US010934261B2

(12) United States Patent
Buckman et al.

(10) Patent No.: US 10,934,261 B2
(45) Date of Patent: Mar. 2, 2021

(54) CALPAIN MODULATORS AND THERAPEUTIC USES THEREOF

(71) Applicant: Blade Therapeutics, Inc., South San Francisco, CA (US)

(72) Inventors: Brad Owen Buckman, Oakland, CA (US); John Beamond Nicholas, Redwood City, CA (US); Shendong Yuan, San Ramon, CA (US); Marc Adler, Orinda, CA (US); Kumaraswamy Emayan, Albany, CA (US); Jingyuan Ma, Palo Alto, CA (US)

(73) Assignee: Blade Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/337,377

(22) PCT Filed: Sep. 27, 2017

(86) PCT No.: PCT/US2017/053629

§ 371 (c)(1),
(2) Date: Mar. 27, 2019

(87) PCT Pub. No.: WO2018/064119

PCT Pub. Date: Apr. 5, 2018

(65) Prior Publication Data

US 2020/0123114 A1 Apr. 23, 2020

Related U.S. Application Data

(60) Provisional application No. 62/554,939, filed on Sep. 6, 2017, provisional application No. 62/459,461, filed on Feb. 15, 2017, provisional application No. 62/459,461, filed on Feb. 15, 2017, provisional application No. 62/401,093, filed on Sep. 28, 2016, provisional application No. 62/401,093, filed on Sep. 28, 2016.

(51) Int. Cl.

| | |
|---|---|
| ***C07D 233/90*** | (2006.01) |
| ***A61P 11/00*** | (2006.01) |
| ***C07C 233/05*** | (2006.01) |
| ***C07D 209/20*** | (2006.01) |
| ***C07D 231/14*** | (2006.01) |
| ***C07D 249/06*** | (2006.01) |
| ***C07D 263/34*** | (2006.01) |
| ***C07D 271/04*** | (2006.01) |
| ***C07D 275/03*** | (2006.01) |
| ***C07D 285/06*** | (2006.01) |
| ***C07D 307/68*** | (2006.01) |
| ***C07D 401/04*** | (2006.01) |
| ***C07D 401/14*** | (2006.01) |
| ***C07D 403/04*** | (2006.01) |
| ***C07D 403/14*** | (2006.01) |
| ***C07D 417/04*** | (2006.01) |
| ***C07D 417/14*** | (2006.01) |

(52) U.S. Cl.

CPC ............ *C07D 233/90* (2013.01); *A61P 11/00* (2018.01); *C07C 233/05* (2013.01); *C07D 209/20* (2013.01); *C07D 231/14* (2013.01); *C07D 249/06* (2013.01); *C07D 263/34* (2013.01); *C07D 271/04* (2013.01); *C07D 275/03* (2013.01); *C07D 285/06* (2013.01); *C07D 307/68* (2013.01); *C07D 401/04* (2013.01); *C07D 401/14* (2013.01); *C07D 403/04* (2013.01); *C07D 403/14* (2013.01); *C07D 417/04* (2013.01); *C07D 417/14* (2013.01)

(58) Field of Classification Search

None

See application file for complete search history.

(56) References Cited

U.S. PATENT DOCUMENTS

| | | | |
|---|---|---|---|
| 4,708,871 | A | 11/1987 | Geysen |
| 4,833,092 | A | 5/1989 | Geysen |
| 4,863,940 | A | 9/1989 | Sharma |
| 5,145,684 | A | 9/1992 | Liversidge et al. |
| 5,223,409 | A | 6/1993 | Ladner et al. |
| 5,331,573 | A | 7/1994 | Balaji et al. |
| 5,403,484 | A | 4/1995 | Ladner et al. |
| 5,463,124 | A | 10/1995 | Jacobi et al. |
| 5,500,807 | A | 3/1996 | Lavin et al. |
| 5,556,762 | A | 9/1996 | Pinilla et al. |
| 5,571,689 | A | 11/1996 | Heuckeroth et al. |
| 5,644,048 | A | 7/1997 | Yau |
| 5,663,143 | A | 9/1997 | Ley et al. |
| 5,750,373 | A | 3/1998 | Gerrard et al. |

(Continued)

FOREIGN PATENT DOCUMENTS

| | | |
|---|---|---|
| CA | 2328440 | 10/1999 |
| CA | 2328720 | 10/1999 |

(Continued)

OTHER PUBLICATIONS

Blum et al., 2003, Complementary use of ion trap / time-of-flight mass spectrometry in combination with capillary high-pressure liquid chromatography: Early characterization of in vivo metabolites of the cathepsin K inhibitor NVP-AAV490 in rat. J Chromatography B. 787:255-270.

Brodney et al., 2015, Utilizing Structures of CYP2D6 and BACE1 Complexes to Reduce Risk of Drug-Drug Interactions with a Novel Series of Centrally Efficacious BACE1 Inhibitors, J Med Chem. 58:3223-3252.

CAS Registry No. 1309010-71-6; STN entry date: Jun. 13, 2011; D-Alanine, N-[(1-phenyl-1H-imidazol-5-yl)carbonyl] in 1 page.

(Continued)

*Primary Examiner* — Joseph R Kosack

(74) *Attorney, Agent, or Firm* — Knobbe Martens Olson & Bear LLP

(57) ABSTRACT

Disclosed herein are small molecule calpain modulator compositions, pharmaceutical compositions, the use and preparation thereof.

44 Claims, No Drawings

(56) References Cited

U.S. PATENT DOCUMENTS

| | | | |
|---|---|---|---|
| 5,852,007 | A | 12/1998 | Chatterjee |
| 5,952,322 | A | 9/1999 | Hoover et al. |
| 6,083,944 | A | 7/2000 | Chatterjee et al. |
| 6,103,720 | A | 8/2000 | Lubisch et al. |
| 6,172,072 | B1 | 1/2001 | Lubisch et al. |
| 6,251,917 | B1 | 6/2001 | Lubisch et al. |
| 6,358,978 | B1 | 3/2002 | Ritzeler et al. |
| 6,380,220 | B1 | 4/2002 | Lubisch et al. |
| 6,436,925 | B1 | 8/2002 | Lubisch et al. |
| 6,448,254 | B1 | 9/2002 | Lubisch et al. |
| 6,482,832 | B1 | 11/2002 | Lubisch et al. |
| 6,506,559 | B1 | 1/2003 | Fire et al. |
| 6,582,827 | B1 | 5/2003 | Lubisch et al. |
| 6,573,099 | B2 | 6/2003 | Graham |
| 6,630,493 | B1 | 10/2003 | Lubisch et al. |
| 6,656,687 | B1 | 12/2003 | Hyldig-Nielsen |
| 7,956,093 | B2 | 6/2011 | Lubisch et al. |
| 7,964,624 | B1 | 6/2011 | Cottrell et al. |
| 8,283,363 | B2 | 10/2012 | Mack et al. |
| 9,434,762 | B2 | 9/2016 | Abell et al. |
| 10,590,084 | B2 | 3/2020 | Buckman et al. |
| 2003/0153519 | A1 | 8/2003 | Kay et al. |
| 2003/0167490 | A1 | 9/2003 | Hunter et al. |
| 2004/0097508 | A1 | 5/2004 | Lubisch et al. |
| 2004/0242542 | A1 | 12/2004 | Shea et al. |
| 2008/0311036 | A1 | 12/2008 | Wang et al. |
| 2010/0144805 | A1 | 6/2010 | Wagner et al. |
| 2010/0216844 | A1 | 8/2010 | Kling et al. |
| 2010/0298326 | A1 | 11/2010 | Kling et al. |
| 2011/0021434 | A1 | 1/2011 | Abell et al. |
| 2011/0059968 | A1 | 3/2011 | Hornberger et al. |
| 2011/0086879 | A1 | 4/2011 | Mack et al. |
| 2011/0152265 | A1 | 6/2011 | Kling et al. |
| 2011/0152325 | A1 | 6/2011 | Kling et al. |
| 2012/0010235 | A1 | 1/2012 | Chu et al. |
| 2014/0005227 | A1 | 1/2014 | Kling et al. |
| 2015/0065477 | A1 | 3/2015 | Kling et al. |
| 2015/0133368 | A1 | 5/2015 | Chang et al. |
| 2015/0368213 | A1 | 12/2015 | Natale et al. |
| 2019/0194139 | A1 | 6/2019 | Buckman et al. |

FOREIGN PATENT DOCUMENTS

| | | |
|---|---|---|
| CA | 2943005 | 9/2015 |
| CN | 105669520 | 6/2016 |
| EP | 0530167 | 3/1993 |
| EP | 1493739 | 1/2005 |
| GB | 2467561 | 8/2010 |
| WO | WO 1984/03506 | 9/1984 |
| WO | WO 1984/03564 | 9/1984 |
| WO | WO 1987/05297 | 9/1987 |
| WO | WO 1991/13889 | 9/1991 |
| WO | WO 1992/13549 | 8/1992 |
| WO | WO 1994/000095 | 1/1994 |
| WO | WO 1995/09859 | 4/1995 |
| WO | WO 1996/12499 | 5/1996 |
| WO | WO 1998/016512 | 4/1998 |
| WO | WO 1998/21186 | 5/1998 |
| WO | WO 1998/41092 | 9/1998 |
| WO | WO 1998/41506 | 9/1998 |
| WO | WO 1999/17790 | 4/1999 |
| WO | WO 1999/50264 | 10/1999 |
| WO | WO 1999/54304 | 10/1999 |
| WO | WO 2000/000823 | 1/2000 |
| WO | WO 2000/039585 | 7/2000 |
| WO | WO 2000/055114 | 9/2000 |
| WO | WO 2000/055125 | 9/2000 |
| WO | WO 2001/089584 | 11/2001 |
| WO | WO 2003/059269 | 7/2003 |
| WO | WO 2003/064440 | 8/2003 |
| WO | WO 2003/080182 | 10/2003 |
| WO | WO 2004/014844 | 2/2004 |
| WO | WO 2004/062601 | 7/2004 |
| WO | WO 2005/000793 | 1/2005 |
| WO | WO 2005/014006 | 2/2005 |
| WO | WO 2005/014534 | 2/2005 |
| WO | WO 2003/091202 | 9/2005 |
| WO | WO 2006/052722 | 5/2006 |
| WO | WO 2007/016476 | 2/2007 |
| WO | WO 2007/025307 | 3/2007 |
| WO | WO 2007/076423 | 7/2007 |
| WO | WO 2007/081530 | 7/2007 |
| WO | WO 2007/089618 | 8/2007 |
| WO | WO 2007/097980 | 8/2007 |
| WO | WO 2007/109080 | 9/2007 |
| WO | WO 2007/141473 | 12/2007 |
| WO | WO 2005/102381 | 3/2008 |
| WO | WO 2008/048121 | 4/2008 |
| WO | WO 2008/080969 | 7/2008 |
| WO | WO 2008/106058 | 9/2008 |
| WO | WO 2008/152093 | 12/2008 |
| WO | WO 2008/154642 | 12/2008 |
| WO | WO 2010/023609 | 3/2010 |
| WO | WO 2010/077836 | 7/2010 |
| WO | WO 2010/094755 | 8/2010 |
| WO | WO 2011/082285 | 7/2011 |
| WO | WO 2011/133346 | 10/2011 |
| WO | WO 2011/133871 | 10/2011 |
| WO | WO 2011/159781 | 12/2011 |
| WO | WO 2012/021788 | 2/2012 |
| WO | WO 2012/040242 | 3/2012 |
| WO | WO 2012/076639 | 6/2012 |
| WO | WO 2012/122420 | 9/2012 |
| WO | WO 2012/122422 | 9/2012 |
| WO | WO 2012/140500 A9 | 10/2012 |
| WO | WO 2013/033396 | 3/2013 |
| WO | WO 2013/076063 | 5/2013 |
| WO | WO 2013/104613 | 7/2013 |
| WO | WO 2013/149800 | 10/2013 |
| WO | WO 2013/166319 | 11/2013 |
| WO | WO 2014/075146 | 5/2014 |
| WO | WO 2015/002915 | 1/2015 |
| WO | WO 2015/073763 | 5/2015 |
| WO | WO 2015/124443 | 8/2015 |
| WO | WO 2015/179441 | 11/2015 |
| WO | WO 2016/027284 | 2/2016 |
| WO | WO 2016/036893 | 3/2016 |
| WO | WO 2016/037157 | 3/2016 |
| WO | WO 2016/089648 | 6/2016 |
| WO | WO 2017/100201 | 6/2017 |
| WO | WO 2017/156071 | 9/2017 |
| WO | WO 2017/156074 | 9/2017 |
| WO | WO 2018/009417 | 1/2018 |
| WO | WO 2018/236913 | 12/2018 |
| WO | WO 2019/190885 | 10/2019 |
| WO | WO 2019/190999 | 10/2019 |
| WO | WO 2019/217465 | 11/2019 |
| WO | WO 2020/006177 | 1/2020 |
| WO | WO 2020/006294 | 1/2020 |

OTHER PUBLICATIONS

Gardiner et al., 2006, Ring closing metathesis of α- and β-amino acid derived dienes, J Organomet Chem. 691:5487-5496.

Kim et al., 2015, Discovery and structure-activity relationships of pyrazolodiazepine derivatives as the first small molecule agonists of the *Drosophila* sex peptide receptor, Bioorg Med Chem. 23:1808-1816.

Kling et al., 2017, Discovery of Novel and Highly Selective Inhibitors of Calpain for the Treatment of Alzheimer's Disease: 243-Phenyl-1H-pyrazol-1-yl)-nicotinamides, J Med Chem. 60:7123-7138.

Li et al., 2015, Synthesis and Cytotoxic Activities of Novel Amino Acid-Conjugates of Pyrrole Derivatives. Youji Huaxue. 35:167-174.

Sasmal et al., 2011, Structure-activity relationship studies of novel pyrazole and imidazole carboxamides as cannabinoid-1 (CB1) antagonists. Bioorg Med Chem Lett. 21(16):4913-4918.

Skogh et al., 2013, Aminocarbonylation of 4-lodo-1H-imidazoles with an Amino Acid Amide Nucleophile: Synthesis of Constrained H-Phe-Phe-NH2 Analogues. J Org Chem. 78:12251-12256.

Zhong et al., 2005, 3-(2-Chloropheny1)-N-(2-cyano-4-methyl-2-pentyl)-5-methylisoxazole-4-carboxamide. Acta Cryst. Section E. E61:o2621-o2622 in 7 pages.

(56) References Cited

OTHER PUBLICATIONS

International Search Report and Written Opinion dated Jan. 2, 2018 for Application No. PCT/US2017/053629, filed Sep. 27, 2017.
Written Opinion (Rule 66) dated Aug. 28, 2018 for Application No. PCT/US2017/053629, filed Sep. 27, 2017.
Written Opinion (Rule 66) dated Dec. 6, 2018 for Application No. PCT/US2017/053629, filed Sep. 27, 2017.
International Preliminary Report on Patentability dated Jan. 22, 2019 for Application No. PCT/US2017/053629, filed Sep. 27, 2017.
Abell et al., 2009, Molecular Modeling, Synthesis, and Biological Evaluation of Macrocyclic Calpain Inhibitors, Angew Chem Int Ed Engl. 48(8):1455-1458.
Bihovsky et al., 2004, 1,2-Benzothiazine 1,1-dioxide α-ketoamide analogues as potent calpain I inhibitors, Bioorg Med Chem Lett. 14(4):1035-1038.
Chatterjee et al., 1999, P2-achiral, P'-extended alpha-ketoamide inhibitors of calpain I. Bioorg Med Chem Lett. 9(16):2371-2374.
Chen et al., 2012, New Tripeptide-Based Macrocyclic Calpain Inhibitors Formed by N-Alkylation of Histidine, Chem Biodiver. 9(11):2473-2484.
Cohrt A. Emil. 2014, Solid-phase synthesis of peptide thioureas and thiazole-containing macrocycles through Ru-catalyzed ring-closing metathesis, ACS Comb Sci. 16(2):71-77 and Supporting Information in 55 pages.
Damalanka et al., 2016, Oxadiazole-Based Cell Permeable Macrocyclic Transition State Inhibitors of Norovirus 3CL Protease, J Med Chem. 59(5):1899-1913.
Donald et al., 1991, C10 N-Acyl Modified FK-506: A Possible Hybrid Analogue of the Transition State of Peptidyl-Prolyl Cis-Trans Isomerization, Tetrahedron Lett., 32(10):1375-1378.
Dourdin et al., 2001, Reduced Cell Migration and Disruption of the Actin Cytoskeleton in Calpain-deficient embryonic Fibroblasts, J Biol Chem. 276(51):48382-48388.
Goll et al., 2003, The Calpain System, Physiol Rev. 83(3):731-801.
Halland et al., 2014, Small Macrocycles As Highly Active Integrin α2β1 Antagonists, ACS Med Chem Lett. 5(2):193-198.
Jánossy et al., 2004, Calpain as a multi-site regulator of cell cycle, Biochem Pharmacol. 67(8):1513-1521.
Jones et al., 2009, Efficient Large-Scale Synthesis of CAT811, a Potent Calpain Inhibitor of Interest in the Treatment of Cataracts, Aust J Chem. 62:671-675.
Jones et al., 2013, A Template-Based Approach to Inhibitors of Calpain 2, 20S Proteasome, and HIV-1 Protease, Chem Med Chem. 8(12):1918-1921.
Jones et al., 2014, The Preparation of Macrocyclic Calpain Inhibitors by Ring Closing Metathesis and Cross Metathesis, Aust J. Chem. 67:1257-1263.
Kim et al., 2011, Synthesis of chromone carboxamide derivatives with antioxidative and calpain inhibitory properties, Eur J Med Chem. 46(5):1721-1728.
Lamouille et al., 2014, Molecular mechanisms of epithelial-mesenchymal transition, Nat Rev Mol Cell Biol. 15(3):178-196 in 46 pages.
Lee et al., 2005, Synthesis and biological evaluation of chromone carboxamides as calpain inhibitors, Bioorg Med Chem Lett., 15(11):2857-2860.
Leloup et al., 2006, Involvement of calpains in growth factor-mediated migration, Int J Biochem Cell Biol. 38(12):2049-2063.
Low et al., 2016, Rational Design of Calpain Inhibitors Based on Calpastatin Peptidomimetics, J Med Chem. 59(11):5403-5415.
Lu et al., 2015, Mechanism of Action of Thalassospiramides, A New Class of Calpain Inhibitors, Sci Rep. 5:8783 in 8 pages.
Lubisch et al., 2002, Discovery of phenyl alanine derived ketoamides carrying benzoyl residues as novel calpain inhibitors, Bioorg Med Chem Lett., 12(10):1335-1338.
Mandadapu et al., 2013, Macrocyclic Inhibitors of 3C and 3C-like Proteases of Picornavirus, Norovirus, and Coronavirus, Bioorg Med Chem Lett. 23(13):3709-3712.
Miettinen et al., 1994, TGF-β Induced Transdifferentiation of Mammary Epithelial Cells to Mesenchymal Cells: Involvement of Type I Receptors, j Cell Biol. 127(6 Pt 2):2021-2036.
Morton et al., 2013, A Macrocyclic Calpain Inhibitor Slows the Development of Inherited Cortical Cataracts in a Sheep Model, Invest Ophthal Visual Science. 54(1):389-395.
Nam et al., 2008, Design and synthesis of 4-quinolinone 2-carboxamides as calpain inhibitors, Bioorg Med Chem Lett., 18(1):205-209.
Nema et al., 2011, Excipients and Their Role in Approved Injectable Products: Current Usage and Future Directions, PDA J Pharm Sci Technol. 65(3):287-332.
Oh et al., 2007, Thalassospiramides A and B, Immunosuppressive Peptides from the Marine Bacterium *Thalassospira* sp., Org Ltts. 9(8):1525-1528.
Pegorier et al., 2010, Bone Morphogenetic Protein (BMP)-4 and BMP-7 regulate differentially Transforming Growth Factor (TGF)-β1 in normal human lung fibroblasts (NHLF), Respir Res. 11:85 in 11 pages.
Pehere et al., 2012, New β-Strand Templates Constrained by Huisgen Cycloaddition, Org Lett. 14(5):1330-1333.
Pehere et al., 2013, New cylindrical peptide assemblies defined by extended parallel β-sheets, Org Biomol Chem. 11(3):425-429.
Pehere et al., 2013, Synthesis and Extended Activity of Triazole-Containing Macrocyclic Protease Inhibitors, Chem Eur J. 19:7975-7981.
Powell et al., 1998, Compendium of Excipients for Parenteral Formulations, pDA; J Pharm Sci Technol. 52(5):238-311.
Ravulapalli et al., 2009, Distinguishing between calpain heterodimerization and homodimerization, FEBS J. 276(4):973-982.
Rotstein et al., 2014, Spirocyclic hypervalent iodine(III)-mediated radiofluorination of non-activated and hindered aromatics, Nature Comm. 5:4365-4371.
Rotstein et al., 2016, Mechanistic Studies and Radiofluorination of Structurally Diverse Pharmaceuticals with Spirocyclic lodonium(III) Ylides, Chem Sci. 7(7):4407-4417.
Santos et al., 2012, Distinct Regulatory Functions of Calpain 1 and 2 during Neural Stem Cell Self-Renewal and Differentiation, PLoS One 7(3):e33468 in 12 pages.
Schád et al., 2002, A novel human small subunit of calpains, Biochem J 342(Pt 2):383-388.
Stoermer et al., 2009, Base-Sensitivity of Arginine Alpha-Ketoamide Inhibitors of Serine Proteases, Aust J Chem. 62(9):988-992.
Stuart et al., 2011, Molecular Modeling: A Search for a Calpain Inhibitor as a New Treatment for Cataractogenesis, J Med Chem. 54(21):7503-7522.
Von Dobeneck et al., 1976, Diaminopyrrolinone, Liebigs Ann Chem., 3:476-486.
Walker et al., 2001, General method for the synthesis of cyclic peptidomimetic compounds, Tetrahed Letts. 42(34):5801-5804.
Wells et al., 2001, 1,2-Benzothiazine 1,1-Dioxide P2-P3 Peptide Mimetic Aldehyde Calpain I Inhibitors, J Med Chem. 44:3488-3503.
Woon et al., 2011, Structure guided development of potent reversibly binding penicillin binding protein inhibitors, ACS Med Chem Lett., 2(3):219-223 and Supporting Information, S1-S46.
Young et al., 2010, Beyond the Canonical 20 Amino Acids: Expanding the Genetic Lexicon, J Biol Chem. 285(15):11039-11044.
CAS Registry No. 2094533-75-0; STN entry date: May 2, 2017; Benzamide, N-(2-amino-1,1-dimethyl-2-oxoethyl)-2-bromo-5-chloro-3-fluoro-, in 1 page.
CAS Registry No. 1629446-68-9; STN entry date: Oct. 21, 2014; Benzamide, 3-cyano-N-[(1S)-1-formyl-2-phenylethyl], in 1 page.
CAS Registry No. 2094410-58-7; STN entry date: May 2, 2017; Benzamide, 2-bromo-5-chloro-N-(1-cyano-2-methoxy-1-methylethyl)-3-fluoro-, in 1 page.
CAS Registry No. 2037707-18-7; STN entry date: Nov. 25, 2016; Alanine, 3-fluoro-N-(2-fluoro-6-methoxybenzoyl)-, in 1 page.
CAS Registry No. 1938924-09-4; STN entry date: Jun. 24, 2016; D-Leucine, N-(2-bromo-6-fluoro-3-methylbenzoyl)-, in 1 page.
CAS Registry No. 2048401-56-3; STN entry date: Dec. 14 2016; 4-Hexenoic acid, 2-[(4,5-dichloro-2-methoxybenzoyl)amino]-, in 1 page.

(56) References Cited

OTHER PUBLICATIONS

CAS Registry No. 2026949-92-6; STN entry date: Nov. 8, 2016; D-Leucine, N-[(6-bromo-3,4-dihydro-3-oxo-2H-1,4-benzoxazin-7-yl)carbonyl]-, in 1 page.
CAS Registry No. 1031704-04-7; STN entry date: Jun. 30, 2008; L-Valine, N-[(5,7,8,10-tetrahydro-7,8-dioxo-6-undecyl-2-phenazinyl)carbonyl]-, in 1 page.
CAS Registry No. 566157-42-4; STN entry date: Aug. 14, 2003; Alanine, N-[(9,10-dihydro-9-oxo-3-acridinyl)carbonyl]-2-methyl-, in 1 page.
CAS Registry No. 289062-66-4; STN entry date: Sep. 14, 2000; Acetic acid, [(2,4-dichlorobenzoyl)amino](phenylthio)-, in 1 page.
CAS Registry No. 15643-65-9; STN entry date: Nov. 16, 1984; Acetic acid, [(3,4-dichlorobenzoyl)amino]phenoxy-, in 1 page.
CAS Reg. No. 1187056-39-8, Entered STN: Oct. 1, 2009; Acetic acid, 2-cyano-2-[(2,6-difluorobenzoyl)amino]-, ethyl ester in 1 page.
CAS Reg. No. 885026-68-6, Entered STN: May 19, 2006; Benzamide, N-(2-butoxy-1-cyano-1-methylethyl)-2,6-dichloro- in 1 page.
CAS Reg. No. 1825463-80-6; STN Entry Date Dec. 9, 2015; Benzamide, N-(cyanocyclopropylmethyl)-6-fluoro-2,3- in 1 page.
CAS Reg No. 1551381-70-4, STN Entry Date: Feb. 20, 2014; Benzamide, N-(1-cyanopropyl)-2,6-difluoro-3-methyl- in 1 page.
CAS Reg No. 1555291-73-0, STN Entry Date: Feb. 25, 2014; Benzamide, 4-chloro-N-(1-cyanobutyl)-2,5-difluoro- in 1 page.
CAS Reg No. 1551443-75-4, STN Entry Date: Feb. 20, 2014; Benzamide, 4-chloro-N-(1-cyano-1-methylpropyl)-2,5-difluoro- in 1 page.
CAS Reg. No. 1347051-33-5, Entered STN: Dec. 1, 2011; 1H-Imidazole-5-hexanoic acid, β-[[[(6S,8aS)-octahydro-4-oxo-2-(phenylmethyl)sulfonyl]pyrrolo[1,2-a]pyrazin-6-yl]carbonyl]amino]-a-oxo-, methyl ester, 1 page.
CAS Reg. No. 1026166-23-3, Entered STN: Jun. 8, 2008 ; Hexanoic acid, 3[[[(1R,25,55)-3-[(2S)-2-cyclohexyl-2-[(3,3-dimethyl-1-oxobutyl)amino]acetyl]-6,6-dimethyl-3-azabicyclo[3.1.0]hex-2-yl]carbonyl]amino]-6,6,6-trifluoro-2-oxo-, 1 page.
CAS Reg. No. 2026817-08-1, Entered STN: Nov. 8, 2016; D-Leucine, N-[[3-(3-thienyl)-1H-pyrazol-4-yl]carbonyl]-, 1 page.
CAS Reg. No. 2049278-49-9, Entered STN: Dec. 15, 2016; 4-Hexenoic acid, 2-[[[1-methyl-3-(2-thienyl)-1H-pyrazol-4-yl]carbonyl]amino]-, 1 page.
CAS Reg. No. 2039960-52-4, Entered STN: Nov. 28, 2016; 5-Hexenoic acid, 2-[[[1-methyl-3-(2-thienyl)-1H-pyrazol-4-yl]carbonyl]amino]-, 1 page.
CAS Reg. No. 2026895-95-2, Entered STN:Nov. 8, 2016; L-Norleucine, N-[[3-(5-chloro-2-thienyl)-1H-pyrazol-4-yl]carbonyl]-, 1 page.
CAS Reg. No. 2026863-64-7, Entered STN: Nov. 8, 2016; L-Norleucine, N-[[4-(5-chloro-2-thienyl)-1H-pyrrol-3-yl]carbonyl]-, 1 page.
CAS Reg. No. 1796920-43-8, Entered STN: Jul. 8, 2015; 1H-Pyrrole-3-carboxamide, N-(2-amino-1-methyl-2-oxoethyl)-4-(5-chloro-2-thienyl)-, 1 page.
Gopalsamy et al., 2004, Identification of [(naphthalene-1-carbonyl)-amino]-acetic acid derivatives as nonnucleoside inhibitors of HCV NSSB RNA dependent RNA polymerase. Bioorg Med Chem Lett. 14(16):4221-4224.
Kling et al., 2018, Mitigating the Metabolic Liability of Carbonyl Reduction: Novel Calpain Inhibitors with P1' Extension, ACS Med Chem Lett. 9(3):221-226.
Li et al., 1996, Novel peptidyl alpha-keto amide inhibitors of calpains and other cysteine proteases, J Med Chem. 39(20):4089-4098.
Lubisch et al., 2003, Benzoylalanine-derived ketoamides carrying vinylbenzyl amino residues: discovery of potent water-soluble calpain inhibitors with oral bioavailability, J Med Chem. 46(12):2404-2412.
Muniappan et al., 2017, Calpain Inhibition Attenuates Adipose Tissue Inflammation and Fibrosis in Diet-induced Obese Mice, Sci Rep. 7:14398.
Nimmrich et al., 2008, Inhibition of Calpain Prevents N-Methyl-D-aspartate-Induced Degeneration of the Nucleus Basalis and Associated Behavioral Dysfunction, J Pharmacol Exp Ther. 327(2):343-352.
Ross et al., 2013, Biosynthetic Multitasking Facilitates Thalassospiramide Structural Diversity in Marine Bacteria, J Am Chem Soc. 135(3):1155-1162.
Singh et al., 2015, Identification of amino acid appended acridines as potential leads to anti-cancer drugs. Bioorg Med Chem Lett. 25(18):3854-3858.
Vengeliene et al., 2016, The Calpain Inhibitor A-705253 Attenuates Alcohol-Seeking and Relapse with Low Side-Effect Profile, Neuropsychopharmacology. 41(4):979-988 [online published Jul. 28, 2015].
Zhang et al., 2016, Family-wide Structural Characterization and Genomic Comparisons Decode the Diversity-oriented Biosynthesis of Thalassospiramides by Marine Proteobacteria, J Biol Chem. 291(53):27228-27238.
Beaucage S.L., Oligodeoxyribonucleotides synthesis. Phosphoramidite approach., (1993) Methods Mol. Biol., 20, 33-61.
Boyer et al., Induction and regulation of epithelial-mesenchymal transitions., (2000) Biochem. Pharmacol, 60, 1091-1099.
Branton et al., TGF-beta and fibrosis., (1999) Microbes Infect, 1(15), 1349-1365.
Brooks et al., CHARMM: A program for macromolecular energy, minimization, and dynamics calculations, (1983) J. Comp. Chem., 4, 187-217.
Burkert et al., Pitfalls in the use of the torsion angle driving method for the calculation of conformational interconversions., (1982) J Comp. Chem, 3, 40-46.
Capaldi et al., Signal amplification through nucleotide extension and excision on a dendritic Dna platform., (2000) Nucleic Acids Res., 28(7), e21.
Chubanov et al., Natural and synthetic modulators of SK (K(ca)2) potassium channels inhibit magnesium- dependent activity of the kinase-coupled cation channel TRPM7., (2012) Br J Pharmacol, 166(4), 1357-1376.
Clackson et al., Making antibody fragments using phage display libraries. (1991) Nature, 352: 624-628.
Coburn et al., Potent and specific inhibition of human immunodeficiency virus type 1 replication by RNA interference., (2002) J. Virol., 76, 9225-9231.
Cohen et al., Molecular Modeling Software and Methods for Medicinal Chemistry, (1990) Journal of Medicinal Chemistry, 33(3), 883-894.
Connolly M.L., Solvent-Accessible Surfaces of Proteins and Nucleic Acids., (1983) Science, 221(4612), 709-713.
Cwirla et al., Peptides on phage: a vast library of peptides for identifying ligands., (1990) Proc. Natl. Acad. Sci. USA, 87, 6378.
Davis et al., The Crystal Structures of Human Calpains 1 and 9 Imply Diverse Mechanisms of Action and Auto inhibition., (2007) J. Mol. Biol., 366, 216-229.
De Maria et al., Calpain Expression and Activity during Lens Fiber Cell Differentiation., (2009) J. Biol. Chem., 284 (20), 13542-50.
Dunbrack et al., Meeting review: the Second Meeting on the Critical Assessment of Techniques for Protein Structure Prediction (CASP2), Asilomar, California, Dec. 13-16, 1996., (1997) Folding and Design, 2, R27; 16 pages.
Egholm et al., PNA hybridizes to complementary oligonucleotides obeying the Watson-Crick hydrogen-bonding rules., (1993) Nature, 365(6446), 566-568.
Friedman et al., Therapy for fibrotic diseases: nearing the starting line., (2013) Sci. Transi. Med., 5(167), 167-17 pages.
Geysen et al., Small peptides induce antibodies with a sequence and structural requirement for binding antigen comparable to antibodies raised against the native protein., (1985) Proc. Natl. Acad. Sci. USA, 82(1), 178-182.
Geysen et al., Strategies for epitope analysis using peptide synthesis., (1987) Journal of Immunological Methods., 102(2), 259-274.
Geysen et al., Use of peptide synthesis to probe viral antigens for epitopes to a resolution of a single amino acid., (1984) Proc. Natl. Acad. Sci. USA, 81, 3998-4002.

(56) References Cited

OTHER PUBLICATIONS

Gooch et al., Invovlement of calcineurin in transforming growth factor-beta-mediated regulation of extracellular maxtrix accumulation., (2004) J. Biol Chem., 279(15), 15561-70.
Goodford P.J., A computational procedure for determining energetically favorable binding sites on biologically important macromolecules., (1985) J. Med. Chem, 28, 849-857.
Goodsell et al., Automated docking of substrates to proteins by simulated annealing., (1990) Protein., 8(3): 195-202.
Hata et al., Calpain 8/nCL-2 and Calpain 9/nCL-4 Constitute an Active Protease Complex, G-Calpain, Involved in Gastric Mucosal Defense., (2010) PloS Genet., 6(7), e1001040 in 14 pages.
Hyrup et al., Peptide nucleic acids (PNA): synthesis, properties and potential applications., (1996) Bioorg Med Chem., 4(1), 5-23.
Iwano et al., Evidence that fibroblasts derive from epithelium during tissue fibrosis., (2002) J Chit Invest., 110(3): 341-350.
Janda et al., RAS and TGF-beta cooperatively regulate epithelial cell plasticity and metastasis: dissection of Ras signaling pathways., (2002) J. Cell Biol, 156, 299-313.
Jones et al. Improved methods for building protein models in electron density maps and the location of errors in these models., (1991) Acta Cryst., A47, 110-119.
Kalluri et al., Epithelial-mesenchymal transition and its implications for fibrosis., (2003) J Clin Invest, 112(12), 1776-1784.
Kang, et al., Antibody redesign by chain shuffling from random combinatorial immunoglobulin libraries., (1991) Proc. Natl. Acad. Sci. USA, 88, 11120-11123.
Kiemer, et al., Identification of genes involved in epithelial-mesenchymal transition and tumor progression., (2001) Oncogene, 20, 6679-6688.
Kim et al., Targeting Calpains: a Therapeutic Strategy for the Treatment of TGFbeta Mediated Mesenchymal Transition and Associated Pathologies., (2014) 64th Annual Meeting of the American Society of Human Genetics.
Kraulis, Molscript: a program to produce both detailed and schematic plots of protein structures., (1991) J Appl Cryst., 24, 946-950.
Kuntz et al., A geometric approach to macromolecule-ligand interactions., (1982) J. Mol. Biol., 161, 269-288.
Kuntz I.D., Structure-Based Strategies for Drug Design and Discovery, (1992) Science 257:1078-1082.
Leask et al., TGF-beta signaling and the fibrotic response., (2004) FASEB J., 18(7), 816-827.
LeBleu et al., Origin and function of myofibroblasts in kidney fibrosis., (2013) Nat Med, 19(8), 1047-1053.
Lee et al., Bleomycin delivery by osmotic minipump: similarity to human scleroderma interstitial lung disease., (2014) Am J Physiol Lung Cell Mol Physiol, 306(8), L736-748.
Lee et al., Molecular Cloning and Characterization of a Novel Tissue-Specific Calpain Predominantly Expressed in the Digestive Tract., (1998) Biol Chem., 379(2), 175-183.
Li et al., Suppression of atherogenesis by delivery of TGFbeta1ACT using adeno-associated virus type 2 in LDLR knockout mice., (2006) Biochem Biophys Res Commun., 344(3): 701-707.
Lowman et al., Selecting high-affinity binding proteins by monovalent phage display., (1991) Biochemistry, 30(45): 10832-10838.
Ma et al., Expression of calpain small subunit 2 in mammalian tissues., (2004) Curr Eye Res., 29(4-5), 337-347.
Mag et al., Synthesis and selective cleavage of an oligodeoxynucleotide containing a bridged internucleotide 5'- phosphorothioate linkage., (1991) Nucleic Acids Res., 19(7): 1437-1441.
Mani et al., The epithelia-mesenchymal transition generates cells with properties of stem cells., (2008) Cell, 122(4), 704-715.
Marks et al., By-passing immunization. Human antibodies from V-gene libraries displayed on phage., (1991), J Mol Biol., 222, 581-597.
McKay et al., Characterization of a Potent and Specific Class of Antisense Oligonucleotide Inhibitor of Human Protein Kinase C-α Expression., (1999) Biol. Chem., 274(3): 1715-1722.
Miranker et al., Functionality maps of binding sites: a multiple copy simultaneous search method., (1991) Proteins. 11(1): 29-34.
Miyazono K., Transforming growth factor-beta signaling in epithelial-mesenchymal transition and progression of cancer., (2009) Proc Jpn Acad Ser. B. Phys. Bio. Sci., 85(8), 314-323.
Navia et al., Use of structural information in drug design., (1992) Current Opinion in Structural Biology, 2(2): 202-210.
Nielsen, P.E., Peptide nucleic acid (PNA): A model structure for the primordial genetic material?, (1993) Origins of life and evolution of biospheres, 23(5), 323-327.
Nieto M.A., The snail superfamily of zinc-finger transcription factors., (2002) Nat Rev Mol Cell Biol., 3, 155-166.
Nishibata et al., Automatic creation of drug candidate structures based on receptor structure. Starting point for artificial lead generation., (1991) Tetrahedron, 47(43), 8985-8990.
Peng et al., Bleomycin induces molecular changes directly relevant to idiopathic pulmonary fibrosis: A model for "active" disease., (2013) Plos One, 8(4), e59348; 15 pages.
Piccirillo et al., TGF-β1 Somatic Gene Therapy Prevents Autoimmune Disease in Nonobese Diabetic Mice., (1998) J Immunol., 161(8): 3950-3956.
Piera-Velazquez et al., Role of endothelial-mesenchymal transition (EndoMT) in the pathogenesis of fibrotic disorders. (2011), Am J Pathol., 179(3), 1074-1080.
Savary et al., Role of TGF-β signaling in EMT, cancer progression and metastasis., (2011) Drug Discovery Today: Disease Models, 8(2-3), 121-126.
Schoofs et al., Epitopes of an influenza viral peptide recognized by antibody at single amino acid resolution., (1988) J Immunol., 140(2): 611-616.
Singh et al., EMT, cancer stem cells and drug resistance: an emerging axis of evil in the war on cancer., (2010) Oncogene, 29(34), 4741-4751.
Smith G.P., Surface presentation of protein epitopes using bacteriophage expression systems., (1991) Current Opin Blotechnol., 2, 668-673.
Stewart et al., Lentivirus-delivered stable gene silencing by RNAi in primary cells., (2003) RNA, 9, 493-501.
Strutz et al., Identification and characterization of a fibroblast marker: FSP1., (1995) J Cell Biol, 130(2): 393-405.
Summerton J., Morpholino antisense oligomers: the case for an RNase H-independent structural type., (1999) Biochim Biophys Acta., 1489, 141-158.
Suzuki et al., Structure, activity, and biology of calpain., (2004) Diabetes, 53(Suppl 1): S12-S18.
Tojo et al., The ALK-5 Inhibitor A-83-01 inhibits Smad signaling and epithelial-to-mesenchymal transition by transforming growth factor-beta. (2005) Cancer Sci, 96(11), 791-800.
Verlinde et al., Structure-based drug design: progress, results and challenges., (1994) Structure, 2, 577-587.
Wahlestedt et al., Potent and nontoxic antisense oligonucleotides containing locked nucleic acids., (2000) PNAS USA, 97(10): 5633-5638.
Weiner et al., A new force field for molecular mechanical simulation of nucleic acids and proteins., (1984) J Am Chem Soc. 106, 765-784.
Willis et al., TGF-beta-induced EMT: mechanisms and implications for fibrotic lung disease., (2007) Amer J Physiol Lung Cell Mol Physiol, 293(3): L525-L534.
Wu et al. Critical role of calpain-mediated cleavage of calcineurin in excitotoxic neurodegeneration. (2004), J Biol Chem. 279(6), 4929-4940.
Wu et al., Detection of epithelial to mesenchymal transition in airways of a bleomycin induced pulmonary fibrosis model derived from an a-smooth muscle actin-Cre transgenic mouse., (2007) Respir Res., 8(1), 1; 11 pages.
Wynn T., Cellular and molecular mechanisms of fibrosis., (2008) J Pathol., 214(2): 199-210.
Xue et al., The Gatekeeper Effect of Epithelial-Mesenchymal Transition Regulates the Frequency of Breast Cancer Metastasis., (2003) Cancer Res., 63, 3386-3394.
Yang et al., Dissection of key events in tubular epithelial to myofibroblast transition and its implications in renal interstitial fibrosis., (2001) Am J Pathol., 159(4): 1465-1475.

(56) References Cited

OTHER PUBLICATIONS

Yoshikawa et al., Isolation of Two Novel Genes, Down-regulated in Gastric Cancer., (2000) Jpn J Cancer Res., 91(5), 459-463.
Zeisberg et al., Renal Fibrosis: Collagen Composition and Assembly Regulates Epithelial-Mesenchymal Transdifferentiation., (2001) Am J Pathol., 159(4): 1313-1321.
Zimmerman et al., The calpain small subunit gene is essential: its inactivation results in embryonic lethality. (2000) IUBMB Life, 50(1), 63-68.
CAS Registry No. 1422551-25-4, N-[(1S)-2-amino-1-(1H-imidazol-5-ylmethyl)-2-oxoethyl]-3-(3-fluorophenyl)- 1H-Pyrazole-4-carboxamide, Entered STN Mar. 7, 2013; 1 page.
Brouillette et al., Supporting Information for Valuable Versatile Reactivity of Thiaaisatoic Anhydrides: Expedient Solid-Phase Synthesis of Thieno [1,4]diazepine-2,5-diones, Synlett (2008) 15:2360-2364; Aug. 22, 2008 pp. 1-58.
Wang et al., Synthesis and Biological Activity of 6-Substituted Pyrrolo [2,3- d]pyrimidine Thienoyl Regioisomers as Inhibitors of de Novo Purine Biosynthesis with Selectivity for Cellular Uptake by High Affinity Folate Receptors and the Proton-Coupled Folate Transporter over the Reduced Folate Carrier. J Med Chem. (2012) 55(4):1758-1770.
Partial Supplementary European Search Report dated Aug. 13, 2020 for Application No. 17857308.5, filed Apr. 26, 2019.
Celatka et al., 2002, Asymmetric symhegis of a C1-C19 fragment of Ulapualide A. Tetrahed Lttrs, 43(39): 704-37046.
Jansen et al., 1961. Some 4-Substituted Gxazoies. J Chem Society pp. 465-411 (see Reaxys-Abs).
Reaxys Database, 2002, Database Accession No. 9305036, Eisevier Life Sciences IP Limited, 1 page.
reaxys Database, 1961, Database Accession No. 849427, Eisevier Life Sciences IP Limited, 2 page.
Extended European Search Report dated Dec. 14, 2020 for Application No. 17857308.5. filed Apr. 26, 2019.
New Zealand Examination Report dated Dec. 2, 2020 for Application No. 752865, filed Apr. 24, 2019.

CALPAIN MODULATORS AND THERAPEUTIC USES THEREOF

CROSS REFERENCE TO RELATED APPLICATIONS

Any and all priority claims identified in the Application Data Sheet, or any correction thereto, are hereby incorporated by reference under 37 CFR 1.57. For example, this application is a U.S. National Phase of International Application No. PCT/US2017/053629, filed on Sep. 27, 2017 and published on Apr. 5, 2018 as WO 2018/064119, which claims the benefit of U.S. Provisional Application 62/401,093, filed on Sep. 28, 2016; U.S. Provisional Application 62/459,461, filed on Feb. 15, 2017; and U.S. Provisional Application 62/554,939, filed on Sep. 6, 2017, which are incorporated herein by reference in their entirety.

BACKGROUND

Field of the Invention

The present invention relates to the fields of chemistry and medicine. More particularly, the present invention relates to non-macrocyclic α-keto amide compounds as small molecule calpain modulators, compositions, their preparation, and their use as therapeutic agents.

Description of the Related Art

Fibrotic disease accounts for an estimated 45% of deaths in the developed world but the development of therapies for such diseases is still in its infancy. The current treatments for fibrotic diseases, such as for idiopathic lung fibrosis, renal fibrosis, systemic sclerosis, and liver cirrhosis, are few in number and only alleviate some of the symptoms of fibrosis while failing to treat the underlying cause.

Despite the current limited understanding of the diverse etiologies responsible for these conditions, similarities in the phenotype of the affected organs, across fibrotic diseases, strongly support the existence of common pathogenic pathways. At present, it is recognized that a primary driver of fibrotic disease is a high transforming growth factor-beta (TGFβ) signaling pathway which can promote the transformation of normally functioning cells into fibrosis-promoting cells. Termed "myofibroblasts," these transformed cells can secrete large amounts of extracellular matrix proteins and matrix degrading enzymes, resulting in the formation of scar tissue and eventual organ failure. This cellular process is transformative and termed "myofibroblast differentiation" (which includes Epithelial-to-Mesenchymal Transition (EpMT) and its variations like Endothelial-to-Mesenchymal Transition (EnMT) and Fibroblast-to-Myofibroblast Transition (FMT)). This process is a major target for the treatment of fibrotic diseases. Myofibroblast differentiation has also been shown to occur within cancer cells that have been chronically exposed to high TGFβ, causing stationary epithelial cells to become motile, invasive, and metastasize. Thus, within the context of cancer, the signaling has been documented to associate with the acquisition of drug resistance, immune system evasion, and development of stem cell properties.

Despite the tremendous potential of myofibroblast differentiation-inhibiting drugs, and the numerous attempts to develop a working treatment, the data gathered thus far has yet to translate into practical therapy. This is partly due to the lack of an ideal target protein. Initial strategies to target the myofibroblast differentiation process focused on proximal inhibition of the TGFβ signaling pathway by various methods, including targeting ligand activators (e.g. alpha-v integrins), ligand-receptor interactions (e.g., using neutralizing antibodies) or TGFβ receptor kinase activity (e.g., small molecule chemical compound drugs to block signal transduction). Unfortunately, TGFβ is a pleiotropic cytokine with many physiological functions such that global suppression of TGFβ signaling was also associated with severe side effects. Additionally, current data suggests that such proximal inhibition may be vulnerable to pathologic workaround strategies (i.e., due to redundancy or compensation), that would limit the utility of such drugs. Further complicating matters is that, in cancer, TGFβ signaling early on functions as an anti-tumorigenic growth inhibitor but later becomes tumor promoting and is another reason why selective inhibition of pathogenic elements of signaling is so strongly desired. In light of these inherent limitations, current treatment strategies have refocused on identification and inhibition of critical distal events in TGFβ signaling, which in theory would preferentially target the pathologic, but not physiological functions of TGFβ signaling.

SUMMARY

A compound having the structure of the formula I:

I

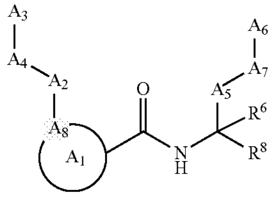

or a pharmaceutically acceptable salt thereof, wherein:

$A_1$ is selected from the group consisting of optionally substituted 5-10 membered heterocyclyl provided the 5-10 membered heterocyclyl is not substituted with oxo, optionally substituted 5-, 8-, or 9-membered heteroaryl, and optionally substituted $C_{3-10}$ carbocyclyl;

$A_2$ is selected from the group consisting of optionally substituted 3-10 membered heterocyclyl, optionally substituted $C_{6-10}$ aryl, optionally substituted 5-10 membered heteroaryl, and optionally substituted $C_{3-10}$ carbocyclyl, $—CR_2—$, —S—, —S(=O)—, $—SO_2—$, —O—, —C(=S)—, —C(=O)—, —NR—, —CH=CH—, —C≡C—, —OC(O)NH—, —NHC(O)NH—, —NHC(O)O—, —NHC(O)—, —NHC(S)NH—, —NHC(S)O—, —NHC(S)—, and single bond;

$A_4$ is selected from the group consisting of optionally substituted $C_6$_10 aryl, optionally substituted 5-10 membered heteroaryl, optionally substituted 3-10 membered heterocyclyl, optionally substituted $C_{3-10}$ carbocyclyl, optionally substituted $C_{1-4}$ alkyl, $—(CR_2)_n—S—(CR_2)_n—$, $—(CR_2)_n—S(=O)—(CR_2)_n—$, $—(CR_2)_n—SO_2—(CR_2)_n—$, $—(CR_2)_n—O—(CR_2)_n—$, $—(CR_2)_n—C(=S)—(CR_2)_n—$, $—(CR_2)_n—C(=O)—(CR_2)_n—$, $—(CR_2)_n—NR—(CR_2)_n—$, $—(CR_2)_n—CH=CH—(CR_2)_n—$, $—(CR_2)_n—OC(O)NH—(CR_2)_n—$, $—(CR_2)_n—NHC(O)NH—(CR_2)_n—$, $—(CR_2)_n—NHC(O)O—(CR_2)_n—$, $—(CR_2)_n—NHC(O)—(CR_2)_n—$, $—(CR_2)_n—NHC(S)NH—(CR_2)_n—$, $—(CR_2)_n—NHC(S)O—(CR_2)_n—$, $—(CR_2)_n—NHC(S)—(CR_2)_n—$, and single bond;

when $A_2$ and $A_4$ are single bond, $A_3$ is directly attached to $A_8$;

$A_3$ is selected from the group consisting of optionally substituted $C_6$_10 aryl, optionally substituted 5-10 membered heteroaryl, optionally substituted 3-10 membered heterocyclyl, and optionally substituted $C_{3-10}$ carbocyclyl, or if $A_2$ is selected from optionally substituted 3-10 membered heterocyclyl, optionally substituted $C_{6-10}$ aryl, optionally substituted 5-10 membered heteroaryl, and optionally substituted $C_{3-10}$ carbocyclyl, then $A_3$ is selected from the group consisting of hydrogen, optionally substituted $C_{6-10}$ aryl, optionally substituted 5-10 membered heteroaryl, optionally substituted 3-10 membered heterocyclyl, optionally substituted $C_{3-10}$ carbocyclyl, —C≡CH, and optionally substituted 2- to 5-membered polyethylene glycol;

$A_5$ is selected from the group consisting of optionally substituted 3-10 membered heterocyclyl, optionally substituted $C_{6-10}$ aryl, optionally substituted 5-10 membered heteroaryl, optionally substituted $C_{3-10}$ carbocyclyl, optionally substituted $C_{1-8}$ alkyl, —S—, —S(═O)—, —$SO_2$—, —O—, —C(═S)—, —C(═O)—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;

$A_6$ is selected from the group consisting of optionally substituted $C_6$_o aryl, optionally substituted 5-10 membered heteroaryl, optionally substituted 3-10 membered heterocyclyl, and optionally substituted $C_{3-10}$ carbocyclyl, optionally substituted $C_{1-8}$ alkyl, optionally substituted $C_{2-8}$ alkenyl, optionally substituted —O—$C_{1-6}$ alkyl, optionally substituted —$OC_{2-6}$ alkenyl, —$OSO_2CF_3$, and any natural or non-natural amino acid side chain;

$A_7$ is selected from the group consisting of optionally substituted $C_6$_o aryl, optionally substituted 5-10 membered heteroaryl, optionally substituted 3-10 membered heterocyclyl, optionally substituted $C_{3-10}$ carbocyclyl, optionally substituted $C_{1-8}$ alkyl, —S—, S(═O)—, —$SO_2$—, —O—, —C(═S)—, —C(═O)—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;

when $A_5$ and $A_7$ are single bond, $A_6$ is directly attached to the carbon to which $R^8$ is attached;

$A_8$ is a ring member of $A_1$ and selected from the group consisting of C, CH, and N;

$R^8$ is selected from the group consisting of —$COR^1$, —CN, —CH═$CHSO_2R$, and —$CH_2NO_2$;

$R^1$ is selected from the group consisting of H, —OH, $C_{1-4}$ haloalkyl, —COOH, —$CH_2NO_2$, —C(═O)NOR, —$NH_2$, —$CONR^2R^3$, —$CH(CH_3)$═$CH_2$, —$CH(CF_3)NR^2R^3$, —C(F)═$CHCH_2CH_3$,

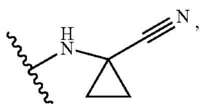, 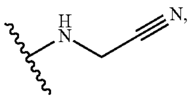, 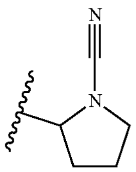,

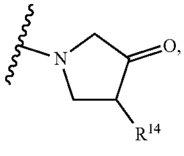, 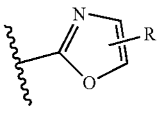,

-continued

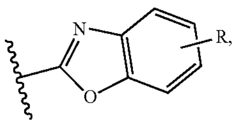, 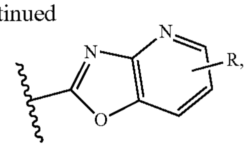,

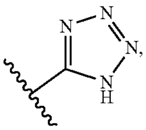, 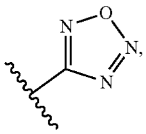, 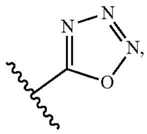,

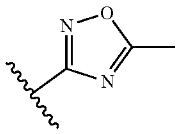, 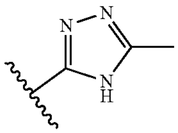,

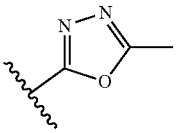, and 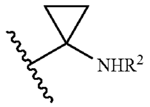;

$R^{14}$ is halo;

each R, $R^2$, and $R^3$ are independently selected from —H, optionally substituted $C_{1-4}$ alkyl, optionally substituted $C_{1-8}$ alkoxyalkyl, optionally substituted 2- to 5-membered polyethylene glycol, optionally substituted $C_{3-7}$ carbocyclyl, optionally substituted 5-10 membered heterocyclyl, optionally substituted $C_6$_10 aryl, and optionally substituted 5-10 membered heteroaryl; and $R^6$ is independently selected from —H and optionally substituted $C_{1-4}$ alkyl.

Other embodiments disclosed herein include a pharmaceutical composition comprising a therapeutically effective amount of a compound disclosed herein and a pharmaceutically acceptable excipient.

Other embodiments disclosed herein include a method of treating diseases and conditions mediated at least in part by the physiologic effects of CAPN1, CAPN2, or CAP9, or combinations thereof, comprising administering to a subject in need thereof a compound disclosed herein.

In some embodiments, compounds disclosed herein are specific inhibitors of one of: CAPN1, CAPN2 or CAPN9.

In some embodiments, compounds disclosed herein are selective inhibitors of one of: CAPN1, CAPN2 or CAPN9.

In some embodiments, compounds disclosed herein are selective inhibitors of: CAPN1 and CAPN2, or CAPN1 and CAPN9, or CAPN2 and CAPN9.

In some embodiments, compounds disclosed herein are effective inhibitors of CAPN1, CAPN2 and/or CAPN9.

In some embodiments, the non-macrocyclic α-keto amide compounds disclosed herein are broadly effective in treating a host of conditions arising from fibrosis or inflammation, and specifically including those associated with myofibroblast differentiation. Accordingly, compounds disclosed herein are active therapeutics for a diverse set of diseases or disorders that include or that produces a symptom which include, but are not limited to: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases or disorders. In other embodiments, the compounds disclosed herein can be used can be used in metabolic and reaction kinetic studies, detection and imaging techniques and radioactive treatments.

In some embodiments, the compounds disclosed herein are used to treat diseases or conditions or that produces a symptom in a subject which include, but not limited to: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases.

In certain embodiments methods are provided for alleviating or ameliorating a condition or disorder, affected at least in part by the enzymatic activity of calpain 1 (CAPN1), calpain 2 (CAPN2), and/or calpain 9 (CAPN9), or mediated at least in part by the enzymatic activity of CAPN1, CAPN2, and/or CAPN9 wherein the condition includes or produces a symptom which includes: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and/or rheumatoid arthritis.

In some embodiments, the methods, compounds, and/or compositions of the present invention are used for prophylactic therapy.

In some embodiments, the CAPN1, CAPN2, and/or CAPN9 inhibiting compounds demonstrate efficacy in animal models of human disease. Specifically, in-vivo treatment of mice, rabbits, and other mammalian subjects with compounds disclosed herein establish the utility of these compounds as therapeutic agents to modulate CAPN1, CAPN2, and/or CAPN9 activities in humans and thereby ameliorate corresponding medical conditions.

Some embodiments provide compounds, pharmaceutical compositions, and methods of use to inhibit myofibroblast differentiation. Some embodiments provide compounds, pharmaceutical compositions, and methods of use for inhibiting CAPN1, CAPN2, and/or CAPN9 or combinations of these enzyme activities such as CAPN1 and CAPN2, or CAPN1 and CAPN9, or CAPN2 and CAPN9. Some embodiments provide methods for treatment of diseases and disorders by inhibiting CAPN1, CAPN2, and/or CAPN9 or combinations of these enzymatic activities.

DETAILED DESCRIPTION

In some embodiments, compounds that are non-macrocyclic α-keto amides are provided that act as calpain modulators. Various embodiments of these compounds include compounds having the structures of Formula I as described above or pharmaceutically acceptable salts thereof. The structure of Formula I encompasses all stereoisomers and racemic mixtures, including the following structures and mixtures thereof:

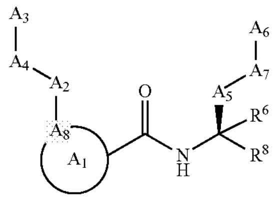

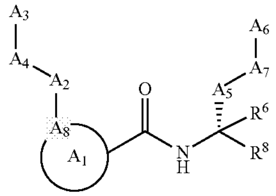

In some embodiments of compounds of Formula (I), the compound is not selected from the group consisting of:

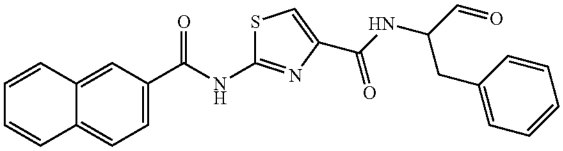

,

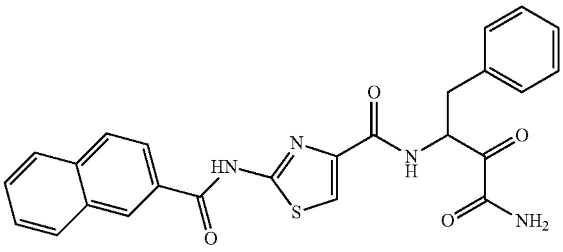

,

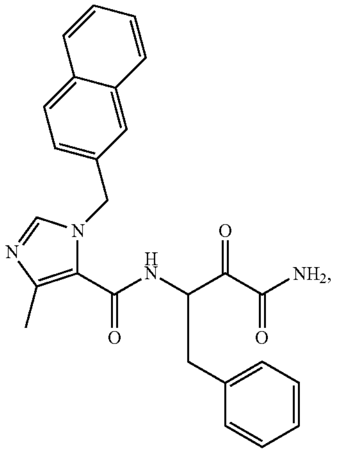

-continued

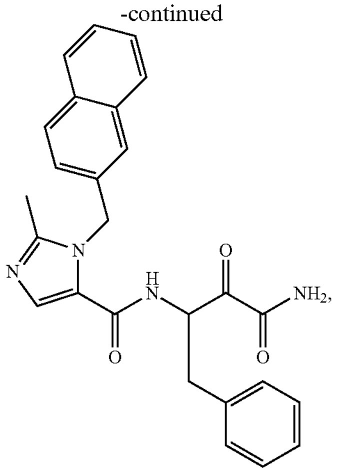

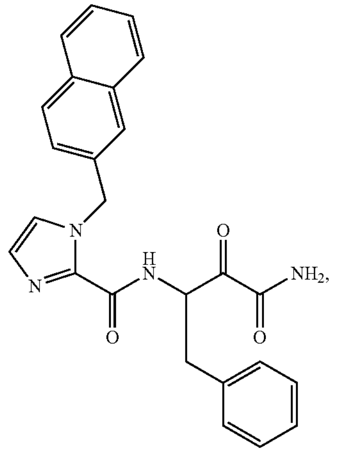

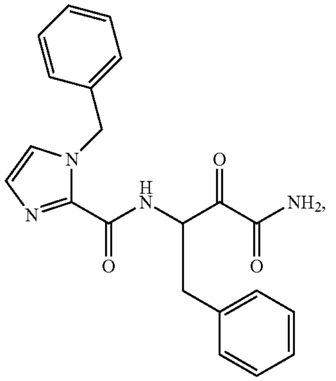

and

-continued

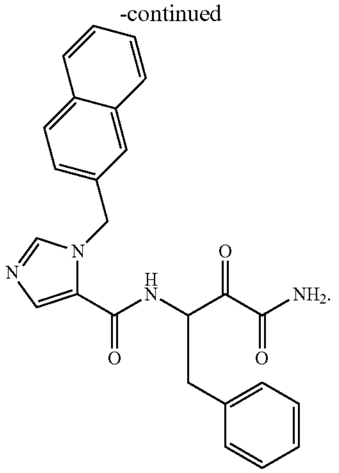

In some embodiments of compounds of Formula (I):

$A_1$ is selected from the group consisting of optionally substituted 6-10 membered heterocyclyl provided the 6-10-membered heterocyclyl is not substituted with oxo; optionally substituted 5-, 8-, or 9-membered heteroaryl; and optionally substituted $C_{3-10}$ carbocyclyl;

$A_2$ is selected from the group consisting of optionally substituted 3-10 membered heterocyclyl, optionally substituted $C_{6-10}$ aryl, optionally substituted 5-10 membered heteroaryl, optionally substituted $C_{3-10}$ carbocyclyl, —$CR_2$—, —S—, —S(═O)—, —$SO_2$—, —O—, —C(═S)—, —C(═O)—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;

$A_4$ is selected from the group consisting of optionally substituted $C_6$_o aryl, optionally substituted 5-10 membered heteroaryl, optionally substituted 3-10 membered heterocyclyl, optionally substituted $C_{3-10}$ carbocyclyl, optionally substituted $C_{1-4}$ alkyl, —S—, S(═O)—, —$SO_2$—, —O—, —C(═S)—, —C(═O)—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;

$A_3$ is selected from the group consisting of optionally substituted $C_6$_o aryl, optionally substituted 5-10 membered heteroaryl, optionally substituted 3-10 membered heterocyclyl, and optionally substituted $C_{3-10}$ carbocyclyl;

$A_6$ is selected from the group consisting of optionally substituted $C_6$_o aryl, optionally substituted 5-10 membered heteroaryl, optionally substituted 3-10 membered heterocyclyl, optionally substituted $C_{3-10}$ carbocyclyl, optionally substituted $C_{1-8}$ alkyl, optionally substituted —O—$C_{1-6}$ alkyl, optionally substituted —$OC_{2-6}$ alkenyl, and any natural or non-natural amino acid side chain; and each R, $R^2$, and $R^3$ are independently selected from —H, optionally substituted $C_{1-4}$ alkyl, optionally substituted $C_{3-7}$ carbocyclyl, optionally substituted 5-10 membered heterocyclyl, optionally substituted $C_{6-10}$ aryl, and optionally substituted 5-10 membered heteroaryl.

Some embodiments of compounds of Formula (I) include compounds having the structure of Formula (I-a):

I-a

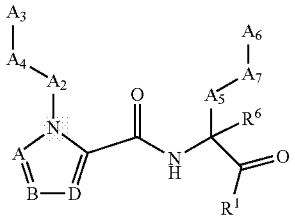

or a pharmaceutically acceptable salt thereof, wherein:

A, B, and D are each independently selected from the group consisting of $C(R^4)$ and N; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$haloalkoxy), halo, hydroxy, and $C_1$-$C_6$ alkoxy.

In some embodiments of compounds of Formula (I-a) or their pharmaceutically acceptable salts; A, B, and D are independently selected from the group consisting of CH and N. In some embodiments, A is N, B is CH, and D is CH. In some embodiments, A is CH, B is N, and D is CH.

Some embodiments of compounds of Formula (I) include compounds having the structure of Formula (I-b):

I-b

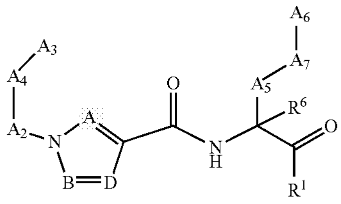

or a pharmaceutically acceptable salt thereof, wherein:

A, B, and D are each independently selected from the group consisting of $C(R^4)$ and N; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$haloalkoxy), halo, hydroxy, and $C_1$-$C_6$ alkoxy.

In some embodiments of compounds of Formula (I-b) or their pharmaceutically acceptable salts; A, B, and D are independently selected from the group consisting of CH and N.

Some embodiments of compounds of Formula (I) include compounds having the structure of Formula (I-c):

I-c

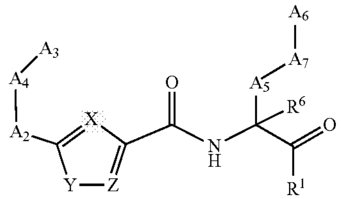

or a pharmaceutically acceptable salt thereof, wherein:

Y is selected from the group consisting of $NR^5$, O, S, and $SO_2$; X and Z are each independently selected from the group consisting of $C(R^4)$ and N; each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl, and $C_{3-7}$ carbocyclyl.

In some embodiments of compounds of Formula (I-c) or their pharmaceutically acceptable salts; X and Z are independently selected from the group consisting of CH and N.

Some embodiments of compounds of Formula (I) include compounds having the structure of Formula (I-d):

I-d

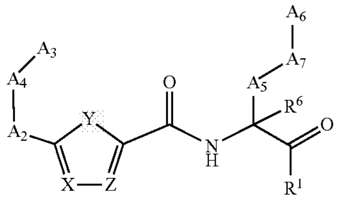

or a pharmaceutically acceptable salt thereof, wherein:

Y is selected from the group consisting of $NR^5$, O, S, and $SO_2$; X and Z are each independently selected from the group consisting of $C(R^4)$ and N; each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl, and $C_{3-7}$ carbocyclyl.

In some embodiments of compounds of Formula (I-d) or their pharmaceutically acceptable salts; X and Z are independently selected from the group consisting of CH and N.

Some embodiments of compounds of Formula (I) include compounds having the structure of Formula (I-e):

I-e

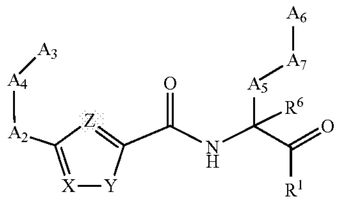

or a pharmaceutically acceptable salt thereof, wherein:

Y is selected from the group consisting of $NR^5$, O, S, and $SO_2$; X and Z are each independently selected from the group consisting of $C(R^4)$ and N; each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl, and $C_{3-7}$ carbocyclyl.

In some embodiments of compounds of Formula (I-e) or their pharmaceutically acceptable salts; X and Z are independently selected from the group consisting of CH and N.

Some embodiments of compounds of Formula (I) include compounds having the structure of Formula (I-f):

I-f

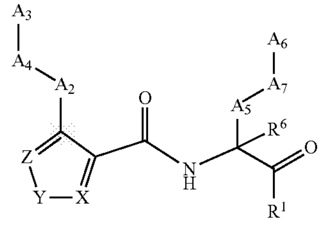

or a pharmaceutically acceptable salt thereof, wherein:
Y is selected from the group consisting of $NR^5$, O, S, and $SO_2$; X and Z are each independently selected from the group consisting of $C(R^4)$ and N; each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl, and $C_{3-7}$ carbocyclyl.

In some embodiments of compounds of Formula (I-f), Z is N, Y is $NR^5$, and X is CH.

In some embodiments of compounds of Formula (I-f), $R^5$ is selected from the group consisting of —H, $C_{1-4}$ alkyl, $C_1$-$C_4$ haloalkyl, and cyclopropyl.

In some embodiments of compounds of Formula (I-f), Z is N, Y is O, and X is $C(R^4)$. In some embodiments of compounds of Formula (I-f), Z is N, Y is S, and X is $C(R^4)$. In some embodiments of compounds of Formula (I-f), Z is $C(R^4)$, Y is S, and X is $C(R^4)$.

In some embodiments of compounds of Formula (I-f), Z is $C(R^4)$, Y is O, and X is $C(R^4)$.

In some embodiments of compounds of Formula (I-f), Z is N, Y is S, and X is N. In some embodiments of compounds of Formula (I-f), Z is N, Y is O, and X is N.

Some embodiments of compounds of Formula (I) include compounds having the structure of formula (I-g):

I-g

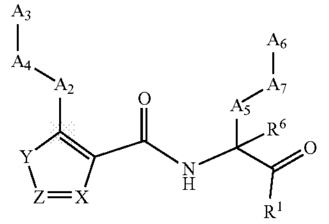

or a pharmaceutically acceptable salt thereof, wherein:
Y is selected from the group consisting of $NR^5$, O, S, and $SO_2$; X and Z are each independently selected from the group consisting of $C(R^4)$ and N; each $R^4$ is independently selected from the group consisting of —H, $C_{1-4}$ alkyl, $C_{1-4}$ haloalkyl $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl and $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$haloalkoxy).

In some embodiments of compounds of Formula (I-g) or their pharmaceutically acceptable salts; X and Z are independently selected from the group consisting of CH and N. In some embodiments of compounds of Formula (I-g), Y is $NR^5$, Z is N, and X is CH.

Some embodiments of compounds of Formula (I) include compounds having the structure of Formula (I-h):

I-h

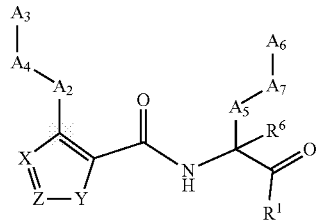

or a pharmaceutically acceptable salt thereof, wherein:
Y is selected from the group consisting of $NR^5$, O, S, and $SO_2$; X and Z are each independently selected from the group consisting of $C(R^4)$ and N; each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl, and $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$haloalkoxy).

In some embodiments of compounds of Formula (I-h) or their pharmaceutically acceptable salts; X and Z are independently selected from the group consisting of CH and N. In some embodiments of compounds of Formula (I-h), X is CH, Z is N, and Y is $NR^5$.

In some embodiments of compounds of Formula (I-h), X is CH, Z is N, and Y is $NR^5$. In some embodiments of compounds of Formula (I-h), X is N, Z is $C(R^4)$, and Y is O.

In some embodiments of compounds of Formula (I-h), wherein $R^4$ is selected from —H and $C_{1-4}$ alkyl.

In some embodiments of compounds of Formula (I-h), X is N, Z is $C(R^4)$, and Y is S. In some embodiments of compounds of Formula (I-h), X is N, Z is N, and Y is S.

Some embodiments of compounds of Formula (I) include compounds having the structure of formula (I-j):

I-j

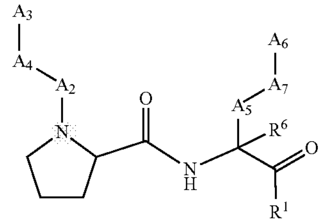

or a pharmaceutically acceptable salt thereof.

Some embodiments of compounds of Formula (I) include compounds having the structure of Formula (I-k):

I-k

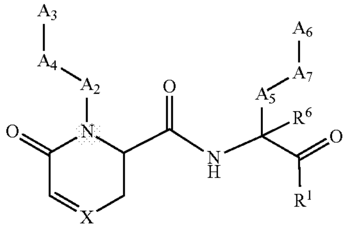

or a pharmaceutically acceptable salt thereof, wherein:

X is selected from the group consisting of $C(OR^5)$, —$C(R^4)$, and N; $R^4$ is selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy; and $R^5$ is selected from the group consisting of —H, $C_{1-4}$ alkyl, $C_{1-4}$ haloalkyl, and $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy).

In some embodiments of compounds of Formula (I-k) or their pharmaceutically acceptable salts; X and Z are independently selected from the group consisting of CH and N.

Some embodiments of compounds of Formula (I) include compounds having the structure of Formula (I-m):

I-m

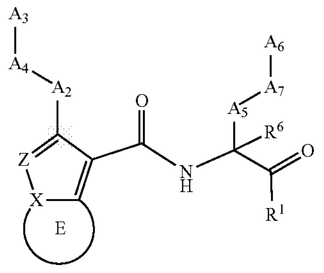

or a pharmaceutically acceptable salt thereof, wherein:

X and Z are independently selected from the group consisting of $C(R^4)$ and N; E is selected from the group consisting of an optionally substituted $C_{5-6}$ carbocyclyl and an optionally substituted 5- to 6-membered heterocyclyl; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

Some embodiments of compounds of Formula (I) include compounds having the structure of Formula (I-n):

I-n

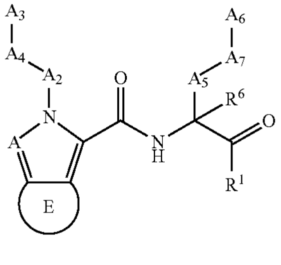

or a pharmaceutically acceptable salt thereof, wherein:

A is selected from the group consisting of $C(R^4)$ and N; E is selected from the group consisting of an optionally substituted $C_{5-6}$ carbocyclyl, an optionally substituted 5- to 6-membered heterocyclyl, an optionally substituted 5- to 6-membered heteroaryl, and an optionally substituted phenyl; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

Some embodiments include compounds of Formula (III)

III

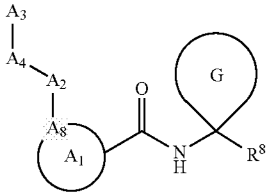

or a pharmaceutically acceptable salt thereof, wherein:

$A_1$ is selected from the group consisting of optionally substituted 5-10 membered heterocyclyl provided the 6-10-membered heterocyclyl is not substituted with oxo; optionally substituted 5-, 8-, or 9-membered heteroaryl; and optionally substituted $C_{3-10}$ carbocyclyl;

$A_2$ is selected from the group consisting of optionally substituted 3-10 membered heterocyclyl, optionally substituted $C_{6-10}$ aryl, optionally substituted 5-10 membered heteroaryl, optionally substituted $C_{3-10}$ carbocyclyl, —$CR_2$—, —S—, —S(═O)—, —$SO_2$—, —O—, —C(═S)—, —C(═O)—, —NR—, —CH═CH—, —C≡C—, —OC(O)NH—, —NHC(O)NH—, —NHC(O)O—, —NHC(O)—, —NHC(S)NH—, —NHC(S)O—, —NHC(S)—, and single bond;

$A_4$ is selected from the group consisting of optionally substituted $C_6$_10 aryl, optionally substituted 5-10 membered heteroaryl, optionally substituted 3-10 membered heterocyclyl, optionally substituted $C_{3-10}$ carbocyclyl, optionally substituted $C_{1-4}$ alkyl, —$(CR_2)_n$—S—$(CR_2)_n$—, —$(CR_2)_n$—S(═O)—$(CR_2)_n$—, —$(CR_2)_n$—$SO_2$—$(CR_2)_n$—, —$(CR_2)_n$—O—$(CR_2)_n$—, —$(CR_2)$—C(═S)—$(CR_2)_n$—, —$(CR_2)_n$—C(═O)—$(CR_2)_n$—, —$(CR_2)_n$—NR—$(CR_2)_n$—, —$(CR_2)_n$—CH═CH—$(CR_2)_n$—, —$(CR_2)_n$—OC(O)NH—$(CR_2)_n$—, —$(CR_2)_n$—NHC(O)NH—$(CR_2)_n$—, —$(CR_2)_n$—NHC(O)O—$(CR_2)_n$—, —$(CR_2)_n$—NHC(O)—$(CR_2)_n$—, —$(CR_2)_n$—NHC(S)NH—$(CR_2)_n$—, —$(CR_2)_n$—NHC(S)O—$(CR_2)_n$—, —$(CR_2)_n$—NHC(S)—$(CR_2)_n$—, and single bond;

when $A_2$ and $A_4$ are single bond, $A_3$ is directly attached to $A_8$; $A_3$ is selected from the group consisting of optionally substituted $C_{6-10}$ aryl, optionally substituted 5-10 membered heteroaryl, optionally substituted 3-10 membered heterocyclyl, and optionally substituted $C_{3-10}$ carbocyclyl, or if $A_2$ is selected from optionally substituted 3-10 membered heterocyclyl, optionally substituted $C_{6-10}$ aryl, optionally substituted 5-10 membered heteroaryl, and optionally substituted $C_{3-10}$ carbocyclyl, then $A_3$ is selected from the group consisting of hydrogen, optionally substituted $C_{6-10}$ aryl, optionally substituted 5-10 membered heteroaryl, optionally substituted 3-10 membered heterocyclyl, optionally substituted $C_{3-10}$ carbocyclyl, —C≡CH, and optionally substituted 2- to 5-membered polyethylene glycol; G is an optionally substituted C3 to $C_7$ carbocyclyl or an optionally substituted 4- to 7-membered heterocyclyl;

$A_8$ is a ring member of $A_1$ and is selected from the group consisting of C and N;

$R^8$ is selected from the group consisting of —$COR^1$, —CN, —CH═$CHSO_2R$, —$CH_2NO_2$;

$R^1$ is selected from the group consisting of H, —OH, $C_{1-4}$ haloalkyl, —COOH, —$CH_2NO_2$, —C(═O)NOR, —$NH_2$, —$CONR^2R^3$, —$CH(CH_3)$═$CH_2$, —$CH(CF_3)NR^2R^3$, —C(F)═$CHCH_2CH_3$,

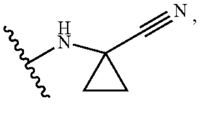,
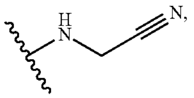,
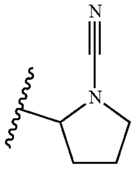,
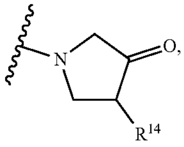,
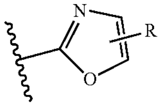,
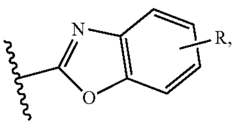,
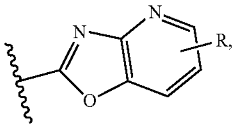,
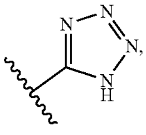,
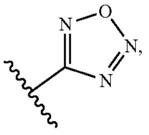,
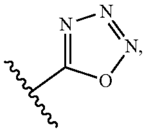,
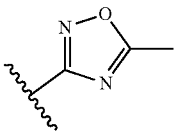,
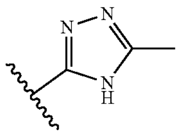,
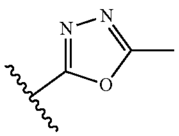, and
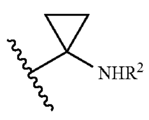;

$R^{14}$ is halo; and each R, $R^2$, and $R^3$ are independently selected from —H, optionally substituted $C_{1-4}$ alkyl, optionally substituted $C_{1-8}$ alkoxyalkyl, optionally substituted 2- to 5-membered polyethylene glycol, optionally substituted $C_{3-7}$ carbocyclyl, optionally substituted 5-10 membered heterocyclyl, optionally substituted $C_{6-10}$ aryl, optionally substituted $C_{6-10}$ aryl $(C_1-C_6)$alkyl, and optionally substituted 5-10 membered heteroaryl; $R^6$ is independently selected from —H and optionally substituted $C_{1-4}$ alkyl; and each n is independently selected to be an integer from 0 to 3.

Some embodiments of compounds of Formulas (III) include compounds having the structure of Formula (III-a):

IIIa

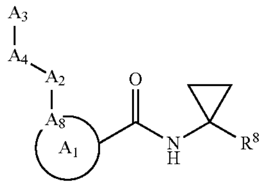

or a pharmaceutically acceptable salt thereof.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), at least one of the optionally substituted moieties of $A_2$, $A_4$, and $A_3$ is substituted with $^{18}F$.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), at least one of the optionally substituted moieties of $A_2$, $A_4$, and $A_3$ is substituted with $C_1-C_6$ alkyl containing one or more $^{11}C$.

In some embodiments of compounds of Formulas (I), (III), (III-a), (I-a), (I-b), (I-c), (I-d), (I-e), (I-f), (I-g), (I-h), (I-j), (I-k), (I-m), (I-n), or (I-p) or their pharmaceutically acceptable salts; $A_3$ is selected from the group consisting of

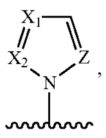,
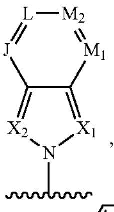,
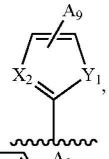,
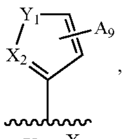,
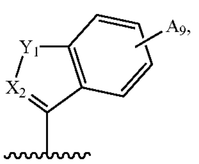
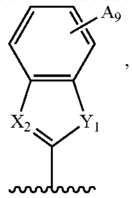,
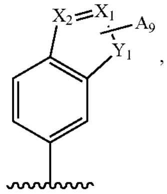,
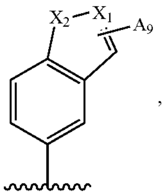,
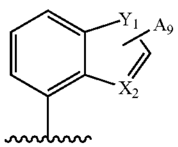 and
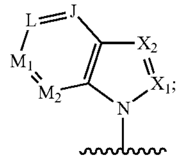;

and $A_9$ is selected from the group consisting of H, $C_{6-10}$ aryl, 5-10 membered heteroaryl, 3-10 membered heterocyclyl, and $C_{3-10}$ carbocyclyl, $C_{1-4}$ alkyl; $X_2$, $X_1$, and Z are each independently selected from the group consisting of $C(R^4)$ and N; $Y_1$ is selected from the group consisting of $NR^5$, O, and S; J, L, $M_1$ and $M_2$ are each independently selected from the group consisting of $C(R^4)$ and N; $R^4$ is selected from the group consisting of —H, $C_{1-4}$ alkyl, $C_{1-4}$ haloalkyl, $C_{3-7}$ carbocyclyl, halo, hydroxy, and $C_1-C_6$ alkoxy; $R^5$ is selected from the group consisting of —H, $C_{1-4}$ alkyl, $C_{1-4}$ haloalkyl, and $C_{3-7}$ carbocyclyl.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is —$CH_2$—.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is —CH═CH—.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is —O—.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is S.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is single bond.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is phenyl.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_3$ is optionally substituted $C_{6-10}$ aryl.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is selected from the group consisting of optionally substituted 3-10 membered heterocyclyl, optionally substituted $C_{6-10}$ aryl, optionally substituted 5- or 7-10 membered heteroaryl, optionally substituted $C_{3-10}$ carbocyclyl, —S—, —S(═O)—, —$SO_2$-, —C(═S)—, —C(═O)—, —NR—, —CH═CH—, —C≡C—, —OC(O)NH—, —NHC(O)NH—, —NHC(O)O—, —NHC(S)NH—, —NHC(S)O—, and —NHC(S)—.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is selected from the group consisting of optionally substituted 3-10 membered heterocyclyl, optionally substituted $C_{6-10}$ aryl, optionally substituted 5-10 membered heteroaryl, optionally substituted $C_{3-10}$ carbocyclyl, and —C≡C—, In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_2$ is selected from the group consisting of optionally substituted 3-10 membered heterocyclyl, optionally substituted $C_{6-10}$ aryl, optionally substituted 5-10 membered heteroaryl, and optionally substituted $C_{3-10}$ carbocyclyl.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_4$ is single bond.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_3$ is selected from the group consisting of phenyl,

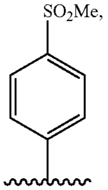,

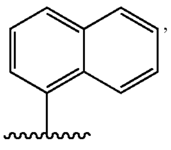,

-continued

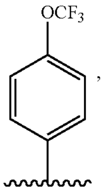,

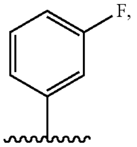,

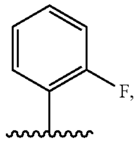, and

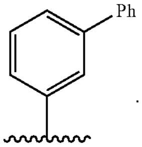.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_3$ is optionally substituted 5-10 membered heteroaryl.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), $A_3$ is selected from the group consisting of

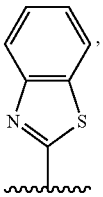,

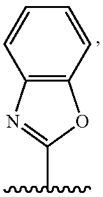,

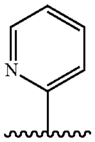,

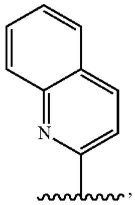,

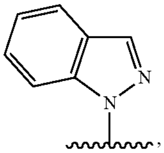,

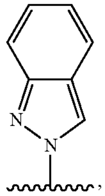, and

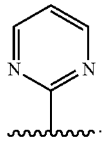.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein $A_2$ is a single bond, $A_4$ is a single bond, and $A_3$ is an optionally substituted $C_{6-10}$ aryl or an optionally substituted 5-10 membered heteroaryl.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein $A_3$ has the structure:

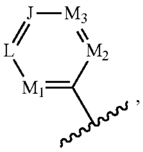, wherein J, L, $M_1$, $M_2$, and $M_3$ are each independently selected from the group consisting of $C(R^4)$ and N; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein each of J, L, $M_1$, $M_2$, and $M_3$ are $C(R^4)$ In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein each $R^4$ is independently selected from —H and halo.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein $M_1$ is halo and each of J, L, $M_2$, and $M_3$ are CH.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein L is halo and each of J, $M_1$, $M_2$, and $M_3$ are CH.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein $A_3$ has a structure selected from the group consisting of:

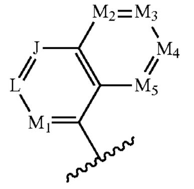

and

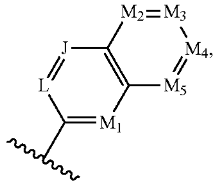

wherein J, L, $M_1$, $M_2$, $M_3$, $M_4$, and $M_5$ are each independently selected from the group consisting of $C(R^4)$ and N; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

In some embodiments of Formulas (I), (III), (III-a), (I-a), (I-b), (I-c), (I-d), (I-e), (I-f), (I-g), (I-h), (I-j), (I-k), (I-m), (I-n), or (I-p), wherein $A_3$ has the structure:

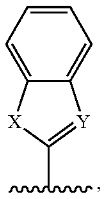

wherein X is selected from the group consisting of $C(R^4)$ and N; Y is selected from O and S; and $R^4$ is selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$haloalkoxy), halo, hydroxy, and $C_1$-$C_6$ alkoxy.

Some embodiments of compounds of Formula (I) include compounds having the structure of Formula (I-o):

I-o

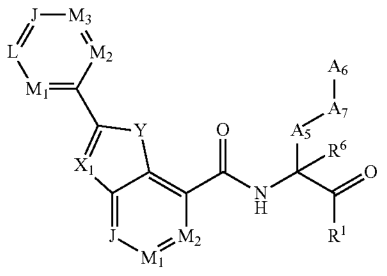

or a pharmaceutically acceptable salt thereof, wherein: Y is selected from the group consisting of $NR^5$, O, S, and $SO_2$; $X_1$ is selected from the group consisting of $C(R^4)$ and N; J, L, $M_1$, $M_2$, and $M_3$ are each independently selected from the group consisting of $C(R^4)$ and N; $R^4$ is selected from the group consisting of —H, $C_{1-4}$ alkyl, $C_{1-4}$ haloalkyl, $C_{3-7}$ carbocyclyl, halo, hydroxy, and $C_1$-$C_6$ alkoxy; $R^5$ is selected from the group consisting of —H, $C_{1-4}$ alkyl, $C_{1-4}$ haloalkyl, and $C_{3-7}$ carbocyclyl (optionally substituted with halo, $C_1$-$C_6$ alkyl, $C_1$-$C_6$alkoxy, $C_1$-$C_6$ haloalkyl, and $C_1$-$C_6$ haloalkoxy).

In some embodiments of compounds of Formula (I-o) or their pharmaceutically acceptable salts; J, L, $M_1$, $M_2$, and $M_3$ are independently selected from the group consisting of CH and N.

In some embodiments of Formulas (I), (I-a), (I-b), (I-c), (I-d), (I-e), (I-f), (I-g), (I-h), (I-j), (I-k), (I-m), (I-n), (I-o), or (I-p), wherein at least one of the optionally substituted moieties of $A_5$, $A_7$, and $A_6$ is substituted with $^{18}F$.

In some embodiments of Formulas (I), (I-a), (I-b), (I-c), (I-d), (I-e), (I-f), (I-g), (I-h), (I-j), (I-k), (I-m), (I-n), (I-o), or (I-p), wherein at least one of the optionally substituted moieties of $A_5$, $A_7$, and $A_6$ is substituted with $C_1$-$C_6$ alkyl containing one or more $^{11}C$.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_6$ is phenyl.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, optionally substituted $C_{1-8}$ alkyl, optionally substituted —O—$C_{1-6}$ alkyl, and optionally substituted —$OC_{2-6}$ alkenyl.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is —$CH_2$—.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is —CH═CH—.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is —O—.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is S.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is single bond.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is optionally substituted $C_{6-10}$ aryl.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_7$ is phenyl.

In some embodiments of Formulas (I), (I-a), (I-b), (I-c), (I-d), (I-e), (I-f), (I-g), (I-h), (I-j), (I-k), (I-m), (I-n), (I-o), or (I-p), As is —$CH_2$—.

In some embodiments of Formulas (I), (I-a), (I-b), (I-c), (I-d), (I-e), (I-f), (I-g), (I-h), (I-j), (I-k), (I-m), (I-n), (I-o), or (I-p), wherein $A_5$ is —$CH_2$— or —$CH_2CH_2$—; $A_7$ is a single bond; and $A_6$ is selected from the group consisting of $C_1$-$C_4$ alkyl, optionally substituted phenyl, optionally substituted 5-10 membered heteroaryl.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_6$ is optionally substituted phenyl.

In some embodiments of Formulas (I), (I-a), (I-b), (I-c), (I-d), (I-e), (I-f), (I-g), (I-h), (I-j), (I-k), (I-m), (I-n), (I-o), or (I-p), wherein $A_6$ is unsubstituted phenyl.

In some embodiments of Formulas (I), (I-a), (I-b), (I-c), (I-d), (I-e), (I-f), (I-g), (I-h), (I-j), (I-k), (I-m), (I-n), (I-o), or (I-p), wherein $A_6$ is phenyl optionally substituted with one or more $C_{1-4}$ alkyl, $C_{3-7}$ carbocyclyl, halo, hydroxy, and $C_1$-$C_6$ alkoxy.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_6$ has the structure:

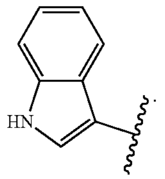

In some embodiments of Formulas (I), (I-a), (I-b), (I-c), (I-d), (I-e), (I-f), (I-g), (I-h), (I-j), (I-k), (I-m), (I-n), (I-o), or (I-p), wherein $A_5$ is a single bond, $A_7$ is a single bond; and $A_6$ is $C_1$-$C_5$ alkyl.

In some embodiments of Formulas (I), (I-a), (I-b), (I-c), (I-d), (I-e), (I-f), (I-g), (I-h), (I-j), (I-k), (I-m), (I-n), (I-o), or (I-p), $A_6$ is selected from the group consisting of ethyl, n-propyl, isopropyl, isobutyl, 2,2-dimethylpropyl, and 1,2-dimethylpropyl.

In some embodiments of Formulas (I), (III), (II-a), (I-a), (I-b), (I-c), (I-d), (I-e), (I-f), (I-g), (I-h), (I-j), (I-k), (I-o), or (I-p) $R^1$ is $CONR^2R^3$.

In some embodiments of Formulas (I), (III), (III-a), (I-a), (I-b), (I-c), (I-d), (I-e), (I-f), (I-g), (I-h), (I-j), (I-k), (I-o), or (I-p) $R^2$ is —H and $R^3$ is optionally substituted $C_{1-4}$ alkyl.

In some embodiments of Formulas (I), (III), (III-a), (I-a), (I-b), (I-c), (I-d), (I-e), (I-f), (I-g), (I-h), (I-j), (I-k), (I-o), or (I-p) wherein $R^2$ is —H and $R^3$ is selected from the group consisting of —H, $C_1$-$C_4$ alkyl optionally substituted with C-amido, and $C_3$-$C_6$ cycloalkyl.

In some embodiments of Formulas (I), (III), (III-a), (I-a), (I-b), (I-c), (I-d), (I-e), (I-f), (I-g), (I-h), (I-j), (I-k), (I-o), or (I-p) $R^3$ is selected from ethyl or cyclopropyl.

In some embodiments of Formulas (I), (III), (III-a), (I-a), (I-b), (I-c), (I-d), (I-e), (I-f), (I-g), (I-h), (I-j), (I-k), (I-o), or (I-p) $R^3$ is methyl substituted with C-amido.

In some embodiments of Formulas (I), (III), (III-a), (I-a), (I-b), (I-c), (I-d), (I-e), (I-f), (I-g), (I-h), (I-j), (I-k), (I-o), or (I-p) $R^3$ is H.

In some embodiments of Formulas (I), (III), (III-a), (I-a), (I-b), (I-c), (I-d), (I-e), (I-f), (I-g), (I-h), (I-j), (I-k), (I-o), or (I-p) $R^3$ is optionally substituted $C_{1-4}$ alkyl.

In some embodiments of Formulas (I), (III), (III-a), (I-a), (I-b), (I-c), (I-d), (I-e), (I-f), (I-g), (I-h), (I-j), (I-k), (I-o), or (I-p) $R^3$ is benzyl.

In some embodiments of Formulas (I), (I-a), (I-b), (I-c), (I-d), (I-e), (I-f), (I-g), (I-h), (I-j), (I-k), (I-m), (I-n), (I-o), or (I-p), $R^6$ is —H and optionally substituted $C_{1-4}$ alkyl.

In some embodiments of Formulas (I), (I-a), (I-b), (I-c), (I-d), (I-e), (I-f), (I-g), (I-h), (I-j), (I-k), (I-m), (I-n), (I-o), or (I-p), $R^6$ is optionally substituted $C_{1-4}$ alkyl.

In some embodiments of Formulas (I), (I-a), (I-b), (I-c), (I-d), (I-e), (I-f), (I-g), (I-h), (I-j), (I-k), (I-m), (I-n), (I-o), or (I-p), $R^6$ is methyl.

In some embodiments of Formula (I), $A_1$ is selected from the group consisting of optionally substituted 6-10 membered heterocyclyl; 5-membered heterocyclyl optionally substituted with one or more $C_{1-4}$ alkyl, $C_{3-7}$ carbocyclyl, halo, hydroxy, or $C_1$-$C_6$ alkoxy; optionally substituted 5-, 8-, or 9-membered heteroaryl; and optionally substituted $C_{3-10}$ carbocyclyl.

In some embodiments of Formula (I), $A_1$ is selected from the group consisting of 5-membered heterocyclyl optionally substituted with one or more $C_{1-4}$ alkyl, $C_{3-7}$ carbocyclyl, halo, hydroxy, or $C_1$-$C_6$ alkoxy and optionally substituted 5-membered heteroaryl.

In some embodiments of Formula (I), $A_1$ is optionally substituted 5-membered heteroaryl.

Some embodiments of compounds of Formula (I) include compounds having the structure of Formula (I-p):

I-p

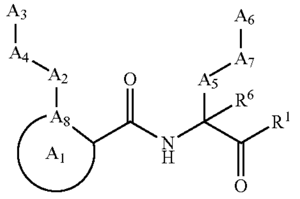

or a pharmaceutically acceptable salt thereof.

Some embodiments provide a compound of Formula (II):

II

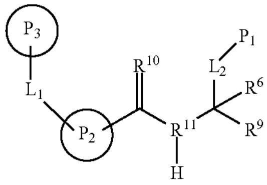

or a pharmaceutically acceptable salt thereof, wherein:

$P_2$ is an optionally substituted cyclic moiety having a size and configuration such that, upon binding of the compound to calpain 9, at least one atom of $P_2$ forms a non-polar interaction with, and is within 5 Å or less of, at least one calpain 9 P2 pocket moiety selected from the group consisting of Gly190, Phe233, Gly253, His254, and Ala255;

$L_1$ is a bond or a moiety consisting of from 1 to 25 atoms selected from the group consisting of carbon, oxygen, nitrogen, hydrogen, and sulfur;

$P_3$ is an optionally substituted cyclic moiety positioned by $L_1$ and having a size and configuration such that, upon binding of the compound to calpain 9, at least one atom of $P_3$ forms a non-polar interaction with, and is within 5 Å or less of, at least one calpain 9 P3 pocket moiety selected from the group consisting of Gly189, Gly190, Ser191, Thr236, and Gly253;

$R^{10}$ is oxo and is positioned by $P_2$ such that, upon binding of the compound to calpain 9, $R^{10}$ forms a polar interaction with, and is within 4 Å or less of, calpain 9 Gly190 amide;

$R^{11}$ is nitrogen and is positioned by the carbons to which it is bonded such that, upon binding of the compound to calpain 9, $R^{11}$ forms a polar interaction with, and is within 4 Å or less of, calpain 9 Gly253 carbonyl;

$L_2$ is a bond or a moiety consisting of from 1 to 25 atoms selected from the group consisting of carbon, oxygen, nitrogen, hydrogen, and sulfur;

$P_1$ is a moiety positioned by $L_2$ and having a size and configuration such that, upon binding of the compound to calpain 9, at least one atom of $P_1$ forms a non-polar interaction with, and is within 5 Å or less of, at least one calpain 9 P1 pocket moiety selected from the group consisting of Gly95, Lys188, Gly189, and Ser242;

$R^9$ is a moiety positioned by the carbon to which it is attached such that, upon binding of the compound to calpain 9, at least one atom of $R^9$ forms a polar interaction with, and is within 4 Å or less of, at least one calpain 9 moiety selected from the group consisting of Gln91, Cys97, and His254; and $R^6$ is selected from —H and optionally substituted $C_{1-4}$ alkyl.

Some embodiments of compounds of Formula (II) include compounds wherein; $R^9$ is —(C═$R^{12}$)(C═$R^{13}$)N$R^2R^3$;

$R^{12}$ is oxo and is positioned such that, upon binding of the compound to calpain 9, $R^{12}$ forms a polar interaction with, and is within 4 Å or less of, calpain 9 His254 imidazole;

$R^{13}$ is oxo and is positioned such that, upon binding of the compound to calpain 9, $R^{13}$ forms a polar interaction with, and is within 4 Å or less of, at least one calpain 9 moiety selected from the group consisting of Gln91 side chain carboxamide and Cys97 backbone amide; and $R^2$ and $R^3$ are independently selected from —H, optionally substituted $C_{1-4}$ alkyl, optionally substituted $C_{3-7}$ carbocyclyl, optionally substituted 5-10 membered heterocyclyl, optionally substituted C6_o aryl, optionally substituted $C_{6-10}$aryl($C_1$-$C_6$)alkyl, and optionally substituted 5-10 membered heteroaryl.

Some embodiments of compounds of Formula (II) include compound wherein $R^{12}$ is positioned such that, upon binding of the compound to calpain 9, $R^{12}$ is within 2.6 to 3.2 Å or less of, calpain 9 His254 imidazole.

Some embodiments of compounds of Formula (II) include compound wherein $R^{12}$ is positioned such that, upon binding of the compound to calpain 9, $R^{12}$ is within 2.6 to 3.0 Å or less of, calpain 9 His254 imidazole.

Some embodiments of compounds of Formula (II) include compound wherein $R^{13}$ is positioned such that, upon binding of the compound to calpain 9, $R^{13}$ is within 2.6 to 3.5 Å to the calpain 9 moieties including both Gln91 side chain carboxamide and Cys97 backbone amide.

Some embodiments of compounds of Formula (II) include compound wherein $R^{13}$ is positioned such that, upon binding of the compound to calpain 9, $R^{13}$ is within 2.6 to 3.2 Å to the calpain 9 moieties including both Gln91 side chain carboxamide and Cys97 backbone amide.

Some embodiments of compounds of Formula (II) include compound wherein $R^9$ is positioned by the carbon to which it is attached such that, upon binding of the compound to calpain 9, at least one atom of $R^9$ forms a polar interaction with, and is within 3.6 Å or less of, at least one calpain 9 moiety selected from the group consisting of Gln91, Cys97, and His254.

Some embodiments of compounds of Formula (II) include compound wherein $R^9$ is positioned by the carbon to which it is attached such that, upon binding of the compound to calpain 9, at least one atom of $R^9$ is within 2.6 to 3.6 Å to the calpain 9 moieties including both Gln91 side chain carboxamide and Cys97 backbone amide.

Some embodiments of compounds of Formula (II) include compound wherein $R^9$ is positioned by the carbon to which it is attached such that, upon binding of the compound to calpain 9, at least one atom of $R^9$ is within 2.9 to 3.2 Å to the calpain 9 moieties including both Gln91 side chain carboxamide and Cys97 backbone amide.

Some embodiments of compounds of Formula (II) include compound wherein a carbon atom in $R^9$ at its point of attachment forms a covalent bond with Cys97

Some embodiments of compounds of Formula (II) include compound wherein the covalent bond length is between 1.7 and 1.9 Å.

Some embodiments of compounds of Formula (II) include compound wherein $P_2$ is an optionally substituted 5-membered heteroaryl.

Some embodiments of compounds of Formula (II) include compound wherein $R^{11}$ is positioned by the carbons to which it is bonded such that, upon binding of the compound to calpain 9, $R^{11}$ forms a polar interaction with, and is within 3.6 Å or less of, calpain 9 Gly253 carbonyl.

Some embodiments of compounds of Formula (II) include compound wherein, $P_2$ has a size and configuration such that, upon binding of the compound to calpain 1, at least one atom of $P_2$ forms a non-polar interaction with, and is within 5 Å or less of, at least one calpain 1 P2 pocket moiety selected from the group consisting of Gly208, Ser251, Gly271, His272, and Ala273;

$P_3$ is positioned by $L_1$ and has a size and configuration such that, upon binding of the compound to calpain 1, at least one atom of $P_3$ forms a non-polar interaction with, and is within 5 Å or less of, at least one calpain 1 P3 pocket moiety selected from the group consisting of Gly207, Gly208, Ser209, Ile254, and Gly271;

$R^{10}$ is positioned by $P_2$ such that, upon binding of the compound to calpain 1, $R^{10}$ forms a polar interaction with, and is within 4 Å or less of, calpain 1 Gly208 amide;

$R^{11}$ is positioned by the carbons to which it is bonded such that, upon binding of the compound to calpain 1, $R^{11}$ forms a polar interaction with, and is within 4 Å or less of, calpain 1 Gly271 carbonyl;

$P_1$ is positioned by $L_2$ and has a size and configuration such that, upon binding of the compound to calpain 1, at least one atom of $P_1$ forms a non-polar interaction with, and is within 5 Å or less of, at least one calpain 1 P1 pocket moiety selected from the group consisting of Gly113, Ser206, Gly207, and Met260; and $R^9$ is positioned by the carbon to which it is attached such that, upon binding of the compound to calpain 1, at least one atom of $R^9$ forms a polar interaction with, and is within 4 Å or less of, at least one calpain 1 moiety selected from the group consisting of Gln109, Cys115, and His272.

Some embodiments of compounds of Formula (II) include compound wherein:

$P_2$ has a size and configuration such that, upon binding of the compound to calpain 2, at least one atom of $P_2$ forms a non-polar interaction with, and is within 5 Å or less of, at least one calpain 2 P2 pocket moiety selected from the group consisting of Gly198, Ser241, Gly261, His262, and Ala263;

$P_3$ is positioned by $L_1$ and has a size and configuration such that, upon binding of the compound to calpain 2, at least one atom of $P_3$ forms a non-polar interaction with, and is within 5 Å or less of, at least one calpain 2 P3 pocket moiety selected from the group consisting of Gly197, Gly198, Ala199, Ile244, and Gly261;

$R^{10}$ is positioned by $P_2$ such that, upon binding of the compound to calpain 2, $R^{10}$ forms a polar interaction with, and is within 4 Å or less of, calpain 2 Gly198 amide;

$R^{11}$ is positioned by the carbons to which it is bonded such that, upon binding of the compound to calpain 2, $R^{11}$ forms a polar interaction with, and is within 4 Å or less of, calpain 2 Gly261 carbonyl;

$P_1$ is positioned by $L_2$ and has a size and configuration such that, upon binding of the compound to calpain 2, at least one atom of $P_1$ forms a non-polar interaction with, and is within 5 Å or less of, at least one calpain 2 P1 pocket moiety selected from the group consisting of Gly103, Ser196, Gly197, and Ser250; and $R^9$ is positioned by the carbon to which it is attached such that, upon binding of the compound to calpain 2, at least one atom of $R^9$ forms a polar interaction with, and is within 4 Å or less of, at least one calpain 2 moiety selected from the group consisting of Gln99, Cys105, and His262.

Some embodiments of compounds of Formula (II) include compound wherein $P_2$ has a size and configuration such that, upon binding of the compound to calpain 9, at least one atom of $P_2$ is within 2.6 to 3.6 Å of Gly190 carbonyl oxygen.

Some embodiments of compounds of Formula (II) include compound wherein $P_2$ has a size and configuration such that, upon binding of the compound to calpain 9, at least one atom of $P_2$ is within 2.9 to 3.3 Å of Gly190 carbonyl oxygen.

Some embodiments of compounds of Formula (II) include compound wherein $P_2$ has a size and configuration such that, upon binding of the compound to calpain 9, at least one atom of $P_2$ is within 2.8 to 4.8 Å of a carbon atom in Phe233.

Some embodiments of compounds of Formula (II) include compound wherein $P_2$ has a size and configuration such that, upon binding of the compound to calpain 9, at least one atom of $P_2$ is within 2.9 to 3.3 Å of a carbon atom in Phe233.

Some embodiments of compounds of Formula (II) include compound wherein $P_2$ has a size and configuration such that, upon binding of the compound to calpain 9, at least one atom of $P_2$ is within 2.6 to 3.7 Å of Gly253 carbonyl oxygen.

Some embodiments of compounds of Formula (II) include compound wherein $P_2$ has a size and configuration such that, upon binding of the compound to calpain 9, at least one atom of $P_2$ is within 2.9 to 3.3 Å of Gly253 carbonyl oxygen.

Some embodiments of compounds of Formula (II) include compound wherein $P_2$ has a size and configuration such that, upon binding of the compound to calpain 9, at least one atom of $P_2$ is within 2.9 to 4.8 of Ala255 nitrogen.

Some embodiments of compounds of Formula (II) include compound wherein $P_2$ has a size and configuration such that, upon binding of the compound to calpain 9, at least one atom of $P_2$ is within 3.2 to 4.0 Å of Ala255 nitrogen.

Some embodiments of compounds of Formula (II) include compound wherein $P_3$ has a size and configuration such that, upon binding of the compound to calpain 9, at least one atom of $P_3$ is within 3.1 to 4.3 Å of Gly189 C-alpha.

Some embodiments of compounds of Formula (II) include compound wherein $P_3$ has a size and configuration such that, upon binding of the compound to calpain 9, at least one atom of $P_3$ is within 3.2 to 4.0 Å of Gly189 C-alpha.

Some embodiments of compounds of Formula (II) include compound wherein $P_3$ has a size and configuration such that, upon binding of the compound to calpain 9, at least one atom of $P_3$ is within 3.0 to 4.3 Å of Gly190 carbonyl oxygen.

Some embodiments of compounds of Formula (II) include compound wherein $P_3$ has a size and configuration such that, upon binding of the compound to calpain 9, at least one atom of $P_3$ is within 3.2 to 4.0 Å of Gly190 carbonyl oxygen.

Some embodiments of compounds of Formula (II) include compound wherein $P_3$ has a size and configuration such that, upon binding of the compound to calpain 9, at least one atom of $P_3$ is within 3.2 to 4.8 of Ser191 nitrogen.

Some embodiments of compounds of Formula (II) include compound wherein $P_3$ has a size and configuration such that, upon binding of the compound to calpain 9, at least one atom of $P_3$ is within 3.2 to 4.0 of Ser191 nitrogen.

Some embodiments of compounds of Formula (II) include compound wherein $R^{10}$ is positioned by $P_2$ such that, upon binding of the compound to calpain 9, $R^{10}$ is within 2.6 to 3.5 Å of, calpain 9 Gly190 amide.

Some embodiments of compounds of Formula (II) include compound wherein $R^{10}$ is positioned by $P_2$ such that, upon binding of the compound to calpain 9, $R^{10}$ is within 2.9 to 3.3 Å of, calpain 9 Gly190 amide.

Some embodiments of compounds of Formula (II) include compound wherein $R^{11}$ is positioned by the carbons to which it is bonded such that, upon binding of the compound to calpain 9, $R^{11}$ is within 2.6 to 3.6 Å or less of, calpain 9 Gly253 carbonyl.

Some embodiments of compounds of Formula (II) include compound wherein $R^{11}$ is positioned by the carbons to which it is bonded such that, upon binding of the compound to calpain 9, $R^{11}$ is within 2.9 to 3.3 Å or less of, calpain 9 Gly253 carbonyl.

Some embodiments of compounds of Formula (II) include compound wherein $P_1$ is positioned by $L_2$ and has a size and configuration such that, upon binding of the compound to calpain 9, at least one atom of $P_1$ is within 3.2 to 4.4 Å Gly95 carbonyl oxygen.

Some embodiments of compounds of Formula (II) include compound wherein $P_1$ is positioned by $L_2$ and has a size and configuration such that, upon binding of the compound to calpain 9, at least one atom of $P_1$ is within 3.2 to 4.0 Å Gly95 carbonyl oxygen.

Some embodiments of compounds of Formula (II) include compound wherein $P_1$ is positioned by $L_2$ and has a size and configuration such that, upon binding of the compound to calpain 9, at least one atom of $P_1$ is within 3.2 to 4.7 Å of Lys188 carbonyl carbon.

Some embodiments of compounds of Formula (II) include compound wherein $P_1$ is positioned by $L_2$ and has a size and configuration such that, upon binding of the compound to calpain 9, at least one atom of $P_1$ is within 2.6 to 4.0 Å of Lys188 carbonyl carbon.

Some embodiments of compounds of Formula (II) include compound wherein $P_1$ is positioned by $L_2$ and has a size and configuration such that, upon binding of the compound to calpain 9, at least one atom of $P_1$ is within 3.0 to 4.1 Å of Gly189 C-alpha.

Some embodiments of compounds of Formula (II) include compound wherein $P_1$ is positioned by $L_2$ and has a size and configuration such that, upon binding of the compound to calpain 9, at least one atom of $P_1$ is within 3.2 to 4.0 Å of Gly189 C-alpha.

Some embodiments provide a compound of Formula (II):

II

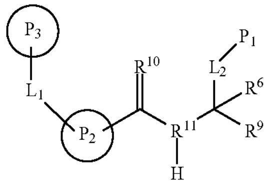

or a pharmaceutically acceptable salt thereof, wherein:

$P_2$ is an optionally substituted cyclic moiety having a size and configuration such that, upon binding of the compound to calpain 1, at least one atom of $P_2$ forms a non-polar interaction with, and is within 5 Å or less of, at least one calpain 1 P2 pocket moiety selected from the group consisting of Gly208, Ser251, Gly271, His272, and Ala273;

$L_1$ is a bond or a moiety consisting of from 1 to 25 atoms selected from the group consisting of carbon, oxygen, nitrogen, hydrogen, and sulfur;

$P_3$ is an optionally substituted cyclic moiety positioned by $L_1$ and having a size and configuration such that, upon binding of the compound to calpain 1, at least one atom of $P_3$ forms a non-polar interaction with, and is within 5 Å or less of, at least one calpain 1 P3 pocket moiety selected from the group consisting of Gly207, Gly208, Ser209, Ile254, and Gly271;

$R^{10}$ is oxo and is positioned by $P_2$ such that, upon binding of the compound to calpain 1, $R^{10}$ forms a polar interaction with, and is within 4 Å or less of, calpain 1 Gly208 amide;

$R^{11}$ is nitrogen and is positioned by the carbons to which it is bonded such that, upon binding of the compound to calpain 1, $R^{11}$ forms a polar interaction with, and is within 4 Å or less of, calpain 1 Gly271 carbonyl;

$L_2$ is a bond or a moiety consisting of from 1 to 25 atoms selected from the group consisting of carbon, oxygen, nitrogen, hydrogen, and sulfur;

$P_1$ is a moiety positioned by $L_2$ and having a size and configuration such that, upon binding of the compound to calpain 1, at least one atom of $P_1$ forms a non-polar interaction with, and is within 5 Å or less of, at least one calpain 1 P1 pocket moiety selected from the group consisting of Gly113, Ser206, Gly207, and Met260;

$R^9$ is a moiety positioned by the carbon to which it is attached such that, upon binding of the compound to calpain 1, at least one atom of $R^9$ forms a polar interaction with, and is within 4 Å or less of, at least one calpain 1 moiety selected from the group consisting of Gln109, Cys115, and His272; and $R^6$ is selected from —H and optionally substituted $C_{1-4}$ alkyl.

Some embodiments of compounds of Formula (II) include compound wherein $R^9$ is $-(C{=}R^{12})(C{=}R^{13})NR^2R^3$;

$R^{12}$ is oxo and is positioned such that, upon binding of the compound to calpain 1, $R^{12}$ forms a polar interaction with, and is within 4 Å or less of, calpain 1 His272 imidazole;

$R^{13}$ is oxo and is positioned such that, upon binding of the compound to calpain 1, $R^{13}$ forms a polar interaction with, and is within 4 Å or less of, at least one calpain 1 moiety selected from the group consisting of Gln109 side chain carboxamide and Cys115 backbone amide; and $R^2$ and $R^3$ are independently selected from —H, optionally substituted $C_{1-4}$ alkyl, optionally substituted $C_{3-7}$ carbocyclyl, optionally substituted 5-10 membered heterocyclyl, optionally substituted $C_{6-10}$ aryl, optionally substituted C10aryl($C_1$-$C_6$)alkyl, and optionally substituted 5-10 membered heteroaryl.

Some embodiments of compounds of Formula (II) include compound wherein $R^9$ is positioned by the carbon to which it is attached such that, upon binding of the compound to calpain 1, at least one atom of $R^9$ forms a polar interaction with, and is within 3.5 Å or less of, at least one calpain 1 moiety selected from the group consisting of Gln109, Cys115, and His272.

Some embodiments of compounds of Formula (II) include compound wherein a carbon atom in $R^9$ at its point of attachment forms a covalent bond with Cys115.

Some embodiments of compounds of Formula (II) include compound wherein the covalent bond length is between 1.7 and 1.9 Å.

Some embodiments of compounds of Formula (II) include compound wherein $P_2$ is an optionally substituted 5-membered heteroaryl.

Some embodiments of compounds of Formula (II) include compound wherein $R^{11}$ is positioned by the carbons to which it is bonded such that, upon binding of the compound to calpain 1, $R^{11}$ forms a polar interaction with, and is within 3.5 Å or less of, calpain 1 Gly271 carbonyl.

Some embodiments provide a compound of Formula (II):

II

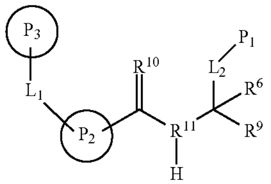

or a pharmaceutically acceptable salt thereof, wherein $P_2$ is an optionally substituted cyclic moiety having a size and configuration such that, upon binding of the compound to calpain 2, at least one atom of $P_2$ forms a non-polar interaction with, and is within 5 Å or less of, at least one calpain 2 P2 pocket moiety selected from the group consisting of Gly198, Ser241, Gly261, His262, and Ala263;

$L_1$ is a bond or a moiety consisting of from 1 to 25 atoms selected from the group consisting of carbon, oxygen, nitrogen, hydrogen, and sulfur;

$P_3$ is an optionally substituted cyclic moiety positioned by $L_1$ and having a size and configuration such that, upon binding of the compound to calpain 2, at least one atom of $P_3$ forms a non-polar interaction with, and is within 5 Å or less of, at least one calpain 2 P3 pocket moiety selected from the group consisting of Gly197, Gly198, Ala199, Ile244, and Gly261;

$R^{10}$ is oxo and is positioned by $P_2$ such that, upon binding of the compound to calpain 2, $R^{10}$ forms a polar interaction with, and is within 4 Å or less of, calpain 2 Gly198 amide;

$R^{11}$ is nitrogen and is positioned by the carbons to which it is bonded such that, upon binding of the compound to calpain 2, $R^{11}$ forms a polar interaction with, and is within 4 Å or less of, calpain 2 Gly261 carbonyl;

$L_2$ is a bond or a moiety consisting of from 1 to 25 atoms selected from the group consisting of carbon, oxygen, nitrogen, hydrogen, and sulfur;

$P_1$ is a moiety positioned by $L_2$ and having a size and configuration such that, upon binding of the compound to calpain 2, at least one atom of $P_1$ forms a non-polar interaction with, and is within 5 Å or less of, at least one calpain 2 P1 pocket moiety selected from the group consisting of Gly103, Ser196, Gly197, and Ser250;

$R^9$ is a moiety positioned by the carbon to which it is attached such that, upon binding of the compound to calpain 2, at least one atom of $R^9$ forms a polar interaction with, and is within 4 Å or less of, at least one calpain 2 moiety selected from the group consisting of Gln99, Cys105, and His262; and $R^6$ is selected from —H and optionally substituted $C_{1-4}$ alkyl.

Some embodiments of compounds of Formula (II) include compound wherein $R^9$ is —(C═$R^{12}$)(C═$R^{13}$)$NR^2R^3$;

$R^{12}$ is oxo and is positioned such that, upon binding of the compound to calpain 2, $R^{12}$ forms a polar interaction with, and is within 4 Å or less of, calpain 2 His262 imidazole;

$R^{13}$ is oxo and is positioned such that, upon binding of the compound to calpain 2, $R^{13}$ forms a polar interaction with, and is within 4 Å or less of, at least one calpain 2 moiety selected from the group consisting of Gln99 side chain carboxamide and Cys105 backbone amide; and $R^2$ and $R^3$ are independently selected from —H, optionally substituted $C_{1-4}$ alkyl, optionally substituted $C_{3-7}$ carbocyclyl, optionally substituted 5-10 membered heterocyclyl, optionally substituted $C_{6-10}$ aryl, optionally substituted C10aryl($C_1$-$C_6$)alkyl, and optionally substituted 5-10 membered heteroaryl.

Some embodiments of compounds of Formula (II) include compound wherein $R^9$ is positioned by the carbon to which it is attached such that, upon binding of the compound to calpain 2, at least one atom of $R^9$ forms a polar interaction with, and is within 3.5 Å or less of, at least one calpain 2 moiety selected from the group consisting of Gln99, Cys105, and His262.

Some embodiments of compounds of Formula (II) include compound wherein a carbon atom in $R^9$ at its point of attachment forms a covalent bond with Cys195.

Some embodiments of compounds of Formula (II) include compound wherein the covalent bond length is between 1.7 and 1.9 Å.

Some embodiments of compounds of Formula (II) include compound wherein $P_2$ is an optionally substituted 5-membered heteroaryl.

Some embodiments of compounds of Formula (II) include compound wherein $R^{11}$ is positioned by the carbons to which it is bonded such that, upon binding of the compound to calpain 2, $R^{11}$ forms a polar interaction with, and is within 3.5 Å or less of, calpain 2 Gly261 carbonyl.

Some embodiments include a compound selected from the group consisting of compounds 1 to 90, compounds 92-94, compound 195, compounds 197 to 235, compounds 238 to 273, compounds 276 to 281, compounds 283 to 299, compounds 303 to 309, compounds 313 to 363, compound 365, compounds 367-410, compounds 413-424, compounds 428-445, compounds 447-448, compounds 454-532, compound 540, compounds 546-588, compounds 591-605, compounds 607-611, compounds 613-630, and pharmaceutically acceptable salts thereof, as such compounds are described herein.

Some embodiments include a compound selected from the group consisting of compounds 91, 196, 274, 282, 310 to 312, 364, 366, 411, 536, 541, and pharmaceutically acceptable salts thereof, as such compounds are described herein.

Some embodiments include a compound selected from the group consisting of:

1

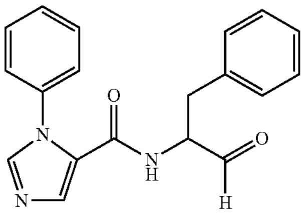

2

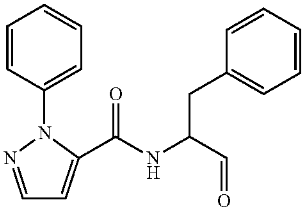

3

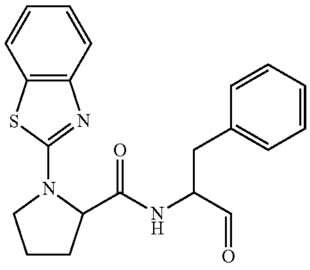

4

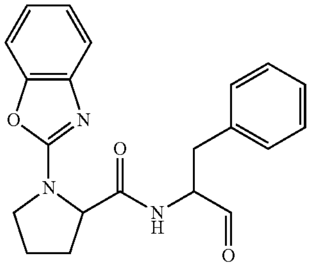

5

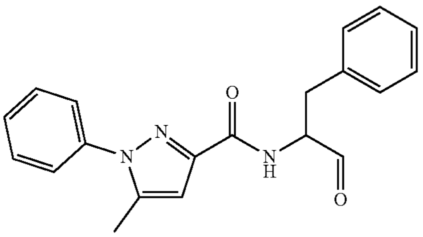

6

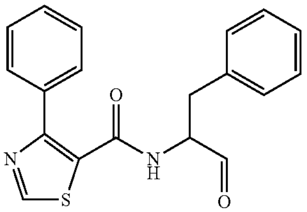

-continued
7
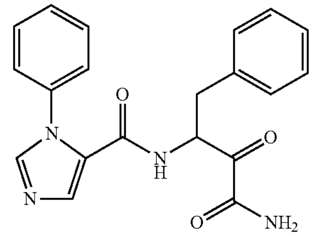
8
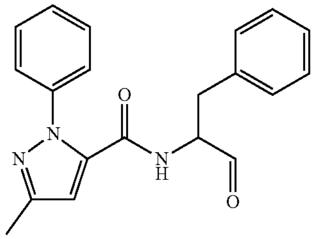
9
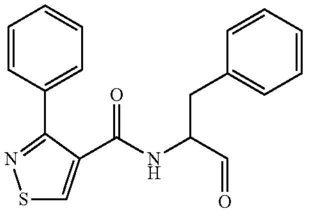
10
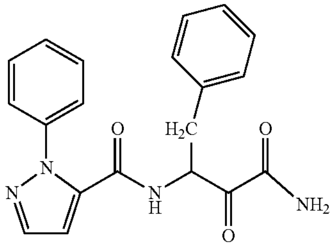
11
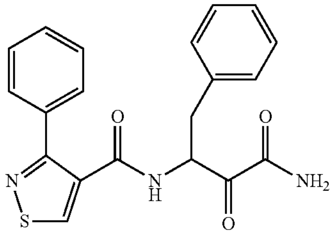
12
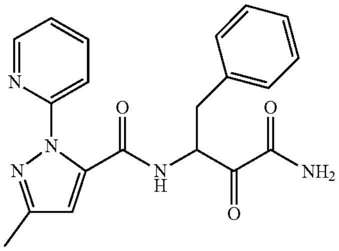
-continued
13
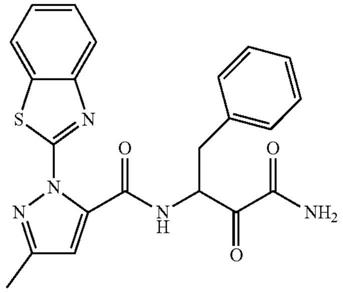
14
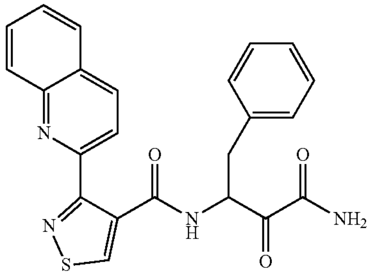
15
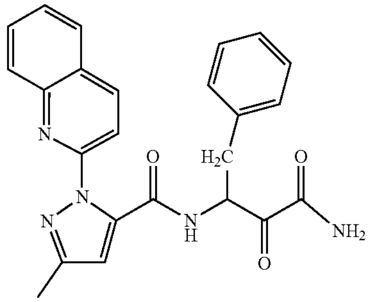
16
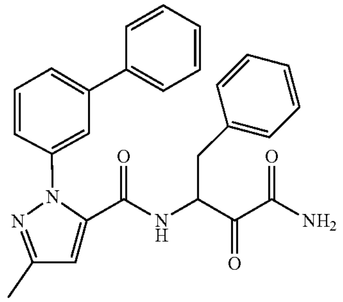
17
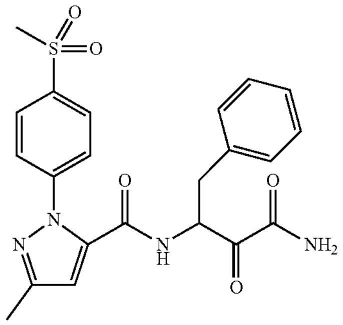

-continued
18
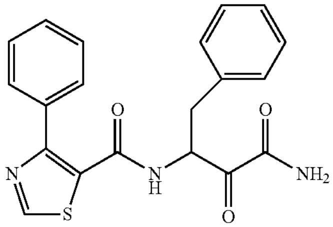
19
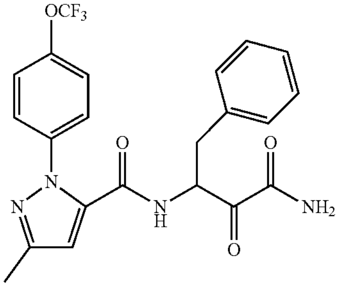
20
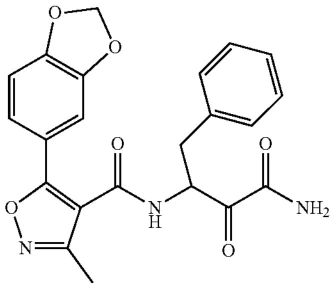
21
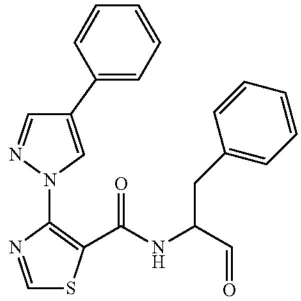
22
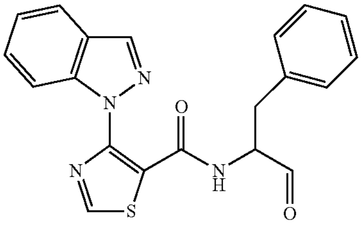
23
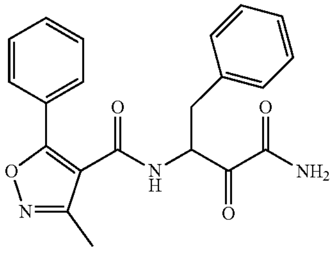
-continued
24
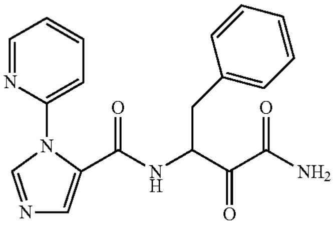
25
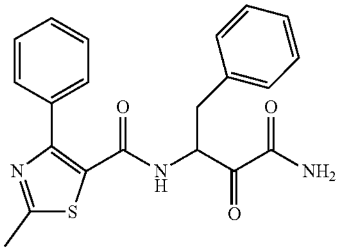
26
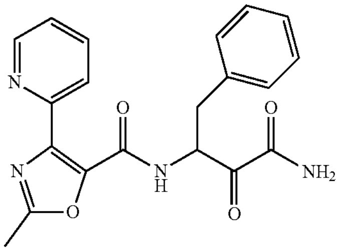
27
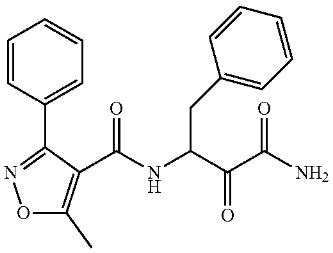
28
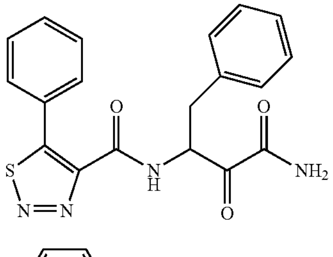
29
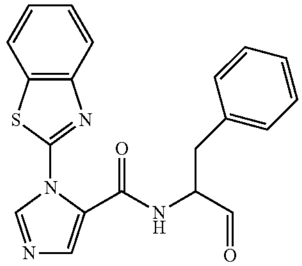

-continued
30
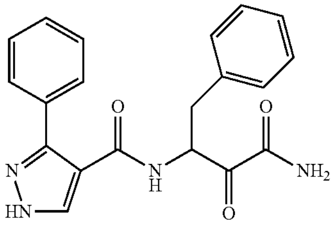
31
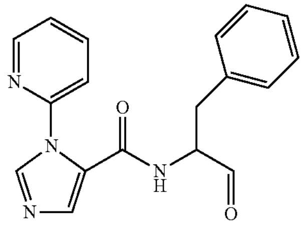
32
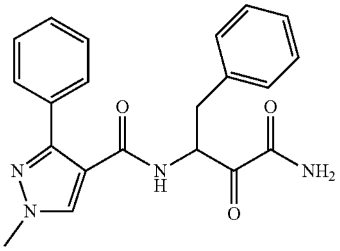
33
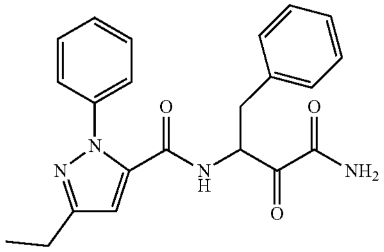
34
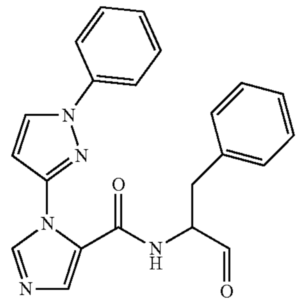
35
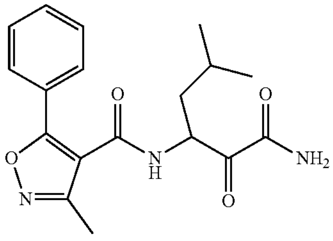
-continued
36
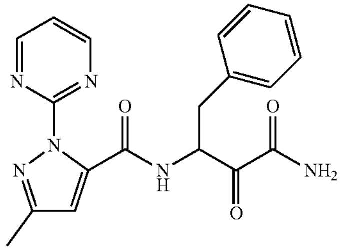
37
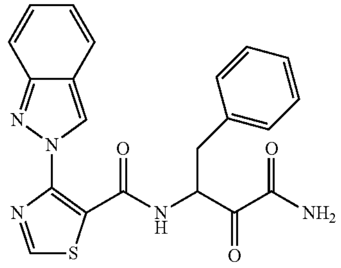
38
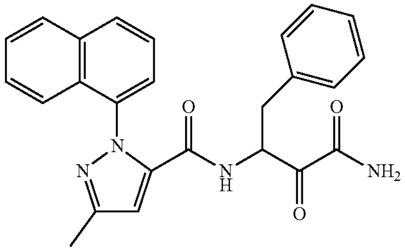
39
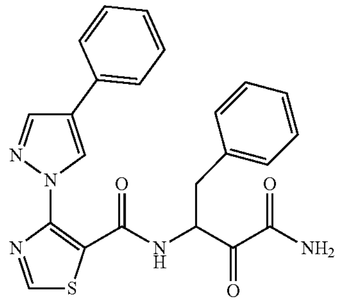
40
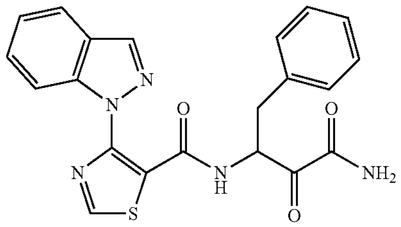
41
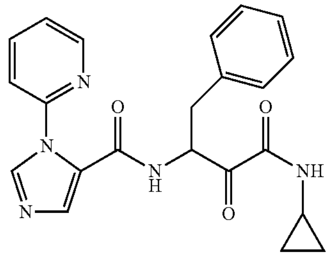

-continued
42
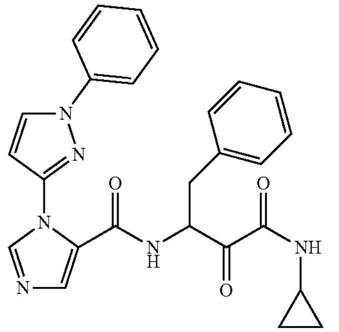
43
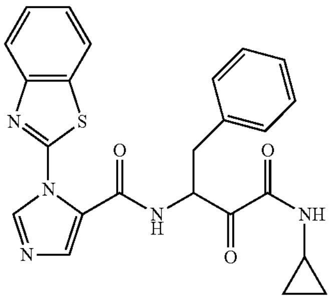
44
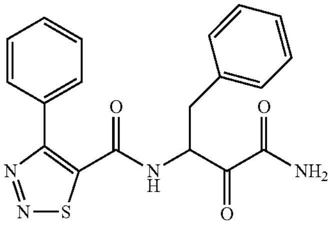
45
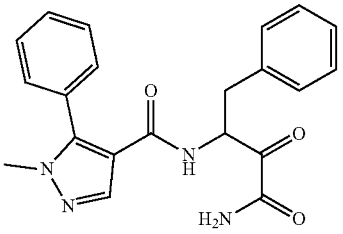
46
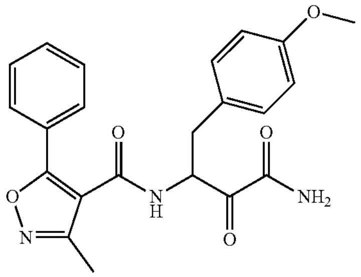
47
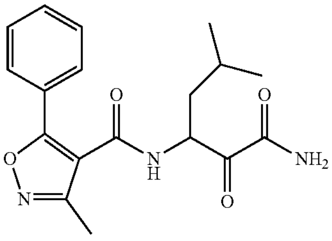
-continued
48
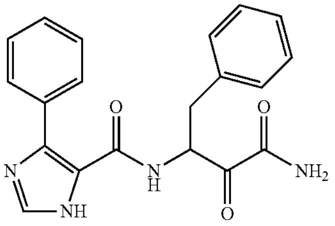
49
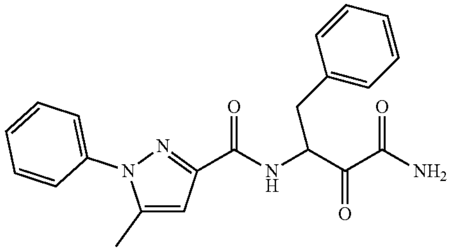
50
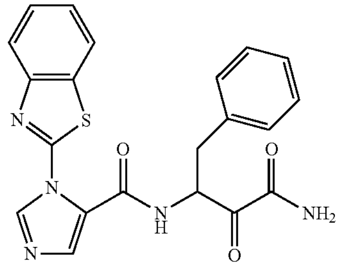
51
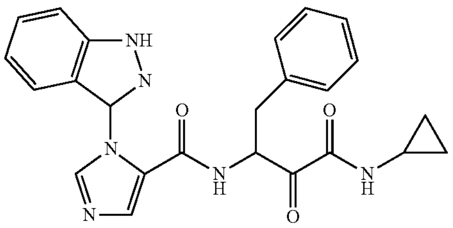
52
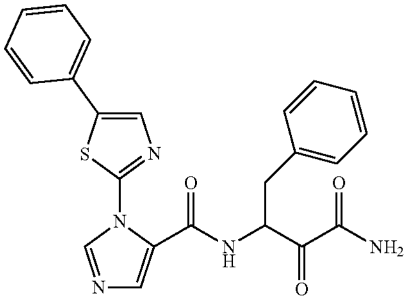
53
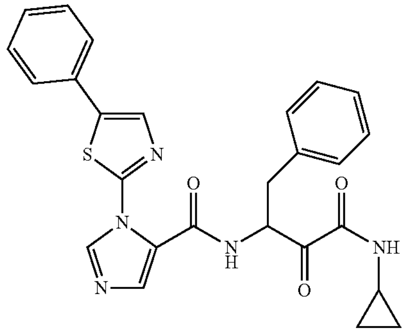

-continued
54
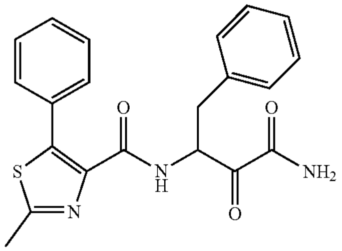
55
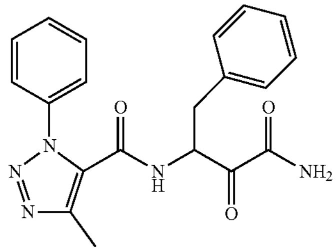
56
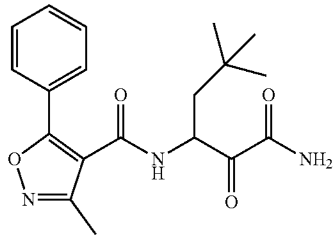
57
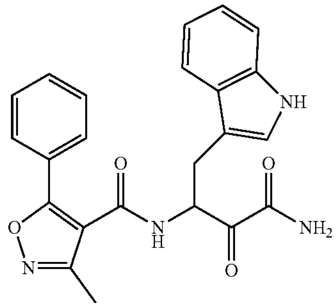
58
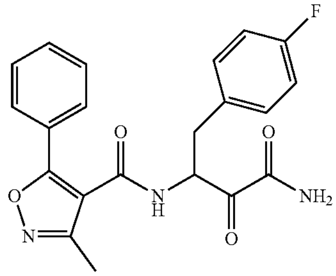
59
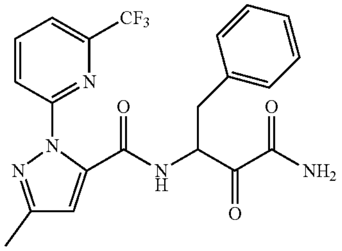
-continued
60
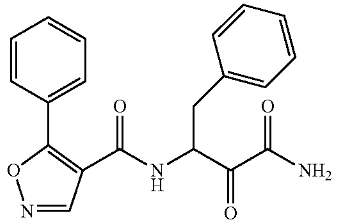
61
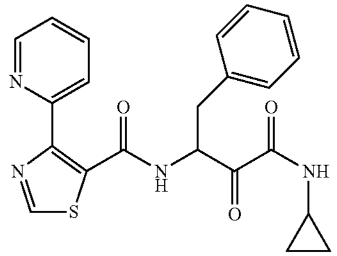
62
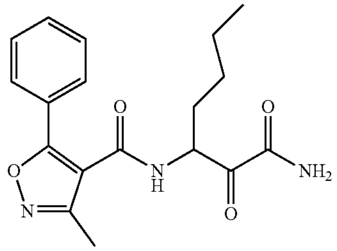
63
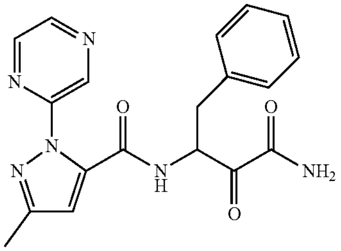
64
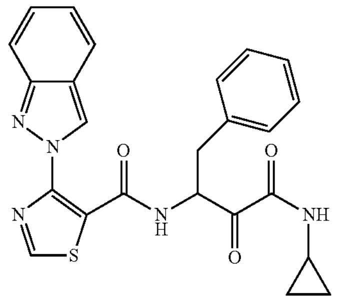
65
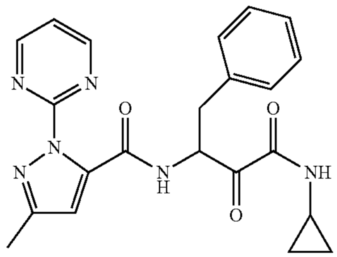

-continued
66
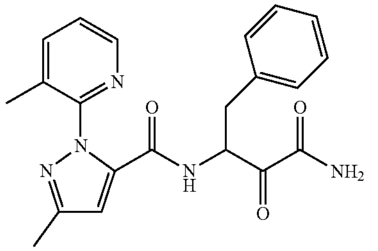
67
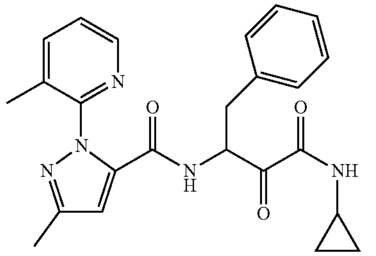
68
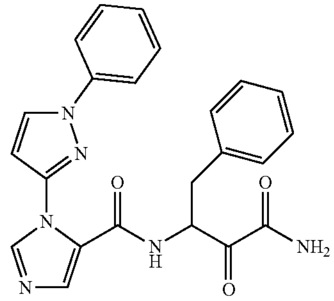
69
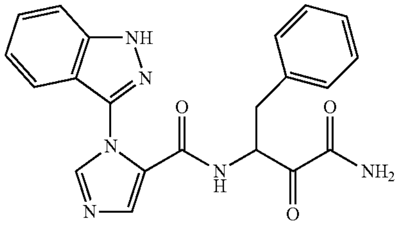
70
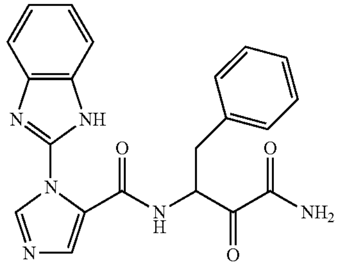
71
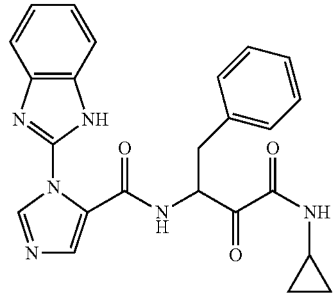
-continued
72
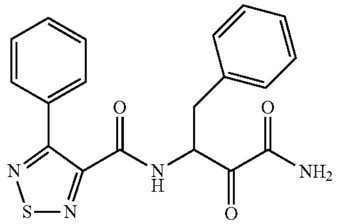
73
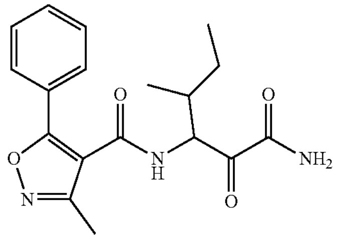
74
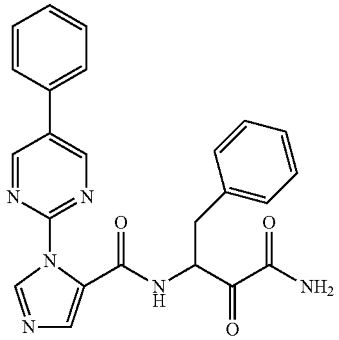
75
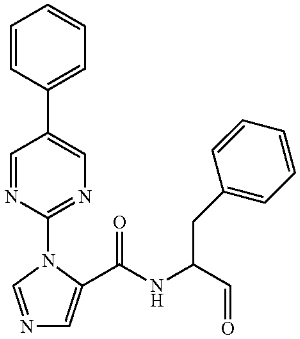
76
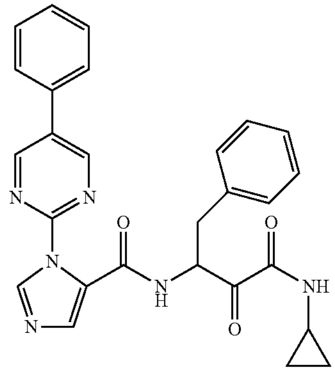

-continued
77
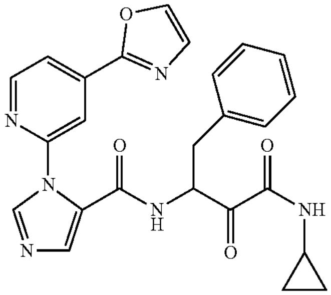
78
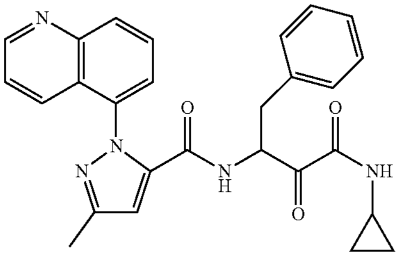
79
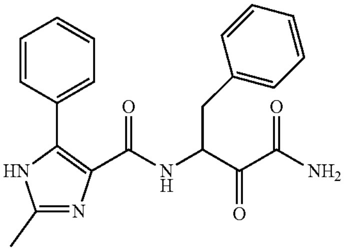
80
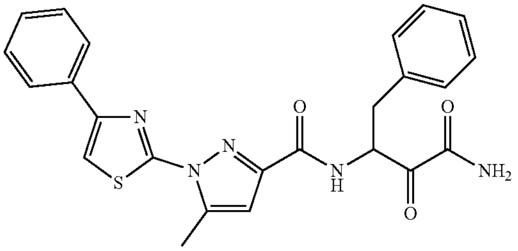
81
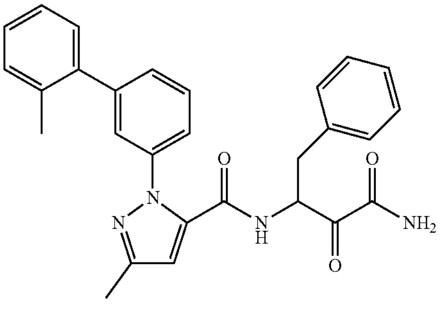
-continued
82
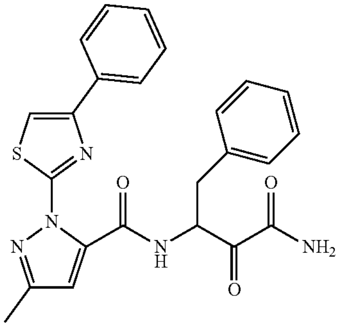
83
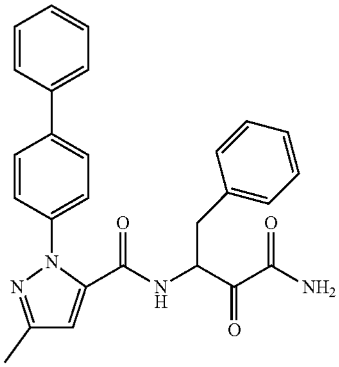
84
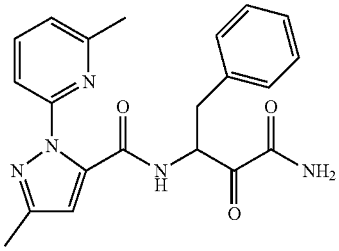
85
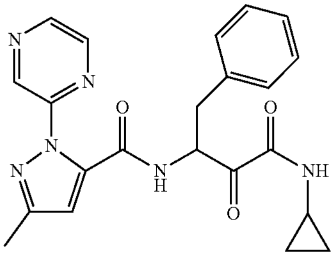
86
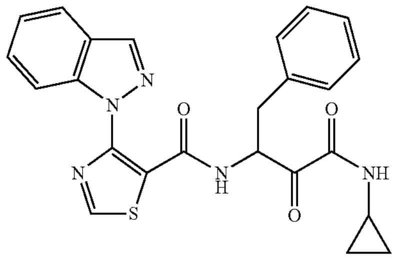

-continued
87
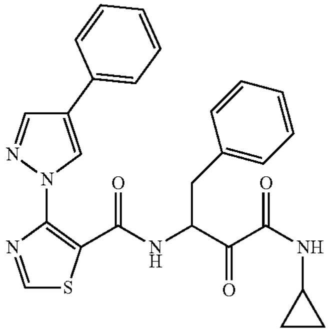
88
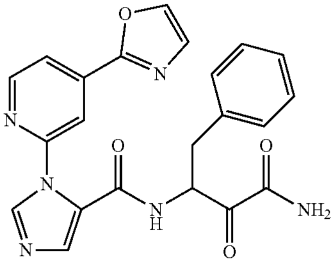
89
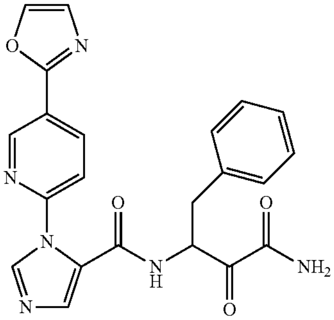
90
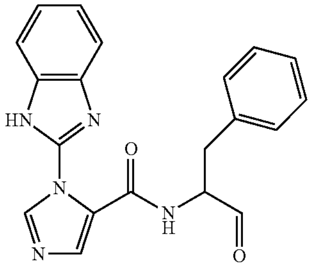
91
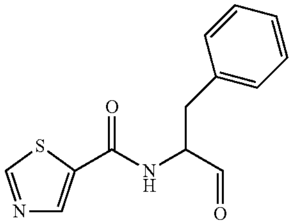
-continued
92
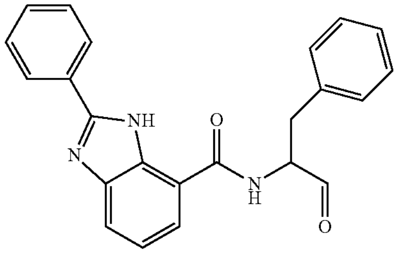
93
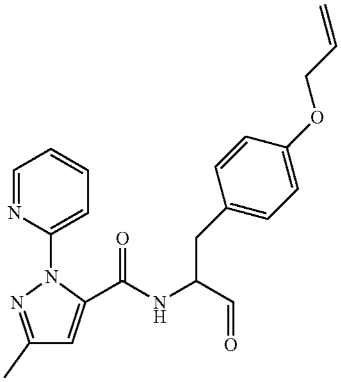
94
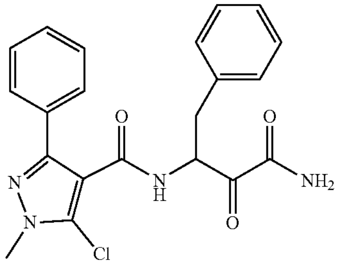
96
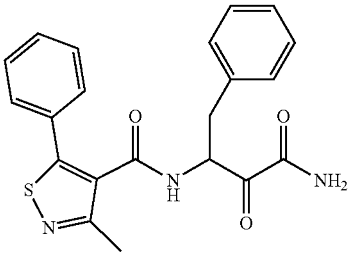
97
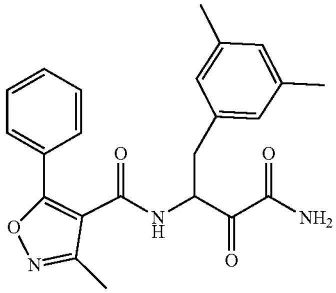

-continued
98
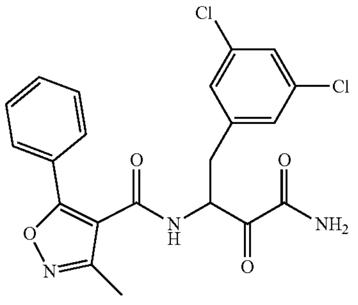
99
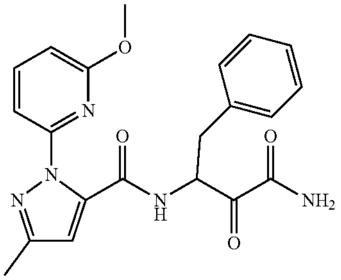
100
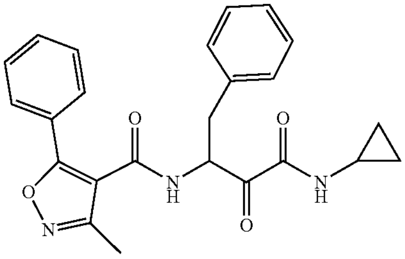
101
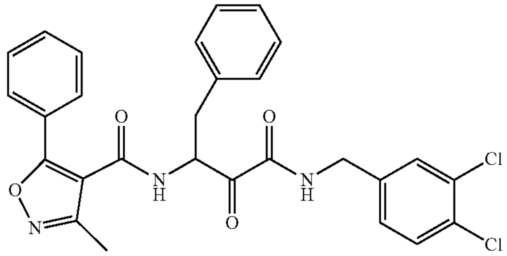
102
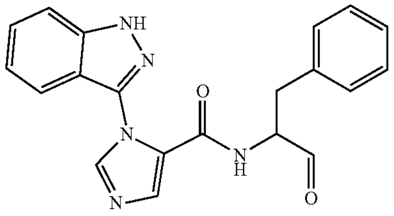
-continued
103
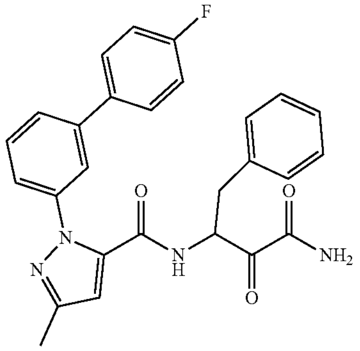
104
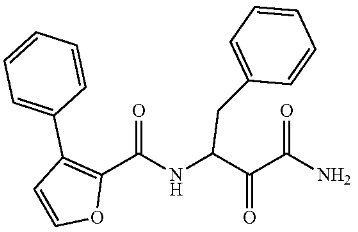
105
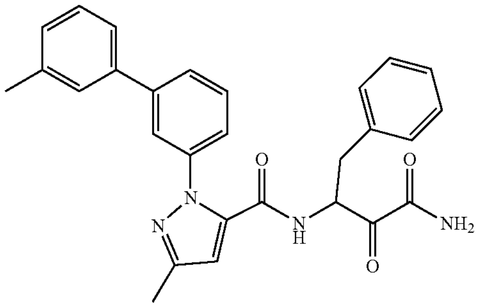
106
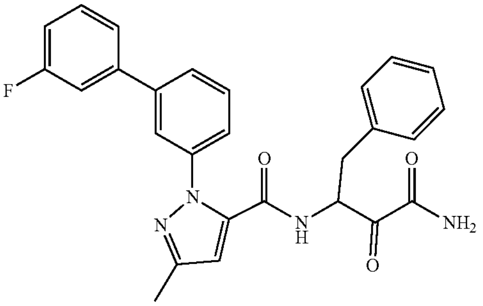
107
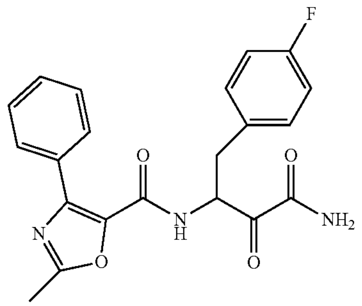

-continued
108
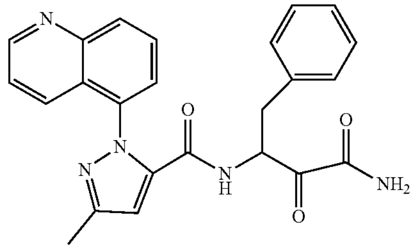
109
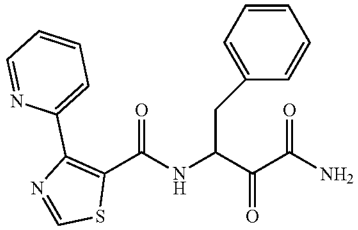
110
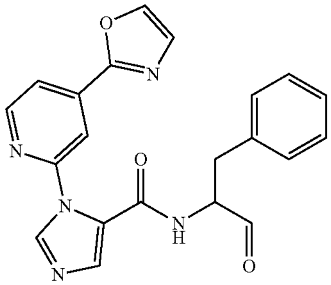
111
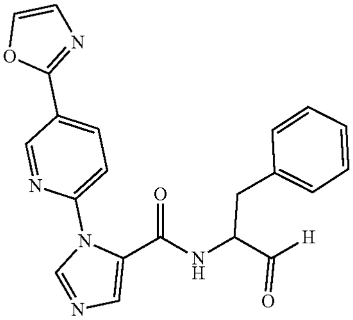
112
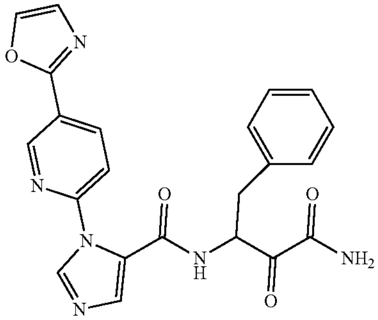
-continued
113
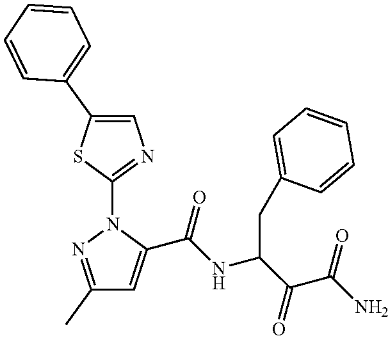
114
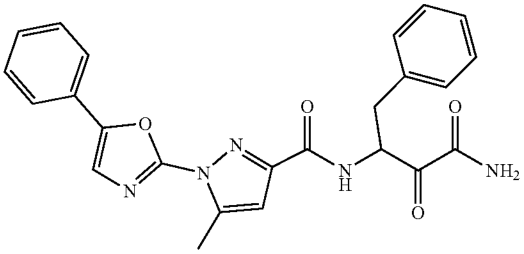
115
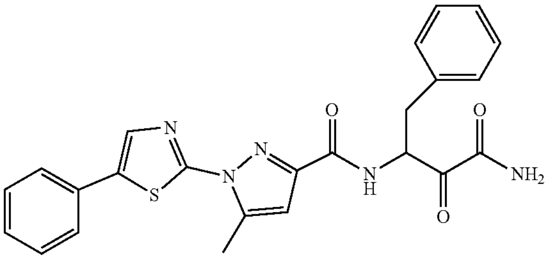
116
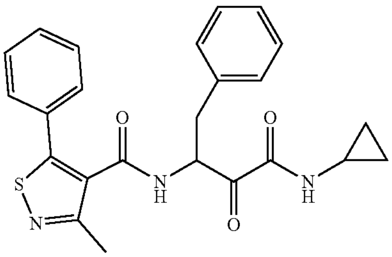
117
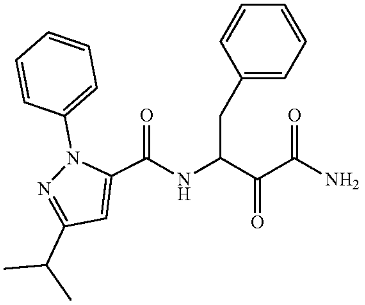

-continued
118
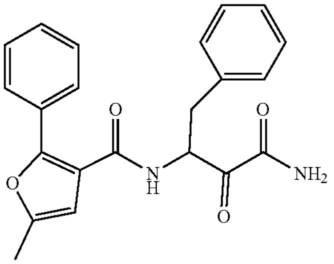
119
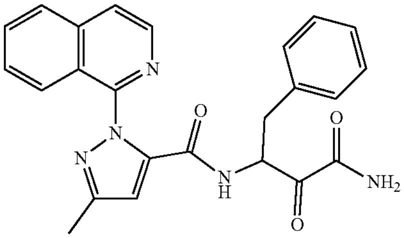
120
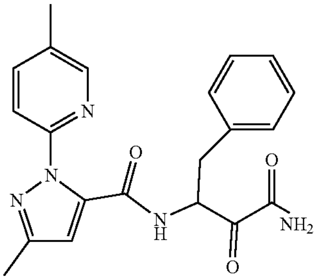
121
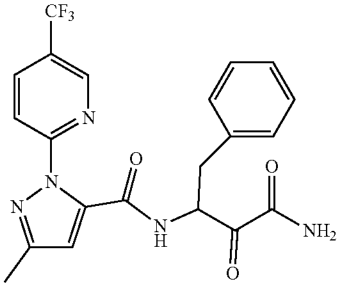
122
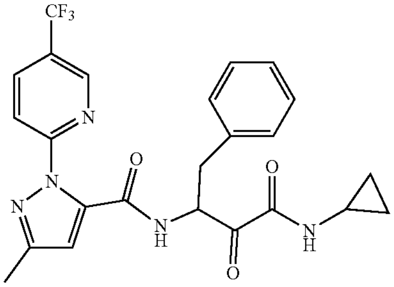
123
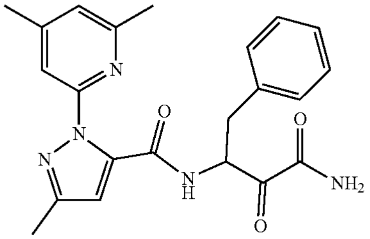
-continued
124
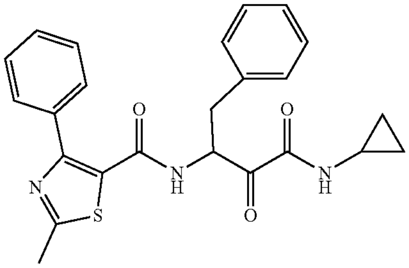
125
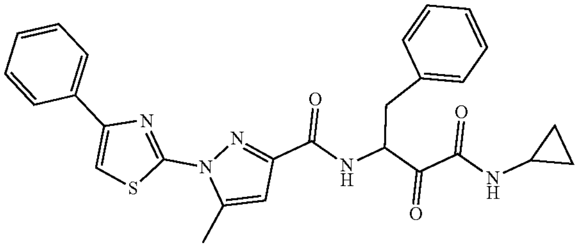
126
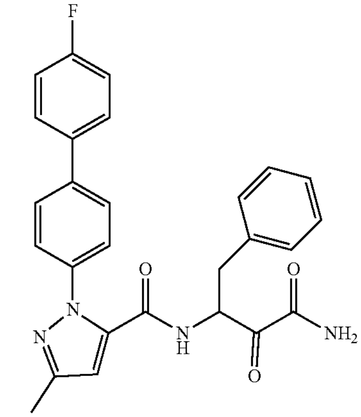
127
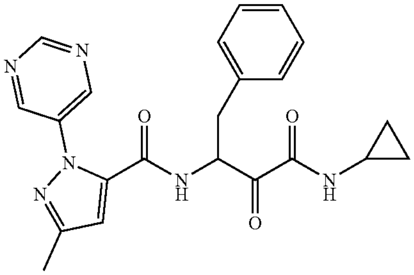
128
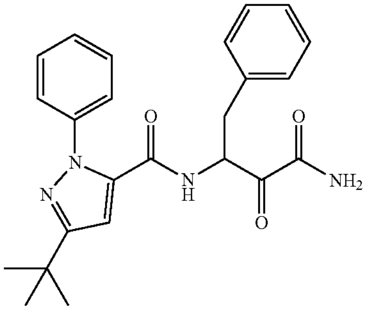

129
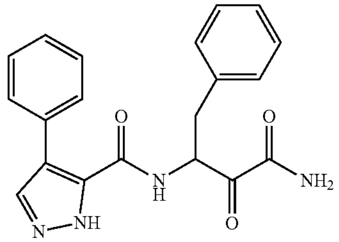
130
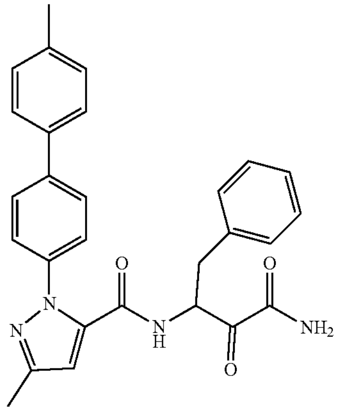
131
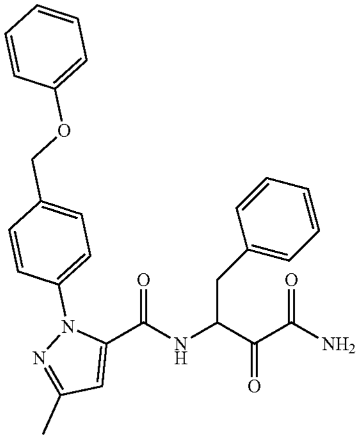
132
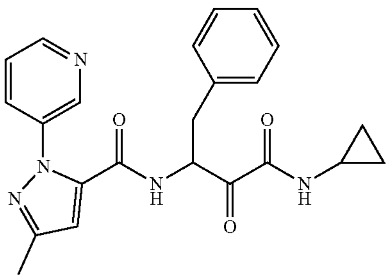
133
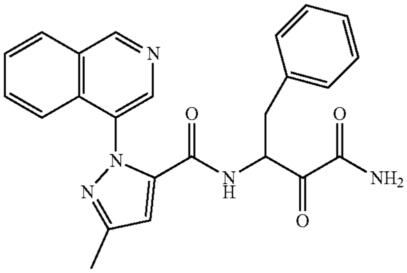
134
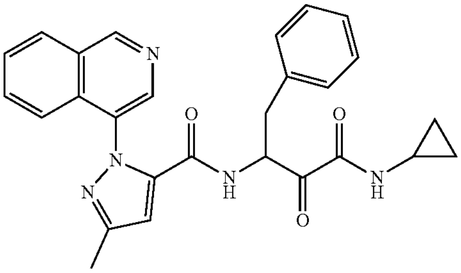
135
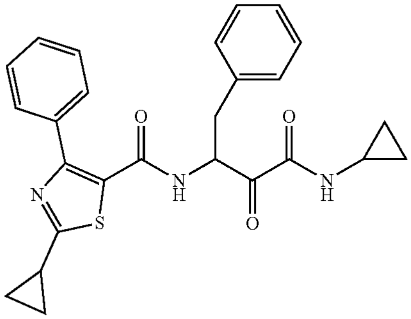
136
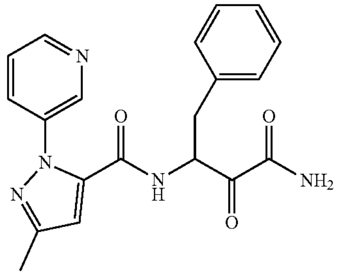
137
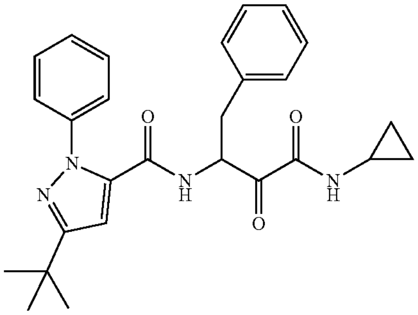

-continued
138
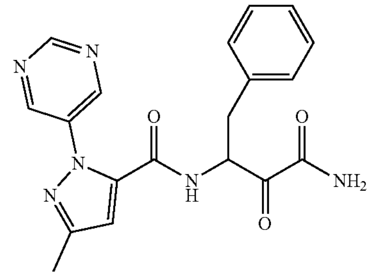
139
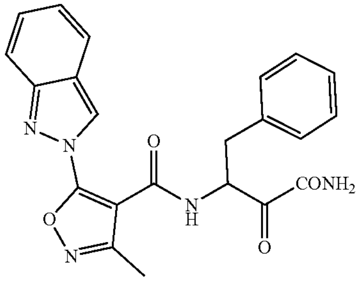
140
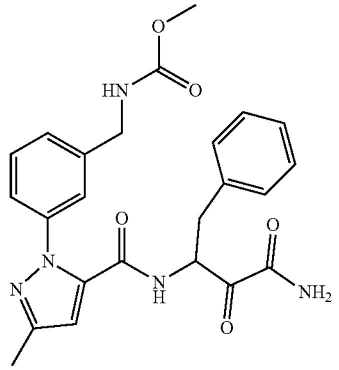
141
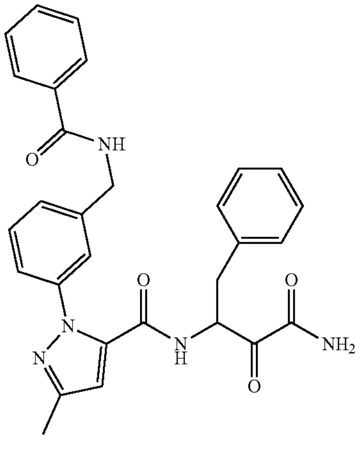
-continued
142
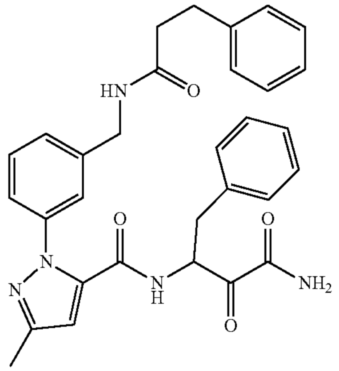
143
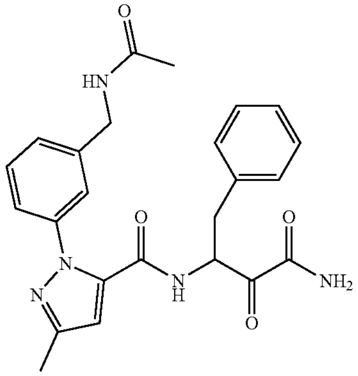
144
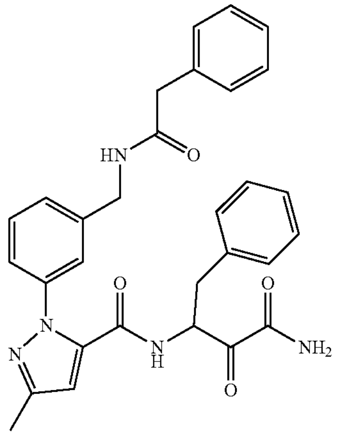
145
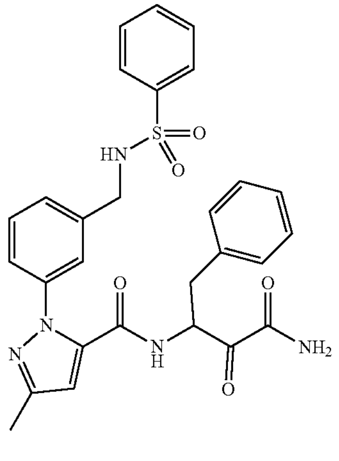

146
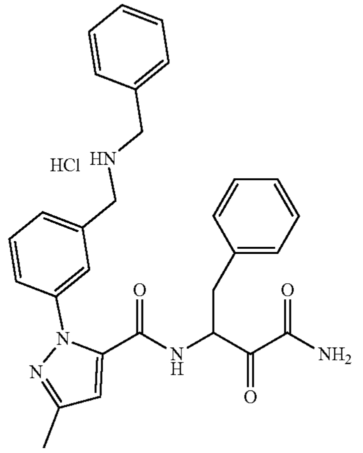
147
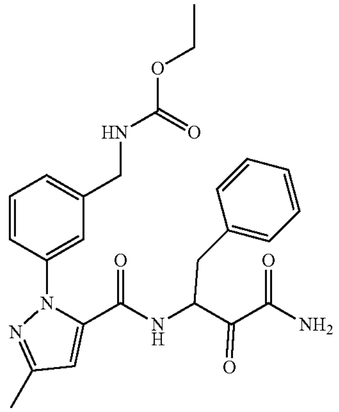
148
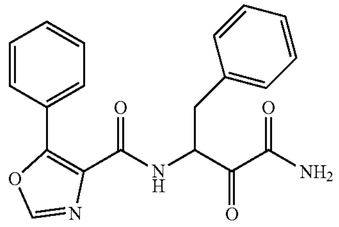
149
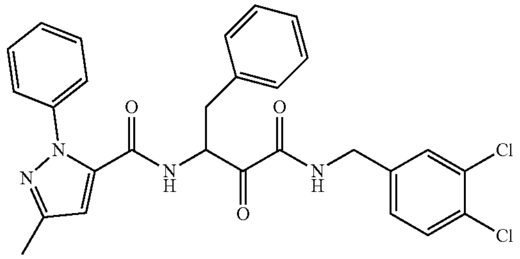
150
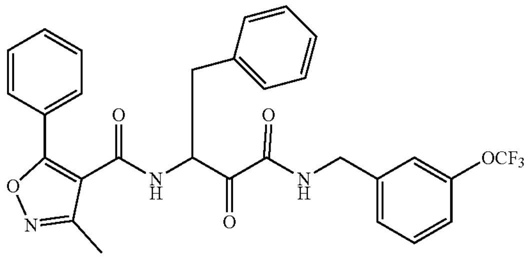
151
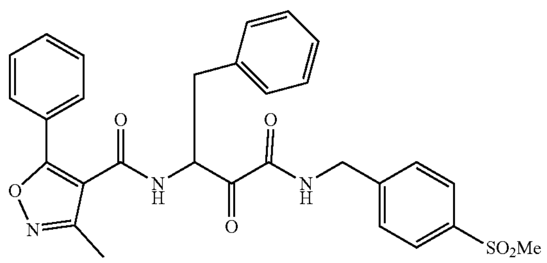
152
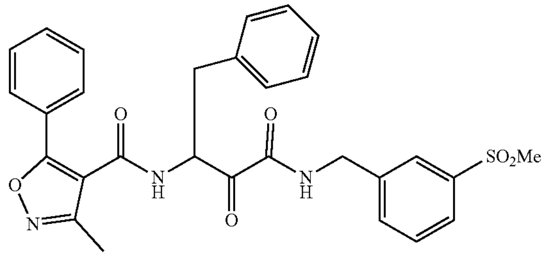
153
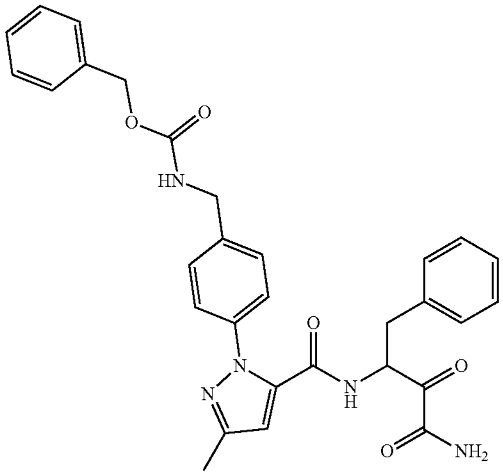
154
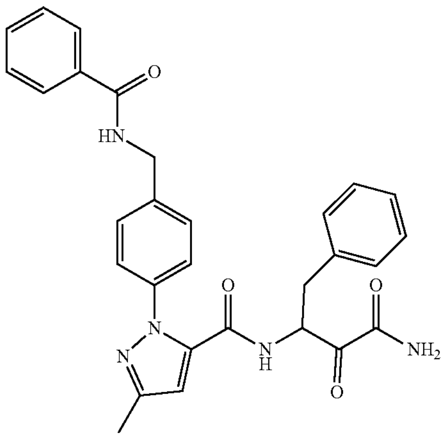

-continued
155
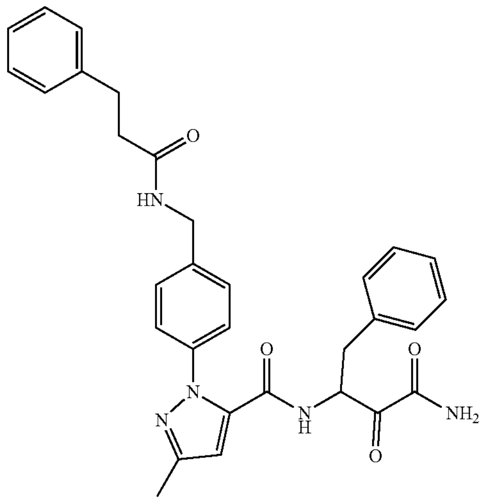
156
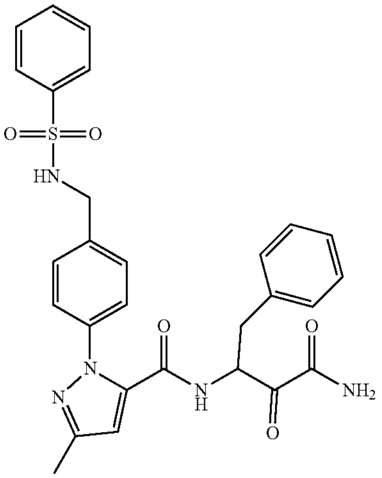
157
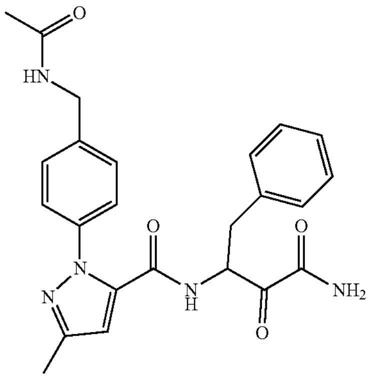
-continued
158
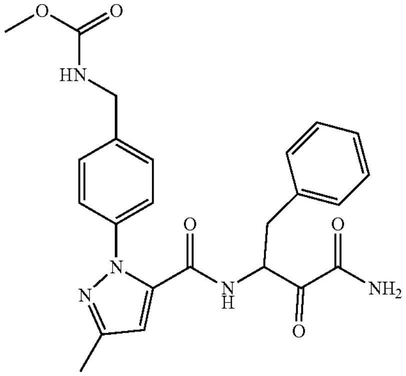
159
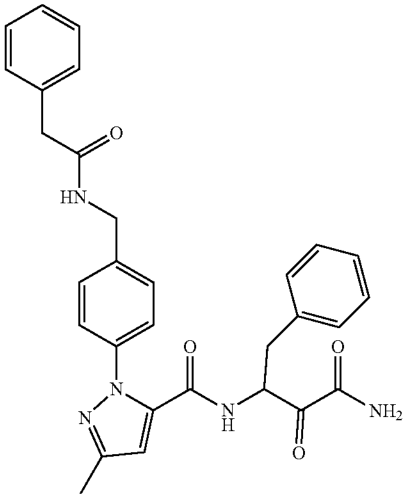
160
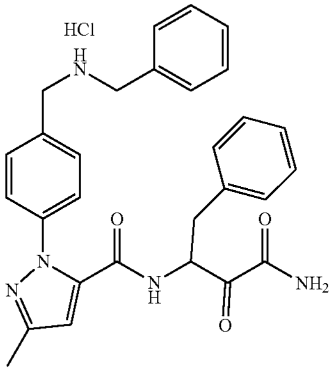
161
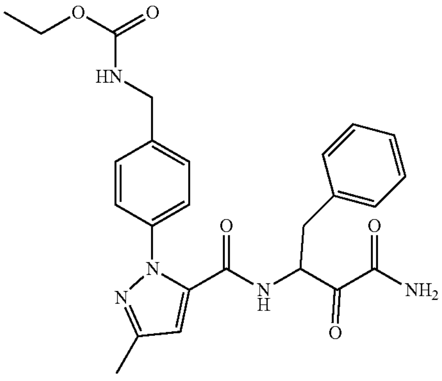

-continued
162
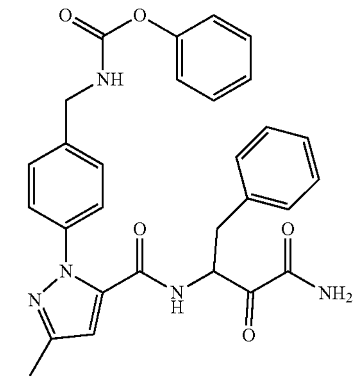
163
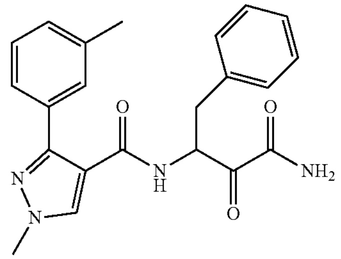
164
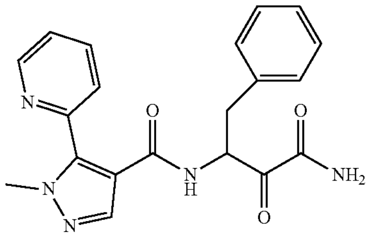
165
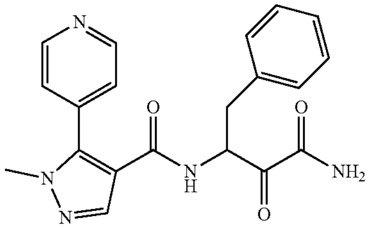
166
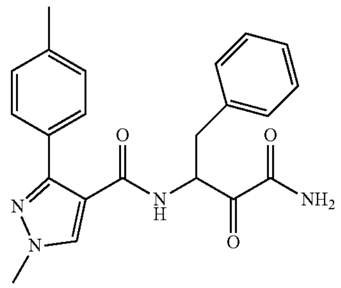
-continued
167
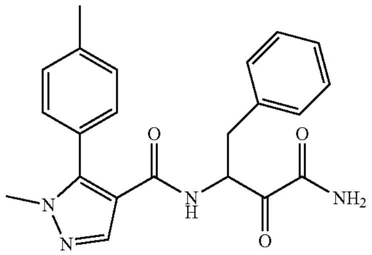
168
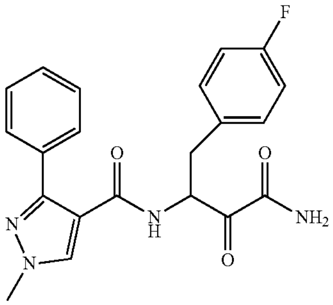
169
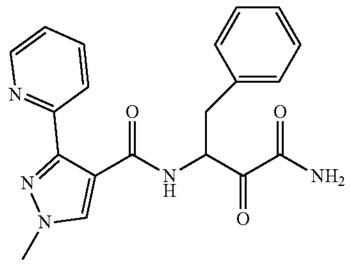
170
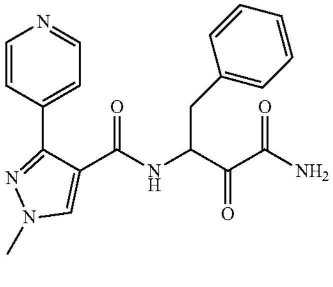
171
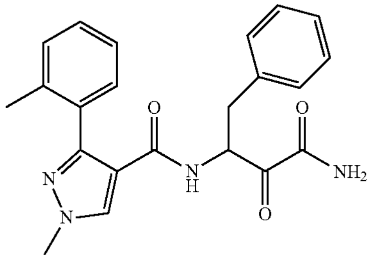
172
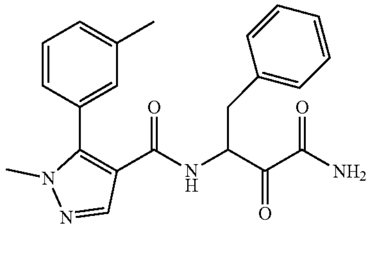

-continued
173
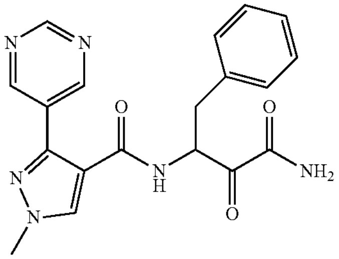
174
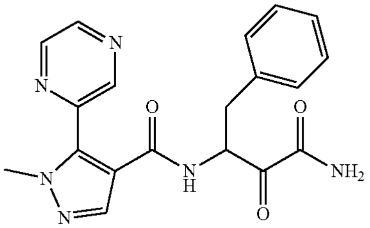
175
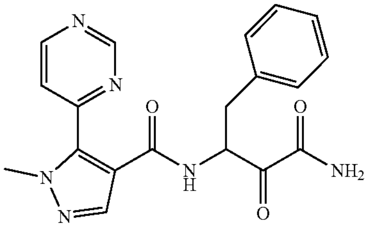
176
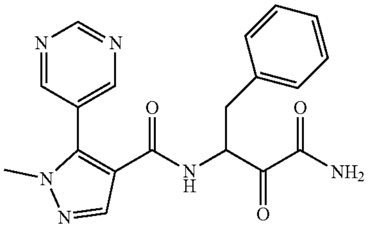
177
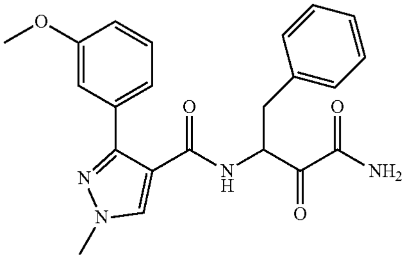
178
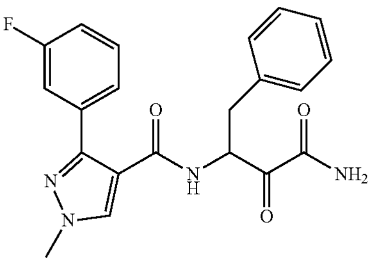
-continued
179
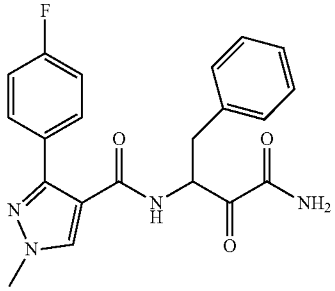
180
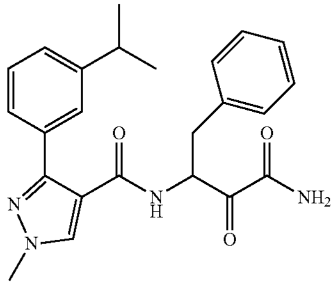
181
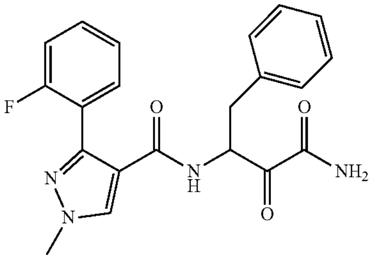
182
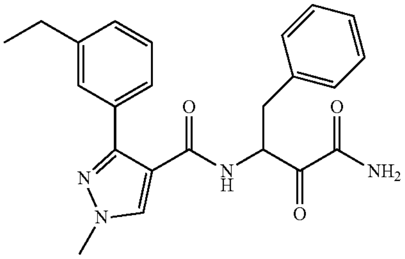
183
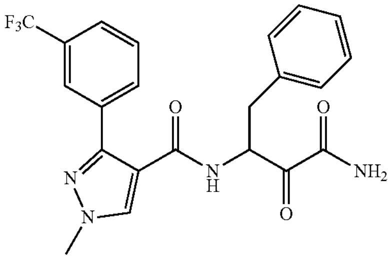

-continued
184
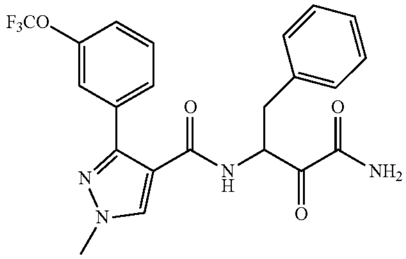
185
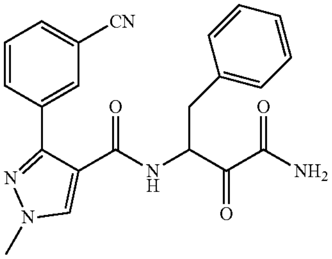
186
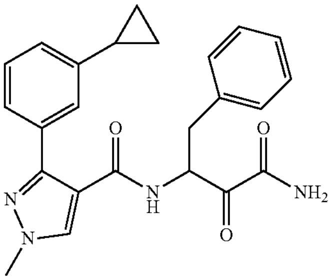
187
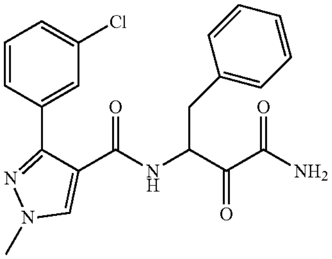
188
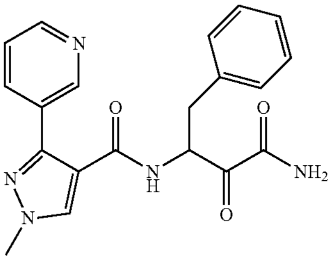
189
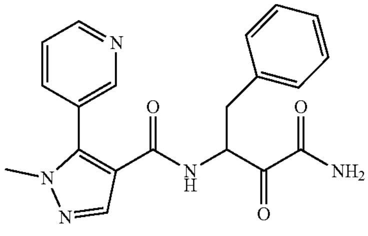
-continued
190
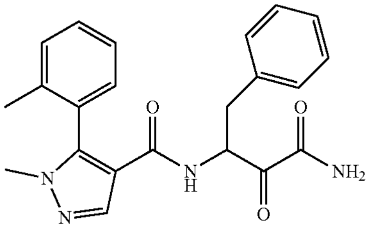
191
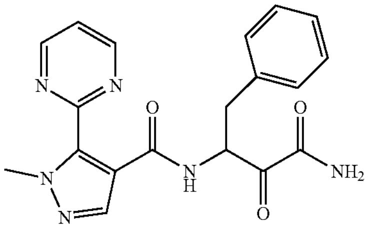
192
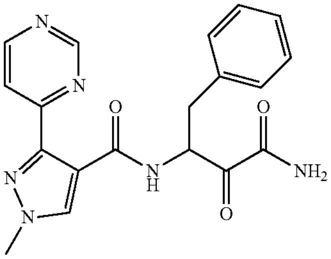
193
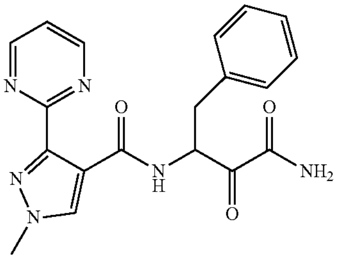
194
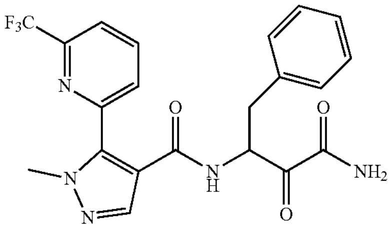
195
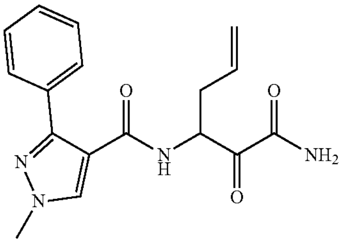

-continued
196
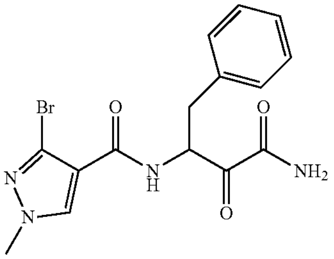
197
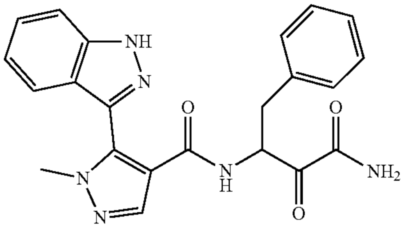
198
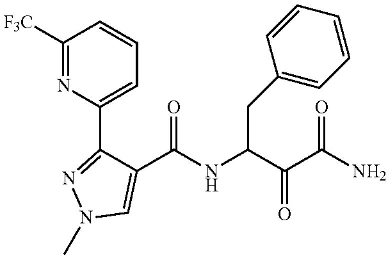
199
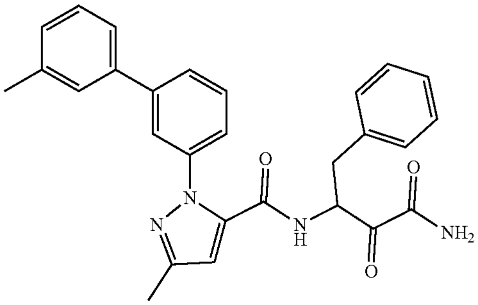
200
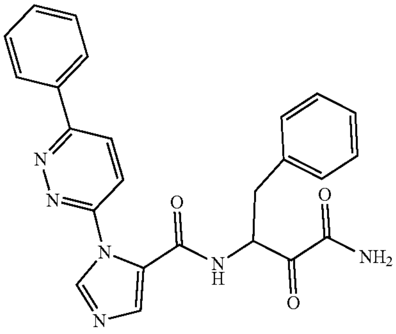
-continued
201
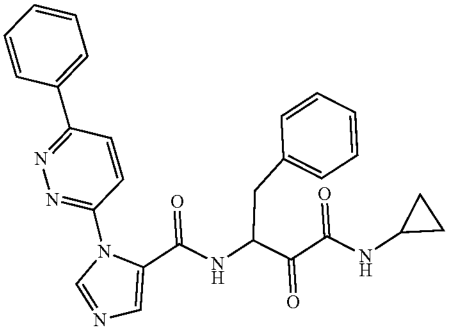
202
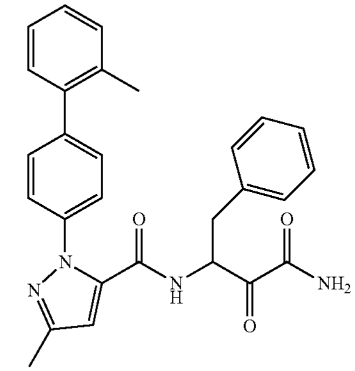
203
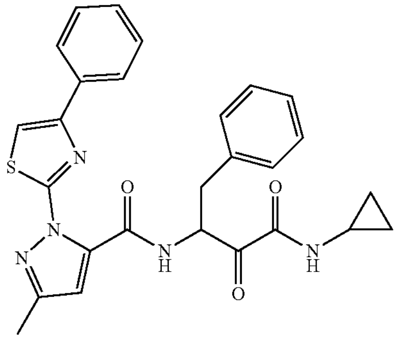
204
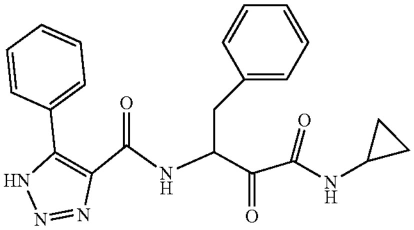
205
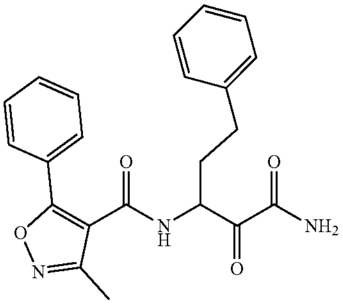

-continued
206
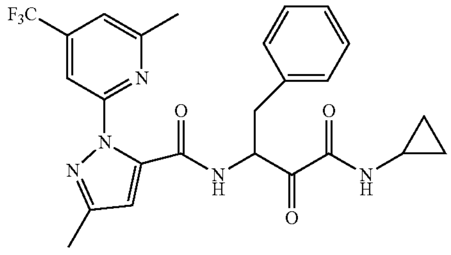
207
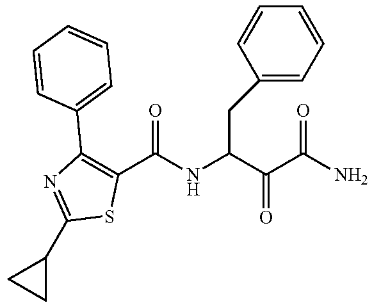
208
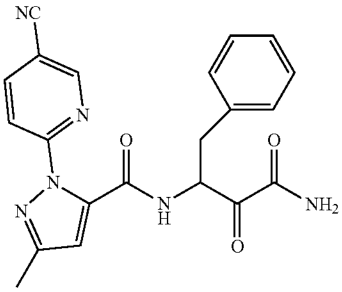
209
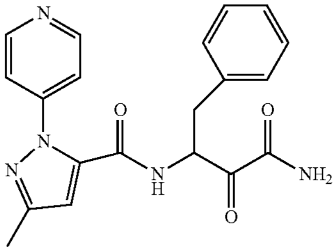
210
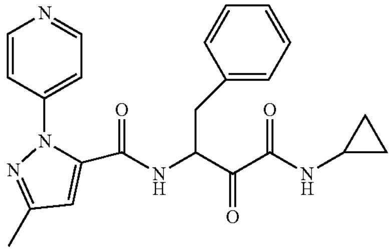
-continued
211
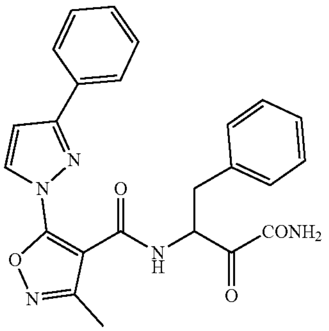
212
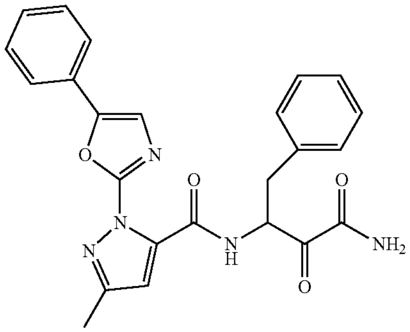
213
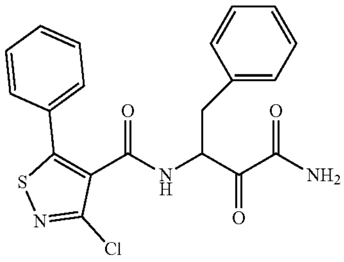
214
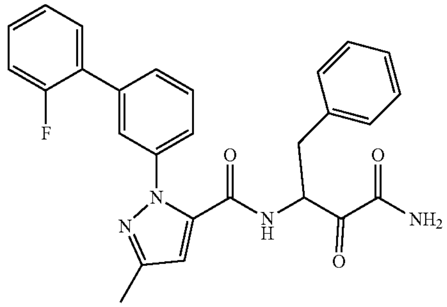
215
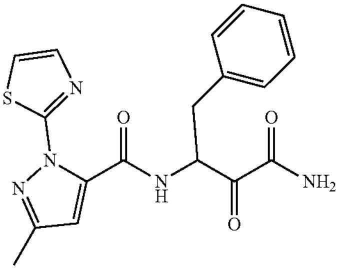

-continued
216
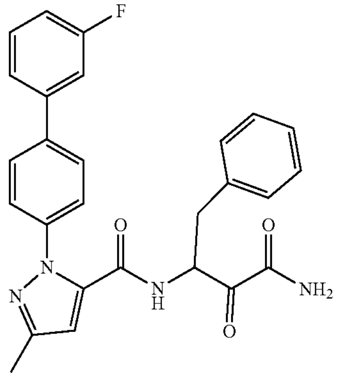
217
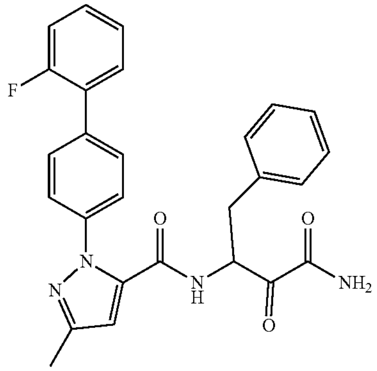
218
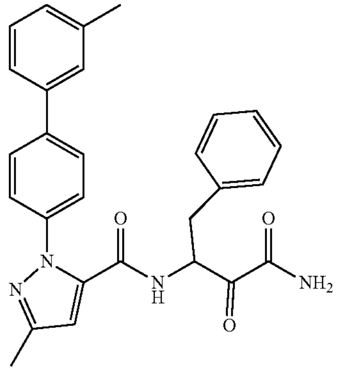
219
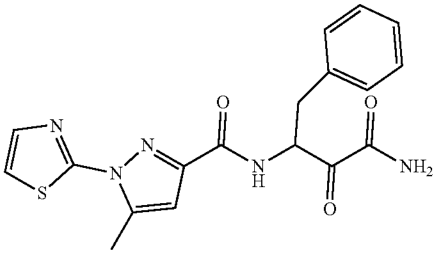
-continued
220
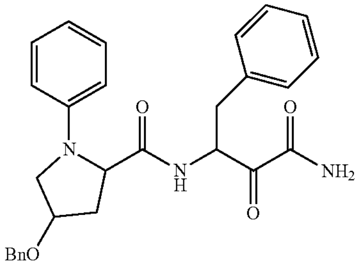
221
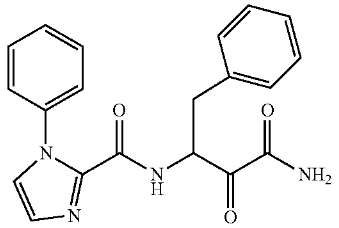
222
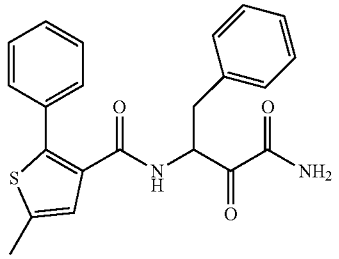
223
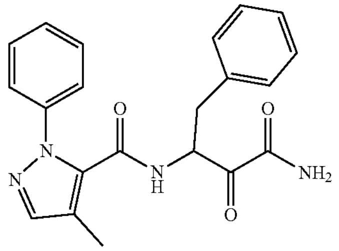
224
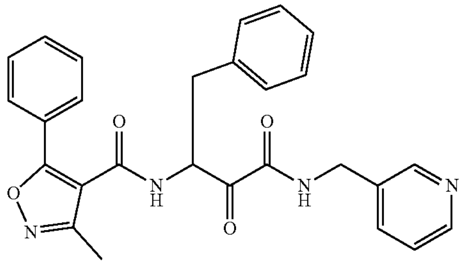
225
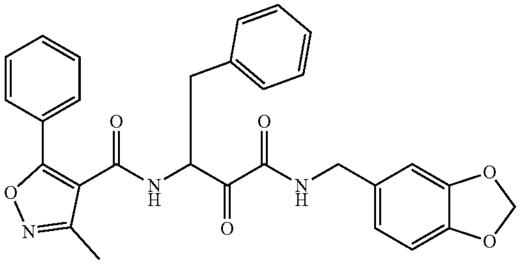

-continued
226
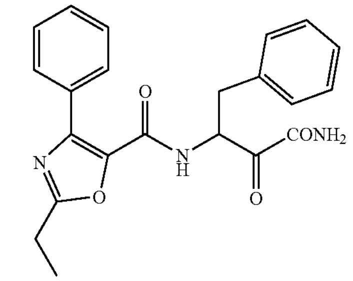
227
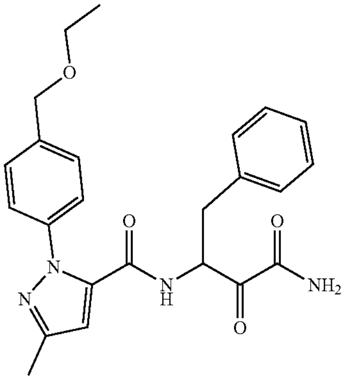
228
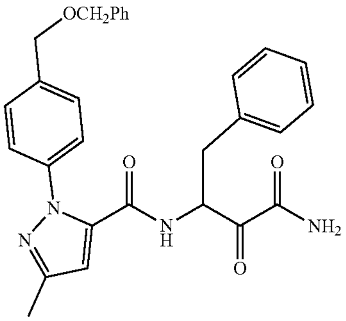
229
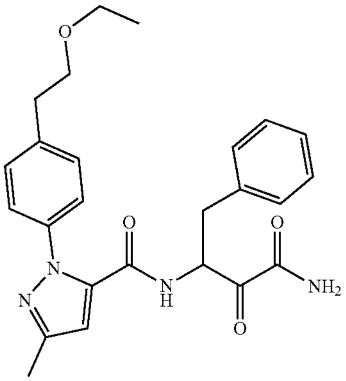
-continued
230
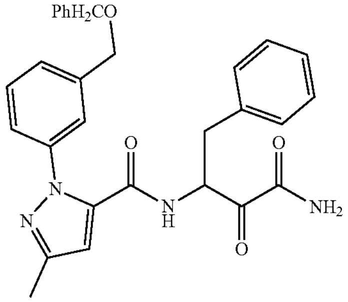
231
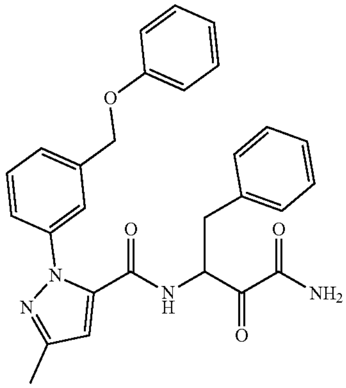
232
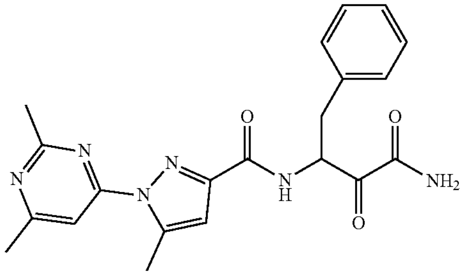
233
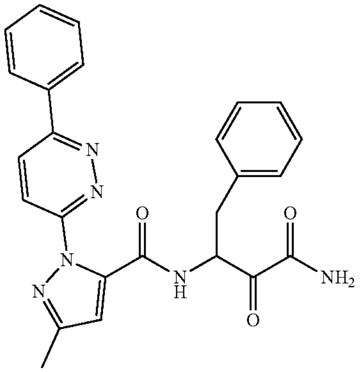
234
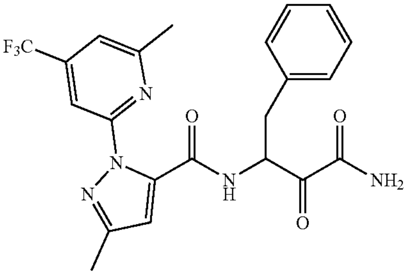

235
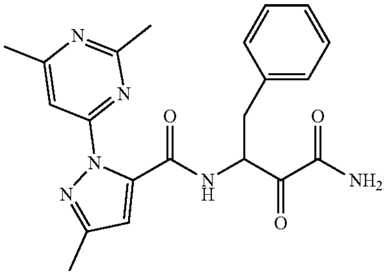
238
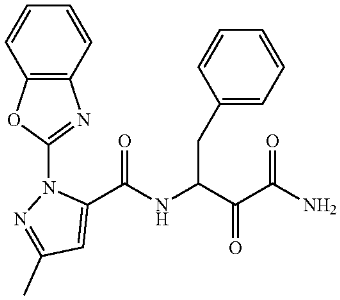
239
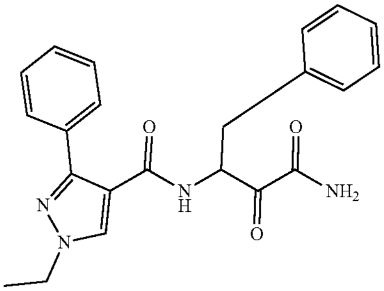
240
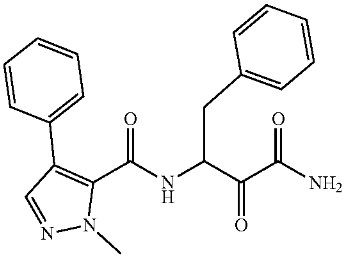
241
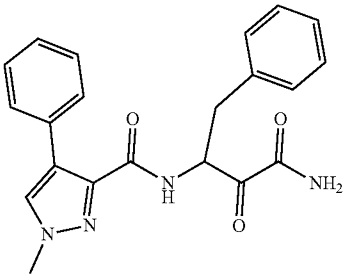
242
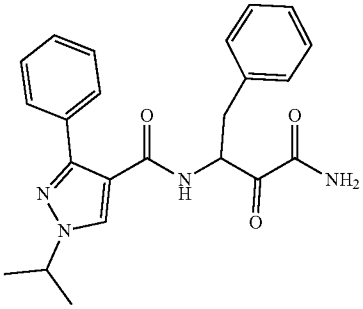
243
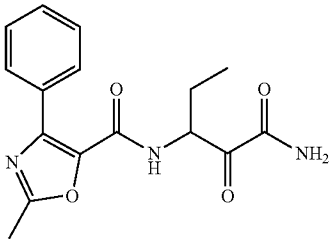
244
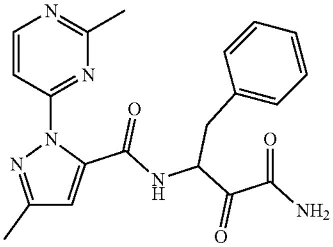
245
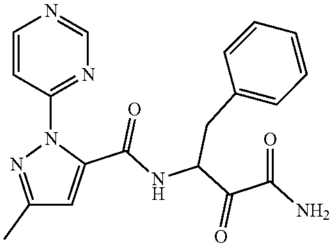
246
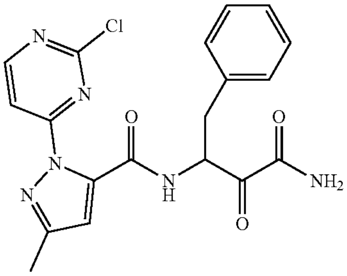

-continued
247
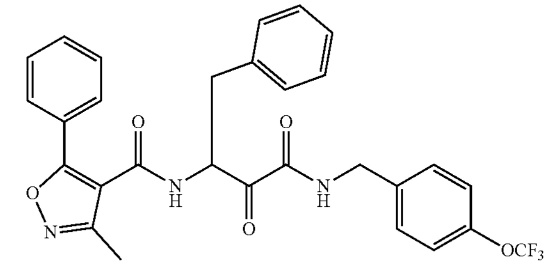
248
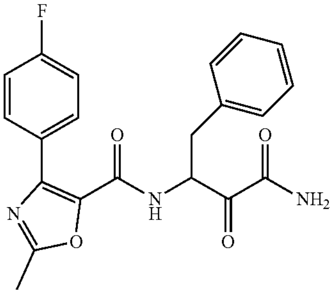
249
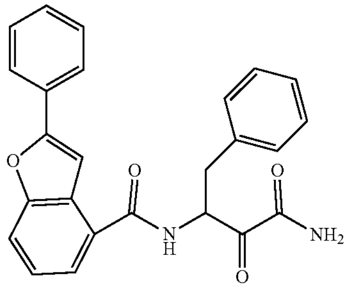
250
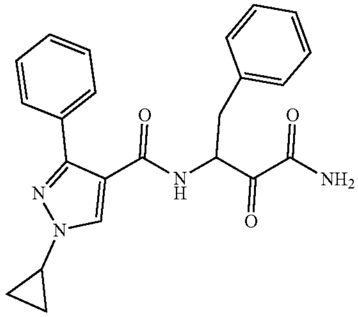
251
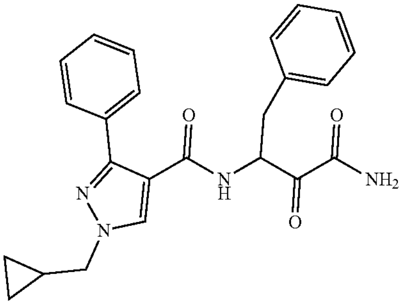
-continued
252
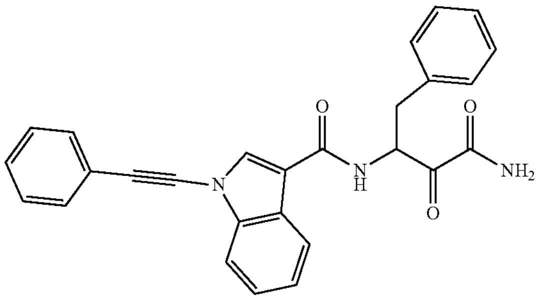
253
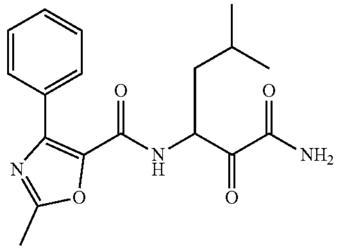
254
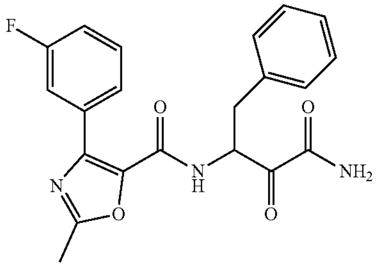
255
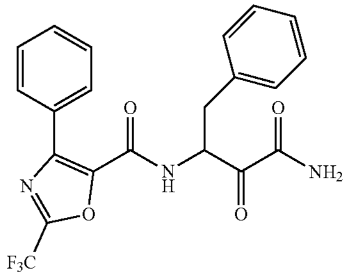
256
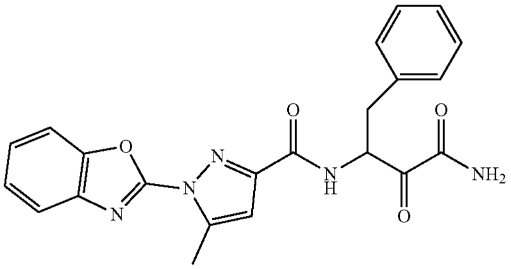

-continued
257
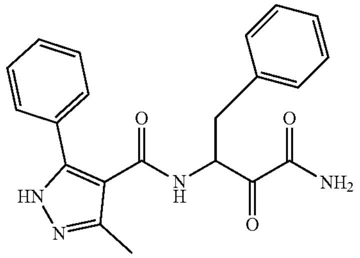
258
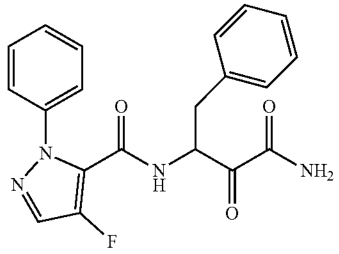
259
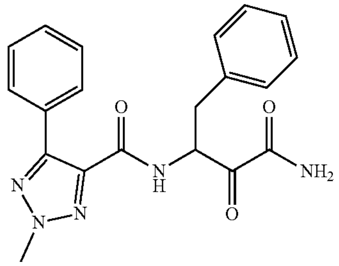
260
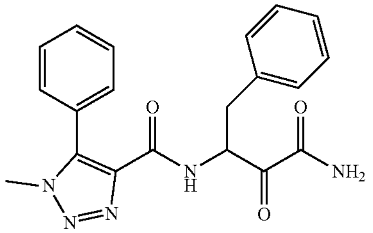
261
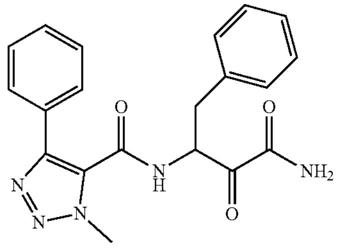
262
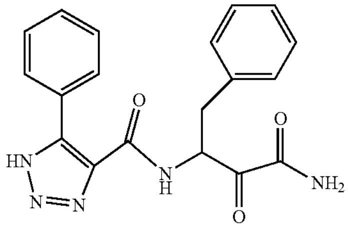
-continued
263
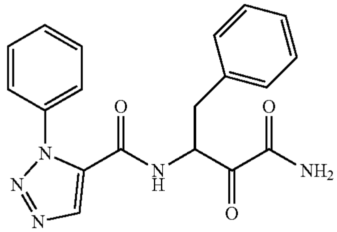
264
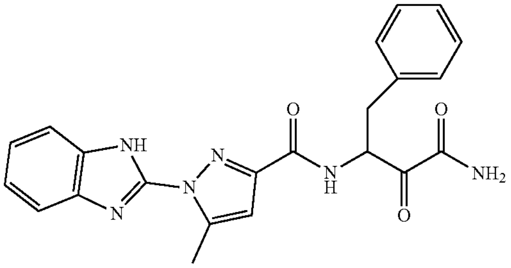
265
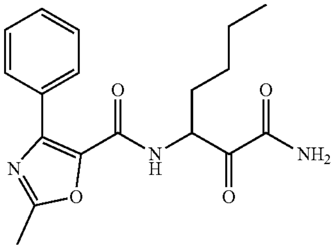
266
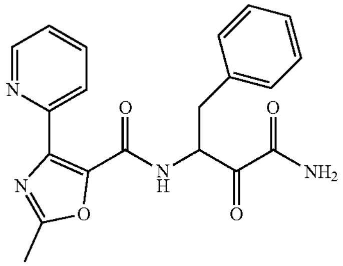
267
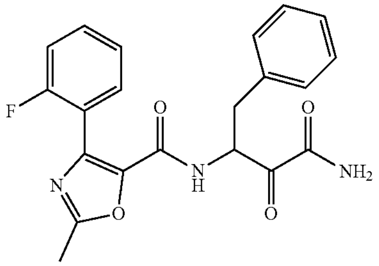
268
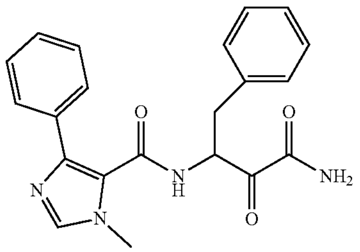

-continued
269
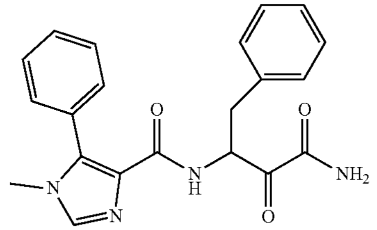
270
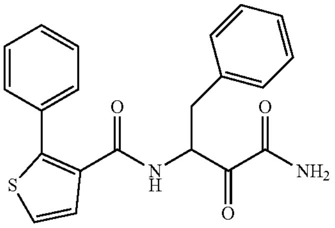
271
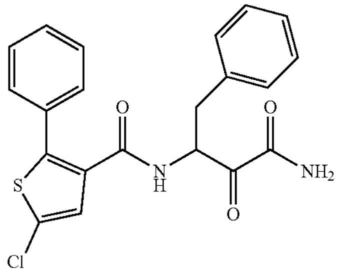
272
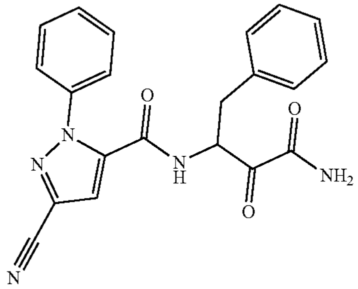
273
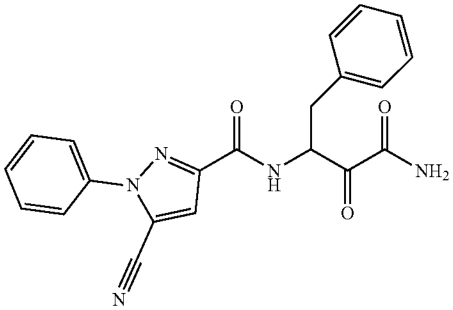
274
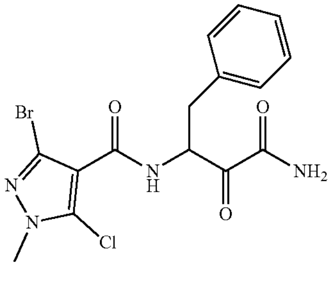
-continued
276
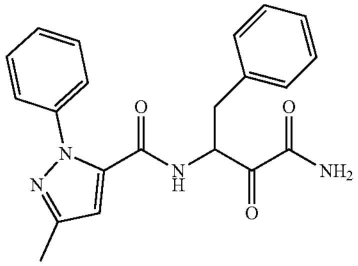
277
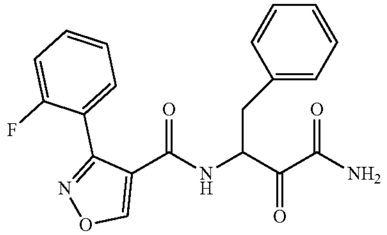
278
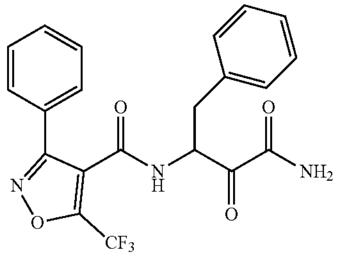
279
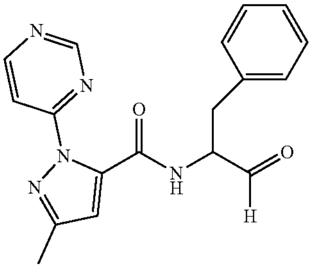
280
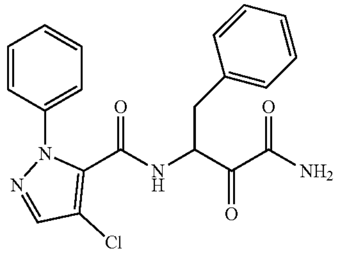
281
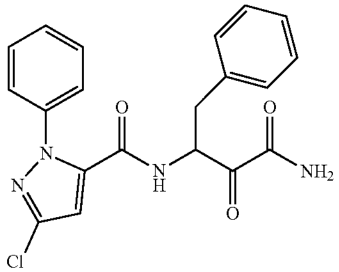

-continued
282
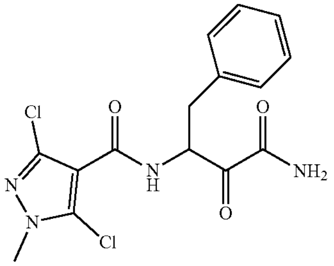
283
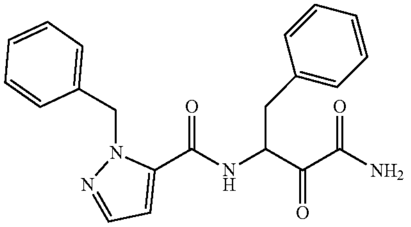
284
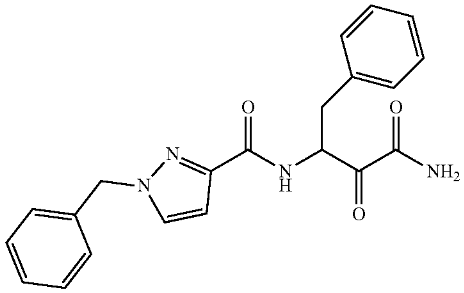
285
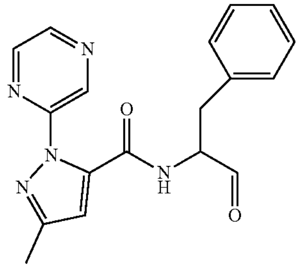
286
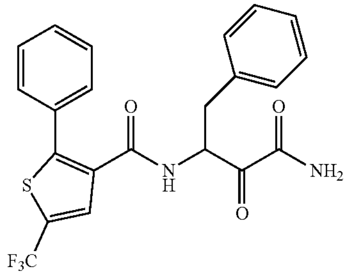
287
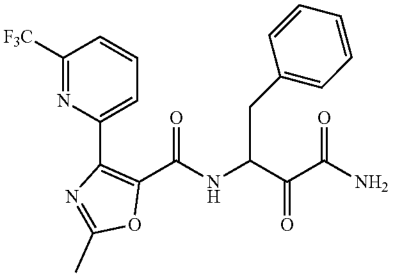
-continued
288
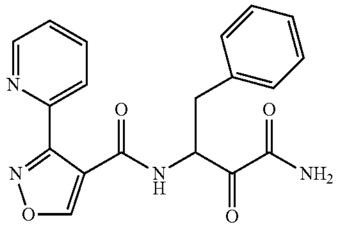
289
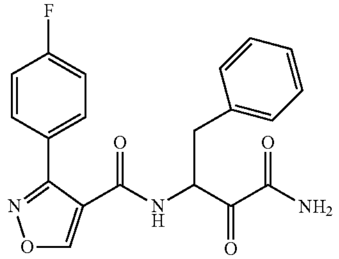
290
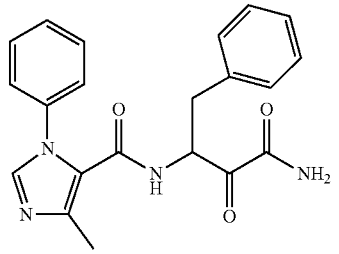
291
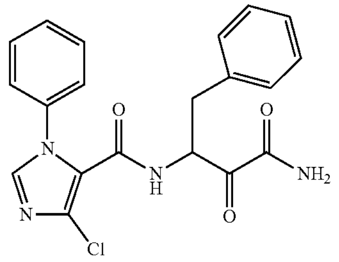
292
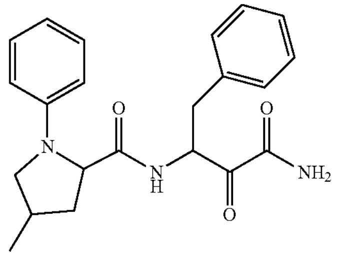
293
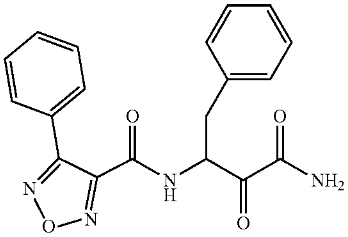

294
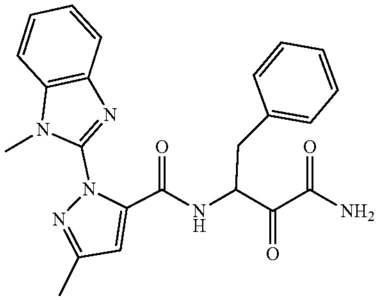
295
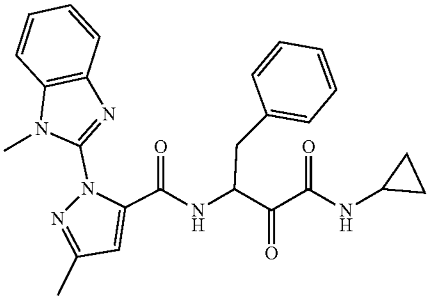
296
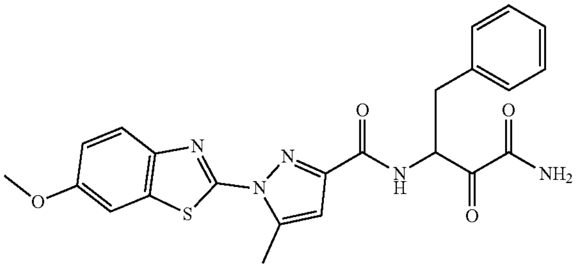
297
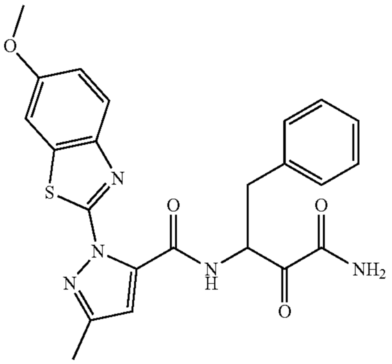
298
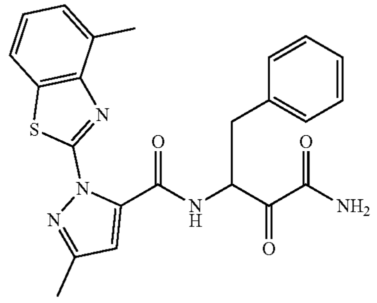
299
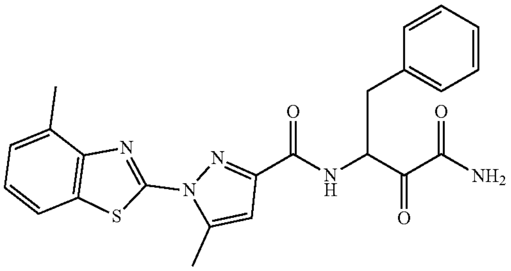
303
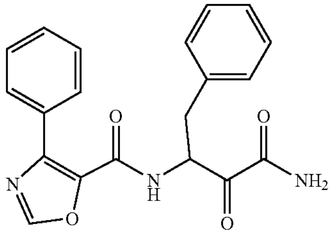
304
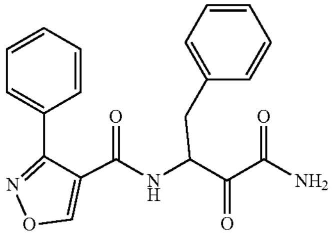
305
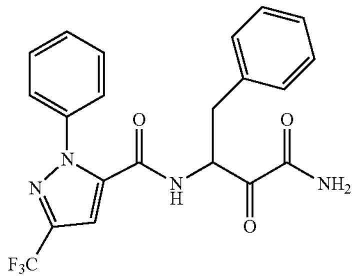
306
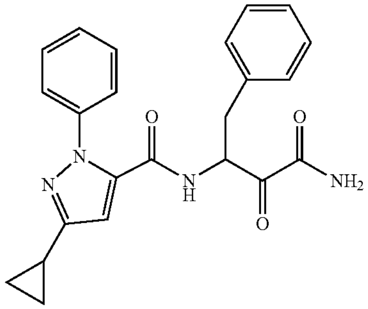
307
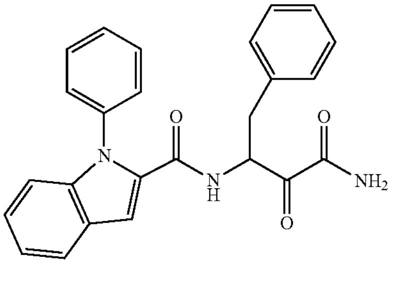

-continued
308
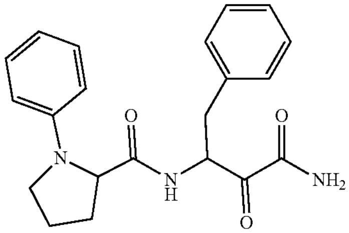
309
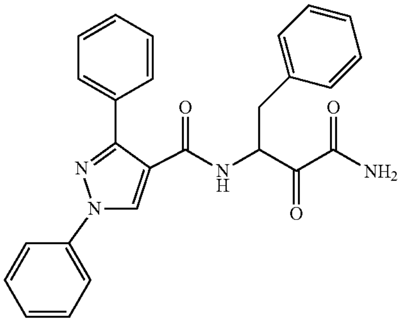
310
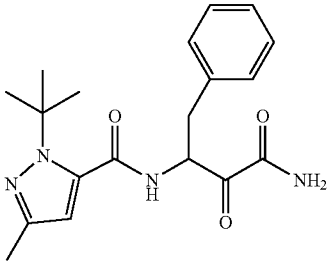
311
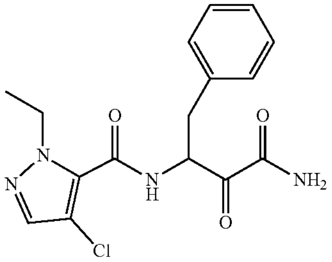
312
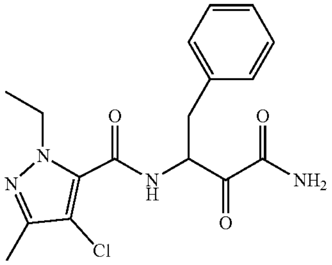
313
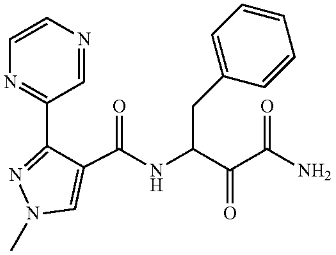
-continued
314
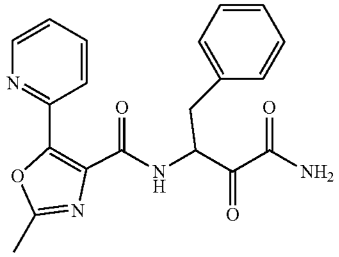
315
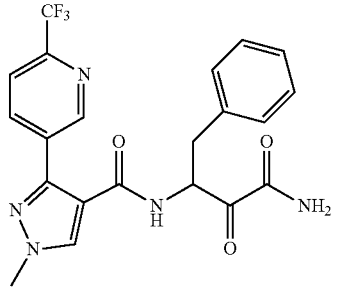
316
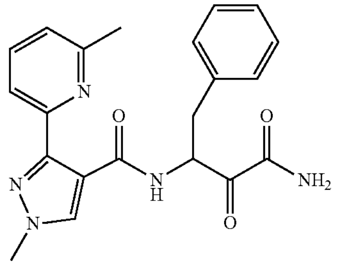
317
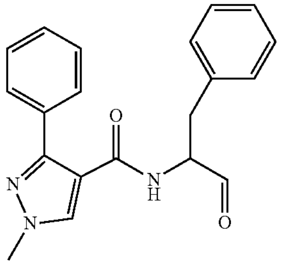
318
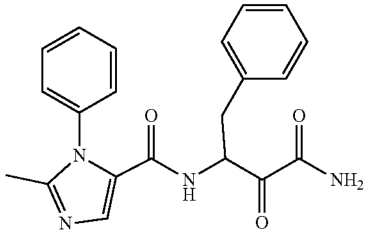
319
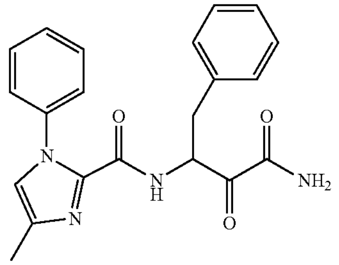

-continued
320
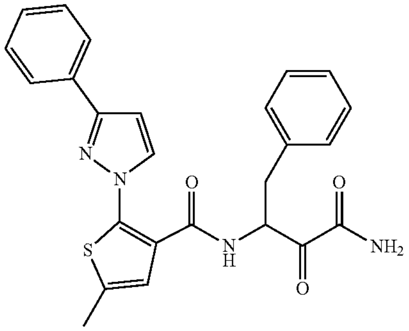
321
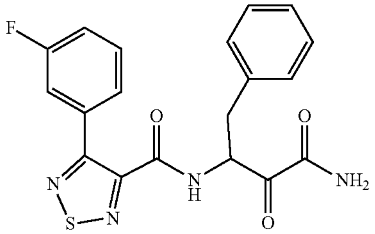
322
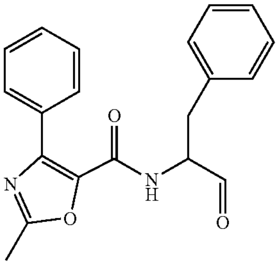
323
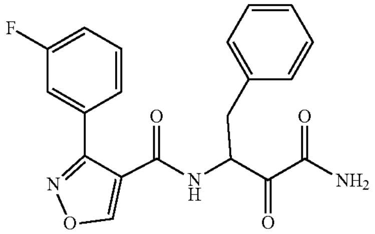
324
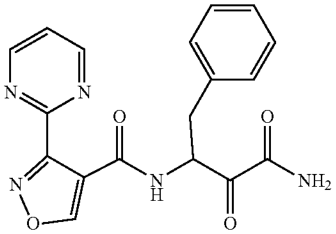
325
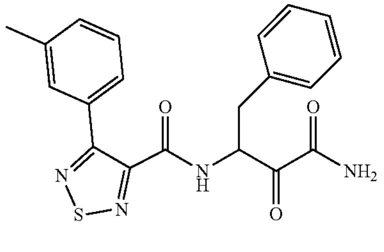
-continued
326
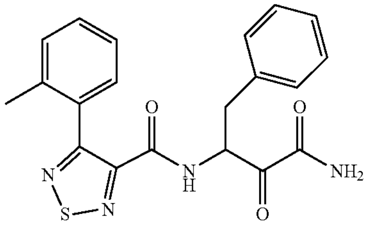
327
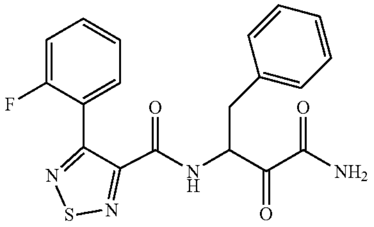
328
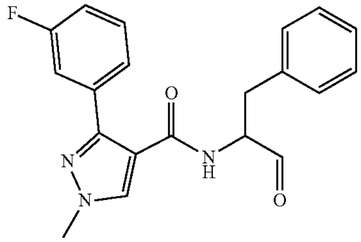
329
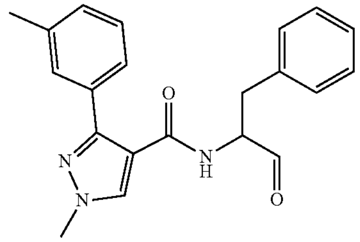
330
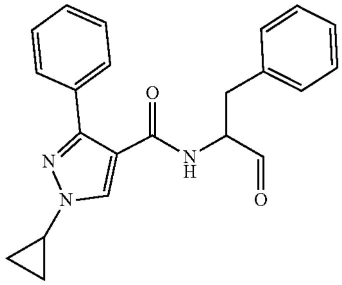
331
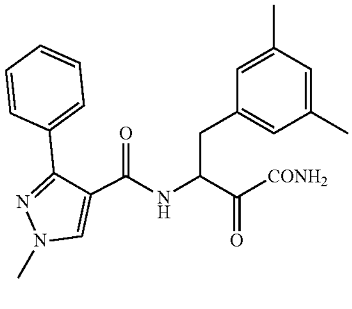

-continued
332
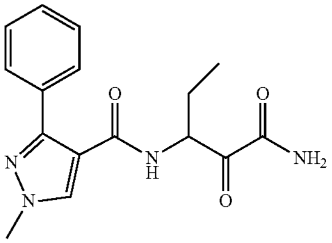
333
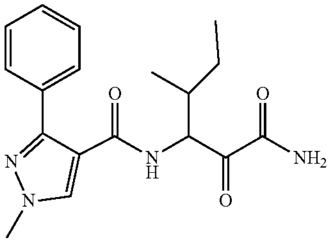
334
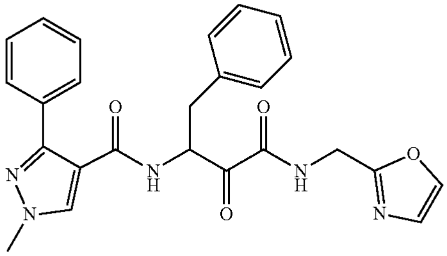
335
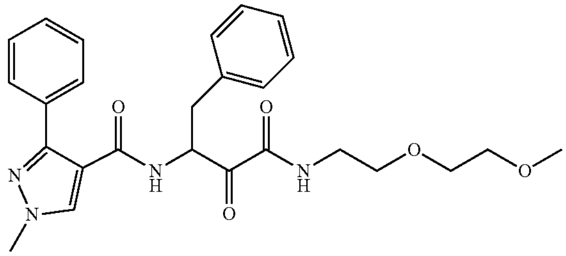
336
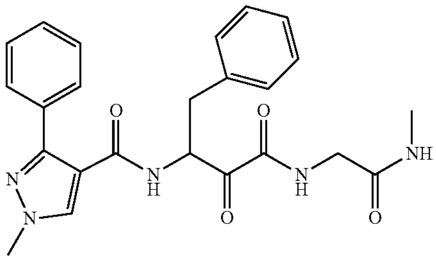
337
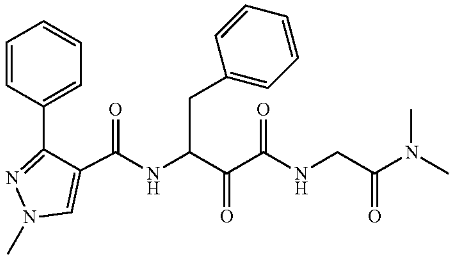
-continued
338
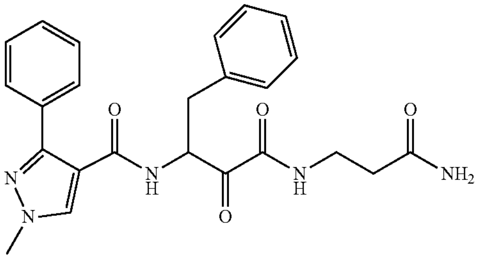
339
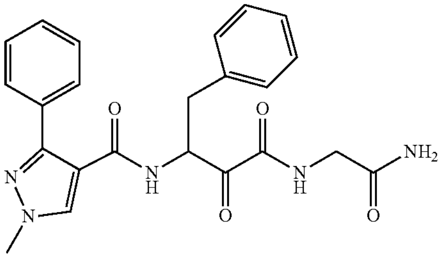
340
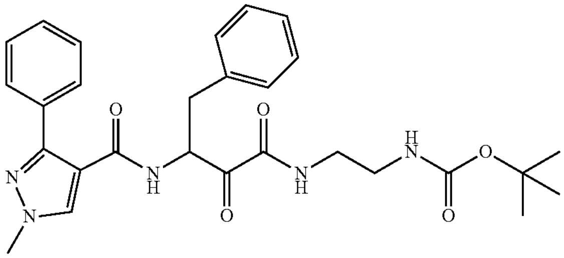
341
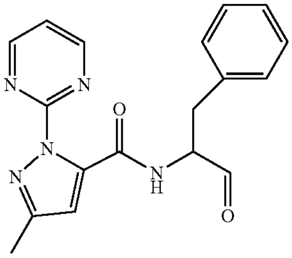
342
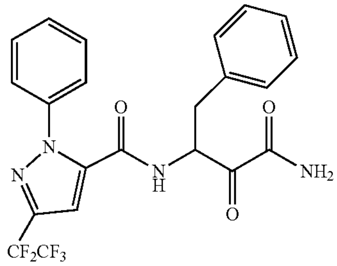

-continued
343
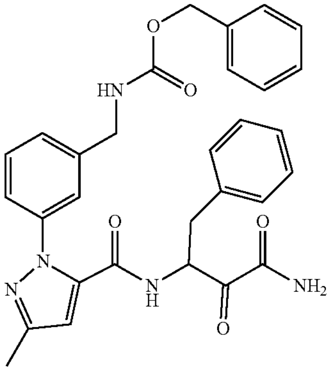
344
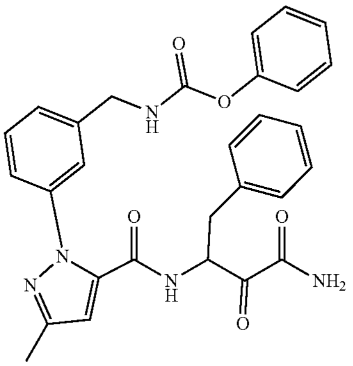
345
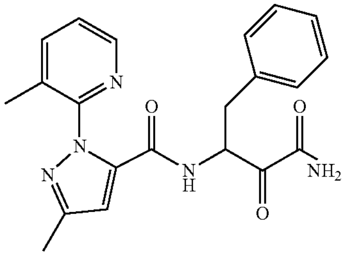
346
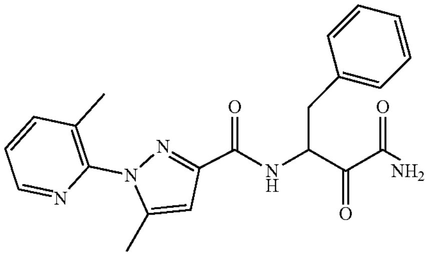
347
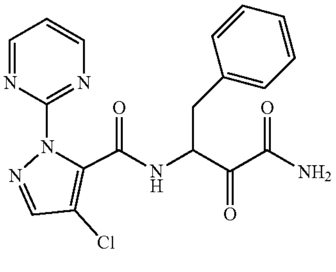
-continued
348
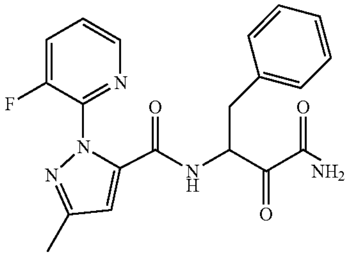
349
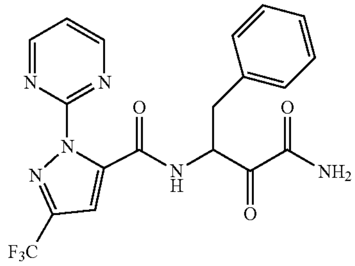
350
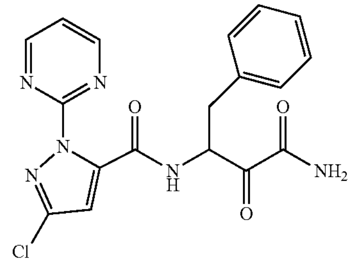
351
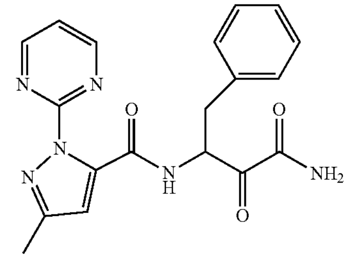
352
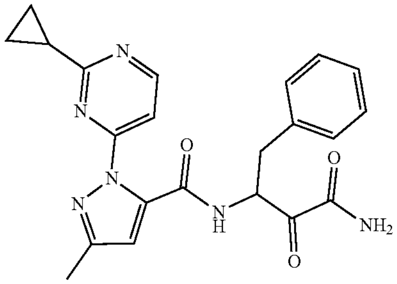
353
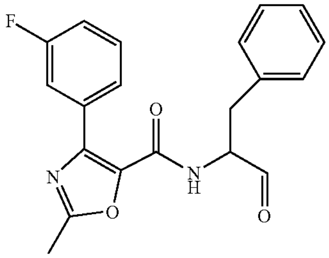

-continued
354
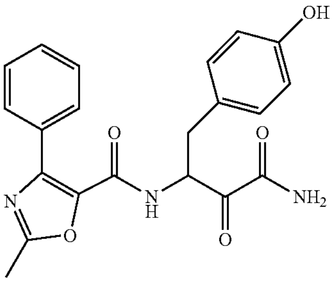
355
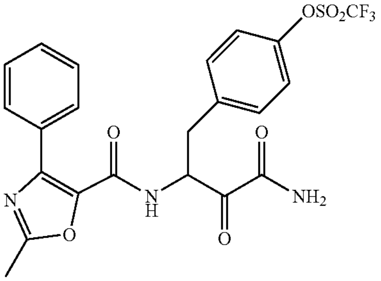
356
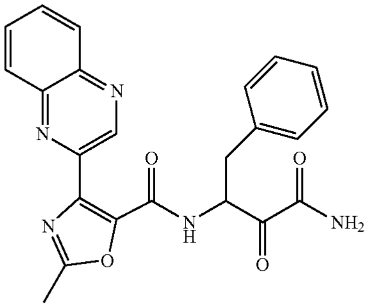
357
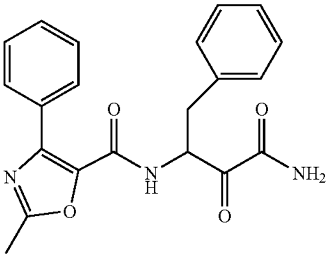
358
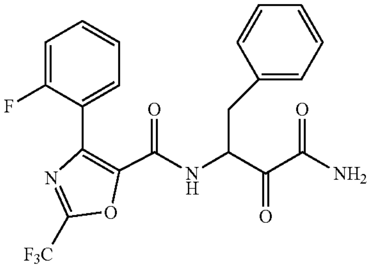
-continued
359
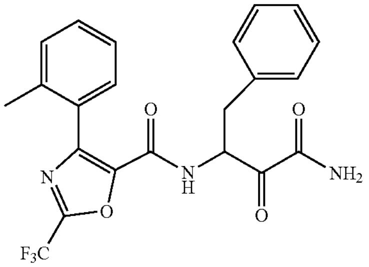
360
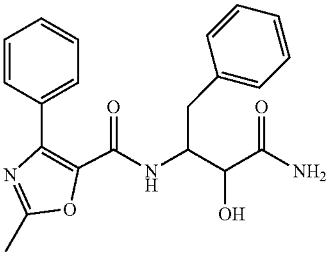
361
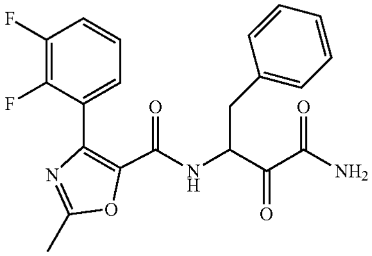
362
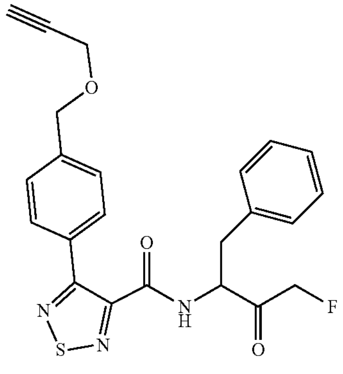
363
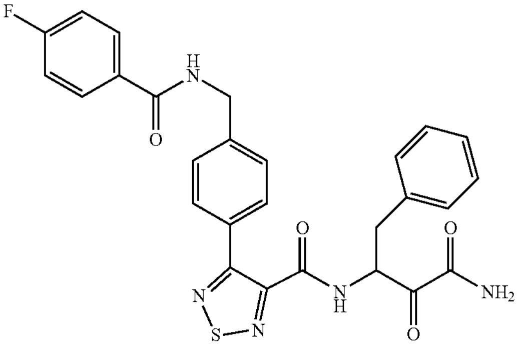

-continued
364
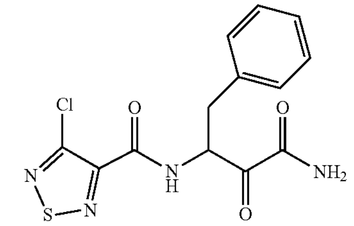
365
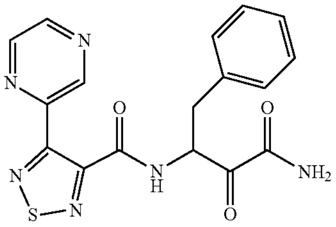
366
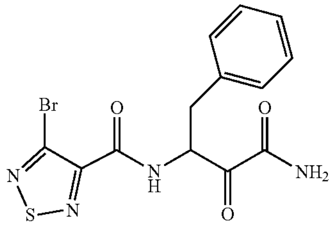
367
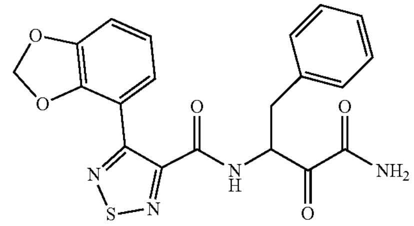
368
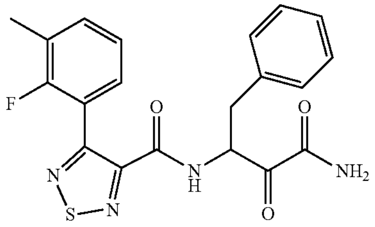
369
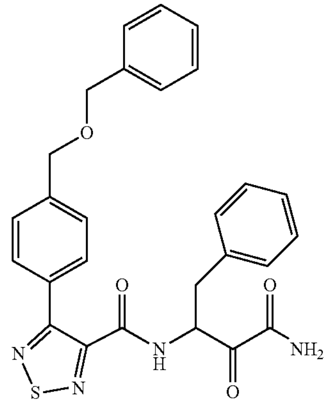
-continued
370
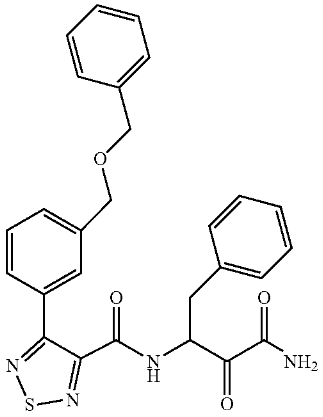
371
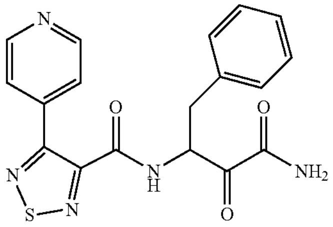
372
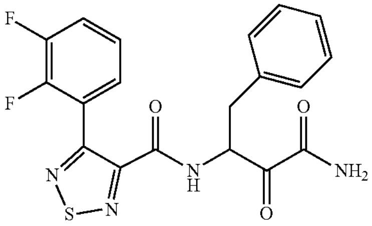
373
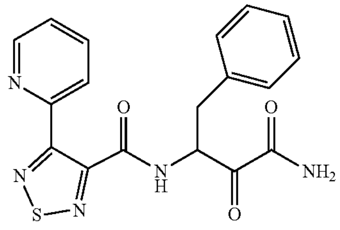
374
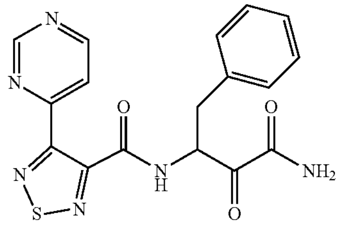
375
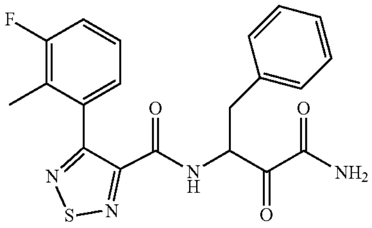

-continued
376
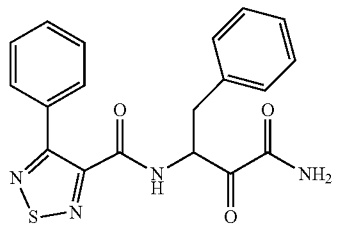
377
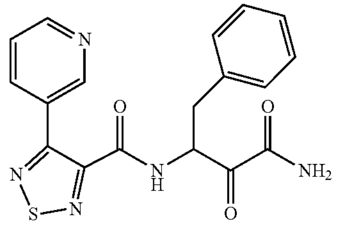
378
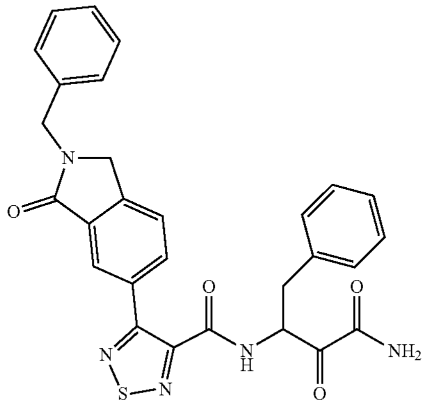
379
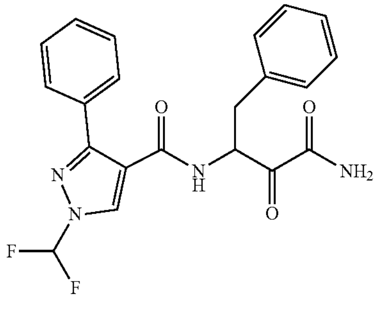
380
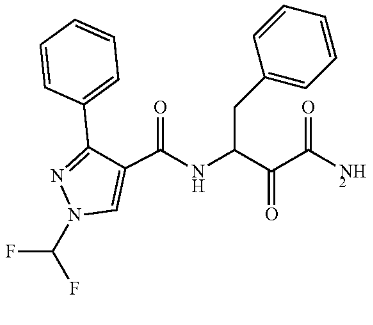
-continued
381
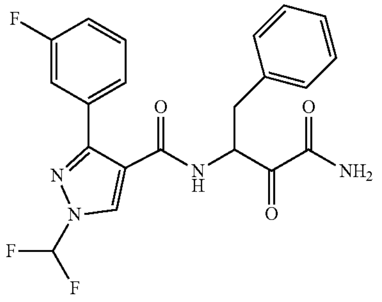
382
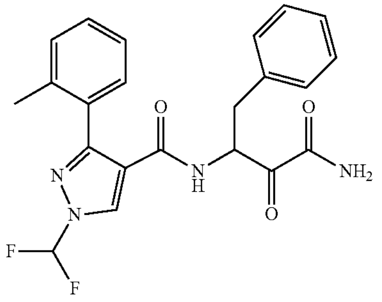
383
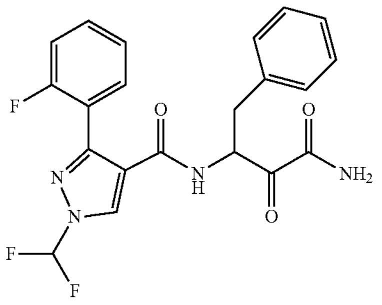
384
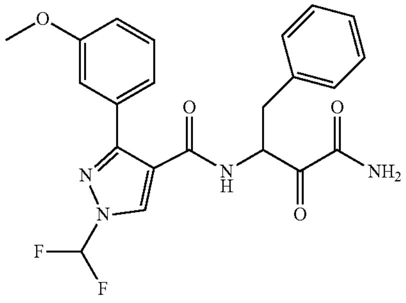
385
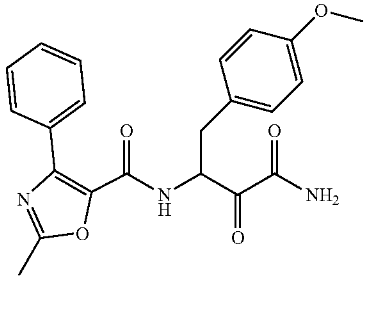

-continued
386
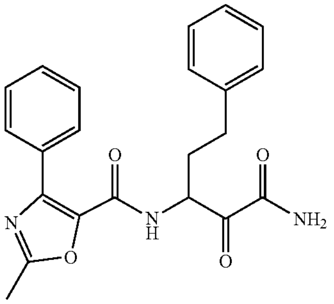
387
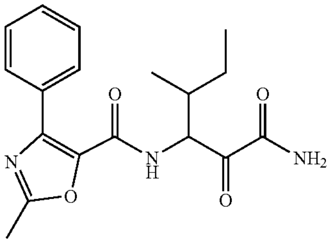
388
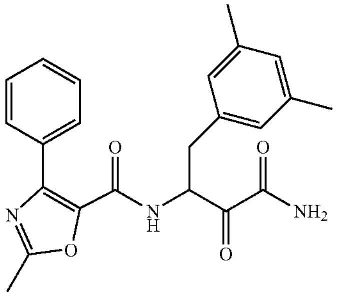
389
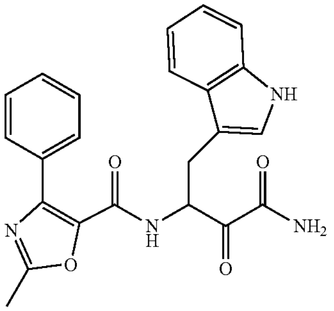
390
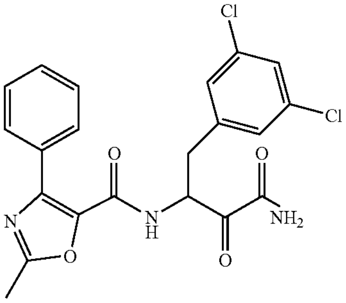
-continued
391
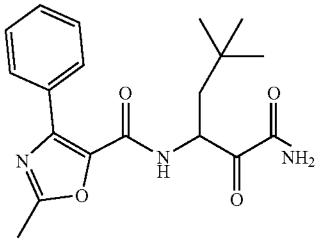
392
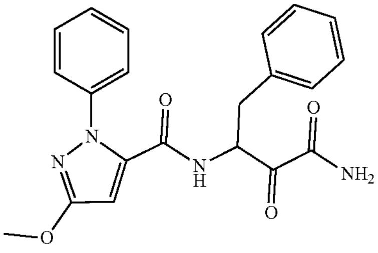
393
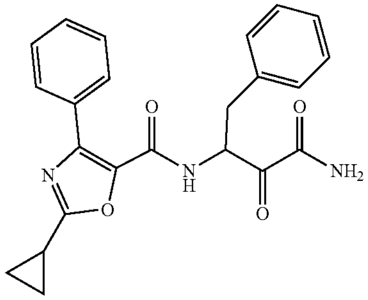
394
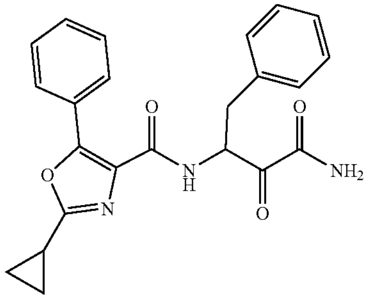
395
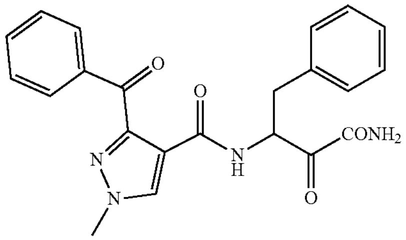

-continued
396
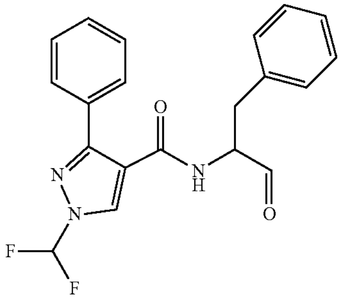
397
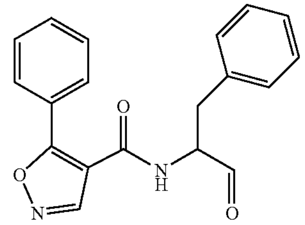
398
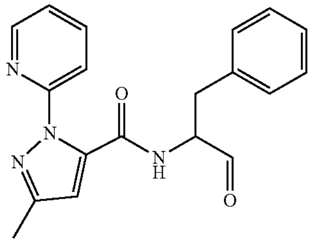
399
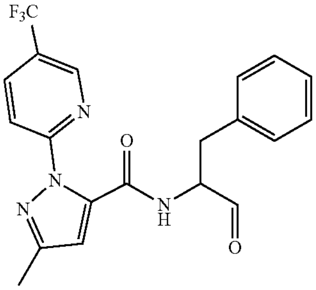
400
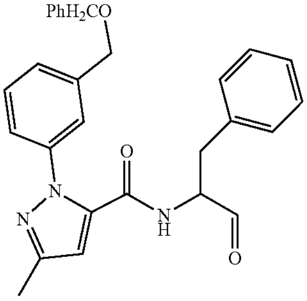
401
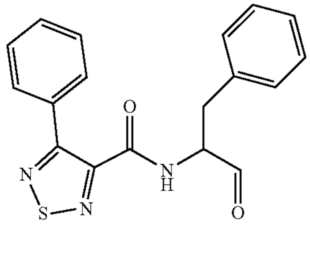
-continued
402
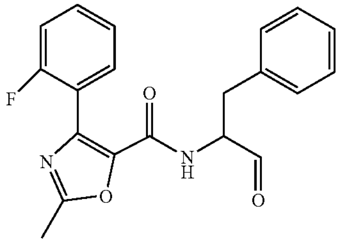
403
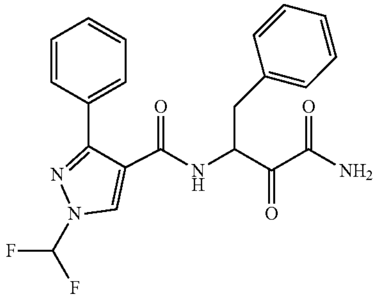
404
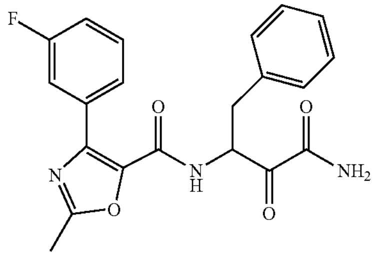
405
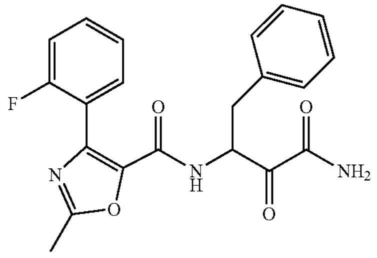
406
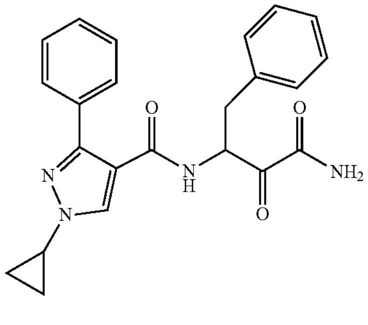
407
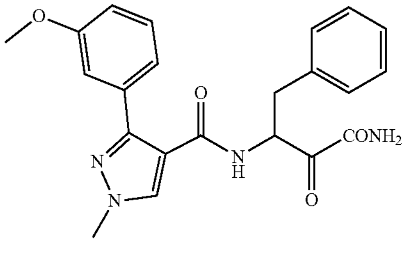

408
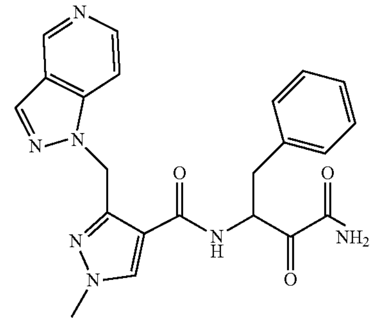
409
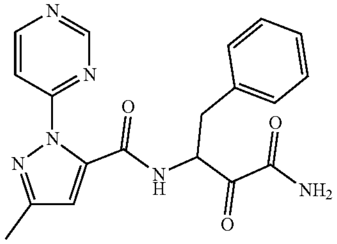
410
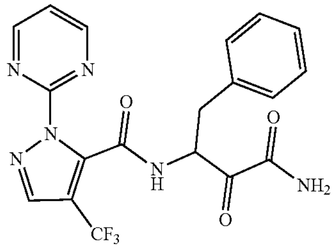
411
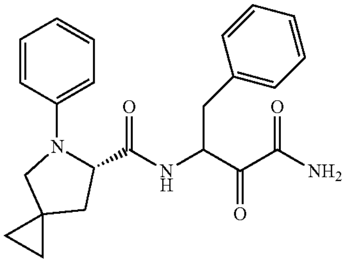
413
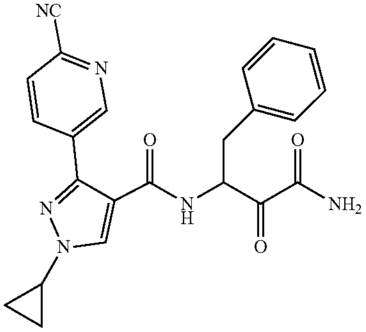
414
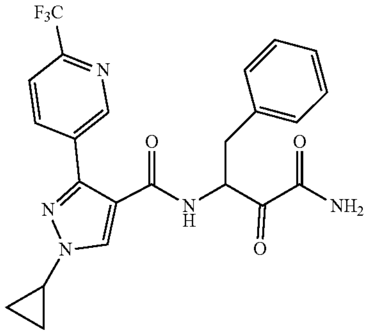
415
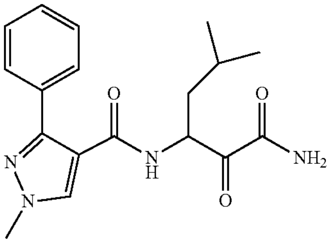
416
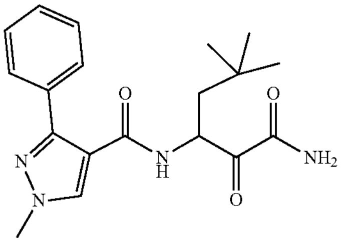
417
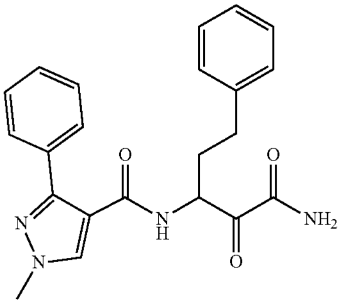
418
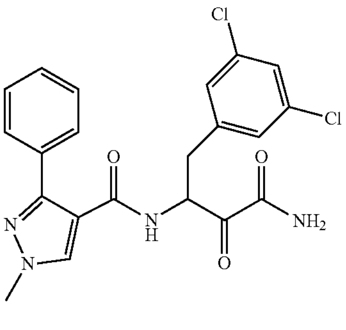

-continued
419
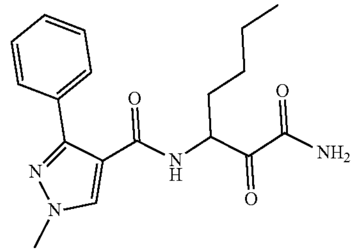
420
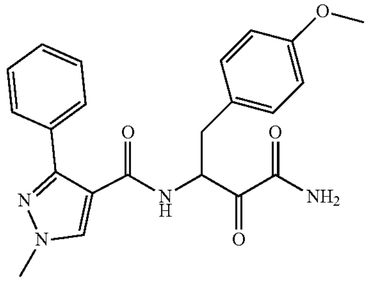
421
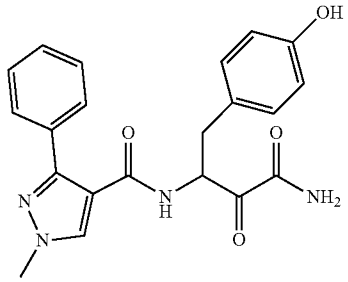
422
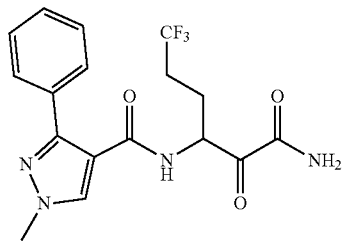
423
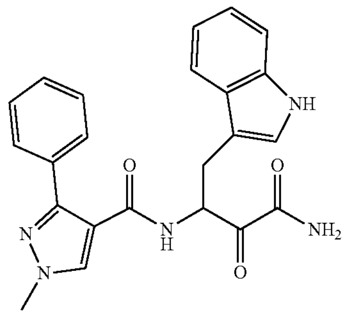
-continued
424
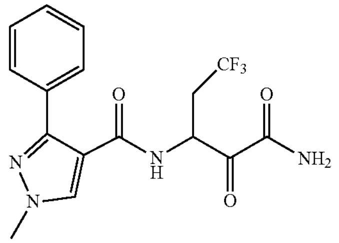
428
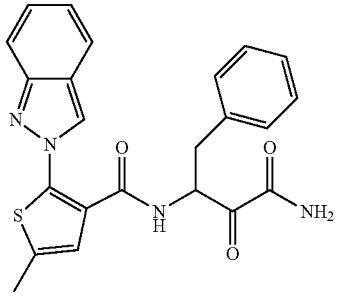
429
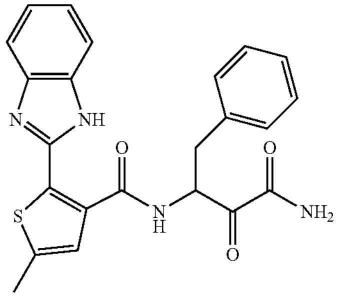
430
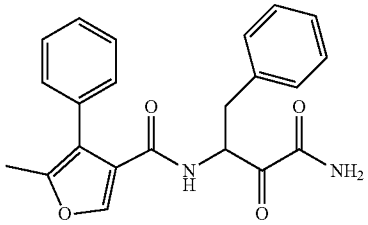
431
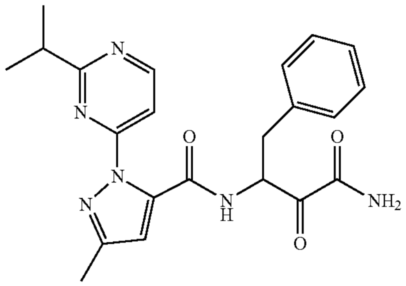

-continued
432
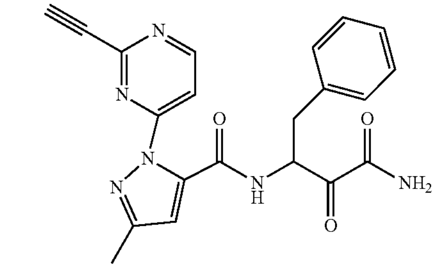
433
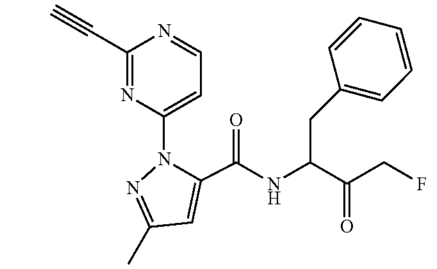
434
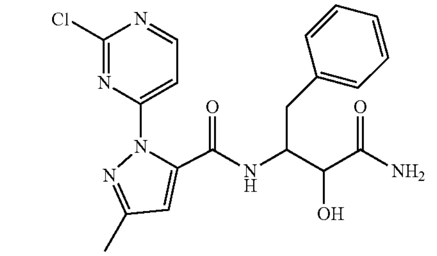
435
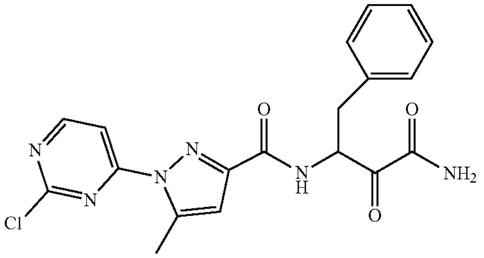
436
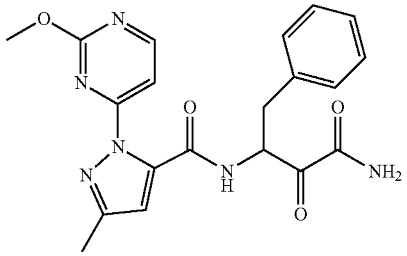
437
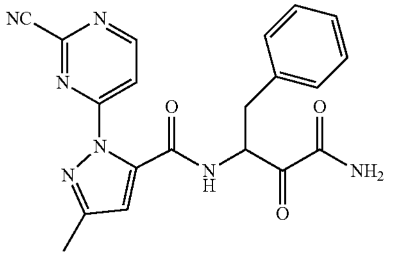
-continued
438
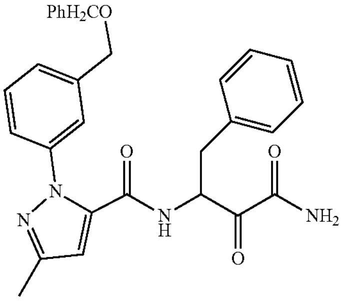
439
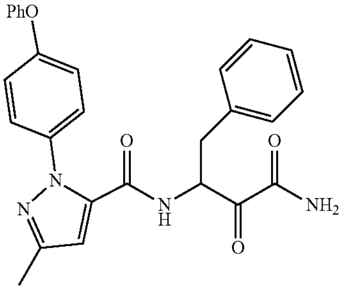
440
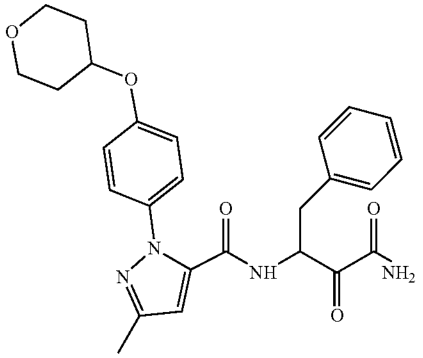
441
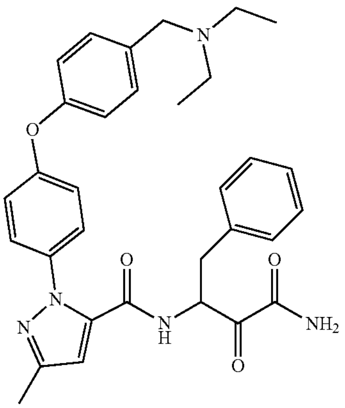

-continued
442
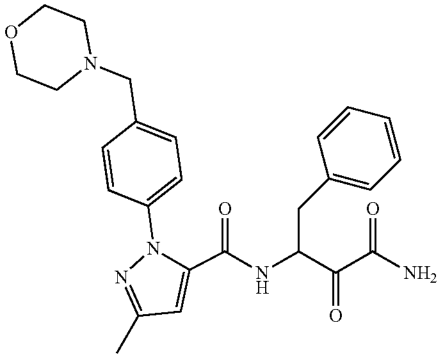
443
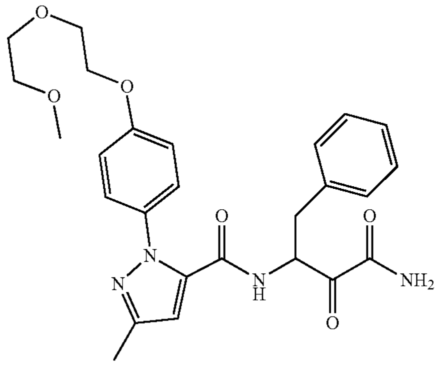
444
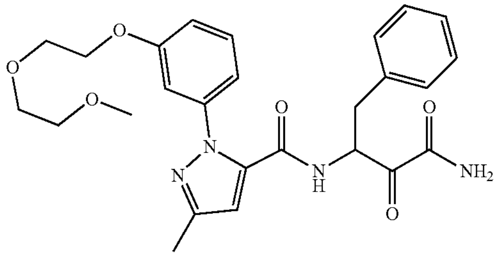
445
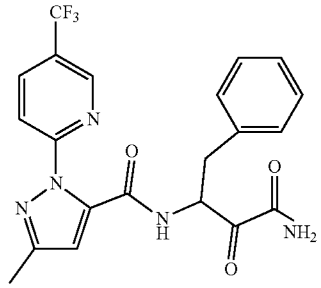
446
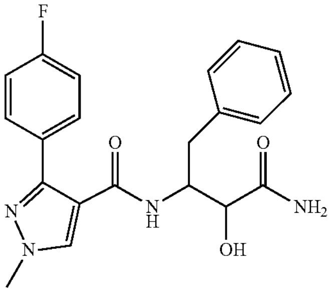
-continued
447
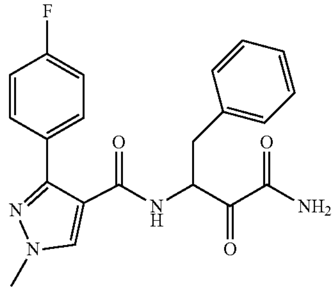
448
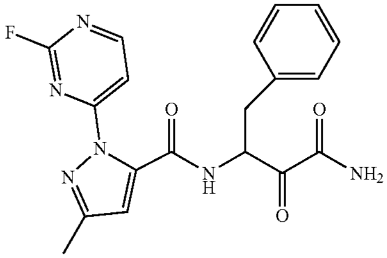
454
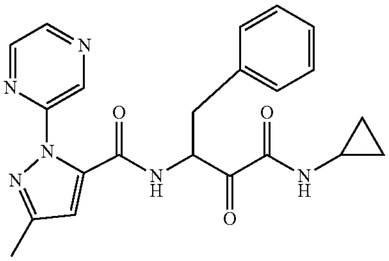
455
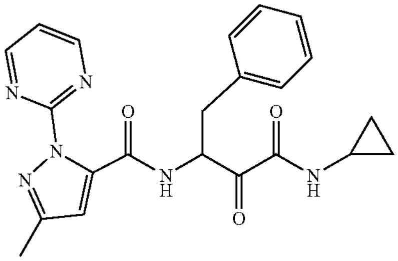
456
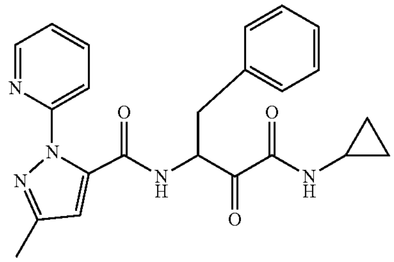
457
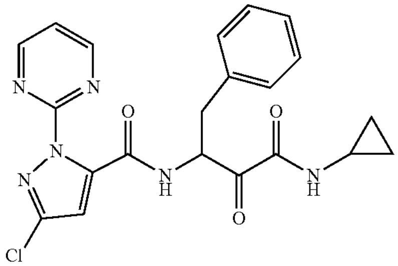

-continued
458
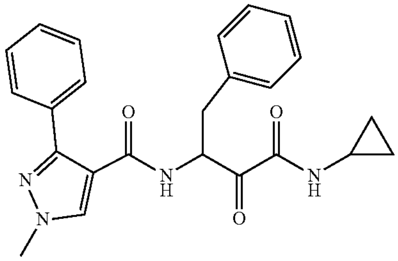
459
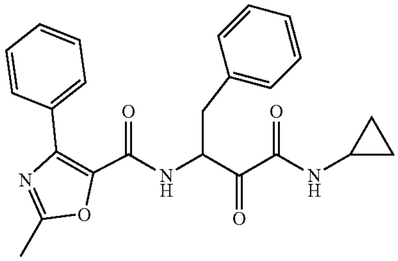
460
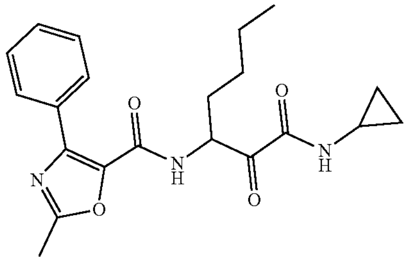
461
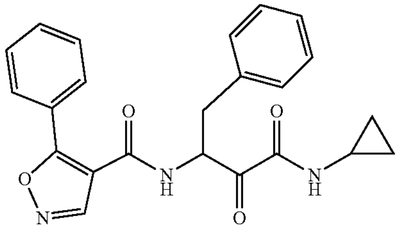
462
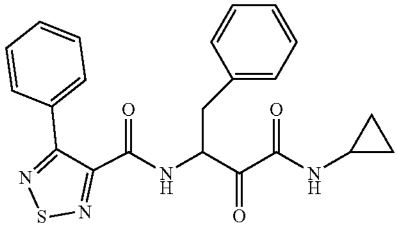
463
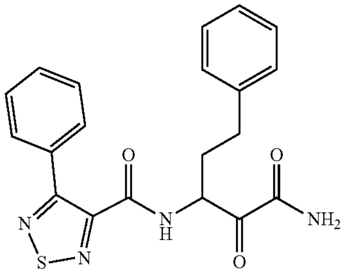
-continued
464
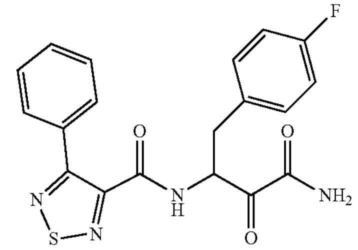
465
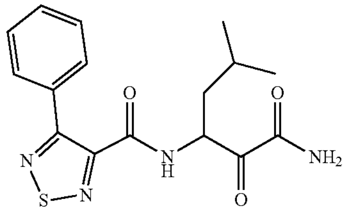
466
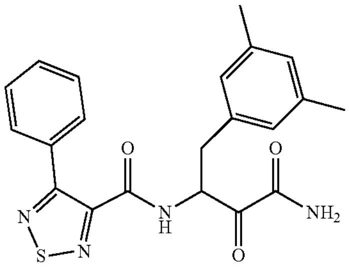
467
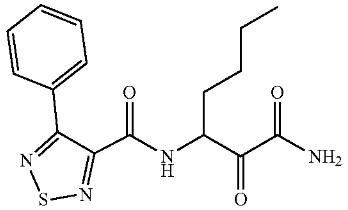
468
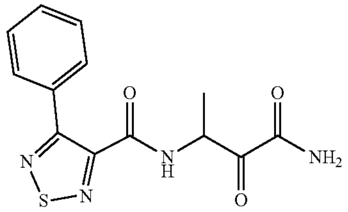
469
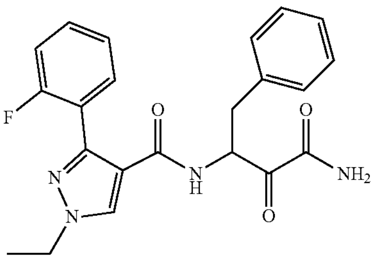

-continued
470
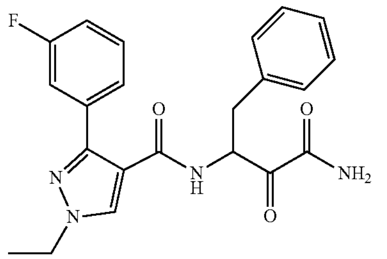
471
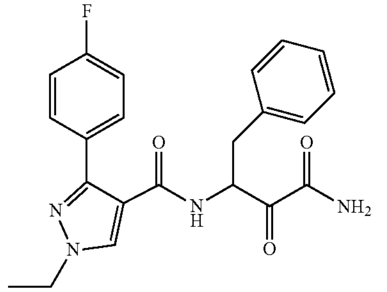
472
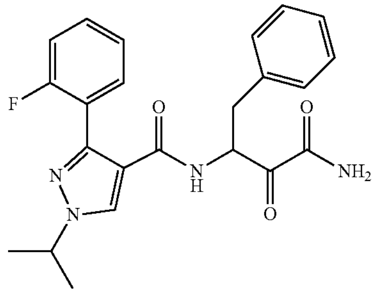
473
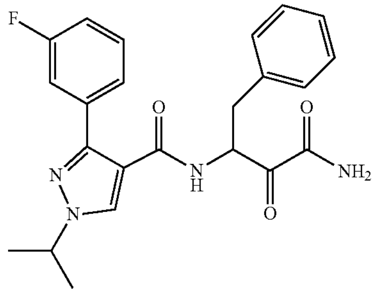
474
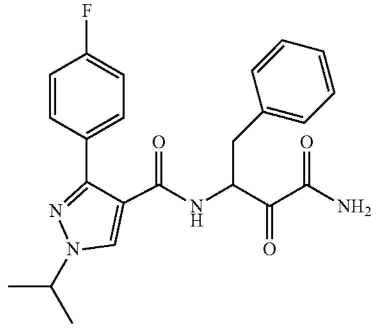
-continued
475
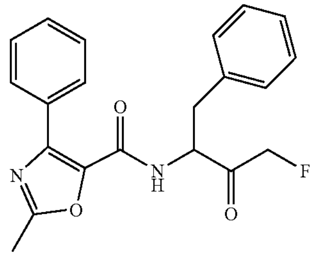
476
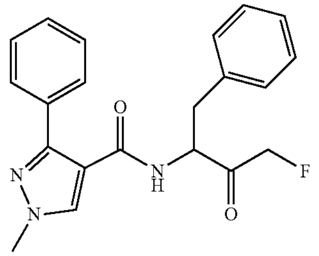
477
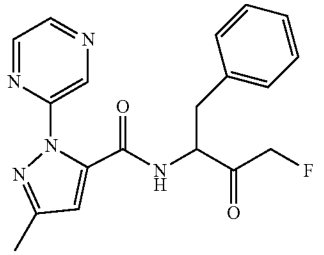
478
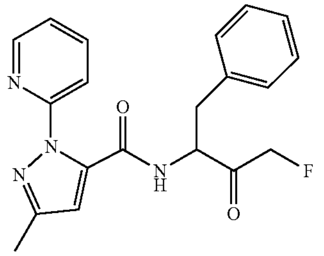
479
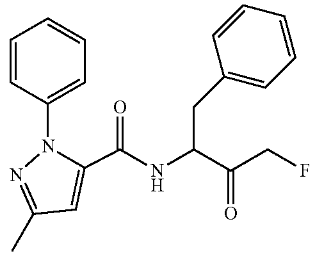
480
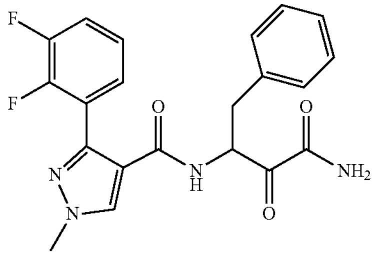

-continued
481
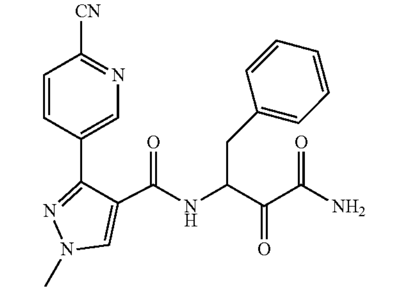
482
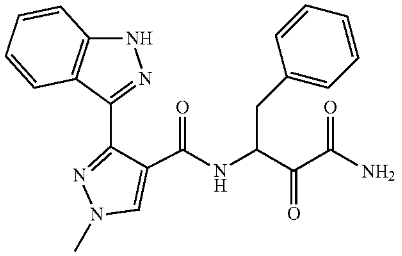
483
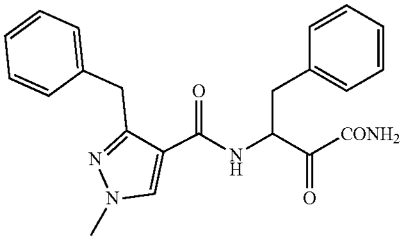
484
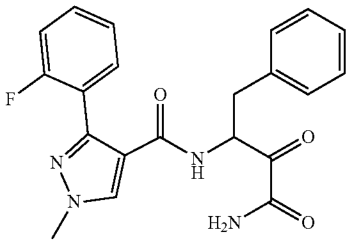
485
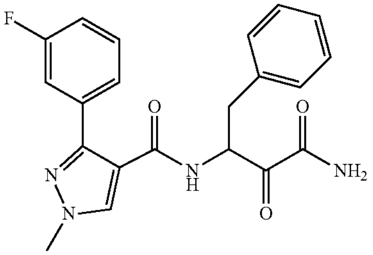
486
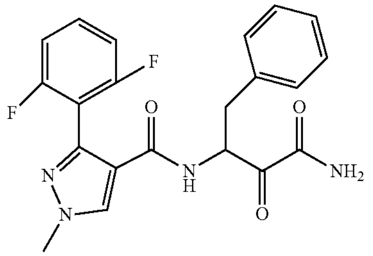
-continued
487
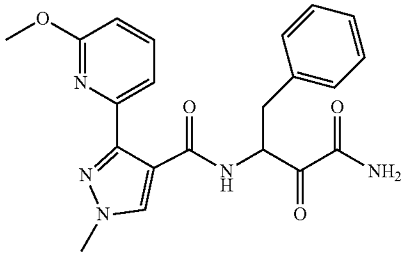
488
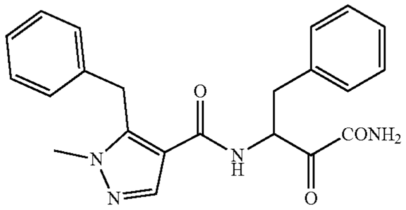
489
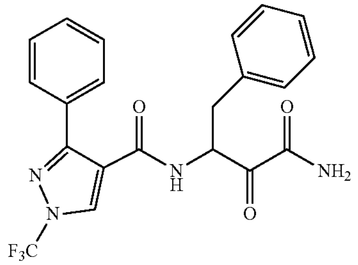
490
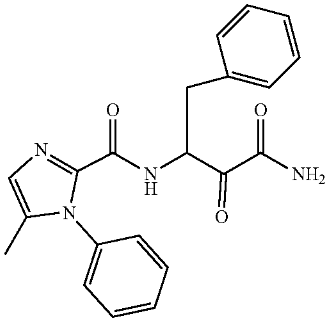
491
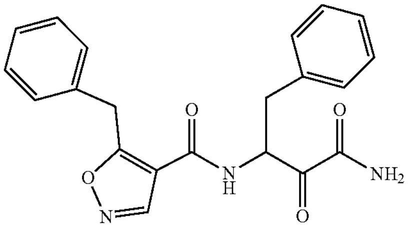
492
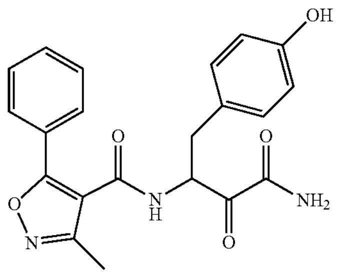

493
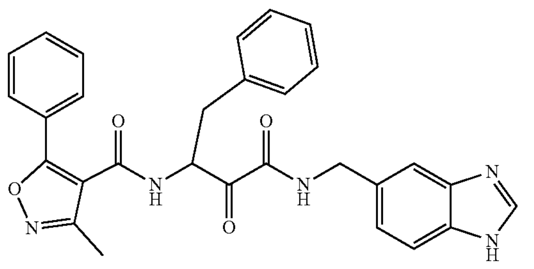
494
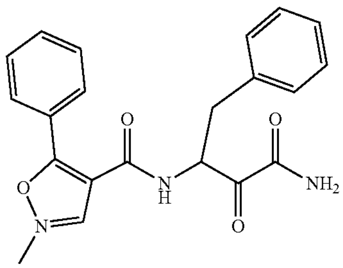
495
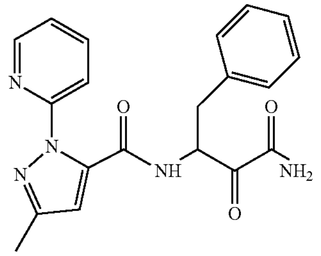
496
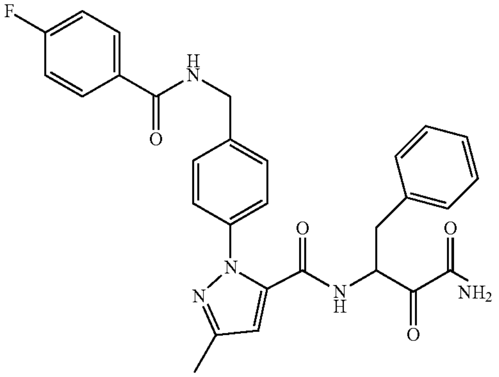
497
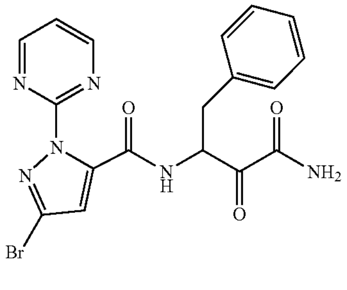
498
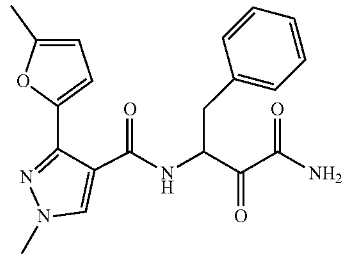
499
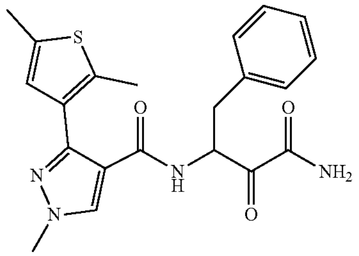
500
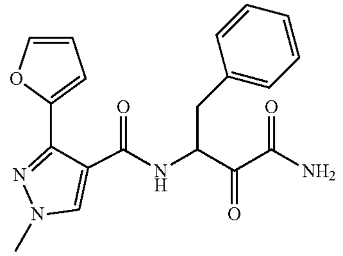
501
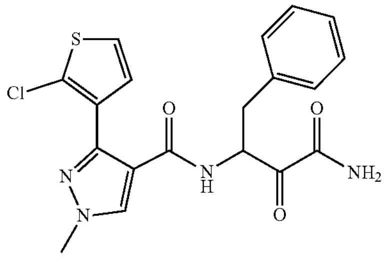
502
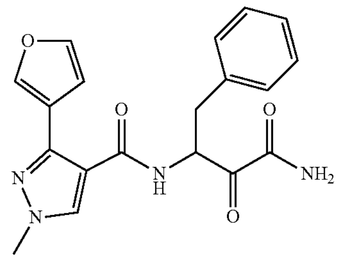
503
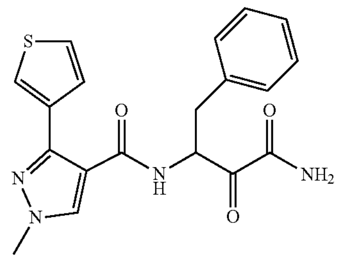

-continued
504
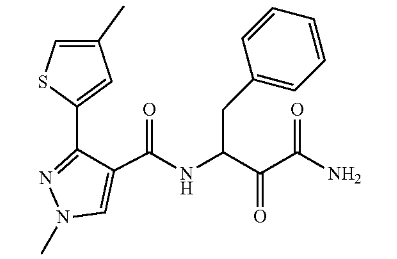
505
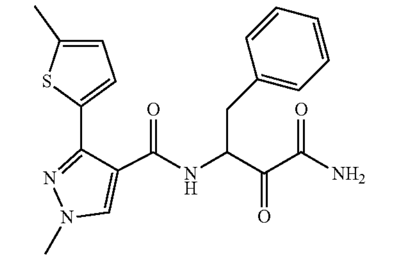
506
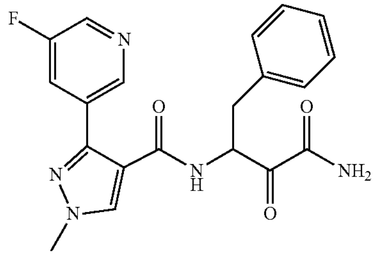
507
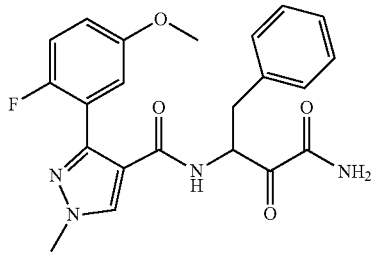
508
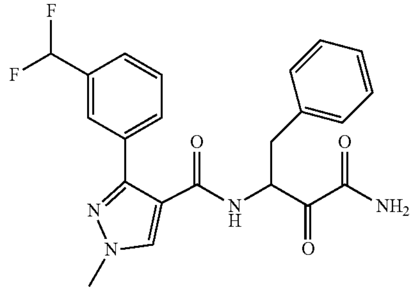
509
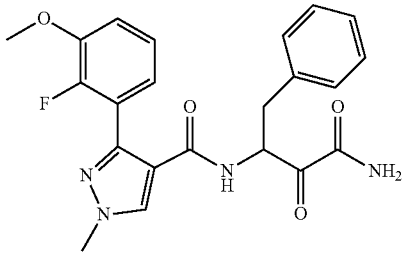
-continued
510
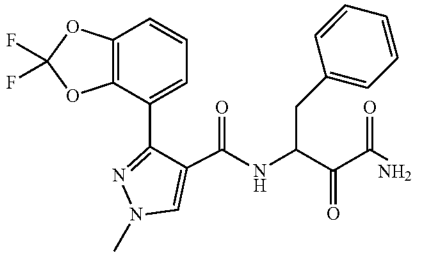
511
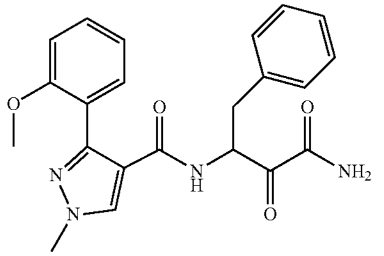
512
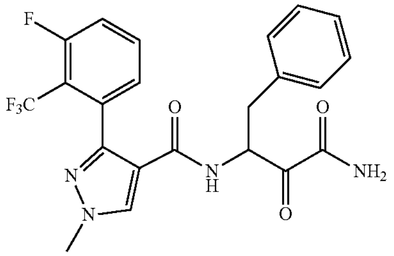
513
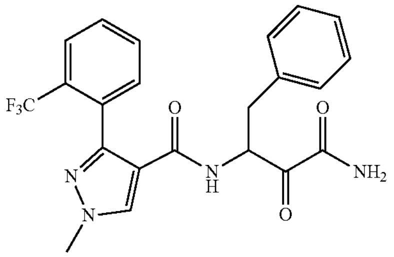
514
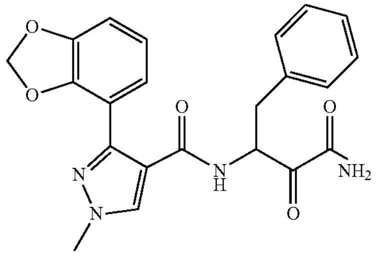
515
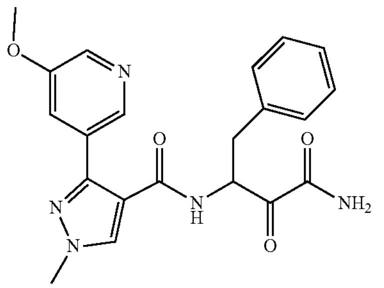

-continued
516
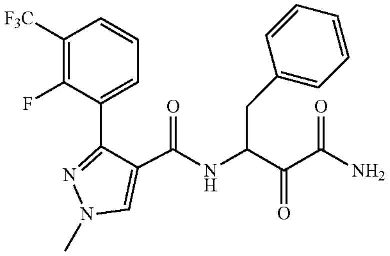
517
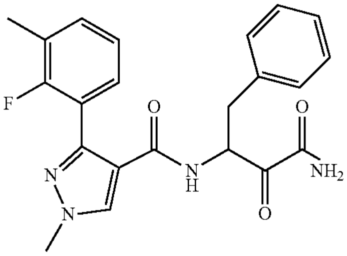
518
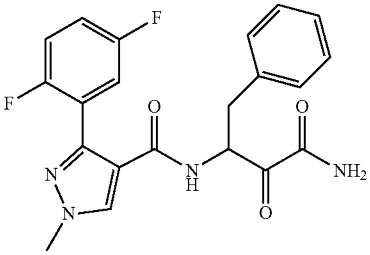
519
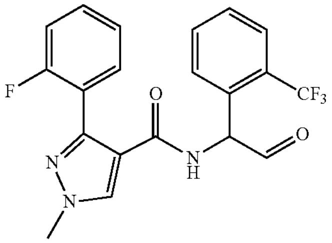
520
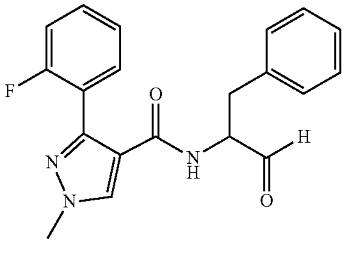
-continued
521
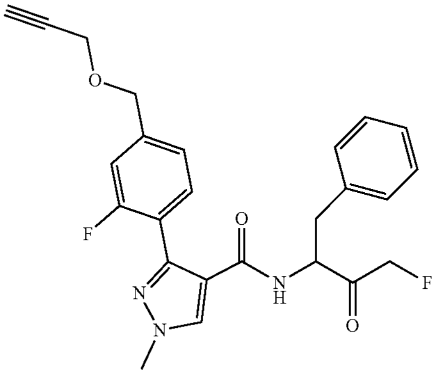
522
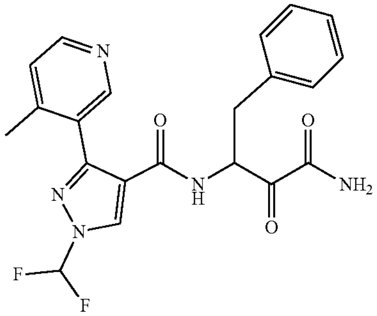
523
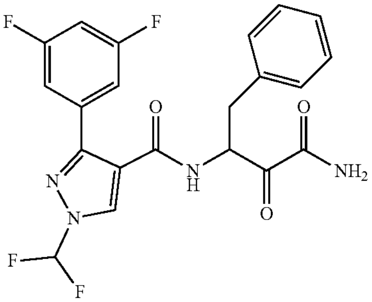
524
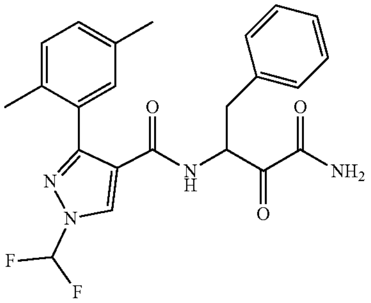
525
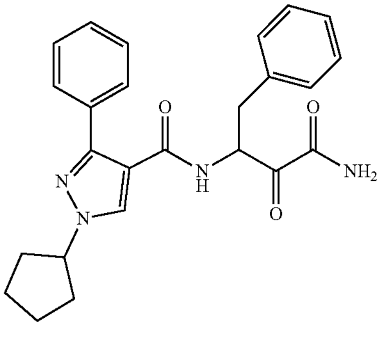

-continued
526
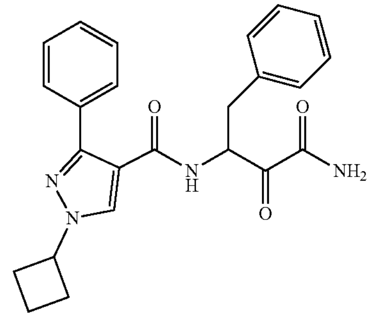
527
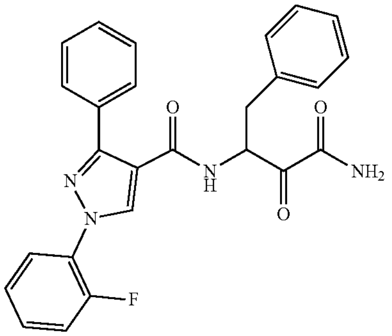
528
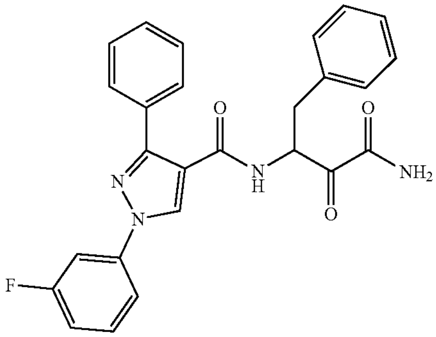
529
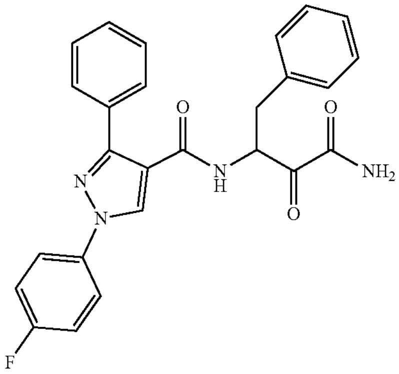
530
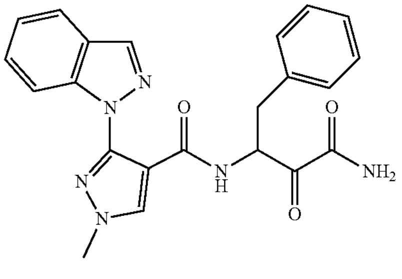
-continued
531
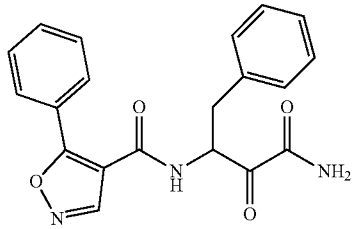
532
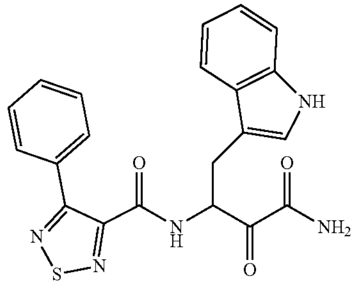
541
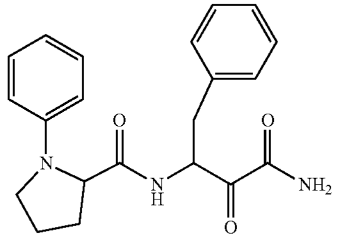
546
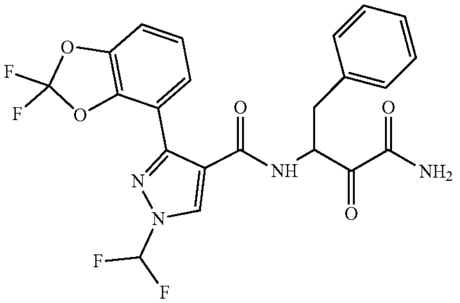
547
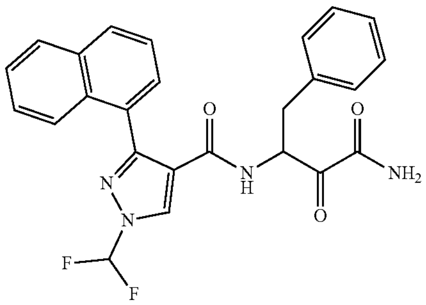

-continued
548
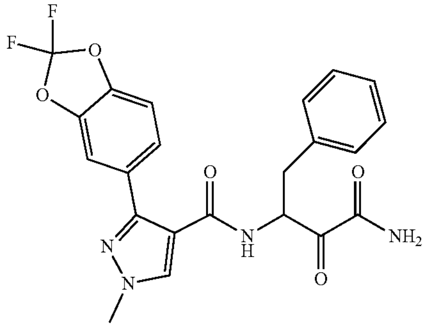
549
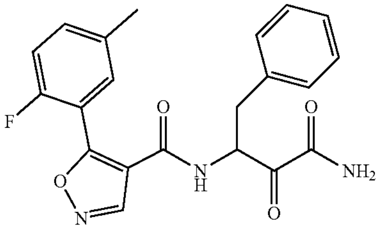
550
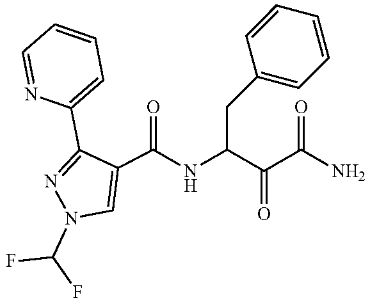
551
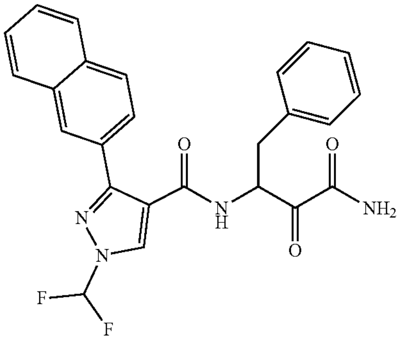
552
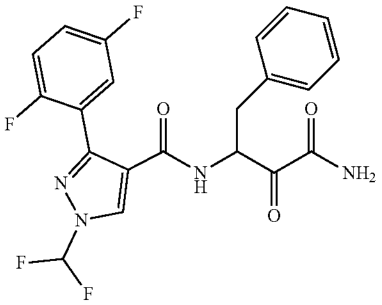
-continued
553
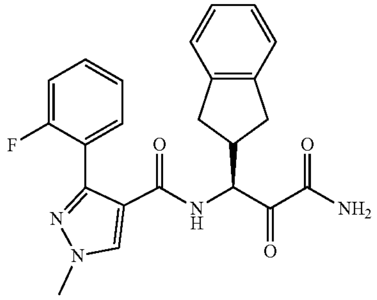
554
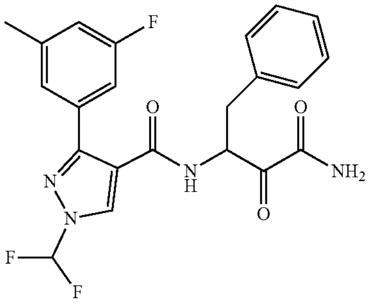
555
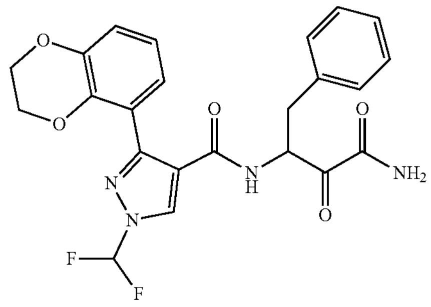
556
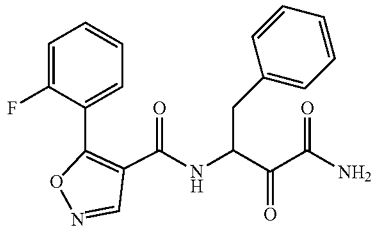
557
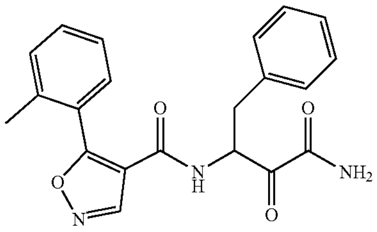
558
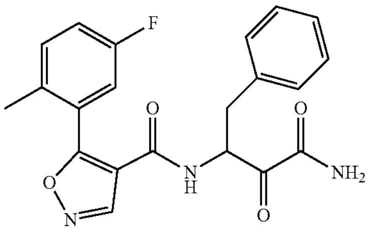

-continued
559
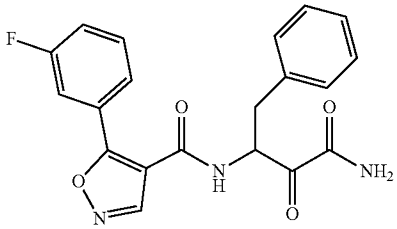
560
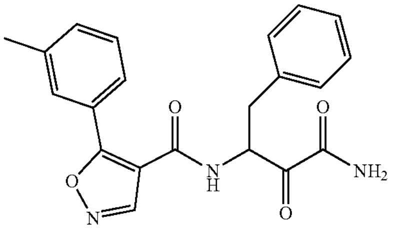
561
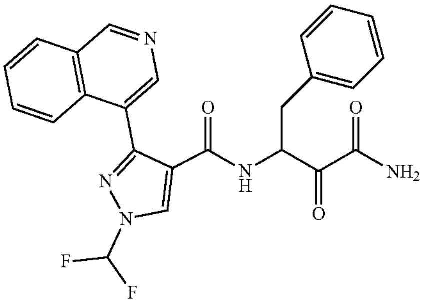
562
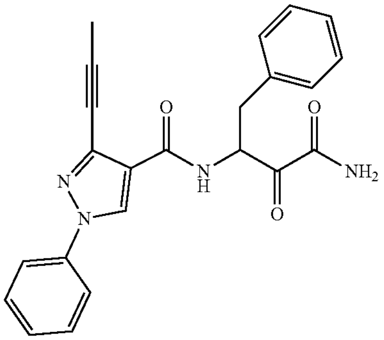
563
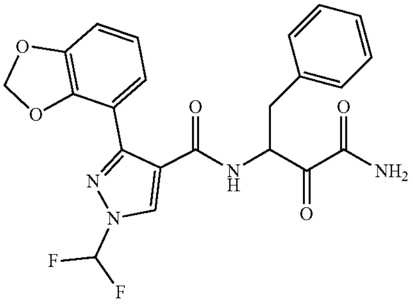
-continued
564
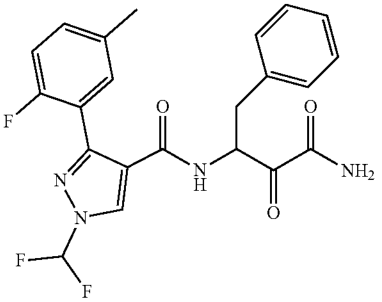
565
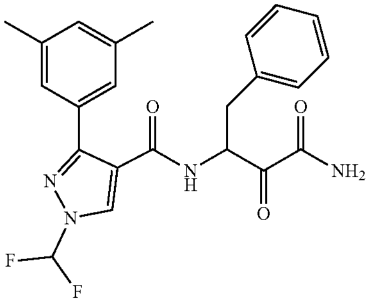
566
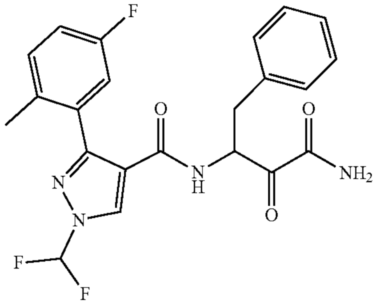
567
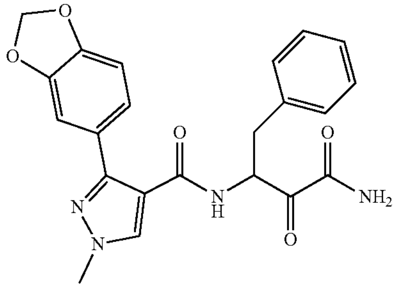
568
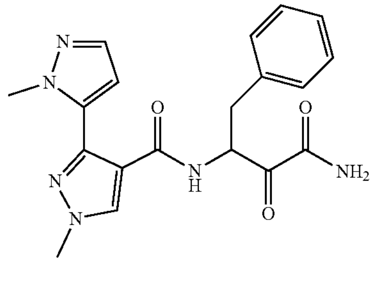

-continued
569
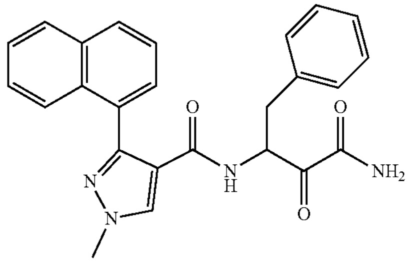
570
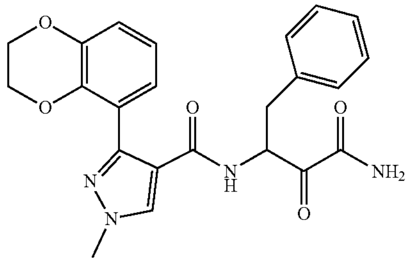
571
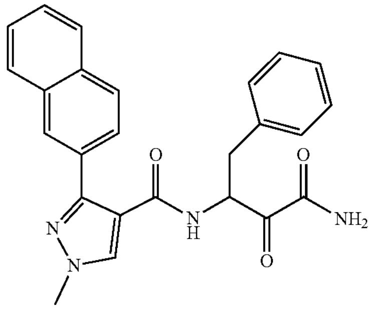
572
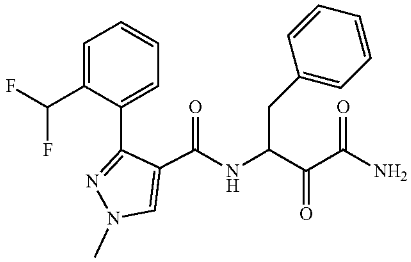
573
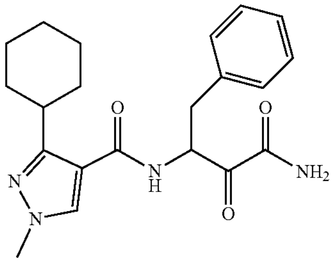
574
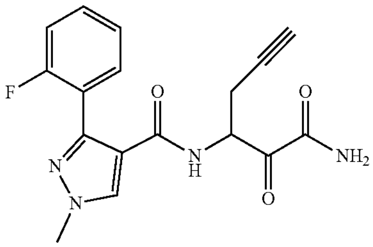
-continued
575
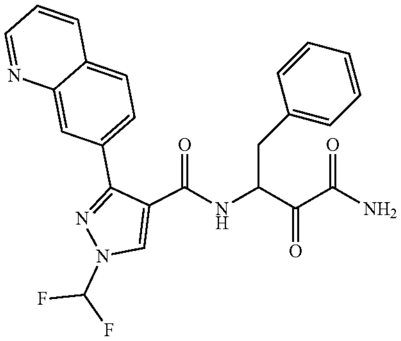
576
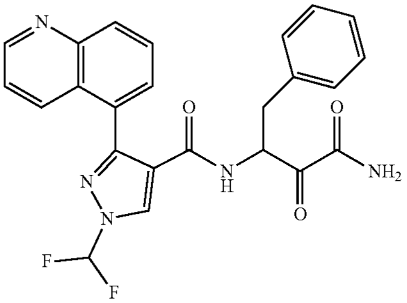
577
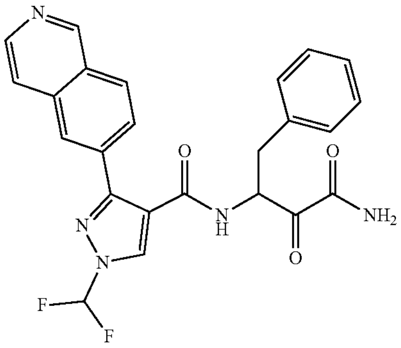
578
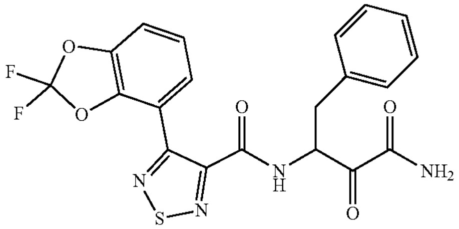
579
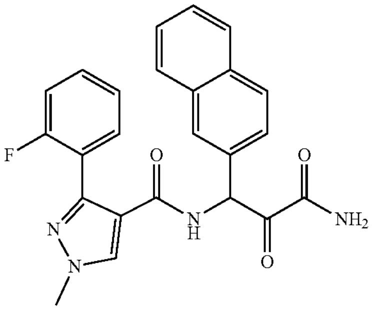

-continued
580
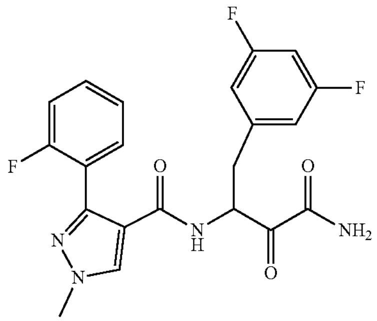
581
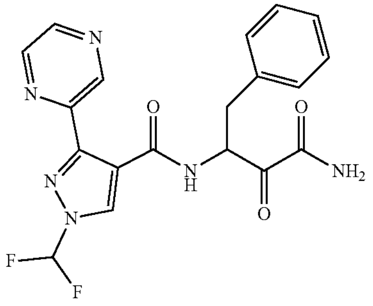
582
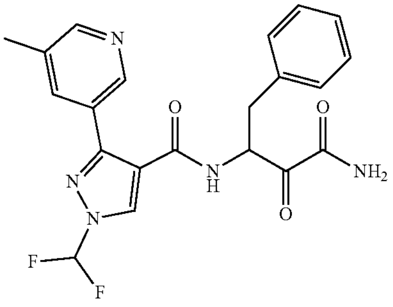
583
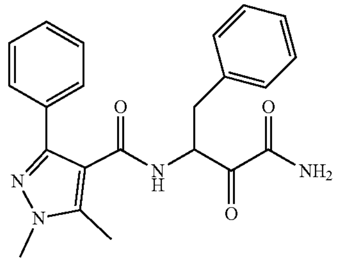
584
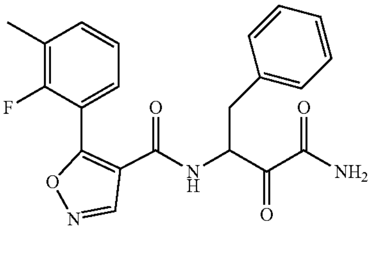
-continued
585
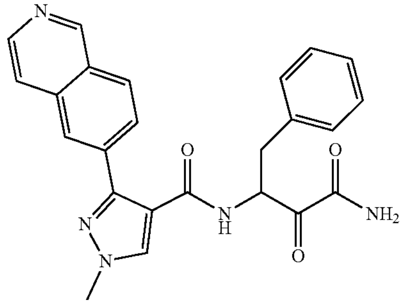
586
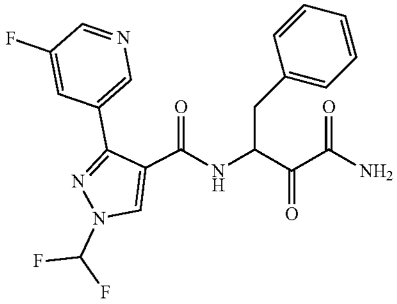
587
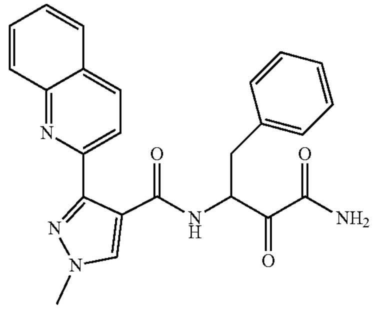
588
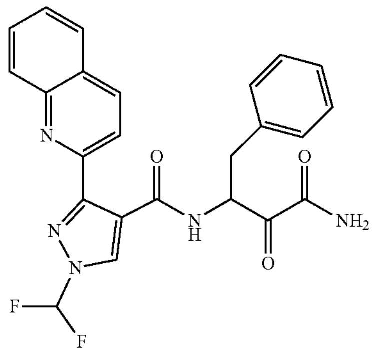
591
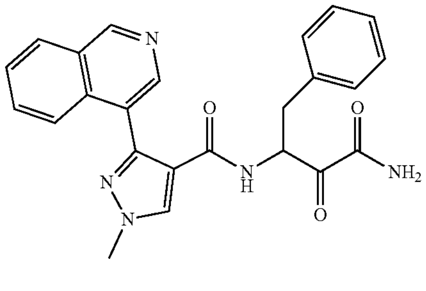

-continued
592
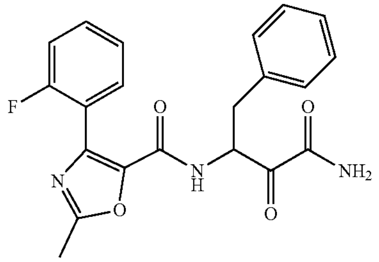
593
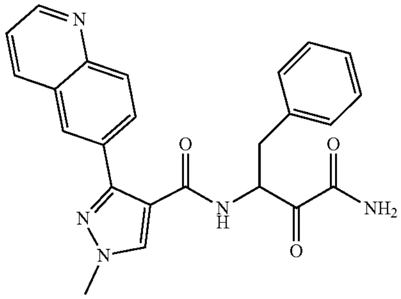
594
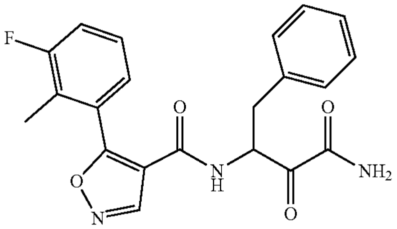
595
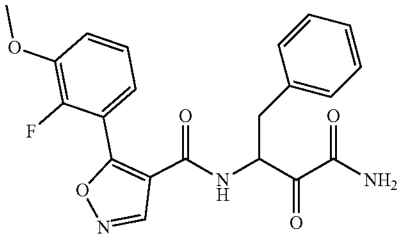
596
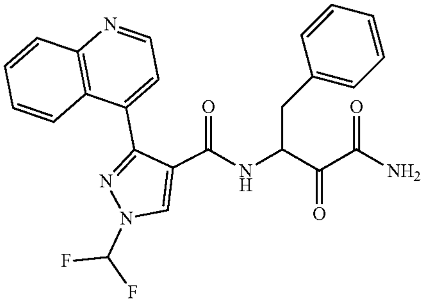
597
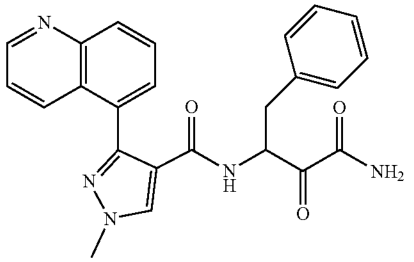
-continued
598
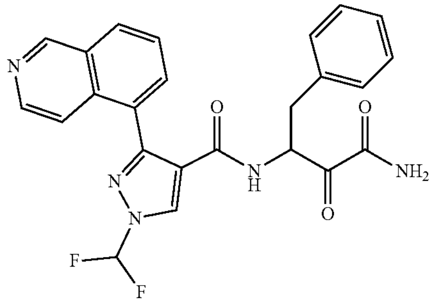
599
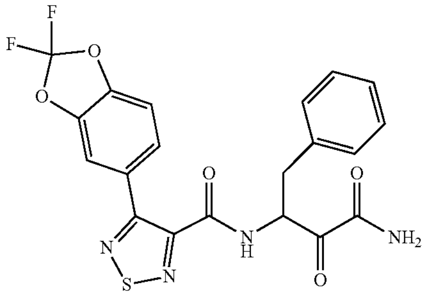
600
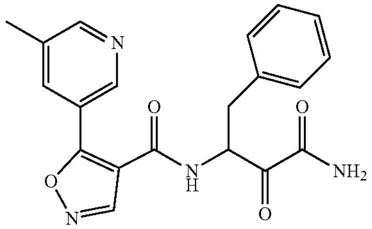
601
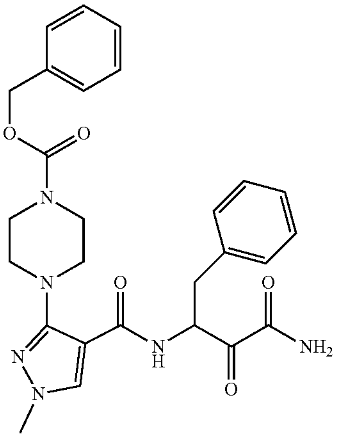
602
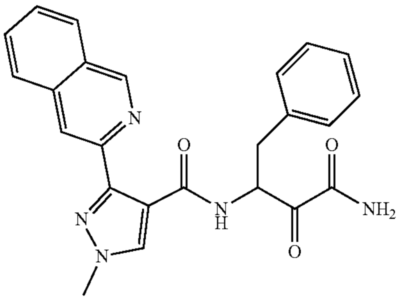

-continued
603
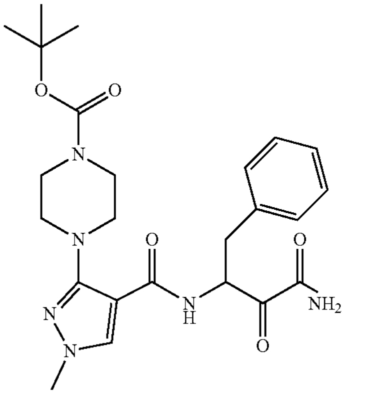
604
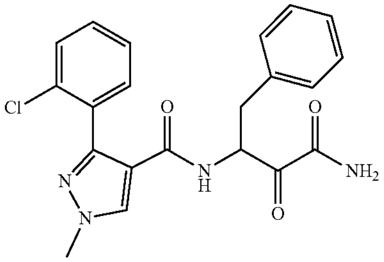
605
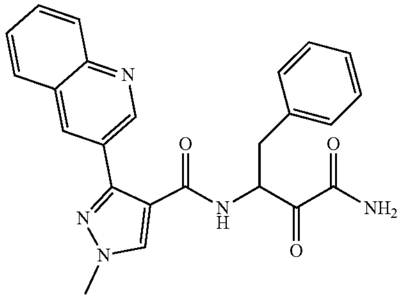
607
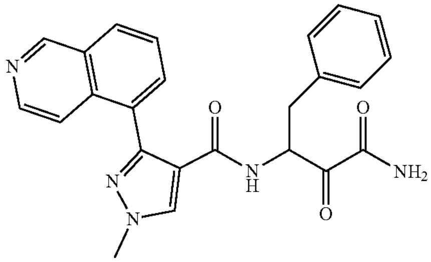
608
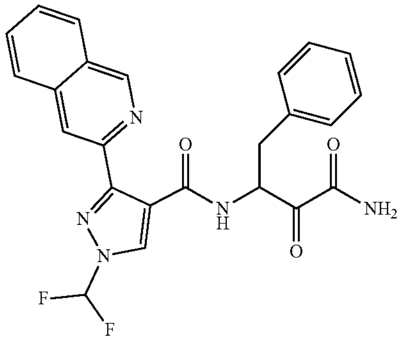
-continued
609
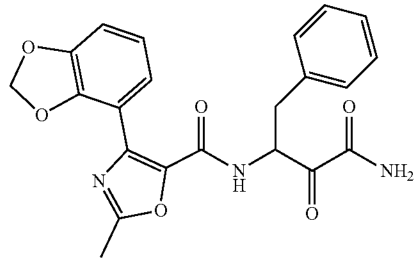
610
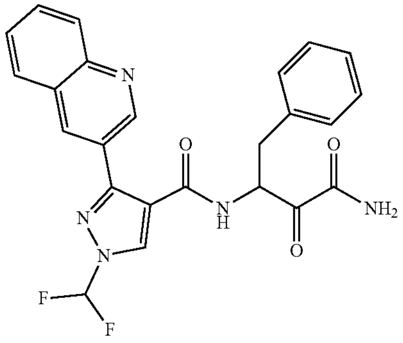
611
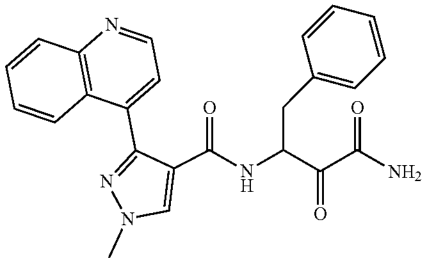
613
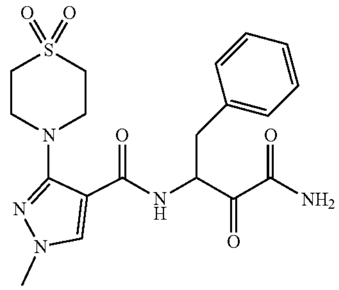
614
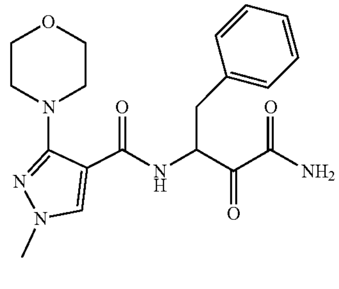

-continued
615
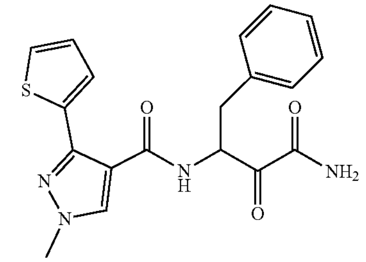
616
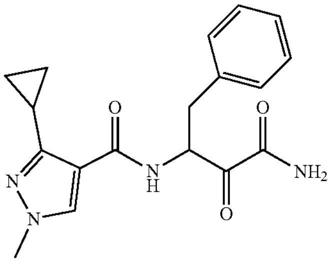
617
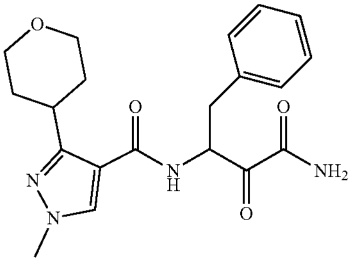
618
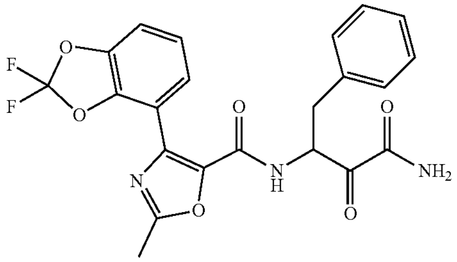
619
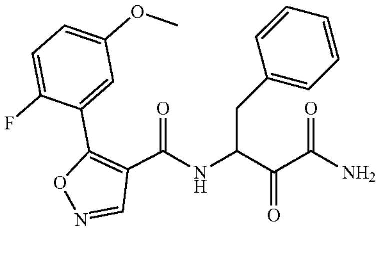
620
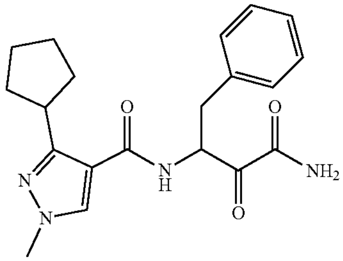
-continued
621
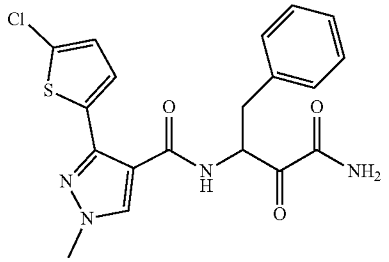
622
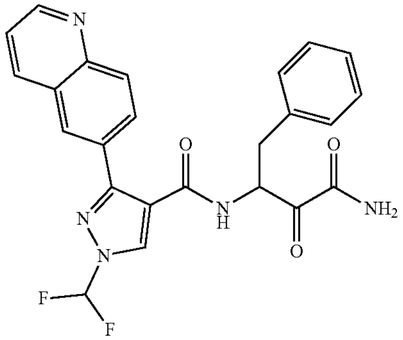
623
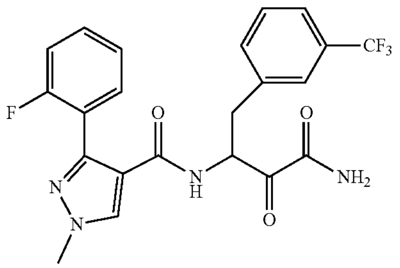
624
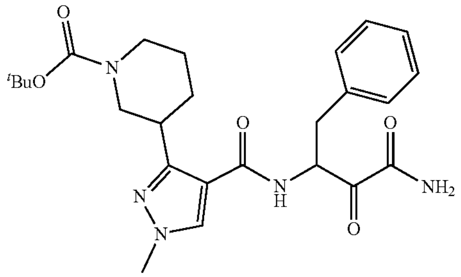
625
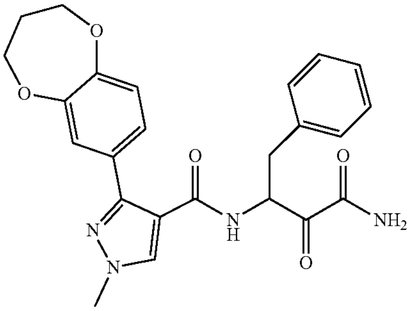

-continued
626
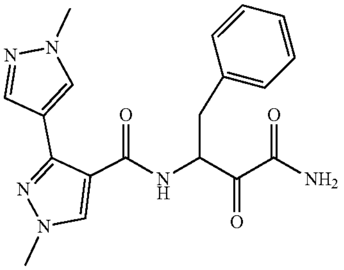
627
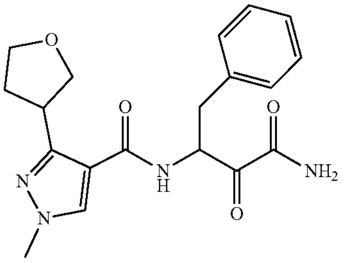
628
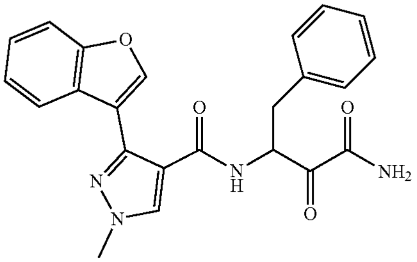
629
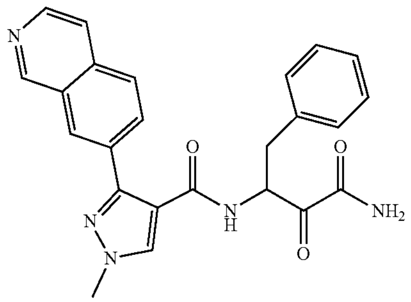
630
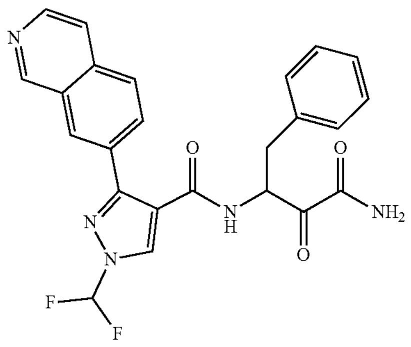
or a pharmaceutically acceptable salt thereof. Various embodiments include the S-enantiomer, the R-enantiomer, or the racemate of the above compounds.
Additional compounds suitable for use as described herein and that can be made by using the methods described herein are presented in Table 1.
TABLE 1
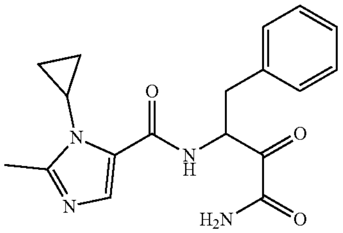 [SMILES: Cc1ncc(C(=O)NC(Cc2ccccc2)C(=O)C(N)=O)n1C1CC1]
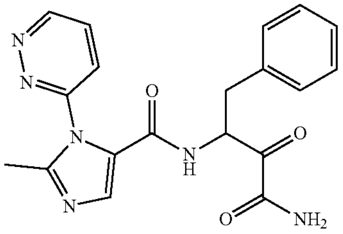
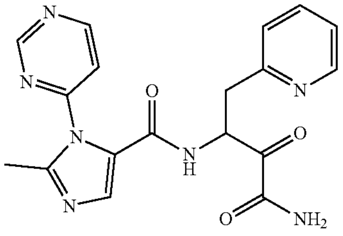 [SMILES: Cc1ncc(C(=O)NC(Cc2ccccn2)C(=O)C(N)=O)n1-c1ccncn1]
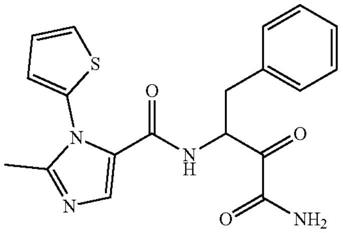
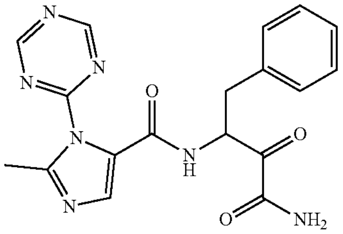 [SMILES: Cc1ncc(C(=O)NC(Cc2ccccc2)C(=O)C(N)=O)n1-c1ncncn1]
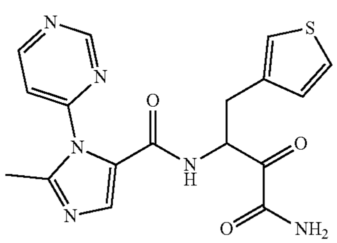 [SMILES: Cc1ncc(C(=O)NC(Cc2ccsc2)C(=O)C(N)=O)n1-c1ccncn1]

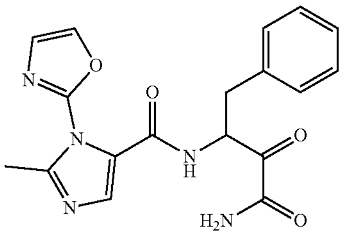 [SMILES: Cc1ncc(C(=O)NC(Cc2ccccc2)C(=O)C(N)=O)n1-c1ncco1]
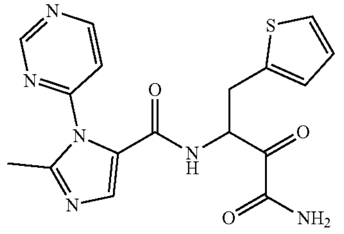
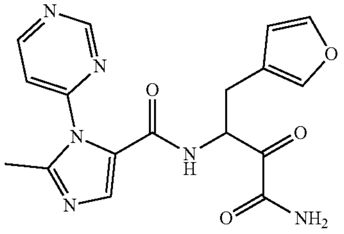
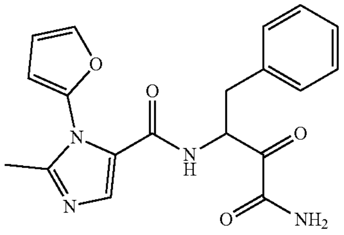 [SMILES: Cc1ncc(C(=O)NC(Cc2ccccc2)C(=O)C(N)=O)n1-c1ccco1]
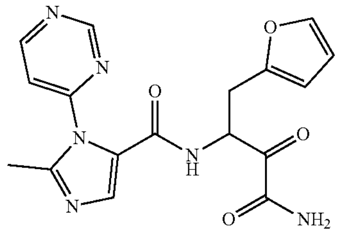
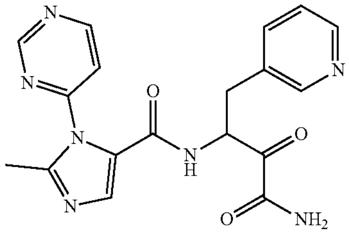
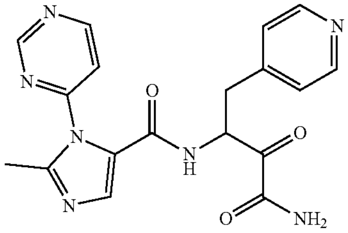
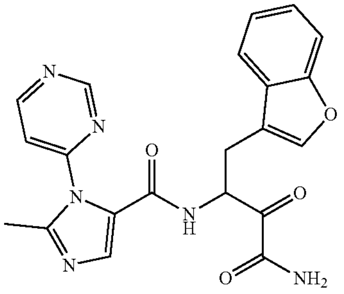
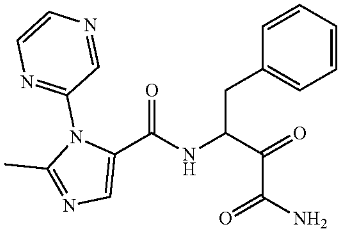
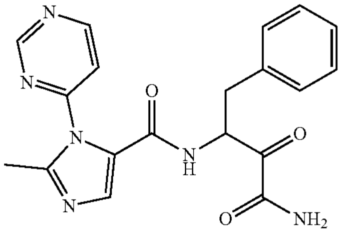
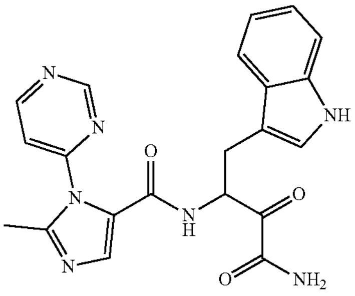
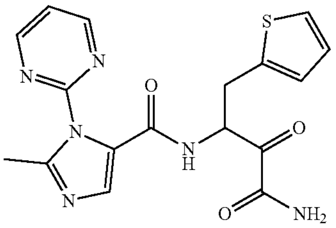

TABLE 1-continued
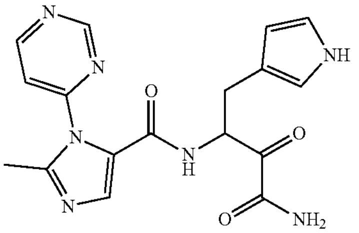
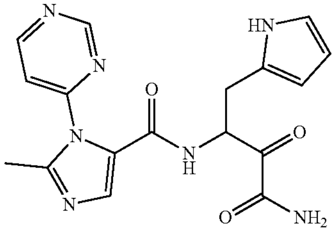
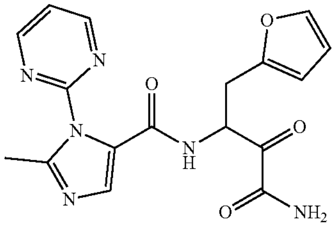 [SMILES: Cc1ncc(C(=O)NC(Cc2ccco2)C(=O)C(N)=O)n1-c1ncccn1]
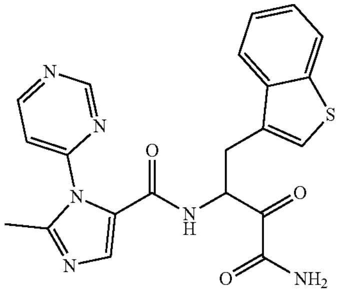
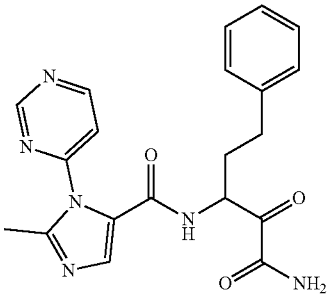 [SMILES: Cc1ncc(C(=O)NC(CCc2ccccc2)C(=O)C(N)=O)n1-c1ccncn1]
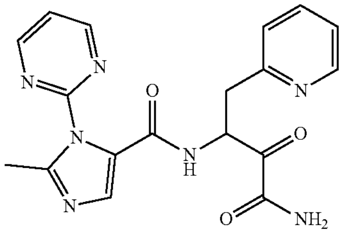
TABLE 1-continued
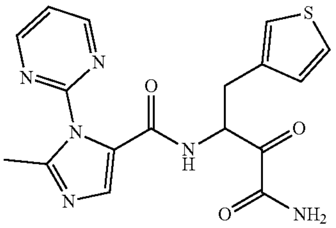 [SMILES: Cc1ncc(C(=O)NC(Cc2ccsc2)C(=O)C(N)=O)n1-c1ncccn1]
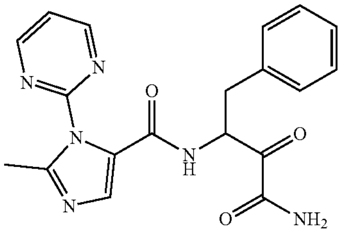
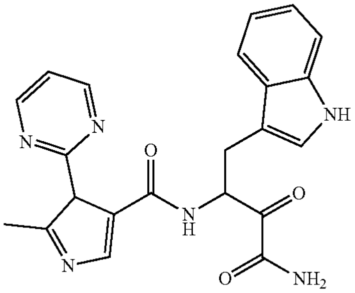 [SMILES: CC1=NC=C(C(=O)NC(Cc2c[nH]c3ccccc23)C(=O)C(N)=O)C1c1ncccn1]
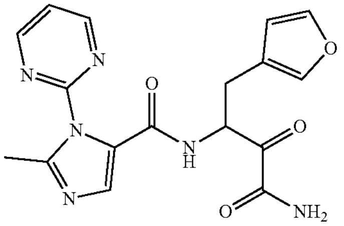 [SMILES: Cc1ncc(C(=O)NC(Cc2ccoc2)C(=O)C(N)=O)n1-c1ncccn1]
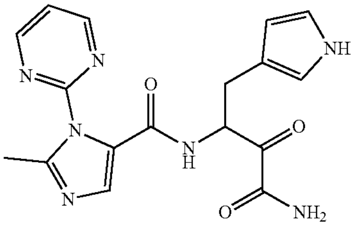
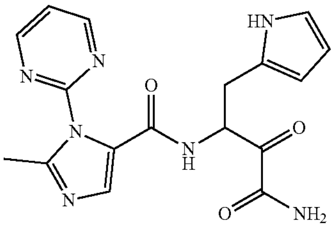

TABLE 1-continued
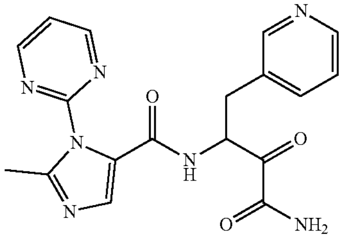
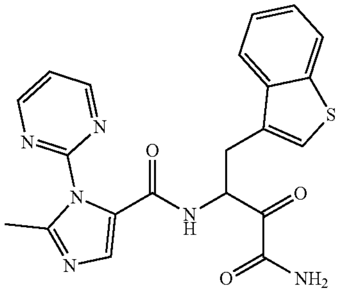
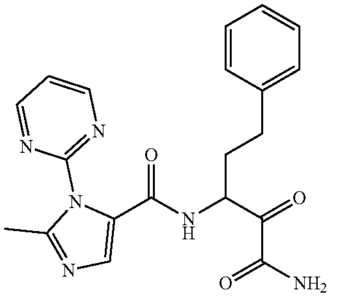 [SMILES: Cc1ncc(C(=O)NC(CCc2ccccc2)C(=O)C(N)=O)n1-c1ncccn1]
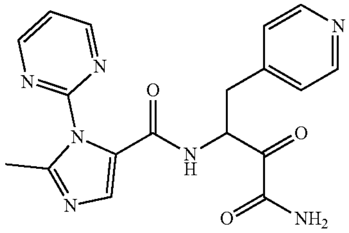 [SMILES: Cc1ncc(C(=O)NC(Cc2ccncc2)C(=O)C(N)=O)n1-c1ncccn1]
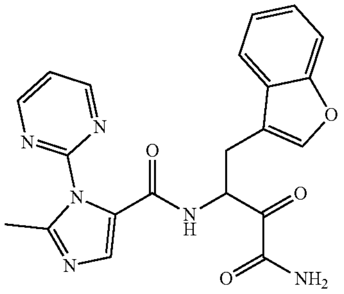 [SMILES: Cc1ncc(C(=O)NC(Cc2coc3ccccc23)C(=O)C(N)=O)n1-c1ncccn1]
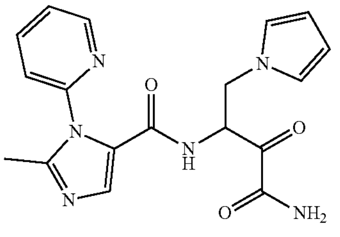 [SMILES: Cc1ncc(C(=O)NC(Cn2cccc2)C(=O)C(N)=O)n1-c1ccccn1]
TABLE 1-continued
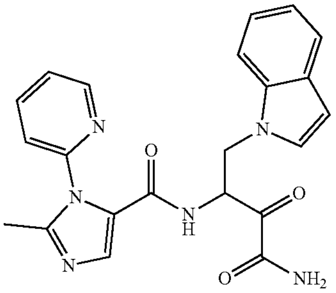 [SMILES: Cc1ncc(C(=O)NC(Cn2ccc3ccccc32)C(=O)C(N)=O)n1-c1ccccn1]
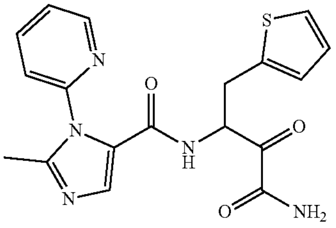
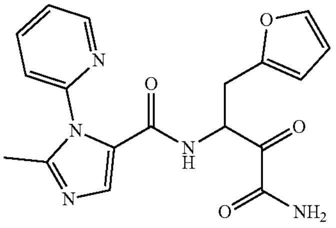
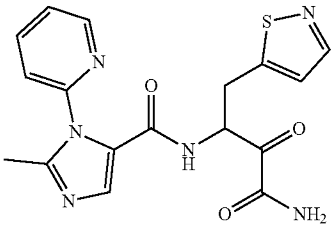
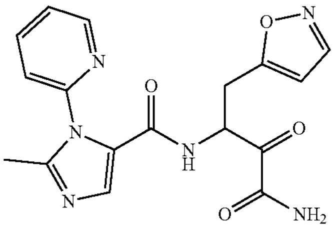
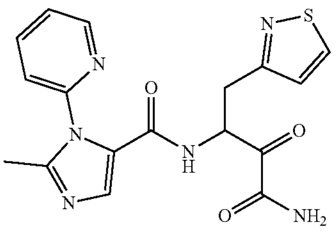 [SMILES: Cc1ncc(C(=O)NC(Cc2ccsn2)C(=O)C(N)=O)n1-c1ccccn1]

TABLE 1-continued
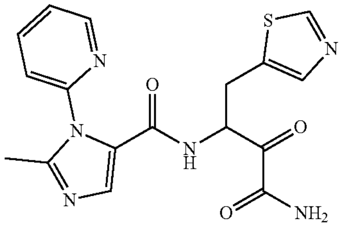 [SMILES: Cc1ncc(C(=O)NC(Cc2cncs2)C(=O)C(N)=O)n1-c1ccccn1]
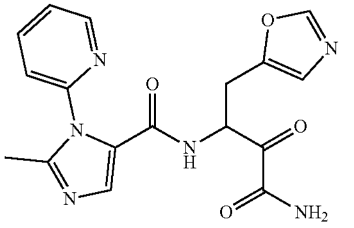 [SMILES: Cc1ncc(C(=O)NC(Cc2cnco2)C(=O)C(N)=O)n1-c1ccccn1]
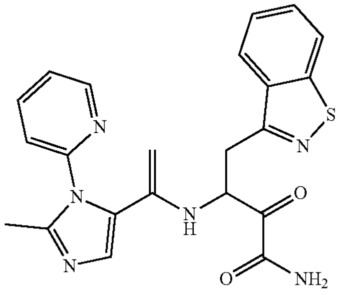 [SMILES: C=C(NC(Cc1nsc2ccccc12)C(=O)C(N)=O)c1cnc(C)n1-c1ccccn1]
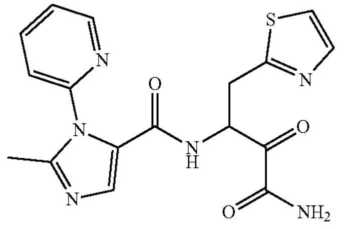
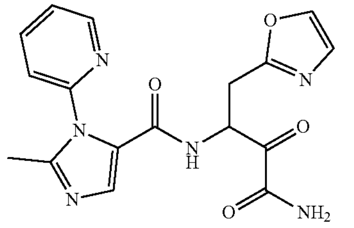
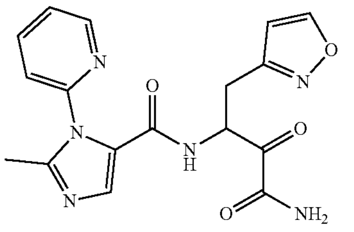 [SMILES: Cc1ncc(C(=O)NC(Cc2ccon2)C(=O)C(N)=O)n1-c1ccccn1]
TABLE 1-continued
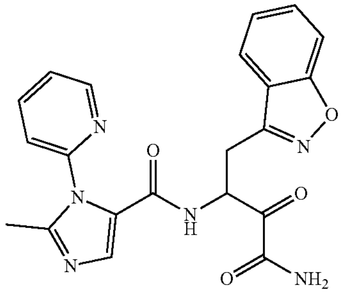 [SMILES: Cc1ncc(C(=O)NC(Cc2noc3ccccc23)C(=O)C(N)=O)n1-c1ccccn1]
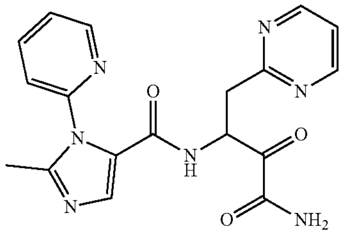 [SMILES: Cc1ncc(C(=O)NC(Cc2ncccn2)C(=O)C(N)=O)n1-c1ccccn1]
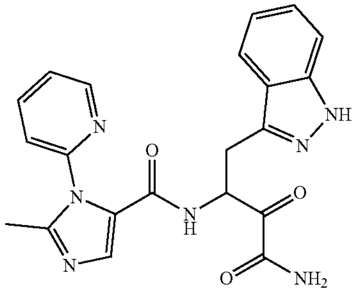 [SMILES: Cc1ncc(C(=O)NC(Cc2n[nH]c3ccccc23)C(=O)C(N)=O)n1-c1ccccn1]
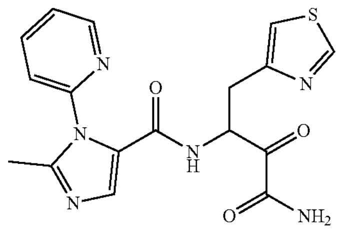 [SMILES: Cc1ncc(C(=O)NC(Cc2cscn2)C(=O)C(N)=O)n1-c1ccccn1]
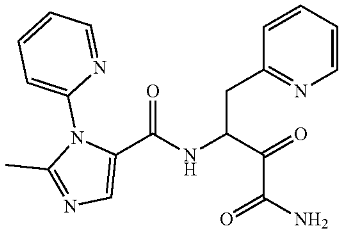
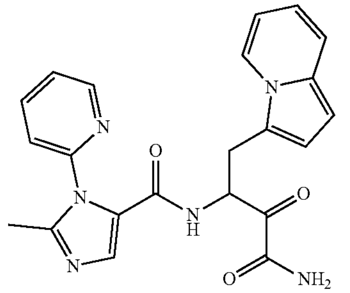 [SMILES: Cc1ncc(C(=O)NC(Cc2ccc3ccccn23)C(=O)C(N)=O)n1-c1ccccn1]

TABLE 1-continued
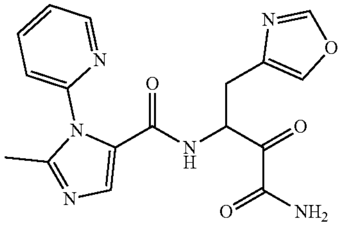 [SMILES: Cc1ncc(C(=O)NC(Cc2cocn2)C(=O)C(N)=O)n1-c1ccccn1]
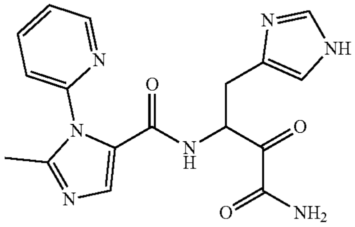
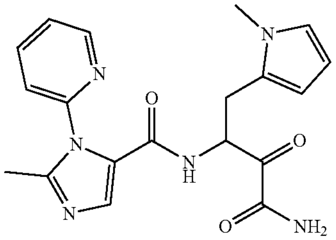 [SMILES: Cc1ncc(C(=O)NC(Cc2cccn2C)C(=O)C(N)=O)n1-c1ccccn1]
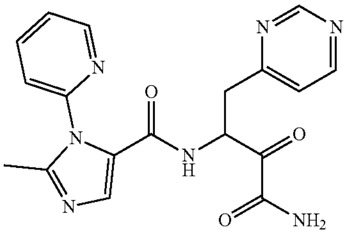
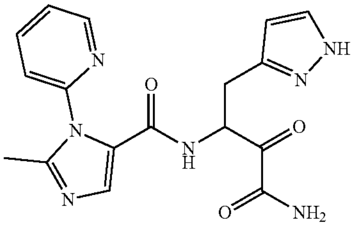
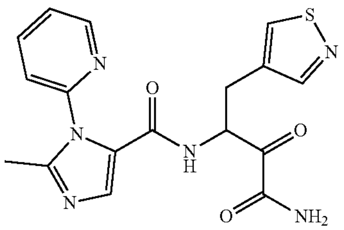 [SMILES: Cc1ncc(C(=O)NC(Cc2cnsc2)C(=O)C(N)=O)n1-c1ccccn1]
TABLE 1-continued
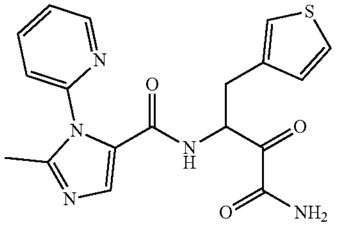
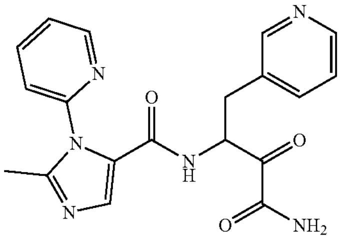 [SMILES: Cc1ncc(C(=O)NC(Cc2cccnc2)C(=O)C(N)=O)n1-c1ccccn1]
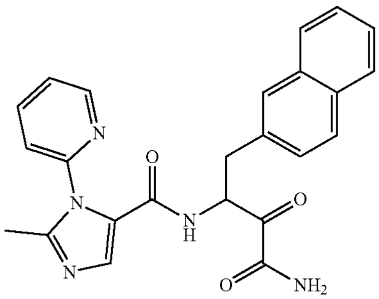 [SMILES: Cc1ncc(C(=O)NC(Cc2ccc3ccccc3c2)C(=O)C(N)=O)n1-c1ccccn1]
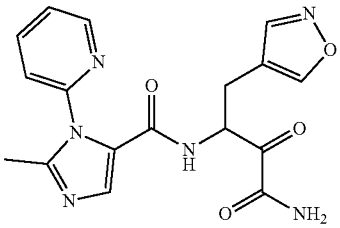 [SMILES: Cc1ncc(C(=O)NC(Cc2cnoc2)C(=O)C(N)=O)n1-c1ccccn1]
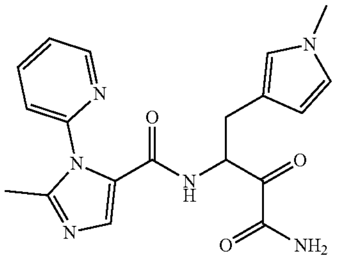 [SMILES: Cc1ncc(C(=O)NC(Cc2ccn(C)c2)C(=O)C(N)=O)n1-c1ccccn1]
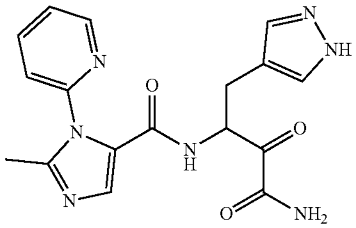 [SMILES: Cc1ncc(C(=O)NC(Cc2cn[nH]c2)C(=O)C(N)=O)n1-c1ccccn1]

TABLE 1-continued
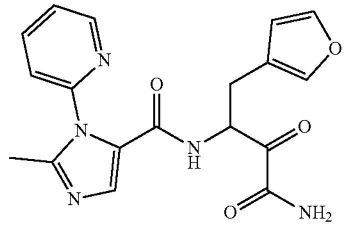
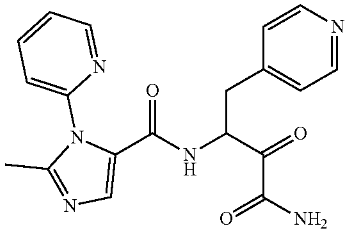 [SMILES: Cc1ncc(C(=O)NC(Cc2ccncc2)C(=O)C(N)=O)n1-c1ccccn1]
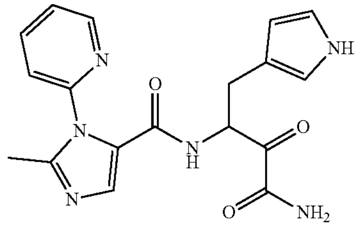 [SMILES: Cc1ncc(C(=O)NC(Cc2cc[nH]c2)C(=O)C(N)=O)n1-c1ccccn1]
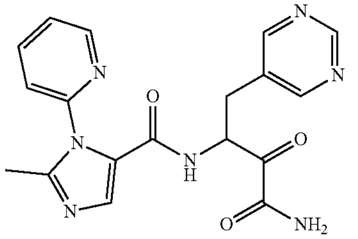 [SMILES: Cc1ncc(C(=O)NC(Cc2cncnc2)C(=O)C(N)=O)n1-c1ccccn1]
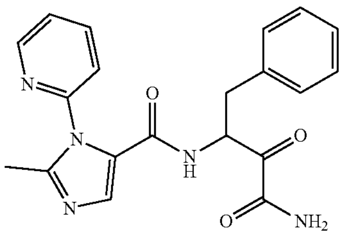
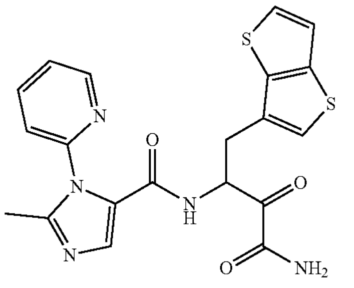 [SMILES: Cc1ncc(C(=O)NC(Cc2csc3ccsc23)C(=O)C(N)=O)n1-c1ccccn1]
TABLE 1-continued
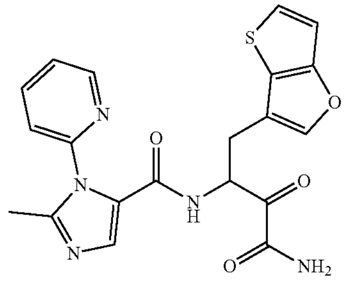 [SMILES: Cc1ncc(C(=O)NC(Cc2coc3ccsc23)C(=O)C(N)=O)n1-c1ccccn1]
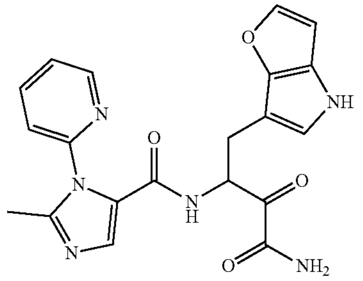 [SMILES: Cc1ncc(C(=O)NC(Cc2c[nH]c3ccoc23)C(=O)C(N)=O)n1-c1ccccn1]
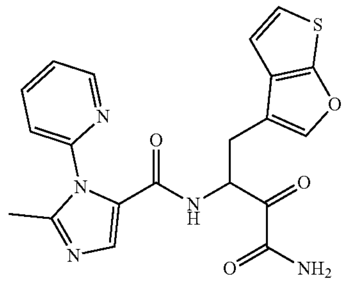 [SMILES: Cc1ncc(C(=O)NC(Cc2coc3sccc23)C(=O)C(N)=O)n1-c1ccccn1]
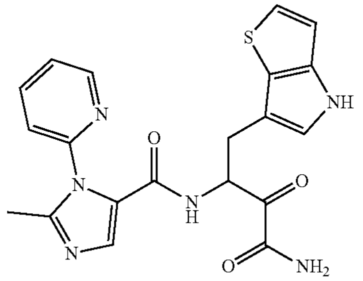 [SMILES: Cc1ncc(C(=O)NC(Cc2c[nH]c3ccsc23)C(=O)C(N)=O)n1-c1ccccn1]
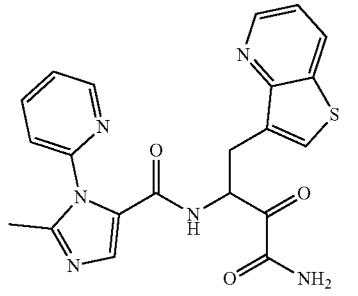 [SMILES: Cc1ncc(C(=O)NC(Cc2csc3cccnc23)C(=O)C(N)=O)n1-c1ccccn1]

TABLE 1-continued
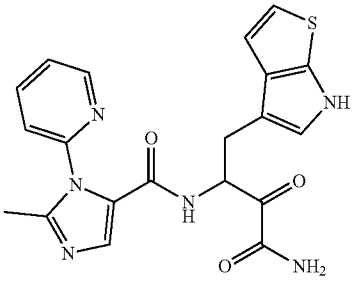
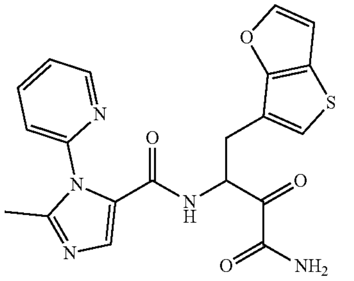 [SMILES: Cc1ncc(C(=O)NC(Cc2csc3ccoc23)C(=O)C(N)=O)n1-c1ccccn1]
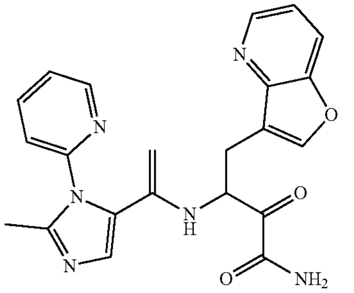 [SMILES: C=C(NC(Cc1coc2cccnc12)C(=O)C(N)=O)c1cnc(C)n1-c1ccccn1]
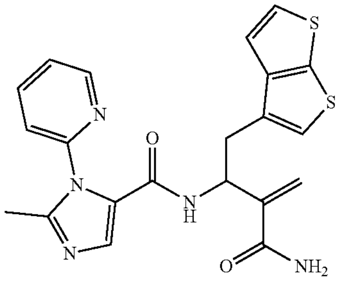 [SMILES: C=C(C(N)=O)C(Cc1csc2sccc12)NC(=O)c1cnc(C)n1-c1ccccn1]
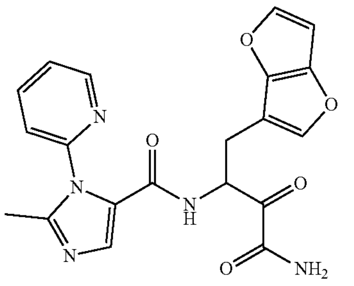 [SMILES: Cc1ncc(C(=O)NC(Cc2coc3ccoc23)C(=O)C(N)=O)n1-c1ccccn1]
TABLE 1-continued
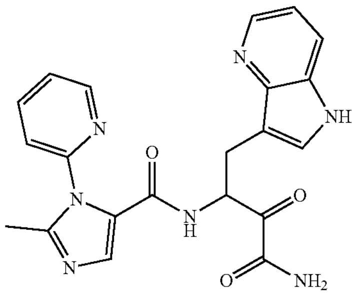 [SMILES: Cc1ncc(C(=O)NC(Cc2c[nH]c3cccnc23)C(=O)C(N)=O)n1-c1ccccn1]
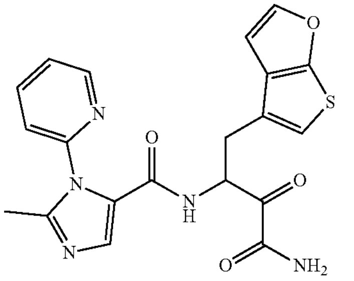 [SMILES: Cc1ncc(C(=O)NC(Cc2csc3occc23)C(=O)C(N)=O)n1-c1ccccn1]
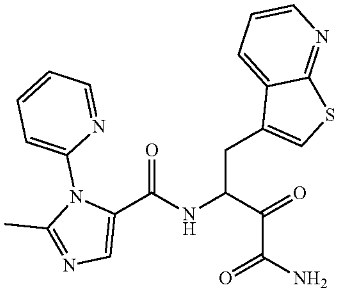
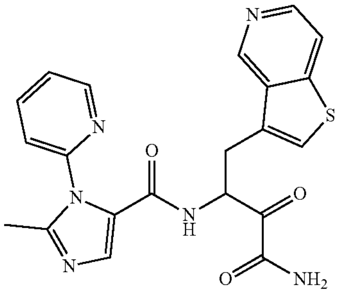
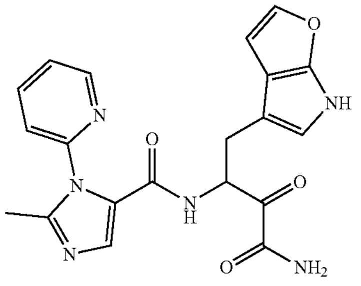 [SMILES: Cc1ncc(C(=O)NC(Cc2c[nH]c3occc23)C(=O)C(N)=O)n1-c1ccccn1]

TABLE 1-continued
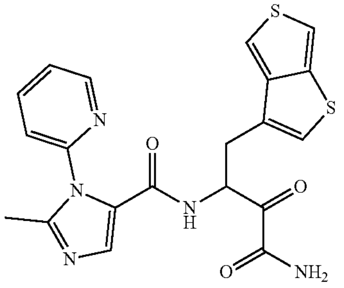 [SMILES: Cc1ncc(C(=O)NC(Cc2csc3cscc23)C(=O)C(N)=O)n1-c1ccccn1]
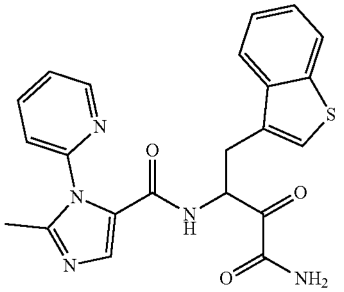
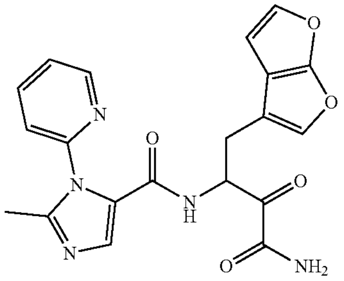 [SMILES: Cc1ncc(C(=O)NC(Cc2coc3occc23)C(=O)C(N)=O)n1-c1ccccn1]
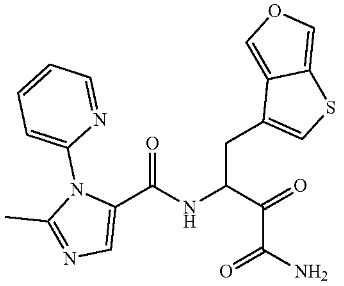 [SMILES: Cc1ncc(C(=O)NC(Cc2csc3cocc23)C(=O)C(N)=O)n1-c1ccccn1]
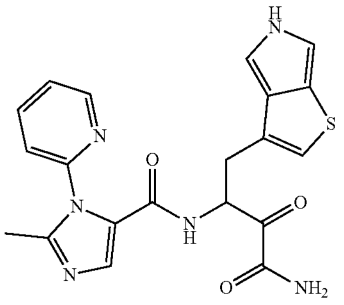 [SMILES: Cc1ncc(C(=O)NC(Cc2csc3c[nH]cc23)C(=O)C(N)=O)n1-c1ccccn1]
TABLE 1-continued
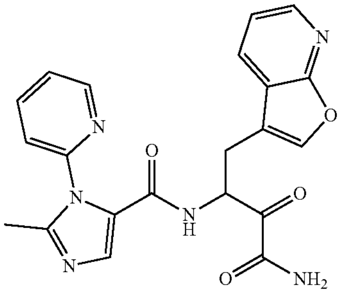
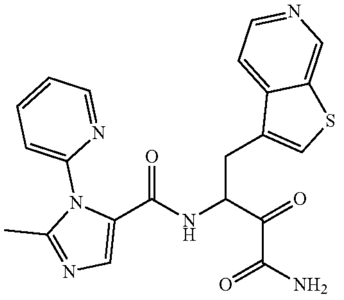 [SMILES: Cc1ncc(C(=O)NC(Cc2csc3cnccc23)C(=O)C(N)=O)n1-c1ccccn1]
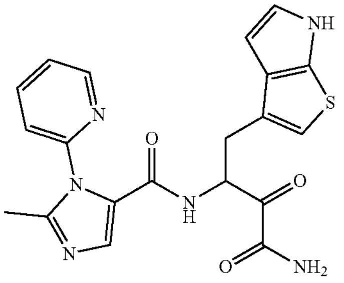 [SMILES: Cc1ncc(C(=O)NC(Cc2csc3[nH]ccc23)C(=O)C(N)=O)n1-c1ccccn1]
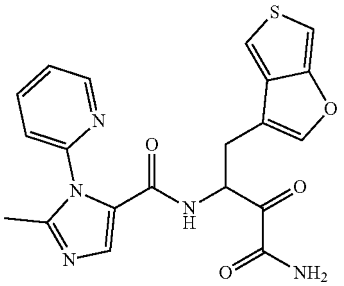 [SMILES: Cc1ncc(C(=O)NC(Cc2coc3cscc23)C(=O)C(N)=O)n1-c1ccccn1]
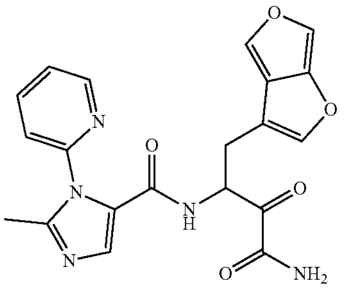 [SMILES: Cc1ncc(C(=O)NC(Cc2coc3cocc23)C(=O)C(N)=O)n1-c1ccccn1]

TABLE 1-continued
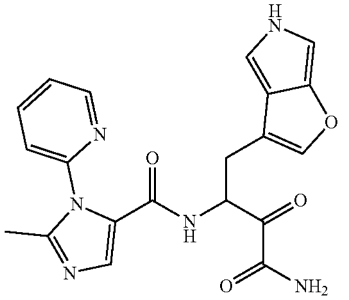 [SMILES: Cc1ncc(C(=O)NC(Cc2coc3c[nH]cc23)C(=O)C(N)=O)n1-c1ccccn1]
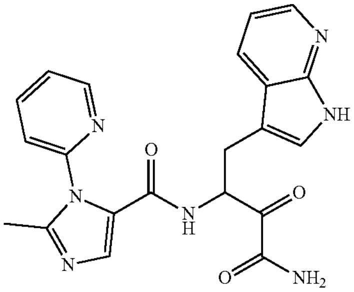
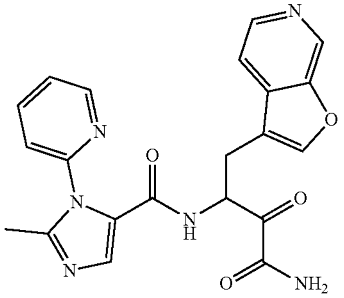 [SMILES: Cc1ncc(C(=O)NC(Cc2coc3cnccc23)C(=O)C(N)=O)n1-c1ccccn1]
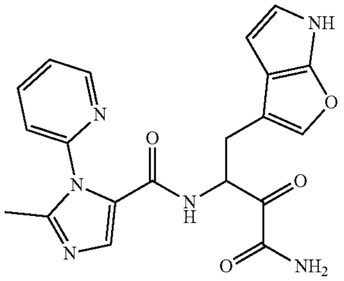 [SMILES: Cc1ncc(C(=O)NC(Cc2coc3[nH]ccc23)C(=O)C(N)=O)n1-c1ccccn1]
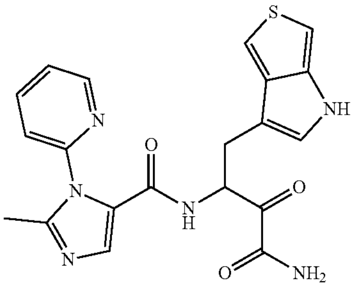 [SMILES: Cc1ncc(C(=O)NC(Cc2c[nH]c3cscc23)C(=O)C(N)=O)n1-c1ccccn1]
TABLE 1-continued
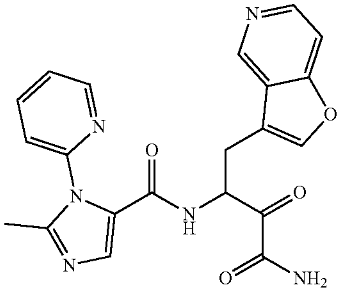
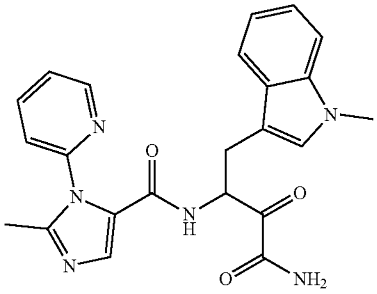
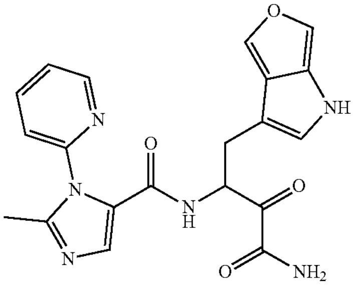
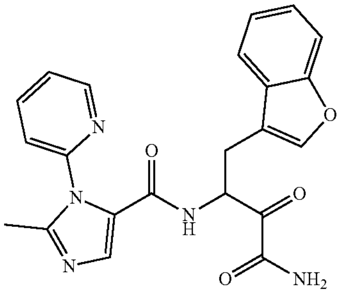
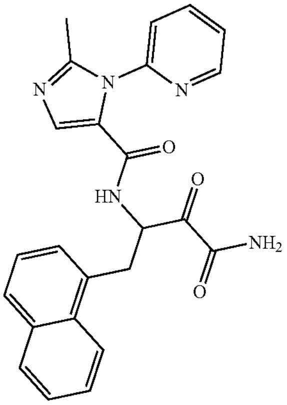 [SMILES: Cc1ncc(C(=O)NC(Cc2cccc3ccccc23)C(=O)C(N)=O)n1-c1ccccn1]

TABLE 1-continued
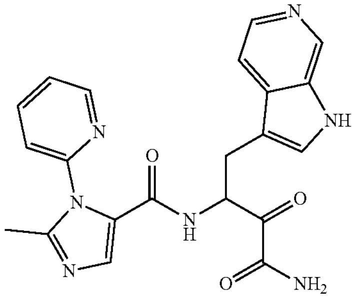 [SMILES: Cc1ncc(C(=O)NC(Cc2c[nH]c3cnccc23)C(=O)C(N)=O)n1-c1ccccn1]
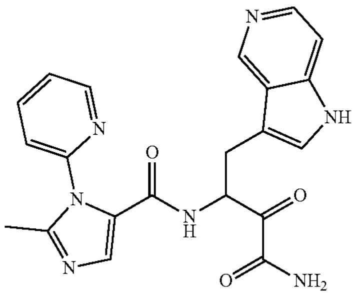
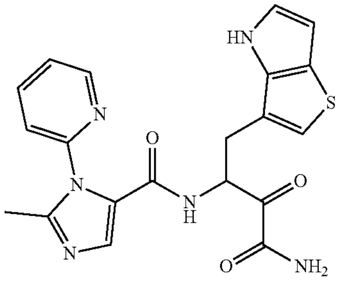 [SMILES: Cc1ncc(C(=O)NC(Cc2csc3cc[nH]c23)C(=O)C(N)=O)n1-c1ccccn1]
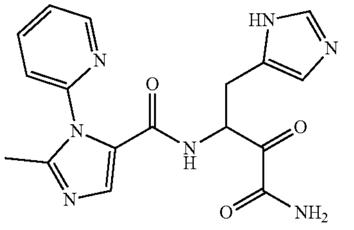 [SMILES: Cc1ncc(C(=O)NC(Cc2cnc[nH]2)C(=O)C(N)=O)n1-c1ccccn1]
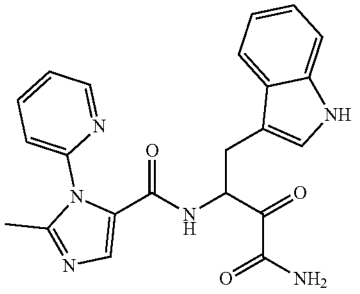 [SMILES: Cc1ncc(C(=O)NC(Cc2c[nH]c3ccccc23)C(=O)C(N)=O)n1-c1ccccn1]
TABLE 1-continued
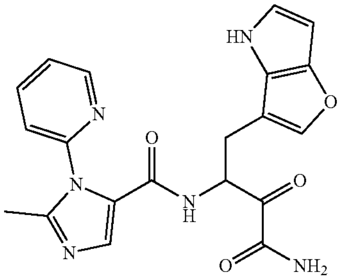 [SMILES: Cc1ncc(C(=O)NC(Cc2coc3cc[nH]c23)C(=O)C(N)=O)n1-c1ccccn1]
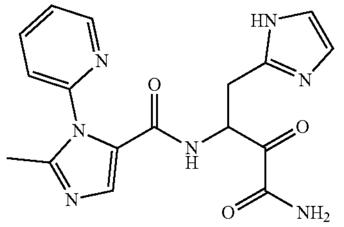 [SMILES: Cc1ncc(C(=O)NC(Cc2ncc[nH]2)C(=O)C(N)=O)n1-c1ccccn1]
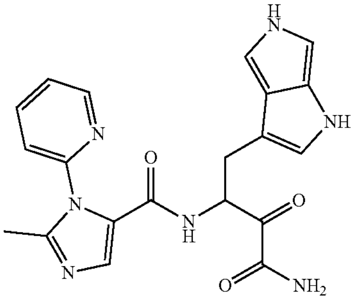 [SMILES: Cc1ncc(C(=O)NC(Cc2c[nH]c3c[nH]cc23)C(=O)C(N)=O)n1-c1ccccn1]
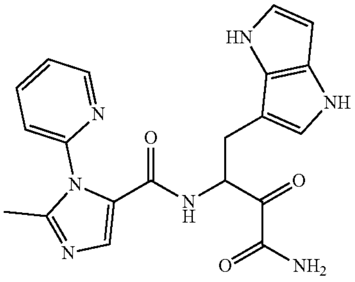
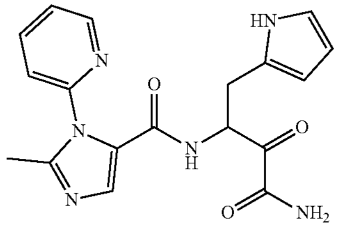 [SMILES: Cc1ncc(C(=O)NC(Cc2ccc[nH]2)C(=O)C(N)=O)n1-c1ccccn1]
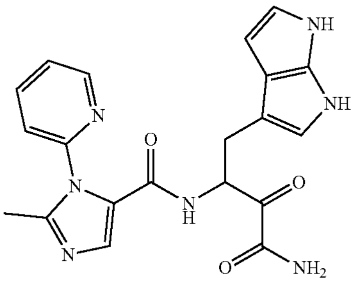 [SMILES: Cc1ncc(C(=O)NC(Cc2c[nH]c3[nH]ccc23)C(=O)C(N)=O)n1-c1ccccn1]

TABLE 1-continued
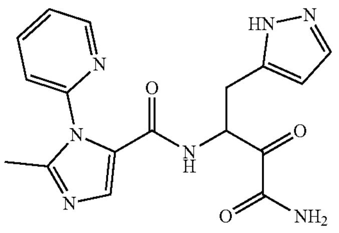 [SMILES: Cc1ncc(C(=O)NC(Cc2ccn[nH]2)C(=O)C(N)=O)n1-c1ccccn1]
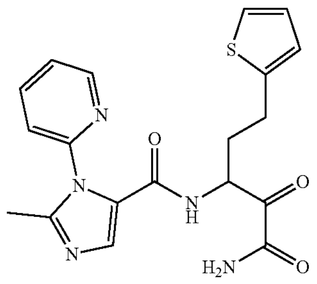 [SMILES: Cc1ncc(C(=O)NC(CCc2cccs2)C(=O)C(N)=O)n1-c1ccccn1]
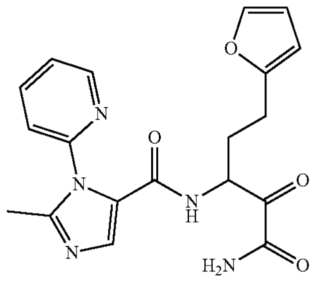 [SMILES: Cc1ncc(C(=O)NC(CCc2ccco2)C(=O)C(N)=O)n1-c1ccccn1]
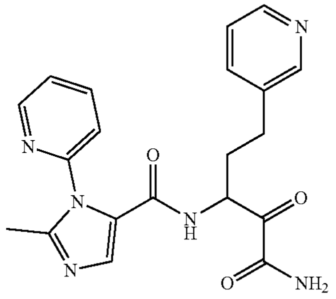 [SMILES: Cc1ncc(C(=O)NC(CCc2cccnc2)C(=O)C(N)=O)n1-c1ccccn1]
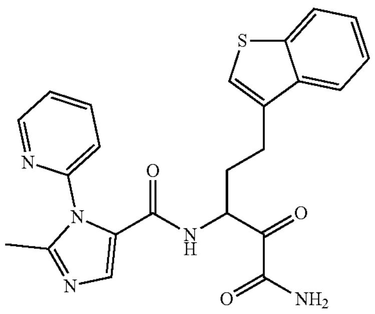 [SMILES: Cc1ncc(C(=O)NC(CCc2csc3ccccc23)C(=O)C(N)=O)n1-c1ccccn1]
TABLE 1-continued
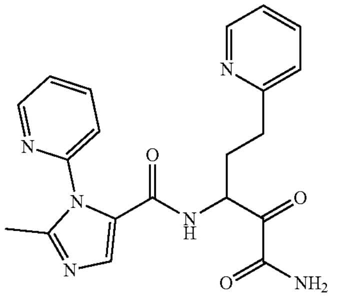
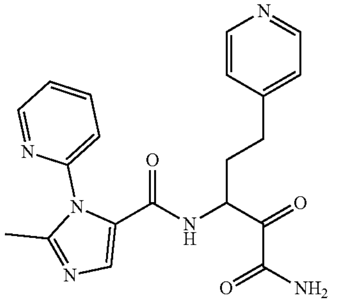 [SMILES: Cc1ncc(C(=O)NC(CCc2ccncc2)C(=O)C(N)=O)n1-c1ccccn1]
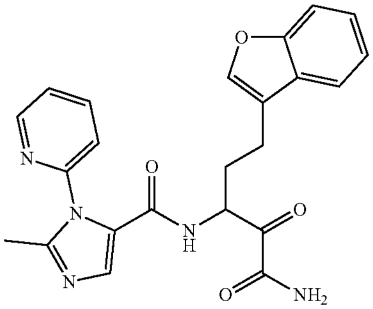 [SMILES: Cc1ncc(C(=O)NC(CCc2coc3ccccc23)C(=O)C(N)=O)n1-c1ccccn1]
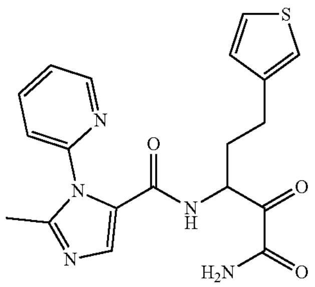 [SMILES: Cc1ncc(C(=O)NC(CCc2ccsc2)C(=O)C(N)=O)n1-c1ccccn1]
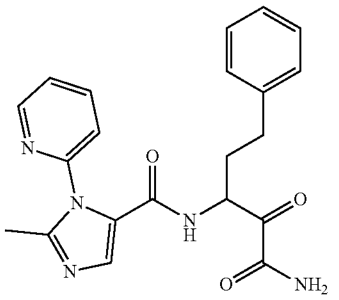

TABLE 1-continued
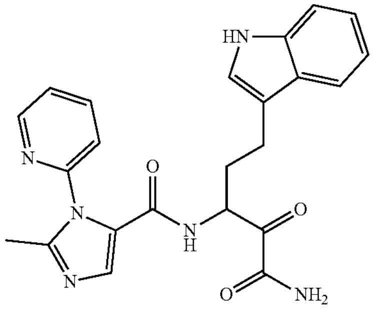 [SMILES: Cc1ncc(C(=O)NC(CCc2c[nH]c3ccccc23)C(=O)C(N)=O)n1-c1ccccn1]
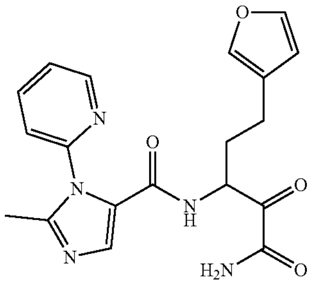 [SMILES: Cc1ncc(C(=O)NC(CCc2ccoc2)C(=O)C(N)=O)n1-c1ccccn1]
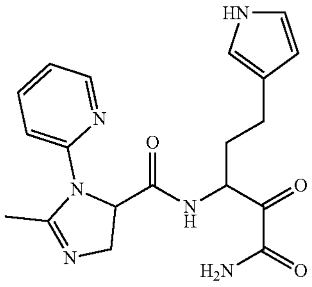 [SMILES: CC1=NCC(C(=O)NC(CCc2cc[nH]c2)C(=O)C(N)=O)N1c1ccccn1]
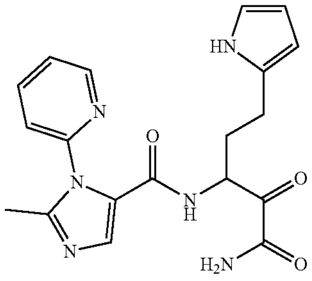 [SMILES: Cc1ncc(C(=O)NC(CCc2ccc[nH]2)C(=O)C(N)=O)n1-c1ccccn1]
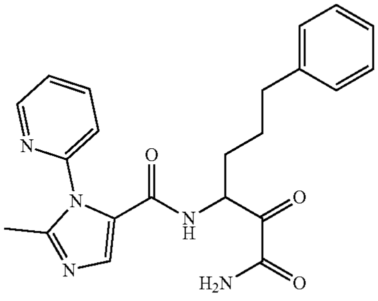 [SMILES: Cc1ncc(C(=O)NC(CCCc2ccccc2)C(=O)C(N)=O)n1-c1ccccn1]
TABLE 1-continued
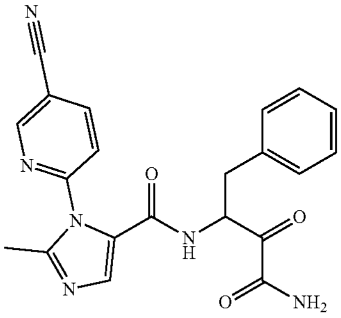 [SMILES: Cc1ncc(C(=O)NC(Cc2ccccc2)C(=O)C(N)=O)n1-c1ccc(C#N)cn1]
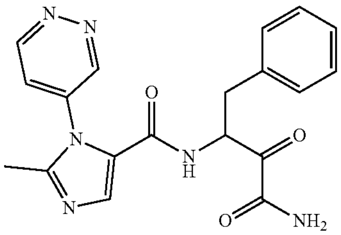 [SMILES: Cc1ncc(C(=O)NC(Cc2ccccc2)C(=O)C(N)=O)n1-c1ccnnc1]
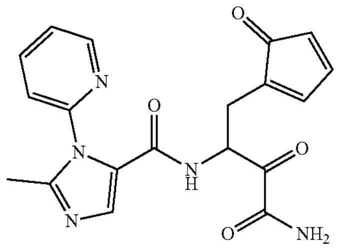 [SMILES: Cc1ncc(C(=O)NC(CC2=CC=CC2=O)C(=O)C(N)=O)n1-c1ccccn1]
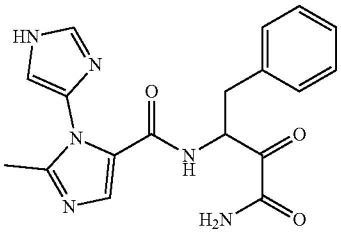 [SMILES: Cc1ncc(C(=O)NC(Cc2ccccc2)C(=O)C(N)=O)n1-c1c[nH]cn1]
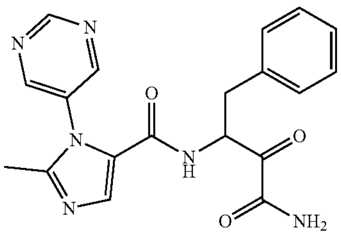 [SMILES: Cc1ncc(C(=O)NC(Cc2ccccc2)C(=O)C(N)=O)n1-c1cncnc1]
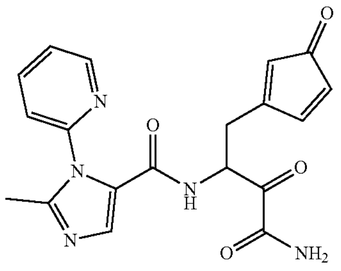 [SMILES: Cc1ncc(C(=O)NC(CC2=CC(=O)C=C2)C(=O)C(N)=O)n1-c1ccccn1]

TABLE 1-continued
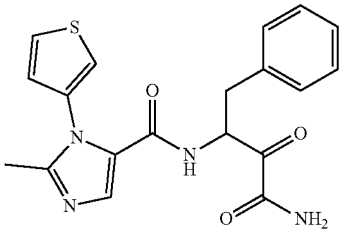 [SMILES: Cc1ncc(C(=O)NC(Cc2ccccc2)C(=O)C(N)=O)n1-c1ccsc1]
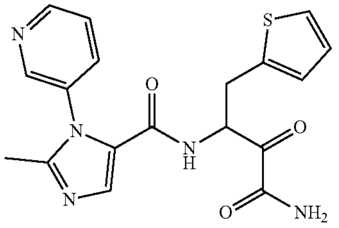
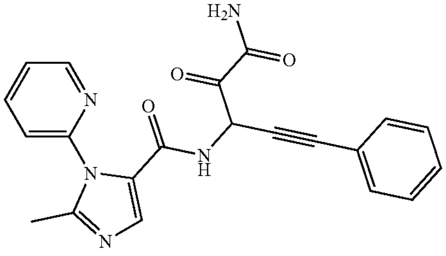 [SMILES: Cc1ncc(C(=O)NC(C#Cc2ccccc2)C(=O)C(N)=O)n1-c1ccccn1]
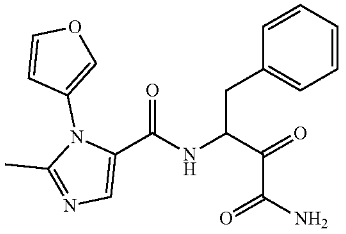 [SMILES: Cc1ncc(C(=O)NC(Cc2ccccc2)C(=O)C(N)=O)n1-c1ccoc1]
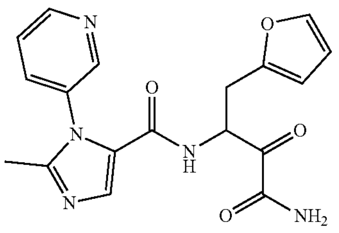 [SMILES: Cc1ncc(C(=O)NC(Cc2ccco2)C(=O)C(N)=O)n1-c1cccnc1]
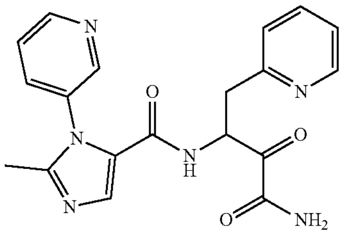 [SMILES: Cc1ncc(C(=O)NC(Cc2ccccn2)C(=O)C(N)=O)n1-c1cccnc1]
TABLE 1-continued
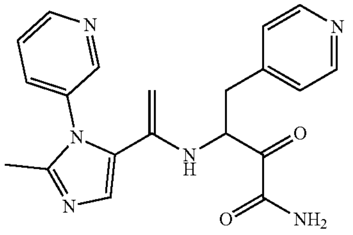 [SMILES: C=C(NC(Cc1ccncc1)C(=O)C(N)=O)c1cnc(C)n1-c1cccnc1]
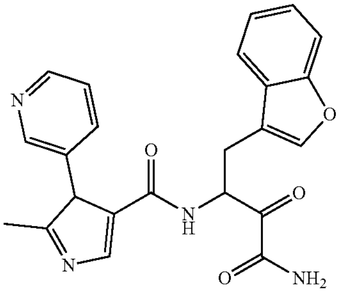 [SMILES: CC1=NC=C(C(=O)NC(Cc2coc3ccccc23)C(=O)C(N)=O)C1c1cccnc1]
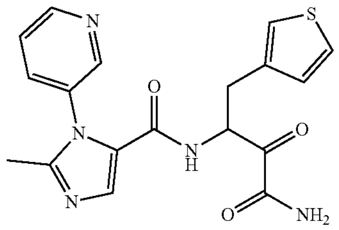 [SMILES: Cc1ncc(C(=O)NC(Cc2ccsc2)C(=O)C(N)=O)n1-c1cccnc1]
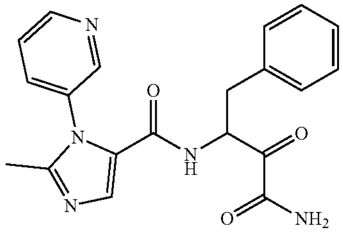 [SMILES: Cc1ncc(C(=O)NC(Cc2ccccc2)C(=O)C(N)=O)n1-c1cccnc1]
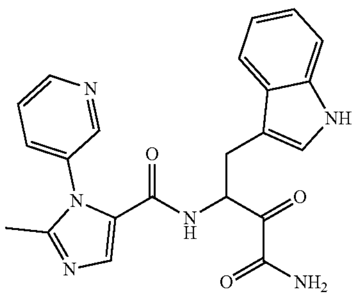 [SMILES: Cc1ncc(C(=O)NC(Cc2c[nH]c3ccccc23)C(=O)C(N)=O)n1-c1cccnc1]
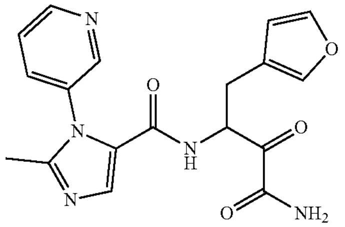 [SMILES: Cc1ncc(C(=O)NC(Cc2ccoc2)C(=O)C(N)=O)n1-c1cccnc1]

TABLE 1-continued
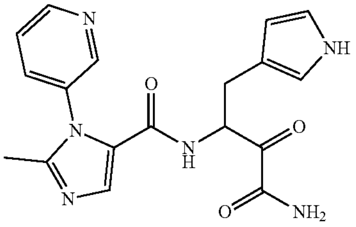 [SMILES: Cc1ncc(C(=O)NC(Cc2cc[nH]c2)C(=O)C(N)=O)n1-c1cccnc1]
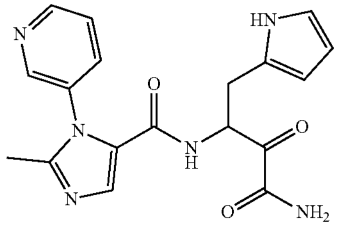 [SMILES: Cc1ncc(C(=O)NC(Cc2ccc[nH]2)C(=O)C(N)=O)n1-c1cccnc1]
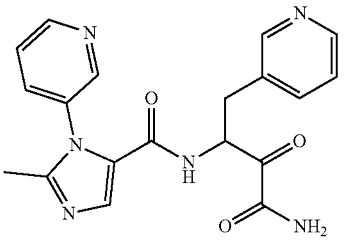 [SMILES: Cc1ncc(C(=O)NC(Cc2cccnc2)C(=O)C(N)=O)n1-c1cccnc1]
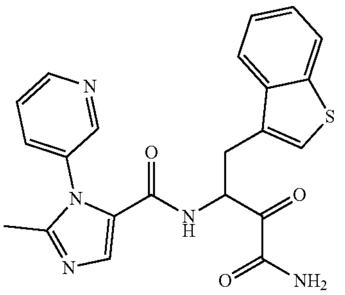 [SMILES: Cc1ncc(C(=O)NC(Cc2csc3ccccc23)C(=O)C(N)=O)n1-c1cccnc1]
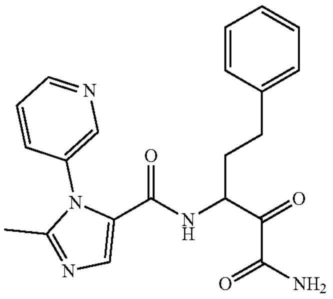 [SMILES: Cc1ncc(C(=O)NC(CCc2ccccc2)C(=O)C(N)=O)n1-c1cccnc1]
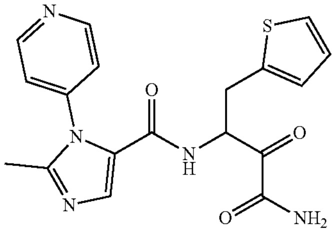
TABLE 1-continued
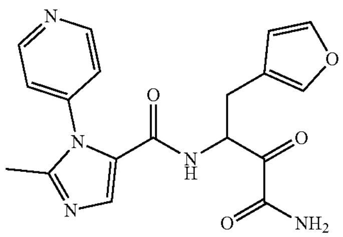 [SMILES: Cc1ncc(C(=O)NC(Cc2ccoc2)C(=O)C(N)=O)n1-c1ccncc1]
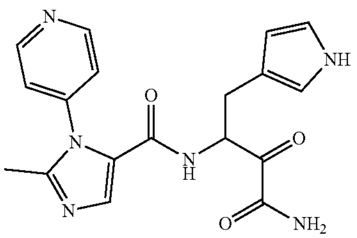 [SMILES: Cc1ncc(C(=O)NC(Cc2cc[nH]c2)C(=O)C(N)=O)n1-c1ccncc1]
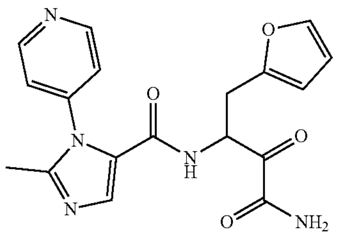 [SMILES: Cc1ncc(C(=O)NC(Cc2ccco2)C(=O)C(N)=O)n1-c1ccncc1]
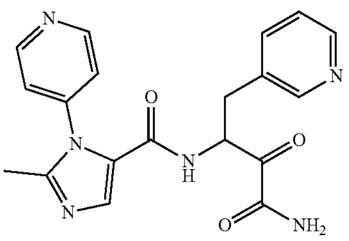 [SMILES: Cc1ncc(C(=O)NC(Cc2cccnc2)C(=O)C(N)=O)n1-c1ccncc1]
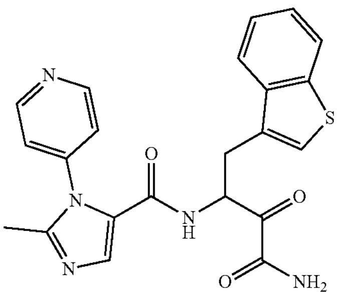 [SMILES: Cc1ncc(C(=O)NC(Cc2csc3ccccc23)C(=O)C(N)=O)n1-c1ccncc1]
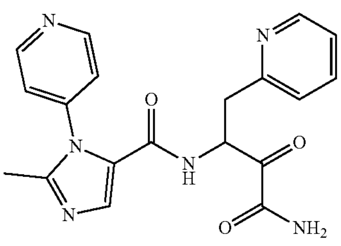 [SMILES: Cc1ncc(C(=O)NC(Cc2ccccn2)C(=O)C(N)=O)n1-c1ccncc1]

TABLE 1-continued
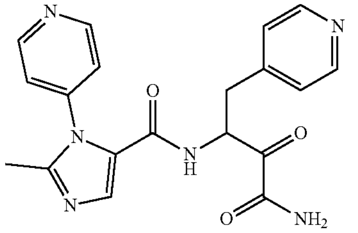 [SMILES: Cc1ncc(C(=O)NC(Cc2ccncc2)C(=O)C(N)=O)n1-c1ccncc1]
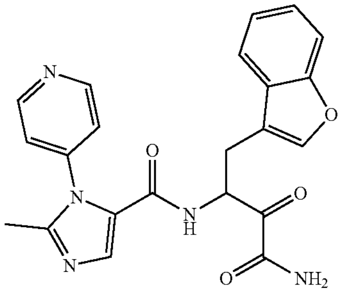 [SMILES: Cc1ncc(C(=O)NC(Cc2coc3ccccc23)C(=O)C(N)=O)n1-c1ccncc1]
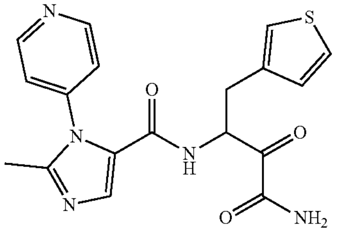 [SMILES: Cc1ncc(C(=O)NC(Cc2ccsc2)C(=O)C(N)=O)n1-c1ccncc1]
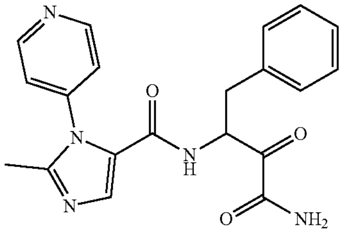
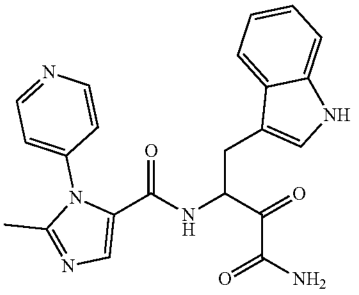 [SMILES: Cc1ncc(C(=O)NC(Cc2c[nH]c3ccccc23)C(=O)C(N)=O)n1-c1ccncc1]
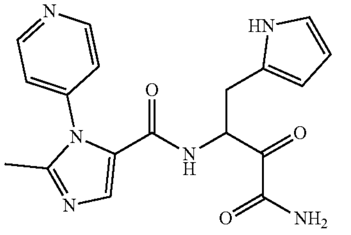 [SMILES: Cc1ncc(C(=O)NC(Cc2ccc[nH]2)C(=O)C(N)=O)n1-c1ccncc1]
TABLE 1-continued
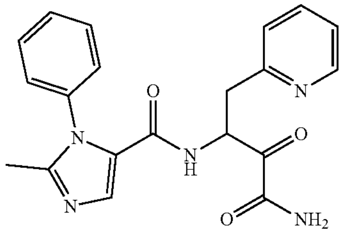
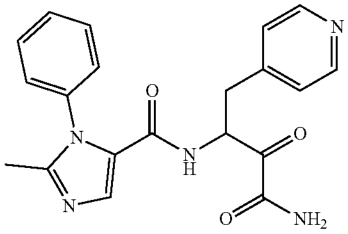 [SMILES: Cc1ncc(C(=O)NC(Cc2ccncc2)C(=O)C(N)=O)n1-c1ccccc1]
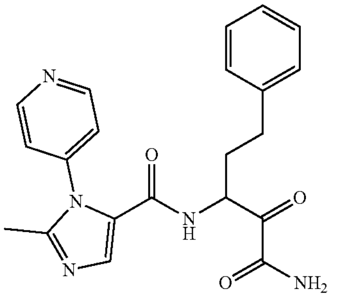 [SMILES: Cc1ncc(C(=O)NC(CCc2ccccc2)C(=O)C(N)=O)n1-c1ccncc1]
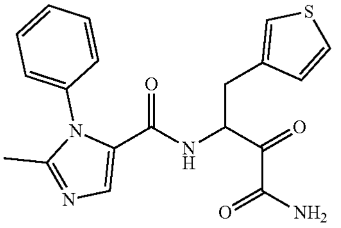 [SMILES: Cc1ncc(C(=O)NC(Cc2ccsc2)C(=O)C(N)=O)n1-c1ccccc1]
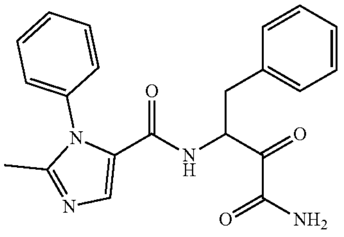
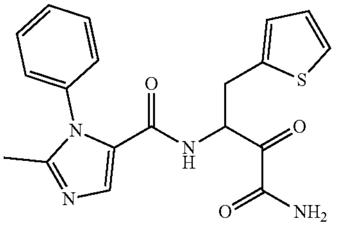 [SMILES: Cc1ncc(C(=O)NC(Cc2cccs2)C(=O)C(N)=O)n1-c1ccccc1]

TABLE 1-continued
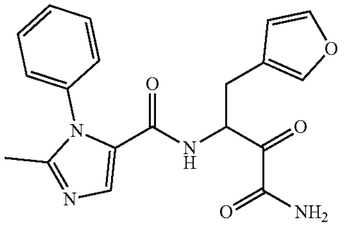 [SMILES: Cc1ncc(C(=O)NC(Cc2ccoc2)C(=O)C(N)=O)n1-c1ccccc1]
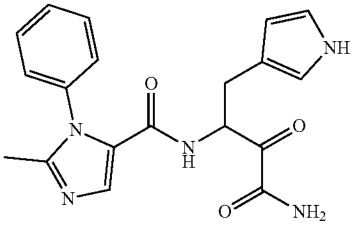 [SMILES: Cc1ncc(C(=O)NC(Cc2cc[nH]c2)C(=O)C(N)=O)n1-c1ccccc1]
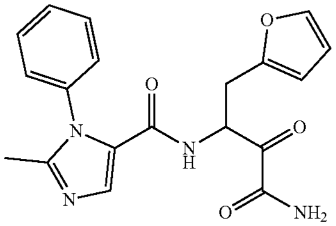 [SMILES: Cc1ncc(C(=O)NC(Cc2ccco2)C(=O)C(N)=O)n1-c1ccccc1]
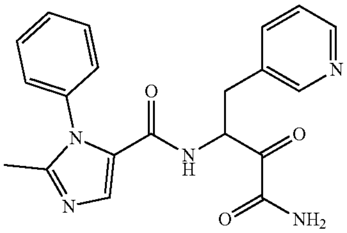
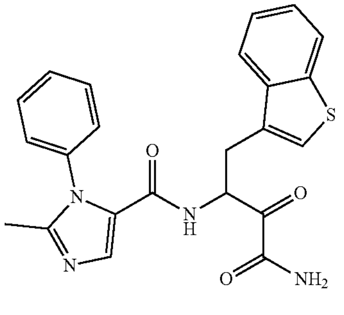 [SMILES: Cc1ncc(C(=O)NC(Cc2csc3ccccc23)C(=O)C(N)=O)n1-c1ccccc1]
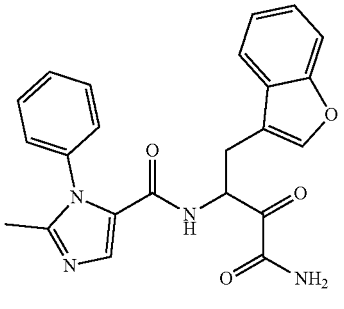
TABLE 1-continued
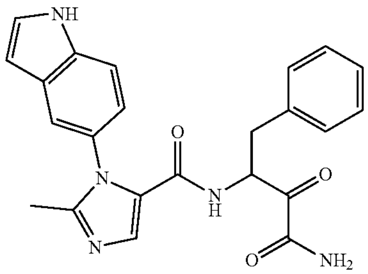 [SMILES: Cc1ncc(C(=O)NC(Cc2ccccc2)C(=O)C(N)=O)n1-c1ccc2[nH]ccc2c1]
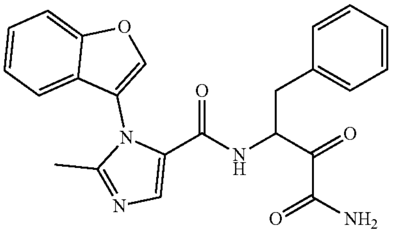
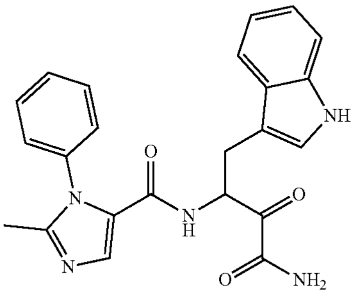 [SMILES: Cc1ncc(C(=O)NC(Cc2c[nH]c3ccccc23)C(=O)C(N)=O)n1-c1ccccc1]
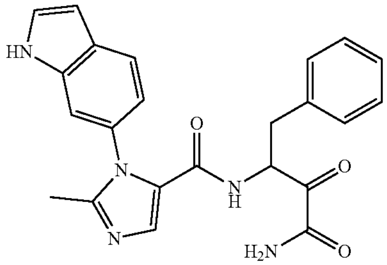 [SMILES: Cc1ncc(C(=O)NC(Cc2ccccc2)C(=O)C(N)=O)n1-c1ccc2cc[nH]c2c1]
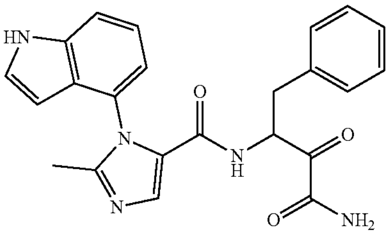 [SMILES: Cc1ncc(C(=O)NC(Cc2ccccc2)C(=O)C(N)=O)n1-c1cccc2[nH]ccc12]
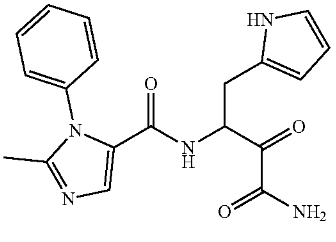

TABLE 1-continued
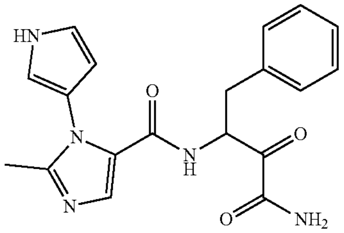 [SMILES: Cc1ncc(C(=O)NC(Cc2ccccc2)C(=O)C(N)=O)n1-c1cc[nH]c1]
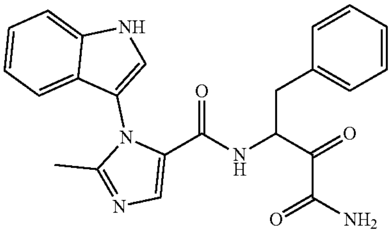 [SMILES: Cc1ncc(C(=O)NC(Cc2ccccc2)C(=O)C(N)=O)n1-c1c[nH]c2ccccc12]
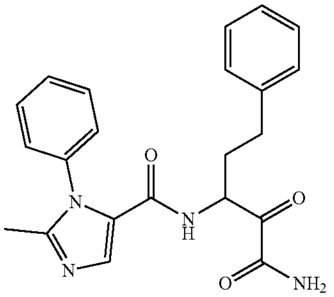 [SMILES: Cc1ncc(C(=O)NC(CCc2ccccc2)C(=O)C(N)=O)n1-c1ccccc1]
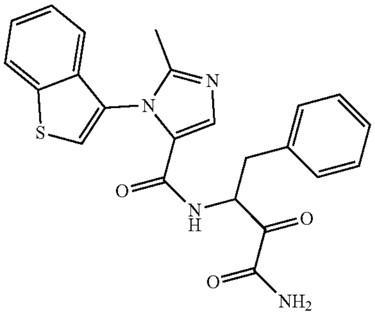 [SMILES: Cc1ncc(C(=O)NC(Cc2ccccc2)C(=O)C(N)=O)n1-c1csc2ccccc12]
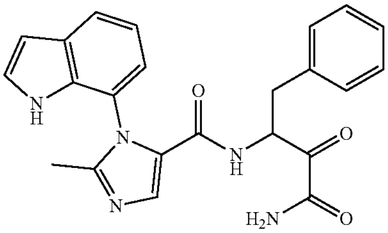 [SMILES: Cc1ncc(C(=O)NC(Cc2ccccc2)C(=O)C(N)=O)n1-c1cccc2cc[nH]c12]
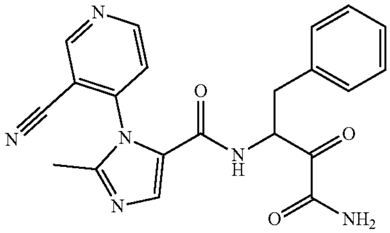 [SMILES: Cc1ncc(C(=O)NC(Cc2ccccc2)C(=O)C(N)=O)n1-c1ccncc1C#N]
TABLE 1-continued
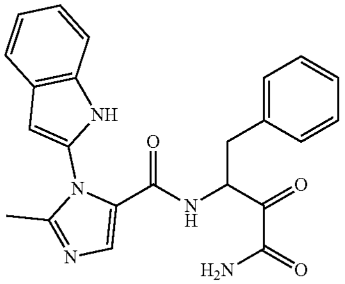 [SMILES: Cc1ncc(C(=O)NC(Cc2ccccc2)C(=O)C(N)=O)n1-c1cc2ccccc2[nH]1]
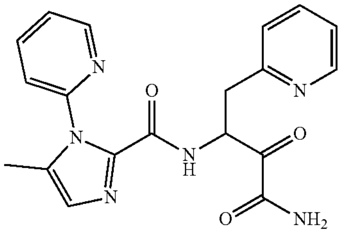 [SMILES: Cc1cnc(C(=O)NC(Cc2ccccn2)C(=O)C(N)=O)n1-c1ccccn1]
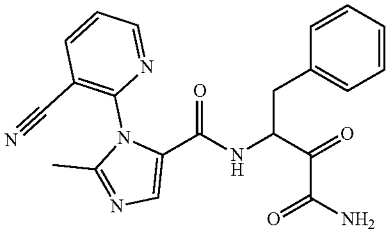 [SMILES: Cc1ncc(C(=O)NC(Cc2ccccc2)C(=O)C(N)=O)n1-c1ncccc1C#N]
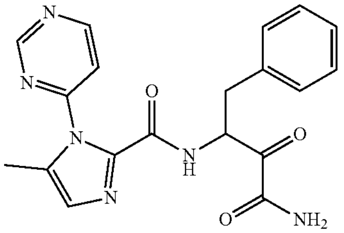
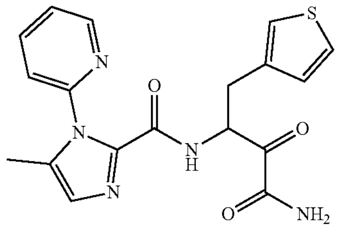 [SMILES: Cc1cnc(C(=O)NC(Cc2ccsc2)C(=O)C(N)=O)n1-c1ccccn1]
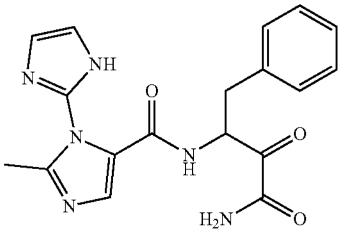

TABLE 1-continued
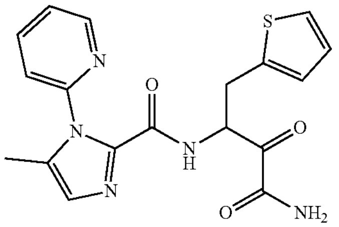 [SMILES: Cc1cnc(C(=O)NC(Cc2cccs2)C(=O)C(N)=O)n1-c1ccccn1]
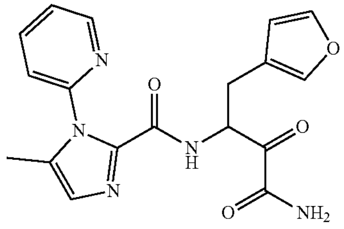 [SMILES: Cc1cnc(C(=O)NC(Cc2ccoc2)C(=O)C(N)=O)n1-c1ccccn1]
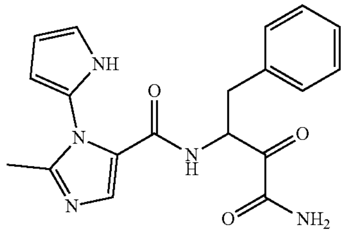 [SMILES: Cc1ncc(C(=O)NC(Cc2ccccc2)C(=O)C(N)=O)n1-c1ccc[nH]1]
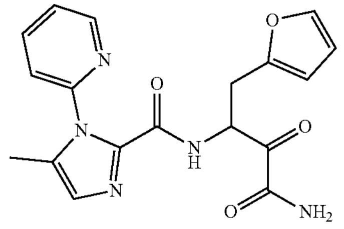 [SMILES: Cc1cnc(C(=O)NC(Cc2ccco2)C(=O)C(N)=O)n1-c1ccccn1]
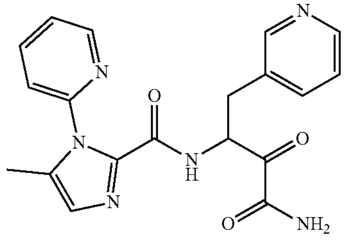
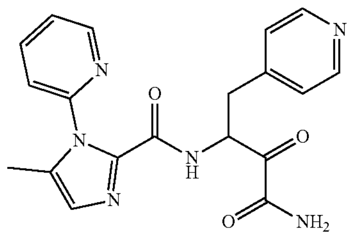
TABLE 1-continued
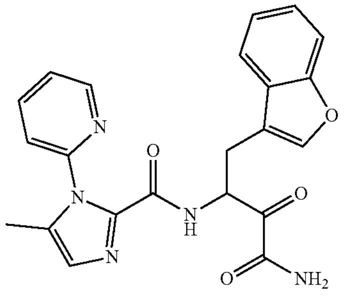 [SMILES: Cc1cnc(C(=O)NC(Cc2coc3ccccc23)C(=O)C(N)=O)n1-c1ccccn1]
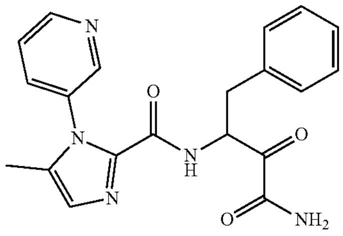
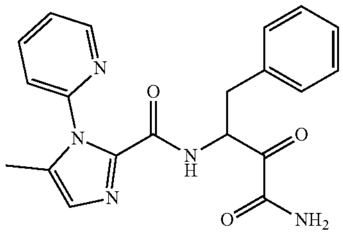
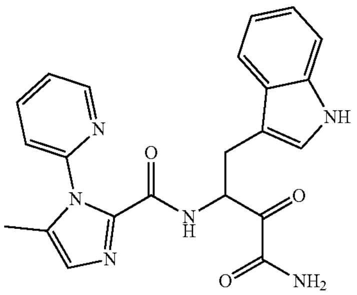 [SMILES: Cc1cnc(C(=O)NC(Cc2c[nH]c3ccccc23)C(=O)C(N)=O)n1-c1ccccn1]
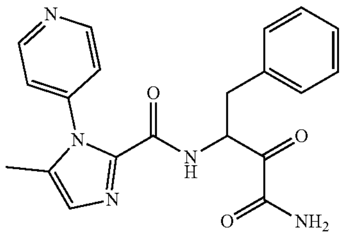
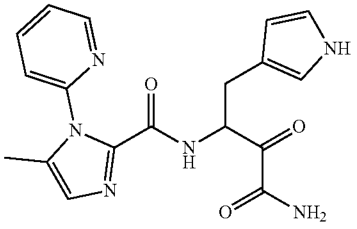 [SMILES: Cc1cnc(C(=O)NC(Cc2cc[nH]c2)C(=O)C(N)=O)n1-c1ccccn1]

TABLE 1-continued
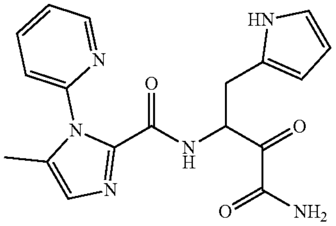 [SMILES: Cc1cnc(C(=O)NC(Cc2ccc[nH]2)C(=O)C(N)=O)n1-c1ccccn1]
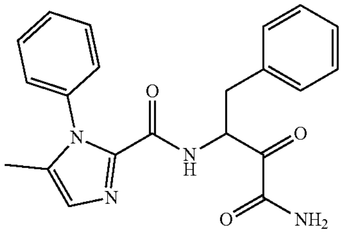
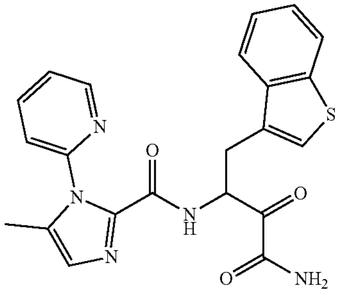 [SMILES: Cc1cnc(C(=O)NC(Cc2csc3ccccc23)C(=O)C(N)=O)n1-c1ccccn1]
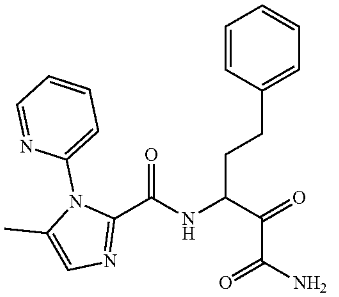 [SMILES: Cc1cnc(C(=O)NC(CCc2ccccc2)C(=O)C(N)=O)n1-c1ccccn1]
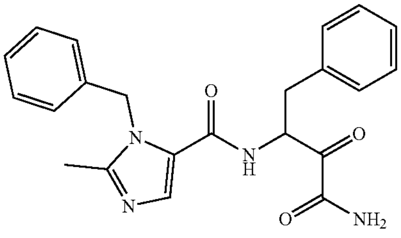 [SMILES: Cc1ncc(C(=O)NC(Cc2ccccc2)C(=O)C(N)=O)n1Cc1ccccc1]
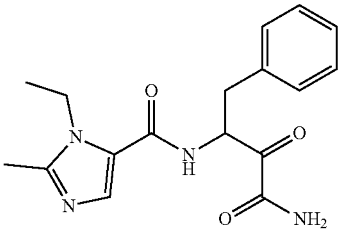 [SMILES: CCn1c(C(=O)NC(Cc2ccccc2)C(=O)C(N)=O)cnc1C]
TABLE 1-continued
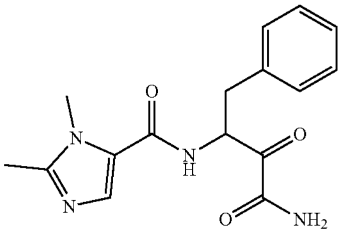 [SMILES: Cc1ncc(C(=O)NC(Cc2ccccc2)C(=O)C(N)=O)n1C]
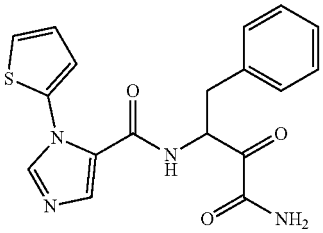 [SMILES: NC(=O)C(=O)C(Cc1ccccc1)NC(=O)c1cncn1-c1cccs1]
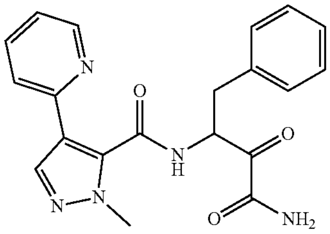 [SMILES: Cn1ncc(-c2ccccn2)c1C(=O)NC(Cc1ccccc1)C(=O)C(N)=O]
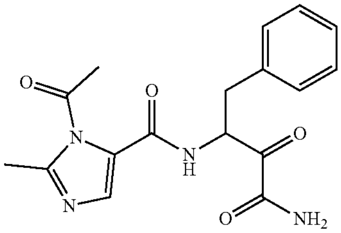 [SMILES: CC(=O)n1c(C(=O)NC(Cc2ccccc2)C(=O)C(N)=O)cnc1C]
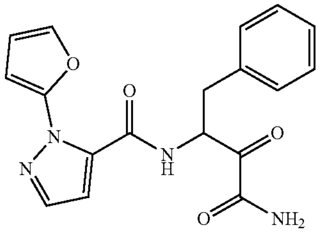 [SMILES: NC(=O)C(=O)C(Cc1ccccc1)NC(=O)c1ccnn1-c1ccco1]
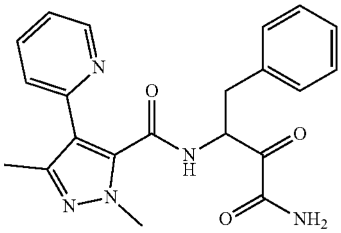 [SMILES: Cc1nn(C)c(C(=O)NC(Cc2ccccc2)C(=O)C(N)=O)c1-c1ccccn1]

TABLE 1-continued
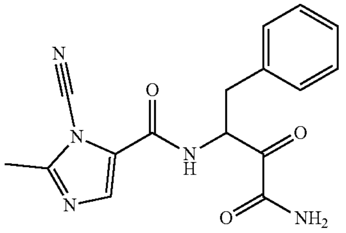 [SMILES: Cc1ncc(C(=O)NC(Cc2ccccc2)C(=O)C(N)=O)n1C#N]
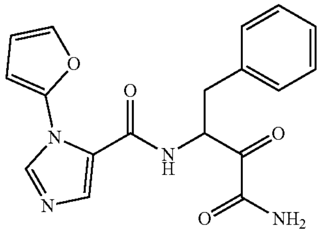 [SMILES: NC(=O)C(=O)C(Cc1ccccc1)NC(=O)c1cncn1-c1ccco1]
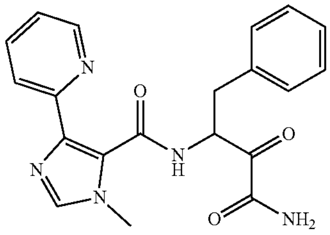 [SMILES: Cn1cnc(-c2ccccn2)c1C(=O)NC(Cc1ccccc1)C(=O)C(N)=O]
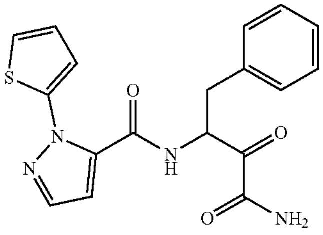 [SMILES: NC(=O)C(=O)C(Cc1ccccc1)NC(=O)c1ccnn1-c1cccs1]
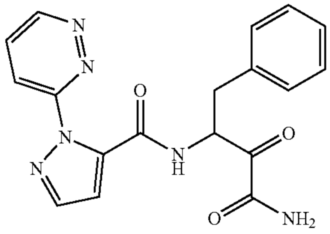 [SMILES: NC(=O)C(=O)C(Cc1ccccc1)NC(=O)c1ccnn1-c1cccnn1]
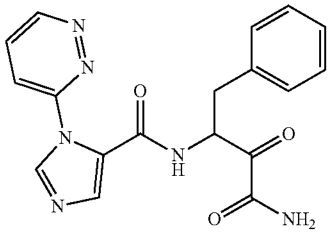 [SMILES: NC(=O)C(=O)C(Cc1ccccc1)NC(=O)c1cncn1-c1cccnn1]
TABLE 1-continued
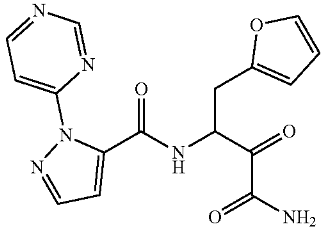 [SMILES: NC(=O)C(=O)C(Cc1ccco1)NC(=O)c1ccnn1-c1ccncn1]
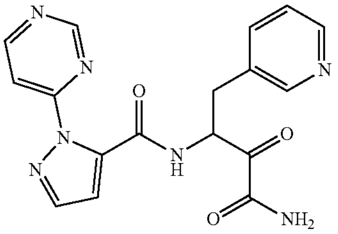 [SMILES: NC(=O)C(=O)C(Cc1cccnc1)NC(=O)c1ccnn1-c1ccncn1]
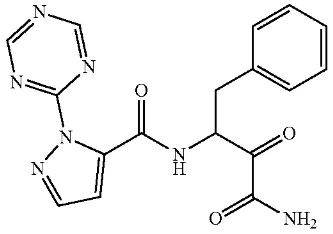 [SMILES: NC(=O)C(=O)C(Cc1ccccc1)NC(=O)c1ccnn1-c1ncncn1]
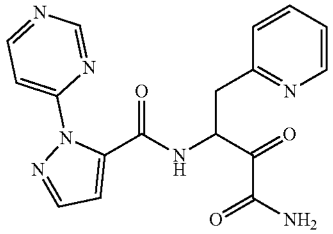 [SMILES: NC(=O)C(=O)C(Cc1ccccn1)NC(=O)c1ccnn1-c1ccncn1]
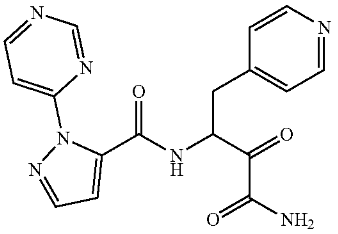 [SMILES: NC(=O)C(=O)C(Cc1ccncc1)NC(=O)c1ccnn1-c1ccncn1]
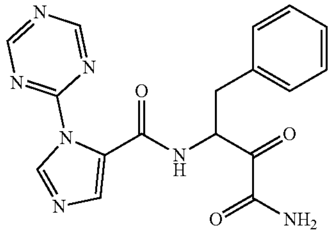 [SMILES: NC(=O)C(=O)C(Cc1ccccc1)NC(=O)c1cncn1-c1ncncn1]

TABLE 1-continued
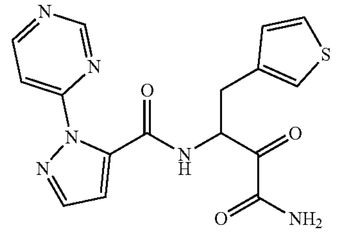 [SMILES: NC(=O)C(=O)C(Cc1ccsc1)NC(=O)c1ccnn1-c1ccncn1]
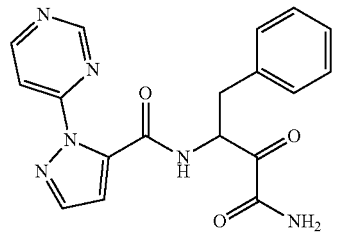 [SMILES: NC(=O)C(=O)C(Cc1ccccc1)NC(=O)c1ccnn1-c1ccncn1]
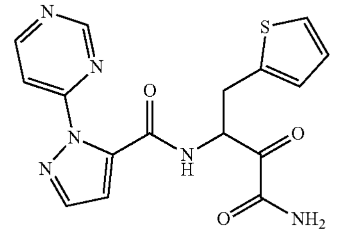 [SMILES: NC(=O)C(=O)C(Cc1cccs1)NC(=O)c1ccnn1-c1ccncn1]
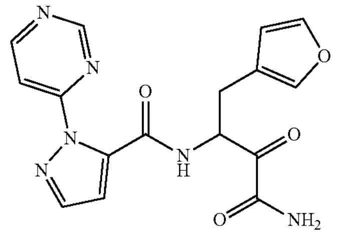 [SMILES: NC(=O)C(=O)C(Cc1ccoc1)NC(=O)c1ccnn1-c1ccncn1]
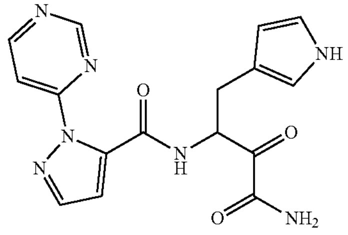
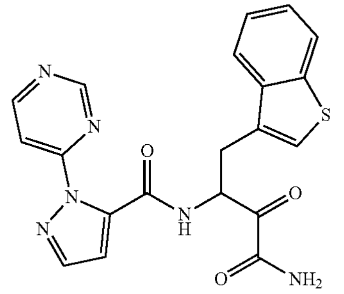
TABLE 1-continued
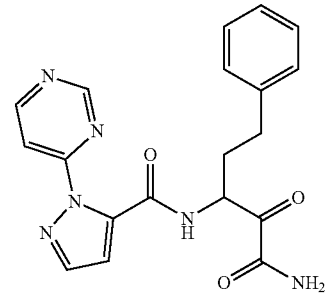 [SMILES: NC(=O)C(=O)C(CCc1ccccc1)NC(=O)c1ccnn1-c1ccncn1]
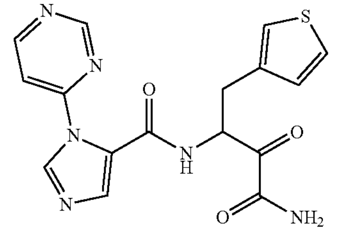 [SMILES: NC(=O)C(=O)C(Cc1ccsc1)NC(=O)c1cncn1-c1ccncn1]
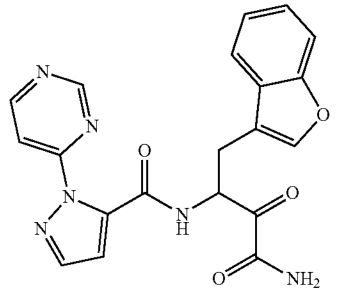
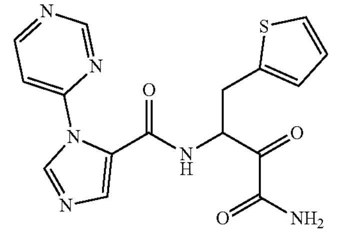 [SMILES: NC(=O)C(=O)C(Cc1cccs1)NC(=O)c1cncn1-c1ccncn1]
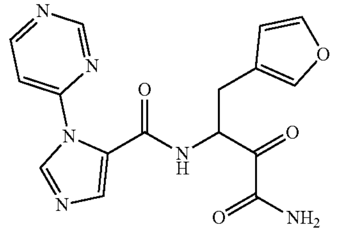 [SMILES: NC(=O)C(=O)C(Cc1ccoc1)NC(=O)c1cncn1-c1ccncn1]
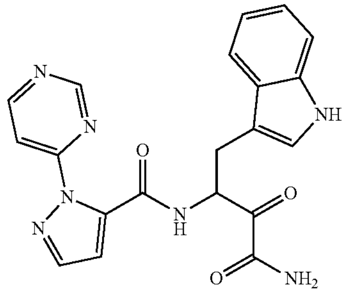

TABLE 1-continued
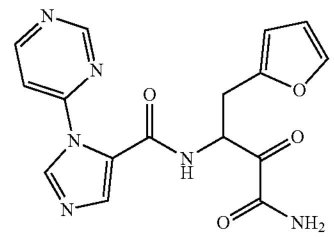 [SMILES: NC(=O)C(=O)C(Cc1ccco1)NC(=O)c1cncn1-c1ccncn1]
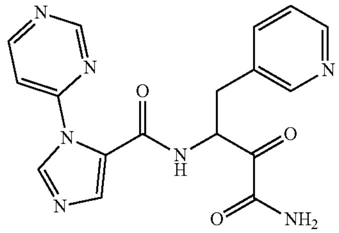 [SMILES: NC(=O)C(=O)C(Cc1cccnc1)NC(=O)c1cncn1-c1ccncn1]
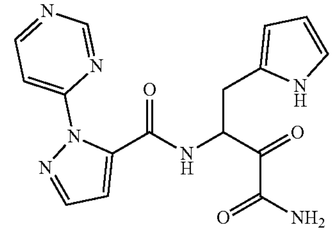 [SMILES: NC(=O)C(=O)C(Cc1ccc[nH]1)NC(=O)c1ccnn1-c1ccncn1]
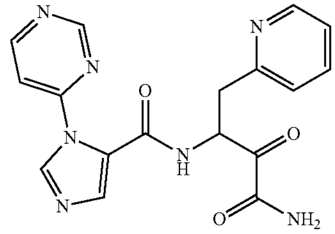 [SMILES: NC(=O)C(=O)C(Cc1ccccn1)NC(=O)c1cncn1-c1ccncn1]
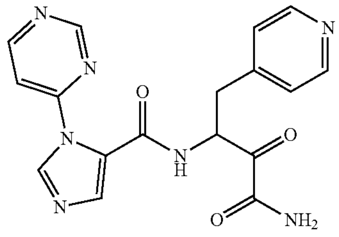 [SMILES: NC(=O)C(=O)C(Cc1ccncc1)NC(=O)c1cncn1-c1ccncn1]
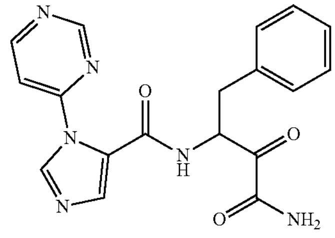 [SMILES: NC(=O)C(=O)C(Cc1ccccc1)NC(=O)c1cncn1-c1ccncn1]
TABLE 1-continued
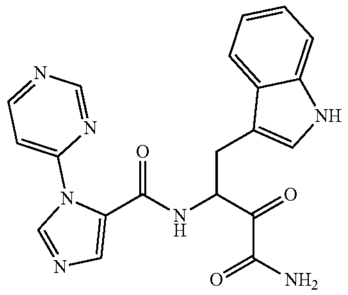
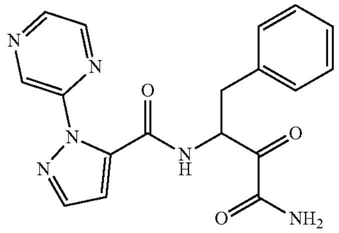
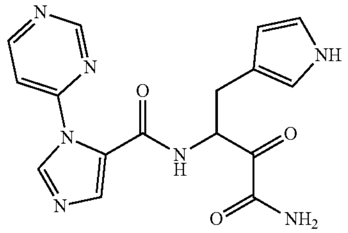 [SMILES: NC(=O)C(=O)C(Cc1cc[nH]c1)NC(=O)c1cncn1-c1ccncn1]
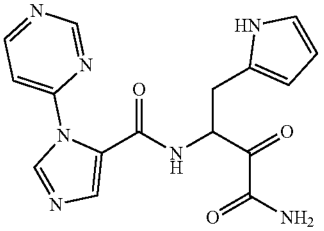 [SMILES: NC(=O)C(=O)C(Cc1ccc[nH]1)NC(=O)c1cncn1-c1ccncn1]
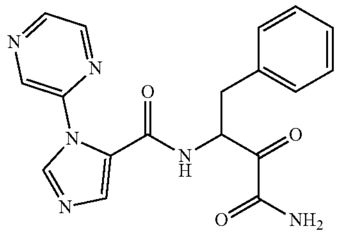
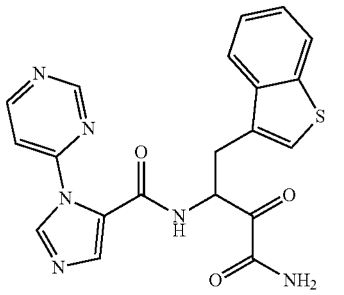

TABLE 1-continued
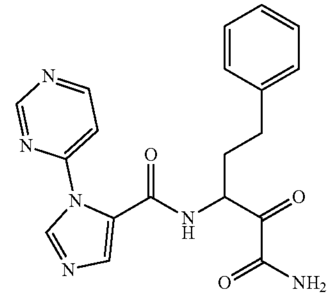
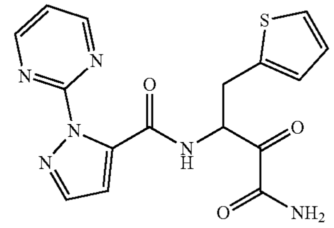
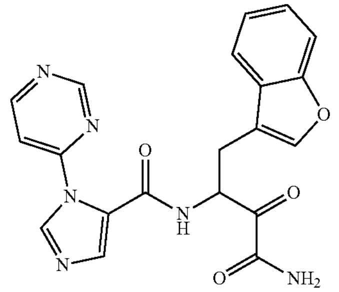
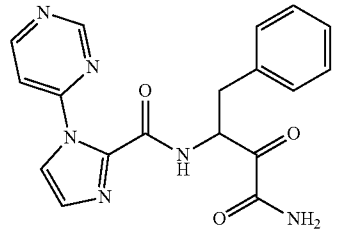
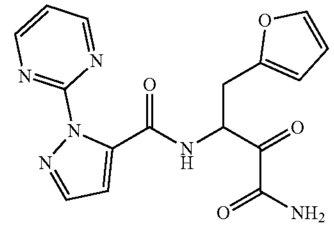
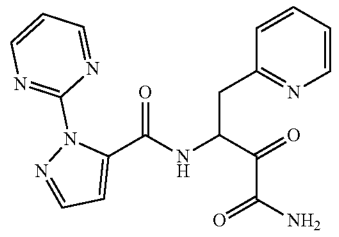 [SMILES: NC(=O)C(=O)C(Cc1ccccn1)NC(=O)c1ccnn1-c1ncccn1]
TABLE 1-continued
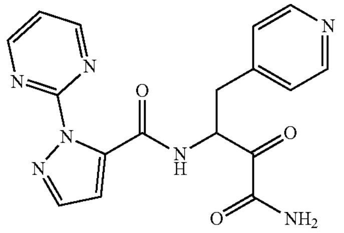 [SMILES: NC(=O)C(=O)C(Cc1ccncc1)NC(=O)c1ccnn1-c1ncccn1]
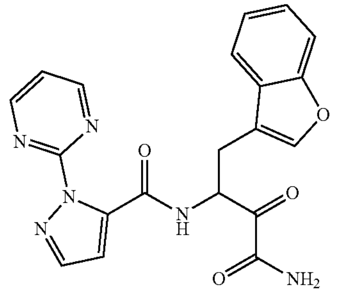
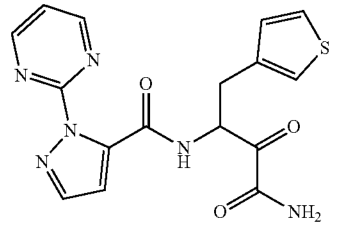 [SMILES: NC(=O)C(=O)C(Cc1ccsc1)NC(=O)c1ccnn1-c1ncccn1]
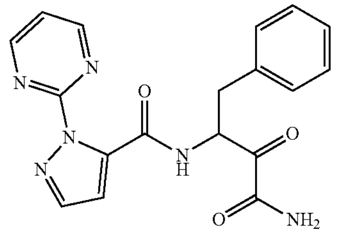 [SMILES: NC(=O)C(=O)C(Cc1ccccc1)NC(=O)c1ccnn1-c1ncccn1]
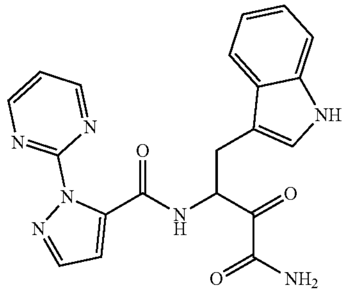
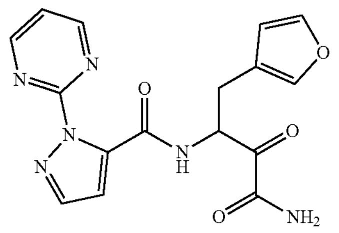

TABLE 1-continued
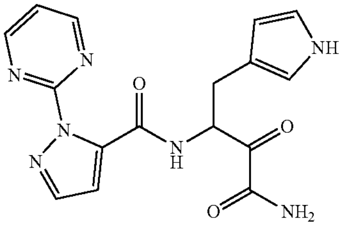
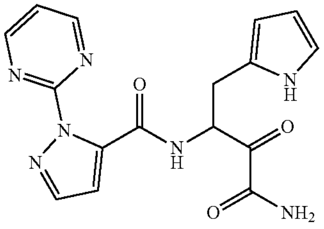
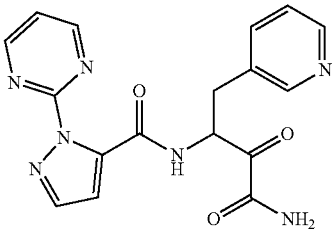 [SMILES: NC(=O)C(=O)C(Cc1cccnc1)NC(=O)c1ccnn1-c1ncccn1]
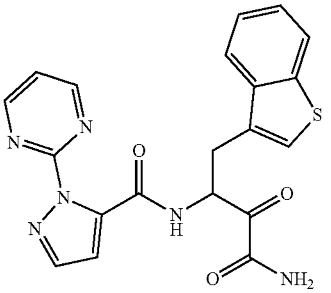
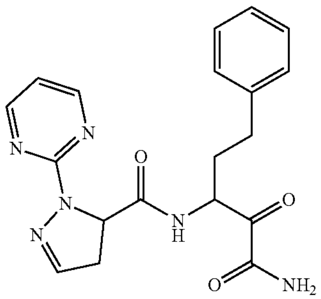
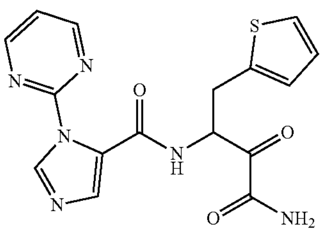
TABLE 1-continued
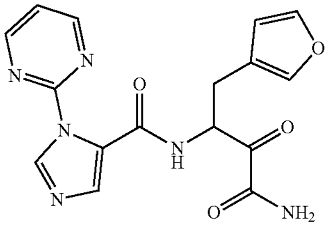
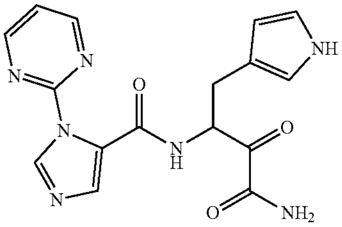
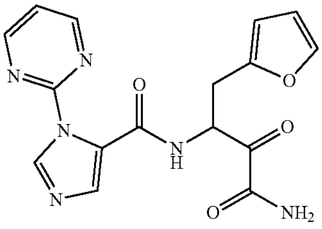
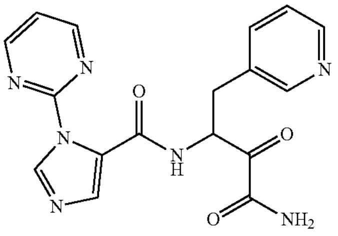
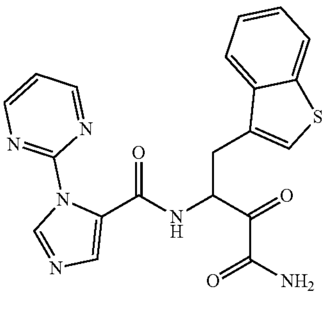 [SMILES: NC(=O)C(=O)C(Cc1csc2ccccc12)NC(=O)c1cncn1-c1ncccn1]
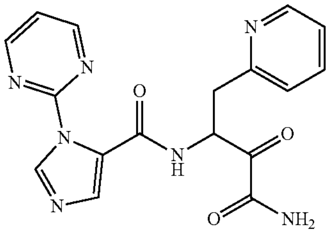

TABLE 1-continued
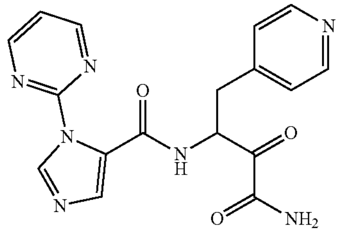 [SMILES: NC(=O)C(=O)C(Cc1ccncc1)NC(=O)c1cncn1-c1ncccn1]
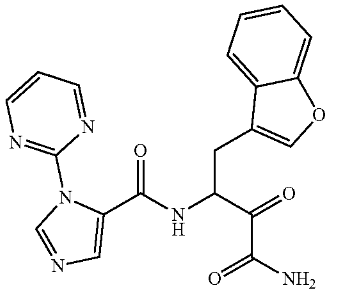 [SMILES: NC(=O)C(=O)C(Cc1coc2ccccc12)NC(=O)c1cncn1-c1ncccn1]
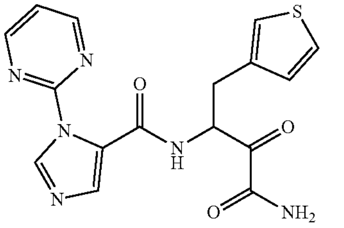
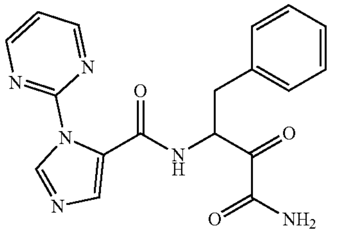 [SMILES: NC(=O)C(=O)C(Cc1ccccc1)NC(=O)c1cncn1-c1ncccn1]
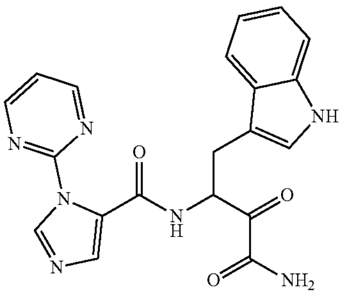
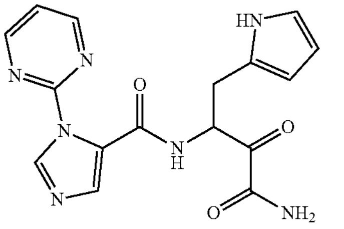
TABLE 1-continued
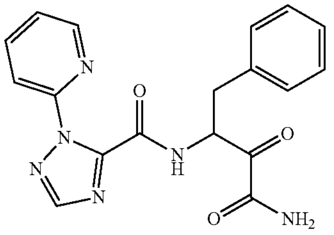 [SMILES: NC(=O)C(=O)C(Cc1ccccc1)NC(=O)c1ncnn1-c1ccccn1]
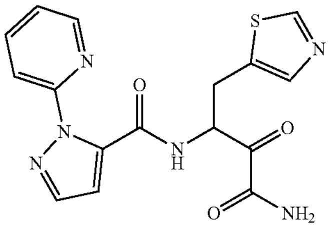 [SMILES: NC(=O)C(=O)C(Cc1cncs1)NC(=O)c1ccnn1-c1ccccn1]
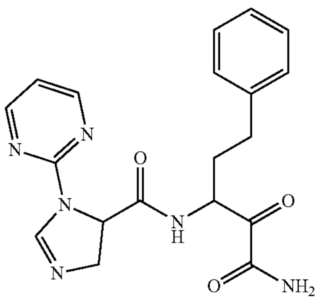 [SMILES: NC(=O)C(=O)C(CCc1ccccc1)NC(=O)C1CN=CN1c1ncccn1]
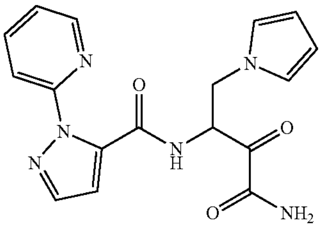 [SMILES: NC(=O)C(=O)C(Cn1cccc1)NC(=O)c1ccnn1-c1ccccn1]
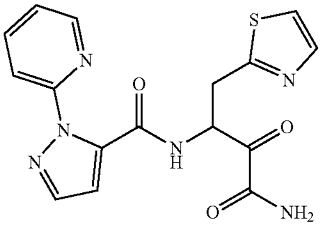 [SMILES: NC(=O)C(=O)C(Cc1nccs1)NC(=O)c1ccnn1-c1ccccn1]
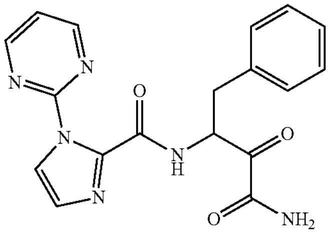 [SMILES: NC(=O)C(=O)C(Cc1ccccc1)NC(=O)c1nccn1-c1ncccn1]

TABLE 1-continued
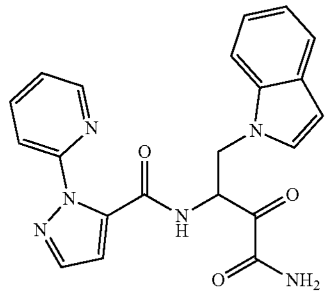 [SMILES: NC(=O)C(=O)C(Cn1ccc2ccccc21)NC(=O)c1ccnn1-c1ccccn1]
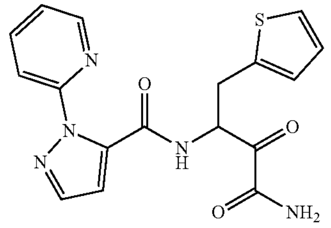
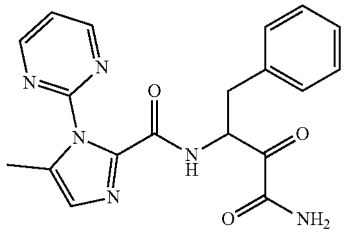
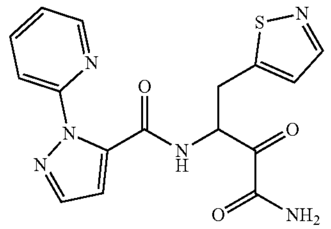 [SMILES: NC(=O)C(=O)C(Cc1ccns1)NC(=O)c1ccnn1-c1ccccn1]
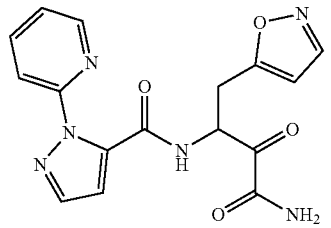 [SMILES: NC(=O)C(=O)C(Cc1ccno1)NC(=O)c1ccnn1-c1ccccn1]
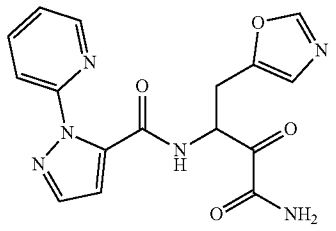 [SMILES: NC(=O)C(=O)C(Cc1cnco1)NC(=O)c1ccnn1-c1ccccn1]
TABLE 1-continued
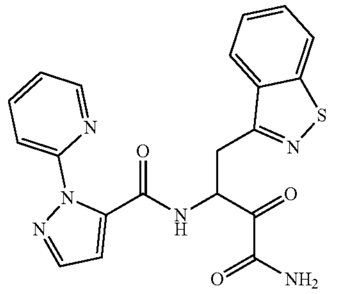
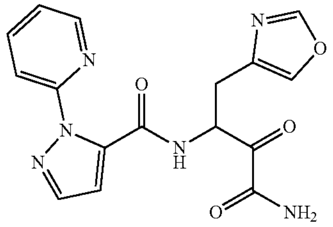
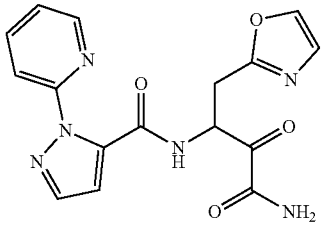 [SMILES: NC(=O)C(=O)C(Cc1ncco1)NC(=O)c1ccnn1-c1ccccn1]
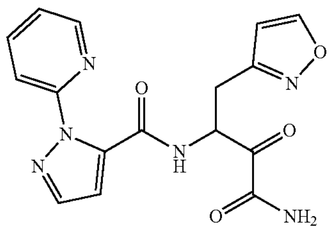
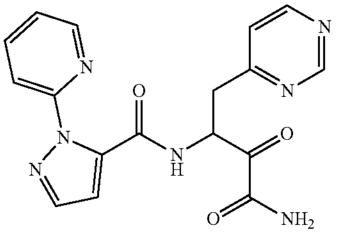 [SMILES: NC(=O)C(=O)C(Cc1ccncn1)NC(=O)c1ccnn1-c1ccccn1]
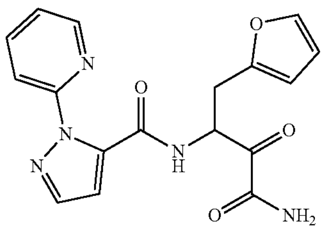

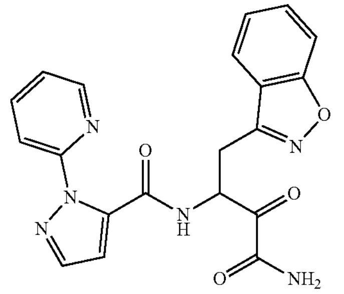 [SMILES: NC(=O)C(=O)C(Cc1noc2ccccc12)NC(=O)c1ccnn1-c1ccccn1]
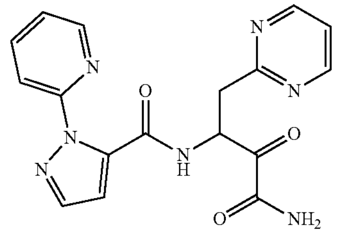 [SMILES: NC(=O)C(=O)C(Cc1ncccn1)NC(=O)c1ccnn1-c1ccccn1]
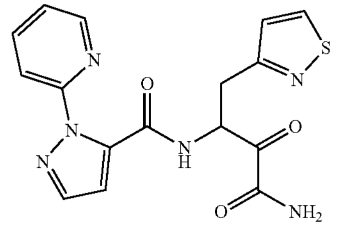 [SMILES: NC(=O)C(=O)C(Cc1ccsn1)NC(=O)c1ccnn1-c1ccccn1]
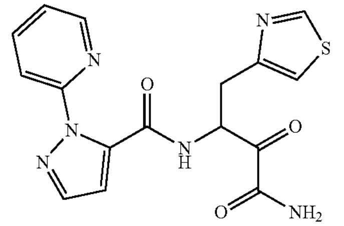
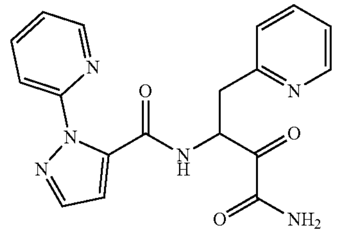 [SMILES: NC(=O)C(=O)C(Cc1ccccn1)NC(=O)c1ccnn1-c1ccccn1]
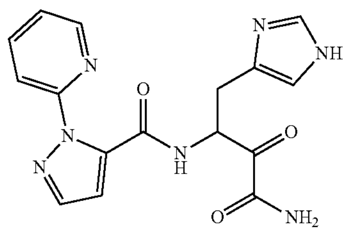
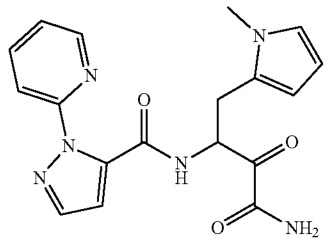 [SMILES: Cn1cccc1CC(NC(=O)c1ccnn1-c1ccccn1)C(=O)C(N)=O]
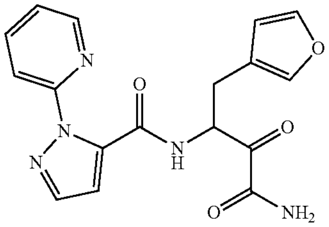
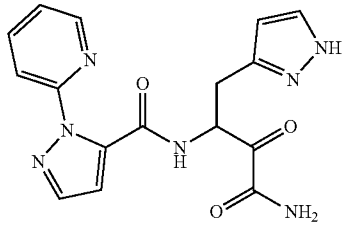 [SMILES: NC(=O)C(=O)C(Cc1cc[nH]n1)NC(=O)c1ccnn1-c1ccccn1]
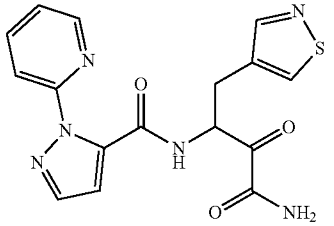 [SMILES: NC(=O)C(=O)C(Cc1cnsc1)NC(=O)c1ccnn1-c1ccccn1]
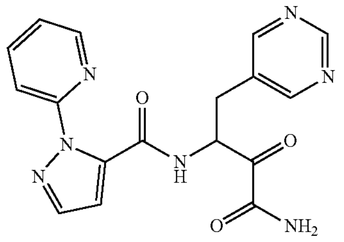 [SMILES: NC(=O)C(=O)C(Cc1cncnc1)NC(=O)c1ccnn1-c1ccccn1]
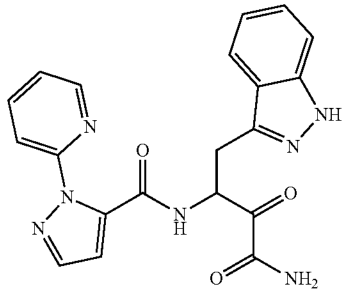

TABLE 1-continued
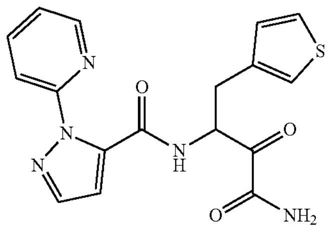
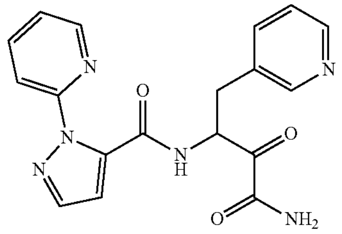 [SMILES: NC(=O)C(=O)C(Cc1cccnc1)NC(=O)c1ccnn1-c1ccccn1]
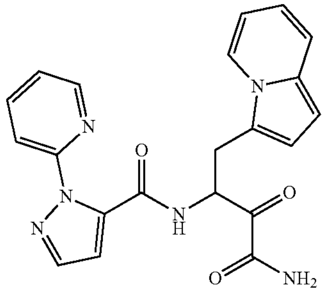 [SMILES: NC(=O)C(=O)C(Cc1ccc2ccccn12)NC(=O)c1ccnn1-c1ccccn1]
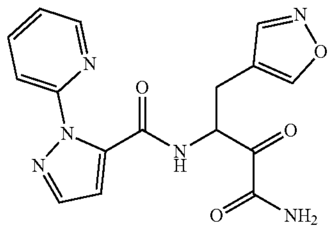
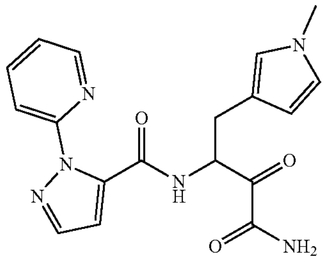 [SMILES: Cn1ccc(CC(NC(=O)c2ccnn2-c2ccccn2)C(=O)C(N)=O)c1]
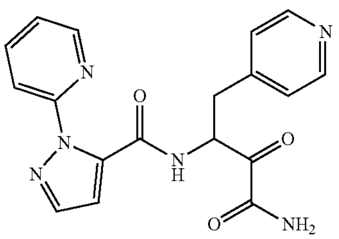 [SMILES: NC(=O)C(=O)C(Cc1ccncc1)NC(=O)c1ccnn1-c1ccccn1]
TABLE 1-continued
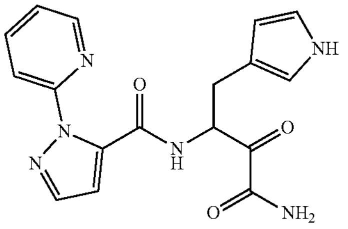
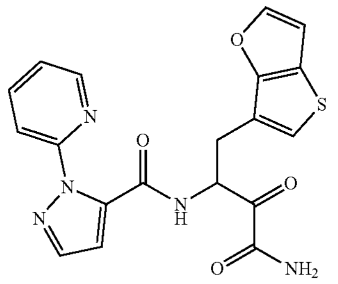
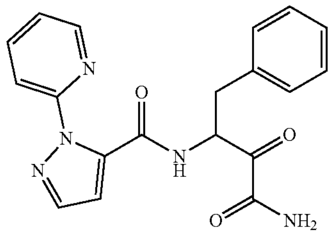 [SMILES: NC(=O)C(=O)C(Cc1ccccc1)NC(=O)c1ccnn1-c1ccccn1]
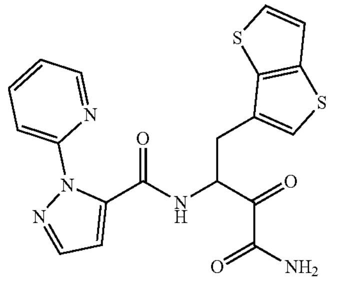 [SMILES: NC(=O)C(=O)C(Cc1csc2ccsc12)NC(=O)c1ccnn1-c1ccccn1]
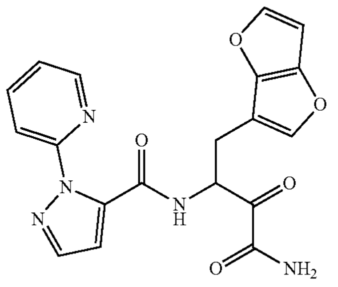 [SMILES: NC(=O)C(=O)C(Cc1coc2ccoc12)NC(=O)c1ccnn1-c1ccccn1]

TABLE 1-continued
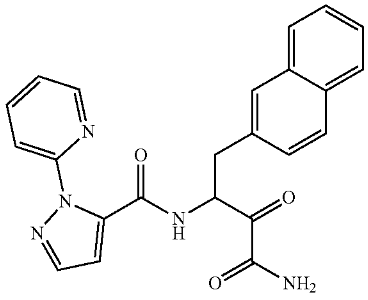
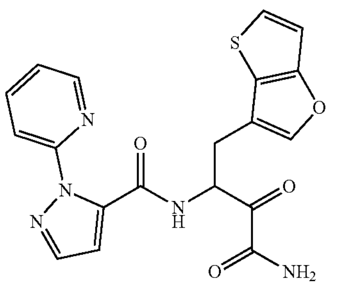
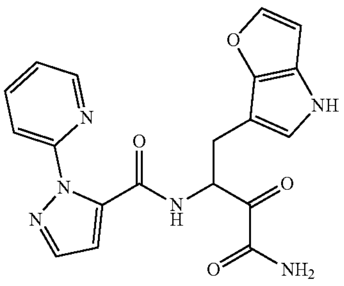 [SMILES: NC(=O)C(=O)C(Cc1c[nH]c2ccoc12)NC(=O)c1ccnn1-c1ccccn1]
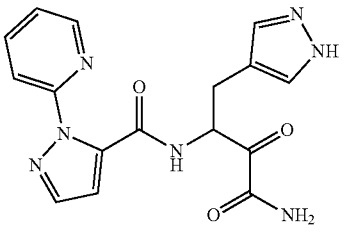 [SMILES: NC(=O)C(=O)C(Cc1cn[nH]c1)NC(=O)c1ccnn1-c1ccccn1]
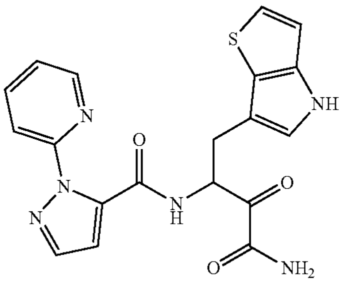 [SMILES: NC(=O)C(=O)C(Cc1c[nH]c2ccsc12)NC(=O)c1ccnn1-c1ccccn1]
TABLE 1-continued
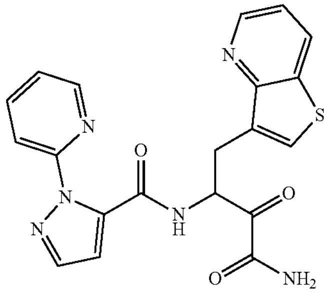
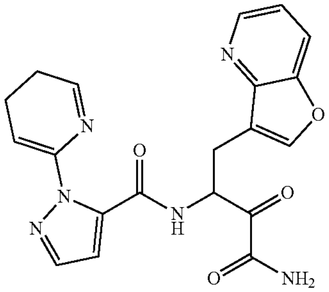 [SMILES: NC(=O)C(=O)C(Cc1coc2cccnc12)NC(=O)c1ccnn1C1=CCCC=N1]
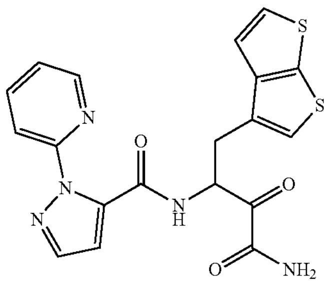
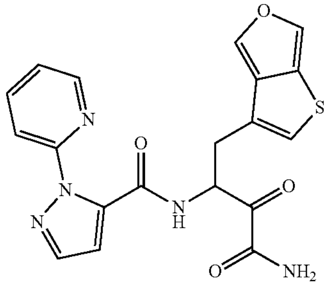 [SMILES: NC(=O)C(=O)C(Cc1csc2cocc12)NC(=O)c1ccnn1-c1ccccn1]
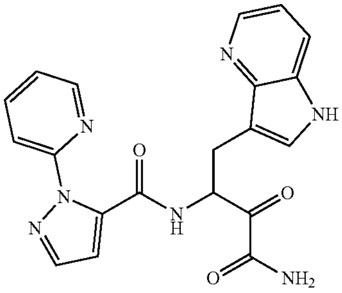

TABLE 1-continued
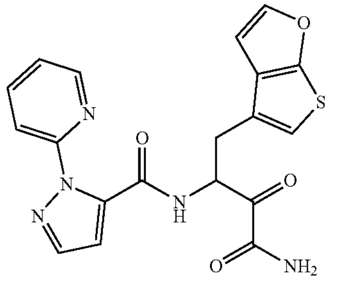
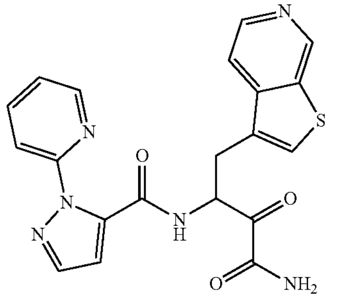 [SMILES: NC(=O)C(=O)C(Cc1csc2cnccc12)NC(=O)c1ccnn1-c1ccccn1]
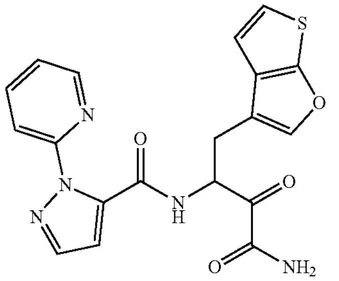
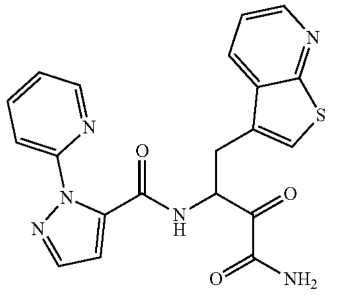
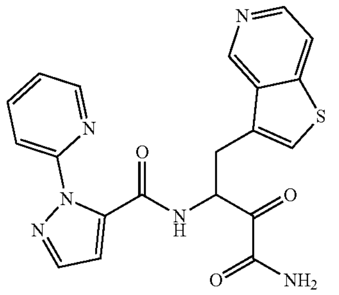
TABLE 1-continued
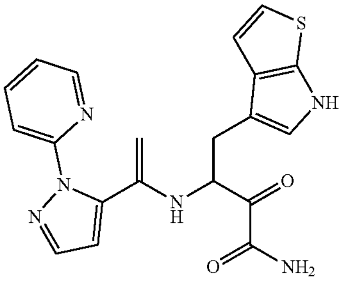 [SMILES: C=C(NC(Cc1c[nH]c2sccc12)C(=O)C(N)=O)c1ccnn1-c1ccccn1]
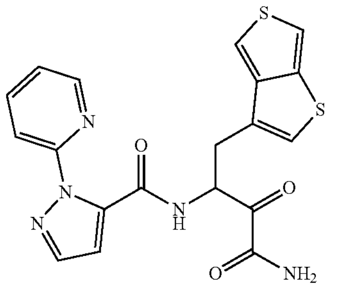 [SMILES: NC(=O)C(=O)C(Cc1csc2cscc12)NC(=O)c1ccnn1-c1ccccn1]
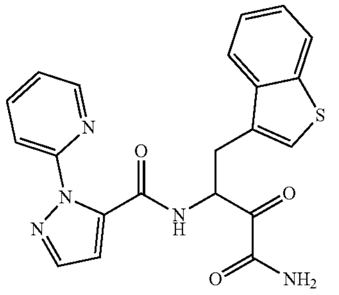
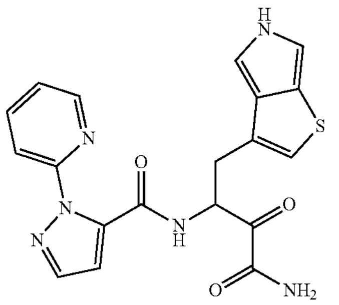
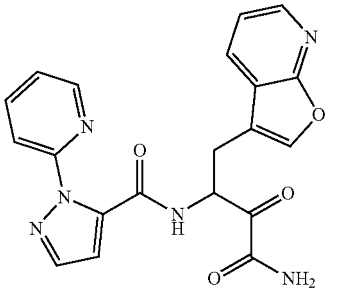

TABLE 1-continued
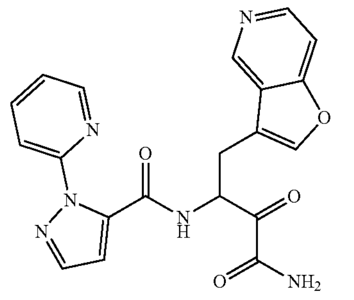 [SMILES: NC(=O)C(=O)C(Cc1coc2ccncc12)NC(=O)c1ccnn1-c1ccccn1]
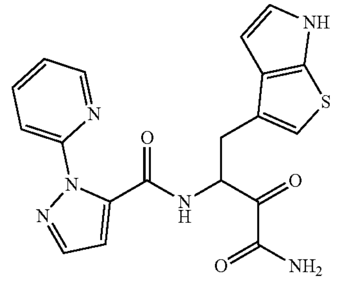 [SMILES: NC(=O)C(=O)C(Cc1csc2[nH]ccc12)NC(=O)c1ccnn1-c1ccccn1]
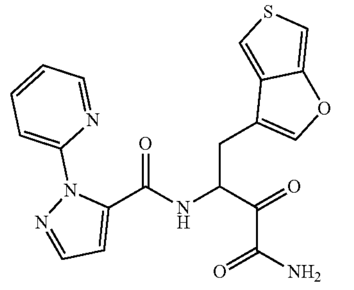 [SMILES: NC(=O)C(=O)C(Cc1coc2cscc12)NC(=O)c1ccnn1-c1ccccn1]
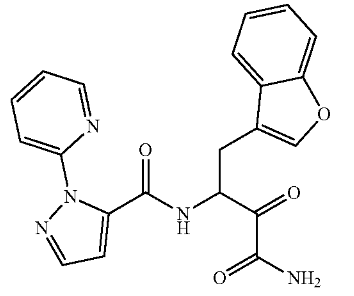 [SMILES: NC(=O)C(=O)C(Cc1coc2ccccc12)NC(=O)c1ccnn1-c1ccccn1]
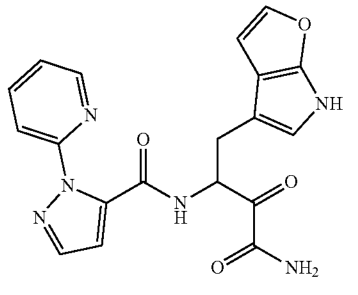
TABLE 1-continued
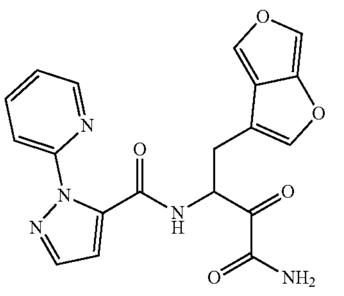 [SMILES: NC(=O)C(=O)C(Cc1coc2cocc12)NC(=O)c1ccnn1-c1ccccn1]
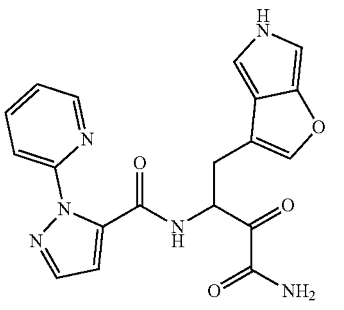
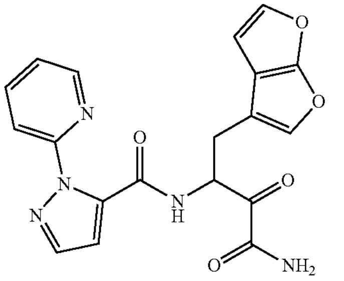 [SMILES: NC(=O)C(=O)C(Cc1coc2occc12)NC(=O)c1ccnn1-c1ccccn1]
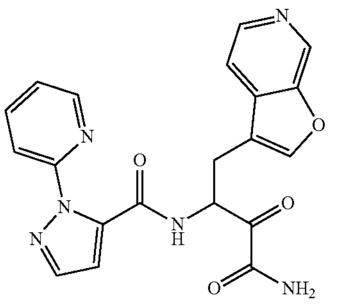 [SMILES: NC(=O)C(=O)C(Cc1coc2cnccc12)NC(=O)c1ccnn1-c1ccccn1]
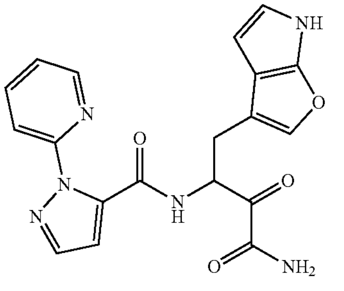

TABLE 1-continued
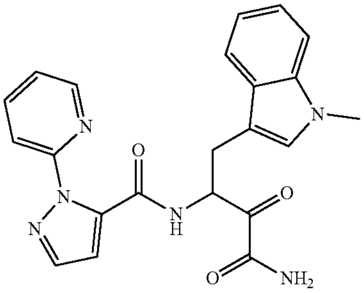 [SMILES: Cn1cc(CC(NC(=O)c2ccnn2-c2ccccn2)C(=O)C(N)=O)c2ccccc21]
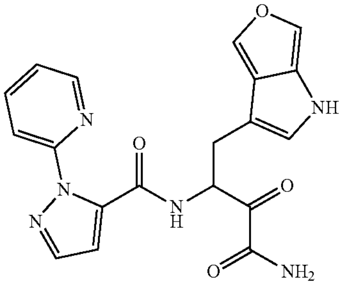
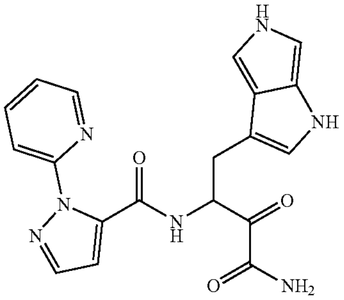
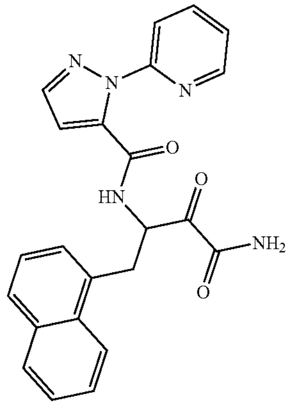 [SMILES: NC(=O)C(=O)C(Cc1cccc2ccccc12)NC(=O)c1ccnn1-c1ccccn1]
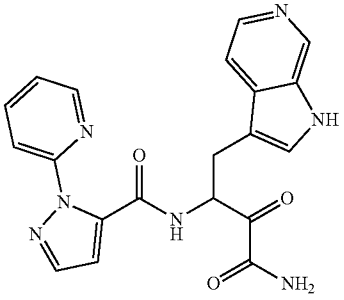 [SMILES: NC(=O)C(=O)C(Cc1c[nH]c2cnccc12)NC(=O)c1ccnn1-c1ccccn1]
TABLE 1-continued
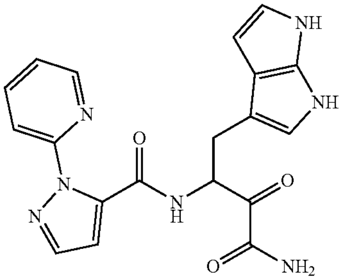
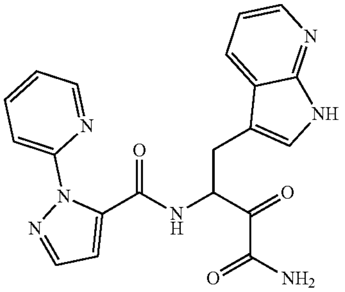 [SMILES: NC(=O)C(=O)C(Cc1c[nH]c2ncccc12)NC(=O)c1ccnn1-c1ccccn1]
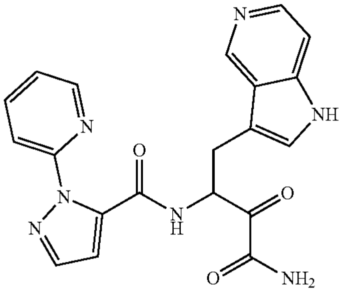 [SMILES: NC(=O)C(=O)C(Cc1c[nH]c2ccncc12)NC(=O)c1ccnn1-c1ccccn1]
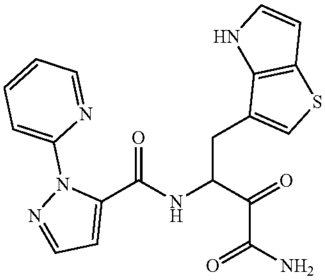 [SMILES: NC(=O)C(=O)C(Cc1csc2cc[nH]c12)NC(=O)c1ccnn1-c1ccccn1]
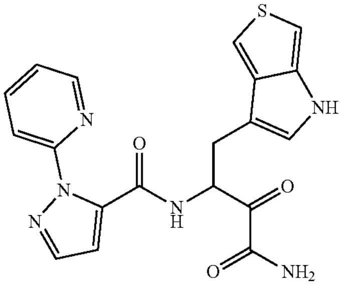

TABLE 1-continued
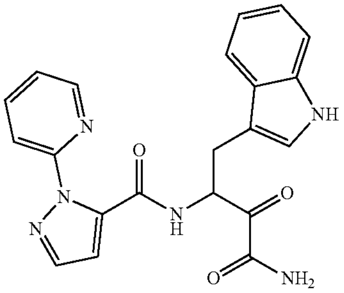 [SMILES: NC(=O)C(=O)C(Cc1c[nH]c2ccccc12)NC(=O)c1ccnn1-c1ccccn1]
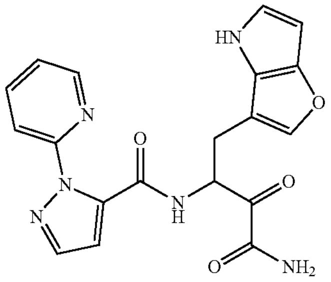
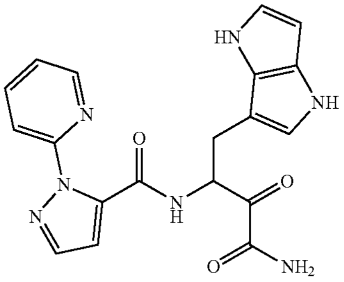
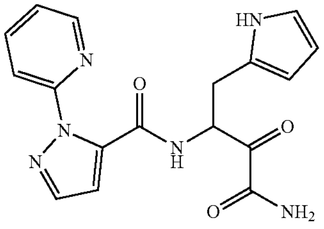 [SMILES: NC(=O)C(=O)C(Cc1ccc[nH]1)NC(=O)c1ccnn1-c1ccccn1]
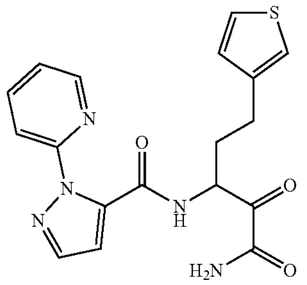 [SMILES: NC(=O)C(=O)C(CCc1ccsc1)NC(=O)c1ccnn1-c1ccccn1]
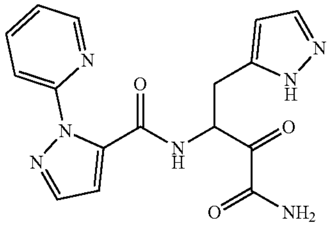 [SMILES: NC(=O)C(=O)C(Cc1ccn[nH]1)NC(=O)c1ccnn1-c1ccccn1]
TABLE 1-continued
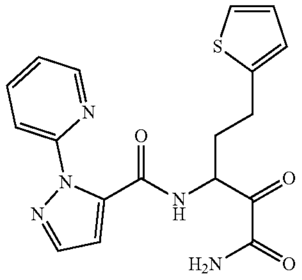 [SMILES: NC(=O)C(=O)C(CCc1cccs1)NC(=O)c1ccnn1-c1ccccn1]
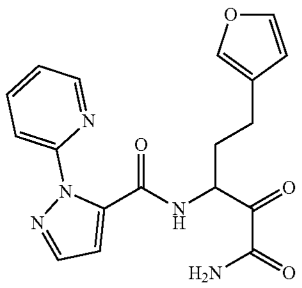
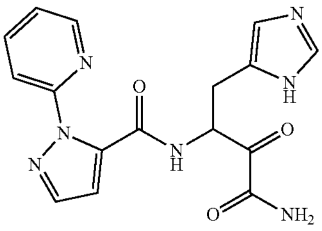 [SMILES: NC(=O)C(=O)C(Cc1cnc[nH]1)NC(=O)c1ccnn1-c1ccccn1]
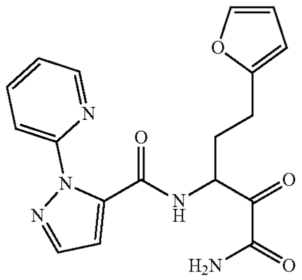 [SMILES: NC(=O)C(=O)C(CCc1ccco1)NC(=O)c1ccnn1-c1ccccn1]
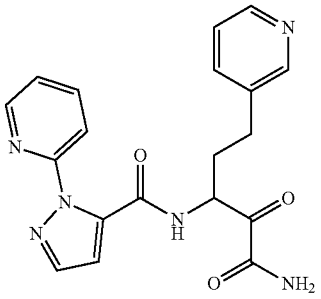 [SMILES: NC(=O)C(=O)C(CCc1cccnc1)NC(=O)c1ccnn1-c1ccccn1]

TABLE 1-continued
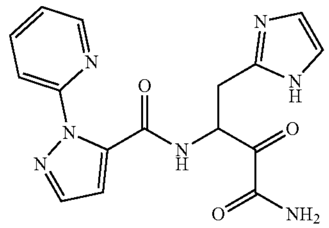 [SMILES: NC(=O)C(=O)C(Cc1ncc[nH]1)NC(=O)c1ccnn1-c1ccccn1]
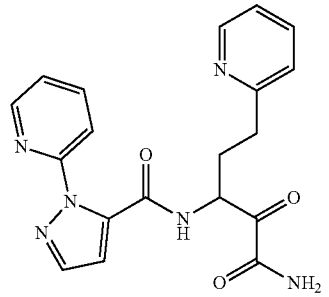 [SMILES: NC(=O)C(=O)C(CCc1ccccn1)NC(=O)c1ccnn1-c1ccccn1]
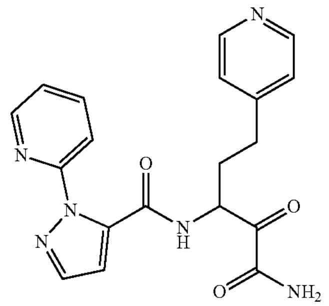 [SMILES: NC(=O)C(=O)C(CCc1ccncc1)NC(=O)c1ccnn1-c1ccccn1]
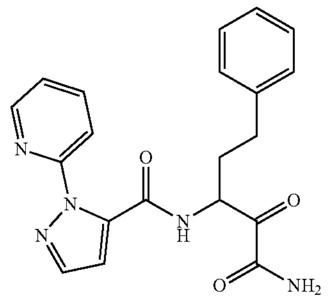
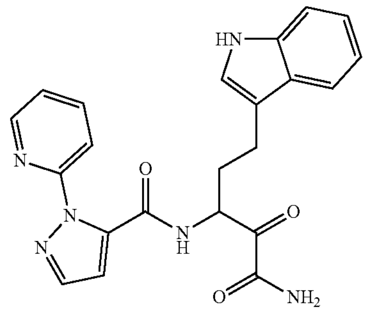 [SMILES: NC(=O)C(=O)C(CCc1c[nH]c2ccccc12)NC(=O)c1ccnn1-c1ccccn1]
TABLE 1-continued
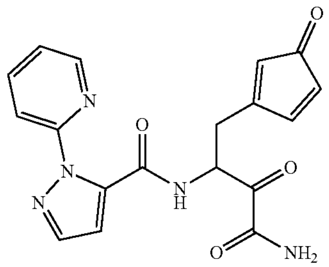 [SMILES: NC(=O)C(=O)C(CC1=CC(=O)C=C1)NC(=O)c1ccnn1-c1ccccn1]
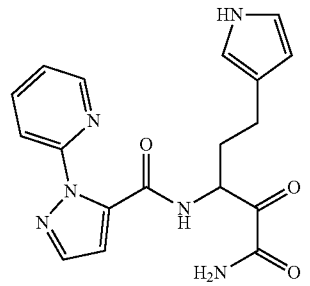 [SMILES: NC(=O)C(=O)C(CCc1cc[nH]c1)NC(=O)c1ccnn1-c1ccccn1]
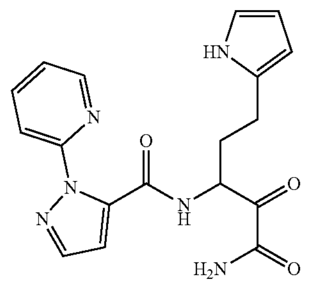 [SMILES: NC(=O)C(=O)C(CCc1ccc[nH]1)NC(=O)c1ccnn1-c1ccccn1]
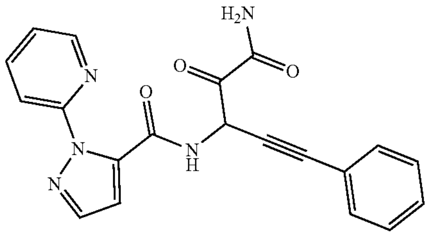 [SMILES: NC(=O)C(=O)C(C#Cc1ccccc1)NC(=O)c1ccnn1-c1ccccn1]
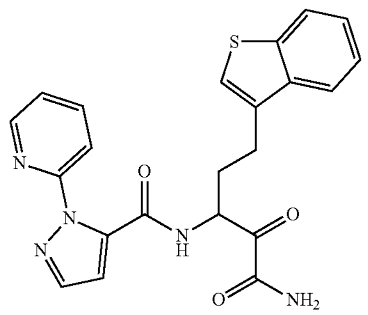 [SMILES: NC(=O)C(=O)C(CCc1csc2ccccc12)NC(=O)c1ccnn1-c1ccccn1]

TABLE 1-continued
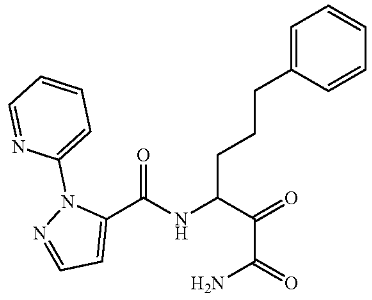 [SMILES: NC(=O)C(=O)C(CCCc1ccccc1)NC(=O)c1ccnn1-c1ccccn1]
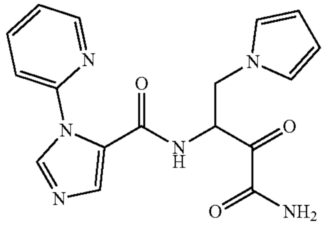 [SMILES: NC(=O)C(=O)C(Cn1cccc1)NC(=O)c1cncn1-c1ccccn1]
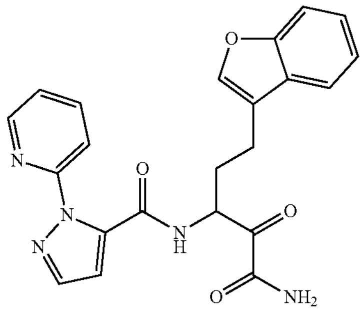 [SMILES: NC(=O)C(=O)C(CCc1coc2ccccc12)NC(=O)c1ccnn1-c1ccccn1]
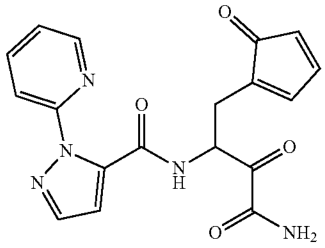 [SMILES: NC(=O)C(=O)C(CC1=CC=CC1=O)NC(=O)c1ccnn1-c1ccccn1]
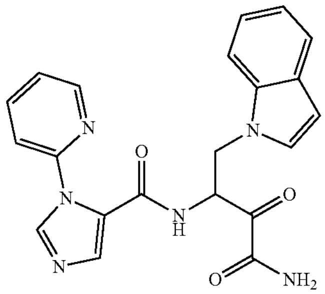 [SMILES: NC(=O)C(=O)C(Cn1ccc2ccccc21)NC(=O)c1cncn1-c1ccccn1]
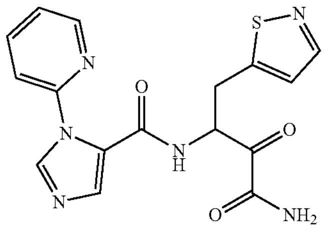 [SMILES: NC(=O)C(=O)C(Cc1ccns1)NC(=O)c1cncn1-c1ccccn1]
TABLE 1-continued
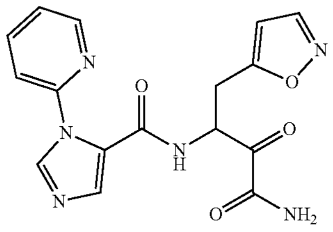 [SMILES: NC(=O)C(=O)C(Cc1ccno1)NC(=O)c1cncn1-c1ccccn1]
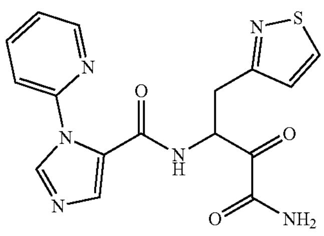 [SMILES: NC(=O)C(=O)C(Cc1ccsn1)NC(=O)c1cncn1-c1ccccn1]
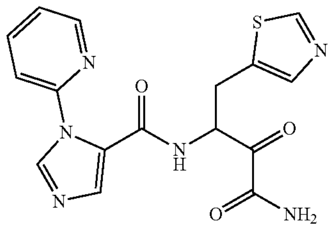 [SMILES: NC(=O)C(=O)C(Cc1cncs1)NC(=O)c1cncn1-c1ccccn1]
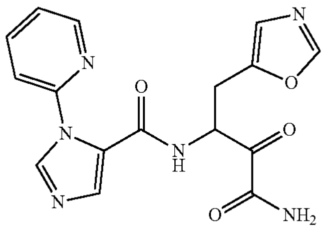 [SMILES: NC(=O)C(=O)C(Cc1cnco1)NC(=O)c1cncn1-c1ccccn1]
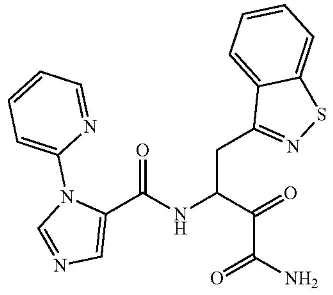 [SMILES: NC(=O)C(=O)C(Cc1nsc2ccccc12)NC(=O)c1cncn1-c1ccccn1]
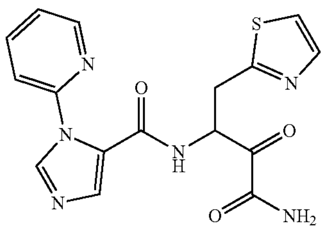 [SMILES: NC(=O)C(=O)C(Cc1nccs1)NC(=O)c1cncn1-c1ccccn1]

TABLE 1-continued
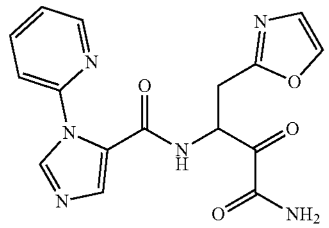 [SMILES: NC(=O)C(=O)C(Cc1ncco1)NC(=O)c1cncn1-c1ccccn1]
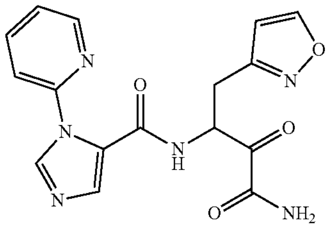 [SMILES: NC(=O)C(=O)C(Cc1ccon1)NC(=O)c1cncn1-c1ccccn1]
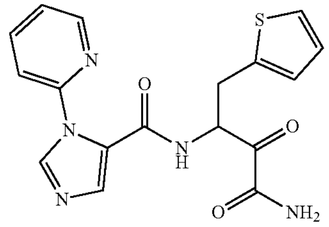 [SMILES: NC(=O)C(=O)C(Cc1cccs1)NC(=O)c1cncn1-c1ccccn1]
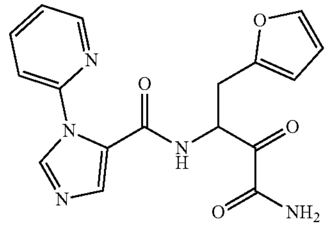 [SMILES: NC(=O)C(=O)C(Cc1ccco1)NC(=O)c1cncn1-c1ccccn1]
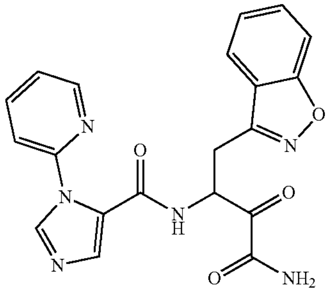 [SMILES: NC(=O)C(=O)C(Cc1noc2ccccc12)NC(=O)c1cncn1-c1ccccn1]
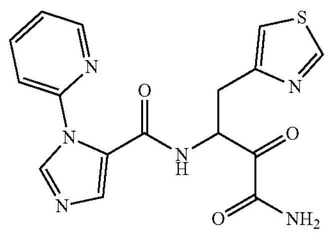 [SMILES: NC(=O)C(=O)C(Cc1cscn1)NC(=O)c1cncn1-c1ccccn1]
TABLE 1-continued
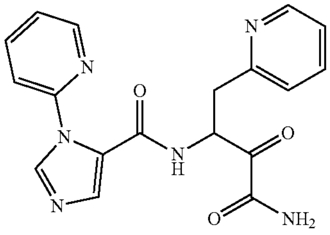
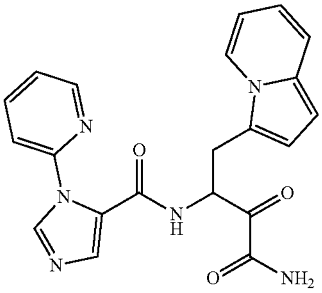 [SMILES: NC(=O)C(=O)C(Cc1ccc2ccccn12)NC(=O)c1cncn1-c1ccccn1]
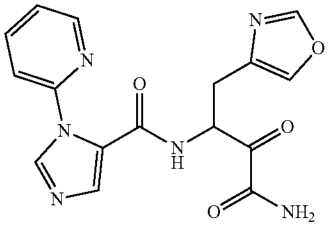
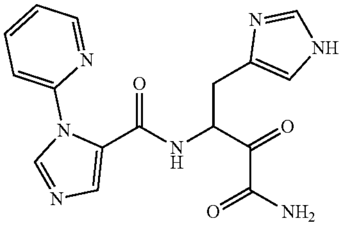 [SMILES: NC(=O)C(=O)C(Cc1c[nH]cn1)NC(=O)c1cncn1-c1ccccn1]
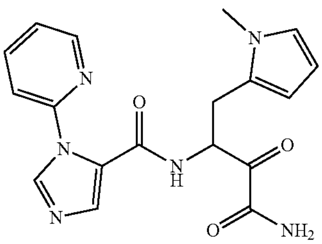 [SMILES: Cn1cccc1CC(NC(=O)c1cncn1-c1ccccn1)C(=O)C(N)=O]
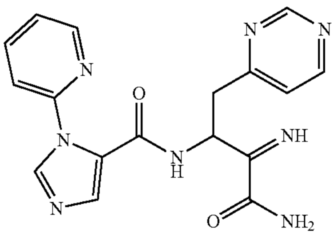 [SMILES: N=C(C(N)=O)C(Cc1ccncn1)NC(=O)c1cncn1-c1ccccn1]

TABLE 1-continued
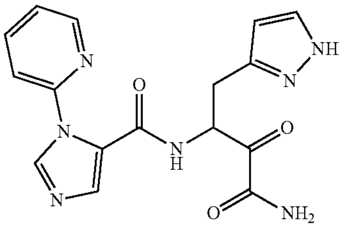
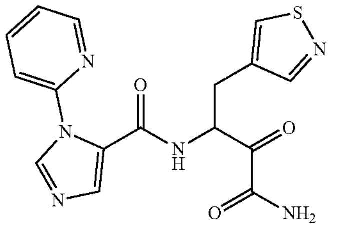 [SMILES: NC(=O)C(=O)C(Cc1cnsc1)NC(=O)c1cncn1-c1ccccn1]
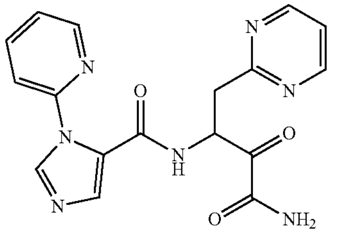 [SMILES: NC(=O)C(=O)C(Cc1ncccn1)NC(=O)c1cncn1-c1ccccn1]
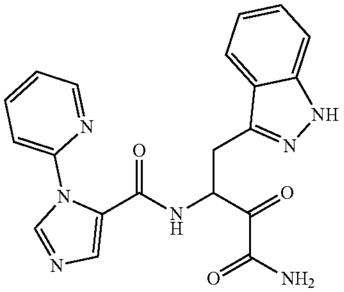
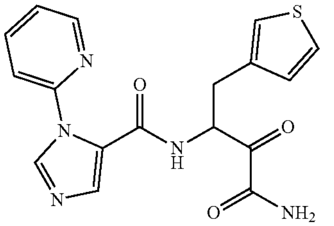 [SMILES: NC(=O)C(=O)C(Cc1ccsc1)NC(=O)c1cncn1-c1ccccn1]
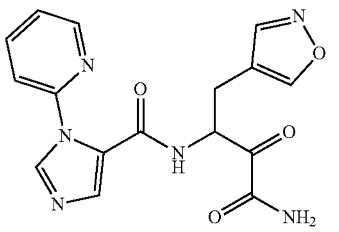
TABLE 1-continued
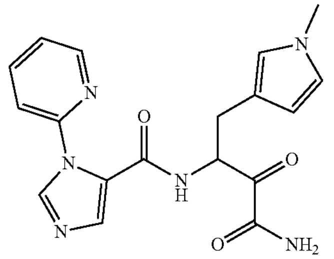 [SMILES: Cn1ccc(CC(NC(=O)c2cncn2-c2ccccn2)C(=O)C(N)=O)c1]
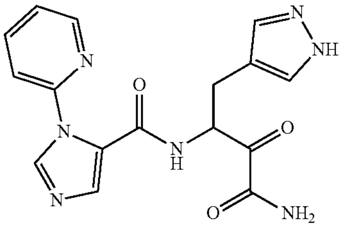
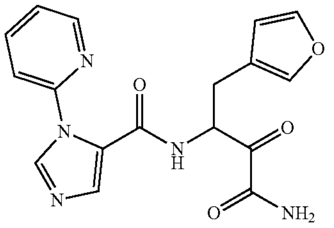
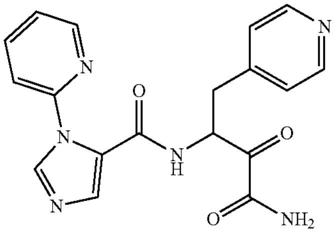 [SMILES: NC(=O)C(=O)C(Cc1ccncc1)NC(=O)c1cncn1-c1ccccn1]
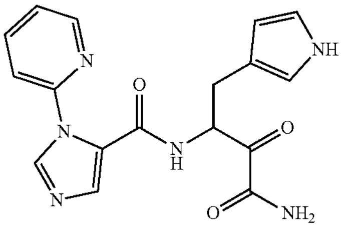
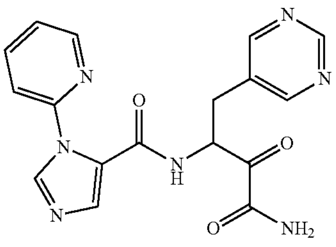 [SMILES: NC(=O)C(=O)C(Cc1cncnc1)NC(=O)c1cncn1-c1ccccn1]

TABLE 1-continued
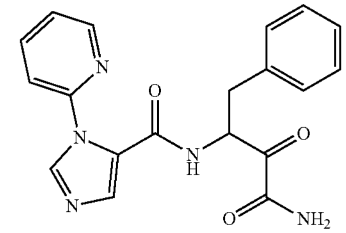 [SMILES: NC(=O)C(=O)C(Cc1ccccc1)NC(=O)c1cncn1-c1ccccn1]
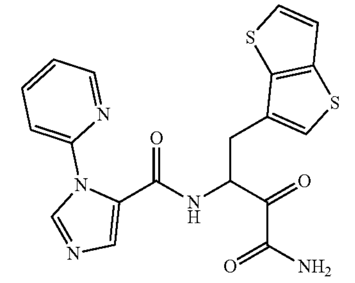 [SMILES: NC(=O)C(=O)C(Cc1csc2ccsc12)NC(=O)c1cncn1-c1ccccn1]
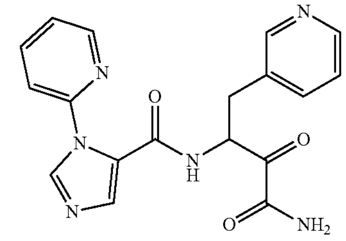 [SMILES: NC(=O)C(=O)C(Cc1cccnc1)NC(=O)c1cncn1-c1ccccn1]
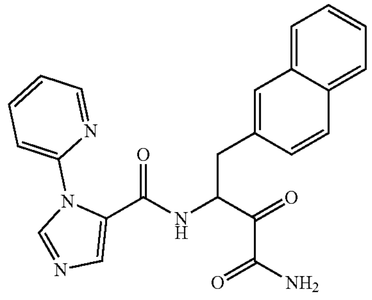 [SMILES: NC(=O)C(=O)C(Cc1ccc2ccccc2c1)NC(=O)c1cncn1-c1ccccn1]
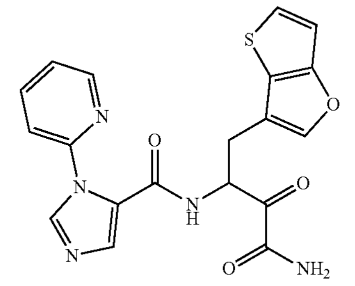 [SMILES: NC(=O)C(=O)C(Cc1coc2ccsc12)NC(=O)c1cncn1-c1ccccn1]
TABLE 1-continued
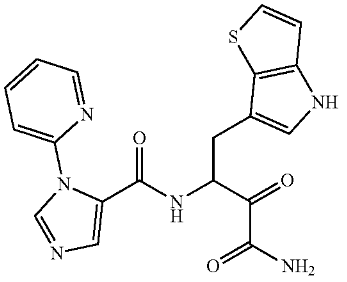 [SMILES: NC(=O)C(=O)C(Cc1c[nH]c2ccsc12)NC(=O)c1cncn1-c1ccccn1]
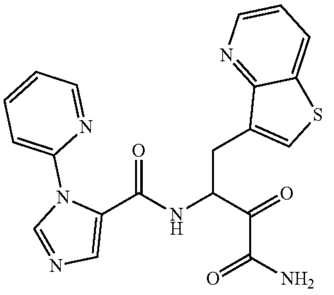
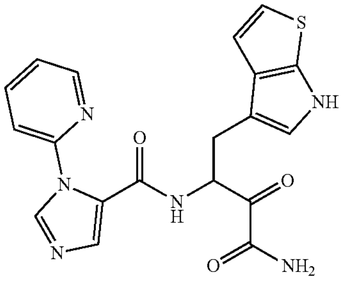 [SMILES: NC(=O)C(=O)C(Cc1c[nH]c2sccc12)NC(=O)c1cncn1-c1ccccn1]
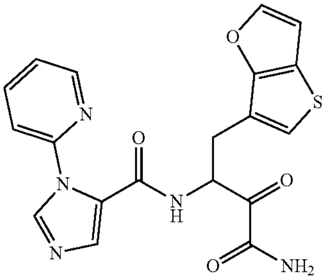 [SMILES: NC(=O)C(=O)C(Cc1csc2ccoc12)NC(=O)c1cncn1-c1ccccn1]
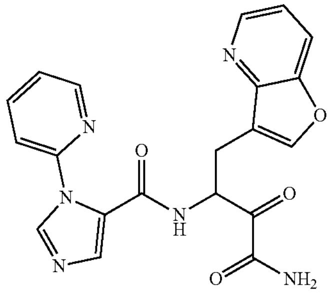

TABLE 1-continued
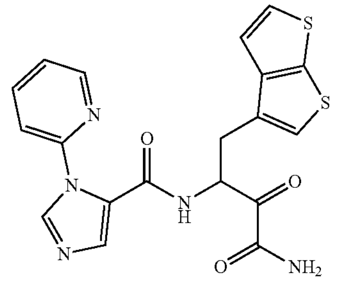 [SMILES: NC(=O)C(=O)C(Cc1csc2sccc12)NC(=O)c1cncn1-c1ccccn1]
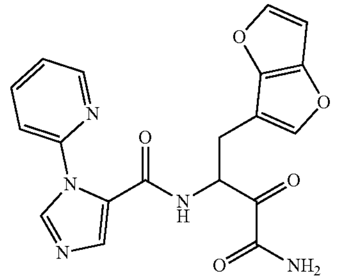 [SMILES: NC(=O)C(=O)C(Cc1coc2ccoc12)NC(=O)c1cncn1-c1ccccn1]
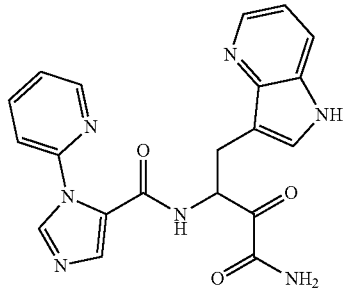
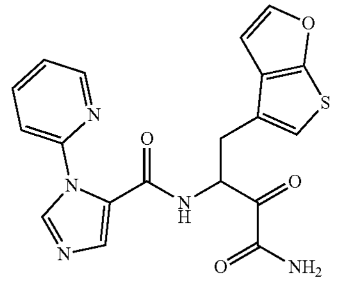 [SMILES: NC(=O)C(=O)C(Cc1csc2occc12)NC(=O)c1cncn1-c1ccccn1]
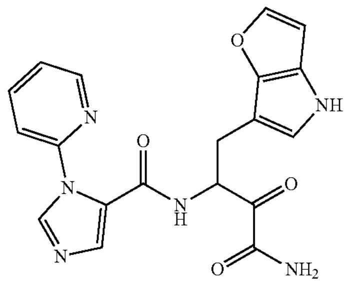
TABLE 1-continued
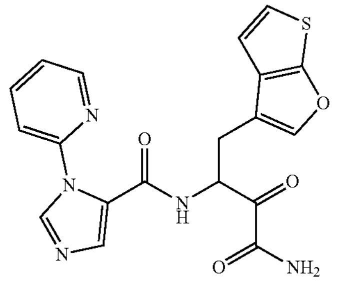 [SMILES: NC(=O)C(=O)C(Cc1coc2sccc12)NC(=O)c1cncn1-c1ccccn1]
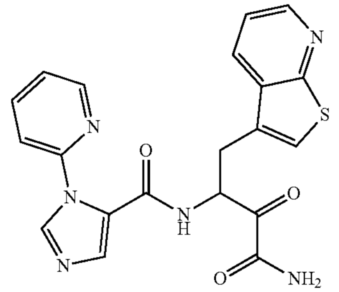
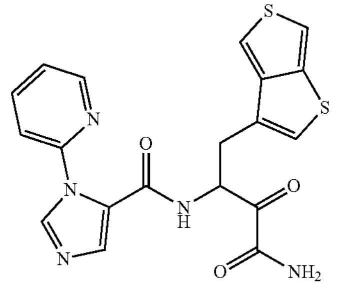 [SMILES: NC(=O)C(=O)C(Cc1csc2cscc12)NC(=O)c1cncn1-c1ccccn1]
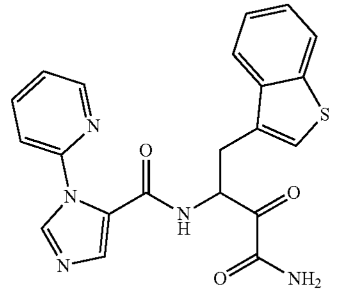
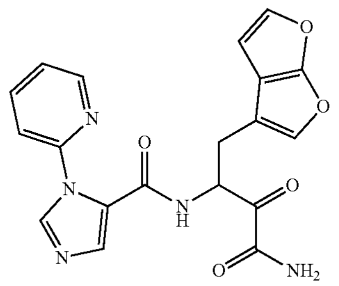 [SMILES: NC(=O)C(=O)C(Cc1coc2occc12)NC(=O)c1cncn1-c1ccccn1]

TABLE 1-continued
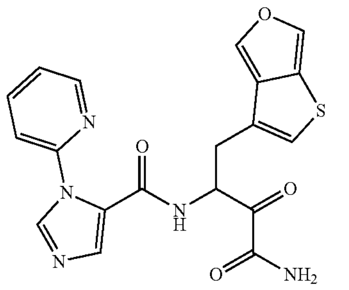 [SMILES: NC(=O)C(=O)C(Cc1csc2cocc12)NC(=O)c1cncn1-c1ccccn1]
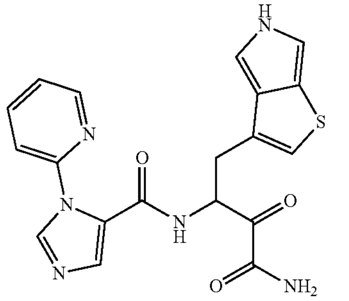 [SMILES: NC(=O)C(=O)C(Cc1csc2c[nH]cc12)NC(=O)c1cncn1-c1ccccn1]
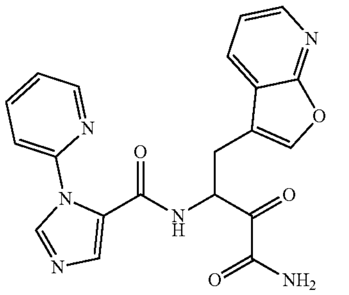
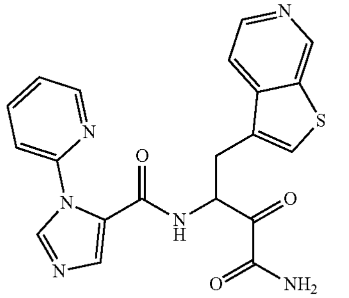 [SMILES: NC(=O)C(=O)C(Cc1csc2cnccc12)NC(=O)c1cncn1-c1ccccn1]
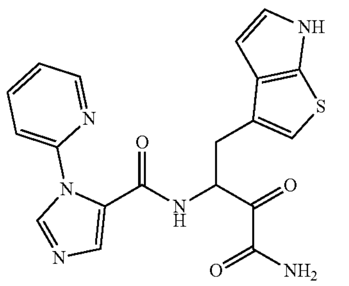 [SMILES: NC(=O)C(=O)C(Cc1csc2[nH]ccc12)NC(=O)c1cncn1-c1ccccn1]
TABLE 1-continued
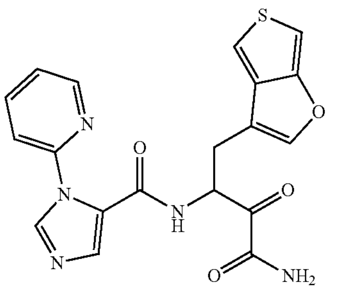 [SMILES: NC(=O)C(=O)C(Cc1coc2cscc12)NC(=O)c1cncn1-c1ccccn1]
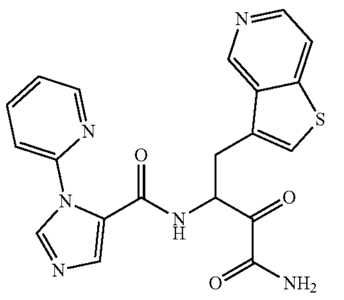
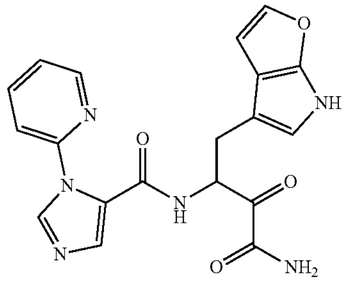 [SMILES: NC(=O)C(=O)C(Cc1c[nH]c2occc12)NC(=O)c1cncn1-c1ccccn1]
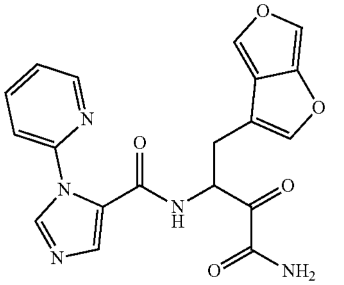 [SMILES: NC(=O)C(=O)C(Cc1coc2cocc12)NC(=O)c1cncn1-c1ccccn1]
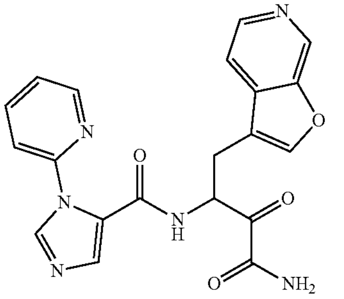

TABLE 1-continued
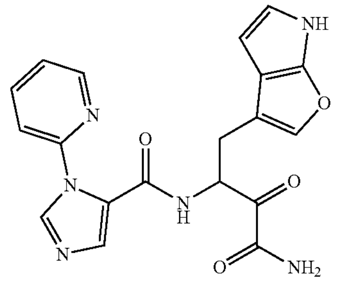 [SMILES: NC(=O)C(=O)C(Cc1coc2[nH]ccc12)NC(=O)c1cncn1-c1ccccn1]
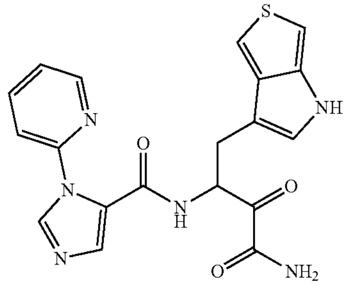 [SMILES: NC(=O)C(=O)C(Cc1c[nH]c2cscc12)NC(=O)c1cncn1-c1ccccn1]
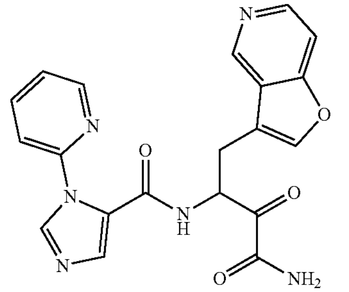
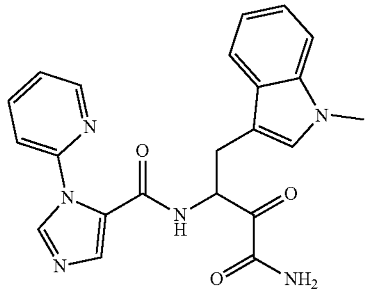
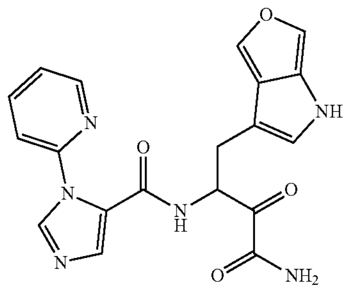 [SMILES: NC(=O)C(=O)C(Cc1c[nH]c2cocc12)NC(=O)c1cncn1-c1ccccn1]
TABLE 1-continued
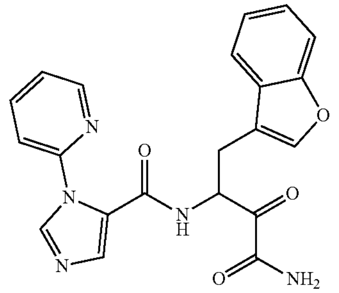
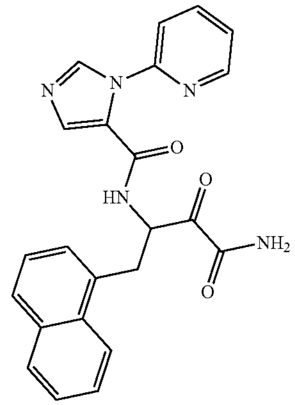 [SMILES: NC(=O)C(=O)C(Cc1cccc2ccccc12)NC(=O)c1cncn1-c1ccccn1]
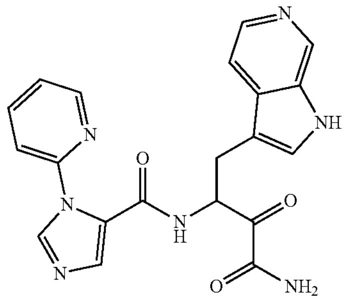
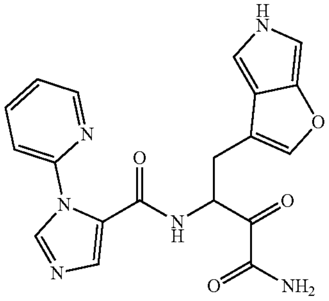 [SMILES: NC(=O)C(=O)C(Cc1coc2c[nH]cc12)NC(=O)c1cncn1-c1ccccn1]
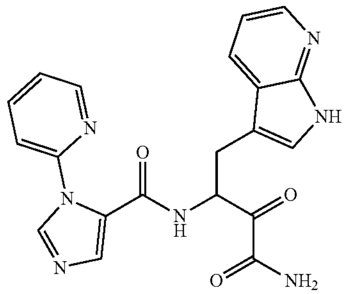

TABLE 1-continued
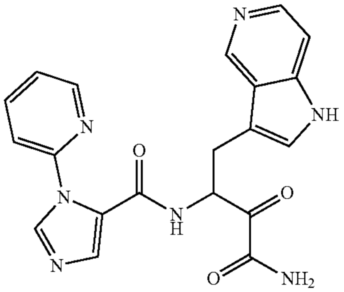
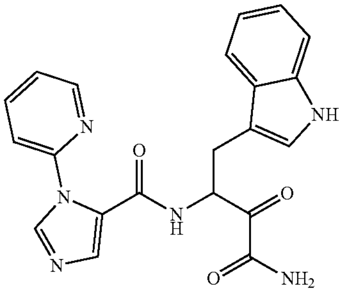
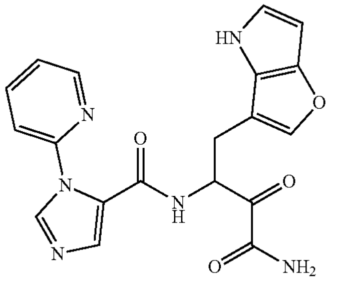
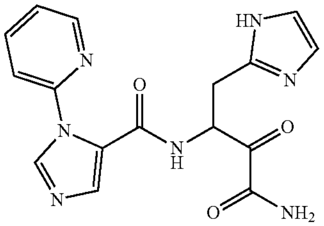 [SMILES: NC(=O)C(=O)C(Cc1ncc[nH]1)NC(=O)c1cncn1-c1ccccn1]
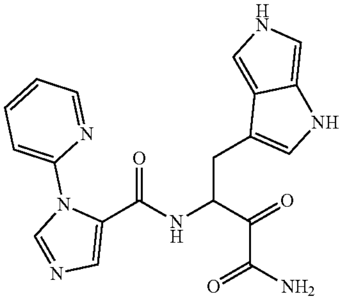 [SMILES: NC(=O)C(=O)C(Cc1c[nH]c2c[nH]cc12)NC(=O)c1cncn1-c1ccccn1]
TABLE 1-continued
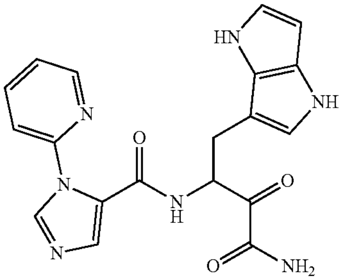 [SMILES: NC(=O)C(=O)C(Cc1c[nH]c2cc[nH]c12)NC(=O)c1cncn1-c1ccccn1]
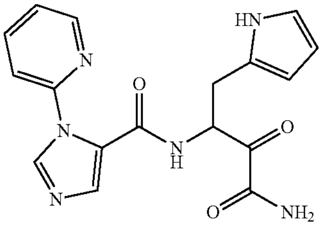
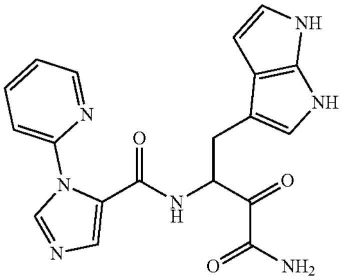 [SMILES: NC(=O)C(=O)C(Cc1c[nH]c2[nH]ccc12)NC(=O)c1cncn1-c1ccccn1]
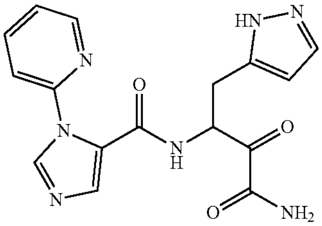 [SMILES: NC(=O)C(=O)C(Cc1ccn[nH]1)NC(=O)c1cncn1-c1ccccn1]
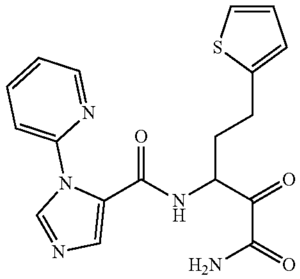 [SMILES: NC(=O)C(=O)C(CCc1cccs1)NC(=O)c1cncn1-c1ccccn1]
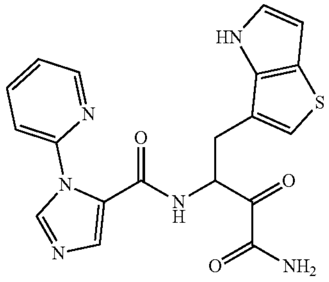 [SMILES: NC(=O)C(=O)C(Cc1csc2cc[nH]c12)NC(=O)c1cncn1-c1ccccn1]

TABLE 1-continued
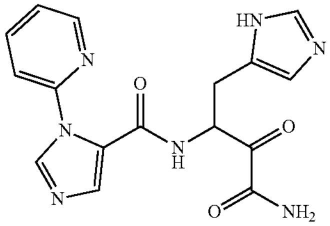 [SMILES: NC(=O)C(=O)C(Cc1cnc[nH]1)NC(=O)c1cncn1-c1ccccn1]
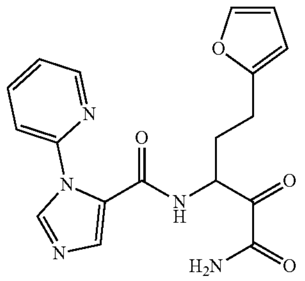 [SMILES: NC(=O)C(=O)C(CCc1ccco1)NC(=O)c1cncn1-c1ccccn1]
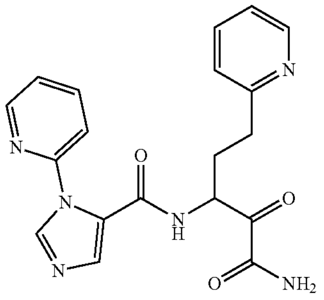 [SMILES: NC(=O)C(=O)C(CCc1ccccn1)NC(=O)c1cncn1-c1ccccn1]
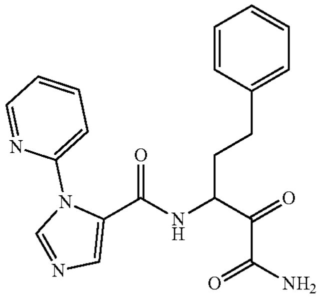
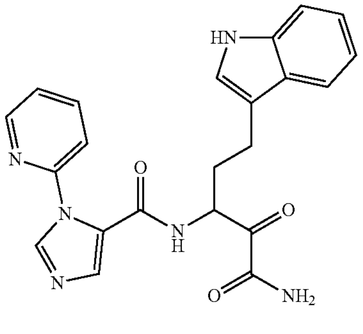
TABLE 1-continued
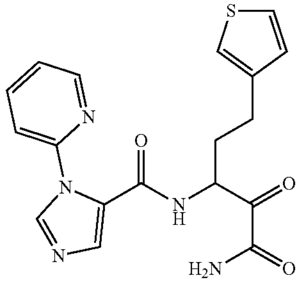 [SMILES: NC(=O)C(=O)C(CCc1ccsc1)NC(=O)c1cncn1-c1ccccn1]
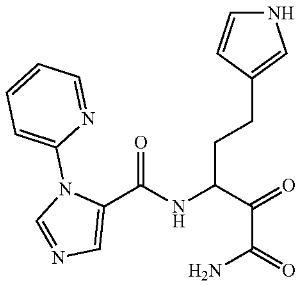 [SMILES: NC(=O)C(=O)C(CCc1cc[nH]c1)NC(=O)c1cncn1-c1ccccn1]
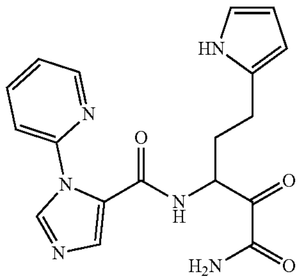 [SMILES: NC(=O)C(=O)C(CCc1ccc[nH]1)NC(=O)c1cncn1-c1ccccn1]
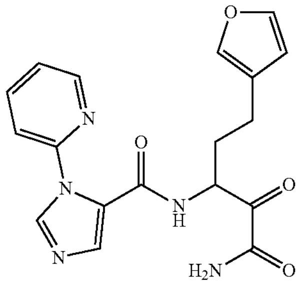 [SMILES: NC(=O)C(=O)C(CCc1ccoc1)NC(=O)c1cncn1-c1ccccn1]
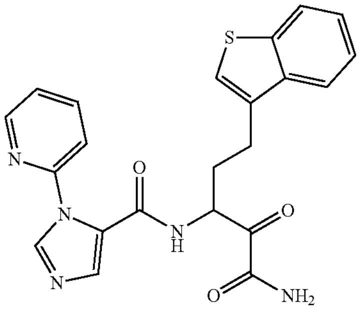

TABLE 1-continued
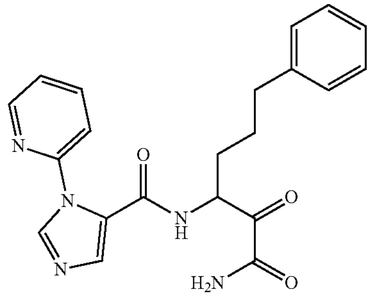 [SMILES: NC(=O)C(=O)C(CCCc1ccccc1)NC(=O)c1cncn1-c1ccccn1]
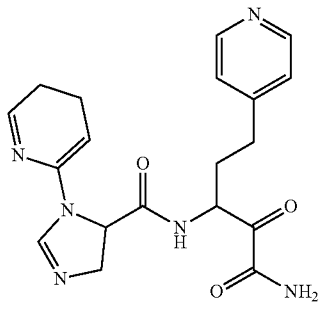 [SMILES: NC(=O)C(=O)C(CCc1ccncc1)NC(=O)C1CN=CN1C1=CCCC=N1]
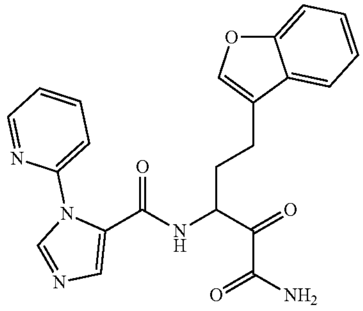
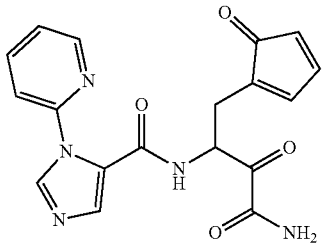 [SMILES: NC(=O)C(=O)C(CC1=CC=CC1=O)NC(=O)c1cncn1-c1ccccn1]
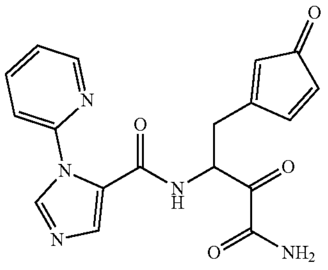
TABLE 1-continued
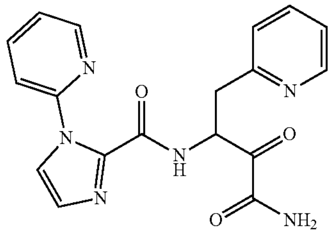 [SMILES: NC(=O)C(=O)C(Cc1ccccn1)NC(=O)c1nccn1-c1ccccn1]
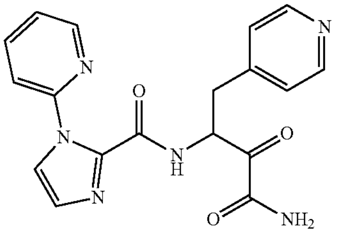 [SMILES: NC(=O)C(=O)C(Cc1ccncc1)NC(=O)c1nccn1-c1ccccn1]
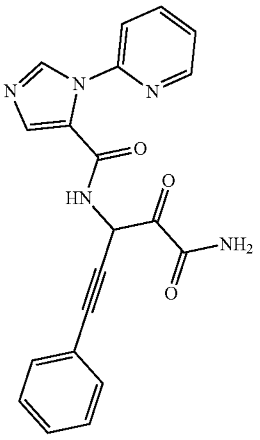 [SMILES: NC(=O)C(=O)C(C#Cc1ccccc1)NC(=O)c1cncn1-c1ccccn1]
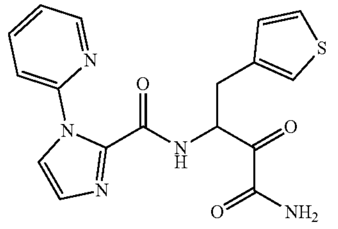 [SMILES: NC(=O)C(=O)C(Cc1ccsc1)NC(=O)c1nccn1-c1ccccn1]
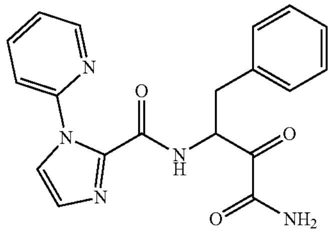 [SMILES: NC(=O)C(=O)C(Cc1ccccc1)NC(=O)c1nccn1-c1ccccn1]
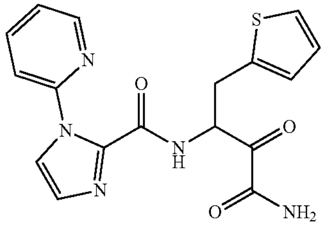 [SMILES: NC(=O)C(=O)C(Cc1cccs1)NC(=O)c1nccn1-c1ccccn1]

TABLE 1-continued
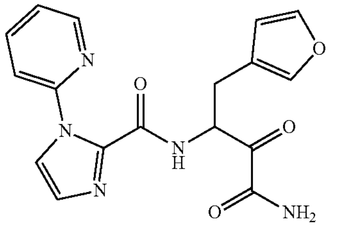 [SMILES: NC(=O)C(=O)C(Cc1ccoc1)NC(=O)c1nccn1-c1ccccn1]
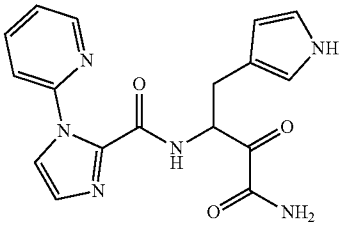 [SMILES: NC(=O)C(=O)C(Cc1cc[nH]c1)NC(=O)c1nccn1-c1ccccn1]
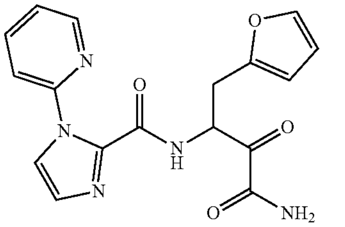 [SMILES: NC(=O)C(=O)C(Cc1ccco1)NC(=O)c1nccn1-c1ccccn1]
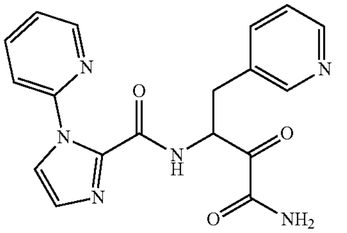 [SMILES: NC(=O)C(=O)C(Cc1cccnc1)NC(=O)c1nccn1-c1ccccn1]
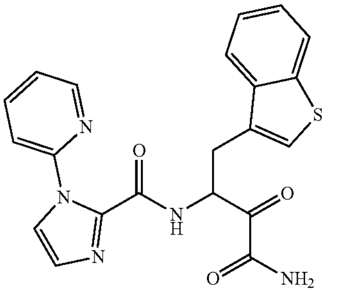 [SMILES: NC(=O)C(=O)C(Cc1csc2ccccc12)NC(=O)c1nccn1-c1ccccn1]
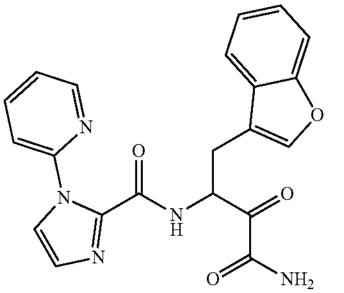 [SMILES: NC(=O)C(=O)C(Cc1coc2ccccc12)NC(=O)c1nccn1-c1ccccn1]
TABLE 1-continued
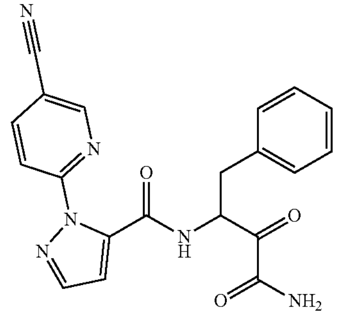 [SMILES: N#Cc1ccc(-n2nccc2C(=O)NC(Cc2ccccc2)C(=O)C(N)=O)nc1]
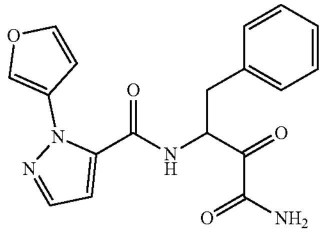 [SMILES: NC(=O)C(=O)C(Cc1ccccc1)NC(=O)c1ccnn1-c1ccoc1]
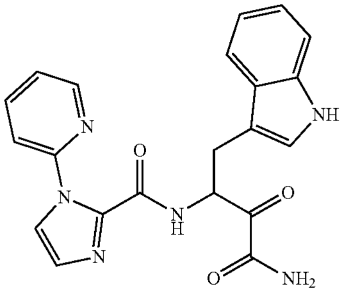 [SMILES: NC(=O)C(=O)C(Cc1c[nH]c2ccccc12)NC(=O)c1nccn1-c1ccccn1]
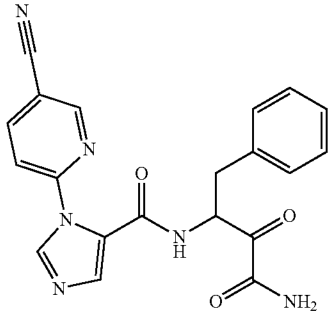 [SMILES: N#Cc1ccc(-n2cncc2C(=O)NC(Cc2ccccc2)C(=O)C(N)=O)nc1]
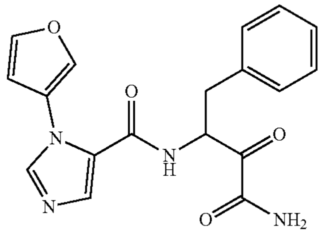 [SMILES: NC(=O)C(=O)C(Cc1ccccc1)NC(=O)c1cncn1-c1ccoc1]

TABLE 1-continued
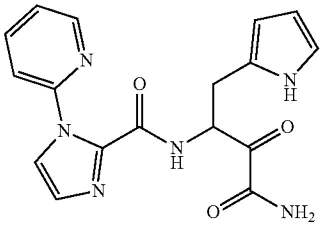 [SMILES: NC(=O)C(=O)C(Cc1ccc[nH]1)NC(=O)c1nccn1-c1ccccn1]
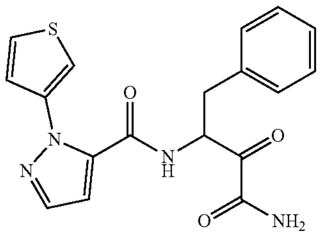 [SMILES: NC(=O)C(=O)C(Cc1ccccc1)NC(=O)c1ccnn1-c1ccsc1]
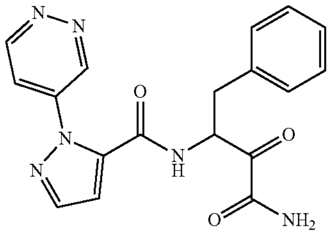 [SMILES: NC(=O)C(=O)C(Cc1ccccc1)NC(=O)c1ccnn1-c1ccnnc1]
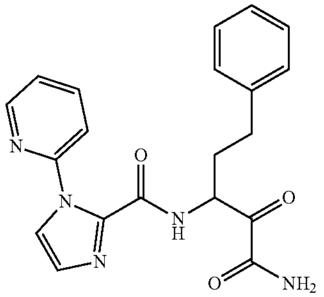 [SMILES: NC(=O)C(=O)C(CCc1ccccc1)NC(=O)c1nccn1-c1ccccn1]
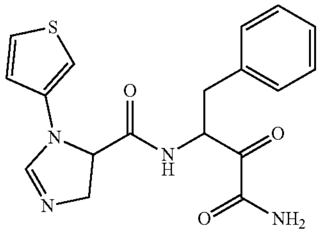 [SMILES: NC(=O)C(=O)C(Cc1ccccc1)NC(=O)C1CN=CN1c1ccsc1]
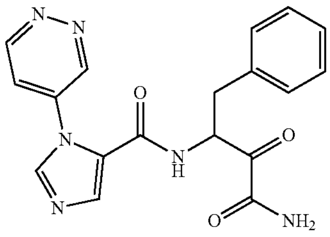 [SMILES: NC(=O)C(=O)C(Cc1ccccc1)NC(=O)c1cncn1-c1ccnnc1]
TABLE 1-continued
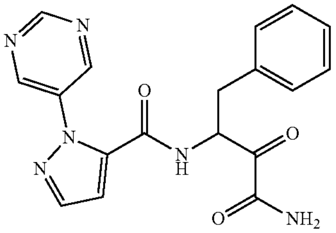 [SMILES: NC(=O)C(=O)C(Cc1ccccc1)NC(=O)c1ccnn1-c1cncnc1]
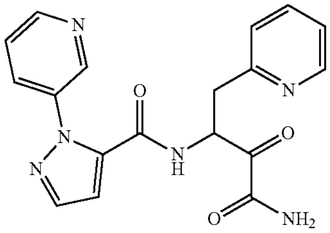 [SMILES: NC(=O)C(=O)C(Cc1ccccn1)NC(=O)c1ccnn1-c1cccnc1]
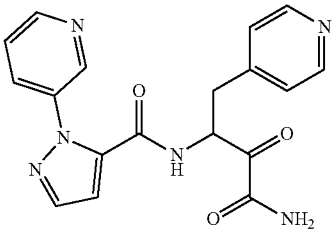 [SMILES: NC(=O)C(=O)C(Cc1ccncc1)NC(=O)c1ccnn1-c1cccnc1]
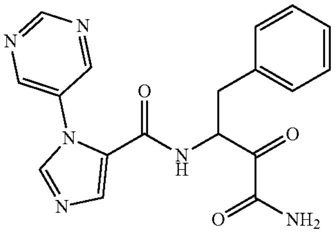 [SMILES: NC(=O)C(=O)C(Cc1ccccc1)NC(=O)c1cncn1-c1cncnc1]
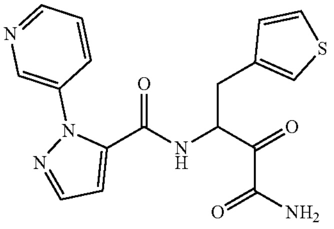 [SMILES: NC(=O)C(=O)C(Cc1ccsc1)NC(=O)c1ccnn1-c1cccnc1]
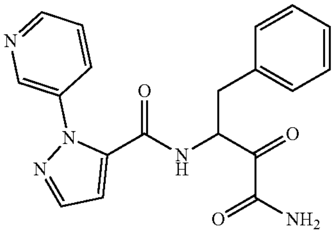 [SMILES: NC(=O)C(=O)C(Cc1ccccc1)NC(=O)c1ccnn1-c1cccnc1]

TABLE 1-continued
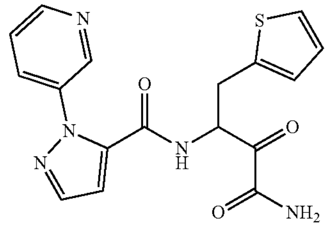 [SMILES: NC(=O)C(=O)C(Cc1cccs1)NC(=O)c1ccnn1-c1cccnc1]
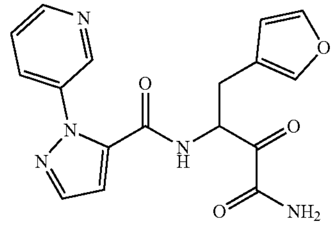 [SMILES: NC(=O)C(=O)C(Cc1ccoc1)NC(=O)c1ccnn1-c1cccnc1]
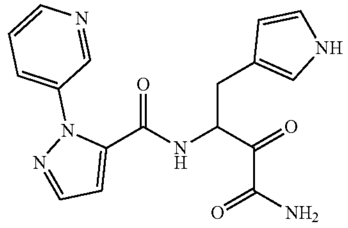 [SMILES: NC(=O)C(=O)C(Cc1cc[nH]c1)NC(=O)c1ccnn1-c1cccnc1]
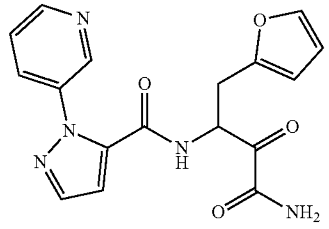 [SMILES: NC(=O)C(=O)C(Cc1ccco1)NC(=O)c1ccnn1-c1cccnc1]
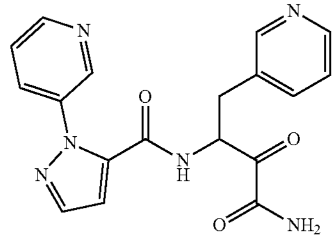 [SMILES: NC(=O)C(=O)C(Cc1cccnc1)NC(=O)c1ccnn1-c1cccnc1]
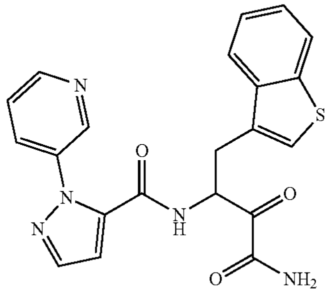 [SMILES: NC(=O)C(=O)C(Cc1csc2ccccc12)NC(=O)c1ccnn1-c1cccnc1]
TABLE 1-continued
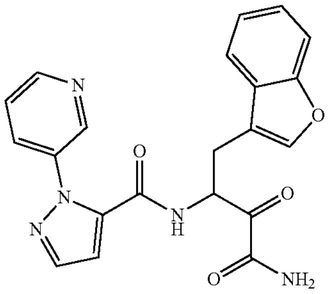 [SMILES: NC(=O)C(=O)C(Cc1coc2ccccc12)NC(=O)c1ccnn1-c1cccnc1]
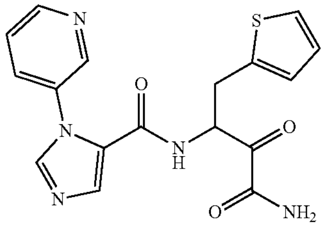 [SMILES: NC(=O)C(=O)C(Cc1cccs1)NC(=O)c1cncn1-c1cccnc1]
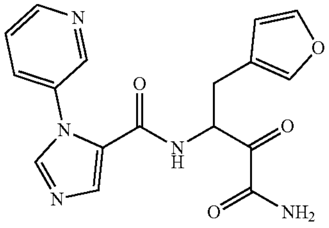 [SMILES: NC(=O)C(=O)C(Cc1ccoc1)NC(=O)c1cncn1-c1cccnc1]
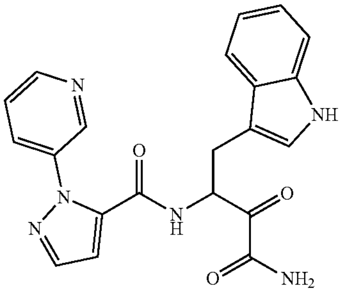 [SMILES: NC(=O)C(=O)C(Cc1c[nH]c2ccccc12)NC(=O)c1ccnn1-c1cccnc1]
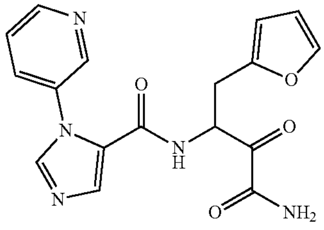 [SMILES: NC(=O)C(=O)C(Cc1ccco1)NC(=O)c1cncn1-c1cccnc1]
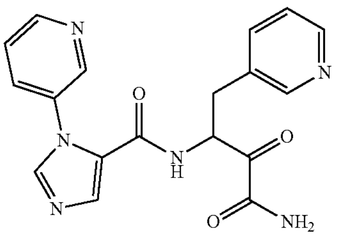 [SMILES: NC(=O)C(=O)C(Cc1cccnc1)NC(=O)c1cncn1-c1cccnc1]

TABLE 1-continued
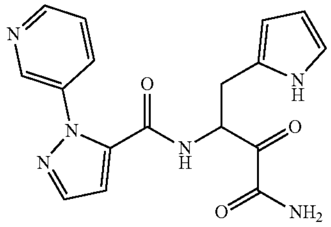 [SMILES: NC(=O)C(=O)C(Cc1ccc[nH]1)NC(=O)c1ccnn1-c1cccnc1]
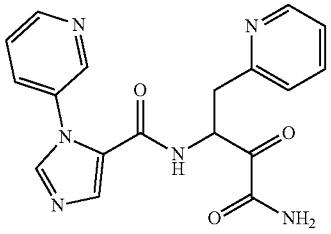 [SMILES: NC(=O)C(=O)C(Cc1ccccn1)NC(=O)c1cncn1-c1cccnc1]
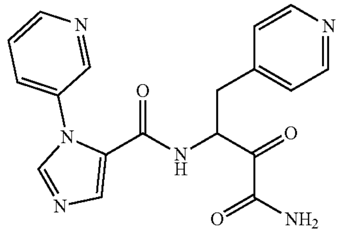 [SMILES: NC(=O)C(=O)C(Cc1ccncc1)NC(=O)c1cncn1-c1cccnc1]
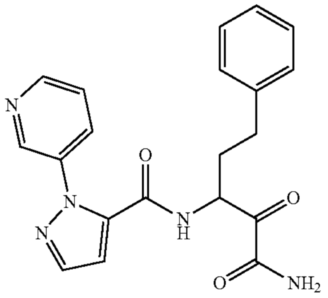 [SMILES: NC(=O)C(=O)C(CCc1ccccc1)NC(=O)c1ccnn1-c1cccnc1]
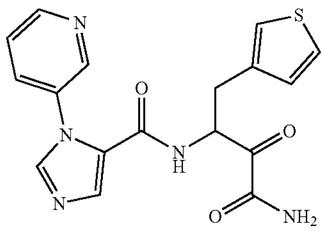 [SMILES: NC(=O)C(=O)C(Cc1ccsc1)NC(=O)c1cncn1-c1cccnc1]
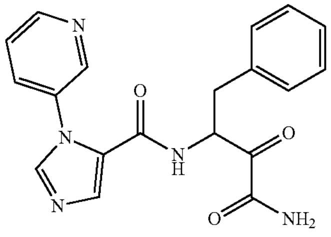 [SMILES: NC(=O)C(=O)C(Cc1ccccc1)NC(=O)c1cncn1-c1cccnc1]
TABLE 1-continued
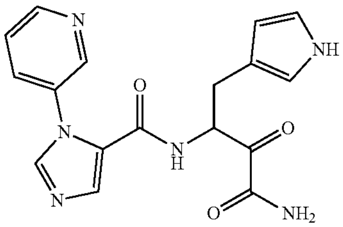 [SMILES: NC(=O)C(=O)C(Cc1cc[nH]c1)NC(=O)c1cncn1-c1cccnc1]
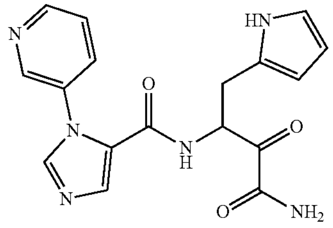 [SMILES: NC(=O)C(=O)C(Cc1ccc[nH]1)NC(=O)c1cncn1-c1cccnc1]
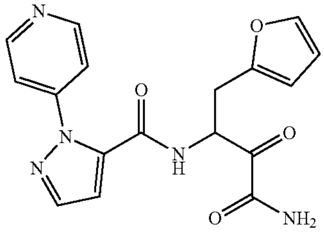 [SMILES: NC(=O)C(=O)C(Cc1ccco1)NC(=O)c1ccnn1-c1ccncc1]
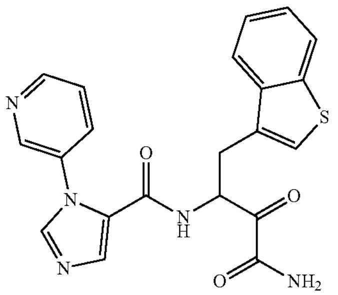 [SMILES: NC(=O)C(=O)C(Cc1csc2ccccc12)NC(=O)c1cncn1-c1cccnc1]
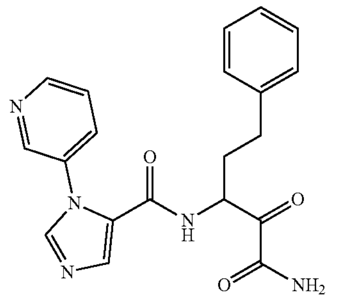 [SMILES: NC(=O)C(=O)C(CCc1ccccc1)NC(=O)c1cncn1-c1cccnc1]
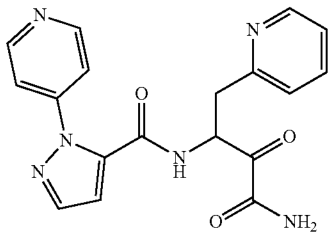 [SMILES: NC(=O)C(=O)C(Cc1ccccn1)NC(=O)c1ccnn1-c1ccncc1]

TABLE 1-continued
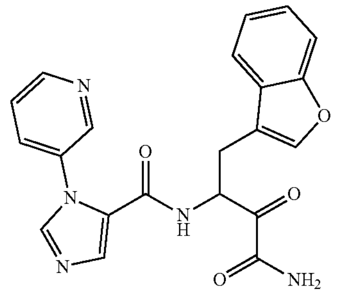 [SMILES: NC(=O)C(=O)C(Cc1coc2ccccc12)NC(=O)c1cncn1-c1cccnc1]
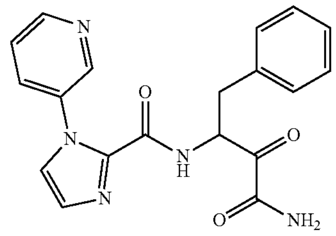 [SMILES: NC(=O)C(=O)C(Cc1ccccc1)NC(=O)c1nccn1-c1cccnc1]
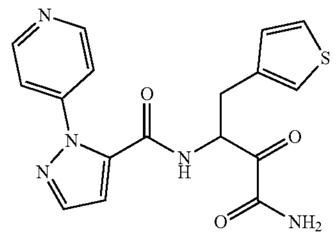
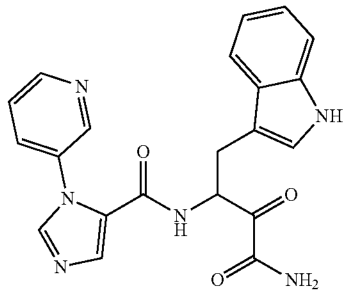 [SMILES: NC(=O)C(=O)C(Cc1c[nH]c2ccccc12)NC(=O)c1cncn1-c1cccnc1]
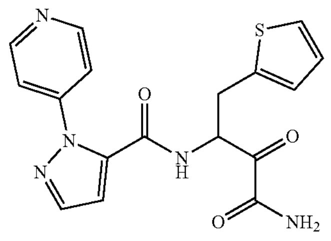
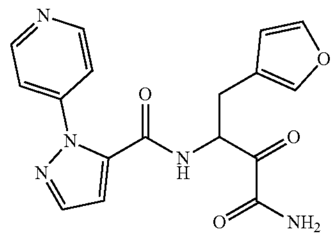 [SMILES: NC(=O)C(=O)C(Cc1ccoc1)NC(=O)c1ccnn1-c1ccncc1]
TABLE 1-continued
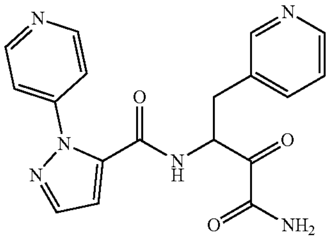 [SMILES: NC(=O)C(=O)C(Cc1cccnc1)NC(=O)c1ccnn1-c1ccncc1]
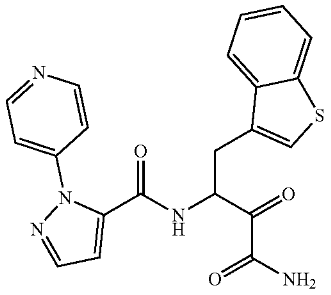 [SMILES: NC(=O)C(=O)C(Cc1csc2ccccc12)NC(=O)c1ccnn1-c1ccncc1]
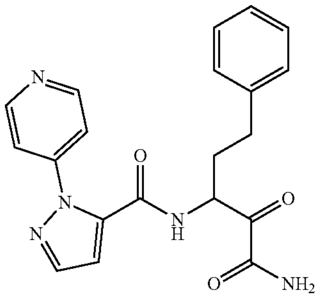 [SMILES: NC(=O)C(=O)C(CCc1ccccc1)NC(=O)c1ccnn1-c1ccncc1]
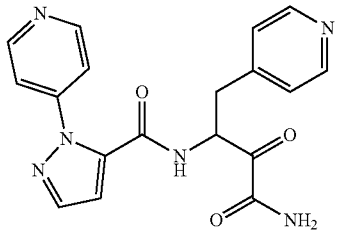 [SMILES: NC(=O)C(=O)C(Cc1ccncc1)NC(=O)c1ccnn1-c1ccncc1]
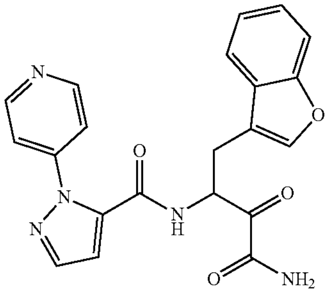 [SMILES: NC(=O)C(=O)C(Cc1coc2ccccc12)NC(=O)c1ccnn1-c1ccncc1]
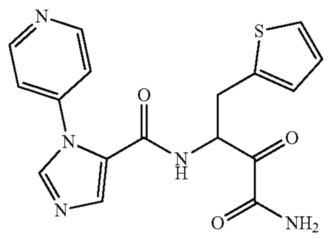

TABLE 1-continued
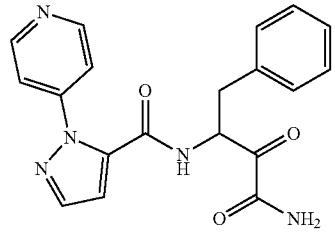
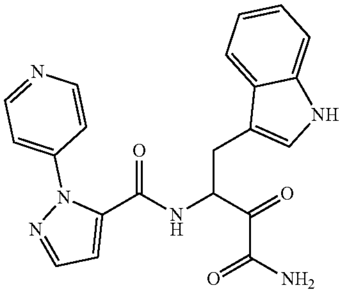 [SMILES: NC(=O)C(=O)C(Cc1c[nH]c2ccccc12)NC(=O)c1ccnn1-c1ccncc1]
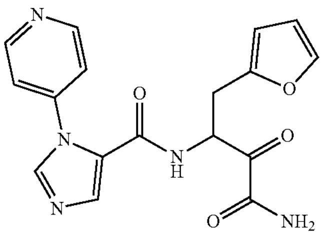 [SMILES: NC(=O)C(=O)C(Cc1ccco1)NC(=O)c1cncn1-c1ccncc1]
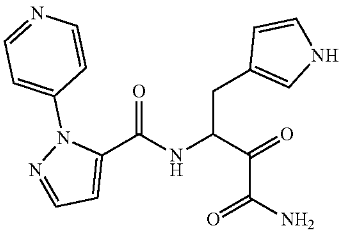 [SMILES: NC(=O)C(=O)C(Cc1cc[nH]c1)NC(=O)c1ccnn1-c1ccncc1]
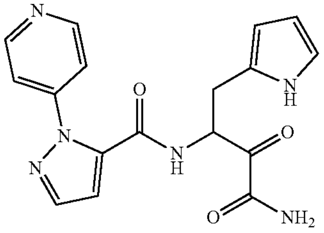 [SMILES: NC(=O)C(=O)C(Cc1ccc[nH]1)NC(=O)c1ccnn1-c1ccncc1]
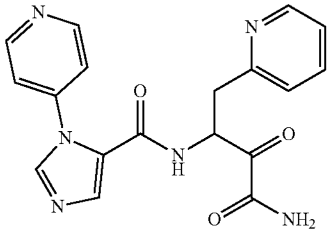 [SMILES: NC(=O)C(=O)C(Cc1ccccn1)NC(=O)c1cncn1-c1ccncc1]
TABLE 1-continued
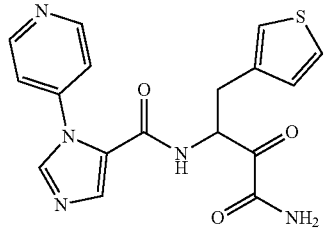 [SMILES: NC(=O)C(=O)C(Cc1ccsc1)NC(=O)c1cncn1-c1ccncc1]
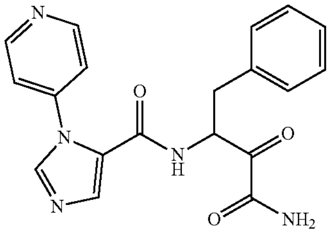 [SMILES: NC(=O)C(=O)C(Cc1ccccc1)NC(=O)c1cncn1-c1ccncc1]
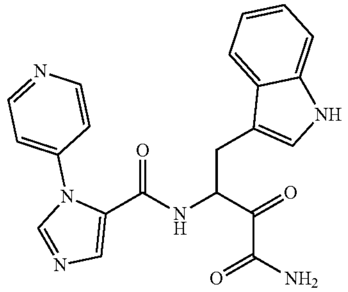 [SMILES: NC(=O)C(=O)C(Cc1c[nH]c2ccccc12)NC(=O)c1cncn1-c1ccncc1]
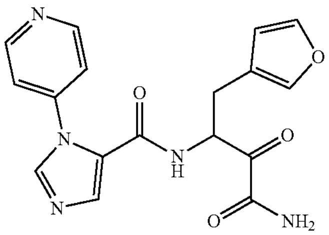 [SMILES: NC(=O)C(=O)C(Cc1ccoc1)NC(=O)c1cncn1-c1ccncc1]
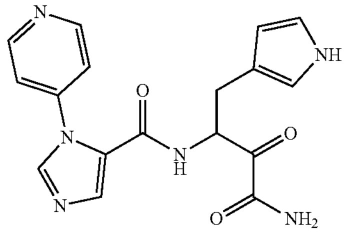
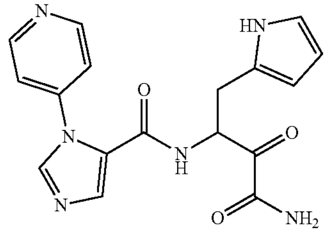

TABLE 1-continued
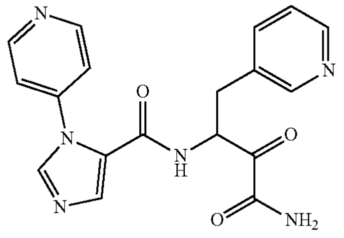 [SMILES: NC(=O)C(=O)C(Cc1cccnc1)NC(=O)c1cncn1-c1ccncc1]
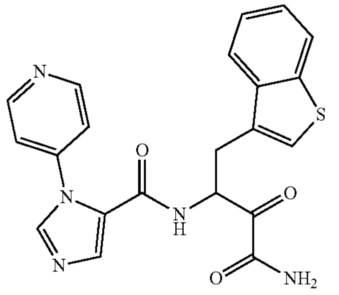 [SMILES: NC(=O)C(=O)C(Cc1csc2ccccc12)NC(=O)c1cncn1-c1ccncc1]
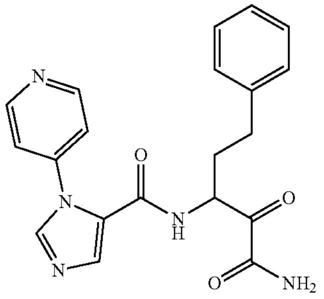 [SMILES: NC(=O)C(=O)C(CCc1ccccc1)NC(=O)c1cncn1-c1ccncc1]
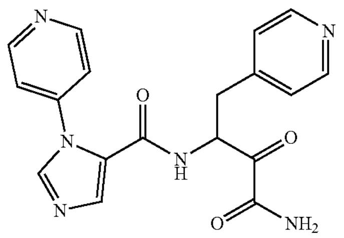 [SMILES: NC(=O)C(=O)C(Cc1ccncc1)NC(=O)c1cncn1-c1ccncc1]
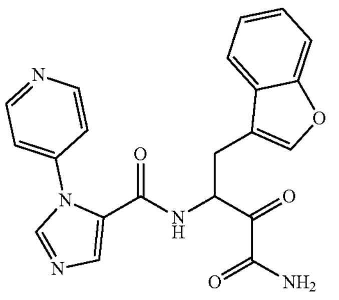 [SMILES: NC(=O)C(=O)C(Cc1coc2ccccc12)NC(=O)c1cncn1-c1ccncc1]
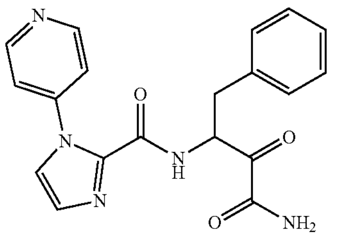 [SMILES: NC(=O)C(=O)C(Cc1ccccc1)NC(=O)c1nccn1-c1ccncc1]
TABLE 1-continued
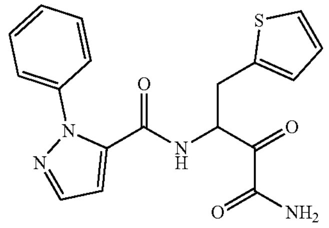 [SMILES: NC(=O)C(=O)C(Cc1cccs1)NC(=O)c1ccnn1-c1ccccc1]
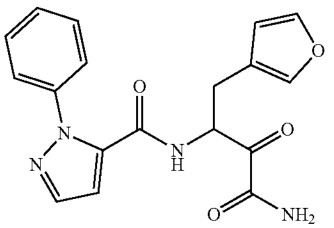 [SMILES: NC(=O)C(=O)C(Cc1ccoc1)NC(=O)c1ccnn1-c1ccccc1]
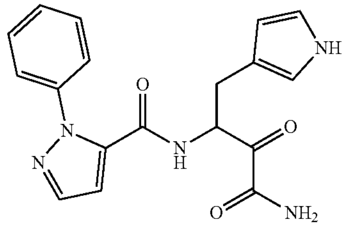 [SMILES: NC(=O)C(=O)C(Cc1cc[nH]c1)NC(=O)c1ccnn1-c1ccccc1]
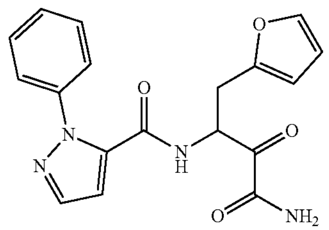 [SMILES: NC(=O)C(=O)C(Cc1ccco1)NC(=O)c1ccnn1-c1ccccc1]
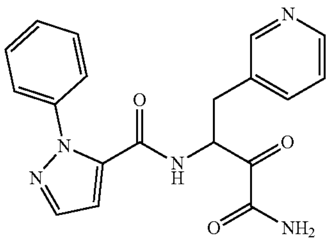 [SMILES: NC(=O)C(=O)C(Cc1cccnc1)NC(=O)c1ccnn1-c1ccccc1]
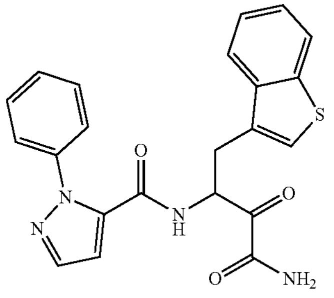 [SMILES: NC(=O)C(=O)C(Cc1csc2ccccc12)NC(=O)c1ccnn1-c1ccccc1]

TABLE 1-continued
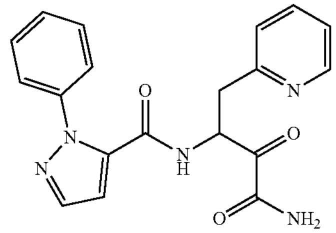 [SMILES: NC(=O)C(=O)C(Cc1ccccn1)NC(=O)c1ccnn1-c1ccccc1]
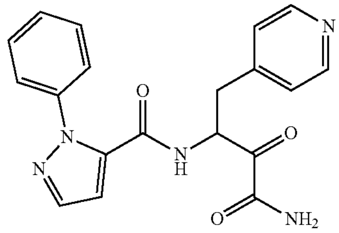 [SMILES: NC(=O)C(=O)C(Cc1ccncc1)NC(=O)c1ccnn1-c1ccccc1]
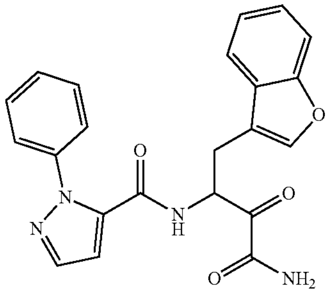 [SMILES: NC(=O)C(=O)C(Cc1coc2ccccc12)NC(=O)c1ccnn1-c1ccccc1]
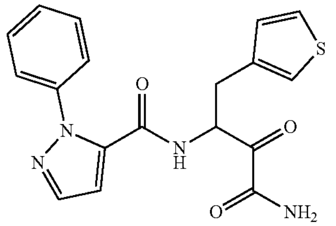 [SMILES: NC(=O)C(=O)C(Cc1ccsc1)NC(=O)c1ccnn1-c1ccccc1]
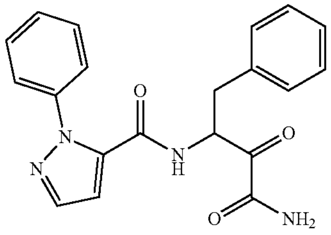 [SMILES: NC(=O)C(=O)C(Cc1ccccc1)NC(=O)c1ccnn1-c1ccccc1]
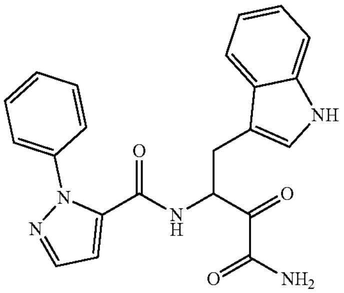 [SMILES: NC(=O)C(=O)C(Cc1c[nH]c2ccccc12)NC(=O)c1ccnn1-c1ccccc1]
TABLE 1-continued
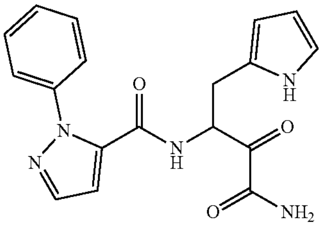 [SMILES: NC(=O)C(=O)C(Cc1ccc[nH]1)NC(=O)c1ccnn1-c1ccccc1]
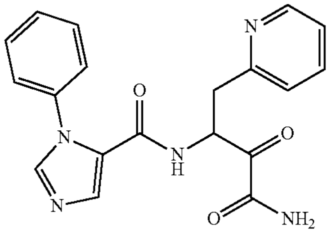 [SMILES: NC(=O)C(=O)C(Cc1ccccn1)NC(=O)c1cncn1-c1ccccc1]
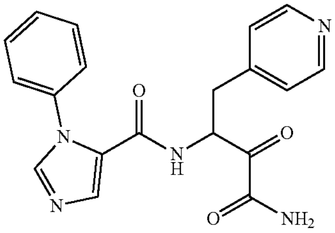 [SMILES: NC(=O)C(=O)C(Cc1ccncc1)NC(=O)c1cncn1-c1ccccc1]
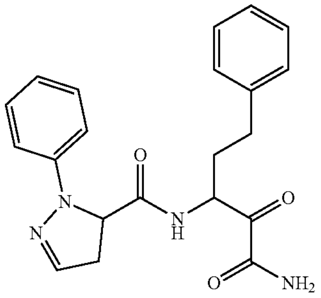 [SMILES: NC(=O)C(=O)C(CCc1ccccc1)NC(=O)C1CC=NN1c1ccccc1]
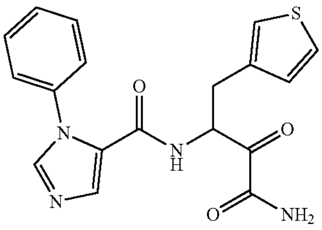 [SMILES: NC(=O)C(=O)C(Cc1ccsc1)NC(=O)c1cncn1-c1ccccc1]
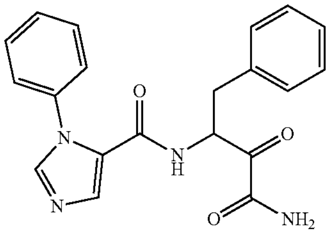

TABLE 1-continued
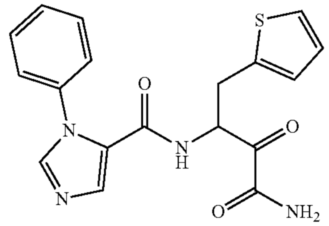 [SMILES: NC(=O)C(=O)C(Cc1cccs1)NC(=O)c1cncn1-c1ccccc1]
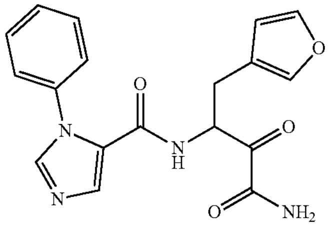 [SMILES: NC(=O)C(=O)C(Cc1ccoc1)NC(=O)c1cncn1-c1ccccc1]
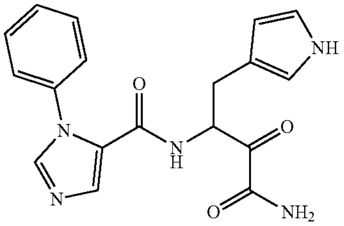 [SMILES: NC(=O)C(=O)C(Cc1cc[nH]c1)NC(=O)c1cncn1-c1ccccc1]
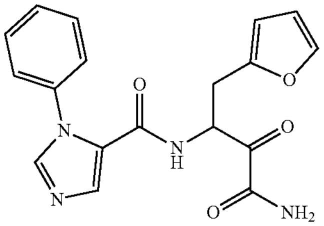 [SMILES: NC(=O)C(=O)C(Cc1ccco1)NC(=O)c1cncn1-c1ccccc1]
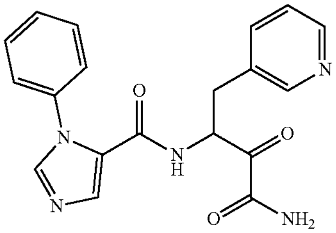 [SMILES: NC(=O)C(=O)C(Cc1cccnc1)NC(=O)c1cncn1-c1ccccc1]
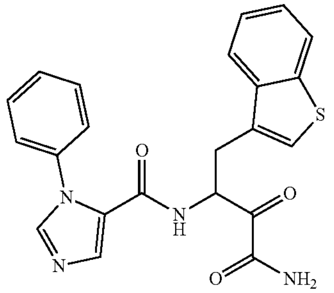 [SMILES: NC(=O)C(=O)C(Cc1csc2ccccc12)NC(=O)c1cncn1-c1ccccc1]
TABLE 1-continued
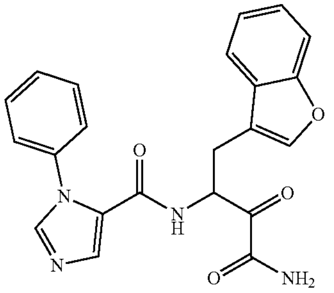 [SMILES: NC(=O)C(=O)C(Cc1coc2ccccc12)NC(=O)c1cncn1-c1ccccc1]
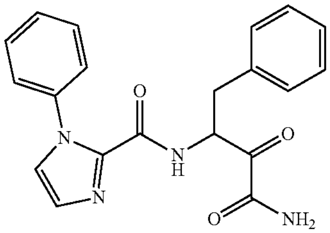 [SMILES: NC(=O)C(=O)C(Cc1ccccc1)NC(=O)c1nccn1-c1ccccc1]
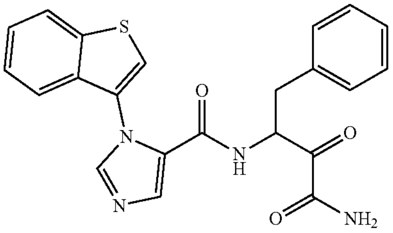 [SMILES: NC(=O)C(=O)C(Cc1ccccc1)NC(=O)c1cncn1-c1csc2ccccc12]
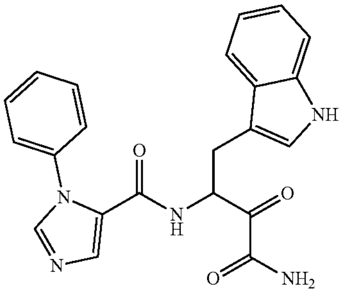 [SMILES: NC(=O)C(=O)C(Cc1c[nH]c2ccccc12)NC(=O)c1cncn1-c1ccccc1]
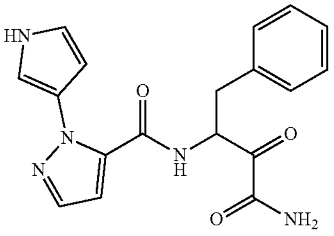 [SMILES: NC(=O)C(=O)C(Cc1ccccc1)NC(=O)c1ccnn1-c1cc[nH]c1]
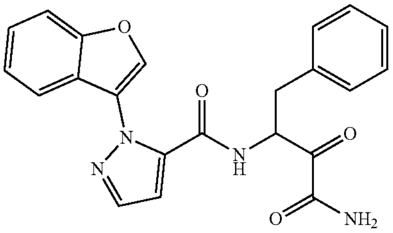 [SMILES: NC(=O)C(=O)C(Cc1ccccc1)NC(=O)c1ccnn1-c1coc2ccccc12]

TABLE 1-continued
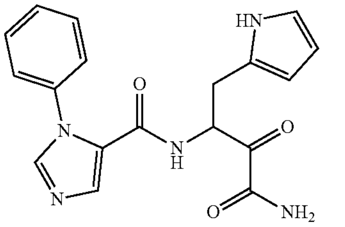 [SMILES: NC(=O)C(=O)C(Cc1ccc[nH]1)NC(=O)c1cncn1-c1ccccc1]
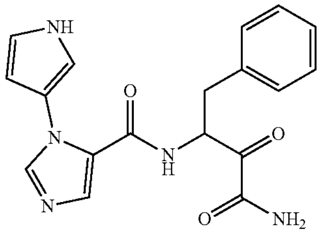 [SMILES: NC(=O)C(=O)C(Cc1ccccc1)NC(=O)c1cncn1-c1cc[nH]c1]
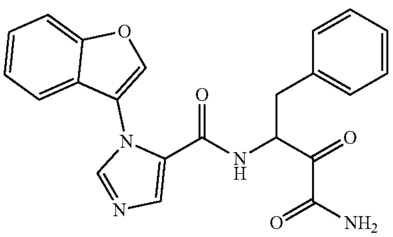 [SMILES: NC(=O)C(=O)C(Cc1ccccc1)NC(=O)c1cncn1-c1coc2ccccc12]
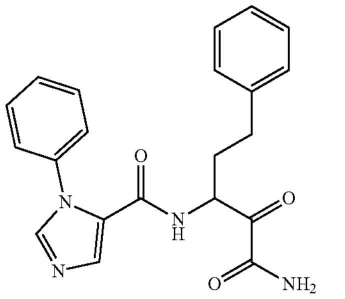 [SMILES: NC(=O)C(=O)C(CCc1ccccc1)NC(=O)c1cncn1-c1ccccc1]
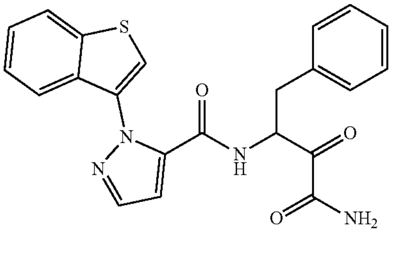 [SMILES: NC(=O)C(=O)C(Cc1ccccc1)NC(=O)c1ccnn1-c1csc2ccccc12]
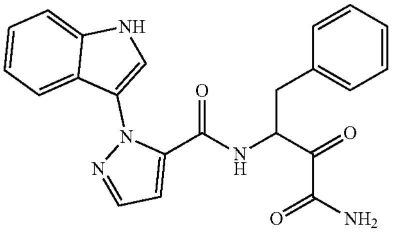
TABLE 1-continued
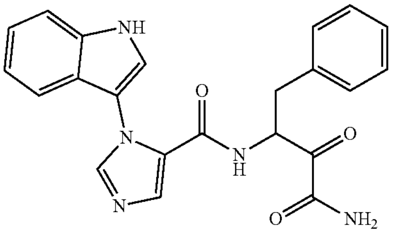 [SMILES: NC(=O)C(=O)C(Cc1ccccc1)NC(=O)c1cncn1-c1c[nH]c2ccccc12]
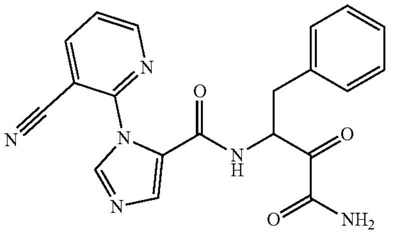 [SMILES: N#Cc1cccnc1-n1cncc1C(=O)NC(Cc1ccccc1)C(=O)C(N)=O]
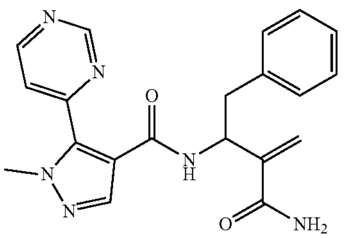 [SMILES: C=C(C(N)=O)C(Cc1ccccc1)NC(=O)c1cnn(C)c1-c1ccncn1]
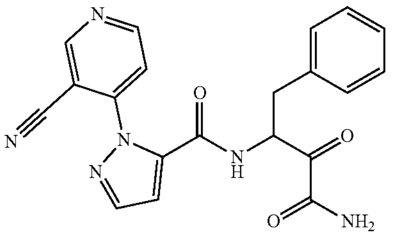 [SMILES: N#Cc1cnccc1-n1nccc1C(=O)NC(Cc1ccccc1)C(=O)C(N)=O]
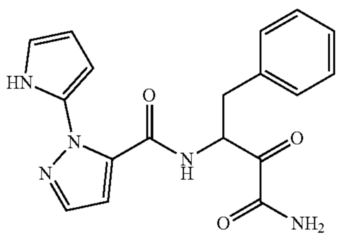 [SMILES: NC(=O)C(=O)C(Cc1ccccc1)NC(=O)c1ccnn1-c1ccc[nH]1]
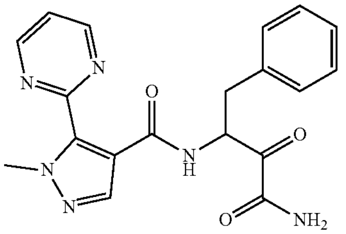 [SMILES: Cn1ncc(C(=O)NC(Cc2ccccc2)C(=O)C(N)=O)c1-c1ncccn1]

TABLE 1-continued
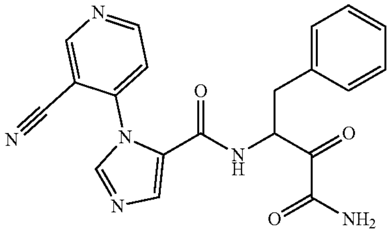 [SMILES: N#Cc1cnccc1-n1cncc1C(=O)NC(Cc1ccccc1)C(=O)C(N)=O]
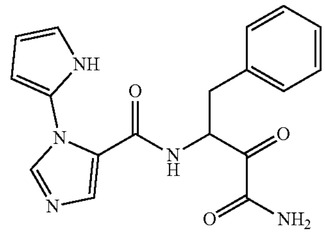 [SMILES: NC(=O)C(=O)C(Cc1ccccc1)NC(=O)c1cncn1-c1ccc[nH]1]
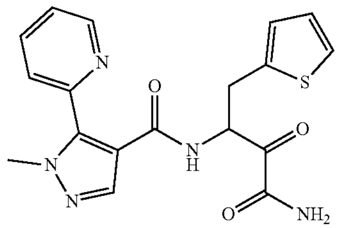 [SMILES: Cn1ncc(C(=O)NC(Cc2cccs2)C(=O)C(N)=O)c1-c1ccccn1]
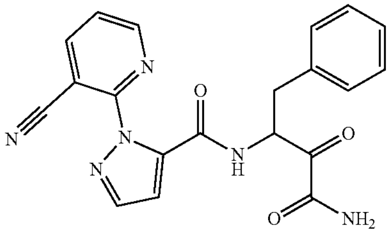 [SMILES: N#Cc1cccnc1-n1nccc1C(=O)NC(Cc1ccccc1)C(=O)C(N)=O]
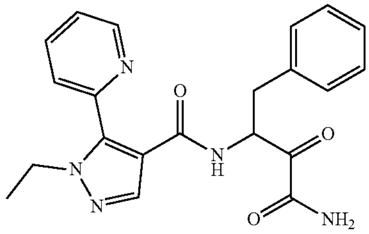 [SMILES: CCn1ncc(C(=O)NC(Cc2ccccc2)C(=O)C(N)=O)c1-c1ccccn1]
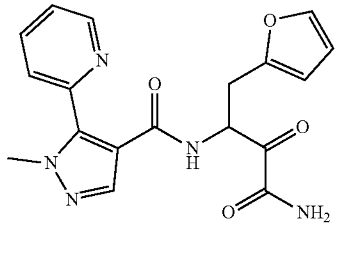 [SMILES: Cn1ncc(C(=O)NC(Cc2ccco2)C(=O)C(N)=O)c1-c1ccccn1]
TABLE 1-continued
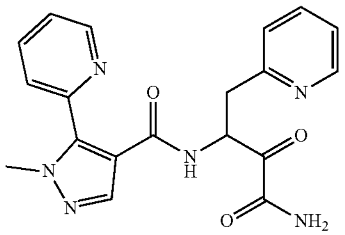 [SMILES: Cn1ncc(C(=O)NC(Cc2ccccn2)C(=O)C(N)=O)c1-c1ccccn1]
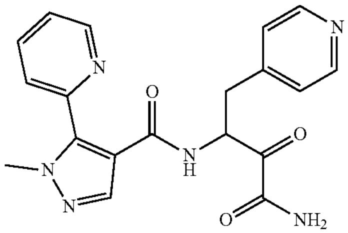 [SMILES: Cn1ncc(C(=O)NC(Cc2ccncc2)C(=O)C(N)=O)c1-c1ccccn1]
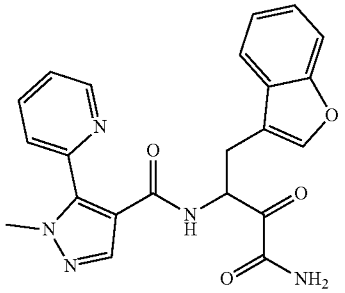 [SMILES: Cn1ncc(C(=O)NC(Cc2coc3ccccc23)C(=O)C(N)=O)c1-c1ccccn1]
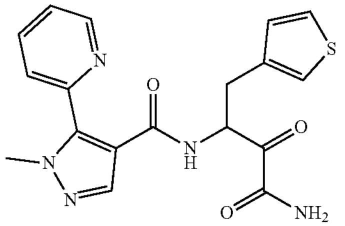 [SMILES: Cn1ncc(C(=O)NC(Cc2ccsc2)C(=O)C(N)=O)c1-c1ccccn1]
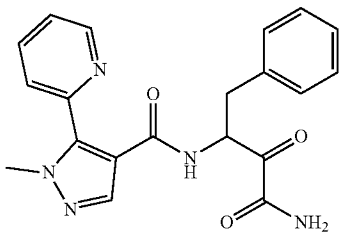 [SMILES: Cn1ncc(C(=O)NC(Cc2ccccc2)C(=O)C(N)=O)c1-c1ccccn1]
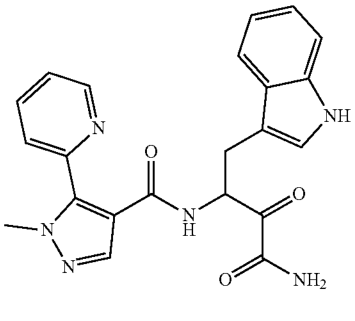 [SMILES: Cn1ncc(C(=O)NC(Cc2c[nH]c3ccccc23)C(=O)C(N)=O)c1-c1ccccn1]

TABLE 1-continued
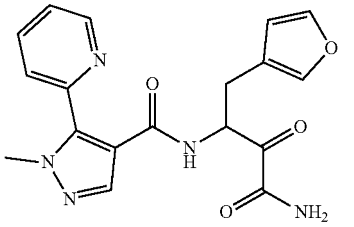 [SMILES: Cn1ncc(C(=O)NC(Cc2ccoc2)C(=O)C(N)=O)c1-c1ccccn1]
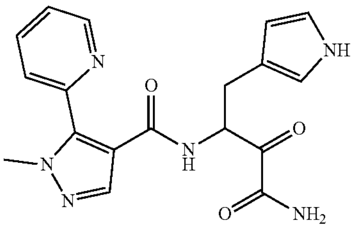 [SMILES: Cn1ncc(C(=O)NC(Cc2cc[nH]c2)C(=O)C(N)=O)c1-c1ccccn1]
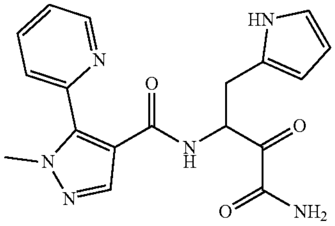 [SMILES: Cn1ncc(C(=O)NC(Cc2ccc[nH]2)C(=O)C(N)=O)c1-c1ccccn1]
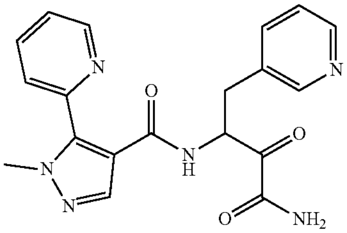 [SMILES: Cn1ncc(C(=O)NC(Cc2cccnc2)C(=O)C(N)=O)c1-c1ccccn1]
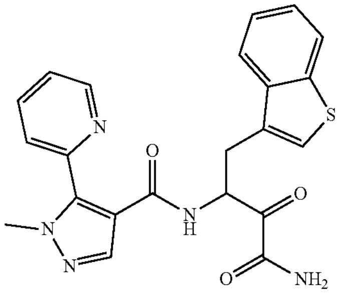 [SMILES: Cn1ncc(C(=O)NC(Cc2csc3ccccc23)C(=O)C(N)=O)c1-c1ccccn1]
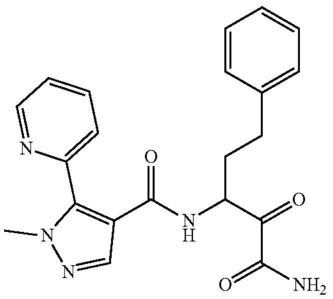 [SMILES: Cn1ncc(C(=O)NC(CCc2ccccc2)C(=O)C(N)=O)c1-c1ccccn1]
TABLE 1-continued
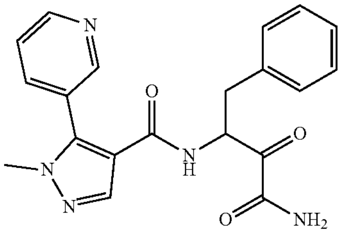 [SMILES: Cn1ncc(C(=O)NC(Cc2ccccc2)C(=O)C(N)=O)c1-c1cccnc1]
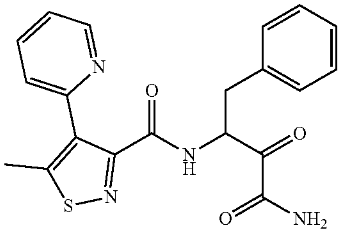 [SMILES: Cc1snc(C(=O)NC(Cc2ccccc2)C(=O)C(N)=O)c1-c1ccccn1]
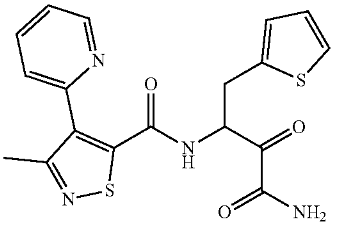 [SMILES: Cc1nsc(C(=O)NC(Cc2cccs2)C(=O)C(N)=O)c1-c1ccccn1]
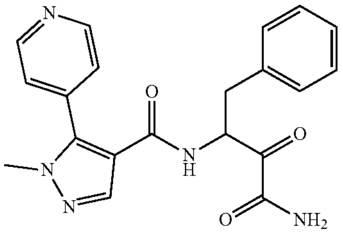 [SMILES: Cn1ncc(C(=O)NC(Cc2ccccc2)C(=O)C(N)=O)c1-c1ccncc1]
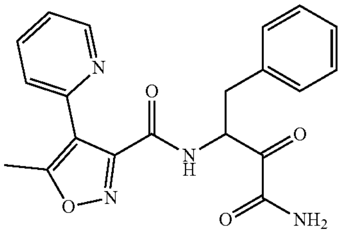
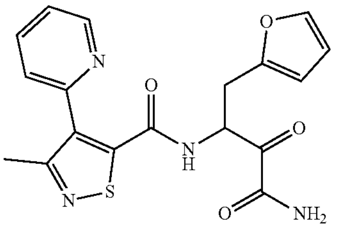 [SMILES: Cc1nsc(C(=O)NC(Cc2ccco2)C(=O)C(N)=O)c1-c1ccccn1]

TABLE 1-continued
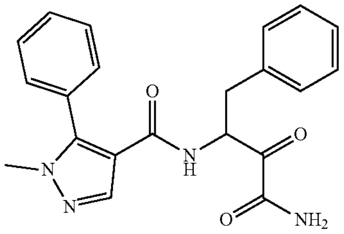 [SMILES: Cn1ncc(C(=O)NC(Cc2ccccc2)C(=O)C(N)=O)c1-c1ccccc1]
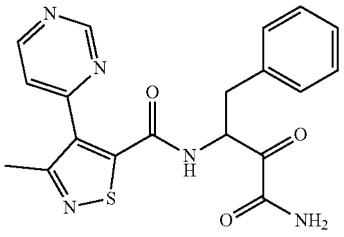 [SMILES: Cc1nsc(C(=O)NC(Cc2ccccc2)C(=O)C(N)=O)c1-c1ccncn1]
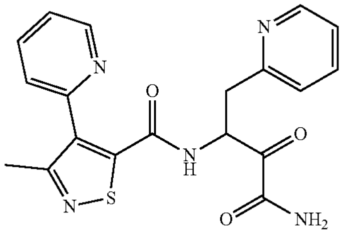 [SMILES: Cc1nsc(C(=O)NC(Cc2ccccn2)C(=O)C(N)=O)c1-c1ccccn1]
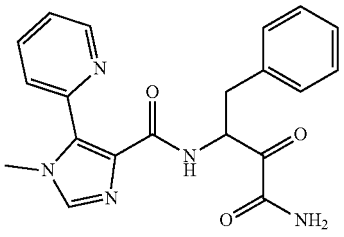 [SMILES: Cn1cnc(C(=O)NC(Cc2ccccc2)C(=O)C(N)=O)c1-c1ccccn1]
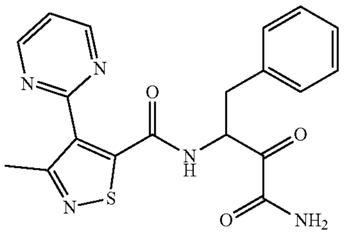
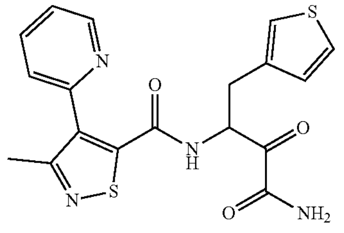 [SMILES: Cc1nsc(C(=O)NC(Cc2ccsc2)C(=O)C(N)=O)c1-c1ccccn1]
TABLE 1-continued
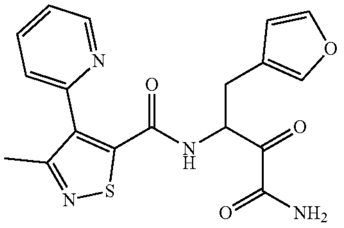 [SMILES: Cc1nsc(C(=O)NC(Cc2ccoc2)C(=O)C(N)=O)c1-c1ccccn1]
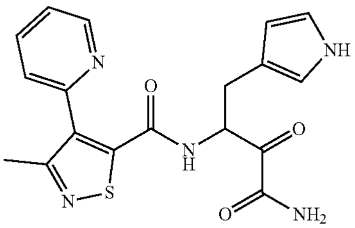 [SMILES: Cc1nsc(C(=O)NC(Cc2cc[nH]c2)C(=O)C(N)=O)c1-c1ccccn1]
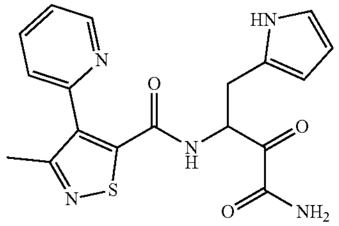 [SMILES: Cc1nsc(C(=O)NC(Cc2ccc[nH]2)C(=O)C(N)=O)c1-c1ccccn1]
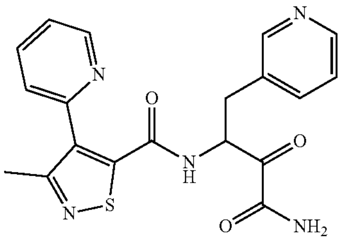
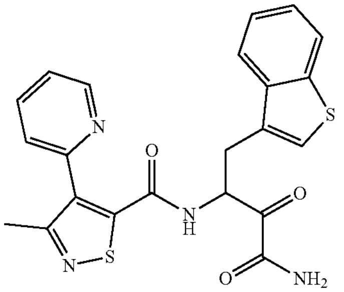 [SMILES: Cc1nsc(C(=O)NC(Cc2csc3ccccc23)C(=O)C(N)=O)c1-c1ccccn1]
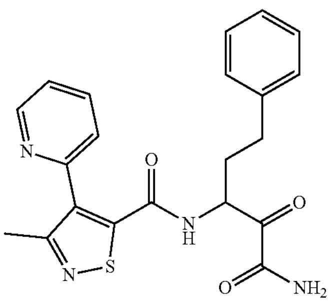

TABLE 1-continued
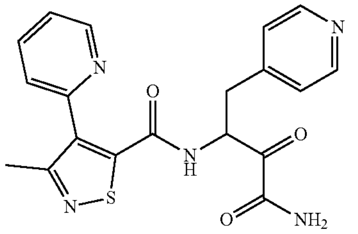 [SMILES: Cc1nsc(C(=O)NC(Cc2ccncc2)C(=O)C(N)=O)c1-c1ccccn1]
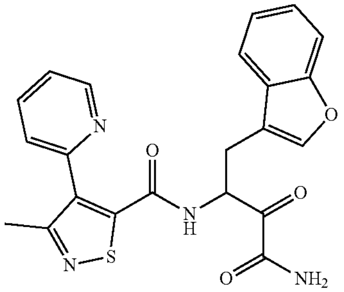 [SMILES: Cc1nsc(C(=O)NC(Cc2coc3ccccc23)C(=O)C(N)=O)c1-c1ccccn1]
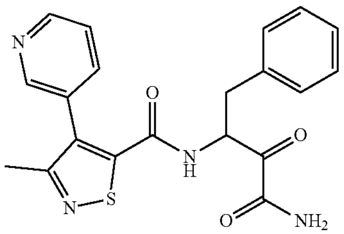 [SMILES: Cc1nsc(C(=O)NC(Cc2ccccc2)C(=O)C(N)=O)c1-c1cccnc1]
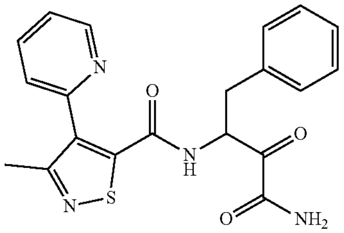 [SMILES: Cc1nsc(C(=O)NC(Cc2ccccc2)C(=O)C(N)=O)c1-c1ccccn1]
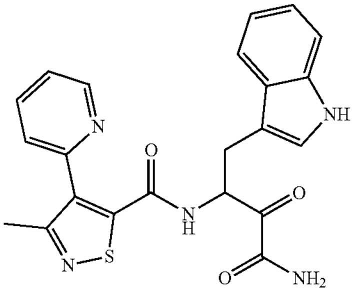 [SMILES: Cc1nsc(C(=O)NC(Cc2c[nH]c3ccccc23)C(=O)C(N)=O)c1-c1ccccn1]
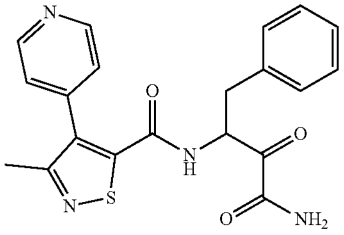 [SMILES: Cc1nsc(C(=O)NC(Cc2ccccc2)C(=O)C(N)=O)c1-c1ccncc1]
TABLE 1-continued
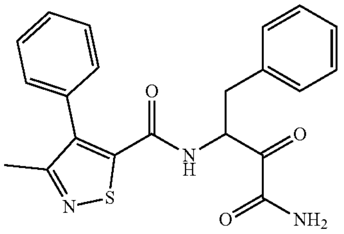 [SMILES: Cc1nsc(C(=O)NC(Cc2ccccc2)C(=O)C(N)=O)c1-c1ccccc1]
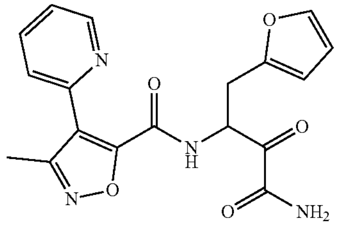 [SMILES: Cc1noc(C(=O)NC(Cc2ccco2)C(=O)C(N)=O)c1-c1ccccn1]
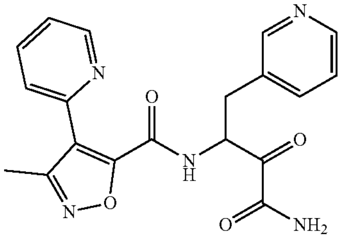
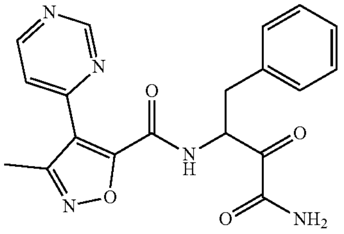 [SMILES: Cc1noc(C(=O)NC(Cc2ccccc2)C(=O)C(N)=O)c1-c1ccncn1]
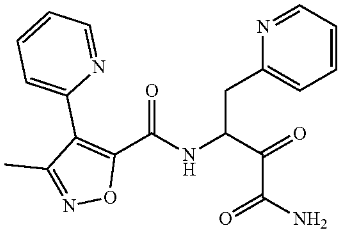 [SMILES: Cc1noc(C(=O)NC(Cc2ccccn2)C(=O)C(N)=O)c1-c1ccccn1]
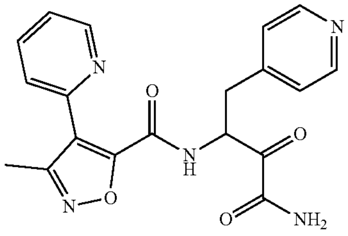 [SMILES: Cc1noc(C(=O)NC(Cc2ccncc2)C(=O)C(N)=O)c1-c1ccccn1]

TABLE 1-continued
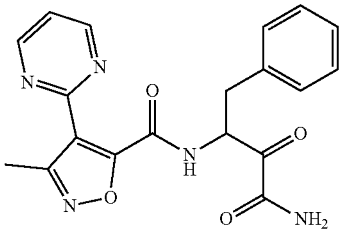 [SMILES: Cc1noc(C(=O)NC(Cc2ccccc2)C(=O)C(N)=O)c1-c1ncccn1]
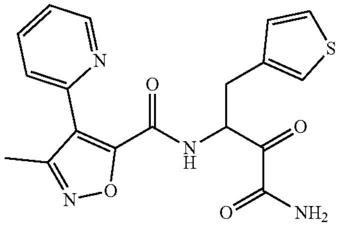 [SMILES: Cc1noc(C(=O)NC(Cc2ccsc2)C(=O)C(N)=O)c1-c1ccccn1]
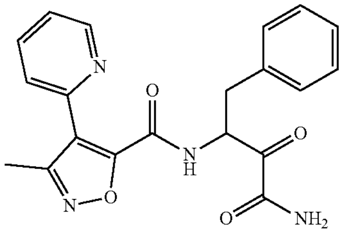 [SMILES: Cc1noc(C(=O)NC(Cc2ccccc2)C(=O)C(N)=O)c1-c1ccccn1]
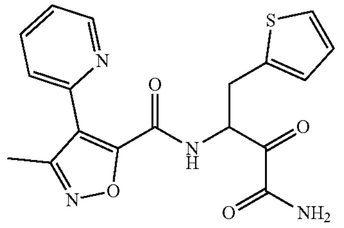 [SMILES: Cc1noc(C(=O)NC(Cc2cccs2)C(=O)C(N)=O)c1-c1ccccn1]
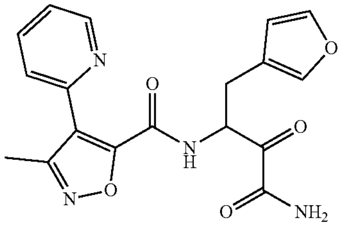 [SMILES: Cc1noc(C(=O)NC(Cc2ccoc2)C(=O)C(N)=O)c1-c1ccccn1]
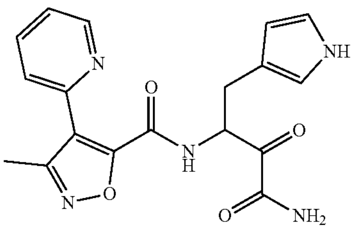 [SMILES: Cc1noc(C(=O)NC(Cc2cc[nH]c2)C(=O)C(N)=O)c1-c1ccccn1]
TABLE 1-continued
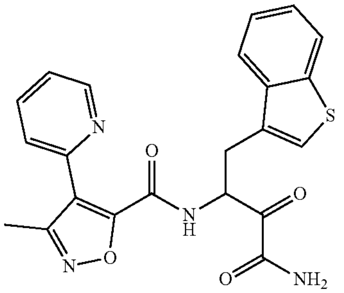 [SMILES: Cc1noc(C(=O)NC(Cc2csc3ccccc23)C(=O)C(N)=O)c1-c1ccccn1]
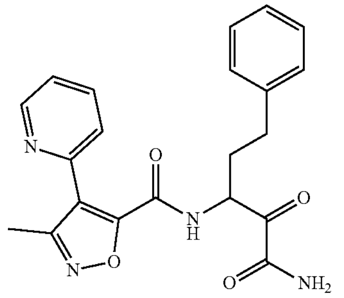 [SMILES: Cc1noc(C(=O)NC(CCc2ccccc2)C(=O)C(N)=O)c1-c1ccccn1]
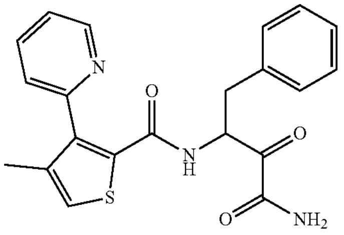
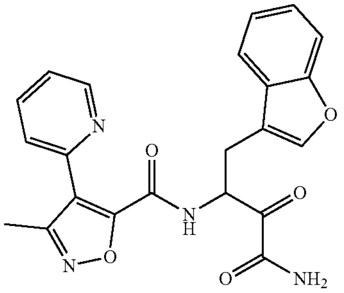 [SMILES: Cc1noc(C(=O)NC(Cc2coc3ccccc23)C(=O)C(N)=O)c1-c1ccccn1]
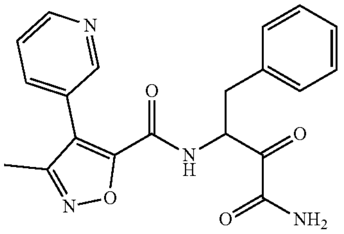 [SMILES: Cc1noc(C(=O)NC(Cc2ccccc2)C(=O)C(N)=O)c1-c1cccnc1]
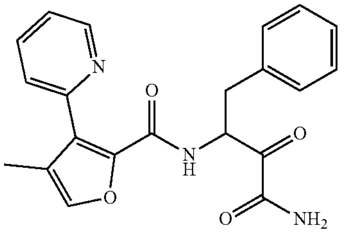 [SMILES: Cc1coc(C(=O)NC(Cc2ccccc2)C(=O)C(N)=O)c1-c1ccccn1]

TABLE 1-continued
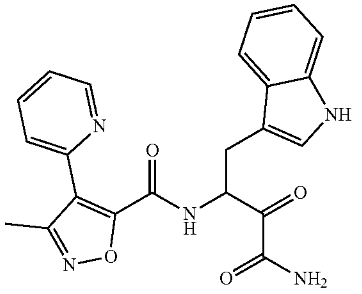 [SMILES: Cc1noc(C(=O)NC(Cc2c[nH]c3ccccc23)C(=O)C(N)=O)c1-c1ccccn1]
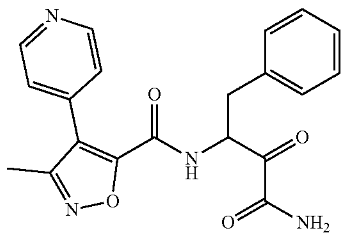 [SMILES: Cc1noc(C(=O)NC(Cc2ccccc2)C(=O)C(N)=O)c1-c1ccncc1]
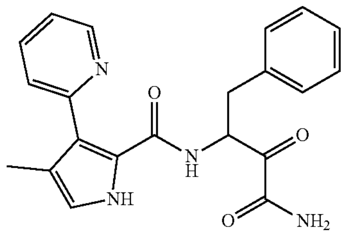 [SMILES: Cc1c[nH]c(C(=O)NC(Cc2ccccc2)C(=O)C(N)=O)c1-c1ccccn1]
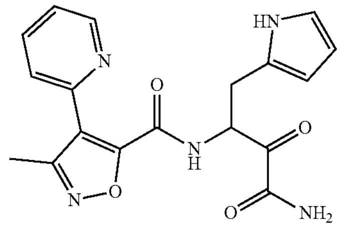 [SMILES: Cc1noc(C(=O)NC(Cc2ccc[nH]2)C(=O)C(N)=O)c1-c1ccccn1]
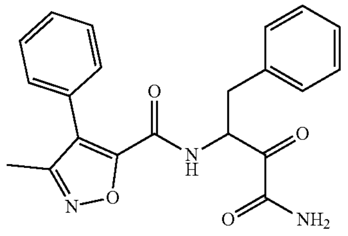 [SMILES: Cc1noc(C(=O)NC(Cc2ccccc2)C(=O)C(N)=O)c1-c1ccccc1]
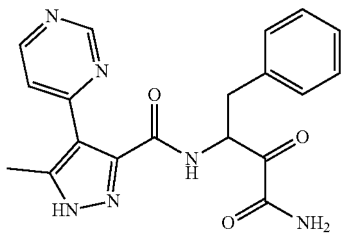
TABLE 1-continued
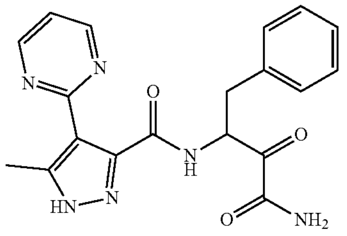
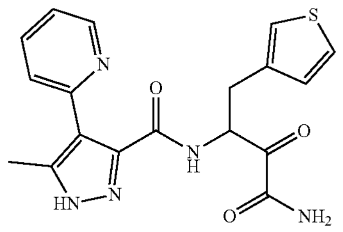
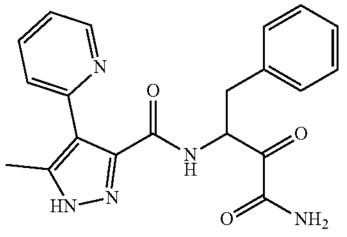
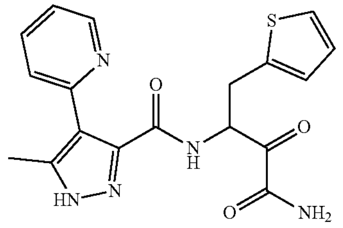 [SMILES: Cc1[nH]nc(C(=O)NC(Cc2cccs2)C(=O)C(N)=O)c1-c1ccccn1]
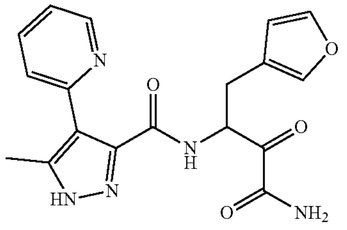
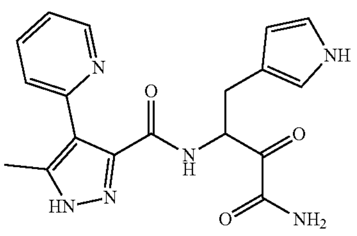 [SMILES: Cc1[nH]nc(C(=O)NC(Cc2cc[nH]c2)C(=O)C(N)=O)c1-c1ccccn1]

TABLE 1-continued
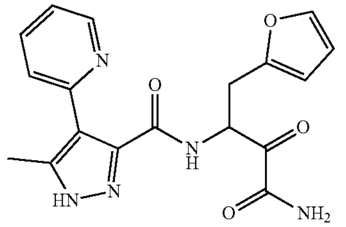 [SMILES: Cc1[nH]nc(C(=O)NC(Cc2ccco2)C(=O)C(N)=O)c1-c1ccccn1]
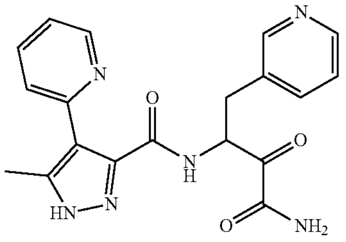
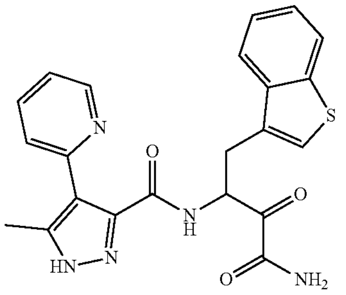 [SMILES: Cc1[nH]nc(C(=O)NC(Cc2csc3ccccc23)C(=O)C(N)=O)c1-c1ccccn1]
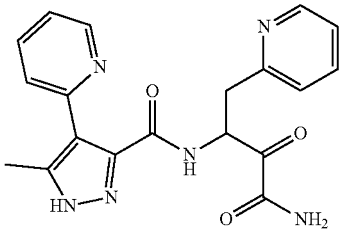 [SMILES: Cc1[nH]nc(C(=O)NC(Cc2ccccn2)C(=O)C(N)=O)c1-c1ccccn1]
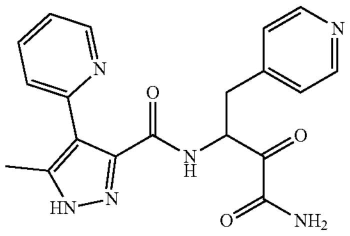
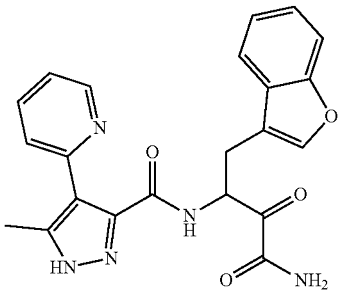 [SMILES: Cc1[nH]nc(C(=O)NC(Cc2coc3ccccc23)C(=O)C(N)=O)c1-c1ccccn1]
TABLE 1-continued
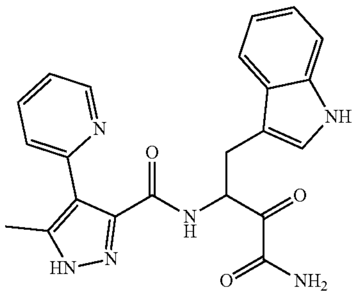 [SMILES: Cc1[nH]nc(C(=O)NC(Cc2c[nH]c3ccccc23)C(=O)C(N)=O)c1-c1ccccn1]
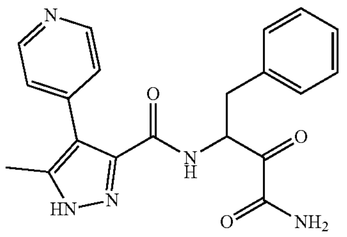
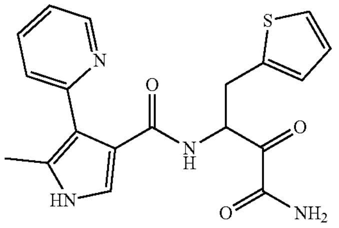 [SMILES: Cc1[nH]cc(C(=O)NC(Cc2cccs2)C(=O)C(N)=O)c1-c1ccccn1]
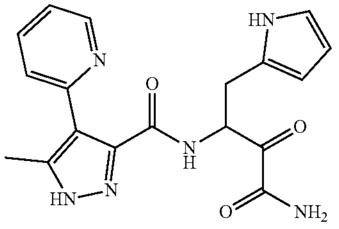
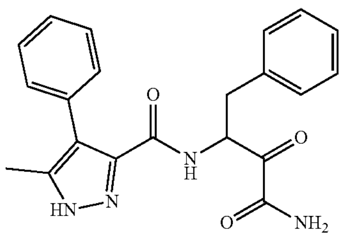
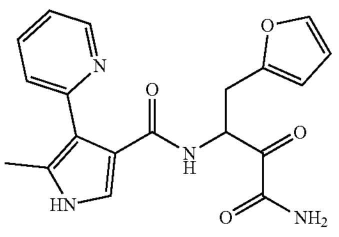 [SMILES: Cc1[nH]cc(C(=O)NC(Cc2ccco2)C(=O)C(N)=O)c1-c1ccccn1]

TABLE 1-continued
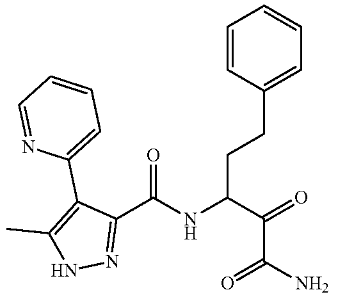 [SMILES: Cc1[nH]nc(C(=O)NC(CCc2ccccc2)C(=O)C(N)=O)c1-c1ccccn1]
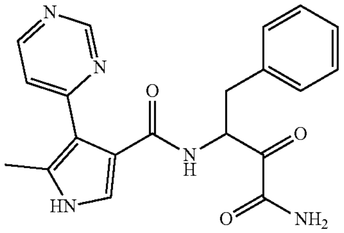
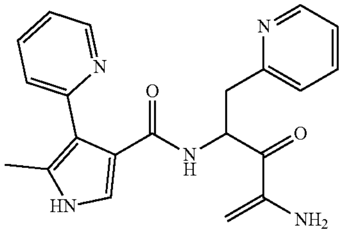
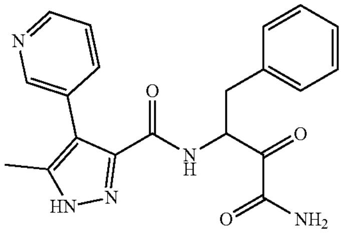
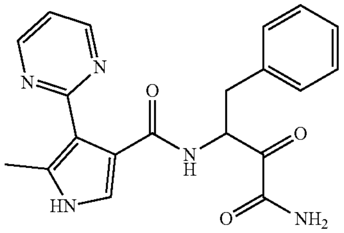
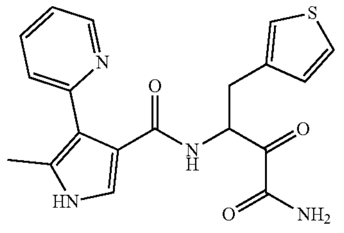 [SMILES: Cc1[nH]cc(C(=O)NC(Cc2ccsc2)C(=O)C(N)=O)c1-c1ccccn1]
TABLE 1-continued
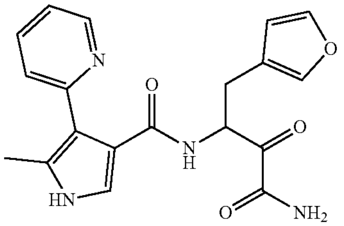 [SMILES: Cc1[nH]cc(C(=O)NC(Cc2ccoc2)C(=O)C(N)=O)c1-c1ccccn1]
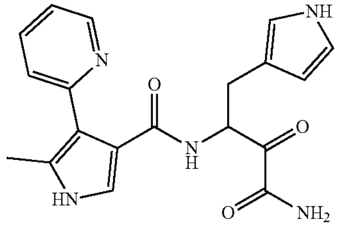 [SMILES: Cc1[nH]cc(C(=O)NC(Cc2cc[nH]c2)C(=O)C(N)=O)c1-c1ccccn1]
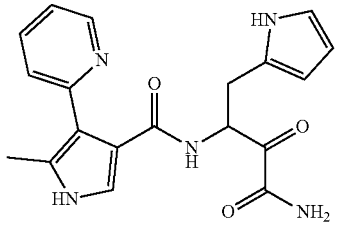 [SMILES: Cc1[nH]cc(C(=O)NC(Cc2ccc[nH]2)C(=O)C(N)=O)c1-c1ccccn1]
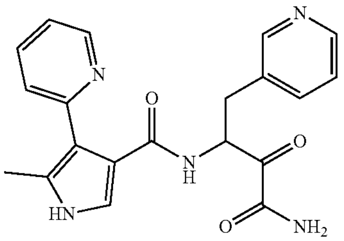 [SMILES: Cc1[nH]cc(C(=O)NC(Cc2cccnc2)C(=O)C(N)=O)c1-c1ccccn1]
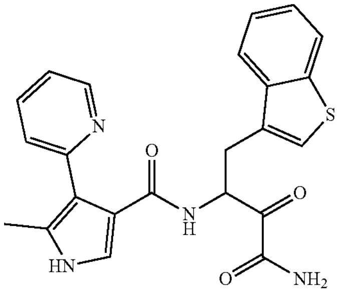 [SMILES: Cc1[nH]cc(C(=O)NC(Cc2csc3ccccc23)C(=O)C(N)=O)c1-c1ccccn1]
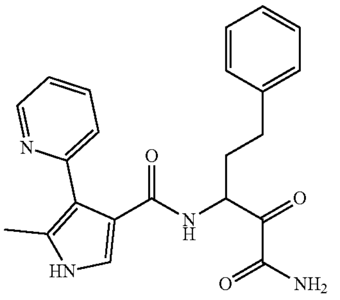

TABLE 1-continued
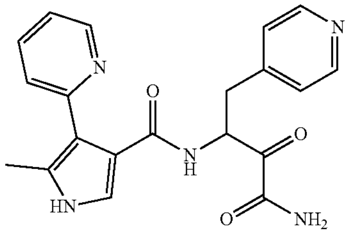 [SMILES: Cc1[nH]cc(C(=O)NC(Cc2ccncc2)C(=O)C(N)=O)c1-c1ccccn1]
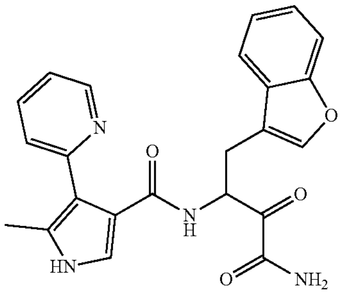 [SMILES: Cc1[nH]cc(C(=O)NC(Cc2coc3ccccc23)C(=O)C(N)=O)c1-c1ccccn1]
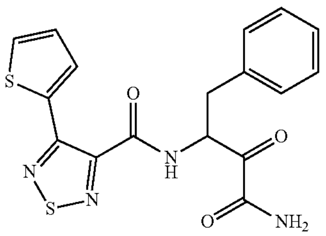 [SMILES: NC(=O)C(=O)C(Cc1ccccc1)NC(=O)c1nsnc1-c1cccs1]
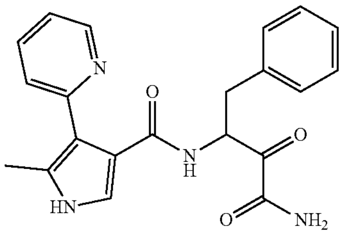 [SMILES: Cc1[nH]cc(C(=O)NC(Cc2ccccc2)C(=O)C(N)=O)c1-c1ccccn1]
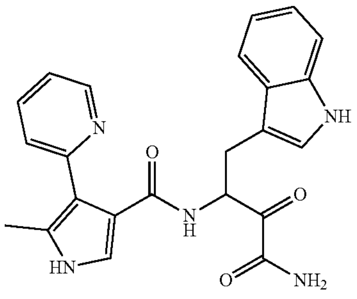 [SMILES: Cc1[nH]cc(C(=O)NC(Cc2c[nH]c3ccccc23)C(=O)C(N)=O)c1-c1ccccn1]
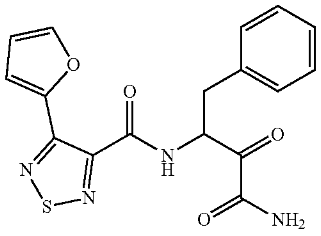 [SMILES: NC(=O)C(=O)C(Cc1ccccc1)NC(=O)c1nsnc1-c1ccco1]
TABLE 1-continued
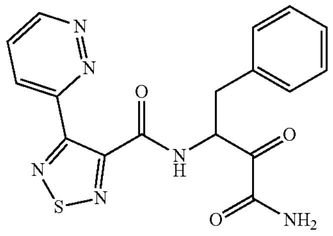 [SMILES: NC(=O)C(=O)C(Cc1ccccc1)NC(=O)c1nsnc1-c1cccnn1]
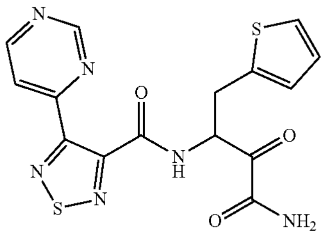 [SMILES: NC(=O)C(=O)C(Cc1cccs1)NC(=O)c1nsnc1-c1ccncn1]
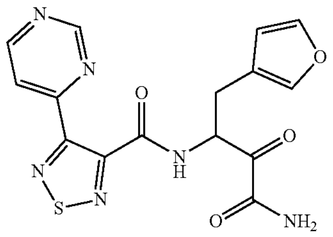 [SMILES: NC(=O)C(=O)C(Cc1ccoc1)NC(=O)c1nsnc1-c1ccncn1]
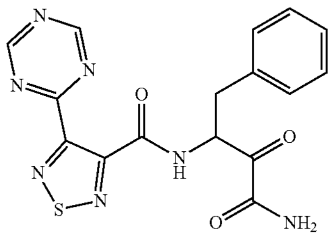 [SMILES: NC(=O)C(=O)C(Cc1ccccc1)NC(=O)c1nsnc1-c1ncncn1]
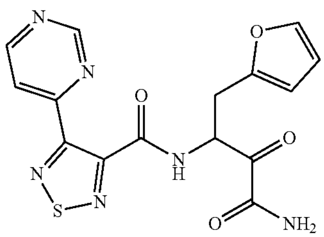 [SMILES: NC(=O)C(=O)C(Cc1ccco1)NC(=O)c1nsnc1-c1ccncn1]
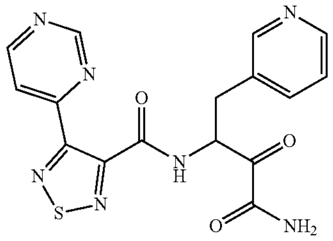 [SMILES: NC(=O)C(=O)C(Cc1cccnc1)NC(=O)c1nsnc1-c1ccncn1]

TABLE 1-continued
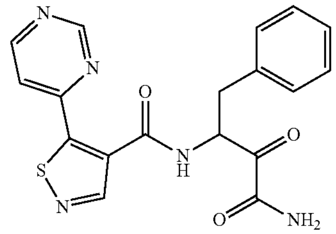 [SMILES: NC(=O)C(=O)C(Cc1ccccc1)NC(=O)c1cnsc1-c1ccncn1]
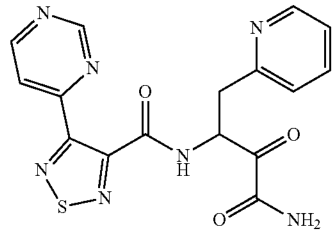 [SMILES: NC(=O)C(=O)C(Cc1ccccn1)NC(=O)c1nsnc1-c1ccncn1]
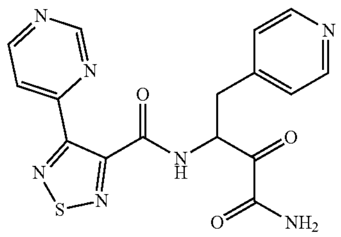 [SMILES: NC(=O)C(=O)C(Cc1ccncc1)NC(=O)c1nsnc1-c1ccncn1]
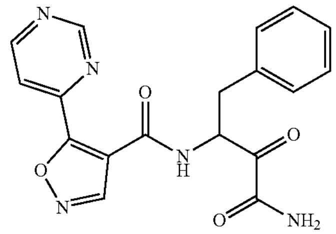 [SMILES: NC(=O)C(=O)C(Cc1ccccc1)NC(=O)c1cnoc1-c1ccncn1]
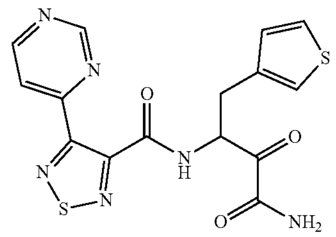 [SMILES: NC(=O)C(=O)C(Cc1ccsc1)NC(=O)c1nsnc1-c1ccncn1]
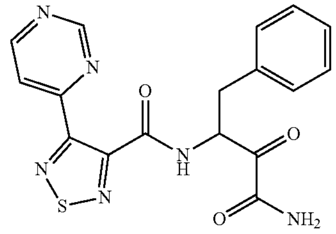 [SMILES: NC(=O)C(=O)C(Cc1ccccc1)NC(=O)c1nsnc1-c1ccncn1]
TABLE 1-continued
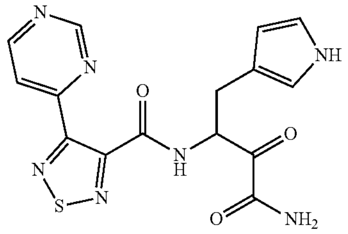 [SMILES: NC(=O)C(=O)C(Cc1cc[nH]c1)NC(=O)c1nsnc1-c1ccncn1]
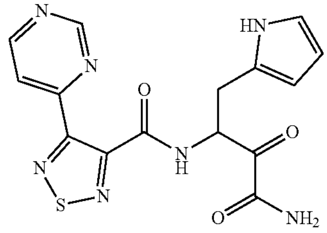 [SMILES: NC(=O)C(=O)C(Cc1ccc[nH]1)NC(=O)c1nsnc1-c1ccncn1]
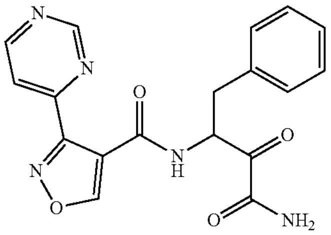 [SMILES: NC(=O)C(=O)C(Cc1ccccc1)NC(=O)c1conc1-c1ccncn1]
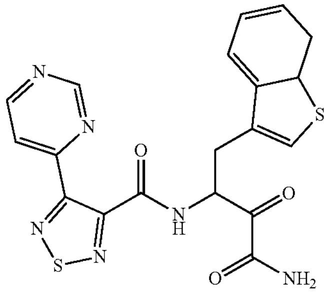 [SMILES: NC(=O)C(=O)C(CC1=CSC2CC=CC=C12)NC(=O)c1nsnc1-c1ccncn1]
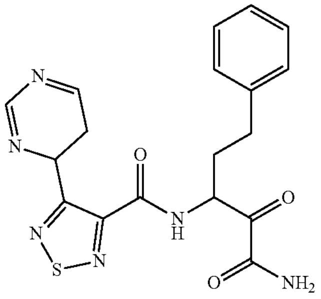 [SMILES: NC(=O)C(=O)C(CCc1ccccc1)NC(=O)c1nsnc1C1CC=NC=N1]
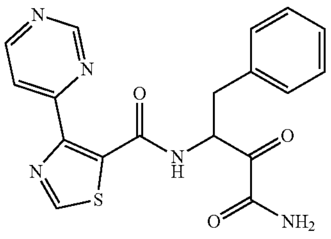 [SMILES: NC(=O)C(=O)C(Cc1ccccc1)NC(=O)c1scnc1-c1ccncn1]

TABLE 1-continued
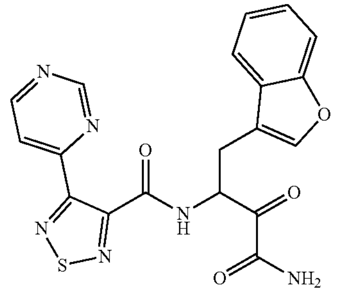
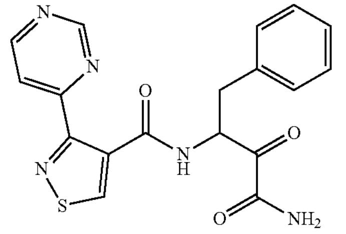 [SMILES: NC(=O)C(=O)C(Cc1ccccc1)NC(=O)c1csnc1-c1ccncn1]
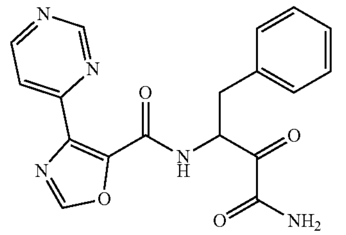 [SMILES: NC(=O)C(=O)C(Cc1ccccc1)NC(=O)c1ocnc1-c1ccncn1]
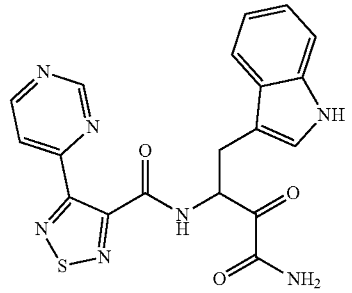
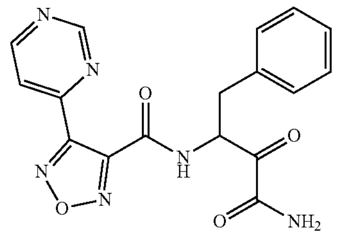
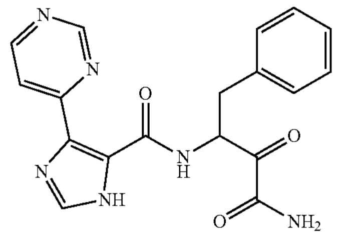 [SMILES: NC(=O)C(=O)C(Cc1ccccc1)NC(=O)c1[nH]cnc1-c1ccncn1]
TABLE 1-continued
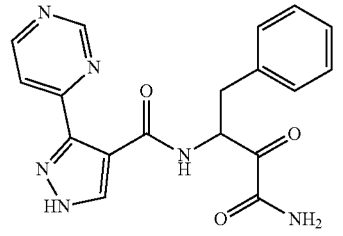 [SMILES: NC(=O)C(=O)C(Cc1ccccc1)NC(=O)c1c[nH]nc1-c1ccncn1]
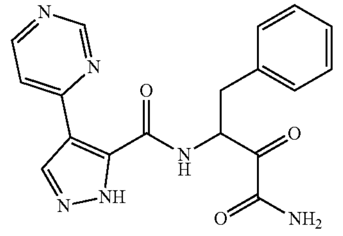 [SMILES: NC(=O)C(=O)C(Cc1ccccc1)NC(=O)c1[nH]ncc1-c1ccncn1]
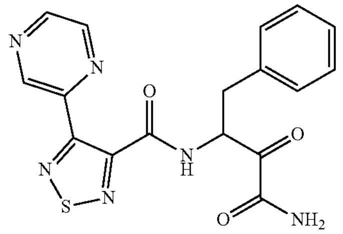 [SMILES: NC(=O)C(=O)C(Cc1ccccc1)NC(=O)c1nsnc1-c1cnccn1]
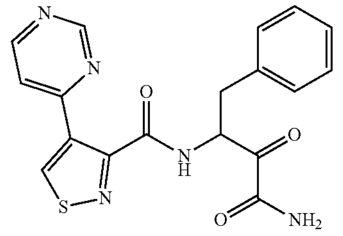 [SMILES: NC(=O)C(=O)C(Cc1ccccc1)NC(=O)c1nscc1-c1ccncn1]
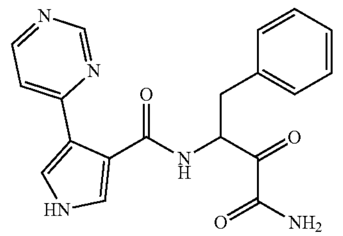 [SMILES: NC(=O)C(=O)C(Cc1ccccc1)NC(=O)c1c[nH]cc1-c1ccncn1]
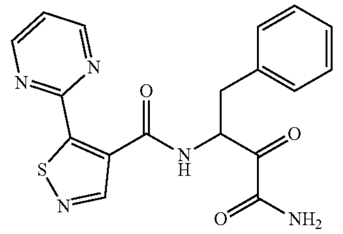 [SMILES: NC(=O)C(=O)C(Cc1ccccc1)NC(=O)c1cnsc1-c1ncccn1]

TABLE 1-continued
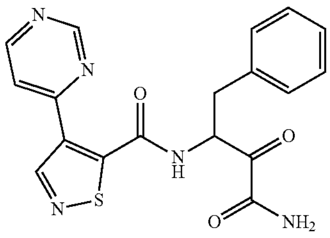 [SMILES: NC(=O)C(=O)C(Cc1ccccc1)NC(=O)c1sncc1-c1ccncn1]
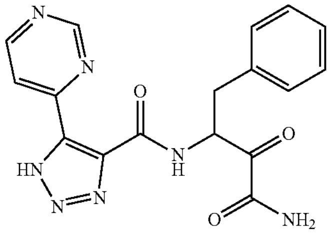 [SMILES: NC(=O)C(=O)C(Cc1ccccc1)NC(=O)c1nn[nH]c1-c1ccncn1]
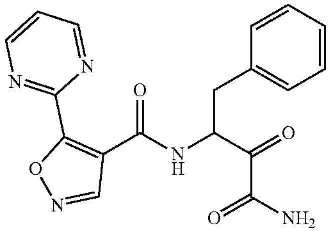 [SMILES: NC(=O)C(=O)C(Cc1ccccc1)NC(=O)c1cnoc1-c1ncccn1]
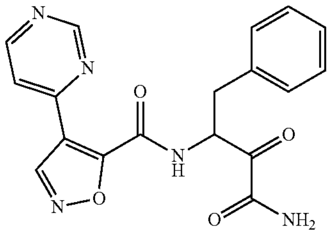 [SMILES: NC(=O)C(=O)C(Cc1ccccc1)NC(=O)c1oncc1-c1ccncn1]
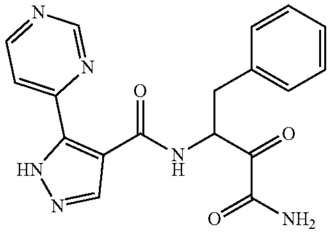 [SMILES: NC(=O)C(=O)C(Cc1ccccc1)NC(=O)c1cn[nH]c1-c1ccncn1]
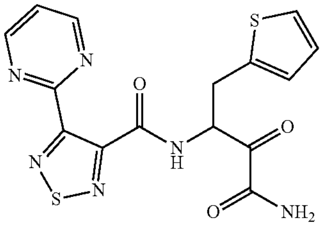
TABLE 1-continued
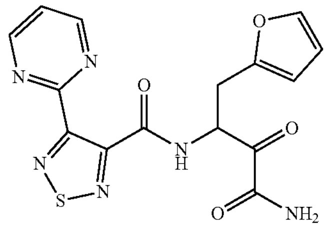
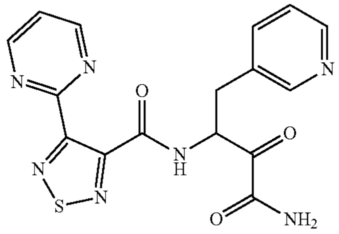 [SMILES: NC(=O)C(=O)C(Cc1cccnc1)NC(=O)c1nsnc1-c1ncccn1]
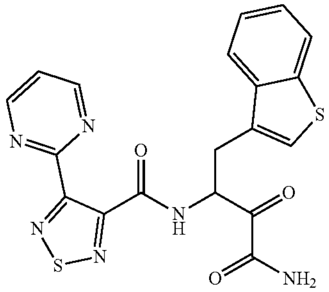
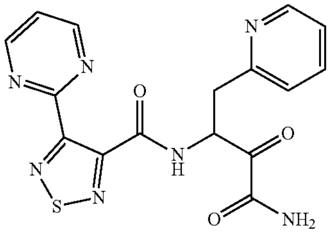 [SMILES: NC(=O)C(=O)C(Cc1ccccn1)NC(=O)c1nsnc1-c1ncccn1]
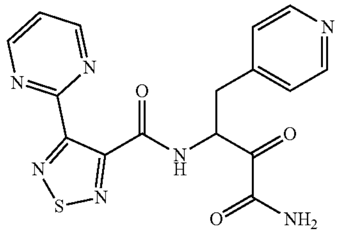 [SMILES: NC(=O)C(=O)C(Cc1ccncc1)NC(=O)c1nsnc1-c1ncccn1]
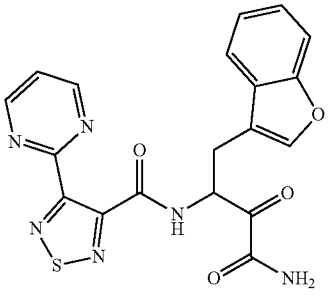

TABLE 1-continued
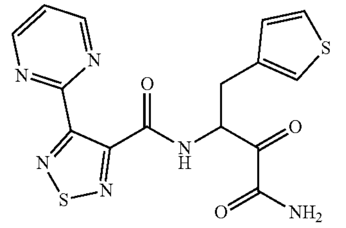 [SMILES: NC(=O)C(=O)C(Cc1ccsc1)NC(=O)c1nsnc1-c1ncccn1]
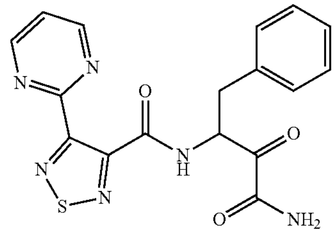 [SMILES: NC(=O)C(=O)C(Cc1ccccc1)NC(=O)c1nsnc1-c1ncccn1]
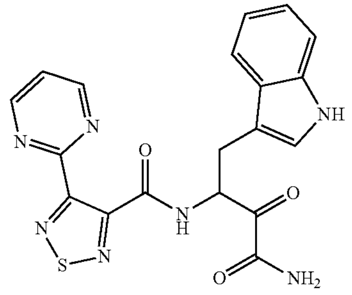
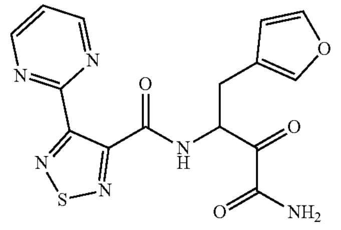 [SMILES: NC(=O)C(=O)C(Cc1ccoc1)NC(=O)c1nsnc1-c1ncccn1]
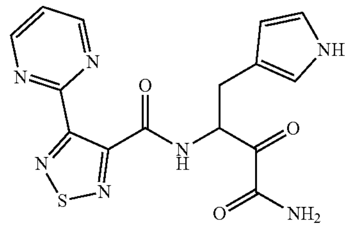 [SMILES: NC(=O)C(=O)C(Cc1cc[nH]c1)NC(=O)c1nsnc1-c1ncccn1]
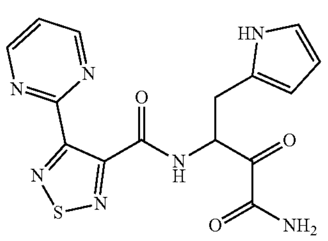
TABLE 1-continued
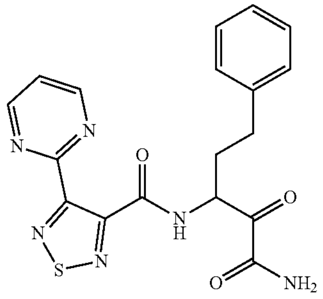 [SMILES: NC(=O)C(=O)C(CCc1ccccc1)NC(=O)c1nsnc1-c1ncccn1]
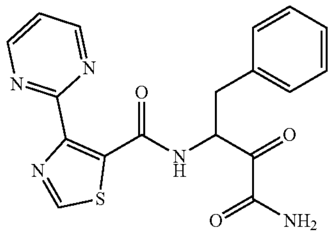
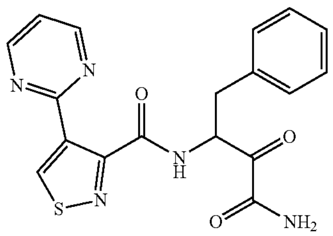
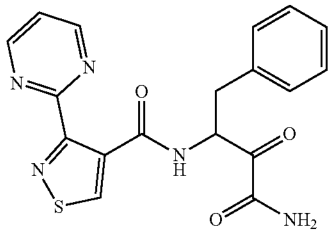
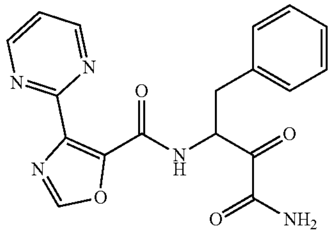 [SMILES: NC(=O)C(=O)C(Cc1ccccc1)NC(=O)c1ocnc1-c1ncccn1]
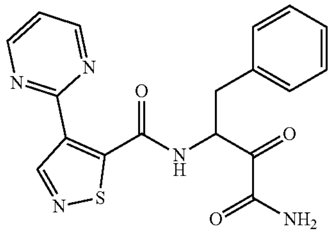 [SMILES: NC(=O)C(=O)C(Cc1ccccc1)NC(=O)c1sncc1-c1ncccn1]

TABLE 1-continued
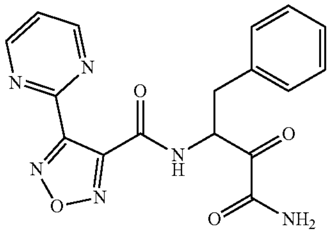
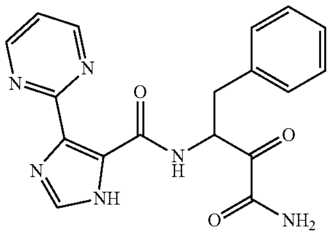 [SMILES: NC(=O)C(=O)C(Cc1ccccc1)NC(=O)c1[nH]cnc1-c1ncccn1]
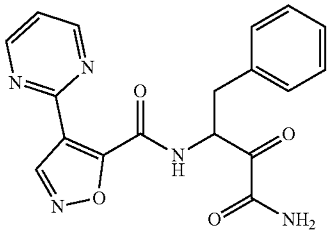 [SMILES: NC(=O)C(=O)C(Cc1ccccc1)NC(=O)c1oncc1-c1ncccn1]
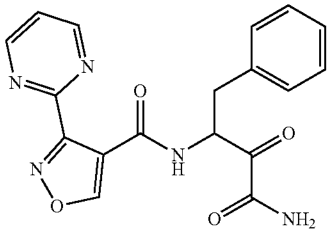
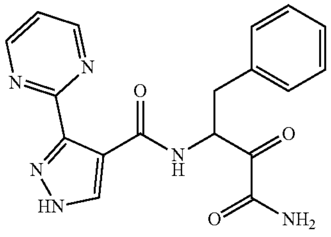 [SMILES: NC(=O)C(=O)C(Cc1ccccc1)NC(=O)c1c[nH]nc1-c1ncccn1]
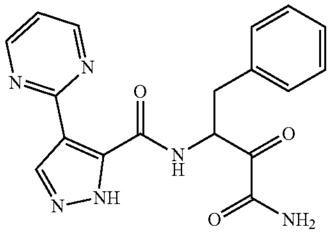 [SMILES: NC(=O)C(=O)C(Cc1ccccc1)NC(=O)c1[nH]ncc1-c1ncccn1]
TABLE 1-continued
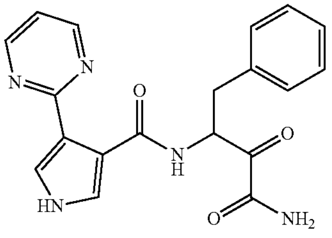 [SMILES: NC(=O)C(=O)C(Cc1ccccc1)NC(=O)c1c[nH]cc1-c1ncccn1]
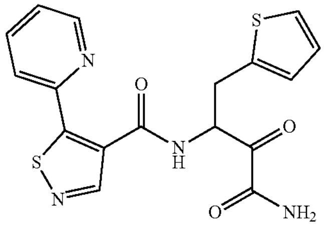
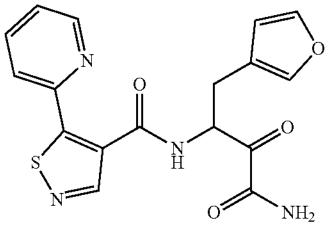
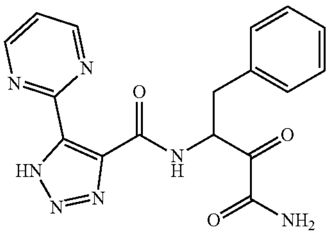
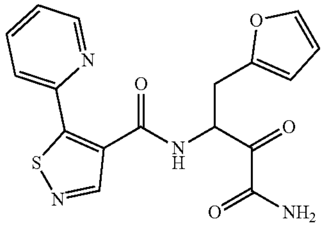
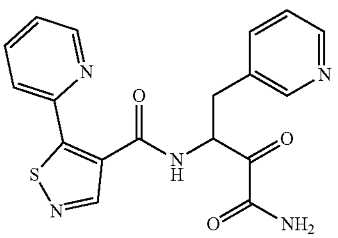 [SMILES: NC(=O)C(=O)C(Cc1cccnc1)NC(=O)c1cnsc1-c1ccccn1]

TABLE 1-continued
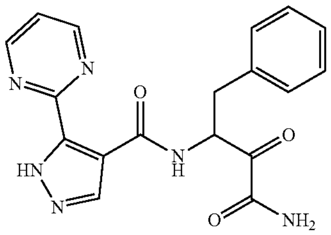
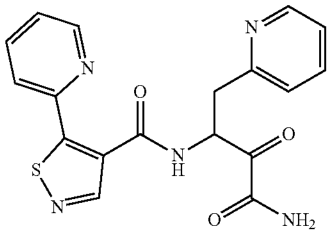
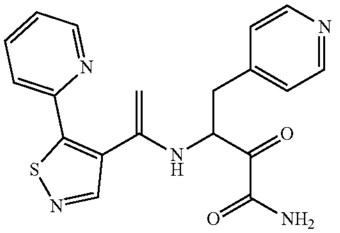 [SMILES: C=C(NC(Cc1ccncc1)C(=O)C(N)=O)c1cnsc1-c1ccccn1]
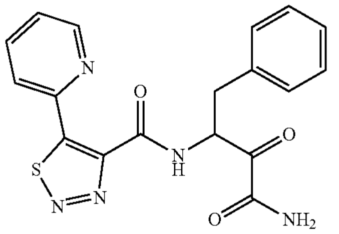
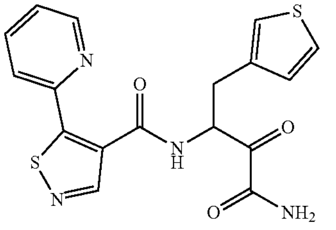 [SMILES: NC(=O)C(=O)C(Cc1ccsc1)NC(=O)c1cnsc1-c1ccccn1]
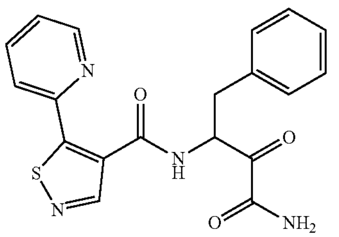
TABLE 1-continued
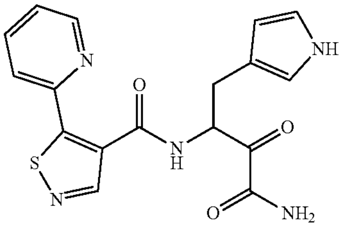 [SMILES: NC(=O)C(=O)C(Cc1cc[nH]c1)NC(=O)c1cnsc1-c1ccccn1]
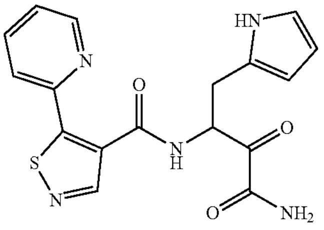 [SMILES: NC(=O)C(=O)C(Cc1ccc[nH]1)NC(=O)c1cnsc1-c1ccccn1]
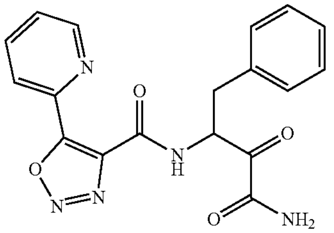
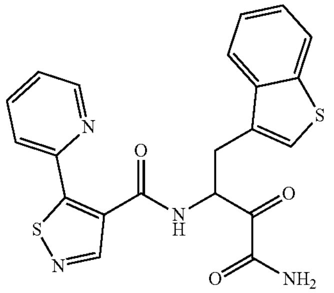
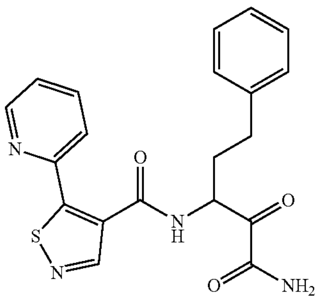 [SMILES: NC(=O)C(=O)C(CCc1ccccc1)NC(=O)c1cnsc1-c1ccccn1]
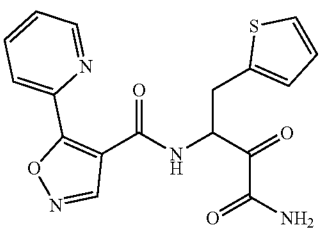

TABLE 1-continued
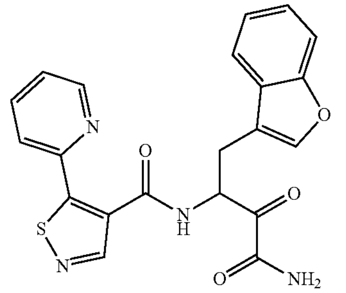
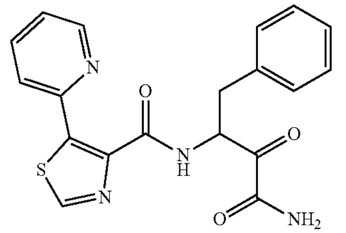
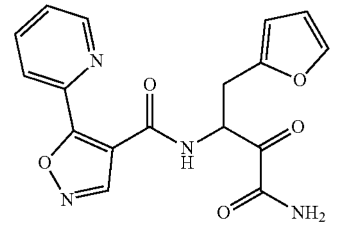 [SMILES: NC(=O)C(=O)C(Cc1ccco1)NC(=O)c1cnoc1-c1ccccn1]
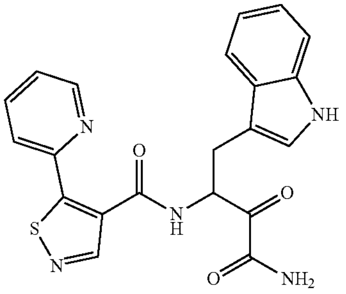 [SMILES: NC(=O)C(=O)C(Cc1c[nH]c2ccccc12)NC(=O)c1cnsc1-c1ccccn1]
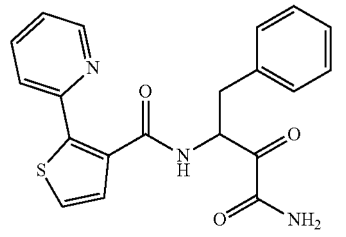
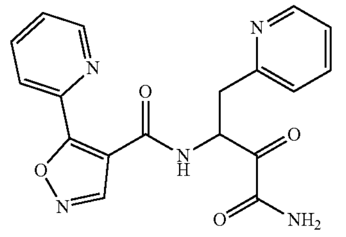
TABLE 1-continued
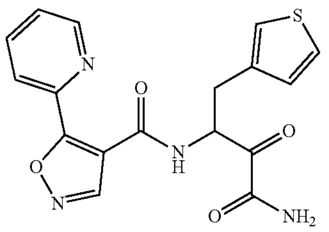 [SMILES: NC(=O)C(=O)C(Cc1ccsc1)NC(=O)c1cnoc1-c1ccccn1]
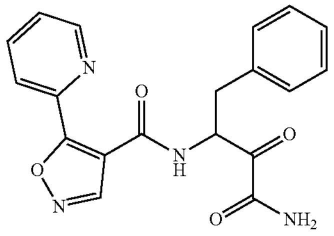
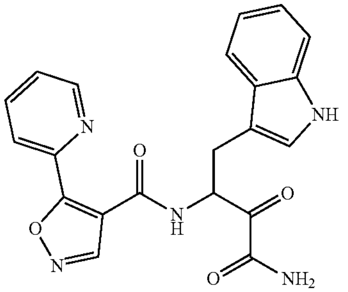 [SMILES: NC(=O)C(=O)C(Cc1c[nH]c2ccccc12)NC(=O)c1cnoc1-c1ccccn1]
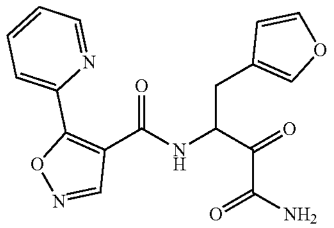 [SMILES: NC(=O)C(=O)C(Cc1ccoc1)NC(=O)c1cnoc1-c1ccccn1]
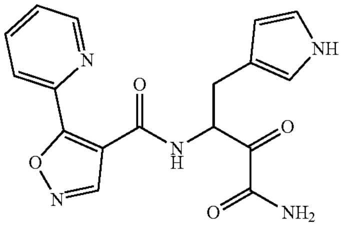
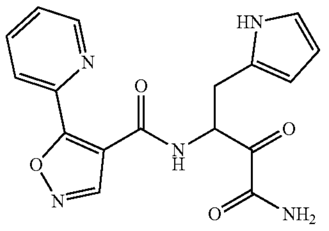 [SMILES: NC(=O)C(=O)C(Cc1ccc[nH]1)NC(=O)c1cnoc1-c1ccccn1]

TABLE 1-continued
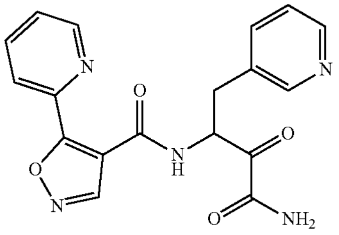 [SMILES: NC(=O)C(=O)C(Cc1cccnc1)NC(=O)c1cnoc1-c1ccccn1]
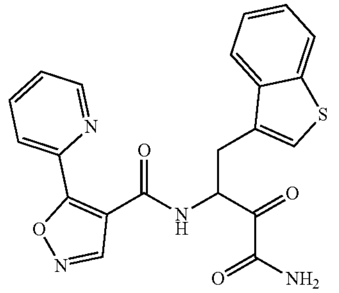 [SMILES: NC(=O)C(=O)C(Cc1csc2ccccc12)NC(=O)c1cnoc1-c1ccccn1]
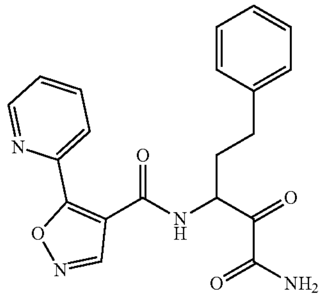 [SMILES: NC(=O)C(=O)C(CCc1ccccc1)NC(=O)c1cnoc1-c1ccccn1]
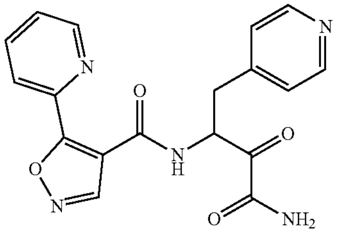
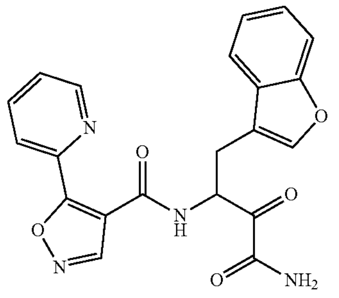 [SMILES: NC(=O)C(=O)C(Cc1coc2ccccc12)NC(=O)c1cnoc1-c1ccccn1]
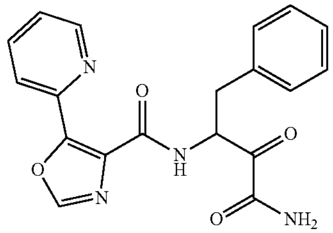
TABLE 1-continued
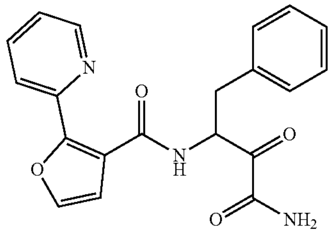
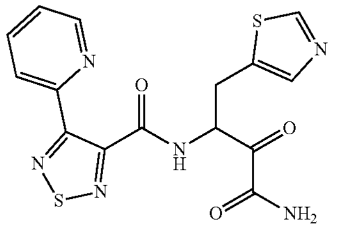
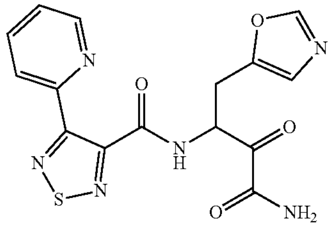 [SMILES: NC(=O)C(=O)C(Cc1cnco1)NC(=O)c1nsnc1-c1ccccn1]
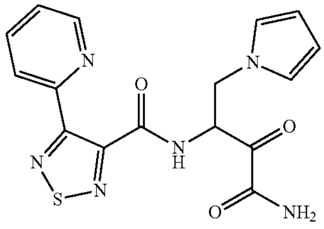 [SMILES: NC(=O)C(=O)C(Cn1cccc1)NC(=O)c1nsnc1-c1ccccn1]
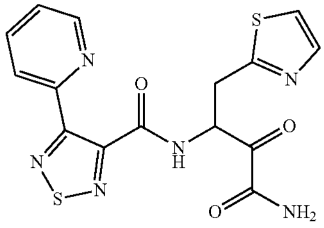 [SMILES: NC(=O)C(=O)C(Cc1nccs1)NC(=O)c1nsnc1-c1ccccn1]
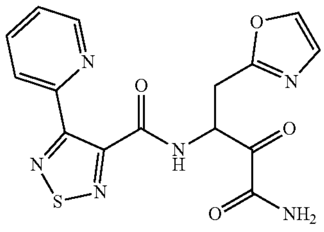 [SMILES: NC(=O)C(=O)C(Cc1ncco1)NC(=O)c1nsnc1-c1ccccn1]

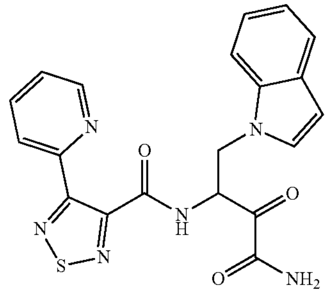 [SMILES: NC(=O)C(=O)C(Cn1ccc2ccccc21)NC(=O)c1nsnc1-c1ccccn1]
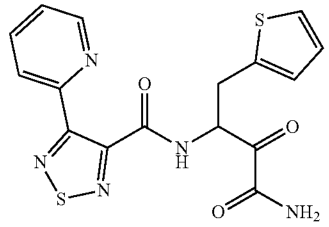 [SMILES: NC(=O)C(=O)C(Cc1cccs1)NC(=O)c1nsnc1-c1ccccn1]
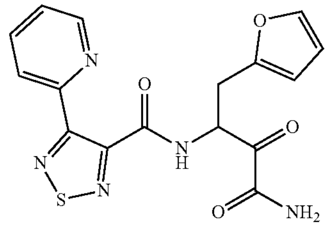 [SMILES: NC(=O)C(=O)C(Cc1ccco1)NC(=O)c1nsnc1-c1ccccn1]
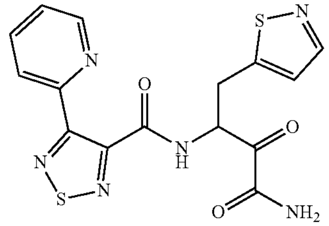 [SMILES: NC(=O)C(=O)C(Cc1ccns1)NC(=O)c1nsnc1-c1ccccn1]
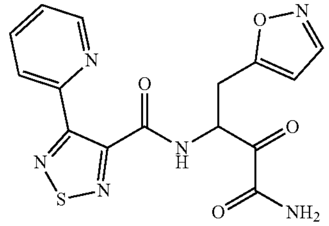 [SMILES: NC(=O)C(=O)C(Cc1ccno1)NC(=O)c1nsnc1-c1ccccn1]
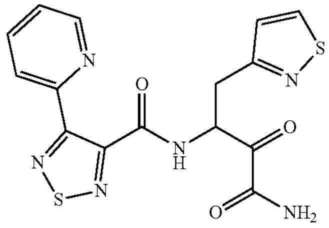 [SMILES: NC(=O)C(=O)C(Cc1ccsn1)NC(=O)c1nsnc1-c1ccccn1]
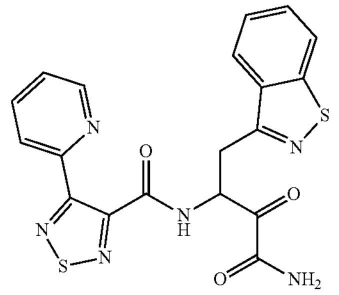 [SMILES: NC(=O)C(=O)C(Cc1nsc2ccccc12)NC(=O)c1nsnc1-c1ccccn1]
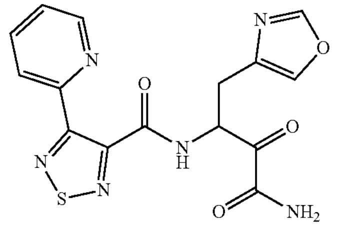 [SMILES: NC(=O)C(=O)C(Cc1cocn1)NC(=O)c1nsnc1-c1ccccn1]
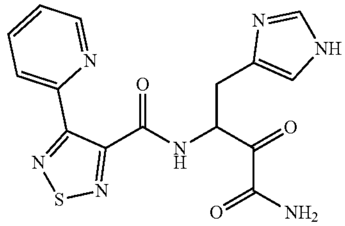 [SMILES: NC(=O)C(=O)C(Cc1c[nH]cn1)NC(=O)c1nsnc1-c1ccccn1]
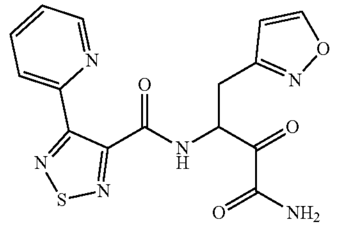 [SMILES: NC(=O)C(=O)C(Cc1ccon1)NC(=O)c1nsnc1-c1ccccn1]
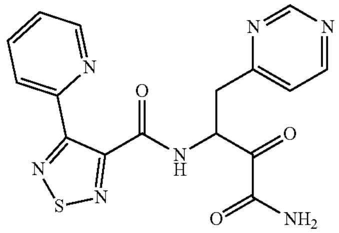 [SMILES: NC(=O)C(=O)C(Cc1ccncn1)NC(=O)c1nsnc1-c1ccccn1]
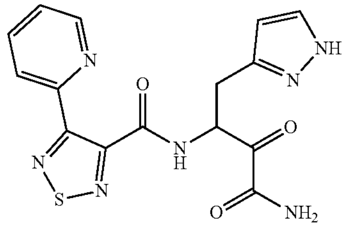 [SMILES: NC(=O)C(=O)C(Cc1cc[nH]n1)NC(=O)c1nsnc1-c1ccccn1]

TABLE 1-continued
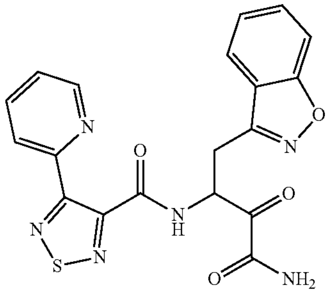 [SMILES: NC(=O)C(=O)C(Cc1noc2ccccc12)NC(=O)c1nsnc1-c1ccccn1]
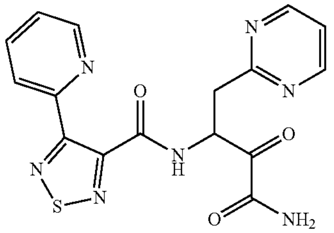 [SMILES: NC(=O)C(=O)C(Cc1ncccn1)NC(=O)c1nsnc1-c1ccccn1]
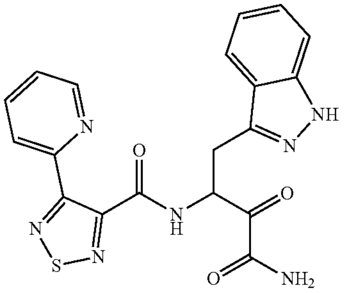 [SMILES: NC(=O)C(=O)C(Cc1n[nH]c2ccccc12)NC(=O)c1nsnc1-c1ccccn1]
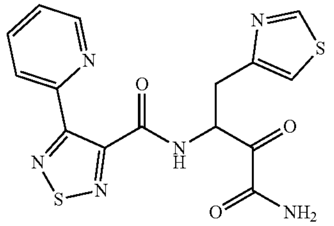 [SMILES: NC(=O)C(=O)C(Cc1cscn1)NC(=O)c1nsnc1-c1ccccn1]
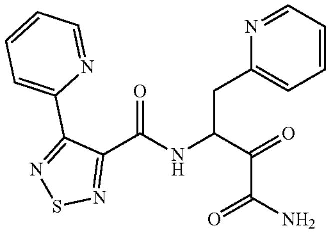
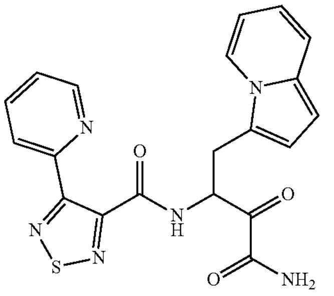 [SMILES: NC(=O)C(=O)C(Cc1ccc2ccccn12)NC(=O)c1nsnc1-c1ccccn1]
TABLE 1-continued
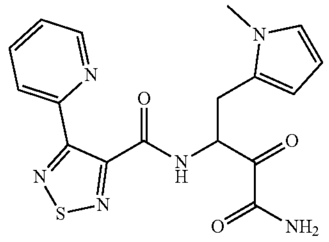 [SMILES: Cn1cccc1CC(NC(=O)c1nsnc1-c1ccccn1)C(=O)C(N)=O]
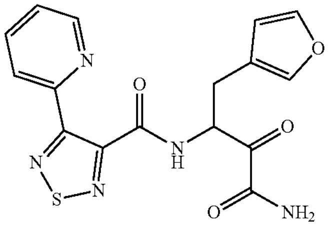 [SMILES: NC(=O)C(=O)C(Cc1ccoc1)NC(=O)c1nsnc1-c1ccccn1]
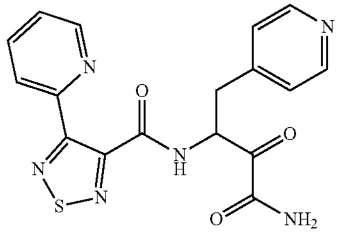
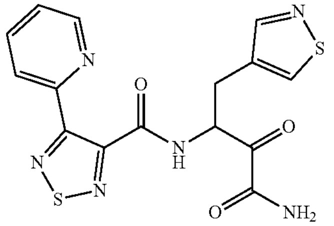 [SMILES: NC(=O)C(=O)C(Cc1cnsc1)NC(=O)c1nsnc1-c1ccccn1]
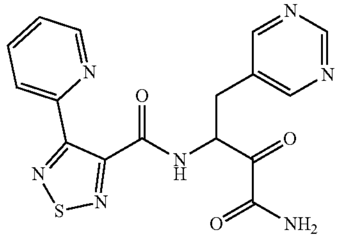 [SMILES: NC(=O)C(=O)C(Cc1cncnc1)NC(=O)c1nsnc1-c1ccccn1]
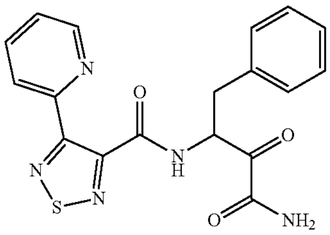

TABLE 1-continued
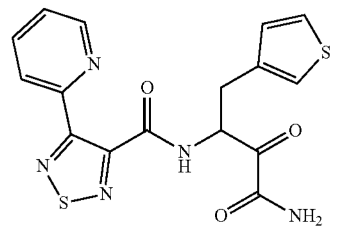 [SMILES: NC(=O)C(=O)C(Cc1ccsc1)NC(=O)c1nsnc1-c1ccccn1]
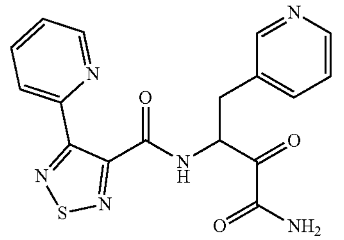 [SMILES: NC(=O)C(=O)C(Cc1cccnc1)NC(=O)c1nsnc1-c1ccccn1]
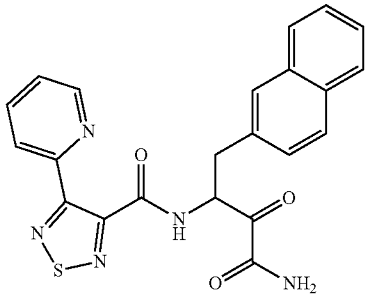 [SMILES: NC(=O)C(=O)C(Cc1ccc2ccccc2c1)NC(=O)c1nsnc1-c1ccccn1]
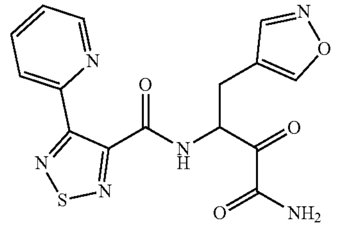 [SMILES: NC(=O)C(=O)C(Cc1cnoc1)NC(=O)c1nsnc1-c1ccccn1]
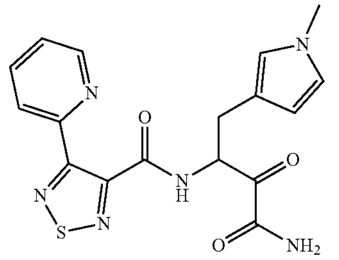 [SMILES: Cn1ccc(CC(NC(=O)c2nsnc2-c2ccccn2)C(=O)C(N)=O)c1]
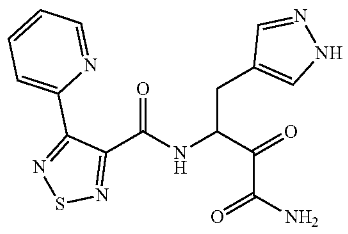 [SMILES: NC(=O)C(=O)C(Cc1cn[nH]c1)NC(=O)c1nsnc1-c1ccccn1]
TABLE 1-continued
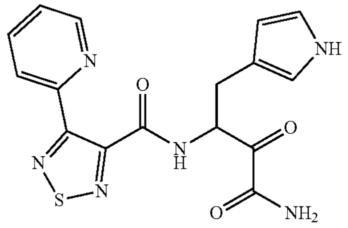
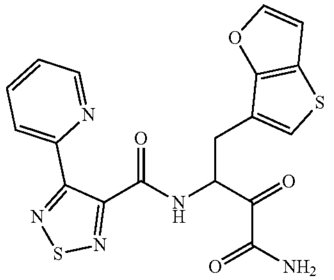 [SMILES: NC(=O)C(=O)C(Cc1csc2ccoc12)NC(=O)c1nsnc1-c1ccccn1]
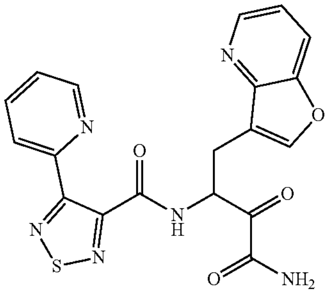 [SMILES: NC(=O)C(=O)C(Cc1coc2cccnc12)NC(=O)c1nsnc1-c1ccccn1]
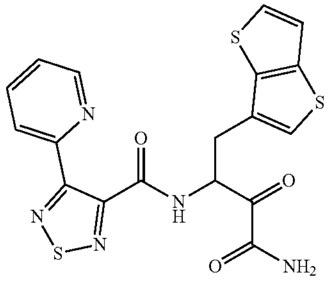 [SMILES: NC(=O)C(=O)C(Cc1csc2ccsc12)NC(=O)c1nsnc1-c1ccccn1]
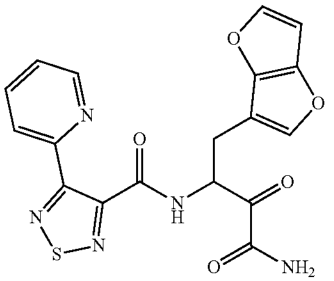 [SMILES: NC(=O)C(=O)C(Cc1coc2ccoc12)NC(=O)c1nsnc1-c1ccccn1]

TABLE 1-continued
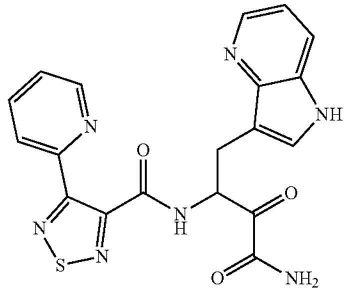 [SMILES: NC(=O)C(=O)C(Cc1c[nH]c2cccnc12)NC(=O)c1nsnc1-c1ccccn1]
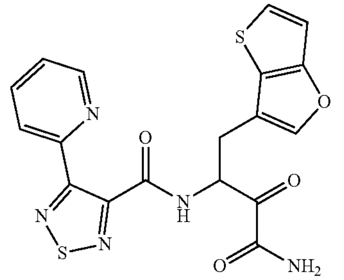 [SMILES: NC(=O)C(=O)C(Cc1coc2ccsc12)NC(=O)c1nsnc1-c1ccccn1]
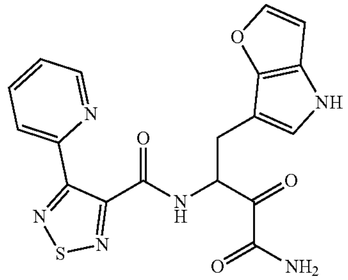 [SMILES: NC(=O)C(=O)C(Cc1c[nH]c2ccoc12)NC(=O)c1nsnc1-c1ccccn1]
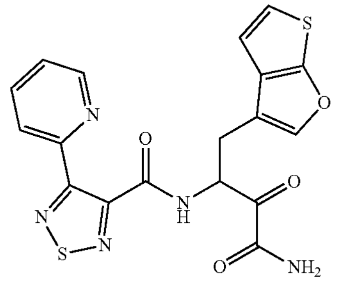 [SMILES: NC(=O)C(=O)C(Cc1coc2sccc12)NC(=O)c1nsnc1-c1ccccn1]
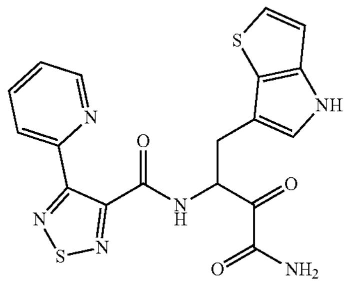 [SMILES: NC(=O)C(=O)C(Cc1c[nH]c2ccsc12)NC(=O)c1nsnc1-c1ccccn1]
TABLE 1-continued
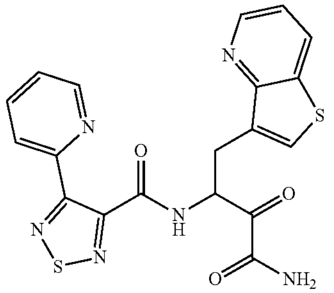 [SMILES: NC(=O)C(=O)C(Cc1csc2cccnc12)NC(=O)c1nsnc1-c1ccccn1]
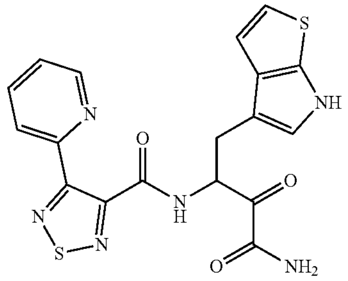 [SMILES: NC(=O)C(=O)C(Cc1c[nH]c2sccc12)NC(=O)c1nsnc1-c1ccccn1]
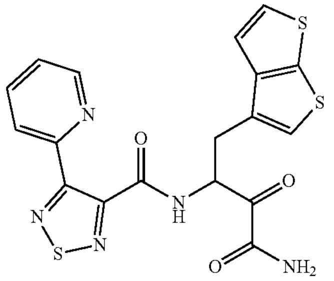 [SMILES: NC(=O)C(=O)C(Cc1csc2sccc12)NC(=O)c1nsnc1-c1ccccn1]
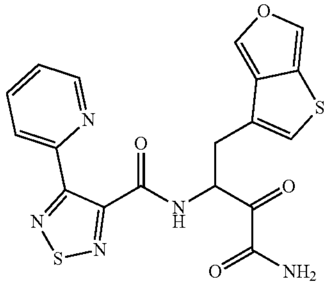 [SMILES: NC(=O)C(=O)C(Cc1csc2cocc12)NC(=O)c1nsnc1-c1ccccn1]
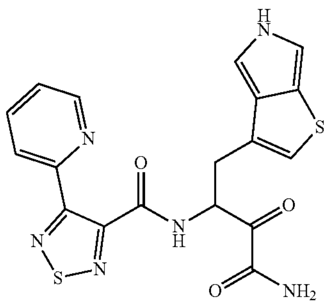 [SMILES: NC(=O)C(=O)C(Cc1csc2c[nH]cc12)NC(=O)c1nsnc1-c1ccccn1]

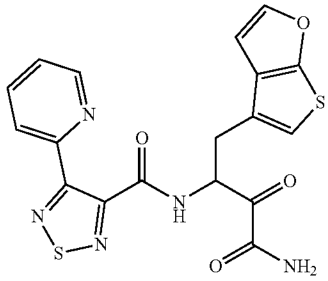 [SMILES: NC(=O)C(=O)C(Cc1csc2occc12)NC(=O)c1nsnc1-c1ccccn1]
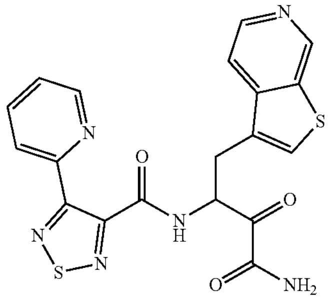 [SMILES: NC(=O)C(=O)C(Cc1csc2cnccc12)NC(=O)c1nsnc1-c1ccccn1]
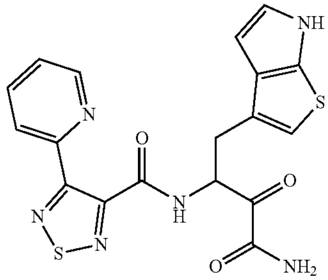 [SMILES: NC(=O)C(=O)C(Cc1csc2[nH]ccc12)NC(=O)c1nsnc1-c1ccccn1]
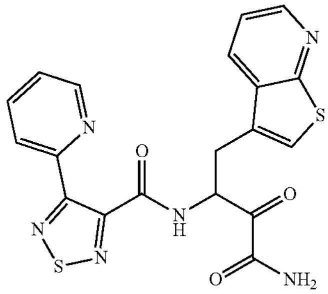 [SMILES: NC(=O)C(=O)C(Cc1csc2ncccc12)NC(=O)c1nsnc1-c1ccccn1]
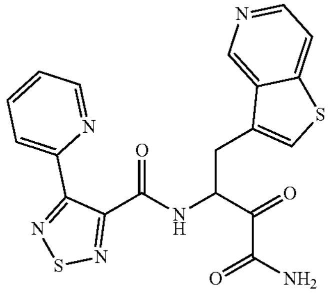 [SMILES: NC(=O)C(=O)C(Cc1csc2ccncc12)NC(=O)c1nsnc1-c1ccccn1]
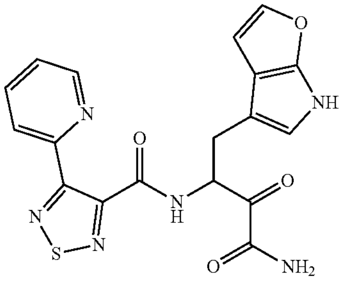
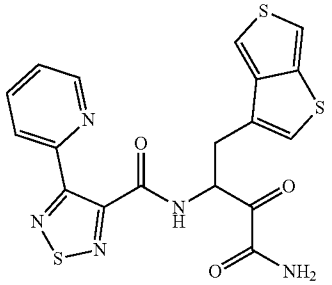 [SMILES: NC(=O)C(=O)C(Cc1csc2cscc12)NC(=O)c1nsnc1-c1ccccn1]
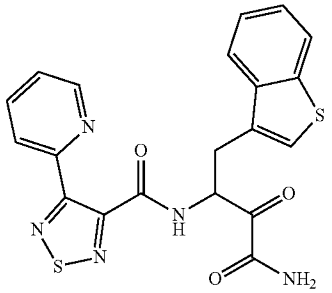 [SMILES: NC(=O)C(=O)C(Cc1csc2ccccc12)NC(=O)c1nsnc1-c1ccccn1]
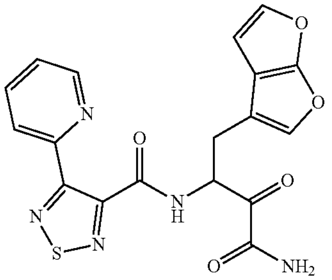
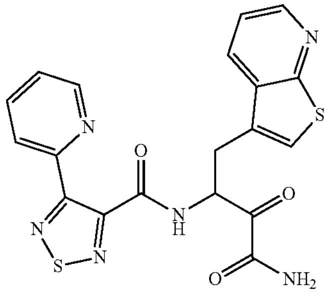 [SMILES: NC(=O)C(=O)C(Cc1csc2ncccc12)NC(=O)c1nsnc1-c1ccccn1]

TABLE 1-continued
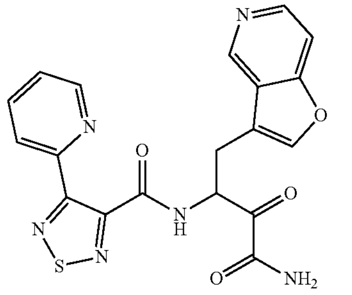 [SMILES: NC(=O)C(=O)C(Cc1coc2ccncc12)NC(=O)c1nsnc1-c1ccccn1]
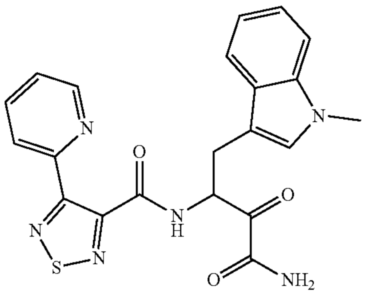 [SMILES: Cn1cc(CC(NC(=O)c2nsnc2-c2ccccn2)C(=O)C(N)=O)c2ccccc21]
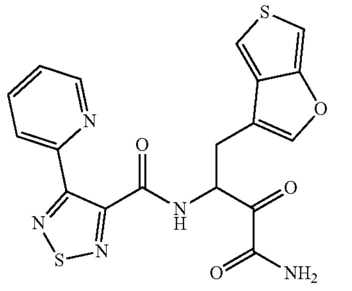 [SMILES: NC(=O)C(=O)C(Cc1coc2cscc12)NC(=O)c1nsnc1-c1ccccn1]
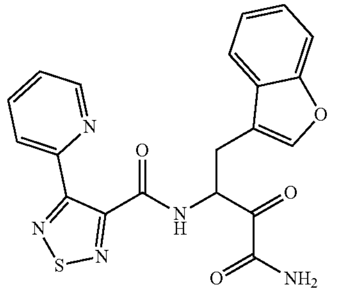
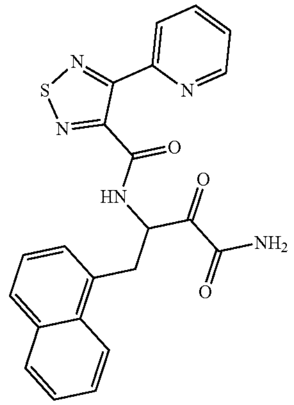 [SMILES: NC(=O)C(=O)C(Cc1cccc2ccccc12)NC(=O)c1nsnc1-c1ccccn1]
TABLE 1-continued
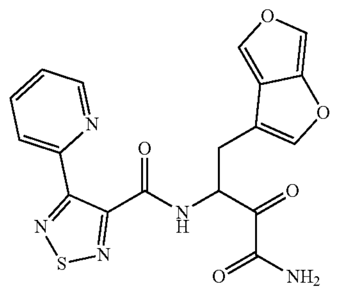 [SMILES: NC(=O)C(=O)C(Cc1coc2cocc12)NC(=O)c1nsnc1-c1ccccn1]
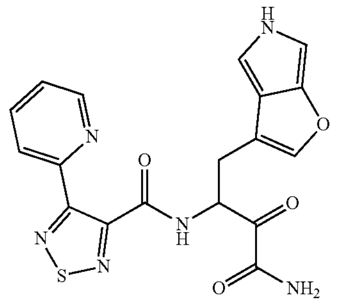 [SMILES: NC(=O)C(=O)C(Cc1coc2c[nH]cc12)NC(=O)c1nsnc1-c1ccccn1]
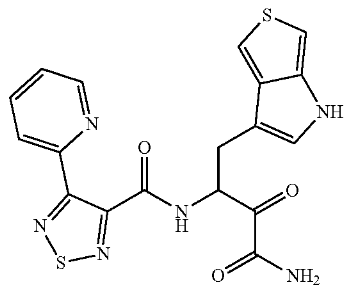 [SMILES: NC(=O)C(=O)C(Cc1c[nH]c2cscc12)NC(=O)c1nsnc1-c1ccccn1]
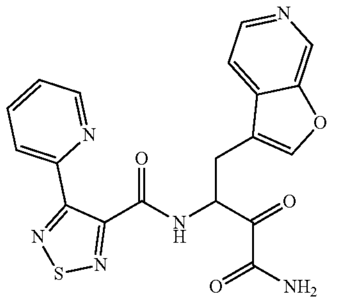 [SMILES: NC(=O)C(=O)C(Cc1coc2cnccc12)NC(=O)c1nsnc1-c1ccccn1]
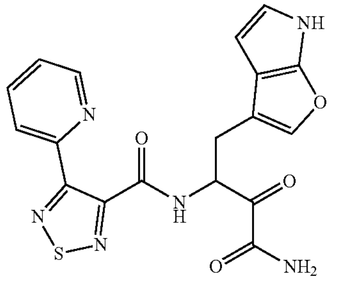

TABLE 1-continued
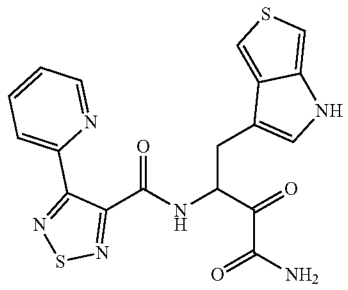 [SMILES: NC(=O)C(=O)C(Cc1c[nH]c2cscc12)NC(=O)c1nsnc1-c1ccccn1]
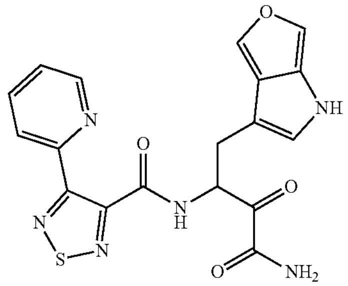 [SMILES: NC(=O)C(=O)C(Cc1c[nH]c2cocc12)NC(=O)c1nsnc1-c1ccccn1]
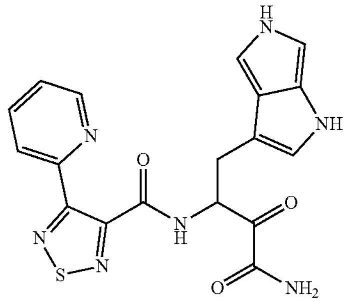 [SMILES: NC(=O)C(=O)C(Cc1c[nH]c2c[nH]cc12)NC(=O)c1nsnc1-c1ccccn1]
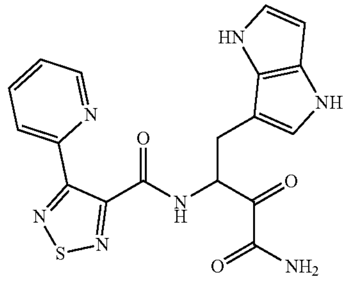
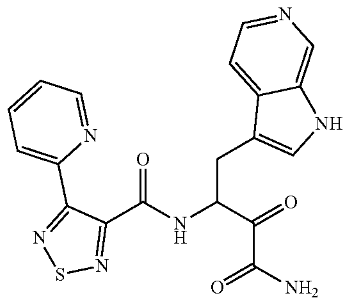 [SMILES: NC(=O)C(=O)C(Cc1c[nH]c2cnccc12)NC(=O)c1nsnc1-c1ccccn1]
TABLE 1-continued
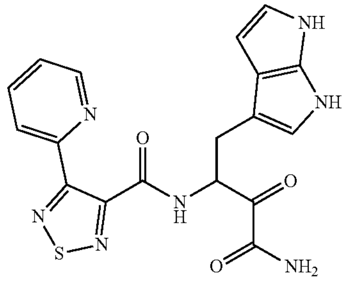 [SMILES: NC(=O)C(=O)C(Cc1c[nH]c2[nH]ccc12)NC(=O)c1nsnc1-c1ccccn1]
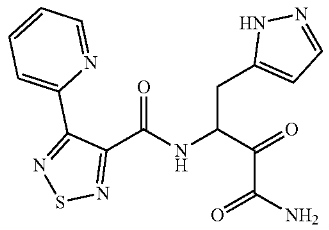 [SMILES: NC(=O)C(=O)C(Cc1ccn[nH]1)NC(=O)c1nsnc1-c1ccccn1]
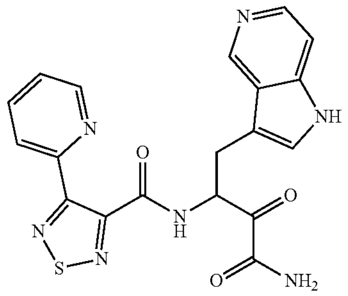 [SMILES: NC(=O)C(=O)C(Cc1c[nH]c2ccncc12)NC(=O)c1nsnc1-c1ccccn1]
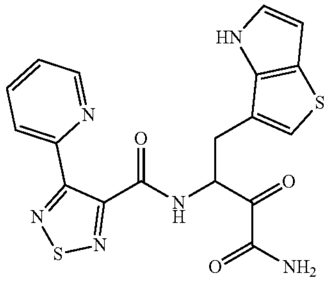 [SMILES: NC(=O)C(=O)C(Cc1csc2cc[nH]c12)NC(=O)c1nsnc1-c1ccccn1]
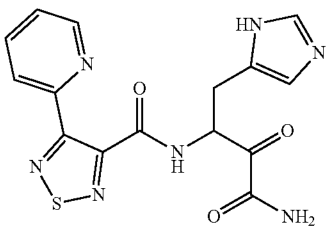
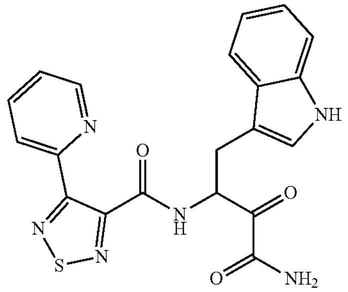 [SMILES: NC(=O)C(=O)C(Cc1c[nH]c2ccccc12)NC(=O)c1nsnc1-c1ccccn1]

TABLE 1-continued
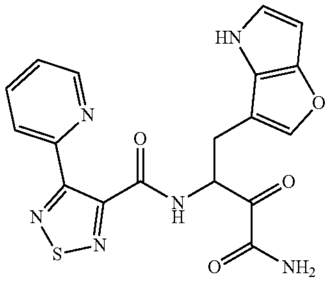
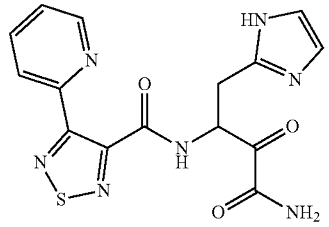
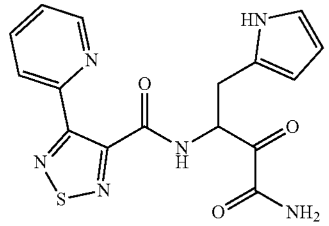
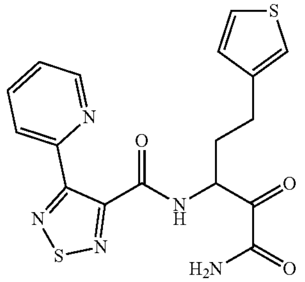 [SMILES: NC(=O)C(=O)C(CCc1ccsc1)NC(=O)c1nsnc1-c1ccccn1]
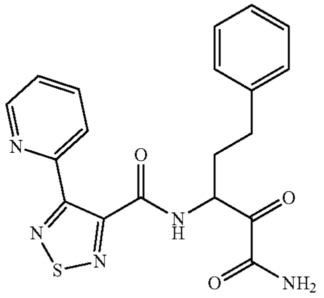 [SMILES: NC(=O)C(=O)C(CCc1ccccc1)NC(=O)c1nsnc1-c1ccccn1]
TABLE 1-continued
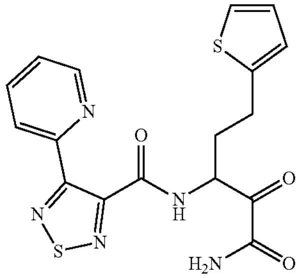 [SMILES: NC(=O)C(=O)C(CCc1cccs1)NC(=O)c1nsnc1-c1ccccn1]
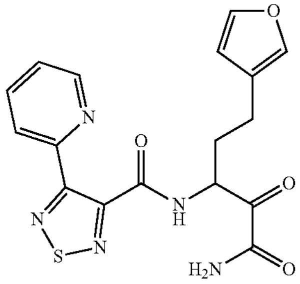 [SMILES: NC(=O)C(=O)C(CCc1ccoc1)NC(=O)c1nsnc1-c1ccccn1]
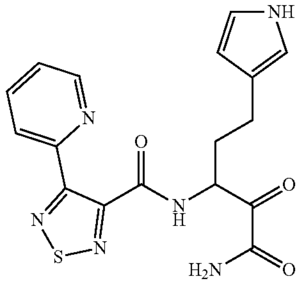 [SMILES: NC(=O)C(=O)C(CCc1cc[nH]c1)NC(=O)c1nsnc1-c1ccccn1]
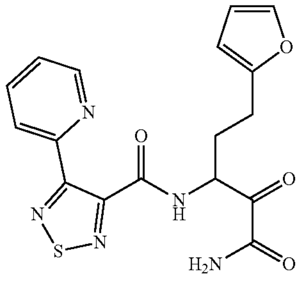 [SMILES: NC(=O)C(=O)C(CCc1ccco1)NC(=O)c1nsnc1-c1ccccn1]
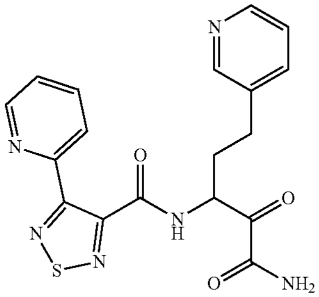 [SMILES: NC(=O)C(=O)C(CCc1cccnc1)NC(=O)c1nsnc1-c1ccccn1]

TABLE 1-continued
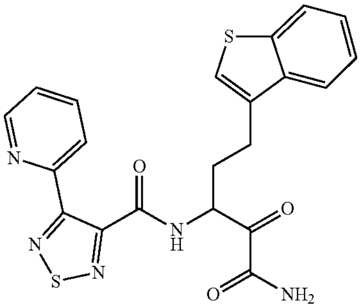
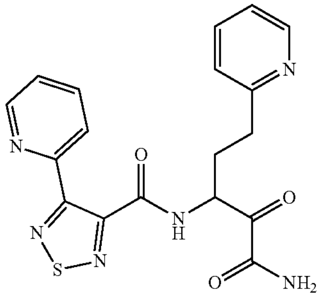 [SMILES: NC(=O)C(=O)C(CCc1ccccn1)NC(=O)c1nsnc1-c1ccccn1]
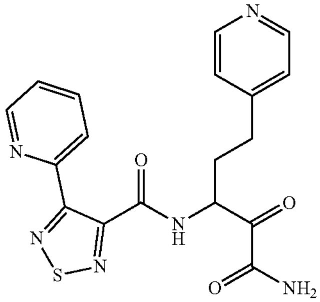 [SMILES: NC(=O)C(=O)C(CCc1ccncc1)NC(=O)c1nsnc1-c1ccccn1]
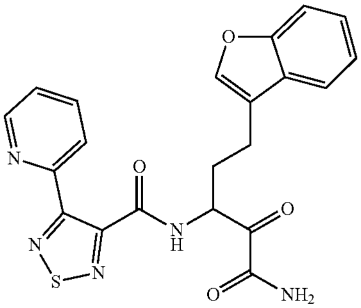
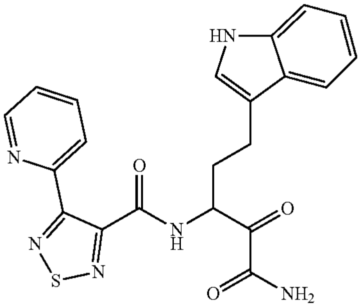 [SMILES: NC(=O)C(=O)C(CCc1c[nH]c2ccccc12)NC(=O)c1nsnc1-c1ccccn1]
TABLE 1-continued
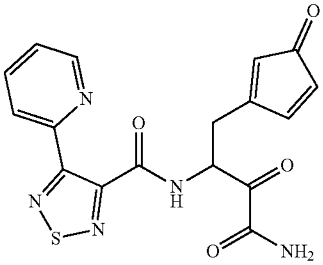 [SMILES: NC(=O)C(=O)C(CC1=CC(=O)C=C1)NC(=O)c1nsnc1-c1ccccn1]
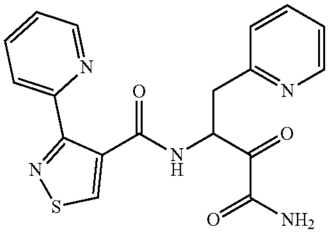 [SMILES: NC(=O)C(=O)C(Cc1ccccn1)NC(=O)c1csnc1-c1ccccn1]
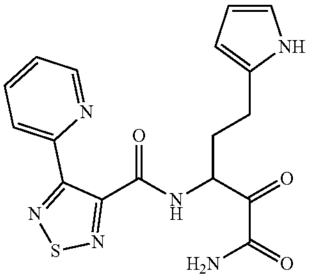 [SMILES: NC(=O)C(=O)C(CCc1ccc[nH]1)NC(=O)c1nsnc1-c1ccccn1]
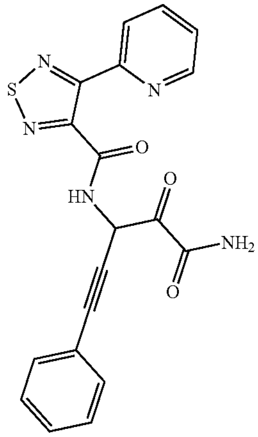 [SMILES: NC(=O)C(=O)C(C#Cc1ccccc1)NC(=O)c1nsnc1-c1ccccn1]
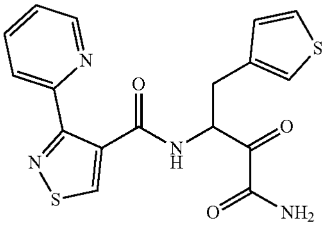

TABLE 1-continued
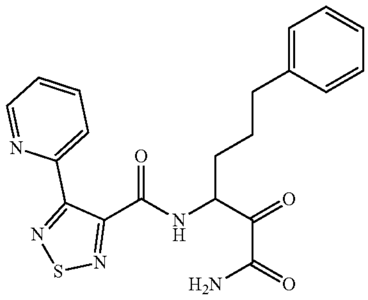 [SMILES: NC(=O)C(=O)C(CCCc1ccccc1)NC(=O)c1nsnc1-c1ccccn1]
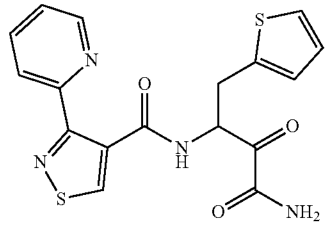
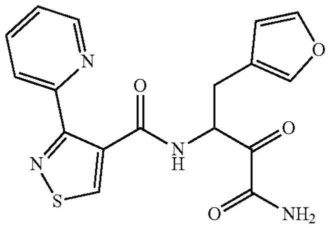
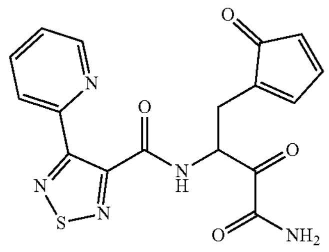 [SMILES: NC(=O)C(=O)C(CC1=CC=CC1=O)NC(=O)c1nsnc1-c1ccccn1]
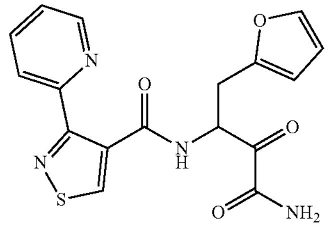
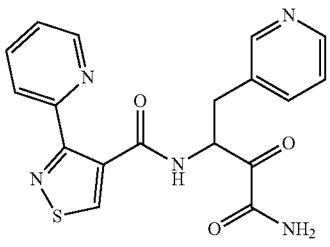
TABLE 1-continued
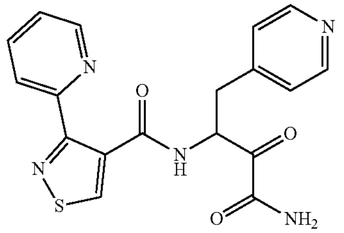 [SMILES: NC(=O)C(=O)C(Cc1ccncc1)NC(=O)c1csnc1-c1ccccn1]
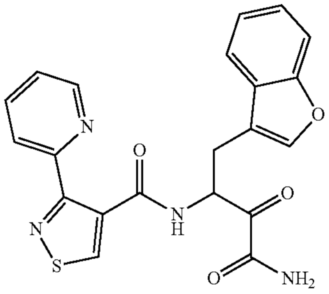
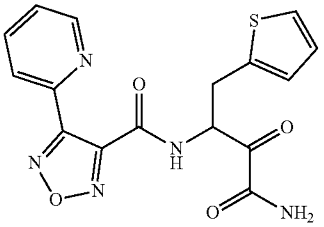
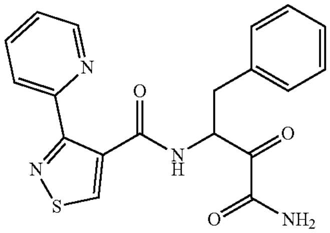 [SMILES: NC(=O)C(=O)C(Cc1ccccc1)NC(=O)c1csnc1-c1ccccn1]
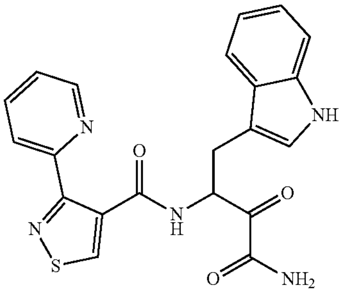 [SMILES: NC(=O)C(=O)C(Cc1c[nH]c2ccccc12)NC(=O)c1csnc1-c1ccccn1]
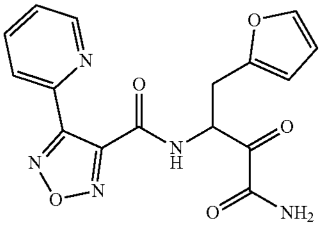

TABLE 1-continued
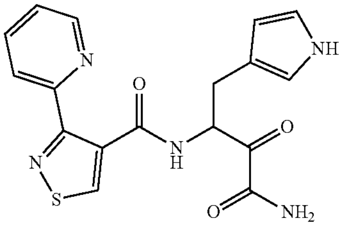
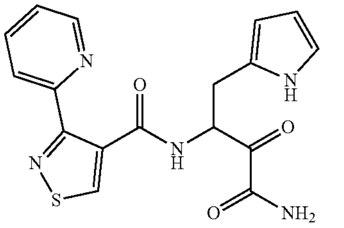
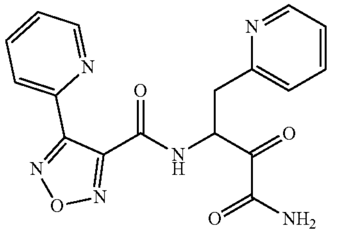
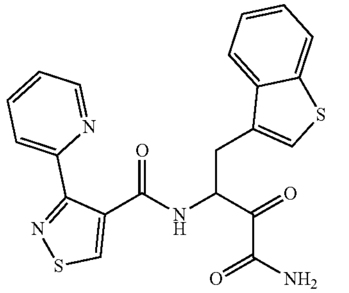 [SMILES: NC(=O)C(=O)C(Cc1csc2ccccc12)NC(=O)c1csnc1-c1ccccn1]
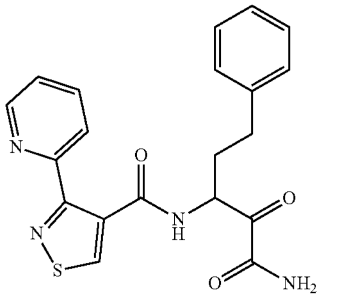 [SMILES: NC(=O)C(=O)C(CCc1ccccc1)NC(=O)c1csnc1-c1ccccn1]
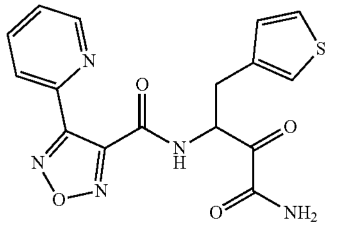
TABLE 1-continued
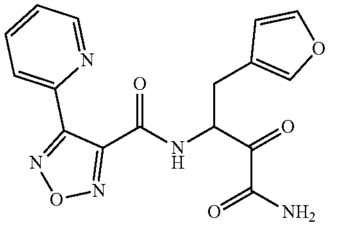
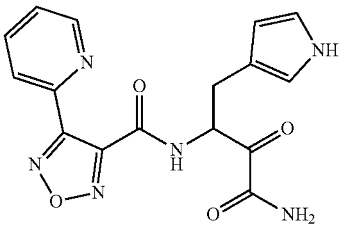
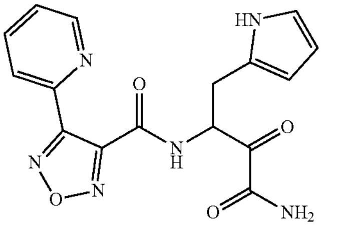
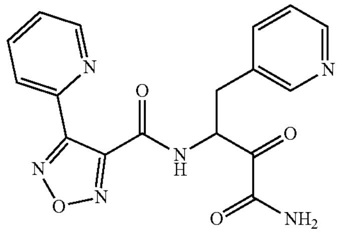
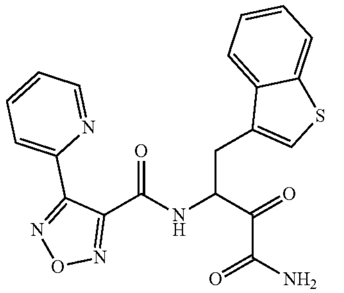
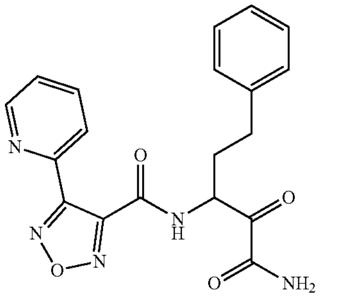 [SMILES: NC(=O)C(=O)C(CCc1ccccc1)NC(=O)c1nonc1-c1ccccn1]

TABLE 1-continued
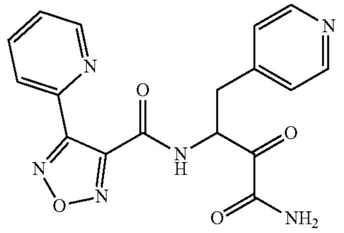
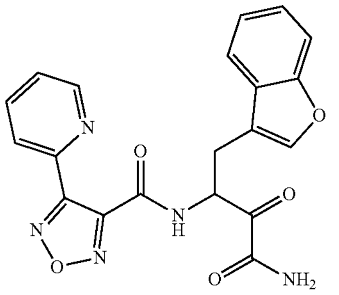 [SMILES: NC(=O)C(=O)C(Cc1coc2ccccc12)NC(=O)c1nonc1-c1ccccn1]
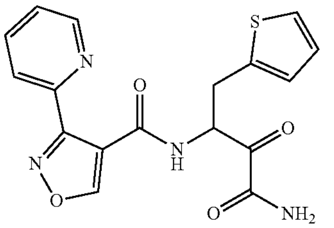
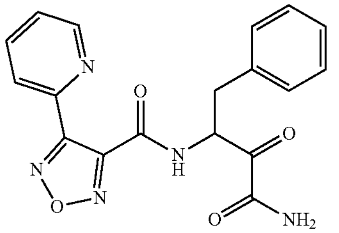
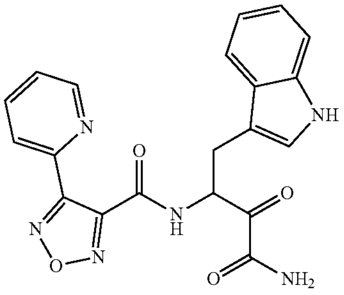 [SMILES: NC(=O)C(=O)C(Cc1c[nH]c2ccccc12)NC(=O)c1nonc1-c1ccccn1]
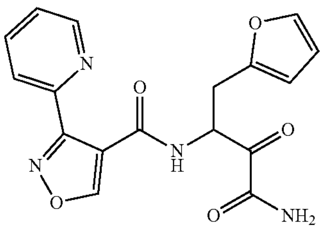
TABLE 1-continued
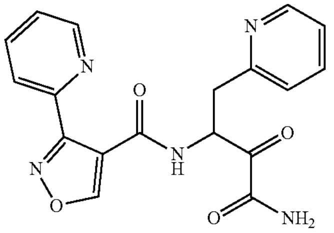
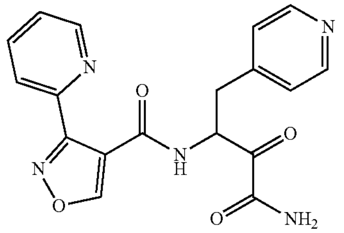
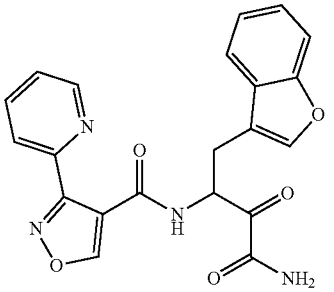 [SMILES: NC(=O)C(=O)C(Cc1coc2ccccc12)NC(=O)c1conc1-c1ccccn1]
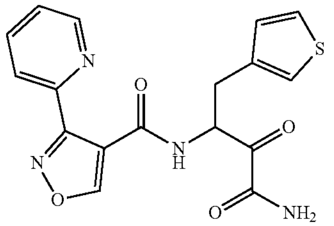
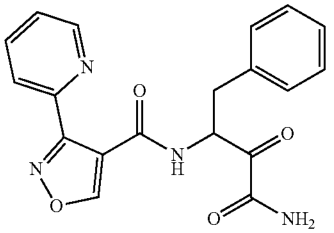
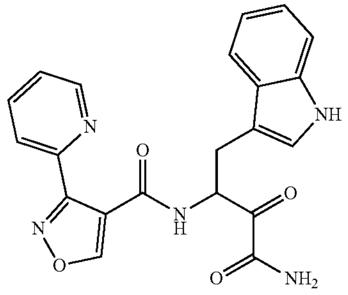 [SMILES: NC(=O)C(=O)C(Cc1c[nH]c2ccccc12)NC(=O)c1conc1-c1ccccn1]

TABLE 1-continued
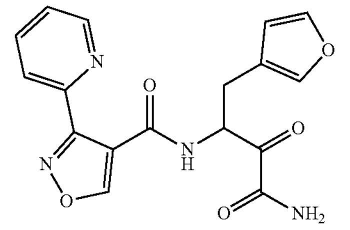
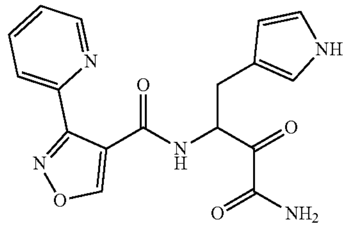
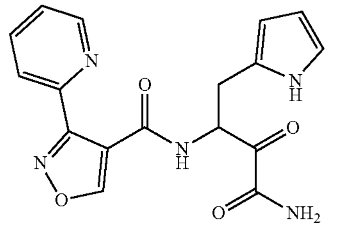 [SMILES: NC(=O)C(=O)C(Cc1ccc[nH]1)NC(=O)c1conc1-c1ccccn1]
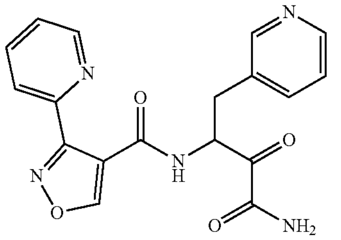
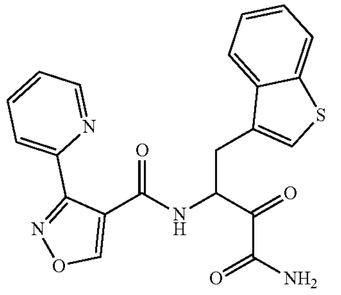 [SMILES: NC(=O)C(=O)C(Cc1csc2ccccc12)NC(=O)c1conc1-c1ccccn1]
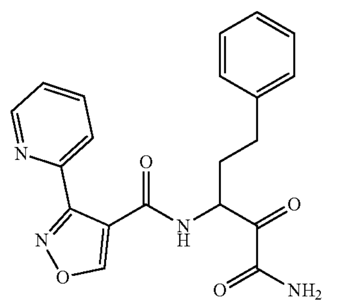 [SMILES: NC(=O)C(=O)C(CCc1ccccc1)NC(=O)c1conc1-c1ccccn1]
TABLE 1-continued
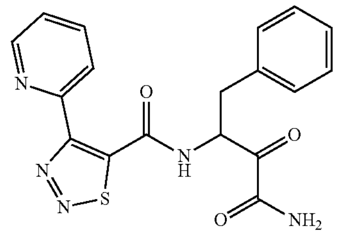 [SMILES: NC(=O)C(=O)C(Cc1ccccc1)NC(=O)c1snnc1-c1ccccn1]
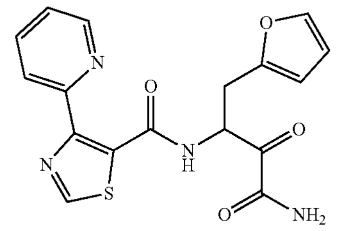 [SMILES: NC(=O)C(=O)C(Cc1ccco1)NC(=O)c1scnc1-c1ccccn1]
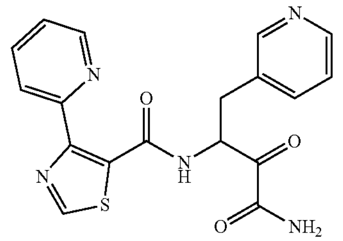 [SMILES: NC(=O)C(=O)C(Cc1cccnc1)NC(=O)c1scnc1-c1ccccn1]
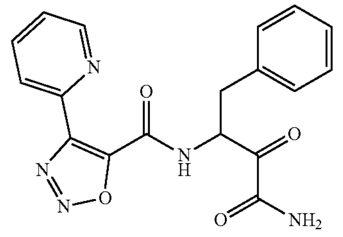
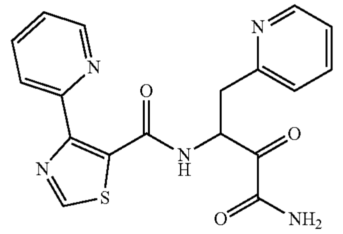
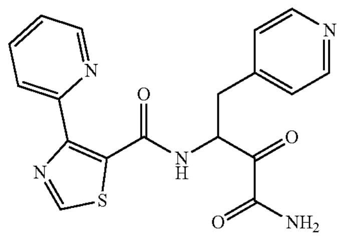 [SMILES: NC(=O)C(=O)C(Cc1ccncc1)NC(=O)c1scnc1-c1ccccn1]

TABLE 1-continued
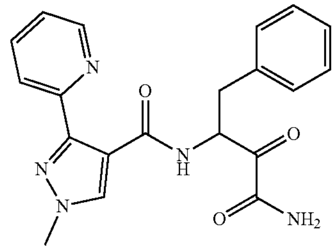 [SMILES: Cn1cc(C(=O)NC(Cc2ccccc2)C(=O)C(N)=O)c(-c2ccccn2)n1]
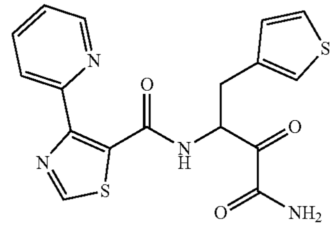
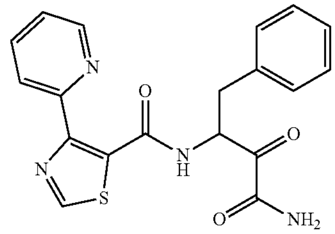
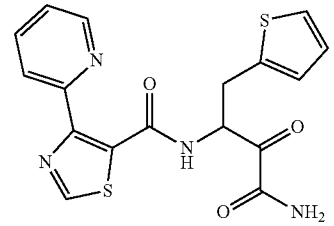 [SMILES: NC(=O)C(=O)C(Cc1cccs1)NC(=O)c1scnc1-c1ccccn1]
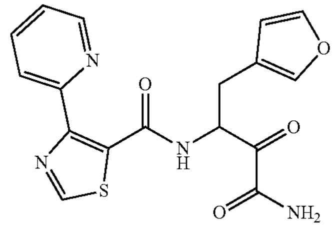 [SMILES: NC(=O)C(=O)C(Cc1ccoc1)NC(=O)c1scnc1-c1ccccn1]
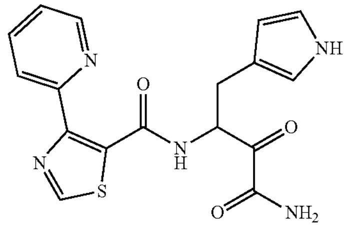 [SMILES: NC(=O)C(=O)C(Cc1cc[nH]c1)NC(=O)c1scnc1-c1ccccn1]
TABLE 1-continued
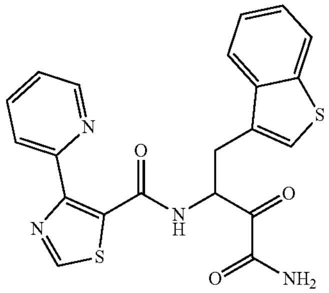 [SMILES: NC(=O)C(=O)C(Cc1csc2ccccc12)NC(=O)c1scnc1-c1ccccn1]
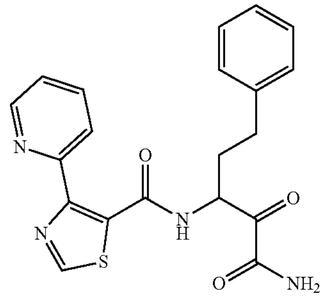 [SMILES: NC(=O)C(=O)C(CCc1ccccc1)NC(=O)c1scnc1-c1ccccn1]
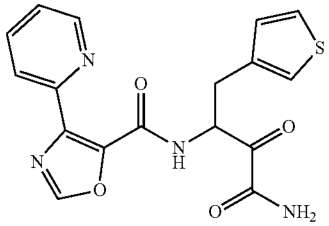 [SMILES: NC(=O)C(=O)C(Cc1ccsc1)NC(=O)c1ocnc1-c1ccccn1]
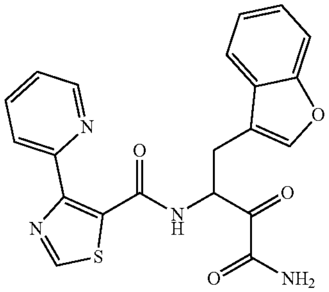 [SMILES: NC(=O)C(=O)C(Cc1coc2ccccc12)NC(=O)c1scnc1-c1ccccn1]
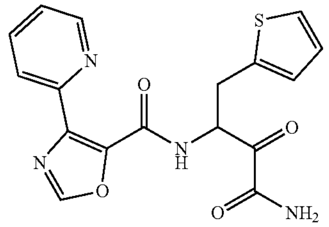 [SMILES: NC(=O)C(=O)C(Cc1cccs1)NC(=O)c1ocnc1-c1ccccn1]
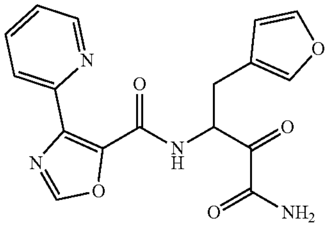 [SMILES: NC(=O)C(=O)C(Cc1ccoc1)NC(=O)c1ocnc1-c1ccccn1]

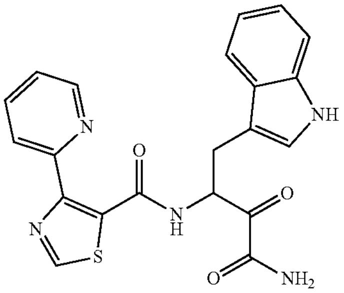 [SMILES: NC(=O)C(=O)C(Cc1c[nH]c2ccccc12)NC(=O)c1scnc1-c1ccccn1]
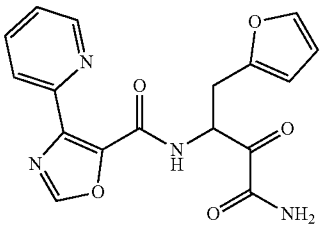 [SMILES: NC(=O)C(=O)C(Cc1ccco1)NC(=O)c1ocnc1-c1ccccn1]
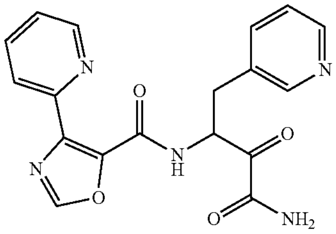 [SMILES: NC(=O)C(=O)C(Cc1cccnc1)NC(=O)c1ocnc1-c1ccccn1]
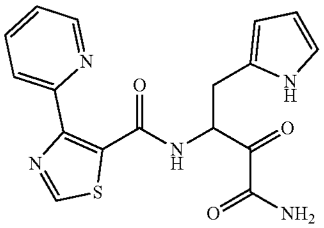 [SMILES: NC(=O)C(=O)C(Cc1ccc[nH]1)NC(=O)c1scnc1-c1ccccn1]
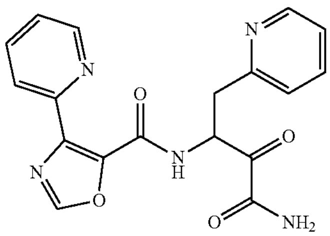
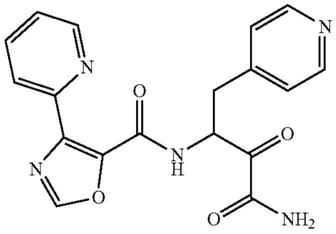
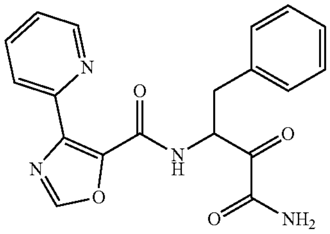
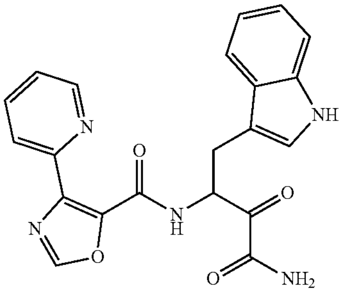 [SMILES: NC(=O)C(=O)C(Cc1c[nH]c2ccccc12)NC(=O)c1ocnc1-c1ccccn1]
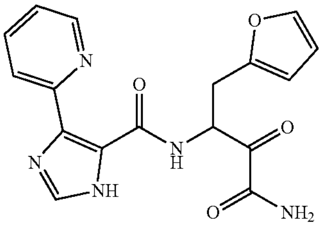 [SMILES: NC(=O)C(=O)C(Cc1ccco1)NC(=O)c1[nH]cnc1-c1ccccn1]
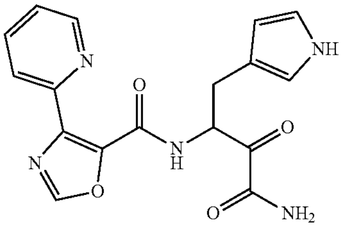 [SMILES: NC(=O)C(=O)C(Cc1cc[nH]c1)NC(=O)c1ocnc1-c1ccccn1]
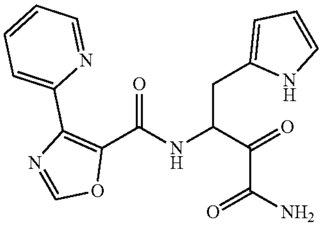 [SMILES: NC(=O)C(=O)C(Cc1ccc[nH]1)NC(=O)c1ocnc1-c1ccccn1]
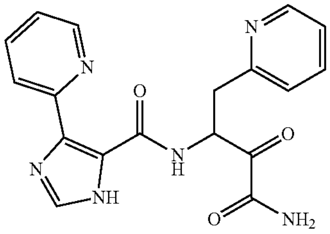

TABLE 1-continued
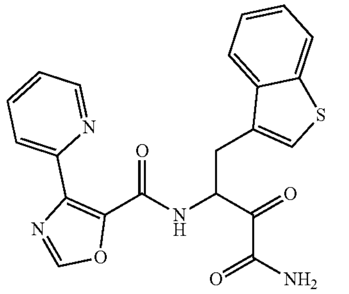 [SMILES: NC(=O)C(=O)C(Cc1csc2ccccc12)NC(=O)c1ocnc1-c1ccccn1]
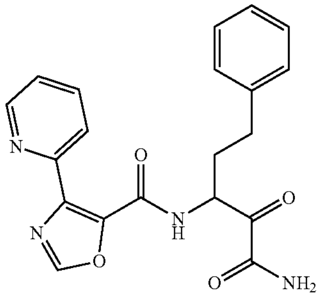 [SMILES: NC(=O)C(=O)C(CCc1ccccc1)NC(=O)c1ocnc1-c1ccccn1]
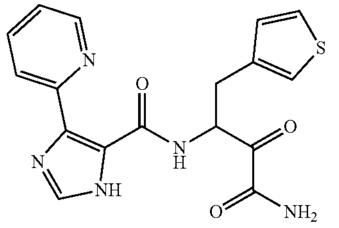 [SMILES: NC(=O)C(=O)C(Cc1ccsc1)NC(=O)c1[nH]cnc1-c1ccccn1]
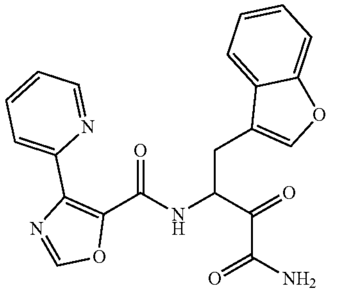 [SMILES: NC(=O)C(=O)C(Cc1coc2ccccc12)NC(=O)c1ocnc1-c1ccccn1]
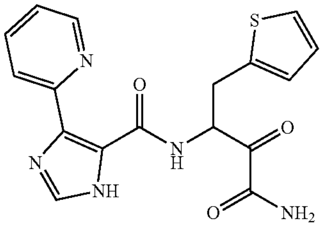 [SMILES: NC(=O)C(=O)C(Cc1cccs1)NC(=O)c1[nH]cnc1-c1ccccn1]
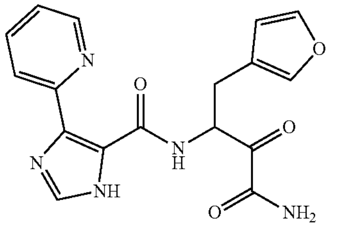 [SMILES: NC(=O)C(=O)C(Cc1ccoc1)NC(=O)c1[nH]cnc1-c1ccccn1]
TABLE 1-continued
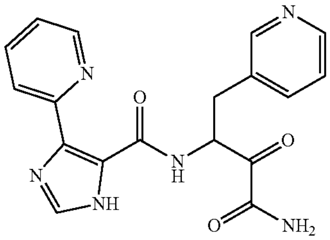 [SMILES: NC(=O)C(=O)C(Cc1cccnc1)NC(=O)c1[nH]cnc1-c1ccccn1]
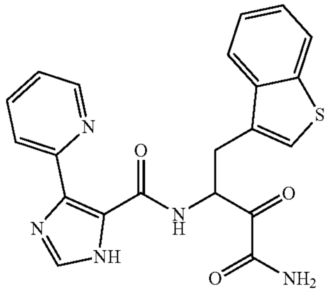 [SMILES: NC(=O)C(=O)C(Cc1csc2ccccc12)NC(=O)c1[nH]cnc1-c1ccccn1]
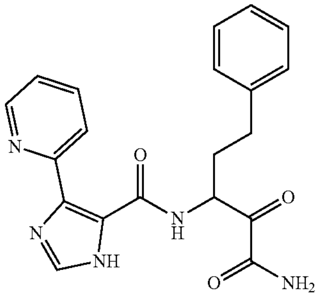 [SMILES: NC(=O)C(=O)C(CCc1ccccc1)NC(=O)c1[nH]cnc1-c1ccccn1]
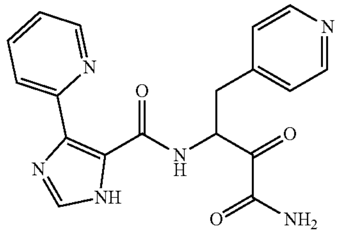 [SMILES: NC(=O)C(=O)C(Cc1ccncc1)NC(=O)c1[nH]cnc1-c1ccccn1]
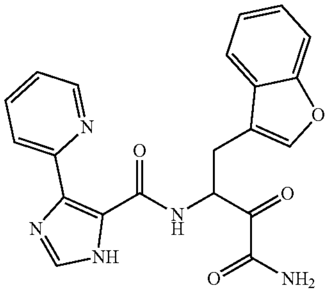 [SMILES: NC(=O)C(=O)C(Cc1coc2ccccc12)NC(=O)c1[nH]cnc1-c1ccccn1]
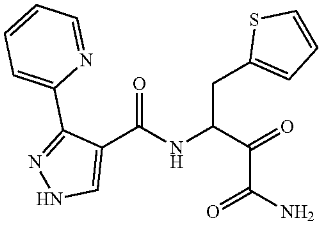

TABLE 1-continued
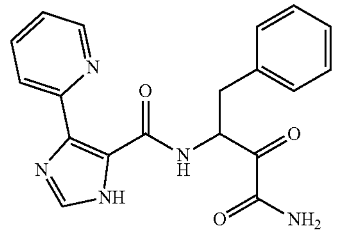
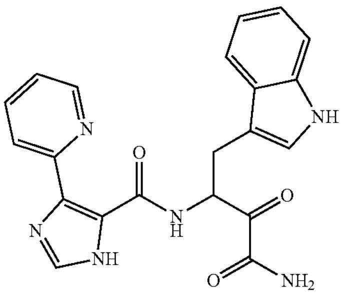 [SMILES: NC(=O)C(=O)C(Cc1c[nH]c2ccccc12)NC(=O)c1[nH]cnc1-c1ccccn1]
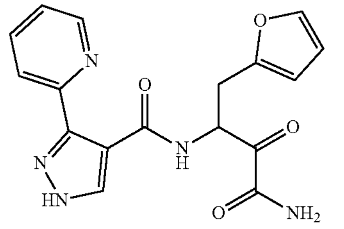 [SMILES: NC(=O)C(=O)C(Cc1ccco1)NC(=O)c1c[nH]nc1-c1ccccn1]
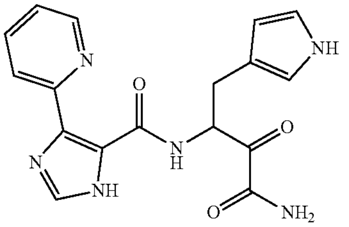 [SMILES: NC(=O)C(=O)C(Cc1cc[nH]c1)NC(=O)c1[nH]cnc1-c1ccccn1]
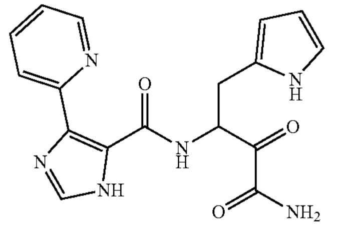 [SMILES: NC(=O)C(=O)C(Cc1ccc[nH]1)NC(=O)c1[nH]cnc1-c1ccccn1]
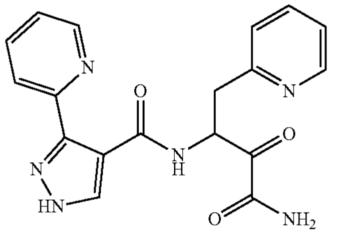
TABLE 1-continued
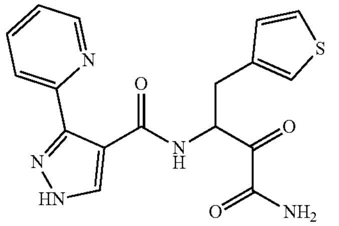 [SMILES: NC(=O)C(=O)C(Cc1ccsc1)NC(=O)c1c[nH]nc1-c1ccccn1]
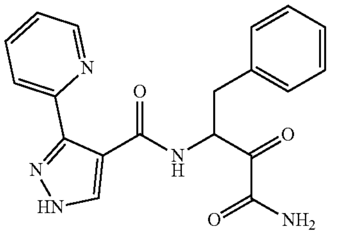
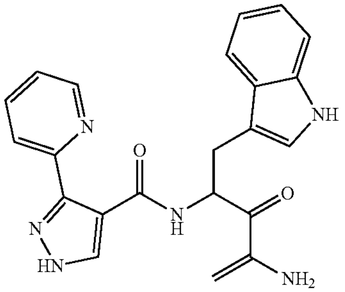 [SMILES: C=C(N)C(=O)C(Cc1c[nH]c2ccccc12)NC(=O)c1c[nH]nc1-c1ccccn1]
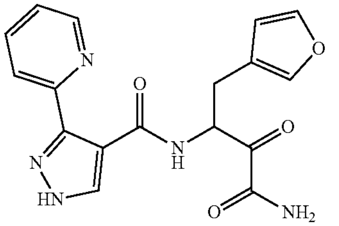
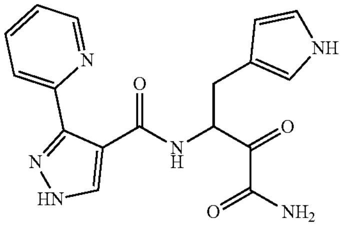
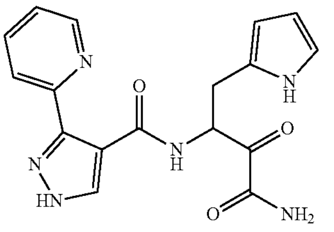 [SMILES: NC(=O)C(=O)C(Cc1ccc[nH]1)NC(=O)c1c[nH]nc1-c1ccccn1]

TABLE 1-continued
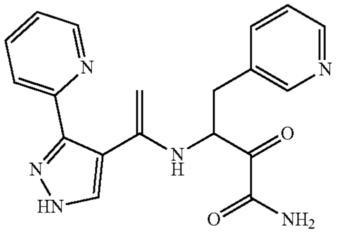 [SMILES: C=C(NC(Cc1cccnc1)C(=O)C(N)=O)c1c[nH]nc1-c1ccccn1]
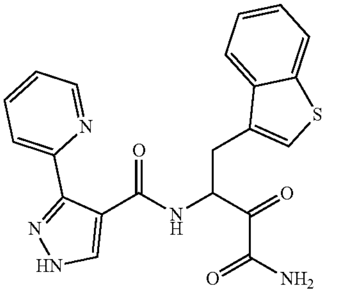 [SMILES: NC(=O)C(=O)C(Cc1csc2ccccc12)NC(=O)c1c[nH]nc1-c1ccccn1]
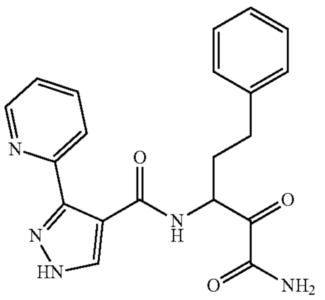 [SMILES: NC(=O)C(=O)C(CCc1ccccc1)NC(=O)c1c[nH]nc1-c1ccccn1]
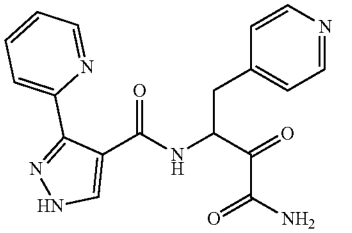 [SMILES: NC(=O)C(=O)C(Cc1ccncc1)NC(=O)c1c[nH]nc1-c1ccccn1]
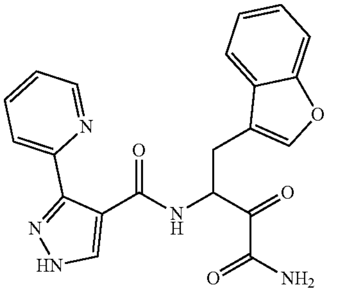 [SMILES: NC(=O)C(=O)C(Cc1coc2ccccc12)NC(=O)c1c[nH]nc1-c1ccccn1]
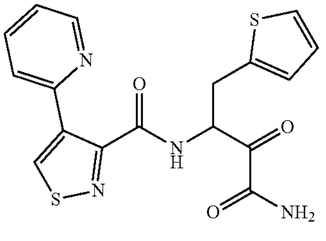
TABLE 1-continued
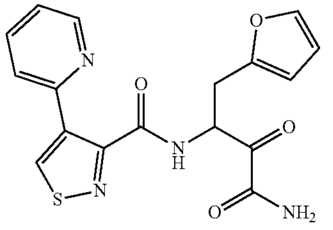
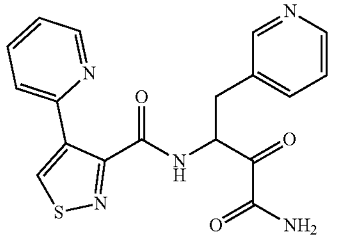 [SMILES: NC(=O)C(=O)C(Cc1cccnc1)NC(=O)c1nscc1-c1ccccn1]
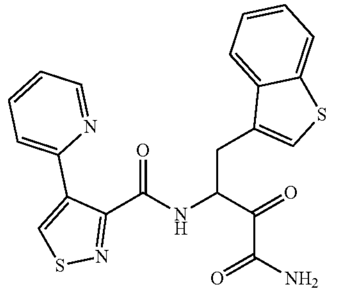 [SMILES: NC(=O)C(=O)C(Cc1csc2ccccc12)NC(=O)c1nscc1-c1ccccn1]
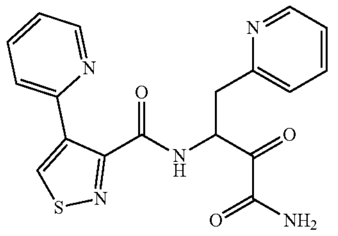 [SMILES: NC(=O)C(=O)C(Cc1ccccn1)NC(=O)c1nscc1-c1ccccn1]
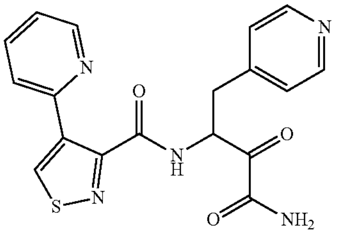 [SMILES: NC(=O)C(=O)C(Cc1ccncc1)NC(=O)c1nscc1-c1ccccn1]
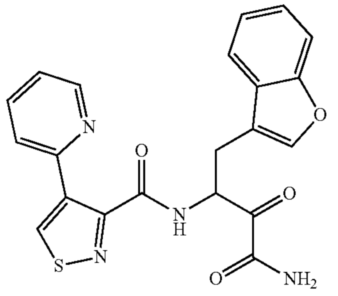 [SMILES: NC(=O)C(=O)C(Cc1coc2ccccc12)NC(=O)c1nscc1-c1ccccn1]

TABLE 1-continued
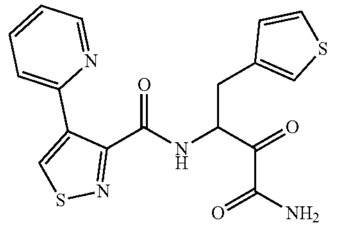
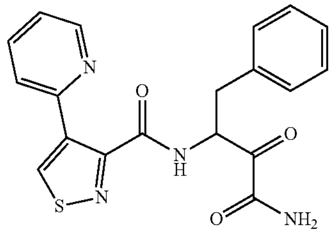 [SMILES: NC(=O)C(=O)C(Cc1ccccc1)NC(=O)c1nscc1-c1ccccn1]
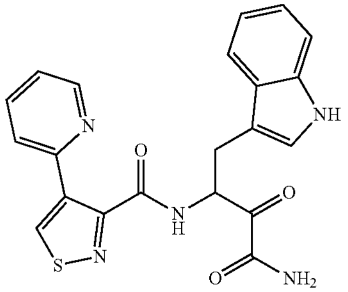 [SMILES: NC(=O)C(=O)C(Cc1c[nH]c2ccccc12)NC(=O)c1nscc1-c1ccccn1]
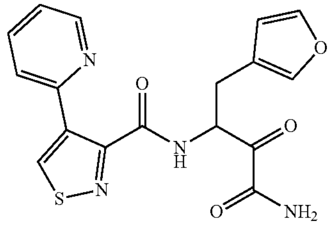 [SMILES: NC(=O)C(=O)C(Cc1ccoc1)NC(=O)c1nscc1-c1ccccn1]
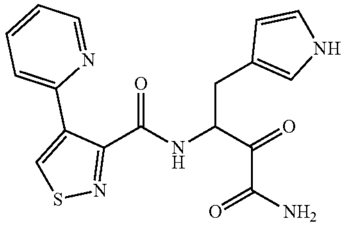
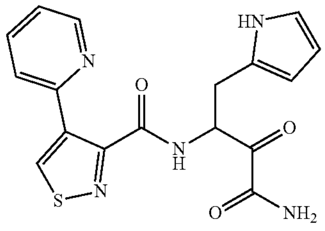
TABLE 1-continued
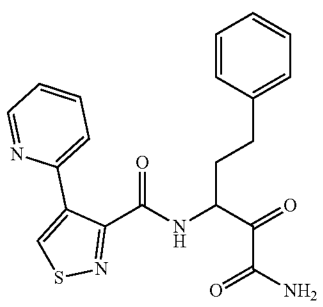 [SMILES: NC(=O)C(=O)C(CCc1ccccc1)NC(=O)c1nscc1-c1ccccn1]
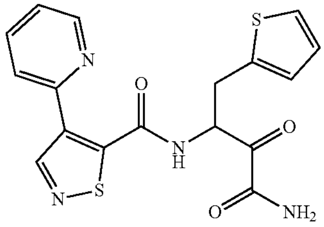
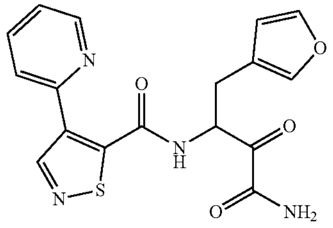
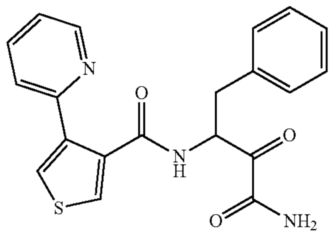 [SMILES: NC(=O)C(=O)C(Cc1ccccc1)NC(=O)c1cscc1-c1ccccn1]
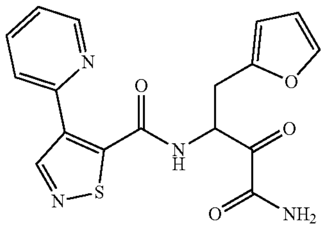 [SMILES: NC(=O)C(=O)C(Cc1ccco1)NC(=O)c1sncc1-c1ccccn1]
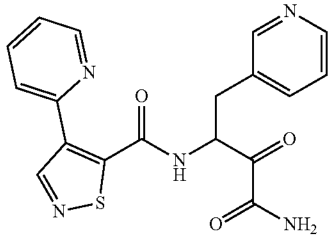 [SMILES: NC(=O)C(=O)C(Cc1cccnc1)NC(=O)c1sncc1-c1ccccn1]

TABLE 1-continued
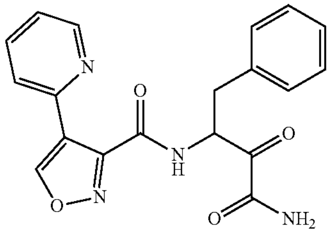 [SMILES: NC(=O)C(=O)C(Cc1ccccc1)NC(=O)c1nocc1-c1ccccn1]
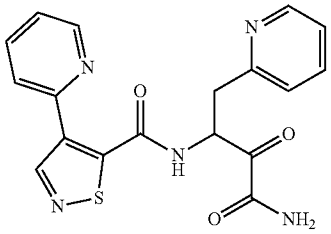
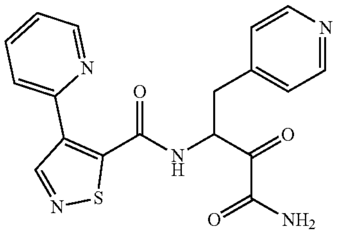
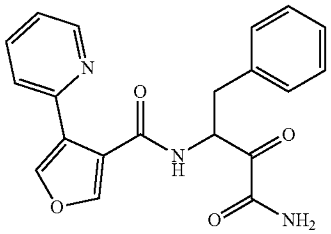 [SMILES: NC(=O)C(=O)C(Cc1ccccc1)NC(=O)c1cocc1-c1ccccn1]
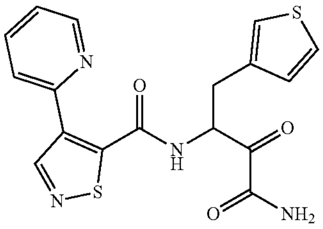 [SMILES: NC(=O)C(=O)C(Cc1ccsc1)NC(=O)c1sncc1-c1ccccn1]
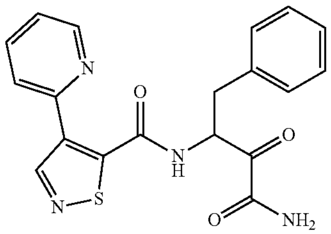 [SMILES: NC(=O)C(=O)C(Cc1ccccc1)NC(=O)c1sncc1-c1ccccn1]
TABLE 1-continued
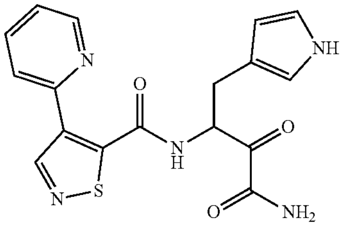
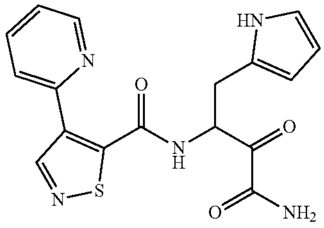 [SMILES: NC(=O)C(=O)C(Cc1ccc[nH]1)NC(=O)c1sncc1-c1ccccn1]
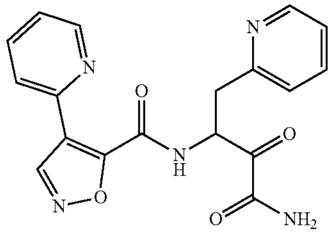
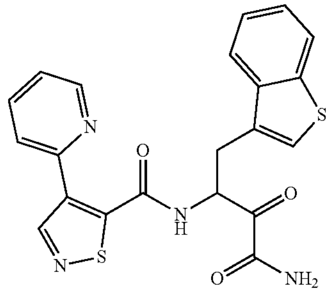 [SMILES: NC(=O)C(=O)C(Cc1csc2ccccc12)NC(=O)c1sncc1-c1ccccn1]
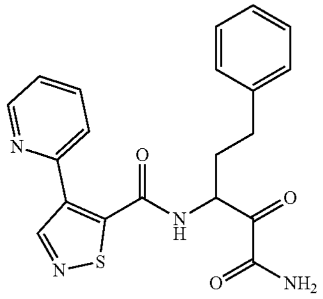 [SMILES: NC(=O)C(=O)C(CCc1ccccc1)NC(=O)c1sncc1-c1ccccn1]
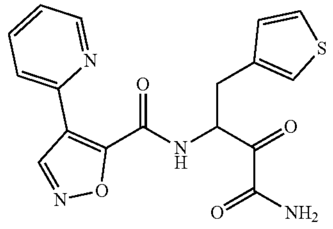

TABLE 1-continued
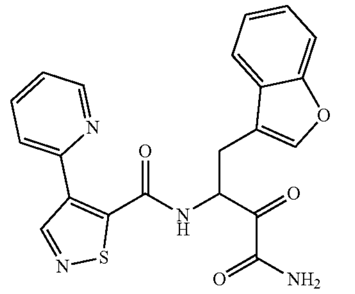 [SMILES: NC(=O)C(=O)C(Cc1coc2ccccc12)NC(=O)c1sncc1-c1ccccn1]
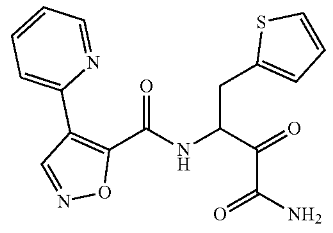
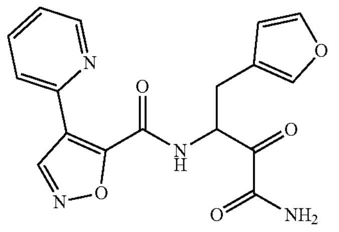 [SMILES: NC(=O)C(=O)C(Cc1ccoc1)NC(=O)c1oncc1-c1ccccn1]
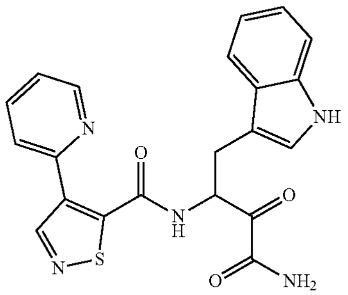 [SMILES: NC(=O)C(=O)C(Cc1c[nH]c2ccccc12)NC(=O)c1sncc1-c1ccccn1]
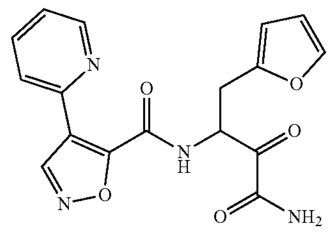 [SMILES: NC(=O)C(=O)C(Cc1ccco1)NC(=O)c1oncc1-c1ccccn1]
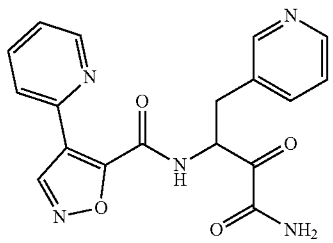
TABLE 1-continued
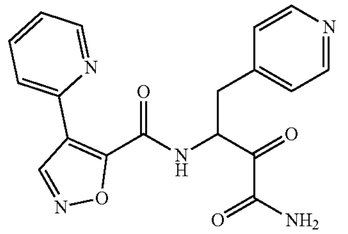 [SMILES: NC(=O)C(=O)C(Cc1ccncc1)NC(=O)c1oncc1-c1ccccn1]
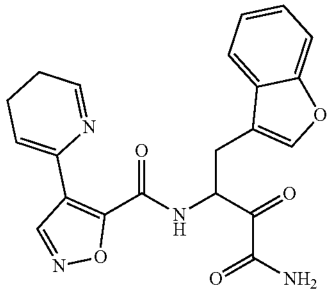 [SMILES: NC(=O)C(=O)C(Cc1coc2ccccc12)NC(=O)c1oncc1C1=CCCC=N1]
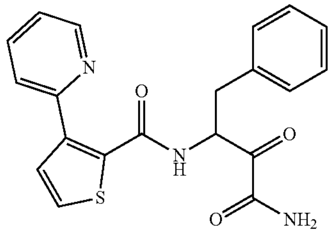 [SMILES: NC(=O)C(=O)C(Cc1ccccc1)NC(=O)c1sccc1-c1ccccn1]
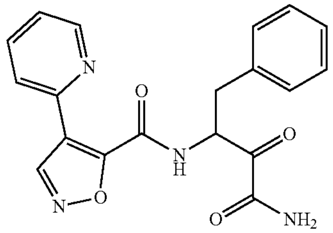
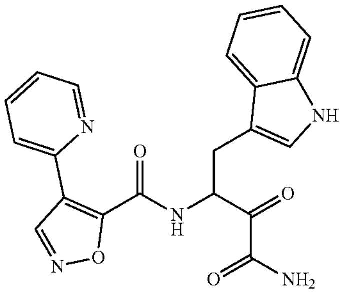 [SMILES: NC(=O)C(=O)C(Cc1c[nH]c2ccccc12)NC(=O)c1oncc1-c1ccccn1]
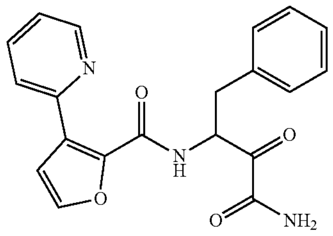

TABLE 1-continued
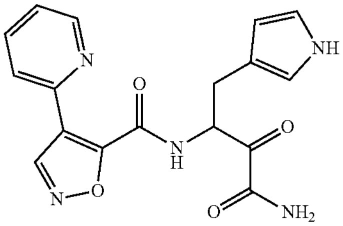
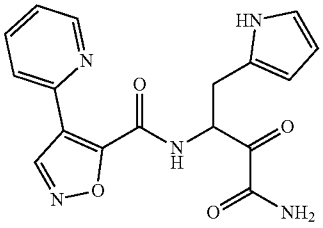 [SMILES: NC(=O)C(=O)C(Cc1ccc[nH]1)NC(=O)c1oncc1-c1ccccn1]
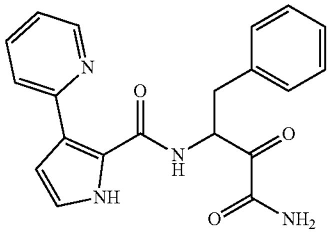
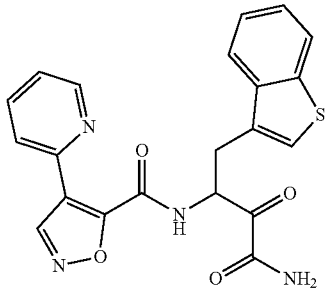 [SMILES: NC(=O)C(=O)C(Cc1csc2ccccc12)NC(=O)c1oncc1-c1ccccn1]
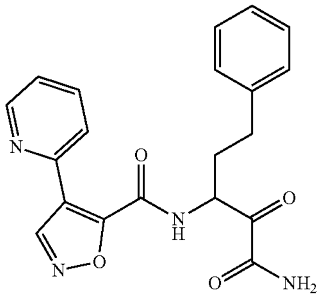 [SMILES: NC(=O)C(=O)C(CCc1ccccc1)NC(=O)c1oncc1-c1ccccn1]
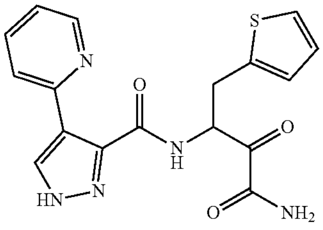
TABLE 1-continued
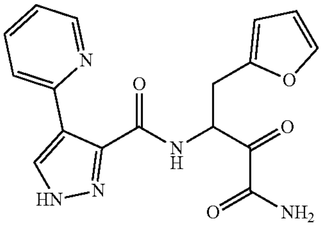 [SMILES: NC(=O)C(=O)C(Cc1ccco1)NC(=O)c1n[nH]cc1-c1ccccn1]
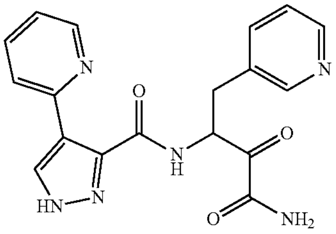
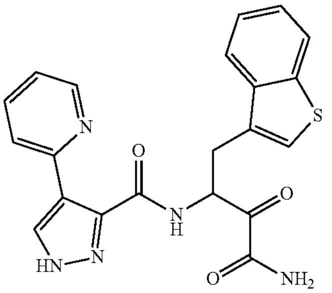 [SMILES: NC(=O)C(=O)C(Cc1csc2ccccc12)NC(=O)c1n[nH]cc1-c1ccccn1]
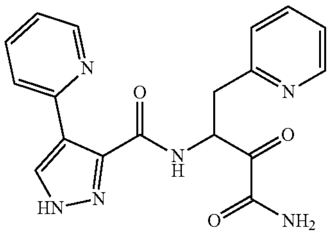 [SMILES: NC(=O)C(=O)C(Cc1ccccn1)NC(=O)c1n[nH]cc1-c1ccccn1]
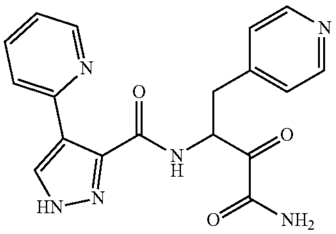
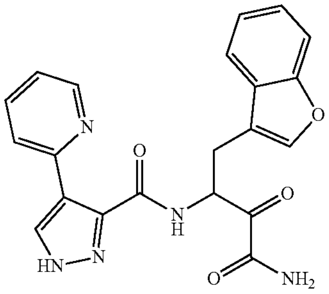 [SMILES: NC(=O)C(=O)C(Cc1coc2ccccc12)NC(=O)c1n[nH]cc1-c1ccccn1]

TABLE 1-continued
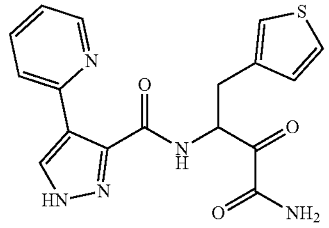 [SMILES: NC(=O)C(=O)C(Cc1ccsc1)NC(=O)c1n[nH]cc1-c1ccccn1]
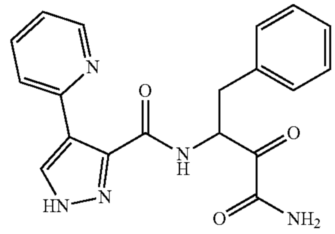
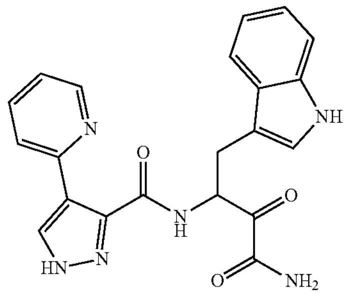 [SMILES: NC(=O)C(=O)C(Cc1c[nH]c2ccccc12)NC(=O)c1n[nH]cc1-c1ccccn1]
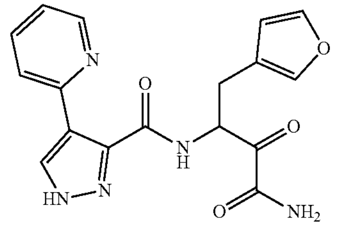 [SMILES: NC(=O)C(=O)C(Cc1ccoc1)NC(=O)c1n[nH]cc1-c1ccccn1]
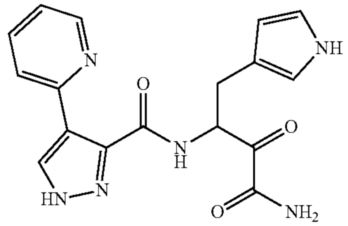 [SMILES: NC(=O)C(=O)C(Cc1cc[nH]c1)NC(=O)c1n[nH]cc1-c1ccccn1]
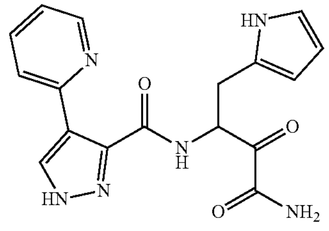 [SMILES: NC(=O)C(=O)C(Cc1ccc[nH]1)NC(=O)c1n[nH]cc1-c1ccccn1]
TABLE 1-continued
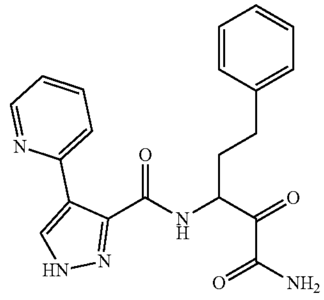 [SMILES: NC(=O)C(=O)C(CCc1ccccc1)NC(=O)c1n[nH]cc1-c1ccccn1]
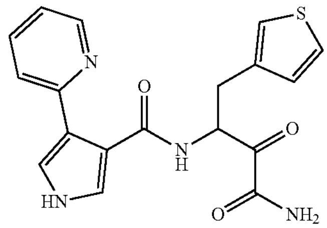 [SMILES: NC(=O)C(=O)C(Cc1ccsc1)NC(=O)c1c[nH]cc1-c1ccccn1]
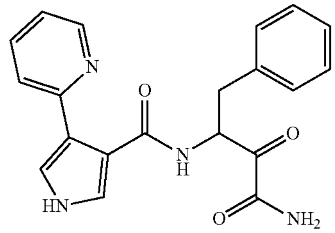
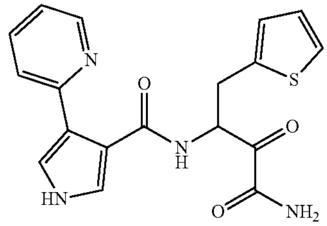 [SMILES: NC(=O)C(=O)C(Cc1cccs1)NC(=O)c1c[nH]cc1-c1ccccn1]
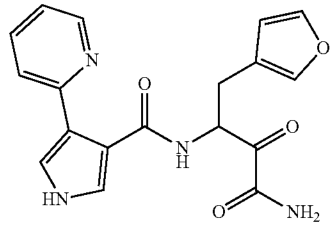 [SMILES: NC(=O)C(=O)C(Cc1ccoc1)NC(=O)c1c[nH]cc1-c1ccccn1]
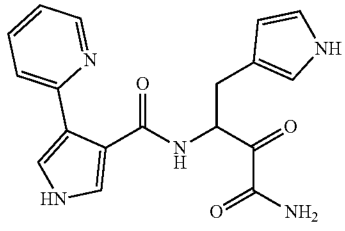 [SMILES: NC(=O)C(=O)C(Cc1cc[nH]c1)NC(=O)c1c[nH]cc1-c1ccccn1]

TABLE 1-continued
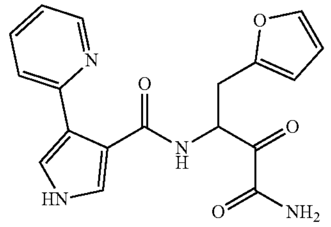
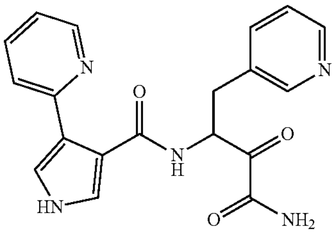 [SMILES: NC(=O)C(=O)C(Cc1cccnc1)NC(=O)c1c[nH]cc1-c1ccccn1]
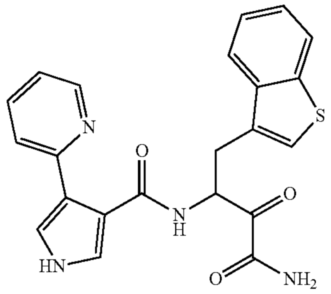
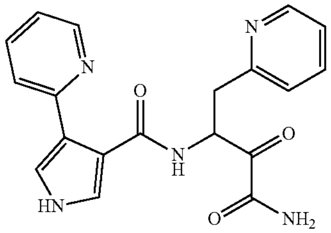 [SMILES: NC(=O)C(=O)C(Cc1ccccn1)NC(=O)c1c[nH]cc1-c1ccccn1]
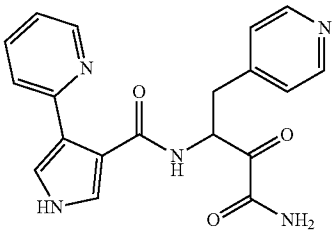 [SMILES: NC(=O)C(=O)C(Cc1ccncc1)NC(=O)c1c[nH]cc1-c1ccccn1]
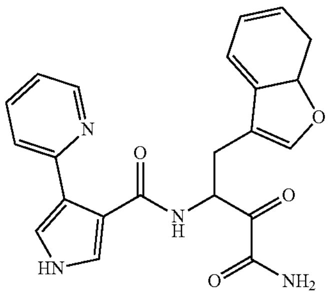 [SMILES: NC(=O)C(=O)C(CC1=COC2CC=CC=C12)NC(=O)c1c[nH]cc1-c1ccccn1]
TABLE 1-continued
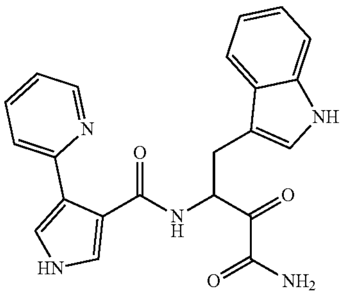
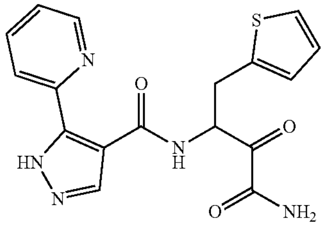
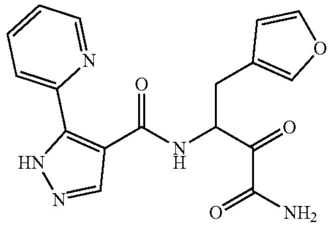
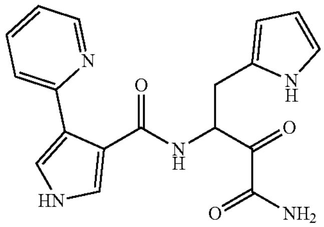
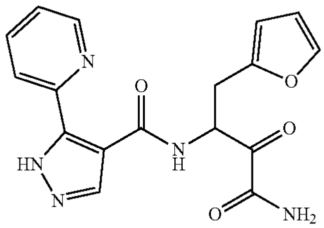
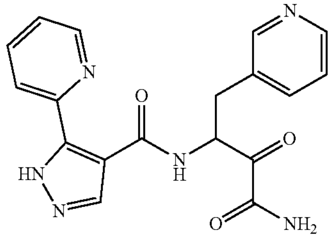 [SMILES: NC(=O)C(=O)C(Cc1cccnc1)NC(=O)c1cn[nH]c1-c1ccccn1]

TABLE 1-continued
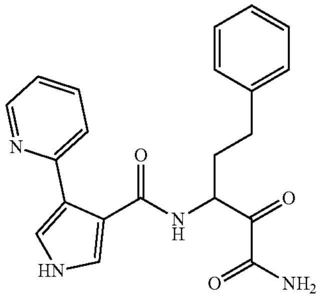 [SMILES: NC(=O)C(=O)C(CCc1ccccc1)NC(=O)c1c[nH]cc1-c1ccccn1]
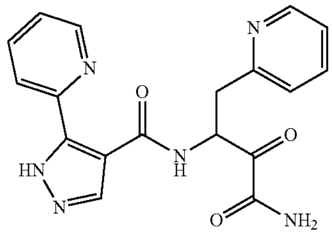 [SMILES: NC(=O)C(=O)C(Cc1ccccn1)NC(=O)c1cn[nH]c1-c1ccccn1]
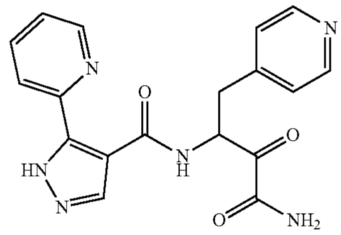 [SMILES: NC(=O)C(=O)C(Cc1ccncc1)NC(=O)c1cn[nH]c1-c1ccccn1]
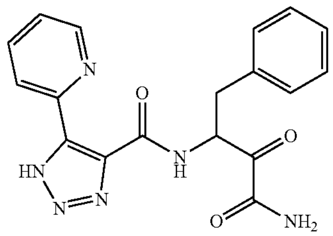 [SMILES: NC(=O)C(=O)C(Cc1ccccc1)NC(=O)c1nn[nH]c1-c1ccccn1]
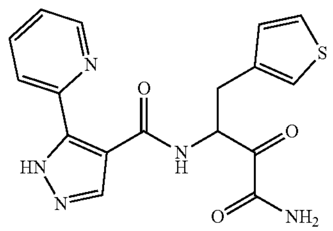 [SMILES: NC(=O)C(=O)C(Cc1ccsc1)NC(=O)c1cn[nH]c1-c1ccccn1]
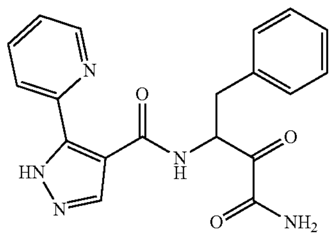 [SMILES: NC(=O)C(=O)C(Cc1ccccc1)NC(=O)c1cn[nH]c1-c1ccccn1]
TABLE 1-continued
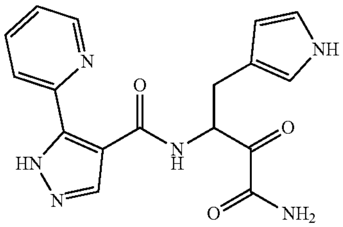
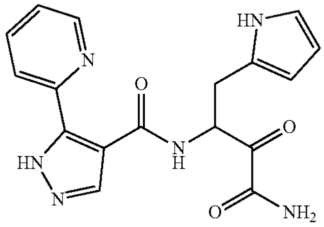
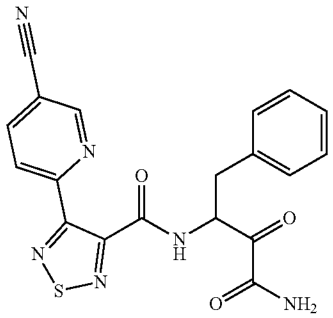 [SMILES: N#Cc1ccc(-c2nsnc2C(=O)NC(Cc2ccccc2)C(=O)C(N)=O)nc1]
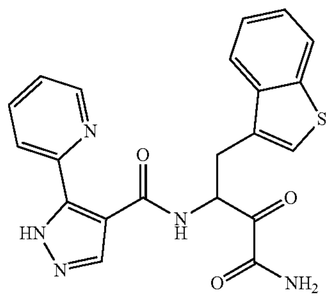
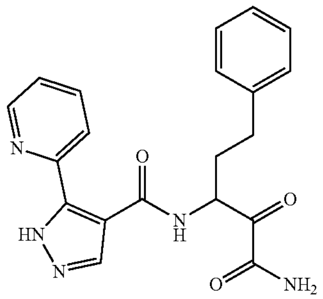 [SMILES: NC(=O)C(=O)C(CCc1ccccc1)NC(=O)c1cn[nH]c1-c1ccccn1]
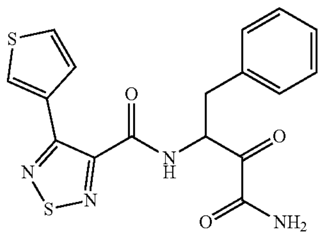 [SMILES: NC(=O)C(=O)C(Cc1ccccc1)NC(=O)c1nsnc1-c1ccsc1]

TABLE 1-continued
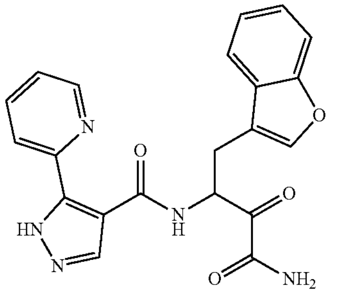
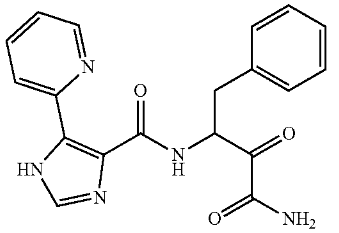 [SMILES: NC(=O)C(=O)C(Cc1ccccc1)NC(=O)c1nc[nH]c1-c1ccccn1]
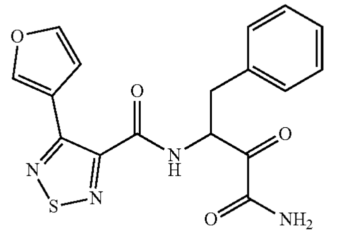 [SMILES: NC(=O)C(=O)C(Cc1ccccc1)NC(=O)c1nsnc1-c1ccoc1]
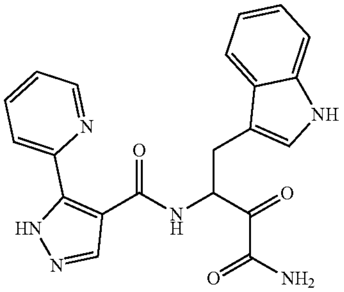
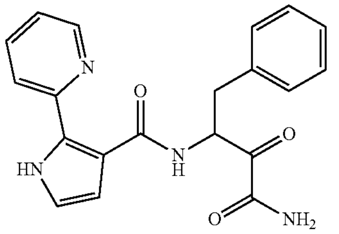 [SMILES: NC(=O)C(=O)C(Cc1ccccc1)NC(=O)c1cc[nH]c1-c1ccccn1]
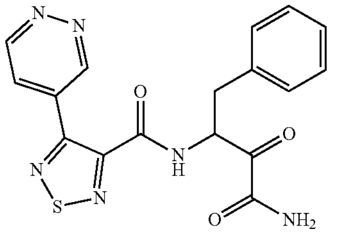
TABLE 1-continued
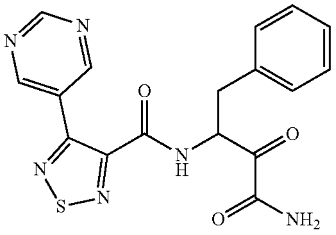 [SMILES: NC(=O)C(=O)C(Cc1ccccc1)NC(=O)c1nsnc1-c1cncnc1]
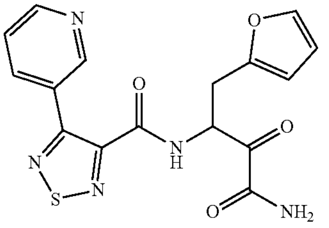
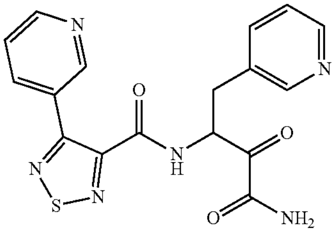 [SMILES: NC(=O)C(=O)C(Cc1cccnc1)NC(=O)c1nsnc1-c1cccnc1]
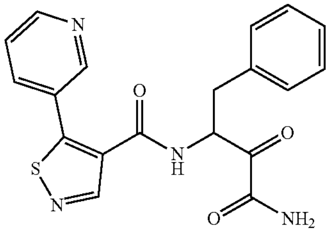 [SMILES: NC(=O)C(=O)C(Cc1ccccc1)NC(=O)c1cnsc1-c1cccnc1]
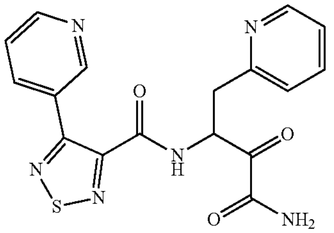
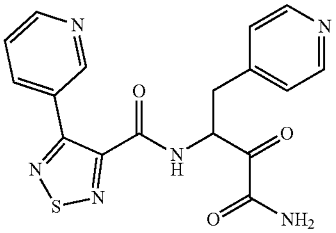 [SMILES: NC(=O)C(=O)C(Cc1ccncc1)NC(=O)c1nsnc1-c1cccnc1]

TABLE 1-continued
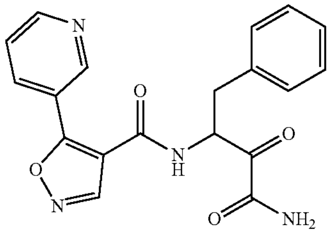 [SMILES: NC(=O)C(=O)C(Cc1ccccc1)NC(=O)c1cnoc1-c1cccnc1]
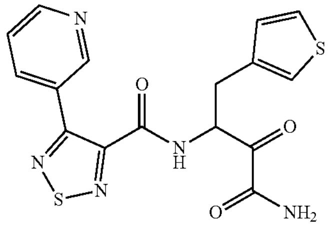
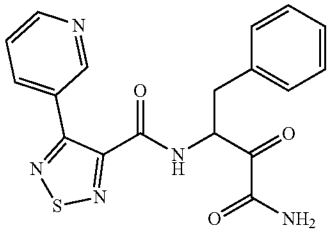
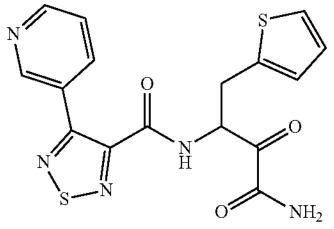 [SMILES: NC(=O)C(=O)C(Cc1cccs1)NC(=O)c1nsnc1-c1cccnc1]
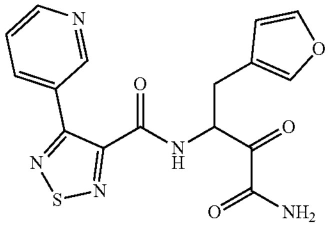 [SMILES: NC(=O)C(=O)C(Cc1ccoc1)NC(=O)c1nsnc1-c1cccnc1]
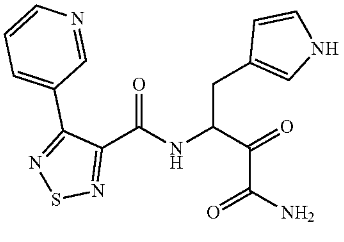
TABLE 1-continued
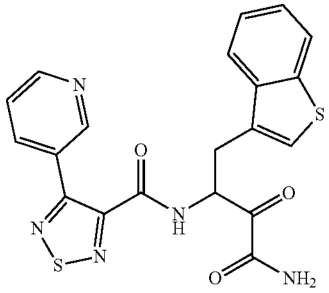
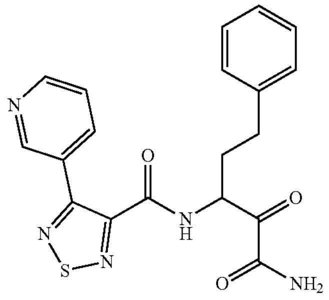 [SMILES: NC(=O)C(=O)C(CCc1ccccc1)NC(=O)c1nsnc1-c1cccnc1]
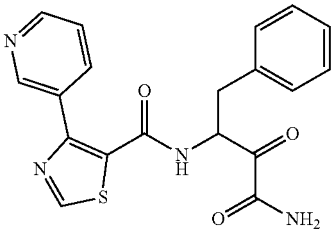 [SMILES: NC(=O)C(=O)C(Cc1ccccc1)NC(=O)c1scnc1-c1cccnc1]
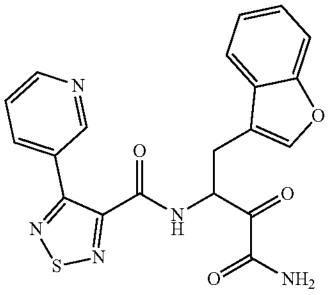
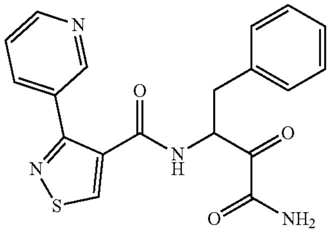
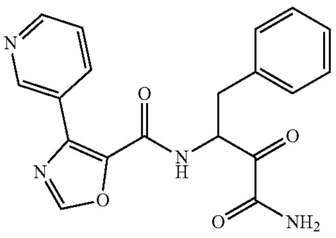 [SMILES: NC(=O)C(=O)C(Cc1ccccc1)NC(=O)c1ocnc1-c1cccnc1]

TABLE 1-continued
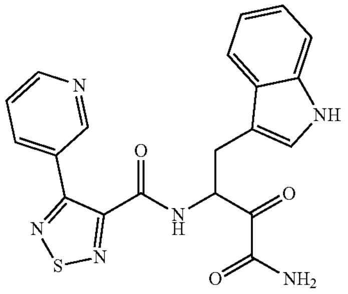
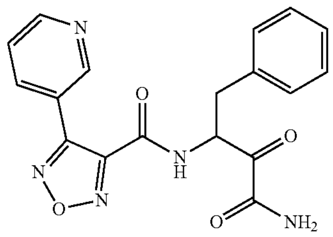
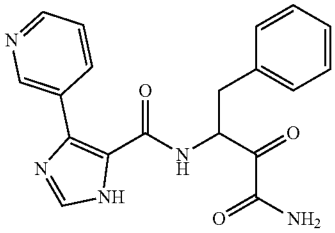 [SMILES: NC(=O)C(=O)C(Cc1ccccc1)NC(=O)c1[nH]cnc1-c1cccnc1]
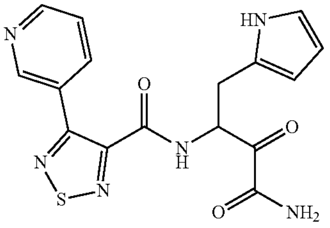 [SMILES: NC(=O)C(=O)C(Cc1ccc[nH]1)NC(=O)c1nsnc1-c1cccnc1]
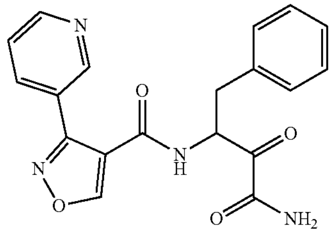
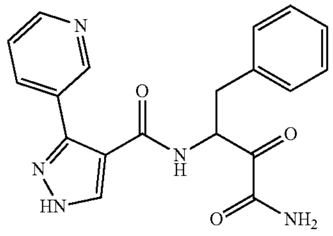
TABLE 1-continued
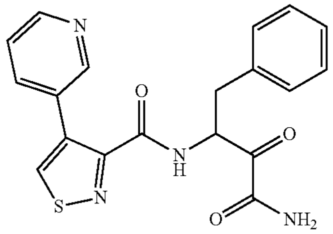
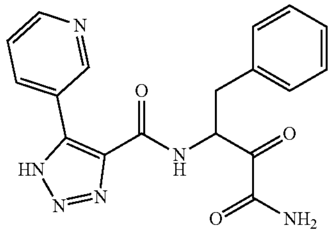 [SMILES: NC(=O)C(=O)C(Cc1ccccc1)NC(=O)c1nn[nH]c1-c1cccnc1]
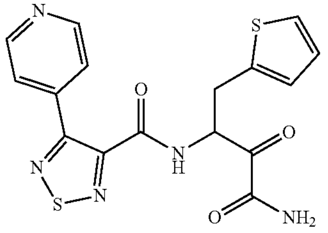
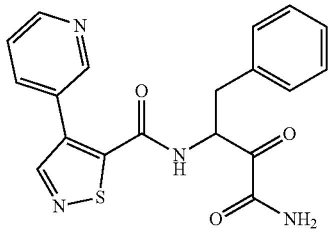 [SMILES: NC(=O)C(=O)C(Cc1ccccc1)NC(=O)c1sncc1-c1cccnc1]
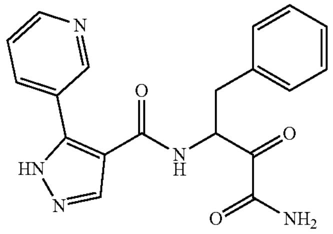 [SMILES: NC(=O)C(=O)C(Cc1ccccc1)NC(=O)c1cn[nH]c1-c1cccnc1]
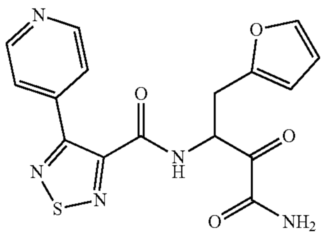 [SMILES: NC(=O)C(=O)C(Cc1ccco1)NC(=O)c1nsnc1-c1ccncc1]

TABLE 1-continued
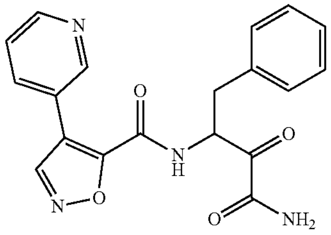 [SMILES: NC(=O)C(=O)C(Cc1ccccc1)NC(=O)c1oncc1-c1cccnc1]
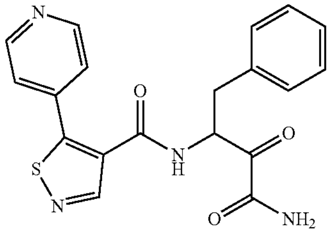 [SMILES: NC(=O)C(=O)C(Cc1ccccc1)NC(=O)c1cnsc1-c1ccncc1]
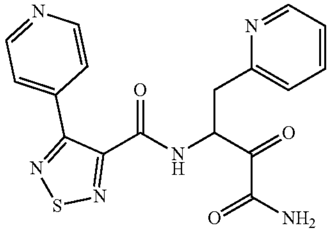
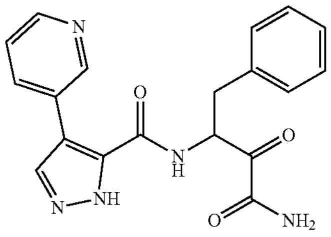 [SMILES: NC(=O)C(=O)C(Cc1ccccc1)NC(=O)c1[nH]ncc1-c1cccnc1]
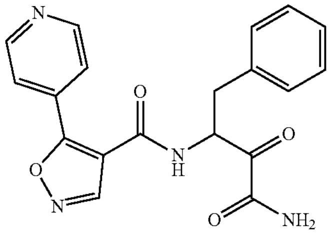 [SMILES: NC(=O)C(=O)C(Cc1ccccc1)NC(=O)c1cnoc1-c1ccncc1]
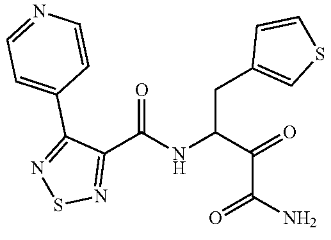
TABLE 1-continued
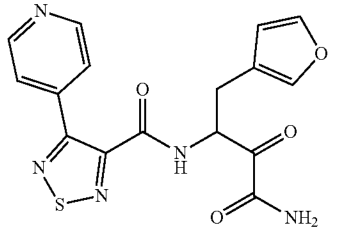 [SMILES: NC(=O)C(=O)C(Cc1ccoc1)NC(=O)c1nsnc1-c1ccncc1]
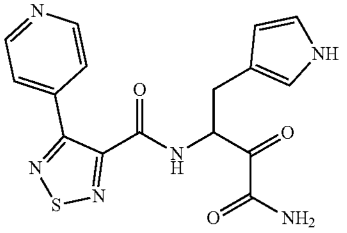
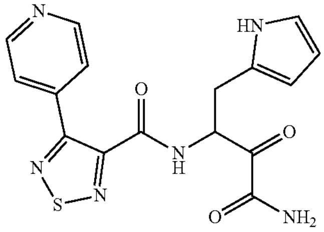
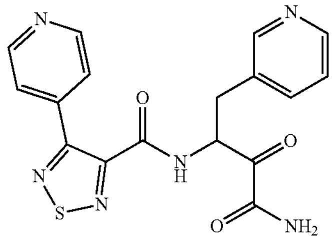
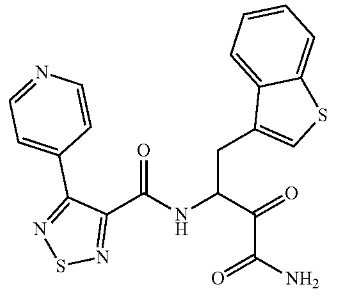 [SMILES: NC(=O)C(=O)C(Cc1csc2ccccc12)NC(=O)c1nsnc1-c1ccncc1]
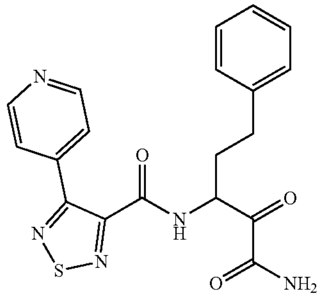 [SMILES: NC(=O)C(=O)C(CCc1ccccc1)NC(=O)c1nsnc1-c1ccncc1]

TABLE 1-continued
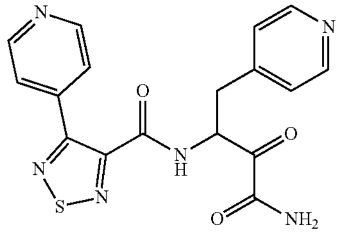
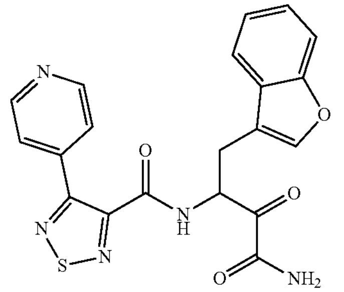 [SMILES: NC(=O)C(=O)C(Cc1coc2ccccc12)NC(=O)c1nsnc1-c1ccncc1]
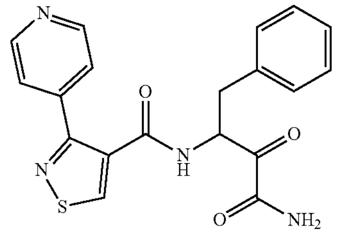 [SMILES: NC(=O)C(=O)C(Cc1ccccc1)NC(=O)c1csnc1-c1ccncc1]
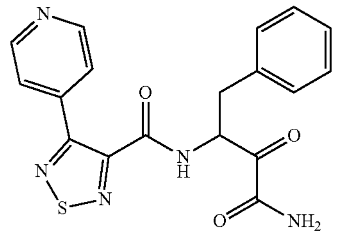
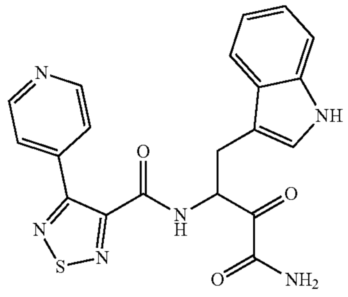 [SMILES: NC(=O)C(=O)C(Cc1c[nH]c2ccccc12)NC(=O)c1nsnc1-c1ccncc1]
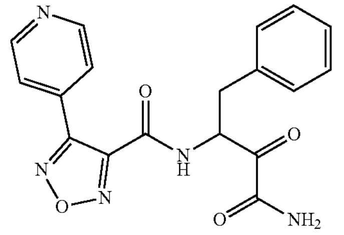
TABLE 1-continued
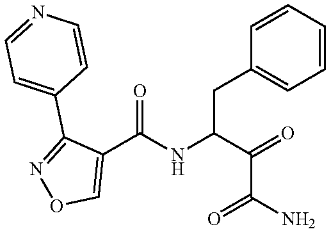
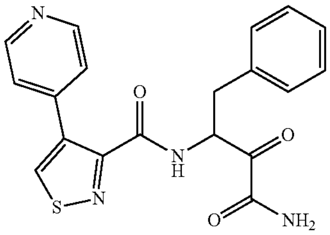
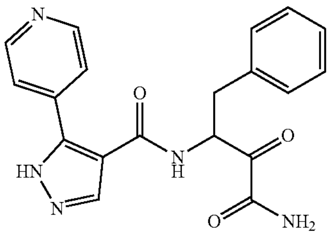 [SMILES: NC(=O)C(=O)C(Cc1ccccc1)NC(=O)c1cn[nH]c1-c1ccncc1]
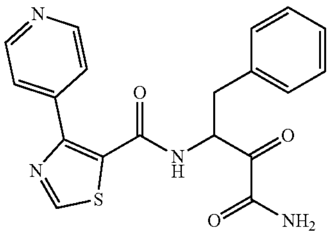
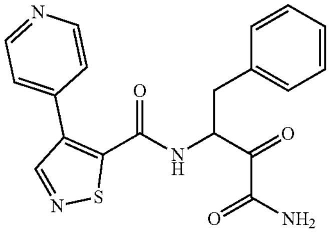
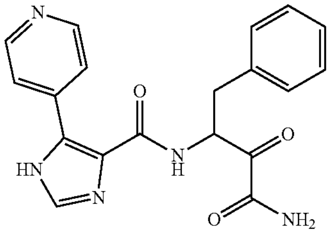 [SMILES: NC(=O)C(=O)C(Cc1ccccc1)NC(=O)c1nc[nH]c1-c1ccncc1]

TABLE 1-continued
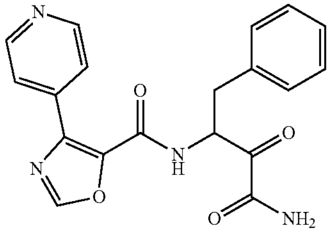
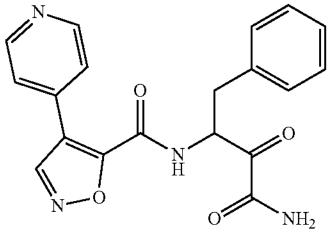
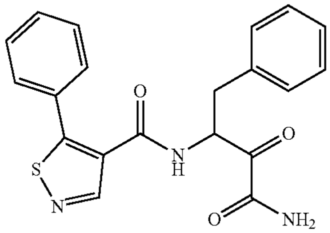 [SMILES: NC(=O)C(=O)C(Cc1ccccc1)NC(=O)c1cnsc1-c1ccccc1]
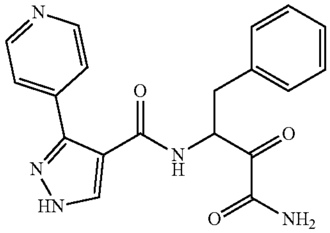
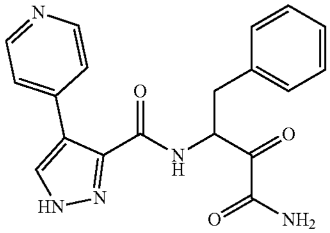
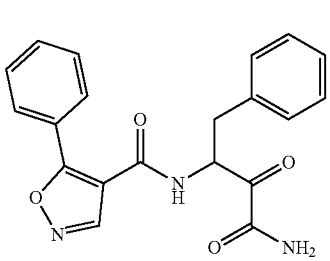 [SMILES: NC(=O)C(=O)C(Cc1ccccc1)NC(=O)c1cnoc1-c1ccccc1]
TABLE 1-continued
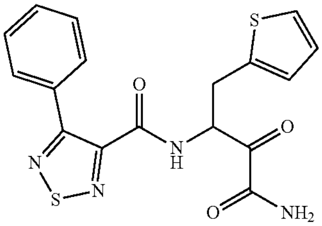
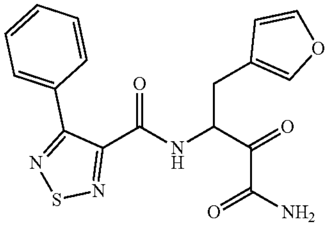
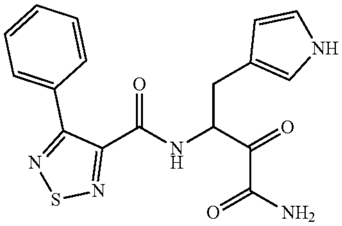
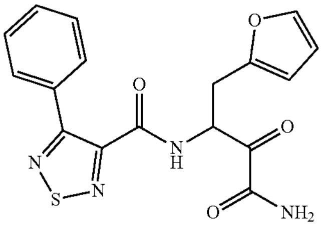
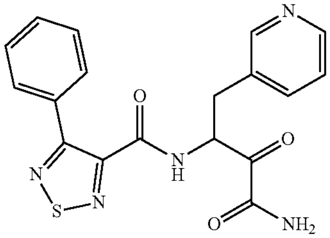
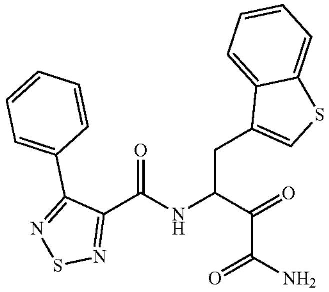 [SMILES: NC(=O)C(=O)C(Cc1csc2ccccc12)NC(=O)c1nsnc1-c1ccccc1]

TABLE 1-continued
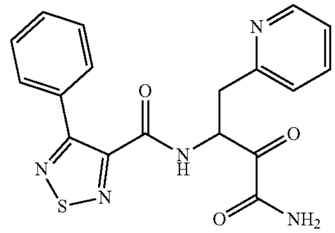
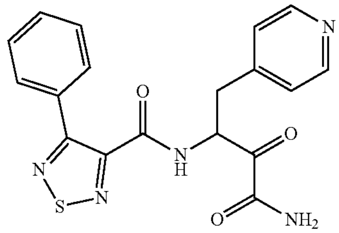
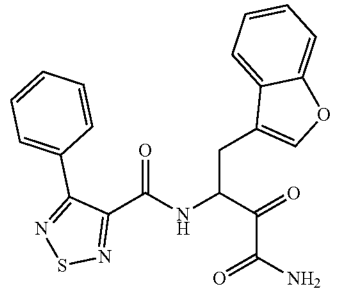 [SMILES: NC(=O)C(=O)C(Cc1coc2ccccc12)NC(=O)c1nsnc1-c1ccccc1]
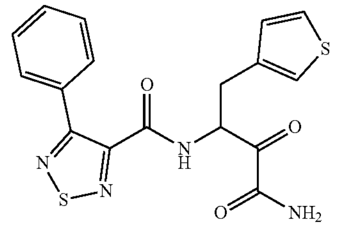
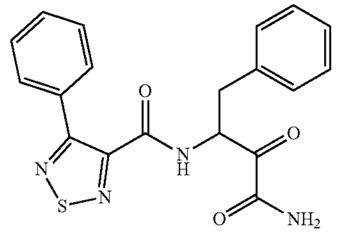
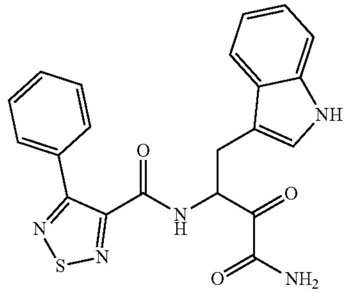 [SMILES: NC(=O)C(=O)C(Cc1c[nH]c2ccccc12)NC(=O)c1nsnc1-c1ccccc1]
TABLE 1-continued
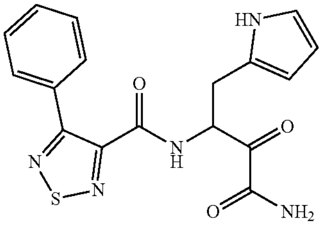
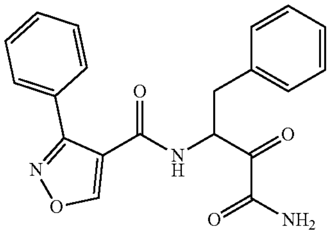
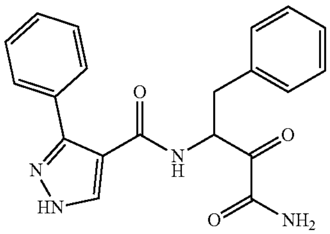
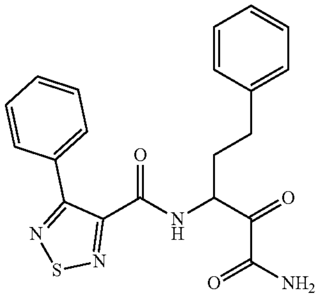
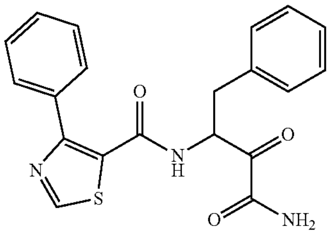
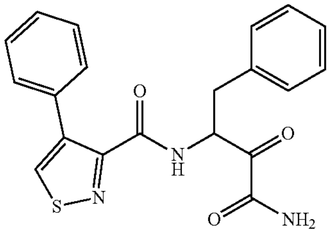

TABLE 1-continued
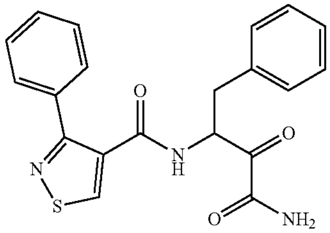
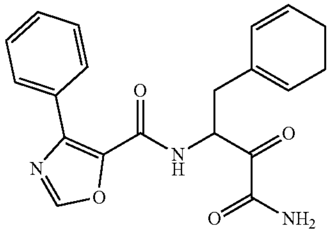 [SMILES: NC(=O)C(=O)C(CC1=CCCC=C1)NC(=O)c1ocnc1-c1ccccc1]
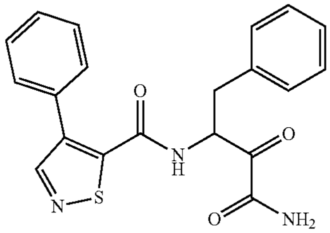
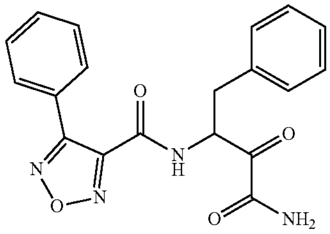
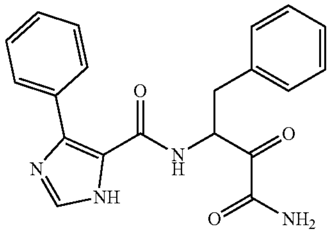
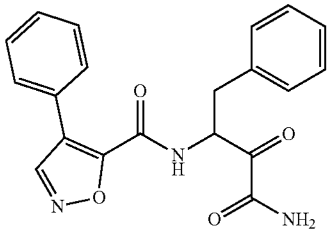
TABLE 1-continued
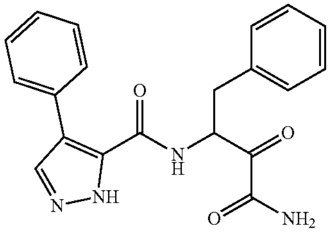
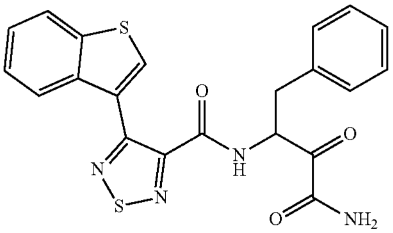 [SMILES: NC(=O)C(=O)C(Cc1ccccc1)NC(=O)c1nsnc1-c1csc2ccccc12]
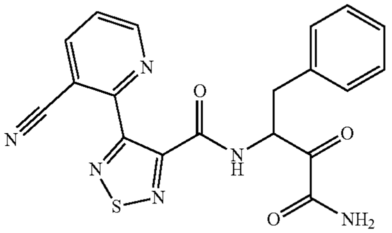 [SMILES: N#Cc1cccnc1-c1nsnc1C(=O)NC(Cc1ccccc1)C(=O)C(N)=O]
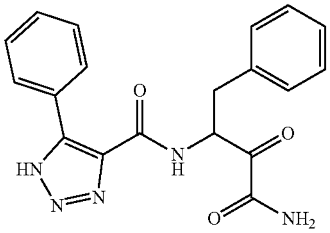 [SMILES: NC(=O)C(=O)C(Cc1ccccc1)NC(=O)c1nn[nH]c1-c1ccccc1]
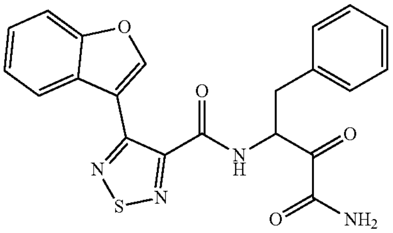 [SMILES: NC(=O)C(=O)C(Cc1ccccc1)NC(=O)c1nsnc1-c1coc2ccccc12]
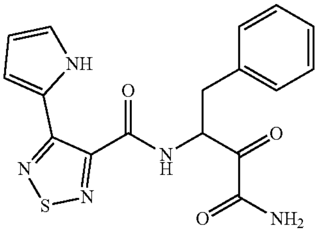

TABLE 1-continued
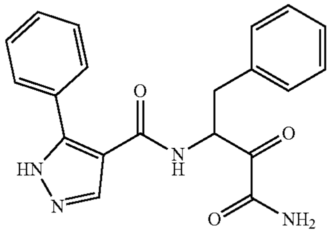 [SMILES: NC(=O)C(=O)C(Cc1ccccc1)NC(=O)c1cn[nH]c1-c1ccccc1]
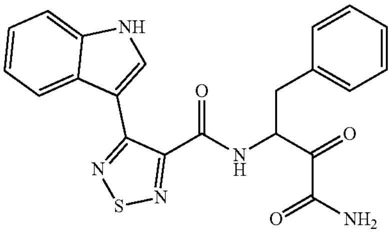 [SMILES: NC(=O)C(=O)C(Cc1ccccc1)NC(=O)c1nsnc1-c1c[nH]c2ccccc12]
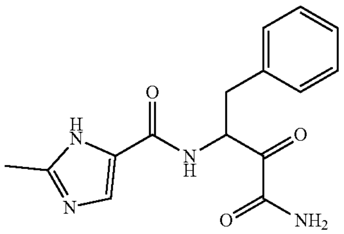 [SMILES: Cc1ncc(C(=O)NC(Cc2ccccc2)C(=O)C(N)=O)[nH]1]
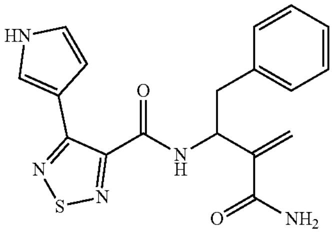 [SMILES: C=C(C(N)=O)C(Cc1ccccc1)NC(=O)c1nsnc1-c1cc[nH]c1]
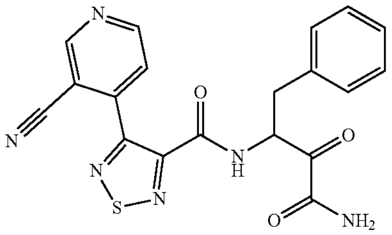 [SMILES: N#Cc1cnccc1-c1nsnc1C(=O)NC(Cc1ccccc1)C(=O)C(N)=O]
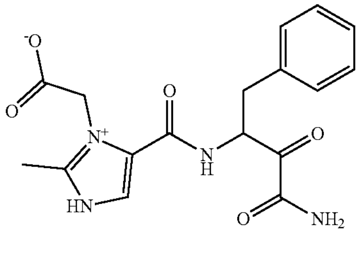
TABLE 1-continued
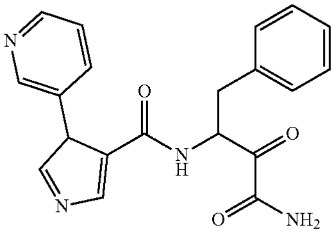 [SMILES: NC(=O)C(=O)C(Cc1ccccc1)NC(=O)C1=CN=CC1c1cccnc1]
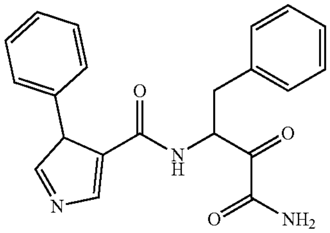
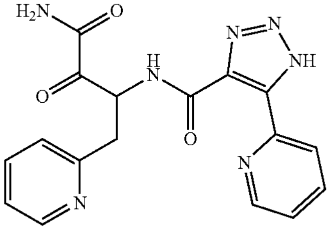 [SMILES: NC(=O)C(=O)C(Cc1ccccn1)NC(=O)c1nn[nH]c1-c1ccccn1]
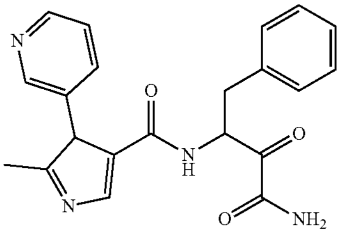 [SMILES: CC1=NC=C(C(=O)NC(Cc2ccccc2)C(=O)C(N)=O)C1c1cccnc1]
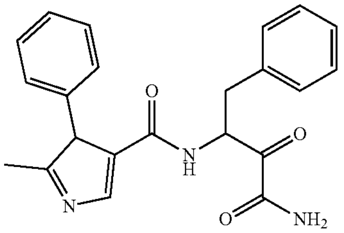 [SMILES: CC1=NC=C(C(=O)NC(Cc2ccccc2)C(=O)C(N)=O)C1c1ccccc1]
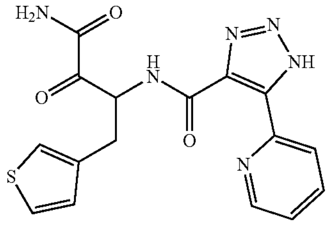 [SMILES: NC(=O)C(=O)C(Cc1ccsc1)NC(=O)c1nn[nH]c1-c1ccccn1]

TABLE 1-continued
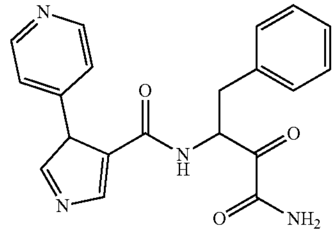
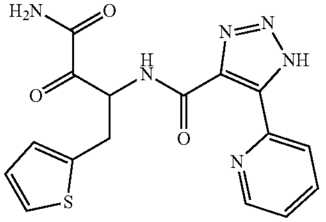 [SMILES: NC(=O)C(=O)C(Cc1cccs1)NC(=O)c1nn[nH]c1-c1ccccn1]
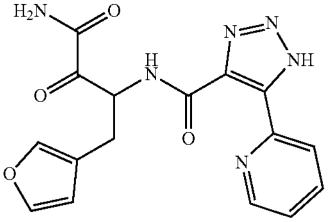 [SMILES: NC(=O)C(=O)C(Cc1ccoc1)NC(=O)c1nn[nH]c1-c1ccccn1]
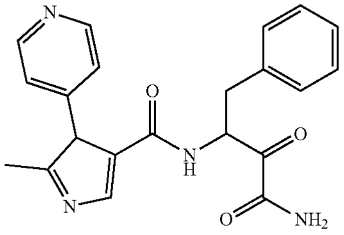 [SMILES: CC1=NC=C(C(=O)NC(Cc2ccccc2)C(=O)C(N)=O)C1c1ccncc1]
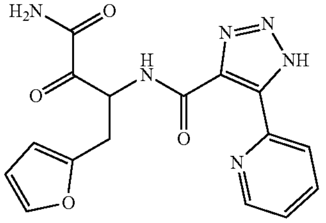 [SMILES: NC(=O)C(=O)C(Cc1ccco1)NC(=O)c1nn[nH]c1-c1ccccn1]
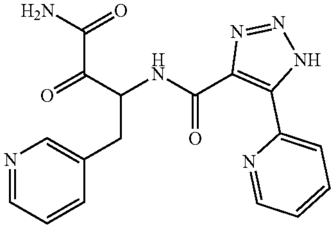 [SMILES: NC(=O)C(=O)C(Cc1cccnc1)NC(=O)c1nn[nH]c1-c1ccccn1]
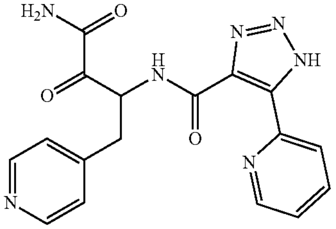 [SMILES: NC(=O)C(=O)C(Cc1ccncc1)NC(=O)c1nn[nH]c1-c1ccccn1]
TABLE 1-continued
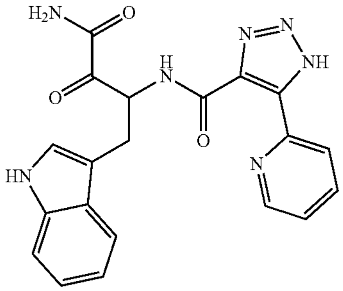 [SMILES: NC(=O)C(=O)C(Cc1c[nH]c2ccccc12)NC(=O)c1nn[nH]c1-c1ccccn1]
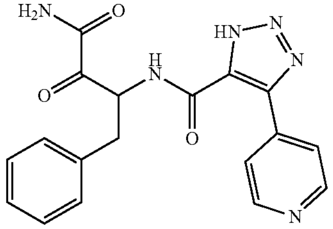 [SMILES: NC(=O)C(=O)C(Cc1ccccc1)NC(=O)c1[nH]nnc1-c1ccncc1]
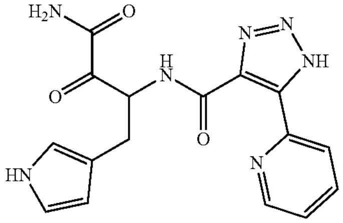 [SMILES: NC(=O)C(=O)C(Cc1cc[nH]c1)NC(=O)c1nn[nH]c1-c1ccccn1]
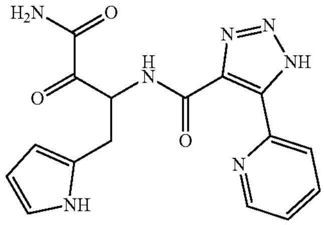
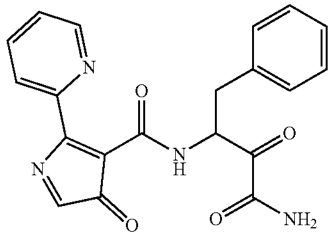 [SMILES: NC(=O)C(=O)C(Cc1ccccc1)NC(=O)C1=C(c2ccccn2)N=CC1=O]
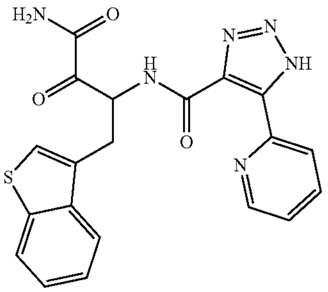 [SMILES: NC(=O)C(=O)C(Cc1csc2ccccc12)NC(=O)c1nn[nH]c1-c1ccccn1]

TABLE 1-continued
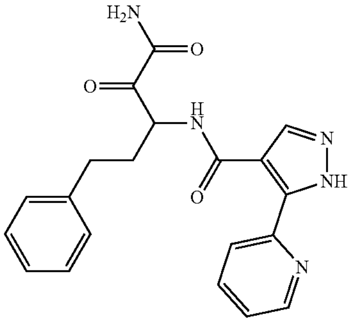 [SMILES: NC(=O)C(=O)C(CCc1ccccc1)NC(=O)c1cn[nH]c1-c1ccccn1]
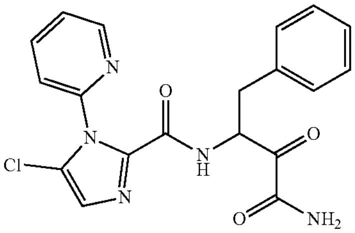 [SMILES: NC(=O)C(=O)C(Cc1ccccc1)NC(=O)c1ncc(Cl)n1-c1ccccn1]
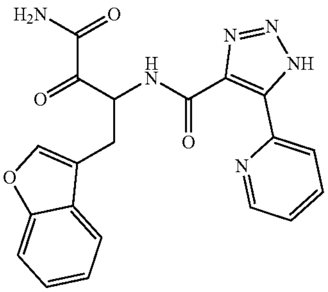 [SMILES: NC(=O)C(=O)C(Cc1coc2ccccc12)NC(=O)c1nn[nH]c1-c1ccccn1]
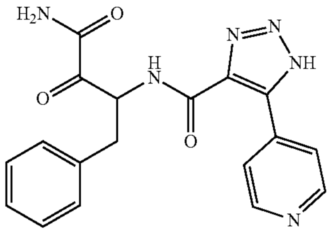 [SMILES: NC(=O)C(=O)C(Cc1ccccc1)NC(=O)c1nn[nH]c1-c1ccncc1]
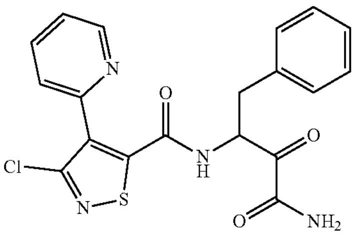 [SMILES: NC(=O)C(=O)C(Cc1ccccc1)NC(=O)c1snc(Cl)c1-c1ccccn1]
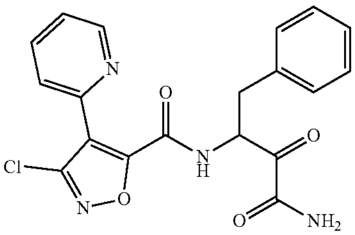 [SMILES: NC(=O)C(=O)C(Cc1ccccc1)NC(=O)c1onc(Cl)c1-c1ccccn1]
TABLE 1-continued
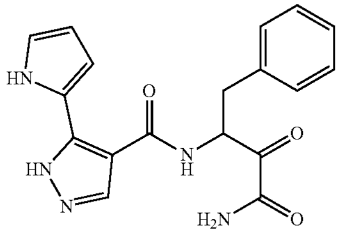 [SMILES: NC(=O)C(=O)C(Cc1ccccc1)NC(=O)c1cn[nH]c1-c1ccc[nH]1]
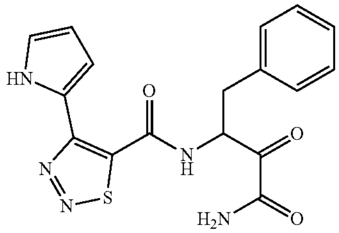 [SMILES: NC(=O)C(=O)C(Cc1ccccc1)NC(=O)c1snnc1-c1ccc[nH]1]
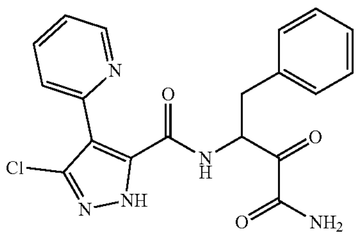 [SMILES: NC(=O)C(=O)C(Cc1ccccc1)NC(=O)c1[nH]nc(Cl)c1-c1ccccn1]
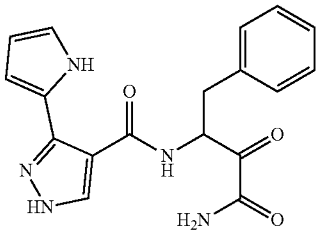 [SMILES: NC(=O)C(=O)C(Cc1ccccc1)NC(=O)c1c[nH]nc1-c1ccc[nH]1]
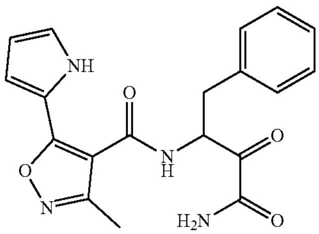 [SMILES: Cc1noc(-c2ccc[nH]2)c1C(=O)NC(Cc1ccccc1)C(=O)C(N)=O]
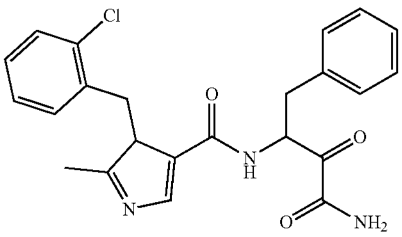 [SMILES: CC1=NC=C(C(=O)NC(Cc2ccccc2)C(=O)C(N)=O)C1Cc1ccccc1Cl]

TABLE 1-continued
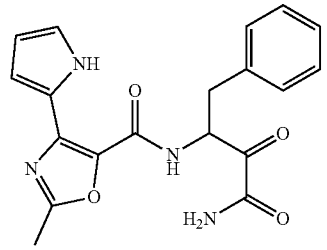 [SMILES: Cc1nc(-c2ccc[nH]2)c(C(=O)NC(Cc2ccccc2)C(=O)C(N)=O)o1]
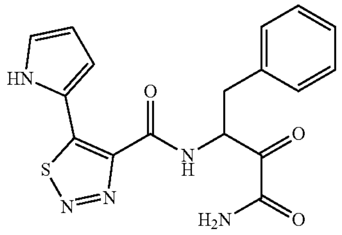 [SMILES: NC(=O)C(=O)C(Cc1ccccc1)NC(=O)c1nnsc1-c1ccc[nH]1]
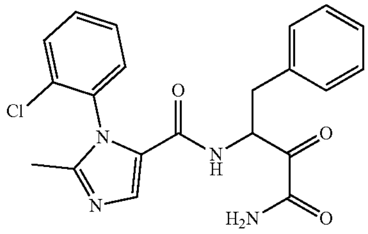 [SMILES: Cc1ncc(C(=O)NC(Cc2ccccc2)C(=O)C(N)=O)n1-c1ccccc1Cl]
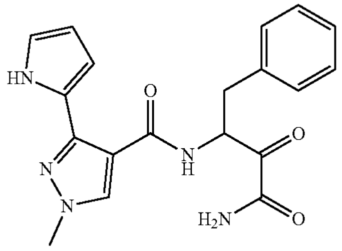 [SMILES: Cn1cc(C(=O)NC(Cc2ccccc2)C(=O)C(N)=O)c(-c2ccc[nH]2)n1]
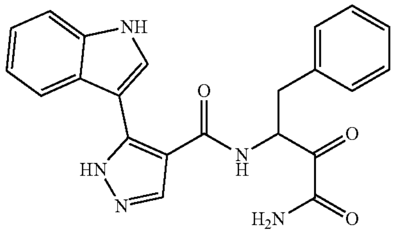 [SMILES: NC(=O)C(=O)C(Cc1ccccc1)NC(=O)c1cn[nH]c1-c1c[nH]c2ccccc12]
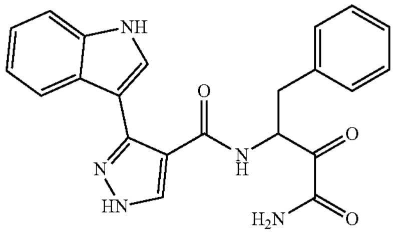 [SMILES: NC(=O)C(=O)C(Cc1ccccc1)NC(=O)c1c[nH]nc1-c1c[nH]c2ccccc12]
TABLE 1-continued
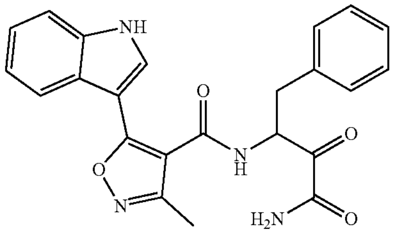
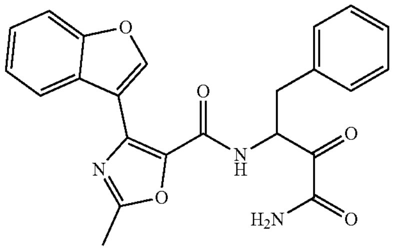
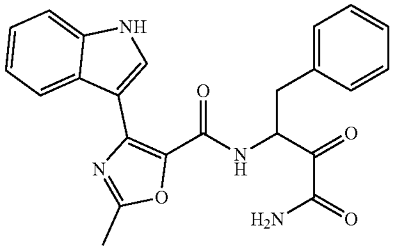 [SMILES: Cc1nc(-c2c[nH]c3ccccc23)c(C(=O)NC(Cc2ccccc2)C(=O)C(N)=O)o1]
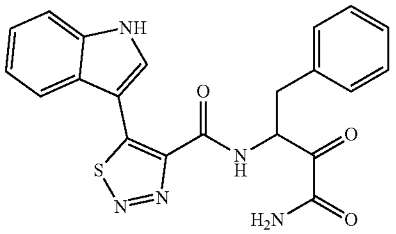 [SMILES: NC(=O)C(=O)C(Cc1ccccc1)NC(=O)c1nnsc1-c1c[nH]c2ccccc12]
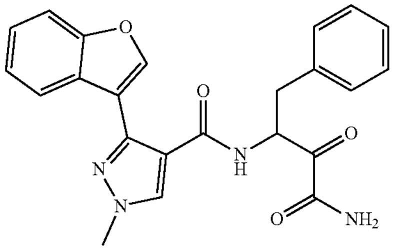
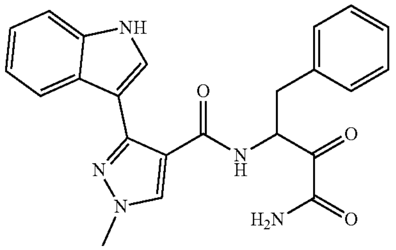 [SMILES: Cn1cc(C(=O)NC(Cc2ccccc2)C(=O)C(N)=O)c(-c2c[nH]c3ccccc23)n1]

TABLE 1-continued
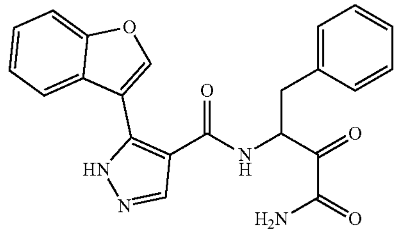 [SMILES: NC(=O)C(=O)C(Cc1ccccc1)NC(=O)c1cn[nH]c1-c1coc2ccccc12]
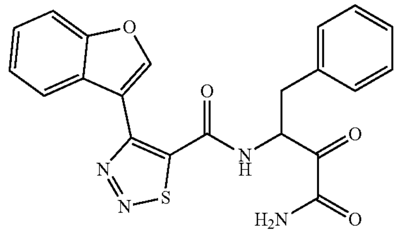 [SMILES: NC(=O)C(=O)C(Cc1ccccc1)NC(=O)c1snnc1-c1coc2ccccc12]
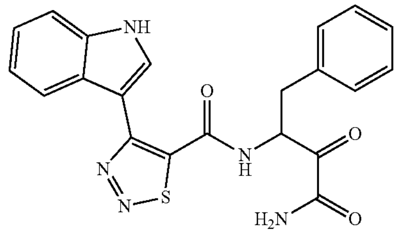 [SMILES: NC(=O)C(=O)C(Cc1ccccc1)NC(=O)c1snnc1-c1c[nH]c2ccccc12]
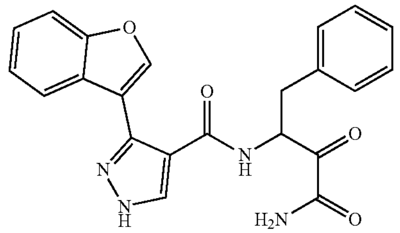 [SMILES: NC(=O)C(=O)C(Cc1ccccc1)NC(=O)c1c[nH]nc1-c1coc2ccccc12]
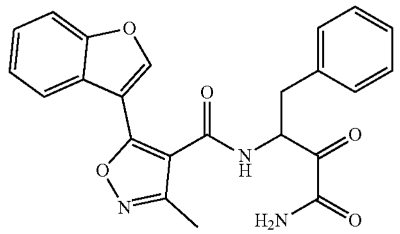 [SMILES: Cc1noc(-c2coc3ccccc23)c1C(=O)NC(Cc1ccccc1)C(=O)C(N)=O]
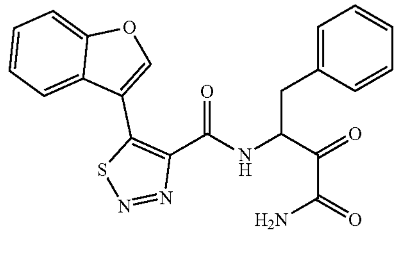 [SMILES: NC(=O)C(=O)C(Cc1ccccc1)NC(=O)c1nnsc1-c1coc2ccccc12]
TABLE 1-continued
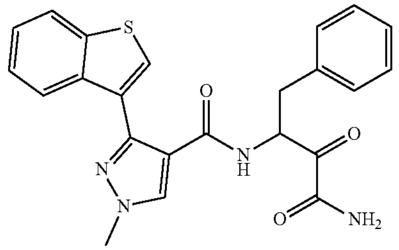 [SMILES: Cn1cc(C(=O)NC(Cc2ccccc2)C(=O)C(N)=O)c(-c2csc3ccccc23)n1]
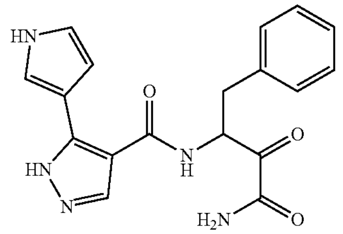 [SMILES: NC(=O)C(=O)C(Cc1ccccc1)NC(=O)c1cn[nH]c1-c1cc[nH]c1]
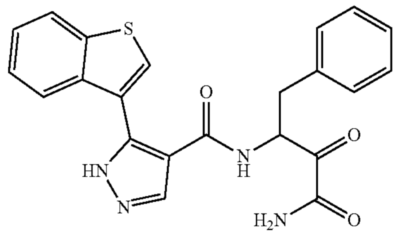
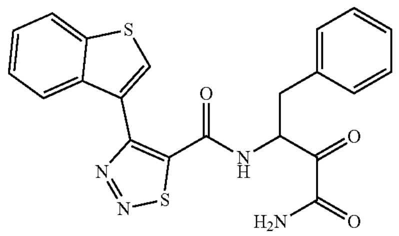 [SMILES: NC(=O)C(=O)C(Cc1ccccc1)NC(=O)c1snnc1-c1csc2ccccc12]
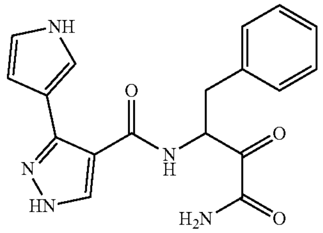 [SMILES: NC(=O)C(=O)C(Cc1ccccc1)NC(=O)c1c[nH]nc1-c1cc[nH]c1]
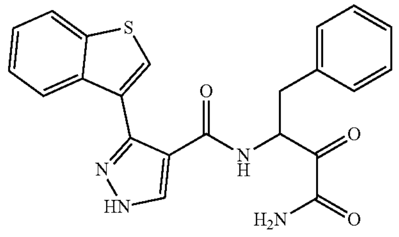 [SMILES: NC(=O)C(=O)C(Cc1ccccc1)NC(=O)c1c[nH]nc1-c1csc2ccccc12]

TABLE 1-continued
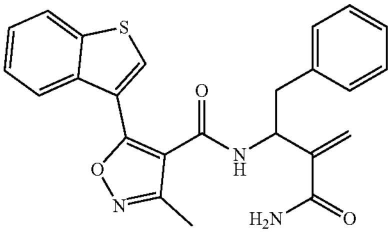
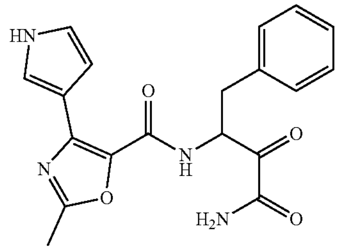 [SMILES: Cc1nc(-c2cc[nH]c2)c(C(=O)NC(Cc2ccccc2)C(=O)C(N)=O)o1]
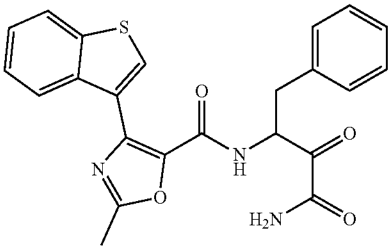
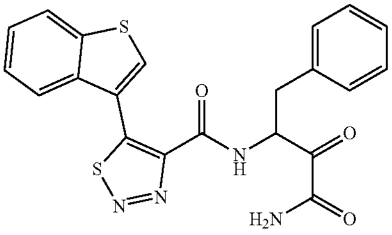 [SMILES: NC(=O)C(=O)C(Cc1ccccc1)NC(=O)c1nnsc1-c1csc2ccccc12]
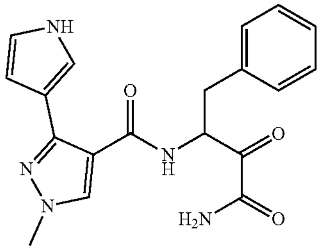 [SMILES: Cn1cc(C(=O)NC(Cc2ccccc2)C(=O)C(N)=O)c(-c2cc[nH]c2)n1]
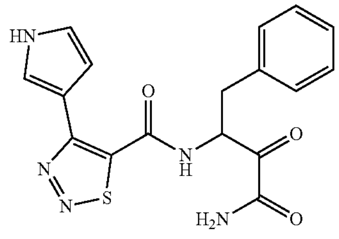 [SMILES: NC(=O)C(=O)C(Cc1ccccc1)NC(=O)c1snnc1-c1cc[nH]c1]
TABLE 1-continued
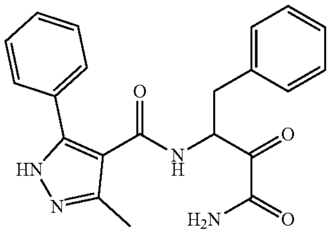 [SMILES: Cc1n[nH]c(-c2ccccc2)c1C(=O)NC(Cc1ccccc1)C(=O)C(N)=O]
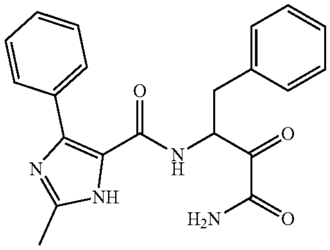 [SMILES: Cc1nc(-c2ccccc2)c(C(=O)NC(Cc2ccccc2)C(=O)C(N)=O)[nH]1]
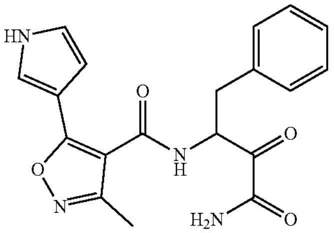 [SMILES: Cc1noc(-c2cc[nH]c2)c1C(=O)NC(Cc1ccccc1)C(=O)C(N)=O]
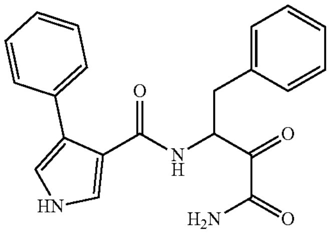 [SMILES: NC(=O)C(=O)C(Cc1ccccc1)NC(=O)c1c[nH]cc1-c1ccccc1]
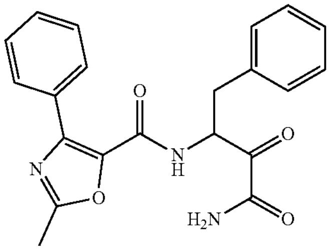 [SMILES: Cc1nc(-c2ccccc2)c(C(=O)NC(Cc2ccccc2)C(=O)C(N)=O)o1]
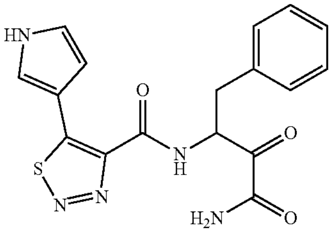 [SMILES: NC(=O)C(=O)C(Cc1ccccc1)NC(=O)c1nnsc1-c1cc[nH]c1]

TABLE 1-continued
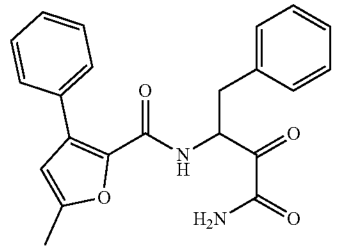 [SMILES: Cc1cc(-c2ccccc2)c(C(=O)NC(Cc2ccccc2)C(=O)C(N)=O)o1]
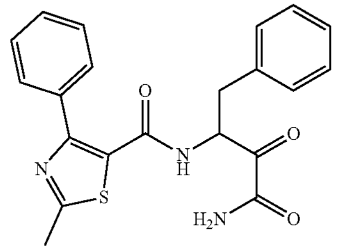 [SMILES: Cc1nc(-c2ccccc2)c(C(=O)NC(Cc2ccccc2)C(=O)C(N)=O)s1]
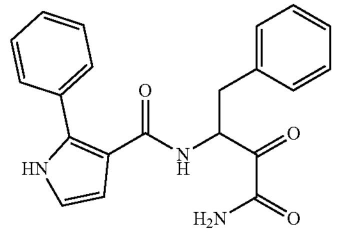 [SMILES: NC(=O)C(=O)C(Cc1ccccc1)NC(=O)c1cc[nH]c1-c1ccccc1]
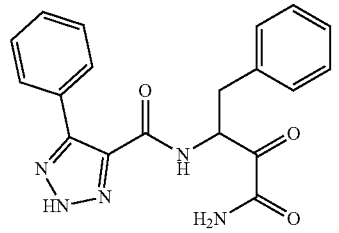
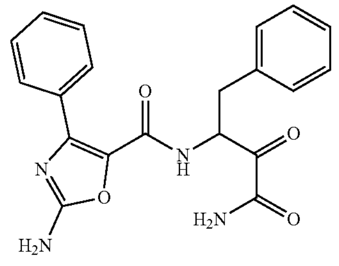 [SMILES: NC(=O)C(=O)C(Cc1ccccc1)NC(=O)c1oc(N)nc1-c1ccccc1]
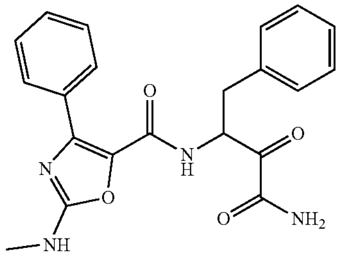 [SMILES: CNc1nc(-c2ccccc2)c(C(=O)NC(Cc2ccccc2)C(=O)C(N)=O)o1]
TABLE 1-continued
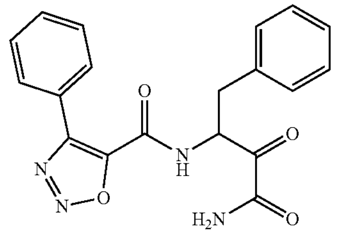 [SMILES: NC(=O)C(=O)C(Cc1ccccc1)NC(=O)c1onnc1-c1ccccc1]
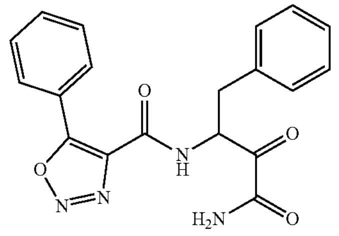 [SMILES: NC(=O)C(=O)C(Cc1ccccc1)NC(=O)c1nnoc1-c1ccccc1]
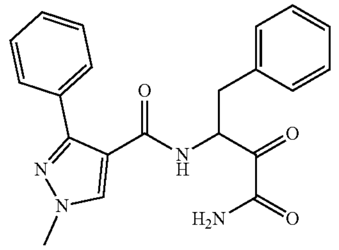 [SMILES: Cn1cc(C(=O)NC(Cc2ccccc2)C(=O)C(N)=O)c(-c2ccccc2)n1]
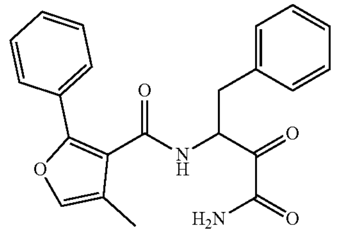 [SMILES: Cc1coc(-c2ccccc2)c1C(=O)NC(Cc1ccccc1)C(=O)C(N)=O]
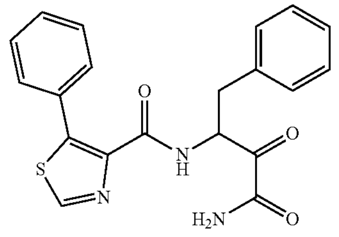 [SMILES: NC(=O)C(=O)C(Cc1ccccc1)NC(=O)c1ncsc1-c1ccccc1]
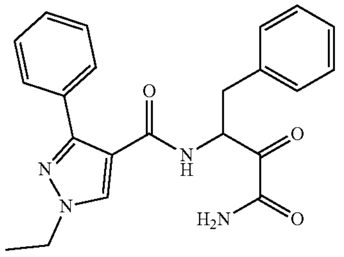 [SMILES: CCn1cc(C(=O)NC(Cc2ccccc2)C(=O)C(N)=O)c(-c2ccccc2)n1]

TABLE 1-continued
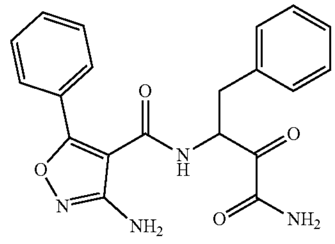 [SMILES: NC(=O)C(=O)C(Cc1ccccc1)NC(=O)c1c(N)noc1-c1ccccc1]
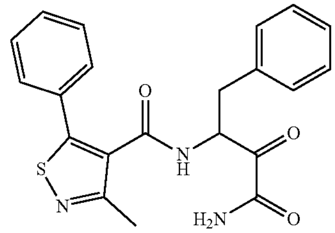 [SMILES: Cc1nsc(-c2ccccc2)c1C(=O)NC(Cc1ccccc1)C(=O)C(N)=O]
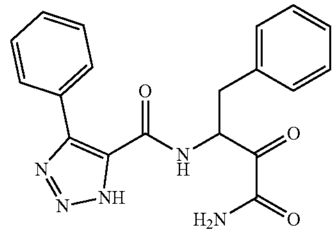
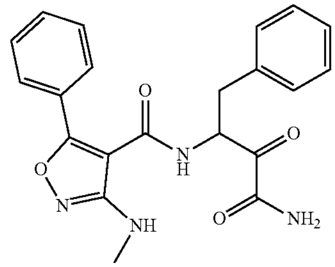 [SMILES: CNc1noc(-c2ccccc2)c1C(=O)NC(Cc1ccccc1)C(=O)C(N)=O]
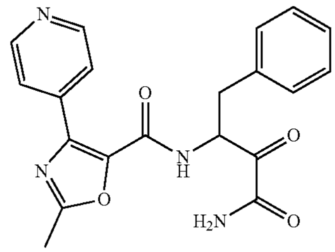 [SMILES: Cc1nc(-c2ccncc2)c(C(=O)NC(Cc2ccccc2)C(=O)C(N)=O)o1]
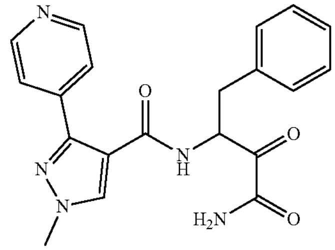 [SMILES: Cn1cc(C(=O)NC(Cc2ccccc2)C(=O)C(N)=O)c(-c2ccncc2)n1]
TABLE 1-continued
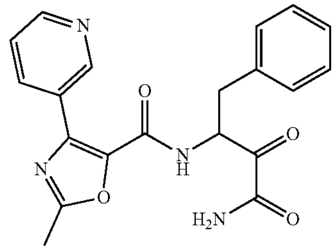 [SMILES: Cc1nc(-c2cccnc2)c(C(=O)NC(Cc2ccccc2)C(=O)C(N)=O)o1]
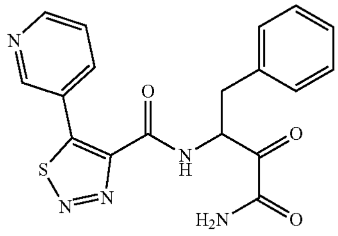 [SMILES: NC(=O)C(=O)C(Cc1ccccc1)NC(=O)c1nnsc1-c1cccnc1]
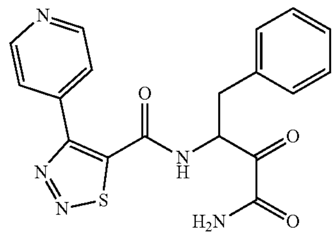 [SMILES: NC(=O)C(=O)C(Cc1ccccc1)NC(=O)c1snnc1-c1ccncc1]
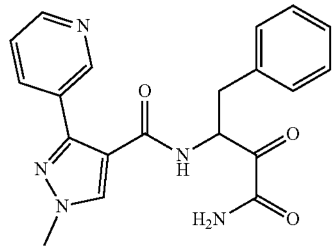 [SMILES: Cn1cc(C(=O)NC(Cc2ccccc2)C(=O)C(N)=O)c(-c2cccnc2)n1]
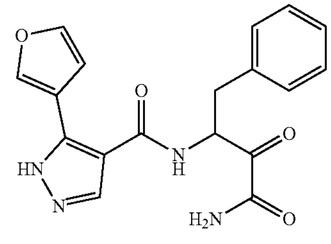 [SMILES: NC(=O)C(=O)C(Cc1ccccc1)NC(=O)c1cn[nH]c1-c1ccoc1]
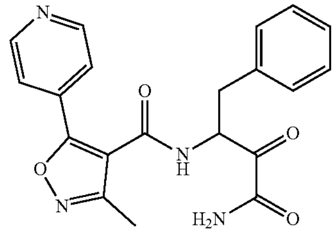 [SMILES: Cc1noc(-c2ccncc2)c1C(=O)NC(Cc1ccccc1)C(=O)C(N)=O]

TABLE 1-continued
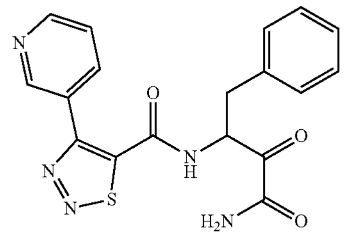 [SMILES: NC(=O)C(=O)C(Cc1ccccc1)NC(=O)c1snnc1-c1cccnc1]
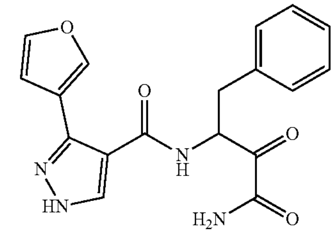 [SMILES: NC(=O)C(=O)C(Cc1ccccc1)NC(=O)c1c[nH]nc1-c1ccoc1]
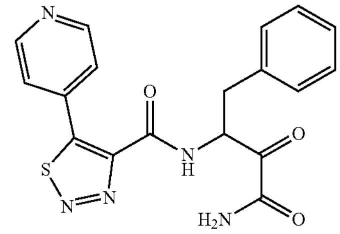 [SMILES: NC(=O)C(=O)C(Cc1ccccc1)NC(=O)c1nnsc1-c1ccncc1]
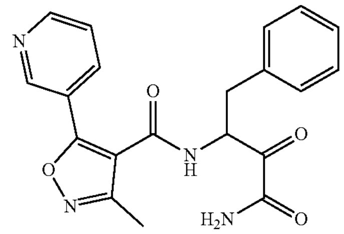 [SMILES: Cc1noc(-c2cccnc2)c1C(=O)NC(Cc1ccccc1)C(=O)C(N)=O]
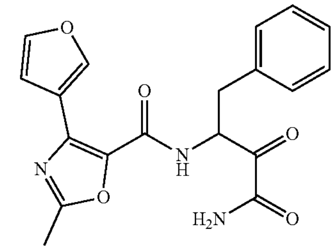 [SMILES: Cc1nc(-c2ccoc2)c(C(=O)NC(Cc2ccccc2)C(=O)C(N)=O)o1]
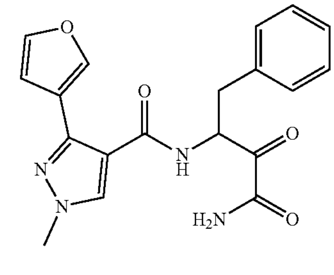
TABLE 1-continued
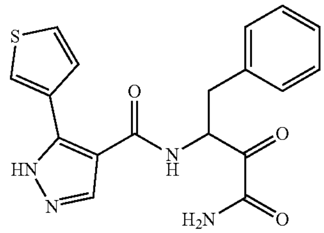 [SMILES: NC(=O)C(=O)C(Cc1ccccc1)NC(=O)c1cn[nH]c1-c1ccsc1]
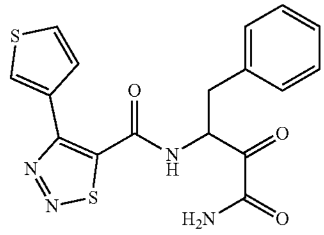 [SMILES: NC(=O)C(=O)C(Cc1ccccc1)NC(=O)c1snnc1-c1ccsc1]
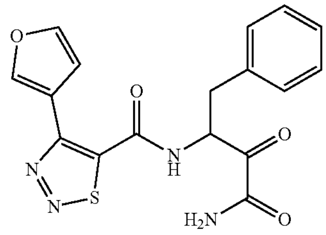 [SMILES: NC(=O)C(=O)C(Cc1ccccc1)NC(=O)c1snnc1-c1ccoc1]
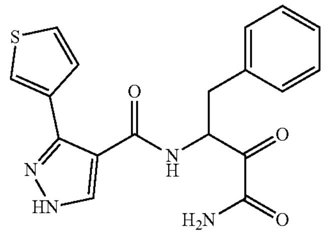 [SMILES: NC(=O)C(=O)C(Cc1ccccc1)NC(=O)c1c[nH]nc1-c1ccsc1]
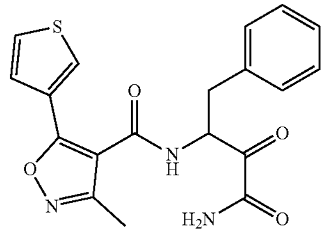 [SMILES: Cc1noc(-c2ccsc2)c1C(=O)NC(Cc1ccccc1)C(=O)C(N)=O]
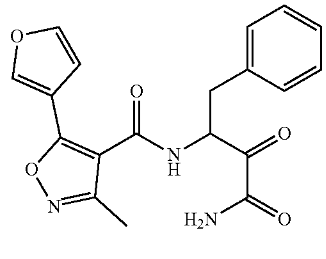 [SMILES: Cc1noc(-c2ccoc2)c1C(=O)NC(Cc1ccccc1)C(=O)C(N)=O]

TABLE 1-continued
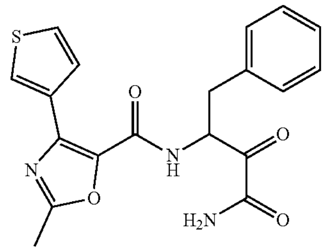 [SMILES: Cc1nc(-c2ccsc2)c(C(=O)NC(Cc2ccccc2)C(=O)C(N)=O)o1]
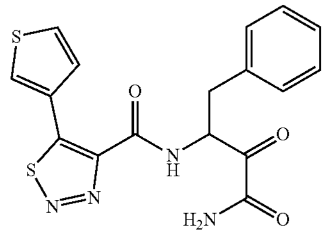
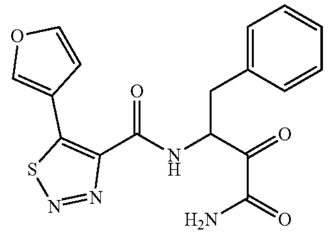 [SMILES: NC(=O)C(=O)C(Cc1ccccc1)NC(=O)c1nnsc1-c1ccoc1]
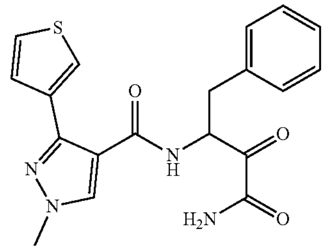 [SMILES: Cn1cc(C(=O)NC(Cc2ccccc2)C(=O)C(N)=O)c(-c2ccsc2)n1]
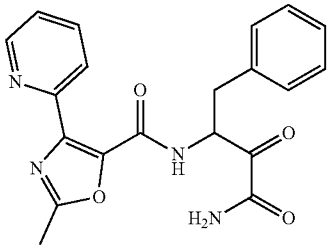 [SMILES: Cc1nc(-c2ccccn2)c(C(=O)NC(Cc2ccccc2)C(=O)C(N)=O)o1]
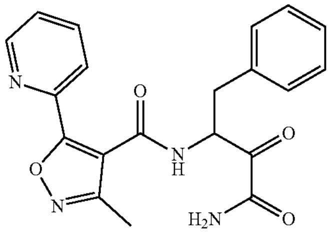 [SMILES: Cc1noc(-c2ccccn2)c1C(=O)NC(Cc1ccccc1)C(=O)C(N)=O]
TABLE 1-continued
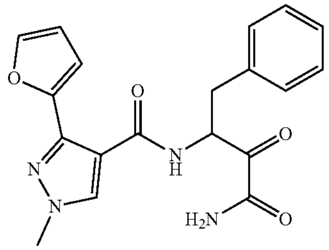 [SMILES: Cn1cc(C(=O)NC(Cc2ccccc2)C(=O)C(N)=O)c(-c2ccco2)n1]
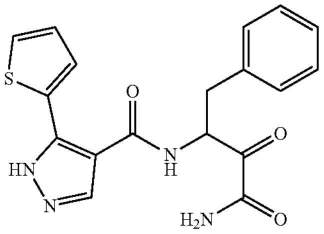
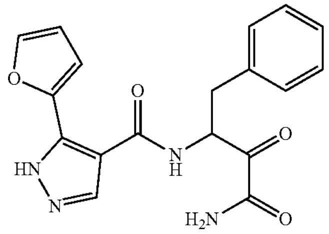 [SMILES: NC(=O)C(=O)C(Cc1ccccc1)NC(=O)c1cn[nH]c1-c1ccco1]
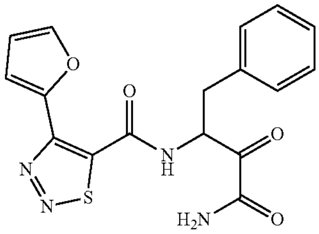 [SMILES: NC(=O)C(=O)C(Cc1ccccc1)NC(=O)c1snnc1-c1ccco1]
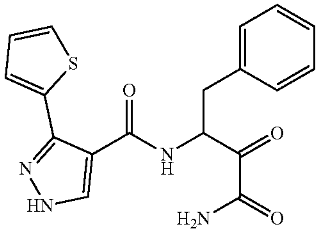
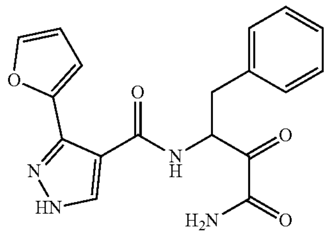 [SMILES: NC(=O)C(=O)C(Cc1ccccc1)NC(=O)c1c[nH]nc1-c1ccco1]

TABLE 1-continued
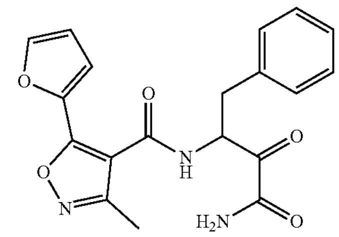 [SMILES: Cc1noc(-c2ccco2)c1C(=O)NC(Cc1ccccc1)C(=O)C(N)=O]
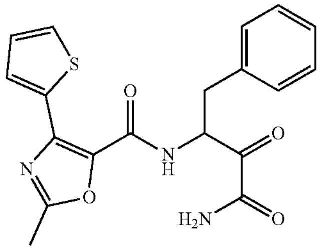 [SMILES: Cc1nc(-c2cccs2)c(C(=O)NC(Cc2ccccc2)C(=O)C(N)=O)o1]
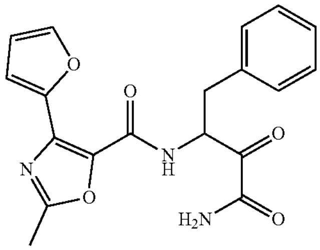 [SMILES: Cc1nc(-c2ccco2)c(C(=O)NC(Cc2ccccc2)C(=O)C(N)=O)o1]
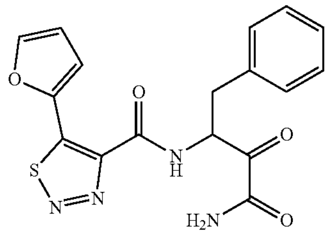 [SMILES: NC(=O)C(=O)C(Cc1ccccc1)NC(=O)c1nnsc1-c1ccco1]
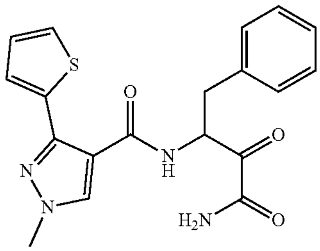 [SMILES: Cn1cc(C(=O)NC(Cc2ccccc2)C(=O)C(N)=O)c(-c2cccs2)n1]
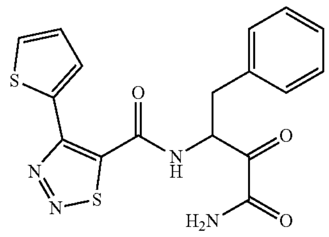 [SMILES: NC(=O)C(=O)C(Cc1ccccc1)NC(=O)c1snnc1-c1cccs1]
TABLE 1-continued
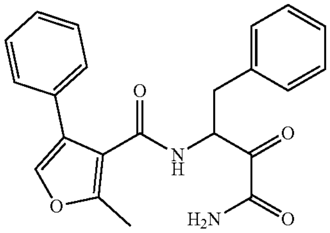 [SMILES: Cc1occ(-c2ccccc2)c1C(=O)NC(Cc1ccccc1)C(=O)C(N)=O]
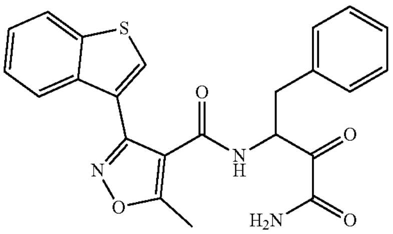 [SMILES: Cc1onc(-c2csc3ccccc23)c1C(=O)NC(Cc1ccccc1)C(=O)C(N)=O]
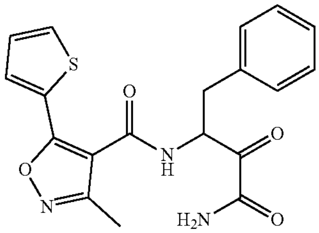
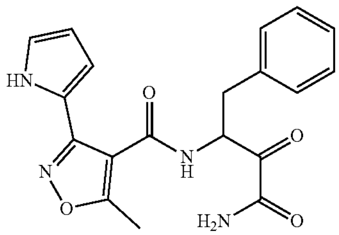 [SMILES: Cc1onc(-c2ccc[nH]2)c1C(=O)NC(Cc1ccccc1)C(=O)C(N)=O]
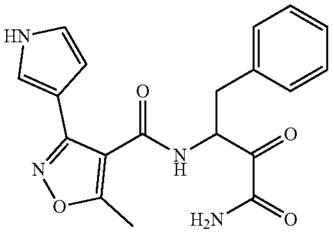 [SMILES: Cc1onc(-c2cc[nH]c2)c1C(=O)NC(Cc1ccccc1)C(=O)C(N)=O]
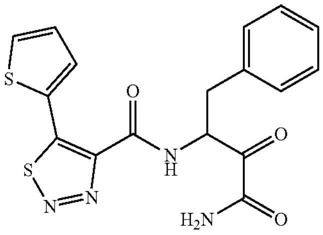 [SMILES: NC(=O)C(=O)C(Cc1ccccc1)NC(=O)c1nnsc1-c1cccs1]

TABLE 1-continued
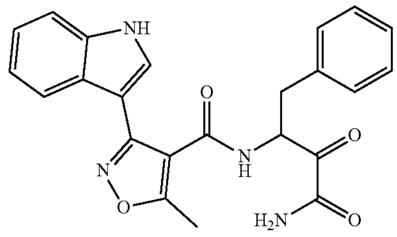 [SMILES: Cc1onc(-c2c[nH]c3ccccc23)c1C(=O)NC(Cc1ccccc1)C(=O)C(N)=O]
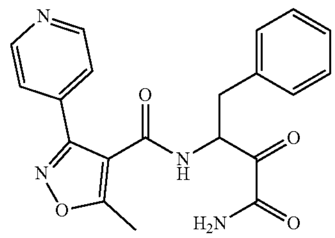 [SMILES: Cc1onc(-c2ccncc2)c1C(=O)NC(Cc1ccccc1)C(=O)C(N)=O]
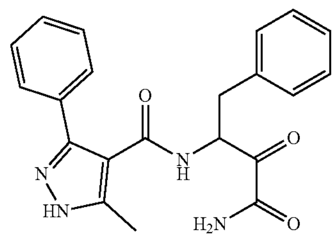 [SMILES: Cc1[nH]nc(-c2ccccc2)c1C(=O)NC(Cc1ccccc1)C(=O)C(N)=O]
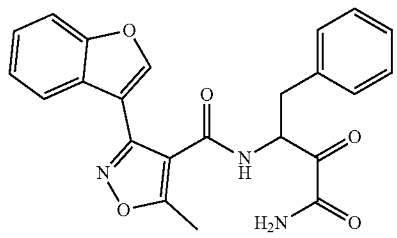 [SMILES: Cc1onc(-c2coc3ccccc23)c1C(=O)NC(Cc1ccccc1)C(=O)C(N)=O]
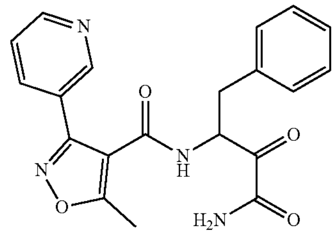 [SMILES: Cc1onc(-c2cccnc2)c1C(=O)NC(Cc1ccccc1)C(=O)C(N)=O]
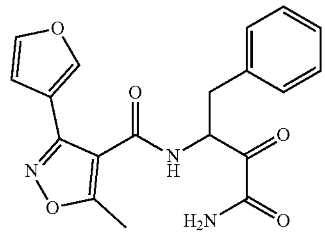 [SMILES: Cc1onc(-c2ccoc2)c1C(=O)NC(Cc1ccccc1)C(=O)C(N)=O]
TABLE 1-continued
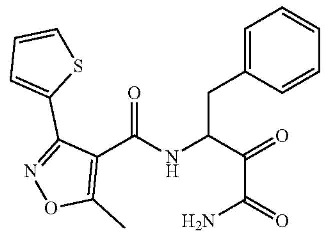
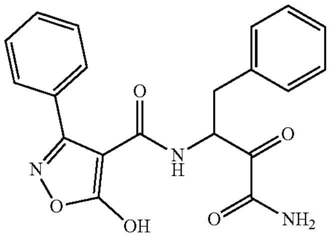 [SMILES: NC(=O)C(=O)C(Cc1ccccc1)NC(=O)c1c(-c2ccccc2)noc1O]
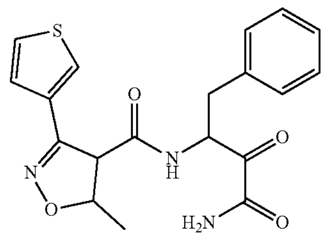 [SMILES: CC1ON=C(c2ccsc2)C1C(=O)NC(Cc1ccccc1)C(=O)C(N)=O]
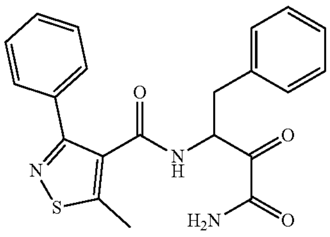 [SMILES: Cc1snc(-c2ccccc2)c1C(=O)NC(Cc1ccccc1)C(=O)C(N)=O]
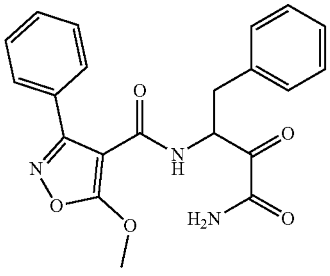 [SMILES: COc1onc(-c2ccccc2)c1C(=O)NC(Cc1ccccc1)C(=O)C(N)=O]
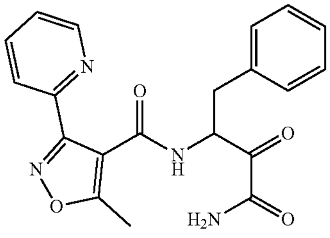 [SMILES: Cc1onc(-c2ccccn2)c1C(=O)NC(Cc1ccccc1)C(=O)C(N)=O]

TABLE 1-continued
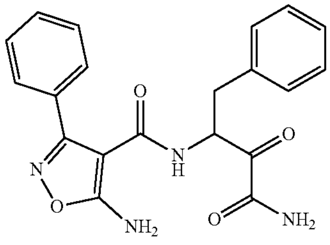 [SMILES: NC(=O)C(=O)C(Cc1ccccc1)NC(=O)c1c(-c2ccccc2)noc1N]
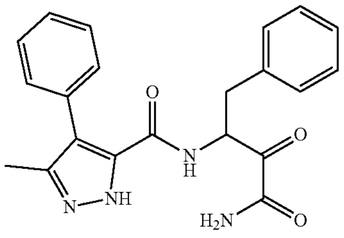 [SMILES: Cc1n[nH]c(C(=O)NC(Cc2ccccc2)C(=O)C(N)=O)c1-c1ccccc1]
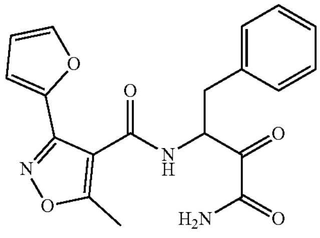 [SMILES: Cc1onc(-c2ccco2)c1C(=O)NC(Cc1ccccc1)C(=O)C(N)=O]
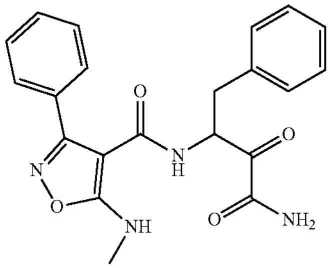 [SMILES: CNc1onc(-c2ccccc2)c1C(=O)NC(Cc1ccccc1)C(=O)C(N)=O]
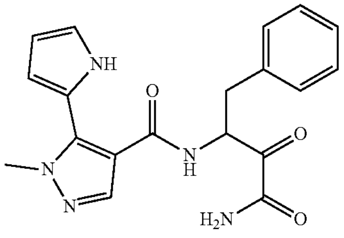 [SMILES: Cn1ncc(C(=O)NC(Cc2ccccc2)C(=O)C(N)=O)c1-c1ccc[nH]1]
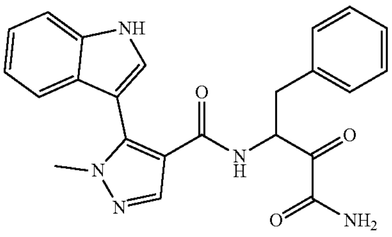 [SMILES: Cn1ncc(C(=O)NC(Cc2ccccc2)C(=O)C(N)=O)c1-c1c[nH]c2ccccc12]
TABLE 1-continued
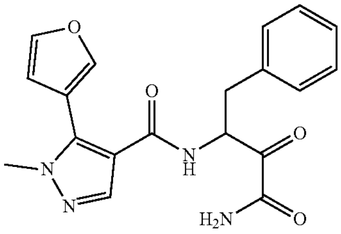 [SMILES: Cn1ncc(C(=O)NC(Cc2ccccc2)C(=O)C(N)=O)c1-c1ccoc1]
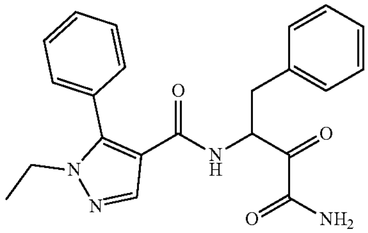 [SMILES: CCn1ncc(C(=O)NC(Cc2ccccc2)C(=O)C(N)=O)c1-c1ccccc1]
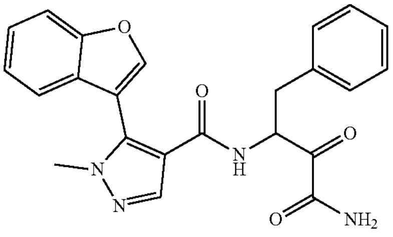 [SMILES: Cn1ncc(C(=O)NC(Cc2ccccc2)C(=O)C(N)=O)c1-c1coc2ccccc12]
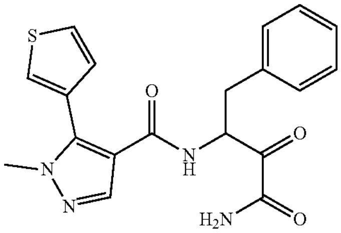 [SMILES: Cn1ncc(C(=O)NC(Cc2ccccc2)C(=O)C(N)=O)c1-c1ccsc1]
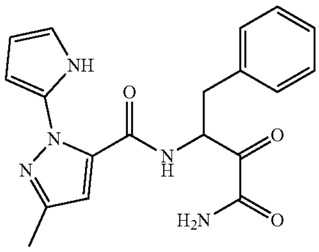 [SMILES: Cc1cc(C(=O)NC(Cc2ccccc2)C(=O)C(N)=O)n(-c2ccc[nH]2)n1]
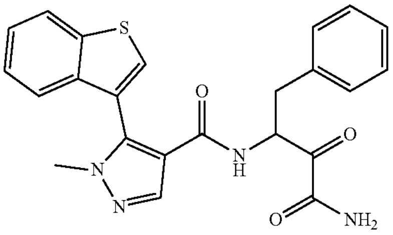 [SMILES: Cn1ncc(C(=O)NC(Cc2ccccc2)C(=O)C(N)=O)c1-c1csc2ccccc12]

TABLE 1-continued
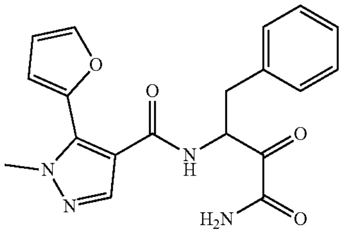 [SMILES: Cn1ncc(C(=O)NC(Cc2ccccc2)C(=O)C(N)=O)c1-c1ccco1]
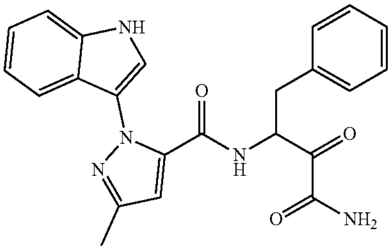 [SMILES: Cc1cc(C(=O)NC(Cc2ccccc2)C(=O)C(N)=O)n(-c2c[nH]c3ccccc23)n1]
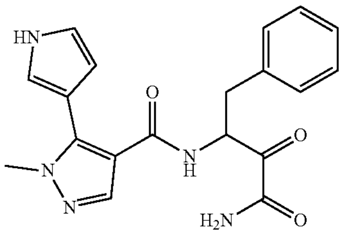 [SMILES: Cn1ncc(C(=O)NC(Cc2ccccc2)C(=O)C(N)=O)c1-c1cc[nH]c1]
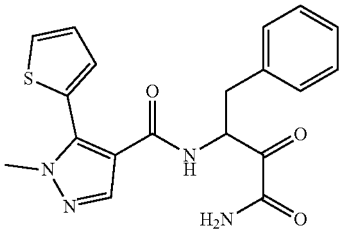 [SMILES: Cn1ncc(C(=O)NC(Cc2ccccc2)C(=O)C(N)=O)c1-c1cccs1]
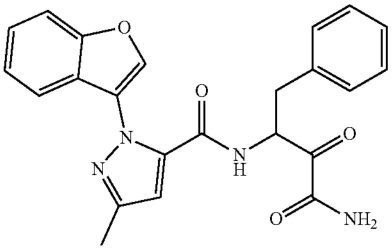 [SMILES: Cc1cc(C(=O)NC(Cc2ccccc2)C(=O)C(N)=O)n(-c2coc3ccccc23)n1]
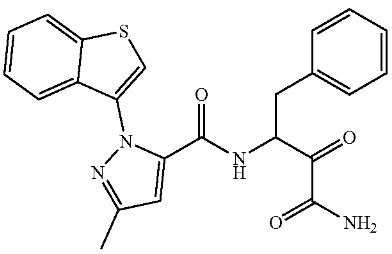 [SMILES: Cc1cc(C(=O)NC(Cc2ccccc2)C(=O)C(N)=O)n(-c2csc3ccccc23)n1]
TABLE 1-continued
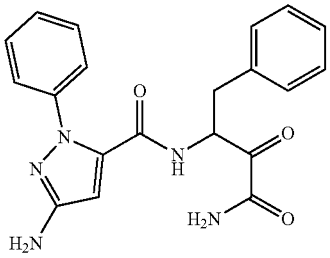 [SMILES: NC(=O)C(=O)C(Cc1ccccc1)NC(=O)c1cc(N)nn1-c1ccccc1]
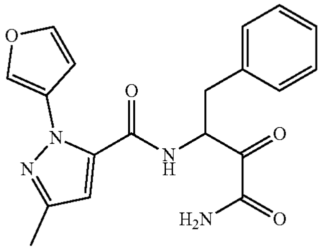 [SMILES: Cc1cc(C(=O)NC(Cc2ccccc2)C(=O)C(N)=O)n(-c2ccoc2)n1]
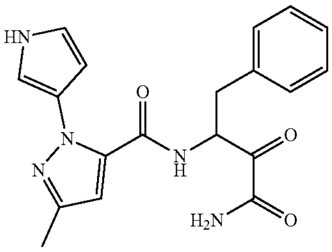 [SMILES: Cc1cc(C(=O)NC(Cc2ccccc2)C(=O)C(N)=O)n(-c2cc[nH]c2)n1]
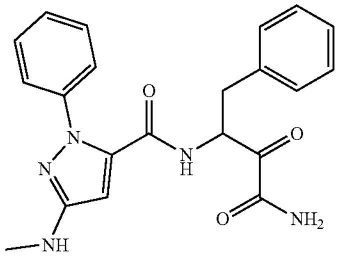 [SMILES: CNc1cc(C(=O)NC(Cc2ccccc2)C(=O)C(N)=O)n(-c2ccccc2)n1]
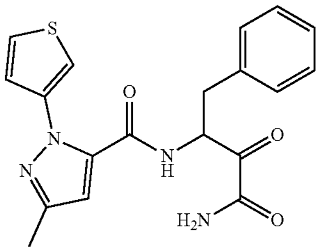 [SMILES: Cc1cc(C(=O)NC(Cc2ccccc2)C(=O)C(N)=O)n(-c2ccsc2)n1]
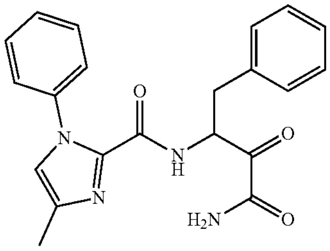 [SMILES: Cc1cn(-c2ccccc2)c(C(=O)NC(Cc2ccccc2)C(=O)C(N)=O)n1]

TABLE 1-continued

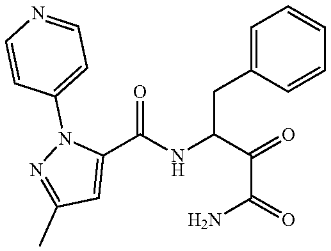 [SMILES: Cc1cc(C(=O)NC(Cc2ccccc2)C(=O)C(N)=O)n(-c2ccncc2)n1]

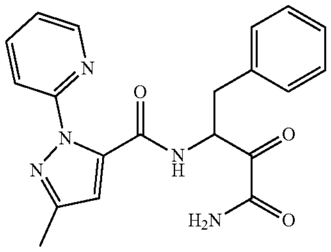 [SMILES: Cc1cc(C(=O)NC(Cc2ccccc2)C(=O)C(N)=O)n(-c2ccccn2)n1]

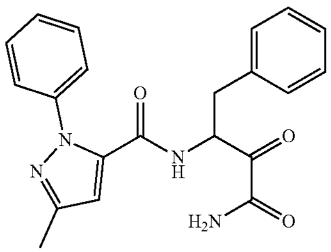 [SMILES: Cc1cc(C(=O)NC(Cc2ccccc2)C(=O)C(N)=O)n(-c2ccccc2)n1]

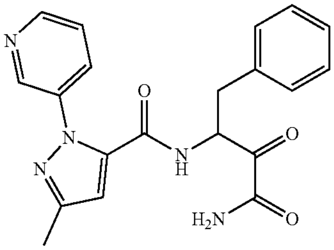 [SMILES: Cc1cc(C(=O)NC(Cc2ccccc2)C(=O)C(N)=O)n(-c2cccnc2)n1]

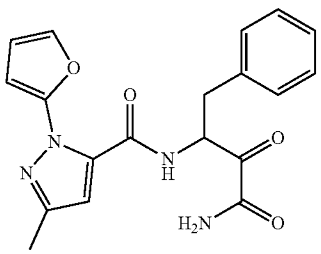 [SMILES: Cc1cc(C(=O)NC(Cc2ccccc2)C(=O)C(N)=O)n(-c2ccco2)n1]

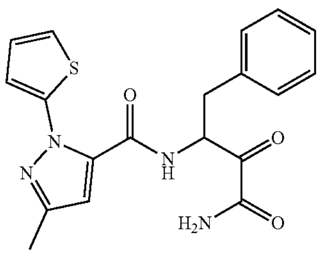 [SMILES: Cc1cc(C(=O)NC(Cc2ccccc2)C(=O)C(N)=O)n(-c2cccs2)n1]

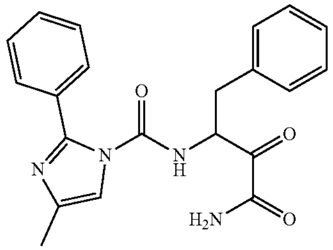 [SMILES: Cc1cn(C(=O)NC(Cc2ccccc2)C(=O)C(N)=O)c(-c2ccccc2)n1]

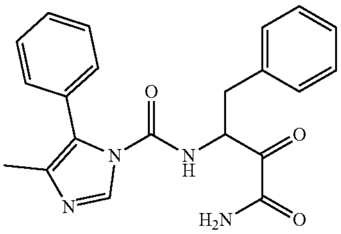 [SMILES: Cc1ncn(C(=O)NC(Cc2ccccc2)C(=O)C(N)=O)c1-c1ccccc1]

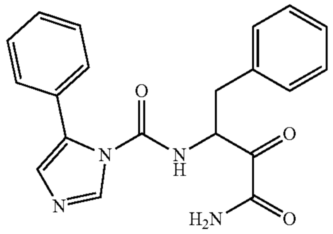 [SMILES: NC(=O)C(=O)C(Cc1ccccc1)NC(=O)n1cncc1-c1ccccc1]

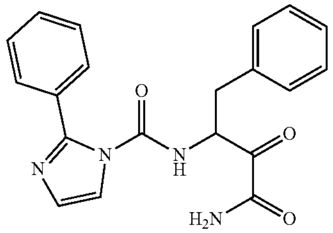 [SMILES: NC(=O)C(=O)C(Cc1ccccc1)NC(=O)n1ccnc1-c1ccccc1]

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopically-Labeled Compounds

Isotopes may be present in the compounds described. Each chemical element as represented in a compound structure may include any isotope of said element. The isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise. Isotopically-labeled compounds of the present embodiments are useful in drug and substrate tissue distribution and target occupancy assays. For example, isotopically labeled compounds are particularly useful in SPECT (single photon emission computed tomography) and in PET (positron emission tomography), as discussed further herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "Cab" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3H_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "haloalkyl" refers to a straight- or branched-chain alkyl group having from 1 to 12 carbon atoms in the chain, substituting one or more hydrogens with halogens. Examples of haloalkyl groups include, but are not limited to, $—CF_3$, $—CHF_2$, $—CH_2F$, $—CH_2CF_3$, $—CH_2CHF_2$, $—CH_2CH_2F$, $—CH_2CH_2Cl$, $—CH_2CF_2CF_3$ and other groups that in light of the ordinary skill in the art and the teachings provided herein, would be considered equivalent to any one of the foregoing examples.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "polyethylene glycol" refers to the formula

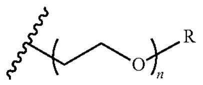

wherein n is an integer greater than one and R is a hydrogen or alkyl. The number of repeat units "n" may be indicated by referring to a number of members. Thus, for example, "2- to 5-membered polyethylene glycol" refers to n being an integer selected from two to five. In some embodiments, R is selected from methoxy, ethoxy, n-propoxy, 1-methylethoxy (isopropoxy), n-butoxy, iso-butoxy, sec-butoxy, and tert-butoxy.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. In various embodiments, the heteroalkyl may have from 1 to 4 heteroatoms, from 1 to 3 heteroatoms, 1 or 2 heteroatoms, or 1 heteroatom. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. In various embodiments, a heteroaryl contains from 1 to 4 heteroatoms, from 1 to 3 heteroatoms, from 1 to 2 heteroatoms, or 1 heteroatom. For example, in various embodiments, a heteroaryl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations.

In various embodiments, a heterocyclyl contains from 1 to 4 heteroatoms, from 1 to 3 heteroatoms, from 1 to 2 heteroatoms, or 1 heteroatom. For example, in various embodiments, a heterocyclyl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—$OC(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)OC(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—$OC(=S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—$N(R_A)OC(=S)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—$C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—$N(R_A)C({=}O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a "natural amino acid side chain" refers to the side-chain substituent of a naturally occurring amino acid. Naturally occurring amino acids have a substituent attached to the α-carbon. Naturally occurring amino acids include Arginine, Lysine, Aspartic acid, Glutamic acid, Glutamine, Asparagine, Histidine, Serine, Threonine, Tyrosine, Cysteine, Methionine, Tryptophan, Alanine, Isoleucine, Leucine, Phenylalanine, Valine, Proline, and Glycine.

As used herein, a "non-natural amino acid side chain" refers to the side-chain substituent of a non-naturally occurring amino acid. Non-natural amino acids include 3-amino acids ($\beta^3$ and $\beta^2$), Homo-amino acids, Proline and Pyruvic acid derivatives, 3-substituted Alanine derivatives, Glycine derivatives, Ring-substituted Phenylalanine and Tyrosine Derivatives, Linear core amino acids and N-methyl amino acids. Exemplary non-natural amino acids are available from Sigma-Aldridge, listed under "unnatural amino acids & derivatives." See also, Travis S. Young and Peter G. Schultz, "Beyond the Canonical 20 Amino Acids: Expanding the Genetic Lexicon," J. Biol. Chem. 2010 285:11039-11044, which is incorporated by reference in its entirety.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

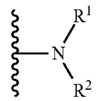

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

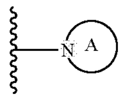

where ring A is a heterocyclyl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

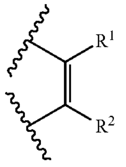

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

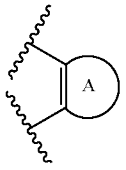

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

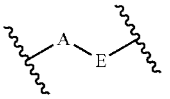

includes the substituent being oriented such that the A is attached at the leftmost attachment point of the molecule as well as the case in which A is attached at the rightmost attachment point of the molecule.

As used herein, the substructure:

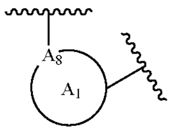

means that the A atom can be in any ring atom position within the ring or ring system $A_1$. The substructure:

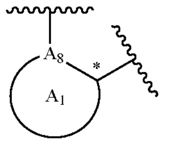

means that the $A_8$ atom is in the ring atom position immediately adjacent (i.e., alpha) to the point of attachment indicated by *.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include $-SO_3H$, $-SO_2HNR$, $-PO_2(R)_2$, $-PO_3(R)_2$, $-CONHNHSO_2R$, $-COHNSO_2R$, and $-CONRCN$, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

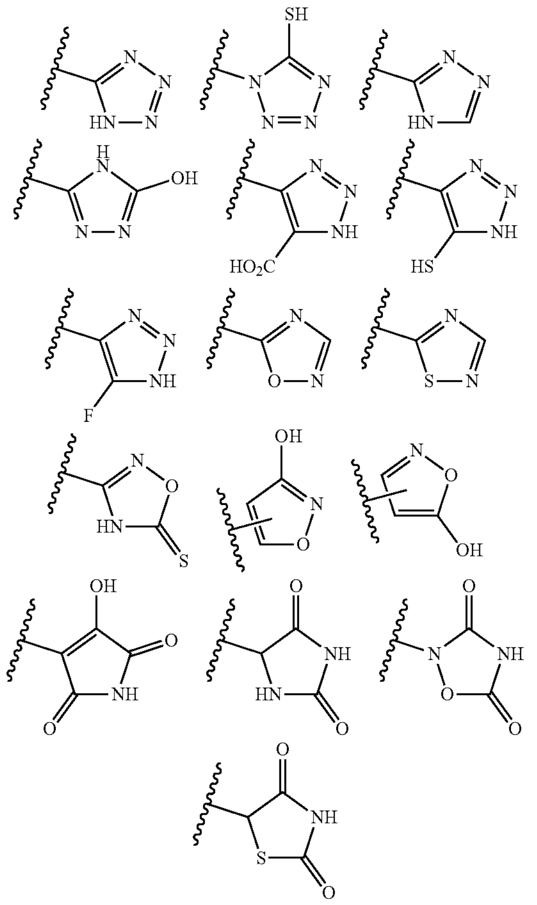

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms “agent”, “substance”, and “compound” are used interchangeably herein.

The term “analog” is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term “mammal” is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term “microbial infection” refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is “suffering” from a microbial infection when excessive numbers of a microbial population are present in or on a mammal’s body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term “pharmaceutically acceptable carrier” or “pharmaceutically acceptable excipient” includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman’s: The Pharmacological Basis of Therapeutics, 8th Ed., Pergamon Press, which is incorporated herein by reference in its entirety.

“Subject” as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An “effective amount” or a “therapeutically effective amount” as used herein refers to an amount of a therapeutic agent that is effective to relieve, to some extent, or to reduce the likelihood of onset of, one or more of the symptoms of a disease or condition, and includes curing a disease or condition. “Curing” means that the symptoms of a disease or condition are eliminated; however, certain long-term or permanent effects may exist even after a cure is obtained (such as extensive tissue damage).

“Treat,” “treatment,” or “treating,” as used herein refers to administering a pharmaceutical composition for prophylactic and/or therapeutic purposes. The term “prophylactic treatment” refers to treating a subject who does not yet exhibit symptoms of a disease or condition, but who is susceptible to, or otherwise at risk of, a particular disease or condition, whereby the treatment reduces the likelihood that the patient will develop the disease or condition. The term “therapeutic treatment” refers to administering treatment to a Methods of Preparation The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)).

If the compounds of the present technology contain one or more chiral centers, such compounds can be prepared or isolated as pure stereoisomers, i.e., as individual enantiomers or d(1) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, -continued

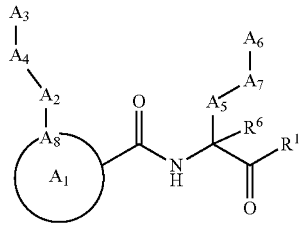

I described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Synthesis of Compounds of Formula I

In one embodiment, the method involves reacting an appropriately substituted intermediate with an acidic hydrogen (IV) with an ester (V) under base catalyzed conditions to yield the ester derivative (VI). The resulting product was then subjected to hydrolysis under basic conditions to yield the carboxylic acid derivative (VII) which was then subjected to amide-coupling conditions with an amino acid derivative (VIII) wherein the carboxylic acid group is functionalized with the $R^1$ group (Scheme 1). Alternatively, the carboxylic acid product (VII) is then subjected to amide coupling conditions with the amino alcohol derivative (VIII-a) to yield the corresponding adduct (IX). The resulting adduct (IX) is subjected to oxidation conditions with DMP oxidation (with hypervalent iodine) or by an oxidizing agent such as PCC (pyridinium chlorochromate) to yield the α-ketoamide product (X). Alternately, the adduct (IX) was subjected to oxidation conditions using EDC and dichloroacetic acid or using IBX as the oxidizing agent to yield the α-ketoamide product (X). The skilled artisan will once again appreciate that there are many other oxidizing conditions and agents which are within the scope of this disclosure to oxidize the hydroxyl group. This synthesis route is generally shown in Scheme 2.

Scheme 1

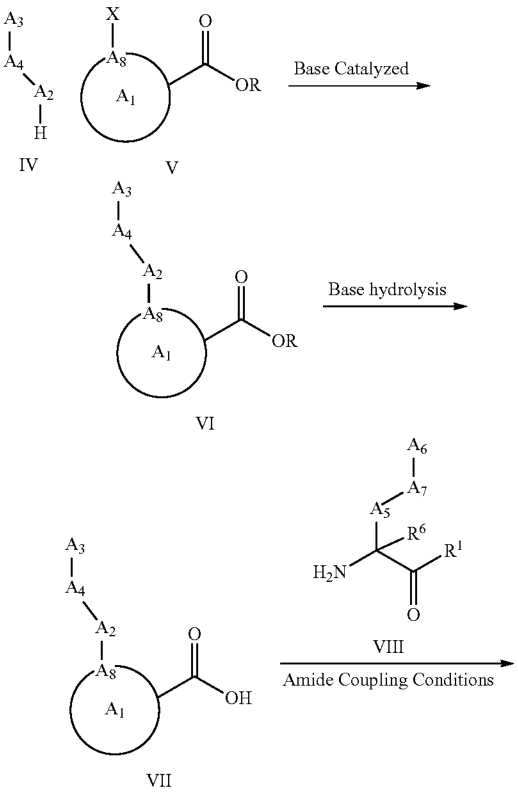

Scheme 2

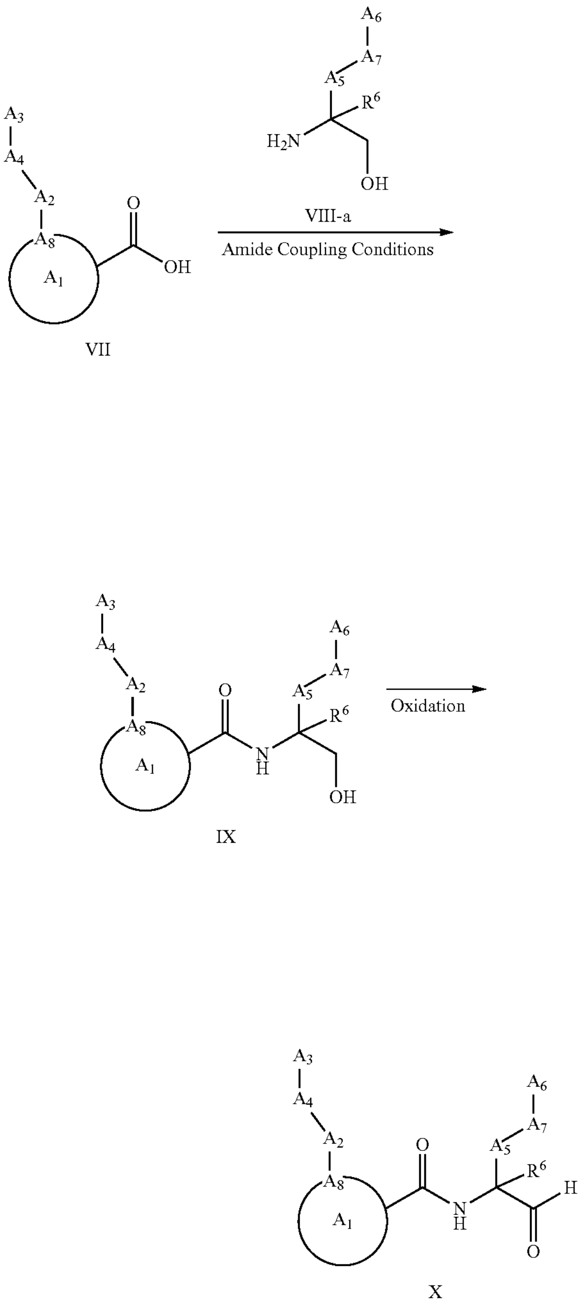

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Uses of Isotopically-Labeled Compounds

Some embodiments provide a method of using isotopically labeled compounds and prodrugs of the present disclosure in: (i) metabolic studies (preferably with $^{14}C$), reaction kinetic studies (with, for example 2H or 3H); (ii) detection or imaging techniques [such as positron emission tomography (PET) or single-photon emission computed tomography (SPECT)] including drug or substrate tissue distribution assays; or (III) in radioactive treatment of patients.

Isotopically labeled compounds and prodrugs of the embodiments thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $^{123}I$ labeled compound may be particularly preferred for SPECT studies. Further substitution with heavier isotopes such as deuterium (i.e., $^{2}H$) may afford certain therapeutic advantages resulting from greater metabolic stability, for example increased in vivo half-life or reduced dosage requirements.

Synthesis of Isotopically Labeled Compounds $^{18}F$ labeled compounds are synthesized as shown in the schemes below. In one embodiment, the method involves reacting the intermediate 450 with a $^{18}F$-labeling agent using conditions as described in Rotstein, et al., Spirocyclic hypervalent iodine(III)-mediated radiofluorination of non-activated and hindered aromatics, *Nature Communications,* 2014, Vol. 5, 4365-4371 and Rotstein, et al., Mechanistic Studies and Radiofluorination of Structurally Diverse Pharmaceuticals with Spirocyclic Iodonium(III) Ylides, *Chemical Science,* 2016, Vol. 7, 4407-4417, both of which are incorporated herein by reference in their entirety, to yield the $^{18}F$-labeled intermediate methyl 2-((ethoxycarbonyl)amino)-3-(4-(fluoro-$^{18}F$)phenyl)propanoate (631) which is then transformed into the final α-ketoamide product represented by the general structure XI (Scheme 3).

Scheme 3

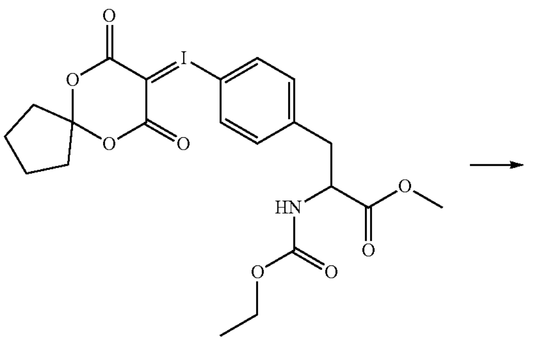

450

-continued

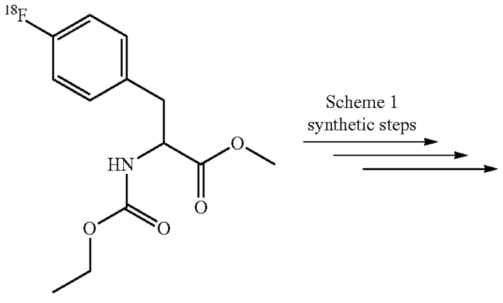

631

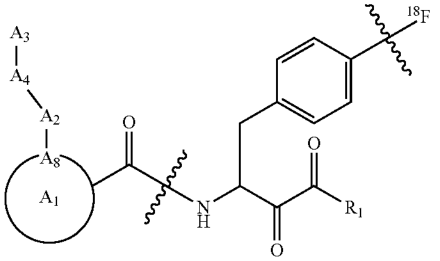

XI

Alternately, $^{18}F$-labeled compound XV is synthesized as shown in Scheme 4. In one embodiment, iodanylidene intermediate XII is used to introduce the $^{18}F$ label yielding using conditions as described in Rotstein, et al., Spirocyclic hypervalent iodine(III)-mediated radiofluorination of non-activated and hindered aromatics, *Nature Communications,* 2014, Vol. 5, 4365-4371 and Rotstein, et al., Mechanistic Studies and Radiofluorination of Structurally Diverse Pharmaceuticals with Spirocyclic Iodonium(III) Ylides, *Chemical Science,* 2016, Vol. 7, 4407-4417 to yield the labeled α-ketoamide product XV. In another embodiment, iodanylidene intermediate (XIV) is (Scheme 4) subjected to oxidation conditions with DMP oxidation (with hypervalent iodine) or by an oxidizing agent such as PCC (pyridinium chlorochromate) to yield the α-ketoamide product (XV). In yet another embodiment, iodanylidene intermediate (XIII) (Scheme 4) is subjected to $^{18}F$-labeling reaction conditions as described earlier followed by hydrolysis of the ester under basic conditions to yield the carboxylic acid derivative which is then subjected to amide-coupling conditions with an amino acid derivative wherein the carboxylic acid group is functionalized with the R group to yield the labeled α-ketoamide product XV.

Scheme 4

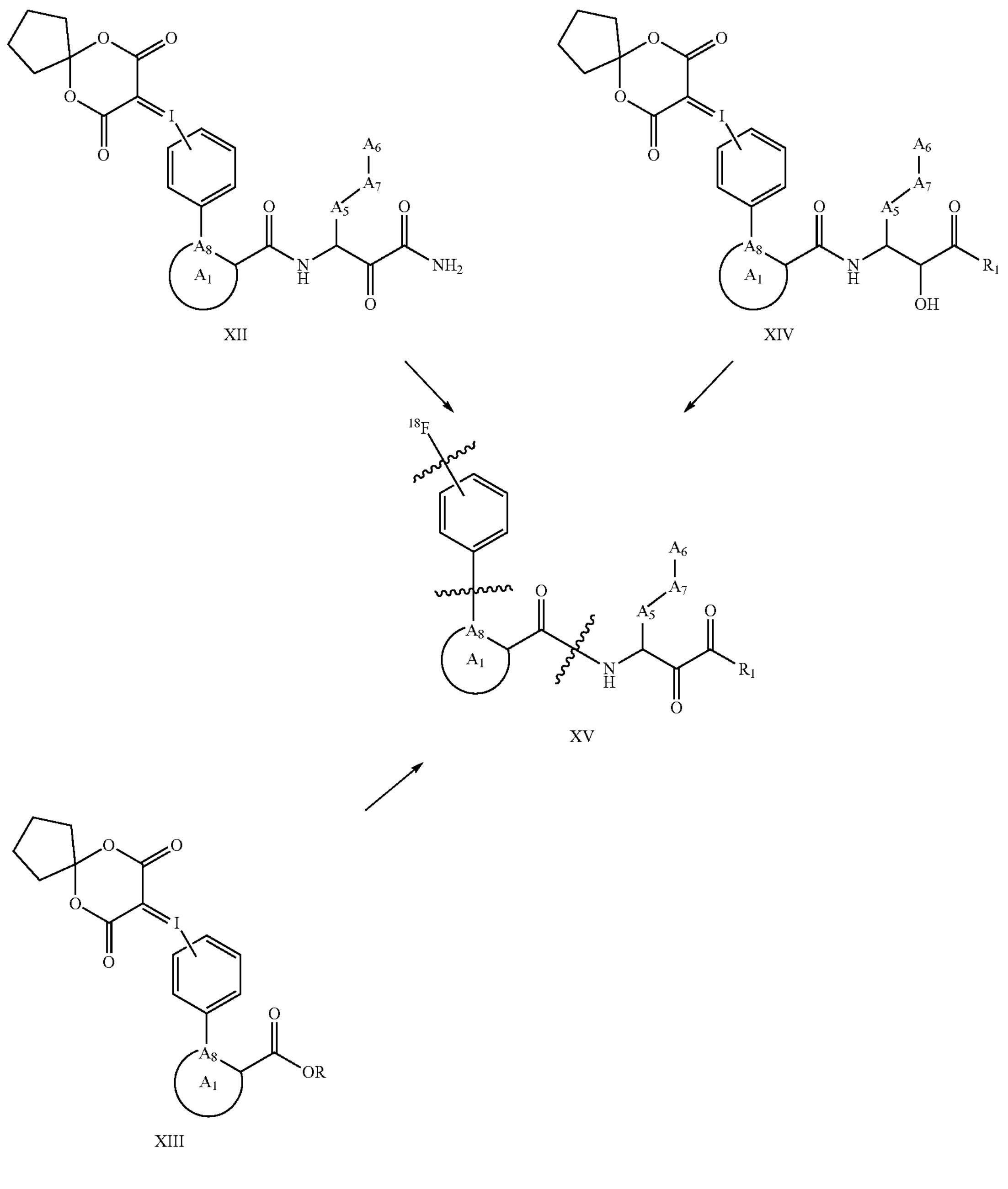

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonary, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

The compounds and compositions described herein, if desired, may be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compounds and compositions described herein are formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01 99.99 wt % of a compound of the present technology based on the total formulation, with the balance being one or more suitable pharmaceutical excipients. Preferably, the compound is present at a level of about 180 wt %. Representative pharmaceutical formulations are described below.

FORMULATION EXAMPLES

The following are representative pharmaceutical formulations containing a compound of Formula I.

Formulation Example 1—Tablet Formulation

The following ingredients are mixed intimately and pressed into single scored tablets.

| Ingredient | Quantity per tablet, mg |
|---|---|
| Compounds disclosed herein | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
|---|---|
| Compounds disclosed herein | 200 |
| lactose, spray-dried | 148 |
| magnesium stearate | 2 |

Formulation Example 3—Suspension Formulation

The following ingredients are mixed to form a suspension for oral administration.

| Ingredient | Amount |
|---|---|
| Compounds disclosed herein | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
|---|---|
| Compounds disclosed herein | 0.2 mg-20 mg |
| sodium acetate buffer solution, 0.4 M | 2.0 mL |
| HC1 (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
|---|---|
| Compounds disclosed herein | 500 mg |
| Witepsol ® H-15 | balance |

Methods of Treatment

The compounds disclosed herein or their tautomers and/or pharmaceutically acceptable salts thereof can effectively act as CAPN1, CAPN2, and/or CAPN9 inhibitors and treat conditions affected at least in part by CAPN1, CAPN2, and/or CAPN9. Some embodiments provide pharmaceutical compositions comprising one or more compounds disclosed herein and a pharmaceutically acceptable excipient. Some embodiments provide a method for treating a fibrotic disease with an effective amount of one or more compounds as disclosed herein.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Some embodiments include combinations of a compound, composition or pharmaceutical composition described herein with any other pharmaceutical compound approved for treating fibrotic or myofibroblast differentiation associated diseases or disorders.

Some embodiments provide a method for inhibiting CAPN1, CAPN2, and/or CAPN9 and/or a method for treating a disease affected at least in part by CAPN1, CAPN2, and/or CAPN9 with an effective amount of one or more compounds as disclosed herein.

The compounds disclosed herein are useful in inhibiting CAPN1, CAPN2, and/or CAPN9 enzymes and/or treating disorders relating to fibrosis or myofibroblast differentiation.

Some embodiments provide a method for inhibiting CAPN1, CAPN2, and/or CAPN9 which method comprises contacting cells (including neurons/microglia/invading macrophages) with an effective amount of one or more compounds as disclosed herein.

Some embodiments provide a method for treating a fibrotic disease, which method comprises administering to a subject an effective amount of one or more compounds or a pharmaceutical composition disclosed herein comprising a pharmaceutically acceptable excipient.

Some embodiments provide a method for treating a disease affected at least in part by CAPN1, CAPN2, and/or CAPN9, which method comprises administering to a subject an effective amount of one or more compounds or a pharmaceutical composition disclosed herein comprising a pharmaceutically acceptable excipient.

Some embodiments provide a method for inhibiting CAPN1, CAPN2, and/or CAPN9 is provided wherein the method comprises contacting cells with an effective amount of one or more compounds disclosed herein. In some embodiments a method for inhibiting CAPN1, CAPN2, and/or CAPN9 is performed in-vitro or in-vivo.

Calpains are also expressed in cells other than neurons, microglia and invading macrophages. In particular, they are important in skeletal muscle and herein inhibition of calpains also refers to inhibition in these cells as well.

Selective Inhibition

Some embodiments provide a method for competitive binding with calpastatin (CAST), the method comprising contacting a compound disclosed herein with CAPN1, CAPN2, and/or CAPN9 enzymes residing inside a subject. In such a method, the compound specifically inhibits one or more of the enzymes selected from the group consisting of: CAPN1, CAPN2, and CAPN9 by at least 2-fold, by at least 3-fold, by at least 4-fold, by at least 5-fold, by at least 10-fold, by at least 15-fold, by at least 20-fold, by at least 50-fold, by at least 100-fold, by at least 150-fold, by at least 200-fold, by at least 400-fold, or by at least 500-fold.

Some embodiments provide a method for selectively inhibiting CAPN1 in the presence of CAPN2 and CAPN9, which includes contacting cells (including neurons/microglia/invading macrophages) with an effective amount of one or more compounds disclosed herein.

Some embodiments provide a method for selectively inhibiting CAPN2 in the presence of CAPN1 and CAPN9, which includes contacting cells (including neurons/microglia/invading macrophages) with an effective amount of one or more compounds disclosed herein.

Some embodiments provide a method for selectively inhibiting CAPN9 in the presence of CAPN2 and CAPN1, which includes contacting cells (including neurons/microglia/invading macrophages) with an effective amount of one or more compounds disclosed herein.

Some embodiments provide a method for selectively inhibiting CAPN1 and CAPN2 in the presence of CAPN9, which includes contacting cells (including neurons/microglia/invading macrophages) with an effective amount of one or more compounds disclosed herein.

Some embodiments provide a method for selectively inhibiting CAPN1 and CAPN9 in the presence of CAPN2, which includes contacting cells (including neurons/microglia/invading macrophages) with an effective amount of one or more compounds disclosed herein.

Some embodiments provide a method for selectively inhibiting CAPN2 and CAPN9 in the presence of CAPN1, which includes contacting cells (including neurons/microglia/invading macrophages) with an effective amount of one or more compounds disclosed herein.

Some embodiments provide a method for treating a fibrotic disease, which method comprises administering to a subject an effective amount of one or more compounds which specifically inhibits CAPN1, CAPN2, and/or CAPN9, said compounds or a pharmaceutical composition comprising one or more compounds disclosed herein and a pharmaceutically acceptable excipient.

Some embodiments provide a method for treating a disease affected at least in part by CAPN1, CAPN2, and/or CAPN9, which method comprises administering to a subject an effective amount of one or more compounds which specifically inhibits CAPN1, CAPN2, and/or CAPN9, said compounds being selected from compounds disclosed herein or a pharmaceutical composition comprising one or more compounds disclosed herein and a pharmaceutically acceptable excipient.

Some embodiments provide a method for treating a fibrotic disease, which method comprises administering to a subject an effective amount of one or more compounds which selectively inhibits CAPN1, CAPN2, and/or CAPN9, said compounds being selected from compounds disclosed herein or a pharmaceutical composition comprising one or more compounds disclosed herein and a pharmaceutically acceptable excipient.

Some embodiments provide a method for treating a disease affected at least in part by CAPN1, CAPN2, and/or CAPN9, which method comprises administering to a subject an effective amount of one or more compounds which selectively inhibits CAPN1, CAPN2, and/or CAPN9, said compounds being selected from compounds disclosed herein or a pharmaceutical composition comprising one or more compounds disclosed herein and a pharmaceutically acceptable excipient.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:5.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:10.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:20.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:50.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:100.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:200.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:250.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:500.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:5.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:10.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:20.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:50.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:100.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:200.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:250.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:500.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:5.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:10.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:20.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:50.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:100.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:200.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:250.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:500.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:5.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:10.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:20.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:50.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:100.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:200.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:250.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:500.

Some embodiments provide a method for prophylactic therapy or treatment of a subject having a fibrotic disorder wherein said method comprising administering an effective amount of one or more compounds disclosed herein to the subject in need thereof.

Some embodiments provide a method for prophylactic therapy or treatment of a subject having a disorder affected by CAPN1, CAPN2, and/or CAPN9 wherein said method comprising administering an effective amount of one or more compounds disclosed herein to the subject in need thereof.

Some embodiments provide a method for inhibiting myofibroblast differentiation (e.g., Epithelial/Endothelial-to-Mesenchymal Transition (EpMT/EnMT)) is provided wherein the method comprises contacting cells with an effective amount of one or more compounds disclosed herein. In one aspect, the method for inhibiting myofibroblast differentiation (e.g., Epithelial/Endothelial-to-Mesenchymal Transition (EpMT/EnMT)) is performed in-vitro or in-vivo.

Some embodiments provide a method for treating a disease or condition selected from the group consisting of or that produces a symptom selected from the group consisting of: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases, wherein which method comprises administering to a subject an effective amount of one or more compounds disclosed herein to a subject in need thereof.

Some embodiments provide a method for treating liver fibrosis.

Some embodiments provide a method for treating cardiac fibrosis.

Some embodiments provide a method for treating fibrosis in rheumatoid arthritis diseases.

Some embodiments provide a method for treating a condition affected by CAPN1, CAPN2, and/or CAPN9, which is in both a therapeutic and prophylactic setting for subjects. Both methods comprise administering of one or more compounds disclosed herein to a subject in need thereof.

Some embodiments provide a method for treating stiff skin syndrome.

Preferred embodiments include combinations of a compound, composition or pharmaceutical composition described herein with other CAPN1, CAPN2, and/or CAPN9 inhibitor agents, such as anti-CAPN1, CAPN2, AND/OR CAPN9 antibodies or antibody fragments, CAPN1, CAPN2, and/or CAPN9 antisense, iRNA, or other small molecule CAPN1, CAPN2, and/or CAPN9 inhibitors.

Some embodiments include combinations of a compound, composition or pharmaceutical composition described herein to inhibit myofibroblast differentiation (e.g., Epithelial/Endothelial-to-Mesenchymal Transition (EpMT/EnMT)). Some embodiments include combinations of one or more of these compounds which are inhibitors of one or more (or all three) CAPN1, CAPN2, and/or CAPN9, alone or in combination with other TGFβ signaling inhibitors, could be used to treat or protect against or reduce a symptom of a fibrotic, sclerotic or post inflammatory disease or condition including: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, postvasectomy pain syndrome, and rheumatoid arthritis.

Some embodiments include a combination of the compounds, compositions and/or pharmaceutical compositions described herein with an additional agent, such as anti-inflammatories including glucocorticoids, analgesics (e.g. ibuprofen), aspirin, and agents that modulate a Th2-immune response, immunosuppressants including methotrexate, mycophenolate, cyclophosphamide, cyclosporine, thalidomide, pomalidomide, leflunomide, hydroxychloroquine, azathioprine, soluble bovine cartilage, vasodilators including endothelin receptor antagonists, prostacyclin analogues, nifedipine, and sildenafil, IL-6 receptor antagonists, selective and non-selective tyrosine kinase inhibitors, Wnt-pathway modulators, PPAR activators, caspase-3 inhibitors, LPA receptor antagonists, B cell depleting agents, CCR2 antagonists, pirfenidone, cannabinoid receptor agonists, ROCK inhibitors, miRNA-targeting agents, toll-like receptor antagonists, CTGF-targeting agents, NADPH oxidase inhibitors, tryptase inhibitors, TGFD inhibitors, relaxin receptor agonists, and autologous adipose derived regenerative cells.

Indications

In some embodiments, the compounds and compositions comprising the compounds described herein can be used to treat a host of conditions arising from fibrosis or inflammation, and specifically including those associated with myofibroblast differentiation. Example conditions include liver fibrosis (alcoholic, viral, autoimmune, metabolic and hereditary chronic disease), renal fibrosis (e.g., resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, medicines, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders), cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic reperfusion injury associated fibrosis, injection fibrosis, cirrhosis, diffuse parenchymal lung disease, post-vasectomy pain syndrome, and rheumatoid arthritis diseases or disorders.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

It will be apparent to the skilled artisan that methods for preparing precursors and functionality related to the compounds claimed herein are generally described in the literature. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like. All the intermediate compounds of the present invention were used without further purification unless otherwise specified.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:

DCM=dichloromethane
DIEA=N,N-Diisopropylethylamine
DIPEA=N,N-Diisopropylethylamine
DMF=N,N-dimethylformamide
DMP=Dess Martin Periodinane
DNs=dinitrosulfonyl
ESBL=extended-spectrum β-lactamase
EtOAc=ethyl acetate
EA=ethyl acetate
FCC=Flash Column Chromatography
HATU=2-(7-aza-1H-benzotriazole-1-yl)-1,1,3,3-tetramethyluronium hexafluorophosphate
MeCN=acetonitrile
NMR=nuclear magnetic resonance
PE=Petroleum Ether
Prep=preparatory
Py=pyridine
Sat.=saturated aqueous
TBDMSCl=tert-butyldimethylsilyl chloride
TBS=tert-butyldimethylsilyl
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Example 1

Compounds 1-2, 5-6, 8, 91-92

(S)—N-(1-oxo-3-phenylpropan-2-yl)-1-phenyl-1H-imidazole-5-carboxamide (1)

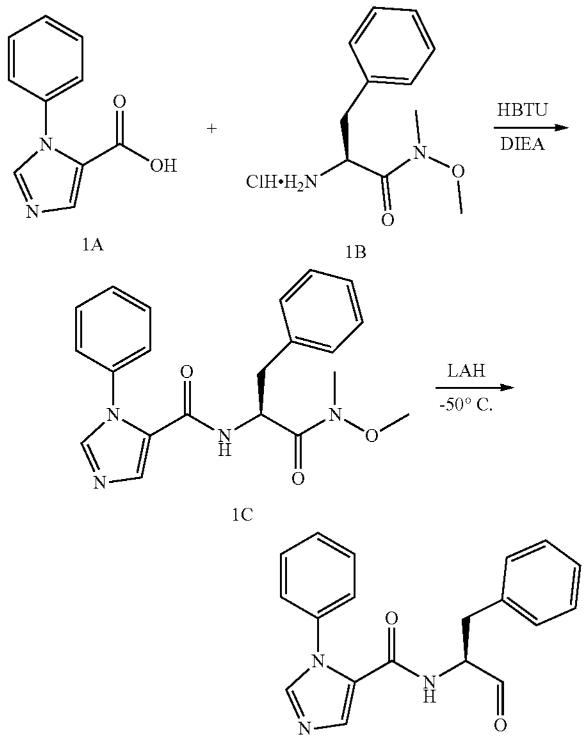

1A 1B

1C

1

A mixture of compound 1A (102 mg, 1.0 eq), compound 1B (160 mg, 1.2 eq) and HBTU (250 mg, 1.25 eq) in DMF (8 mL) was stirred at room temperature for 5 mins, and then DIEA (0.3 mL, 3.0 eq) was added. After stirred at room temperature for 30 mins, the reaction mixture was diluted with 50 mL ethyl acetate and 20 mL Hexane, washed with water, saturated $NaHCO_3$ and brine and concentrated in vacuo to afford intermediate compound 1C (190 mg, yield 92%).

A solution of compound 1C (190 mg, 1.0 eq) in dry THF (15 mL) was cooled to −50° C. under $N_2$, and then was added a solution of 1N LAH in THF (0.55 mL, 1.1 eq) dropwise at −50° C. The reaction mixture was stirred at −30° C. to −10° C. for 2 hrs, quenched with saturated $NaHCO_3$ at −20° C., and then extracted with 3×30 mL ethyl acetate. The combined organic phase was dried over $Na_2SO_4$ to give the crude mixture, which was purified on silica gel column. Compound 1 (105 mg, 65%): MS (ESI) m/z (M+H)+: 320.3; $^1$H NMR (400 MHz, $CDCl_3$): δ 9.64 (s, 1H), 7.65 (s, 1H), 7.56 (s, 1H), 7.46 (m, 3H), 7.26-7.33 (m, 5H), 7.09 (m, 2H), 6.29 (d, 1H), 4.81 (m, 1H), 3.19 (d, 2H) ppm (S)—N-(1-oxo-3-phenylpropan-2-yl)-1-phenyl-1H-pyrazole-5-carboxamide (2)

((S)-5-methyl-N-(1-oxo-3-phenylpropan-2-yl)-1-phenyl-1H-pyrazole-3-carboxamide (5)

(S)—N-(1-oxo-3-phenylpropan-2-yl)-4-phenylthiazole-5-carboxamide (6)

(S)-3-methyl-N-(1-oxo-3-phenylpropan-2-yl)-1-phenyl-1H-pyrazole-5-carboxamide (8)

Compounds 2, 5, 6 and 8 were prepared as in Example 1 using the corresponding carboxylic acid, respectively. Compound 2: MS (ESI) m/z $(M+H)^+$: 320.2; $^1$H NMR (400 MHz, DMSO): δ 9.6 (s, 1H), 9.15 (d, 1H), 7.73 (s, 1H), 7.4-7.2 (m, 10H), 6.8 (s, 1H), 4.53 (m, 1H), 3.25 (dd, 1H), 2.8 (dd, 1H) ppm.

Compound 5: MS (ESI) m/z $(M+H)^+$: 334.3; $^1$H NMR (400 MHz, $CDCl_3$): δ 9.67 (s, 1H), 7.54-7.4 (m, 6H), 7.3-7.2 (m, 5H), 6.73 (s, 1H), 4.82 (m, 1H), 3.21 (d, 2H), 2.33 (s, 3H) ppm.

Compound 6: MS (ESI) m/z $(M+H)^+$: 337.5; $^1$H NMR (400 MHz, $CDCl_3$): δ 9.56 (s, 1H), 8.88 (s, 1H), 7.5-7.34 (m, 5H), 7.27-7.2 (m, 3H), 6.94 (m, 2H), 6.35 (d, 1H), 4.73 (m, 1H), 3.1 (dd, 1H), 3.08 (dd, 1H) ppm.

Compound 8: MS (ESI) m/z $(M+H)^+$: 334.3; $^1$H NMR (400 MHz, DMSO): δ 9.59 (s, 0.6H), 9.01 (d, 0.6H), 8.35 (d, 0.4H), 7.38-7.06 (m, 10H), 6.58 (s, 0.6H), 6.48 (s, 0.4H), 4.82 (m, 0.2H), 4.54 (m, 0.6H), 3.98 (m, 0.4H), 3.25 (dd, 0.6H), 2.98 (dd, 0.4H), 2.78 (dd, 0.6H), 2.7 (dd, 0.4H), 2.48 (s, 1.8 HO, 2.21 (s, 1.2H) ppm.

91A

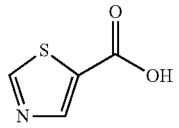

92A

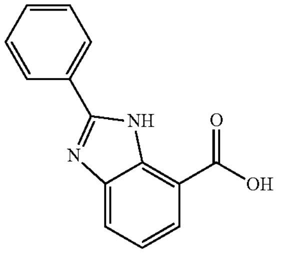

(S)—N-(1-oxo-3-phenylpropan-2-yl)thiazole-5-carboxamide (91)

Compound 91 was prepared as in Example 1 from the corresponding starting materials, compounds 91A and 1B. Compound 91: $^1$H NMR (400 MHz, $CDCl_3$): δ 9.69 (s, 1H), 8.85 (s, 1H), 8.21 (s, 1H), 7.06 (d, 1H), 7.32-7.18 (m, 8H), 4.88 (m, 1H), 3.26 (m, 2H) ppm. MS (ESI) m/z $(M+H)^+$ 261.3.

(S)—N-(1-oxo-3-phenylpropan-2-yl)-2-phenyl-1H-benzo[d]imidazole-7-carboxamide (92)

Compound 92 was prepared as in Example 1 using the corresponding carboxylic acid. $^1$H NMR (400 MHz, $CDCl_3$): δ 12.07 (s, 1H), 11.92 (d, 1H), 9.84 (s, 1H), 8.1-8.0 (m, 3H), 7.5-7.46 (m, 10H), 7.32-7.18 (m, 8H), 5.04 (m, 1H), 3.34 (d, 2H) ppm. MS (ESI) m/z $(M+H)^+$370.4.

Example 2

Compounds 3-4

(S)-1-(benzo[d]thiazol-2-yl)-N—((S)-1-oxo-3-phenylpropan-2-yl)pyrrolidine-2-carboxamide (3)

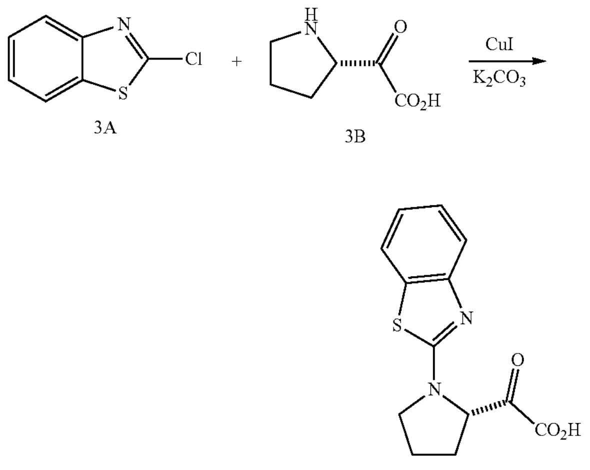

3A 3B

3C

A mixture of compound 3A (500 mg, 1.0 eq), compound 3B (738 mg, 1.0 eq), CuI (124 mg, 0.15 eq) and $K_2CO_3$ (1.8 g, 3.0 eq) in DMA (15 mL) was heated at 100° C. for 18 hrs, and then the inorganic was removed by filtration. The mixture was diluted with water (50 mL), adjusted pH ~6, and then extracted with 3x50 mL acetate to afford intermediate compound 3C. Compound 3 was prepared as in Example 1 using the corresponding carboxylic acid, intermediate compound 3C. Compound 3: MS (ESI) m/z (M+H)+: 380.2; $^1$H NMR (400 MHz, $CDCl_3$): δ 9.66 (s, 1H), 8.32 (d, 1H), 7.63 (d, 1H), 7.52 (d, 1H), 7.30 (t, 1H), 7.10 (t, 1H), 6.92-7.01 (m, 5H), 4.69 (m, 2H), 3.45 (m, 1H), 3.36 (m, 1H), 3.17 (dd, 1H), 2.90 (dd, 1H), 2.55 (m, 1H), 2.03 (m, 3H) ppm.

(S)-1-(benzo[d]oxazol-2-yl)-N—((S)-1-oxo-3-phenylpropan-2-yl)pyrrolidine-2-carboxamide (4)

Compound 4 was prepared as in Example 2 using the corresponding starting materials. MS (ESI) m/z $(M+H)^+$: 364.3; $^1$H NMR (400 MHz, $CDCl_3$): δ 9.65 (s, 1H), 7.69 (br d, 1H), 7.37 (d, 1H), 7.33 (t, 1H), 7.18 (t, 1H), 6.98-7.10 (m, 6H), 4.71 (m, 2H), 4.59 (m, 1H), 3.61 (m, 2H), 3.19 (dd, 1H), 2.97 (dd, 1H), 2.41 (m, 1H), 1.91-2.12 (m, 3H) ppm.

Example 3

(S)—N-(1-oxo-3-phenylpropan-2-yl)-3-phenylisothiazole-4-carboxamide (9)

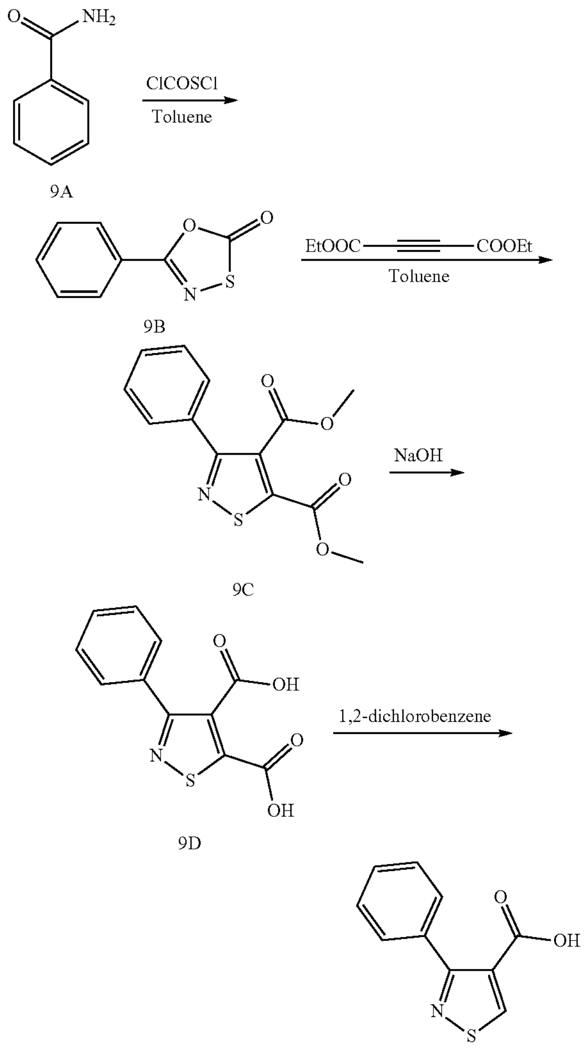

9A 9B 9C 9D 9E

To a suspension of compound 9A (1.2 g) in toluene (15 ml) was added chlorocarbonylsulfenyl chloride (1.3 ml). The mixture was heated at 100° C. for 2 hrs to obtain a clear solution (gas evolution was observed). When TLC showed complete conversion, the reaction mixture was concentrated and the solid residue was triturated with hexane, filtered and dried to yield compound 9B.

To a solution of compound 9B (1.4 g) in α,α,α-trifluorotoluene (10 mL) was added diethyl acetylenedicarboxylate (2.0 ml). After heated in the microwave at 170° C. for 1 hr, the reaction mixture was concentrated. and the oily residue was purified by flash column chromatography. The product-containing fractions were combined, concentrated, and the residue was triturated with hexane, filtered and dried to yield compound 9C.

A solution of compound 9C (2.1 g) and NaOH (1.4 g) in water (20 mL) was refluxed for 2.5 hrs. The reaction mixture was cooled, diluted with water (150 mL) and acidified with concentrated HCl (aqueous). A precipitate was formed. The water layer was extracted with EtOAc (2×200 mL; the precipitate slowly dissolved). The combined organic layers were washed with brine, dried ($Na_2SO_4$) and concentrated to yield compound 9D.

A suspension of compound 9D (1.8 g) in 1,2-dichlorobenzene (20 mL) was refluxed for 20 mins (gas formation is observed). The reaction mixture was cooled diluted with hexane (50 mL) and filtered to precipitate the product. To a suspension of the crude product in water (40 mL) was added 1N NaOH (10 ml). The water layer was extracted with ethyl acetate (2×100 mL) and acidified with concentrated HCl to pH ~3. The product was extracted with EtOAc (2×100 mL). The combined organic layers were washed with brine, dried ($Na_2SO_4$) and concentrated to yield intermediate compound 9E.

Compound 9 was prepared as in Example 1 using the corresponding carboxylic acid, intermediate compound 9E. MS (ESI) m/z $(M+H)^+$: 359.1; $^1H$ NMR (400 MHz, $CDCl_3$): δ 9.59 (s, 1H), 9.16 (s, 1H), 7.56-7.5 (m, 2H), 7.48-7.4 (m, 3H), 7.27-7.22 (m, 3H), 6.94 (m, 2H), 6.15 (d, 1H), 4.79 (m, 1H), 3.1 (d, 2H) ppm.

Example 4

Compounds 7, 10-11, 14, 18, 20

(S)—N-(4-amino-3,4-dioxo-1-phenylbutan-2-yl)-1-phenyl-1H-imidazole-5-carboxamide (7)

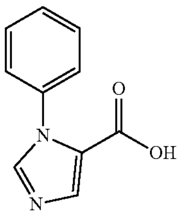

+

7A

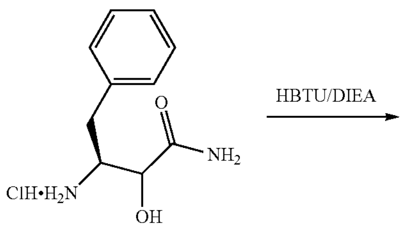

7B

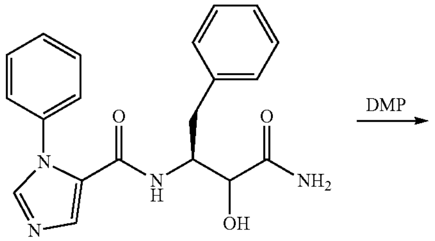

7C

-continued

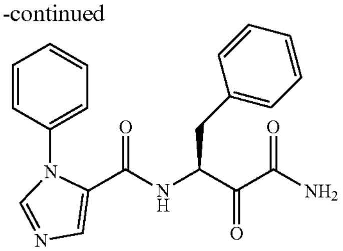

7

A mixture of compound 7A (50 mg, 1.0 eq), compound 7B (74 mg, 1.2 eq) and HBTU (126 mg, 1.25 eq) in DMF (3 mL) was stirred at room temperature for 5 mins, and then DIEA (0.15 mL, 3.0 eq) was added. After stirred at room temperature for 30 mins, the reaction mixture was diluted with ethyl acetate (30 mL) and hexane (10 mL), washed with 1N HCl, water, saturated $NaHCO_3$ and brine and concentrated in vacuo to afford intermediate compound 7C (65 mg, yield 67%) as white solid.

To a solution of compound 7C (65 mg, 1.0 eq) in dry DCM (10 ml) and DMSO (2 mL) was added DMP (305 mg, 4.0 eq). After stirred at room temperature for 1 hr, the mixture was diluted with DCM (30 mL), quenched by adding 10% aqueous $Na_2S_2O_3$/saturated aqueous $NaHCO_3$ (v/v=1/1, 10 mL). The organic layer was separated by extracting the aqueous layer with DCM (30 mL×5). The combined organic layer was washed with $H_2O$ (10 mL), brine (10 mL), dried over $Na_2SO_4$, filtered and concentrated to afford white solid, which was then triturated in $CH_2Cl_2$/Hexane to provide pure product compound 7 (29 mg, yield 45%). MS (ESI) m/z $(M+H)^+$: 363.4; $^1H$ NMR (400 MHz, $CDCl_3$): δ 7.66 (s, 1H), 7.57 (s, 1H), 7.45 (m, 3H), 7.26-7.35 (m, 5H), 7.05 (m, 2H), 6.72 (s, 1H), 6.24 (d, 1H), 5.58 (m, 2H), 4.81 (m, 1H), 3.38 (dd, 1H), 3.14 (dd, 1H) ppm.

(S)—N-(4-amino-3,4-dioxo-1-phenylbutan-2-yl)-1-phenyl-1H-pyrazole-5-carboxamide (10)

Prepared as in Example 4 using the corresponding carboxylic acid. MS (ESI) m/z $(M+H)^+$: 363.3; $^1H$ NMR (400 MHz, DMSO): δ 9.15 (d, 1H), 8.11 (s, 1H), 7.71 (s, 1H), 7.4-7.2 (m, 10H), 7.07 (d, 1H), 6.72 (s, 1H), 5.26 (m, 1H), 2.81 (dd, 1H), 2.64 (dd, 1H) ppm.

9E

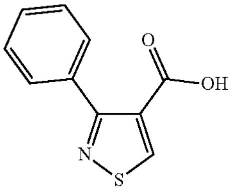

14E

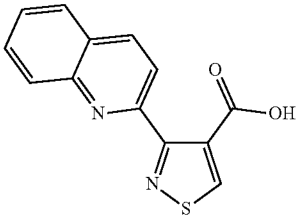

(S)—N-(4-amino-3,4-dioxo-1-phenylbutan-2-yl)-3-phenylisothiazole-4-carboxamide (11)

Prepared as in Example 4 using the corresponding carboxylic acid, intermediate compound 9E. MS (ESI) m/z $(M+H)^{+}$380.2; $^{1}$H NMR (400 MHz, DMSO): δ 9.15 (d, 1H), 9.05 (s, 1H), 8.14 (s, 1H), 7.89 (s, 1H), 7.5-7.4 (m, 2H), 7.3-7.2 (m, 8H), 5.34 (m, 1H), 3.2 (d, 2H) ppm.

(S)-1-(benzo[d]oxazol-2-yl)-N—((S)-1-oxo-3-phenylpropan-2-yl)pyrrolidine-2-carboxamide (14)

Intermediate compound 14E was prepared as in Example 3. Compound 14 was then prepared as in Example 4 using the corresponding intermediate carboxylic acid, compound 14E. Compound 14: MS (ESI) m/z $(M+H)^{+}$: 431.5; $^{1}$H NMR (400 MHz, DMSO): δ 9.14 (s, 1H), 9.05 (d, 1H), 8.16 (d, 1H), 7.9 (s, 1H), 7.62-7.56 (m, 2H), 7.3-7.2 (m, 8H), 5.36 (m, 1H), 3.17 (dd, 1H), 2.78 (dd, 1H) ppm.

(S)—N-(4-amino-3,4-dioxo-1-phenylbutan-2-yl)-4-phenylthiazole-5-carboxamide (18)

Prepared as in Example 4 using the corresponding carboxylic acid. MS (ESI) m/z $(M+H)^{+}$: 380.1; $^{1}$H NMR (400 MHz, DMSO): δ 10.11 (d, 1H), 9.33 (s, 1H), 8.49 (d, 1H), 8.13 (s, 1H), 8.07 (d, 1H), 8.03 (d, 1H), 7.85 (s, 1H), 7.74 (m, 2H), 7.65 (m, 1H), 7.12-7 (m, 5H), 5.51 (m, 1H), 3.18 (dd, 1H) 2.89 (dd, 1H) ppm.

(S)—N-(4-amino-3,4-dioxo-1-phenylbutan-2-yl)-5-(benzo[d][1,3]dioxol-5-yl)-3-methylisoxazole-4-carboxamide (20)

Prepared as in Example 4 using the corresponding carboxylic acid. MS (ESI) m/z $(M+H)^{+}$: 422.1; $^{1}$H NMR (400 MHz, DMSO-d6): δ 8.88 (d, 1H), 8.19 (s, 1H), 7.91 (s, 1H), 7.17-7.30 (m, 7H), 6.94 (d, 1H), 6.11 (s, 2H), 5.45 (m, 1H), 3.22 (dd, 1H), 2.72 (dd, 1H), 2.03 (s, 3H) ppm.

Example 5

Compounds 12-13, 15-17, 19, 27, 44, 47, 54, 60, 94, 117-118, 128, 148, 207, 235, 303-305, 309-312, 23, 39, 456, 461, 492

(S)—N-(4-amino-3,4-dioxo-1-phenylbutan-2-yl)-3-methyl-1-(pyridin-2-yl)-1H-pyrazole-5-carboxamide (12)

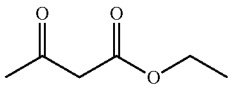

12A

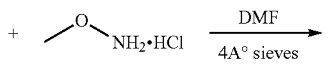

12B

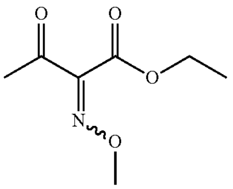

12C

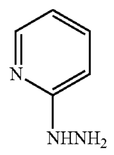

12D

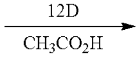

-continued

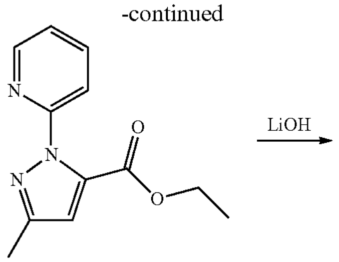

12E

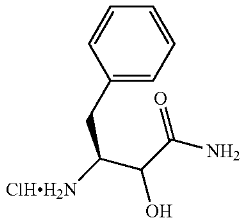

12G

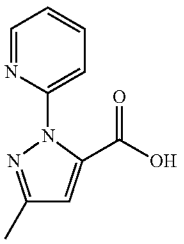

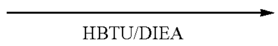

12F

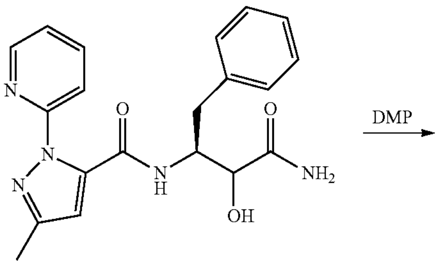

12H

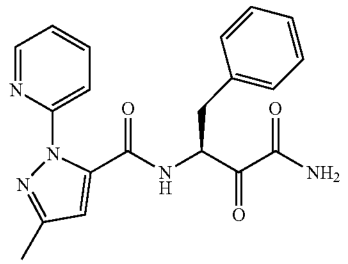

12

To a solution of compound 12A (5.0 g, 1.0 eq) and compound 12B (2.64 g, 1.0 eq) in dry DMF (20 mL) was added 4A° molecular sieve (5.0 g, powder). The resulting mixture was stirred room temperature under $N_2$ for 20 hrs, filtrated to remove the molecular sieves, diluted with hexane (80 mL) and ethyl acetate (80 mL), and then washed with 3×50 mL water, 50 mL saturated $NaHCO_3$ and brine. The crude mixture was purified on silica gel column to provide compound 12C (3.2 g, yield 48%) as clear oil.

A mixture of compound 12C (350 mg, 1.0 eq) and compound 12D (190 mg, 1.0 eq) in acetic acid (8 mL) was heated at 100° C. for 1 hr. The residue, upon in-vacuo removal of solvent, was suspended in ethyl acetate (80 mL), washed with saturated $NaHCO_3$ and brine. The crude mixture was purified on silica gel column to provide compound 12E (100 mg, yield 25%). Compound 12E (100 mg) was treated with LiOH in MeOH/water to afford compound 12F (87 mg, yield 100%).

A mixture of compound 12F (85 mg, 1.0 eq), compound 12G (116 mg, 1.2 eq) and HBTU (190 mg, 1.2 eq) in DMF (5 mL) was stirred at room temperature for 5 mins, and then DIEA (0.3 mL, 4.0 eq) was added. After stirred at room temperature for 30 mins, the mixture was diluted with 50 mL ethyl acetate and 20 mL hexane, washed with 1N HCl, water, saturated $NaHCO_3$ and brine and concentrated in vacuo to afford intermediate compound 12H (150 mg, yield 94%) as white solid.

To a solution of compound 12H (150 mg, 1.0 eq) in dry DCM (20 ml) and DMSO (2.5 mL) was added DMP (673 mg, 4.0 eq). After stirred at room temperature for 1 hr, the mixture was diluted with DCM (80 mL), quenched by adding 10% $Na_2S_2O_3$/saturated $NaHCO_3$ (v/v=1/1, 20 mL). The organic layer was separated. The aqueous layer was extracted with DCM (30 mL×2). The combined organic layer was washed with $H_2O$ (10 mL), brine (10 mL), dried over $Na_2SO_4$, filtered and concentrated to afford white solid. The solid was triturated in $CH_2Cl_2$/Hexane to provide pure compound 12 (95 mg, yield 64%). MS (ESI) m/z $(M+H)^+$: 378.3; $^1H$ NMR (400 MHz, DMSO-d6): δ 9.15 (d, 1H), 8.21 (d, 1H), 7.91 (t, 1H), 7.82 (s, 1H), 7.54 (d, 1H), 7.17-7.32 (m, 6H), 6.49 (s, 1H), 5.29 (m, 1H), 3.15 (dd, 1H), 2.84 (dd, 1H), 2.23 (s, 3H) ppm.

(S)—N-(4-amino-3,4-dioxo-1-phenylbutan-2-yl)-1-(benzo[d]thiazol-2-yl)-3-methyl-1H-pyrazole-5-carboxamide (13)

(S)—N-(4-amino-3,4-dioxo-1-phenylbutan-2-yl)-3-methyl-1-(quinolin-2-yl)-1H-pyrazole-5-carboxamide (15)

(S)-1-([1,1'-biphenyl]-3-yl)-N-(4-amino-3,4-dioxo-1-phenylbutan-2-yl)-3-methyl-1H-pyrazole-5-carboxamide (16)

(S)—N-(4-amino-3,4-dioxo-1-phenylbutan-2-yl)-3-methyl-1-(4-(methylsulfonyl)phenyl)-1H-pyrazole-5-carboxamide (17)

(S)—N-(4-amino-3,4-dioxo-1-phenylbutan-2-yl)-3-methyl-1-(4-(trifluoromethoxy)phenyl)-1H-pyrazole-5-carboxamide (19)

Compounds 13, 15-17 and 19 were prepared, respectively, as in Example 5 by utilizing the corresponding hydrazine derivative.

Compound 13: MS (ESI) m/z $(M+H)^+$: 434.3; $^1H$ NMR (400 MHz, DMSO-d6): δ 10.09 (d, 1H), 8.10 (d, 1H), 7.99 (d, 1H), 7.83 (s, 1H), 7.62 (d, 1H), 7.40 (m, 2H), 7.04-7.24 (m, 5H), 6.68 (s, 1H), 5.51 (m, 1H), 3.16 (dd, 1H), 2.95 (dd, 1H), 2.24 (s, 3H) ppm.

Compound: 15: MS (ESI) m/z $(M+H)^+$: 428.4; 4H NMR (400 MHz, DMSO): δ 9.28 (d, 0.5H), 8.77 (d, 0.5H), 8.45 (d, 1H), 8 (d, 1H), 7.9-7.5 (6H), 7.2-7.1 (6H), 5.4 (m, 0.5H 4.44 (m, 0.5H), 3.2-2.7 (m, 2H) ppm.

Compound 16: MS (ESI) m/z $(M+H)^+$: 453.3; $^1H$ NMR (400 MHz, DMSO-d6): δ 9.10 (d, 1H), 8.09 (s, 1H), 7.87 (s, 1H), 7.35-7.62 (m, 8H), 7.19-7.29 (m, 5H), 7.09 (d, 1H), 6.61 (s, 1H), 5.30 (m, 1H), 3.17 (dd, 1H), 2.81 (dd, 1H), 2.25 (s, 3H) ppm.

Compound 17: MS (ESI) m/z $(M+H)^+$: 455.3; $^1H$ NMR (400 MHz, DMSO-d6): δ 9.27 (d, 1H), 8.14 (s, 1H), 7.88 (m, 2H), 7.82 (d, 1H), 7.35-7.62 (m, 8H), 7.19-7.45 (m, 7H), 6.62 (s, 1H), 5.25 (m, 1H), 3.19 (m, 4H), 2.82 (dd, 1H), 2.25 (s, 3H) ppm.

Compound 19: MS (ESI) m/z $(M+H)^+$: 461.3; $^1H$ NMR (400 MHz, DMSO-d6): δ 9.15 (d, 1H), 8.11 (s, 1H), 7.87 (s, 1H), 7.82 (d, 1H), 7.21-7.35 (m, 9H), 6.61 (s, 1H), 5.23 (m, 1H), 3.20 (dd, 1H), 2.82 (dd, 1H), 2.24 (s, 3H) ppm.

27A

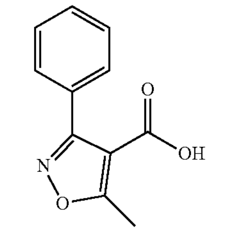

44A

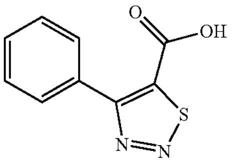

54A

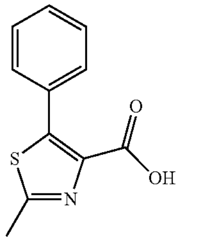

60A

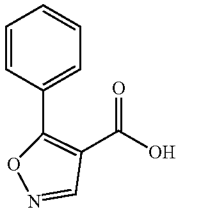

94A

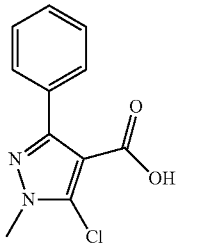

117A

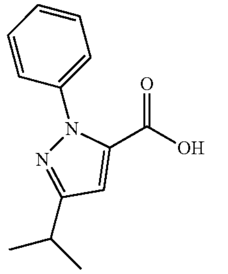

-continued

118A

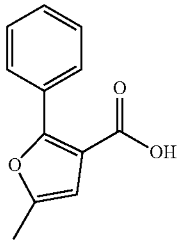

128A

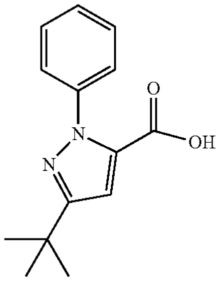

148A

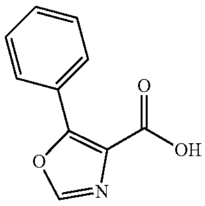

135A

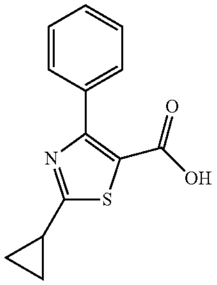

235A

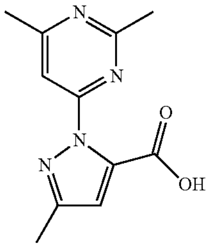

12G

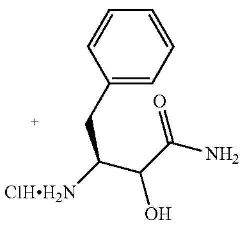

(S)—N-(4-amino-3,4-dioxo-1-phenylbutan-2-yl)-5-methyl-3-phenylisoxazole-4-carboxamide (27)

Compound 27 (30.0 mg, 43.0% yield, white solid) was prepared as in Example 12 from the corresponding carboxylic acid, compound 27A. Compound 27: $^1$H NMR (400 MHz, DMSO-$d_6$) δ 8.94 (d, J=7.6 Hz, 1H), 8.17 (s, 1H), 7.90 (s, 1H), 7.49-7.41 (m, 3H), 7.41-7.34 (m, 2H), 7.33-7.21 (m, 5H), 5.42-5.35 (m, 1H), 3.29-3.21 (m, 1H), 2.80-2.70 (m, 1H), 2.35-2.27 (m, 3H). MS (ESI) m/z $(M+H)^+$378.1.

(S)—N-(4-amino-3,4-dioxo-1-phenylbutan-2-yl)-4-phenyl-1,2,3-thiadiazole-5-carboxamide (44)

Compound 44 (42.4 mg, yield: 47.7%, white solid) was prepared as in Example 12 from the corresponding intermediate carboxylic acid, compound 44A. Compound 44: $^1$H NMR (400 MHz, DMSO-$d_6$) δ 9.60 (br d, J=7.5 Hz, 1H), 8.19 (s, 1H), 7.93 (s, 1H), 7.79-7.67 (m, 2H), 7.52-7.39 (m, 3H), 7.34-7.21 (m, 5H), 5.52-5.39 (m, 1H), 3.23 (dd, J=14.0, 3.5 Hz, 1H), 2.78 (dd, J=13.6, 10.5 Hz, 1H). MS (ESI) m/z $(M+H)^+$381.0.

(S)—N-(4-amino-3,4-dioxo-1-phenylbutan-2-yl)-2-methyl-5-phenylthiazole-4-carboxamide (54)

Compound 54 (75 mg, yield: 75.4%, white solid) was prepared as in Example 12 from the corresponding intermediate carboxylic acid, compound 54A. $^1$H NMR (400 MHz, DMSO-$d_6$) δ 8.46 (br d, J=7.7 Hz, 1H) 8.05 (br s, 1H) 7.81 (br s, 1H) 7.43-7.29 (m, 1H) 7.41-7.29 (m, 1H) 7.29-7.29 (m, 1H) 7.41-7.29 (m, 1H) 7.30-7.28 (m, 1H) 7.28-7.08 (m, 5H) 5.37 (td, J=8.1, 4.5 Hz, 1H) 3.22-3.09 (m, 1H) 3.17 (br dd, J=14.0, 4.1 Hz, 1H) 3.06-2.92 (m, 1H) 2.72-2.60 (m, 3H). MS (ESI) m/z $(M+H)^+$394.0.

(S)—N-(4-amino-3,4-dioxo-1-phenylbutan-2-yl)-5-phenylisoxazole-4-carboxamide (60)

Compound 60 (40 mg, yield 36.20%, white solid) was prepared as in Example 5 from the corresponding carboxylic acid, compound 60A. Compound 60: $^1$H NMR (400 MHz, DMSO-$d_6$) δ 9.02 (d, J=7.5 Hz, 1H), 8.83 (s, 1H), 8.16 (s, 1H), 7.92-7.78 (m, 3H), 7.59-7.42 (m, 3H), 7.35-7.17 (m, 4H), 5.43-5.34 (m, 1H), 3.27-3.17 (m, 1H), 2.90-2.79 (m, 1H). MS (ESI) m/z $(M+H)^+$364.1.

(S)—N-(4-amino-3,4-dioxo-1-phenylbutan-2-yl)-5-chloro-1-methyl-3-phenyl-1H-pyrazole-4-carboxamide (94)

Compound 94 was prepared as in Example 5 from the corresponding intermediate carboxylic acid, compound 94A. Compound 94: $^1$H NMR (400 MHz, DMSO): δ 8.8 (d, 1H), 8.16 (s, 1H), 7.89 (s, 1H), 7.5-7.46 (m, 2H), 7.32-7.18 (m, 8H), 5.41 (m, 1H), 3.82 (s, 3H), 3.17 (dd, 1H), 2.76 (dd, 1H) ppm. MS (ESI) m/z $(M+H)^+$410.9.

(S)—N-(4-amino-3,4-dioxo-1-phenylbutan-2-yl)-3-isopropyl-1-phenyl-1H-pyrazole-5-carboxamide (117)

Compound 117 (10 mg, yield 18.29%, white solid) was prepared as in Example 5 from the corresponding intermediate carboxylic acid, compound 117A. Compound 117: $^1$H NMR (400 MHz, DMSO-$d_6$) δ 8.36 (d, J=7.8 Hz, 1H), 8.09 (s, 1H), 7.84 (s, 1H), 7.63-7.47 (m, 5H), 7.32-7.14 (m, 5H), 6.66 (s, 1H), 5.50-5.39 (m, 1H), 3.23-3.13 (m, 1H), 3.09-2.89 (m, 2H), 1.12 (d, J=6.8 Hz, 6H). MS (ESI) m/z $(M+H)^+$405.2.

(S)—N-(4-amino-3,4-dioxo-1-phenylbutan-2-yl)-5-methyl-2-phenylfuran-3-carboxamide (118)

Compound 118 (58 mg, yield: 55.4%, white solid) was prepared as in Example 5 from the corresponding intermediate carboxylic acid, compound 118A. Compound 118: $^1$H NMR (400 MHz, DMSO-$d_6$) δ 8.54 (d, J=7.5 Hz, 1H), 8.08 (s, 1H), 7.81 (s, 1H), 7.68 (d, J=7.0 Hz, 2H), 7.35-7.26 (m, 7H), 7.23-7.17 (m, 1H), 6.39 (d, J=0.9 Hz, 1H), 5.30 (br d, J=0.7 Hz, 1H), 3.19-3.12 (m, 1H), 2.88-2.79 (m, 1H), 2.33-2.29 (m, 3H). MS (ESI) m/z (M+H)+377.1.

(S)—N-(4-amino-3,4-dioxo-1-phenylbutan-2-yl)-3-(tert-butyl)-1-phenyl-1H-pyrazole-5-carboxamide (128)

Compound 128 (101.7 mg, 68.04% yield, white solid) was prepared as in Example 5 from the corresponding intermediate carboxylic acid, compound 128A. Compound 128: $^1$H NMR (400 MHz, $CDCl_3$) δ 7.55-7.44 (m, 3H), 7.42-7.35 (m, 2H), 7.34-7.28 (m, 1H), 7.25-7.14 (m, 5H), 6.74 (br s, 1H), 6.70 (s, 1H), 5.73-5.64 (m, 1H), 5.53 (br s, 1H), 3.44-3.35 (m, 1H), 3.18-3.09 (m, 1H), 1.16 (s, 9H). MS (ESI) m/z $(M+1)^+$419.3.

(S)—N-(4-amino-3,4-dioxo-1-phenylbutan-2-yl)-5-phenyloxazole-4-carboxamide (148)

Compound 148 (10 mg, yield: 30.8%, white solid) was prepared as in Example 5 from the corresponding intermediate carboxylic acid, compound 148A. Compound 148: $^1$H NMR (400 MHz, DMSO-$d_6$) δ 8.57 (s, 1H), 8.44 (d, J=7.7 Hz, 1H), 8.14-8.03 (m, 3H), 7.85 (s, 1H), 7.49-7.42 (m, 3H), 7.30-7.15 (m, 5H), 5.49-5.40 (m, 1H), 3.26-3.17 (m, 1H), 3.12-3.02 (m, 1H). MS (ESI) m/z $(M+H)^+$364.1.

(S)—N-(4-amino-3,4-dioxo-1-phenylbutan-2-yl)-2-cyclopropyl-4-phenylthiazole-5-carboxamide (207)

Compound 207 (54.0 mg, 44.09% yield, white solid) was prepared as in Example 5 from the corresponding intermediate carboxylic acid, compound 135A. Compound 207: $^1$H NMR (400 MHz, $CDCl_3$) δ 7.52-7.45 (m, 2H), 7.43-7.38 (m, 3H), 7.21-7.17 (m, 3H), 6.79-6.77 (m, 2H), 6.70 (s, 1H), 6.19-6.17 (d, J=6.0 Hz, 1H), 5.53 (s, 1H), 5.50-5.45 (m, 1H), 3.25-3.21 (m, 1H), 2.90-2.85 (m, 1H), 2.33-2.27 (m, 1H), 1.19-1.16 (m, 2H), 1.13-1.10 (m, 2H). MS (ESI) m/z $(M+1)^+$ 420.1.

(S)—N-(4-amino-3,4-dioxo-1-phenylbutan-2-yl)-1-(2,6-dimethylpyrimidin-4-yl)-3-methyl-1H-pyrazole-5-carboxamide (235)

Compound 235 (61.6 mg, 51.11% yield, white solid) was prepared as in Example 5 from the corresponding intermediate carboxylic acid, compound 235A. Compound 235: $^1$H NMR (400 MHz, $CDCl_3$) δ 9.83 (d, J=7.2 Hz, 1H), 7.57 (s, 1H), 7.21-7.16 (m, 3H), 7.11-7.06 (m, 2H), 6.87 (s, 1H), 6.75 (br s, 1H), 5.84-5.76 (m, 1H), 5.56 (br s, 1H), 3.49-3.31 (m, 2H), 2.55 (s, 3H), 2.34-2.32 (m, 6H). MS (ESI) m/z $(M+1)^+$407.1.

((S)—N-(1-amino-1,2-dioxopentan-3-yl)-3-methyl-5-phenylisoxazole-4-carboxamide (47)

Compound 47 (90.00 mg, yield 60.4%, white solid) was prepared as in Example 5 from the corresponding starting materials, 23A and 47A. Compound 47: $^1$H NMR (400 MHz, DMSO-$d_6$) δ 8.98 (d, J=6.6 Hz, 1H), 8.12 (br s, 1H), 7.88-7.79 (m, 3H), 7.57-7.50 (m, 3H), 5.12-5.02 (m, 1H), 2.32 (s, 3H), 1.95-1.77 (m, 1H), 1.65-1.48 (m, 1H), 0.93 (t, J=7.4 Hz, 3H). MS (ESI) m/z $(M+H)^+$316.1.

(S)—N-(4-amino-3,4-dioxo-1-phenylbutan-2-yl)-4-phenyloxazole-5-carboxamide (303)

(S)—N-(4-amino-3,4-dioxo-1-phenylbutan-2-yl)-3-phenylisoxazole-4-carboxamide (304)

(S)—N-(4-amino-3,4-dioxo-1-phenylbutan-2-yl)-1-phenyl-3-(trifluoromethyl)-1H-pyrazole-5-carboxamide (305)

(S)—N-(4-amino-3,4-dioxo-1-phenylbutan-2-yl)-1,3-diphenyl-1H-pyrazole-4-carboxamide (309)

(S)—N-(4-amino-3,4-dioxo-1-phenylbutan-2-yl)-1-(tert-butyl)-3-methyl-1H-pyrazole-5-carboxamide (310)

(S)—N-(4-amino-3,4-dioxo-1-phenylbutan-2-yl)-4-chloro-1-ethyl-1H-pyrazole-5-carboxamide (311)

(S)—N-(4-amino-3,4-dioxo-1-phenylbutan-2-yl)-4-chloro-1-ethyl-3-methyl-1H-pyrazole-5-carboxamide (312)

Compounds 303-305 and 309-312 were prepared as in Example 5 from the corresponding carboxylic acid with compound 12G, respectively.

Compound 303: $^1$H NMR (400 MHz, DMSO-$d_6$) δ $^1$H NMR (400 MHz, DMSO): δ 8.51 (s, 1H), 7.9-7.85 (m, 2H), 7.81 (d, 1H), 7.4-7.0 (m, 10H), 4.53 (m, 1H), 2.98 (dd, 1H), 2.57 (dd, 1H) ppm. MS (ESI) m/z $(M+H)^+$364.3.

Compound 304: $^1$H NMR (400 MHz, DMSO-$d_6$) δ 9.2-8.9 (m, 1H), 8.11 (m, 1H), 7.7-7.1 (m, 12H), 5.3 (m, 0.5H), 4.4 (m, 0.5H), 2.85-2.55 (m, 2H) ppm. MS (ESI) m/z $(M+H)^+$364.3.

Compound 305: $^1$H NMR (400 MHz, DMSO-$d_6$) δ 9.3 (d, 1H), 8.07 (s, 1H), 7.83 (s, 1H), 7.4-7.1 (m, 10H), 5.24 (m, 1H), 3.14 (dd, 1H), 2.74 (dd, 1H) ppm. MS (ESI) m/z $(M+H)^+$431.3.

Compound 309: $^1$H NMR (400 MHz, DMSO-$d_6$) δ 8.7 (m, 1H), 8.49 (d, 1H), 8.1-7.1 (m, 17H), 5.31 (m, 0.5H), 4.6-4.4 (m, 0.5H), 3.1-2.7 (m, 2H) ppm. MS (ESI) m/z $(M+H)^+$439.3.

Compound 310: $^1$H NMR (400 MHz, DMSO-$d_6$) δ 7.75 (d, 1H), 7.4-7.1 (m, 5H), 6.38 (s, 1H), 6.1 (d, 2H), 4.48 (m, 1H), 3.02 (dd, 1H), 2.52 (dd, 1H) 2.08 (s, 3H), 1.31 (s, 9H) ppm. MS (ESI) m/z $(M+H)^+$379.3.

Compound 311: $^1$H NMR (400 MHz, DMSO-$d_6$) δ 8.89 (d, 1H), 8.13 (d, 1H), 7.86 (s, 1H), 7.33 (s, 1H), 7.3-7.1 (m, 5H), 6.8 (s, 1H), 5.38 (m, 1H), 3.99 (q, 2H), 3.21 (dd, 1H), 2.78 (dd, 1H) 1.11 (t, 3H) ppm. MS (ESI) m/z $(M+H)^+$349.2.

Compound 312: $^1$H NMR (400 MHz, DMSO-$d_6$) δ 8.74 (d, 1H), 8.1 (s, 1H), 7.83 (s, 1H), 7.4-7.2 (m, 5H), 6.58 (s, 1H), 5.29 (m, 1H), 4.25 (q, 2H), 3.18 (dd, 1H), 2.87 (dd, 1H), 2.13 (s, 3H), 1.15 (t, 3H) ppm. MS (ESI) m/z $(M+H)^+$ 329.1.

(S)—N-(4-amino-3,4-dioxo-1-phenylbutan-2-yl)-3-methyl-5-phenylisoxazole-4-carboxamide (23)

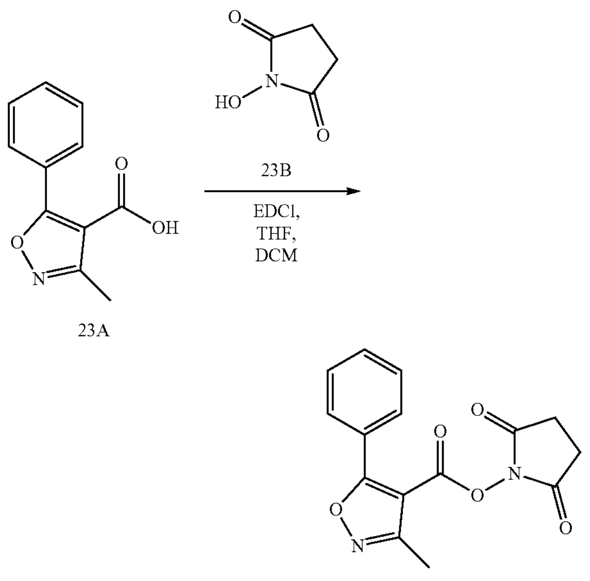

23B

23A

23C

To a solution of compound 23A (500 mg, 2.46 mmol) in THF (10 mL) was added 23B (311 mg, 2.71 mmol) and EDCI (566 mg, 2.95 mmol) with DCM (10 mL). The mixture was stirred at 25° C. for 3 hrs. The reaction mixture was concentrated and diluted with EA (20 mL). Then the mixture was washed with HCl (1M, 20 mL), saturated aqueous $NaHCO_3$ (20 mL), dried over $Na_2SO_4$ and concentrated. Compound 23C (800 mg, crude, yellow oil): $^1H$ NMR (400 MHz, DMSO-$d_6$) δ 7.93-7.88 (m, 2H), 7.69-7.63 (m, 1H), 7.62-7.56 (m, 2H), 2.87 (s, 4H), 2.54-2.51 (m, 3H).

Compound 23 (30.0 mg, yield 35.0%, white solid) was prepared as in Example 5 from the corresponding intermediate compounds 23C and 12G. Compound 23: $^1H$ NMR (400 MHz, DMSO-$d_6$) δ 9.08 (br d, J=8.0 Hz, 1H), 8.22 (s, 1H), 7.94 (s, 1H), 7.64 (br d, J=7.2 Hz, 2H), 7.55-7.41 (m, 3H), 7.35-7.21 (m, 5H), 5.54-5.45 (m, 1H), 3.29-3.23 (m, 1H), 2.81-2.71 (m, 1H), 2.09 (s, 3H). MS (ESI) m/z $(M+H)^+$ 378.0.

(S)—N-(4-amino-3,4-dioxo-1-phenylbutan-2-yl)-4-(4-phenyl-1H-pyrazol-1-yl)thiazole-5-carboxamide (39)

Compound 39 (5.20 mg, 26.12% yield, white solid) was prepared as in Example 5 from the corresponding starting materials, compounds 21F and 12G. Compound 39: $^1H$ NMR ($CDCl_3$, 400 MHz): δ 11.75 (d, J=4.8 Hz, 1H), 8.73-8.71 (m, 1H), 8.73 (s, 1H), 8.66 (s, 1H), 7.69 (s, 1H), 7.54 (d, J=7.6 Hz, 2H), 7.45-7.41 (m, 2H), 7.35-7.31 (m, 1H), 7.29-7.27 (m, 1H), 7.25-7.21 (m, 4H), 6.78 (br s, 1H), 5.82-5.74 (m, 1H), 5.48 (br s, 1H), 3.46-3.41 (m, 1H), 3.27-3.20 (m, 1H). MS (ESI) m/z $(M+H)^+$446.1.

N-(4-(cyclopropylamino)-3,4-dioxo-1-phenylbutan-2-yl)-3-methyl-1-(pyridin-2-yl)-1H-pyrazole-5-carboxamide (456)

Compound 456 (240 mg, 86.0% yield, white solid) was prepared as in compound 12 from the corresponding starting materials, compounds 12F and 3-amino-N-cyclopropyl-2-hydroxy-4-phenylbutanamide hydrochloride. Compound 456: $^1H$ NMR ($CDCl_3$, 400 MHz): δ 9.15 (d, J=7.2 Hz, 1H), 8.80 (d, J=5.2 Hz, 1H), 8.21-8.17 (m, 1H), 7.92-7.86 (m, 1H), 7.55 (d, J=8.4 Hz, 1H), 7.33-7.16 (m, 6H), 6.50 (s, 1H), 5.36-5.27 (m, 1H), 3.17-3.09 (m, 1H), 2.88-2.79 (m, 1H), 2.79-2.70 (m, 1H), 2.24 (s, 3H), 0.69-0.53 (m, 4H). MS (ESI) m/z $(M+H)^+$418.2.

N-(4-(cyclopropylamino)-3,4-dioxo-1-phenylbutan-2-yl)-5-phenylisoxazole-4-carboxamide (461)

Compound 461 (270 mg, 68.77% yield, white solid) was prepared as in compound 12 from the corresponding starting materials, compounds 60A and 3-amino-N-cyclopropyl-2-hydroxy-4-phenylbutanamide hydrochloride. Compound 461: $^1H$ NMR ($CDCl_3$, 400 MHz): δ 9.04 (d, J=7.5 Hz, 1H), 8.87 (d, J=4.8 Hz, 1H), 8.82 (s, 1H), 7.85 (d, J=7.3 Hz, 2H), 7.59-7.44 (m, 3H), 7.36-7.19 (m, 5H), 5.37 (br.s., 1H), 3.27-3.17 (m, 1H), 2.90-2.73 (m, 2H), 0.72-0.51 (m, 4H). MS (ESI) m/z $(M+H)^+$404.1.

(S)—N-(4-amino-1-(4-hydroxyphenyl)-3,4-dioxobutan-2-yl)-3-methyl-5-phenylisoxazole-4-carboxamide (492)

Compound 492 (35 mg, 60.9% yield, white solid) was prepared as in compound 12 from the corresponding starting materials, compounds 23A and (3S)-3-amino-4-(4-(tert-butoxy)phenyl)-2-hydroxybutanamide followed by removal of the tert-butyl group to obtain the final compound 492. Compound 492: $^1H$ NMR (DMSO-$d_6$, 400 MHz): δ 9.29 (s, 1H), 9.01 (d, J=7.5 Hz, 1H), 8.19 (s, 1H), 7.92 (s, 1H), 7.66-7.41 (m, 5H), 7.07 (d, J=8.4 Hz, 2H), 6.68 (d, J=8.6 Hz, 2H), 5.46-5.29 (m, 1H), 3.13 (br d, J=10.8 Hz, 1H), 2.63 (br d, J=2.9 Hz, 1H), 2.13 (s, 3H). MS (ESI) m/z $(M+H)^+$394.1.

N-(4-amino-3,4-dioxo-1-phenylbutan-2-yl)-3-methyl-1-(pyridin-2-yl)-1H-pyrazole-5-carboxamide (495)

Compound 495 (4.0 g, 44.68% yield, white solid) was prepared as in compound 12 from the corresponding starting materials, compounds 12F and 3-amino-2-hydroxy-4-phenylbutanamide hydrochloride to obtain the final compound 495. Compound 495: $^1H$ NMR (DMSO-$d_6$, 400 MHz): δ 7.74 (br d, J=9.0 Hz, 1H), 7.31 (d, J=8.5 Hz, 2H), 7.20-7.08 (m, 5H), 7.04 (d, J=9.0 Hz, 1H), 6.97 (d, J=8.5 Hz, 2H), 5.40 (d, J=6.3 Hz, 1H), 4.96 (s, 2H), 4.79 (d, J=2.3 Hz, 2H), 4.48-4.15 (m, 2H), 3.97-3.86 (m, 1H), 3.68 (t, J=8.2 Hz, 1H), 3.63-3.49 (m, 2H), 2.98 (dd, J=3.4, 13.9 Hz, 1H), 2.70-2.59 (m, 1H), 1.78 (qd, J=6.8, 13.6 Hz, 1H), 0.72 (d, J=6.8 Hz, 3H), 0.69-0.62 (m, 1H), 0.67 (d, J=6.8 Hz, 2H). MS (ESI) m/z $(M+Na)^+$493.1.

N-(4-amino-3,4-dioxo-1-phenylbutan-2-yl)-5-phenylisoxazole-4-carboxamide (531)

Compound 531 (4.0 g, 44.68% yield, white solid) was prepared as in compound 12 from the corresponding starting materials, compounds 60A and 3-amino-2-hydroxy-4-phenylbutanamide hydrochloride to obtain the final compound 531. Compound 531: $^1$H NMR ($CD_3CN$, 400 MHz): δ 8.52 (s, 1H), 7.84-7.75 (m, 2H), 7.57-7.51 (m, 1H), 7.51-7.43 (m, 2H), 7.32-7.23 (m, 3H), 7.23-7.17 (m, 2H), 7.17-7.07 (m, 1H), 7.06-6.93 (m, 1H), 6.23 (s, 1H), 5.55-5.47 (m, 1H), 3.29 (dd, J=4.9, 14.1 Hz, 1H), 2.92 (dd, J=8.9, 14.0 Hz, 1H). MS (ESI) m/z $(M+H)^+$364.1.

Example 6

Compounds 21-22, 322, 29, 31, 75, 90, 279

(S)—N-(1-oxo-3-phenylpropan-2-yl)-4-(4-phenyl-1H-pyrazol-1-yl)thiazole-5-carboxamide (21)

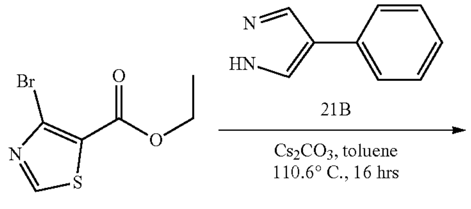

21A

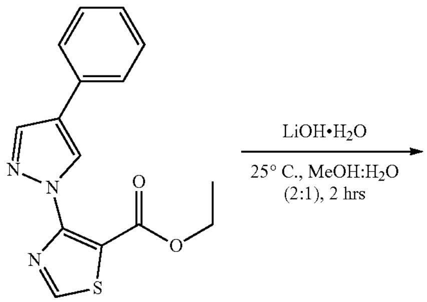

21C

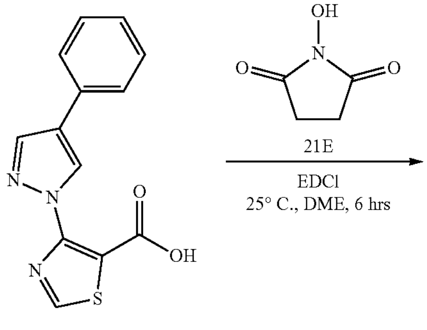

21D

-continued

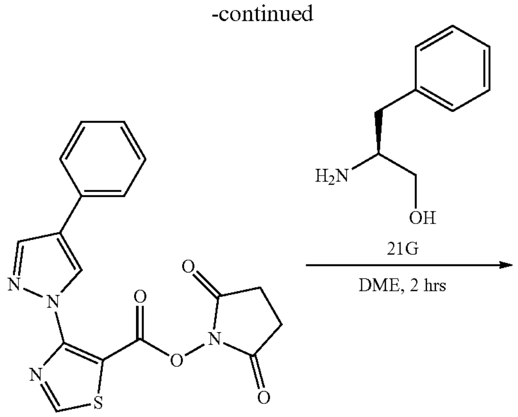

21F

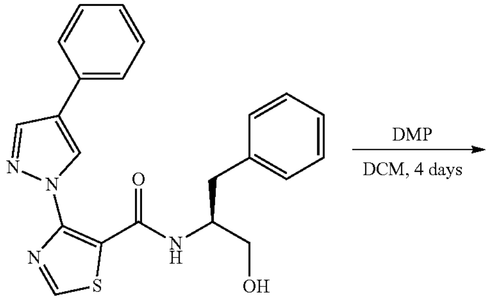

21H

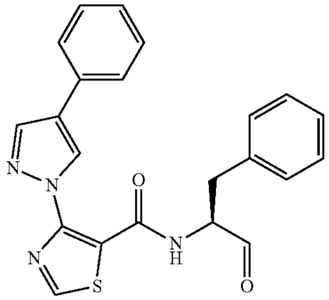

21

A mixture consisting of compound 21A (500 mg, 2.12 mmol), compound 21B (306 mg, 2.12 mmol) and $Cs_2CO_3$ (2.07 g, 6.36 mmol) was stirred at 110.6° C. for 16 hrs. The reaction mixture was cooled to room-temperature, filtered and concentrated under reduced pressure to give a residue. The residue was purified by flash silica gel chromatography (Petroleum ether:Ethyl acetate=3:2 and then Acetic acid: Ethyl acetate=1:100) to afford compound 21C (80 mg, 12.61% yield) as a light yellow solid, and compound 21D (125 mg, 21.73% yield) as a yellow solid.

Compound 21C: $^1$H NMR ($CDCl_3$, 400 MHz): δ 8.85 (s, 1H), 8.49 (s, 1H), 8.07 (s, 1H), 7.57 (d, J=7.6 Hz, 2H), 7.40 (t, J=7.6 Hz, 2H), 7.30-7.26 (m, 1H), 4.41-4.32 (m, 2H), 1.34 (t, J=7.2 Hz, 3H).

Compound 21D: $^1$H NMR ($CDCl_3$, 400 MHz): δ14.70 (br. s., 1H), 9.33 (s, 1H), 8.87 (d, J=0.8 Hz, 1H), 8.41 (d, J=0.8 Hz, 1H), 7.75-7.71 (m, 2H), 7.43-7.38 (m, 2H), 7.30-7.24 (m, 1H). MS (ESI) m/z $(M+H)^+$ 271.8.

To a solution of compound 21C (80 mg, 267.25 umol) in MeOH (5 mL) and $H_2O$ (2.5 mL) was added LiOH (19.20 mg, 801.75 umol) in one portion at 25° C. under $N_2$. The mixture was stirred at 25° C. for 2 hrs. The mixture was concentrated under reduced pressure to give a residue. The residue was diluted with water (10 mL) and adjusted with 1N HCl to pH ~3, extracted with ethyl acetate 90 mL (30 mL×3). The combined organic layers were washed with brine 30 mL, dried over anhydrous $Na_2SO_4$, filtered and concentrated under reduced pressure to afford intermediate compound 21D (71.1 mg, 98.07% yield) as white solid. $^1H$ NMR ($CDCl_3$, 400 MHz): δ 8.84 (s, 1H), 8.78 (d, J=0.8 Hz, 1H), 8.13 (d, J=0.8 Hz, 1H), 7.60-7.56 (m, 2H), 7.45 (t, J=7.6 Hz, 2H), 7.39-7.34 (m, 1H). MS (ESI) m/z $(M+H)^+$ 271.8.

To a solution of compound 21D (80 mg, 294.89 umol) and 1-hydroxypyrrolidine-2,5-dione (21E) (35.6 mg, 309.63 umol) in DME (3.50 mL) was added EDCI (84.8 mg, 442.34 umol) in one portion at 25° C. under $N_2$. The resultant mixture was stirred at 25° C. for 6 hrs. The mixture was concentrated under reduced pressure, diluted with EtOAc (100 mL), washed with 1N HCl (10 mL) and saturated aqueous $NaHCO_3$ (10 mL×3), and then washed with brine (20 mL). The organic phase was dried with anhydrous $Na_2SO_4$, filtered and concentrated in vacuum to afford intermediate compound 21F (100 mg, crude) as yellow oil. MS (ESI) m/z $(M+H)^+$368.9.

A mixture consisting of compound 21F (100 mg, 271.47 umol) and compound 21G (41.1 mg, 271.47 umol) in DME (3 mL) was stirred at 25° C. for 2 hrs. The mixture was concentrated in vacuum, diluted with ethyl acetate (100 mL), washed with 1N HCl (10 mL) and saturated aqueous $NaHCO_3$ (10 mL×3), and then washed with brine (20 mL). The organic phase was dried with anhydrous $Na_2SO_4$, filtered and concentrated in vacuum to give a residue. The residue was purified by flash silica gel chromatography (Petroleum ether:Ethyl acetate=3:2) to afford compound 21H (65 mg, 59.20% yield). $^1H$ NMR ($CDCl_3$, 400 MHz): δ 10.54 (d, J=7.6 Hz, 1H), 9.21 (d, J=0.4 Hz, 1H), 8.93 (s, 1H), 8.40 (s, 1H), 7.78 (d, J=7.6 Hz, 2H), 7.45-7.38 (m, 2H), 7.31-7.26 (m, 1H), 7.24-7.18 (m, 4H), 7.15-7.10 (m, 1H), 4.96-4.89 (m, 1H), 4.13-4.02 (m, 1H), 3.52-3.43 (m, 2H), 2.97-2.91 (m, 1H), 2.82-2.74 (m, 1H). MS (ESI) m/z (M+H)+405.0.

DMP (63 mg, 148.34 umol) was added to a solution of compound 21H (30 mg, 74.17 umol) in dichloromethane (6 mL). The mixture was stirred at 25° C. for 12 hrs. Additional DMP (63 mg, 148.34 umol) was added and the mixture was stirred for additional 6 hrs at 25° C. Additional DMP (157 mg, 0.37 mmol) was added. After stirred for additional 39 hrs, the mixture was diluted with dichloromethane (35 mL), quenched by the addition of 10% $Na_2S_2O_3$/saturated aqueous $NaHCO_3$ (v/v=1/1, ~35 mL). The organic layer was separated and the aqueous layer was extracted with DCM (20 mL×2). The combined organic layer was washed with $H_2O$ (10 mL), brine (10 mL), dried over anhydrous $MgSO_4$, filtered and concentrated. The residue was triturated with i-$Pr_2O$ (3 mL). The insoluble substance was collected and dried in vacuum. Compound 21 (20 mg, 67% yield, pale yellow solid): $^1H$ NMR ($CDCl_3$, 400 MHz): δ 11.71 (br. d, J=6.0 Hz, 1H), 9.67 (s, 1H), 8.68 (s, 1H), 8.60 (s, 1H), 7.66 (s, 1H), 7.48-7.46 (m, 2H), 7.36-7.34 (m, 3H), 7.24-7.22 (m, 2H), 7.20-7.16 (m, 3H), 4.86-4.81 (m, 1H), 3.21-3.18 (m, 2H). MS (ESI) m/z $(M+H)^+$403.1.

(S)-4-(1H-indazol-1-yl)-N-(1-oxo-3-phenylpropan-2-yl)thiazole-5-carboxamide (22)

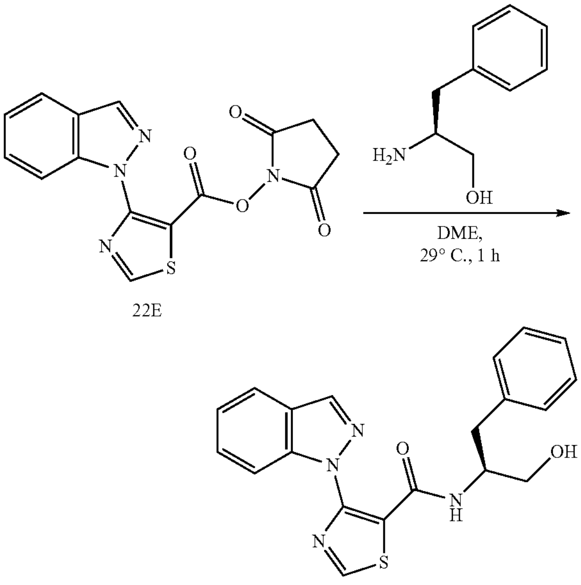

22E

22G

Compound 22 (4.70 mg, 16.87% yield, yellow solid) was prepared as in Example 6 from the corresponding starting materials through intermediate compound 22E and then compound 22G. Compound 22: $^1H$ NMR ($CD_3CN$, 400 MHz): δ 10.41 (br. s, 1H), 9.67 (s, 1H), 9.04 (s, 1H), 8.21-8.19 (m, 1H), 8.15 (s, 1H), 7.91-7.89 (m, 1H), 7.61-7.58 (m, 1H), 7.40-7.37 (m, 1H) 7.12-7.10 (m, 5H) 4.77-4.72 (m, 1H), 3.29-3.24 (m, 1H), 3.11-3.05 (m, 1H). MS (ESI) m/z $(M+H)^+$377.0.

(S)-2-methyl-n-(1-oxo-3-phenylpropan-2-yl)-4-phenyloxazole-5-carboxamide (322)

Compound 322 (102.9 mg, 36.1% yield, off-white solid) was prepared as in Example 6 from the corresponding intermediate compounds 107B and 21G ((S)-2-amino-3-phenylpropan-1-ol). Compound 322: $^1H$ NMR (400 MHz, $CDCl_3$) δ 9.70 (s, 1H), 8.17-8.09 (m, 2H), 7.47-7.36 (m, 3H), 7.35-7.26 (m, 3H), 7.19 (d, J=6.84 Hz, 2H), 6.82 (d, J=6.00 Hz, 1H), 4.96-4.86 (m, 1H), 3.40-3.28 (m, 1H), 3.26-3.19 (m, 1H), 2.55 (s, 3H). MS (ESI) m/z $(M+1)^+$335.1.

(S)-1-(benzo[d]thiazol-2-yl)-N-(1-oxo-3-phenylpropan-2-yl)-1H-imidazole-5-carboxamide (29)

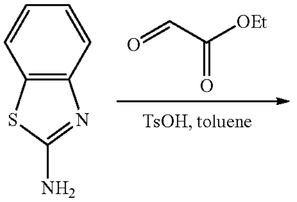

29A

-continued

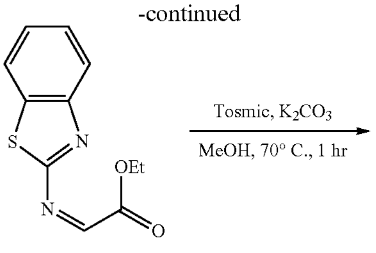

29B

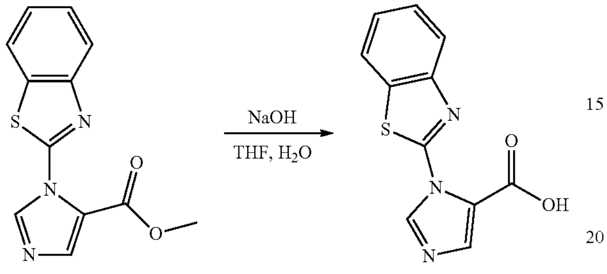

29C 29D

A mixture of compound 29A (20 g, 133 mmol), ethyl 2-oxoacetate (136 g, 665 mmol), TsOH.$H_2O$ (2.5 g, 13.3 mmol) in toluene (200 mL) was stirred at 120° C. for 1 hour. TLC (Petroleum ether:Ethyl acetate=3:1, $R_f$=0.5) indicated reactant 29A was almost consumed and one new spot formed. LCMS showed one peak with desired MS was detected. The reaction mixture was concentrated under reduced pressure to give a residue. The residue was purified by column chromatography (Petroleum ether:Ethyl acetate=20:1 to 5:1) to give compound 29B (30.0 g, crude) as a yellow oil. $^1$H NMR (400 MHz, $CDCl_3$) δ 9.40 (s, 1H), 7.98-7.78 (m, 1H), 7.77-7.57 (m, 1H), 7.55-7.31 (m, 1H), 7.30-7.07 (m, 1H), 5.38-5.26 (m, 1H), 4.33-4.21 (m, 3H). MS (ESI) m/z $(M+H)^+$234.9.

A mixture of methyl 29B (10 g, 45.4 mmol), Tosmic (17.7 g, 90.8 mmol), $K_2CO_3$ (9.4 g, 68.1 mmol) in MeOH (200 mL) was stirred at 70° C. for 0.5 hour. TLC (Petroleum ether:Ethyl acetate=3:1, $R_f$=0.4) indicated 29B was consumed completely and some new spots formed. The reaction mixture was filtered and concentrated under reduced pressure to give a residue. The residue was purified by column chromatography (Petroleum ether:Ethyl acetate=20:1 to 3:1) to give compound 29C (1.2 g, yield: 10.2%) as a yellow solid. $^1$H NMR (400 MHz, $CDCl_3$) δ 8.22 (d, J=0.9 Hz, 1H), 8.06 (d, J=7.9 Hz, 1H), 7.93-7.88 (m, 3H), 7.58 (dt, J=1.3, 7.7 Hz, 1H), 7.52-7.49 (m, 1H), 7.49-7.43 (m, 1H), 4.58 (s, 1H), 3.87 (s, 3H), 2.51 (s, 1H). MS (ESI) m/z $(M+H)^+$259.9.

To a solution of 29C (1.1 g, 4.24 mmol in THF (30 mL), $H_2O$ (5 mL) was added NaOH (339 mg, 8.48 mmol). The reaction mixture was stirred at 25° C. for 3 hrs. LCMS showed 29C was consumed completely and one main peak with desired MS was detected. The reaction mixture was concentrated to give a residue. The residue was dissolved in water (10 mL), adjusted by aqueous HCl (2M) to pH ~5, filtered and the filtered cake was concentrated to give the product 29D (600 mg, yield: 57.7%) as a gray solid. $^1$H NMR (400 MHz, DMSO-$d_6$) δ 8.48 (d, J=1.1 Hz, 1H), 8.22-8.18 (m, 1H), 8.06 (dd, J=0.8, 8.0 Hz, 1H), 7.81 (d, J=0.9 Hz, 1H), 7.64-7.53 (m, 2H). MS (ESI) m/z $(M+H)^+$ 245.9.

Compound 29 (55.00 mg, yield: 76.12%, offwhite solid) was prepared as in Example 21 from the corresponding intermediate compounds 29D and 21G. Compound 29: $^1$H NMR (400 MHz, $CDCl_3$) δ 9.75 (s, 1H), 9.01 (d, J=6.2 Hz, 1H), 8.14 (s, 1H), 7.90-7.75 (m, 3H), 7.57-7.42 (m, 2H), 7.19-7.00 (m, 5H), 5.04-4.94 (m, 1H), 3.37-3.21 (m, 2H). MS (ESI) m/z $(M+H)^+$377.2.

(S)—N-(1-oxo-3-phenylpropan-2-yl)-1-(pyridin-2-yl)-1H-imidazole-5-carboxamide (31)

Compound 31 (25 mg, yield: 57.86%, light yellow solid) was prepared as in Example 6 from the corresponding intermediate compounds 24E and 21G. Compound 31: $^1$H NMR (400 MHz, $CDCl_3$) δ 9.70 (s, 1H), 8.45-8.39 (m, 1H), 7.94 (d, J=1.1 Hz, 1H), 7.89-7.82 (m, 1H), 7.67-7.59 (m, 2H), 7.39-7.32 (m, 2H), 7.30-7.27 (m, 1H), 7.26-7.21 (m, 2H), 7.17-7.11 (m, 2H), 4.87 (q, J=6.6 Hz, 1H), 3.25 (dd, J=2.5, 6.5 Hz, 2H). MS (ESI) m/z $(M+H)^+$321.1.

(S)—N-(4-amino-3,4-dioxo-1-phenylbutan-2-yl)-1-(5-phenylpyrimidin-2-yl)-1H-imidazole-5-carboxamide (75)

Compound 75 (43.1 mg, yield: 66.6%, white solid) was prepared as in Example 6 from the corresponding intermediate compounds 74E and 21G. Compound 75: $^1$H NMR ($CDCl_3$, 400 MHz) δ 9.79 (s, 1H), 9.61 (br d, J=6.0 Hz, 1H), 8.75 (s, 2H), 8.65 (s, 1H), 7.84 (s, 1H), 7.58-7.53 (m, 5H), 7.25-7.14 (m, 5H), 5.06-5.01 (m, 1H), 3.43-3.38 (m, 1H), 3.33-3.28 (m, 1H). MS (ESI) m/z $(M+H)^+$398.1.

(S)-1-(1H-benzo[d]imidazol-2-yl)-n-(1-oxo-3-phenylpropan-2-yl)-1H-imidazole-5-carboxamide (90)

Compound 90 (20 mg, yield: 44.4%, white solid) was prepared as in Example 6 from the corresponding intermediate compounds 70D and 21G ((S)-2-amino-3-phenylpropan-1-ol). Compound 90: $^1$H NMR (400 MHz, $CDCl_3$) δ 12.77 (br s, 1H), 12.87-12.63 (m, 1H), 9.75 (s, 1H), 8.85 (s, 1H), 7.71 (br s, 1H), 7.57 (s, 1H), 7.50 (br s, 1H), 7.36-7.27 (m, 4H), 7.19 (br d, J=6.8 Hz, 2H), 6.99 (br d, J=5.3 Hz, 1H), 4.93 (q, J=6.7 Hz, 1H), 3.32 (d, J=6.4 Hz, 2H). MS (ESI) m/z $(M+H)^+$360.1.

(S)-3-methyl-n-(1-oxo-3-phenylpropan-2-yl)-1-(pyrimidin-4-yl)-1H-pyrazole-5-carboxamide (279)

Compound 279 (102.0 mg, 304.15 umol, 55.26% yield, white solid) was prepared as in Example 6 from the corresponding intermediate compounds 245D and 21G ((S)-2-amino-3-phenylpropan-1-ol). Compound 279: $^1$H NMR (400 MHz, $CDCl_3$): δ 9.88 (d, J=5.6 Hz, 1H), 9.76 (s, 1H), 8.74 (d, J=5.6 Hz, 1H), 8.61 (s, 1H), 7.91-7.87 (m, 1H), 7.27-7.23 (m, 3H), 7.19-7.17 (m, 2H), 8.89 (s, 1H), 5.02-4.97 (m, 1H), 3.40-3.35 (m, 1H), 3.30-3.25 (m, 1H), 2.34 (s, 1H). MS (ESI) m/z $(M+1)^+$336.1.

Example 7

(S)—N-(4-amino-3,4-dioxo-1-phenylbutan-2-yl)-1-(pyridin-2-yl)-1H-imidazole-5-carboxamide (24)

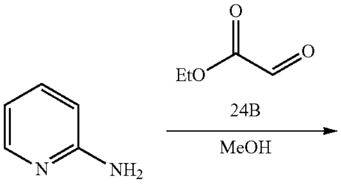

24A

-continued

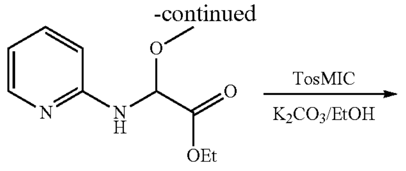

24C

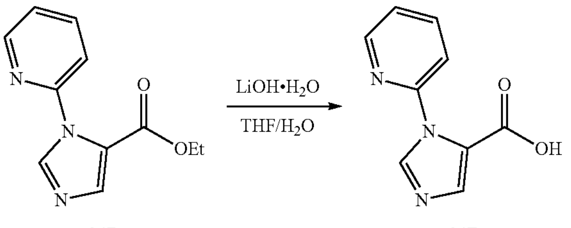

24D 24E

To a solution of compound 24B (16.2 g, 79.7 mmol) in MeOH (25 mL) was added compound 24A (5 g, 53.1 mmol). The mixture was stirred at 80° C. for 6 hrs. TLC (Petroleum ether:Ethyl acetate=2:1, $R_f$=0.24) indicated compound 24A was remained and one major new spot with lower polarity was detected. Then the reaction mixture was concentrated under reduced pressure to give a residue. Then the residue was purified by column chromatography ($SiO_2$, Petroleum ether:Ethyl acetate=30:1 to 15:1) to give compound 24C (6 g, yield: 53.7%) as a yellow oil.

To a mixture of compound 24C (6 g, 28.5 mmol) in EtOH (15 mL) was added TosMIC (8.3 g, 42.8 mmol), $K_2CO_3$ (11.8 g, 85.6 mmol). The mixture was stirred at 80° C. for 12 hrs. TLC (Petroleum ether:Ethyl acetate=1:1, $R_f$=0.70) indicated compound 24C remained and one major new spot with higher polarity was detected. Then the reaction mixture was filtered and concentrated under reduced pressure to give a residue. The residue was purified by column chromatography ($SiO_2$, Petroleum ether:Ethyl acetate=30:1 to 3:1) to give compound 24D (1.60 g, yield: 25.8%) as a white solid. $^1$H NMR (400 MHz, $CDCl_3$) δ 8.61-8.54 (m, 1H), 7.98 (s, 1H), 7.92-7.83 (m, 2H), 7.45-7.38 (m, 2H), 4.25 (q, J=7.1 Hz, 2H), 1.28 (t, J=7.2 Hz, 4H).

To a solution of compound 24D (1.6 g, 7.37 mmol) in THF (15 mL) and $H_2O$ (5 mL) was added LiOH.$H_2O$ (618 mg, 14.7 mmol). The reaction mixture was stirred at 25° C. for 12 hrs. LCMS showed compound 24D was consumed completely and one main peak with desired MS was detected. Then the mixture was adjusted to pH ~5 by adding HCl (1M), and then white solid was precipitate out. The white solid was filtered and dried over to give compound 24E (1 g, yield: 71.7%) as a white solid. MS (ESI) m/z $(M+H)^+$189.1.

Compound 24 (20 mg, yield: 33.5%, yellow solid) was prepared as in Example 5 from the corresponding intermediate carboxylic acid, compound 24E, and compound 12G. Compound 24: $^1$H NMR (400 MHz, DMSO-$d_6$) δ 8.95 (d, J=7.6 Hz, 1H), 8.50-8.38 (m, 1H), 8.12 (s, 1H), 8.03 (br.s., 1H), 7.89-7.85 (m, 1H), 7.80 (br.s., 1H), 7.53 (s, 1H), 7.43-7.40 (m, 1H), 7.33-7.25 (m, 4H), 7.24-7.19 (m, 1H), 7.15 (d, J=8.4 Hz, 1H), 5.25-5.20 (m, 1H), 3.17 (dd, J=4.0, 14.4 Hz, 1H), 2.83 (dd, J=10.0, 13.6 Hz, 1H). MS (ESI) m/z $(M+H)^+$364.1.

Example 8

(S)—N-(4-amino-3,4-dioxo-1-phenylbutan-2-yl)-2-methyl-4-phenylthiazole-5-carboxamide (25)

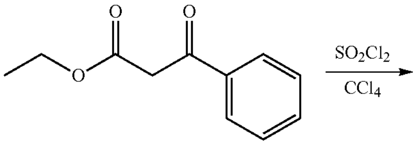

25A

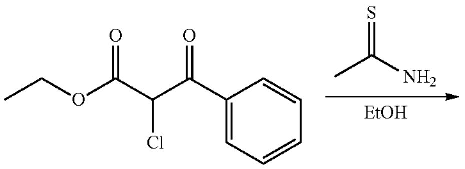

25B

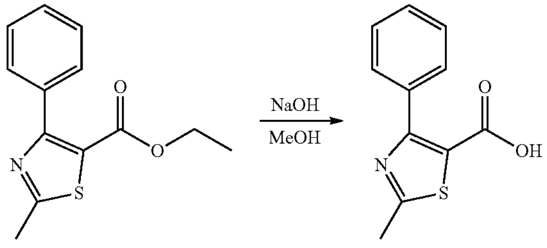

25C 25D

To a solution of compound 25A (20 g, 104 mmol) in $CCl_4$ (200 ml) was added $SO_2Cl_2$ (14 g, 104 mmol) at 45-50° C. during a period of 0.3 h. Then the mixture was stirred at 45-50° C. for 1 h. The reaction mixture was diluted with ice-water (200 mL). The organic layer was separated, washed with $H_2O$ (200 mL×2), brine (200 mL) dried over anhydrous $MgSO_4$, filtered and concentrated under reduced pressure to afford compound 25B (25.g, crude) as pale yellow oil, which was used for next step directly. $^1$H NMR ($CDCl_3$, 400 MHz): δ 8.03-7.98 (m, 2H), 7.67-7.62 (m, 1H), 7.54-7.50 (m, 2H), 5.62 (s, 1H), 4.32-4.26 (q, J=7.2 Hz, 2H), 1.25 (t, J=7.2 Hz, 3H).

A mixture of compound 25B (6.8 g, 30 mmol) and thioacetamide (2.25 g, 30.0 mmol) in EtOH (75 mL) was heated to 80° C. and stirred for 6 hrs. The solvent was distilled off under reduced pressure. The residue was purified by a silica gel column chromatography (eluent: Petroleum Ether/Ethyl Acetate=50/1) to afford compound 25C (3.0 g, yield 40.4%) as yellow oil. $^1$H NMR ($CDCl_3$, 400 MHz): δ 7.77-7.71 (m, 2H), 7.47-7.40 (m, 3H), 4.28 (q, J=7.2 Hz, 2H), 2.77 (s, 3H), 1.29 (t, J=7.2 Hz, 3H).

A solution of NaOH (2N, 12 mL, 24 mmol) was added to a solution of compound 25C (1.24 g, 5.01 mmol) in MeOH/$H_2O$ mixture (39 mL/13 mL). The mixture was stirred at 25° C. for 3 hrs. The mixture was diluted with $H_2O$ (5 mL). The volatile solvent was removed by evaporation. The residue was treated with HCl (1N) until pH ~3. The precipitate was collected by filtration, dried under reduced pressure to afford compound 25D (650 mg, yield 59.2%) as white solid, which was used directly in next step. $^1$H NMR (DMSO-$d_6$, 400 MHz): δ 7.72-7.65 (m, 2H), 7.43-7.36 (m, 3H), 2.68 (s, 3H).

Compound 25 (25 mg, yield 42%, white solid) was prepared as in Example 5 from the corresponding intermediate carboxylic acid, compound 25D. Compound 25: $^1$H NMR (DMSO-$d_6$, 400 MHz): δ 8.81 (d, J=7.6 Hz, 1H), 8.12 (s, 1H), 7.86 (s, 1H), 7.55-7.53 (m, 2H), 7.31-7.19 (m, 8H), 5.35-5.31 (m, 1H), 3.15 (dd, J=3.6, 13.8 Hz, 1H), 2.77 (dd, J=9.9, 13.8 Hz, 1H), 2.67 (s, 3H). MS (ESI) m/z $(M+H)^+$ 394.1.

Example 9

(S)—N-(4-amino-3,4-dioxo-1-phenylbutan-2-yl)-2-methyl-4-phenyloxazole-5-carboxamide (26)

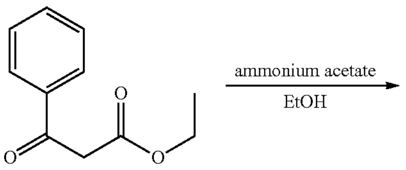

26A

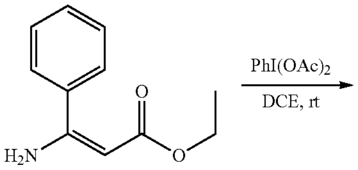

26B

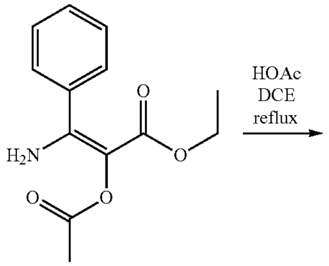

26C

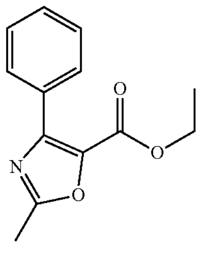

26D

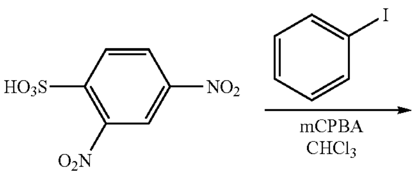

26E

-continued

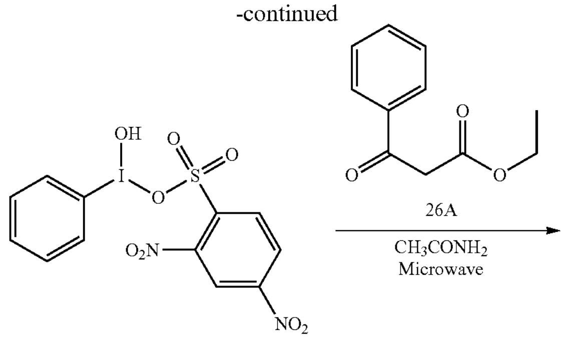

26F

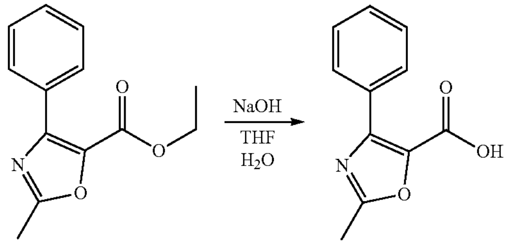

26G 26H

To a mixture of compound 26A (7.2 g, 37.46 mmol, 6.5 mL) and ammonium acetate (5.8 g, 74.92 mmol) were mixed in EtOH (70 mL) and refluxed at 80° C. for 16 hrs. After removal of the solvent, the residue was dissolved in water (50 mL), extracted with EtOAc (100 mL×2). This combined organic phase was washed with sat. $NaHCO_3$ (50 mL×2) and brine (50 mL), dried over $Na_2SO_4$, filtered and the solvent was removed in vacuo. The residue was purified by column chromatography ($SiO_2$, Petroleum ether/Ethyl acetate=20:1 to 10:1) to give compound 26B (3.5 g, yield: 48.9%) as yellow oil. $^1$H NMR ($CDCl_3$, 400 MHz): δ 7.57-7.53 (m, 2H), 7.48-7.37 (m, 3H), 5.07-4.89 (m, 1H), 4.22-4.11 (m, 2H), 1.33-1.25 (m, 3H).

To a mixture of compound 26B (2 g, 10.46 mmol) in DCE (4 mL) was added $PhI(OAc)_2$ (4.4 g, 13.60 mmol) in one portion at 25° C. under $N_2$. The mixture was stirred at 25° C. for 16 hrs. The reaction mixture was quenched with saturated aqueous $NaHCO_3$ (50 mL) and extracted with DCM (50 mL×3). The organic layers were combined and dried over anhydrous $Na_2SO_4$. The residue was purified by column chromatography ($SiO_2$, Petroleum ether/Ethyl acetate=20:1 to 5:1) to give compound 26C (400 mg, yield: 15.3%) as yellow oil. $^1$H NMR ($CDCl_3$, 400 MHz): δ 7.58 (dd, J=1.1, 7.7 Hz, 1H), 7.44-7.39 (m, 4H), 4.28-4.21 (m, 2H), 1.94 (s, 3H), 1.66-1.60 (m, 1H), 1.62 (br s, 1H), 1.30-1.26 (m, 3H).

To a mixture of compound 26C (400 mg, 1.60 mmol) in DCE (5 mL) and AcOH (10 mL) was stirred at 90° C. for 16 hrs. The solvent was removed. The residue was purified by column chromatography ($SiO_2$, Petroleum ether/Ethyl acetate=10:1 to 5:1) to give compound 26D (220 mg, yield: 53.0%) as yellow oil. $^1$H NMR ($CDCl_3$, 400 MHz): δ 8.11-7.89 (m, 2H), 7.56-7.32 (m, 3H), 4.40 (t, J=7.3 Hz, 2H), 2.59 (s, 3H), 1.39 (q, J=7.1 Hz, 3H). MS (ESI) m/z $(M+H)^+$ 231.8.

To a mixture of iodobenzene (2.5 g, 12.25 mmol, 1.4 mL) and compound 26E (3.59 g, 13.48 mmol) in $CHCl_3$ (25 mL), was added m-CPBA (2.33 g, 13.48 mmol). The mixture was stirred for 2 hrs at 25° C. under an $N_2$ atmosphere. After the reaction, MTBE (20 mL) was added to the reaction mixture, and the resulting mixture was filtered and the solid was washed with MTBE (30 mL) Compound 26F was obtained as a white solid Ethyl 3-oxo-3-phenyl-propanoate 26A (500 mg, 2.60 mmol) and compound 26F (1.58 g, 3.38 mmol) in $CH_3CN$ (30 mL) were heated to reflux for 1 h at 80° C., and acetamide (461 mg, 7.80 mmol) was added to the mixture. The reaction mixture was heated at 120° C. for 0.1 h under microwave irradiation. After being cooled to room temperature, the suspension was diluted with saturated $NaHCO_3$ solution (30 mL), extracted with EtOAc (10 mL×2), dried over $Na_2SO_4$, filtered, and concentrated in vacuo. The residue was purified by column chromatography ($SiO_2$, Petroleum ether/Ethyl acetate=10/1) and by preparatory-TLC ($SiO_2$, Petroleum ether/Ethyl acetate=5/1). Compound 26G (50 mg, yield: 8.32%) was obtained as a white solid. $^1H$ NMR ($CDCl_3$, 400 MHz): δ 8.06-7.93 (m, 2H), 7.48-7.39 (m, 3H), 4.38 (q, J=7.1 Hz, 2H), 2.58 (s, 3H), 1.37 (t, J=7.1 Hz, 3H). MS (ESI) m/z $(M+H)^+$231.8.

To a mixture of compound 26G (60 mg, 259.46 umol) in THF (2 mL) and $H_2O$ (2 mL) was added NaOH (1 M, 778 uL) in one portion at 0° C. The mixture was stirred at 25° C. for 16 hrs. The mixture was extracted with MTBE (2×30 mL) and washed with water (3×30 mL). The water layers were acidified to pH ~4 with 1N HCl, then, the solution extracted with EtOAc (3×30 mL). The organic layers were dried over $Na_2SO_4$ and concentrated to give compound 5 (50 mg, yield: 86.6%) as yellow oil, which was used directly for next step without further purification. $^1H$ NMR ($CDCl_3$, 400 MHz): δ 8.05-8.01 (m, 2H), 7.48-7.43 (m, 3H), 2.62 (s, 3H). MS (ESI) m/z $(M+H)^+$203.8.

Compound 26 (15 mg, yield: 23.0%, white solid) was prepared as in Example 5 from the corresponding intermediate carboxylic acid, compound 26H. Compound 26: $^1H$ NMR ($CDCl_3$, 400 MHz): δ 8.08 (br d, J=6.6 Hz, 2H), 7.41 (br d, J=6.8 Hz, 2H), 7.32-7.24 (m, 4H), 7.13 (br d, J=6.6 Hz, 2H), 6.77 (br s, 2H), 5.76-5.68 (m, 1H), 5.55 (br s, 1H), 3.45 (br dd, J=5.3, 14.3 Hz, 1H), 3.24 (br dd, J=7.3, 14.1 Hz, 1H), 2.56 (s, 3H). MS (ESI) m/z $(M+H)^+$378.1.

Example 10

(S)—N-(4-amino-3,4-dioxo-1-phenylbutan-2-yl)-5-phenyl-1,2,3-thiadiazole-4-carboxamide (28)

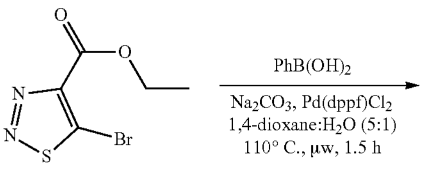

28A

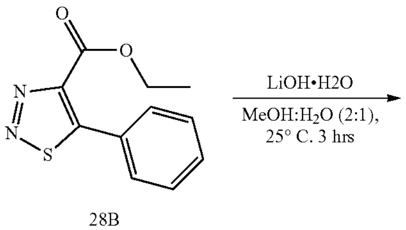

28B

-continued

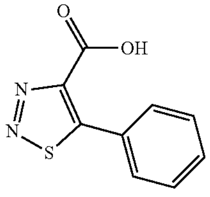

28C

A mixture consisting of compound 28A (200 mg, 843.63 umol), phenyl boronic acid (23 mg, 110.98 umol) and $Na_2CO_3$ (22.4 mg, 2.11 mmol) was stirred at 110° C. for 1.5 hrs under microwave. The reaction mixture was cooled to room-temperature, filtered and concentrated under reduced pressure to give a residue. The residue was purified by Pre-HPLC (base condition) to afford compound 28B (23 mg, yield 11.64%) as a light yellow oil. $^1H$ NMR ($CDCl_3$, 400 MHz): δ7.44-7.58 (m, 5H), 4.44 (q, J=7.20 Hz, 2H), 1.32 (t, J=7.17 Hz, 3H).

To a mixture of compound 28B (50 mg, 213.43 umol) in MeOH (3 mL) and $H_2O$ (1.50 mL) was added $LiOH.H_2O$ (26.9 mg, 640.29 umol) in one portion and the mixture was stirred at 25° C. for 3 hrs. The reaction mixture was concentrated under reduced pressure to remove MeOH. The residue was diluted with $H_2O$ (8 mL), adjusted to pH ~3 with 1N HCl, and then extracted with EtOAc (30 mL×3). The combined organic layers were washed with brine (20 mL), dried over anhydrous $Na_2SO_4$, filtered and concentrated under reduced pressure to give intermediate compound 28C (38 mg, crude) as brown solid. $^1H$ NMR ($CDCl_3$, 400 MHz): δ 7.63-7.57 (m, 2H), 7.54-7.45 (m, 3H). MS (ESI) m/z $(M+1)^+$206.7.

Compound 28 (18.9 mg, 38.00% yield, white solid) was prepared as in Example 5 from the corresponding intermediate carboxylic acid, compound 28C. Compound 28: $^1H$ NMR ($CDCl_3$, 400 MHz): δ 8.07 (d, J=7.2 Hz, 1H), 7.59-7.53 (m, 2H), 7.49-7.41 (m, 3H), 7.33-7.27 (m, 3H), 7.23-7.19 (m, 2H), 6.77 (br s, 1H), 5.84-5.76 (m, 1H), 5.52 (br s, 1H), 3.51-3.45 (m, 1H), 3.25-3.18 (m, 1H). MS (ESI) m/z $(M+1)^+$381.1.

Example 11

(S)—N-(4-amino-3,4-dioxo-1-phenylbutan-2-yl)-3-phenyl-1H-pyrazole-4-carboxamide (30)

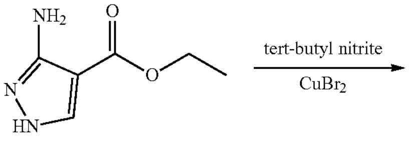

30A

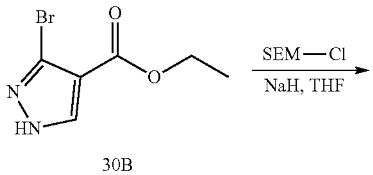

30B

-continued

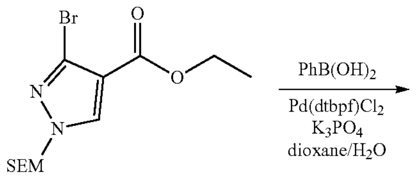

30C

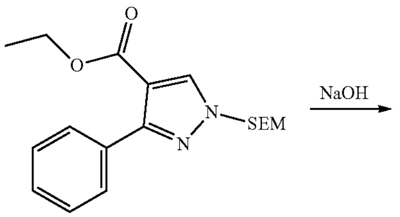

30D

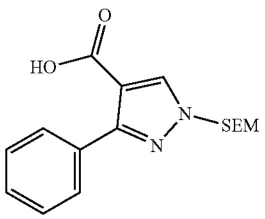

30E

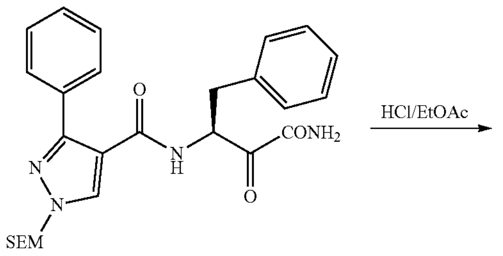

30G

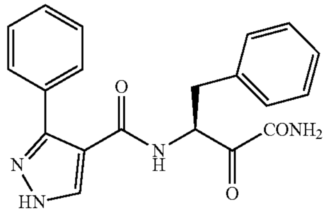

30

To a solution of t-BuONO (3.8 mL, 30.94 mmol) in $CH_3CN$ (60 mL) was added $CuBr_2$ (6.91 g, 30.94 mmol). The mixture was stirred at 25° C. for 1 h under $N_2$. Then compound 30A (4 g, 25.78 mmol) was added portionwise. The mixture was then heated to 70° C. and stirred for 12 hrs. The reaction was washed with $H_2O$ (100 mL), extracted with EtOAc (100 mL×2). The organics were collected, dried with $Na_2SO_4$, filtered and concentrated to afford intermediate compound 30B (6 g, crude) as black brown oil. MS (ESI) m/z $(M+H)^+$218.9, 220.9.

To a solution of NaH (1.64 g, 41.09 mmol, 60% purity) in THF (80 mL) at 0° C. was added a solution of compound 30B (6 g, 27.39 mmol) in THF (20 mL). After addition, the mixture was warmed up to 25° C. and stirred for 2 hrs. Then the solution was cooled to 0° C. and a solution of SEM-Cl (5.34 mL, 30.13 mmol) in THF (100 mL) was added at 0° C. The mixture was then warmed up to 25° C. and stirred for 12 hrs. The reaction was quenched with $H_2O$ (100 mL) dropwise. The mixture was extracted with EtOAc (100 mL×2). The organics were collected and concentrated. The residue was purified by column (Petroleum Ether:Ethyl Acetate=10:1) to afford compound 30C (3 g, yield: 31.14%) as yellow oil.

To a solution of compound 30C (2.60 g, 7.44 mmol) and $PhB(OH)_2$ (1.09 g, 8.93 mmol) in dioxane (36 mL) and $H_2O$ (12 mL) was added $Pd(dtbpf)Cl_2$ (485 mg, 0.74 mmol) and $K_3PO_4$ (4.74 g, 22.32 mmol). The mixture was stirred at 70° C. under $N_2$ for 2 hrs. The reaction was diluted with $H_2O$ (20 mL), extracted with EtOAc (20 mL×2). The organics were collected and concentrated. The residue was purified by column (Petroleum Ether:Ethyl Acetate=10:1) to afford compound 30D (2.40 g, yield: 93.1%) as colorless oil. MS (ESI) m/z $(M+H)^+$347.1. $^1$H NMR (400 MHz, DMSO-$d_6$) δ 8.60 (s, 1H), 7.78-7.72 (m, 2H), 7.56-7.34 (m, 3H), 5.52 (s, 2H), 4.25-4.16 (m, 2H), 3.70-3.62 (m, 2H), 1.26 (t, J=7.1 Hz, 3H), 0.94-0.85 (m, 2H), 0.03-0.02 (m, 9H).

A solution of compound 30D (200 mg, 577.20 umol) in MeOH (4 mL), and then NaOH (230 mg, 5.77 mmol) in $H_2O$ (4 mL) was added dropwise. The mixture was stirred at 25° C. for 19 hrs. The reaction mixture was diluted by addition $H_2O$ (10 mL), and then extracted with MTBE (10 mL×2). The water layers were neutralized by 1N HCl to pH ~3, and extracted with EtOAc (10 mL×3). The combined organic layers were washed with brine (20 mL), dried over $Na_2SO_4$, filtered and concentrated under reduced pressure to give the compound 30E (140 mg, yield: 76.17%) as a yellow oil. $^1$H-NMR (400 MHz, DMSO-$d_6$) δ 12.41 (br s, 1H), 8.54 (s, 1H), 7.81-7.74 (m, 2H), 7.53-7.36 (m, 3H), 5.50 (s, 2H), 3.66 (t, J=8.0 Hz, 2H), 0.90 (t, J=7.9 Hz, 2H), 0.01-0.04 (m, 9H).

Compound 30G (140 mg, yield: 93.72%, white solid) was prepared as in Example 5 from the corresponding intermediate carboxylic acid, compound 30E. Compound 30G: $^1$H-NMR (400 MHz, DMSO-$d_6$) δ 8.54 (d, J=7.3 Hz, 1H), 8.25 (s, 1H), 8.15-8.00 (m, 1H), 7.87 (s, 1H), 7.66-7.52 (m, 2H), 7.43-7.23 (m, 9H), 5.46 (br d, J=6.8 Hz, 1H), 5.38-5.30 (m, 1H), 3.76-3.57 (m, 2H), 3.27-3.12 (m, 1H), 2.96-2.76 (m, 1H), 0.94-0.89 (m, 2H), 0.03-0.00 (m, 9H).

To a solution of compound 30G (18.00 mg, 36.54 umol) in ethyl acetate (1.00 mL) was added 4M HCl/EtOAc (5.00 mL). Then the reaction was stirred at 30° C. for 4 hrs. The reaction mixture was added petroleum ether (50 mL), the mixture was stirred for 3 mins, filtered and the desired solid was dried in vacuo to give compound 30 (6.00 mg, yield: 45.31%) as white solid. $^1$H NMR (400 MHz, DMSO-d6) δ 8.34 (d, J=7.5 Hz, 1H), 8.02 (s, 1H), 7.99-7.95 (m, 1H), 7.77 (s, 1H), 7.59-7.53 (m, 2H), 7.35-7.28 (m, 4H), 7.28-7.23 (m, 5H), 7.23-7.16 (m, 2H), 5.30-5.21 (m, 1H), 3.19-3.10 (m, 1H), 2.83 (dd, J=9.8, 13.8 Hz, 1H). MS (ESI) m/z $(M+H)^+$ 363.1.

Example 12

Compounds 32, 458, 476-479, 521

(S)—N-(4-amino-3,4-dioxo-1-phenylbutan-2-yl)-1-methyl-3-phenyl-1H-pyrazole-4-carboxamide (32)

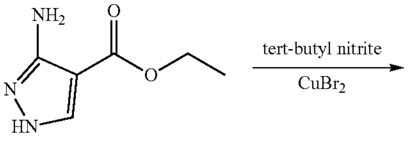

32A

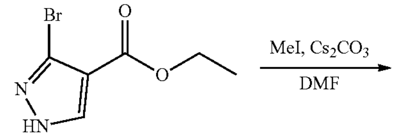

32B

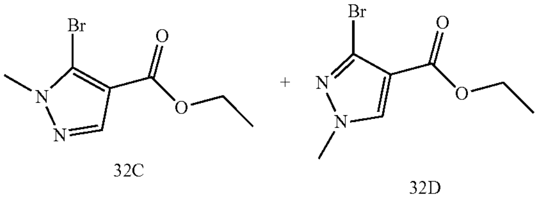

32C

32D

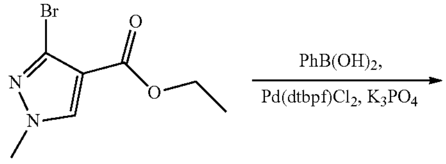

32D

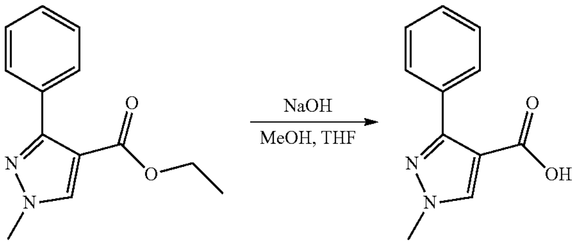

32E

32F

To a solution of t-BuONO (3.19 g, 30.94 mmol, 3.67 mL) in $CH_3CN$ (60 mL) was added $CuBr_2$ (6.91 g, 30.94 mmol). The mixture was stirred at 25° C. for 1 hour under $N_2$. Then compound 32A (4.00 g, 25.78 mmol) was added portion-wise. After heated to 70° C. and stirred for 12 hrs, the mixture was concentrated and diluted with ethyl acetate (100 mL). The mixture was then washed with HCl (1M, 100 mL), saturated $NaHCO_3$ (100 mL), brine (100 mL), dried over $Na_2SO_4$ and concentrated to obtain intermediate compound 32B (5.6 g, crude) as yellow oil. MS (ESI) m/z $(M+H)^+$ 220.9.

To a solution of compound 32B (5.6 g, 25.57 mmol) in DMF (200 mL) was added MeI (14.52 g, 102.28 mmol, 6.37 mL) and $Cs_2CO_3$ (33.32 g, 102.28 mmol). The mixture was stirred at 25° C. for 12 hrs. The mixture was diluted with $H_2O$ (1000 mL) and extracted with ethyl acetate (500 mL), then the organic layer was washed with brine (500 mL×3), dried over $Na_2SO_4$ and concentrated. The residue (4 g) was purified by preparatory-HPLC (basic condition). The residue was purified by column chromatography (SiO2, Petroleum ether/Ethyl acetate=10/1 to 5:1). Compound 32C (1 g, yield: 16.8%) was obtained as a white solid. Compound 32D (2 g, yield: 33.6%) was obtained as a white solid.

Compound 32C: $^1H$ NMR (400 MHz, DMSO-$d_6$) δ 7.93 (s, 1H), 4.24-4.18 (m, 2H), 3.85 (s, 3H), 1.28-1.23 (m, 3H).

Compound 32D: $^1H$ NMR (400 MHz, DMSO-$d_6$) δ 8.33 (s, 1H), 4.22-4.16 (m, 2H), 3.83 (s, 3H), 1.26-1.22 (m, 3H).

A mixture of ethyl compound 32D (500.0 mg, 2.15 mmol), phenylboronic acid (314.6 mg, 2.58 mmol), Pd(dtbpf)$Cl_2$ (140.1 mg, 215.00 umol), $K_3PO_4$ (1.37 g, 6.45 mmol) in dioxane (30 mL) and $H_2O$ (10 mL) was degassed and purged with $N_2$ for 3 times. After stirred at 70° C. for 1 hour under $N_2$ atmosphere, the mixture was concentrated and diluted with ethyl acetate (30 mL). The mixture was then washed with HCl (1M, 50 mL), saturated aqueous $NaHCO_3$ (50 mL), brine (50 mL), dried over $Na_2SO_4$ and concentrated to obtain intermediate compound 32E (480 mg, crude) as a brown oil. MS (ESI) m/z $(M+H)^+$230.9.

To a solution of compound 32E (380.0 mg, 1.65 mmol) in MeOH (5 mL) and THF (5 mL) was added NaOH (2 M, 16.5 mL). The mixture was stirred at 60° C. for 1 hour. The mixture was concentrated and diluted with $H_2O$ (10 mL), the mixture was extracted with ethyl acetate (10 mL), the water phase was added HCl (1M) until pH ~3, then the mixture was extracted with ethyl acetate (20 mL), the organic layer was washed with brine (10 mL), dried over $Na_2SO_4$ and concentrated. Compound 32F (320 mg, yield: 95.9%) was obtained as a brown solid. $^1H$ NMR (400 MHz, DMSO-$d_6$) δ 12.03-11.85 (m, 1H), 8.27 (s, 1H), 7.74-7.68 (m, 2H), 7.40-7.30 (m, 3H), 3.87 (s, 3H).

Compound 32 (40.0 mg, yield: 64.7%, white solid) was prepared as in Example 5 from the corresponding intermediate carboxylic acid, compound 32F. Compound 32: $^1H$ NMR (400 MHz, DMSO-$d_6$) δ 8.33 (d, J=7.2 Hz, 1H), 8.05 (s, 2H), 7.81 (br s, 1H), 7.63-7.53 (m, 2H), 7.39-7.20 (m, 8H), 5.33-5.26 (m, 1H), 3.93-3.86 (m, 3H), 3.21-3.13 (m, 1H), 2.88-2.79 (m, 1H). MS (ESI) m/z $(M+H)^+$377.1.

N-(4-(cyclopropylamino)-3,4-dioxo-1-phenylbutan-2-yl)-1-methyl-3-phenyl-1H-pyrazole-4-carboxamide (458)

Compound 458 (270 mg, yield: 67.4%, white solid) was prepared as in compound 12 from the corresponding intermediate carboxylic acid, compound 32F and 3-amino-N-cyclopropyl-2-hydroxy-4-phenylbutanamide hydrochloride. Compound 458: $^1H$ NMR (400 MHz, DMSO-$d_6$) δ 8.80 (d, J=4.4 Hz, 1H), 8.38 (d, J=7.3 Hz, 1H), 8.05 (s, 1H), 7.56 (s, 2H), 7.36-7.17 (m, 8H), 5.28 (s, 1H), 3.89 (s, 3H), 3.16 (d, J=11.2 Hz, 1H), 2.89-2.73 (m, 2H), 0.71-0.52 (m, 4H). MS (ESI) m/z $(M+H)^+$417.1.

(S)—N-(4-fluoro-3-oxo-1-phenylbutan-2-yl)-1-methyl-3-phenyl-1H-pyrazole-4-carboxamide (476)

Compound 476 (36.8 mg, yield: 34.22%, white solid) was prepared as in compound 12 from the corresponding intermediate carboxylic acid, compound 32F and (2S,3S)-3-amino-1-fluoro-4-phenylbutan-2-ol hydrochloride. Compound 476: $^1H$ NMR (400 MHz, $CDCl_3$) δ 7.91 (s, 1H), 7.52-7.47 (m, 2H), 7.46-7.37 (m, 3H), 7.25-7.19 (m, 3H), 6.94-6.84 (m, 2H), 6.06 (d, J=6.4 Hz, 1H), 5.03-4.71 (m, 3H), 3.93 (s, 3H), 3.09-3.01 (m, 1H), 2.85-2.76 (m, 1H). MS (ESI) m/z $(M+H)^+$366.1.

(S)—N-(4-fluoro-3-oxo-1-phenylbutan-2-yl)-3-methyl-1-(pyrazin-2-yl)-1H-pyrazole-5-carboxamide (477)

Compound 477 (110 mg, yield: 90.33%, white solid) was prepared as in compound 12 from the corresponding intermediate carboxylic acid, compound 85B and (2S,3S)-3-amino-1-fluoro-4-phenylbutan-2-ol hydrochloride. Compound 477: $^1$H NMR (400 MHz, $CDCl_3$) δ 9.20 (s, 1H), 9.08-9.00 (m, 1H), 8.50-8.48 (m, 1H), 8.11 (s, 1H), 7.27-7.24 (m, 3H), 7.17-7.12 (m, 2H), 6.79 (s, 1H), 5.33-5.24 (m, 1H), 5.11-4.79 (m, 2H), 3.45-3.33 (m, 1H), 3.15-3.11 (m, 1H), 2.38 (s, 3H). MS (ESI) m/z $(M+H)^+$368.1.

(S)—N-(4-fluoro-3-oxo-1-phenylbutan-2-yl)-3-methyl-1-(pyridin-2-yl)-1H-pyrazole-5-carboxamide (478)

Compound 478 (82 mg, yield: 54.97%, white solid) was prepared as in compound 12 from the corresponding intermediate carboxylic acid, compound 12F and (2S,3S)-3-amino-1-fluoro-4-phenylbutan-2-ol hydrochloride. Compound 478: $^1$H NMR (400 MHz, $CDCl_3$) δ 10.70 (d, J=6.40 Hz, 1H), 8.14 (d, J=4.40 Hz, 1H), 7.92-7.83 (m, 2H), 7.26-7.14 (m, 6H), 6.88 (s, 1H), 5.24-5.20 (m, 1H), 5.05-4.74 (m, 2H), 3.29-3.18 (m, 2H), 2.35 (s, 3H). MS (ESI) m/z $(M+1)^+$367.2.

(S)—N-(4-fluoro-3-oxo-1-phenylbutan-2-yl)-3-methyl-1-phenyl-1H-pyrazole-5-carboxamide (479)

Compound 479 (100 mg, yield: 82.06%, white solid) was prepared as in compound 12 from the corresponding intermediate carboxylic acid, 3-methyl-1-phenyl-1H-pyrazole-5-carboxylic acid and (2S,3S)-3-amino-1-fluoro-4-phenylbutan-2-ol hydrochloride. Compound 479: $^1$H NMR (400 MHz, $CDCl_3$) δ 7.46-7.28 (m, 8H), 7.08-7.03 (m, 2H), 6.51 (s, 1H), 6.28 (br d, J=7.0 Hz, 1H), 5.20-5.13 (m, 1H), 5.03-4.73 (m, 2H), 3.22-3.15 (m, 1H), 3.02-2.95 (m, 1H), 2.35 (s, 3H). MS (ESI) m/z $(M+H)^+$366.1.

(S)—N-(4-fluoro-3-oxo-1-phenylbutan-2-yl)-3-(2-fluoro-4-((prop-2-yn-1-yloxy)methyl)phenyl)-1-methyl-1H-pyrazole-4-carboxamide (521)

Compound 521 (250 mg, yield: 78.40%, white solid) was prepared using coupling conditions as in compound 476 from the corresponding intermediate ethyl 3-iodo-1-methyl-1H-pyrazole-4-carboxylate and (2-fluoro-4-(hydroxymethyl)phenyl)boronic acid followed by alkylation with 3-bromoprop-1-yne and then the intermediate obtained was subjected to hydrolysis and coupling with (2S,3S)-3-amino-1-fluoro-4-phenylbutan-2-ol hydrochloride as in compound 12 to yield compound 521. Compound 521: $^1$H NMR (400 MHz, $CDCl_3$) δ 7.89 (s, 1H), 7.40 (t, J=7.6 Hz, 1H), 7.24-7.13 (m, 5H), 6.94-6.92 (m, 2H), 5.97 (d, J=6.4 Hz, 1H), 5.09-5.01 (m, 1H), 4.96-4.83 (m, 1H), 4.83-4.70 (m, 1H), 4.66 (s, 2H), 4.19 (d, J=2.4 Hz, 2H), 3.95 (s, 3H), 3.03 (d, J=6.4 Hz, 1H), 2.95-2.88 (m, 1H), 2.49 (t, J=2.3 Hz, 1H). MS (ESI) m/z $(M+H)^+$452.2.

Example 13

(S)—N-(4-amino-3,4-dioxo-1-phenylbutan-2-yl)-3-ethyl-1-phenyl-1H-pyrazole-5-carboxamide (33)

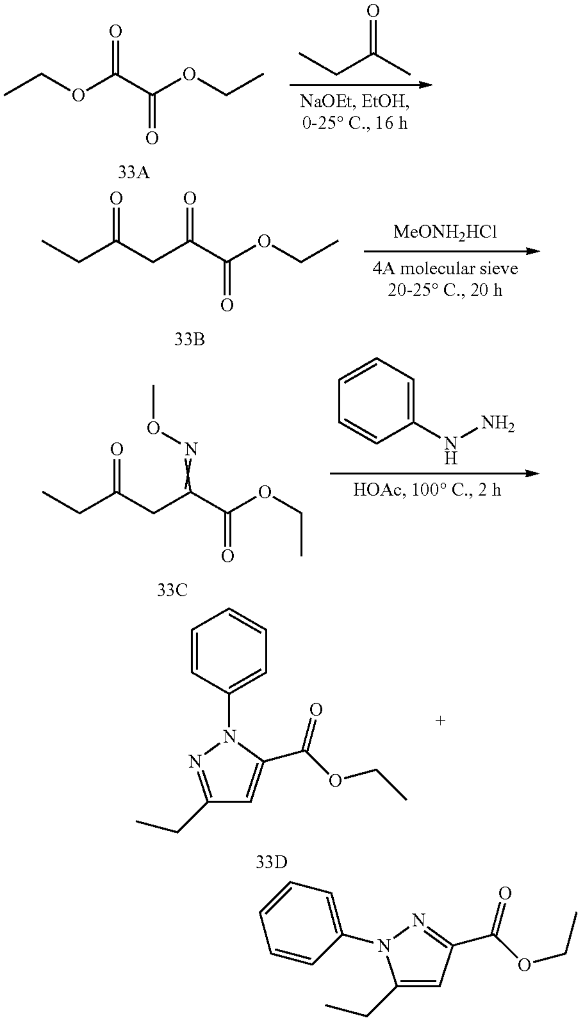

33A

33B

33C

33D

33E

A mixture of compound 33A (46.73 mL, 342.14 mmol) and butan-2-one (30.46 mL, 342.14 mmol) was added dropwise to the solution of NaOEt (prepared by Na (9.5 g) in EtOH (200 mL)) at 0° C. Then the reaction was stirred at 20-25° C. for 16 hrs. The reaction was adjusted to pH ~6-7 with HCl (2M) and then removed the solvent to give a residue, which was diluted with ethyl acetate (500 mL), washed with brine (150 mL), dried over $Na_2SO_4$ and concentrated to give the crude product which was purified by flash column chromatography (Petroleum Ether:Ethyl Acetate=1:0 to 10:1) to give compound 33B (23.0 g, yield: 39.0%) as a yellow oil. $^1$H NMR ($CDCl_3$, 400 MHz) δ 14.34 (br s, 1H), 6.31 (s, 1H), 4.28 (q, J=7.2 Hz, 2H), 2.47 (q, J=7.3 Hz, 2H), 1.34-1.27 (m, 3H), 1.11 (t, J=7.5 Hz, 3H).

The mixture of compound 33B (10 g, 58.08 mmol), O-methylhydroxylamine (4.85 g, 58.08 mmol, HCl) and 4A° molecular sieve (10 g) in DMF (100 mL) was stirred at 20-25° C. for 20 hrs. Filtered to remove the 4A° molecular sieve and the filtrate was diluted with $H_2O$ (800 mL), extracted with ethyl acetate (300 mL×3). The organic phase was combined and washed with brine (300 mL×3) and concentrated to give the crude product, which was purified by flash column chromatography (Petroleum Ether:Ethyl Acetate=1:0 to 5:1) to give compound 33C (3.5 g, yield: 29.95%) as a yellow oil. $^1H$ NMR ($CDCl_3$, 400 MHz) δ 4.41-4.29 (m, 2H), 4.06 (s, 3H), 3.71 (s, 2H), 2.60-2.46 (m, 2H), 1.42-1.32 (m, 3H), 1.08 (t, J=7.3 Hz, 3H).

The mixture of compound 33C (3.5 g, 17.39 mmol) and phenylhydrazine (1.88 g, 17.39 mmol) in AcOH (20 mL) was stirred at 100° C. for 2 hrs. The solvent was removed and the residue was adjusted to pH ~7-8 with saturated $NaHCO_3$ aqueous and extracted with ethyl acetate (60 mL×2). The organic phase were combined and washed with brine (50 mL), concentrated to give a residue, which was purified by flash column chromatography (Petroleum Ether: Ethyl Acetate=1:0 to 5:1) to give compound 33D (0.3 g, 1.23 mmol, 7.05% yield) as a yellow solid and compound 33E (3.0 g, 12.21 mmol, yield 70.19%) as a yellow oil.

Compound 33D: $^1H$ NMR ($CDCl_3$, 400 MHz) δ 7.50-7.37 (m, 5H), 6.87 (s, 1H), 4.24 (q, J=7.0 Hz, 2H), 2.76 (q, J=7.5 Hz, 2H), 1.32 (t, J=7.5 Hz, 3H), 1.25 (t, J=7.2 Hz, 3H). MS (ESI) m/z $(M+H)^+$245.0. Compound 33E: $^1H$ NMR ($CDCl_3$, 400 MHz) δ 7.46-7.31 (m, 1H), 6.70 (s, 1H), 4.35 (q, J=7.1 Hz, 1H), 2.58 (q, J=7.4 Hz, 1H), 1.33 (t, J=7.2 Hz, 1H), 1.16 (t, J=7.5 Hz, 1H). MS (ESI) m/z $(M+H)^+$245.0.

The mixture of compound 33D (3.0 g, 12.28 mmol) and $LiOH.H_2O$ (3.09 g, 73.68 mmol) in MeOH (10 mL) and $H_2O$ (3 mL) was stirred at 25° C. for 16 hrs. The reaction was adjusted with HCl (2M) to pH ~3-4 and removed the solvent. The residue was extracted with ethyl acetate (100 mL×3) and combined, washed with brine (100 mL), dried over $Na_2SO_4$. Filter and the filtrate were concentrated to give compound 33F (2.7 g, crude) as a yellow solid. $^1H$ NMR ($CDCl_3$, 400 MHz) δ 8.58 (br s, 1H), 7.46-7.34 (m, 5H), 6.89 (s, 1H), 2.73 (q, J=7.6 Hz, 2H), 1.28 (t, J=7.6 Hz, 3H). MS (ESI) m/z $(M+H)^+$216.9.

The mixture of compound 33F (2.7 g, 12.49 mmol) and 1-hydroxypyrrolidine-2,5-dione (1.44 g, 12.49 mmol) in THF (20 mL) was stirred at 0° C. for 15 min, then solution of DCC (2.6 g, 12.61 mmol, 2.55 mL) in THF (10 mL) was added dropwise at 0° C. and stirred at 25-30° C. for 16 hrs. After filtered and the filtrate was concentrated to give compound 33G (4.0 g, crude) as a yellow solid. The product was used directly in next step.

The mixture of compound 33G (0.2 g, 638.35 umol), compound 12G (147.3 mg, 638.35 umol, HCl) and DIEA (0.25 mL, 1.28 mmol) in DMF (10 mL) was stirred at 20-25° C. for 16 hrs. The reaction was diluted with $H_2O$ (60 mL) and ethyl acetate (30 mL) and stirred at 20-25° C. for 0.5 h. White solid precipitated out and was filtered, the filter cake was washed with $H_2O$ (10 mL×2) and dried over under reduced pressure to give compound 33H (100.0 mg, yield: 39.24%) as a white solid. $^1H$ NMR (DMSO-$d_6$, 400 MHz) δ 8.53-8.11 (m, 1H), 7.40-7.20 (m, 10H), 7.16-7.01 (m, 2H), 6.59 (s, 1H), 5.96-5.69 (m, 1H), 4.49-4.36 (m, 1H), 4.03-3.90 (m, 1H), 2.96-2.70 (m, 2H), 2.62 (q, J=7.7 Hz, 2H), 1.22 (t, J=7.5 Hz, 3H). MS (ESI) m/z $(M+H)^+$393.0.

The mixture of compound 33H (100 mg, 254.81 umol) and DMP (540.4 mg, 1.27 mmol, 394.44 uL) in DMSO (5.0 mL) was stirred at 25-30° C. for 16 hrs. The reaction was diluted with DCM (20 mL) and quenched with a mixture of saturated $NaHCO_3$ aqueous and $Na_2S_2O_3$ aqueous (10%) (80 mL, 1:1) and stirred at 20-25° C. for 0.5 hours. White solid precipitated out and was filtered, the filter cake was washed with $H_2O$ (3 mL×2) and dried under reduced pressure to give compound 33 (20.0 mg, yield: 20%) as a white solid. $^1H$ NMR (DMSO-$d_6$, 400 MHz) δ 9.10 (d, J=7.9 Hz, 1H), 8.10 (s, 1H), 7.85 (s, 1H), 7.36-7.20 (m, 8H), 7.18-7.10 (m, 2H), 6.58 (s, 1H), 5.30-5.21 (m, 1H), 3.18 (dd, J=3.5, 13.9 Hz, 1H), 2.80 (dd, J 10.6, 13.7 Hz, 1H), 2.60 (q, J=7.7 Hz, 2H), 1.20 (t, J=7.6 Hz, 3H). MS (ESI) m/z $(M+H)^+$ 391.1.

Example 14

(S)—N-(1-oxo-3-phenylpropan-2-yl)-1-(1-phenyl-1H-pyrazol-3-yl)-1H-imidazole-5-carboxamide (34)

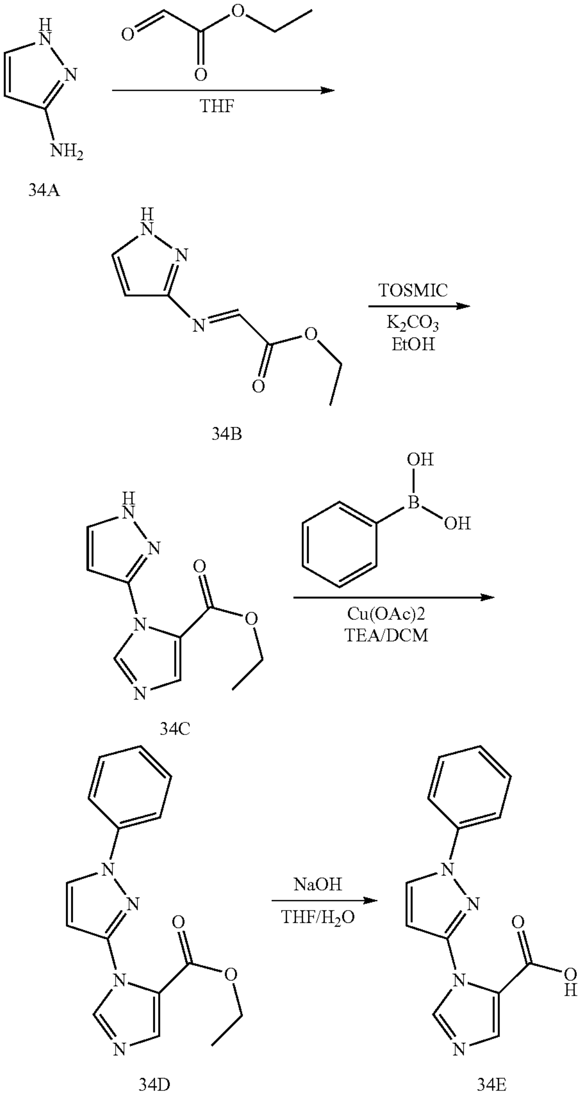

34A
34B
34C
34D
34E

To a solution of 34A (15 g, 180.53 mmol) in THF (200 mL) was added ethyl 2-oxoacetate (47.9 g, 234.69 mmol). The mixture was stirred at 25° C. for 0.5 h. The reaction mixture was filtered and concentrated under reduced pressure to give intermediate compound 34B (55.3 g, crude) as brown solid. MS (ESI) m/z $(M+H)^+$167.8.

To a solution of 34B (40 g, 239 mmol) in EtOH (400 mL) was added $K_2CO_3$ (50 g, 362 mol) and 1-(isocyanomethyl-sulfonyl)-4-methyl-benzene (40 g, 204.88 mmol). The mixture was stirred at 90° C. for 0.5 h. The reaction mixture was filtered and concentrated under reduced pressure to give a residue. The residue was purified by column chromatography ($SiO_2$, Petroleum ether:Ethyl acetate=1:0 to 5:2) to afford compound 34C (12 g, yield: 24.3%) as brown solid. $^1H$ NMR (400 MHz, $CDCl_3$) δ 11.80-11.35 (m, 1H), 7.87 (d, J=1.10 Hz, 1H), 7.84 (d, J=1.10 Hz, 1H), 7.58 (d, J=2.43 Hz, 1H), 6.45 (d, J=2.43 Hz, 1H), 4.25 (q, J=7.06 Hz, 2H), 1.29 (t, J=7.17 Hz, 3H). MS (ESI) m/z $(M+H)^+$207.0.

A mixture of 34C (5 g, 24.3 mmol), phenylboronic acid (4.4 g, 36.4 mmol), $Cu(OAc)_2$ (4.4 g, 24.3 mmol), triethylamine (7.4 g, 72.8 mmol) in DCM (200 mL) was degassed and purged with 02 for 3 times, and then the mixture was stirred at 25° C. for 10 hrs under 02 atmosphere. The reaction mixture was filtered and concentrated under reduced pressure to give a residue. The residue was purified by column chromatography ($SiO_2$, Petroleum ether:Ethyl acetate=1:0 to 2:1). Compound 34D (2.3 g, yield: 33.6%) was obtained as a white solid. $^1H$ NMR (400 MHz, $CDCl_3$) δ 8.04-7.94 (m, 2H), 7.87 (s, 1H), 7.71 (br d, J=7.7 Hz, 2H), 7.49 (br t, J=7.1 Hz, 2H), 7.36 (br d, J=7.1 Hz, 1H), 7.27 (d, J=2.0 Hz, 2H), 6.70-6.61 (m, 1H), 4.29 (dd, J=2.1, 7.2 Hz, 2H), 1.38-1.22 (m, 3H). MS (ESI) m/z $(M+H)^+$282.9.

To a solution of 34D (2.5 g, 8.86 mmol) in THF (30 mL) and $H_2O$ (6 mL) was added NaOH (708 mg, 17.7 mmol). The mixture was stirred at 80° C. for 1.5 hrs. The reaction mixture was concentrated under reduced pressure to remove THF, and then washed with EtOAc (20 mL). The aqueous layer was acidized with 1M HCl (to pH ~5) and then extracted with EtOAc (30 mL×3). The combined organic layer was washed with $H_2O$ (40 mL), brine (40 mL), dried over $Na_2SO_4$, filtered and concentrated to afford intermediate compound 34E (1.90 g, yield: 84.31%) as yellow solid. $^1H$ NMR (400 MHz, DMSO-$d_6$) δ 8.62 (d, J=2.6 Hz, 1H), 8.19 (s, 1H), 7.86 (d, J=7.9 Hz, 2H), 7.76 (s, 1H), 7.53 (t, J=7.9 Hz, 2H), 7.39-7.31 (m, 1H), 6.77 (d, J=2.6 Hz, 1H). MS (ESI) m/z $(M+H)^+$254.9.

Compound 34 (50 mg, yield: 62.8%, white solid) was prepared as in Example 6 from the corresponding intermediate compounds 34E and 21G. Compound 34: $^1H$ NMR (400 MHz, $CDCl_3$) δ 9.66 (s, 1H), 7.95 (d, J=2.4 Hz, 1H), 7.89 (s, 1H), 7.67 (s, 1H), 7.58 (d, J=8.2 Hz, 2H), 7.45 (t, J=7.8 Hz, 2H), 7.36-7.31 (m, 1H), 7.26-7.19 (m, 4H), 7.08 (d, J=6.4 Hz, 2H), 6.55 (d, J=2.4 Hz, 1H), 4.84 (q, J=6.4 Hz, 1H), 3.21 (d, J=6.4 Hz, 2H). MS (ESI) m/z $(M+H_2O+H)^+$ 404.1.

Example 15

Compounds 35, 205

(S)—N-(1-amino-5-methyl-1,2-dioxohexan-3-yl)-3-methyl-5-phenylisoxazole-4-carboxamide (35)

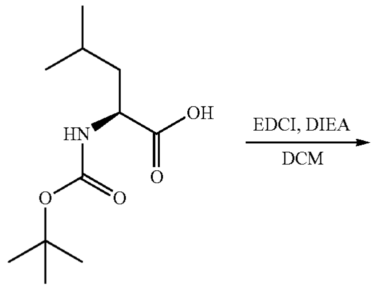

35A

-continued

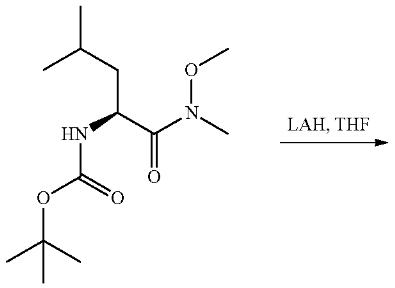

35B

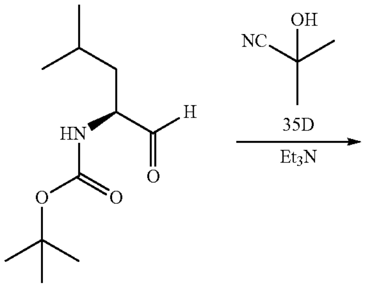

35C

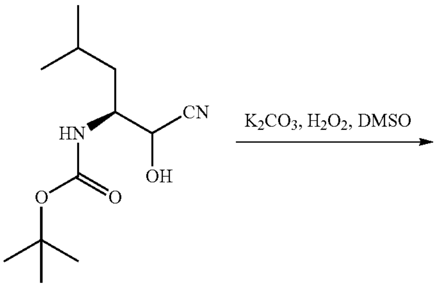

35E

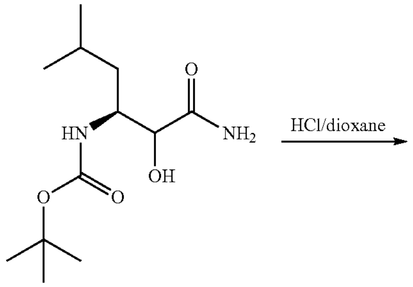

35F

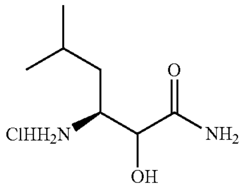

35G

To a solution of compound 35A (20 g, 86.47 mmol), N-methoxymethanamine (12.65 g, 129.71 mmol, HCl), HOBt (11.68 g, 86.47 mmol) in DCM (400 mL) was added DIEA (33.53 g, 259.41 mmol, 45.31 mL) at 0° C. After that, the reaction mixture was stirred at 0° C. for 0.1 h, and then EDCI (19.89 g, 103.76 mmol) was added, after addition, the reaction mixture was stirred at 25° C. for 16 hrs. The reaction mixture was concentrated to give a residue and the residue was dissolved in EtOAc (400 mL), washed with 1N HCl (400 mL×2), sat.$NaHCO_3$ (400 mL×2) and brine (400 mL). The organic phase was dried over $Na_2SO_4$ and concentrated. The residue was purified by column chromatography ($SiO_2$, Petroleum Ether~Petroleum Ether:EtOAc=10:1). Compound 35B (40.32 g, yield: 84.98%) was obtained as a colorless oil. $^1H$ NMR (400 MHz, $CDCl_3$) δ 5.04 (br d, J=9.0 Hz, 1H), 4.71 (br s, 1H), 3.77 (s, 3H), 3.18 (s, 3H), 1.80-1.63 (m, 2H), 1.42 (s, 10H), 0.93 (dd, J=6.5, 14.2 Hz, 6H).

To a mixture of LAH (1.53 g, 40.41 mmol) in THF (200 mL) was added dropwise a solution of compound 35B (10.08 g, 36.74 mmol) in THF (100 mL) at 0° C. under $N_2$ atmosphere. After addition, the reaction mixture was stirred at 0° C. for 2 hrs. EtOAc (150 mL) was added dropwise into the reaction mixture at 0° C. and acidified to pH ~1~2 with 1N HCl, then added saturated aqueous $NaHCO_3$ (150 mL×3) and brine (150 mL). The organic layer was dried over $Na_2SO_4$ and concentrated. The compound 35C (27.89 g, yield: 88.15%) was obtained as a yellow oil, which was used for next step directly without purification. $^1H$ NMR (400 MHz, $CDCl_3$): δ 9.71-9.32 (m, 1H), 4.99 (br s, 1H), 4.20 (br d, J=2.9 Hz, 1H), 1.79-1.69 (m, 1H), 1.67-1.57 (m, 1H), 1.43-1.40 (m, 10H), 0.93 (dd, J=1.4, 6.5 Hz, 6H).

To a solution of compound 35C (4 g, 18.58 mmol), compound 35D (3.16 g, 37.16 mmol, 3.40 mL) and $Et_3N$ (2.26 g, 22.30 mmol, 3.09 mL) in dry DCM (40 mL) was stirred at 25° C. for 16 hrs. The reaction mixture was diluted with 50 mL DCM, washed with 0.5N HCl (100 mL), water (100 mL) and brine (100 mL). The organic phase was dried over $Na_2SO_4$, concentrated. Then the residue was purified by column chromatography ($SiO_2$, Petroleum Ether: EtOAc=10:1). Compound 35E (3.9 g, yield: 86.63%) was obtained as a yellow oil. $^1H$ NMR (400 MHz, $CDCl_3$): δ 4.80 (br s, 1H), 4.58-4.36 (m, 1H), 4.02-3.91 (m, 0.5H), 3.77 (br s, 0.5H), 1.75-1.60 (m, 2H), 1.51-1.33 (m, 10H), 1.03-0.89 (m, 6H)

To a solution of compound 35E (15 g, 61.90 mmol) and $K_2CO_3$ (17.11 g, 123.80 mmol) in DMSO (300 mL) was added $H_2O_2$ (70.17 g, 2.15 mol, 60 mL) under $N_2$ at 0° C. After addition, the reaction mixture was stirred at 0° C. for 1 h. Then the reaction mixture was diluted with water (150 mL) and quenched with saturated aqueous $Na_2S_2O_3$ (300 mL) slowly at ice water. The mixture was extracted with EtOAc (300 mL×3) and the combined extracts were washed with saturated aqueous $Na_2S_2O_3$ (300 mL×3). The organic layer was dried over $Na_2SO_4$ and concentrated. The residue was diluted with EtOAc (20 mL) and MTBE (200 mL), the solid was collected and dried in vacuo. Compound 35F (15.15 g, yield: 47.01%) was obtained as a white solid. $^1H$ NMR (400 MHz, DMSO-$d_6$) δ 7.31-6.96 (m, 2H), 6.33 (br d, J=9.0 Hz, 0.6H), 5.95 (d, J=9.5 Hz, 0.4H), 5.44 (br d, J=5.1 Hz, 1H), 3.93-3.65 (m, 2H), 1.57-1.47 (m, 1H), 1.41-1.23 (m, 10H), 0.95-0.70 (m, 7H).

To a solution of compound 35F (5.42 g, 20.82 mmol) in dioxane (10 mL) was added HC/dioxane (4M, 55 mL) at 25° C. After addition, the reaction mixture was stirred at 25° C. for 2 hrs. The reaction was concentrated, and 40 mL of MTBE was added into the reaction mixture and the mixture was stirred for 5 min. Then the mixture was filtered to afford desired compound. Compound 35G (3.8 g, yield: 92.80%) was obtained as a white solid. $^1H$ NMR (400 MHz, DMSO-$d_6$) δ 8.12 (br s, 1.5H), 7.87 (br s, 0.5H), 7.57-7.35 (m, 2H), 4.22 (d, J=2.5 Hz, 0.7H), 4.02 (d, J=3.8 Hz, 0.3H), 3.57 (s, 1H), 3.45 (br d, J=3.5 Hz, 1H), 1.81-1.58 (m, 1H), 1.54-1.33 (m, 1.3H), 1.21 (ddd, J=4.3, 9.5, 14.1 Hz, 0.7H), 0.93-0.67 (m, 6H).

Compound 35 (48 mg, yield: 44.55%, white solid) was prepared as in Example 5 from the corresponding intermediate compounds 23A and 35G. Compound 35: $^1H$ NMR (400 MHz, DMSO-$d_6$) δ 8.99 (br d, J=7.1 Hz, 1H), 8.13 (s, 1H), 7.89-7.77 (m, 3H), 7.54-7.48 (m, 3H), 5.20 (ddd, J=3.3, 7.0, 10.6 Hz, 1H), 2.29 (s, 3H), 1.74-1.62 (m, 1H), 1.56-1.36 (m, 2H), 0.92 (d, J=6.4 Hz, 3H), 0.89-0.84 (m, 3H).

(S)—N-(1-amino-1,2-dioxo-5-phenylpentan-3-yl)-3-methyl-5-phenylisoxazole-4-carboxamide (205)

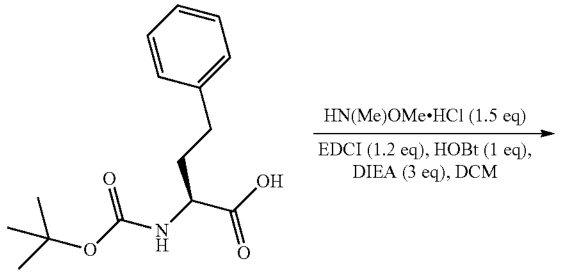

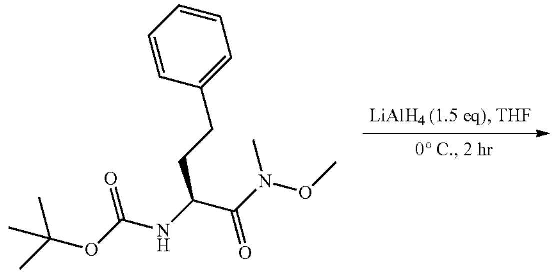

205A

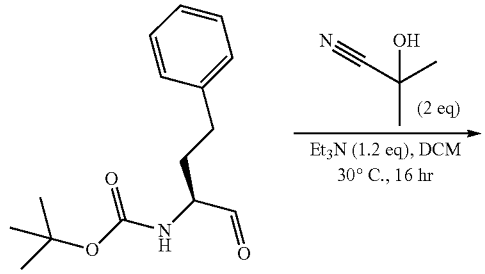

205B

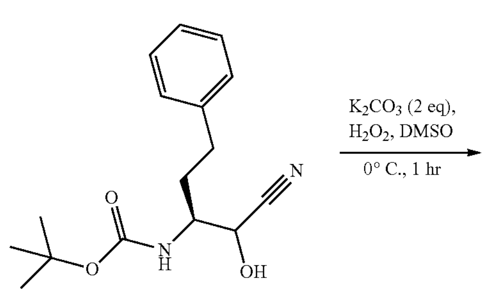

205C

-continued

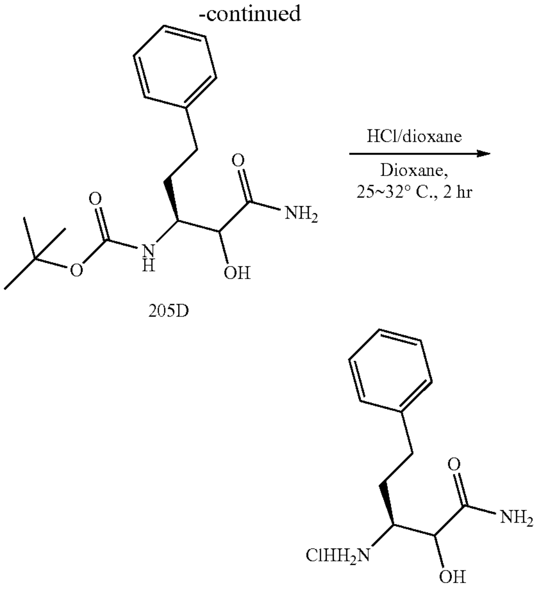

205D

205E

To a mixture of (S)-2-((tert-butoxycarbonyl)amino)-4-phenylbutanoic acid (5 g, 17.90 mmol) and N-methoxymethanamine (2.76 g, 28.26 mmol, HCl), HOBt (2.55 g, 18.84 mmol) in DCM (100.00 mL) was added dropwise DIEA (9.88 mL, 56.53 mmol) and EDCI (4.33 g, 22.61 mmol) in portion at 0° C. under $N_2$. The mixture was stirred at 0° C. for 30 min, then the mixture was stirred at 25° C. for 16 hours. The reaction mixture was diluted with $H_2O$ (200 mL). The two layers were separated and the aqueous phase was extracted with Ethyl Acetate (2×150 mL). The combined organic layers were washed with 0.5N HCl (2×150 mL) and $NaHCO_3$ (2×150 mL), dried over $Na_2SO_4$, filtered and concentrated under reduced pressure to give a residue. The residue was purified by column chromatography ($SiO_2$, Petroleum ether/Ethyl acetate=10:1 to 3:1) to afford compound 205A (4.15 g, 68.32% yield) as a white solid. $^1$H NMR (400 MHz, DMSO-$d_6$) δ 7.35-7.23 (m, 2H), 7.22-7.04 (m, 4H), 4.45-4.21 (m, 1H), 3.59 (s, 3H), 3.06 (s, 3H), 2.81-2.68 (m, 1H), 2.61-2.54 (m, 1H), 1.86-1.65 (m, 2H), 1.45-1.29 (s, 9H).

To a solution of $LiAlH_4$ (88.3 mg, 2.32 mmol) in THF (15 mL) was added drop wise a solution of compound 205A (500 mg, 1.55 mmol) in THF (15 mL) at 0° C. under $N_2$ atmosphere. After addition, the reaction mixture was stirred at 0° C. for 2 hours. The mixture was diluted with ethyl acetate (100 mL) and washed with 1N HCl (20 mL), saturated $NaHCO_3$ (2×20 mL), brine (15 mL). The organic layer was dried over $Na_2SO_4$ and concentrated to afford compound 205B (400 mg, 1.52 mmol) as a yellow oil. $^1$H NMR (400 MHz, DMSO-$d_6$) δ 9.4 (s, 1H), 7.33-7.05 (m, 5H), 3.82-3.72 (m, 1H), 2.71-2.51 (m, 2H), 1.97-1.9 (m, 1H), 1.81-1.66 (m, 1H), 1.51-1.25 (m, 10H).

A solution of compound 205B (1.86 g, 7.06 mmol), 2-hydroxy-2-methylpropanenitrile (1.29 mL, 14.12 mmol) and $Et_3N$ (1.17 mL, 8.47 mmol) in dry DCM (60 mL) was stirred at 30° C. for 16 hours. The reaction mixture was diluted with DCM (50 mL), washed with 0.5N HCl (20 mL), water (20 mL) and brine (20 mL). The organic phase was dried over $Na_2SO_4$, concentrated. The residue was purified by column chromatography ($SiO_2$, Petroleum ether/Ethyl acetate=5/1 to 3:1) to afford compound 205C (900 mg, 43.90% yield) as a white solid. $^1$H NMR (400 MHz, DMSO-$d_6$) δ 7.44-7.21 (m, 51H), 6.75-6.58 (m, 1H), 4.70-4.29 (m, 1H), 3.80-3.51 (m, 1H), 2.86-2.68 (m, 1H), 2.62-2.59 (m, 1H), 2.04-1.64 (m, 2H), 1.53-1.43 (m, 9H).

To a solution of compound 205C (900 mg, 3.1 mmol) and $K_2CO_3$ (856.9 mg, 6.2 mmol) in DMSO (18 mL) was added $H_2O_2$ (3.06 mL, 106.14 mmol) at 0° C. After addition, the reaction mixture was stirred at 0° C. for 1 h. The reaction mixture was diluted with water (200 mL) and quenched with saturated aqueous $Na_2S_2O_3$ (500 mL) slowly at ice water. The mixture was extracted with EtOAc (3×500 mL) and the combined extracts were washed with saturated aqueous $Na_2S_2O_3$ (2×300 mL). The organic layer was dried over $Na_2SO_4$ and concentrated. The mixture was treated with MTBE and then it was filtered to afford Compound 205D (500 mg, 52.30% yield) as white solid. $^1$H NMR ($CDCl_3$, 400 MHz): δ 7.34-7.11 (m, 1H), 6.81-6.67 (m, 1H), 5.54-5.35 (m, 1H), 5.19-5.05 (m, 2H), 4.28-4.12 (m, 1H), 3.85-3.72 (s, 1H), 2.81-2.54 (m, 2H), 2.24-1.99 (m, 2H), 2.98-2.78 (m, 1H), 1.65-1.41 (m, 9H).

To a solution of compound 205D (250 mg, 810.71 umol) in dioxane (2 mL) was added HCl/dioxane (4M, 1.06 mL) at 25° C. After addition, the reaction was stirred at 32° C. for 2 hours and concentrated. The residue was purified by column chromatography ($SiO_2$, Petroleum ether/Ethyl acetate=10:1 to 1:2) to afford compound 205E (180 mg, 90.64% yield) as white solid. $^1$H NMR (400 MHz, DMSO-$d_6$): δ 8.15-8.02 (m, 1H), 8.01-7.75 (m, 1H), 7.65-7.48 (m, 2H), 7.37-7.26 (m, 2H), 7.25-7.05 (m, 5H), 6.52-6.24 (s, 1H), 4.16-4.05 (m, 1H), 3.45-3.39 (m, 1H), 1.95-1.61 (m, 2H), 1.41-1.28 (m, 2H).

Compound 205 (23.5 mg, 31.69% yield, yellow solid) was prepared as in Example 5 from the corresponding intermediate compounds 23A and 205E. Compound 205: $^1$H NMR (400 MHz, $CDCl_3$) δ 7.84-7.72 (m, 2H), 7.60-7.50 (m, 3H), 7.26-7.12 (m, 4H), 7.07-7.00 (m, 2H), 6.66 (br s, 1H), 6.19 (br s, 1H), 5.51-5.34 (m, 2H), 2.66-2.54 (m, 2H), 2.47 (s, 3H), 2.38-2.25 (m, 1H), 1.99-1.85 (m, 1H). MS (ESI) m/z $(M+H)^+$392.1.

Example 16

Compounds 36, 49, 409, 455

(S)—N-(4-amino-3,4-dioxo-1-phenylbutan-2-yl)-3-methyl-1-(pyrimidin-2-yl)-1H-pyrazole-5-carboxamide (36)

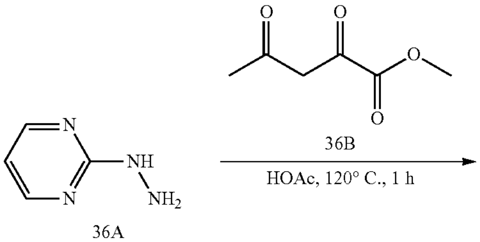

36B

36A

-continued

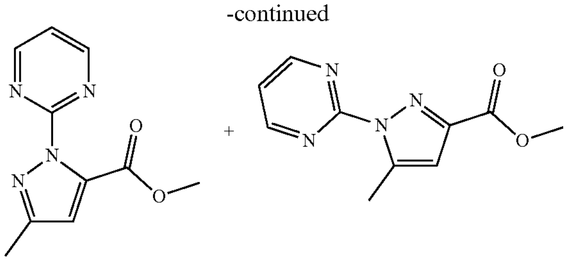

36C

36D

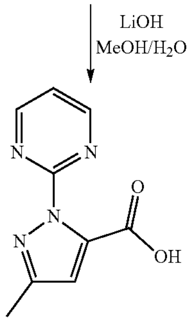

36F

To a solution of compound 36B (1.31 g, 9.08 mmol) in AcOH (50 mL) was added compound 36A (1 g, 9.08 mmol). The mixture was stirred at 120° C. for 1 h. The mixture was in DCM (50 mL). The organic layer was washed with water (10 mL), $NaHCO_3$ to pH ~8~9 and dried over $Na_2SO_4$ and concentrated. The residue was purified by column chromatography ($SiO_2$, Petroleum ether/Ethyl acetate=10:1 to 5:1) to afford compounds 36C and 36D. Compound 36C (500 mg, 2.29 mmol, 25.24% yield, white solid): $^1H$ NMR (400 MHz, DMSO-$d_6$) δ 9.03-8.79 (m, 2H), 7.67-7.45 (m, 1H), 6.87 (s, 1H), 3.73 (s, 3H), 2.29 (s, 3H). Compound 36D (1 g, 50.47% yield, white solid): $^1H$ NMR (400 MHz, DMSO-$d_6$) δ 9.03-8.89 (m, J=4.9 Hz, 2H), 7.67-7.55 (m, 1H), 6.81 (s, 1H), 3.84 (s, 3H), 2.60 (s, 3H).

Intermediate compound 36F (39.6 mg, 90% yield, white solid) was prepared as in Example 85 from compound 36C. MS (ESI) m/z $(M+1)^+$205. Compound 36 (15.5 mg, 43.77% yield, brown solid) was prepared as in Example 5 from the corresponding intermediate compound 36F. Compound 36: $^1H$ NMR (400 MHz, DMSO-$d_6$) δ 8.99-8.95 (m, 2H), 8.50-8.39 (m, 1H), 8.11 (s, 1H), 7.85 (s, 1H), 7.65-7.57 (m, 1H), 7.31-7.17 (m, 5H), 6.68 (s, 1H), 5.51-5.45 (m, 1H), 3.26-3.18 (m, 1H), 3.13-3.03 (m, 1H), 2.58 (s, 3H).

(S)—N-(4-amino-3,4-dioxo-1-phenylbutan-2-yl)-3-methyl-1-(pyrimidin-2-yl)-1H-pyrazole-5-carboxamide (49)

Following the procedure as used for compound 36, compound 49 (21 mg, 38.4% yield, white solid) was prepared from the corresponding intermediate compound 36D. $^1H$ NMR (400 MHz, DMSO-$d_6$) δ 9.08-8.98 (m, 1H), 8.76-8.70 (m, 2H), 8.05 (s, 1H), 7.82 (s, 1H), 7.49-7.44 (m, 1H), 7.35-7.26 (m, 4H), 7.26-7.19 (m, 1H), 6.58 (s, 1H), 5.31-5.25 (m, 1H), 3.19-3.09 (m, 1H), 2.90-2.78 (m, 1H), 2.27 (s, 3H). MS (ESI) m/z $(M+Na)^+$379.

N-(4-amino-3,4-dioxo-1-phenylbutan-2-yl)-3-methyl-1-(pyrimidin-4-yl)-1H-pyrazole-5-carboxamide (409)

Following the procedure as used for compound 36, compound 409 (4225.7 mg, 80.2% yield, white solid) was prepared from the corresponding starting materials, namely 4-hydrazinylpyrimidine and intermediate compound 274D. $^1H$ NMR (400 MHz, DMSO-$d_6$) δ 9.22 (d, J=7.2 Hz, 1H), 8.84 (d, J=5.6 Hz, 1H), 8.75 (s, 1H), 8.14 (s, 1H), 7.89 (s, 1H), 7.78-7.74 (m, 1H), 7.31-7.21 (m, 5H), 6.52 (s, 1H), 5.41-5.33 (m, 1H), 3.22-3.12 (m, 1H), 2.90-2.78 (m, 1H), 2.28 (s, 3H). MS (ESI) m/z $(M+1)^+$379.0.

N-(4-(cyclopropylamino)-3,4-dioxo-1-phenylbutan-2-yl)-3-methyl-1-(pyrimidin-2-yl)-1H-pyrazole-5-carboxamide (455)

Following the procedure as used for compound 36, compound 455 (180 mg, 71.6% yield, white solid) was prepared from the corresponding starting materials, namely 36F and 3-amino-N-cyclopropyl-2-hydroxy-4-phenylbutanamide. $^1H$ NMR (400 MHz, DMSO-$d_6$) δ 9.05-9.00 (m, 1H), 9.03 (d, J=7.3 Hz, 1H), 8.78 (d, J=5.1 Hz, 1H), 8.69 (d, J=4.9 Hz, 2H), 7.44 (t, J=4.9 Hz, 1H), 7.29-7.18 (m, 5H), 6.56 (s, 1H), 5.31-5.24 (m, 1H), 3.12 (dd, J=3.7, 13.9 Hz, 1H), 2.84-2.71 (m, 2H), 2.24 (s, 2H), 2.27-2.19 (m, 1H), 0.67-0.54 (m, 4H). MS (ESI) m/z $(M+H)^+$419.2.

Example 17

(S)—N-(4-amino-3,4-dioxo-1-phenylbutan-2-yl)-4-(2H-indazol-2-yl)thiazole-5-carboxamide (37)

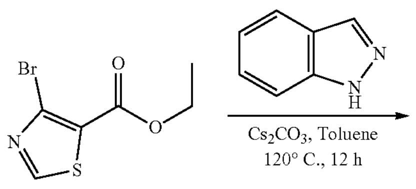

37A

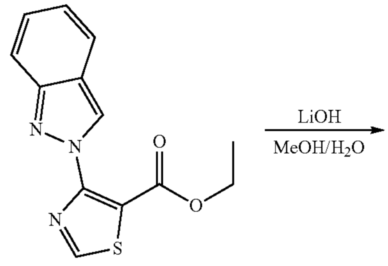

37B

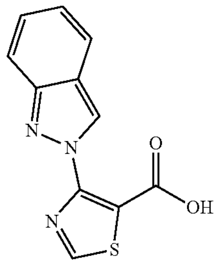

37D

A mixture of compound 37A (250 mg, 2.12 mmol), $Cs_2CO_3$ (2.07 g, 6.36 mmol) in toluene (40 mL) was stirred at 110° C. for 13 hrs. The mixture was concentrated. The residue was purified by column chromatography ($SiO_2$, Petroleum ether/Ethyl acetate=10/1 to 5:1) to afford compound 37B (43.75 mg, 7.55% yield) as white solid. MS (ESI) m/z $(M+1)^+$274. $^1H$ NMR (400 MHz, $CDCl_3$) δ 8.93 (s, 1H), 8.68 (s, 1H), 7.85-7.65 (m, 2H), 7.39-7.30 (m, 1H), 7.17-7.05 (m, 1H), 4.44-4.24 (m, 2H), 1.28 (m, 3H).

A mixture of compound 37B (35 mg, 128.06 umol), LiOH (9.2 mg, 384.18 umol) in water (1 mL) and MeOH (5 mL) was stirred at 27° C. for 2 hrs. MeOH was evaporated. To the residue was added water (10 mL). The mixture was extracted with MTBE (5 mL) and separated. The aqueous layer was acidified to pH ~3 with 1N HCl and extracted with ethyl acetate (3×20 mL). The combined organic layers were dried and concentrated to afford compound 37D (25.3 mg, 80.55% yield) as brown solid.

Compound 37 (4 mg, 8.47 umol, yield 5.95%, yellow solid) was prepared as in Example 5 from the corresponding intermediate carboxylic acid, compound 37D. Compound 37: $^1H$ NMR (400 MHz, $CDCl_3$) δ 12.72-12.49 (m, 1H), 8.97 (s, 1H), 8.80 (s, 1H), 7.80-7.64 (m, 1H), 7.46-7.29 (m, 2H), 7.20-6.98 (m, 6H), 6.83-6.72 (m, 1H), 5.97-5.84 (m, 1H), 5.52-5.40 (m, 1H), 3.56-3.33 (m, 2H).

Example 18

(S)—N-(4-amino-3,4-dioxo-1-phenylbutan-2-yl)-3-methyl-1-(naphthalen-1-yl)-1H-pyrazole-5-carboxamide (38)

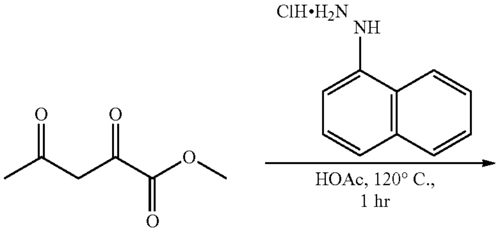

38A

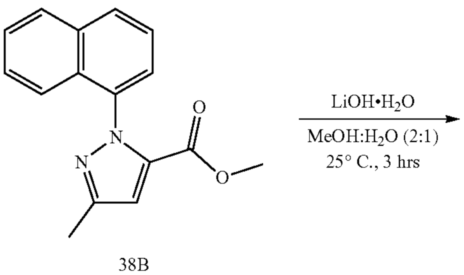

38B

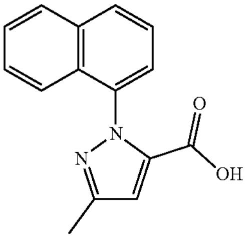

38C

A mixture consisting of compound naphthalen-1-yl hydrazine hydrochloride (4.05 g, 20.81 mmol) and compound 38A (3.0 g, 20.81 mmol) in AcOH (30 mL) was stirred at 120° C. for 1 hour. The reaction mixture was cooled to 25° C., concentrated under reduced pressure and diluted with $CH_2Cl_2$ (100 mL). The organic phase was washed with sat. $NaHCO_3$ (20 mL×2), dried over anhydrous $Na_2SO_4$, filtered, and the filtration was concentrated under reduced pressure to give a residue, which was purified by flash silica gel chromatography (Petroleum ether:Ethyl acetate=4:1) to afford compound 38B (154.3 mg, 2.79% yield) as a brown solid. $^1H$ NMR ($CDCl_3$, 400 MHz): δ 7.96 (d, J=8.0 Hz, 1H), 7.91 (d, J=8.4 Hz, 1H), 7.57-7.52 (m, 1H), 7.51-7.47 (m, 2H), 7.46-7.41 (m, 1H), 7.22 (d, J=8.4 Hz, 1H), 6.90 (s, 1H), 3.62 (s, 3H), 2.43 (s, 3H). MS (ESI) m/z $(M+1)^+$267.1.

To a mixture of compound 38B (160 mg, 570.78 umol) in MeOH (10 mL) and $H_2O$ (5 mL) was added $LiOH.H_2O$ (71.9 mg, 1.71 mmol) in one portion and the mixture was stirred at 25° C. for 3 hrs. The reaction mixture was concentrated under reduced pressure to remove MeOH. The residue was diluted with $H_2O$ (10 mL), adjusted to pH ~3 with 1N HCl, and then extracted with EtOAc (40 mL×3). The combined organic layers were washed with brine (30 mL), dried over anhydrous $Na_2SO_4$, filtered and concentrated under reduced pressure to give intermediate compound 38C (140 mg, yield 97.23%) as a white solid. $^1H$ NMR ($CDCl_3$, 400 MHz): δ 7.96-7.83 (m, 2H), 7.52-7.44 (m, 2H), 7.44-7.36 (m, 2H), 7.15 (d, J=8.4 Hz, 1H), 6.87 (s, 1H), 2.37 (s, 3H). MS (ESI) m/z $(M+1)^+$252.9.

Compound 38 (10.6 mg, yield 13.31%, white solid) was prepared as in Example 5 from the corresponding intermediate carboxylic acid, compound 38C. Compound 38: $^1H$ NMR (400 MHz, $CDCl_3$) δ 8.00-7.89 (m, 2H), 7.57-7.43 (m, 4H), 7.28 (d, J=8.4 Hz, 1H), 7.22-7.10 (m, 3H), 6.82-6.72 (m, 2H), 6.69 (s, 1H), 6.54 (br s, 1H), 6.16 (d, J=6.8 Hz, 1H), 5.48-5.33 (m, 2H), 3.19-3.09 (m, 1H), 2.94-2.84 (m, 1H), 2.40 (s, 3H). MS (ESI) m/z $(M+1)^+$427.2.

Example 19

(S)—N-(4-amino-3,4-dioxo-1-phenylbutan-2-yl)-4-(1H-indazol-1-yl)thiazole-5-carboxamide (40)

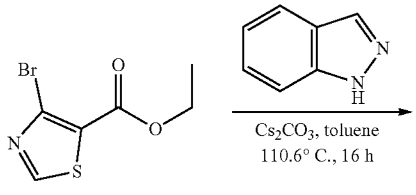

40A

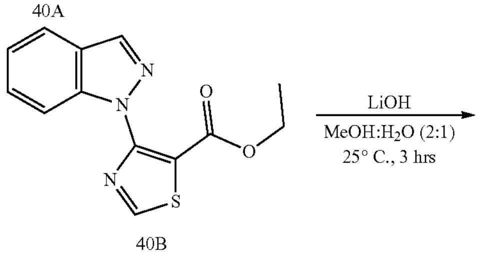

40B

-continued

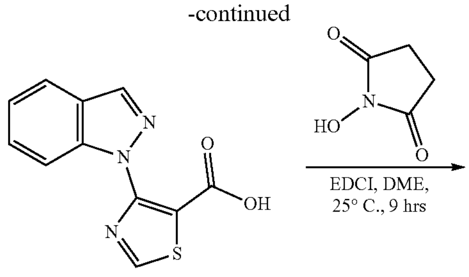

40C

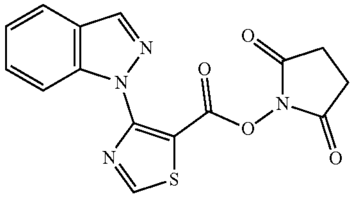

40D

A mixture consisting of compound 40A (500 mg, 2.12 mmol), indazole (250.5 mg, 2.12 mmol), $Cs_2CO_3$ (2.07 g, 6.36 mmol) in toluene (40 mL) was stirred at 110.6° C. for 16 hrs. The reaction mixture was cooled to 25° C., filtered, concentrated under reduced pressure. The obtained residue was purified by preparatory-HPLC (HCl condition) to afford compound 40B (56 mg, 9.67% yield) as a light yellow solid. $^1H$ NMR ($CDCl_3$, 400 MHz): δ 8.94 (s, 1H), 8.26 (s, 1H), 7.80 (d, J=8.0 Hz, 1H), 7.62 (d, J=8.4 Hz, 1H), 7.48-7.43 (m, 1H), 7.28-7.24 (m, 1H), 4.24 (q, J=7.2 Hz, 2H), 1.17-1.12 (m, 1H), 1.14 (t, J=7.2 Hz, 2H).

To a mixture of compound 40B (50 mg, 182.94 umol) in MeOH (2 mL) was added LiOH (13.1 mg, 548.83 umol) in one portion and the mixture was stirred at 25° C. for 3 hrs. The reaction mixture was concentrated under reduced pressure to remove MeOH. The residue was diluted with $H_2O$ (8 mL), adjusted to pH ~3 with 1 N HCl, and then extracted with EtOAc (30 mL×3). The combined organic layers were washed with brine (20 mL), dried over anhydrous $Na_2SO_4$, filtered and concentrated under reduced pressure to give intermediate compound 40C (42 mg, 93.61% yield) as a white solid. $^1H$ NMR ($CDCl_3$, 400 MHz): δ 8.95 (s, 1H), 8.73 (d, J=8.4 Hz, 1H), 8.38 (s, 1H), 7.89 (d, J=8.0 Hz, 1H), 7.67 (t, J=7.6 Hz, 1H), 7.43 (t, J=7.6 Hz, 1H).

To a solution consisting of compound 40C (42 mg, 171.25 umol) and 1-hydroxypyrrolidine-2,5-dione (20.7 mg, 179.81 umol) in DME (5 mL) was added EDCI (49.24 mg, 256.87 umol) in one portion at 25° C. under $N_2$. The mixture was stirred at 25° C. for 9 hrs. The reaction mixture was concentrated under reduced pressure to remove DME. The residue was diluted with EtOAc (60 mL), washed with 1N HCl (10 mL) and saturated aqueous $NaHCO_3$ (10 mL×3). The organic layers was washed with brine (20 mL), dried over anhydrous $Na_2SO_4$, filtered and concentrated under reduced pressure to afford intermediate compound 40D (60 mg, crude) as a light yellow oil. MS (ESI) m/z $(M+1)^+$342.8.

Compound 40 (15.10 mg, 50.57% yield, white solid) was prepared as in Example 6 from the corresponding starting materials, compounds 40D and 12G. Compound 40: $^1H$ NMR ($CDCl_3$, 400 MHz): δ 11.07 (d, J=6.0 Hz, 1H), 8.85 (s, 1H), 8.33-8.28 (m, 1H), 7.86 (d, J=0.8 Hz, 1H), 7.77 (d, J=8.0 Hz, 1H), 7.57-7.52 (m, 1H), 7.35-7.31 (m, 1H), 7.16-7.08 (m, 5H), 6.77 (br s, 1H), 5.81-5.75 (m, 1H), 5.55 (br s, 1H), 3.43-3.37 (m, 1H), 3.26-3.19 (m, 1H). MS (ESI) m/z $(M+1)^+$420.1.

Example 20

Compounds 41-43, 64-65, 67, 71, 76, 87, 100, 116, 132, 134-135, 137, 203-204

(S)—N-(4-(cyclopropylamino)-3,4-dioxo-1-phenylbutan-2-yl)-1-(pyridin-2-yl)-1H-imidazole-5-carboxamide (41)

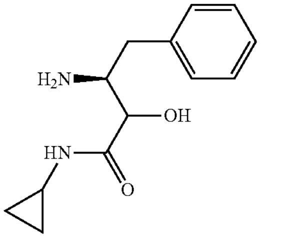

41B

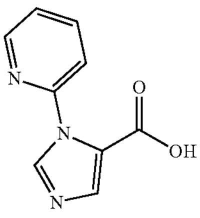

24E

HBTU, DIEA, DMF

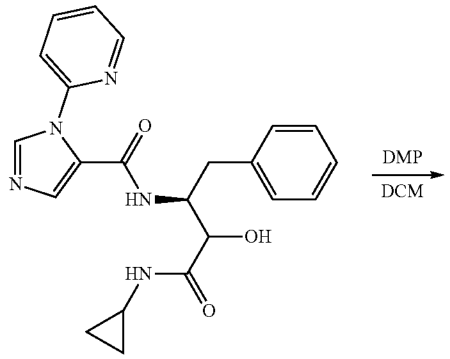

41A

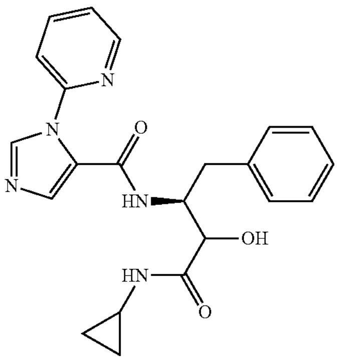

41

To a mixture of compound 24E (100 mg, 528 umol) and compound 41B (148 mg, 634 umol) in DMF (1.5 mL) was added HBTU (240 mg, 634 umol) in one portion at 25° C. and stirred for 5 mins, and then DIEA (273 mg, 2.1 mmol) was added. The mixture was stirred at 25° C. for 30 mins. LCMS showed compound 24E remained and desired MS was detected. Then the residue was purified by preparatory-HPLC (TFA condition) to give compound 41A (130 mg, yield: 60.6%) as a white solid. $^1$H NMR (400 MHz, Methanol-d4) δ 9.12 (br s, 1H), 8.49 (br d, J=3.8 Hz, 1H), 7.95-7.74 (m, 2H), 7.50 (br s, 1H), 7.37-7.16 (m, 5H), 7.13-7.01 (m, 1H), 4.69-4.52 (m, 1H), 4.22-4.03 (m, 1H), 3.29 (br s, 1H), 3.11-2.74 (m, 2H), 2.69-2.51 (m, 1H), 0.77-0.59 (m, 2H), 0.56-0.38 (m, 2H). MS (ESI) m/z $(M+H)^+$405.2.

To a solution of compound 41A (130 mg, 320 umol) in DCM (10 mL) was added DMP (543 mg, 1.3 mmol, 397 uL) in one portion at 0° C. The mixture was stirred at 25° C. for 10 mins. LCMS showed compound 41A was consumed completely and one main peak with desired MS was detected. Then the mixture was diluted with DCM (80 mL), quenched by adding 10% $Na_2S_2O_3$/saturated aqueous $NaHCO_3$ (v/v=1/1, 20 mL). The organic layer was separated, and the aqueous layer was extracted with DCM (30 mL×2). The combined organic layer was washed with $H_2O$ (10 mL), brine (10 mL), dried over $Na_2SO_4$, filtered and concentrated to afford white solid. Then the residue was purified by re-crystallization from isopropyl ether (20 mL) to give compound 41 (20.6 mg, yield: 30.9%) as a white solid. $^1$H NMR (400 MHz, DMSO-$d_6$) δ 8.96 (d, J=7.8 Hz, 1H), 8.79 (br d, J=5.0 Hz, 1H), 8.45 (br d, J=4.6 Hz, 1H), 8.14 (s, 1H), 7.88 (t, J=7.8 Hz, 1H), 7.57 (s, 1H), 7.44 (dd, J=7.0, 5.2 Hz, 1H), 7.34-7.28 (m, 4H), 7.24 (br d, J=4.2 Hz, 1H), 7.18 (d, J=8.2 Hz, 1H), 5.32-5.22 (m, 1H), 3.31 (s, 1H), 3.19 (dd, J=13.8, 3.6 Hz, 1H), 2.89-2.71 (m, 2H), 0.70-0.64 (m, 2H), 0.60-0.55 (m, 2H). MS (ESI) m/z $(M+H)^+$403.2.

(S)—N-(4-(cyclopropylamino)-3,4-dioxo-1-phenylbutan-2-yl)-1-(1-phenyl-1H-pyrazol-3-yl)-1H-imidazole-5-carboxamide (42)

Compound 42 (19.3 mg, yield: 55.2%, yellow solid) was prepared as in Example 20 from the corresponding intermediate carboxylic acid, compound 34E. $^1$H NMR (400 MHz, DMSO-$d_6$) δ 8.91 (d, J=7.7 Hz, 1H), 8.82 (d, J=5.1 Hz, 1H), 8.57 (d, J=2.6 Hz, 1H), 8.14 (s, 1H), 7.83 (d, J=7.9 Hz, 2H), 7.63 (s, 1H), 7.53 (t, J=8.0 Hz, 2H), 7.36 (t, J=7.4 Hz, 1H), 7.32 (d, J=4.4 Hz, 4H), 7.27-7.20 (m, 1H), 6.48 (d, J=2.6 Hz, 1H), 5.34-5.26 (m, 1H), 3.21 (dd, J=13.8, 3.6 Hz, 1H), 2.86 (dd, J=13.8, 10.3 Hz, 1H), 2.81-2.72 (m, 1H), 0.71-0.63 (m, 2H), 0.62-0.53 (m, 2H). MS (ESI) m/z $(M+H)^+$469.1.

(S)-1-(benzo[d]thiazol-2-yl)-N-(4-(cyclopropylamino)-3,4-dioxo-1-phenylbutan-2-yl)-1H-imidazole-5-carboxamide (43)

Compound 43 (24.4 mg, yield: 43%, white solid) was prepared as in Example 20 from the corresponding intermediate carboxylic acid, compound 29D. Compound 43: $^1$H NMR (400 MHz, DMSO-$d_6$) δ 9.13 (d, J=7.7 Hz, 1H), 8.77 (br d, J=4.9 Hz, 1H), 8.39 (s, 1H), 8.08 (d, J=7.9 Hz, 1H), 7.96 (d, J=8.2 Hz, 1H), 7.67 (s, 1H), 7.59-7.43 (m, 2H), 7.27 (d, J=4.0 Hz, 4H), 7.22-7.12 (m, 1H), 5.34-5.16 (m, 1H), 3.18 (dd, J=13.9, 3.3 Hz, 1H), 2.83 (dd, J=13.7, 10.1 Hz, 1H), 2.72 (br d, J=4.2 Hz, 1H), 0.69-0.58 (m, 2H), 0.54 (br d, J=2.9 Hz, 2H). MS (ESI) m/z $(M+H)^+$460.1

(S)—N-(4-(cyclopropylamino)-3,4-dioxo-1-phenylbutan-2-yl)-3-methyl-1-(pyrimidin-2-yl)-1H-pyrazole-5-carboxamide (65)

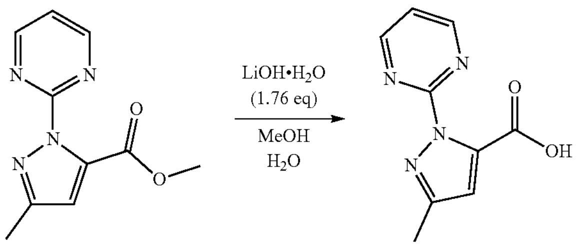

65A 65B

A mixture of compound 65A (80 mg, 366.62 umol) in MeOH (5 mL) and $H_2O$ (1 mL) was added $LiOH.H_2O$ (27.1 mg, 645.87 umol). The mixture was stirred at 31° C. for 1 h. The mixture was evaporated to remove MeOH, then it was washed with water (3×50 mL) and extracted with MTBE (2×50 mL). The water layers were acidized to pH ~4 with 1N HCl, then, the solution extracted with ethyl acetate (3×100 mL). The organic layers were dried over $Na_2SO_4$ and concentrated to give compound 65B (50 mg, 66.79% yield) was obtained as white solid.

Compound 65 (11.8 mg, 87.93% yield, white solid) was prepared as in Example 20 from the corresponding intermediate compounds 65B and 41B. Compound 65: $^1$H NMR (400 MHz, DMSO-$d_6$) δ 8.94 (s, 2H), 8.87-8.79 (m, 1H), 8.51-8.44 (m, 1H), 7.62-7.55 (m, 1H), 7.34-7.09 (m, 5H), 6.65 (s, 1H), 5.53-5.39 (m, 1H), 3.26-3.12 (m, 4H), 3.10-3.00 (m, 1H), 2.81-2.71 (m, 1H), 2.56 (s, 3H), 0.71-0.54 (m, 4H). MS (ESI) m/z $(M+H)^+$419.2.

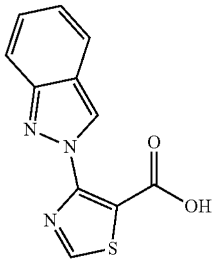

64A

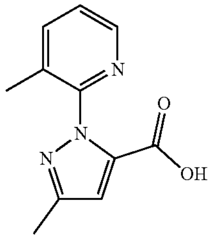

67A

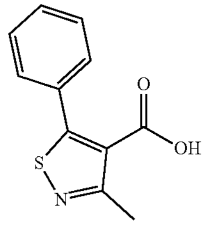

96D

+

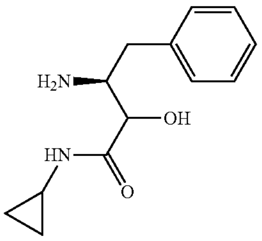

41B

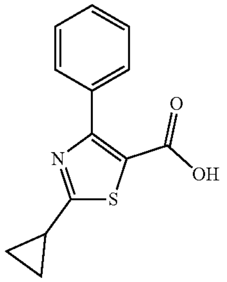

135A

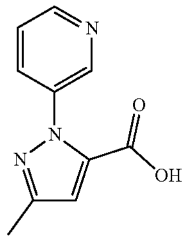

136C

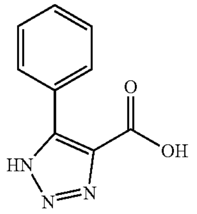

204A

(S)—N-(4-(cyclopropylamino)-3,4-dioxo-1-phenylbutan-2-yl)-4-(2H-indazol-2-yl)thiazole-5-carboxamide (64)

Compound 64 (48.2 mg 87.93% yield, white solid) was prepared as in Example 20 from the corresponding intermediate carboxylic acid, compound 64A. Compound 64: $^1H$ NMR (400 MHz, DMSO-$d_6$) δ11.99-11.83 (m, 1H), 9.33 (s, 1H), 9.16 (s, 1H), 8.95-8.84 (m, 1H), 7.93-7.80 (m, 1H), 7.56-7.50 (m, 1H), 7.44-7.33 (m, 1H), 7.27-7.15 (m, 1H), 7.12-6.99 (m, 5H), 5.71-5.60 (m, 1H), 3.34-3.24 (m, 3H), 3.19-3.10 (m, 1H), 2.84-2.74 (m, 1H), 0.73-0.54 (m, 4H). MS (ESI) m/z $(M+H)^+$460.1.

(S)—N-(4-(cyclopropylamino)-3,4-dioxo-1-phenylbutan-2-yl)-3-methyl-1-(3-methylpyridin-2-yl)-1H-pyrazole-5-carboxamide (67)

Compound 67 (30.8 mg, 38.6% yield, white solid) was prepared as in Example 20 from the corresponding intermediate carboxylic acid, compound 67A. Compound 67: $^1H$ NMR ($CDCl_3$, 400 MHz) δ 8.24 (d, J=4.4 Hz, 1H), 7.67 (d, J=7.6 Hz, 1H), 7.2 (d, J=7.2 Hz, 1H), 7.34-7.26 (m, 2H), 7.25-7.20 (m, 3H), 6.99 (d, J=4.4 Hz, 2H), 6.86 (s, 1H), 6.56 (s, 1H), 5.66-5.58 (m, 1H), 3.38-3.29 (m, 1H), 3.21-3.13 (m, 1H), 2.82-2.74 (m, 1H), 2.34 (s, 3H), 2.16 (s, 3H), 0.91-0.84 (m, 2H), 0.64-0.57 (m, 2H). MS (ESI) m/z $(M+H)^+$432.1.

(S)-1-(1H-benzo[d]imidazol-2-yl)-N-(4-(cyclopropylamino)-3,4-dioxo-1-phenylbutan-2-yl)-1H-imidazole-5-carboxamide (71)

Compound 71 (75 mg, yield: 78.1%, white solid) was prepared as in Example 20 from the corresponding intermediate carboxylic acid, compound 70D. Compound 71: $^1H$ NMR (400 MHz, DMSO-$d_6$) δ 12.93 (br s, 1H), 9.25 (br s, 1H), 8.74 (d, J=4.9 Hz, 1H), 8.29 (s, 1H), 7.83 (s, 1H), 7.52 (br s, 2H), 7.30-7.18 (m, 6H), 7.18-7.13 (m, 1H), 5.42-5.25 (m, 1H), 3.17 (dd, J=3.5, 13.7 Hz, 1H), 2.83 (dd, J=10.0, 13.8 Hz, 1H), 2.74-2.64 (m, 1H), 0.70-0.42 (m, 4H). MS (ESI) m/z $(M+H)^+$443.0.

(S)—N-(4-(cyclopropylamino)-3,4-dioxo-1-phenylbutan-2-yl)-1-(5-phenylpyrimidin-2-yl)-1H-imidazole-5-carboxamide (76)

Compound 76 (24.7 mg, yield: 44.7%, white solid) was prepared as in Example 20 from the corresponding intermediate compound 74E. Compound 76: $^1H$ NMR ($CDCl_3$, 400 MHz) δ 9.46 (br d, J=6.4 Hz, 1H), 8.66 (s, 2H), 8.62 (s, 1H), 7.80 (s, 1H), 7.57-7.49 (m, 5H), 7.22-7.16 (m, 2H), 7.16-7.07 (m, 3H), 6.93 (br s, 1H), 5.86-5.82 (m, 1H), 3.53-3.46 (m, 1H), 3.41-3.32 (m, 1H), 2.86-2.82 (m, 1H), 0.92-0.86 (m, 2H), 0.64-0.62 (m, 2H). MS (ESI) m/z $(M+H)^+$481.0.

(S)—N-(4-(cyclopropylamino)-3,4-dioxo-1-phenylbutan-2-yl)-4-(4-phenyl-1H-pyrazol-1-yl)thiazole-5-carboxamide (87)

Compound 87 (60.0 mg, 75.3% yield, white solid) was prepared as in Example 20 from the corresponding intermediate carboxylic acid, compound 21D. $^1H$ NMR (400 MHz, $CDCl_3$) δ11.72 (br. d, J=6.0 Hz, 1H), 8.73 (s, 1H), 8.68-8.64 (m, 1H), 7.76-7.72 (m, 1H), 7.58-7.52 (m, 2H), 7.48-7.40 (m, 2H), 7.37-7.30 (m, 1H), 7.29-7.21 (m, 5H), 6.97-6.91 (m, 1H), 5.86-5.74 (m, 1H), 3.53-3.41 (m, 1H), 3.29-3.17 (m, 1H), 2.88-2.75 (m, 1H), 0.93-0.82 (m, 2H), 0.68-0.58 (m, 2H). MS (ESI) m/z $(M+1)^+$486.1.

(S)—N-(4-(cyclopropylamino)-3,4-dioxo-1-phenylbutan-2-yl)-3-methyl-5-phenylisoxazole-4-carboxamide (100)

Compound 100 (85 mg, yield: 83.27%, white solid) was prepared as in Example 20 from the corresponding intermediate carboxylic acid, compound 23A. Compound 100: $^1H$ NMR (400 MHz, DMSO-$d_6$) δ 9.09 (d, J=7.5 Hz, 1H), 8.94

(br d, J=5.1 Hz, 1H), 7.62 (d, J=7.1 Hz, 2H), 7.53-7.46 (m, 1H), 7.44-7.39 (m, 2H), 7.32-7.20 (m, 5H), 5.48 (ddd, J=3.3, 7.6, 10.7 Hz, 1H), 3.25 (br dd, J=3.2, 14.0 Hz, 1H), 2.85-2.67 (m, 2H), 2.07 (s, 3H), 0.73-0.56 (m, 4H). MS (ESI) m/z $(M+H)^+$418.1.

(S)—N-(4-(cyclopropylamino)-3,4-dioxo-1-phenylbutan-2-yl)-3-methyl-5-phenylisothiazole-4-carboxamide (116)

Compound 116 (88.00 mg, 87.41% yield, off-white solid) was prepared as in Example 20 from the corresponding intermediate carboxylic acid, compound 96D. Compound 116: $^1$H NMR (400 MHz, $CDCl_3$) δ 7.44 (s, 5H), 7.20-7.09 (m, 3H), 6.86 (br s, 1H), 6.77-6.68 (m, 2H), 5.93 (br d, J=6.6 Hz, 1H), 5.68-5.57 (m, 1H), 3.24-3.14 (m, 1H), 2.99-2.89 (m, 1H), 2.83-2.73 (m, 1H), 2.46 (s, 3H), 0.93-0.81 (m, 2H), 0.69-0.53 (m, 2H). MS (ESI) m/z $(M+H)^+$434.1.

(S)—N-(4-(cyclopropylamino)-3,4-dioxo-1-phenylbutan-2-yl)-3-methyl-1-(pyridin-3-yl)-1H-pyrazole-5-carboxamide (132)

Compound 132 (72.8 mg, 60.40% yield, white solid) was prepared as in Example 20 from the corresponding intermediate carboxylic acid, compound 136C. Compound 132: $^1$H NMR (400 MHz, $CDCl_3$): δ 8.61 (d, J=2.4 Hz, 1H), 8.57-8.54 (m, 1H), 7.72-7.66 (m, 1H), 7.34-7.26 (m, 4H), 7.10-7.05 (m, 2H), 7.03-6.94 (m, 1H), 6.64-6.56 (m, 1H), 6.44 (s, 1H), 5.62-5.54 (m, 1H), 3.44-3.36 (m, 1H), 3.18-3.10 (m, 1H), 2.85-2.76 (m, 1H), 2.33 (s, 3H), 0.92-0.85 (m, 2H), 0.66-0.59 (m, 2H). MS (ESI) m/z $(M+1)^+$418.1.

(S)—N-(4-(cyclopropylamino)-3,4-dioxo-1-phenylbutan-2-yl)-1-(isoquinolin-4-yl)-3-methyl-1H-pyrazole-5-carboxamide (134)

Compound 134 (57.4 mg, 62.9% yield, yellow solid) was prepared as in Example 20 from the corresponding intermediate carboxylic acid, compound 133D. Compound 134: $^1$H NMR (400 MHz, $CDCl_3$) δ 9.31 (br s, 1H), 8.47 (br s, 1H), 8.06 (d, J=7.6 Hz, 1H), 7.74-7.61 (m, 2H), 7.43 (d, J=8.0 Hz, 1H), 7.25-7.20 (m, 3H), 6.92 (br s, 2H), 6.84 (br s, 1H), 6.60 (s, 1H), 6.46 (d, J=7.2 Hz, 1H), 5.50-5.41 (m, 1H), 3.30-3.22 (m, 1H), 3.14-3.04 (m, 1H), 2.79-2.70 (m, 1H), 2.40 (s, 3H), 0.87-0.82 (m, 2H), 0.63-0.53 (m, 2H). MS (ESI) m/z $(M+H)^+$468.1.

(S)-2-cyclopropyl-N-(4-(cyclopropylamino)-3,4-dioxo-1-phenylbutan-2-yl)-4-phenylthiazole-5-carboxamide (135)

Compound 135 (52.8 mg, 53.03% yield, white solid) was prepared as in Example 20 from the corresponding intermediate carboxylic acid, compound 135A. Compound 135: $^1$H NMR ($CDCl_3$, 400 MHz) δ 1H NMR (400 MHz, CDCl3) δ 7.53-7.45 (m, 2H), 7.45-7.35 (m, 3H), 7.22-7.11 (m, 3H), 6.85 (br s, 1H), 6.80-6.70 (m, 2H), 6.17 (d, J=6.4 Hz, 1H), 5.54-5.45 (m, 1H), 3.27-3.22 (m, 1H), 2.89-2.84 (m, 1H), 2.80-2.75 (m, 1H), 2.33-2.26 (m, 1H), 1.20-1.14 (m, 2H), 1.13-1.08 (m, 2H), 0.91-0.79 (m, 2H), 0.64-0.54 (m, 2H). MS (ESI) m/z $(M+H)^+$460.1.

(S)-3-(tert-butyl)-N-(4-(cyclopropylamino)-3,4-dioxo-1-phenylbutan-2-yl)-1-phenyl-1H-pyrazole-5-carboxamide (137)

Compound 137 (96.70 mg, 64.74% yield, white solid) was prepared as in Example 20 from the corresponding intermediate carboxylic acid, compound 128A. Compound 137: $^1$H NMR (400 MHz, $CDCl_3$) δ 7.54-7.45 (m, 3H), 7.41-7.36 (m, 2H), 7.31-7.27 (m, 1H), 7.25-7.13 (m, 5H), 6.87 (br s, 1H), 6.69 (s, 1H), 5.77-5.68 (m, 1H), 3.44-3.36 (m, 1H), 3.17-3.09 (m, 1H), 2.82-2.74 (m, 1H), 1.16 (s, 9H), 0.89-0.81 (m, 2H), 0.64-0.54 (m, 2H). MS (ESI) m/z $(M+H)^+$459.2.

(S)—N-(4-(cyclopropylamino)-3,4-dioxo-1-phenylbutan-2-yl)-3-methyl-1-(4-phenylthiazol-2-yl)-1H-pyrazole-5-carboxamide (203)

Compound 203 (30 mg, yield 60.18%, white solid) was prepared as in Example 20 from the corresponding intermediate carboxylic acid, compound 82D. Compound 203: $^1$H NMR ($CDCl_3$, 400 MHz) δ 7.69-7.64 (m, 2H), 7.41-7.33 (m, 3H), 7.22 (s, 1H), 7.12-7.06 (m, 3H), 7.01-6.94 (m, 3H), 6.84 (br s, 1H), 5.65-5.58 (m, 1H), 3.41-3.34 (m, 1H), 2.97-2.89 (m, 1H), 2.79-2.71 (m, 1H), 2.32 (s, 3H), 0.86-0.80 (m, 2H), 0.61-0.53 (m, 2H). MS (ESI) m/z $(M+H)^+$ 500.1.

(S)—N-(4-(cyclopropylamino)-3,4-dioxo-1-phenylbutan-2-yl)-5-phenyl-1H-1,2,3-triazole-4-carboxamide (204)

Compound 204 (4 mg, 8.9% yield, white solid) was prepared as in Example 20 from the corresponding intermediate carboxylic acid, compound 204A. Compound 204: $^1$H NMR ($CDCl_3$, 400 MHz) T=80: δ 8.55 (br s, 1H), 8.41 (d, J=7.2 Hz, 1H), 7.82-7.78 (m, 2H), 7.50-7.35 (m, 4H), 7.32-7.20 (m, 5H), 5.51-5.45 (m, 1H), 3.30-3.22 (m, 1H), 3.05 (br s, 1H), 2.81-2.74 (m, 1H), 0.71-0.66 (m, 2H), 0.64-0.59 (m, 2H). MS (ESI) m/z $(M+H)^+$404.1.

Example 21

(S)—N-(4-amino-3,4-dioxo-1-phenylbutan-2-yl)-1-methyl-5-phenyl-1H-pyrazole-4-carboxamide (45)

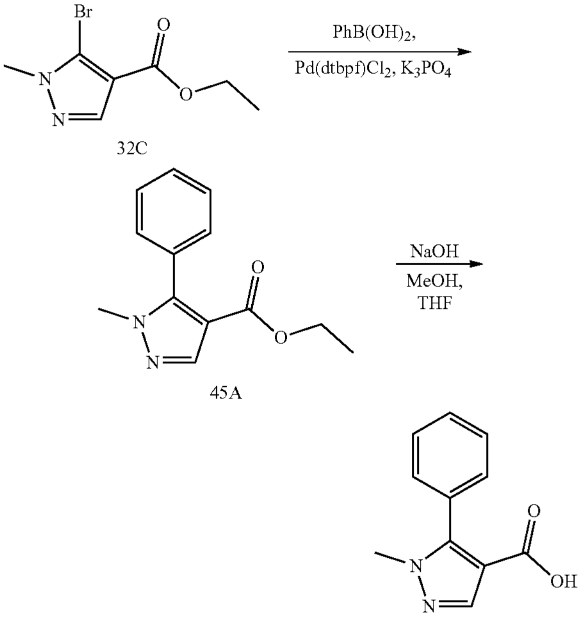

32C

45A

45B

A mixture of ethyl compound 32C (500.0 mg, 2.15 mmol), phenylboronic acid (262.1 mg, 2.15 mmol), Pd(dtbpf)$Cl_2$ (140.1 mg, 215.00 umol), $K_3PO_4$ (1.37 g, 6.45 mmol) in dioxane (30 mL) and $H_2O$ (10 mL) was degassed and purged with $N_2$ for 3 times, and then the mixture was stirred at 70° C. for 1 hour under $N_2$ atmosphere. The mixture was concentrated and diluted with ethyl acetate (30 mL), washed with HCl (1M, 50 mL), saturated aqueous $NaHCO_3$ (50 mL), brine (50 mL), dried over $Na_2SO_4$ and concentrated to afford intermediate compound 45A (490 mg, crude) as a brown oil. MS (ESI) m/z $(M+H)^+$230.9.

To a solution of compound 45A (490.0 mg, 2.13 mmol) in MeOH (5 mL) and THF (5 mL) was added NaOH (2M, 21.28 mL). The mixture was stirred at 60° C. for 1 hour. The mixture was concentrated and diluted with $H_2O$ (10 mL), the mixture was extracted with ethyl acetate (10 mL), the water phase was added HCl (1M) until pH ~3, then the mixture was extracted with ethyl acetate (20 mL), the organic layer was washed with brine (10 mL), dried over $Na_2SO_4$ and concentrated. Compound 45B (400 mg, yield: 93.0%) was obtained as a brown solid. $^1$H NMR (400 MHz, DMSO-$d_6$) δ 12.09 (br s, 1H), 7.87 (s, 1H), 7.50-7.40 (m, 5H), 3.63 (s, 3H).

Compound 45 (50.0 mg, yield: 71.4%, white solid) was prepared as in Example 5 from the corresponding intermediate carboxylic acid, compound 45B. Compound 45: $^1$H NMR (400 MHz, $CDCl_3$) δ 7.97 (s, 1H), 7.55-7.43 (m, 3H), 7.32-7.27 (m, 2H), 7.23-7.15 (m, 3H), 6.85-6.65 (m, 3H), 5.80-5.71 (m, 1H), 5.55-5.40 (m, 2H), 3.71-3.60 (m, 3H), 3.29-3.19 (m, 1H), 2.94-2.84 (m, 1H), 2.94-2.84 (m, 1H). MS (ESI) m/z $(M+H)^+$377.1.

Example 22

(S)—N-(4-amino-1-(4-methoxyphenyl)-3,4-dioxobutan-2-yl)-3-methyl-5-phenylisoxazole-4-carboxamide (46)

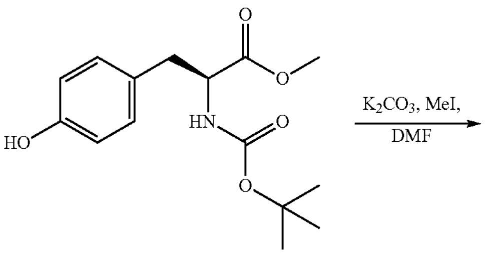

46A

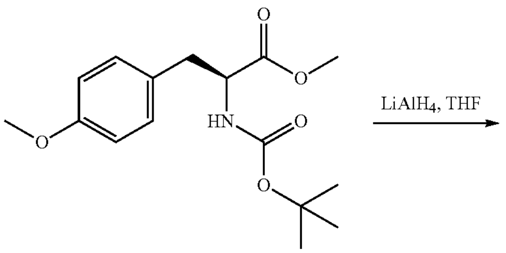

46B

-continued

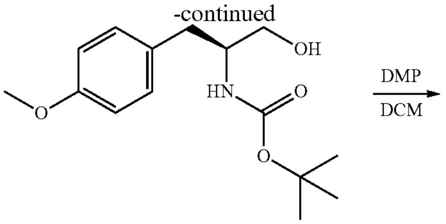

46C

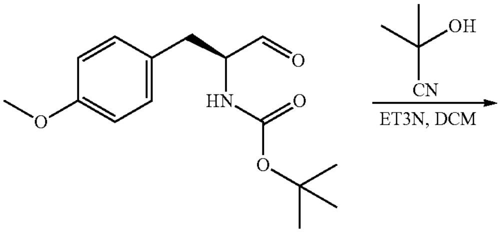

46D

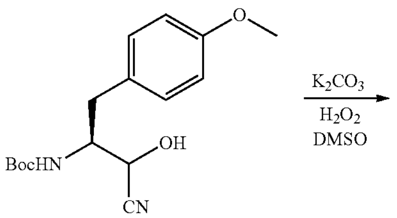

46E

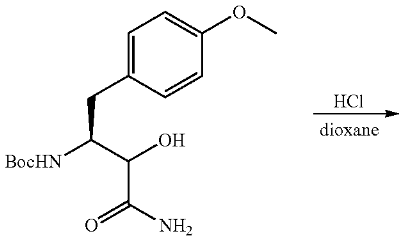

46F

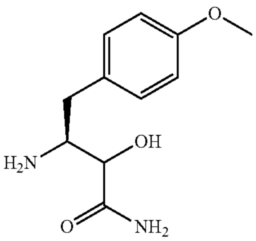

46G

To a solution of compound 46A (13 g, 44.02 mmol, 1 eq) in DMF (150 mL) was added $K_2CO_3$ (12.17 g, 88.04 mmol, 2 eq) at 0° C. After addition, the mixture was stirred at this temperature for 0.2 h, and then $CH_3I$ (8.97 g, 63.20 mmol, 3.93 mL) was added dropwise at 0° C. The resulting mixture was stirred at 25° C. for 18.8 hours. The reaction mixture was diluted with EtOAc (50 mL). The combined organic layers were washed with brine (100 mL×2), dried over $Na_2SO_4$, filtered and concentrated under reduced pressure to give the compound 46B (13.4 g, yield: 98.4%) as a colorless oil. $^1$H NMR (400 MHz, $CDCl_3$) δ 7.04 (d, J=8.6 Hz, 2H), 6.84 (d, J=7.7 Hz, 2H), 4.96 (br d, J=7.3 Hz, 1H), 4.55 (br d, J=7.1 Hz, 1H), 3.79 (s, 3H), 3.72 (s, 3H), 3.09-2.94 (m, 2H), 1.43 (s, 9H).

To a solution of LAH (490 mg, 12.92 mmol, 2 eq.) in THF (10 mL) was degassed and purged with $N_2$ for 3 times at 0°

C. and the mixture of compound 46B (2 g, 6.46 mmol, 1 eq) in THF (30 mL) was added dropwise, and then the mixture was stirred at 0° C. for 2 hrs under $N_2$ atmosphere. The reaction mixture was quenched by addition $H_2O$ (0.5 mL), then add NaOH (15% in $H_2O$, 0.5 mL), $H_2O$ (1.5 mL), and then diluted with EtOAc (20 mL), dried over $Na_2SO_4$, and stirred for 30 min, then filtered to give the organic layers. The combined organic layers were washed with brine (20 mL×2), dried over $Na_2SO_4$, filtered and concentrated under reduced pressure to give the compound 46C (1.48 g, yield: 81.4%) was obtained as a colorless oil. $^1$H NMR (400 MHz, $CDCl_3$) δ 7.12 (d, J=8.4 Hz, 2H), 6.89-6.78 (m, 2H), 4.69 (br s, 1H), 3.88-3.80 (m, 1H), 3.79 (s, 3H), 3.69-3.48 (m, 2H), 2.77 (d, J=7.1 Hz, 2H), 1.41 (s, 9H).

A solution of DMP (1.51 g, 3.56 mmol) in DCM (10 mL) was degassed and purged with $N_2$ for 3 times, and then compound 46C (500 mg, 1.78 mmol) in DCM (10 mL) was added dropwise, and then the mixture was stirred at 25° C. for 20 hrs under $N_2$ atmosphere. The reaction mixture was quenched by addition of saturated aqueous $Na_2S_2O_3$ (15 mL) and saturated aqueous $NaHCO_3$ (15 mL), and then diluted with DCM (10 mL) and extracted with $H_2O$ (20 mL×3). The combined organic layers were washed with brine (20 mL), dried over $Na_2SO_4$, filtered and concentrated under reduced pressure to give the compound 46D (430 mg, yield: 86.48%) was obtained as a yellow solid. $^1$H NMR (400 MHz, $CDCl_3$) δ 9.62 (s, 1H), 7.13-7.02 (m, 2H), 6.84 (br d, J=8.6 Hz, 2H), 5.05 (br d, J=5.5 Hz, 1H), 4.46-4.32 (m, 1H), 3.78 (s, 3H), 3.06 (br d, J=6.4 Hz, 2H), 1.43 (s, 9H).

To a solution of compound 46D (1.53 g, 5.48 mmol) in DCM (20 mL) was added compound 2-hydroxy-2-methyl-propanenitrile (3.30 g, 38.78 mmol, 3.55 mL) and $Et_3N$ (832 mg, 8.22 mmol, 1.14 mL). The mixture was stirred at 25° C. for 2 hrs. The reaction mixture was quenched by addition 1N HCl (20 mL), and then diluted with $H_2O$ (20 mL) and extracted with DCM (20 mL×2). The combined organic layers were washed with brine (20 mL×3), dried over $Na_2SO_4$, filtered and concentrated under reduced pressure to give a residue. The residue was purified by column chromatography ($SiO_2$, Petroleum ether/Ethyl acetate=10/1 to 4:1) to give the compound 46E (980 mg, yield: 58.37%) was obtained as a white solid. $^1$H NMR (400 MHz, $CDCl_3$) δ 7.16-6.97 (m, 2H), 6.90-6.71 (m, 2H), 4.96-4.72 (m, 1H), 4.52-4.37 (m, 1H), 3.74-3.72 (m, 3H), 3.07-2.66 (m, 2H), 1.37 (s, 9H).

To a solution of compound 46E (980 mg, 3.20 mmol) and $K_2CO_3$ (885 mg, 6.40 mmol) in DMSO (15 mL) was added $H_2O_2$ (9.3 mL, purity: 30%). The mixture was stirred at 0° C. for 2 hrs. The reaction mixture was diluted with $H_2O$ (100 mL) and extracted with EtOAc (30 mL×3). The combined organic layers were washed with brine (50 mL×2), dried over $Na_2SO_4$, filtered and concentrated under reduced pressure to give the compound 46F (560 mg, yield: 53.95%) was obtained as a white solid. $^1$H NMR (400 MHz, $CDCl_3$) δ 7.16-6.97 (m, 2H), 6.90-6.71 (m, 2H), 4.96-4.72 (m, 1H), 4.52-4.37 (m, 1H), 3.74-3.72 (m, 3H), 3.07-2.66 (m, 2H), 1.37 (s, 9H).

To a solution of compound 46F (500 mg, 1.54 mmol) in EtOAc (5 mL) was added HCl/EtOAc (4 M, 5 mL). The mixture was stirred at 25° C. for 1 h. The reaction mixture was diluted with MTBE (20 mL), and filtered to give the compound 46G (300 mg, yield: 73.97%, HCl) was obtained as a white solid. $^1$H NMR (400 MHz, DMSO-$d_6$) δ 8.06-7.81 (m, 3H), 7.51 (br s, 2H), 7.26-7.07 (m, 2H), 6.95-6.79 (m, 2H), 6.65-6.35 (m, 1H), 4.21-3.78 (m, 1H), 3.71 (d, J=1.5 Hz, 3H), 3.53 (br s, 1H), 2.87-2.62 (m, 2H).

Compound 46 (65 mg, yield: 65.3%, white solid) was prepared as in Example 15 from the corresponding intermediate compounds, 23A and 46G. Compound 46: $^1$H NMR (400 MHz, DMSO-$d_6$) δ 9.05-8.64 (m, 1H), 8.18 (s, 1H), 7.90 (s, 1H), 7.67-7.55 (m, 2H), 7.53-7.32 (m, 3H), 7.24-7.10 (m, 2H), 6.89-6.76 (m, 2H), 5.48-5.36 (m, 1H), 3.74-3.65 (m, 3H), 3.23-2.95 (m, 1H), 2.76-2.58 (m, 1H), 2.17-2.00 (m, 3H). MS (ESI) m/z $(M+H)^+$408.1.

Example 23

(S)—N-(4-amino-3,4-dioxo-1-phenylbutan-2-yl)-4-phenyl-1H-imidazole-5-carboxamide (48)

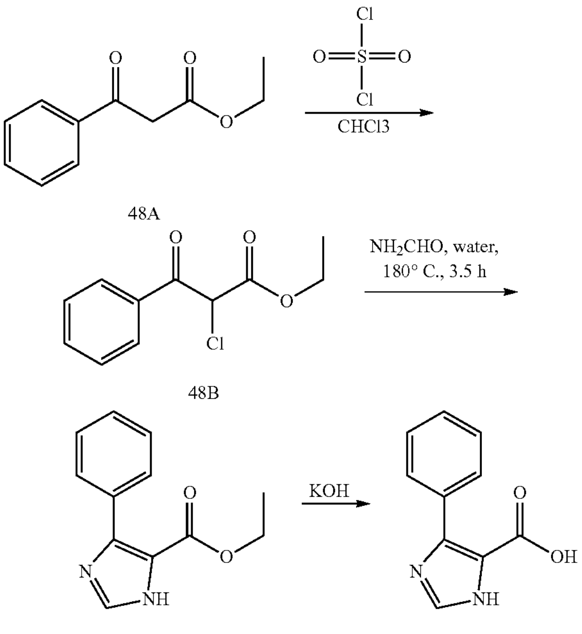

48A

48B

48C

48D

To a solution of compound 48A (40 g) in $CHCl_3$ (200 mL) cooled to 0° C. was added dropwise sulfuryl dichloride (34 g). The mixture was warmed to 30° C. for 0.5 h and heated at 70° C. for 5 hrs. After cooling to room temperature, the reaction mixture was diluted with chloroform (40 mL), washed with aqueous $NaHCO_3$ (40 mL×2), water (20 mL) and then brine (30 mL) successively. The organic phase was dried over $Na_2SO_4$ and evaporated to afford compound 48B (47 g, crude) was obtained as a yellow solid. $^1$H NMR (400 MHz, $CDCl_3$) δ 8.06-7.87 (m, 2H), 7.67-7.56 (m, 1H), 7.52-7.42 (m, 1H), 7.48-7.39 (m, 1H), 7.48-7.39 (m, 1H), 7.67-7.38 (m, 1H), 7.26 (s, 1H), 5.61 (s, 1H), 5.29-5.26 (m, 1H), 4.39-4.21 (m, 2H), 1.70 (s, 1H), 1.40-1.14 (m, 3H).

A solution of compound 48B (20 g) in $NH_2CHO$ (40 g, 882.40 mmol, 35 mL) and Water (3.2 g, 176.48 mmol) was heated at 180° C. for 3.5 hrs. The mixture was allowed to cool to room temperature, then water (50 ml) was added and the mixture was extracted with DCM (100 mL×3). The combined organic layers were washed with brine (100 mL), dried over $Na_2SO_4$, filtered and concentrated under reduced pressure to give a residue. The residue was purified by flash silica gel chromatography (Eluent of 0~100% Ethyl acetate/Petroleum ether gradient @ 40 mL/min) to afford compound 48C (1.3 g) as yellow solid. $^1$H NMR (400 MHz, DMSO-$d_6$) δ 8.09 (d, J=7.3 Hz, 7H), 4.28-4.08 (m, 2H), 1.24 (br t, J=6.8 Hz, 1H), 1.29-1.10 (m, 1H).

To a solution of ethyl compound 48C (800 mg, 3.70 mmol) in EtOH (20 mL) was added a solution of KOH (2.1 g, 37.00 mmol) in $H_2O$ (20 mL) at 0° C. After addition, the reaction mixture was stirred at 70° C. for 16 hrs 20 mL of water was added into the reaction mixture and the mixture was extracted with MTBE (20 mL). The aqueous layer was acidified with 1N HCl to pH ~4 and filtered to afford desired compound. The filtrate was extracted with EtOAc (50 mL×3). The combined extracts were washed with brine (50 mL) and dried over $Na_2SO_4$, the mixture was concentrated in vacuum to afford desired compound 48D (500 mg, yield 71.81%) as white solid. $^1$H NMR (400 MHz, DMSO-$d_6$) δ 13.42-12.33 (m, 1H), 7.97-7.67 (m, 3H), 7.48-7.21 (m, 3H).

Compound 48 (10 mg, yield 25.1%, light yellow solid) was prepared as in Example 5 from the corresponding intermediate carboxylic acid, compound 48D. Compound 48: $^1$H NMR (400 MHz, DMSO-$d_6$) δ 8.30-8.17 (m, 1H), 8.00-7.53 (m, 5H), 7.46-7.13 (m, 8H), 5.50-5.30 (m, 1H), 4.31-4.05 (m, 1H), 3.32-3.21 (m, 1H), 2.71-2.61 (m, 1H). MS (ESI) m/z $(M+H)^+$363.2.

Example 24

(S)—N-(4-amino-3,4-dioxo-1-phenylbutan-2-yl)-1-(benzo[d]thiazol-2-yl)-1H-imidazole-5-carboxamide (50)

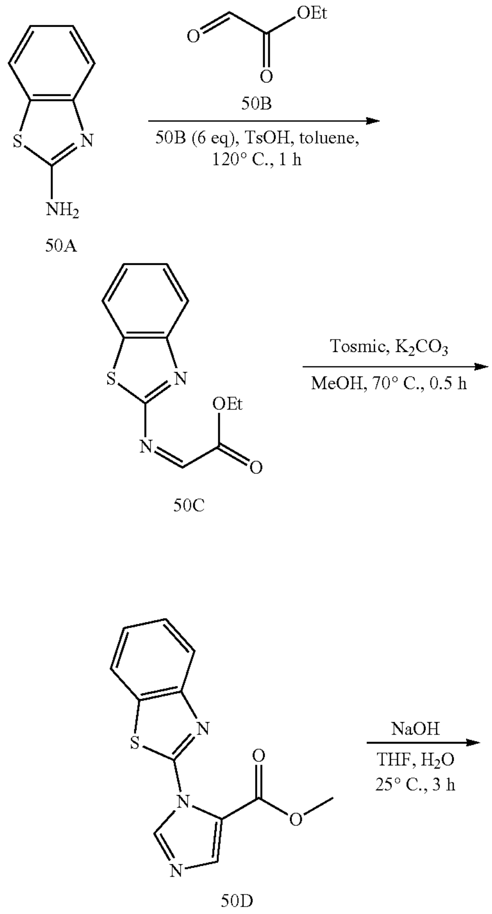

-continued

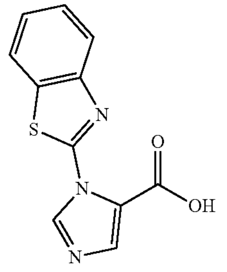

50E

A mixture of compound 50A (20 g, 133 mmol), compound 50B (136 g, 665 mmol), $TsOH.H_2O$ (2.5 g, 13.3 mmol) in toluene (200 mL) was stirred at 120° C. for 1 hour. TLC (Petroleum ether:Ethyl acetate=3:1, $R_f$~0.5) indicated 50A was almost consumed and one new spot formed. The reaction mixture was concentrated under reduced pressure to give a residue. The residue was purified by column chromatography (Petroleum ether:Ethyl acetate=20:1 to 5:1) to give compound 50C (30 g, crude) as a yellow oil. $^1$H NMR (400 MHz, $CDCl_3$) δ 9.40 (s, 1H), 7.98-7.78 (m, 1H), 7.77-7.57 (m, 1H), 7.55-7.31 (m, 1H), 7.30-7.07 (m, 1H), 5.38-5.26 (m, 1H), 4.33-4.21 (m, 3H). MS (ESI) m/z $(M+H)^+$234.9.

A mixture of methyl 50C (10 g, 45.4 mmol), TosMIC (17.7 g, 90.8 mmol), $K_2CO_3$ (9.4 g, 68.1 mmol) in MeOH (200 mL) was stirred at 70° C. for 0.5 hour. TLC (Petroleum ether:Ethyl acetate=3:1, $R_f$=0.4) indicated 50C was consumed completely and some new spots formed. The reaction mixture was filtered and concentrated under reduced pressure to give a residue. The residue was purified by column chromatography (Petroleum ether:Ethyl acetate=20:1 to 3:1) to give compound 50D (1.2 g, yield: 10.2%) as a yellow solid. $^1$H NMR (400 MHz, $CDCl_3$) δ 8.22 (d, J=0.9 Hz, 1H), 8.06 (d, J=7.9 Hz, 1H), 7.93-7.88 (m, 3H), 7.58 (dt, J=1.3, 7.7 Hz, 1H), 7.52-7.49 (m, 1H), 7.49-7.43 (m, 1H), 4.58 (s, 1H), 3.87 (s, 3H), 2.51 (s, 1H). MS (ESI) m/z $(M+H)^+$259.9.

To a solution of 50D (1.1 g, 4.24 mmol in THF (30 mL), $H_2O$ (5 mL) was added NaOH (339 mg, 8.48 mmol). The reaction mixture was stirred at 25° C. for 3 hrs. LCMS showed 50D was consumed completely and one main peak with desired MS was detected. The reaction mixture was concentrated to give a residue. The residue was dissolved in water (10 mL), adjusted pH ~5 by aqueous HCl, filtered and the filtered cake was concentrated to give the product 50E (0.6 g, yield: 57.7%) as a gray solid. $^1$H NMR (400 MHz, DMSO-$d_6$) δ 8.48 (d, J=1.1 Hz, 1H), 8.22-8.18 (m, 1H), 8.06 (dd, J=0.8, 8.0 Hz, 1H), 7.81 (d, J=0.9 Hz, 1H), 7.64-7.53 (m, 2H). MS (ESI) m/z $(M+H)^+$245.9.

Compound 50 (12.9 mg, yield: 18.8%, white solid) was prepared as in Example 5 from the corresponding intermediate carboxylic acid, compound 50E. Compound 50: $^1$H NMR (400 MHz, DMSO-$d_6$) δ 9.11 (br d, J=7.7 Hz, 1H) 8.39 (s, 1H) 8.12-8.03 (m, 2H) 7.96 (d, J=8.2 Hz, 1H) 7.81 (s, 1H) 7.66 (s, 1H) 7.57-7.45 (m, 2H) 7.26 (d, J=4.2 Hz, 4H) 7.20-7.16 (m, 1H) 5.33-5.20 (m, 1H) 3.18 (br dd, J=13.9, 3.5 Hz, 1H) 2.90-2.76 (m, 1H). MS (ESI) m/z $(M+H)^+$420.0.

Example 25

(S)—N-(4-(cyclopropylamino)-3,4-dioxo-1-phenylbutan-2-yl)-1-(1H-indazol-3-yl)-1H-imidazole-5-carboxamide (51)

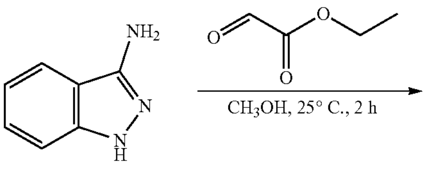

51A

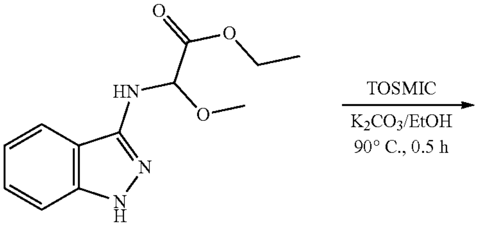

51B

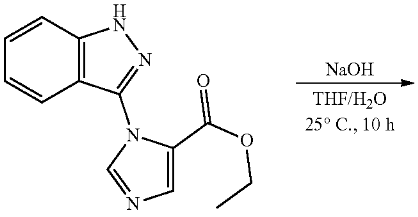

51C

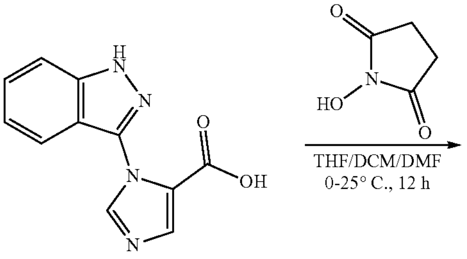

51D

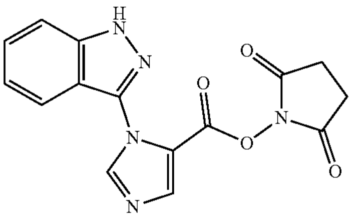

51E

To a solution of 51A (8.7 g, 65.3 mmol) in MeOH (90 mL) was added ethyl 2-oxoacetate (20 g, 98.01 mmol). After stirred at 25° C. for 2 hours, the mixture was filtered and concentrated to give crude product 51B (15 g, crude) as brown solid, which was used for the next step without purification.

To a solution of 51B (15 g, 69.1 mmol) in EtOH (400 mL) was added $K_2CO_3$ (14.5 g, 104 mmol) and TosMIC (11.6 g 59.4 mmol). After stirred at 90° C. for 0.5 hour, the reaction mixture was filtered and concentrated under reduced pressure to give a residue. The residue was purified by column chromatography ($SiO_2$, Petroleum ether/Ethyl acetate=1:0 to 1:1) to give compound 51C (2.9 g, yield: 16.4%) as a yellow solid. $^1H$ NMR (400 MHz, $CDCl_3$) δ11.04 (br s, 1H), 7.98 (d, J=0.7 Hz, 1H), 7.91 (s, 1H), 7.48-7.41 (m, 3H), 7.25-7.19 (m, 1H), 4.24-4.14 (m, 2H), 1.14 (t, J=7.1 Hz, 3H).

To a solution of 51C (2.9 g, 11.3 mmol) in THF (40 mL) and $H_2O$ (8 mL) was added NaOH (905 mg, 22.6 mmol). The mixture was stirred at 25° C. for 10 hours. The mixture was concentrated under reduced pressure to remove the organic solvent, and extracted with EtOAc (20 mL). The aqueous layer was acidized with 1M HCl to pH ~5 and then extracted with EtOAc (30 mL×3). The combined organic layer was washed with $H_2O$ (40 mL), brine (40 mL), dried over $Na_2SO_4$, filtered and concentrated to give 51D (1.5 g, yield: 58.1%) as yellow solid. $^1H$ NMR (400 MHz, DMSO-$d_6$) δ 13.35 (s, 1H), 8.16 (s, 1H), 7.83 (s, 1H), 7.61 (d, J=8.3 Hz, 1H), 7.47-7.41 (m, 2H), 7.20-7.15 (m, 1H). MS (ESI) m/z $(M+H)^+$228.9.

To a solution of 51D (500 mg, 2.19 mmol) and 1-hydroxypyrrolidine-2,5-dione (252 mg, 2.19 mmol) in THF (10 mL), DCM (5 mL) and DMF (10 mL) was added EDCI (420 mg, 2.19 mmol) at 0° C. After addition, the mixture was stirred at 25° C. for 12 h. The solvent was removed under vacuum. The residue was diluted with EtOAc (50 mL), washed with 1N HCl (20 mL), saturated $NaHCO_3$ (20 mL) and brine (20 mL). The organics were combined, dried over $Na_2SO_4$, filtered, and concentrated to give crude 51E (476 mg, yield: 66.8%) as yellow solid. $^1H$ NMR (400 MHz, DMSO-$d_6$) δ 13.52 (s, 1H), 8.57 (s, 1H), 8.32 (s, 1H), 7.63 (d, J=8.6 Hz, 1H), 7.49-7.43 (m, 2H), 7.24-7.17 (m, 1H), 2.77 (s, 5H).

Compound 51 (28.5 mg, yield: 29.1%, yellow solid) was prepared as in Example 20 from the corresponding intermediate compounds 51E and 41B. Compound 51: $^1H$ NMR (400 MHz, $CDCl_3$) δ 10.66 (br s, 1H), 7.86 (s, 1H), 7.73 (s, 1H), 7.49-7.34 (m, 3H), 7.34-7.28 (m, 1H), 7.23-7.10 (m, 4H), 7.09-6.90 (m, 3H), 5.65-5.53 (m, 1H), 3.33 (dd, J 14.1, 5.1 Hz, 1H), 3.15 (dd, J=14.1, 7.3 Hz, 1H), 2.75 (td, J=7.2, 3.6 Hz, 1H), 0.76-0.86 (m, 2H), 0.55 (br d, J=2.6 Hz, 2H). MS (ESI) m/z $(M+H)^+$443.1.

Example 26

(S)—N-(4-amino-3,4-dioxo-1-phenylbutan-2-yl)-1-(5-phenylthiazol-2-yl)-1H-imidazole-5-carboxamide (52)

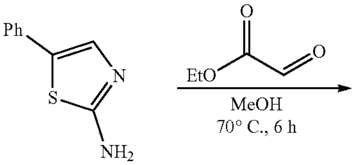

52A

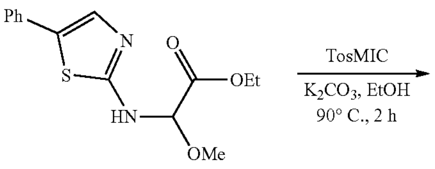

52B

-continued

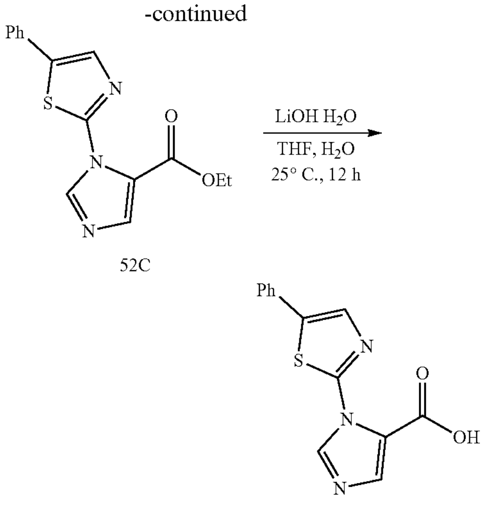

52C

52D

A mixture of compound 52A (4.2 g, 23.8 mmol) and ethyl 2-oxoacetate (14.6 g, 71.4 mmol) in MeOH (40 mL) was stirred at 70° C. for 6 hours. TLC (Petroleum ether:Ethyl acetate=2:1, $R_f$~0.7) indicated compound 52A was consumed completely, and one major new spot with lower polarity was detected. The reaction mixture was concentrated. The residue was purified by column chromatography ($SiO_2$, Petroleum ether:Ethyl acetate=20:1 to 10:1) to give compound 52B (7 g, crude) as a yellow oil.

To a mixture of compound 52B (7 g, 23.9 mmol) and $K_2CO_3$ (6.6 g, 47.8 mmol) in EtOH (15 mL) was added TosMIC (6.9 g, 35.9 mmol). The mixture was stirred at 90° C. for 2 hours. TLC (Petroleum ether:Ethyl acetate=2:1, $R_f$~0.55) indicated compound 52B was consumed completely, and one major new spot with larger polarity was detected. The reaction mixture was concentrated to give residue. The crude product was purified by silica gel chromatography eluted with Petroleum ether:Ethyl acetate=15:1 to 5:1 to give compound 52C (6 g, crude) as a yellow solid. MS (ESI) m/z $(M+H)^+$299.9.

To a solution of compound 52C (3.5 g, 11.69 mmol) in THF (20 mL) and $H_2O$ (6 mL) was added $LiOH.H_2O$ (981 mg, 23.3 mmol) in one portion. The mixture was stirred at 25° C. for 12 hours. TLC (Petroleum ether:Ethyl acetate=1:1, $R_f$~0.25) indicated compound 52C was consumed completely and one new spot formed. The mixture was adjusted to pH ~5 by adding HCl (2M), and then white solid was precipitate out, filtered and dried under reduced pressure to give compound 52D (1.5 g, yield: 47.3%) as a white solid. $^1$H NMR (400 MHz, DMSO-$d_6$) δ 8.37 (s, 1H), 8.19 (s, 1H), 7.76-7.70 (m, 3H), 7.53-7.46 (m, 2H), 7.45-7.38 (m, 1H).

Compound 52 (50.9 mg, yield: 43%, white solid) was prepared as in Example 5 from the corresponding intermediate carboxylic acid, compound 52D. Compound 52: $^1$H NMR (400 MHz, DMSO-$d_6$) δ 9.05 (d, J=7.5 Hz, 1H), 8.32 (s, 1H), 8.11 (s, 2H), 7.85 (s, 1H), 7.71-7.66 (m, 3H), 7.48 (t, J=7.5 Hz, 2H), 7.44-7.39 (m, 1H), 7.30 (d, J=4.4 Hz, 4H), 7.23-7.19 (m, 1H), 5.35-5.25 (m, 1H), 3.21 (dd, J=3.7, 13.8 Hz, 1H), 2.85 (dd, J=10.3, 13.8 Hz, 1H). MS (ESI) m/z $(M+H)^+$446.0.

Example 27

(S)—N-(4-(cyclopropylamino)-3,4-dioxo-1-phenylbutan-2-yl)-1-(5-phenylthiazol-2-yl)-1H-imidazole-5-carboxamide (53)

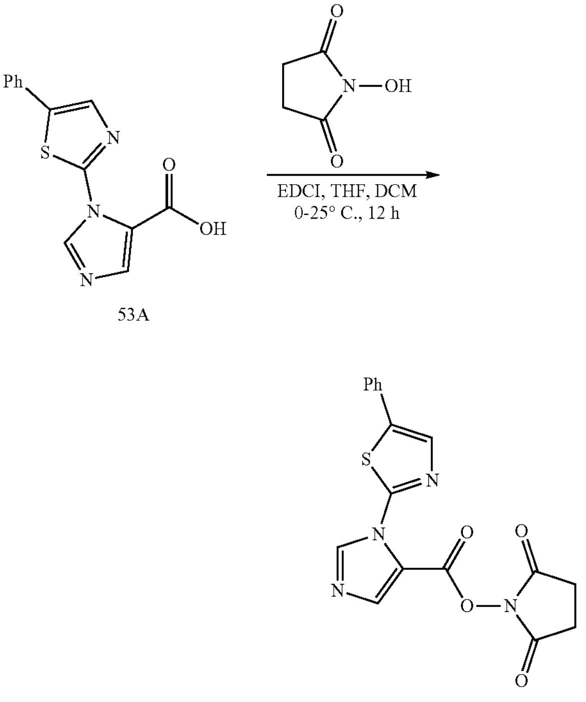

53A

53B

To a mixture of compound 53A (600 mg, 2.21 mmol) and compound 1-hydroxypyrrolidine-2,5-dione (254 mg, 2.21 mmol) in THF (10 mL) at 0° C. was added a solution of EDCI (423 mg, 2.21 mmol) in DCM (5 mL) dropwise. The mixture was stirred at 25° C. for 12 hours. TLC (Petroleum ether:Ethyl acetate=1:1, $R_f$~0.4) indicated compound 53A was consumed completely, and one major new spot with lower polarity was detected. The reaction mixture was concentrated to remove solvent. The residue was diluted with EtOAc (50 mL), washed with $H_2O$ (20 mL), saturated $NaHCO_3$ (20 mL), brine (20 mL). The organics were collected, dried with $Na_2SO_4$, filtered, and concentrated to give desired intermediate compound 53B (700 mg, yield: 85.9%) as a yellow solid. $^1$H NMR (400 MHz, $CDCl_3$) δ 8.29 (s, 1H), 8.20 (s, 1H), 7.86 (s, 1H), 7.57 (d, J=6.5 Hz, 2H), 7.48-7.36 (m, 3H), 7.27 (s, 1H), 2.88 (s, 4H).

Compound 53 (41 mg, yield: 34.3%, white solid) was prepared as in Example 20 from the corresponding intermediate compound 53B. Compound 53: $^1$H NMR (400 MHz, DMSO-$d_6$) δ 9.08 (d, J=7.7 Hz, 1H), 8.82 (d, J=5.0 Hz, 1H), 8.32 (d, J=0.8 Hz, 1H), 8.11 (s, 1H), 7.72-7.64 (m, 3H), 7.52-7.46 (m, 2H), 7.44-7.39 (m, 1H), 7.30 (d, J=4.4 Hz, 4H), 7.24-7.18 (m, 1H), 5.31-5.22 (m, 1H), 3.21 (dd, J=13.7, 3.6 Hz, 1H), 2.90-2.70 (m, 2H), 0.66-0.54 (m, 4H). MS (ESI) m/z $(M+H)^+$486.1.

Example 28

(S)—N-(4-amino-3,4-dioxo-1-phenylbutan-2-yl)-4-methyl-1-phenyl-1H-1,2,3-triazole-5-carboxamide (55)

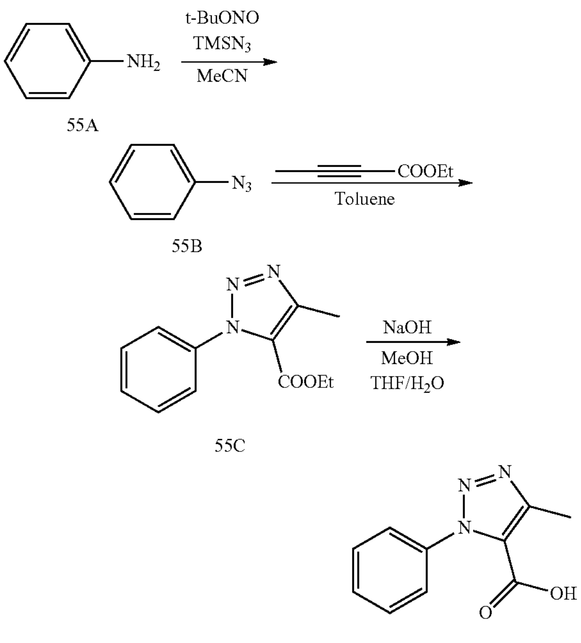

55A 55B 55C 55D

A solution of compound 55A (2.5 g, 26.8 mmol) in MeCN (50 mL) was added t-BuONO (4.15 g, 40.3 mmol) at 0° C. followed with $TMSN_3$ (4.64 g, 40.3 mmol). The reaction mixture was stirred at 20° C. for 1 hr. The solvent was evaporated to give intermediate compound 55B (4 g, crude) as yellow oil.

A mixture of compound 55B (4 g, crude) and compound ethyl but-2-ynoate (1 g, 8.92 mmol) in toluene (20 mL) was stirred at 110° C. for 5 hrs. The solvent was evaporated. The crude product was purified by silica gel column chromatography (Petroleum ether:Ethyl acetate=20:1~5:1) to give compound 55C (150 mg, yield: 7.27%) as yellow oil. $^1H$ NMR (400 MHz, $CDCl_3$) δ 7.54-7.49 (m, 2H), 7.44-7.40 (m, 2H), 7.37 (d, J=5.1 Hz, 1H), 4.25 (q, J=7.1 Hz, 2H), 1.21 (t, J=7.1 Hz, 3H).

A solution of compound 55C (150 mg, 649 umol) in THF (2 mL) and $H_2O$ (2 mL) was added NaOH (51.9 mg). The reaction mixture was stirred at 20° C. for 30 min. TLC showed a new peak with higher polarity was generated. The solvent was evaporated and 1M HCl was added until pH ~6. The mixture was filtered and the cake was dried to give compound 55D (120 mg, yield: 91.0%) as a yellow solid.

Compound 55 (46 mg, 121 umol, yield: 42.0%, yellow solid) was prepared as in Example 5 from the corresponding intermediate carboxylic acid, compound 55D. Compound 55: $^1H$ NMR (400 MHz, DMSO-$d_6$) δ 9.36 (br d, J=7.9 Hz, 1H), 8.20 (s, 1H), 7.94 (s, 1H), 7.51-7.43 (m, 3H), 7.36-7.28 (m, 7H), 5.38 (br t, J=7.7 Hz, 1H), 3.26 (br s, 1H), 2.82-2.73 (m, 1H), 2.21 (s, 3H). MS (ESI) m/z $(M+H)^+$378.1.

Example 29

(S)—N-(4-amino-3,4-dioxo-1-phenylbutan-2-yl)-4-methyl-1-phenyl-1H-1,2,3-triazole-5-carboxamide (56)

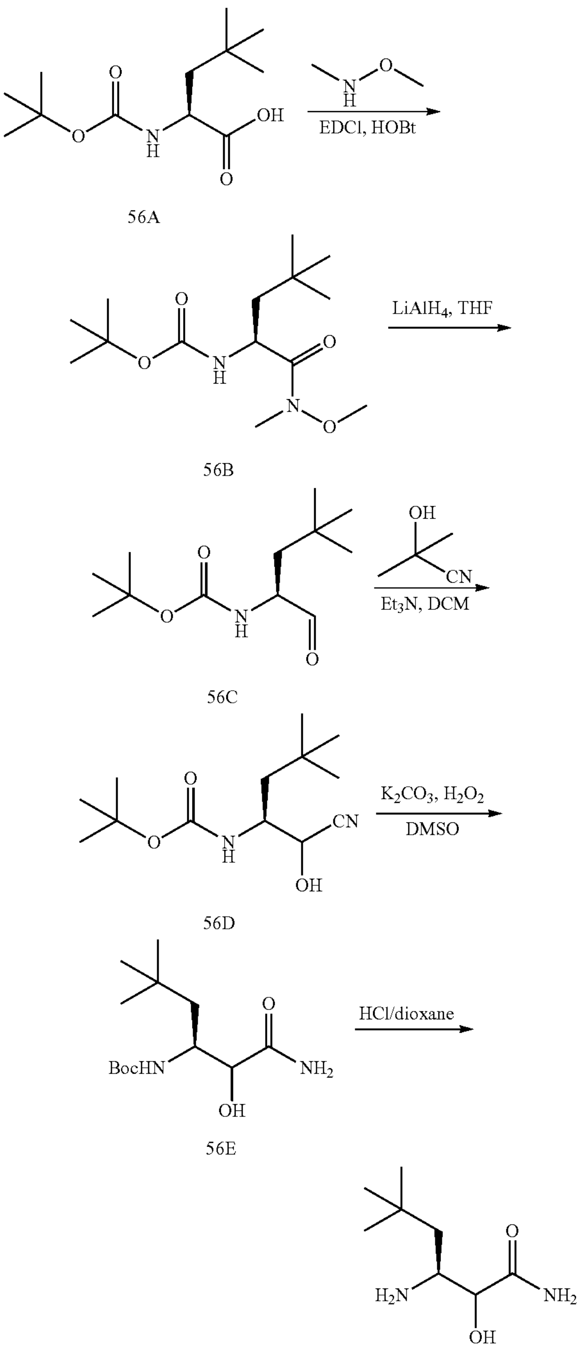

56A 56B 56C 56D 56E 56F

A mixture of compound 56A (1.0 g, 4.08 mmol), compound N,O-dimethylhydroxylamine (478 mg, 4.90 mmol, HCl), HOBt (552 mg, 4.08 mmol) and NMM (1.24 g, 12.24 mmol, 1.35 mL) in $CHCl_3$ (20 mL) was degassed and purged with $N_2$ for 3 times at 0° C., then EDCI (1.17 g, 6.12 mmol)

was added in portions. The mixture was stirred at 25° C. for 20 hrs under $N_2$ atmosphere. The reaction mixture was quenched by addition $H_2O$ (20 mL), and then diluted with DCM (10 mL). The combined organic layers were washed with 1N HCl (15 mL×2), saturated aqueous $NaHCO_3$ (15 mL×2) and brine (20 mL), dried over $Na_2SO_4$, filtered and concentrated under reduced pressure to give the compound 56B (1.15 g, yield: 97.7%) was obtained as a white solid. $^1$H NMR (400 MHz, DMSO-$d_6$) δ 6.97 (br d, J=8.8 Hz, 1H), 4.47 (br t, J=8.4 Hz, 1H), 3.73-3.64 (m, 3H), 3.06 (s, 3H), 1.51-1.27 (m, 11H), 0.87 (s, 9H).

To a solution of LAH (303 mg, 7.98 mmol) in THF (10 mL) was degassed and purged with $N_2$ for 3 times at 0° C., and the mixture of compound 56B (1.15 g, 3.99 mmol) in THF (20 mL) was added dropwise, and then the mixture was stirred at 0° C. for 2 hrs under $N_2$ atmosphere. The reaction mixture was quenched by add EtOAc (10 mL), then add 1N HCl (50 mL), and then diluted with EtOAc (20 mL), dried over $Na_2SO_4$, and stirred for 30 min, then filtered to give the organic layers. The combined organic layers were washed with brine (20 mL×2), dried over $Na_2SO_4$, filtered and concentrated under reduced pressure to give the compound 56C (900 mg, yield: 98.4%) was obtained as a white solid. $^1$H NMR (400 MHz, $CDCl_3$) δ 9.55 (s, 1H), 4.83 (br s, 1H), 4.24 (br s, 1H), 1.86-1.55 (m, 2H), 1.44 (s, 9H), 1.03-0.91 (m, 9H).

To a solution of compound 56C (900 mg, 3.92 mmol) in DCM (20 mL) was added compound 2-hydroxy-2-methyl-propanenitrile (2.33 g, 27.32 mmol, 2.50 mL) and $Et_3N$ (595 mg, 5.88 mmol, 815 uL). The mixture was stirred at 25° C. for 2 hrs. The reaction mixture was quenched by addition 1N HCl (20 mL), and then diluted with $H_2O$ (20 mL) and extracted with DCM (20 mL×2). The combined organic layers were washed with brine (20 mL×3), dried over $Na_2SO_4$, filtered and concentrated under reduced pressure to give the compound 56D (930 mg, yield: 92.55%) was obtained as a white solid. $^1$H NMR (400 MHz, $CDCl_3$) δ 5.06-4.66 (m, 1H), 4.55-4.35 (m, 1H), 4.05-3.73 (m, 1H), 1.80-1.65 (m, 2H), 1.45 (br d, J=6.8 Hz, 9H), 1.10-0.80 (m, 9H).

To a solution of compound 56D (930 mg, 3.63 mmol) and $K_2CO_3$ (1.00 g, 7.26 mmol) in DMSO (15 mL) was added $H_2O_2$ (4.12 g, 36.30 mmol, 3.49 mL, purity: 30%). The mixture was stirred at 0° C. for 2 hrs. The reaction mixture was diluted with $H_2O$ (50 mL) and extracted with EtOAc (20 mL×2). The combined organic layers were washed with brine (30 mL×2), dried over $Na_2SO_4$, filtered and concentrated under reduced pressure to give a residue. The residue was stirred in DCM (0.1 mL) and PE (5 mL) for 30 min and filtered to give the compound 56E (480 mg, yield: 48.20%) was obtained as a white solid. $^1$H NMR (400 MHz, $CDCl_3$) δ 6.83 (br s, 1H), 5.65 (br s, 1H), 5.27-5.06 (m, 1H), 4.99-4.82 (m, 1H), 4.23-4.00 (m, 1H), 3.88 (br t, J=8.6 Hz, 1H), 1.77 (br s, 1H), 1.60-1.51 (m, 1H), 1.42 (d, J=9.3 Hz, 9H), 0.94 (d, J=10.1 Hz, 9H).

To a solution of compound 56E (480 mg, 1.75 mmol) in EtOAc (5 mL) was added HCl/EtOAc (4M, 5 mL). The mixture was stirred at 25° C. for 1 h. The reaction mixture was diluted with PE (20 mL), filtered and concentrated under reduced pressure to give the compound 56F (360 mg, yield: 97.63%, HCl) was obtained as a white solid. $^1$H NMR (400 MHz, DMSO-$d_6$) δ 8.00 (br s, 1H), 7.92-7.70 (m, 1H), 7.58-7.41 (m, 2H), 4.21-3.93 (m, 1H), 3.33 (br d, J=3.5 Hz, 2H), 1.76-1.24 (m, 2H), 0.86 (s, 9H).

Compound 56 (94.20 mg, yield: 85.26%, white solid) was prepared as in Example 35 from the corresponding intermediate compounds, 23A and 56F. Compound 56: $^1$H NMR (400 MHz, DMSO-$d_6$) δ 8.98-8.61 (m, 1H), 8.20-7.95 (m, 1H), 7.85-7.71 (m, 2H), 7.57-7.37 (m, 3H), 5.25 (br t, J=6.8 Hz, 1H), 2.35-2.20 (m, 3H), 1.63-1.28 (m, 2H), 0.98-0.76 (m, 9H). MS (ESI) m/z $(M+H)^+$358.2.

Example 30

(S)—N-(4-amino-1-(1 h-indol-3-yl)-3,4-dioxobutan-2-yl)-3-methyl-5-phenylisoxazole-4-carboxamide (57)

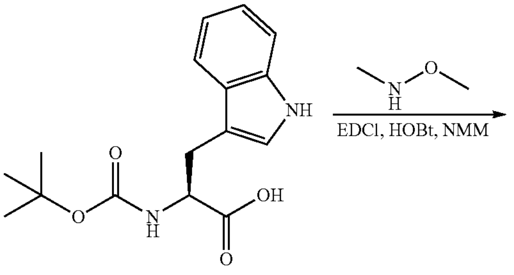

57A

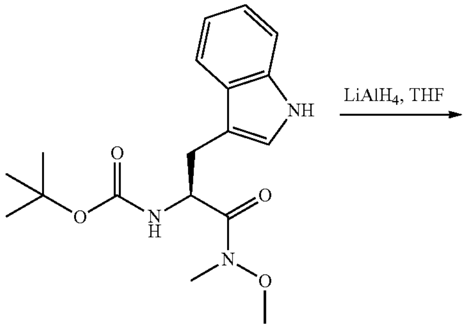

57B

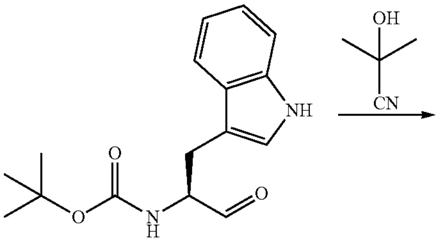

57C

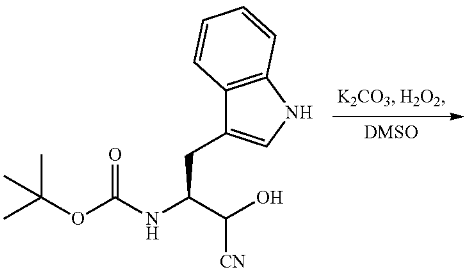

57D

-continued

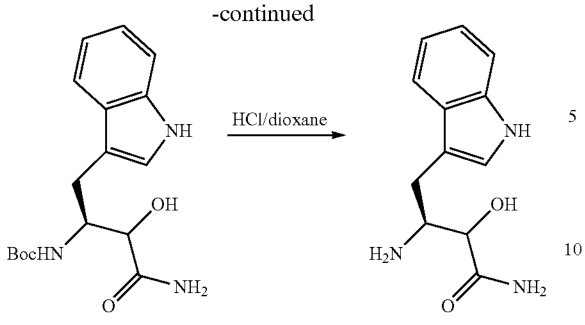

57E 57F

A mixture of compound 57A (5.00 g, 16.43 mmol), compound N,O-dimethylhydroxylamine (1.76 g, 18.07 mmol, HCl), HOBt (2.22 g, 16.43 mmol) and NMM (4.99 g, 49.29 mmol, 5.42 mL) in $CHCl_3$ (150 mL) was degassed and purged with $N_2$ for 3 times at 0° C., then EDCI (4.72 g, 24.65 mmol) was added in portions, and then the mixture was stirred at 25° C. for 23 hrs under $N_2$ atmosphere. The reaction mixture was quenched by addition $H_2O$ (100 mL), and then diluted with 1N HCl (200 mL) and extracted with $NaHCO_3$ (50 mL×2). The combined organic layers were washed with brine (200 mL), dried over $Na_2SO_4$, filtered and concentrated under reduced pressure to give a residue. The residue was purified by column chromatography ($SiO_2$, Petroleum ether/Ethyl acetate=6/1 to 1/1) to give the compound 57B (5.94 g) was obtained as a yellow solid. $^1H$ NMR (400 MHz, DMSO-$d_6$) δ 10.79 (br s, 1H), 7.50 (d, J=7.7 Hz, 1H), 7.32 (d, J=8.2 Hz, 1H), 7.19-7.11 (m, 1H), 7.07-6.96 (m, 3H), 4.59 (br s, 1H), 3.70 (br s, 3H), 3.10 (s, 3H), 3.03-2.94 (m, 1H), 2.89-2.77 (m, 1H), 1.29 (s, 9H).

To a solution of LAH (330 mg, 8.64 mmol) in THF (10 mL), and then compound 57B (2.00 g, 5.76 mmol) in THF (20 mL) was added dropwise. The mixture was stirred at 0° C. for 2 hrs. The reaction mixture was quenched by addition EtOAc (10 mL) at 0° C., and then diluted with 1N HCl (40 mL) and extracted with EtOAc (20 mL×2). The combined organic layers were washed with 1N HCl (40 mL) and $NaHCO_3$ (30 mL×2) and brine (100 mL), dried over $Na_2SO_4$, filtered and concentrated under reduced pressure to give the compound 57C (1.55 g, yield: 93.33%) was obtained as a yellow solid. $^1H$ NMR (400 MHz, DMSO-$d_6$) δ11.02-10.75 (m, 1H), 9.52 (s, 1H), 7.50 (br d, J=7.7 Hz, 1H), 7.32 (d, J=7.9 Hz, 1H), 7.25 (br d, J=7.3 Hz, 1H), 7.14 (d, J=1.8 Hz, 1H), 7.05 (t, J=7.2 Hz, 1H), 7.00-6.92 (m, 1H), 4.14-4.05 (m, 1H), 3.19-3.10 (m, 1H), 2.95-2.85 (m, 1H), 2.52-2.45 (m, 4H), 1.39-1.23 (m, 9H).

To a solution of compound 57C (1.50 g, 5.20 mmol) in DCM (30.00 mL) was added compound N,O-dimethylhydroxylamine (885 mg, 10.40 mmol, 960 uL) and $Et_3N$ (790 mg, 7.80 mmol, 1.08 mL). After stirred at 25° C. for 20 hrs, the reaction mixture was quenched by addition 0.5N HCl 30 mL, and then extracted with DCM (30 mL×2). The combined organic layers were washed with brine (30 mL×2), dried over $Na_2SO_4$, filtered and concentrated under reduced pressure. Compound 57D (1.74 g, yellow solid): $^1H$ NMR (400 MHz, $CDCl_3$) δ 9.64 (s, 1H), 8.14 (br s, 1H), 7.60 (d, J=7.7 Hz, 1H), 7.37 (d, J=8.2 Hz, 1H), 7.24-7.18 (m, 1H), 7.17-7.11 (m, 1H), 7.03 (d, J=2.2 Hz, 1H), 5.14 (br s, 1H), 4.51 (br d, J=6.6 Hz, 1H), 3.41-3.16 (m, 2H), 1.44 (s, 9H).

To a solution of compound 57D (1.74 g, 5.52 mmol) and $K_2CO_3$ (1.53 g, 11.04 mmol) in DMSO (25.00 mL) was added $H_2O_2$ (6.43 g, 189.00 mmol, 5.45 mL) at 0° C. The mixture was stirred at 0° C. for 1 h. The reaction mixture was diluted with $H_2O$ (50 mL), and then quenched by addition $Na_2S_2O_3$ (50 mL) and extracted with EtOAc (50 mL×3) and $Na_2S_2O_3$ (50 mL×3). The combined organic layers were washed with brine (50 mL), dried over $Na_2SO_4$, filtered and concentrated under reduced pressure to give a residue. The residue was purified by column chromatography ($SiO_2$, Petroleum ether/Ethyl acetate=1/2 to 0:1) to give the compound 57E (689.60 mg, yield: 37.47%) was obtained as a yellow solid. $^1H$ NMR (400 MHz, $CDCl_3$) δ 8.06 (br s, 1H), 7.70 (d, J=8.3 Hz, 1H), 7.38 (d, J=7.8 Hz, 1H), 7.25-7.06 (m, 4H), 5.42 (br s, 1H), 5.19-5.04 (m, 1H), 4.21-4.08 (m, 3H), 3.30-3.12 (m, 2H), 1.41 (s, 9H).

To a solution of compound 57E (680.00 mg, 2.04 mmol) in EtOAc (5.00 mL) was added HCl/EtOAc (5.00 mL). The mixture was stirred at 25° C. for 2.5 hrs. The reaction mixture was concentrated under reduced pressure to remove solvent to give the compound 57F (400.00 mg, yield: 72.69%, HCl) was obtained as a brown solid. $^1H$ NMR (400 MHz, DMSO-$d_6$) δ 11.01 (br s, 1H), 7.92 (br s, 2H), 7.70-7.46 (m, 3H), 7.39-7.26 (m, 2H), 7.12-6.95 (m, 2H), 4.01-3.89 (m, 1H), 3.81-3.64 (m, 1H), 3.14 (s, 2H), 3.08-2.80 (m, 2H).

Compound 57 (11.20 mg, yield: 29.41%, white solid) was prepared as in Example 15 from the corresponding intermediate compounds, 23A and 57F. Compound 57: $^1H$ NMR (400 MHz, DMSO-$d_6$) δ10.89 (br s, 1H), 9.03 (d, J=7.3 Hz, 1H), 8.23 (s, 1H), 7.95 (s, 1H), 7.70 (d, J=7.8 Hz, 1H), 7.63 (d, J=7.5 Hz, 2H), 7.48 (br d, J=7.5 Hz, 1H), 7.39 (t, J=7.4 Hz, 3H), 7.17 (d, J=1.8 Hz, 1H), 7.13-6.96 (m, 2H), 5.56 (br s, 1H), 2.97-2.87 (m, 1H), 2.70-2.54 (m, 1H), 2.11 (s, 3H). MS (ESI) m/z $(M+H)^+$417.1.

Example 31

(S)—N-(4-amino-1-(1H-indol-3-yl)-3,4-dioxobutan-2-yl)-3-methyl-5-phenylisoxazole-4-carboxamide (58)

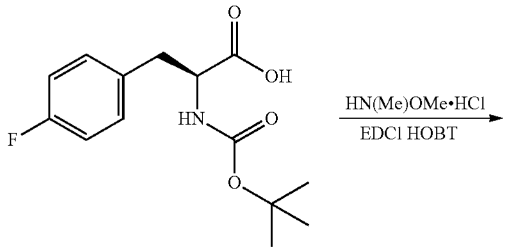

58A

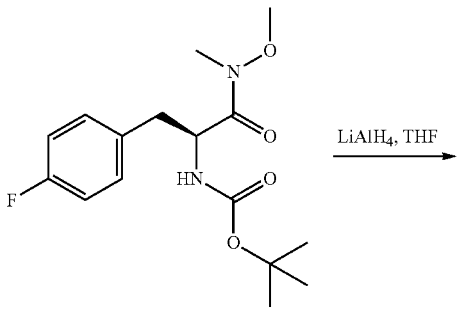

58B

-continued

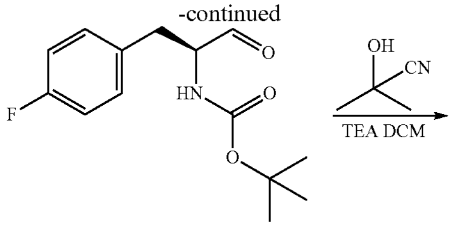

58c

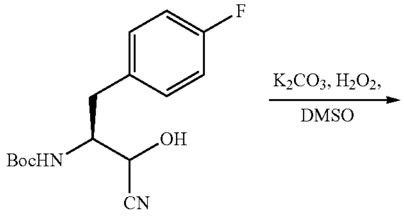

58D

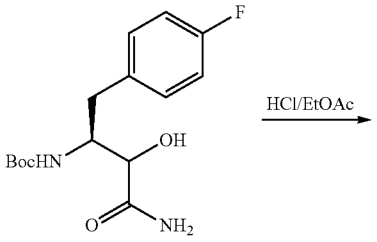

58E

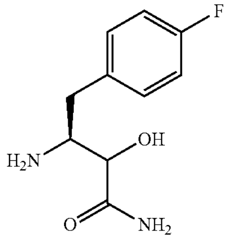

58F

To a solution of N-methoxymethanamine (1.89 g 19.42 mmol), compound 58A (5.0 g, 17.65 mmol), HOBt (2.38 g, 17.65 mmol) and NMM (52.95 mmol, 5.8 mL) in $CHCl_3$ (100 mL) was degassed and purged with $N_2$ for 3 times at 0° C., then EDCI (5.1 g, 26.48 mmol) was added in portions. The mixture was stirred at 25° C. for 16 hrs under $N_2$ atmosphere. The reaction mixture was washed with $H_2O$ (100 mL). The organic layers were washed with 1 mol/L HCl (100 mL×2), saturated $NaHCO_3$ (100 mL×2) and saturated brine (100 ml), dried over $Na_2SO_4$, filtered and concentrated under reduced pressure to give a residue. The residue was purified by flash silica gel chromatography (ISCO®; 80 g SepaFlash® Silica Flash Column, Eluent of 0 30% Ethyl acetate/Petroleum ether gradient @ 40 mL/min) to afford compound 58B (4.00 g, yield 69.4%) as white solid. $^1H$ NMR (400 MHz, $CDCl_3$) δ 7.11 (dd, J=5.6, 8.3 Hz, 2H), 6.94 (t, J=8.7 Hz, 2H), 5.18 (br d, J=7.9 Hz, 1H), 4.98-4.80 (m, 1H), 4.13-4.07 (m, 2H), 3.72-3.64 (m, 4H), 3.14 (s, 3H), 3.08-2.94 (m, 1H), 2.91-2.70 (m, 1H), 2.02 (s, 2H), 1.78 (br s, 1H), 1.37 (s, 10H), 1.28-1.20 (m, 3H).

To $LiAlH_4$ (128 mg 3.37 mmol) in 100 mL of dry flask was added dropwise THF (15 mL) at 0° C. After addition, the mixture was stirred at this temperature, and then a solution of compound 58B (1.0 g 3.06 mmol) in THF (15 mL) was added dropwise to the above mixture at 0° C. The resulting mixture was stirred at 0° C. for 1.5 hrs. The reaction mixture was quenched by slowly added EtOAc (20 mL) at 0° C., and then added 1N HCl (20 mL) and extracted with EtOAc (30 mL×2). The combined organic layers were washed with $NaHCO_3$ (30 mL×2) and brine (20 mL), dried over $Na_2SO_4$, filtered and concentrated under reduced pressure to give the compound 58C (810 mg, yield 99.0%) as white solid. $^1H$ NMR (400 MHz, $CDCl_3$) δ 9.65 (br s, 1H), 9.63 (br s, 1H), 7.21-7.08 (m, 2H), 7.00 (br d, J=8.6 Hz, 2H), 5.05 (br s, 1H), 4.42 (br s, 1H), 3.09-3.02 (m, 1H), 3.11 (br d, J=6.2 Hz, 1H), 1.51-1.38 (m, 9H).

To a solution of compound 58C (3.2 g, 11.86 mmol) and 2-hydroxy-2-methylpropanenitrile (2.2 mL, 23.72 mmol) in DCM (30 mL) was added TEA (2 mL, 14.23 mmol). After addition, the reaction mixture was stirred at 28° C. for 14 hrs. The reaction mixture was diluted with 30 mL of DCM and the mixture was quenched by addition 0.5N HCl 30 mL. The organic layer were washed with $H_2O$ (30 mL) and brine (50 mL), dried over $Na_2SO_4$, filtered and concentrated under reduced pressure to give compound 58D (3.4 g, yield 89.2%) as a white solid. $^1H$ NMR (400 MHz, $CDCl_3$) δ 7.15-7.07 (m, 2H), 7.01-6.90 (m, 2H), 4.94-4.70 (m, 1H), 4.52-4.36 (m, 1H), 4.16-3.67 (m, 1H), 3.11-2.78 (m, 2H), 1.57-1.47 (m, 2H).

To a solution of compound 58D (3.42 g 11.62 mmol) and $K_2CO_3$ (3.21 g, 23.24 mmol) in DMSO (30 mL) was added $H_2O_2$ (395.08 mmol, 12 mL) at 0° C. After addition, the reaction mixture was stirred at 0° C. for 1.5 hrs. The reaction mixture was diluted with water (100 mL) and quenched with saturated aqueous $Na_2S_2O_3$ slowly into ice water. The mixture was extracted with EtOAc (200 mL×3) and the combined extracts were washed with saturated aqueous $Na_2S_2O_3$ (100 mL×3). The organic layer was dried over $Na_2SO_4$, concentrated and to yield a residue. The residue was diluted with EtOAc (10 mL) and filtered to give the compound 58E (2.25 g, yield 61.99%) as a white solid. $^1H$ NMR (400 MHz, DMSO-$d_6$) δ 7.25 (br s, 6H), 6.62-6.03 (m, 1H), 5.75-5.55 (m, 1H), 4.02-3.67 (m, 2H), 2.80-2.52 (m, 2H), 2.52-2.51 (m, 1H), 1.26 (d, J=3.7 Hz, 9H). MS (ESI) m/z ($M+Na^+$) 334.9.

To a solution of compound 58E (1 g 3.20 mmol) in EtOAc (10 mL) was added HCl/EtOAc (4 mmol, 20 mL). The mixture was stirred at 28° C. for 2 hrs. The reaction mixture diluted with MTBE and filtered to give the compound 58F (750 mg, yield 94.25%) as white solid. $^1H$ NMR (400 MHz, DMSO-$d_6$) δ 8.25-7.94 (m, 3H), 7.58-7.43 (m, 2H), 7.41-7.33 (m, 1H), 7.30-7.23 (m, 1H), 7.41-7.23 (m, 1H), 7.20-7.05 (m, 2H), 6.90-6.37 (m, 1H), 6.80-6.25 (m, 1H), 4.24 (br s, 1H), 3.88-3.81 (m, 1H), 3.85 (br s, 1H), 3.68-3.50 (m, 1H), 2.96-2.76 (m, 2H). MS (ESI) m/z $(M+H)^+$213.1.

Compound 58 (130 mg, yield 78.40%, light yellow solid) was prepared as in Example 15 from the corresponding intermediate compounds, 23A and 58F. Compound 58: $^1H$ NMR (400 MHz, DMSO-$d_6$) δ 9.05 (d, J=7.7 Hz, 1H), 8.20 (br s, 1H), 7.93 (brs, 1H), 7.66-7.59 (m, 2H), 7.55-7.49 (m, 1H), 7.48-7.41 (m, 2H), 7.35-7.26 (m, 2H), 7.17-7.06 (m, 2H), 5.51-5.40 (m, 1H), 3.28-3.19 (m, 1H), 2.81-2.69 (m, 1H), 2.11 (s, 3H). MS (ESI) m/z $(M+H)^+$396.1.

Example 32

(S)—N-(4-amino-1-(1H-indol-3-yl)-3,4-dioxobutan-2-yl)-3-methyl-5-phenylisoxazole-4-carboxamide (59)

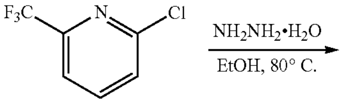

59A

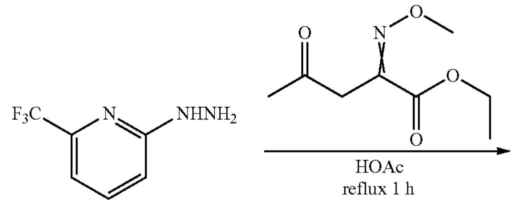

59B

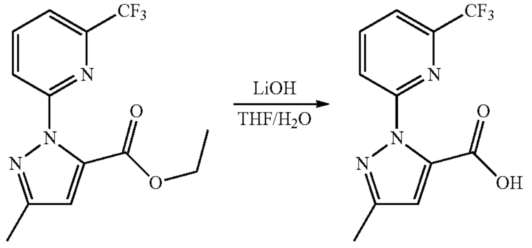

59C 59D

To a solution of compound 59A (10 g, 55.08 mmol) in EtOH (30 mL) was added $NH_2NH_2.H_2O$ (32 mL, 550.80 mmol). After addition, the reaction mixture was stirred at 80° C. for 14 hrs. The reaction mixture was concentrated and the residue was dissolved into 150 mL of EtOAc, the mixture was washed with water (50 mL) and brine (50 mL), then dried over $Na_2SO_4$ and concentrated in vacuum to afford compound 59B (9.7 g, yield 99.4%) as white solid. $^1H$ NMR (400 MHz, DMSO-$d_6$) δ 8.02 (s, 1H), 7.71-7.53 (m, 1H), 7.03-6.79 (m, 2H), 4.23 (s, 2H).

To a solution of compound 59B (1 g, 5.65 mmol) in AcOH (10 mL) was added ethyl 2-methoxyimino-4-oxo-pentanoate (1.1 g, 5.65 mmol). After addition, the reaction mixture was stirred at 120° C. for 14 hrs. The mixture was concentrated in vacuum and the residue was dissolved into 80 mL of EtOAc, the mixture was washed with 30 mL of saturated aqueous $NaHCO_3$ and brine (30 mL). The mixture was dried over $Na_2SO_4$ and concentrated in vacuum. The residue was purified by column chromatography ($SiO_2$, Petroleum ether/Ethyl acetate=20/1 to 10:1) to afford desired compound 59C (1.2 g, yield: 71%) as white solid. $^1H$ NMR (400 MHz, DMSO-$d_6$) δ 8.34-8.25 (m, 1H), 8.05 (d, J=8.2 Hz, 1H), 7.93 (d, J=7.5 Hz, 1H), 6.86 (s, 1H), 4.18 (q, J=7.1 Hz, 2H), 2.29 (s, 3H), 1.11 (t, J=7.1 Hz, 3H). MS (ESI) m/z $(M+H)^+$299.9.

To a solution of compound 59C (700 mg, 2.34 mmol) in THF (10 mL) was added a solution of $LiOH.H_2O$ (393 mg, 9.36 mmol) in $H_2O$ (10 mL) at 0° C. After addition, the reaction mixture was stirred at 28° C. for 16 hrs, 20 mL of MTBE was added into the reaction mixture, then the mixture was separated and the aqueous layer was acidified by 1N HCl to pH 4, the mixture was filtered to afford white solid which was dried to afford compound 59D (330 mg, yield 51.95%) as white solid. $^1H$ NMR (400 MHz, DMSO-$d_6$) δ 13.48 (br s, 1H), 8.31-8.22 (m, 1H), 8.02-7.89 (m, 2H), 6.81 (s, 1H), 2.27 (s, 3H). MS (ESI) m/z $(M+H)^+$271.8.

Compound 59 (50 mg, yield: 37.9%, white solid) was prepared as in Example 5 from the corresponding intermediate carboxylic acid, compound 59D. Compound 59: $^1H$ NMR (400 MHz, DMSO-$d_6$) δ 9.07 (d, J=7.3 Hz, 1H), 8.27-8.16 (m, 1H), 8.04 (s, 1H), 7.89-7.77 (m, 3H), 7.30-7.19 (m, 5H), 6.59 (s, 1H), 5.40-5.28 (m, 1H), 3.15 (dd, J=4.0, 13.8 Hz, 1H), 2.82 (dd, J=9.5, 13.8 Hz, 1H), 2.30 (s, 3H). MS (ESI) m/z $(M+H)^+$446.1.

Example 33

(S)—N-(4-amino-3,4-dioxo-1-phenylbutan-2-yl)-5-phenylisoxazole-4-carboxamide (61)

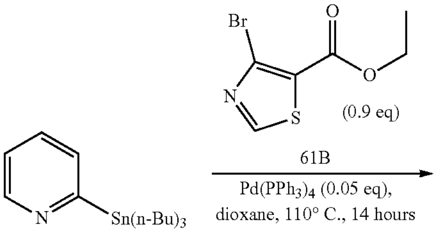

61B

61A

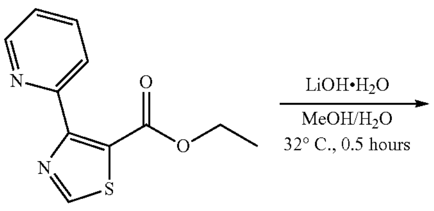

61C

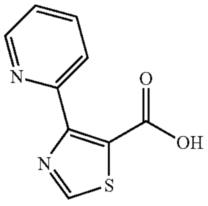

61D

A mixture of compound 61B (500 mg, 2.12 mmol), compound 61A (859 mg, 2.33 mmol), $Pd(PPh_3)_4$ (122 mg, 106 umol) was stirred at 105° C. for 14 hours. The mixture was concentrated. The residue was purified by column chromatography ($SiO_2$, Petroleum ether/Ethyl acetate=3/1 to 1/1) to afford compound 61C (376 mg, 74.95% yield) as yellow oil. MS (ESI) m/z $(M+H)^+$234.9.

To a solution of compound 61C (320 mg, 1.37 mmol) in MeOH (20 mL) was added $LiOH.H_2O$ (144 mg, 3.43 mmol). The mixture was stirred at 32° C. for 0.5 h. MeOH was evaporated. To the residue was added water (20 mL). The mixture was extracted with MTBE (5 mL) and separated. The aqueous layer was acidified to pH ~3 with 1N HCl and extracted with Ethyl Acetate (3x20 mL). The combined organic layers were dried over $Na_2SO_4$ and concentrated to afford compound 61D (220 mg, 77.9% yield) as white solid.

Compound 61 (21.8 mg, 21.78% yield, white solid) was prepared as in Example 20 from the corresponding intermediate carboxylic acid, compound 61D. Compound 61: $^1$H NMR (400 MHz, DMSO-$d_6$) δ 13.06-12.79 (m, 1H), 9.27 (s, 1H), 8.95-8.84 (m, 1H), 8.42-8.32 (m, 1H), 8.32-8.24 (m, 1H), 8.13-8.00 (m, 1H), 7.55-7.45 (m, 1H), 7.21-7.10 (m, 3H), 7.22-7.03 (m, 2H), 5.70-5.59 (m, 1H), 3.32-3.25 (m, 1H), 3.20-3.12 (m, 1H), 2.85-2.74 (m, 1H), 0.72-0.63 (m, 2H), 0.63-0.54 (m, 2H). MS (ESI) m/z $(M+H)^+$421.1.

Example 34

(S)—N-(1-amino-1,2-dioxoheptan-3-yl)-3-methyl-5-phenylisoxazole-4-carboxamide (62)

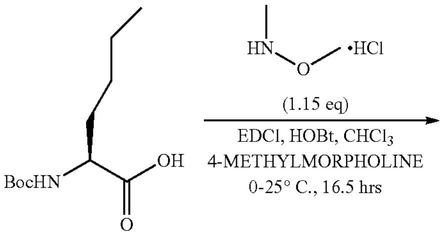

62A

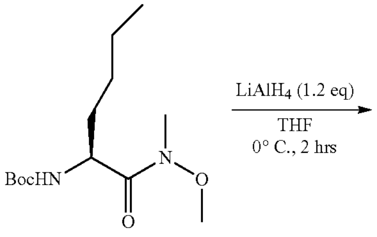

62B

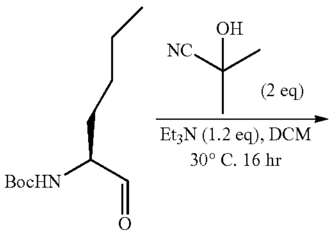

62C

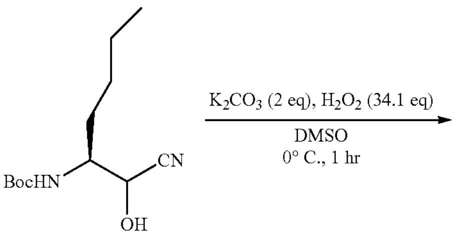

62D

-continued

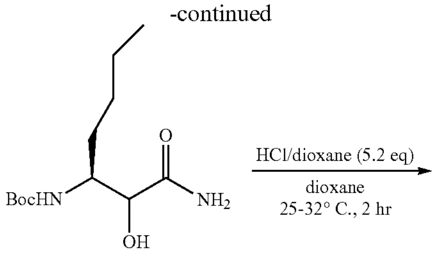

62E

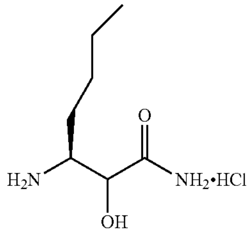

62F

To a mixture of compound 62A (2 g, 8.65 mmol) and compound N,O-dimethylhydroxylamine hydrochloride (970.3 mg, 9.95 mmol), HOBt (1.34 g, 9.95 mmol) in $CHCl_3$ (40 mL) was added dropwise 4-methylmorpholine (2.62 g, 25.95 mmol) and EDCI (2.32 g, 12.11 mmol) in portion at 0° C. under $N_2$ atmosphere. The mixture was stirred at 0° C. for 30 min, and then the mixture was stirred at 25° C. for 16 hours. The reaction mixture was diluted with $H_2O$ (5 mL). The two layers were separated and the aqueous phase was extracted with EA (5 mL×2). The combined organic layers were washed with 0.5N HCl (5 mL×2) and $NaHCO_3$ (5 mL×2), dried over $Na_2SO_4$, filtered and concentrated under reduced pressure to give compound 62B (1.7 g, yield 71.7%) as colorless oil. $^1$H NMR ($CDCl_3$, 400 MHz): δ 5.19-5.06 (m, 1H), 4.66 (br s, 1H), 3.77 (s, 3H), 3.20 (s, 3H), 1.76-1.66 (m, 1H), 1.55-1.39 (m, 10H), 1.37-1.28 (m, 4H), 0.93-0.83 (m, 3H). MS (ESI) m/z $(M-Boc+H)^+$175.0.

To a solution of $LiAlH_4$ (258.7 mg, 6.82 mmol) in THF (36 mL) was added drop wise a solution of compound 62B (1.7 g, 6.2 mmol) in THF (18 mL) at 0° C. under $N_2$ atmosphere. After addition, the reaction mixture was stirred at 0° C. for 2 hours. The mixture was diluted with ethyl acetate (100 mL), washed with 1N HCl (20 mL), saturated $NaHCO_3$ (20 mL×2), brine (15 mL). The organic layer was dried over anhydrous $Na_2SO_4$ and concentrated to give compound 62C (1.5 g, crude) as yellow oil. $^1$H NMR ($CDCl_3$, 400 MHz) δ 9.58 (s, 1H), 5.03 (br s, 1H), 4.28-4.16 (m, 1H), 1.58-1.19 (m, 15H), 1.01-0.80 (m, 3H).

A solution of compound 62C (1.5 g, 6.97 mmol), compound 2-hydroxy-2-methylpropanenitrile (1.3 mL, 13.94 mmol) and $Et_3N$ (1.16 mL, 8.36 mmol) in dry DCM (30 mL) was stirred at 30° C. for 16 hours. The reaction mixture was diluted with DCM (50 mL), washed with 0.5N HCl (20 mL), water (20 mL) and brine (20 mL). The organic phase was dried over $Na_2SO_4$, concentrated. The residue was purified by column chromatography ($SiO_2$, Petroleum Ether/Ethyl Acetate=5/1 to 3:1) to afford compound 62D (1.12 g, 66.32% yield) as white solid. $^1$H NMR (400 MHz, $CDCl_3$) δ 5.44-4.34 (m, 3H), 3.94-3.83 (m, 1H), 3.74-3.61 (m, 1H), 3.98-3.55 (m, 1H), 1.66-1.28 (m, 14H), 0.99-0.90 (m, 3H).

The mixture of compound 62D (1.12 g, 4.62 mmol) and $K_2CO_3$ (1.28 g, 9.24 mmol) in DMSO (18 mL) was added $H_2O_2$ (4.6 mL, 158.19 mmol) at 0° C. After addition, the reaction mixture was stirred at 0° C. for 1 h. After the reaction, MTBE (20 mL) was added to the reaction mixture, and the resulting mixture was filtered and the solid was washed with MTBE (30 mL) to afford compound 62E (1.1 g, 91.46% yield) as white solid. $^1$H NMR (400 MHz, DMSO-d6) δ7.32-7.08 (m, 2H), 6.42-5.86 (m, 1H), 5.54-5.30 (m, 1H), 3.88-3.59 (m, 2H), 1.42-1.21 (m, 15H), 0.92-0.78 (m, 3H).

The solution of compound 62E (600 mg, 20.82 mmol) in dioxane (10 mL) was added HCl/dioxane (3 mL, 4M) at 25° C. The reaction mixture was stirred at 25° C. for 2 hours. The mixture was filtered to afford compound 62F (320 mg, 70.7%, yield, HCl) was obtained as white solid. $^1$H NMR (400 MHz, DMSO-$d_6$) δ 7.90 (br s, 2H), 7.54-7.35 (m, 2H), 6.26-6.17 (m, 1H), 4.09 (br s, 1H), 1.66-1.37 (m, 2H), 1.37-1.12 (m, 5H), 0.93-0.72 (m, 3H)

Compound 62 (9.1 mg, yield: 38.6%, white solid) was prepared as in Example 15 from the corresponding intermediate compounds, 23A and 62F. Compound 62: $^1$H NMR ($CDCl_3$, 400 MHz): δ 7.84-7.67 (m, 2H), 7.57-7.43 (m, 3H), 6.73 (s, 1H), 6.17-6.03 (m, 1H), 5.52-5.29 (m, 2H), 2.46 (s, 3H), 1.99-1.84 (m, 1H), 1.41-1.04 (m, 5H), 0.90-0.78 (m, 3H). MS (ESI) m/z $(M+H)^+$344.1.

Example 35

Compounds 63, 454

(S)—N-(4-amino-3,4-dioxo-1-phenylbutan-2-yl)-3-methyl-1-(pyrazin-2-yl)-1H-pyrazole-5-carboxamide (63)

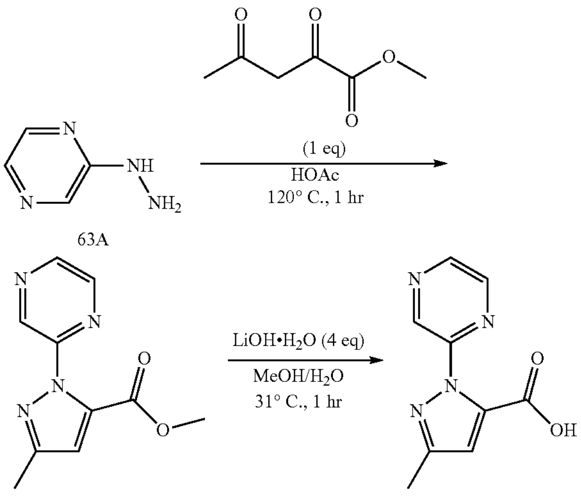

63A

63B

63C

To a solution of compound methyl 2,4-dioxopentanoate (100 mg, 693.82 umol) in AcOH (20 mL) was added compound 63A (76.4 mg, 693.82 umol). The mixture was stirred at 120° C. for 1 hour. The mixture was in DCM (5 mL). The organic layer was washed with water (10 mL), $NaHCO_3$ to pH ~89 and dried over $Na_2SO_4$ and concentrated to afford compound 63B (500 mg, 25.24% yield) as white solid.

To a solution of compound 63B (61 mg, 279.55 umol) in MeOH (6 mL) and $H_2O$ (1 mL) was added $LiOH.H_2O$ (46.9 mg, 1.12 mmol). The mixture was stirred at 31° C. for 1 h. MeOH was evaporated. To the residue was added water (10 mL) and the mixture was extracted with MTBE (5 mL) and separated. The aqueous layer was acidified to pH ~3 with 1N HCl and extracted with ethyl acetate (3×20 mL). The combined organic layers were dried over $Na_2SO_4$ and concentrated to afford the product. (50 mg, 87.59% yield) as white solid.

Compound 63 (25.1 mg, 63.1% yield, white solid) was prepared as in Example 5 from the corresponding intermediate carboxylic acid, compound 63C. Compound 63: $^1$H NMR (400 MHz, $CDCl_3$) δ 9.16 (s, 2H), 9.08-8.97 (m, 1H), 8.44 (s, 1H), 7.95 (s, 1H), 7.20 (s, 3H), 7.08 (s, 2H), 5.78 (m, 1H), 5.54 (s, 1H), 3.45 (m, 1H), 3.38-3.24 (m, 1H), 2.36 (s, 3H). MS (ESI) m/z $(M+H)^+$379.1.

N-(4-(cyclopropylamino)-3,4-dioxo-1-phenylbutan-2-yl)-3-methyl-1-(pyrazin-2-yl)-1H-pyrazole-5-carboxamide (454)

Compound 454 (210 mg, 91.7% yield, white solid) was prepared as in compound 12 from the corresponding intermediate carboxylic acid, compound 63C and 3-amino-N-cyclopropyl-2-hydroxy-4-phenylbutanamide hydrochloride. Compound 454: $^1$H NMR (400 MHz, DMSO-$d_6$) δ 9.07 (d, J=7.2 Hz, 1H), 8.84-8.77 (m, 2H), 8.57 (d, J=2.8 Hz, 1H), 8.31-8.27 (m, 1H), 7.30-7.17 (m, 5H), 6.64 (s, 1H), 5.33-5.25 (m, 1H), 3.17-3.09 (m, 1H), 2.83-2.70 (m, 2H), 2.27 (s, 3H), 0.69-0.53 (m, 4H). MS (ESI) m/z $(M+H)^+$419.2.

Example 36

(S)—N-(4-amino-3,4-dioxo-1-phenylbutan-2-yl)-3-methyl-1-(3-methylpyridin-2-yl)-1H-pyrazole-5-carboxamide (66)

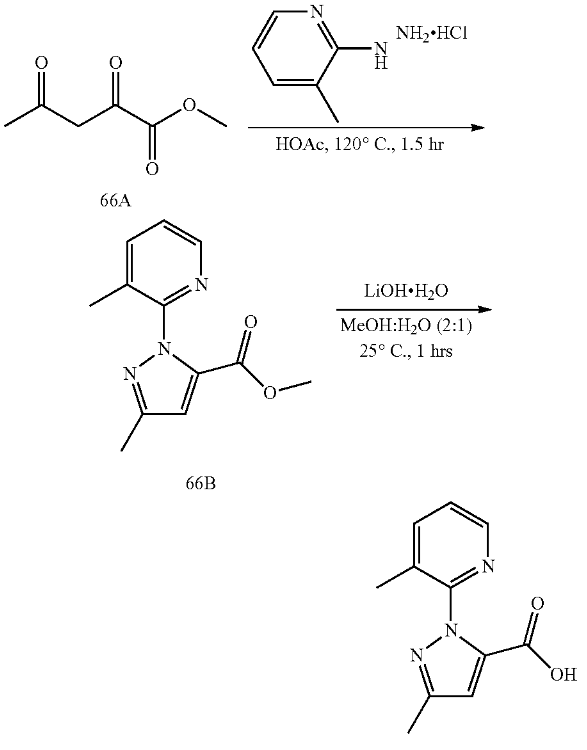

66A

66B

66C

A mixture of compound 2-hydrazinyl-3-methylpyridine hydrochloride (2 g, 12.53 mmol) and compound 66A (1.81 g, 12.53 mmol) in AcOH (30 mL) was degassed and purged with $N_2$ for 3 times, and then stirred at 120° C. for 1.5 hrs under $N_2$ atmosphere. The resultant mixture was concentrated under reduced pressure to remove AcOH and diluted with DCM (10 mL), neutralized with saturated aqueous $NaHCO_3$. The mixture was extracted with DCM (20 mL×3) and the combined organic layers were dried over anhydrous $Na_2SO_4$, filtered and concentrated under reduced pressure to give a residue, which was purified by flash silica gel chromatography (Petroleum ether:Ethyl acetate=1:0 to 0:1) to afford compound 66B (800.0 mg, 27.6% yield) as a white solid and compound 66B-1 (110.0 mg, 4.04% yield) as a white solid and crude 66B-1 (800.0 mg).

Compound 66B: Methyl 3-methyl-1-(3-methylpyridin-2-yl)-1H-pyrazole-5-carboxylate: $^1$H NMR ($CDCl_3$, 400 MHz) δ 8.42-8.37 (m, 1H), 7.70 (d, J=7.6 Hz, 1H), 7.33 (d, J=7.6 Hz, 1H), 6.79 (s, 1H), 3.74 (s, 3H), 2.38 (s, 3H), 2.14 (s, 3H).

Compound 66B-1: Methyl 5-methyl-1-(3-methylpyridin-2-yl)-1H-pyrazole-3-carboxylate: $^1$H NMR ($CDCl_3$, 400 MHz) δ 8.42 (d, J=3.6 Hz, 1H), 7.72 (d, J=6.8 Hz, 1H), 7.34 (d, J=7.6 Hz, 1H), 6.74 (s, 1H), 3.92 (s, 3H), 2.26 (s, 3H), 2.20 (s, 3H).

To a mixture of compound 66B (200.0 mg, 864.86 umol) in MeOH (10 mL) and $H_2O$ (5 mL) was added $LiOH.H_2O$ (145.2 mg, 3.46 mmol) in one portion. After stirred at 25° C. for 1 hour, the reaction mixture was concentrated under reduced pressure to remove MeOH. The residue was diluted with $H_2O$ (10 mL), adjusted to pH ~3 with 1N HCl, and then extracted with EtOAc (40 mL×3). The combined organic layers were washed with brine (30 mL), dried over anhydrous $Na_2SO_4$, filtered and concentrated under reduced pressure to give compound 66C (150 mg, 79.84% yield, white solid). Compound 66C: $^1$H NMR (DMSO-$d_6$, 400 MHz) δ 13.11 (br s, 1H), 8.31 (d, J=3.7 Hz, 1H), 7.84 (d, J=7.3 Hz, 1H), 7.47-7.40 (m, 1H), 6.78 (s, 1H), 2.25 (s, 3H), 2.03 (s, 3H). MS (ESI) m/z $(M+1)^+$218.1.

Compound 66 (24.5 mg, 54.7% yield, white solid) was prepared as in Example 5 from the corresponding intermediate carboxylic acid, compound 66C. Compound 66: $^1$H NMR ($CDCl_3$, 400 MHz) δ 8.23 (d, J=3.6 Hz, 1H), 7.67 (d, J=7.2 Hz, 1H), 7.34 (d, J=7.2 Hz, 1H), 7.27 (br s, 1H), 7.25-7.21 (m, 3H), 7.04-6.99 (m, 2H), 6.70 (br s, 1H), 6.57 (s, 1H), 5.65-5.6 (m, 1H), 5.57 (br s, 1H), 3.37-3.29 (m, 1H), 3.2-3.14 (m, 1H), 2.34 (s, 3H), 2.17 (s, 3H). MS (ESI) m/z $(M+H)^+$392.2.

Example 37

(S)—N-(4-amino-3,4-dioxo-1-phenylbutan-2-yl)-1-(1-phenyl-1H-pyrazol-3-yl)-1H-imidazole-5-carboxamide (68)

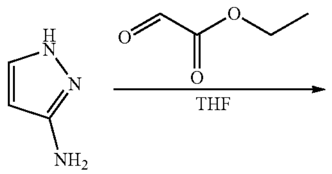

68A

-continued

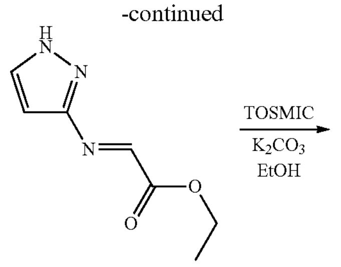

68B

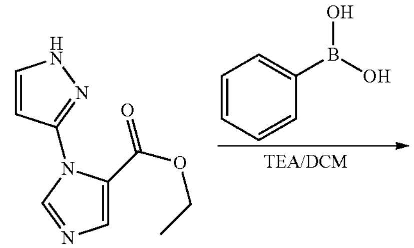

68C

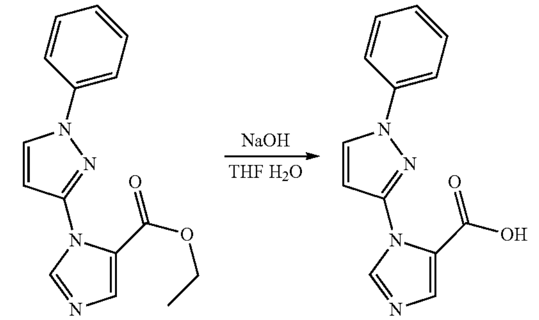

68D 68E

To a solution of 68A (15 g, 181 mmol) in THF (200 mL) was added ethyl 2-oxoacetate (47.9 g, 235 mmol). The mixture was stirred at 25° C. for 0.5 h. The reaction mixture was filtered and concentrated under reduced pressure to give intermediate compound 68B (55.3 g, crude) as brown solid. MS (ESI) m/z $(M+H)^+$167.8.

To a solution of 68B (40 g, 239 mmol) in EtOH (400 mL) was added $K_2CO_3$ (50 g, 362 mmol) and TosMIC (40 g, 204.88 mmol). The mixture was stirred at 90° C. for 0.5 h. The reaction mixture was filtered and concentrated under reduced pressure to give a residue. The residue was purified by column chromatography ($SiO_2$, Petroleum ether:Ethyl acetate=1:0 to 5:2) to afford compound 68C (12 g, yield: 24.3%) as brown solid. $^1$H NMR (400 MHz, $CDCl_3$) δ 11.80-11.35 (m, 1H), 7.87 (d, J=1.10 Hz, 1H), 7.84 (d, J=1.10 Hz, 1H), 7.58 (d, J=2.43 Hz, 1H), 6.45 (d, J=2.43 Hz, 1H), 4.25 (q, J=7.06 Hz, 2H), 1.29 (t, J=7.17 Hz, 3H). MS (ESI) m/z $(M+H)^+$207.0.

A mixture of 68C (5 g, 24.3 mmol), phenylboronic acid (4.4 g, 36.4 mmol), $Cu(OAc)_2$ (4.4 g, 24.3 mmol), TEA (7.4 g, 72.8 mmol) in DCM (200 mL) was degassed and purged with 02 for 3 times, and then the mixture was stirred at 25° C. for 10 hours under 02 atmosphere. The reaction mixture was filtered and concentrated under reduced pressure to give a residue. The residue was purified by column chromatography ($SiO_2$, Petroleum ether:Ethyl acetate=1:0 to 2:1). Compound 68D (2.3 g, yield: 33.6%) was obtained as a white solid. $^1$H NMR (400 MHz, $CDCl_3$) δ 8.04-7.94 (m, 2H), 7.87 (s, 1H), 7.71 (br d, J=7.7 Hz, 2H), 7.49 (br t, J=7.1

Hz, 2H), 7.36 (br d, J=7.1 Hz, 1H), 7.27 (d, J=2.0 Hz, 2H), 6.70-6.61 (m, 1H), 4.29 (dd, J=2.1, 7.2 Hz, 2H), 1.38-1.22 (m, 3H). MS (ESI) m/z $(M+H)^+$282.9.

To a solution of 68D (2.5 g, 8.86 mmol) in THF (30 mL) and $H_2O$ (6 mL) was added NaOH (708 mg, 17.7 mmol). The mixture was stirred at 80° C. for 1.5 hour. The reaction mixture was concentrated under reduced pressure to remove THF, and then washed with EtOAc (20 mL). The aqueous layer was acidized with 1M HCl to pH ~5 and then extracted with EtOAc (30 mL×3). The combined organic layer was washed with $H_2O$ (40 mL), brine (40 mL), dried over $Na_2SO_4$, filtered and concentrated to afford crude intermediate compound 68E (1.90 g, yield: 84.3%) as yellow solid. $^1H$ NMR (400 MHz, DMSO-$d_6$) δ 8.62 (d, J=2.6 Hz, 1H), 8.19 (s, 1H), 7.86 (d, J=7.9 Hz, 2H), 7.76 (s, 1H), 7.53 (t, J=7.9 Hz, 2H), 7.39-7.31 (m, 1H), 6.77 (d, J=2.6 Hz, 1H). MS (ESI) m/z $(M+H)^+$254.9.

Compound 68 (33.5 mg, yield: 42.1%, white solid) was prepared as in Example 5 from the corresponding intermediate carboxylic acid, compound 68E. Compound 68: $^1H$ NMR (400 MHz, DMSO-$d_6$) δ 8.86 (d, J=7.7 Hz, 1H), 8.51 (d, J=2.6 Hz, 1H), 8.10 (d, J=0.9 Hz, 1H), 8.06 (s, 1H), 7.79 (dd, J=8.7, 1.0 Hz, 3H), 7.60 (d, J=0.9 Hz, 1H), 7.46-7.53 (m, 2H), 7.30-7.36 (m, 1H), 7.24-7.29 (m, 4H), 7.16-7.23 (m, 1H), 6.44 (d, J=2.6 Hz, 1H), 5.23-5.32 (m, 1H), 3.17 (dd, J=13.8, 3.9 Hz, 1H), 2.83 (dd, J=13.9, 10.4 Hz, 1H). MS (ESI) m/z $(M+H)^+$429.1.

Example 38

(S)—N-(4-amino-3,4-dioxo-1-phenylbutan-2-yl)-1-(1H-indazol-3-yl)-1H-imidazole-5-carboxamide (69)

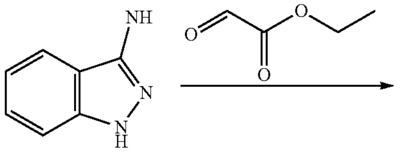

69A

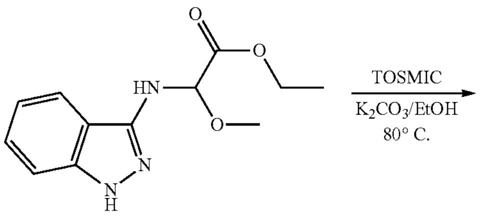

69B

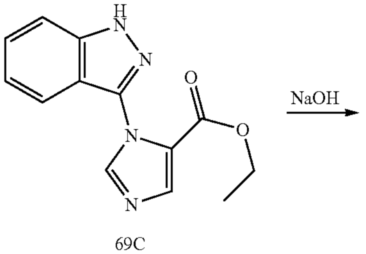

69C

-continued

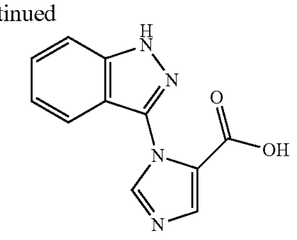

69D

To a solution of 69A (8.7 g, 65.3 mmol) in MeOH (90 mL) was added ethyl 2-oxoacetate (20 g, 98.01 mmol). The mixture was stirred at 25° C. for 2 hours. The mixture was filtered and concentrated to give intermediate compound 69B (15 g, crude) as brown solid.

To a solution of 69B (15 g, 69.1 mmol) in EtOH (400 mL) was added $K_2CO_3$ (14.5 g, 104 mmol) and TosMIC (11.6 g 59.4 mmol). The mixture was stirred at 90° C. for 0.5 hour. The reaction mixture was filtered and concentrated under reduced pressure to give a residue. The residue was purified by column chromatography ($SiO_2$, Petroleum ether:Ethyl acetate=1:0 to 1:1) to give compound 69C (2.9 g, yield: 16.4%) as a yellow solid. $^1H$ NMR (400 MHz, $CDCl_3$) δ 11.04 (br s, 1H), 7.98 (d, J=0.7 Hz, 1H), 7.91 (s, 1H), 7.48-7.41 (m, 3H), 7.25-7.19 (m, 1H), 4.24-4.14 (m, 2H), 1.14 (t, J=7.1 Hz, 3H).

To a solution of 69C (2.9 g, 11.3 mmol) in THF (40 mL) and $H_2O$ (8 mL) was added NaOH (905 mg, 22.6 mmol). The mixture was stirred at 25° C. for 10 hours. The mixture was concentrated under reduced pressure to remove the organic solvent, and extracted with EtOAc (20 mL). The aqueous layer was acidized with 1M HCl to pH ~5 and then extracted with EtOAc (30 mL×3). The combined organic layer was washed with $H_2O$ (40 mL), brine (40 mL), dried over $Na_2SO_4$, filtered and concentrated to give 69D (1.5 g, yield: 58.1%) as yellow solid. $^1H$NMR (400 MHz, DMSO-$d_6$) δ 13.35 (s, 1H), 8.16 (s, 1H), 7.83 (s, 1H), 7.61 (d, J=8.3 Hz, 1H), 7.47-7.41 (m, 2H), 7.20-7.15 (m, 1H). MS (ESI) m/z $(M+H)^+$228.9.

Compound 69 (16.7 mg, yield: 20.9%, yellow solid) was prepared as in Example 5 from the corresponding intermediate carboxylic acid, compound 69D. Compound 69: $^1H$ NMR (400 MHz, DMSO-$d_6$) δ13.16 (br s, 1H), 8.84 (br d, J=7.7 Hz, 1H), 8.08-7.95 (m, 2H), 7.80-7.70 (m, 2H), 7.52 (d, J=8.4 Hz, 1H), 7.36 (br t, J=7.5 Hz, 1H), 7.30-7.23 (m, 4H), 7.22-7.13 (m, 3H), 7.08-7.01 (m, 1H), 5.21-5.12 (m, 1H), 3.17-3.09 (m, 1H), 2.84-2.75 (m, 1H). MS (ESI) m/z $(M+H)^+$403.1.

Example 39

(S)—N-(4-amino-3,4-dioxo-1-phenylbutan-2-yl)-1-(1H-benzo[d]imidazol-2-yl)-1H-imidazole-5-carboxamide (70)

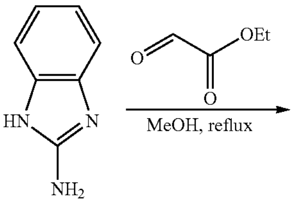

70A

-continued

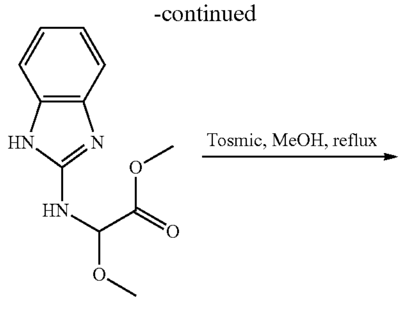

70B

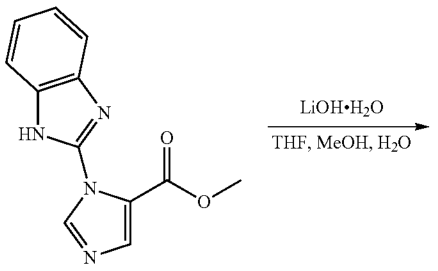

70C

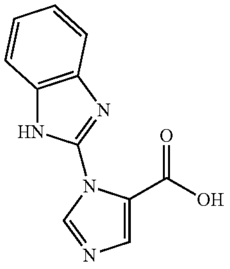

70D

A mixture of 70A (10 g, 75.1 mmol), ethyl 2-oxoacetate (30.6 g, 150 mmol) in MeOH (300 mL) was stirred at 70° C. for 12 hour under $N_2$ atmosphere. LCMS showed 70A was consumed completely and one peak with desired MS was detected. The reaction mixture was concentrated under reduced pressure to give crude product 70B (15 g, crude) as yellow oil. MS (ESI) m/z $(M+H)^+$235.9.

A mixture of 70B (15 g, 63.7 mmol), $K_2CO_3$ (13.2 g, 95.6 mmol), TosMIC (24.9 g, 127 mmol) in MeOH (300 mL) was stirred at 70° C. for 1 hour. LCMS showed 70B was consumed completely and one small peak with desired MS was detected. TLC (Petroleum ether:Ethyl acetate=1:1, $R_f$~0.3) indicated 70B was consumed completely and one new spot formed. The reaction mixture was filtered and concentrated under reduced pressure to give a residue. The residue was purified by column chromatography (Petroleum ether/Ethyl acetate=10/1 to 1:1) to give 70C (350 mg, yield: 2.3%) as a yellow oil. $^1$H NMR (400 MHz, $CDCl_3$) δ 12.52 (br s, 1H) 8.96 (s, 1H) 7.98 (s, 1H) 7.69 (br d, J=4.4 Hz, 1H) 7.48 (br s, 1H) 7.28 (br dd, J=5.8, 2.8 Hz, 2H) 3.99 (s, 3H). MS (ESI) m/z $(M+H)^+$243.1.

A mixture of 70C (350 mg, 1.44 mmol), $LiOH.H_2O$ (120 mg, 2.88 mmol) in THF (5 mL), $H_2O$ (2 mL) was stirred at 25° C. for 4 hours. LCMS showed 70C was consumed completely and one peak with desired MS was detected. The reaction mixture was added aqueous HCl (1M) to adjust the pH ~5, filtered and the filtered cake was concentrated under reduced pressure. The filtered cake was washed with water. Compound 70D (230 mg, yield: 70.1%) was obtained as a white solid. $^1$H NMR (400 MHz, DMSO-$d_6$) δ 8.57 (d, J=1.3 Hz, 1H) 7.38-7.63 (m, 3H) 7.03-7.22 (m, 1H) 7.03-7.17 (m, 1H). MS (ESI) m/z $(M+H)^+$229.0.

Compound 70 (40 mg, yield: 46.7%, white solid) was prepared as in Example 5 from the corresponding intermediate carboxylic acid, compound 70D. Compound 70: $^1$HNMR (400 MHz, DMSO-$d_6$) δ12.94 (br s, 1H), 9.31 (br s, 1H), 8.38-8.23 (m, 1H), 8.04 (br s, 1H), 7.87-7.74 (m, 2H), 7.60-7.43 (m, 2H), 7.29-7.10 (m, 6H), 5.33 (br t, J=6.6 Hz, 1H), 3.17 (br dd, J=3.1, 13.9 Hz, 1H), 3.22-3.09 (m, 1H), 2.84 (br dd, J=10.3, 13.8 Hz, 1H), 2.91-2.74 (m, 1H). MS (ESI) m/z $(M+H)^+$403.1.

Example 40

(S)—N-(4-amino-3,4-dioxo-1-phenylbutan-2-yl)-4-phenyl-1,2,5-thiadiazole-3-carboxamide (72)

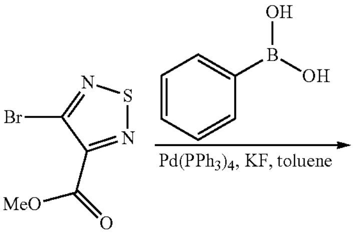

72A

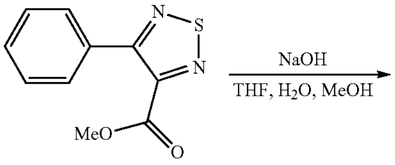

72B

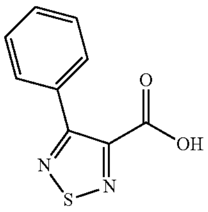

72C

A mixture of compound 72A (800 mg, 3.59 mmol) and phenylboronic acid (1.31 g, 10.8 mmol) in toluene (10 mL) and $H_2O$ (500 uL) was added KF (417 mg, 7.18 mmol) and $Pd(PPh_3)_4$ (414 mg, 359 umol) under $N_2$. Then the reaction mixture was stirred at 100° C. under $N_2$ for 16 hrs. The solvent was evaporated. The crude product was purified by silica gel column (petroleum ether:ethyl acetate=20:1 to 5:1) to give compound 72B (400 mg, crude) as an oil. $^1$H NMR (400 MHz, $CDCl_3$) δ 7.70-7.68 (m, 2H), 7.48-7.46 (m, 3H), 3.94 (s, 3H).

A solution of compound 72B (500 mg, 2.27 mmol) in THF (5 mL), $H_2O$ (5 mL) and MeOH (5 mL) was added NaOH (182 mg, 4.54 mmol). The reaction mixture was stirred at 20° C. for 1 hr. 1M HCl was added to the reaction mixture until pH ~4. The solvent was evaporated to give a crude product 72C (500 mg, crude) as a white solid. The crude product was used in the next step without purification.

Compound 72 (50.5 mg, yield: 43.9%, white solid) was prepared as in Example 5 from the corresponding intermediate carboxylic acid, compound 72C. Compound 72: $^1$H NMR (400 MHz, DMSO-d$_6$) δ 9.42 (d, J=7.7 Hz, 1H), 8.18 (s, 1H), 7.91 (s, 1H), 7.60-7.55 (m, 2H), 7.48-7.43 (m, 1H), 7.42-7.36 (m, 2H), 7.31-7.22 (m, 5H), 5.51 (ddd, J=3.6, 7.7, 10.0 Hz, 1H), 3.23 (dd, J=3.6, 14.0 Hz, 1H), 2.87 (dd, J=10.1, 14.1 Hz, 1H). MS (ESI) m/z (M+H)$^+$381.0.

Example 41

N-((3S,4R)-1-amino-4-methyl-1,2-dioxohexan-3-yl)-3-methyl-5-phenylisoxazole-4-carboxamide (73)

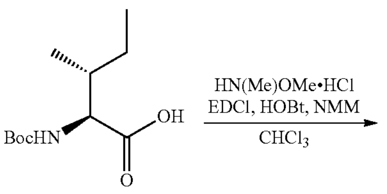

73A

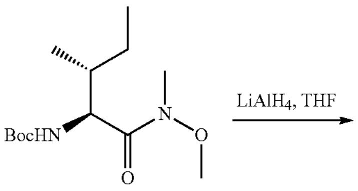

73B

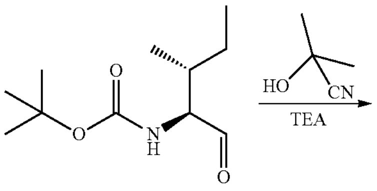

73C

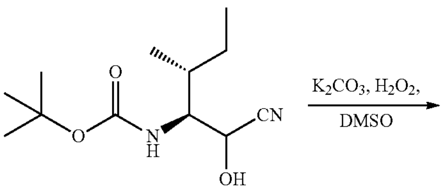

73D

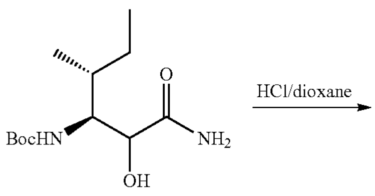

73E

-continued

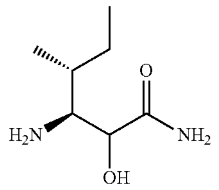

73F

A mixture of N-methoxymethanamine (2.32 g, 23.78 mmol), compound 73A (5.00 g, 21.62 mmol), HOBt (2.92 g, 21.62 mmol) and NMM (6.56 g, 64.86 mmol) in $CHCl_3$ (100 mL) was degassed and purged with $N_2$ for 3 times at 0° C., then EDCI (6.22 g, 32.43 mmol) was added in portions. The mixture was stirred at 25° C. for 16 hrs under $N_2$ atmosphere. The reaction mixture was quenched by addition $H_2O$ (100 mL). The organic layers were washed with HCl (1N, 100 mL×2), and saturated $NaHCO_3$ (100 mL×2), and saturated brine (50 mL), dried over $Na_2SO_4$, filtered and concentrated under reduced pressure to give a residue. The residue was purified by flash silica gel chromatography (Eluent of 0-10% Ethyl acetate/Petroleum ether gradient) to give compound 73B (5.0 g, yield: 84.3%) as a colorless oil. $^1$H NMR (400 MHz, $CDCl_3$) δ 5.10 (d, J=9.5 Hz, 1H), 4.67-4.53 (m, 1H), 3.76 (s, 3H), 3.20 (s, 3H), 1.70 (qt, J=6.8, 9.9 Hz, 1H), 1.54-1.51 (m, 1H), 1.41 (s, 9H), 1.15-1.07 (m, 1H), 0.91-0.85 (m, 6H). MS (ESI) m/z (M+Na$^+$) 296.9.

To a solution of $LiAlH_4$ (350 mg, 9.22 mmol) in THF (30 mL) was added a solution of compound 73B (2.30 g, 8.38 mmol) in THF (30 mL) at 0° C. After addition, the reaction mixture was stirred for 1 hr at 5° C. The reaction mixture was quenched by addition of ethyl acetate (10 mL) and HCl (1N, 10 mL), and extracted with EtOAc (100 mL×2). The combined organic layers were washed with HCl (1N, 30 mL×2), sat. $NaHCO_3$ (30 mL×3), and brines (30 mL), dried over $Na_2SO_4$, filtered and concentrated under reduced pressure to give compound 73C (1.50 g, yield: 83.2%) as a colourless oil. $^1$H NMR (400 MHz, DMSO-d$_6$) δ 9.45 (d, J=1.3 Hz, 1H), 7.22 (br d, J=7.5 Hz, 1H), 3.79 (br t, J=6.4 Hz, 1H), 1.89-1.75 (m, 1H), 1.42-1.32 (m, 10H), 1.25-1.10 (m, 1H), 0.86 (d, J=6.8 Hz, 3H), 0.81 (t, J=7.4 Hz, 3H). MS (ESI) m/z (M+H)$^+$216.0.

To a solution of compound 73C (1.5 g, 6.97 mmol) in DCM (10 mL) was added 2-hydroxy-2-methylpropanenitrile (1.28 mL, 13.93 mmol) and TEA (1.16 mL, 8.36 mmol), and then stirred at 25° C. for 14 hours. The reaction mixture was diluted with DCM (25 mL), washed with HCl (1N, 20 mL×2), $H_2O$ (30 mL), and brine (30 mL), dried over $Na_2SO_4$, filtered and concentrated under reduced pressure to give compound 73D (1.5 g, yield: 88.8%) as a colorless liquid. $^1$H NMR (400 MHz, $CDCl_3$) δ 5.24-5.08 (m, 1H), 4.92-4.56 (m, 1H), 3.90-3.25 (m, 1H), 2.04-1.80 (m, 1H), 1.66-1.52 (m, 1H), 1.50-1.40 (m, 9H), 1.33-1.09 (m, 2H), 1.02-0.75 (m, 6H).

To a solution of compound 73D (1.50 g, 6.19 mmol) and $K_2CO_3$ (1.71 g, 12.38 mmol) in DMSO (15 mL) was added $H_2O_2$ (7.21 g, 211.95 mmol) at 0° C. After addition, the reaction mixture was stirred at 0° C. for 1 h. The reaction mixture was diluted with water (20 mL) and quenched with saturated aqueous $Na_2S_2O_3$ slowly at ice water. The mixture was extracted with EtOAc (50 mL×3) and the combined extracts were washed with saturated aqueous $Na_2S_2O_3$ (30 mL×3). The organic layer was dried over $Na_2SO_4$, filtered and concentrated under reduced pressure to give a residue. The residue was purified by flash silica gel chromatography (eluent of 0 20% Ethyl acetate/Petroleum ethergradient) to give compound 73E (870 mg, yield: 54.0%) as a white solid. $^1$H NMR (400 MHz, DMSO-$d_6$) δ 7.31-6.97 (m, 2H), 6.29-5.87 (m, 1H), 5.44-5.12 (m, 1H), 3.99-3.80 (m, 1H), 3.71-3.50 (m, 1H), 1.67-1.41 (m, 2H), 1.39-1.30 (m, 9H), 1.11-0.92 (m, 1H), 0.89-0.75 (m, 6H). MS (ESI) m/z $(M+Na)^+$282.9.

To a solution of compound 73E (870 mg, 3.34 mmol) in EtOAc (10 mL) was added HCl/EtOAc (4M, 16.70 mL) at 0° C. After addition, the reaction mixture was stirred at 25° C. for 2 hrs. The reaction mixture was concentrated under reduced pressure to remove solvent. The residue was washed with MTBE (30 mL), filtered to give compound 73F (620 mg, yield: 94.4%) as a white solid. $^1$H NMR (400 MHz, DMSO-$d_6$) δ 8.14-7.71 (m, 3H), 7.64-7.37 (m, 2H), 6.57-6.28 (m, 1H), 4.32-3.99 (m, 1H), 3.21 (br s, 1H), 1.82-1.43 (m, 2H), 1.30-1.03 (m, 1H), 0.99-0.71 (m, 6H). MS (ESI) m/z $(M+H)^+$161.1.

Compound 73 (100 mg, yield: 63.6%, white solid) was prepared as in Example 15 from the corresponding intermediate compounds, 23A and 73F. Compound 73: $^1$H NMR (400 MHz, DMSO-$d_6$) δ 8.92 (d, J=7.0 Hz, 1H), 8.15 (s, 1H), 7.96-7.65 (m, 3H), 7.62-7.44 (m, 3H), 5.19 (t, J=6.5 Hz, 1H), 3.33 (br s, 1H), 2.30 (s, 3H), 2.10-1.94 (m, 1H), 1.36-1.13 (m, 2H), 0.92 (d, J=6.8 Hz, 3H), 0.81 (t, J=7.4 Hz, 3H). MS (ESI) m/z $(M+H)^+$344.1.

Example 42

(S)—N-(4-amino-3,4-dioxo-1-phenylbutan-2-yl)-1-(5-phenylpyrimidin-2-yl)-1H-imidazole-5-carboxamide (74)

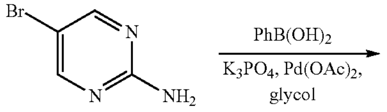

74A

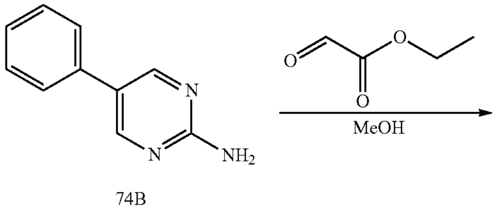

74B

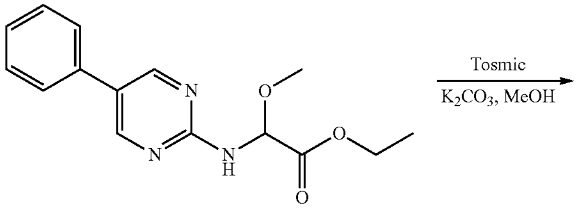

74C

-continued

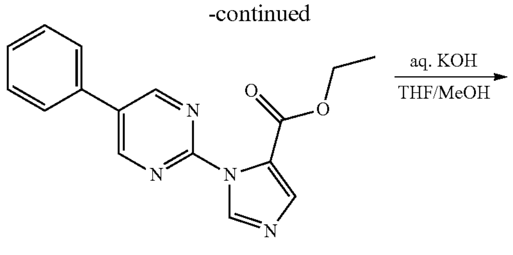

74D

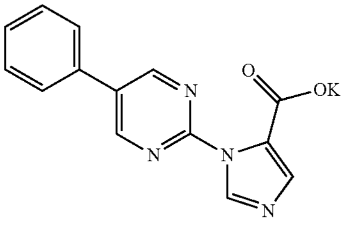

74E

The mixture of compound 74A (10.0 g, 57.47 mmol), phenylboronic acid (10.5 g, 86.21 mmol), $K_3PO_4$ (24.4 g, 114.94 mmol), $Pd(OAc)_2$ (1.3 g, 5.75 mmol) in ethylene glycol (200 mL) was stirred at 80° C. for 12 hrs. The reaction mixture was added to $H_2O$ (200 mL), the insoluble substance was removed by filtration; the filtrate was extracted with ethyl acetate (200 mL×3). The combined organic layer was washed with saturated aqueous $NaHCO_3$ (150 mL×3), saturated aqueous NaCl (150 mL×3), dried over $Na_2SO_4$ and concentrated in vacuum. The resulting solid was treated with ethyl acetate (10 mL). The precipitate was filtered and dried in vacuum to afford compound 74B (4.97 g, yield: 50.5%) as light yellow solid. $^1$H NMR (DMSO-d6, 400 MHz) δ 8.55 (s, 2H), 7.62-7.58 (m, 2H), 7.43-7.40 (m, 2H), 7.33-7.27 (m, 1H), 6.76 (br.s., 2H).

The mixture of compound 74B (3.0 g, 17.35 mmol) and compound ethyl 2-oxoacetate (2.3 g, 22.55 mmol) in MeOH (50 mL) was stirred at 80° C. for 12 hrs. The reaction mixture was concentrated and the solid was filtered. The resulting solid was treated with MeOH (10 mL), filtered and dried in vacuum to afford compound 74C (3.23 g, yield: 64.8%) as light yellow solid. $^1$H NMR (DMSO-$d_6$, 400 MHz) δ 8.71 (s, 2H), 8.24 (d, J=8.8 Hz, 1H), 7.67-7.63 (m, 2H), 7.47-7.41 (m, 2H), 7.37-7.31 (m, 1H), 5.64 (d, J=8.8 Hz, 1H), 4.19-4.10 (m, 2H), 3.33 (s, 3H), 1.21 (t, J=7.2 Hz, 3H).

The mixture of compound 74C (500 mg, 1.74 mmol), Tosmic (680 mg, 3.48 mmol), $K_2CO_3$ (720 mg, 5.22 mmol) in absolute EtOH (50 mL) was stirred at 65° C. for 2 hrs. The reaction mixture was concentrated under reduced pressure; the resulting residue was added in water (30 mL) and extracted with ethyl acetate (30 mL×3). The combined organic layers were dried over $Na_2SO_4$, filtered and concentrated. The residue was purified by column chromatography ($SiO_2$, petroleum ether/ethyl acetate=15:1 to 8:1) to afford compound 4 (293 mg, yield: 52.2%) as white solid. $^1$H NMR (DMSO-$d_6$, 400 MHz) δ 9.30 (s, 2H), 8.46 (s, 1H), 7.89 (t, J=7.2 Hz, 2H), 7.76 (s, 1H), 7.59-7.49 (m, 3H), 4.23-4.13 (m, 2H), 1.17 (t, J=7.2 Hz, 3H). MS (ESI) m/z $(M+H)^+$295.1.

To the mixture of compound 74D (1.15 g, 3.91 mmol) in THF (10 mL) and MeOH (10 mL) was added KOH (2M, 1.96 mL, 3.92 mmol) dropwise at 25° C. The mixture was stirred at 25° C. for 23 hrs, and then concentrated under reduced pressure to afford intermediate compound 74E (2 g, crude).

Compound 74 (14.9 mg, yield 28.2%, white solid) was prepared as in Example 5 from the corresponding intermediate compounds 74E and 12G. $^1$H NMR (DMSO-$d_6$, 400 MHz) δ 9.60 (br d, J=6.4 Hz, 1H), 8.64 (br s, 3H), 7.82 (s, 1H), 7.59-7.50 (m, 6H), 7.22-7.11 (m, 5H), 5.83 (m, 1H), 5.61 (br s, 1H), 3.52-3.44 (m, 1H), 3.40-3.31 (m, 1H). MS (ESI) m/z $(M+H)^+$441.0.

Example 43

Compounds 77, 88

(S)—N-(4-(cyclopropylamino)-3,4-dioxo-1-phenylbutan-2-yl)-1-(4-(oxazol-2-yl)pyridin-2-yl)-1H-imidazole-5-carboxamide (77)

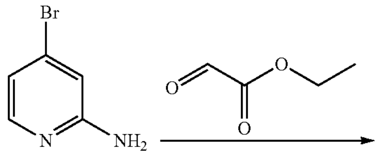

77A

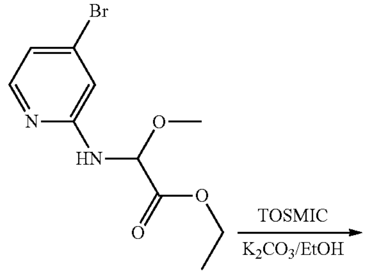

77B

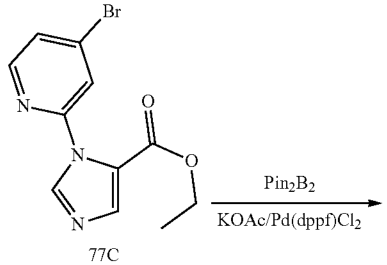

77C

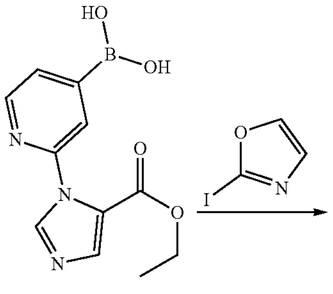

77D

-continued

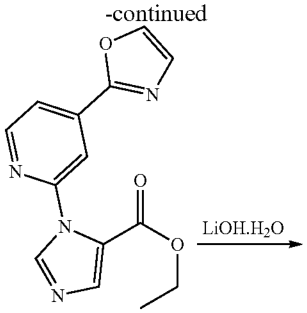

77E

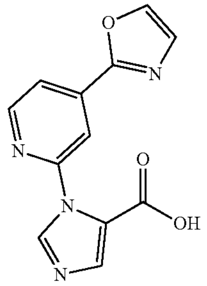

77F

A mixture of 77A (20 g, 115.60 mmol) and ethyl 2-oxoacetate (30.7 g, 150.28 mmol) in MeOH (300 mL) was heated to 80° C. for 3 hrs. LCMS showed desired MS. TLC (Petroleum ether:Ethyl acetate=3:1, $R_f$~0.8) showed new point, the mixture was concentrated and residue purified by silica gel column (Petroleum ether:Ethyl acetate=20:1). Compound 77B (28.9 g, yield 86.5%, yellow solid): $^1$H NMR (400 MHz, $CDCl_3$) δ 7.96 (d, J=5.2 Hz, 1H), 6.86 (dd, J=5.2, 1.75 Hz, 1H), 6.77 (d, J=1.3 Hz, 1H), 5.75 (br s, 1H), 5.61 (d, J=8.3 Hz, 1H), 4.29 (q, J=7.0 Hz, 2H), 3.41 (s, 3H), 1.37-1.31 (m, 3H).

A mixture of 77B (15 g, 51.9 mmol) and $K_2CO_3$ (21.5 g, 156 mmol) in EtOH (300 mL) was stirred at 80° C. for 0.5 hr, then TosMIC (15.2 g, 77.82 mmol) was added, the resulting mixture was stirred at 80° C. for another 2 hrs. LCMS showed desired MS, most of ethanol was removed and a precipitate was formed, the solid was filtered and washed with water (100 mL×2), the solid was dried and concentrated to give 77C (6.4 g, yield: 41.7%), as yellow solid. $^1$H NMR (400 MHz, $CDCl_3$) δ 8.38 (d, J=5.2 Hz, 1H), 7.97 (s, 1H), 7.85 (s, 1H), 7.61 (s, 1H), 7.56 (dd, J=5.26 1.3 Hz, 1H), 4.27 (q, J=7.02 Hz, 2H), 1.29 (t, J=7.02 Hz, 3H).

Compound 77C (3 g, 10.13 mmol), $Pin_2B_2$ (2.57 g, 10.13 mmol), KOAc (2.98 g, 30.4 mmol) and Pd(dppf)$Cl_2$ (741 mg, 1.01 mmol) in dioxane (100 mL) was de-gassed and then heated at 70° C. for 4 hours under $N_2$. LCMS showed desired MS, TLC (Ethyl acetate:Methanol=10:1, $R_f$~0), the mixture was filtered and the filtrate was concentrated, the residue was purified by silica gel chromatography (DCM: Methanol=5:1) to give 77D (1.70 g, crude) as black solid.

Compound 77D (300 mg, 1.15 mmol), 2-iodooxazole (157 mg, 805.00 umol), Pd(dppf)$Cl_2$ (84.1 mg, 115.00 umol) and $Na_2CO_3$ (244 mg, 2.30 mmol) in toluene (2 mL), EtOH (2 mL), $H_2O$ (1 mL) was de-gassed and then heated to 120° C. for 1 h under microwave condition. LCMS showed desired MS, the mixture was added water (5 mL) and extracted with ethyl acetate (10 mL×2), the organic phases were dried and concentrated, the residue was purified by preparatory-TLC (Petroleum ether:Ethyl acetate=1:1) to give 77E (80 mg, yield: 24.5%) as yellow solid.

A mixture of 77E (80 mg, 281.42 umol) and $LiOH.H_2O$ (17.7 mg, 422.13 umol) in THF (5 mL), $H_2O$ (1 mL) was stirred at 25° C. for 12 hrs. LCMS showed desired MS, THF was removed under vacuum, the water layer was extracted with ethyl acetate (10 mL×2), the water layer was adjusted to pH ~6 with 1N HCl and lyophilized, the residue was purified by preparatory-HPLC (TFA) to give 77F (35 mg, yield: 48.5%), as white solid. $^1H$ NMR (400 MHz, methanol-$d_4$) δ 8.70 (d, J=5.3 Hz, 1H), 8.25 (s, 1H), 8.16 (s, 1H), 8.11 (s, 1H), 8.08 (d, J=5.1 Hz, 1H), 7.81 (s, 1H), 7.46 (s, 1H).

Compound 77 (38.4 mg, yield: 64.3%, white solid) was prepared as in Example 41 from the corresponding intermediate carboxylic acid, compound 77F. Compound 77: $^1H$ NMR (400 MHz, DMSO-$d_6$) δ 8.93 (d, J=7.5 Hz, 1H), 8.74 (d, J=5.1 Hz, 1H), 8.60 (d, J=5.7 Hz, 1H), 8.39 (d, J=0.7 Hz, 1H), 8.22 (d, J=0.7 Hz, 1H), 7.94 (dd, J=1.4, 5.2 Hz, 1H), 7.82 (s, 1H), 7.65 (d, J=0.7 Hz, 1H), 7.54 (d, J=0.7 Hz, 1H), 7.28 (d, J=4.4 Hz, 4H), 7.20 (qd, J=4.2, 8.5 Hz, 1H), 5.30-5.22 (m, 1H), 3.16 (dd, J=3.9, 13.8 Hz, 1H), 2.85 (dd, J=10.1, 13.9 Hz, 1H), 2.77-2.68 (m, 1H), 0.67-0.59 (m, 2H), 0.58-0.50 (m, 2H). MS (ESI) m/z $(M+H)^+$471.1.

(S)—N-(4-amino-3,4-dioxo-1-phenylbutan-2-yl)-1-(4-(oxazol-2-yl)pyridin-2-yl)-1H-imidazole-5-carboxamide (88)

Compound 88 (18.5 mg, yield: 46.5%, white solid) was prepared as in Example 5 from the corresponding intermediate carboxylic acid, compound 77F. $^1H$ NMR (400 MHz, DMSO-$d_6$) δ 8.93 (d, J=7.5 Hz, 1H), 8.58 (d, J=5.3 Hz, 1H), 8.37 (s, 1H), 8.21 (s, 1H), 8.01 (br s, 1H), 7.91 (d, J=5.1 Hz, 1H), 7.79 (s, 2H), 7.62 (s, 1H), 7.52 (s, 1H), 7.25 (d, J=4.2 Hz, 4H), 7.18 (br dd, J=4.5, 8.7 Hz, 1H), 5.25-5.17 (m, 1H), 3.14 (dd, J=3.6, 14.0 Hz, 1H), 2.83 (dd, J=10.5, 13.8 Hz, 1H). MS (ESI) m/z $(M+H)^+$431.1.

Example 44

(S)—N-(4-(cyclopropylamino)-3,4-dioxo-1-phenylbutan-2-yl)-3-methyl-1-(quinolin-5-yl)-1H-pyrazole-5-carboxamide (78)

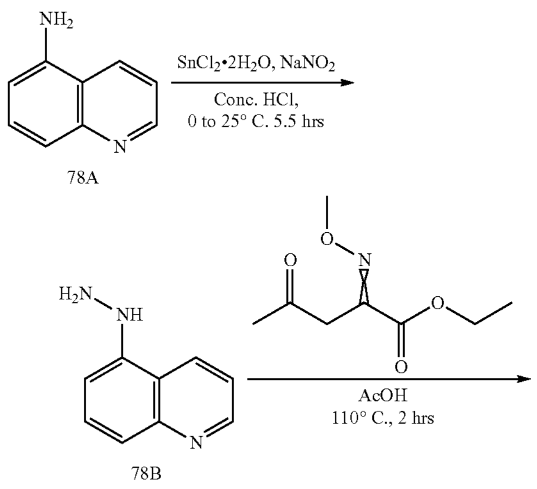

78A

78B

-continued

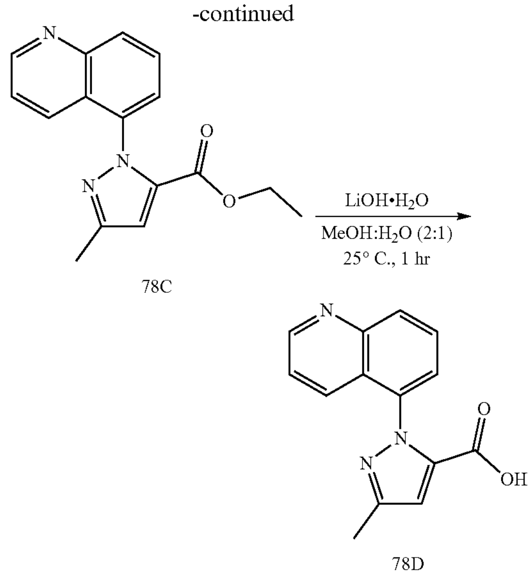

78C

78D

A mixture consisting of compound 78A (1.0 g, 6.94 mmol) in conc. HCl (4.00 mL) at 0° C. was added $NaNO_2$ (526.8 mg, 7.63 mmol) dropwise and the resultant mixture was stirred at 0° C. for 0.5 hour. The reaction mixture was warmed to 25° C. over 0.5 hour, and then cooled to 0° C. The $SnCl_2.2H_2O$ (3.13 g, 13.88 mmol, in 1.2 mL conc. HCl) was added dropwise to the reaction mixture, and stirred at 0° C. for 0.5 hour. The resulting mixture was allowed to warm to room temperature with vigorous stirring over 4 hours and then concentrated under reduced pressure to remove solvent. The residue was filtered, and the cake was washed with ethanol (30 mL×3), and then dried under reduced pressure to afford compound 78B (700.0 mg, 51.55% yield) as a yellow solid. $^1H$ NMR (DMSO-$d_6$, 400 MHz) δ 9.95 (br s, 1H), 9.25-9.13 (m, 2H), 8.04-7.95 (m, 2H), 7.88 (d, J=8.8 Hz, 1H), 7.26 (d, J=7.6 Hz, 1H), 7.28-7.23 (m, 1H).

To a mixture of compound 78B (500 mg, 3.14 mmol) and compound ethyl 2-(methoxyimino)-4-oxopentanoate (588 mg, 3.14 mmol) in AcOH (1 mL) was degassed and purged with $N_2$ for 3 times, and then the mixture was stirred at 110° C. for 2 hrs under $N_2$ atmosphere. The reaction mixture was concentrated under reduced pressure to remove AcOH. The residue was diluted with $CH_2Cl_2$ (100 mL), adjusted to pH ~7-8 with saturated aqueous $NaHCO_3$, and then extracted with $CH_2Cl_2$ (40 mL×2). The organic phase was dried over anhydrous $Na_2SO_4$, filtered, and concentrated under reduced pressure to give a residue, which was purified by column chromatography ($SiO_2$, Petroleum ether/Ethyl acetate=1:0 to 1:0) to give compound 78C (200 mg, 22.6% yield) as a yellow solid. $^1H$ NMR ($CDCl_3$, 400 MHz) δ 8.93 (d, J=4.0 Hz, 1H), 8.23 (d, J=8.4 Hz, 1H), 7.78 (t, J=8.0 Hz, 1H), 7.64 (d, J=8.4 Hz, 1H), 7.56 (d, J=7.2 Hz, 1H), 7.38 (d, J=8.8 Hz, 1H), 6.93 (s, 1H), 4.05 (q, J=7.2 Hz, 2H), 2.41 (s, 3H), 1.00 (t, J=7.2 Hz, 3H). MS (ESI) m/z $(M+1)^+$282.0.

Intermediate compound 78D (135 mg, 74.98% yield, white solid) was prepared as in Example 85 from compound 78C. Compound 78D: $^1H$ NMR (DMSO-d6, 400 MHz) δ 8.97 (d, J=4.0 Hz, 1H), 8.17 (d, J=8.4 Hz, 1H), 7.89-7.82 (m, 1H), 7.67-7.52 (m, 3H), 6.97 (s, 1H), 2.32 (s, 3H). MS (ESI) m/z $(M+1)^+$253.9.

Compound 78 (8.8 mg, 16.77% yield, yellow solid) was prepared as in Example 20 from the corresponding intermediate carboxylic acid, compound 78D. Compound 78: $^1H$ NMR ($CDCl_3$, 400 MHz): δ 8.95 (d, J=4.0 Hz, 1H), 8.22 (d, J=8.4 Hz, 1H), 7.76-7.66 (m, 2H), 7.49 (d, J=6.4 Hz, 1H), 7.38 (d, J=8.4 Hz, 1H), 7.24-7.16 (m, 3H), 6.87 (d, J=7.6 Hz, 2H), 6.79 (br s, 1H), 6.64 (s, 1H), 6.33 (d, J=7.2 Hz, 1H), 5.49-5.42 (m, 1H), 3.27-3.19 (m, 1H), 3.08-2.98 (m, 1H), 2.78-2.69 (m, 1H), 0.90-0.83 (m, 2H), 0.61-0.50 (m, 2H). MS (ESI) m/z $(M+H)^+$468.1.

Example 45

Compounds 79, 146, 160, 264

(S)—N-(4-amino-3,4-dioxo-1-phenylbutan-2-yl)-2-methyl-5-phenyl-1H-imidazole-4-carboxamide (79)

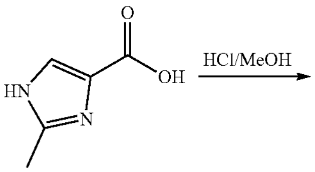

79A

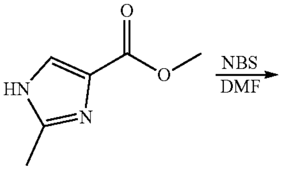

79B

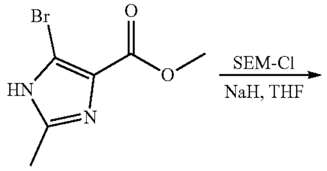

79C

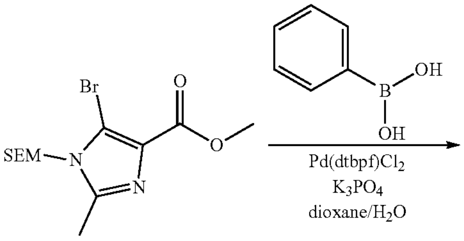

79D

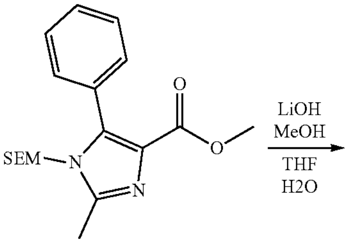

79E

-continued

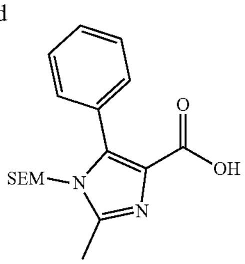

79F

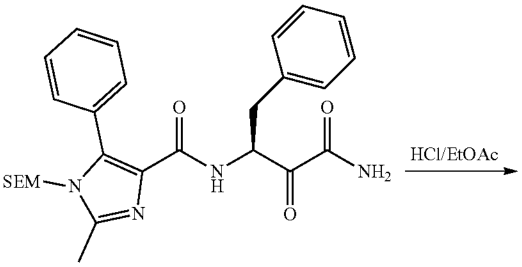

79H

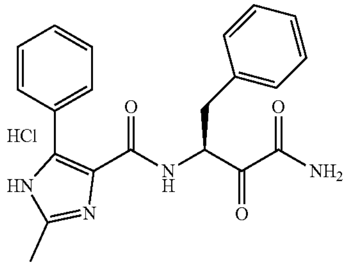

79

The solution of compound 79A (500 mg, 3.96 mmol) in HCl/MeOH (4 M, 50 mL) was stirred at 80° C. for 12 hrs. The solvent was removed in vacuo. The residue was adjusted to pH ~8 with saturated aqueous $NaHCO_3$. The solution was extracted with EtOAc (100 mL×3). The organics were collected, dried with $Na_2SO_4$, filtered and concentrated. Compound 79B (360 mg, yield: 64.87%, light yellow solid): $^1H$ NMR ($CDCl_3$, 400 MHz) δ 7.90-7.88 (m, 1H), 7.34-7.31 (m, 1H), 7.15-7.09 (m, 2H), 5.72-5.63 (m, 1H), 4.87-4.76 (m, 2H), 2.90-2.86 (m, 2H), 1.92-1.87 (m, 2H), 1.50-1.47 (m, 2H), 1.26-1.14 (m, 8H).

To a solution of compound 79B (360 mg, 2.57 mmol) in DMF (5 mL) at 0° C. was added NBS (550 mg, 3.08 mmol). The mixture was then warmed up to 25° C. and stirred for 12 hrs. The reaction was washed with $H_2O$ (10 mL), extracted with DCM (20 mL). The organics were collected, dried with $Na_2SO_4$, filtered and concentrated to afford intermediate compound 79C (550 mg, crude) as yellow solid. MS (ESI) m/z $(M+2)^+$220.7.

To a solution of NaH (151 mg, 3.76 mmol, 60% purity) in THF (8 mL) at 0° C. was added a solution of compound 79C (550 mg, 2.51 mmol) in THF (2 mL) dropwise. After addition, the mixture was warmed up to 25° C. and stirred for 1 h. Then SEM-C1 (0.5 mL, 2.76 mmol) was added. The mixture was stirred at 25° C. for 12 hrs. The reaction was quenched with $H_2O$ (10 mL), extracted with EtOAc (20 mL×2). The organics were collected and concentrated. The residue was purified by column (Petroleum Ether:Ethyl Acetate=5:1) to afford compound 79D (180 mg, yield: 20.51%) as colorless oil. MS (ESI) m/z $(M+2)^+$350.9.

To a solution of compound 79D (180 mg, 0.52 mmol) and phenylboronic acid (76 mg, 0.62 mmol) in dioxane (12 mL) and $H_2O$ (4 mL) was added Pd(dtbpf)$Cl_2$ (34 mg, 0.052 mmol) and $K_3PO_4$ (330 mg, 1.55 mmol). The mixture was stirred at 80° C. under $N_2$ for 2 hrs. The reaction was washed with $H_2O$ (10 mL), extracted with EtOAc (15 mL×2). The organics were collected and concentrated. The residue was purified by column (Petroleum Ether:Ethyl Acetate=5:1) to afford compound 79E (150 mg, yield: 84.0%) as yellow oil. MS (ESI) m/z $(M+H)^+$347.0.

To a solution of compound 79E (180 mg, 0.52 mmol) in THF (5 mL), MeOH (5 mL) and $H_2O$ (5 mL) was added LiOH.$H_2O$ (110 mg, 2.60 mmol). The mixture was stirred at 25° C. for 12 hrs. The reaction was acidified with 1N HCl to pH ~3. The mixture was extracted with EtOAc (10 mL×2). The organics were collected, dried with $Na_2SO_4$, filtered and concentrated to afford compound 79F (130 mg, crude) as yellow oil. MS (ESI) m/z $(M+H)^+$333.0. Intermediate compound 79H (65 mg, crude, yellow oil) was prepared as in Example 5 from the corresponding carboxylic acid, compound 79F. Compound 79H: MS (ESI) m/z $(M+H)^+$507.2.

To a solution of compound 79H (65 mg, 0.13 mmol) in EtOAc (5 mL) was added HCl/EtOAc (4 M, 10 mL) dropwise. After addition, the mixture was stirred at 25° C. for 12 hrs. The solvent was removed in vacuo. The residue was purified by prep-HPLC (HCl) to afford compound 79 (10.00 mg, yield: 18.7%) as white solid. $^1H$ NMR (400 MHz, $D_2O$) δ 7.45-7.28 (m, 3H), 7.23-6.97 (m, 7H), 4.46-4.38 (m, 1H), 3.02-2.93 (m, 1H), 2.48-2.41 (m, 3H), 2.39-2.29 (m, 1H). MS (ESI) m/z $(M+H)^+$377.1.

(S)—N-(4-amino-3,4-dioxo-1-phenylbutan-2-yl)-1-(3-((benzylamino)methyl)phenyl)-3-methyl-1H-pyrazole-5-carboxamide (146)

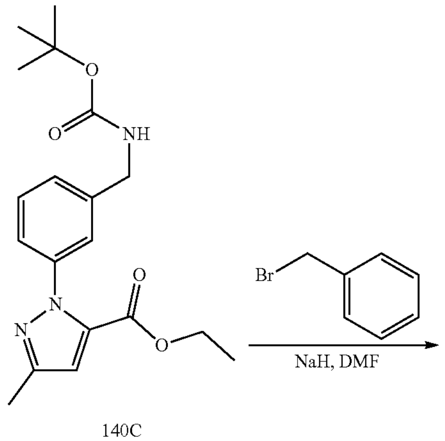

140C

-continued

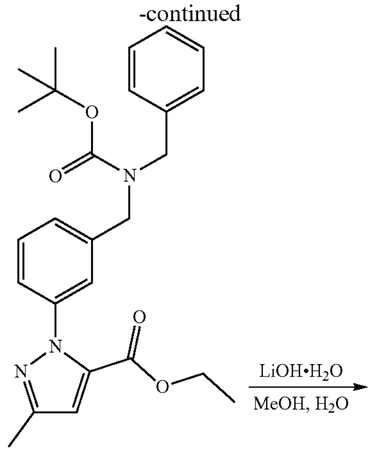

146A

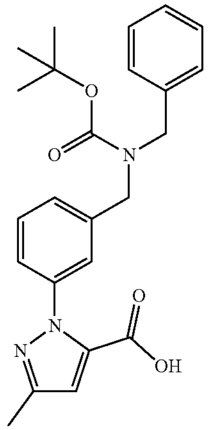

146B

To a mixture of compound 140C (250 mg, 0.72 mmol) and benzyl bromide (310 mg, 1.8 mmol) in DMF (10 mL) was added NaH (87 mg, 2.2 mmol, 60% purity) in batches at 0° C. under $N_2$. The mixture was stirred at 25° C. for 3 h. The mixture was quenched with $NH_4Cl$ (10 mL), diluted with $H_2O$ (30 mL), extracted with ethyl acetate (20 mL×3). The organic phase was combined and washed with brine (30 mL×2), dried over $Na_2SO_4$, filtered and concentrated to give a residue. The residue was purified by Flash Column Chromatography (SiO2, Petroleum ether/Ethyl acetate=I/O to 5/1) to afford compound 146A (182 mg, yield: 57.7%) as colorless clear liquid.

To a mixture of compound 146A (180 mg, 0.41 mmol) in MeOH (10 mL) and $H_2O$ (2 mL) was added LiOH.$H_2O$ (52 mg, 1.24 mmol) in one portion at 25° C. The mixture was stirred at 25° C. for 3 h. The reaction mixture was concentrated under reduced pressure to move MeOH. Then the residue was diluted with water (15 mL) and extracted with MTBE (20 mL), the aqueous phase was acidified with aqueous HCl (1M) till pH ~5~6 and extracted with ethyl acetate (20 mL×2). The combined organic layers were washed with brine (40 mL) and dried over $Na_2SO_4$, filtered and concentrated to afford compound 146B (158 mg, yield: 90.8%) as colorless liquid, which was used directly for next step without purification. $^1H$ NMR (DMSO-$d_6$, 400 MHz): δ 7.44-7.39 (m, 1H), 7.37-7.30 (m, 3H), 7.26 (q, J=6.9 Hz, 5H), 6.81 (s, 1H), 4.48-4.26 (m, 4H), 2.25 (s, 3H), 1.39 (s, 9H).

Compound 146 was prepared as in Example 45 from the intermediate compound 146B. Compound 146 (40.0 mg, yield 74.6%, white solid): $^1$H NMR ($D_2O$, 400 MHz): δ 7.51-7.42 (m, 6H), 7.41-7.36 (m, 1H), 7.36-7.27 (m, 5H), 7.25 (s, 1H), 6.78 (d, J=8.6 Hz, 1H), 6.60 (s, 1H), 4.52-4.43 (m, 1H), 4.30-4.18 (m, 4H), 3.24-3.15 (m, 1H), 2.82-2.71 (m, 1H), 2.29 (s, 3H). MS (ESI) m/z (M−HCl+H)$^+$496.2.

(S)—N-(4-amino-3,4-dioxo-1-phenylbutan-2-yl)-1-(4-((benzylamino)methyl)phenyl)-3-methyl-1H-pyrazole-5-carboxamide hydrochloride (160)

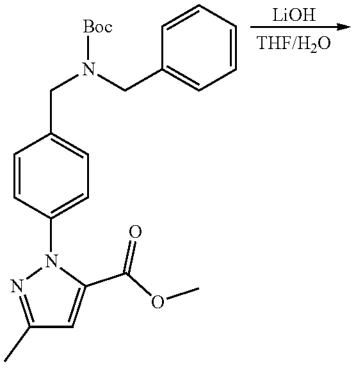

160A

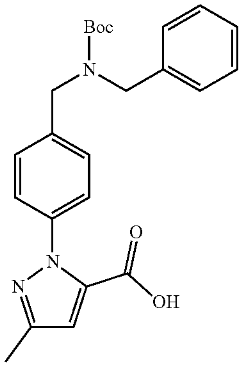

160B

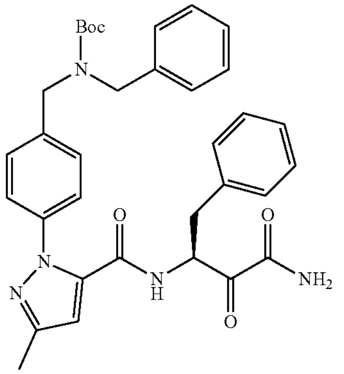

160D

To a solution of compound 153E (350 mg, 1.01 mmol) and benzyl bromide (432 mg, 2.53 mmol, 0.3 mL) in DMF (10 mL) was added NaH (121 mg, 3.03 mmol, 60% purity) at 0° C. The mixture was stirred at 25° C. for 1 h. The mixture was quenched with $NH_4Cl$ (5 mL), diluted with $H_2O$ (20 mL), extracted with ethyl acetate (20 mL×3), the organic phase was combined, and washed with NaCl (30 mL×2), dried over $Na_2SO_4$, concentrated to give a residue. The residue was purified by column chromatography ($SiO_2$, Petroleum ether/Ethyl acetate=20/1 to 5/1) to give compound 160A (400 mg, yield: 41.47%) as a yellow oil. $^1$H NMR (400 MHz, $CDCl_3$) δ 8.02 (dd, J=1.1 Hz, 1H), 7.37-7.25 (m, 9H), 6.88-6.75 (m, 1H), 4.49-4.28 (m, 4H), 2.98-2.88 (m, 4H), 2.46-2.30 (m, 3H), 1.57-1.41 (m, 8H). MS (ESI) m/z (M−56)$^+$380.0.

To a mixture of compound 160A (400 mg, 918.46 umol) in THF (10 mL) and $H_2O$ (10 mL) was added $LiOH.H_2O$ (116 mg, 2.76 mmol) in portion at 25° C. and stirred for 2.5 h. The mixture was diluted with $H_2O$ (10 mL) and concentrated to remove THF, then the water was extracted with MTBE (30 mL×2). The water layers were acidified to pH ~2 with 1N HCl, then, the solution extracted with ethyl acetate (30 mL×3). The organic layers were dried over $Na_2SO_4$ and concentrated to give intermediate compound 160B (350 mg, yield: 86.82%) as white solid. $^1$H NMR (400 MHz, $CDCl_3$) δ 7.40-7.20 (m, 9H), 6.85 (s, 1H), 4.43 (s, 2H), 4.33 (dd, J=13.9 Hz, 2H), 2.34 (s, 3H), 1.47 (s, 8H). MS (ESI) m/z (M−56)$^+$366.1.

Compound 160 was prepared as in Example 79 from the corresponding carboxylic acid, compound 160B, and then through intermediate compound 160D. Compound 160 (30 mg, yield: 53.02%, light yellow solid): $^1$H NMR (400 MHz, DMSO-d6) δ 9.62-9.57 (m, 1H), 9.15 (d, J=7.9 Hz, 1H), 8.12 (s, 1H), 7.88 (s, 1H), 7.58-7.49 (m, 4H), 7.44 (dd, J=6.8 Hz, 3H), 7.36-7.27 (m, 5H), 7.22 (d, J=8.4 Hz, 2H), 6.61 (s, 1H), 5.35-5.28 (m, 1H), 4.18 (s, 4H), 3.25-3.18 (m, 1H), 2.83 (dd, J=10.6, 13.9 Hz, 1H), 2.26 (s, 3H). MS (ESI) m/z (M+H)$^+$496.2.

(S)—N-(4-amino-3,4-dioxo-1-phenylbutan-2-yl)-1-(1H-benzo[d]imidazol-2-yl)-5-methyl-1H-pyrazole-3-carboxamide (264)

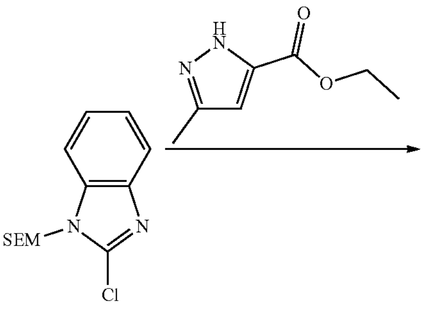

264A

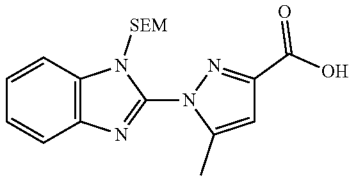

264B

-continued

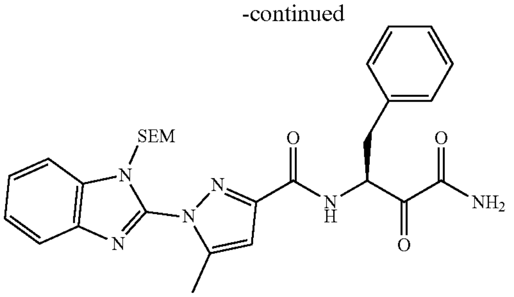

264D 2-chloro-1H-benzo[d]imidazole (5 g, 32.8 mmol) was added to a solution of NaH (1.31 g, 32.8 mmol, 60%) in DMF (50 mL) below 10° C. After addition, the reaction mixture was stirred at 20° C. for 2 h. Then SEM-Cl (5.46 g, 32.8 mmol) was added to the reaction mixture. The reaction mixture was stirred at 20° C. for 16 hrs. Water (150 mL) and EtOAc (150 mL) were added. The organic layer was separated and washed by brine (100 mL), concentrated to give a residue. The crude product was purified by silica gel column (petroleum ether:ethyl acetate=20: 1-4:1) to give compound 264A (3.50 g, yield: 37.8%) as an oil. $^1$H NMR (400 MHz, $CDCl_3$) δ 7.78-7.71 (m, 1H), 7.54-7.48 (m, 1H), 7.41-7.32 (m, 2H), 5.62 (s, 2H), 3.66-3.59 (m, 2H), 0.99-0.93 (m, 2H), 0.07 (d, J=2.0 Hz, 2H), 0.00 (s, 9H).

Compound 264 was prepared as in Example 79 from the corresponding intermediate compound 264B, and then through intermediate compound 264D. Compound 264 (31.8 mg, yield: 28.0%, off-white solid): $^1$H NMR (400 MHz, $CDCl_3$) δ 13.04 (br s, 1H), 8.39 (d, J=7.6 Hz, 1H), 8.13 (br s, 1H), 7.88 (br s, 1H), 7.67 (br d, J=7.2 Hz, 1H), 7.53 (br d, J=7.5 Hz, 1H), 7.34-7.19 (m, 7H), 6.79 (s, 1H), 5.51 (dt, J=4.0, 8.2 Hz, 1H), 3.27 (br d, J=4.0 Hz, 1H), 3.02 (dd, J=9.3, 13.9 Hz, 1H), 2.73 (s, 3H). MS (ESI) m/z $(M+H)^+$417.2.

Example 46

(S)—N-(4-amino-3,4-dioxo-1-phenylbutan-2-yl)-5-methyl-1-(4-phenylthiazol-2-yl)-1H-pyrazole-3-carboxamide (80)

(S)—N-(4-(cyclopropylamino)-3,4-dioxo-1-phenylbutan-2-yl)-5-methyl-1-(4-phenylthiazol-2-yl)-1H-pyrazole-3-carboxamide (125)

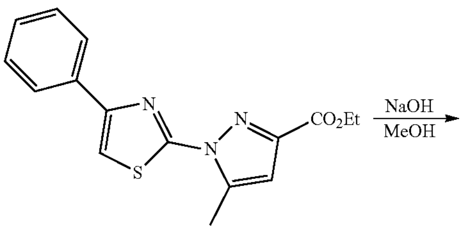

80A

-continued

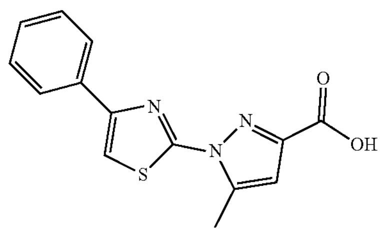

80B

Intermediate compound 80B (182.00 mg, 99.95% yield, white solid): $^1$H NMR (DMSO-$d_6$, 400 MHz) δ 8.02 (s, 1H), 7.96 (br d, J=7.5 Hz, 2H), 7.47 (br t, J=7.5 Hz, 2H), 7.41-7.32 (m, 1H), 6.80 (s, 1H), 2.78 (s, 3H).

Compound 80 (44 mg, 64.6% yield, white solid) was prepared as in Example 5 from the corresponding intermediate compounds 80B and 12G. Compound 80: $^1$H NMR (DMSO-$d_6$, 400 MHz) δ 8.53 (br d, J=7.3 Hz, 1H), 8.12 (br s, 1H), 8.04-7.94 (m, 3H), 7.86 (br s, 1H), 7.52-7.44 (m, 2H), 7.39 (br d, J=6.4 Hz, 1H), 7.32-7.17 (m, 5H), 6.76 (s, 1H), 5.43 (br s, 1H), 3.24 (br d, J=12.1 Hz, 1H), 3.12-3.03 (m, 1H), 2.78 (s, 3H). MS (ESI) m/z $(M+H)^+$460.1.

Compound 125 (118 mg, yield 77.6%, white solid) was prepared as in Example 20 from the corresponding intermediate carboxylic compounds 80B and 41B. Compound 125: $^1$H NMR (DMSO-$d_6$, 400 MHz) δ 8.84 (br s, 1H), 8.60-8.53 (m, 1H), 8.06-7.94 (m, 3H), 7.52-7.44 (m, 2H), 7.42-7.35 (m, 1H), 7.29 (br s, 4H), 7.21 (br s, 1H), 6.76 (s, 1H), 5.44 (br s, 1H), 3.27-3.19 (m, 1H), 3.11-3.02 (m, 1H), 2.78 (br s, 4H), 0.72-0.57 (m, 4H). MS (ESI) m/z $(M+H)^+$500.1.

Example 47

(S)—N-(4-amino-3,4-dioxo-1-phenylbutan-2-yl)-3-methyl-1-(2'-methyl-[1,1'-biphenyl]-3-yl)-1H-pyrazole-5-carboxamide (81)

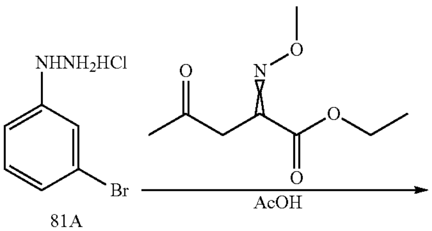

81A

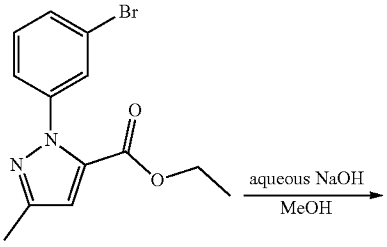

81B

-continued

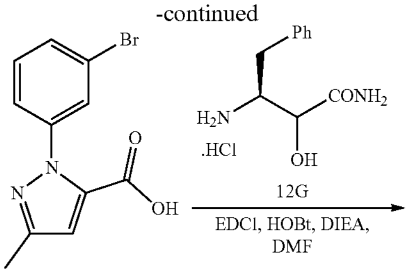

81C

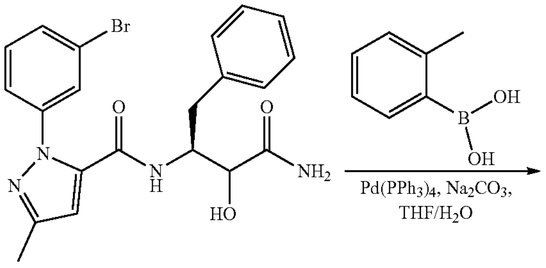

81D

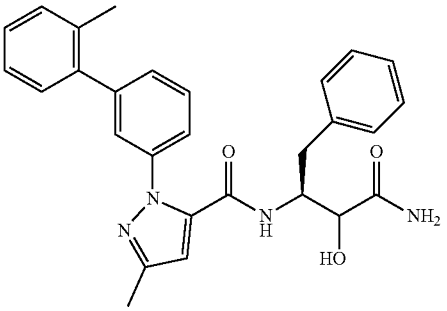

81E

To a mixture of compound 81A (25 g, 111.86 mmol) and compound ethyl 2-(methoxyimino)-4-oxopentanoate (22 g, 117.45 mmol) in AcOH (150 mL) was stirred at 110° C. for 2 hrs. The reaction mixture was concentrated under reduced pressure to remove a large amount of AcOH. The residue was acidified with saturated aqueous $NaHCO_3$ till pH ~7-8. The precipitate was collected by filtration and the cake was triturated with petroleum ether (20 mL), filtered and dried in vacuum to afford compound 81B (26.41 g, yield: 74.0%) as gray solid. $^1H$ NMR (DMSO-$d_6$, 400 MHz) δ 7.71-7.68 (m, 1H), 7.65 (td, J=1.5, 7.7 Hz, 1H), 7.50-7.38 (m, 2H), 6.95-6.84 (m, 1H), 4.18 (q, J=7.0 Hz, 2H), 2.27 (s, 3H), 1.17 (t, J=7.0 Hz, 3H). MS (ESI) m/z $(M+H)^+$310.8.

To a mixture of compound 81B (5 g, 16.17 mmol) in MeOH (20.00 mL) was added NaOH (2M, 40 mL) in one portion at 25° C. The mixture was stirred at 25° C. for 2 hrs. The reaction mixture was concentrated under reduced pressure to remove MeOH. The residue was added $H_2O$ (10 mL) and ethyl acetate (20 mL), and then the mixture was acidified with 1M HCl till the aqueous phase pH ~5-6. The separated aqueous layer was extracted with ethyl acetate (30×3 mL), the combined organic layers were washed with brine (60 mL), dried over $Na_2SO_4$, filtered under reduced pressure to give crude product. The crude product was treated with isopropyl ether (15 mL), the precipitate was filtered and dried in vacuum to afford compound 81C (4.21 g, yield: 80.67%) as white solid. $^1H$ NMR (DMSO-$d_6$, 400 MHz) δ 7.65-7.58 (m, 2H), 7.45-7.36 (m, 2H), 6.83 (s, 1H), 2.23 (s, 3H). MS (ESI) m/z $(M+H)^+$282.8.

To a solution of compound 81C (1 g, 3.56 mmol) in DMF (50 mL) was added HOBt (144 mg, 1.07 mmol), compound 12G (903 mg, 3.92 mmol, HCl) and DIEA (1.38 g, 10.68 mmol). After stirring for 5 min, EDCI (682 mg, 3.56 mmol) was added at 0° C. Then the reaction mixture was stirred at 25° C. for 9 hrs. The reaction mixture was concentrated under reduced pressure to move DMF, and to the residue was added ethyl acetate (100 mL) and respectively washed with $H_2O$ (80 mL), saturated aqueous $NaHCO_3$ (80 mL×2), brine (80 mL×3). The organic phase was dried over $Na_2SO_4$ and concentrated. The crude product was treated with i-propyl ether. The solid was collected and dried in vacuum to afford compound 81D (1.3 g, yield: 79.85%) as white solid. $^1H$ NMR (DMSO-$d_6$, 400 MHz) δ 8.55-8.18 (m, 1H), 7.54-7.45 (m, 2H), 7.34 (br d, J=18.5 Hz, 1H), 7.30-7.14 (m, 7H), 7.00-6.89 (m, 1H), 6.58 (d, J=1.5 Hz, 1H), 5.98-5.73 (m, 1H), 4.44-4.33 (m, 1H), 4.00-3.89 (m, 1H), 2.93-2.87 (m, 0.5H), 2.84-2.73 (m, 1H), 2.71 (br s, 0.6H), 2.22 (s, 3H).

To a mixture of compound 81D (150 mg, 328.00 umol) and compound o-tolylboronic acid (89.2 mg, 656.00 umol) in THF (50 mL) and $H_2O$ (10 mL) was added $Na_2CO_3$ (70 mg, 656.00 umol) and $Pd(PPh_3)_4$ (38 mg, 32.80 umol) in one portion at 25° C. under $N_2$. The mixture was stirred at 80° C. for 12 hrs. Then to the reaction mixture was added $H_2O$ (100 mL) and extracted with ethyl acetate (100 mL×3). The combined organic layer was washed with saturated aqueous $NaHCO_3$ (150 mL×3), brine (150 mL×3), dried over $Na_2SO_4$ and concentrated to afford compound 81E (110 mg, yield: 71.58%) was obtained as white solid. $^1H$ NMR (DMSO-$d_6$, 400 MHz) δ 8.50-8.11 (m, 1H), 7.38-7.32 (m, 2H), 7.31-7.22 (m, 6H), 7.18 (br s, 5H), 7.10 (br d, J=6.4 Hz, 1H), 7.00 (br.dd, J=8.0, 16.4 Hz, 1H), 6.57 (s, 1H), 5.96-5.69 (m, 1H), 4.51-4.30 (m, 1H), 4.03-3.85 (m, 1H), 2.92-2.63 (m, 2H), 2.27-2.12 (m, 6H). MS (ESI) m/z $(M+H)^+$469.2.

The mixture of compound 81E (70 mg, 149.4 umol) in DCM (10 mL) and DMSO (0.5 mL) was added DMP (190 mg, 448.2 umol) in one portion at 0° C. The mixture was stirred at 0° C. for 5 min, then heated to 25° C. and stirred for 1.5 hours. The reaction was quenched by 20 mL of 10% aqueous $Na_2S_2O_3$ solution and 20 mL of saturated aqueous $NaHCO_3$ solution and then extracted with DCM (30 mL×3). The combined organic phase was washed with brine (40 mL×3), dried over anhydrous $Na_2SO_4$, filtered and concentrated in vacuum. The residue was treated with i-propyl ether/CH3CN (v/v=10/1, 10 mL). The solid was collected and dried in vacuum to afford compound 81 (48.3 mg, yield: 66.3%) as white solid. $^1H$ NMR (DMSO-$d_6$, 400 MHz) δ 9.11 (br d, J=8.0 Hz, 1H), 8.18-7.79 (m, 2H), 7.49-7.37 (m, 1H), 7.29-7.26 (m, 8H), 7.21-7.12 (m, 4H), 6.60 (s, 1H), 5.32 (br.s., 1H), 3.21-3.18 (m, 1H), 2.86-2.76 (m, 1H), 2.25 (br.s., 3H), 2.18 (br.s., 3H). MS (ESI) m/z $(M+H)^+$467.1.

Example 48

(S)—N-(4-amino-3,4-dioxo-1-phenylbutan-2-yl)-3-methyl-1-(4-phenylthiazol-2-yl)-1H-pyrazole-5-carboxamide (82)

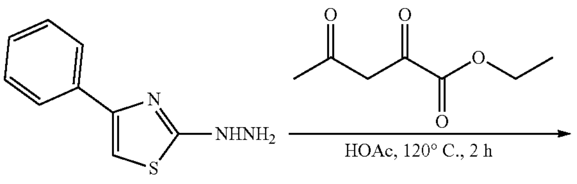

82A

-continued

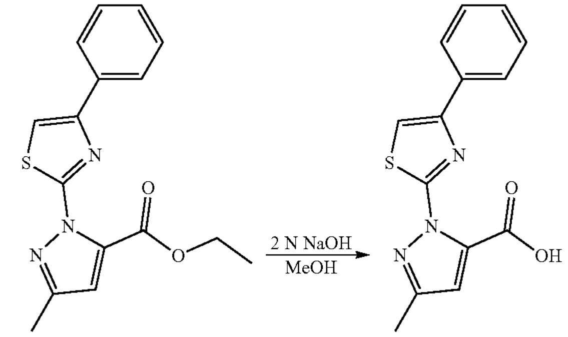

82B 82D

To a solution of compound 82A (2.0 g, 10.46 mmol) in $CH_3COOH$ (30.0 mL) was added compound ethyl 2,4-dioxopentanoate (1.65 g, 10.46 mmol, 1.48 mL) dropwise, then the mixture was heated to 120° C. and stirred for 2 hrs and removed the solvent under reduced pressure. The residue was dissolved in ethyl acetate (20 mL) and treated with $NaHCO_3$ until pH 8, and then the organic layer was collected and evaporated under reduced pressure. The residue was purified by flash column chromatography (Petroleum Ether/Ethyl Acetate: 0 to 10/1).

Compound 82B (660.0 mg, 2.11 mmol, 20.14% yield) was obtained as white solid. Compound 82B (low polarity): $^1H$ NMR ($CDCl_3$, 400 MHz) δ 7.88-7.83 (m, 2H), 7.43-7.38 (m, 3H), 7.36-7.31 (m, 1H), 6.71 (s, 1H), 4.33 (q, J=7.2 Hz, 2H), 2.37 (s, 3H), 1.24 (t, J=7.2 Hz, 3H).

To a solution of compound 82B (650.0 mg, 2.07 mmol) in MeOH (10.00 mL) was added NaOH (2M, 6.00 mL) drop wise and the mixture was stirred at 25° C. for 2 hrs. The reaction was diluted with $H_2O$ (10 mL) and extracted with MBTE (10 mL×2). The water phase was treated with HCl (1M) until pH ~4, then the precipitate was filtered and dried under reduced pressure. Compound 82D (540.0 mg, 91.3% yield) was obtained as white solid. $^1H$ NMR (DMSO-$d_6$, 400 MHz) δ 8.04 (s, 1H), 7.88 (d, J=7.1 Hz, 2H), 7.47-7.41 (m, 2H), 7.38-7.33 (m, 1H), 6.83 (s, 1H), 2.27 (s, 3H)

Compound 82 (20.0 mg, 42.74% yield, white solid) was prepared as in Example 5 from the corresponding intermediate carboxylic acid, compound 82D. Compound 82: $^1H$ NMR (DMSO-$d_6$, 400 MHz) δ 9.49 (d, J=7.6 Hz, 1H), 8.12 (s, 1H), 7.94 (s, 1H), 7.88 (br s, 1H), 7.78 (br d, J=7.2 Hz, 2H), 7.42-7.37 (m, 2H), 7.35-7.29 (m, 1H), 7.22-7.12 (m, 5H), 6.55 (s, 1H), 5.55-5.47 (m, 1H), 3.16 (m, 1H), 2.80 (m, 1H), 2.27 (s, 3H). MS (ESI) m/z $(M+H)^+$403.1.

Example 49

Compounds 83, 126, 130

(S)-1-([1,1'-biphenyl]-4-yl)-N-(4-amino-3,4-dioxo-1-phenylbutan-2-yl)-3-methyl-1H-pyrazole-5-carboxamide (83)

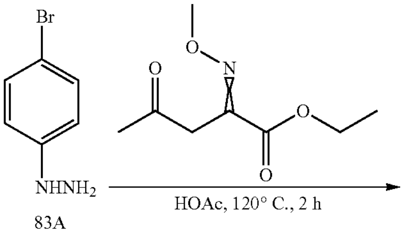

83A

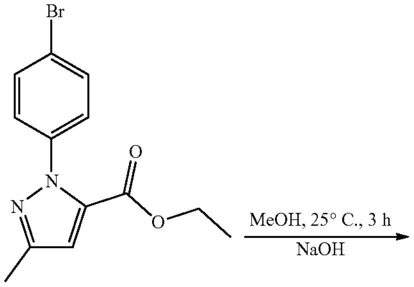

83B

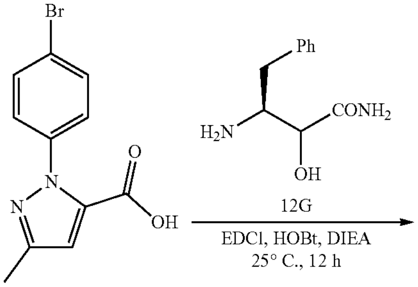

83C

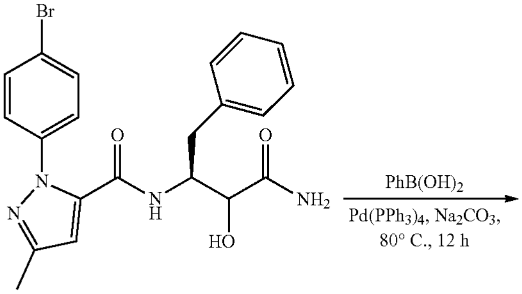

83D

-continued

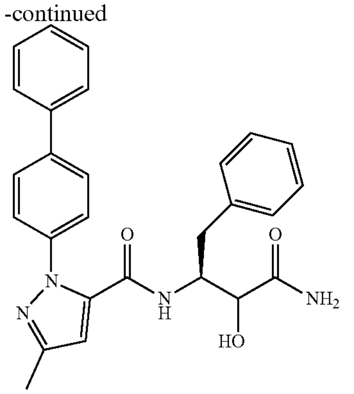

83E

To a solution of compound 83A (20.0 g, 89.49 mmol, HCl) in $CH_3COOH$ (150.0 mL) was added compound ethyl 2-(methoxyimino)-4-oxopentanoate (14.0 g, 89.49 mmol), then the mixture was heated to 120° C. and stirred for 2 hrs and removed the solvent under reduced pressure. The residue was dissolved in ethyl acetate (150 mL), treated with $NaHCO_3$ until pH ~7 and filtered. The solid was treated with petroleum ether. Compound 83B (22.0 g, 71.16 mmol, 79.52% yield) was obtained as yellow solid. $^1H$ NMR ($CDCl_3$, 400 MHz) δ 7.56 (d, J=8.4 Hz, 2H), 7.31-7.24 (m, 2H), 6.81 (s, 1H), 4.23 (q, J=7.2 Hz, 2H), 2.34 (s, 3H), 1.26 (t, J=7.2 Hz, 3H).

To a solution of compound 83B (5.0 g, 16.17 mmol) in MeOH (40.0 mL) was added NaOH (2M, 45.0 mL) dropwise and the mixture was stirred at 25° C. for 3 hrs and removed the solvent under reduced pressure, then the mixture was diluted with $H_2O$ (30 mL) and extracted with MTBE (60 mL×2). Water phase was treated with HCl (1M) until pH ~4, and then the precipitate was filtered and dried under reduced pressure. The water phase was extracted with ethyl acetate (50 mL×2), the organic layer (extracted with ethyl acetate) was evaporated under reduced pressure. The solid collected was compound 83C (3.75 g, 82.5% yield) obtained as white solid. $^1H$ NMR (DMSO-$d_6$, 400 MHz) δ 7.62 (d, J=8.8 Hz, 2H), 7.36 (d, J=8.8 Hz, 2H), 6.81 (s, 1H), 2.23 (s, 3H).

Compound 83 (25.0 mg, 61.24% yield, white solid) was prepared as in Example 47 from the corresponding intermediate compounds 83C, 12G and phenylboronic acid. Compound 83: $^1H$ NMR ($CDCl_3$, 400 MHz) δ 9.49 (d, J=7.3 Hz, 1H), 8.12 (s, 1H), 7.94 (s, 1H), 7.88 (br s, 1H), 7.78 (br d, J=7.3 Hz, 2H), 7.48-7.27 (m, 4H), 7.26-6.96 (m, 7H), 6.55 (s, 1H), 5.55-5.47 (m, 1H), 3.16 (br dd, J=4.2, 14.1 Hz, 1H), 2.80 (br dd, J=9.7, 13.9 Hz, 1H), 2.27 (s, 3H), 2.06 (s, 1H). MS (ESI) m/z $(M+H)^+$453.1.

(S)—N-(4-amino-3,4-dioxo-1-phenylbutan-2-yl)-1-(4'-fluoro-[1,1'-biphenyl]-4-yl)-3-methyl-1H-pyrazole-5-carboxamide (126)

Compound 126 (32 mg, yield 25.5%, light yellow solid) was prepared as in Example 63 from the corresponding starting materials, compound 83D and (4-fluorophenyl)boronic acid. Compound 126: $^1H$ NMR ($CD_3CN$, 400 MHz) δ 7.73-7.67 (m, 2H), 7.63-7.59 (m, 2H), 7.37-7.22 (m, 10H), 7.02 (br s, 1H), 6.54 (s, 1H), 6.27 (br s, 1H), 5.42 (ddd, J=4.5, 7.8, 9.5 Hz, 1H), 3.32 (dd, J=4.5, 13.8 Hz, 1H), 2.93 (dd, J=9.6, 14.0 Hz, 1H), 2.31 (s, 3H). MS (ESI) m/z $(M+H)^+$471.1.

(S)—N-(4-amino-3,4-dioxo-1-phenylbutan-2-yl)-1-(4'-fluoro-[1,1'-biphenyl]-4-yl)-3-methyl-1H-pyrazole-5-carboxamide (130)

Compound 130 (30 mg, yield 34.7%, light yellow solid) was prepared as in Example 105 from the corresponding starting materials, compound 83D and p-tolylboronic acid. Compound 130: $^1H$ NMR (DMSO-$d_6$, 400 MHz) δ 9.14 (br d, J=7.7 Hz, 1H), 8.11 (br s, 1H), 7.87 (br s, 1H), 7.60-7.55 (m, 3H), 7.33-7.22 (m, 10H), 6.56-6.50 (m, 1H), 5.24 (br s, 1H), 3.20 (br d, J=13.5 Hz, 1H), 2.87-2.78 (m, 1H), 2.33 (s, 3H), 2.24 (s, 3H). MS (ESI) m/z $(M+H)^+$467.1.

Example 50

(S)—N-(4-amino-3,4-dioxo-1-phenylbutan-2-yl)-3-methyl-1-(6-methylpyridin-2-yl)-1H-pyrazole-5-carboxamide (84)

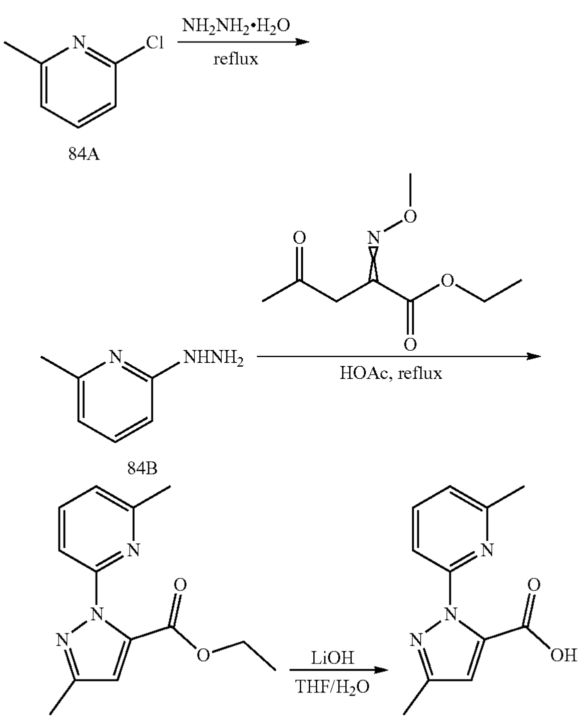

84A

84B

84C

84D

A mixture of compound 84A (5 g, 39.19 mmol) and $NH_2NH_2.H_2O$ (20 g, 391.94 mmol) was heated under reflux (119° C.) for 36 hours. The reaction mixture was concentrated under reduced pressure to remove the unreacted hydrazine hydrate. The residue was diluted with $H_2O$ (30 mL) and extracted with DCM (30 mL×3). The combined organic layers were washed with brines (30 mL), dried over $Na_2SO_4$, filtered and concentrated under reduced pressure to give a residue. The residue was purified by re-crystallization from Petroleum Ether (15 mL) at −10° C. to give compound 84B (2.40 g, yield: 49.35%) as a black brown solid. $^1H$ NMR (400 MHz, DMSO-$d_6$) δ 7.39-7.29 (m, 1H), 7.25 (s, 1H), 6.51 (d, J=8.4 Hz, 1H), 6.39 (d, J=7.3 Hz, 1H), 4.06 (s, 2H), 2.26 (s, 3H). MS (ESI) m/z $(M+H)^+$127.8.

To a solution of compound 84B (970 mg, 7.88 mmol) in AcOH (20 mL) was added compound ethyl 2-(methoxyimino)-4-oxopentanoate (1.36 g, 7.88 mmol). The mixture was stirred at 120° C. for 20 hrs. The reaction mixture was concentrated under reduced pressure to remove solvent. The residue was diluted with $H_2O$ (30 mL) and extracted with ethyl acetate (10 mL×3). The combined organic layers were washed with saturated aqueous $NaHCO_3$ (15 mL×3), dried over $Na_2SO_4$, filtered and concentrated under reduced pressure to give a residue. The residue was purified by flash silica gel chromatography, and then by preparatory-HPLC (HCl condition) to give compound 84C (160 mg, yield: 8.22%) was obtained as a white solid. $^1H$ NMR (400 MHz, DMSO-$d_6$) δ 7.88 (t, J=7.8 Hz, 1H), 7.50 (d, J=8.0 Hz, 1H), 7.28 (d, J=7.5 Hz, 1H), 6.76 (s, 1H), 4.20 (d, J=7.3 Hz, 2H), 2.43 (s, 3H), 2.28 (s, 3H), 1.14 (t, J=7.0 Hz, 3H). MS (ESI) m/z $(M+H)^+$246.0.

To a solution of compound 84C (100 mg, 432.43 umol) in THF (5 mL) was added a solution of $LiOH.H_2O$ (91 mg, 2.16 mmol) in $H_2O$ (5 mL) at 0° C. After addition, the reaction mixture was stirred for 14 hrs at 25° C. The reaction mixture was diluted with $H_2O$ (10 mL) and extracted with MTBE (30 mL). The aqueous phase was neutralized by 1N HCl to the pH 4 and then was extracted with EtOAc (30 mL×3). The combined organic layers were washed with brine (30 mL), dried over $Na_2SO_4$, filtered and concentrated under reduced pressure to give compound 84D (50 mg, yield: 53.2%) as a red solid. $^1H$ NMR (400 MHz, $CDCl_3$) δ 8.06 (d, J=8.4 Hz, 1H), 7.89 (t, J=8.0 Hz, 1H), 7.20-7.14 (m, 2H), 2.64 (s, 3H), 2.36 (s, 3H). MS (ESI) m/z $(M+H)^+$217.9.

Compound 84 (70 mg, yield: 54.12%, white solid) was prepared as in Example 5 from the corresponding intermediate carboxylic acid, compound 84D. Compound 84: $^1H$ NMR (400 MHz, DMSO-$d_6$) δ 9.09 (d, J=7.3 Hz, 1H), 8.04 (s, 1H), 7.81 (s, 1H), 7.76 (t, J=7.7 Hz, 1H), 7.32 (d, J=7.9 Hz, 1H), 7.29-7.17 (m, 5H), 7.15 (d, J=7.5 Hz, 1H), 6.44 (s, 1H), 5.37-5.25 (m, 1H), 3.13 (dd, J=4.0, 13.9 Hz, 1H), 2.82 (dd, J=9.7, 13.9 Hz, 1H), 2.24 (s, 6H). MS (ESI) m/z $(M+H)^+$392.1.

Example 51

(S)—N-(4-(cyclopropylamino)-3,4-dioxo-1-phenylbutan-2-yl)-3-methyl-1-(pyrazin-2-yl)-1H-pyrazole-5-carboxamide (85)

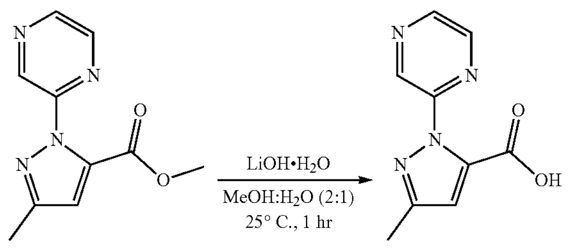

63B 85B

To a mixture of compound 63B (200 mg, 916.55 umol) in MeOH (10 mL) and $H_2O$ (5 mL) was added $LiOH.H_2O$ (153.8 mg, 3.67 mmol) in one portion and the mixture was stirred at 25° C. for 1 hour. The reaction mixture was concentrated under reduced pressure to remove MeOH. The residue was diluted with $H_2O$ (10 mL), adjusted to pH ~3 with 1N HCl, and then extracted with EtOAc (40 mL×3). The combined organic layers were washed with brine (30 mL), dried over anhydrous $Na_2SO_4$, filtered and concentrated under reduced pressure to afford intermediate compound 85B (160 mg, 85.49% yield) as a white solid. $^1H$ NMR (400 MHz, $CDCl_3$) δ 9.60 (br s, 1H), 8.67 (br s, 1H), 8.32 (br s, 1H), 7.25 (br s, 1H), 2.41 (br s, 3H). MS (ESI) m/z $(M+1)^+$205.0.

Compound 85 (30.7 mg, 59.7% yield, white solid) was prepared as in Example 20 from the corresponding intermediate carboxylic acid, compound 85B. Compound 85: $^1H$ NMR (400 MHz, $CDCl_3$) δ 8.95 (d, J=4.0 Hz, 1H), 8.22 (d, J=8.4 Hz, 1H), 7.76-7.66 (m, 2H), 7.49 (d, J=6.4 Hz, 1H), 7.38 (d, J=8.4 Hz, 1H), 7.24-7.16 (m, 3H), 6.87 (d, J=7.6 Hz, 2H), 6.79 (br s, 1H), 6.64 (s, 1H), 6.33 (d, J=7.2 Hz, 1H), 5.49-5.42 (m, 1H), 3.27-3.19 (m, 1H), 3.08-2.98 (m, 1H), 2.78-2.69 (m, 1H), 0.90-0.83 (m, 2H), 0.61-0.50 (m, 2H). MS (ESI) m/z $(M+H)^+$419.1.

Example 52

(S)—N-(4-(cyclopropylamino)-3,4-dioxo-1-phenylbutan-2-yl)-4-(1H-indazol-1-yl)thiazole-5-carboxamide (86)

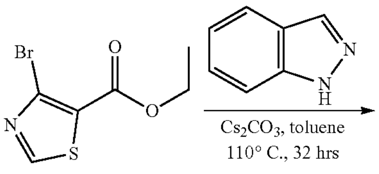

86A

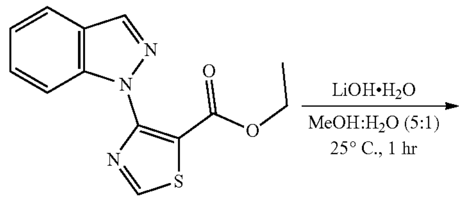

86B

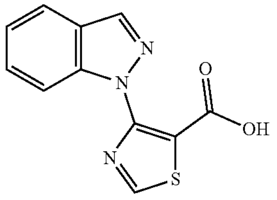

86C

A mixture consisting of compound 86A (250 mg, 1.06 mmol), 1H-indazole (125.2 mg, 1.06 mmol) and $Cs_2CO_3$ (1.04 g, 3.18 mmol) in toluene (15 mL) was stirred at 110° C. for 32 hours. The reaction mixture was cooled to room-temperature, filtered, and concentrated under reduced pressure to give a residue, which was purified by preparatory-HPLC (HCl condition) to afford compound 86B (20 mg, 6.90% yield) as a white solid. $^1H$ NMR ($CDCl_3$, 400 MHz) δ 8.87 (s, 1H), 8.19 (d, J=0.8 Hz, 1H), 7.75-7.70 (m, 1H), 7.54 (d, J=8.4 Hz, 1H), 7.41-7.35 (m, 1H), 7.22-7.17 (m, 2H), 4.17 (q, J=7.2 Hz, 2H), 1.07 (t, J=7.2 Hz, 3H).

To a mixture of 86B (40 mg, 146.35 umol) in MeOH (5 mL) and $H_2O$ (1 mL) was added $LiOH.H_2O$ (24.6 mg, 585.40 umol) in one portion and the mixture was stirred at 25° C. for 1 hour. The reaction mixture was concentrated under reduced pressure to remove MeOH and the residue was diluted with $H_2O$ (10 mL), adjusted to pH ~3 with 1N HCl, and then extracted with EtOAc (40 mL×3). The combined organic layers were washed with brine (30 mL), dried over anhydrous $Na_2SO_4$, filtered and concentrated under reduced pressure to afford intermediate compound 86C (30 mg, 83.58% yield) as a white solid. MS (ESI) m/z $(M+1)^+$ 245.8.

Compound 86 (5.4 mg, 10.0% yield, white solid) was prepared as in Example 20 from the corresponding intermediate carboxylic acid, compound 86C. Compound 86: $^1H$ NMR (400 MHz, $CDCl_3$) δ 10.97 (d, J=5.2 Hz, 1H), 8.78 (s, 1H), 8.23 (d, J=6.4 Hz, 1H), 7.82 (s, 1H), 7.71 (d, J=3.2 Hz, 1H), 7.54-7.44 (m, 1H), 7.32-7.23 (m, 1H), 7.11-6.96 (m, 5H), 6.85 (br s, 1H), 5.79-5.66 (m, 1H), 3.40-3.29 (m, 1H), 3.21-3.09 (m, 1H), 2.78-2.69 (m, 1H), 0.80 (d, J=6.2 Hz, 2H), 0.55 (br s, 2H). MS (ESI) m/z $(M+H)^+$460.1.

Example 53

(S)—N-(4-(cyclopropylamino)-3,4-dioxo-1-phenylbutan-2-yl)-1-(5-(oxazol-2-yl)pyridin-2-yl)-1H-imidazole-5-carboxamide (89)

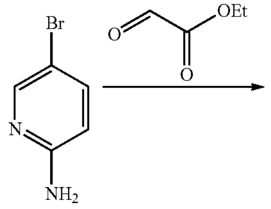

89A

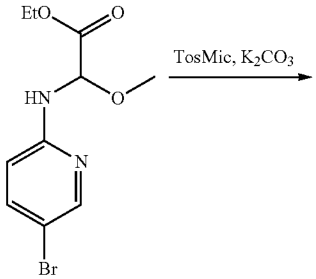

89B

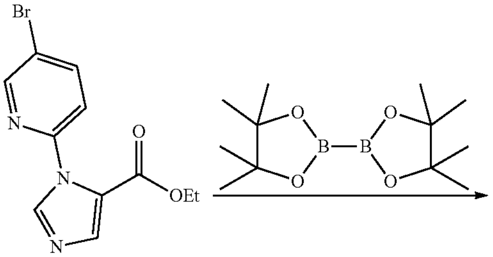

89C

-continued

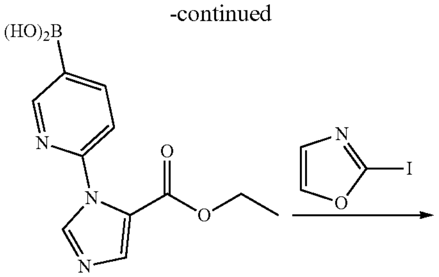

89D

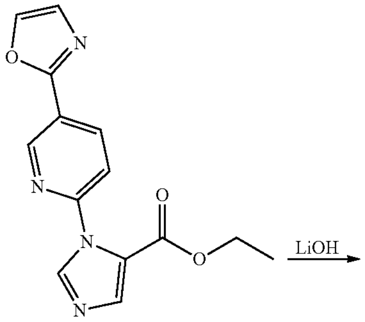

89E

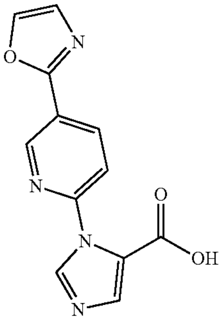

89F

To a solution of compound 89A (40 g, 231 mmol) in MeOH (500 mL) was added ethyl 2-oxoacetate (188 g, 924 mmol) at 25° C. The reaction mixture was stirred at 70° C. for 1 hr. The reaction mixture was concentrated to give a residue. The residue was purified by column chromatography ($SiO_2$, Petroleum ether:Ethyl acetate=50:1 to 30:1). Compound 89B (70 g, crude) was obtained as yellow oil. MS (ESI) m/z $(M+H)^+$258.8.

To a solution of compound 89B (35 g, 136 mmol) in EtOH (300 mL) was added TosMIC (66.4 g, 340 mmol) and $K_2CO_3$ (28.2 g, 204 mmol) at 25° C. The reaction mixture was stirred at 70° C. for 1 hr. The reaction mixture was filtered and the filtrate was concentrated to give a residue. The residue was purified by column chromatography ($SiO_2$, Petroleumether:Ethylacetate=20:1 to 3:1). Compound 89C (17 g) was obtained as a yellow solid. $^1H$ NMR (400 MHz, $CDCl_3$) δ 8.62 (d, J=2.4 Hz, 1H), 8.00-7.96 (m, 2H), 7.86 (d, J=0.9 Hz, 1H), 7.36-7.32 (m, 1H), 4.27 (q, J=7.1 Hz, 2H), 1.31 (t, J=7.2 Hz, 3H). MS (ESI) m/z $(M+H)^+$297.0.

To a solution of compound 89C (5 g, 16.8 mmol) in dioxane (100 mL) was added bis(pinacolato)diboron (8.58 g, 33.7 mmol), KOAc (16.5 g, 168 mmol) at 25° C. The mixture was degassed and purged with $N_2$ for 3 times, followed by addition of $Pd(dppf)Cl_2$ (617 mg, 844 umol). The reaction mixture was degassed and purged with $N_2$ for 3 times and stirred at 75° C. for 4 hrs. The reaction mixture was concentrated to give a residue. The residue was purified by column chromatography ($SiO_2$, Petroleum ether:Ethyl acetate=20:1 to Dichloromethane:Methanol=5:1). Compound 89D (2.7 g, yield: 61.2%) was obtained as a white solid. $^1H$ NMR (400 MHz, methanol-$d_4$) δ 8.63 (br s, 1H), 8.06 (s, 2H), 7.76 (s, 1H), 7.36 (br d, J=7.1 Hz, 1H), 4.14 (q, J=7.1 Hz, 2H), 1.14 (t, J=7.2 Hz, 3H). MS (ESI) m/z $(M+H)^+$261.9.

To a solution of compound 89D (500 mg, 1.92 mmol) in dioxane (4 mL) was added 2-iodooxazole (561.48 mg, 2.88 mmol) $K_2CO_3$ (796.09 mg, 5.76 mmol) $H_2O$ (1 mL) at 25° C. The reaction mixture was degassed and purged with $N_2$. Then Pd(dppf)$Cl_2$ (140 mg, 192 umol) was added. The mixture was degassed and purged with $N_2$ and stirred at 150° C. for 1 hr under microwave conditions. The reaction mixture was concentrated to give a residue. The residue was purified by column chromatography ($SiO_2$, Petroleum ether: Ethyl acetate=10:1~1.5:1). Compound 89E (300 mg, crude) was obtained as a grey solid. MS (ESI) m/z $(M+H)^+$285.0.

To a solution of compound 89E (200 mg, 703 umol) in THF (2 mL) $H_2O$ (500 uL) was added $LiOH.H_2O$ (59 mg, 1.41 mmol) and stirred at 25° C. for 12 hrs. The reaction mixture was acidified by HCl (1N) to pH ~5, and the precipitation was filtered to give a crude product. Compound 89F (60 mg, crude) was obtained as a grey solid. MS (ESI) m/z $(M+H)^+$257.0.

Compound 89 (35 mg, yield: 65.4%, white solid) was prepared as in Example 20 from the corresponding intermediate carboxylic acid, compound 89F. Compound 89: $^1H$ NMR (400 MHz, DMSO-$d_6$) δ 9.04-8.93 (m, 2H), 8.77 (br d, J=5.1 Hz, 1H), 8.38-8.28 (m, 2H), 8.20 (s, 1H), 7.56 (s, 1H), 7.46 (s, 1H), 7.34 (d, J=8.6 Hz, 1H), 7.29-7.22 (m, 4H), 5.32-5.14 (m, 1H), 3.28 (br s, 1H), 3.20-3.10 (m, 1H), 2.81 (br dd, J=10.1, 13.7 Hz, 1H), 2.77-2.69 (m, 1H), 0.73-0.42 (m, 4H). MS (ESI) m/z $(M+H)^+$471.1.

Example 54

(S)—N-(1-(4-(allyloxy)phenyl)-3-oxopropan-2-yl)-3-methyl-1-(pyridin-2-yl)-1H-pyrazole-5-carboxamide (93)

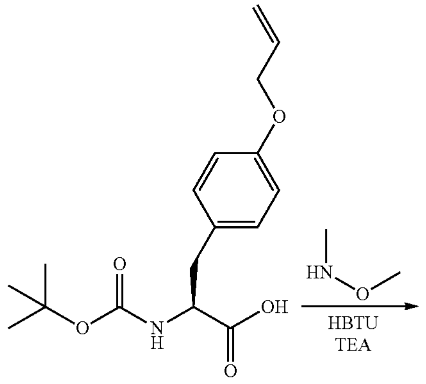

93A

-continued

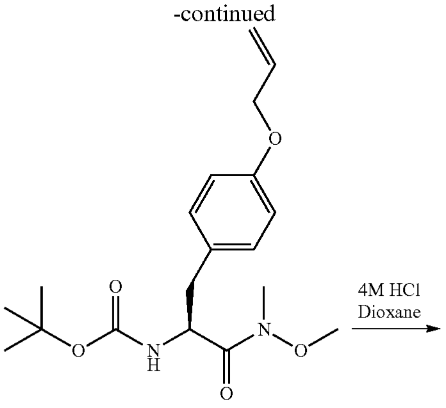

93B

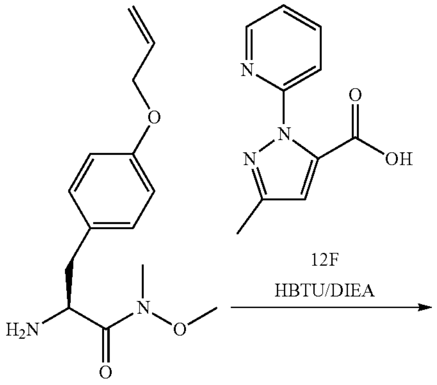

93C

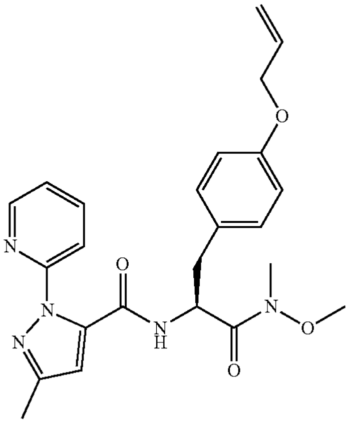
93D

Compound 93A (1 g, 1.0 eq), N,O-dimethylhydroxylamine (607 mg, 2 eq) and HBTU (1.36 g, 1.15 eq) were combined in 10 mL DMF, the mixture was stirred at room temperature for 5 mins, and then TEA (1.3 mL, 3.0 eq) was added. The resulting mixture was stirred at room temperature for 1 h. The mixture was diluted with 100 mL ethyl acetate and 20 mL Hexane, washed with 0.25N HCl, water, saturated aqueous $NaHCO_3$, and brine and concentrated in vacuo to afford intermediate compound 93B (1 g, yield 88%) as white solid.

To a solution of compound 93B (1 g, 1.0 eq) in 6 mL dry DCM was added 3 mL of 4M HCl in Dioxane. Resulting mixture was stirred at room temperature for 2 hrs. DCM and Dioxane were removed under vacuo, residue was diluted with EtOAc, washed with saturated aqueous $NaHCO_3$ and brine and concentrated in vacuo to afford intermediate compound 93C (650 mg, yield 90%) as white solid.

Compound 93C (125 mg, 1.0 eq), compound 12F (115 mg, 1.2 eq) and HBTU (226 mg, 1.25 eq) were combined in 5 mL DMF, the mixture was stirred at room temperature for 5 mins, and then DIEA (0.23 mL, 3.0 eq) was added. The resulting mixture was stirred at room temperature for 30 mins. The mixture was diluted with 50 mL ethyl acetate and 20 mL Hexane, washed with water, saturated aqueous $NaHCO_3$ and brine and concentrated in vacuo to afford intermediate compound 93D (180 mg, yield 85%).

Compound 6 (90 mg, 1.0 eq) was dissolved in 8 mL dry THF, cooled to −50° C. under $N_2$. A solution of 1N LAH in THF (0.22 mL, 1.1 eq) was added dropwise at −50° C. The resulting mixture was stirred at −30 to −10° C. for 2 hrs. The reaction was quenched with saturated aqueous $NaHCO_3$ at −20° C., and then extracted with 3×15 mL acetate. The combined organic phase was dried over $Na_2SO_4$. The crude mixture was purified on silica gel column to provide compound 93 (40 mg, 51%).

Example 55

(S)—N-(4-amino-3,4-dioxo-1-phenylbutan-2-yl)-3-methyl-5-phenylisothiazole-4-carboxamide (96)

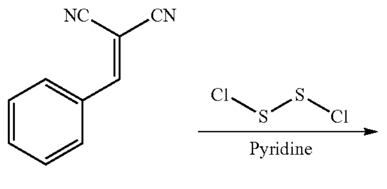

96A

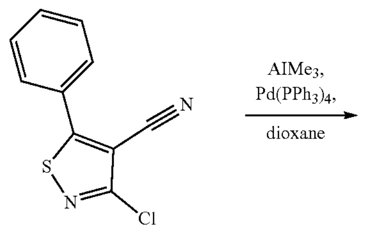

96B

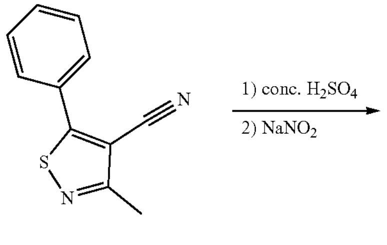

96C

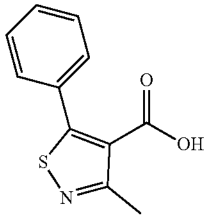

96D

To a solution of benzaldehyde (10.00 g, 94.23 mmol) and malononitrile (6.54 g, 98.94 mmol) in EtOH (75.00 mL) was added catalytic piperidine (80.24 mg, 942.30 umol). Then the reaction was stirred at 90° C. for 2 h. Yellow solid was precipitated out when the reaction mixture was cooled to room temperature, the mixture was filtered, the desired yellow solid was washed with EtOH (20 mL) and dried in vacuo to give intermediate compound 96A (23.00 g, 79.2% yield) as yellow solid. $^1$H NMR (400 MHz, CHLOROFORM-d) δ 7.91 (d, J=7.7 Hz, 2H), 7.79 (s, 1H), 7.67-7.60 (m, 1H), 7.58-7.50 (m, 2H).

To a mixture of compound 96A (17.50 g, 113.51 mmol) and chlorosulfanyl thiohypochlorite (70.00 g, 518.36 mmol, 41.42 mL) was added pyridine (900.00 mg, 11.38 mmol). Then the reaction was stirred at 140° C. for 16 h. The reaction mixture was cooled to room temperature and quenched with ice/$H_2O$ (200 mL) and EtOAc (500 mL), yellow solid was was precipitate out, filtered and the filtrate was extracted with EtOAc (100 mL×2), the combined organic was washed with brine (100 mL), dried over $Na_2SO_4$, filtered and the filtrate was concentrated in vacuo. The residue was purified by flash silica gel chromatography (ISCO®; 120 g SepaFlash® Silica Flash Column, eluent of 0~10% Ethyl acetate/Petroleum ether gradient @50 mL/min) to give compound 96B (21.00 g, 70.4% yield) as light yellow solid. $^1$H NMR (400 MHz, CHLOROFORM-d) δ 7.77 (br d, J=7.1 Hz, 2H), 7.65-7.53 (m, 3H).

To a mixture of compound 96B (2.00 g, 9.06 mmol) in dioxane (150.00 mL) was added $AlMe_3$ (2M, 20.00 mL) and $Pd(PPh_3)_4$ (1.05 g, 906.00 umol) under $N_2$, Then the reaction was stirred at 110° C. for 3 h. The reaction mixture was cooled to room temperature and quenched with ice/$H_2O$ (100 mL) and EtOAc (150 mL), yellow solid was precipitate out, filtered and the filtrate was extracted with EtOAc (60 mL×2), the combined organic was washed with brine (70 mL), dried over $Na_2SO_4$, filtered and the filtrate was concentrated in vacuo. The residue was purified by flash silica gel chromatography (ISCO®; 40 g SepaFlash® Silica Flash Column, eluent of 0~10% Ethyl acetate/Petroleum ether gradient @ 40 mL/min) to give compound 96C (700.00 mg, 16.59% yield, 43% purity) as light yellow solid. $^1$H NMR (400 MHz, CHLOROFORM-d) δ 7.79-7.75 (m, 2H), 7.56-7.51 (m, 3H), 2.67 (s, 3H). MS (ESI) m/z (M+H)+200.9.

To compound 96C (490.00 mg, 2.45 mmol) was added $H_2SO_4$ (9.20 g, 93.81 mmol, 5.00 mL), and the reaction was stirred at 135° C. for 1.5 h. Then the reaction was cooled to 0° C. and a solution of $NaNO_2$ (339.79 mg, 4.92 mmol) in $H_2O$ (2.00 mL) was added to the above mixture and the reaction mixture was stirred at 70° C. for 1 h. The reaction mixture was cooled to room temperature and poured into ice/$H_2O$ (40 mL) and EtOAc (40 mL), extracted with EtOAc (50 mL×2), the combined organic was extracted with 0.1N NaOH (40 mL×2), the desired basic water phase was then added 1N HCl to pH <4, then extracted with EtOAc (40 mL×3) and washed with brine (40 mL), dried over $Na_2SO_4$, filtered and the filtrate was concentrated in vacuo to give compound 96D (410.00 mg, 76.25% yield) as light yellow solid. $^1$H NMR (400 MHz, DMSO-$d_6$) δ 7.49 (s, 5H), 2.57 (s, 3H). MS (ESI) m/z $(M+H)^+$219.9.

Compound 96 (35 mg, yield: 65.86%, white solid) was prepared as in Example 5 from the corresponding intermediate carboxylic acid, compound 96D. Compound 96: $^1$H NMR (400 MHz, $CD_3CN$) δ 7.48-7.33 (m, 5H), 7.29-7.17 (m, 3H), 7.15-7.06 (m, 3H), 7.01 (br s, 1H), 6.26 (br s, 1H), 5.56 (ddd, J=4.4, 7.5, 9.5 Hz, 1H), 3.23 (dd, J=4.3, 14.2 Hz, 1H), 2.77 (dd, J=9.5, 14.3 Hz, 1H), 2.28 (s, 3H). MS (ESI) m/z $(M+H)^+$394.1.

Example 56

(S)—N-(4-amino-1-(3,5-dimethylphenyl)-3,4-dioxobutan-2-yl)-3-methyl-5-phenylisoxazole-4-carboxamide (97)

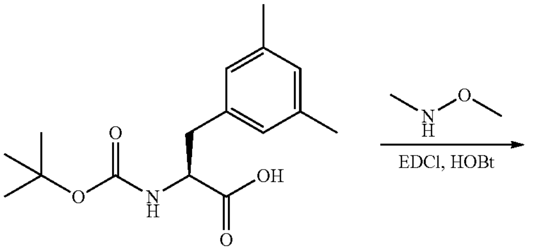

97A

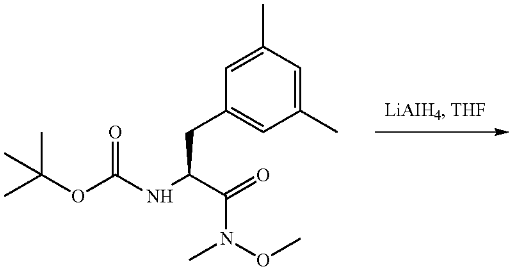

97B

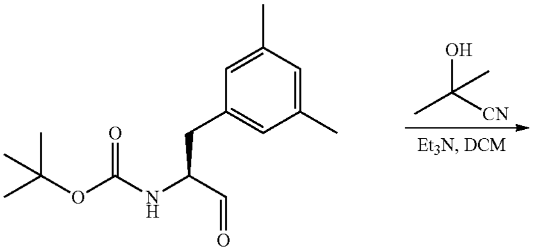

97C

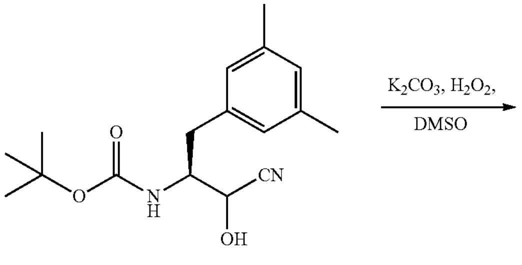

97D

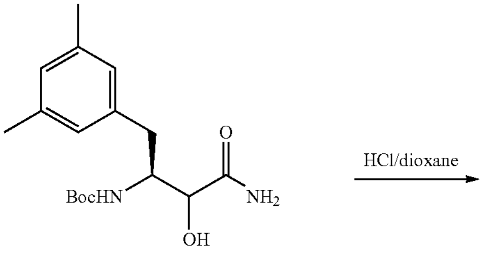

97E

-continued

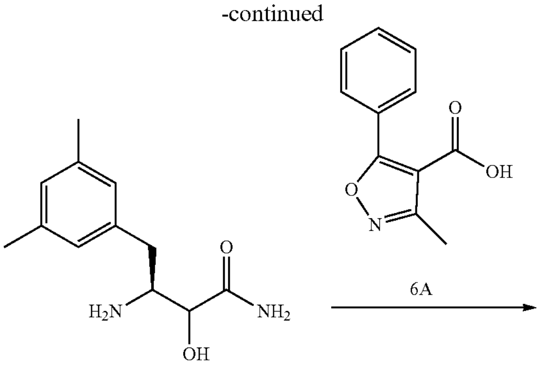

97F

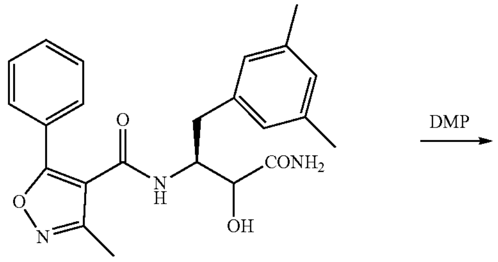

97G

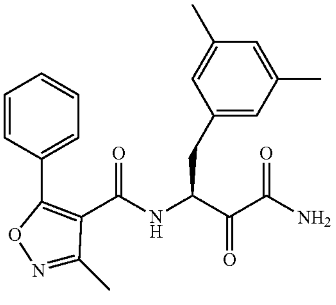

97

A mixture of compound 97A (1.0 g, 3.41 mmol), compound N,O-dimethylhydroxylamine (400 mg, 4.09 mmol, HCl), HOBt (460 mg, 3.41 mmol) and NMM (1.03 g, 10.23 mmol, 1.12 mL) in $CHCl_3$ (20 mL) was degassed and purged with $N_2$ for 3 times at 0° C., then EDCI (980 mg, 5.12 mmol) was added in portions. The mixture was stirred at 25° C. for 20 h under $N_2$ atmosphere. The reaction mixture was quenched by addition $H_2O$ (20 mL), and then diluted with DCM (10 mL). The combined organic layers were washed with 1N HCl (15 mL×2), saturated aqueous $NaHCO_3$ (15 mL×2) and brine (20 mL), dried over $Na_2SO_4$, filtered and concentrated under reduced pressure to give the compound 97B (1.13 g, yield: 98.5%) was obtained as a white solid. $^1H$ NMR (400 MHz, DMSO-$d_6$) δ 7.08 (br d, J=8.2 Hz, 1H), 6.82 (s, 3H), 4.55 (br s, 1H), 3.71 (br s, 3H), 3.09 (s, 3H), 2.82-2.72 (m, 1H), 2.68-2.58 (m, 1H), 2.22 (s, 6H), 1.32 (s, 9H).

To a solution of LAH (255 mg, 6.72 mmol) in THF (10 mL) was degassed and purged with $N_2$ for 3 times at 0° C., and the mixture of compound 97B (1.13 g, 3.36 mmol) in THF (20 mL) was added dropwise, and then the mixture was stirred at 0° C. for 2 h under $N_2$ atmosphere. The reaction mixture was quenched by addition EtOAc (10 mL), then added 1N HCl (50 mL), and then diluted with EtOAc (20 mL), dried over $Na_2SO_4$, and stirred for 30 min, then filtered to give the organic layers. The combined organic layers were washed with brine (20 mL×2), dried over $Na_2SO_4$, filtered and concentrated under reduced pressure to give the compound 97C (860 mg, yield: 92.3%) was obtained as a white solid. $^1H$ NMR (400 MHz, DMSO-$d_6$) δ 9.48 (s, 1H), 7.24 (br d, J=7.7 Hz, 1H), 6.85-6.73 (m, 3H), 4.08-3.94 (m, 1H), 3.04-2.91 (m, 1H), 2.70-2.57 (m, 1H), 2.20 (s, 6H), 1.39-1.19 (m, 9H).

To a solution of compound 97C (860 mg, 3.10 mmol) in DCM (10 mL) was added compound 2-hydroxy-2-methyl-propanenitrile (530 mg, 6.20 mmol, 570 μL) and $Et_3N$ (470 mg, 4.65 mmol, 650 μL). The mixture was stirred at 25° C. for 22 h. The reaction mixture was quenched by addition 1N HCl (20 mL), and then diluted with $H_2O$ (20 mL) and extracted with DCM (20 mL×2). The combined organic layers were washed with brine (20 mL×3), dried over $Na_2SO_4$, filtered and concentrated under reduced pressure to give the compound 97D (930.00 mg, yield: 98.6%) was obtained as a yellow solid. $^1H$ NMR (400 MHz, DMSO-$d_6$) δ 7.19-6.99 (m, 1H), 6.91-6.78 (m, 3H), 6.77-6.51 (m, 1H), 4.66-4.34 (m, 1H), 3.84 (br s, 1H), 2.99-2.81 (m, 1H), 2.75-2.60 (m, 1H), 2.27 (br s, 6H), 1.40-1.20 (m, 9H).

To a solution of compound 97D (930 mg, 3.63 mmol) and $K_2CO_3$ (850 mg, 6.11 mmol) in DMSO (10 mL) was added $H_2O_2$ (3.46 g, 30.55 mmol, 2.94 mL, purity: 30%). The mixture was stirred at 0° C. for 2 h. The reaction mixture was diluted with $H_2O$ (100 mL) and extracted with EtOAc (30 mL×3). The combined organic layers were washed with brine (50 mL×2), dried over $Na_2SO_4$, filtered and concentrated under reduced pressure to give a residue. The residue was stirred in DCM (3 mL) and PE (25 mL) for 30 min and filtered to give the compound 5 (970 mg, yield: 98.32%) was obtained as a white solid. $^1H$ NMR (400 MHz, DMSO-d6) δ 7.42-7.08 (m, 1H), 6.86-6.45 (m, 3H), 6.21-5.49 (m, 1H), 4.06-3.82 (m, 1H), 3.31 (s, 1H), 2.72-2.52 (m, 2H), 2.26-2.13 (m, 6H), 1.40-1.18 (m, 9H).

To a solution of compound 97E (970 mg, 3.01 mmol) in EtOAc (5 mL) was added HCl/EtOAc (4M, 5 mL). The mixture was stirred at 25° C. for 3 h. The reaction mixture was diluted with PE (20 mL), filtered and concentrated under reduced pressure to give the compound 97F (370 mg, yield: 43.7%, HCl) was obtained as a white solid. $^1H$ NMR (400 MHz, DMSO-$d_6$) δ 8.09-7.89 (m, 3H), 7.58 (br s, 2H), 6.96 (br s, 2H), 6.89 (s, 1H), 4.26 (br s, 1H), 3.89 (br s, 1H), 3.69-3.57 (m, 1H), 2.91-2.73 (m, 2H), 2.30 (br s, 6H). MS (ESI) m/z $(M+H)^+$223.1.

A mixture of compound 97F (310 mg, 1.18 mmol, HCl), compound 6A (200 mg, 984.30 umol), HOBT (133 mg, 984.30 umol) and DIEA (520 uL, 2.95 mmol) in DCM (15 mL) was added EDCI (285 mg, 1.48 mmol), and then the mixture was stirred at 25° C. for 18 h. The reaction mixture was washed with $H_2O$ (20 mL×2). The combined organic layers were washed with HCl (1N, 30 mL), saturated aqueous $NaHCO_3$ (30 mL) and brine (50 mL), dried over $Na_2SO_4$, filtered and concentrated under reduced pressure to give a residue. The residue was stirred in Petroleum Ether (5 mL) and DCM (1 mL) for 30 min and filtered to give the compound 97G (270 mg, yield: 61.9%) was obtained as a white solid. $^1H$ NMR (400 MHz, DMSO-$d_6$) δ 8.59-8.24 (m, 1H), 7.64-7.51 (m, 2H), 7.49-7.28 (m, 5H), 6.89-6.77 (m, 3H), 5.98-5.63 (m, 1H), 4.61-4.49 (m, 1H), 4.11-3.86 (m, 1H), 2.86-2.59 (m, 2H), 2.21-2.03 (m, 9H). MS (ESI) m/z $(M+H)^+$408.1.

To a solution of compound 97G (100 mg, 245.42 umol) in DCM (10 mL) was added DMP (320 mg, 736.26 umol) at 0° C. The mixture was stirred at 25° C. for 7 h. The reaction mixture was quenched by addition saturated aqueous $Na_2S_2O_3$ (15 mL) and saturated aqueous $NaHCO_3$ (15 mL), the mixture was stirred for 0.2 h, and then diluted with DCM (10 mL) and extracted with $H_2O$ (20 mL×3). The combined organic layers were washed with brine (20 mL), dried over $Na_2SO_4$, filtered and concentrated under reduced pressure to give a residue. The residue was stirred in Petroleum Ether (15 mL) and EtOAc (1 mL) for 30 min and filtered to give the compound 97 (60 mg, yield: 60.3%) was obtained as a white solid. $^1H$ NMR (400 MHz, DMSO-d6) δ9.01 (br d, J=7.5 Hz, 1H), 8.18 (br s, 1H), 7.90 (br s, 1H), 7.64 (br d, J=7.3 Hz, 2H), 7.53-7.46 (m, 1H), 7.45-7.38 (m, 2H), 6.92-6.81 (m, 3H), 5.40 (br t, J=7.3 Hz, 1H), 3.15 (br d, J=10.6 Hz, 1H), 2.72-2.58 (m, 1H), 2.18 (s, 6H), 2.11 (s, 3H). MS (ESI) m/z $(M+H)^+$406.1.

Example 57

(S)—N-(4-amino-1-(3,5-dimethylphenyl)-3,4-dioxobutan-2-yl)-3-methyl-5-phenylisoxazole-4-carboxamide (98)

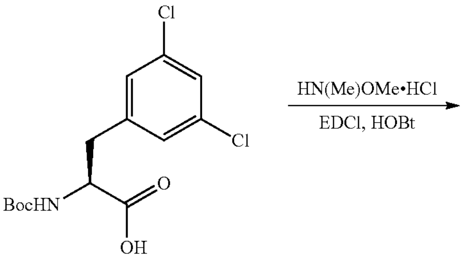

98A

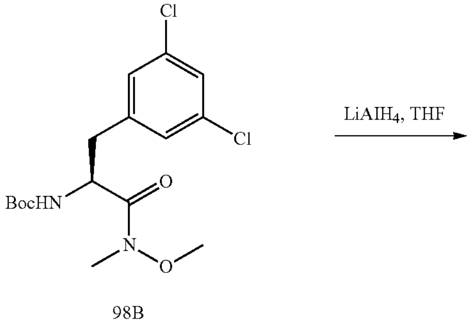

98B

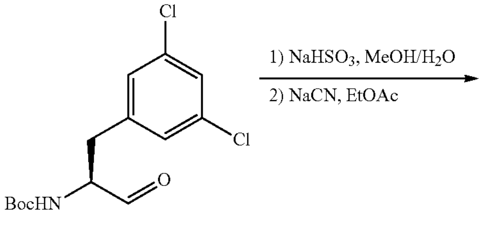

98C

-continued

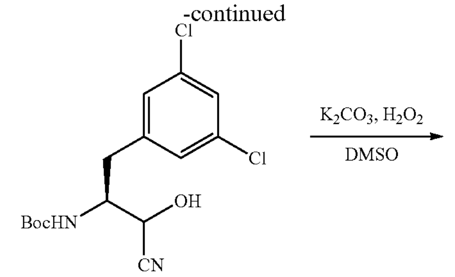

98D

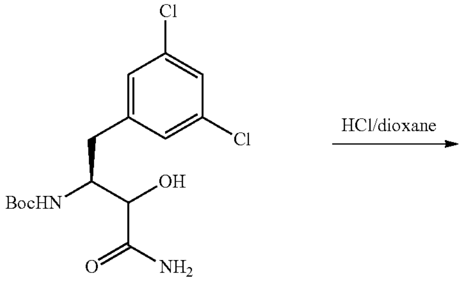

98E

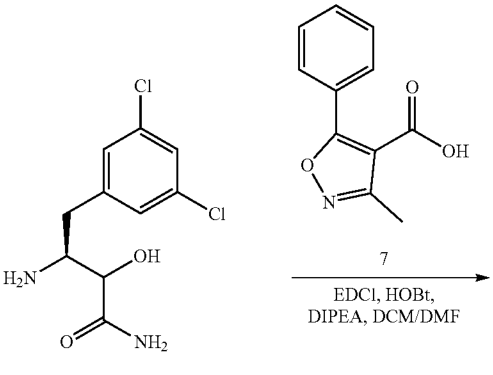

98F

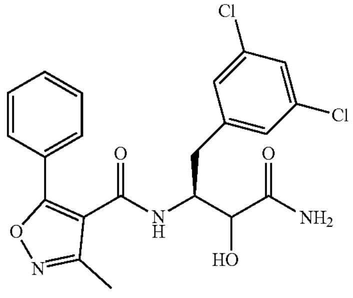

98G

To a solution of compound 98A (1.0 g, 2.99 mmol) and N-methoxymethanamine (321 mg, 3.29 mmol, HCl) in $CHCl_3$ (30 mL) was added HOBt (404 mg, 2.99 mmol) and EDCI (803 mg, 4.19 mmol). Then NMM (1.3 mL, 11.96 mmol) was added into the reaction mixture. After addition, the reaction mixture was stirred at 28° C. for 14 h. The reaction mixture was concentrated in vacuum and the residue was dissolved into 80 mL of EtOAc. The mixture was washed with 1N HCl (30 mL×2) and saturated aqueous $NaHCO_3$ (30 mL×2), then brine (30 mL). The mixture was dried over $Na_2SO_4$ and concentrated in vacuum to afford compound 98B (1.1 g, yield 82.9%) as white solid. $^1$H NMR (400 MHz, DMSO-$d_6$) δ 7.44 (s, 1H), 7.34-7.19 (m, 3H), 4.55 (br s, 1H), 3.71 (br s, 3H), 3.17-3.00 (m, 3H), 2.90-2.80 (m, 1H), 2.76-2.67 (m, 1H), 1.29 (s, 8H). MS (ESI) m/z $(M-56)^+$320.9.

To a solution of $LiAlH_4$ (122 mg, 3.21 mmol) in THF (10 mL) was added a solution of compound 98B (1.1 g, 2.92 mmol) in THF (20 mL) at 0° C. under $N_2$ atmosphere. After addition, the reaction mixture was stirred at 0° C. for 1 h. 2 mL of EtOAc was added into the reaction mixture at 0° C. and the mixture was stirred for 10 min. Then 2 mL of 1N HCl was added into the reaction mixture slowly. After addition, the mixture was diluted with 80 mL of EtOAc and the mixture was washed with 1 N HCl (30 mL×2), brine (30 mL). Then the mixture was dried over $Na_2SO_4$ and concentrated in vacuum to afford compound 98C (800 mg, yield 80.9%) as white solid. $^1$H NMR (400 MHz, DMSO-$d_6$) δ 9.52 (s, 1H), 7.53-7.17 (m, 4H), 4.20-4.08 (m, 1H), 3.19-3.08 (m, 1H), 2.72-2.63 (m, 1H), 1.37-1.27 (m, 9H).

To a solution of compound 98C (800 mg, 2.51 mmol) in MeOH (10 mL) was added dropwise a solution of $NaHSO_3$ (261 mg, 2.51 mmol) in $H_2O$ (15 mL) at 0-5° C. After that, the reaction mixture was stirred at 25° C. for 5 h. NaCN (129 mg, 2.64 mmol) in $H_2O$ (20 mL) was added into the reaction mixture followed by EtOAc (40 mL). After that, the reaction mixture was stirred at 25° C. for 14 h. The organic layer was separated and washed with brine (30 mL), then dried over $Na_2SO_4$. The mixture was concentrated to afford compound 98D (800 mg, yield 92.33%) as light yellow gum. $^1$H NMR (400 MHz, DMSO-$d_6$) δ 7.46-7.22 (m, 3H), 7.16-7.02 (m, 1H), 6.89-6.70 (m, 1H), 4.65-4.30 (m, 1H), 3.95-3.76 (m, 1H), 3.07-2.87 (m, 1H), 2.76-2.55 (m, 1H), 1.32-1.20 (m, 8H).

To a solution of compound 98D (800 mg, 2.32 mmol) and $K_2CO_3$ (641 mg, 4.64 mmol) in DMSO (8 mL) was added $H_2O_2$ (2 mL, 22.25 mmol, 30% purity) at 0° C. After addition, the reaction mixture was stirred at 0° C. for 1 h. The reaction mixture was diluted with ice water (20 mL) and 50 mL of saturated aqueous $Na_2SO_3$. The mixture was extracted with EtOAc (50 mL×3) and the combined extracts were washed with saturated aqueous $Na_2SO_3$ (50 mL×2). The organic layer was dried over $Na_2SO_4$ and concentrated to afford crude compound. The crude compound was diluted with MTBE (5 mL) and filtered to afford compound 98E (800 mg, yield 94.9%) as white solid. $^1$H NMR (400 MHz, DMSO-$d_6$) δ 7.48-7.12 (m, 5H), 6.73-6.20 (m, 1H), 5.86-5.63 (m, 1H), 4.04-3.71 (m, 2H), 2.86-2.54 (m, 1H), 1.34-1.19 (m, 9H). MS (ESI) m/z $(M+23)^+$384.9.

To a solution of compound 98E (800 mg, 2.20 mmol) in EtOAc (10 mL) was added HCl/EtOAc (4M, 55 mL). After addition, the reaction mixture was stirred at 26° C. for 1 h. 20 mL of Petroleum ether was added into the reaction mixture and the mixture was filtered to afford compound 98F (400 mg, yield 58.87%, HCl) as white solid. $^1$H NMR (400 MHz, DMSO-d6) δ8.35 (br s, 1H), 8.14 (br s, 1H), 7.62-7.41 (m, 3H), 7.33 (d, J=1.8 Hz, 1H), 6.90-6.50 (m, 1H), 4.28 (br s, 1H), 3.94-3.84 (m, 1H), 3.77-3.56 (m, 1H), 3.03-2.80 (m, 2H).

To a solution of compound 7 (100 mg, 492.15 umol) and compound 98F (162 mg, 541.37 umol, HCl) in DMF (10 mL) was added HOBT (67 mg, 492.15 umol) and DIEA (340 uL, 1.97 mmol), then EDCI (133 mg, 689.01 umol) was added. After addition, the reaction mixture was stirred at 26° C. for 14 h. The mixture was diluted with 30 mL of EtOAc. The mixture was washed with 1N HCl (15 mL×2) and saturated aqueous $NaHCO_3$ (15 mL×3), then brine (20 mL). The residue was dried over $Na_2SO_4$ and concentrated in vacuum. The residue was diluted with 4 mL of EtOAc and filtered to afford compound 98G (110 mg, yield 45.87%) as white solid. $^1$H NMR (400 MHz, DMSO-$d_6$) δ 8.65-8.26 (m, 1H), 7.60-7.30 (m, 9H), 7.28-7.17 (m, 1H), 6.04-5.65 (m, 1H), 4.73-4.56 (m, 1H), 4.11-4.06 (m, 0.5H), 4.01-3.95 (m, 0.5H), 3.01-2.70 (m, 2H), 2.18-2.09 (m, 3H). MS (ESI) m/z $(M+H)^+$448.1.

To a solution of compound 98G (110 mg, 245.37 umol) in DCM (30 mL) and DMSO (4 mL) was added DMP (416 mg, 981.48 umol). After addition, the reaction mixture was stirred at 26° C. for 2 h. 10 mL of saturated aqueous $Na_2S_2O_3$ and 10 mL of saturated aqueous $NaHCO_3$ was added into the reaction mixture, and the mixture was stirred for 20 min. Then the mixture was separated, the organic layer was washed with 10 mL of saturated aqueous $Na_2S_2O_3$ and 10 mL of saturated aqueous $NaHCO_3$, then water (20 mL) and brine (20 mL). The mixture was dried over $Na_2SO_4$ and concentrated in vacuum to afford compound 98 (30 mg, yield 24.66%) as light yellow solid. $^1$H NMR (400 MHz, DMSO-$d_6$) δ 9.08 (d, J=7.5 Hz, 1H), 8.21 (s, 1H), 7.94 (s, 1H), 7.68-7.58 (m, 2H), 7.54-7.42 (m, 4H), 7.34 (d, J=1.8 Hz, 2H), 5.45-5.33 (m, 1H), 3.28-3.19 (m, 1H), 2.83-2.73 (m, 1H), 2.12 (s, 3H). MS (ESI) m/z $(M+H)^+$446.0.

Example 58

(S)—N-(4-amino-3,4-dioxo-1-phenylbutan-2-yl)-1-(6-methoxypyridin-2-yl)-3-methyl-1H-pyrazole-5-carboxamide (99)

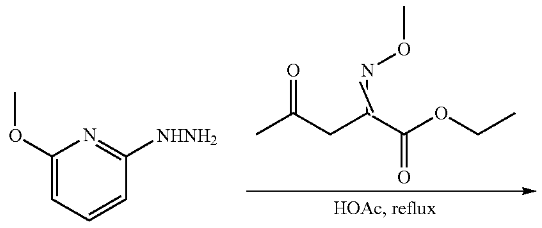

99B

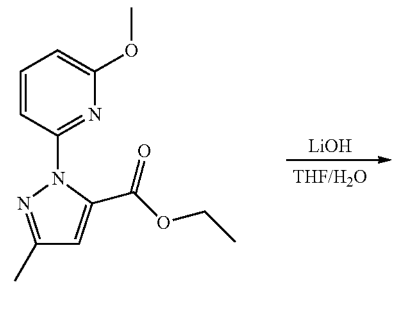

99C

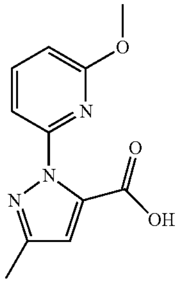

99D

A mixture of compound 2-chloro-6-methoxypyridine (5.0 g, 34.83 mmol) in $NH_2NH_2$—$H_2O$ (17.44 g, 348.30 mmol, 16.93 mL) was stirred at 120° C. for 16 h. The reaction mixture was concentrated under reduced pressure to give a residue. then diluted with $H_2O$ (30 mL) and extracted with ethyl acetate (40 mL). The combined organic layers were washed with brine (50 mL), dried over $Na_2SO_4$, filtered and concentrated under reduced pressure to give a residue. The residue was purified by column chromatography ($SiO_2$, Petroleum ether/Ethyl acetate=5:1 to 1:1) to give compound 99B (1.06 g, 21.87% yield) as a yellow oil. $^1$H NMR (400 MHz, $CDCl_3$) δ 7.41 (t, J=7.8 Hz, 1H), 6.24-6.08 (m, 2H), 5.73 (br s, 1H), 3.86 (s, 3H), 3.83-2.75 (m, 2H). MS (ESI) m/z $(M+H)^+$140.1.

A mixture of compound 99B (1.00 g, 7.19 mmol) and ethyl 2-(methoxyimino)-4-oxopentanoate (1.35 g, 7.19 mmol) in HOAc (20.00 mL) was stirred at 120° C. for 16 h. The reaction mixture was concentrated under reduced pressure to remove HOAc. The residue was diluted with $H_2O$ (20 mL) and extracted with ethyl acetate (20 mL). The combined organic layers were washed with brine (20 mL), dried over $Na_2SO_4$, concentrated under reduced pressure to give a residue. The residue was purified by column chromatography ($SiO_2$, Petroleum ether/Ethyl acetate=1:0 to 5:1) and further purified by preparatory-HPLC (TFA condition) to give compound 99C (487.00 mg, 25.87% yield) was obtained as a yellow oil. $^1$H NMR (400 MHz, $CDCl_3$) δ 7.70 (t, J=7.9 Hz, 1H), 7.21 (d, J=7.5 Hz, 1H), 6.71 (d, J=8.2 Hz, 1H), 6.66 (s, 1H), 4.27 (q, J=7.2 Hz, 2H), 3.85 (s, 3H), 2.36 (s, 3H), 1.25 (t, J=7.2 Hz, 3H). MS (ESI) m/z $(M+H)^+$261.9.

To a solution of compound 99C (487.00 mg, 1.99 mmol) in THF (15.00 mL) was added $LiOH.H_2O$ (417.50 mg, 9.95 mmol) in $H_2O$ (5.00 mL). The mixture was stirred at 28° C. for 16 h. The reaction mixture was diluted with $H_2O$ (10 mL) and extracted with MTBE (15 mL×2), the water phase was added 1N HCl to pH=3-4, extracted with EA (15 mL×2). The combined organic layers were washed with brine (15 mL), dried over $Na_2SO_4$, filtered and concentrated under reduced pressure to give intermediate compound 99D (396 mg, 91.61% yield) as a white solid. Compound 99D: $^1$H NMR (400 MHz, DMSO-d6) δ 7.86 (t, J=7.8 Hz, 1H), 7.26 (d, J=7.5 Hz, 1H), 6.80 (d, J=8.2 Hz, 1H), 6.67 (s, 1H), 3.80 (s, 3H), 2.26 (s, 3H). MS (ESI) m/z $(M+H)^+$234.1.

Compound 99 (10.00 mg, 13.78% yield, white solid) was prepared as in Example 5 from the corresponding intermediate carboxylic acid, compound 99D. Compound 99: $^1$H NMR (400 MHz, $CDCl_3$) δ 7.68 (br t, J=7.9 Hz, 1H), 7.26-7.18 (m, 4H), 7.12-7.01 (m, 3H), 6.73 (br s, 1H), 6.68-6.60 (m, 1H), 6.65 (br d, J=8.2 Hz, 1H), 6.50 (s, 1H), 5.73-5.64 (m, 1H), 5.50 (br s, 1H), 3.67 (s, 3H), 3.45-3.35 (m, 1H), 3.25-3.11 (m, 1H), 2.33 (s, 3H). MS (ESI) m/z $(M+H)^+$408.1.

Example 59

Compounds 101, 493

(S)—N-(4-((3,4-dichlorobenzyl)amino)-3,4-dioxo-1-phenylbutan-2-yl)-3-methyl-5-phenylisoxazole-4-carboxamide (101)

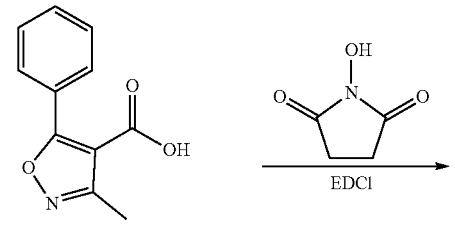

23A

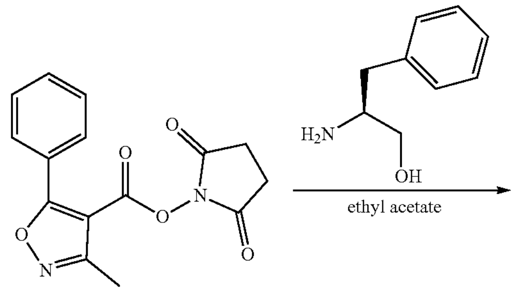

101A

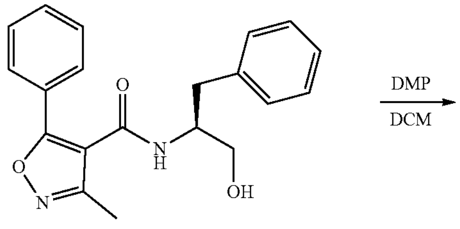

101B

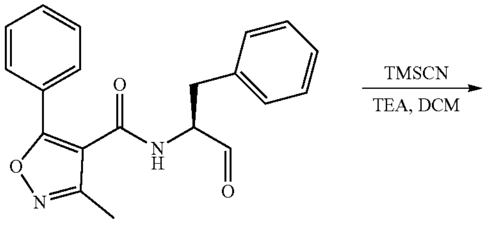

101C

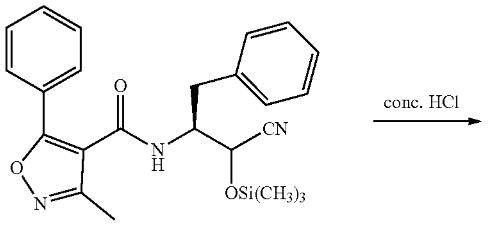

101D

-continued

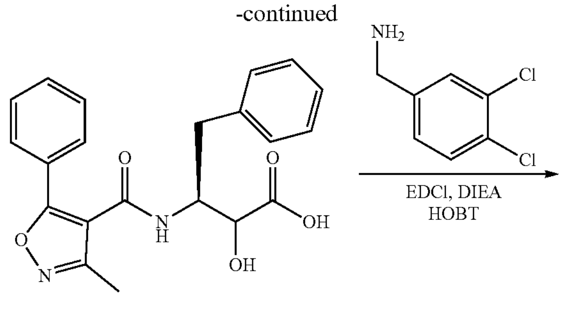

101E

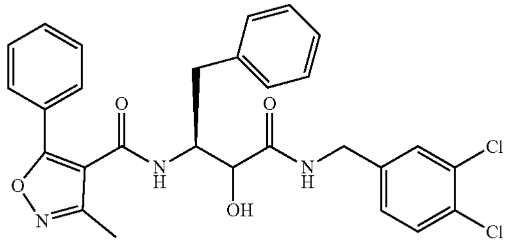

101F

To a solution of compound 23A (20.00 g, 98.43 mmol) in THF (300 mL) was added 1-hydroxypyrrolidine-2,5-dione (12.46 g, 108.27 mmol) and EDCI (22.64 g, 118.12 mmol) with DCM (200 mL). The mixture was stirred at 25° C. for 12 hours. The reaction mixture was concentrated and diluted with ethyl acetate (200 mL). Then the mixture was washed with HCl (1M, 200 mL), saturated aqueous $NaHCO_3$ (200 mL), dried over $Na_2SO_4$ and concentrated. Compound 101A (28.00 g, crude) was obtained as a yellow oil. $^1H$ NMR (400 MHz, DMSO-$d_6$) δ 7.94-7.88 (m, 2H), 7.69-7.63 (m, 1H), 7.62-7.56 (m, 2H), 2.87 (br s, 4H), 2.50-2.48 (m, 3H).

To a solution of compound 101A (28.00 g, 93.25 mmol) in DMF (200 mL) was added (2S)-2-amino-3-phenyl-propan-1-ol (15.51 g, 102.57 mmol). The mixture was stirred at 25° C. for 12 hour. The mixture was diluted with $H_2O$ (1000 mL), extracted with ethyl acetate (1000 mL), the organic layer was washed with HCl (aqueous 1000 mL), $NaHCO_3$ (aqueous 1000 mL), dried over $Na_2SO_4$ and concentrated. Compound 3 (20.00 g, yield 63.8%) was obtained as a white solid. $^1H$ NMR (400 MHz, DMSO-$d_6$) δ 8.45 (br d, J=8.8 Hz, 1H), 7.66-7.61 (m, 2H), 7.53-7.40 (m, 3H), 7.32-7.18 (m, 5H), 4.97-4.92 (m, 1H), 4.33-4.23 (m, 1H), 3.54-3.41 (m, 2H), 3.01-2.97 (m, 1H), 2.69-2.57 (m, 1H), 2.06 (s, 3H).

To a solution of compound 101B (3.00 g, 8.92 mmol) in DCM (100 mL) was added DMP (5.67 g, 13.38 mmol). The mixture was stirred at 25° C. for 3 hour. The mixture quenched with 10% $Na_2S_2O_3$ (aqueous):saturated $NaHCO_3$ (aqueous) (1:1, 200 mL), extracted with DCM (200 mL) and washed with brine (200 mL×3). The combined organic layers were dried over $Na_2SO_4$ and concentrated. Compound 101C (2.70 g, yield 90.5%) was obtained as a white solid. $^1H$ NMR (400 MHz, DMSO-$d_6$) δ 9.66 (s, 1H), 8.91 (d, J=8.4 Hz, 1H), 7.67-7.63 (m, 2H), 7.53-7.47 (m, 1H), 7.46-7.40 (m, 2H), 7.29-7.19 (m, 5H), 4.79-4.72 (m, 1H), 3.37-3.32 (m, 1H), 2.81-2.72 (m, 1H), 2.09 (s, 3H).

To a solution of compound 101C (500.0 mg, 1.50 mmol) in DCM (20 mL) was added TMSCN (223.2 mg, 2.25 mmol, 280 uL) and TEA (15.2 mg, 150.00 umol, 20 uL). The mixture was stirred at 0° C. for 3 hours. The mixture was concentrated, diluted with ethyl acetate (20 mL), washed with water (20 mL), brine (20 mL), dried over $Na_2SO_4$ and concentrated to obtain compound 10D (600.0 mg, crude) as colorless oil.

To a solution of compound 101D (600.0 mg, 1.41 mmol) in THF (10 mL) was added HCl (10 mL). The mixture was stirred at 60° C. for 12 hours. The mixture was diluted with $H_2O$ (200 mL), extracted with ethyl acetate (100 mL), the organic layer was washed with $NaHCO_3$ (aqueous 100 mL), the water phase was added HCl (1M) until pH ~1, then extracted with ethyl acetate (100 mL), the organic layer was washed with brine (100 mL), dried over $Na_2SO_4$ and concentrated. Compound 101E (240.0 mg, crude) was obtained as a colorless oil and used in next step directly.

To a solution of compound 101E (200.0 mg, 526 umol) in THF (10.00 mL) was added (3,4-dichlorophenyl)methanamine (92.6 mg, 525.78 umol, 70 uL), DIEA (203.85 mg, 1.58 mmol, 275.48 uL), HOBt (71.04 mg, 525.78 umol) and EDCI (120.95 mg, 630.93 umol). The mixture was stirred at 25° C. for 4 hours. The mixture was concentrated and diluted with ethyl acetate (50 mL), washed with HCl (1M, 50 mL), saturated $NaHCO_3$ (aqueous 50 mL), brine (50 mL×3), dried over $Na_2SO_4$ and concentrated. The mixture was triturated with $CH_3CN$ (5 mL) and filtered. Compound 101F (70.0 mg, yield 24.7%) obtained as a white solid. $^1H$ NMR (400 MHz, DMSO-$d_6$) δ 8.63-8.53 (m, 1H), 8.30 (d, J=9.2 Hz, 1H), 7.58-7.10 (m, 13H), 6.20-5.94 (m, 1H), 4.68-4.57 (m, 1H), 4.32-4.16 (m, 2H), 4.08-3.99 (m, 1H), 2.97-2.67 (m, 2H), 2.07-1.96 (m, 1H), 2.07-1.96 (m, 2H).

To a solution of compound 101F (60.0 mg, 111.44 umol) in DCM (10 mL) and DMSO (1.00 mL) was added DMP (141.8 mg, 334.32 umol). The mixture was stirred at 25° C. for 3 hours. The mixture quenched with 10% $Na_2S_2O_3$ (aqueous):saturated $NaHCO_3$ (aqueous) (1:1, 20 mL), extracted with DCM (10 mL) and washed with brine (20 mL×3). The combined organic layers were dried over $Na_2SO_4$ and concentrated. Compound 101 (33.2 mg, yield 55.5%) was obtained as a white solid. $^1H$ NMR (400 MHz, DMSO-$d_6$) δ 9.52-9.43 (m, 1H), 9.12 (d, J=7.6 Hz, 1H), 7.69-7.38 (m, 7H), 7.35-7.20 (m, 6H), 5.53-5.42 (m, 1H), 4.40-4.32 (m, 2H), 3.31-3.19 (m, 1H), 2.93-2.71 (m, 1H), 2.12-2.00 (m, 3H). MS (ESI) m/z $(M+H)^+$536.1.

(S)—N-(4-(((1H-benzo[d]imidazol-5-yl)methyl) amino)-3,4-dioxo-1-phenylbutan-2-yl)-3-methyl-5-phenylisoxazole-4-carboxamide (493)

Compound 493 (20 mg, 23.4% yield, yellow solid) was prepared as in compound 101 from the corresponding intermediate carboxylic acid, compound 101E and (1-((2-(trimethylsilyl)ethoxy)methyl)-1H-benzo[d]imidazol-5-yl)methanamine followed by removal of the 2-(trimethylsilyl) ethoxy)methyl group to obtain compound 493. Compound 493: $^1H$ NMR (400 MHz, DMSO-$d_6$) δ 8.07 (s, 1H), 7.67-7.59 (m, 3H), 7.56 (br s, 1H), 7.52-7.38 (m, 4H), 7.30 (br s, 1H), 7.25-7.14 (m, 4H), 6.89 (br d, J=6.2 Hz, 2H), 6.12 (br d, J=6.8 Hz, 1H), 5.72-5.63 (m, 1H), 4.62 (br d, J=5.5 Hz, 2H), 3.37 (br dd, J=4.7, 14.0 Hz, 1H), 2.99 (br dd, J=7.9, 14.3 Hz, 1H), 2.33 (s, 3H). MS (ESI) m/z $(M+H)^+$378.1.

Example 60

(S)-1-(1H-indazol-3-yl)-N-(1-oxo-3-phenylpropan-2-yl)-1H-imidazole-5-carboxamide (102)

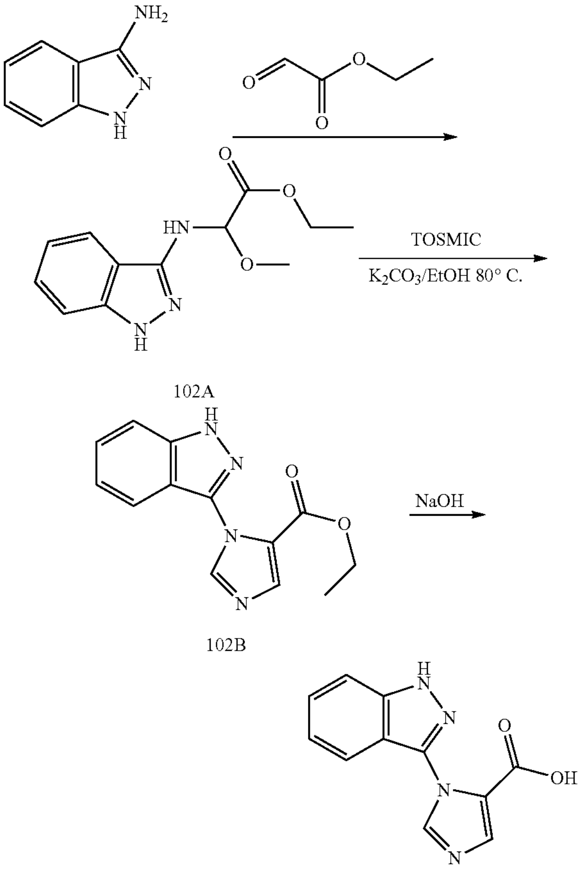

102A

102B

102C

To a solution of 1H-indazol-3-amine (8.7 g, 65.3 mmol) in MeOH (90 mL) was added ethyl 2-oxoacetate (20 g, 98.01 mmol). The mixture was stirred at 25° C. for 2 hours. The mixture was filtered and concentrated to give crude product 102A (15 g, crude) as brown solid, which was used for the next step without purification.

To a solution of 102A (15 g, 69.1 mmol) in EtOH (400 mL) was added $K_2CO_3$ (14.5 g, 104 mmol) and TosMIC (11.6 g 59.4 mmol). The mixture was stirred at 90° C. for 0.5 hour. The reaction mixture was filtered and concentrated under reduced pressure to give a residue. The residue was purified by column chromatography ($SiO_2$, Petroleum ether/Ethyl acetate=1:0 to 1:1) to give compound 102B (2.9 g, yield: 16.4%) as yellow solid. $^1H$ NMR (400 MHz, $CDCl_3$) δ 11.04 (br s, 1H), 7.98 (d, J=0.7 Hz, 1H), 7.91 (s, 1H), 7.48-7.41 (m, 3H), 7.25-7.19 (m, 1H), 4.24-4.14 (m, 2H), 1.14 (t, J=7.1 Hz, 3H).

To a solution of 102B (2.9 g, 11.3 mmol) in THF (40 mL) and $H_2O$ (8 mL) was added NaOH (905 mg, 22.6 mmol). The mixture was stirred at 25° C. for 10 hours. The mixture was concentrated under reduced pressure to remove the organic solvent, and extracted with EtOAc (20 mL). The aqueous layer was acidified with 1M HCl to pH ~5 and then extracted with EtOAc (30 mL×3). The combined organic layer was washed with $H_2O$ (40 mL), brine (40 mL), dried over $Na_2SO_4$, filtered and concentrated to give 102C (1.5 g, yield: 58.1%) as yellow solid. $^1H$ NMR (400 MHz, DMSO-$d_6$) δ 13.35 (s, 1H), 8.16 (s, 1H), 7.83 (s, 1H), 7.61 (d, J=8.3 Hz, 1H), 7.47-7.41 (m, 2H), 7.20-7.15 (m, 1H). MS (ESI) m/z $(M+H)^+$228.9.

Compound 102 (20 mg, yield 52.9%, pale yellow solid) was prepared as in Example 6 from the corresponding intermediate compounds 102C and 21G ((S)-2-amino-3-phenylpropan-1-ol). Compound 102: $^1H$ NMR (DMSO-$d_6$, 400 MHz) δ 13.22 (s, 1H), 9.48 (s, 1H), 8.95 (d, J=8.0 Hz, 1H), 8.07 (s, 1H), 7.72 (s, 1H), 7.59-7.51 (m, 1H), 7.42-7.40 (m, 1H), 7.31-7.24 (m, 2H), 7.24-7.18 (m, 4H), 7.12-7.06 (m, 1H), 7.06-7.06 (m, 1H), 4.34-4.23 (m, 1H), 3.19-3.15 (m, 1H), 2.77-2.74 (m, 1H). MS (ESI) m/z $(M+H)^+$360.1.

Example 61

(S)—N-(4-amino-3,4-dioxo-1-phenylbutan-2-yl)-3-methyl-1-(3'-methyl-[1,1'-biphenyl]-3-yl)-1H-pyrazole-5-carboxamide (105)

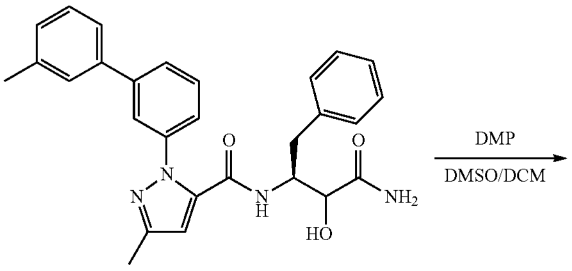

105A

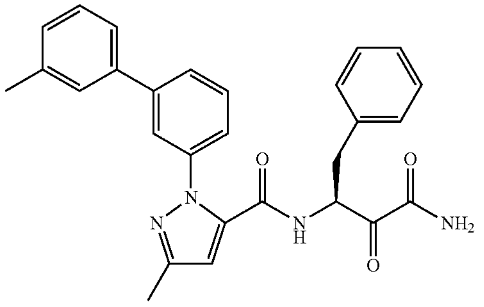

105

To a mixture of compound 103A (150 mg, 0.33 mmol) and m-tolylboronic acid (89 mg, 0.66 mmol) in THF (50 mL) was added $H_2O$ (10 mL), $Na_2CO_3$ (70 mg, 0.66 mmol) and $Pd(PPh_3)_4$ (38 mg, 0.033 mmol) in one portion at 25° C. under $N_2$. The mixture was stirred at 80° C. for 12 h. The reaction mixture was added $H_2O$ (100 mL) and extracted with EA (100 mL×3). The combined organic layer was washed with saturated aqueous $NaHCO_3$ (150 mL×3), brine (150 mL×3), dried over $Na_2SO_4$ and concentrated. The crude product was treated with i-propyl ether/CH3CN (10/1, 10 mL). The solid was collected and dried in vacuo to afford compound 2A (72.7 mg, yield 42.70%) as gray solid. Compound 105A: $^1H$ NMR (DMSO-$d_6$, 400 MHz) δ 8.51-8.10 (m, 1H), 7.60-7.52 (m, 2H), 7.47-7.38 (m, 2H), 7.36-7.28 (m, 3H), 7.26-7.12 (m, 7H), 7.03-6.93 (m, 1H), 6.57 (d, J=3.3 Hz, 1H), 5.93-5.73 (m, 1H), 4.49-4.29 (m, 1H), 4.04-3.86 (m, 1H), 2.90-2.81 (m, 1H), 2.81-2.72 (m, 1H), 2.35 (s, 3H), 2.24 (s, 3H). MS (ESI) m/z $(M+H)^+$469.2.

To a mixture of compound 105A (65 mg, 0.14 mmol) in DCM (10 mL) and DMSO (1 mL) was added DMP (177 mg, 0.42 mmol) in one portion at 0° C. The mixture was stirred at 0° C. for 10 min, then temperature to 25° C. and stirred for 2 hours. The reaction was quenched by 20 mL of 10% $Na_2S_2O_3$ aqueous solution and 20 mL of saturated aqueous $NaHCO_3$ solution and then extracted with DCM (30 mL×3). The combined organic phase was washed with brine (40 mL×3), dried over anhydrous $Na_2SO_4$, filtered and concentrated in vacuo. The residue was purified by preparatory-HPLC (basic condition) to afford compound 105 (35.0 mg, yield 53.6%) as white solid. $^1H$ NMR (DMSO-$d_6$, 400 MHz) δ 9.08 (d, J=7.7 Hz, 1H), 8.08-8.00 (m, 1H), 7.84 (br s, 1H), 7.60-7.52 (m, 2H), 7.45-7.37 (m, 3H), 7.36-7.30 (m, 1H), 7.28-7.25 (m, 3H), 7.23-7.16 (m, 3H), 7.12-7.06 (m, 1H), 6.60 (br s, 1H), 5.29 (br s, 1H), 3.22-3.14 (m, 1H), 2.86-2.76 (m, 1H), 2.35 (s, 3H), 2.28-2.22 (m, 3H). MS (ESI) m/z $(M+H)^+$467.2.

Example 62

Compounds 103, 106, 216-218, 214

(S)—N-(4-amino-3,4-dioxo-1-phenylbutan-2-yl)-1-(4'-fluoro-[1,1'-biphenyl]-3-yl)-3-methyl-1H-pyrazole-5-carboxamide (103)

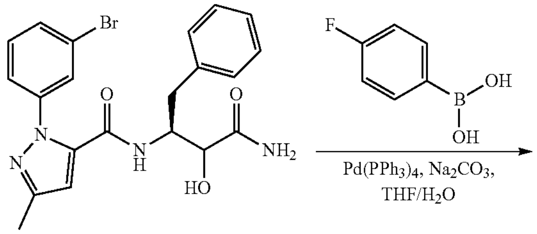

103A

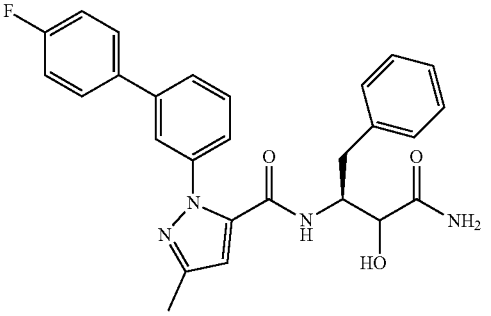

103B

Compound 103B (110 mg, yield 70.98%, off-white solid) was prepared as in Example 49 from the corresponding intermediate compounds 103A and (4-fluorophenyl)boronic acid. Compound 103B: $^1H$ NMR (DMSO-$d_6$, 400 MHz) δ 8.45 (d, J=9.0 Hz, 0.5H), 8.15 (d, J=9.0 Hz, 0.5H), 7.68-7.52 (m, 4H), 7.40-7.13 (m, 10H), 7.02 (br d, J=8.4 Hz, 0.5H), 6.94 (br d, J=7.9 Hz, 0.5H), 6.59 (d, J=2.4 Hz, 1H), 5.93-5.74 (m, 1H), 4.49-4.32 (m, 1H), 4.02-3.88 (m, 1H), 2.95-2.66 (m, 2H), 2.26-2.19 (m, 3H).

Compound 103 (78 mg, yield 68.93%, pale yellow solid) was prepared as in Example 61 from the corresponding intermediate compounds 103B. Compound 103: $^1$H NMR (DMSO-$d_6$, 400 MHz) δ 9.09 (d, J=7.7 Hz, 1H), 8.09 (s, 1H), 7.86 (s, 1H), 7.65 (dd, J=5.4, 8.7 Hz, 2H), 7.58 (br d, J=7.7 Hz, 1H), 7.52 (s, 1H), 7.41 (t, J=7.8 Hz, 1H), 7.32-7.25 (m, 6H), 7.23-7.19 (m, 1H), 7.11 (br d, J=7.9 Hz, 1H), 6.60 (s, 1H), 5.35-5.25 (m, 1H), 3.18 (dd, J=3.5, 13.7 Hz, 1H), 2.81 (dd, J=10.4, 13.7 Hz, 1H), 2.25 (s, 3H). MS (ESI) m/z $(M+H)^+$471.1.

(S)—N-(4-amino-3,4-dioxo-1-phenylbutan-2-yl)-1-(3'-fluoro-[1,1'-biphenyl]-3-yl)-3-methyl-1 h-pyrazole-5-carboxamide (106)

Compound 106 (18.7 mg, yield 46.2%, light yellow solid) was prepared as in Example 61 from the corresponding starting materials, compound 103A and (3-fluorophenyl) boronic acid. Compound 106: $^1$H NMR (DMSO-$d_6$, 400 MHz) δ 9.08 (br d, J=7.7 Hz, 1H), 8.05 (br s, 1H), 7.85 (br s, 1H), 7.69-7.62 (m, 1H), 7.60-7.56 (m, 1H), 7.52-7.43 (m, 3H), 7.43-7.37 (m, 1H), 7.33-7.24 (m, 4H), 7.24-7.15 (m, 2H), 7.13-7.05 (m, 1H), 6.62 (s, 1H), 5.35-5.25 (m, 1H), 3.20-3.15 (m, 1H), 2.86-2.76 (m, 1H), 2.28-2.21 (m, 3H). MS (ESI) m/z $(M+H)^+$471.1.

(S)—N-(4-amino-3,4-dioxo-1-phenylbutan-2-yl)-1-(3'-fluoro-[1,1'-biphenyl]-4-yl)-3-methyl-1H-pyrazole-5-carboxamide (216)

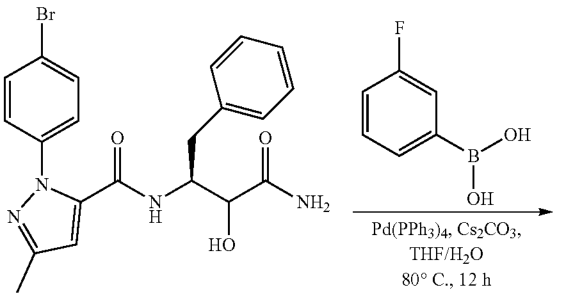

83D

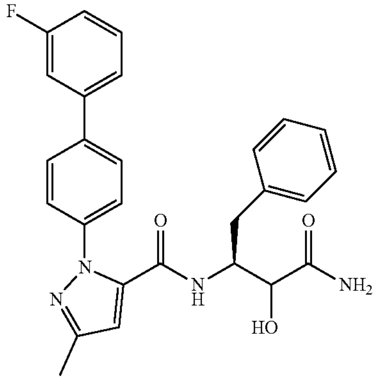

216A

Compound 216 (26 mg, yield 16.7%, yellow solid) was prepared as in Example 62 from the corresponding starting materials, compound 83D and (3-fluorophenyl)boronic acid. Compound 216: $^1$H NMR ($CDCl_3$, 400 MHz) δ 7.59 (br d, J=7.7 Hz, 2H), 7.47-7.35 (m, 4H), 7.33-7.27 (m, 4H), 7.05 (br d, J=6.4 Hz, 3H), 6.75 (br s, 1H), 6.49 (s, 1H), 6.42-6.33 (m, 1H), 5.66-5.50 (m, 2H), 3.39 (br dd, J=5.0, 13.8 Hz, 1H), 3.16 (br dd, J=7.4, 14.0 Hz, 1H), 2.40-2.29 (m, 3H). MS (ESI) m/z $(M+H)^+$471.1.

(S)—N-(4-amino-3,4-dioxo-1-phenylbutan-2-yl)-1-(2'-fluoro-[1,1'-biphenyl]-4-yl)-3-methyl-1H-pyrazole-5-carboxamide (217)

Compound 217 was prepared as in Example 62 from the corresponding starting materials, compound 83D and (2-fluorophenyl)boronic acid. Compound 217 (13 mg, yield 14.49%, yellow solid): $^1$H NMR ($CDCl_3$, 400 MHz) δ 7.59 (d, J=7.3 Hz, 2H), 7.49-7.39 (m, 3H), 7.37-7.26 (m, 3H), 7.24-7.13 (m, 3H), 7.02 (br d, J=6.0 Hz, 2H), 6.72 (br s, 1H), 6.49 (s, 1H), 6.37-6.29 (m, 1H), 5.62-5.49 (m, 2H), 3.36 (dd, J=5.3, 14.1 Hz, 1H), 3.11 (dd, J=7.4, 14.0 Hz, 1H), 2.38-2.29 (m, 3H). MS (ESI) m/z $(M+H)^+$471.2.

(S)—N-(4-amino-3,4-dioxo-1-phenylbutan-2-yl)-3-methyl-1-(3'-methyl-[1,1'-biphenyl]-4-yl)-1H-pyrazole-5-carboxamide (218)

Compound 218 was prepared as in Example 62 from the corresponding starting materials, compound 83D and m-tolylboronic acid. Compound 218 (yield 36.1%, yellow solid): $^1$H NMR ($CDCl_3$, 400 MHz) δ 9.16 (d, J=7.7 Hz, 1H), 8.11 (s, 1H), 7.87 (s, 1H), 7.60 (d, J=8.6 Hz, 2H), 7.50-7.43 (m, 2H), 7.38-7.28 (m, 5H), 7.26-7.21 (m, 3H), 7.18 (br d, J=7.5 Hz, 1H), 6.54 (s, 1H), 5.28-5.18 (m, 1H), 3.20 (br dd, J=3.6, 13.8 Hz, 1H), 2.83 (dd, J=10.6, 13.7 Hz, 1H), 2.37 (s, 3H), 2.24 (s, 3H).

(S)—N-(4-amino-3,4-dioxo-1-phenylbutan-2-yl)-1-(2'-fluoro-[1,1'-biphenyl]-3-yl)-3-methyl-1H-pyrazole-5-carboxamide (214)

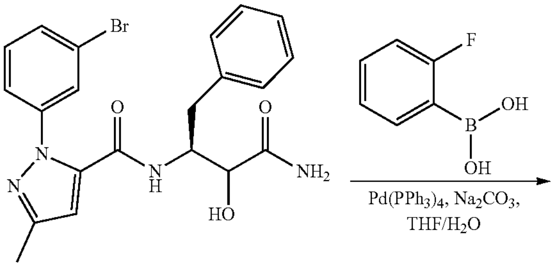

103A

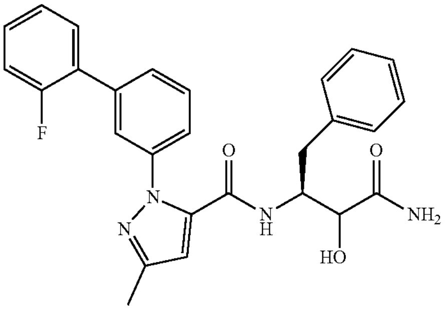

214A

Compound 214 was prepared as in Example 62 from the corresponding starting materials, compound 103A and (2-fluorophenyl)boronic acid. Compound 214 (20 mg, yield 29.5%, white solid): $^1$H NMR ($CDCl_3$, 400 MHz) δ 7.62-7.55 (m, 2H), 7.52-7.43 (m, 2H), 7.41-7.30 (m, 2H), 7.26-7.22 (m, 3H), 7.21-7.13 (m, 2H), 7.03-6.94 (m, 2H), 6.65 (br s, 1H), 6.49 (s, 1H), 6.33-6.26 (m, 1H), 5.56-5.52 (m, 1H), 5.37 (br s, 1H), 3.38-3.31 (m, 1H), 3.17-3.09 (m, 1H), 2.36-2.30 (m, 3H). MS (ESI) m/z $(M+H)^+$471.1.

Example 63

(S)—N-(4-amino-3,4-dioxo-1-phenylbutan-2-yl)-3-phenylfuran-2-carboxamide (104)

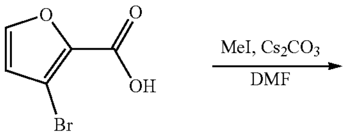

104A

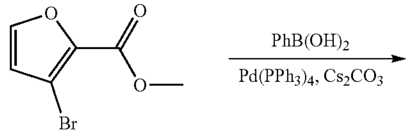

104B

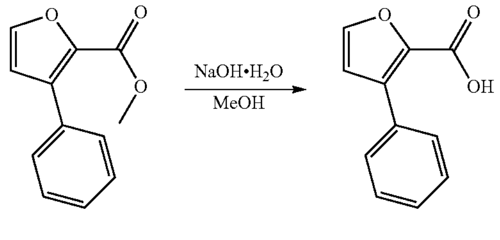

104C 104D

To a solution of i-$Pr_2$NH (3 mL, 18.71 mmol) in anhydrous THF (13 mL) was added n-BuLi (7 mL, 18.71 mmol) dropwise at −78° C. and stirred at 0° C. for 30 min. Then a solution of 3-bromofuran (2.5 g, 17.01 mmol) in THF (13 mL) was added to the mixture drop wise at −78° C. and the mixture was stirred at −78° C. for 30 minutes. Anhydrous $CO_2$ was poured into the solution at −78° C. for 30 minutes. The reaction was quenched with $H_2O$ (20 mL) and extracted with ethyl acetate (20 mL), then water phase was treated with HCl until pH ~3. The precipitation was filtered and dried under reduced pressure. Compound 104A (1.8 g, crude) was obtained as yellow solid. $^1$H NMR (DMSO-$d_6$, 400 MHz) δ 7.96 (d, J=1.8 Hz, 1H), 6.89 (d, J=1.8 Hz, 1H).

$Cs_2CO_3$ (2.13 g, 6.55 mmol) was added to a solution of compound 104A (500 mg, 2.62 mmol) in DMF (10 mL). Then MeI (652.43 uL, 10.48 mmol) was added to the mixture. The mixture was stirred at 25° C. for 13 h. The mixture was diluted with ethyl acetate (35 mL) and $H_2O$ (30 mL). The organic layer was separated and the aqueous layer was washed extracted with ethyl acetate (20 mL×2). The combined organic layer was washed brine (30 mL), dried over MgSO4, filtered and concentrated. The residue was purified by Flash column chromatography (Petroleum Ether/Ethyl Acetate=15/1). Compound 104B (250 mg, yield 46.54%) was obtained as white solid. $^1$H NMR ($CDCl_3$, 400 MHz) δ 7.50 (d, J=2.0 Hz, 1H), 6.61 (d, J=2.0 Hz, 1H), 3.94-3.92 (m, 3H)

To a solution of Compound 104B (221 mg, 1.08 mmol) in THF (4 mL) and $H_2O$ (2 mL) was added phenylboronic acid (263 mg, 2.16 mmol) and $Cs_2CO_3$ (553 mg, 1.70 mmol), followed by $Pd(PPh_3)_4$ (125 mg, 108.00 umol), then the mixture was heated to 80° C. and stirred for 12 h. The reaction mixture was cooled to the room temperature and $H_2O$ (6 mL) was added to quenched the reaction. The mixture was extracted with ethyl acetate (10 mL×2). The combined organic layer was washed with $H_2O$ (10 mL), brine (10 mL), dried over $Na_2SO_4$, filtered, evaporated under reduced pressure. The residue was purified by FCC (PE/EA: 0 to 10/1). Compound 104C (180 mg, yield 82.42%) was obtained as yellow oil. $^1$H NMR ($CDCl_3$, 400 MHz) δ 7.61-7.55 (m, 3H), 7.45-7.35 (m, 3H), 6.64 (d, J=1.8 Hz, 1H), 3.86 (s, 3H)

To a solution Compound 104C (170 mg, 840.71 umol) in MeOH (5 mL) was added NaOH (2 M, 2 mL) dropwise, then the mixture was stirred at 25° C. for 2 h. The reaction was diluted with $H_2O$ (5 mL) and removed solvent under reduced pressure, then the mixture was extracted with MTBE (5 mL). The water phase was treated with HCl (1 M) until pH ~3, then water phase was extracted with ethyl acetate (5 mL×3). The organic layer was washed with brine, dried over anhydrous $Na_2SO_4$, evaporated under reduced pressure. Compound 104D (120 mg, yield 75.85%) was obtained as white solid which was used directly in next step. $^1$H NMR (DMSO-$d_6$, 400 MHz) δ 7.90 (d, J=1.8 Hz, 1H), 7.59-7.53 (m, 2H), 7.39-7.28 (m, 3H), 6.80 (d, J=1.8 Hz, 1H)

Compound 104 (35 mg, yield 44.0%, yellow solid) was prepared as in Example 5 from the corresponding intermediate carboxylic acid, compound 104D. Compound 104: $^1$H NMR (DMSO-$d_6$, 400 MHz) δ 8.56 (d, J=7.5 Hz, 1H), 8.07 (s, 1H), 7.88 (d, J=1.8 Hz, 1H), 7.81 (s, 1H), 7.61-7.54 (m, 2H), 7.36-7.29 (m, 3H), 7.29-7.25 (m, 4H), 7.21-7.17 (m, 1H), 6.90-6.83 (m, 1H), 5.39-5.29 (m, 1H), 3.21-3.12 (m, 1H), 3.01-2.92 (m, 1H). MS (ESI) m/z $(M+H)^+$363.1

Example 64

Compounds 107, 243, 253, 265, 168, 459, 460, 475

(S)—N-(4-amino-1-(4-fluorophenyl)-3,4-dioxobutan-2-yl)-2-methyl-4-phenyloxazole-5-carboxamide (107)

(S)—N-(1-amino-1,2-dioxopentan-3-yl)-2-methyl-4-phenyloxazole-5-carboxamide (243)

(S)—N-(1-amino-5-methyl-1,2-dioxohexan-3-yl)-2-methyl-4-phenyloxazole-5-carboxamide (253)

(S)—N-(1-amino-1,2-dioxoheptan-3-yl)-2-methyl-4-phenyloxazole-5-carboxamide (265)

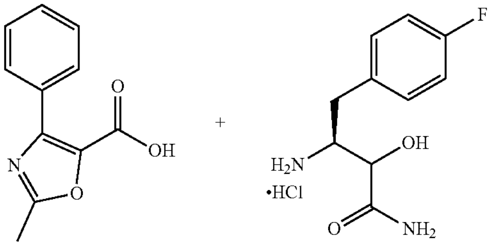

107B 58F

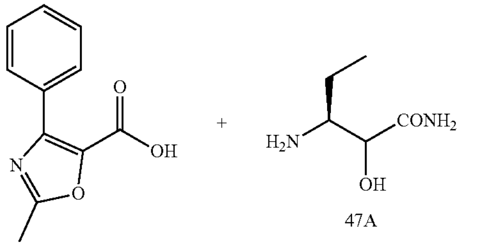

107B 47A

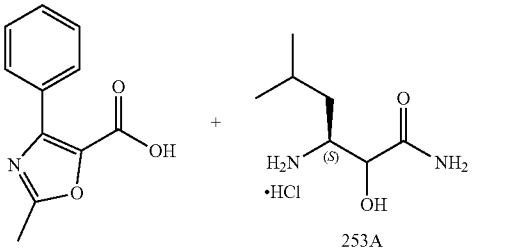

107B 253A

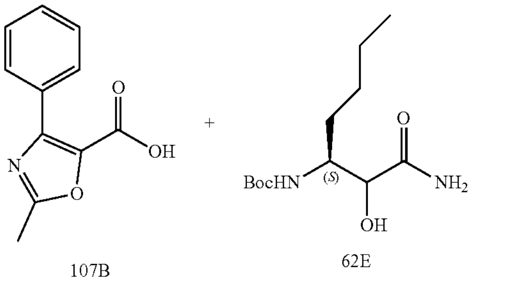

107B 62E

Compounds 107, 243, 253 and 265 were prepared as in Example 5 from the corresponding starting materials, respectively-compound 107B and compound 58F, 47A, 253A or 62E.

Compound 107 (77.3 mg, 51.80% yield, white solid): $^1H$ NMR (400 MHz, $CDCl_3$) δ 8.12-8.05 (m, 2H), 7.46-7.36 (m, 3H), 7.12-7.05 (m, 2H), 7.00-6.94 (m, 2H), 6.79-6.70 (m, 2H), 5.72-5.64 (m, 1H), 5.53 (br s, 1H), 5.57-5.47 (m, 1H), 3.46-3.38 (m, 1H), 3.24-3.16 (m, 1H), 2.56 (s, 3H). MS (ESI) m/z $(M+H)^+$396.1.

Compound 243 (52.8 mg, 42.87% yield, yellow solid): $^1H$ NMR (400 MHz, $CDCl_3$): δ 8.13 (d, J=6.8 Hz, 2H), 7.47-7.33 (m, 3H), 6.91-6.81 (m, 1H), 6.75 (br s, 1H), 5.53-5.36 (m, 2H), 2.58 (s, 3H), 2.20-2.08 (m, 1H), 1.88-1.76 (m, 1H), 0.99 (t, J=7.2 Hz, 3H). MS (ESI) m/z $(M+H)^+$316.1.

Compound 253 (6.5 mg, 6.42% yield, white solid): $^1H$ NMR ($CDCl_3$, 400 MHz): δ 8.19-8.09 (m, 2H), 7.50-7.34 (m, 3H), 6.84-6.68 (m, 2H), 5.55-5.38 (m, 2H), 2.60 (s, 3H), 1.87-1.74 (m, 2H), 1.63-1.58 (m, 1H), 1.04 (d, J=6.4 Hz, 3H), 0.98 (d, J=6.4 Hz, 3H). MS (ESI) m/z $(M+H)^+$344.1.

Compound 265 (79.7 mg, 94.04% purity, white solid): $^1H$ NMR (400 MHz, DMSO-$d_6$) δ 8.73 (d, J=6.8 Hz, 1H), 8.13-8.03 (m, 3H), 7.79 (s, 1H), 7.45-7.35 (m, 3H), 5.17-5.10 (m, 1H), 2.56 (s, 3H), 1.87-1.76 (m, 1H), 1.73-1.60 (m, 1H), 1.45-1.26 (m, 4H), 0.93-0.83 (m, 3H). MS (ESI) m/z $(M+H)^+$344.1.

(S)—N-(4-amino-1-(4-fluorophenyl)-3,4-dioxobutan-2-yl)-1-methyl-3-phenyl-1H-pyrazole-4-carboxamide (168)

Prepared as in Example 64 from the corresponding starting materials, compounds 32F and 58F. Compound 168 (21.3 mg, yield: 45.1%, light yellow solid): $^1H$ NMR (400 MHz, DMSO-$d_6$) δ 8.38 (br d, J=7.7 Hz, 1H), 8.12-7.99 (m, 2H), 7.81 (s, 1H), 7.54 (br d, J=3.7 Hz, 2H), 7.36-7.24 (m, 5H), 7.12 (br t, J=8.7 Hz, 2H), 5.30-5.20 (m, 1H), 3.89 (s, 3H), 3.19-3.09 (m, 1H), 2.87-2.74 (m, 1H). MS (ESI) m/z $(M+H)^+$395.1.

N-(4-(cyclopropylamino)-3,4-dioxo-1-phenylbutan-2-yl)-2-methyl-4-phenyloxazole-5-carboxamide (459)

Prepared as in compound 107 from the corresponding starting materials, compounds 107B and 3-amino-N-cyclopropyl-2-hydroxy-4-phenylbutanamide hydrochloride. Compound 459 (210 mg, yield: 65.2%, white solid): $^1H$ NMR (400 MHz, DMSO-$d_6$) δ 8.88-8.79 (m, 2H), 8.06-7.99 (m, 2H), 7.43-7.34 (m, 3H), 7.33-7.26 (m, 4H), 7.25-7.18 (m, 1H), 5.48-5.35 (m, 1H), 3.26-3.17 (m, 1H), 3.05-2.94 (m, 1H), 2.82-2.71 (m, 1H), 2.55 (s, 3H), 0.70-0.52 (m, 4H). MS (ESI) m/z $(M+H)^+$418.2.

N-(1-(cyclopropylamino)-1,2-dioxoheptan-3-yl)-2-methyl-4-phenyloxazole-5-carboxamide (460)

Prepared as in compound 107 from the corresponding starting materials, compounds 107B and 3-amino-N-cyclopropyl-2-hydroxyheptanamide hydrochloride. Compound 460 (180 mg, yield: 53.3%, white solid): $^1H$ NMR (400 MHz, DMSO-$d_6$) δ 8.76 (br s, 2H), 8.10 (br s, 2H), 7.40 (br s, 3H), 5.12 (br s, 1H), 2.77 (br s, 1H), 2.56 (br s, 3H), 1.81 (br s, 1H), 1.68 (br s, 1H), 1.32 (br s, 4H), 0.88 (br s, 3H), 0.70-0.52 (m, 4H). MS (ESI) m/z $(M+H)^+$384.2.

(S)—N-(4-fluoro-3-oxo-1-phenylbutan-2-yl)-2-methyl-4-phenyloxazole-5-carboxamide (475)

Prepared as in compound 107 from the corresponding starting materials, compounds 107B and (2S,3S)-3-amino- 1-fluoro-4-phenylbutan-2-ol hydrochloride. Compound 475 (75 mg, yield: 50.28%, white solid): $^1H$ NMR (400 MHz, $CDCl_3$) δ 8.13-8.08 (m, 2H), 7.47-7.38 (m, 3H), 7.36-7.28 (m, 3H), 7.18 (d, J=6.6 Hz, 2H), 6.81-6.76 (m, 1H), 5.31-5.22 (m, 1H), 5.05-4.89 (m, 1H), 4.88-4.72 (m, 1H), 3.29-3.22 (m, 1H), 3.17-3.10 (m, 1H), 2.57 (s, 3H). MS (ESI) m/z $(M+H)^+$367.1.

Example 65

(S)—N-(4-amino-3,4-dioxo-1-phenylbutan-2-yl)-3-methyl-1-(quinolin-5-yl)-1H-pyrazole-5-carboxamide (108)

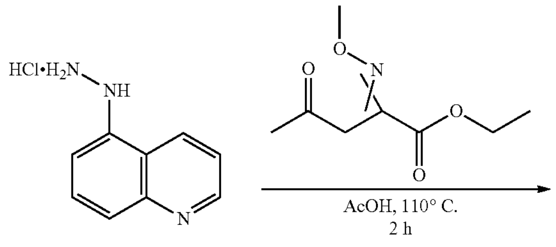

108A

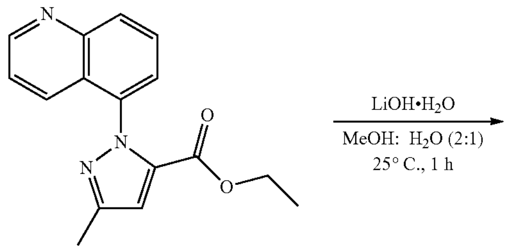

108B

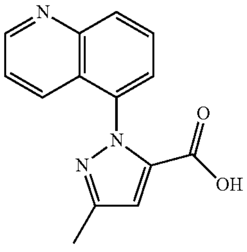

108D

A mixture consisting of quinolin-5-amine (5 g, 34.68 mmol) in conc. HCl (20 mL) at 0° C. was added $NaNO_2$ (2.63 g, 38.15 mmol) dropwise and the resultant mixture was stirred at 0° C. for 0.5 hour. The reaction mixture was warmed to 25° C. over 0.5 hour, and then cooled to 0° C. The $SnCl_2.2H_2O$ (15.65 g, 68.36 mmol, in 20 mL conc. HCl) was added dropwise to the reaction mixture, and stirred at 0° C. for 0.5 hour. The resulting mixture was allowed to warm to 25° C. with vigorous stirring over 4 hours. The reaction mixture was concentrated under reduced pressure to remove solvent. The residue was diluted with ethanol 90 mL (30 mL×3), filtered and concentrated under reduced pressure to afford compound 108A (5.2 g, 76.64% yield, HCl) as a yellow solid. $^1H$ NMR (DMSO-$d_6$, 400 MHz): δ 9.98 (br s, 1H), 9.26-9.15 (m, 2H), 8.07-7.97 (m, 2H), 7.89 (d, J=8.8 Hz, 1H), 7.27 (d, J=7.8 Hz, 1H).

To a mixture of compound 108A (2 g, 12.56 mmol, HCl) and ethyl 2-(methoxyimino)-4-oxopentanoate (1.91 g, 10.22 mmol) in AcOH (20 mL) was degassed and purged with $N_2$ for 3 times, and then the mixture was stirred at 110° C. for 2 h under $N_2$ atmosphere. The reaction mixture was concentrated under reduced pressure to remove AcOH. The residue was diluted with $CH_2Cl_2$ (100 mL), adjusted to pH ~7-8 with saturated aqueous $NaHCO_3$, and then extracted with $CH_2Cl_2$ (40 mL×2). The organic phase was dried over anhydrous $Na_2SO_4$, filtered, and concentrated under reduced pressure to give a residue, which was purified by column chromatography ($SiO_2$, Petroleum ether/Ethyl acetate=1:0 to 0:1) to give compound 108B (1.2 g, 41.78% yield) as a yellow solid and compound 108C (150 mg, 5.22% yield) as a yellow solid. Compound 108B: $^1H$ NMR ($CDCl_3$, 400 MHz): δ 8.93 (d, J=4.0 Hz, 1H), 8.23 (d, J=8.4 Hz, 1H), 7.78 (t, J=8.0 Hz, 1H), 7.64 (d, J=8.4 Hz, 1H), 7.56 (d, J=7.2 Hz, 1H), 7.38 (d, J=8.8 Hz, 1H), 6.93 (s, 1H), 4.05 (q, J=7.2 Hz, 2H), 2.41 (s, 3H), 1.00 (t, J=7.2 Hz, 3H).

Compound 108C: $^1H$ NMR ($CDCl_3$, 400 MHz): δ$^1H$ NMR (400 MHz, DMSO-$d_6$) δ 8.98-8.87 (m, 1H), 8.27 (d, J=8.8 Hz, 1H), 7.83-8.77 (m, 1H), 7.68-7.56 (m, 2H), 7.45-7.40 (m, 1H), 6.85 (s, 1H), 4.42 (q, J=7.2 Hz, 2H), 2.13 (s, 3H), 1.40 (t, J=7.2 Hz, 3H).

To a mixture of 108B (250 mg, 888.7 umol) in MeOH (10 mL) and $H_2O$ (5 mL) was added $LiOH.H_2O$ (149.2 mg, 3.55 mmol) in one portion and the mixture was stirred at 25° C. for 1 hour. The reaction mixture was concentrated under reduced pressure to remove MeOH. The residue was diluted with $H_2O$ (10 mL), adjusted to pH ~3 with 1N HCl, and then extracted with DCM (40 mL×3). The combined organic layers were washed with brine (30 mL), dried over anhydrous $Na_2SO_4$, filtered and concentrated under reduced pressure to afford intermediate compound 108D (200 mg, 88.03% yield) as a white solid. $^1H$ NMR (DMSO-$d_6$, 400 MHz): δ 8.97 (d, J=4.0 Hz, 1H), 8.17 (d, J=8.8 Hz, 1H), 7.89-7.79 (m, 1H), 7.67-7.62 (m, 1H), 7.61-7.52 (m, 2H), 6.96 (s, 1H), 5.76 (s, 1H), 2.32 (s, 3H). MS (ESI) m/z $(M+1)^+$253.9.

Compound 108 (21.2 mg, 23.11% yield, white solid) was prepared as in Example 107 from the corresponding intermediate compounds 108D and 12G. Compound 108: $^1H$ NMR ($CDCl_3$, 400 MHz): δ 8.95 (d, J=2.8 Hz, 1H), 8.22 (d, J=8.8 Hz, 1H), 7.77-7.66 (m, 2H), 7.50 (d, J=7.2 Hz, 1H), 7.39 (d, J=8.4 Hz, 1H), 7.24-7.18 (m, 3H), 6.89 (d, J=5.6 Hz, 2H), 6.63 (s, 2H), 6.28 (d, J=7.2 Hz, 1H), 5.53-5.39 (m, 2H), 3.24 (d, J=14.4 Hz, 1H), 3.03 (d, J=14.4 Hz, 1H), 2.39 (s, 3H). MS (ESI) m/z $(M+H)^+$428.1.

Example 66

(S)—N-(4-amino-3,4-dioxo-1-phenylbutan-2-yl)-4-(pyridin-2-yl)thiazole-5-carboxamide (109)

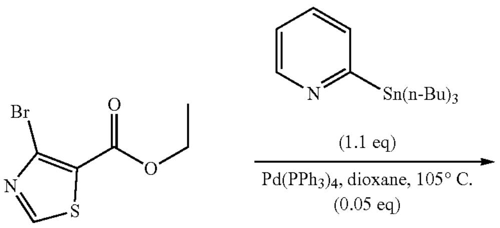

-continued

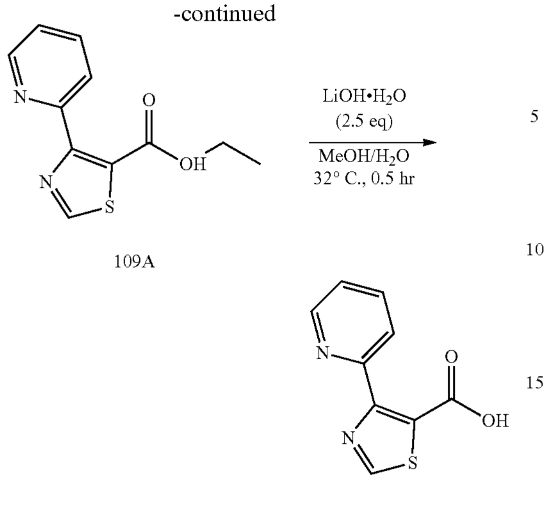

109A

109B

A mixture of ethyl 4-bromothiazole-5-carboxylate (500 mg, 2.12 mmol), 2-(tributylstannyl)pyridine (858.5 mg, 2.33 mmol), $Pd(PPh_3)_4$ (122.5 mg, 106 umol) in dioxane (15 mL) was stirred at 105° C. for 14 h. The mixture was concentrated. The residue was purified by column chromatography ($SiO_2$, Petroleum ether/Ethyl acetate=3:1 to 1:1) to afford compound 109A (221 mg, 44.05% yield) as yellow oil. MS (ESI) m/z $(M+H)^+$235.0.

To a solution of compound 109A (221 mg, 943.36 umol) in MeOH (10 mL) and water (2 mL) was added LiOH.$H_2O$ (99 mg, 2.36 mmol, 2.5 eq). The mixture was stirred at 32° C. for 0.5 hr. MeOH was evaporated. To the residue was added water (20 mL). The mixture was extracted with MTBE (5 mL) and separated. The aqueous layer was acidified to pH ~3 with 1N HCl and extracted with ethyl acetate (3×20 mL). The combined organic layers were dried over $Na_2SO_4$ and concentrated to afford compound 109B (155 mg, 79.68% yield) as white solid. $^1$H NMR (400 MHz, DMSO-$d_6$) δ 9.37 (s, 1H), 8.84 (br d, J=4.8 Hz, 1H), 8.57 (d, J=8.0 Hz, 1H), 8.34 (br t, J=7.4 Hz, 1H), 7.78 (t, J=6.2 Hz, 1H).

Compound 109 (5.7 mg, 13.91% yield, yellow solid) was prepared as in Example 5 from the corresponding intermediate carboxylic acid, compound 109B. Compound 109: MS (ESI) m/z $(M+H)^+$381.0. $^1$H NMR (400 MHz, $CDCl_3$) δ 13.47-13.34 (m, 1H), 8.85 (s, 1H), 8.43 (d, J=8.0 Hz, 1H), 8.03 (d, J=5.2 Hz, 1H), 7.96-7.79 (m, 1H), 7.26-7.22 (m, 1H), 7.20-7.06 (m, 5H), 6.81 (br s, 1H), 5.94-5.86 (m, 1H), 5.68 (br s, 1H), 3.49-3.33 (m, 2H).

Example 67

(S)-1-(4-(oxazol-2-yl)pyridin-2-yl)-n-(1-oxo-3-phenylpropan-2-yl)-1H-imidazole-5-carboxamide (110)

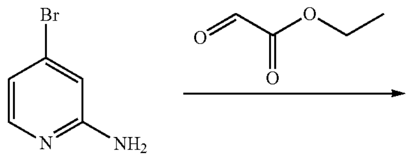

-continued

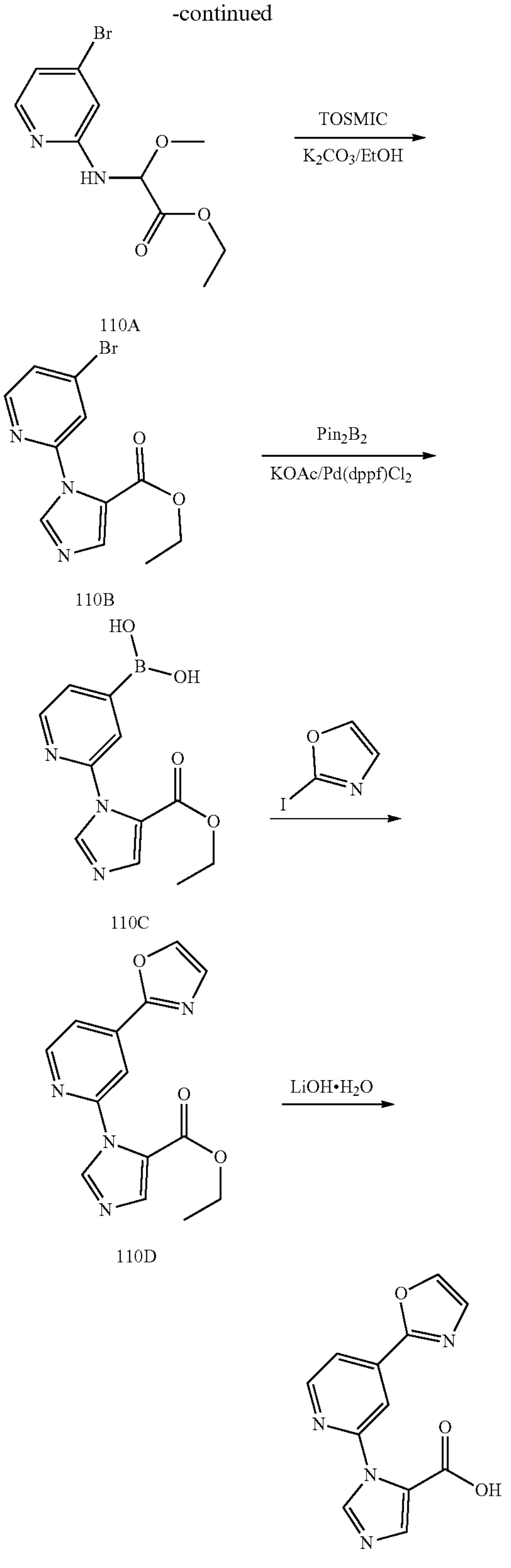

110A

110B

110C

110D

110E

A mixture of 4-bromopyridin-2-amine (20 g, 115.60 mmol) and ethyl 2-oxoacetate (30.7 g, 150.28 mmol) in MeOH (300 mL) was heated to 80° C. for 3 h. The mixture was concentrated, the residue was purified by silica gel column (Petroleum ether:Ethyl acetate=20:1). Compound 110A (28.9 g, yield: 86.5%, yellow solid): $^1H$ NMR (400 MHz, $CDCl_3$) δ 7.96 (d, J=5.2 Hz, 1H), 6.86 (dd, J=5.2, 1.75 Hz, 1H), 6.77 (d, J=1.3 Hz, 1H), 5.75 (br s, 1H), 5.61 (d, J=8.3 Hz, 1H), 4.29 (q, J=7.0 Hz, 2H), 3.41 (s, 3H), 1.37-1.31 (m, 3H).

A mixture of 110A (15 g, 51.9 mmol) and $K_2CO_3$ (21.5 g, 156 mmol) in EtOH (300 mL) was stirred at 80° C. for 0.5 hr, then 1-(isocyanomethylsulfonyl)-4-methyl-benzene (15.2 g, 77.82 mmol) was added, the resulting mixture was stirred at 80° C. for another 2 h. Most of ethanol was removed and a precipitate was formed, the solid was filtered and washed with water (100 mL×2), the solid was dried and concentrated to give 110B (6.4 g, yield: 41.7%), as yellow solid. $^1H$ NMR (400 MHz, $CDCl_3$) δ 8.38 (d, J=5.2 Hz, 1H), 7.97 (s, 1H), 7.85 (s, 1H), 7.61 (s, 1H), 7.56 (dd, J=5.26, 1.3 Hz, 1H), 4.27 (q, J=7.02 Hz, 2H), 1.29 (t, J=7.02 Hz, 3H).

110B (3 g, 10.13 mmol), $Pin_2B_2$ (2.57 g, 10.13 mmol), KOAc (2.98 g, 30.4 mmol) and $Pd(dppf)Cl_2$ (741 mg, 1.01 mmol) in dioxane (100 mL) was de-gassed and then heated at 70° C. for 4 hours under $N_2$. The mixture was filtered and the filtrate was concentrated, the residue was purified by silica gel chromatography (DCM:Methanol=5:1) to give 110C (1.70 g, crude) as black solid.

110C (300 mg, 1.15 mmol), 2-iodooxazole (157 mg, 805.00 umol), $Pd(dppf)Cl_2$ (84.1 mg, 115.00 umol) and $Na_2CO_3$ (244 mg, 2.30 mmol) in toluene (2 mL), EtOH (2 mL), $H_2O$ (1 mL) was degassed and then heated to 120° C. for 1 hour under microwave condition. LCMS showed desired MS, the mixture was added water (5 mL) and extracted with ethyl acetate (10 mL×2), the organic phases were dried and concentrated, the residue was purified by preparatory-TLC (Petroleum ether:Ethyl acetate=1:1) to give 110D (80 mg, yield: 24.5%), as yellow solid.

A mixture of 110D (80 mg, 281.42 umol) and $LiOH.H_2O$ (17.7 mg, 422.13 umol) in THF (5 mL), $H_2O$ (1 mL) was stirred at 25° C. for 12 h. LCMS showed desired MS, THF was removed under vacuum, the water layer was extracted with ethyl acetate (10 mL×2), the water layer was adjusted to pH ~6 with 1N HCl and lyophilized, the residue was purified by prep-HPLC (FA) to give 110E (35 mg, yield: 48.5%), as white solid. $^1H$ NMR (400 MHz, methanol-$d_4$) δ 8.70 (d, J=5.3 Hz, 1H), 8.25 (s, 1H), 8.16 (s, 1H), 8.11 (s, 1H), 8.08 (d, J=5.1 Hz, 1H), 7.81 (s, 1H), 7.46 (s, 1H).

Compound 110 (38 mg, yield: 58.8%, white solid) was prepared as in Example 6 from the corresponding intermediate compounds 110E and 21G ((S)-2-amino-3-phenylpropan-1-ol). Compound 110: $^1H$ NMR (400 MHz, $CDCl_3$) δ 9.69 (s, 1H), 8.52 (d, J=5.1 Hz, 1H), 7.98 (br d, J=9.9 Hz, 2H), 7.92 (br d, J=5.1 Hz, 1H), 7.81 (s, 1H), 7.59 (s, 1H), 7.52 (br d, J=5.3 Hz, 1H), 7.34 (s, 1H), 7.31-7.17 (m, 4H), 7.13 (br d, J=7.1 Hz, 2H), 4.84 (q, J=6.5 Hz, 1H), 3.33-3.18 (m, 2H). MS (ESI) m/z $(M+H)^+$388.1.

Example 68

Compounds 111-112

(S)-1-(5-(oxazol-2-yl)pyridin-2-yl)-n-(1-oxo-3-phenylpropan-2-yl)-1H-imidazole-5-carboxamide (111)

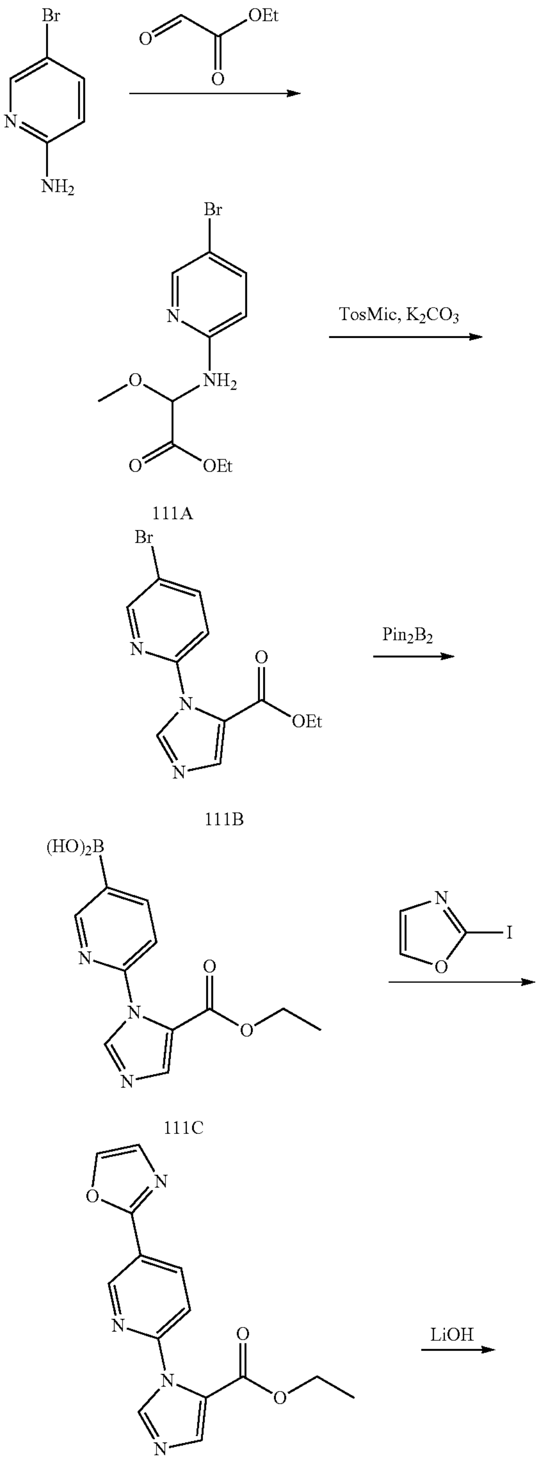

111A

111B

111C

111D

-continued

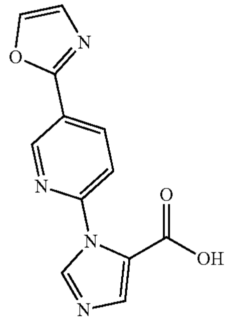

111E

Compound 111E (60 mg, crude, grey solid) was prepared as in Example 110 from the corresponding starting materials, 5-bromopyridin-2-amine. Compound 111E: MS (ESI) m/z $(M+H)^+$257.0. Compound 111 (55 mg, yield: 76.9%, white solid) was prepared as in Example 21 from the corresponding intermediate compounds 111E and 21G ((S)-2-amino-3-phenylpropan-1-ol). Compound 111: $^1$H NMR (400 MHz, $CDCl_3$) δ 9.71 (s, 1H), 9.05 (d, J=1.5 Hz, 1H), 8.42 (dd, J=2.2, 8.4 Hz, 1H), 8.02 (s, 1H), 7.79 (s, 1H), 7.57 (s, 1H), 7.39 (d, J=8.4 Hz, 1H), 7.34 (br d, J=6.4 Hz, 1H), 7.31 (s, 1H), 7.28-7.24 (m, 2H), 7.22-7.17 (m, 1H), 7.14 (br d, J=7.1 Hz, 2H), 4.87 (q, J=6.5 Hz, 1H), 3.24 (d, J=6.4 Hz, 2H). MS (ESI) m/z $(M+H)^+$388.1.

(S)—N-(4-amino-3,4-dioxo-1-phenylbutan-2-yl)-1-(5-(oxazol-2-yl)pyridin-2-yl)-1H-imidazole-5-carboxamide (112)

Compound 112 (20 mg, yield: 48.2%, white solid) was prepared as in Example 5 from the corresponding starting materials, compounds 111E and 12G. $^1$H NMR (400 MHz, DMSO-$d_6$) δ 9.06 (d, J=7.5 Hz, 1H), 8.99 (d, J=1.8 Hz, 1H), 8.39 (dd, J=2.4, 8.4 Hz, 1H), 8.34 (s, 1H), 8.26-8.21 (m, 1H), 8.08 (s, 1H), 7.84 (s, 1H), 7.57 (s, 1H), 7.48 (s, 1H), 7.34 (d, J=8.4 Hz, 1H), 7.31-7.25 (m, 4H), 7.24-7.16 (m, 1H), 7.24-7.16 (m, 1H), 5.28-5.13 (m, 1H), 3.18 (dd, J=3.7, 13.9 Hz, 1H), 2.85 (dd, J=10.3, 13.8 Hz, 1H). MS (ESI) m/z $(M+H)^+$431.1.

Example 69

Compounds 113, 115

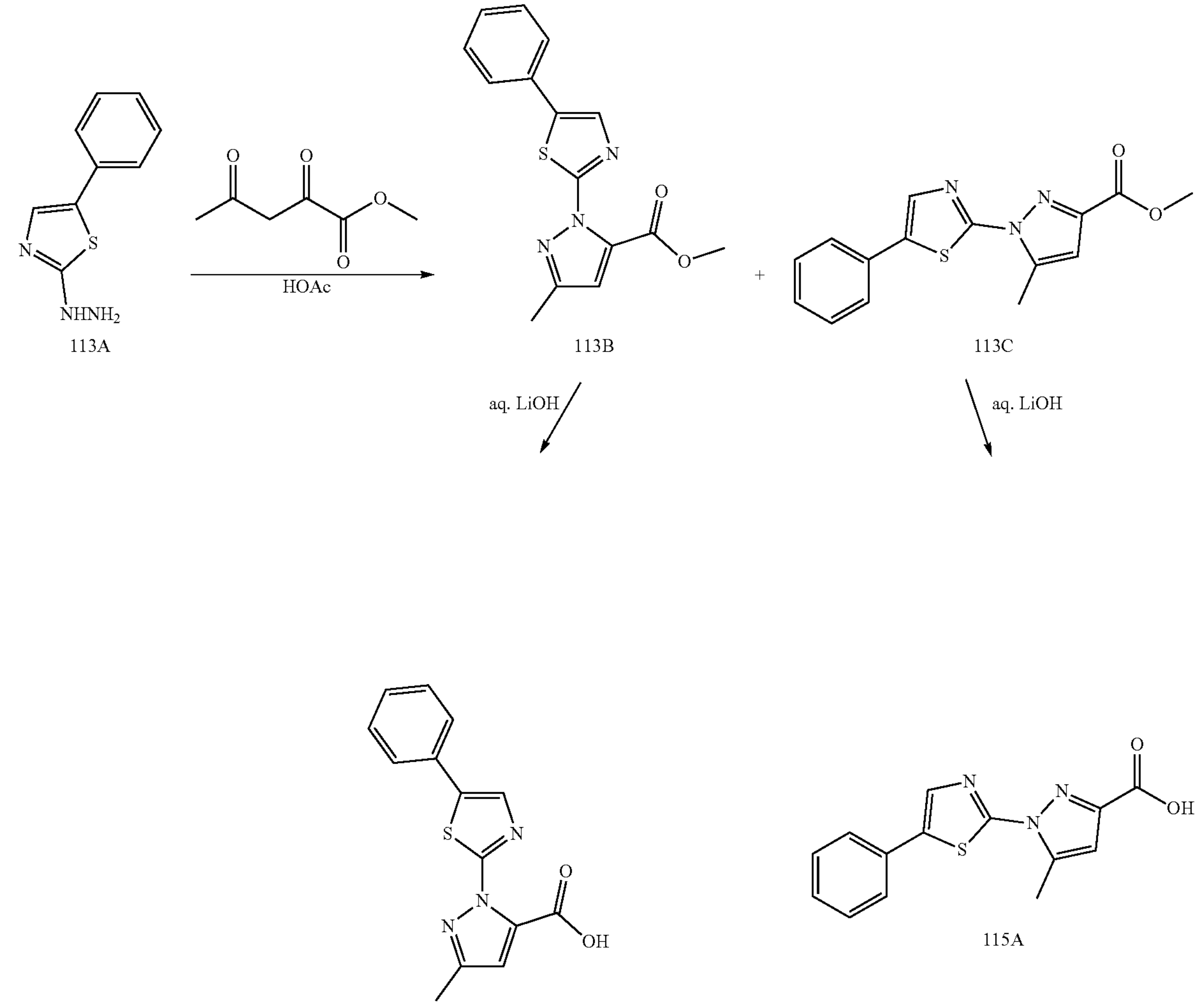

113A

113B

113C

113D

115A (S)—N-(4-amino-3,4-dioxo-1-phenylbutan-2-yl)-3-methyl-1-(5-phenylthiazol-2-yl)-1H-pyrazole-5-carboxamide (113)

5-phenylthiazol-2-amine (850 mg, 4.82 mmol) was added to concentrated hydrochloric acid (5 mL). While being stirred at 0° C., the aqueous solution of $NaNO_2$ (998 mg, 14.5 mmol) in $H_2O$ (3 mL) was dropped slowly into the mixture, and the mixture was stirred for 1 hr. Then hydrochloric acid solution of $SnC_2.2H_2O$ (3.26 g, 14.4 mmol) was added drop-wise slowly, and the mixture was stirred at 25° C. for 3 h. LCMS showed 5-phenylthiazol-2-amine was consumed completely and one peak with desired MS was detected. The reaction mixture was filtered. The filtered cake was wash with water (20 mL), and concentrated under reduced pressure to give the product 113A (1 g, crude) as a yellow solid. MS (ESI) m/z $(M+H)^+$191.9.

A mixture of compound 113A (1 g, 5.23 mmol), methyl 2,4-dioxopentanoate (754 mg, 5.23 mmol) in HOAc (15 mL) was stirred at 120° C. for 1 hr. The reaction mixture was filtered, the filtrate was concentrated under reduced pressure to remove the solvent, and adjusted the pH to 8 9 with the saturated aqueous $NaHCO_3$. Then the mixture was extracted with Ethyl acetate (60 mL×3). The combined organic layers were dried over $Na_2SO_4$, filtered and concentrated under reduced pressure to give a residue. Firstly, the residue was purified by column chromatography (Petroleum ether:Ethyl acetate=50:1 to 10:1) to give the pure compound 113C (300 mg) and the mixture of 113B & 113C (300 mg). And then the mixture of 113B & 113C (300 mg) was purified by preparatory-HPLC (TFA condition) to give 113B (30 mg) and 113C (120 mg) both as a yellow solid.

Compound 113B: $^1H$ NMR (400 MHz, $CDCl_3$) δ 7.79 (br s, 1H), 7.60-7.51 (m, 2H), 7.46-7.38 (m, 2H), 7.38-7.29 (m, 1H), 6.75 (br s, 1H), 4.05-3.71 (m, 3H), 2.54-2.16 (m, 3H). MS (ESI) m/z $(M+H)^+$300.0.

Compound 113C: $^1H$ NMR (400 MHz, $CDCl_3$) δ 7.74 (s, 1H), 7.58-7.53 (m, 2H), 7.46-7.40 (m, 2H), 7.38-7.32 (m, 1H), 7.26 (s, 1H), 6.72 (d, J=0.7 Hz, 1H), 3.96 (s, 3H), 2.75 (s, 3H). MS (ESI) m/z $(M+H)^+$300.0.

To a solution of 113B (30 mg, 100 umol) in THF (5 mL), $H_2O$ (1 mL) was added $LiOH.H_2O$ (6.31 mg, 150 umol). The mixture was stirred at 25° C. for 12 hours. The reaction mixture was added aqueous HCl to adjust the pH ~5. Then the mixture was freezed. Compound 113D (35 mg, crude) was obtained as a white solid. $^1H$ NMR (400 MHz, DMSO-$d_6$) δ 8.07 (s, 1H), 7.68 (d, J=7.3 Hz, 2H), 7.49-7.41 (m, 2H), 7.40-7.32 (m, 1H), 6.79 (s, 1H), 2.25 (s, 3H).

Compound 113 (20 mg, yield: 66.4%, white solid) was prepared as in Example 5 from the corresponding intermediate compounds 113D and 12G. Compound 113: $^1H$ NMR (400 MHz, $CDCl_3$) δ 11.73 (br d, J=5.5 Hz, 1H), 7.55-7.45 (m, 2H), 7.42 (br t, J=7.3 Hz, 2H), 7.38-7.31 (m, 1H), 7.23 (br dd, J=3.9, 8.0 Hz, 6H), 7.03 (s, 1H), 6.80 (br s, 1H), 5.87-5.70 (m, 1H), 5.58 (br s, 1H), 3.43 (br dd, J=4.5, 14.2 Hz, 1H), 3.22 (br dd, J=8.2, 14.3 Hz, 1H), 2.31 (s, 3H). MS (ESI) m/z $(M+H)^+$460.1.

(S)—N-(4-amino-3,4-dioxo-1-phenylbutan-2-yl)-5-methyl-1-(5-phenylthiazol-2-yl)-1H-pyrazole-3-carboxamide (115)

Following the procedure as used for compound 113, compound 115 (62.0 mg, yield: 68.3%, white solid) was prepared from the corresponding intermediate carboxylic acid, compound 115A. Compound 115: $^1H$ NMR (400 MHz, $CDCl_3$) δ 7.71 (s, 1H), 7.56 (d, J=7.3 Hz, 2H), 7.48-7.40 (m, 2H), 7.39-7.33 (m, 2H), 7.33-7.27 (m, 2H), 7.26 (s, 1H), 7.19 (br d, J=6.8 Hz, 2H), 6.76 (br s, 1H), 6.65 (s, 1H), 5.77-5.62 (m, 1H), 5.52 (br s, 1H), 3.43 (dd, J=5.5, 13.9 Hz, 1H), 3.26 (dd, J=7.1, 13.9 Hz, 1H), 2.71 (s, 3H). MS (ESI) m/z $(M+23)^+$460.1.

Example 70

(S)—N-(4-amino-3,4-dioxo-1-phenylbutan-2-yl)-5-methyl-1-(5-phenyloxazol-2-yl)-1H-pyrazole-3-carboxamide (114)

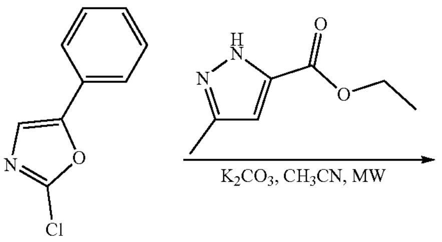

114A

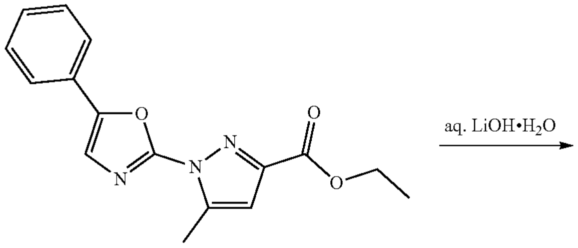

114B

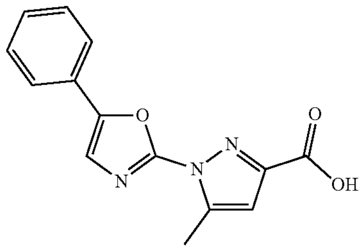

114C

To a solution of 5-phenyloxazole (800 mg, 5.51 mmol) in THF (10 mL) was added n-BuLi (2.5 M, 2.76 mL) drop-wise at −78° C. and stirred for 30 min, then hexachloroethane (1.96 g, 8.27 mmol) in THF (2 mL) was added, the reaction mixture was slowly warmed to 25° C. and stirred for 12 h. The mixture was poured into ice-water (20 mL) and extracted ethyl acetate (10 mL×2), the organic phases were washed with brine (10 mL), dried over $Na_2SO_4$, filtered and concentrated, the residue was purified by silica gel column (Petroleum ether:Ethyl acetate=10:1) to give 114A (900 mg, yield: 90.9%) as yellow oil. $^1H$ NMR (400 MHz, $CDCl_3$-d) δ 7.58 (d, J=7.3 Hz, 2H), 7.45-7.38 (m, 2H), 7.38-7.31 (m, 1H), 7.27 (s, 1H).

A mixture of 114A (90 mg, 501 umol), ethyl 3-methyl-H-pyrazole-5-carboxylate (92.7 mg, 601 umol) and $K_2CO_3$ (103 mg, 752 umol) in $CH_3CN$ (3 mL) was stirred at 120° C. for 2 hr under microwave condition. The mixture was diluted with ethyl acetate (20 mL) and water (20 mL), the organic phase was dried over $Na_2SO_4$, filtered and concentrated, the residue was purified by preparatory-TLC (Petroleum ether:Ethyl acetate=5:1) to give 114B (0.14 g, yield: 60.4%) as yellow oil, $^1$H NMR (400 MHz, $CDCl_3$) δ 7.76-7.67 (m, 2H), 7.47-7.41 (m, 2H), 7.39-7.32 (m, 2H), 6.75 (d, J=0.9 Hz, 1H), 4.44 (q, J=7.2 Hz, 2H), 2.67 (d, J=0.7 Hz, 3H), 1.43 (t, J=7.2 Hz, 3H).

A mixture of 114B (140 mg, 471 umol) and $LiOH.H_2O$ (39.5 mg, 942 umol) in THF (5 mL), $H_2O$ (1 mL) was stirred at 25° C. for 2 h. The organic solvent was removed under vacuum, the water layer was adjusted to pH ~5 with 1N HCl and filtered, the water layer was extracted with DCM (10 mL×3), the organic phases were washed with brine (10 mL), dried over $Na_2SO_4$, filtered and concentrated, the residue combined the filtrate cake to give 114C (120 mg, crude), as white solid. $^1$H NMR (400 MHz, DMSO-$d_6$) δ 7.88 (s, 1H), 7.81-7.71 (m, 2H), 7.52 (t, J=7.7 Hz, 2H), 7.46-7.40 (m, 1H), 6.81 (d, J=0.7 Hz, 1H), 2.62 (s, 3H).

Compound 114 (53 mg, yield: 66.5%, white solid) was prepared as in Example 5 from the corresponding carboxylic acid, compound 114C. Compound 114: $^1$H NMR (400 MHz, DMSO-$d_6$) δ 8.59 (d, J=7.7 Hz, 1H), 8.10 (s, 1H), 7.87 (s, 1H), 7.84 (s, 1H), 7.76 (d, J=7.3 Hz, 2H), 7.52 (t, J=7.7 Hz, 2H), 7.45-7.38 (m, 1H), 7.31-7.22 (m, 4H), 7.19 (qd, J=4.3, 8.8 Hz, 1H), 6.72 (d, J=0.7 Hz, 1H), 5.49-5.40 (m, 1H), 3.25-3.17 (m, 1H), 3.06 (dd, J=9.4, 14.0 Hz, 1H), 2.57 (s, 3H). MS (ESI) m/z $(M+H)^+$444.1.

Example 71

(S)—N-(4-amino-3,4-dioxo-1-phenylbutan-2-yl)-1-(isoquinolin-1-yl)-3-methyl-1H-pyrazole-5-carboxamide (119)

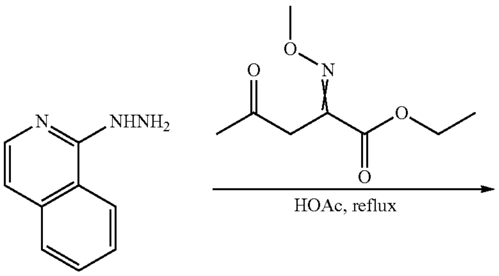

119A

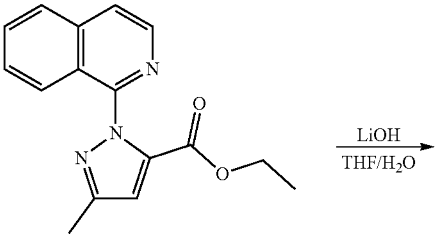

119B

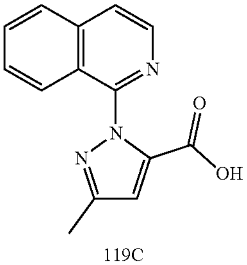

119C

To a mixture of 1-chloroisoquinoline (5.0 g, 30.56 mmol) in dioxane (10.00 mL) was added $NH_2NH_2$—$H_2O$ (305.62 mmol, 15 mL). The mixture was stirred at 80° C. for 16 h. The reaction mixture was washed with $H_2O$ (100 mL). The reaction mixture diluted with MTBE and filtered to give compound 119A (4.27 g, 87.77% yield) as a yellow solid. $^1$H NMR (400 MHz, DMSO-$d_6$) δ 8.16 (d, J=8.3 Hz, 1H), 7.87 (d, J=5.8 Hz, 1H), 7.72-7.65 (m, 1H), 7.64-7.56 (m, 1H), 7.48-7.41 (m, 1H), 6.90 (d, J=5.8 Hz, 1H). MS (ESI) m/z $(M+H)^+$160.1.

A mixture of compound 119A (4.20 g, 26.38 mmol) and ethyl 2-(methoxyimino)-4-oxopentanoate (4.94 g, 26.38 mmol) in HOAc (40.00 mL) was stirred at 120° C. for 48 h. The reaction mixture was concentrated under reduced pressure to remove HOAc. The residue was diluted with $H_2O$ (20 mL) and extracted with ethyl acetate (40 mL). The combined organic layers were washed with brine (40 mL), dried over $Na_2SO_4$, concentrated under reduced pressure to give a residue. The residue was purified by column chromatography ($SiO_2$, Petroleum ether/Ethyl acetate=10/1 to 0:1) to give compound 119B (238.00 mg, 3.08% yield) was obtained as a yellow oil. $^1$H NMR (400 MHz, $CDCl_3$) δ 8.46 (br d, J=5.5 Hz, 1H), 7.92 (d, J=8.2 Hz, 1H), 7.79 (d, J=5.5 Hz, 1H), 7.72 (t, J=7.4 Hz, 1H), 7.67-7.53 (m, 2H), 6.92 (s, 1H), 4.06 (q, J=7.1 Hz, 2H), 2.43 (s, 3H), 0.99 (t, J=7.2 Hz, 3H). MS (ESI) m/z $(M+H)^+$282.

To a solution of compound 119B (238.00 mg, 846.04 umol) in THF (6.00 mL) was added $LiOH.H_2O$ (177.50 mg, 4.23 mmol) in $H_2O$ (2.00 mL). The mixture was stirred at 28° C. for 16 h. The reaction mixture was diluted with $H_2O$ (10 mL) and extracted with MTBE (15 mL×2), the water phase was added 1N HCl to pH ~3~4, extracted with ethyl acetate (15 mL×2). The combined organic layers were washed with brine (15 mL), dried over $Na_2SO_4$, filtered and concentrated under reduced pressure to give intermediate compound 119C (201.00 mg, 92.87% yield) as a yellow solid. Compound 119C: $^1$H NMR (400 MHz, DMSO-$d_6$) δ 8.42 (d, J=5.5 Hz, 1H), 8.12 (d, J=8.2 Hz, 1H), 8.01 (d, J=5.7 Hz, 1H), 7.85 (t, J=7.2 Hz, 1H), 7.69 (t, J=7.4 Hz, 1H), 7.56 (d, J=8.4 Hz, 1H), 6.92 (s, 1H), 2.32 (s, 3H). MS (ESI) m/z $(M+H)^+$254.1.

Compound 119 (20.00 mg, 35.64% yield, light yellow solid) was prepared as in Example 5 from the corresponding intermediate carboxylic acid, compound 119C. Compound 119: $^1$H NMR (400 MHz, $CDCl_3$) δ 8.23 (br d, J=6.2 Hz, 1H), 7.94-7.85 (m, 3H), 7.75 (br t, J=7.8 Hz, 1H), 7.69 (br d, J=5.3 Hz, 1H), 7.62 (br t, J=7.7 Hz, 1H), 7.12 (br d, J=7.1 Hz, 1H), 7.09-7.03 (m, 2H), 6.92 (br d, J=7.1 Hz, 2H), 6.73 (s, 1H), 6.67 (br s, 1H), 5.65-5.59 (m, 1H), 5.51 (br s, 1H), 3.36-3.28 (m, 1H), 3.21-3.14 (m, 1H), 2.41 (s, 3H). MS (ESI) m/z $(M+H)^+$428.1.

Example 72

(S)—N-(4-amino-3,4-dioxo-1-phenylbutan-2-yl)-3-methyl-1-(5-methylpyridin-2-yl)-1H-pyrazole-5-carboxamide (120)

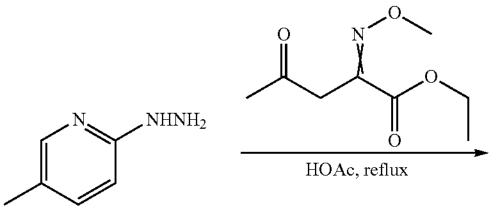

120A

-continued

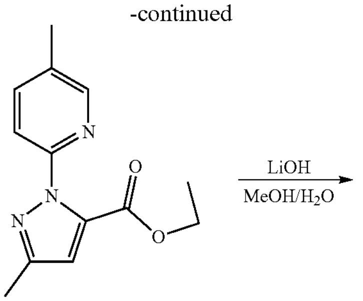

120B

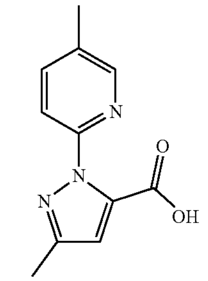

120D

A mixture of 2-fluoro-5-methylpyridine (10.00 g, 89.99 mmol, 9.35 mL) in $NH_2NH_2.H_2O$ (53.00 g, 899.93 mmol, 51.5 mL) was degassed and purged with $N_2$ 3 times, and then the mixture was stirred at 120° C. for 15 h under $N_2$ atmosphere. The reaction mixture was concentrated under reduced pressure to remove solvent. The residue was diluted with $H_2O$ (30 mL) and extracted with ethyl acetate (20 mL×2). The combined organic layers were washed with brine (20 mL×2), dried over $Na_2SO_4$, filtered and concentrated under reduced pressure to give the compound 120A (6.09 g, yield: 54.9%) was obtained as a light pink solid. $^1H$ NMR (400 MHz, $CDCl_3$) δ 7.95 (s, 1H), 7.32 (dd, J=2.0, 8.4 Hz, 1H), 6.63 (d, J=8.4 Hz, 1H), 5.68 (br s, 1H), 2.20 (s, 3H).

A mixture of compound 120A (2 g, 16.24 mmol), ethyl 2-(methoxyimino)-4-oxopentanoate (3.04 g, 16.24 mmol) in HOAc (20 mL) was stirred at 120° C. for 20 h. The reaction mixture was concentrated under reduced pressure to remove solvent. The residue was diluted with $H_2O$ (15 mL) and extracted with ethyl acetate (20 mL×2). The combined organic layers were washed with $NaHCO_3$ (20 mL×3), and then washed with brine (20 mL×2), dried over $Na_2SO_4$, filtered and concentrated under reduced pressure to give a residue. The residue was purified by preparatory-HPLC (HCl condition) to give the compound 120B (340 mg, yield: 8.5%) was obtained as a white solid. Compound 120B: $^1H$ NMR (400 MHz, DMSO-$d_6$) δ 8.27 (s, 1H), 7.82 (dd, J=1.8, 8.3 Hz, 1H), 7.58 (d, J=8.3 Hz, 1H), 6.77 (s, 1H), 4.19 (q, J=7.0 Hz, 2H), 2.35 (s, 3H), 2.28 (s, 3H), 1.14 (t, J=7.0 Hz, 3H).

To a solution of compound 120B (340 mg, 1.39 mmol) in THF (10 mL) was added $LiOH.H_2O$ (291 mg, 6.95 mmol) in $H_2O$ (3 mL). The mixture was stirred at 25° C. for 30 h. The reaction mixture was diluted with $H_2O$ (15 mL) and extracted with MTBE (10 mL). The combined water layers were adjusted to pH ~6 by adding 1N HCl, and then extracted with ethyl acetate (20 mL×2). The combined organic layers were washed with brine (20 mL), dried over $Na_2SO_4$, filtered and concentrated under reduced pressure to give the compound 120D (300 mg, yield: 99.4%) was obtained as a white solid. $^1H$ NMR (400 MHz, DMSO-$d_6$)

δ 13.50 (br s, 1H), 8.26 (s, 1H), 7.79 (dd, J=1.8, 8.2 Hz, 1H), 7.54 (d, J=8.2 Hz, 1H), 6.73 (s, 1H), 2.33 (s, 3H), 2.24 (s, 3H).

Compound 120 (15 mg, yield: 54.1% light yellow solid) was prepared as in Example 5 from the corresponding intermediate carboxylic acid, compound 120D. Compound 120: $^1H$ NMR (400 MHz, DMSO-$d_6$) δ 9.21 (d, J=7.3 Hz, 1H), 8.09 (s, 1H), 8.04 (s, 1H), 7.85 (s, 1H), 7.73 (dd, J=1.6, 8.2 Hz, 1H), 7.44 (d, J=8.3 Hz, 1H), 7.31-7.23 (m, 5H), 6.53 (s, 1H), 5.35-5.26 (m, 1H), 3.16 (dd, J=4.0, 14.1 Hz, 1H), 2.87 (dd, J=9.8, 14.1 Hz, 1H), 2.31 (s, 3H), 2.26 (s, 3H).

Example 73

Compounds 121-122, 445

(S)—N-(4-amino-3,4-dioxo-1-phenylbutan-2-yl)-3-methyl-1-(5-methylpyridin-2-yl)-1H-pyrazole-5-carboxamide (121)

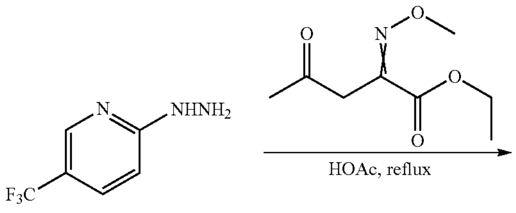

121A

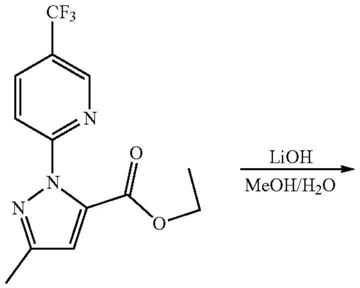

121B

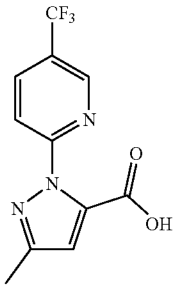

121D

Intermediate compound 121D (650 mg, yield: 89.8%, white solid) was prepared as in Example 120 from the corresponding starting materials, compound 121A and 2-chloro-5-(trifluoromethyl)pyridine. Compound 121A: $^1H$ NMR (400 MHz, DMSO-$d_6$) δ 13.55 (br s, 1H), 8.86 (s, 1H), 8.39 (dd, J=2.3, 8.5 Hz, 1H), 7.91 (d, J=8.4 Hz, 1H), 6.81 (s, 1H), 2.27 (s, 3H).

Compound 121 (35.9 mg, yield: 55.2%, white solid) was prepared as in Example 12 from the corresponding intermediate carboxylic acid, compound 121D. Compound 121: $^1H$ NMR (400 MHz, DMSO-$d_6$) δ 9.15 (d, J=7.3 Hz, 1H), 8.45 (s, 1H), 8.29 (dd, J=2.1, 8.7 Hz, 1H), 8.11 (s, 1H), 7.88-7.80 (m, 2H), 7.28-7.24 (m, 4H), 7.22-7.17 (m, 1H), 6.51 (s, 1H), 5.36-5.28 (m, 1H), 3.14 (dd, J=3.6, 14.0 Hz, 1H), 2.81 (dd, J=9.9, 14.1 Hz, 1H), 2.27 (s, 3H).

(S)—N-(4-(cyclopropylamino)-3,4-dioxo-1-phenylbutan-2-yl)-3-methyl-1-(5-(trifluoromethyl)pyridin-2-yl)-1H-pyrazole-5-carboxamide (122)

Compound 122 (54.1 mg, yield: 87.9%, white solid) was prepared as in Example 20 from the corresponding intermediate carboxylic acid, compound 121D. Compound 122: $^1$H NMR (400 MHz, DMSO-$d_6$) δ 9.16 (d, J=7.3 Hz, 1H), 8.85 (d, J=5.1 Hz, 1H), 8.42 (s, 1H), 8.30 (dd, J=2.1, 8.7 Hz, 1H), 7.83 (d, J=8.6 Hz, 1H), 7.29-7.23 (m, 4H), 7.22-7.16 (m, 1H), 6.51 (s, 1H), 5.38-5.30 (m, 1H), 3.14 (dd, J=3.7, 14.1 Hz, 1H), 2.86-2.72 (m, 2H), 2.27 (s, 3H), 0.68-0.55 (m, 4H).

N-(4-amino-3,4-dioxo-1-phenylbutan-2-yl)-3-methyl-1-(5-(trifluoromethyl)pyridin-2-yl)-1H-pyrazole-5-carboxamide (445)

Compound 445 (140 mg, yield: 47.4%, white solid) was prepared as in compound 121 from the corresponding intermediates 121D and 274D. Compound 445: $^1$H NMR (400 MHz, DMSO-$d_6$) δ 9.16 (d, J=7.5 Hz, 1H), 8.50-8.43 (m, 1H), 8.31 (dd, J=2.2, 8.8 Hz, 1H), 8.12 (s, 1H), 7.90-7.81 (m, 2H), 7.29-7.18 (m, 4H), 6.53 (s, 1H), 5.38-5.29 (m, 1H), 3.16 (dd, J=4.0, 14.1 Hz, 1H), 2.83 (dd, J=9.9, 14.1 Hz, 1H), 2.28 (s, 3H). MS (ESI) m/z $(M+H)^+$446.1.

Example 74

Compounds 123-124

(S)—N-(4-amino-3,4-dioxo-1-phenylbutan-2-yl)-1-(4,6-dimethylpyridin-2-yl)-3-methyl-1H-pyrazole-5-carboxamide (123)

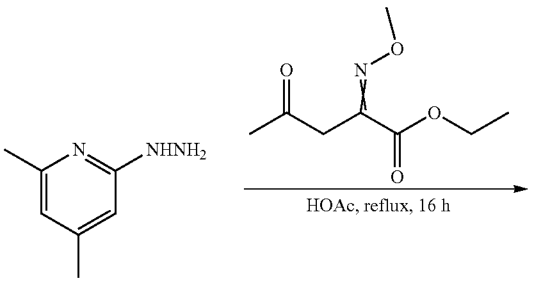

123A

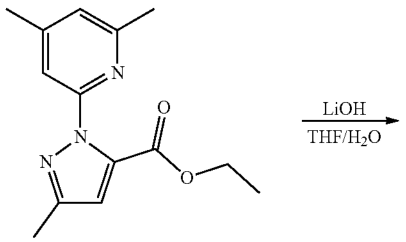

123B

-continued

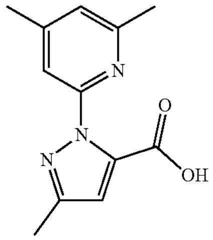

123C

Intermediate compound 123C (210 mg, yield: 78.29%, white solid) was prepared as in Example 120 from the corresponding starting materials, compound 123A and 2-chloro-5-(trifluoromethyl)pyridine. $^1$H NMR (400 MHz, DMSO-$d_6$) δ 7.38 (s, 1H), 7.14 (s, 1H), 6.77 (s, 1H), 2.40 (s, 3H), 2.37 (s, 3H), 2.26 (s, 3H). MS (ESI) m/z $(M+H)^+$232.0.

Compound 123 (40 mg, yield: 38.78%, light yellow solid) was prepared as in Example 5 from the corresponding intermediate carboxylic acid, compound 123C. Compound 123: $^1$H NMR (400 MHz, DMSO-$d_6$) δ 9.13 (d, J=7.3 Hz, 1H), 8.04 (s, 1H), 7.81 (s, 1H), 7.28-7.18 (m, 6H), 6.99 (s, 1H), 6.44 (s, 1H), 5.41-5.21 (m, 1H), 3.12 (dd, J=4.0, 13.9 Hz, 1H), 2.82 (dd, J=9.7, 13.9 Hz, 1H), 2.31 (s, 3H), 2.23 (s, 3H), 2.19 (s, 3H). MS (ESI) m/z $(M+H)^+$406.1.

(S)—N-(4-(cyclopropylamino)-3,4-dioxo-1-phenylbutan-2-yl)-2-methyl-4-phenylthiazole-5-carboxamide (124)

Compound 124 (40 mg, yield: 57.35%, white solid) was prepared as in Example 41 from the corresponding carboxylic acid, 2-methyl-4-phenylthiazole-5-carboxylic acid. $^1$H NMR (400 MHz, $CDCl_3$) δ 7.58-7.50 (m, 2H), 7.49-7.36 (m, 3H), 7.22-7.13 (m, 3H), 6.84 (br s, 1H), 6.80-6.69 (m, 2H), 6.22 (br d, J=6.3 Hz, 1H), 5.58-5.46 (m, 1H), 3.26 (dd, J=4.9, 14.2 Hz, 1H), 2.89 (dd, J=7.5, 14.1 Hz, 1H), 2.79 (qt, J=3.8, 7.4 Hz, 1H), 2.71 (s, 3H), 0.94-0.82 (m, 2H), 0.66-0.55 (m, 2H). MS (ESI) m/z $(M+H)^+$434.1.

Example 75

(S)—N-(4-(cyclopropylamino)-3,4-dioxo-1-phenylbutan-2-yl)-5-methyl-1-(4-phenylthiazol-2-yl)-1H-pyrazole-3-carboxamide (127)

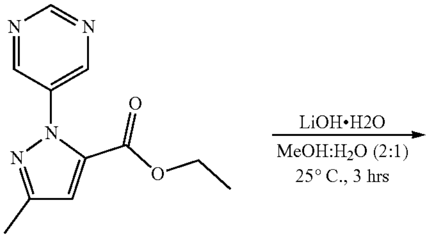

127A

-continued

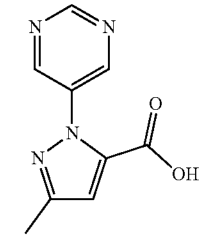

127B

Intermediate compound 127B (150 mg, 94.78% yield, white solid) was prepared as in Example 85 from compound 127A. Compound 127B: $^1H$ NMR (400 MHz, DMSO-$d_6$): δ 9.20 (s, 1H), 8.99 (s, 2H), 6.94 (s, 1H), 2.27 (s, 3H).

Compound 127 (55.3 mg, 45.18% yield, white solid) was prepared as in Example 20 from the corresponding intermediate carboxylic acid, compound 127B. Compound 127: $^1H$ NMR (400 MHz, $CDCl_3$): δ 9.15 (s, 1H), 8.76 (s, 2H), 7.35-7.28 (m, 3H), 7.13-7.09 (m, 2H), 6.95 (br s, 1H), 6.66-6.60 (m, 1H), 6.47 (s, 1H), 5.60-5.54 (m, 1H), 3.46-3.38 (m, 1H), 3.20-3.13 (m, 1H), 2.87-2.77 (m, 1H), 2.35 (s, 3H), 0.92-0.87 (m, 2H), 0.66-0.61 (m, 2H). MS (ESI) m/z $(M+1)^+$419.1.

Example 76

(S)—N-(4-amino-3,4-dioxo-1-phenylbutan-2-yl)-4-phenyl-1H-pyrazole-5-carboxamide (129)

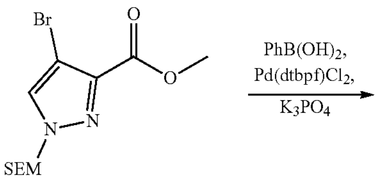

129A

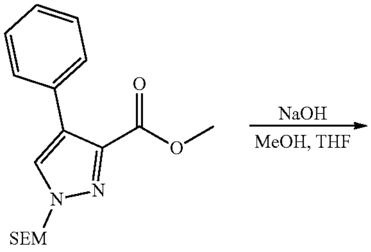

129B

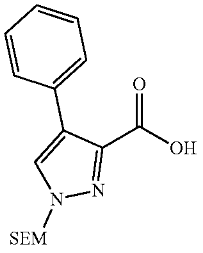

129C

-continued

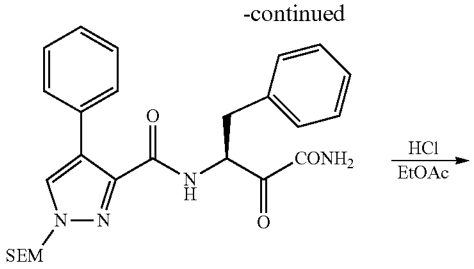

129E

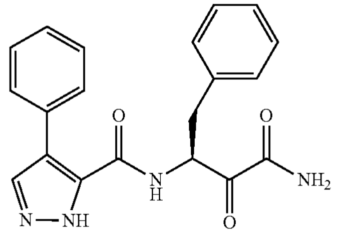

129

To a solution of NaH (1.46 g, 36.59 mmol, 60% purity) in THF (80 mL) was added methyl 4-bromo-1H-pyrazole-3-carboxylate (5.00 g, 24.39 mmol) ith THF (20 mL) at 0° C. After addition, the mixture was warmed to 25° C. and stirred for 2 h. Then the mixture was cooled to 0° C. and a solution of SEM-Cl (4.47 g, 26.83 mmol, 4.8 mL) in THF (100 mL). The mixture was stirred at 25° C. for 12 h. The mixture was diluted with $H_2O$ (200 mL), the organic layer was washed with HCl (1M, 100 mL), saturated $NaHCO_3$ (100 mL), brine (100 mL), dried over $Na_2SO_4$ and concentrated. The residue was purified by column chromatography ($SiO_2$, Petroleum ether/Ethyl acetate=10/1 to 3:1). Compound 129A (3.40 g, yield 41.6%) was obtained as a colorless oil. $^1H$ NMR (400 MHz, DMSO-$d_6$) δ 8.39 (s, 1H), 5.51 (s, 2H), 3.87 (s, 3H), 3.62-3.56 (m, 2H), 0.95-0.81 (m, 2H), 0.07--0.07 (m, 9H).

A mixture of compound 2 (3.40 g, 10.14 mmol), phenylboronic acid (1.48 g, 12.17 mmol), ditert-butyl(cyclopentyl) phosphane; dichloropalladium; iron (660.9 mg, 1.01 mmol), $K_3PO_4$ (6.46 g, 30.42 mmol) in dioxane (30 mL) and $H_2O$ (10 mL) was degassed and purged with $N_2$ 3 times, and then the mixture was stirred at 70° C. for 1 hour under $N_2$ atmosphere. The mixture was concentrated under reduced pressure. The residue was purified by column chromatography ($SiO_2$, Petroleum ether/Ethyl acetate=10/1 to 3:1). Compound 129B (3.00 g, crude) was obtained as a brown oil. $^1H$ NMR (400 MHz, DMSO-$d_6$) δ 8.26 (s, 1H), 7.51-7.32 (m, 5H), 5.53 (s, 2H), 3.78 (s, 3H), 3.67-3.59 (m, 2H), 0.94-0.82 (m, 2H), 0.06--0.07 (m, 9H).

To a solution of compound 129B (3.00 g, 9.02 mmol) in MeOH (100 mL) and THF (100 mL) was added NaOH (2M, 90 mL). The mixture was stirred at 60° C. for 1 hour. The mixture was concentrated and diluted with $H_2O$ (200 mL), the mixture was extracted with ethyl acetate (200 mL), the water phase was added HCl (1M) until pH ~3, then the mixture was extracted with ethyl acetate (200 mL), the organic layer was washed with brine (200 mL), dried over $Na_2SO_4$ and concentrated. Compound 129C (300.0 mg, yield 10.4%) was obtained as a brown oil. $^1H$ NMR (400 MHz, DMSO-$d_6$) δ 8.20 (s, 1H), 7.51-7.47 (m, 2H), 7.43-7.37 (m, 2H), 7.35-7.30 (m, 1H), 5.50 (s, 2H), 3.67-3.61 (m, 2H), 0.92-0.87 (m, 2H), 0.03--0.03 (m, 9H).

Intermediate compound 129E (70.0 mg, crude, colorless oil) was prepared as in Example 5 from the corresponding carboxylic acid, compound 129C. Compound 129E: $^1H$ NMR (400 MHz, DMSO-$d_6$) δ 8.45 (d, J=7.6 Hz, 1H), 8.25-8.21 (m, 1H), 8.20-8.13 (m, 1H), 7.90 (s, 1H), 7.44-7.38 (m, 2H), 7.36-7.19 (m, 8H), 5.51-5.43 (m, 3H), 3.68-3.60 (m, 2H), 3.26-3.18 (m, 1H), 3.08-2.99 (m, 1H), 0.95-0.87 (m, 2H), 0.06--0.05 (m, 9H).

To a solution of compound 129E (70.0 mg, 142.09 umol) in ethyl acetate (10 mL) was added HCl/EtOAc (4M, 710 uL). The mixture was stirred at 25° C. for 3 hours. The mixture was concentrated. The residue was purified by prep-HPLC (HCl condition). Compound 129 (20.0 mg, HCl, yield 34.4%) was obtained as a white solid. $^1$H NMR (400 MHz, $D_2O$) δ 7.74-7.61 (m, 1H), 7.41-7.33 (m, 2H), 7.30-7.09 (m, 10H), 4.54-4.53 (m, 1H), 3.00-2.92 (m, 2H). MS (ESI) m/z $(M+H)^+$363.1.

Example 77

(S)—N-(4-amino-3,4-dioxo-1-phenylbutan-2-yl)-3-methyl-1-(4-(phenoxymethyl)phenyl)-1H-pyrazole-5-carboxamide (131)

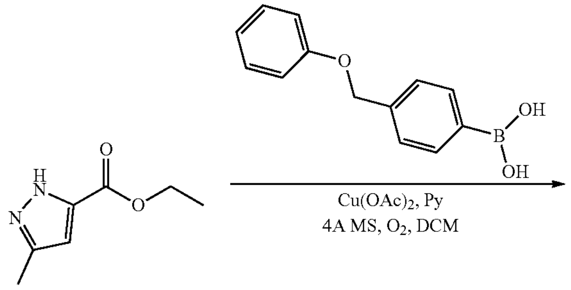

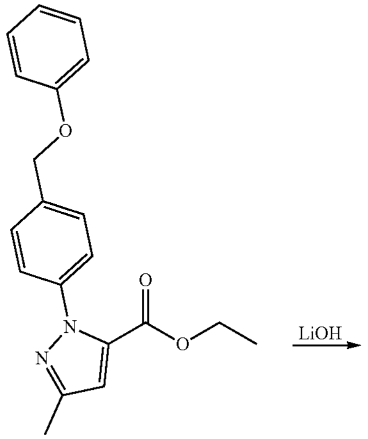

131A

-continued

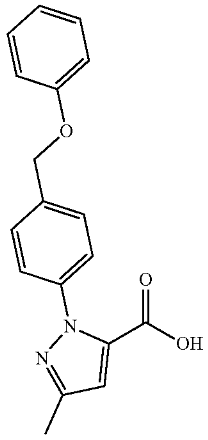

131C

To a mixture of ethyl 3-methyl-1H-pyrazole-5-carboxylate (250 mg, 1.62 mmol), [4-(phenoxymethyl)phenyl]boronic acid (554.7 mg, 2.43 mmol), 4A° MS (8 g) and pyridine (141 mg, 1.78 mmol, 0.15 mL) in DCM (50 mL) was added $Cu(OAc)_2$ (383 mg, 2.11 mmol), the mixture was stirred at 25° C. for 16 h under 02 balloon (15 psi). The reaction mixture was filtered to get rid of 4A° MS and catalyst, and then the filtrate was concentrated. The residue was purified by column chromatography ($SiO_2$, Petroleum ether/Ethyl acetate=5/1) and by preparatory-TLC ($SiO_2$, Petroleum ether/Ethyl acetate=5/1).

Compound 131A (69.3 mg, yield: 13.03%) was obtained as a yellow oil. $^1$H NMR (400 MHz, $CDCl_3$) δ 7.99-7.93 (m, 2H), 7.91-7.82 (m, 2H), 7.80-7.68 (m, 2H), 7.46-7.40 (m, 3H), 5.59 (s, 2H), 4.68 (q, J=7.1 Hz, 2H), 2.81 (s, 3H), 2.05 (s, 1H), 1.69 (t, J=7.2 Hz, 3H). MS (ESI) m/z $(M+H)^+$337.1.

To a solution of compound 131A (69.3 mg, 206.02 umol), in THF (5 mL) and $H_2O$ (3 mL) was added LiOH.$H_2O$ (26 mg, 618.06 umol). After stirred at 25° C. for 3 h, the reaction mixture was added $H_2O$ (10 mL) and extracted with MTBE (20 mL). The organic layer was washed with $H_2O$ (10 mL). The combined aqueous layer was acidified to pH ~1-2 with 1N HCl, extracted with ethyl acetate (20 mL×3), dried over $Na_2SO_4$, filtered and concentrated. Compound 131C (70 mg, crude, white solid): $^1$H NMR (400 MHz, DMSO-$d_6$) δ 13.23 (br s, 1H), 7.57-7.51 (m, 2H), 7.43 (d, J=8.3 Hz, 2H), 7.35-7.27 (m, 2H), 7.05 (d, J=7.8 Hz, 2H), 6.96 (t, J=7.3 Hz, 1H), 6.83 (s, 1H), 5.17 (s, 2H), 2.26 (s, 3H).

Compound 131 (37.2 mg, yield: 45.9%, white solid) was prepared as in Example 5 from the corresponding intermediate carboxylic acid, compound 131C. Compound 131: $^1$H NMR (400 MHz, DMSO-$d_6$) δ 9.12 (br d, J=7.5 Hz, 1H), 8.11 (br s, 1H), 7.86 (s, 1H), 7.39 (br d, J=8.2 Hz, 2H), 7.33-7.26 (m, 6H), 7.23 (br d, J=6.4 Hz, 1H), 7.17 (br d, J=8.2 Hz, 2H), 7.01 (br d, J=8.2 Hz, 2H), 6.93 (t, J=7.4 Hz, 1H), 6.56 (s, 1H), 5.31-5.22 (m, 1H), 5.09 (s, 2H), 3.19 (br dd, J=3.2, 13.8 Hz, 1H), 2.82 (br dd, J=10.9, 13.6 Hz, 1H), 2.23 (s, 3H). MS (ESI) m/z $(M+H)^+$483.1.

Example 78

(S)—N-(4-amino-3,4-dioxo-1-phenylbutan-2-yl)-1-(isoquinolin-4-yl)-3-methyl-1H-pyrazole-5-carboxamide (133)

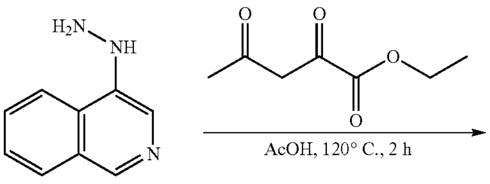

133A

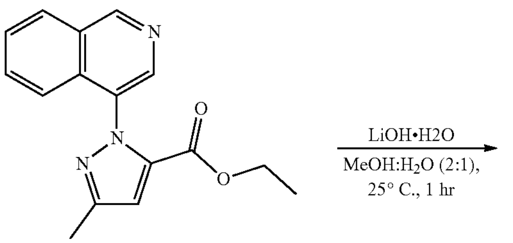

133B

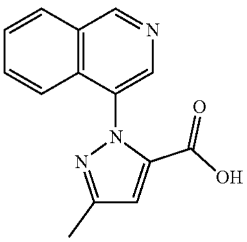

133D

To a solution of isoquinolin-4-amine (1.4 g, 9.71 mmol) in 5N aqueous hydrochloric acid (12 mL) at 0° C. was added a solution of $NaNO_2$ (670 mg, 9.71 mmol) in deionized water (1 mL). The reaction mixture was stirred at 0° C. for 0.5 h and a solution of $SnCl_2.2H_2O$ (5.48 g, 24.28 mmol) dissolved in concentrated hydrochloric acid (5 mL) was added dropwise. The mixture was stirred at 25° C. for 2 h. The mixture was adjusted to pH ~12-14 with 20% aqueous NaOH. The mixture was extracted with 2:1 $CHCl_3$/iPrOH (200 mL). The organic layer was dried ($Na_2SO_4$), filtered, and concentrated in vacuo. The residue was purified by column chromatography ($SiO_2$, Petroleum ether/Ethyl acetate=I/O to 0:1) and then dried under reduced pressure to afford compound 133A (720 mg, 46.55% yield) as a brown solid. $^1H$ NMR (DMSO-$d_6$, 400 MHz): δ 9.95 (br s, 1H), 9.25-9.13 (m, 2H), 8.04-7.95 (m, 2H), 7.88 (d, J=8.8 Hz, 1H), 7.26 (d, J=7.6 Hz, 1H), 7.28-7.23 (m, 1H).

To a mixture of compound 133A (620 mg, 3.89 mmol) and ethyl 2,4-dioxopentanoate (615.9 mg, 3.89 mmol) in AcOH (5 mL) was degassed and purged with $N_2$ for 3 times, and then the mixture was stirred at 120° C. for 2 hours under $N_2$ atmosphere. The reaction mixture was concentrated under reduced pressure to remove AcOH. The residue was diluted with EtOAc 10 mL and adjusted with saturated $NaHCO_3$ and then finally extracted with EtOAc (30 mL×3). The combined organic layers were dried by $Na_2SO_4$, filtered and concentrated under reduced pressure to give a crude product. The reaction solution was purified by column chromatography ($SiO_2$, Petroleum ether/Ethyl acetate=I/O to 0/1) to give compound 133B (600.00 mg, 45.16% yield) as a yellow oil. Compound 133B: $^1H$ NMR ($CDCl_3$, 400 MHz): δ 9.34 (s, 1H), 8.54 (s, 1H), 8.07 (d, J=7.6 Hz, 1H), 7.72-7.61 (m, 2H), 7.37 (d, J=8.0 Hz, 1H), 6.96 (s, 1H), 4.05 (q, J=7.2 Hz, 2H), 2.42 (s, 3H), 0.98 (t, J=7.2 Hz, 3H). MS (ESI) m/z $(M+1)^+$282.1.

To a mixture of 133B (200 mg, 711 umol) in MeOH (10 mL) and $H_2O$ (5 mL) was added $LiOH.H_2O$ (119.3 mg, 2.84 mmol) in one portion and the mixture was stirred at 25° C. for 1 hour. The reaction mixture was concentrated under reduced pressure to remove MeOH. The residue was diluted with $H_2O$ (5 mL), adjusted to pH ~3 with 1N HCl, and then extracted with EtOAc (40 mL×3). The combined organic layers were dried over anhydrous $Na_2SO_4$, filtered and concentrated under reduced pressure to afford intermediate compound 133D (150 mg, 75.43% yield) as a yellow solid. $^1H$ NMR (DMSO-$d_6$, 400 MHz): δ9.45 (s, 1H), 8.54 (s, 1H), 8.28 (d, J=7.6 Hz, 1H), 7.86-7.73 (m, 2H), 7.27 (d, J=8.4 Hz, 1H), 6.99 (s, 1H), 2.33 (s, 3H). MS (ESI) m/z $(M+1)^+$254.0.

Compound 133 (22.2 mg, 31.49% yield, white solid) was prepared as in Example 5 from the corresponding intermediate carboxylic acid, compound 133D. Compound 133: $^1H$ NMR ($CDCl_3$, 400 MHz): δ 9.30 (s, 1H), 8.46 (s, 1H), 8.06 (d, J=8.0 Hz, 1H), 7.73-7.63 (m, 2H), 7.47 (d, J=8.4 Hz, 1H), 7.26-7.24 (m, 3H), 6.97-6.95 (m, 2H), 6.66 (br s, 1H), 6.59 (s, 1H), 6.48 (d, J=7.2 Hz, 1H), 5.65 (br s, 1H), 5.41-5.36 (m, 1H), 3.28-3.24 (m, 1H), 3.11-3.06 (m, 1H), 2.40 (s, 3H). MS (ESI) m/z $(M+H)^+$428.1.

Example 79

(S)—N-(4-amino-3,4-dioxo-1-phenylbutan-2-yl)-3-methyl-1-(pyridin-3-yl)-1H-pyrazole-5-carboxamide (136)

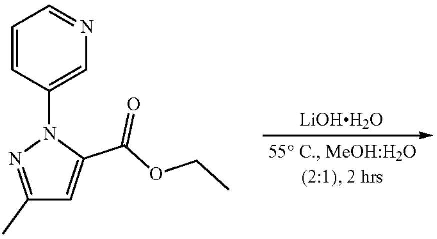

136A

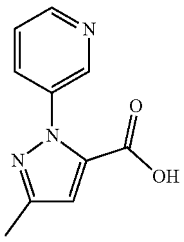

136C

To a solution of ethyl 3-methyl-1-(pyridin-3-yl)-1H-pyrazole-5-carboxylate (2.0 g, 12.97 mmol) and pyridin-3-ylboronic acid (1.59 g, 12.97 mmol) in pyridine (30 mL) was added $Cu(OAc)_2$ (1.18 g, 6.49 mmol). The mixture was stirred at 55° C. for 18 hrs. The mixture filtered and concentrated in vacuum. The residue was purified by flash silica gel chromatography (ISCO®; 80 g SepaFlash® Silica Flash Column, Eluent of 050% Ethyl acetate/Petroleum ether gradient @ 40 mL/min). Compound 136A (850 mg, 28.34% yield, white solid): $^1$H NMR (400 MHz, $CDCl_3$): δ 8.69 (d, J=2.0 Hz, 1H), 8.65-8.62 (m, 1H), 7.80-7.77 (m, 1H), 7.42-7.38 (m, 1H), 6.86 (s, 1H), 4.27-4.21 (m, 2H), 2.37 (s, 3H), 1.27-1.23 (m, 3H).

Compound 136C (160 mg, 60.57% yield, white solid) was prepared as in Example 85. Compound 136C: $^1$H NMR (400 MHz, DMSO-$d_6$): δ 8.65-8.55 (m, 2H), 7.91-7.85 (m, 1H), 7.53-7.47 (m, 1H), 6.88 (s, 1H), 2.26 (s, 3H).

Compound 136 (46.2 mg, 54.66% yield, yellow solid) was prepared as in Example 5 from the corresponding intermediate compounds 136C and 12G. Compound 136: $^1$H NMR (400 MHz, $CDCl_3$) δ 8.61 (d, J=2.4 Hz, 1H), 8.58-8.55 (m, 1H), 7.74-7.69 (m, 1H), 7.36-7.28 (m, 4H), 7.12-7.07 (m, 2H), 6.79 (br s, 1H), 6.55-6.48 (m, 1H), 6.43 (s, 1H), 5.69 (br s, 1H), 5.56-5.49 (m, 1H), 3.43-3.36 (m, 1H), 3.20-3.13 (m, 1H), 2.33 (s, 3H). MS (ESI) m/z $(M+H)^+$ 378.1.

Example 80

(S)—N-(4-amino-3,4-dioxo-1-phenylbutan-2-yl)-3-methyl-1-(pyrimidin-5-yl)-1H-pyrazole-5-carboxamide (138)

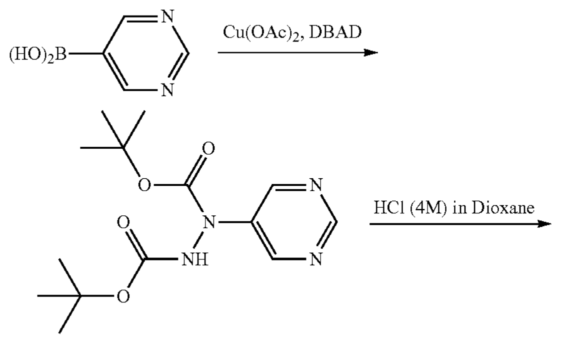

138A

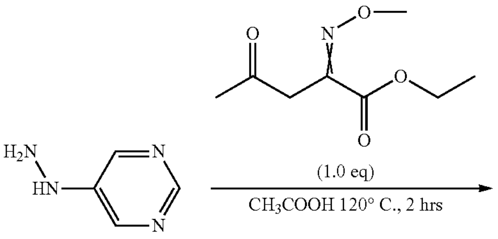

138B

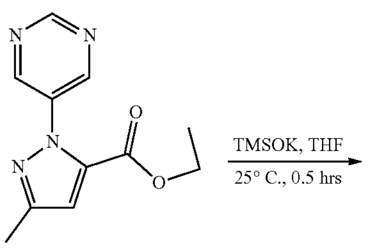

138C

-continued

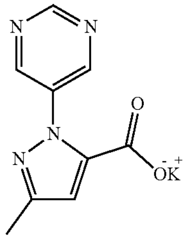

138D

To a solution of pyrimidin-5-ylboronic acid (5.00 g, 40.35 mmol) in MeOH (32 mL) was added $Cu(OAc)_2$ (732.8 mg, 4.04 mmol) and DBAD (9.29 g, 40.35 mmol). The resulting mixture was stirred at 60° C. for 1 hour. The reaction mixture was cooled to 25° C., concentrated under reduced pressure, diluted with water (50 mL), and extracted with ethyl acetate (80 mL×3). The extract was dried over anhydrous $Na_2SO_4$ and concentrated under reduced pressure to give the title compound as yellow oil, which was used in the next step without purification. Compound 138A (9.00 g, 71.87% yield) was obtained as a yellow oil. $^1$H NMR (400 MHz, $CDCl_3$) δ 8.96 (s, 1H), 8.89 (br s, 1H), 1.53-1.50 (m, 18H).

To a solution of compound 138A (9.00 g, 25.00 mmol) in 1,4-dioxane (60 mL) was added 4M HCl 1,4-dioxane (60 mL) and the mixture was stirred at room-temperature for 30 hours. The suspension was filtered, and the residue was washed with ethyl acetate (100 mL×2) and dried under reduced pressure to afford the title compound (3.45 g, crude), which was used in the next step without purification. Compound 138B (3.45 g, 81.17% yield, HCl) was obtained as a white solid. $^1$H NMR (400 MHz, DMSO-$d_6$) δ 8.80 (s, 1H), 8.61 (s, 2H).

To a solution of compound 138B (800.0 mg, 5.46 mmol, HCl) in $CH_3COOH$ (12 mL) was added ethyl 2-(methoxyimino)-4-oxopentanoate (1.02 g, 5.46 mmo), then the mixture was stirred at 120° C. for 2 hours. The mixture was diluted with $CH_2Cl_2$ (70 mL) and washed by saturated sodium bicarbonate (20 mL×2) and saturated brine (20 mL×2), the organic layer was dried over anhydrous $Na_2SO_4$, filtered and concentrated in vacuum. The residue was purified by flash column chromatography ($SiO_2$, petroleum ether:ethyl acetate=10/1 to 3/1). Compound 138C (250.0 mg, 19.72% yield) was obtained as a white solid.

To a solution of compound 138C (50.0 mg, 215.29 umol) in THF (3.00 mL) was added TMSOK (55.2 mg, 430.58 umol), then the mixture was stirred at 25° C. for 0.5 hour. The mixture was diluted with petroleum ethyl (20 mL) and the precipitate was filtered to give intermediate compound 138D (45.0 mg, 86.27% yield) as a white solid. MS (ESI) m/z $(M+1)^+$204.9.

Compound 138 (10.0 mg, 14.63% yield) was prepared as in Example 5 from the corresponding intermediate carboxylic acid, compound 138D. Compound 138: $^1$H NMR (400 MHz, $CDCl_3$): δ 9.15 (s, 1H), 8.78 (s, 2H), 7.35-7.31 (m, 3H), 7.13 (d, J=6.4 Hz, 2H), 6.82 (s, 1H), 6.58 (d, J=7.2 Hz, 1H), 6.47 (s, 1H), 5.57-5.52 (m, 1H), 5.46-5.58 (m, 1H), 3.45-3.40 (m, 1H), 3.21-3.15 (m, 1H), 2.35 (s, 3H). MS (ESI) m/z $(M+1)^+$379.1.

Example 81

(S)—N-(4-amino-3,4-dioxo-1-phenylbutan-2-yl)-5-(2H-indazol-2-yl)-3-methylisoxazole-4-carboxamide (139)

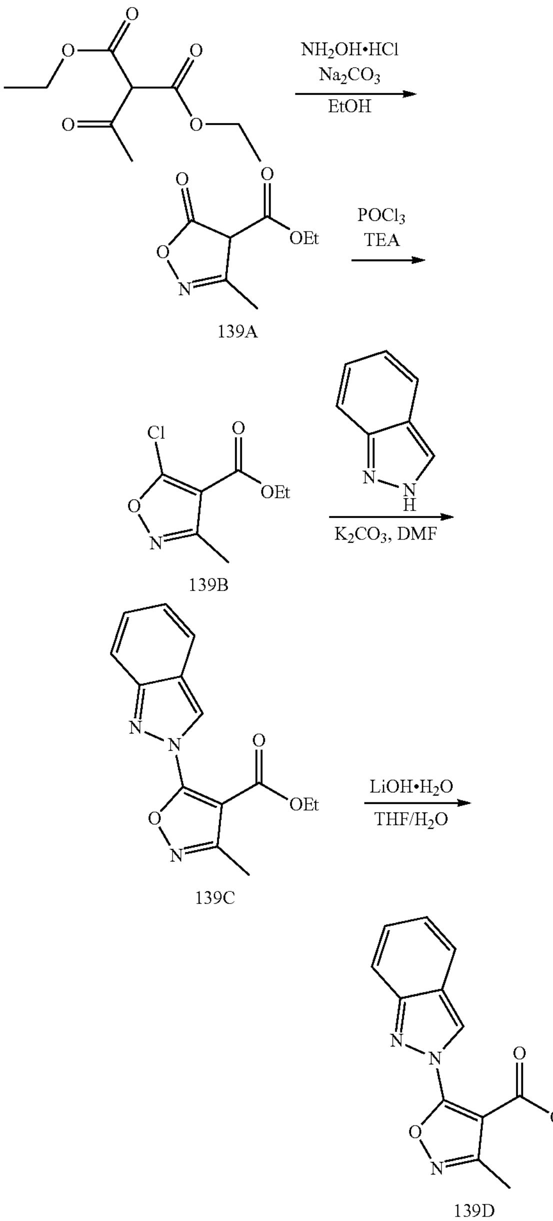

139A

139B

139C

139D

To a solution of diethyl 2-acetylmalonate (5 g, 24.7 mmol) in EtOH (50 mL) was added $NH_2OH.HCl$ (1.9 g, 27.2 mmol) and $Na_2CO_3$ (1.3 g, 12.4 mmol) in one portion, the mixture was stirred at 90° C. for 2 hours. Then the contents were poured into ice-cold water (6 mL), and then filtered to give intermediate compound 139A (3.2 g, yield: 75.6%) as a pale yellow solid. $^1H$ NMR (400 MHz, $CDCl_3$) δ 4.37 (q, J=7.0 Hz, 2H), 2.43-2.37 (m, 3H), 1.38 (t, J=7.2 Hz, 3H). MS (ESI) m/z $(M+H)^+$126.2.

To compound 139A (3 g, 17.5 mmol) was added $POCl_3$ (21.5 g, 140.2 mmol, 13 mL) in one portion. Then TEA (1.8 g, 17.5 mmol) were added. The mixture was stirred at 110° C. for 24 hours under $N_2$. Then ice water (15 mL) was added in to the mixture, and the aqueous phase was extracted with EtOAc (25 mL×3), the combined organic layer was washed with brine, dried over $Na_2SO_4$, and concentrated to give intermediate compound 139B (2.6 g, 13.7 mmol, yield: 78.2%) as brown oil. $^1H$ NMR (400 MHz, $CDCl_3$) δ 4.36 (q, J=7.1 Hz, 2H), 2.48 (s, 3H), 1.38 (t, J=7.2 Hz, 5H).

To a mixture of compound 139B (400 mg, 2.1 mmol) and 2H-indazole (299 mg, 2.5 mmol) in DMF (3 mL) was added $K_2CO_3$ (1.2 g, 8.4 mmol) in one portion. The mixture was stirred at 80° C. for 12 hours. Then $H_2O$ (9 mL) was added into the mixture, and the aqueous phase was extracted with EtOAc (15 mL×3), and the combined organic layer was concentrated to give a residue. The residue was purified by column chromatography ($SiO_2$, Petroleum ether:Ethyl acetate=300:1 to 40:1) to give compound 139C (340 mg, yield: 59.4%) as a pale yellow solid. $^1H$ NMR (400 MHz, $CDCl_3$) δ 8.33 (s, 1H), 7.82 (d, J=7.9 Hz, 1H), 7.68 (d, J=8.8 Hz, 1H), 7.57-7.51 (m, 1H), 7.35 (t, J=7.7 Hz, 1H), 4.24 (q, J=7.0 Hz, 2H), 2.56 (s, 3H), 1.13 (t, J=7.2 Hz, 3H).

To a solution of compound 139C (100 mg, 368.6 umol) in THF (2 mL) and $H_2O$ (500 uL) was added $LiOH.H_2O$ (15.5 mg, 368.6 umol) in one portion. The mixture was stirred at 25° C. for 12 hours. Then the pH of the aqueous phase was adjusted to about 5 by adding HCl (1M), and the residue concentrated on a rotary evaporator to give intermediate compound 139D (83 mg, yield: 92.6%) as a white solid. $^1H$ NMR (400 MHz, DMSO-d6) δ 8.62 (s, 1H), 7.94 (d, J=7.9 Hz, 1H), 7.59 (d, J=3.5 Hz, 2H), 7.41-7.35 (m, 1H), 3.30 (br s, 3H). MS (ESI) m/z $(M+H)^+$243.9.

Compound 139 (18 mg, yield: 24.8%, white solid) was prepared as in Example 5 from the corresponding intermediate carboxylic acid, compound 139D. Compound 139: $^1H$ NMR (400 MHz, $CDCl_3$) δ 10.32 (br d, J=5.7 Hz, 1H), 8.17 (d, J=8.6 Hz, 1H), 7.93 (s, 1H), 7.81 (d, J=7.9 Hz, 1H), 7.65 (t, J=7.4 Hz, 1H), 7.43 (t, J=7.5 Hz, 1H), 7.19-7.12 (m, 5H), 6.77 (br s, 1H), 5.77-5.69 (m, 1H), 5.49 (br s, 1H), 3.42 (dd, J=5.1, 14.3 Hz, 1H), 3.20 (dd, J=7.9, 14.3 Hz, 1H), 2.57 (s, 3H). MS (ESI) m/z $(M+H)^+$418.0.

Example 82 methyl (s)-(3-(5-((4-amino-3,4-dioxo-1-phenylbutan-2-yl)carbamoyl)-3-methyl-1H-pyrazol-1-yl)benzyl)carbamate (140)

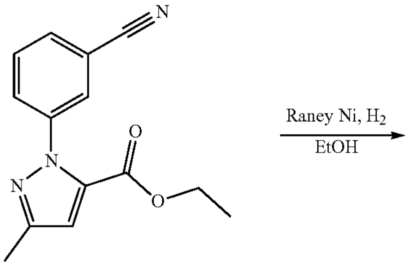

140A

-continued

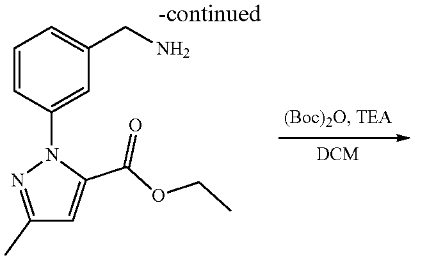

140B

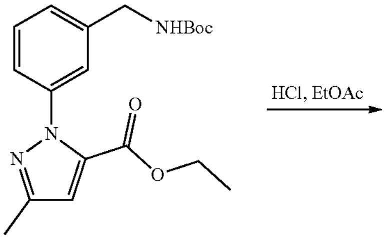

140C

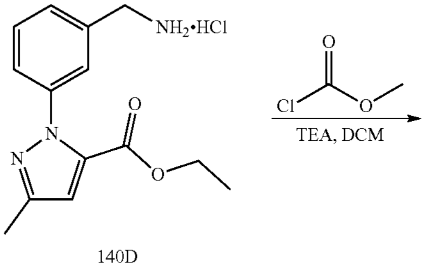

140D

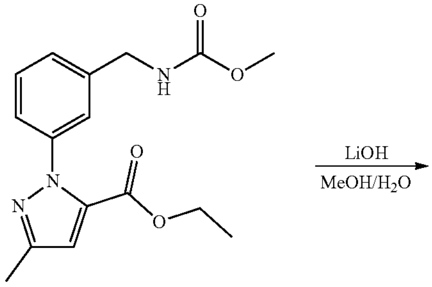

140E

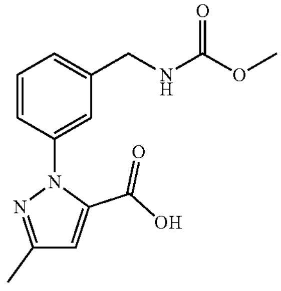

140F

To a solution of 3-hydrazinylbenzonitrile (30.0 g, 176.9 mmol, HCl salt) in HOAc (500 mL) was added ethyl 2-methoxyimino-4-oxo-pentanoate (33.1 g, 176.9 mmol). The mixture was stirred at 100° C. for 12 hours. The mixture was concentrated, diluted with ethyl acetate (200 mL), washed with $NaHCO_3$ (aqueous, 200 mL), brine (200 mL), dried over $Na_2SO_4$ and concentrated. The residue was purified by column chromatography ($SiO_2$, Petroleum ether/Ethyl acetate=1:0 to 5:1). The product obtained was triturated with Petroleum ether/Ethyl acetate=10:1 (100 mL) and filtered. Compound 140A (20.0 g, yield 44.3%) was obtained as a white solid. $^1$H NMR (400 MHz, DMSO-$d_6$) δ 8.05-8.02 (m, 1H), 7.93-7.88 (m, 1H), 7.83-7.78 (m, 1H), 7.70-7.63 (m, 1H), 6.94 (s, 1H), 4.21-4.13 (m, 2H), 2.26 (s, 3H), 1.19-1.11 (m, 3H).

To a solution of compound 140A (9.00 g, 35.26 mmol) in MeOH (500 mL) was added Raney-Ni (1.51 g) and $NH_3.H_2O$ (4 mL). The mixture was stirred at 25° C. under $H_2$ at 40 psi for 12 hours. The mixture was concentrated, diluted with ethyl acetate (500 mL), washed with HCl (500 mL), the water phase was added $NaHCO_3$ (aqueous) until pH ~11. Then the mixture was extracted with ethyl acetate (500 mL), washed with brine (500 mL), dried over $Na_2SO_4$ and concentrated to afford intermediate compound 140B (15 g, crude) as a yellow oil.

To a solution of compound 140B (9.6 g, 37.06 mmol) in DCM (100 mL) was added TEA (7 mL, 55.6 mmol), then $Boc_2O$ (9 mL, 40.77 mmol) was added to the mixture and the mixture was stirred at 25° C. for 12 h. The reaction was washed with citric acid (10%, 100 mL), extracted with DCM (100 mL×2), washed with $H_2O$ (100 mL), dried over anhydrous $Na_2SO_4$, filtered, evaporated under reduced pressure. The crude product was purified by Flash Column Chromatography (Petroleum Ether/Ethyl Acetate=5/1) to afford compound 140C (8.5 g, yield 63.8%) as yellow oil. $^1$H NMR (DMSO-$d_6$, 400 MHz) δ 7.50-7.44 (m, 1H), 7.43-7.37 (m, 1H), 7.32-7.24 (m, 3H), 6.88 (s, 1H), 4.20-4.13 (m, 4H), 2.27 (s, 3H), 1.37 (s, 9H), 1.20-1.14 (m, 3H).

To a suspension of compound 140C (4.5 g, 13.03 mmol) in EA (350 mL) was added HCl/EtOAc (4 M, 35 mL) and the mixture was stirred at 25° C. for 2 h. The reaction was evaporated under reduced pressure to afford compound 140D (3.3 g, yield 89.9%, HCl) as white solid, which was used directly in next step.

To a solution of compound 140D (1 g, 3.4 mmol, HCl) in DCM (20 mL) was added TEA (1.4 mL, 10.1 mmol), followed by compound methylchloroformate (1.6 mL, 20.1 mmol), then the mixture was stirred at 25° C. for 1 h. The reaction was diluted with $H_2O$ (10 mL), the mixture was extracted DCM (20 mL×2). The organic layer was collected, washed with brine (20 mL×3), dried over anhydrous $Na_2SO_4$, filtered, and concentrated under reduced pressure. The product was purified by Flash Column Chromatography (Petroleum Ether/Ethyl Acetate, 0 to 10/1) to afford compound 140E (400 mg, yield 37.3%) was obtained as white solid. $^1$H NMR (DMSO-$d_6$, 400 MHz) δ 7.77 (br t, J=6.2 Hz, 1H), 7.43-7.38 (m, 1H), 7.33-7.25 (m, 3H), 6.88 (s, 1H), 4.23 (d, J=6.2 Hz, 2H), 4.16 (q, J=7.1 Hz, 2H), 3.55 (s, 3H), 2.26 (s, 3H), 1.14 (t, J=7.1 Hz, 3H).

Compound 140F (230 mg, yield 64.6%, white solid) was prepared as in Example 85 from the intermediate compound 140E. $^1$H NMR (DMSO-d6, 400 MHz) δ 7.76 (br t, J=6.1 Hz, 1H), 7.42-7.35 (m, 1H), 7.31-7.22 (m, 3H), 6.82 (s, 1H), 4.23 (br d, J=6.2 Hz, 2H), 3.55 (s, 3H), 2.25 (s, 3H)

Compound 140 (35 mg, yield 21.1%, white solid) was prepared as in Example 5 from the corresponding intermediate carboxylic acid, compound 140F. Compound 140: $^1$H NMR ($CD_3CN$, 400 MHz) δ 7.40-7.17 (m, 10H), 7.07 (br d, J=18.3 Hz, 2H), 6.47 (br s, 1H), 6.26 (br s, 1H), 6.09 (br s, 1H), 5.34 (br s, 1H), 4.29 (br s, 2H), 3.60 (br s, 3H), 3.27 (br d, J=9.5 Hz, 1H), 2.99-2.85 (m, 1H), 2.27 (br s, 3H). MS (ESI) m/z $(M+H)^+$464.2.

Example 83

(S)—N-(4-amino-3,4-dioxo-1-phenylbutan-2-yl)-1-(3-(benzamidomethyl)phenyl)-3-methyl-1H-pyrazole-5-carboxamide (141)

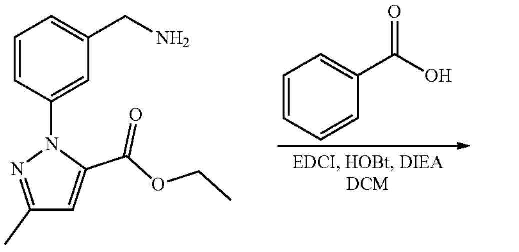

140D

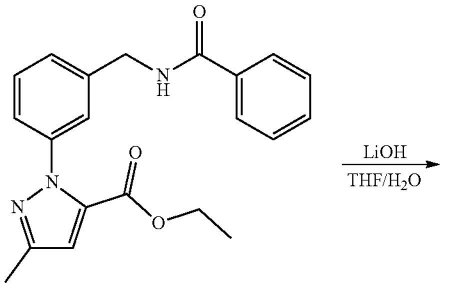

141A

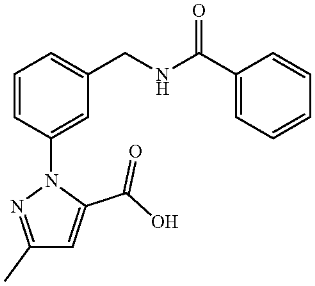

141B

To a solution of compound 140D (300 mg, 1.22 mmol) and benzoic acid (150 mg, 1.22 mmol) in DCM (10 mL) was added HOBt (330 mg, 2.44 mmol), DIEA (0.5 mL, 3.05 mmol) and EDCI (470 mg, 2.44 mmol). The mixture was stirred at 25° C. for 12 h. The solvent was removed in vacuo. The residue was dissolved in EtOAc (20 mL), washed with 1N HCl (20 mL). The organics were collected, washed with saturated $NaHCO_3$ (20 mL). The organics were collected, washed with brine (20 mL), dried with $Na_2SO_4$, filtered and concentrated to afford compound 141A (400 mg, crude) as yellow oil. MS (ESI) m/z $(M+H)^+$364.0.

To a solution of compound 141A (400 mg, 1.14 mmol) in THF (5 mL) and $H_2O$ (5 mL) was added $LiOH.H_2O$ (241 mg, 5.72 mmol). The mixture was stirred at 25° C. for 12 h. The reaction was acidified with 1N HCl to pH ~4, extracted with EtOAc (15 mL×2). The organics were collected and concentrated. The residue was purified by preparatory-HPLC (Neutral conditions) to afford compound 141B (100 mg, yield: 26.16%) as white solid. MS (ESI) m/z $(M+Na)^+$ 358.0.

Compound 141 (4.4 mg, yield: 14.40%, white solid) was prepared as in Example 5 from the corresponding intermediate carboxylic acid, compound 141B. Compound 141: MS (ESI) m/z $(M+H)^+$510.0. $^1H$ NMR (400 MHz, DMSO-$d_6$) (8.86-8.68 (m, 2H), 7.94-7.88 (m, 2H), 7.84-7.57 (m, 2H), 7.54-7.20 (m, 11H), 7.11-6.99 (m, 1H), 6.55 (s, 1H), 5.33-5.24 (m, 1H), 4.56-4.48 (m, 2H), 3.26-3.18 (m, 1H), 2.95-2.86 (m, 1H), 2.25 (s, 3H).

Example 84

(S)—N-(4-amino-3,4-dioxo-1-phenylbutan-2-yl)-3-methyl-1-(3-((3-phenylpropanamido)methyl)phenyl)-1H-pyrazole-5-carboxamide (142)

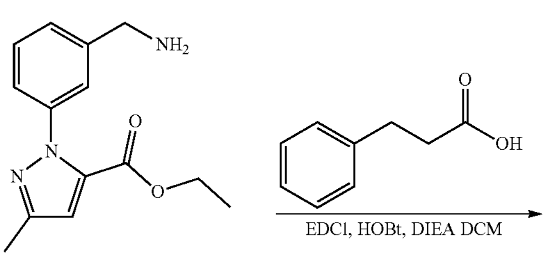

140D

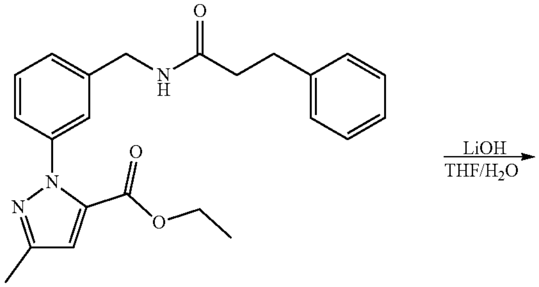

142A

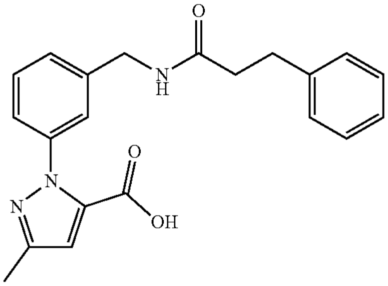

142B

To a solution of compound 140D (500 mg, 2.04 mmol) and 3-phenylpropanoic acid (310 mg, 2.04 mmol) in DCM (20 mL) was added DIEA (0.9 mL, 5.10 mmol), HOBt (552 mg, 4.08 mmol) and EDCI (783 mg, 4.08 mmol). The mixture was stirred at 25° C. for 12 h. The solvent was removed in vacuo. The residue was dissolved in EtOAc (30 mL), washed with 1N HCl (30 mL). The organics were collected, washed with saturated (30 mL), brine (30 mL), dried with $Na_2SO_4$, filtered, collected and dried in vacuo to afford intermediate compound 22 (700 mg, crude) as yellow oil. MS (ESI) m/z $(M+Na)^+$414.0.

To a solution of compound 142A (700 mg, 1.85 mmol) in THF (10 mL) and $H_2O$ (10 mL) was added $LiOH.H_2O$ (390 mg, 9.27 mmol). The mixture was stirred at 25° C. for 12 h. The residue was acidified with 1N HCl to pH ~4. The solution was extracted with EtOAc (20 mL×2). The organics were collected and concentrated. The residue was purified by preparatory-HPLC (Neutral) to afford compound 142B (210 mg, yield: 31.24%) as white solid. MS (ESI) m/z $(M+Na)^+$386.0.

Compound 142 (49.5 mg, yield: 37.88%, white solid) was prepared as in Example 5 from the corresponding intermediate carboxylic acid, compound 142B. Compound 142: MS (ESI) m/z $(M+H)^+$538.2. $^1$H NMR (400 MHz, DMSO-$d_6$) (8.80-8.68 (m, 1H), 8.18-8.08 (m, 1H), 7.88-7.54 (m, 2H), 7.33-7.02 (m, 15H), 6.59-6.49 (m, 1H), 5.33-5.26 (m, 1H), 4.32-4.25 (m, 2H), 3.26-3.20 (m, 1H), 2.95-2.90 (m, 1H), 2.90-2.85 (m, 2H), 2.49-2.45 (m, 2H), 2.28-2.22 (m, 3H).

Example 85

(S)-1-(3-(acetamidomethyl)phenyl)-N-(4-amino-3,4-dioxo-1-phenylbutan-2-yl)-3-methyl-1H-pyrazole-5-carboxamide (143)

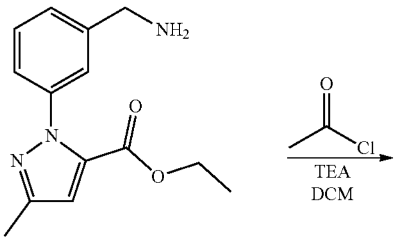

140D

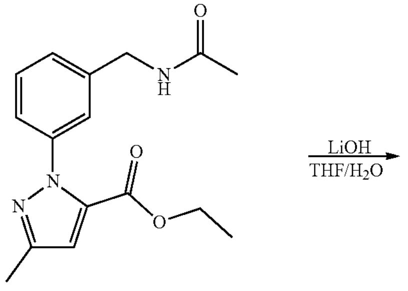

143A

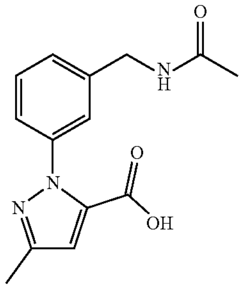

143B

To a solution of compound 140D (500 mg, 2.04 mmol) and acetyl chloride (160 mg, 2.04 mmol) in DCM (20 mL) was added TEA (0.7 mL, 5.10 mmol). The mixture was stirred at 25° C. for 12 h. The reaction was washed with 1N HCl (10 mL). The organics were collected, dried with $Na_2SO_4$, filtered and concentrated to afford intermediate compound 143A (580 mg, crude) as yellow oil. MS (ESI) m/z $(M+Na)^+$323.9.

To a solution of compound 143A (580 mg, 2.02 mmol) in THF (10 mL) and $H_2O$ (10 mL) was added LiOH.$H_2O$ (424 mg, 10.09 mmol). The mixture was stirred at 25° C. for 12 h. The reaction was acidified with 1N HCl to pH ~4. The solution was extracted with EtOAc (20 mL×2). The organics were collected and concentrated. The residue was purified by preparatory-HPLC (Neutral) to afford compound 26 (100 mg, yield: 18.11%) as white solid. MS (ESI) m/z $(M+Na)^+$ 295.9.

Compound 143 (6.2 mg, yield: 12.26%, white solid) was prepared as in Example 5 from the corresponding intermediate carboxylic acid, compound 143B. Compound 143: MS (ESI) m/z $(M+H)^+$448.1. $^1$H NMR (400 MHz, DMSO-$d_6$) δ8.78-8.67 (m, 0.6H), 8.19-8.05 (m, 1H), 7.85-7.72 (m, 1H), 7.67-7.53 (m, 0.6H), 7.36-6.87 (m, 10H), 6.59-6.46 (m, 1H), 6.30-5.89 (m, 1H), 5.33-5.23 (m, 0.6H), 4.52-4.40 (m, 0.6H), 4.32-4.22 (m, 2H), 3.27-3.19 (m, 0.5H), 2.96-2.85 (m, 0.6H), 2.77-2.66 (m, 1H), 2.29-2.19 (m, 3H), 1.89 (s, 3H).

Example 86

(S)—N-(4-amino-3,4-dioxo-1-phenylbutan-2-yl)-3-methyl-1-(3-((2-phenylacetamido)methyl)phenyl)-1H-pyrazole-5-carboxamide (144)

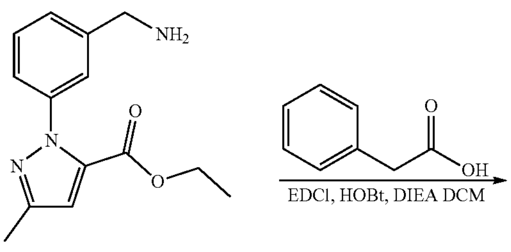

220B

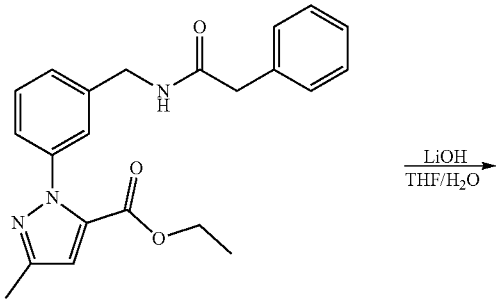

144A

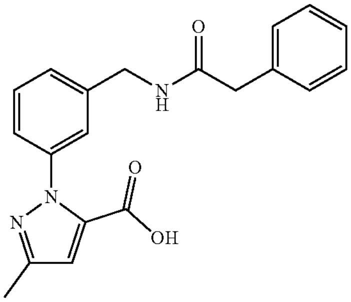

144B

To a solution of compound 140D (500 mg, 2.04 mmol) and 2-phenylacetic acid (278 mg, 2.04 mmol) in DCM (20 mL) was added DIEA (0.9 mL, 5.10 mmol), HOBt (552 mg, 4.08 mmol) and EDCI (783 mg, 4.08 mmol). The mixture was stirred at 25° C. for 12 h. The solvent was removed in vacuo. The residue was dissolved in EtOAc (30 mL), washed with 1N HCl (30 mL). The organics were collected, washed with saturated $NaHCO_3$ (30 mL). The organics were collected, washed with brine (30 mL). The organics were collected, dried with $Na_2SO_4$, filtered and concentrated to afford intermediate compound 144A (700.00 mg, crude) as yellow oil. MS (ESI) m/z $(M+H)^+$378.0.

To a solution of compound 144A (700 mg, 1.93 mmol) in THF (10 mL) and $H_2O$ (10 mL) was added LiOH.$H_2O$ (405 mg, 9.63 mmol). The mixture was stirred at 25° C. for 12 h. The reaction was acidified with 1N HCl to pH ~4. The solution was extracted with EtOAc (15 mL×2). The organics were collected and concentrated. The residue was purified by preparatory-HPLC (Neutral) to give compound 144B (260 mg, yield: 38.56%) as yellow oil. MS (ESI) m/z $(M+H)^+$349.9.

Compound 144 (36 mg, yield: 45.17%, white solid) was prepared as in Example 5 from the corresponding starting materials, compounds 144B and 12G. Compound 144: MS (ESI) m/z $(M+H)^+$524.2. $^1$H NMR (400 MHz, DMSO-$d_6$) δ 9.07 (d, J=7.6 Hz, 1H), 8.66-8.49 (m, 1H), 8.08 (br. s, 1H), 7.84 (br. s, 1H), 7.34-7.10 (m, 13H), 6.94-6.86 (m, 1H), 6.53 (s, 1H), 5.27-5.16 (m, 1H), 4.32-4.16 (m, 2H), 3.44 (s, 2H), 3.22-3.10 (m, 1H), 2.85-2.73 (m, 1H), 2.22 (s, 3H).

Example 87

(S)—N-(4-amino-3,4-dioxo-1-phenylbutan-2-yl)-3-methyl-1-(3-(phenylsulfonamidomethyl)phenyl)-1H-pyrazole-5-carboxamide (145)

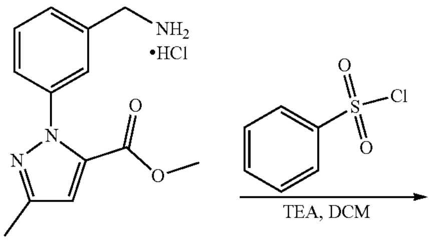

140D

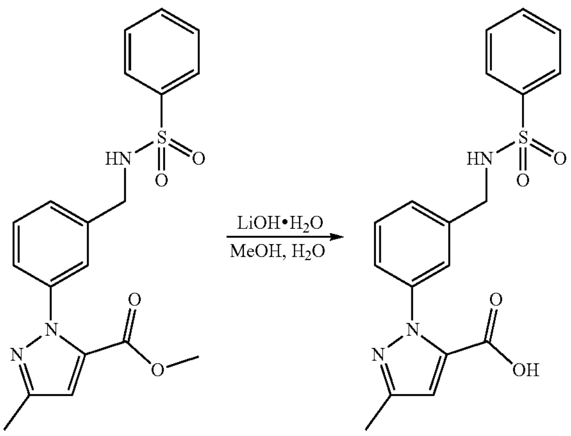

145A 145B

To a mixture of compound 140D (300 mg, 1.1 mmol, HCl salt) in DCM (20 mL) was added TEA (0.44 mL, 3.2 mmol) in one portion. Benzenesulfonyl chloride (0.15 mL, 1.2 mmol) was added dropwise to the mixture at 0° C. for 30 min and then stirred at 25° C. for 1 h. The reaction mixture was washed with 0.5N HCl (10 mL), saturated aqueous $NaHCO_3$ (10 mL) and brine (10 mL). The separated organic layer was dried over $Na_2SO_4$, filtered and concentrated under reduced pressure to give a residue. The residue was triturated with $CH_3CN$ (2 mL). The solid was collected and dried in vacuum to afford compound 145A (330 mg, yield 79.2%) as white solid. MS (ESI) m/z $(M+H)^+$386.0.

To a mixture of compound 145A (150 mg, 0.39 mmol) in MeOH (10 mL) and $H_2O$ (0.5 mL) was added LiOH.$H_2O$ (81.6 mg, 1.9 mmol) in one portion. The mixture was stirred at 25° C. for 12 h. The reaction mixture was concentrated under reduced pressure to move MeOH. Then the residue was diluted with water (15 mL) and extracted with ethyl acetate (10 mL), the aqueous phase was acidified with aqueous HCl (1M) till pH ~67 and extracted with ethyl acetate (20 mL×3). The combined organic layers were washed with brine (40 mL) and dried over $Na_2SO_4$, filtered and concentrated to afford intermediate compound 145B (140 mg, crude) as white solid. $^1$H NMR (DMSO-$d_6$, 400 MHz): δ 8.29-8.22 (m, 1H), 7.85-7.78 (m, 2H), 7.65-7.54 (m, 3H), 7.38-7.23 (m, 4H), 6.82 (s, 1H), 4.04 (d, J=6.0 Hz, 2H), 2.26 (s, 3H).

Compound 145 (30 mg, yield 46.8%, white solid) was prepared as in Example 12 from the corresponding intermediate carboxylic acid, compound 145B. Compound 145: $^1$H NMR ($CDCl_3$, 400 MHz): δ 7.86-7.81 (m, 2H), 7.58-7.46 (m, 3H), 7.37-7.26 (m, 5H), 7.15-7.06 (m, 5H), 6.41 (s, 1H), 6.24-6.18 (m, 1H), 6.16-6.10 (m, 2H), 5.38-5.31 (m, 1H), 4.20-4.08 (m, 2H), 3.34-3.27 (m, 1H), 3.10-3.03 (m, 1H), 2.30 (s, 3H). MS (ESI) m/z $(M+H)^+$546.1.

Example 88

Ethyl (S)-(3-(5-((4-amino-3,4-dioxo-1-phenylbutan-2-yl)carbamoyl)-3-methyl-1H-pyrazol-1-yl)benzyl) carbamate (147)

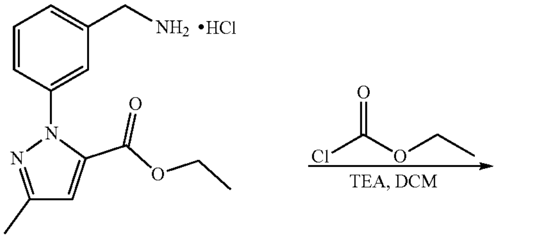

140D

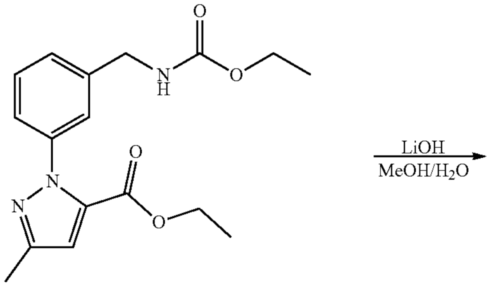

147A

-continued

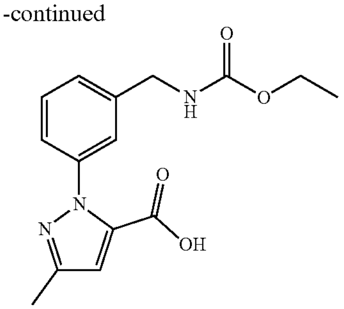

147B

To a solution of compound 140D (1 g, 3.38 mmol, HCl salt) in DCM (20 mL) was added TEA (1.4 mL, 10.14 mmol), ethylchloroformate (1.9 mL, 20.27 mmol) dropwise, then the mixture was stirred at 25° C. for 1 h. The reaction was diluted with $H_2O$ (10 mL), the mixture was extracted DCM (20 mL×2). The combined organic layer was washed with brine (20 mL×3), dried over anhydrous $Na_2SO_4$, filtered, concentrated under reduced pressure. The product was purified by Flash Column Chromatography (Petroleum Ether/Ethyl Acetate: 0 to 10/1) to afford compound 147A (570 mg, yield 50.9%) as white solid. $^1$H NMR (DMSO-$d_6$, 400 MHz) δ 7.72 (br t, J=6.1 Hz, 1H), 7.43-7.37 (m, 1H), 7.32-7.25 (m, 3H), 6.88 (s, 1H), 4.23 (br d, J=6.2 Hz, 2H), 4.15 (q, J=7.1 Hz, 2H), 4.03-3.97 (m, 2H), 2.26 (s, 3H), 1.16-1.12 (m, 6H).

To a solution of compound 147A (560 mg, 1.69 mmol) in MeOH (15 mL) was added LiOH (2 M, 5 mL) dropwise and then the mixture was stirred at 25° C. for 1 h. The reaction was diluted with $H_2O$ (10 mL) and concentrated under reduced pressure. The mixture was extracted with TBME (10 mL) and the water phase was treated with HCl (1M) until pH ~5. The mixture was extracted with ethyl acetate (15 mL×3), the combined organic layer was washed with brine (20 mL), dried over anhydrous $Na_2SO_4$, filtered, concentrated under reduced pressure to afford compound 147B (420 mg, yield 81.9%) was obtained as white solid, which was used directly in next step. $^1$H NMR (DMSO-$d_6$, 400 MHz) δ 7.69 (br t, J=6.2 Hz, 1H), 7.38-7.33 (m, 1H), 7.27-7.20 (m, 3H), 6.78 (s, 1H), 4.19 (br d, J=6.2 Hz, 2H), 3.97 (q, J=7.1 Hz, 2H), 2.22 (s, 3H), 1.16-1.10 (m, 3H).

Compound 147 (45 mg, yield 27.4%, white solid) was prepared as in Example 5 from the corresponding intermediate carboxylic acid, compound 147B. Compound 147: $^1$H NMR ($CD_3CN$, 400 MHz) δ 7.37-7.22 (m, 9H), 7.10 (br d, J=7.7 Hz, 2H), 6.49 (s, 1H), 6.33 (br s, 1H), 6.10 (br s, 1H), 5.40-5.31 (m, 1H), 4.31 (br d, J=6.2 Hz, 2H), 4.08 (q, J=7.1 Hz, 2H), 3.29 (dd, J=4.5, 14.0 Hz, 1H), 2.93 (dd, J=9.4, 14.0 Hz, 1H), 2.29 (s, 3H), 1.21 (t, J=7.2 Hz, 3H). MS (ESI) m/z $(M+H)^+$478.2.

Example 89

(S)—N-(4-((3,4-dichlorobenzyl)amino)-3,4-dioxo-1-phenylbutan-2-yl)-3-methyl-1-phenyl-1H-pyrazole-5-carboxamide (149)

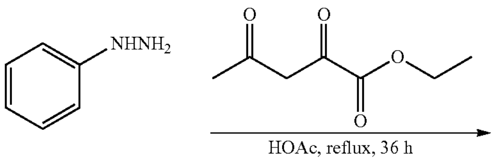

-continued

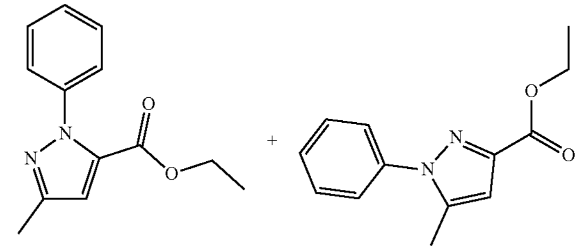

149A 149B

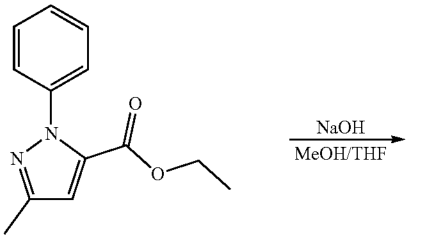

149A

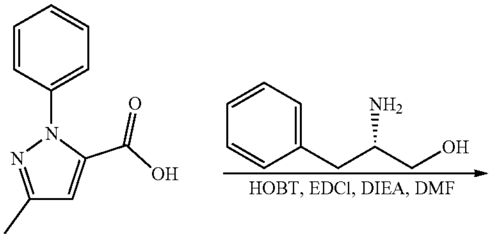

149C

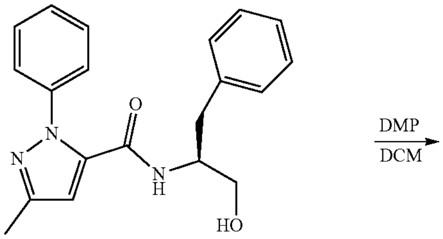

149D

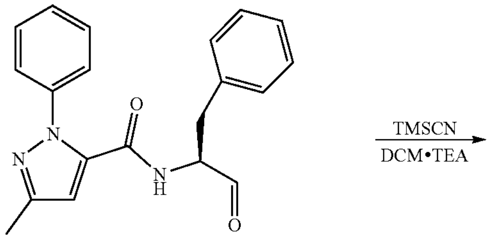

149E

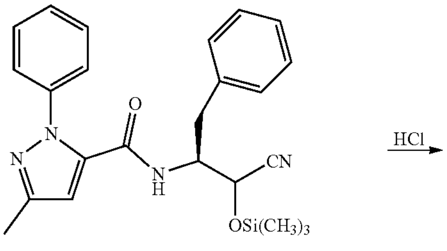

149F

-continued

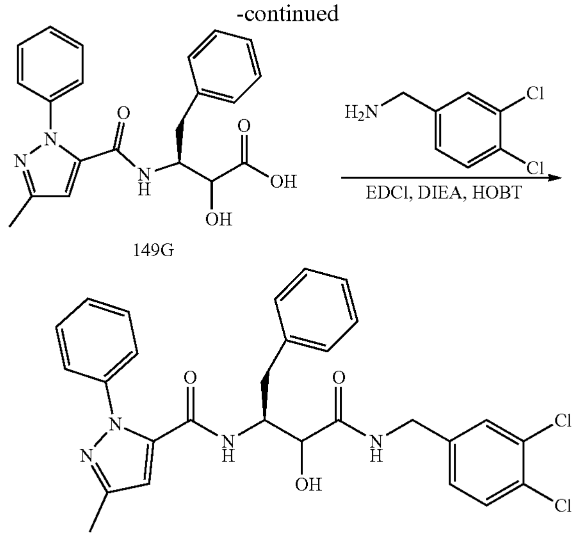

149G

149H

To a solution of phenylhydrazine (1.00 g, 9.25 mmol, 910 uL) in HOAc (20 mL) was added ethyl 2,4-dioxopentanoate (1.46 g, 9.25 mmol, 1.3 mL). The mixture was stirred at 100° C. for 12 hours. The mixture was concentrated and diluted with ethyl acetate (50 mL), washed with $NaHCO_3$ (aqueous, 50 mL×3), brine (50 mL), dried over $Na_2SO_4$ and concentrated. The residue was purified by preparatory-HPLC (TFA condition). Compound 149A (700.0 mg, yield 32.9%) was obtained as a yellow oil. Compound 149B (1.00 g, yield 46.9%) was obtained as a yellow oil.

Compound 149A: $^1$H NMR (400 MHz, DMSO-$d_6$) δ 7.48-7.36 (m, 5H), 6.87 (s, 1H), 4.18-4.10 (m, 2H), 2.25 (s, 3H), 1.16-1.11 (m, 3H).

Compound 149B: $^1$H NMR (400 MHz, DMSO-$d_6$) δ 7.61-7.44 (m, 5H), 6.75 (s, 1H), 4.31-4.23 (m, 2H), 2.31 (s, 3H), 1.30-1.24 (m, 3H).

To a solution of compound 149A (700.0 mg, 3.04 mmol) in THF (20 mL) and MeOH (20 mL) was added NaOH (2M, 30). The mixture was stirred at 25° C. for 12 hours. The mixture was concentrated, diluted with $H_2O$ (20 mL), extracted with ethyl acetate (20 mL), the water phase was added HCl (1M) until pH ~1, then the mixture was extracted with ethyl acetate (20 mL), the organic layer was washed with brine (20 mL), dried over $Na_2SO_4$ and concentrated. Compound 149C (600.0 mg, yield 97.6%) was obtained as a colorless oil. $^1$H NMR (400 MHz, DMSO-$d_6$) δ 13.21 (br s, 1H), 7.49-7.31 (m, 5H), 6.81 (s, 1H), 2.24 (s, 3H).

To a solution of compound 149C (600.0 mg, 2.97 mmol) in THF (20 mL) was added DIEA (1.54 g, 11.88 mmol, 2 mL), (2S)-2-amino-3-phenyl-propan-1-ol (448.7 mg, 2.97 mmol), HOBt (401.3 mg, 2.97 mmol) and EDCI (683.2 mg, 3.56 mmol). The mixture was stirred at 25° C. for 12 hours. The mixture was concentrated and diluted with ethyl acetate (50 mL), washed with HCl (1M, 50 mL), saturated $NaHCO_3$ (aqueous, 50 mL), brine (50 mL×3), dried over $Na_2SO_4$ and concentrated. Compound 149D (600.0 mg, yield 60.2%) was obtained as a white solid. $^1$H NMR (400 MHz, DMSO-$d_6$) δ 8.38 (d, J=8.8 Hz, 1H), 7.32-7.17 (m, 8H), 7.12-7.07 (m, 2H), 6.50 (s, 1H), 4.89-4.83 (m, 1H), 4.10-3.99 (m, 1H), 3.48-3.35 (m, 2H), 2.95-2.87 (m, 1H), 2.68-2.59 (m, 1H), 2.21 (s, 3H).

To a solution of compound 149D (600.0 mg, 1.79 mmol) in DCM (200 mL) was added DMP (1.14 g, 2.69 mmol). The mixture was stirred at 25° C. for 2 hours. The mixture quenched with 10% $Na_2S_2O_3$ (aqueous):saturated $NaHCO_3$ (aqueous) (1:1, 200 mL), extracted with DCM (100 mL) and washed with brine (20 mL×3). The combined organic layers were dried over $Na_2SO_4$ and concentrated. Compound 149E (500.0 mg, yield 83.8%) was obtained as a white solid. $^1$H NMR (400 MHz, DMSO-$d_6$) δ 9.58 (s, 1H), 9.03 (d, J=8.0 Hz, 1H), 7.36-7.13 (m, 10H), 6.57 (s, 1H), 4.56-4.49 (m, 1H), 3.28-3.21 (m, 1H), 2.81-2.72 (m, 1H), 2.25-2.17 (m, 3H).

To a solution of compound 149E (500.0 mg, 1.50 mmol) in DCM (10 mL) was added TEA (15.2 mg, 150.00 umol, 20 uL) and TMSCN (223.2 mg, 2.25 mmol, 280 uL). The mixture was stirred at 0° C. for 3 hours. The mixture was washed with $H_2O$ (100 mL), brine (100 mL), dried over $Na_2SO_4$ and concentrated to obtain intermediate compound 149F (600.0 mg, crude) as a colorless oil.

To a solution of compound 149F (600.0 mg, 1.39 mmol) in THF (30 mL) was added HCl (10 mL). After stirred at 60° C. for 12 hours, the mixture was diluted with $H_2O$ (100 mL), extracted with ethyl acetate (50 mL). The organic layer was washed with $NaHCO_3$ (aq, 50 mL). The water phase was added HCl (1M) until pH ~1, and then extracted with ethyl acetate (500 mL). The organic layer was washed with brine (50 mL), dried over $Na_2SO_4$ and concentrated to obtain intermediate compound 149G (500.0 mg, crude) as colorless oil.

To a solution of compound 149G (500.0 mg, 1.32 mmol) in THF (10 mL) was added (3,4-dichlorophenyl)methanamine (255.6 mg, 1.45 mmol, 190 uL), HOBt (178.4 mg, 1.32 mmol), DIEA (682.4 mg, 5.28 mmol, 920 uL) and EDCI (303.7 mg, 1.58 mmol) with DCM (10 mL). The mixture was stirred at 25° C. for 12 hours. The mixture was concentrated and diluted with ethyl acetate (30 mL), washed with HCl (1M, 30 mL), saturated $NaHCO_3$ (aqueous, 30 mL), brine (30 mL), dried over $Na_2SO_4$ and concentrated. The crude product was purified by preparatory-HPLC (TFA condition). The product obtained (70 mg) was triturated with $CH_3CN$ (5 mL) and filtered. Compound 149H (30.0 mg, 4.23%) was obtained as a white solid. $^1$H NMR (400 MHz, DMSO-$d_6$) δ 8.67-8.50 (m, 1H), 8.11 (d, J=9.6 Hz, 1H), 7.50-7.41 (m, 1H), 7.39-7.34 (m, 1H), 7.32-7.14 (m, 9H), 7.07-6.96 (m, 2H), 6.47-6.36 (m, 1H), 4.46-4.36 (m, 1H), 4.34-4.10 (m, 2H), 4.06-3.99 (m, 1H), 2.95-2.71 (m, 2H), 2.26-2.13 (m, 2H), 2.26-2.13 (m, 1H).

To a solution of compound 149H (30.0 mg, 55.82 umol) in DCM (10 mL) and DMSO (1 mL) was added DMP (47.4 mg, 111.64 umol). The mixture was stirred at 25° C. for 48 hours. The mixture was quenched with 10% $Na_2S_2O_3$ (aqueous):saturated $NaHCO_3$ (aqueous) (1:1, 20 mL), extracted with DCM (10 mL) and washed with brine (20 mL×3). The combined organic layers were dried over $Na_2SO_4$ and concentrated. The crude product was triturated with $CH_3CN$ (3 mL) and filtered. Compound 149 (15.0 mg, yield 40.0%) was obtained as a white solid. $^1$H NMR (400 MHz, DMSO-$d_6$) δ 9.36-9.30 (m, 1H), 9.11 (br d, J=7.6 Hz, 1H), 7.54-7.48 (m, 2H), 7.33-7.19 (m, 9H), 7.13 (br d, J=6.6 Hz, 2H), 6.52 (s, 1H), 5.29-5.22 (m, 1H), 4.34-4.28 (m, 2H), 3.22-3.15 (m, 1H), 2.89-2.80 (m, 1H), 2.26-2.18 (m, 3H). MS (ESI) m/z $(M+H)^+$535.1.

Example 90

Compounds 150-152

(S)—N-(3,4-dioxo-1-phenyl-4-((3-(trifluoromethoxy)benzyl)amino)butan-2-yl)-3-methyl-5-phenylisoxazole-4-carboxamide (150)

150A

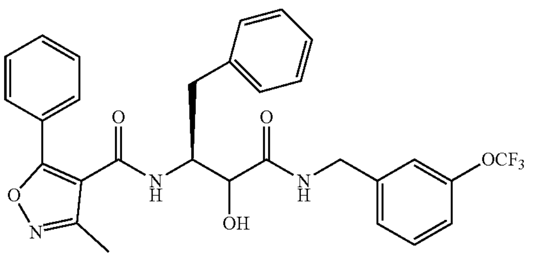

To a solution of compound 101E (500.0 mg, 1.31 mmol) in THF (10 mL) was added [3-(trifluoromethoxy)phenyl] methanamine (251.3 mg, 1.31 mmol), DIEA (509.6 mg, 3.94 mmol, 690 uL), HOBt (177.6 mg, 1.31 mmol) and EDCI (302.4 mg, 1.58 mmol) with DCM (5 mL). After stirred at 25° C. for 12 hours, the mixture was concentrated and diluted with ethyl acetate (50 mL), washed with HCl (1M, 50 mL), saturated aqueous $NaHCO_3$ (50 mL), brine (50 mL×3), dried over $Na_2SO_4$ and concentrated. The crude product (0.30 g) was triturated with $CH_3CN$ (5 mL) and filtered. Compound 150A (140.0 mg, yield 19.3%, white solid): $^1$H NMR (400 MHz, DMSO-$d_6$) δ 8.75-8.53 (m, 1H), 8.31 (d, J=9.6 Hz, 1H), 7.59-7.08 (m, 14H), 6.21-5.91 (m, 1H), 4.71-4.56 (m, 1H), 4.40-4.24 (m, 2H), 4.22-4.01 (m, 1H), 2.98-2.67 (m, 2H), 2.09-1.96 (m, 3H).

To a solution of compound 150A (60.0 mg, 108.40 umol) in DCM (10 mL) and DMSO (1 mL) was added DMP (137.9 mg, 325.20 umol). After stirred at 25° C. for 4 hour, the mixture was quenched with 10% $Na_2S_2O_3$ (aqueous):saturated aq. $NaHCO_3$ (1:1, 20 mL), extracted with DCM (10 mL) and washed with brine (20 mL×3). The combined organic layers were dried over $Na_2SO_4$ and concentrated. The crude product was triturated with $CH_3CN$ (3 mL) and filtered. Compound 150 (50.0 mg, yield 82.8%, white solid): $^1$H NMR (400 MHz, DMSO-$d_6$) δ 9.54-9.45 (m, 1H), 9.11 (d, J=7.6 Hz, 1H), 7.67-7.57 (m, 2H), 7.54-7.36 (m, 4H), 7.34-7.18 (m, 8H), 5.52-5.43 (m, 1H), 4.40 (br d, J=6.0 Hz, 2H), 3.27-3.18 (m, 1H), 2.84-2.72 (m, 1H), 2.04 (s, 3H). MS (ESI) m/z $(M+H)^+$552.1.

(S)-3-methyl-N-(4-((4-(methylsulfonyl)benzyl)amino)-3,4-dioxo-1-phenylbutan-2-yl)-5-phenylisoxazole-4-carboxamide (151)

(S)-3-methyl-N-(4-((3-(methylsulfonyl)benzyl)amino)-3,4-dioxo-1-phenylbutan-2-yl)-5-phenylisoxazole-4-carboxamide (152)

Compounds 151 and 152 were prepared as in Example 150 from compound 101E and the corresponding amine, respectively. Compound 151 (40.0 mg, 63.6% yield, white solid): $^1$H NMR (400 MHz, DMSO-$d_6$) δ 9.58-9.51 (m, 1H), 9.12 (d, J=7.2 Hz, 1H), 7.86 (d, J=8.4 Hz, 2H), 7.65-7.59 (m, 2H), 7.56-7.38 (m, 5H), 7.31-7.19 (m, 5H), 5.53-5.44 (m, 1H), 4.48-4.42 (m, 2H), 3.29-3.21 (m, 1H), 3.20-3.10 (m, 3H), 2.83-2.73 (m, 1H), 2.08-1.96 (m, 3H). MS (ESI) m/z $(M+H)^+$546.1.

Compound 152 (42.0 mg, 68.8% yield, white solid): $^1$H NMR (400 MHz, DMSO-$d_6$) δ 9.59-9.51 (m, 1H), 9.11 (d, J=7.6 Hz, 1H), 7.91-7.78 (m, 2H), 7.67-7.57 (m, 4H), 7.53-7.37 (m, 3H), 7.34-7.17 (m, 5H), 5.53-5.45 (m, 1H), 4.46 (br d, J=6.4 Hz, 2H), 3.29-3.21 (m, 1H), 3.20-3.10 (m, 3H), 2.83-2.72 (m, 1H), 2.09-1.98 (s, 3H). MS (ESI) m/z $(M+H)^+$546.1

Example 91 benzyl (S)-(4-(5-((4-amino-3,4-dioxo-1-phenylbutan-2-yl)carbamoyl)-3-methyl-1H-pyrazol-1-yl)benzyl)carbamate (153)

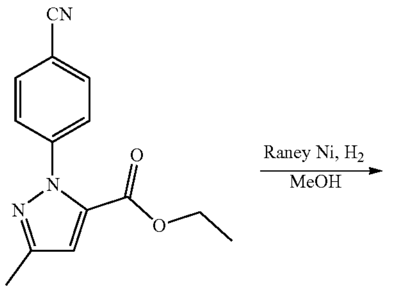

153B

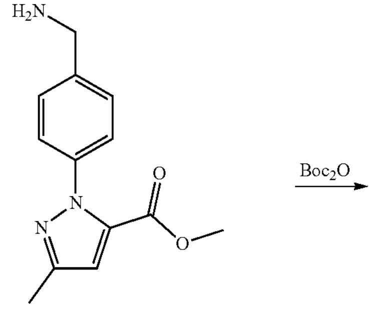

153D

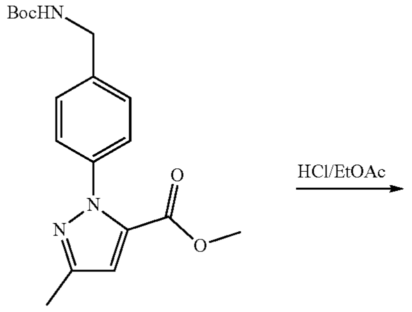

153E

-continued

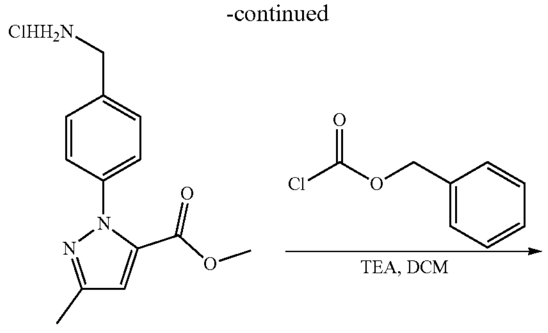

153F

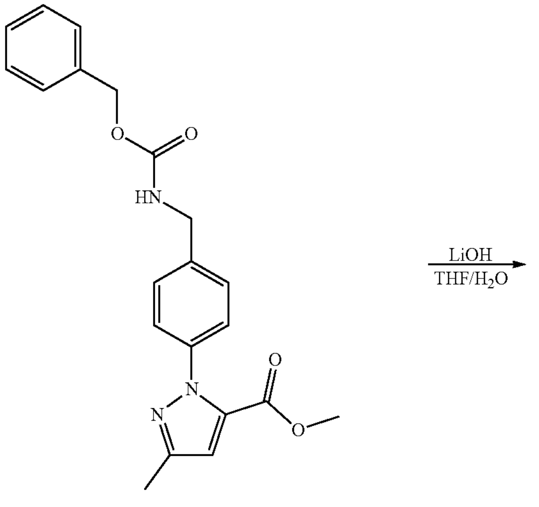

153G

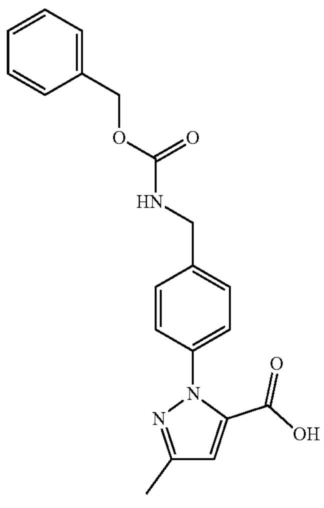

153H

To a solution of 4-hydrazinylbenzonitrile (20 g, 117.92 mmol, HCl) in HOAc (200 mL) was added ethyl 2-methoxyimino-4-oxo-pentanoate (23.18 g, 123.82 mmol), then the mixture was heated to 110° C. and stirred for 12 h and then removed the solvent under reduced pressure. The residue was dissolved in ethyl acetate (200 mL) and treated with $NaHCO_3$ until pH ~8 and then the organic layer was collected and evaporated under reduced pressure. The residue was purified by column chromatography ($SiO_2$, Petroleum ether/Ethyl acetate=15/1 to 3/1) to give compound 153B (5 g, yield: 16.61%) as a white solid. Compound 153B: $^1H$ NMR (400 MHz, $CDCl_3$) δ 7.71 (dd, J=7.9 Hz, 2H), 7.53 (br d, J=7.5 Hz, 2H), 6.84 (s, 1H), 4.23 (q, J=7.0 Hz, 2H), 2.33 (s, 3H), 1.25 (t, J=7.1 Hz, 3H). MS (ESI) m/z $(M+H)^+$255.9.

To a solution of compound 153B (6.5 g, 25.46 mmol) in MeOH (70 mL) was added Raney-Ni (1.09 g, 12.73 mmol) and $NH_3.H_2O$ (2.68 g, 76.38 mmol, 3 mL) under argon. The suspension was degassed under vacuum and purged with $H_2$ 3 times. The mixture was stirred at 30° C. for 16 h under $H_2$ (40 psi). The reaction mixture was filtered and the filtrate was concentrated under reduced pressure to give intermediate compound 153D (6.6 g, crude) as a yellow oil. $^1H$ NMR (400 MHz, DMSO-$d_6$) δ 7.46-7.36 (m, 2H), 7.35-7.29 (m, 2H), 6.87 (s, 1H), 3.77 (s, 2H), 3.71 (s, 3H), 2.26 (s, 3H).

To a mixture of compound 153D (3.3 g, 13.45 mmol) in DCM (40 mL) was added $Et_3N$ (2.04 g, 20.17 mmol, 2.8 mL) and $Boc_2O$ (3.52 g, 16.14 mmol, 3.7 mL) in portion at 25° C. under $N_2$. The mixture was stirred at 25° C. for 1.5 h. The reaction mixture was diluted with DCM (20 mL), and washed with $H_2O$ (50 mL). The organic layer was separated and the aqueous layer was extracted with DCM (20 mL×2). The combined organic layers was washed with brine (30 mL×2), dried over anhydrous $Na_2SO_4$, filtered and concentrated. The residue was purified by column chromatography ($SiO_2$, Petroleum ether/Ethyl acetate=5/1 to 2/1) to give compound 153E (3.3 g, yield: 64.86%) as yellow oil. $^1H$ NMR (400 MHz, $CDCl_3$) δ 7.37 (s, 4H), 6.80 (s, 1H), 4.38 (dd, J=5.1 Hz, 2H), 3.78 (s, 3H), 2.36 (s, 3H), 1.47 (s, 9H). MS (ESI) m/z $(M+H)^+$346.1.

To a mixture of compound 153E (3.3 g, 9.55 mmol) in ethyl acetate (20 mL) was added HCl/EtOAc (4M, 20 mL) dropwise at 0° C. The reaction mixture was stirred at 25° C. for 2 h. The mixture was concentrated to give intermediate compound 153F (2.7 g, crude, HCl) as white solid. $^1H$ NMR (400 MHz, $CDCl_3$) δ 8.62 (s, 1H), 7.63 (dd, J=7.9 Hz, 2H), 7.40 (dd, J=7.5 Hz, 2H), 6.80 (s, 1H), 4.16 (s, 2H), 3.74 (s, 3H), 2.34 (s, 3H).

To a mixture of compound 153F (300 mg, 1.06 mmol, HCl) in DCM (20 mL) was added $Et_3N$ (268.15 mg, 2.65 mmol, 0.4 mL) and benzyl carbonochloridate (181 mg, 1.06 mmol, 0.2 mL) in portion at 25° C. and stirred for 1.5 h. The reaction mixture was treated with DCM (20 mL), added with $H_2O$ (30 mL). The organic layer was separated and washed with brine (30 mL), dried over anhydrous $Na_2SO_4$, filtered and concentrated. The residue was purified by column chromatography ($SiO_2$, Petroleum ether/Ethyl acetate=5/1 to 1/1) to give compound 153G (350 mg, yield: 87.03%) as off-white solid. $^1H$ NMR (400 MHz, $CDCl_3$) δ 7.42-7.29 (m, 9H), 6.82-6.78 (m, 1H), 5.16 (s, 2H), 4.45 (dd, J=6.2 Hz, 2H), 3.80-3.77 (m, 3H), 2.39-2.34 (m, 3H). MS (ESI) m/z $(M+H)^+$380.0.

To a mixture of compound 153G (350 mg, 922.48 umol) in THF (10 mL) and $H_2O$ (10 mL) was added $LiOH.H_2O$ (116 mg, 2.77 mmol) in portion at 25° C. and stirred for 1.5 h. The mixture was diluted with $H_2O$ (10 mL) and concentrated to remove THF, then, the water was extracted with MTBE (30 mL×2). The water layers were acidified to pH ~2 with 1N HCl, then, the solution extracted with ethyl acetate (30 mL×3). The organic layers were dried over $Na_2SO_4$ and concentrated to give intermediate compound 153H (300 mg, yield: 89.04%) as white solid. $^1H$ NMR (400 MHz, $CDCl_3$) δ 7.35 (dd, J=5.3, 8.2 Hz, 6H), 7.30-7.16 (m, 2H), 7.14-6.98 (m, 1H), 6.90-6.82 (m, 1H), 5.15 (s, 2H), 4.47-4.30 (m, 2H), 2.46-2.28 (m, 3H). MS (ESI) m/z $(M+H)^+$366.1.

Compound 153 (35 mg, yield: 50.19%, white solid) was prepared as in Example 5 from the corresponding intermediate carboxylic acid, compound 153H. Compound 153: $^1H$ NMR (400 MHz, DMSO-$d_6$) δ 9.04 (d, J=7.7 Hz, 1H), 8.09

(s, 1H), 7.84 (br s, 2H), 7.38-7.17 (m, 12H), 7.09 (d, J=8.2 Hz, 2H), 6.53 (s, 1H), 5.27 (t, J=7.5 Hz, 1H), 5.04 (s, 2H), 4.20 (d, J=6.0 Hz, 2H), 3.19 (dd, J=3.3, 14.1 Hz, 1H), 2.86-2.75 (m, 1H), 2.22 (s, 3H). MS (ESI) m/z $(M+H)^+$ 540.2.

Example 92

Compounds 154-159, 496

(S)—N-(4-amino-3,4-dioxo-1-phenylbutan-2-yl)-1-(4-(benzamidomethyl)phenyl)-3-methyl-1H-pyrazole-5-carboxamide (154)

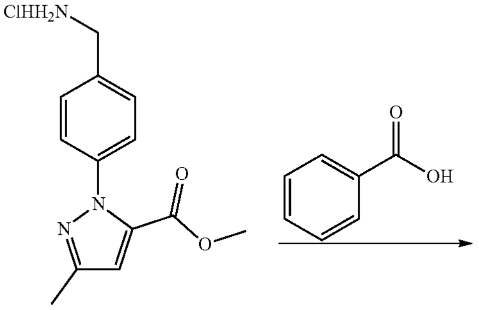

153F

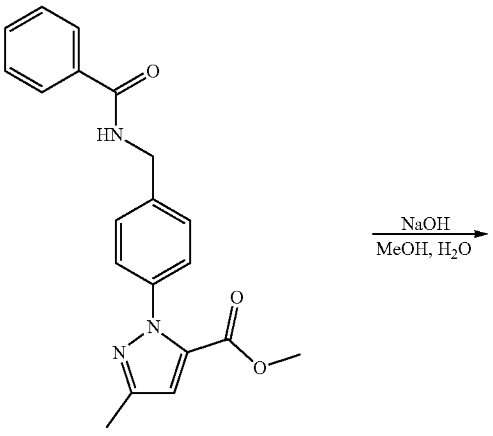

154A

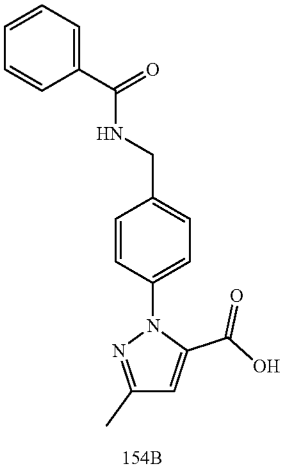

154B

To a mixture of compound 153F (300 mg, 1.06 mmol, HCl), benzoic acid (155 mg, 1.27 mmol, 0.2 mL), HOBt (286 mg, 2.12 mmol) and DIEA (343 mg, 2.65 mmol, 0.5 mL) in DCM (20 mL) was added EDCI (406 mg, 2.12 mmol) in portion at 25° C. and stirred for 4 h. The reaction mixture was treated with DCM (10 mL), washed with $H_2O$ (20 mL). The organic layer was separated and the aqueous layer was extracted with DCM (10 mL×2). The combined organic layer was washed with 0.5N HCl (20 mL×2), $NaHCO_3$ (20 mL×2) and brine (30 mL), dried over $Na_2SO_4$, filtered and the solvent was removed in vacuo. The residue was purified by column chromatography ($SiO_2$, Petroleum ether/Ethyl acetate=5/1 to 1/1) to give compound 154A (280 mg, yield: 75.61%) as offwhite solid. $^1H$ NMR (400 MHz, $CDCl_3$) δ 7.81 (dd, J=6.4 Hz, 2H), 7.58-7.40 (m, 7H), 6.85-6.78 (m, 1H), 6.48 (br s, 1H), 4.72 (br d, J=5.1 Hz, 2H), 3.84-3.77 (m, 3H), 2.41-2.34 (m, 4H). MS (ESI) m/z $(M+Na)^+$372.0.

To a mixture of compound 154A (280 mg, 801.42 umol) in MeOH (10 mL) and $H_2O$ (10 mL) was added NaOH (2M, 2 mL) in portion at 25° C. and stirred for 3 h. The mixture was concentrated to remove MeOH and then the water was extracted with MTBE (30 mL×2). The water layer were acidized to pH ~2 with 1N HCl, then the solution extracted with ethyl acetate (20 mL×2). The organic layers were dried over $Na_2SO_4$ and concentrated to give intermediate compound 154B (200 mg, yield: 74.41%) as white solid. $^1H$ NMR (400 MHz, $CDCl_3$) δ 7.79 (dd, J=8.2 Hz, 2H), 7.50-7.31 (m, 7H), 6.78 (s, 1H), 4.62 (s, 2H), 2.31 (s, 3H). MS (ESI) m/z $(M+H)^+$336.0.

Compound 154 (20 mg, yield: 29.53%, white solid) was prepared as in Example 5 from the corresponding intermediate carboxylic acid, compound 154B. Compound 154: $^1H$ NMR (400 MHz, DMSO-$d_6$) δ 9.11-9.04 (m, 2H), 8.11 (s, 1H), 7.96-7.91 (m, 2H), 7.86 (s, 1H), 7.56-7.47 (m, 3H), 7.30 (d, J=4.4 Hz, 3H), 7.27 (d, J=8.6 Hz, 2H), 7.23-7.19 (m, 1H), 7.12 (d, J=8.4 Hz, 2H), 6.55 (s, 1H), 5.32-5.26 (m, 1H), 4.51 (br d, J=5.7 Hz, 2H), 3.21 (dd, J=3.5, 13.9 Hz, 1H), 2.86-2.78 (m, 1H), 2.25 (s, 3H). MS (ESI) m/z $(M+H)^+$ 510.1.

(S)—N-(4-amino-3,4-dioxo-1-phenylbutan-2-yl)-3-methyl-1-(4-((3-phenylpropanamido)methyl)phenyl)-1H-pyrazole-5-carboxamide (155)

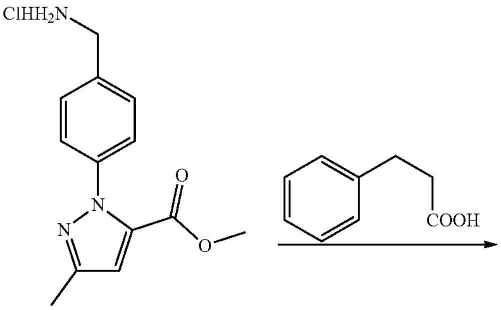

153F

-continued

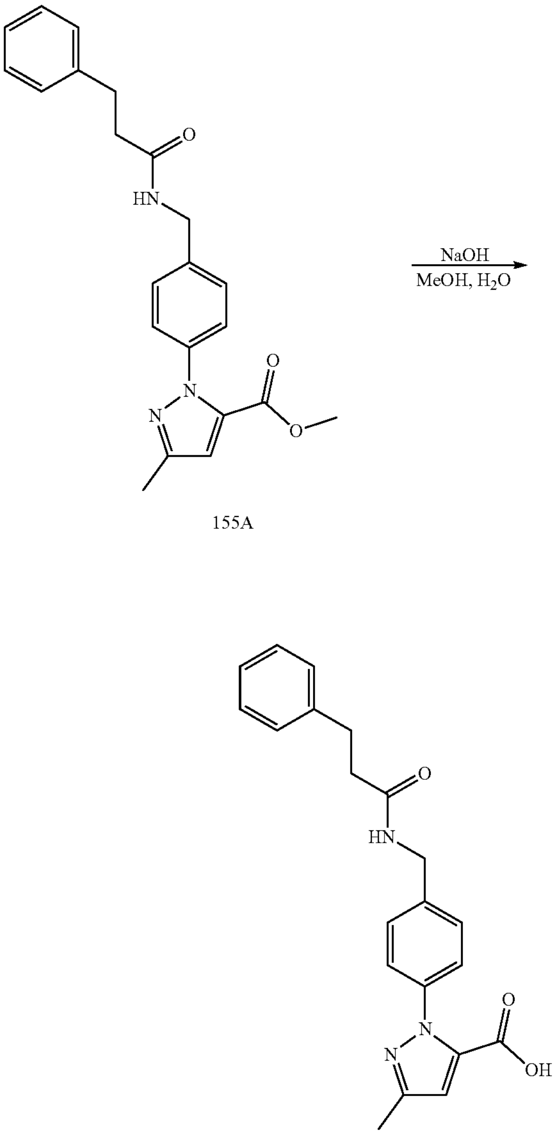

155A

155B

Following the procedure as used for compound 154B, intermediate compound 155B (200 mg, yield: 74.41%, white solid) was prepared from compound 153F through 155A. Compound 155B: $^1H$ NMR (400 MHz, $CDCl_3$) δ 7.28-7.12 (m, 8H), 6.94 (s, 1H), 6.78 (s, 1H), 4.42-4.31 (m, 2H), 2.94 (t, J=7.5 Hz, 2H), 2.50 (t, J=7.2 Hz, 2H), 2.31 (s, 3H). MS (ESI) m/z $(M+H)^+$364.1.

Compound 155 (20 mg, yield: 27.16%, light yellow solid) was prepared as in Example 12 from the corresponding intermediate carboxylic acid, compound 155B. Compound 155: $^1H$ NMR (400 MHz, DMSO-$d_6$) δ 9.06 (d, J=7.7 Hz, 1H), 8.38 (t, J=5.8 Hz, 1H), 8.11 (s, 1H), 7.87 (s, 1H), 7.33-7.29 (m, 4H), 7.27 (d, J=7.5 Hz, 2H), 7.24-7.18 (m, 3H), 7.13-7.07 (m, 4H), 6.56 (s, 1H), 5.30 (dd, J=2.6 Hz, 1H), 4.27 (d, J=5.7 Hz, 2H), 3.25-3.19 (m, 1H), 2.87-2.83 (m, 2H), 2.53 (d, J=2.0 Hz, 1H), 2.49-2.44 (m, 2H), 2.25 (s, 3H). MS (ESI) m/z $(M+H)^+$538.2.

(S)—N-(4-amino-3,4-dioxo-1-phenylbutan-2-yl)-3-methyl-1-(4-(phenylsulfonamidomethyl)phenyl)-1H-pyrazole-5-carboxamide (156)

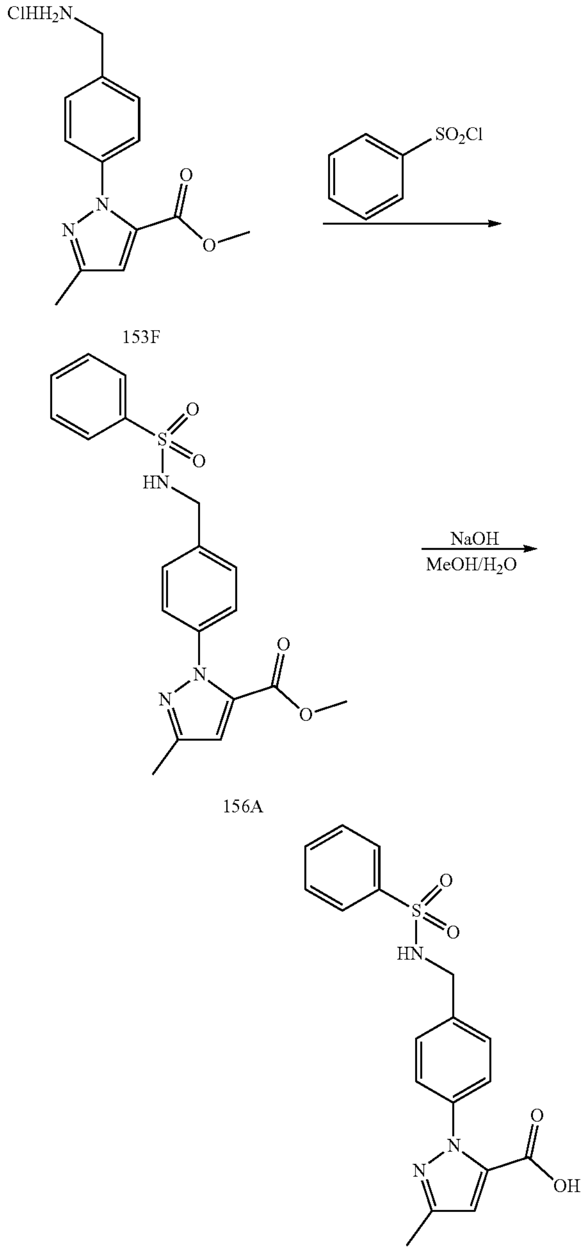

153F

156A

156B

Following the procedure as used for compound 154B, intermediate compound 156B (250 mg, yield: 86.48%, white solid) was prepared from compound 153F through 156A. Compound 156B: $^1H$ NMR (400 MHz, $CDCl_3$) δ 7.85 (dd, J=7.7 Hz, 2H), 7.61-7.43 (m, 3H), 7.29-7.20 (m, 4H), 6.78 (s, 1H), 4.09 (s, 2H), 2.30 (s, 3H). MS (ESI) m/z $(M+H)^+$ 372.0.

Compound 156 (45 mg, yield: 78.05%, white solid) was prepared as in Example 12 from the corresponding intermediate carboxylic acid, compound 156B. Compound 156: $^1H$ NMR (400 MHz, DMSO-$d_6$) δ 9.10-9.01 (m, 1H), 8.19 (br s, 1H), 8.09 (s, 1H), 7.86-7.79 (m, 3H), 7.63-7.56 (m, 3H), 7.32-7.25 (m, 5H), 7.19 (d, J=8.4 Hz, 2H), 7.07 (d, J=8.4 Hz, 2H), 6.52 (s, 1H), 5.26 (br s, 1H), 3.97 (d, J=5.3 Hz, 2H), 3.23-3.13 (m, 1H), 2.87-2.75 (m, 1H), 2.22 (s, 3H). MS (ESI) m/z $(M+H)^+$546.1.

(S)-1-(4-(acetamidomethyl)phenyl)-N-(4-amino-3,4-dioxo-1-phenylbutan-2-yl)-3-methyl-1H-pyrazole-5-carboxamide (157)

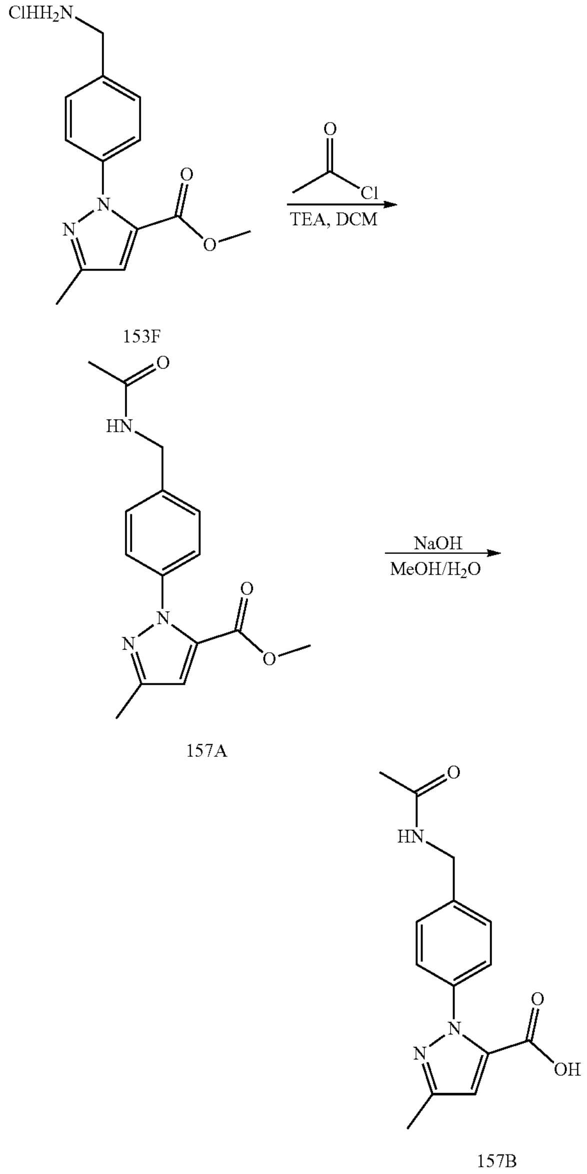

153F

157A

157B

Following the procedure as used for compound 154B, intermediate compound 157B (162 mg, yield: 94.62%, white solid) was prepared from compound 153F through 157A. Compound 157B: $^1H$ NMR (400 MHz, DMSO-$d_6$) δ 13.20 (br s, 1H), 8.43 (br t, J=5.8 Hz, 1H), 7.37-7.25 (m, 4H), 6.79 (s, 1H), 4.29 (d, J=6.0 Hz, 2H), 2.23 (s, 3H), 1.88 (s, 3H).

Compound 157 (17 mg, yield: 33.13%, gray solid) was prepared as in Example 5 from the corresponding intermediate carboxylic acid, compound 157B. Compound 157: $^1H$ NMR (400 MHz, DMSO-$d_6$) δ 8.71 (br d, J=7.5 Hz, 1H), 8.12 (br s, 1H), 7.83-7.54 (m, 2H), 7.31-7.18 (m, 9H), 6.55 (s, 1H), 5.35-5.27 (m, 1H), 4.28 (d, J=6.0 Hz, 2H), 3.25 (d, J=4.3 Hz, 0.5H), 3.21 (d, J=4.0 Hz, 0.5H), 2.94 (s, 0.5H), 2.91 (d, J=4.3 Hz, 0.5H), 2.25 (s, 3H), 1.91 (s, 3H). MS (ESI) m/z $(M+H)^+$448.1.

methyl (S)-(4-(5-((4-amino-3,4-dioxo-1-phenylbutan-2-yl)carbamoyl)-3-methyl-1H-pyrazol-1-yl)benzyl)carbamate (158)

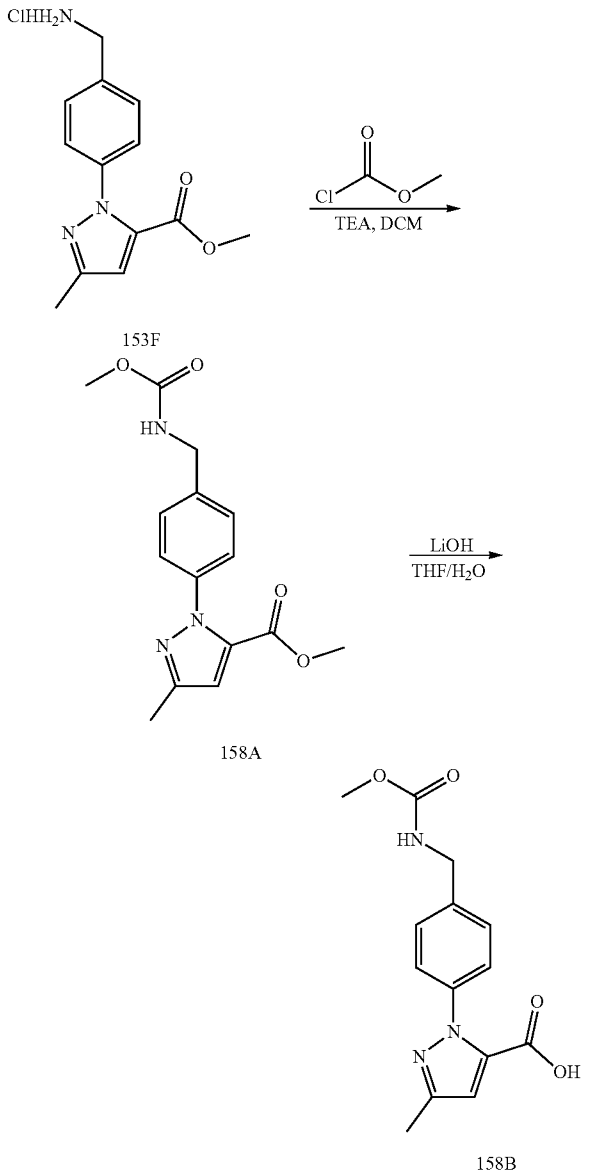

153F

158A

158B

Following the procedure as used for compound 154B, intermediate compound 158B (150 mg, yield: 62.91%, white solid) was prepared from compound 153F through 158A. Compound 158B: $^1H$ NMR (400 MHz, $CDCl_3$) δ 7.36-7.28 (m, 4H), 6.78 (s, 1H), 4.36 (s, 2H), 3.67 (s, 3H), 2.34-2.30 (m, 3H). MS (ESI) m/z $(M+H)^+$289.9.

Compound 158 (12 mg, yield: 22.68%, light yellow solid) was prepared as in Example 5 from the corresponding intermediate carboxylic acid, compound 158B. Compound 158: ¹H NMR (400 MHz, DMSO-$d_6$) δ 9.08 (dd, J=7.5 Hz, 1H), 8.13 (s, 1H), 7.87 (br s, 1H), 7.74 (s, 1H), 7.35-7.17 (m, 7H), 7.16-7.07 (m, 2H), 6.54 (s, 1H), 5.34-5.24 (m, 1H), 4.19 (dd, J=6.0 Hz, 2H), 3.57 (s, 3H), 3.28-3.18 (m, 1H), 2.82 (dd, J=10.9, 13.3 Hz, 1H), 2.24 (s, 3H). MS (ESI) m/z $(M+H)^+$464.1.

(S)—N-(4-amino-3,4-dioxo-1-phenylbutan-2-yl)-3-methyl-1-(4-((2-phenylacetamido)methyl)phenyl)-1H-pyrazole-5-carboxamide (159)

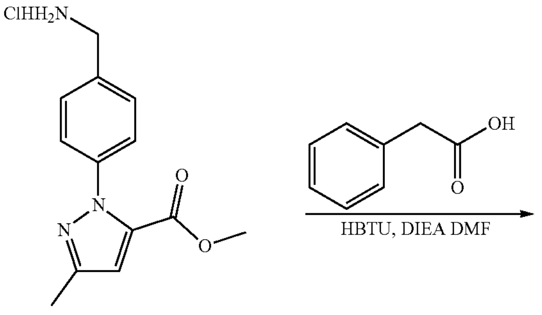

153F

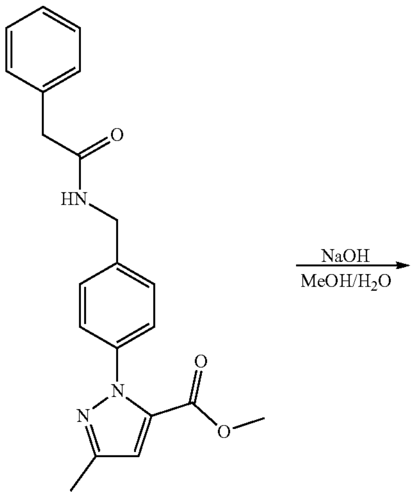

159A

-continued

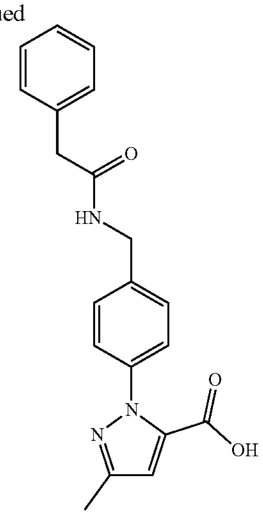

159B

To a mixture of compound 153F (300 mg, 1.06 mmol, HCl) and 2-phenylacetic acid (173 mg, 1.27 mmol, 0.16 mL) in DMF (10 mL) was added DIEA (548 mg, 4.24 mmol, 0.75 mL) and HBTU (603 mg, 1.59 mmol) in one portion at 25° C. The mixture was stirred at 25° C. for 1.5 h. The mixture was diluted with 30 mL ethyl acetate and 20 mL $H_2O$, the organic layer was separated and washed with 1N HCl (20 mL×2), saturated $NaHCO_3$ (20 mL×2) and brine (20 mL), the organic layer was dried with over $Na_2SO_4$, and filtered and organic layer was concentrated in vacuum. The residue was purified by column chromatography ($SiO_2$, Petroleum ether/Ethyl acetate=4/1). Compound 159A (190 mg, yield: 49.32%) was obtained as a yellow oil. ¹H NMR (400 MHz, DMSO-$d_6$) δ 8.62 (br t, J=5.8 Hz, 1H), 7.36-7.14 (m, 9H), 6.91-6.78 (m, 1H), 4.31 (d, J=6.0 Hz, 2H), 3.69 (s, 3H), 3.48 (s, 2H), 2.24 (s, 3H).

To a solution of compound 159A (190 mg, 522.83 umol) in MeOH (8 mL) and $H_2O$ (5 mL) was added NaOH (84 mg, 2.09 mmol). The mixture was stirred at 25° C. for 2 h. The reaction mixture was concentrated and added 10 mL of water and the mixture was extracted with MTBE (10 mL×2), the aqueous layer was acidified by 1N HCl to pH ~2~3 at 0° C., and extracted with EtOAc (10 mL×2), the organic phase was dried over $Na_2SO_4$, and concentrated to give a residue. Compound 159B (143 mg, yield: 78.28%) was obtained as a white solid, which was used for next step directly. ¹H NMR (400 MHz, DMSO-$d_6$) δ 8.62 (br t, J=5.7 Hz, 1H), 7.34-7.24 (m, 8H), 7.24-7.19 (m, 1H), 6.76 (s, 1H), 4.30 (d, J=5.7 Hz, 2H), 3.48 (s, 2H), 2.22 (s, 3H).

Compound 159 (25 mg, yield: 33.34%, white solid) was prepared as in Example 5 from the corresponding intermediate carboxylic acid, compound 159B. Compound 159: ¹H NMR (400 MHz, DMSO-$d_6$) δ 8.31 (br s, 1H), 7.40-7.05 (m, 17H), 6.56 (s, 1H), 5.31 (dd, J=4.3, 9.8 Hz, 1H), 4.31 (d, J=4.3 Hz, 2H), 3.52 (s, 2H), 3.23 (dd, J=4.3, 14.1 Hz, 1H), 2.91 (dd, J=10.0, 13.8 Hz, 1H), 2.25 (s, 3H). MS (ESI) m/z $(M+H)^+$524.2.

N-(4-amino-3,4-dioxo-1-phenylbutan-2-yl)-1-(4-((4-fluorobenzamido)methyl)phenyl)-3-methyl-1H-pyrazole-5-carboxamide (496)

Compound 496 (246.9 mg, yield: 80.2%, white solid) was prepared as in compound 154 using intermediate 153F and 4-fluorobenzoyl chloride and the resulting product was subjected to reactions as in compound 12 to obtain compound 496. Compound 496: $^1$H NMR (400 MHz, DMSO-$d_6$) δ 99.20-9.05 (m, 2H), 8.13 (s, 1H), 8.05-7.96 (m, 2H), 7.87 (s, 1H), 7.40-7.16 (m, 9H), 7.16-7.08 (m, 2H), 6.54 (s, 1H), 5.32-5.22 (m, 1H), 4.55-4.45 (m, 2H), 3.22-3.14 (m, 1H), 2.83-2.73 (m, 1H), 2.24 (s, 3H). MS (ESI) m/z $(M+H)^+$ 526.2.

Example 93 methyl (S)-(4-(5-((4-amino-3,4-dioxo-1-phenylbutan-2-yl)carbamoyl)-3-methyl-1H-pyrazol-1-yl)benzyl)carbamate (161)

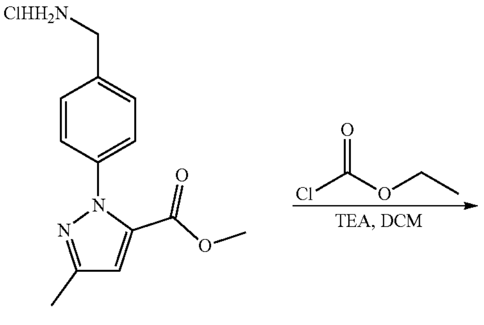

153F

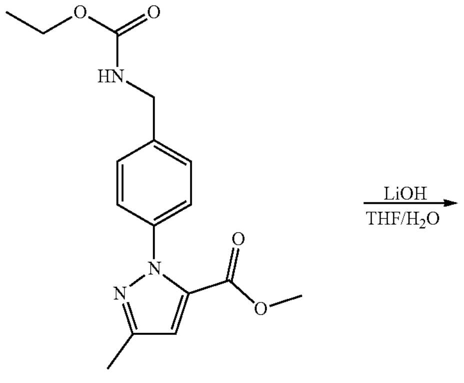

161A

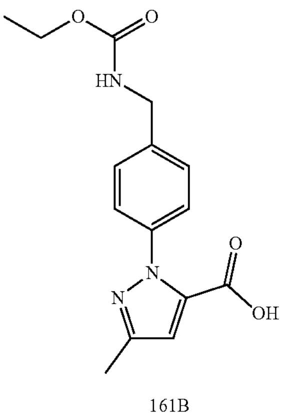

161B

To a mixture of compound 153F (450 mg, 1.60 mmol, HCl) in DCM (15.00 mL) was added TEA (485 mg, 4.79 mmol, 0.7 mL) and ethyl carbonochloridate (452 mg, 4.17 mmol, 0.4 mL) in portion at 25° C. and stirred for 2 h. The reaction mixture was treated with DCM (20 mL), washed with $H_2O$ (30 mL). The organic layer was separated and washed with brine (30 mL), dried over anhydrous $NaSO_4$, filtered and concentrated. The residue was purified by column chromatography ($SiO_2$, Petroleum ether/Ethyl acetate=5/1 to 1/1) to give compound 161A (400 mg, yield: 52.81%) as offwhite solid. $^1$H NMR (400 MHz, $CDCl_3$) δ 7.37 (br s, 4H), 6.80 (dd, J=3.5 Hz, 1H), 4.43 (s, 2H), 4.20-4.09 (m, 2H), 3.79 (d, J=3.7 Hz, 3H), 2.36 (dd, J=3.5 Hz, 3H), 1.27 (td, J=3.5, 7.1 Hz, 3H). MS (ESI) m/z $(M+H)^+$318.0.

To a mixture of compound 161A (400 mg, 1.26 mmol) in THF (10 mL) and $H_2O$ (10 mL) was added $LiOH.H_2O$ (159 mg, 3.78 mmol) in portion at 25° C. and stirred for 0.5 h. The mixture was diluted with $H_2O$ (10 mL) and concentrated to remove THF, then, the water was extracted with MTBE (30 mL×2). The water layers were acidified to pH ~2 with 1N HCl, then, the solution extracted with ethyl acetate (30 mL×3). The organic layers were dried over $Na_2SO_4$ and concentrated to give intermediate compound 161B (300 mg, yield: 78.50%) as white solid. $^1$H NMR (400 MHz, $CDCl_3$) δ 7.33 (s, 4H), 6.79 (s, 1H), 4.35 (s, 2H), 4.23-4.03 (m, 2H), 2.38-2.27 (m, 3H), 1.41-1.19 (m, 4H). MS (ESI) m/z $(M+H)^+$304.0.

Compound 161 (25 mg, yield: 22.8%, white solid) was prepared as in Example 5 from the corresponding intermediate carboxylic acid, compound 161B. Compound 161: $^1$H NMR (400 MHz, DMSO-$d_6$) δ 9.07 (dd, J=8.2 Hz, 1H), 8.12 (s, 1H), 7.87 (s, 1H), 7.69 (s, 1H), 7.42-7.27 (m, 5H), 7.20 (dd, J=7.9 Hz, 2H), 7.16-7.06 (m, 2H), 6.54 (s, 1H), 5.34-5.24 (m, 1H), 4.18 (dd, J=5.5 Hz, 2H), 4.02 (q, J=7.1 Hz, 2H), 3.21 (dd, J=2.9, 13.2 Hz, 1H), 2.92-2.77 (m, 1H), 2.24 (s, 3H), 1.18 (br t, J=7.1 Hz, 3H). MS (ESI) m/z $(M+H)^+$ 478.1.

Example 94 phenyl (S)-(4-(5-((4-amino-3,4-dioxo-1-phenylbutan-2-yl)carbamoyl)-3-methyl-1H-pyrazol-1-yl)benzyl)carbamate (162)

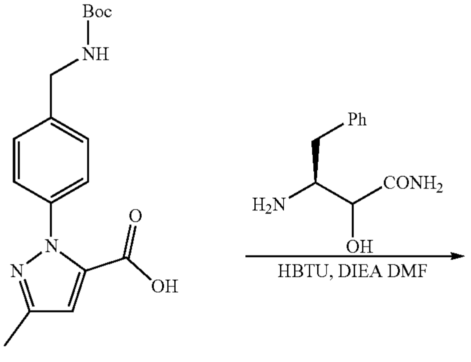

162A

-continued

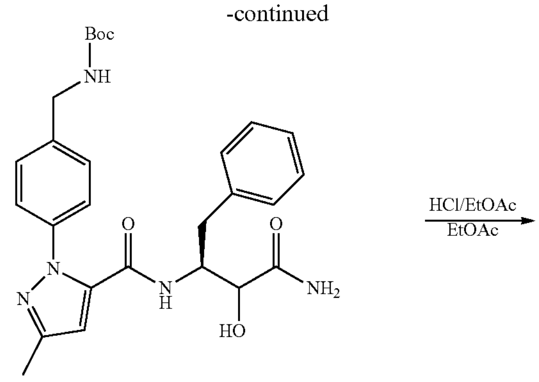

162B

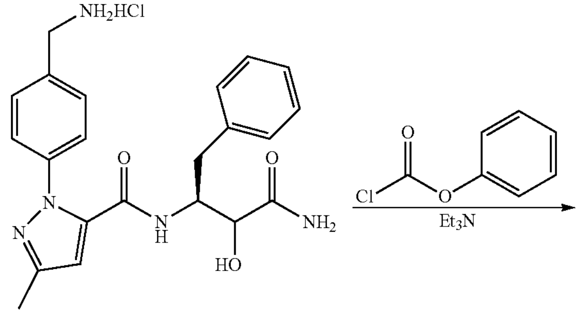

162C

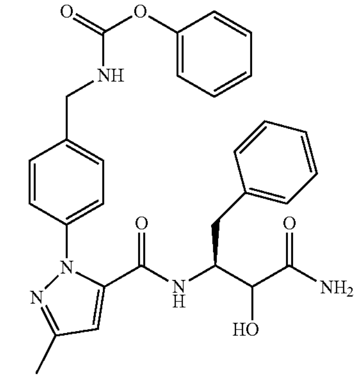

162D

To a mixture of compound 153E (300 mg, 868.58 umol) in THF (10 mL) and $H_2O$ (10 mL) was added $LiOH.H_2O$ (109 mg, 2.61 mmol) in portion at 25° C. and stirred for 12 h. The mixture was diluted with $H_2O$ (10 mL) and concentrated to remove THF, then, the water was extracted with MTBE (30 mL×2). The water layers were acidified to pH ~2 with 1N HCl, then, the solution extracted with ethyl acetate (30 mL×3). The organic layers were dried over $Na_2SO_4$ and concentrated to give intermediate compound 162A (250 mg, yield: 86.86%) as white solid. $^1$H NMR (400 MHz, $CDCl_3$) δ 7.41-7.30 (m, 2H), 7.27-7.04 (m, 2H), 6.86 (s, 1H), 4.43-4.26 (m, 2H), 2.46-2.32 (m, 3H), 1.60-1.40 (m, 9H). MS (ESI) m/z $(M+H)^+$332.0.

To a mixture of compound 12G (209 mg, 905.33 umol, HCl) and compound 162A (250 mg, 754.44 umol) in DMF (10 mL) was added DIEA (244 mg, 1.89 mmol, 0.3 mL) and HBTU (343 mg, 905.33 umol) in portion at 25° C. and stirred for 1.5 h. The reaction mixture was treated with ethyl acetate (40 mL), washed with $H_2O$ (50 mL×2). The organic layer was washed with brine (30 mL), dried over $Na_2SO_4$, filtered and the solvent was removed in vacuo. The residue was triturated in DCM (2 mL) and petroleum ether (10 mL), the solid was collected and was dried in vacuo to give compound 162B (300 mg, yield: 75.76%) as white solid. $^1$H NMR (400 MHz, DMSO-$d_6$) δ 8.72-8.41 (m, 1H), 7.95 (s, 1H), 7.45-7.20 (m, 7H), 7.12 (dd, J=8.4 Hz, 2H), 7.02-6.91 (m, 2H), 6.70-6.48 (m, 1H), 6.08 (d, J=5.5 Hz, 1H), 4.45 (s, 1H), 4.12-3.98 (m, 2H), 2.89 (s, 1H), 2.87-2.80 (m, 1H), 2.73 (s, 1H), 2.28-2.14 (m, 3H), 1.52-1.33 (m, 9H). MS (ESI) m/z $(M-56)^+$452.1.

To a mixture of compound 162B (300 mg, 591.04 umol) in EA (10 mL) was added HCl/EtOAc (4M, 10 mL) dropwise at 0° C. The reaction mixture was stirred at 25° C. for 2 h. The mixture was concentrated to give intermediate compound 162C (250 mg, yield: 95.28%, HCl) as white solid. $^1$H NMR (400 MHz, DMSO-$d_6$) δ 8.71-8.64 (m, 2H), 7.53-7.35 (m, 3H), 7.34-7.17 (m, 7H), 7.03 (dd, J=8.4 Hz, 2H), 6.65 (s, 1H), 4.59-4.30 (m, 1H), 4.15 (s, 2H), 2.88 (s, 1H), 2.83 (dd, J=11.9 Hz, 1H), 2.72 (s, 1H), 2.22 (s, 3H).

To a mixture of compound 162C (120 mg, 270.31 umol, HCl) in DCM (10 mL) was added $Et_3N$ (68 mg, 675.78 umol, 0.1 mL) and phenyl carbonochloridate (51 mg, 324.38 umol, 0.1 mL) in portion at 25° C. and stirred for 1 h. The reaction mixture was treated with DCM (20 mL), added with $H_2O$ (30 mL). The organic layer was separated and washed with brine (30 mL), dried over anhydrous $NaSO_4$, filtered and concentrated. The residue was purified by preparatory-HPLC (HCl condition) to give compound 162D (70 mg, yield: 47.71%) as off-white solid. $^1$H NMR (400 MHz, DMSO-$d_6$) δ 9.36 (s, 1H), 8.50 (dd, J=9.0 Hz, 1H), 7.41-7.11 (m, 14H), 7.08 (s, 1H), 7.02 (dd, J=8.4 Hz, 1H), 6.99 (dd, J=8.4 Hz, 1H), 6.78-6.72 (m, 2H), 6.57-6.50 (m, 1H), 4.43 (s, 1H), 4.31-4.22 (m, 2H), 3.99 (s, 1H), 2.87-2.75 (m, 2H), 2.74-2.65 (m, 2H), 2.27-2.20 (m, 3H). MS (ESI) m/z $(M+H)^+$528.1.

To a mixture of compound 162D (40 mg, 75.82 umol) in DMSO (3 mL) and DCM (15 mL) was added DMP (96 mg, 227.46 umol) in one portion at 25° C. under $N_2$. The mixture was stirred at 25° C. for 1.5 h. The reaction mixture was diluted with DCM (10 mL), $NaHCO_3$ (5 mL) and $Na_2S_2O_3$ (10 mL), then stirred for 10 min and layers were separated. The organic layers were washed with water (50 mL×2), dried over $Na_2SO_4$, filtered and concentrated under reduced pressure to give a residue. The residue was triturated in DCM (2 mL) and petroleum ether (10 mL), the solid was collected and was dried in vacuo to give compound 162 (25 mg, yield: 51.13%) as a white solid. $^1$H NMR (400 MHz, DMSO-$d_6$) δ 9.15 (d, J=8.0 Hz, 1H), 8.39 (t, J=6.0 Hz, 1H), 8.14 (s, 1H), 7.88 (s, 1H), 7.41-7.19 (m, 11H), 7.14 (dd, J=8.0 Hz, 3H), 6.68-6.51 (m, 1H), 5.41-5.22 (m, 1H), 4.29 (dd, J=6.0 Hz, 2H), 3.21 (dd, J=3.5, 13.6 Hz, 1H), 2.85 (dd, J=10.8, 13.8 Hz, 1H), 2.25 (s, 3H). MS (ESI) m/z $(M+H)^+$ 526.1.

Example 95

(S)—N-(4-amino-3,4-dioxo-1-phenylbutan-2-yl)-1-methyl-3-(m-tolyl)-1H-pyrazole-4-carboxamide (163)

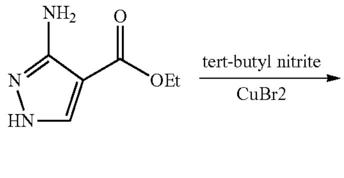

-continued
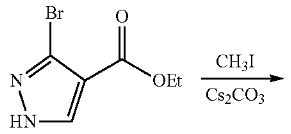
163A
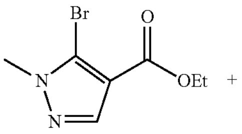
163B
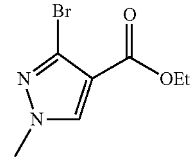
163C
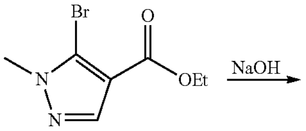
163B
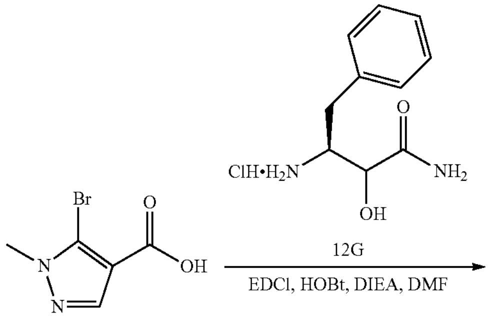
163D
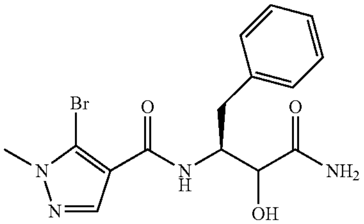
163E
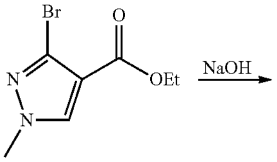
163C
-continued
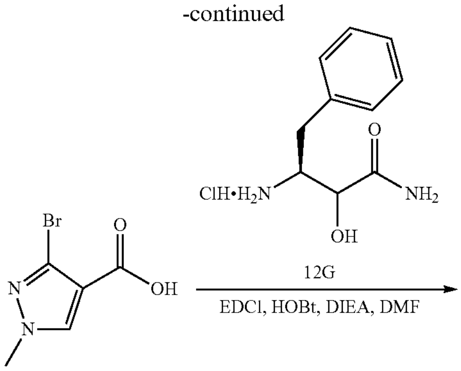
163F
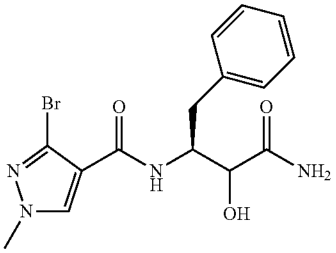
163G
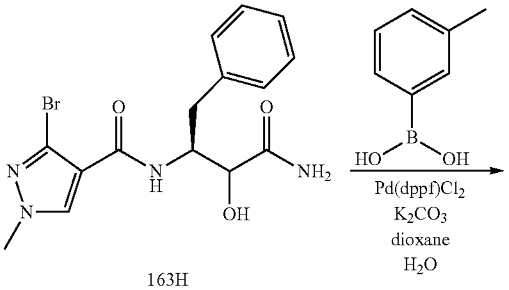
163H
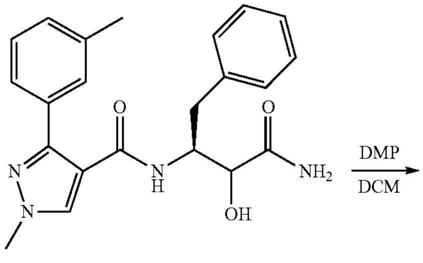
163J
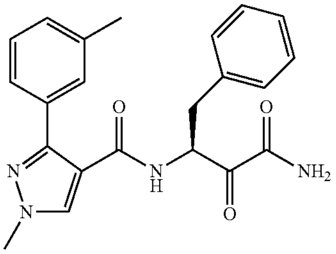
163
To a solution of t-BuONO (3.8 mL, 30.94 mmol) in $CH_3CN$ (60 mL) was added $CuBr_2$ (6.91 g, 30.94 mmol). The mixture was stirred at 25° C. for 1 h under $N_2$. Then ethyl 3-amino-1H-pyrazole-4-carboxylate (4 g, 25.78 mmol) was added in portions. The mixture was then heated to 70° C. and stirred for 12 h. The reaction was washed with $H_2O$ (100 mL), extracted with EtOAc (100 mL×2). The organics were collected, dried with $Na_2SO_4$, filtered and concentrated to afford intermediate compound 163A (6 g, crude) as black oil. MS (ESI) m/z $(M+2)^+$220.9.

To a solution of compound 163A (10 g, 45.65 mmol) and $Cs_2CO_3$ (29.75 g, 91.30 mmol) in DMF (250 mL) was added MeI (19.44 g, 136.95 mmol, 8.53 mL). The mixture was stirred at 25° C. for 16 h. The mixture was filtered, the filtrate was diluted with $H_2O$ (500 mL), and extracted with ethyl acetate (100 mL×3), dried over $Na_2SO_4$, concentrated to give a residue. The residue was purified by column chromatography ($SiO_2$, Petroleum ether/Ethyl acetate=5/1). Compound 163B (2.5 g, yield: 23.50%) was obtained as a yellow oil, and Compound 163C (5.5 g, yield: 51.70%) was obtained as a white solid.

Compound 163B: $^1$H NMR (400 MHz, $CDCl_3$) δ 7.93 (s, 1H), 4.31 (q, J=7.1 Hz, 2H), 3.95-3.87 (m, 3H), 1.36 (t, J=7.1 Hz, 3H).

Compound 163C: $^1$H NMR (400 MHz, $CDCl_3$) δ 7.82 (s, 1H), 4.30 (q, J=7.1 Hz, 2H), 3.99-3.77 (m, 3H), 1.35 (t, J=7.2 Hz, 3H).

To a solution of compound 163B (600 mg, 2.57 mmol) in MeOH (10 mL) and $H_2O$ (10 mL) was added NaOH (514 mg, 12.85 mmol). The mixture was stirred at 25° C. for 3 h. The reaction mixture was concentrated and added 20 mL of water, the mixture was extracted with MTBE (10 mL×2), the aqueous layer was acidified by 1N HCl to pH ~2~3 at 0° C., and extracted with EtOAc (20 mL×2), the organic phase was dried over $Na_2SO_4$, concentrated to give a residue. Compound 163D (480 mg, yield: 91.05%) was obtained as a white solid. $^1$H NMR (400 MHz, DMSO-$d_6$) δ 12.65 (s, 1H), 8.13 (s, 1H), 3.82 (s, 3H).

To a solution of Compound 163D (450 mg, 2.20 mmol), (3S)-3-amino-2-hydroxy-4-phenyl-butanamide 12G (761 mg, 3.30 mmol, HCl) and HOBT (445 mg, 3.30 mmol) in DCM (20 mL) was added DIEA (1.14 g, 8.80 mmol, 1.54 mL) and EDCI (843 mg, 4.40 mmol). The mixture was stirred at 25° C. for 16 h. The mixture was diluted with $CHCl_3$:iPrOH=3:1 (50 mL), washed with 1N HCl (30 mL), saturated aqueous $NaHCO_3$ (30 mL) and brine (30 mL). The organic layer was dried over anhydrous $Na_2SO_4$ and concentrated in vacuo. The solid was triturated in ethyl acetate (30 mL), filtered. Compound 163E (550 mg, yield: 61.64%) was obtained as a yellow solid. $^1$H NMR (400 MHz, DMSO-$d_6$) δ 8.09-7.95 (m, 1H), 7.78 (d, J=8.8 Hz, 0.6H), 7.46 (d, J=9.0 Hz, 0.4H), 7.38-7.07 (m, 6H), 6.01-5.86 (m, 1H), 4.54-4.33 (m, 1H), 4.00 (dd, J=3.4, 5.2 Hz, 1H), 3.85-3.74 (m, 4H), 2.93-2.67 (m, 1H), 2.62 (dd, J=2.3, 13.8 Hz, 1H). MS (ESI) m/z $(M+H)^+$381.0.

To a solution of compound 163C (2.6 g, 11.16 mmol) in MeOH (10 mL) and $H_2O$ (10 mL) was added $LiOH.H_2O$ (2.34 g, 55.80 mmol). The mixture was stirred at 25° C. for 12 h. The reaction mixture was concentrated and added 20 mL of water and the mixture was extracted with MTBE (20 mL×2), the aqueous layer was acidified by 1N HCl to pH ~2~3 at 0° C., and extracted with EtOAc (30 mL×2), the organic phase was dried over $Na_2SO_4$ and concentrated to give a residue. Compound 163F (2.2 g, yield: 96.16%) was obtained as a gray solid, which was used for next step directly. $^1$H NMR (400 MHz, DMSO-$d_6$) δ 12.55 (br s, 1H), 8.24 (s, 1H), 3.81 (s, 3H).

To a mixture of compound 163F (2.2 g, 10.73 mmol) and compound 12G (2.97 g, 12.88 mmol HCl) in DMF (20 mL) and HOBt (2.17 g, 16.10 mmol) and DIEA (4.16 g, 32.19 mmol, 5.62 mL) and EDCI (4.11 g, 21.46 mmol) in one portion at 25° C. The mixture was stirred at 25° C. for 12 h. The reaction mixture was diluted with $H_2O$ (40 mL) and extracted with $CHCl_3$:isopropanol (v:v=3:1; 30×3 mL), then the organic phase was washed with 1N HCl (20 mL×2) and saturated aqueous $NaHCO_3$ (20 mL×2). The mixture was dried over $Na_2SO_4$ and concentrated. The residue was diluted with EtOAc (15 mL) the solid was collected and dried in vacuo. Compound 163G (2.9 g, yield: 68.06%) was obtained as a white solid. $^1$H NMR (400 MHz, DMSO-$d_6$) δ 8.18 (s, 1H), 7.61 (br d, J=8.8 Hz, 1H), 7.31 (br d, J=2.4 Hz, 2H), 7.24-7.13 (m, 5H), 5.89 (d, J=5.7 Hz, 1H), 4.51-4.40 (m, 1H), 4.00-3.97 (m, 1H), 3.79 (s, 3H), 2.80-2.76 (m, 1H), 2.65-2.58 (m, 1H). MS (ESI) m/z $(M+H)^+$381.0.

Compound 163G (200 mg, 525 umol), m-tolylboronic acid (85.6 mg, 629 umol), Pd(dppf)$Cl_2$ (38.4 mg, 52.5 umol) and $K_2CO_3$ (145 mg, 1.05 mmol) in dioxane (5 mL) was de-gassed and then heated to 100° C. for 12 hours under $N_2$. The mixture was filtered and concentrated, the residue was purified by prep-TLC (Dichloromethane:Methanol=10:1) to give compound 163H (100 mg, yield: 48.6%), as white solid. $^1$H NMR (400 MHz, DMSO-$d_6$) δ 7.99 (d, J=19.4 Hz, 1H), 7.37 (br s, 1H), 7.31-7.06 (m, 11H), 5.76 (br s, 1H), 4.52-4.31 (m, 1H), 3.98 (br s, 1H), 3.83 (s, 3H), 3.80 (br s, 1H), 2.87-2.72 (m, 1H), 2.71-2.56 (m, 1H), 2.26 (d, J=6.8 Hz, 3H).

A mixture of compound 163H (100 mg, 255 umol) and DMP (432 mg, 1.02 mmol) in DCM (10 mL), DMSO (2 mL) was stirred at 25° C. for 1 hr. The mixture was diluted DCM (20 mL), quenched with saturated aqueous $NaHCO_3$ (20 mL), saturated aqueous $Na_2S_2O_3$ (20 mL) and stirred for 20 min, the mixture was extracted with DCM (20 mL×2), the combined organic phase was washed with water (20 mL), brine (20 mL), dried over $Na_2SO_4$, filtered and concentrated, the residue was stirred in DCM and n-hexane for 20 min, the solid was filtered and dried to give 163 (43.5 mg, yield: 43.7%) as white solid. $^1$H NMR (400 MHz, DMSO-$d_6$) δ 8.23 (br d, J=7.3 Hz, 1H), 8.08-7.97 (m, 2H), 7.78 (s, 1H), 7.38 (s, 1H), 7.31 (br d, J=7.5 Hz, 1H), 7.28-7.13 (m, 6H), 7.11-7.05 (m, 1H), 5.31-5.21 (m, 1H), 3.85 (s, 3H), 3.12 (dd, J=3.7, 13.9 Hz, 1H), 2.79 (dd, J=9.7, 13.9 Hz, 1H), 2.25 (s, 3H). MS (ESI) m/z $(M+H)^+$391.1.

Example 96

Compounds 164, 169, 480-488, 498-518, 530, 548, 567-573, 585, 587, 591, 593, 597, 601-605, 607, 611, 613-617, 620-621, 624-629

(S)—N-(4-amino-3,4-dioxo-1-phenylbutan-2-yl)-1-methyl-5-(pyridin-2-yl)-1H-pyrazole-4-carboxamide (164)

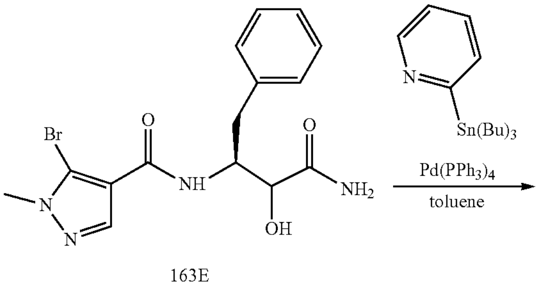

163E

-continued

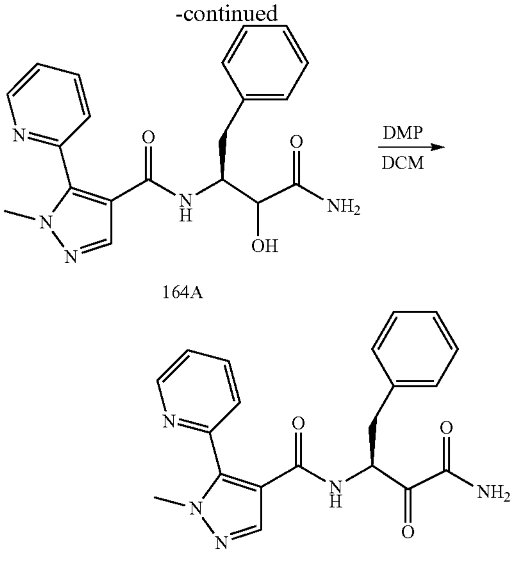

164A

164

To the mixture of 163E (200 mg, 527 umol) and tributyl (2-pyridyl)stannane (388 mg, 1.05 mmol) in toluene (5 mL) was added $Pd(PPh_3)_4$ (60.9 mg, 52.7 umol) under $N_2$ (15 psi). After stirred at 110° C. for 10 h, the mixture was concentrated in vacuum to get residue. The residue was purified by preparatory-HPLC (acid) to get compound 164A (85 mg, yield: 42.5%) as light yellow solid. $^1$H NMR (400 MHz, $CDCl_3$-d) δ 8.97 (br d, J=7.06 Hz, 1H), 8.72 (br d, J=7.28 Hz, 1H), 8.55 (dd, J=17.64, 4.85 Hz, 1H), 8.03-7.95 (m, 1H), 7.88-7.79 (m, 1H), 7.43-7.31 (m, 2H), 7.13-6.99 (m, 6H), 5.49 (br d, J=10.14 Hz, 1H), 4.27-4.17 (m, 2H), 3.89 (d, J=3.53 Hz, 3H), 3.26-2.91 (m, 2H).

Compound 164 (31 mg, yield: 41.6%, white solid) was prepared as in Example 105 from the intermediate compound 164A. Compound 164: $^1$H NMR (400 MHz, $CDCl_3$-d) δ 8.51 (br d, J=6.4 Hz, 1H), 8.43 (d, J=5.1 Hz, 1H), 8.01 (s, 1H), 7.84 (br t, J=7.8 Hz, 1H), 7.49 (d, J=7.9 Hz, 1H), 7.32 (dd, J=5.3, 7.1 Hz, 1H), 7.21-7.09 (m, 3H), 6.96 (br d, J=5.7 Hz, 2H), 6.75 (br s, 1H), 5.70-5.60 (m, 2H), 3.89 (s, 3H), 3.33 (dd, J=5.1, 14.3 Hz, 1H), 3.15 (dd, J=7.1, 14.1 Hz, 1H). MS (ESI) m/z $(M+H)^+$378.1.

(S)—N-(4-amino-3,4-dioxo-1-phenylbutan-2-yl)-1-methyl-3-(pyridin-2-yl)-1H-pyrazole-4-carboxamide (169)

Compound 169 (20 mg, yield: 48.2%, white solid) was prepared as in compound 163 from the corresponding starting materials, compound 163G and tributyl(2-pyridyl)stannane. $^1$H NMR (400 MHz, DMSO-$d_6$) δ 11.88 (br d, J=7.9 Hz, 1H), 8.32 (br d, J=5.3 Hz, 1H), 8.20 (s, 1H), 8.08 (d, J=8.3 Hz, 1H), 7.91 (t, J=7.7 Hz, 1H), 7.74 (br s, 1H), 7.52 (br s, 1H), 7.40-7.32 (m, 1H), 7.20-7.05 (m, 5H), 5.64-5.47 (m, 1H), 3.91 (s, 3H), 3.27 (dd, J=4.8, 14.5 Hz, 1H), 3.12-3.07 (m, 1H). MS (ESI) m/z $(M+H)^+$378.1.

N-(4-amino-3,4-dioxo-1-phenylbutan-2-yl)-3-(2,3-difluorophenyl)-1-methyl-1H-pyrazole-4-carboxamide (480)

Compound 480 (60 mg, yield: 48.13%, white solid) was prepared as in compound 163 from the corresponding starting materials, compound 163G and (2,3-difluorophenyl) boronic acid. $^1$H NMR (400 MHz, DMSO-$d_6$) δ 8.39 (d, J=7.3 Hz, 1H), 8.30 (s, 1H), 8.03 (s, 1H), 7.78 (s, 1H), 7.45-7.34 (m, 1H), 7.33-7.13 (m, 7H), 5.28-5.22 (m, 1H), 3.92 (s, 3H), 3.13 (dd, J=3.6, 13.8 Hz, 1H), 2.83 (dd, J=10.1, 13.9 Hz, 1H). MS (ESI) m/z $(M+H)^+$413.1.

N-(4-amino-3,4-dioxo-1-phenylbutan-2-yl)-3-(6-cyanopyridin-3-yl)-1-methyl-1H-pyrazole-4-carboxamide (481)

Compound 481 (15 mg, yield: 37.47%, white solid) was prepared as in compound 163 from the corresponding starting materials, compound 163G and (6-cyanopyridin-3-yl) boronic acid. $^1$H NMR (400 MHz, DMSO-$d_6$) δ 8.91 (d, J=1.8 Hz, 1H), 8.67 (d, J=7.3 Hz, 1H), 8.25 (s, 1H), 8.15 (dd, J=2.0, 8.2 Hz, 1H), 8.08 (s, 1H), 7.97 (d, J=8.2 Hz, 1H), 7.81 (s, 1H), 7.27 (d, J=4.4 Hz, 4H), 7.24-7.17 (m, 1H), 5.27 (t, J=3.0 Hz, 1H), 3.94 (s, 3H), 3.15 (dd, J=3.7, 13.9 Hz, 1H), 2.86-2.74 (m, 1H). MS (ESI) m/z $(M+H)^+$403.2.

N-(4-amino-3,4-dioxo-1-phenylbutan-2-yl)-3-(1H-indazol-3-yl)-1-methyl-1H-pyrazole-4-carboxamide (482)

Compound 482 (18 mg, yield: 14.77%, white solid) was prepared as in compound 163 from the corresponding starting materials, compound 163C and 3-(4,4,5,5-tetramethyl-1,3,2-dioxaborolan-2-yl)-1-((2-(trimethylsilyl)ethoxy) methyl)-1H-indazole and the final compound 482 was obtained by removal of the 2-(trimethylsilyl)ethoxy)methyl group. $^1$H NMR (400 MHz, DMSO-$d_6$) δ 11.10 (br s, 1H), 9.57 (br s, 1H), 8.44 (d, J=8.0 Hz, 1H), 8.08 (s, 1H), 7.46-7.38 (m, 2H), 7.24 (s, 6H), 6.84 (br s, 1H), 5.70 (br s, 1H), 5.50 (br s, 1H), 3.97 (s, 3H), 3.42-3.32 (m, 1H), 3.26-3.20 (m, 1H). MS (ESI) m/z $(M+H)^+$417.0.

N-(4-amino-3,4-dioxo-1-phenylbutan-2-yl)-3-benzyl-1-methyl-1H-pyrazole-4-carboxamide (483)

Compound 483 (65 mg, yield: 66.57%, white solid) was prepared using the procedures similar to compound 163 from the corresponding starting materials, compound ethyl 3-iodo-1-methyl-1H-pyrazole-4-carboxylate and 2-benzyl-4,4,5,5-tetramethyl-1,3,2-dioxaborolane and the final compound 483 was obtained by removal of the 2-(trimethylsilyl) ethoxy)methyl group. $^1$H NMR (400 MHz, DMSO-$d_6$) δ 8.33 (d, J=7.1 Hz, 1H), 8.19 (s, 1H), 8.05 (s, 1H), 7.79 (s, 1H), 7.31-7.23 (m, 4H), 7.20-7.07 (m, 6H), 5.31-5.23 (m, 1H), 4.05 (s, 2H), 3.77 (s, 3H), 3.20-3.09 (m, 1H), 2.91-2.80 (m, 1H). MS (ESI) m/z $(M+H)^+$391.1.

N-(4-amino-3,4-dioxo-1-phenylbutan-2-yl)-3-(2-fluorophenyl)-1-methyl-1H-pyrazole-4-carboxamide (484)

Compound 484 (3.35 g, white solid) was prepared using the procedures similar to compound 163 from the corresponding starting materials, compound 163C and (2-fluorophenyl)boronic acid and the final compound 484 was obtained. $^1$H NMR (400 MHz, DMSO-$d_6$) δ 8.30 (d, J=7.3 Hz, 1H), 8.26 (s, 1H), 8.04 (s, 1H), 7.79 (s, 1H), 7.41-7.11 (m, 9H), 5.30-5.18 (m, 1H), 3.90 (s, 3H), 3.12 (dd, J=3.6, 14.0 Hz, 1H), 2.83 (dd, J=9.8, 13.8 Hz, 1H). MS (ESI) m/z $(M+H)^+$395.0.

N-(4-amino-3,4-dioxo-1-phenylbutan-2-yl)-3-(3-fluorophenyl)-1-methyl-1H-pyrazole-4-carboxamide hydrochloride (485)

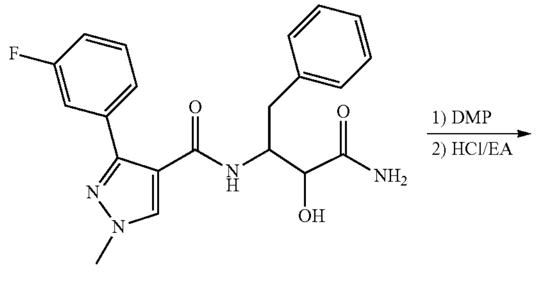

590

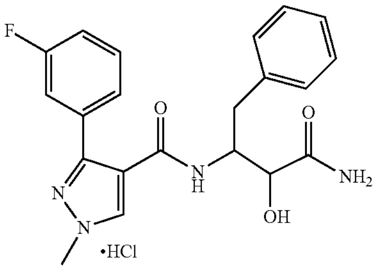

485

Compound 485 was synthesized from intermediate 590 which was synthesized using 163H. Compound 485 (3.1 g, yield: 79.85% white solid) was prepared from intermediate 590 using the procedures similar to compound 163 from the corresponding starting materials and the final compound 485 was obtained. $^1$H NMR (400 MHz, DMSO-d6) δ 8.51 (d, J=7.3 Hz, 1H), 8.12 (s, 2H), 7.85 (br s, 1H), 7.46 (d, J=8.3 Hz, 2H), 7.39-7.28 (m, 5H), 7.25-7.20 (m, 1H), 7.14 (t, J=8.0 Hz, 1H), 5.43-5.25 (m, 1H), 3.18 (dd, J=3.4, 13.7 Hz, 1H), 2.84 (dd, J=10.3, 13.8 Hz, 1H). MS (ESI) m/z $(M+H)^+$ 395.1.

N-(4-amino-3,4-dioxo-1-phenylbutan-2-yl)-3-(2,6-difluorophenyl)-1-methyl-1H-pyrazole-4-carboxamide (486)

Compound 486 (60 mg, yield: 43.0% light yellow solid) was prepared using the procedures similar to compound 163 from the corresponding starting materials, compound 163C and (2,6-difluorophenyl)boronic acid and the final compound 486 was obtained. $^1$H NMR (400 MHz, $CDCl_3$) δ 7.94 (s, 1H), 7.41-7.33 (m, 1H), 7.22-7.17 (m, 3H), 6.99-6.93 (m, 2H), 6.88 (dd, J=3.0, 6.3 Hz, 2H), 6.67 (br s, 1H), 6.01 (br d, J=7.1 Hz, 1H), 5.63-5.57 (m, 1H), 5.53 (br s, 1H), 3.97 (s, 3H), 3.27 (dd, J=5.3, 14.1 Hz, 1H), 3.09 (dd, J=6.6, 14.1 Hz, 1H). MS (ESI) m/z $(M+H)^+$413.1

N-(4-amino-3,4-dioxo-1-phenylbutan-2-yl)-3-(6-methoxypyridin-2-yl)-1-methyl-1H-pyrazole-4-carboxamide (487)

Compound 487 (10 mg, yield: 20.06% white solid) was prepared using the procedures similar to compound 163 from the corresponding starting materials, compound 163C and 2-methoxy-6-(tributylstannyl)pyridine and the final compound 487 was obtained. $^1$H NMR (400 MHz, $CD_3CN$)

δ 11.02 (d, J=5.5 Hz, 1H), 8.01 (s, 1H), 7.81 (t, J=7.9 Hz, 1H), 7.60 (d, J=7.5 Hz, 1H), 7.14-7.06 (m, 5H), 7.00-6.88 (m, 1H), 6.81 (d, J=8.2 Hz, 1H), 6.23-6.01 (m, 1H), 5.21-5.15 (m, 1H), 3.85 (s, 3H), 3.73 (s, 3H), 3.27 (dd, J=4.4, 13.9 Hz, 1H), 2.97 (dd, J=9.9, 13.9 Hz, 1H). MS (ESI) m/z $(M+H)^+$408.1.

N-(4-amino-3,4-dioxo-1-phenylbutan-2-yl)-5-benzyl-1-methyl-1H-pyrazole-4-carboxamide (488)

Compound 488 (35.6 mg, yield: 35.57%, white solid) was prepared using the procedures similar to compound 163 from the corresponding starting materials, compound ethyl 5-iodo-1-methyl-1H-pyrazole-4-carboxylate and 2-benzyl-4,4,5,5-tetramethyl-1,3,2-dioxaborolane and the final compound 488 was obtained. $^1$H NMR (400 MHz, DMSO-$d_6$) δ 8.40 (d, J=7.8 Hz, 1H), 8.03 (br. s, 1H), 7.92 (s, 1H), 7.77 (br. s, 1H), 7.31-7.03 (m, 10H), 5.32-5.23 (m, 1H), 4.36-4.24 (m, 2H), 3.58 (s, 3H), 3.19-3.10 (m, 1H), 2.89-2.79 (m, 1H). MS (ESI) m/z $(M+H)^+$391.1.

N-(4-amino-3,4-dioxo-1-phenylbutan-2-yl)-1-methyl-3-(5-methylfuran-2-yl)-1H-pyrazole-4-carboxamide (498)

Compound 498 (70 mg, yield: 54.1%, light yellow solid) was prepared using the procedures similar to compound 163 from the corresponding starting materials, compound ethyl 3-iodo-1-methyl-1H-pyrazole-4-carboxylate and (5-methylfuran-2-yl)boronic acid and the final compound 498 was obtained. $^1$H NMR (400 MHz, DMSO-$d_6$) δ 8.38-8.22 (m, 1H), 8.20-8.01 (m, 2H), 7.91-7.71 (m, 1H), 7.31-7.17 (m, 5H), 6.90 (d, J=3.1 Hz, 1H), 6.08 (d, J=2.2 Hz, 1H), 5.47-5.20 (m, 1H), 3.87 (s, 3H), 3.17 (dd, J=3.9, 13.8 Hz, 1H), 2.88 (dd, J=9.7, 14.1 Hz, 1H), 2.29-2.19 (m, 3H). MS (ESI) m/z $(M+H)^+$381.1.

N-(4-amino-3,4-dioxo-1-phenylbutan-2-yl)-3-(2,5-dimethylthiophen-3-yl)-1-methyl-1H-pyrazole-4-carboxamide (499)

Compound 499 (110 mg, yield: 64.9%, white solid) was prepared using the procedures similar to compound 163 from the corresponding starting materials, compound ethyl 3-iodo-1-methyl-1H-pyrazole-4-carboxylate and (2,5-dimethyl-3-thienyl)boronic acid and the final compound 499 was obtained. $^1$H NMR (400 MHz, DMSO-$d_6$) δ 8.14-8.00 (m, 2H), 7.87-7.73 (m, 2H), 7.34-7.12 (m, 5H), 6.58 (d, J=1.1 Hz, 1H), 5.28 (ddd, J=4.0, 7.3, 9.5 Hz, 1H), 3.91-3.79 (m, 3H), 3.14 (dd, J=4.0, 13.9 Hz, 1H), 2.77 (dd, J=9.4, 14.0 Hz, 1H), 2.33 (s, 3H), 2.22-2.12 (m, 3H). MS (ESI) m/z $(M+H)^+$411.1.

N-(4-amino-3,4-dioxo-1-phenylbutan-2-yl)-3-(FURAN-2-yl)-1-methyl-1H-pyrazole-4-carboxamide (500)

Compound 500 (55 mg, yield: 91.2%, white solid) was prepared using the procedures similar to compound 163 from the corresponding starting materials, compound ethyl 3-iodo-1-methyl-1H-pyrazole-4-carboxylate and 2-furylboronic acid and the final compound 500 was obtained. $^1$H NMR (400 MHz, DMSO-$d_6$) δ 8.37 (d, J=7.1 Hz, 1H), 8.14 (s, 1H), 8.07 (br s, 1H), 7.81 (br s, 1H), 7.61 (s, 1H), 7.28 (s, 4H), 7.20 (br s, 1H), 6.99 (d, J=2.9 Hz, 1H), 6.48 (br s, 1H), 5.37-5.28 (m, 1H), 3.88 (s, 3H), 3.18 (dd, J=3.5, 13.7 Hz, 1H), 2.86 (dd, J=9.7, 13.9 Hz, 1H). MS (ESI) m/z $(M+H)^+$367.1

N-(4-amino-3,4-dioxo-1-phenylbutan-2-yl)-3-(2-chlorothiophen-3-yl)-1-methyl-1H-pyrazole-4-carboxamide (501)

Compound 501 (110 mg, yield: 68.3%, white solid) was prepared using the procedures similar to compound 163 from the corresponding starting materials, compound ethyl 3-iodo-1-methyl-1H-pyrazole-4-carboxylate and (2-chlorothiophen-3-yl)boronic acid and the final compound 501 was obtained. $^1H$ NMR (400 MHz, DMSO-$d_6$) δ 8.13 (s, 1H), 7.80-7.46 (m, 3H), 7.35 (d, J=5.8 Hz, 1H), 7.30-7.24 (m, 2H), 7.23-7.16 (m, 3H), 6.98 (d, J=5.8 Hz, 1H), 5.31 (m, 1H), 3.89 (s, 3H), 3.17 (dd, J=4.4, 13.9 Hz, 1H), 2.88 (dd, J=8.9, 13.9 Hz, 1H). MS (ESI) m/z $(M+H)^+$417.1.

N-(4-amino-3,4-dioxo-1-phenylbutan-2-yl)-3-(furan-3-yl)-1-methyl-1H-pyrazole-4-carboxamide (502)

Compound 502 (160 mg, yield: 63.78%, white solid) was prepared using the procedures similar to compound 163 from the corresponding starting materials, compound ethyl 3-iodo-1-methyl-1H-pyrazole-4-carboxylate and furan-3-ylboronic acid and the final compound 502 was obtained. $^1H$ NMR (400 MHz, DMSO-$d_6$) δ 8.35 (d, J=7.6 Hz, 1H), 8.22-8.18 (m, 1H), 8.13 (s, 1H), 8.04 (br. s, 1H), 7.76 (br. s, 1H), 7.61-7.57 (m, 1H), 7.31-7.14 (m, 5H), 6.80-6.75 (m, 1H), 5.32-5.23 (m, 1H), 3.85 (s, 3H), 3.19-3.11 (m, 1H), 2.88-2.78 (m, 1H). MS (ESI) m/z $(M+H)^+$367.1.

N-(4-amino-3,4-dioxo-1-phenylbutan-2-yl)-1-methyl-3-(thiophen-3-yl)-1H-pyrazole-4-carboxamide (503)

Compound 503 (65 mg, yield: 47.7%, light yellow solid) was prepared using the procedures similar to compound 163 from the corresponding starting materials, compound ethyl 3-iodo-1-methyl-1H-pyrazole-4-carboxylate and thiophen-3-ylboronic acid and the final compound 503 was obtained. $^1H$ NMR (400 MHz, DMSO-$d_6$) δ 8.37 (d, J=7.3 Hz, 1H), 8.04 (s, 2H), 7.92 (s, 1H), 7.77 (br s, 1H), 7.50-7.34 (m, 2H), 7.30-7.22 (m, 4H), 7.18 (dd, J=4.4, 8.6 Hz, 1H), 5.38-5.18 (m, 1H), 3.84 (s, 3H), 3.22-3.08 (m, 1H), 2.81 (dd, J=9.9, 13.9 Hz, 1H). MS (ESI) m/z $(M+H)^+$383.1.

N-(4-amino-3,4-dioxo-1-phenylbutan-2-yl)-1-methyl-3-(4-methylthiophen-2-yl)-1H-pyrazole-4-carboxamide (504)

Compound 504 (100 mg, yield: 65.93%, light yellow solid) was prepared using the procedures similar to compound 163 from the corresponding starting materials, compound ethyl 3-iodo-1-methyl-1H-pyrazole-4-carboxylate and (4-methylthiophen-2-yl)boronic acid and the final compound 504 was obtained. $^1H$ NMR (400 MHz, DMSO-$d_6$) δ 8.37 (d, J=7.2 Hz, 1H), 8.09 (s, 1H), 8.06 (br. s, 1H), 7.78 (br. s, 1H), 7.57-7.54 (m, 1H), 7.29-7.23 (m, 4H), 7.22-7.15 (m, 1H), 6.99-6.95 (m, 1H), 5.34-5.27 (m, 1H), 3.83 (s, 3H), 3.19-3.10 (m, 1H), 2.88-2.77 (m, 1H), 2.14 (s, 3H). MS (ESI) m/z $(M+H)^+$397.1.

N-(4-amino-3,4-dioxo-1-phenylbutan-2-yl)-1-methyl-3-(5-methylthiophen-2-yl)-1H-pyrazole-4-carboxamide (505)

Compound 505 (130 mg, yield: 61%, light yellow solid) was prepared using the procedures similar to compound 163 from the corresponding starting materials, compound ethyl 3-iodo-1-methyl-1H-pyrazole-4-carboxylate and (5-methylthiophen-2-yl)boronic acid and the final compound 505 was obtained. $^1H$ NMR (400 MHz, DMSO-$d_6$) δ 8.68 (s, 1H), 8.57 (d, J=7.5 Hz, 1H), 8.53-8.48 (m, 1H), 8.23 (s, 1H), 8.08 (s, 1H), 7.92-7.86 (m, 1H), 7.81 (s, 1H), 7.34-7.25 (m, 4H), 7.23-7.18 (m, 1H), 5.36-5.28 (m, 1H), 3.94 (s, 3H), 3.17 (dd, J=3.9, 14.0 Hz, 1H), 2.83 (dd, J=10.0, 14.0 Hz, 1H). MS (ESI) m/z $(M+H)^+$396.1.

N-(4-amino-3,4-dioxo-1-phenylbutan-2-yl)-3-(5-fluoropyridin-3-yl)-1-methyl-1H-pyrazole-4-carboxamide (506)

Compound 506 (35 mg, yield: 20.4%, white solid) was prepared using the procedures similar to compound 163 from the corresponding starting materials, compound ethyl 3-iodo-1-methyl-1H-pyrazole-4-carboxylate and (5-fluoropyridin-3-yl)boronic acid and the final compound 506 was obtained. $^1H$ NMR (400 MHz, DMSO-$d_6$) δ 8.40 (d, J=7.3 Hz, 1H), 8.16-8.03 (m, 2H), 7.81 (s, 1H), 7.54 (d, J=3.5 Hz, 1H), 7.29 (d, J=4.2 Hz, 4H), 7.24-7.19 (m, 1H), 6.66 (dd, J=1.0, 3.6 Hz, 1H), 5.34-5.29 (m, 1H), 3.85 (s, 3H), 3.17 (dd, J=3.7, 13.9 Hz, 1H), 2.84 (dd, J=9.9, 13.9 Hz, 1H), 2.40 (s, 3H). MS (ESI) m/z $(M+H)^+$397.1.

N-(4-amino-3,4-dioxo-1-phenylbutan-2-yl)-3-(2-fluoro-5-methoxyphenyl)-1-methyl-1H-pyrazole-4-carboxamide (507)

Compound 507 (34 mg, yield: 15.75%, white solid) was prepared using the procedures similar to compound 163 from the corresponding starting materials, compound ethyl 3-iodo-1-methyl-1H-pyrazole-4-carboxylate and (2-fluoro-5-methoxyphenyl)boronic acid and the final compound 507 was obtained. $^1H$ NMR (400 MHz, DMSO-$d_6$) δ 8.14 (s, 1H), 7.68 (br d, J=7.0 Hz, 2H), 7.51 (br s, 1H), 7.30-7.15 (m, 5H), 7.10-7.01 (m, 1H), 6.98-6.87 (m, 2H), 5.28 (ddd, J=4.6, 7.3, 8.8 Hz, 1H), 3.90 (s, 3H), 3.75 (s, 3H), 3.15 (dd, J=4.5, 14.1 Hz, 1H), 2.87 (dd, J=8.9, 14.2 Hz, 1H). $^{19}F$ NMR (376 MHz, DMSO-$d_6$) δ−124.53 (br d, J=88.69 Hz, 1F). MS (ESI) m/z $(M+Na)^+$447.2.

N-(4-amino-3,4-dioxo-1-phenylbutan-2-yl)-3-(3-(difluoromethyl)phenyl)-1-methyl-1H-pyrazole-4-carboxamide (508)

Compound 508 (140 mg, yield: 69.98%, white solid) was prepared using the procedures similar to compound 163 from the corresponding starting materials, compound ethyl 3-iodo-1-methyl-1H-pyrazole-4-carboxylate and (3-(difluoromethyl)phenyl)boronic acid and the final compound 508 was obtained. $^1H$ NMR (400 MHz, DMSO-$d_6$) δ 8.43 (d, J=7.6 Hz, 1H), 8.09 (s, 1H), 8.02 (br. s, 1H), 7.85-7.81 (m, 1H), 7.78 (br. s, 1H), 7.73-7.67 (m, 1H), 7.51-7.46 (m, 1H), 7.44-7.39 (m, 1H), 7.30-7.16 (m, 5H), 7.15-6.84 (m, 1H), 5.32-5.23 (m, 1H), 3.89 (s, 3H), 3.19-3.11 (m, 1H), 2.87-2.76 (m, 1H). MS (ESI) m/z $(M+H)^+$427.1.

N-(4-amino-3,4-dioxo-1-phenylbutan-2-yl)-3-(2-fluoro-3-methoxyphenyl)-1-methyl-1H-pyrazole-4-carboxamide (509)

Compound 509 (190 mg, yield: 66.92%, white solid) was prepared using the procedures similar to compound 163 from the corresponding starting materials, compound ethyl 3-iodo-1-methyl-1H-pyrazole-4-carboxylate and (2-fluoro- 3-methoxyphenyl)boronic acid and the final compound 509 was obtained. $^1$H NMR (400 MHz, DMSO-$d_6$) δ 8.18 (s, 1H), 8.13 (d, J=7.6 Hz, 1H), 7.96 (br. s, 1H), 7.73 (br. s, 1H), 7.30-7.16 (m, 5H), 7.14-7.01 (m, 2H), 6.87-6.79 (m, 1H), 5.27-5.16 (m, 1H), 3.88 (s, 3H), 3.80 (s, 3H), 3.14-3.06 (m, 1H), 2.84-2.74 (m, 1H). MS (ESI) m/z (M+H)$^+$425.1.

N-(4-amino-3,4-dioxo-1-phenylbutan-2-yl)-3-(2,2-difluorobenzo[d][1,3]dioxol-4-yl)-1-methyl-1H-pyrazole-4-carboxamide (510)

Compound 510 (70 mg, yield: 34%, white solid) was prepared using the procedures similar to compound 163 from the corresponding starting materials, compound ethyl 3-iodo-1-methyl-1H-pyrazole-4-carboxylate and (2,2-difluorobenzo[d][1,3]dioxol-4-yl)boronic acid and the final compound 510 was obtained. $^1$H NMR (400 MHz, DMSO-$d_6$) δ 8.44 (d, J=7.5 Hz, 1H), 8.19 (s, 1H), 7.98 (s, 1H), 7.76 (s, 1H), 7.35 (d, J=7.8 Hz, 1H), 7.31-7.12 (m, 7H), 5.34-5.21 (m, 1H), 3.93 (s, 3H), 3.14 (dd, J=3.6, 13.9 Hz, 1H), 2.82 (dd, J=9.9, 14.2 Hz, 1H). MS (ESI) m/z (M+H)$^+$457.1.

N-(4-amino-3,4-dioxo-1-phenylbutan-2-yl)-3-(2-methoxyphenyl)-1-methyl-1H-pyrazole-4-carboxamide (511)

Compound 511 (23 mg, yield: 8.04%, white solid) was prepared using the procedures similar to compound 163 from the corresponding starting materials, compound ethyl 3-iodo-1-methyl-1H-pyrazole-4-carboxylate and (2-methoxyphenyl)boronic acid and the final compound 511 was obtained. $^1$H NMR (400 MHz, DMSO-$d_6$) δ 8.04 (s, 1H), 7.72 (br s, 1H), 7.55 (br s, 1H), 7.37 (br t, J=7.9 Hz, 1H), 7.28-7.10 (m, 5H), 7.08-6.90 (m, 4H), 5.30 (br d, J=4.3 Hz, 1H), 3.91-3.81 (m, 3H), 3.66-3.54 (m, 3H), 3.12 (br d, J=4.3 Hz, 1H), 2.76 (dd, J=8.8, 14.1 Hz, 1H). MS (ESI) m/z (M+Na)$^+$407.2.

N-(4-amino-3,4-dioxo-1-phenylbutan-2-yl)-3-(3-fluoro-2-(trifluoromethyl)phenyl)-1-methyl-1H-pyrazole-4-carboxamide (512)

Compound 512 (60 mg, yield: 21.65%, white solid) was prepared using the procedures similar to compound 163 from the corresponding starting materials, compound ethyl 3-iodo-1-methyl-1H-pyrazole-4-carboxylate and 2-(3-fluoro-2-(trifluoromethyl)phenyl)-4,4,5,5-tetramethyl-1,3,2-dioxaborolane and the final compound 512 was obtained. $^1$H NMR (400 MHz, DMSO-$d_6$) δ 8.28 (s, 1H), 8.21 (d, J=7.5 Hz, 1H), 7.99 (s, 1H), 7.76 (s, 1H), 7.67-7.59 (m, 1H), 7.52-7.43 (m, 1H), 7.31-7.17 (m, 5H), 7.05 (d, J=7.7 Hz, 1H), 5.25-5.16 (m, 1H), 3.90 (s, 3H), 3.11 (dd, J=3.6, 14.0 Hz, 1H), 2.79 (dd, J=10.0, 14.0 Hz, 1H). $^{19}$F NMR (376 MHz, DMSO-$d_6$) δ−55.03 (d, J=18.3 Hz, 3F), −114.43 (tdd, J=6.1, 12.3, 18.7 Hz, 1F). MS (ESI) m/z (M+Na)$^+$463.2.

N-(4-amino-3,4-dioxo-1-phenylbutan-2-yl)-1-methyl-3-(2-(trifluoromethyl)phenyl)-1H-pyrazole-4-carboxamide (513)

Compound 513 (45 mg, yield: 54.58%, white solid) was prepared using the procedures similar to compound 163 from the corresponding starting materials, compound ethyl 3-iodo-1-methyl-1H-pyrazole-4-carboxylate and (2-(trifluoromethyl)phenyl)boronic acid and the final compound 513 was obtained. $^1$H NMR (400 MHz, DMSO-$d_6$) δ 8.25 (s, 1H), 7.99 (br d, J=7.1 Hz, 2H), 7.80-7.69 (m, 2H), 7.62-7.52 (m, 2H), 7.30-7.17 (m, 6H), 5.20 (ddd, J=3.9, 7.4, 9.7 Hz, 1H), 3.89 (s, 3H), 3.17-3.03 (m, 1H), 2.78 (dd, J=9.7, 13.9 Hz, 1H). $^{19}$F NMR (376 MHz, DMSO-$d_6$) δ−57.15 (s, 3F). MS (ESI) m/z (M+H)$^+$445.2.

N-(4-amino-3,4-dioxo-1-phenylbutan-2-yl)-3-(benzo[d][1,3]dioxol-4-yl)-1-methyl-1H-pyrazole-4-carboxamide (514)

Compound 514 (92 mg, yield: 34.71%, light yellow solid) was prepared using the procedures similar to compound 163 from the corresponding starting materials, compound ethyl 3-iodo-1-methyl-1H-pyrazole-4-carboxylate and benzo[d][1,3]dioxol-4-ylboronic acid and the final compound 514 was obtained. $^1$H NMR (400 MHz, DMSO-$d_6$) δ 2.82 (dd, J=13.89, 9.48 Hz, 1H) 3.12 (dd, J=14.00, 4.08 Hz, 1H) 3.88 (s, 3H) 5.16-5.34 (m, 1H) 5.77 (s, 1H) 5.87 (s, 1H) 6.76-6.90 (m, 3H) 7.18-7.31 (m, 5H) 7.77 (s, 1H) 8.00 (s, 1H) 8.07 (s, 1H) 8.11 (d, J=7.28 Hz, 1H). MS (ESI) m/z (M+H)$^+$421.1.

N-(4-amino-3,4-dioxo-1-phenylbutan-2-yl)-3-(5-methoxypyridin-3-yl)-1-methyl-1H-pyrazole-4-carboxamide (515)

Compound 515 (60 mg, yield: 20.6%, yellow solid) was prepared using the procedures similar to compound 163 from the corresponding starting materials, compound ethyl 3-iodo-1-methyl-1H-pyrazole-4-carboxylate and (5-methoxypyridin-3-yl)boronic acid and the final compound 515 was obtained. $^1$H NMR (400 MHz, DMSO-$d_6$) δ 8.50 (d, J=7.5 Hz, 1H), 8.39 (d, J=1.5 Hz, 1H), 8.22 (d, J=2.6 Hz, 1H), 8.17 (s, 1H), 8.06 (s, 1H), 7.80 (s, 1H), 7.59 (dd, J=1.8, 2.9 Hz, 1H), 7.29 (d, J=4.4 Hz, 4H), 7.24-7.18 (m, 1H), 5.35-5.26 (m, 1H), 3.93 (s, 3H), 3.79 (s, 3H), 3.16 (dd, J=3.6, 13.8 Hz, 1H), 2.83 (dd, J=9.9, 13.9 Hz, 1H). MS (ESI) m/z (M+H)$^+$ 408.2.

N-(4-amino-3,4-dioxo-1-phenylbutan-2-yl)-3-(2-fluoro-3-(trifluoromethyl)phenyl)-1-methyl-1H-pyrazole-4-carboxamide (516)

Compound 516 (85 mg, yield: 78.65%, light yellow solid) was prepared using the procedures similar to compound 163 from the corresponding starting materials, compound ethyl 3-iodo-1-methyl-1H-pyrazole-4-carboxylate and (2-fluoro-3-(trifluoromethyl)phenyl)boronic acid and the final compound 516 was obtained. $^1$H NMR (400 MHz, DMSO-$d_6$) δ 8.42 (d, J=7.5 Hz, 1H), 8.29 (s, 1H), 8.00 (s, 1H), 7.79-7.72 (m, 2H), 7.63 (br t, J=7.1 Hz, 1H), 7.37 (t, J=7.7 Hz, 1H), 7.31-7.18 (m, 5H), 5.29-5.19 (m, 1H), 3.93 (s, 3H), 3.13 (dd, J=3.5, 14.1 Hz, 1H), 2.82 (dd, J=10.1, 13.9 Hz, 1H). $^{19}$F NMR (376 MHz, DMSO-$d_6$) δ−59.92 (s, 1F), −59.96 (s, 1F), −116.72-116.79 (m, 1F), −116.80-116.86 (m, 1F). MS (ESI) m/z (M+H)+463.1.

N-(4-amino-3,4-dioxo-1-phenylbutan-2-yl)-3-(2-fluoro-3-methylphenyl)-1-methyl-1H-pyrazole-4-carboxamide (517)

Compound 517 (170 mg, yield: 53.97%, light yellow solid) was prepared using the procedures similar to compound 163 from the corresponding starting materials, compound ethyl 3-iodo-1-methyl-1H-pyrazole-4-carboxylate and (2-fluoro-3-methylphenyl)boronic acid and the final compound 517 was obtained. $^1$H NMR (400 MHz, DMSO-$d_6$) δ 8.20 (s, 1H), 8.13 (d, J=7.5 Hz, 1H), 8.02 (s, 1H), 7.78 (s, 1H), 7.31-7.20 (m, 6H), 7.15-7.10 (m, 1H), 7.07-7.02 (m, 1H), 5.25 (ddd, J=3.9, 7.3, 9.5 Hz, 1H), 3.91 (s, 3H), 3.75 (s, 3H), 3.13 (dd, J=4.0, 13.9 Hz, 1H), 2.82 (dd, J=9.7, 13.9 Hz, 1H). 2.21 (d, J=1.5 Hz, 3H). $^{19}$F NMR (376 MHz, DMSO-$d_6$) δ −116.59-120.74 (m, 1F). MS (ESI) m/z $(M+H)^+$409.2.

N-(4-amino-3,4-dioxo-1-phenylbutan-2-yl)-3-(2,5-difluorophenyl)-1-methyl-1H-pyrazole-4-carboxamide (518)

Compound 518 (35.9 mg, yield: 24.08%, light yellow solid) was prepared using the procedures similar to compound 163 from the corresponding starting materials, compound ethyl 3-iodo-1-methyl-1H-pyrazole-4-carboxylate and (2,5-difluorophenyl)boronic acid and the final compound 518 was obtained. $^1$H NMR (400 MHz, DMSO-$d_6$) δ 8.33 (d, J=7.3 Hz, 1H), 8.23 (s, 1H), 8.02 (s, 1H), 7.78 (s, 1H), 7.31-7.17 (m, 8H), 5.29-5.21 (m, 1H), 3.92 (s, 3H), 3.13 (dd, J=3.6, 14.0 Hz, 1H), 2.82 (dd, J=9.8, 13.8 Hz, 1H). $^{19}$F NMR (376 MHz, DMSO-$d_6$) δ−119.41 (tdd, J=4.8, 8.7, 17.7 Hz, 1F), −119.69-120.11 (m, 1F). MS (ESI) m/z $(M+H)^+$413.1.

N-(4-amino-3,4-dioxo-1-phenylbutan-2-yl)-3-(1H-indazol-1-yl)-1-methyl-1H-pyrazole-4-carboxamide (530)

Compound 530 (85 mg, yield: 39.2%, light yellow solid) was prepared using the corresponding starting materials, compound ethyl 3-iodo-1-methyl-1H-pyrazole-4-carboxylate and 1H-indazole and alkylated using $K_3PO_4$, CuI, and (1R,2R)—N1,N2-dimethylcyclohexane-1,2-diamine, followed by subjecting the resulting intermediate to procedures such as in compound 12 to obtain compound 530. $^1$H NMR (400 MHz, DMSO-$d_6$) δ 9.41 (d, J=5.8 Hz, 1H), 8.28 (d, J=2.3 Hz, 2H), 8.00 (d, J=8.5 Hz, 1H), 7.91 (d, J=8.0 Hz, 1H), 7.79 (br s, 1H), 7.68-7.48 (m, 2H), 7.33 (t, J=7.4 Hz, 1H), 7.19-7.04 (m, 5H), 5.47 (dt, J=4.8, 7.7 Hz, 1H), 3.95 (s, 3H), 3.23 (dd, J=4.6, 14.2 Hz, 1H), 2.94 (dd, J=8.4, 14.2 Hz, 1H). MS (ESI) m/z $(M+H)^+$417.1.

N-(4-amino-3,4-dioxo-1-phenylbutan-2-yl)-3-(2,2-difluorobenzo[d][1,3]dioxol-5-yl)-1-methyl-1H-pyrazole-4-carboxamide (548)

Compound 548 (130 mg, yield: 53.1%, white solid) was prepared using the corresponding starting materials, compound ethyl 3-iodo-1-methyl-1H-pyrazole-4-carboxylate (198A) and (2,2-difluorobenzo[d][1,3]dioxol-5-yl)boronic acid, followed by subjecting the resulting intermediate to procedures such as in compound 12 to obtain compound 548. $^1$H NMR (400 MHz, DMSO-$d_6$) δ 8.48 (d, J=7.5 Hz, 1H), 8.14-8.04 (m, 2H), 7.82 (s, 1H), 7.57 (d, J=1.5 Hz, 1H), 7.46 (dd, J=1.8, 8.4 Hz, 1H), 7.36-7.17 (m, 5H), 5.38-5.19 (m, 1H), 3.90 (s, 3H), 3.17 (dd, J=4.0, 13.9 Hz, 1H), 2.83 (dd, J=9.9, 13.9 Hz, 1H). MS (ESI) m/z $(M+H)^+$457.1.

N-(4-amino-3,4-dioxo-1-phenylbutan-2-yl)-3-(benzo[d][1,3]dioxol-5-yl)-1-methyl-1H-pyrazole-4-carboxamide (567)

Compound 567 (125 mg, yield: 72.7%, yellow solid) was prepared using the corresponding starting materials, compound ethyl 3-iodo-1-methyl-1H-pyrazole-4-carboxylate (198A) and benzo[d][1,3]dioxol-5-ylboronic acid, followed by subjecting the resulting intermediate to procedures such as in compound 12 to obtain compound 567. $^1$H NMR (400 MHz, DMSO-$d_6$) δ 8.29 (d, J=7.5 Hz, 1H), 8.08-7.99 (m, 2H), 7.80 (s, 1H), 7.32-7.19 (m, 5H), 7.16-7.08 (m, 2H), 6.83 (d, J=8.2 Hz, 1H), 6.01 (s, 2H), 5.33-5.24 (m, 1H), 3.86 (s, 3H), 3.16 (dd, J=4.1, 13.8 Hz, 1H), 2.82 (dd, J=9.9, 14.1 Hz, 1H). MS (ESI) m/z $(M+H)^+$421.1.

N-(4-amino-3,4-dioxo-1-phenylbutan-2-yl)-1,2'-dimethyl-1H, 2'H-[3,3'-bipyrazole]-4-carboxamide (568)

Compound 568 (24 mg, yield: 12.0%, white solid) was prepared using the corresponding starting materials, compound ethyl 3-iodo-1-methyl-1H-pyrazole-4-carboxylate (198A) and (1-methyl-1H-pyrazol-5-yl)boronic acid, followed by subjecting the resulting intermediate to procedures such as in compound 12 to obtain compound 568. $^1$H NMR (400 MHz, DMSO-$d_6$) δ 8.28-8.10 (m, 1H), 7.99-7.69 (m, 2H), 7.59 (br s, 1H), 7.40-7.10 (m, 6H), 6.42-6.29 (m, 1H), 5.31 (br s, 1H), 3.98-3.85 (m, 3H), 3.77-3.57 (m, 3H), 3.19 (br d, J=13.6 Hz, 1H), 2.92-2.81 (m, 1H). MS (ESI) m/z $(M+H)^+$381.1.

N-(4-amino-3,4-dioxo-1-phenylbutan-2-yl)-1-methyl-3-(naphthalen-1-yl)-1H-pyrazole-4-carboxamide (569)

Compound 569 (125 mg, yield: 72.0%, off-white solid) was prepared using the corresponding starting materials, compound ethyl 3-iodo-1-methyl-1H-pyrazole-4-carboxylate (198A) and naphthalen-1-ylboronic acid, followed by subjecting the resulting intermediate to procedures such as in compound 12 to obtain compound 569. $^1$H NMR (400 MHz, DMSO-$d_6$) δ 8.32 (s, 1H), 8.02 (s, 1H) 8.03-7.89 (m, 3H), 7.82 (d, J=7.3 Hz, 1H), 7.76 (s, 1H), 7.68 (d, J=8.4 Hz, 1H), 7.53-7.44 (m, 2H), 7.40 (dt, J=1.1, 7.6 Hz, 1H), 7.35 (dd, J=1.1, 7.1 Hz, 1H), 7.28-7.15 (m, 3H), 7.08-7.00 (m, 2H), 5.15 (ddd, J=4.0, 7.4, 9.4 Hz, 1H), 3.96 (s, 3H), 3.04 (dd, J=3.5, 13.9 Hz, 1H), 2.67 (dd, J=9.7, 13.7 Hz, 1H). MS (ESI) m/z $(M+H)^+$427.2.

N-(4-amino-3,4-dioxo-1-phenylbutan-2-yl)-3-(2,3-dihydrobenzo[b][1,4]dioxin-5-yl)-1-methyl-1H-pyrazole-4-carboxamide (570)

Compound 570 (41.8 mg, yield: 45.3%, off-white solid) was prepared using the corresponding starting materials, compound ethyl 3-iodo-1-methyl-1H-pyrazole-4-carboxylate (198A) and (2,3-dihydrobenzo[b][1,4]dioxin-5-yl)boronic acid, followed by subjecting the resulting intermediate to procedures such as in compound 12 to obtain compound 570. $^1$H NMR (400 MHz, DMSO-$d_6$) δ 8.09-7.93 (m, 2H), 7.83-7.69 (m, 2H), 7.31-7.10 (m, 5H), 6.88-6.73 (m, 3H), 5.34-5.22 (m, 1H), 4.15-4.06 (m, 2H), 4.02-3.93 (m, 1H), 3.91-3.82 (m, 4H), 3.11 (dd, J=4.0, 13.9 Hz, 1H), 2.79 (dd, J=9.3, 13.9 Hz, 1H). MS (ESI) m/z $(M+H)^+$435.1.

N-(4-amino-3,4-dioxo-1-phenylbutan-2-yl)-1-methyl-3-(naphthalen-2-yl)-1H-pyrazole-4-carboxamide (571)

Compound 571 (41.8 mg, yield: 45.3%, off-white solid) was prepared using the corresponding starting materials, compound ethyl 3-iodo-1-methyl-1H-pyrazole-4-carboxylate (198A) and naphthalen-2-ylboronic acid, followed by subjecting the resulting intermediate to procedures such as in compound 12 to obtain compound 571. $^1$H NMR (400 MHz, DMSO-$d_6$) δ 8.45 (d, J=7.3 Hz, 1H), 8.18-8.06 (m, 3H), 7.92-7.81 (m, 4H), 7.72 (dd, J=1.4, 8.5 Hz, 1H), 7.55-7.45 (m, 2H), 7.33-7.19 (m, 5H), 5.36-5.27 (m, 1H), 3.94 (s, 3H), 3.17 (dd, J=3.9, 14.0 Hz, 1H), 2.84 (dd, J=10.0, 13.8 Hz, 1H). MS (ESI) m/z $(M+H)^+$427.1.

N-(4-amino-3,4-dioxo-1-phenylbutan-2-yl)-3-(2-(difluoromethyl)phenyl)-1-methyl-1H-pyrazole-4-carboxamide (572)

Compound 572 (110 mg, yield: 40.9%, light yellow solid) was prepared using the corresponding starting materials, compound ethyl 3-iodo-1-methyl-1H-pyrazole-4-carboxylate (198A) and 1-bromo-2-(difluoromethyl)benzene and 4,4,4',4',5,5,5',5'-octamethyl-2,2'-bi(1,3,2-dioxaborolane) in presence of palladium catalyst, followed by subjecting the resulting intermediate to procedures such as in compound 12 to obtain compound 572. $^1$H NMR (400 MHz, DMSO-$d_6$) δ 8.31-8.21 (m, 2H), 8.03 (s, 1H), 7.79 (s, 1H), 7.64 (d, J=7.5 Hz, 1H), 7.55-7.42 (m, 2H), 7.33-7.17 (m, 6H), 7.00-6.66 (m, 1H), 5.30-5.18 (m, 1H), 3.92 (s, 3H), 3.13 (dd, J=3.6, 13.7 Hz, 1H), 2.79 (dd, J=10.0, 13.8 Hz, 1H). $^{19}$F NMR (376 MHz, DMSO-$d_6$) δ−107.64-110.93 (m, 2F). MS (ESI) m/z $(M+H)^+$396.

N-(4-amino-3,4-dioxo-1-phenylbutan-2-yl)-3-cyclohexyl-1-methyl-1H-pyrazole-4-carboxamide (573)

Compound 573 (172 mg, yield: 81.1%, white solid) was prepared using the corresponding starting materials, compound ethyl 3-iodo-1-methyl-1H-pyrazole-4-carboxylate (198A) and 2-(cyclohex-1-en-1-yl)-4,4,5,5-tetramethyl-1,3,2-dioxaborolane followed by hydrogenolysis of the resulting product which then followed by subjecting the resulting intermediate to procedures such as in compound 12 to obtain compound 573. $^1$H NMR (400 MHz, DMSO-$d_6$) δ 8.11 (d, J=7.3 Hz, 1H), 8.02 (s, 2H), 7.76 (s, 1H), 7.28-7.21 (m, 4H), 7.20-7.11 (m, 1H), 5.24 (ddd, J=3.6, 7.1, 10.3 Hz, 1H), 3.74 (s, 3H), 3.11 (dd, J=3.7, 13.9 Hz, 1H), 3.05-2.96 (m, 1H), 2.79 (dd, J=10.0, 13.8 Hz, 1H), 1.76-1.55 (m, 5H), 1.39-1.05 (m, 5H). MS (ESI) m/z $(M+H)^+$383.3.

N-(4-amino-3,4-dioxo-1-phenylbutan-2-yl)-3-(isoquinolin-6-yl)-1-methyl-1H-pyrazole-4-carboxamide (585)

Compound 585 (120 mg, yield: 60.0%, light yellow solid) was prepared using the corresponding starting materials, compound ethyl 3-iodo-1-methyl-1H-pyrazole-4-carboxylate (198A) and isoquinolin-7-ylboronic acid followed by subjecting the resulting intermediate to procedures such as in compound 12 to obtain compound 585. $^1$H NMR (400 MHz, DMSO-$d_6$) δ 9.28 (s, 1H), 8.56 (d, J=7.3 Hz, 1H), 8.48 (d, J=5.8 Hz, 1H), 8.20 (s, 1H), 8.16-8.08 (m, 2H), 8.04 (d, J=8.8 Hz, 1H), 7.90-7.77 (m, 3H), 7.29 (d, J=4.3 Hz, 4H), 7.25-7.18 (m, 1H), 5.38-5.25 (m, 1H), 3.95 (s, 3H), 3.18 (dd, J=3.8, 14.1 Hz, 1H), 2.85 (dd, J=10.0, 13.8 Hz, 1H). MS (ESI) m/z $(M+H)^+$428.1.

N-(4-amino-3,4-dioxo-1-phenylbutan-2-yl)-1-methyl-3-(quinolin-2-yl)-1H-pyrazole-4-carboxamide (587)

Compound 587 (70 mg, yield: 49.7%, light pink solid) was prepared using the corresponding starting materials, compound ethyl 3-iodo-1-methyl-1H-pyrazole-4-carboxylate (198A) and 2-bromoquinoline and 4,4,4',4',5,5,5',5'-octamethyl-2,2'-bi(1,3,2-dioxaborolane) in presence of palladium catalyst, followed by subjecting the resulting intermediate to procedures such as in compound 12 to obtain compound 587. $^1$H NMR (400 MHz, DMSO-$d_6$) δ 12.08 (br d, J=8.0 Hz, 1H), 8.50 (br d, J=8.8 Hz, 1H), 8.36 (s, 1H), 8.26 (br d, J=8.8 Hz, 1H), 8.14 (br s, 1H), 8.02 (br d, J=7.5 Hz, 1H), 7.84 (br s, 1H), 7.74-7.59 (m, 3H), 7.07-6.90 (m, 5H), 5.75-5.66 (m, 1H), 3.98 (s, 3H), 3.31-3.26 (m, 1H), 3.18-3.08 (m, 1H). MS (ESI) m/z $(M+H)^+$428.1.

N-(4-amino-3,4-dioxo-1-phenylbutan-2-yl)-3-(isoquinolin-4-yl)-1-methyl-1H-pyrazole-4-carboxamide (591)

Compound 591 (35 mg, yield: 56.3%, white solid) was prepared using the corresponding starting materials, compound ethyl 3-iodo-1-methyl-1H-pyrazole-4-carboxylate (198A) and 4-isoquinolylboronic acid followed by subjecting the resulting intermediate to procedures such as in compound 12 to obtain compound 591. $^1$H NMR (400 MHz, DMSO-$d_6$) δ 9.26 (s, 1H), 8.36-8.30 (m, 2H), 8.25-8.21 (m, 1H), 8.14-8.09 (m, 1H), 7.93 (s, 1H), 7.71 (br s, 1H), 7.68-7.60 (m, 3H), 7.27-7.20 (m, 2H), 7.19-7.13 (m, 3H), 5.17-5.09 (m, 1H), 3.95 (s, 3H), 3.09-3.02 (m, 1H), 2.77-2.69 (m, 1H). MS (ESI) m/z $(M+H)^+$428.1.

N-(4-amino-3,4-dioxo-1-phenylbutan-2-yl)-1-methyl-3-(quinolin-6-yl)-1H-pyrazole-4-carboxamide (593)

Compound 593 (30 mg, 29.9% yield; pale yellow solid) was prepared using the corresponding starting materials, compound ethyl 3-iodo-1-methyl-1H-pyrazole-4-carboxylate (198A) and quinolin-6-ylboronic acid followed by subjecting the resulting intermediate to procedures such as in compound 12 to obtain compound 593. $^1$H NMR (400 MHz, DMSO-$d_6$) δ 8.86 (br s, 1H), 8.50 (br.d, J=6.6 Hz, 1H), 8.31 (br.d, J=7.9 Hz, 1H), 8.20 (br.s, 1H), 8.09 (br.d, J=9.5 Hz, 2H), 7.93 (br.s, 2H), 7.81 (br s, 1H), 7.53-7.47 (m, 1H), 7.30-7.15 (m, 5H), 5.29 (br.s, 1H), 3.92 (s, 3H), 3.16 (br.d, J=11.5 Hz, 1H), 2.88-2.78 (m, 1H). MS (ESI) m/z $(M+H)^+$ 428.1

N-(4-amino-3,4-dioxo-1-phenylbutan-2-yl)-1-methyl-3-(quinolin-5-yl)-1H-pyrazole-4-carboxamide (597)

Compound 597 (20 mg, yield: 25.1%, yellow solid) was prepared using the corresponding starting materials, compound ethyl 3-iodo-1-methyl-1H-pyrazole-4-carboxylate (198A) and quinolin-5-ylboronic acid followed by subjecting the resulting intermediate to procedures such as in compound 12 to obtain compound 597. $^1$H NMR (400 MHz, DMSO-$d_6$) δ 8.88 (dd, J=1.8, 4.0 Hz, 1H), 8.34-8.19 (m, 1H), 8.17-7.97 (m, 2H), 7.81-7.35 (m, 6H), 7.27-7.03 (m, 5H), 5.29-5.11 (m, 1H), 4.02-3.90 (m, 3H), 3.07-3.0 (m, 1H), 2.80-2.74 (m, 1H). MS (ESI) m/z $(M+H)^+$428.1.

N-(4-amino-3,4-dioxo-1-phenylbutan-2-yl)-3-(isoquinolin-3-yl)-1-methyl-1H-pyrazole-4-carboxamide (602)

Compound 602 (55 mg, yield: 36.3%, white solid) was prepared using the corresponding starting materials, compound ethyl 3-iodo-1-methyl-1H-pyrazole-4-carboxylate (198A) and 3-bromoisoquinoline and 4,4,4',4',5,5,5',5'-octamethyl-2,2'-bi(1,3,2-dioxaborolane) in presence of palladium catalyst, followed by subjecting the resulting intermediate to procedures such as in compound 12 to obtain compound 602. $^1$H NMR (400 MHz, DMSO-$d_6$) δ 12.07 (d, J=7.1 Hz, 1H), 8.98 (s, 1H), 8.51 (s, 1H), 8.28 (s, 1H), 8.10 (d, J=7.5 Hz, 3H), 7.89-7.79 (m, 2H), 7.75-7.67 (m, 1H), 7.15-7.06 (m, 4H), 7.04-6.97 (m, 1H), 5.64-5.53 (m, 1H), 4.03-3.84 (m, 3H), 3.27 (dd, J=5.0, 14.0 Hz, 1H), 3.10 (dd, J=7.7, 14.1 Hz, 1H). MS (ESI) m/z $(M+H)^+$428.2.

N-(4-amino-3,4-dioxo-1-phenylbutan-2-yl)-3-(2-chlorophenyl)-1-methyl-1H-pyrazole-4-carboxamide (604)

Compound 604 (120 mg, yield: 58.6%, pale yellow solid) was prepared using the corresponding starting materials, compound ethyl 3-iodo-1-methyl-1H-pyrazole-4-carboxylate (198A) and (2-chlorophenyl)boronic acid followed by subjecting the resulting intermediate to procedures such as in compound 12 to obtain compound 604. $^1$H NMR (400 MHz, DMSO-$d_6$) δ 8.19 (s, 1H), 8.03 (d, J=7.3 Hz, 1H), 7.97 (s, 1H), 7.73 (s, 1H), 7.39-7.15 (m, 9H), 5.24-5.19 (m, 1H), 3.87 (s, 3H), 3.08 (dd, J=3.6, 14.0 Hz, 1H), 2.76 (dd, J=9.8, 14.0 Hz, 1H). MS (ESI) m/z $(M+H)^+$411.1.

N-(4-amino-3,4-dioxo-1-phenylbutan-2-yl)-1-methyl-3-(quinolin-3-yl)-1H-pyrazole-4-carboxamide (605)

Compound 605 (140 mg, yield: 55.6%, white solid) was prepared using the corresponding starting materials, compound ethyl 3-iodo-1-methyl-1H-pyrazole-4-carboxylate (198A) and quinolin-3-ylboronic acid followed by subjecting the resulting intermediate to procedures such as in compound 12 to obtain compound 605. $^1$H NMR (400 MHz, DMSO-$d_6$) δ 9.08 (s, 1H), 8.65-8.45 (m, 2H), 8.23 (s, 1H), 8.08 (br s, 1H), 7.99 (dd, J=8.3, 12.7 Hz, 2H), 7.85-7.70 (m, 2H), 7.60 (t, J=7.4 Hz, 1H), 7.34-7.13 (m, 5H), 5.36-5.20 (m, 1H), 4.05-3.89 (m, 3H), 3.18-2.78 (m, 2H). MS (ESI) m/z $(M+H)^+$428.2.

N-(4-amino-3,4-dioxo-1-phenylbutan-2-yl)-3-(isoquinolin-5-yl)-1-methyl-1H-pyrazole-4-carboxamide (607)

Compound 607 (50 mg, yield: 34.6%, white solid) was prepared using the corresponding starting materials, compound ethyl 3-iodo-1-methyl-1H-pyrazole-4-carboxylate (198A) and isoquinolin-5-ylboronic acid followed by subjecting the resulting intermediate to procedures such as in compound 12 to obtain compound 607. $^1$H NMR (400 MHz, DMSO-$d_6$) δ 9.41-9.21 (m, 1H), 8.52-8.27 (m, 2H), 8.23-7.93 (m, 3H), 7.81-7.48 (m, 4H), 7.32-7.09 (m, 5H), 5.22-5.10 (m, 1H), 4.06-3.90 (m, 3H), 3.09 (dd, J=3.2, 13.8 Hz, 1H), 2.76 (dd, J=9.8, 13.8 Hz, 1H). MS (ESI) m/z $(M+H)^+$ 428.1.

N-(4-amino-3,4-dioxo-1-phenylbutan-2-yl)-1-methyl-3-(quinolin-4-yl)-1H-pyrazole-4-carboxamide (611)

Compound 611 (55 mg, yield: 78.2%, light yellow solid) was prepared using the corresponding starting materials, compound ethyl 3-iodo-1-methyl-1H-pyrazole-4-carboxylate (198A) and quinolin-4-ylboronic acid followed by subjecting the resulting intermediate to procedures such as in compound 12 to obtain compound 611. $^1$H NMR (400 MHz, DMSO-$d_6$) δ 8.86-8.76 (m, 1H), 8.41-8.34 (m, 1H), 8.07-7.88 (m, 2H), 7.85-7.58 (m, 3H), 7.49 (t, J=7.8 Hz, 1H), 7.33-7.11 (m, 7H), 5.21-5.11 (m, 1H), 4.30 (br s, 1H), 4.04-3.93 (m, 3H), 3.10 (dd, J=3.5, 14.1 Hz, 1H), 2.78 (dd, J=10.1, 13.9 Hz, 1H). MS (ESI) m/z $(M+H)^+$428.1.

N-(4-amino-3,4-dioxo-1-phenylbutan-2-yl)-1-methyl-3-(thiophen-2-yl)-1H-pyrazole-4-carboxamide (615)

Compound 615 (122 mg, yield: 73.0%, white solid) was prepared using the corresponding starting materials, compound 1-methyl-3-(thiophen-2-yl)-1H-pyrazole-4-carboxylic acid and 3-amino-2-hydroxy-4-phenylbutanamide hydrochloride using the procedures such as in compound 12 to obtain compound 615. $^1$H NMR (400 MHz, DMSO-$d_6$) δ 8.42 (d, J=7.3 Hz, 1H), 8.10 (s, 1H), 8.06 (s, 1H), 7.79 (s, 1H), 7.73 (d, J=3.5 Hz, 1H), 7.41 (dd, J=1.1, 5.1 Hz, 1H), 7.28 (d, J=4.2 Hz, 4H), 7.24-7.18 (m, 1H), 6.97 (dd, J=3.6, 5.0 Hz, 1H), 5.49-5.20 (m, 1H), 3.85 (s, 3H), 3.16 (dd, J=3.5, 13.9 Hz, 1H), 2.83 (dd, J=10.1, 13.9 Hz, 1H). MS (ESI) m/z $(M+H)^+$383.1.

N-(4-amino-3,4-dioxo-1-phenylbutan-2-yl)-3-cyclopropyl-1-methyl-1H-pyrazole-4-carboxamide (616)

Compound 616 (120 mg, yield: 71.5%, white solid) was prepared using the corresponding starting materials, compound 3-cyclopropyl-1-methyl-H-pyrazole-4-carboxylic acid and 3-amino-2-hydroxy-4-phenylbutanamide hydrochloride using the procedures such as in compound 12 to obtain compound 616. $^1$H NMR (400 MHz, DMSO-$d_6$) δ 8.08 (d, J=7.5 Hz, 1H), 8.04 (s, 1H), 8.03 (br s, 1H), 7.77 (s, 1H), 7.27 (d, J=4.4 Hz, 4H), 7.20-7.16 (m, 1H), 5.31-5.26 (m, 1H), 3.71 (s, 3H), 3.15 (dd, J=3.9, 13.8 Hz, 1H), 2.84 (dd, J=9.9, 13.9 Hz, 1H), 2.41-2.35 (m, 1H), 0.77-0.70 (m, 2H), 0.69-0.65 (m, 2H). MS (ESI) m/z $(M+H)^+$341.2.

N-(4-amino-3,4-dioxo-1-phenylbutan-2-yl)-1-methyl-3-(tetrahydro-2H-pyran-4-yl)-1H-pyrazole-4-carboxamide (617)

Compound 617 (55 mg, yield: 34.4%, white solid) was prepared using the corresponding starting materials, compound 1-methyl-3-(tetrahydro-2H-pyran-4-yl)-1H-pyrazole-4-carboxylic acid and 3-amino-2-hydroxy-4-phenylbutanamide hydrochloride using the procedures such as in compound 12 to obtain compound 617. $^1$H NMR (400 MHz, DMSO-$d_6$) δ 8.20 (d, J=7.5 Hz, 1H), 8.07 (s, 1H), 8.01 (s, 1H), 7.75 (s, 1H), 7.30-7.21 (m, 4H), 7.19-7.14 (m, 1H), 5.31-5.15 (m, 1H), 3.80 (d, J=9.5 Hz, 2H), 3.76 (s, 3H), 3.29-3.20 (m, 3H), 3.11 (dd, J=3.5, 13.9 Hz, 1H), 2.79 (dd, J=10.0, 13.8 Hz, 1H), 1.65-1.52 (m, 4H). MS (ESI) m/z $(M+H)^+$385.1.

N-(4-amino-3,4-dioxo-1-phenylbutan-2-yl)-3-cyclopentyl-1-methyl-1H-pyrazole-4-carboxamide (620)

Compound 620 (70 mg, yield: 53.1%, white solid) was prepared using the corresponding starting materials, compound 3-cyclopentyl-1-methyl-1H-pyrazole-4-carboxylic acid and 3-amino-2-hydroxy-4-phenylbutanamide hydrochloride using the procedures such as in compound 12 to obtain compound 620. $^1$H NMR (400 MHz, DMSO-$d_6$) δ 8.14 (br d, J=7.3 Hz, 1H), 8.06-8.02 (m, 2H), 7.77 (br.s, 1H), 7.29 (d, J=4.3 Hz, 4H), 7.24-7.17 (m, 1H), 5.29-5.21 (m, 1H), 3.77 (s, 3H), 3.42 (br.t, J=8.0 Hz, 1H), 3.14 (br.dd, J=3.5, 13.8 Hz, 1H), 2.83 (br.dd, J=10.2, 13.4 Hz, 1H), 1.80 (br.d, J=7.8 Hz, 2H), 1.69-1.45 (m, 6H). MS (ESI) m/z $(M+H)^+$369.2.

N-(4-amino-3,4-dioxo-1-phenylbutan-2-yl)-3-(5-chlorothiophen-2-yl)-1-methyl-1H-pyrazole-4-carboxamide (621)

Compound 621 (25 mg, yield: 25.1%, pale-yellow solid) was prepared using the corresponding starting materials, compound 3-(5-chlorothiophen-2-yl)-1-methyl-H-pyrazole-4-carboxylic acid and 3-amino-2-hydroxy-4-phenylbutanamide hydrochloride using the procedures such as in compound 12 to obtain compound 621. $^1$H NMR (400 MHz, DMSO-$d_6$) δ 8.53 (br d, J=6.8 Hz, 1H), 8.22-8.04 (m, 2H), 7.87-7.61 (m, 2H), 7.35-6.97 (m, 6H), 5.33 (br s, 1H), 3.88 (br s, 3H), 3.19 (br d, J=14.1 Hz, 1H), 2.92-2.79 (m, 1H). MS (ESI) m/z $(M+H)^+$417.0.

tert-butyl 3-(4-((4-amino-3,4-dioxo-1-phenylbutan-2-yl)carbamoyl)-1-methyl-1H-pyrazol-3-yl)piperidine-1-carboxylate (624)

Compound 624 (100 mg, yield: 33.04%, white solid) was prepared using the corresponding starting materials, compound 3-(1-(tert-butoxycarbonyl)piperidin-3-yl)-1-methyl-1H-pyrazole-4-carboxylic acid and 3-amino-2-hydroxy-4-phenylbutanamide hydrochloride using the procedures such as in compound 12 to obtain compound 624. $^1$H NMR (400 MHz, DMSO-$d_6$) δ 8.27-8.18 (m, 1H), 8.12 (s, 1H), 8.02 (d, J=2.9 Hz, 1H), 7.78 (s, 1H), 7.32-7.13 (m, 5H), 5.29 (s, 1H), 4.02-3.85 (m, 2H), 3.82-3.75 (m, 3H), 3.20-3.09 (m, 2H), 3.19-2.99 (m, 1H), 2.99-2.78 (m, 2H), 2.73-2.64 (m, 1H), 1.84 (s, 1H), 1.62 (s, 1H), 1.48 (d, J=11.9 Hz, 1H), 1.39-1.27 (m, 10H). MS (ESI) m/z $(M+H)^+$484.2.

N-(4-amino-3,4-dioxo-1-phenylbutan-2-yl)-3-(3,4-dihydro-2H-benzo[b][1,4]dioxepin-7-yl)-1-methyl-1H-pyrazole-4-carboxamide (625)

Compound 625 (70 mg, yield: 58.6%, yellow solid) was prepared using the corresponding starting materials, compound 3-(3,4-dihydro-2H-benzo[b][1,4]dioxepin-7-yl)-1-methyl-1H-pyrazole-4-carboxylic acid and 3-amino-2-hydroxy-4-phenylbutanamide hydrochloride using the procedures such as in compound 12 to obtain compound 625. $^1$H NMR (400 MHz, DMSO-$d_6$) δ 8.29 (d, J=7.3 Hz, 1H), 8.09-7.94 (m, 2H), 7.80 (s, 1H), 7.32-7.14 (m, 7H), 6.90-6.83 (m, 1H), 5.39-5.22 (m, 1H), 4.16-4.07 (m, 4H), 3.88-3.82 (m, 3H), 3.16 (dd, J=4.0, 13.7 Hz, 1H), 2.82 (dd, J=9.8, 13.8 Hz, 1H), 2.13-2.06 (m, 2H). MS (ESI) m/z $(M+H)^+$449.1.

N-(4-amino-3,4-dioxo-1-phenylbutan-2-yl)-1,1'-dimethyl-1H, 1'H-[3,4'-bipyrazole]-4-carboxamide (626)

Compound 626 (55 mg, yield: 34.4%, white solid) was prepared using the corresponding starting materials, compound 1,1'-dimethyl-1H, 1'H-[3,4'-bipyrazole]-4-carboxylic acid and 3-amino-2-hydroxy-4-phenylbutanamide hydrochloride using the procedures such as in compound 12 to obtain compound 626. $^1$H NMR (400 MHz, DMSO-$d_6$) δ 8.06 (d, J=17.6 Hz, 2H), 7.94 (s, 1H), 7.76-7.45 (m, 3H), 7.31-7.23 (m, 4H), 7.23-7.15 (m, 1H), 5.37-5.28 (m, 1H), 3.83 (d, J=8.3 Hz, 6H), 3.22 (dd, J=4.1, 13.7 Hz, 1H), 2.95 (dd, J=8.9, 14.4 Hz, 1H). MS (ESI) m/z $(M+H)^+$381.2.

N-(4-amino-3,4-dioxo-1-phenylbutan-2-yl)-1-methyl-3-(tetrahydrofuran-3-yl)-1H-pyrazole-4-carboxamide (627)

Compound 627 (40 mg, yield: 25.1%, pale yellow solid) was prepared using the corresponding starting materials, compound 1-methyl-3-(tetrahydrofuran-3-yl)-1H-pyrazole-4-carboxylic acid and 3-amino-2-hydroxy-4-phenylbutanamide hydrochloride using the procedures such as in compound 12 to obtain compound 627. $^1$H NMR (400 MHz, DMSO-$d_6$) δ 8.06 (s, 1H), 8.00-7.87 (m, 1H), 7.69 (s, 0.5H), 7.57-7.44 (m, 0.7H), 7.30-7.03 (m, 6H), 5.33-5.23 (m, 1H), 3.92 (dt, J=2.6, 7.7 Hz, 1H), 3.86-3.81 (m, 1H), 3.79 (s, 3H), 3.77-3.73 (m, 1H), 3.71 (d, J=7.8 Hz, 1H), 3.62-3.54 (m, 1H), 3.20 (dd, J=4.3, 14.1 Hz, 1H), 2.96-2.88 (m, 1H), 2.09 (q, J=7.3 Hz, 2H). MS (ESI) m/z $(M+H)^+$371.2.

N-(4-amino-3,4-dioxo-1-phenylbutan-2-yl)-3-(benzofuran-3-yl)-1-methyl-1H-pyrazole-4-carboxamide (628)

Compound 628 (143 mg, yield: 98.6%, white solid) was prepared using the corresponding starting materials, compound 3-(benzofuran-3-yl)-1-methyl-1H-pyrazole-4-carboxylic acid and 3-amino-2-hydroxy-4-phenylbutanamide hydrochloride using the procedures such as in compound 12 to obtain compound 628. $^1$H NMR (400 MHz, DMSO-d6) δ 8.56 (d, J=7.3 Hz, 1H), 8.24 (s, 1H), 8.10 (s, 1H), 7.82 (s, 1H), 7.63 (d, J=6.8 Hz, 1H), 7.56-7.50 (m, 2H), 7.33-7.15 (m, 7H), 5.36 (ddd, J=3.9, 7.3, 9.8 Hz, 1H), 3.94 (s, 3H), 3.24-3.14 (m, 1H), 2.87 (dd, J=10.0, 14.0 Hz, 1H). MS (ESI) m/z $(M+H)^+$417.1.

N-(4-amino-3,4-dioxo-1-phenylbutan-2-yl)-3-(isoquinolin-3-yl)-1-methyl-1H-pyrazole-4-carboxamide (629)

Compound 629 (25 mg, yield: 50.14%, pale yellow solid) was prepared using the corresponding starting materials, compound ethyl 3-iodo-1-methyl-1H-pyrazole-4-carboxylate (198A) and 7-bromoisoquinoline and 4,4,4',4',5,5,5',5'-octamethyl-2,2'-bi(1,3,2-dioxaborolane) in presence of palladium catalyst, followed by subjecting the resulting intermediate to procedures such as in compound 12 to obtain compound 629. $^1$H NMR (400 MHz, DMSO-$d_6$) δ 9.27 (s, 1H), 8.54 (d, J=7.5 Hz, 1H), 8.49 (d, J=5.7 Hz, 1H), 8.35 (s, 1H), 8.15 (s, 1H), 8.11 (s, 1H), 8.00-7.94 (m, 1H), 7.92-7.87 (m, 1H), 7.85-7.78 (m, 2H), 7.30-7.17 (m, 5H), 5.36-5.26 (m, 1H), 3.95 (s, 3H), 3.18 (dd, J=4.0, 13.9 Hz, 1H), 2.85 (dd, J=9.9, 13.9 Hz, 1H). MS (ESI) m/z $(M+H)^+$428.2.

benzyl 4-(4-((4-amino-3,4-dioxo-1-phenylbutan-2-yl)carbamoyl)-1-methyl-1H-pyrazol-3-yl)piperazine-1-carboxylate (601)

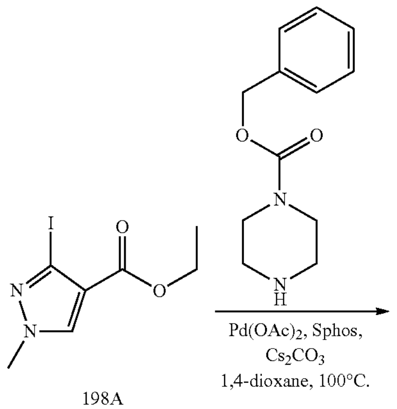

198A

-continued

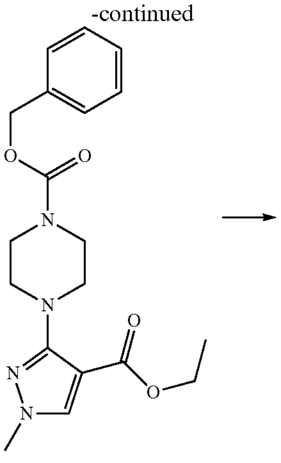

601A

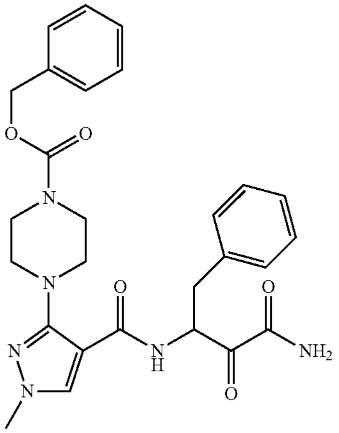

601

To the solution of compound 198A (500 mg, 1.79 mmol) and benzyl piperazine-1-carboxylate (590 mg, 2.68 mmol) in 1,4-dioxane (20 mL) was added $Pd(OAc)_2$ (40 mg, 0.18 mmol), $Cs_2CO_3$ (116 mg, 3.57 mmol) and Sphos (147 mg, 0.36 mmol) under $N_2$ atmosphere. The reaction was stirred at 100° C. for 16 h. The reaction mixture was filtered and washed with EtOAc (10 mL). The organic phase was concentrated under reduced pressure to give a residue. The residue was purified on Combi flash (eluent: PE ~10%~30% EtOAc/PE) to afford the compound 601A (183 mg, yield 25.7%) as a yellow oil.

Compound 601 (55 mg, yield: 78.8%, pink solid) was prepared using the corresponding starting materials, compound benzyl 4-(4-(ethoxycarbonyl)-1-methyl-H-pyrazol-3-yl)piperazine-1-carboxylate (601A) and 3-amino-2-hydroxy-4-phenylbutanamide hydrochloride using the procedures such as in compound 12 to obtain compound 601. $^1$H NMR (400 MHz, DMSO-$d_6$) δ 8.28-8.15 (m, 2H), 8.03 (s, 1H), 7.92 (s, 1H), 7.43-7.33 (m, 5H), 7.28-7.21 (m, 2H), 7.19-7.13 (m, 1H), 7.06 (d, J=7.0 Hz, 2H), 5.53 (q, J=6.3 Hz, 1H), 5.13-5.04 (m, 2H), 3.79-3.68 (m, 3H), 3.33-3.18 (m, 5H), 3.17-3.08 (m, 1H), 2.86 (br s, 2H), 2.81-2.75 (m, 2H). MS (ESI) m/z $(M+H)^+$519.2.

tert-butyl 4-(4-((4-amino-3,4-dioxo-1-phenylbutan-2-yl)carbamoyl)-1-methyl-1H-pyrazol-3-yl)piperazine-1-carboxylate (603)

Intermediate 603A was prepared using the same procedure as for intermediate 601A using tert-butyl piperazine-1-carboxylate.

Compound 603 (18 mg, yield: 41.6%, white solid) was prepared using the corresponding starting materials, compound tert-butyl 4-(4-(ethoxycarbonyl)-1-methyl-1H-pyrazol-3-yl)piperazine-1-carboxylate (603A) and 3-amino-2-hydroxy-4-phenylbutanamide hydrochloride using the procedures such as in compound 12 to obtain compound 603. $^1$H NMR (400 MHz, DMSO-$d_6$) δ 8.07 (d, J=7.5 Hz, 1H), 7.98-7.81 (m, 2H), 7.80-7.61 (m, 1H), 7.30-7.24 (m, 2H), 7.22-7.19 (m, 1H), 7.13 (d, J=7.5 Hz, 2H), 5.56-5.45 (m, 1H), 3.76-3.67 (m, 3H), 3.42 (br s, 1H), 3.35-3.28 (m, 2H), 3.27-3.21 (m, 2H), 3.15-3.13 (m, 1H), 2.88 (d, J=6.3 Hz, 2H), 2.84-2.77 (m, 2H), 1.44 (s, 9H). MS (ESI) m/z $(M+H)^+$485.2.

N-(4-amino-3,4-dioxo-1-phenylbutan-2-yl)-3-(1,1-dioxidothiomorpholino)-1-methyl-1H-pyrazole-4-carboxamide (613)

Intermediate 613A was prepared using the same procedure as for intermediate 601A using thiomorpholine 1,1-dioxide.

Compound 613 (70 mg, yield: 33.7%, light yellow solid) was prepared using the corresponding starting materials, compound ethyl 3-(1,1-dioxidothiomorpholino)-1-methyl-1H-pyrazole-4-carboxylate (613A) and 3-amino-2-hydroxy-4-phenylbutanamide hydrochloride using the procedures such as in compound 12 to obtain compound 613. $^1$H NMR (400 MHz, DMSO-$d_6$) δ 8.15 (d, J=7.0 Hz, 2H), 8.05 (s, 1H), 7.87 (s, 1H), 7.31-7.26 (m, 2H), 7.23 (br d, J=7.0 Hz, 1H), 7.16 (d, J=6.8 Hz, 2H), 5.48-5.31 (m, 1H), 3.75 (s, 3H), 3.42 (m, 4H), 3.25-3.20 (m, 1H), 3.14-3.07 (m, 2H), 3.06-2.98 (m, 3H). MS (ESI) m/z $(M+H)^+$434.1.

N-(4-amino-3,4-dioxo-1-phenylbutan-2-yl)-1-methyl-3-morpholino-1H-pyrazole-4-carboxamide (614)

Intermediate 614A was prepared using the same procedure as for intermediate 601A using morpholine.

Compound 614 (45 mg, yield: 86.3%, yellow solid) was prepared using the corresponding starting materials, compound ethyl 1-methyl-3-morpholino-1H-pyrazole-4-carboxylate (614A) and 3-amino-2-hydroxy-4-phenylbutanamide hydrochloride using the procedures such as in compound 12 to obtain compound 614. $^1$H NMR (400 MHz, DMSO-$d_6$) δ 8.21-8.11 (m, 2H), 7.98 (s, 1H), 7.91-7.84 (m, 1H), 7.26-7.21 (m, 2H), 7.18 (s, 1H), 7.07 (d, J=6.8 Hz, 2H), 5.52-5.44 (m, 1H), 3.71 (s, 3H), 3.55-3.47 (m, 2H), 3.46-3.39 (m, 2H), 3.23 (dd, J=5.3, 14.1 Hz, 1H), 3.06 (dd, J=7.1, 14.1 Hz, 1H), 2.89-2.82 (m, 2H), 2.80-2.75 (m, 2H). MS (ESI) m/z $(M+H)^+$386.2.

Example 97

Compounds 165-167, 170-173, 176-190, 315, 407, 408, 446, 447

(S)—N-(4-amino-3,4-dioxo-1-phenylbutan-2-yl)-1-methyl-5-(pyridin-4-yl)-1H-pyrazole-4-carboxamide (165)

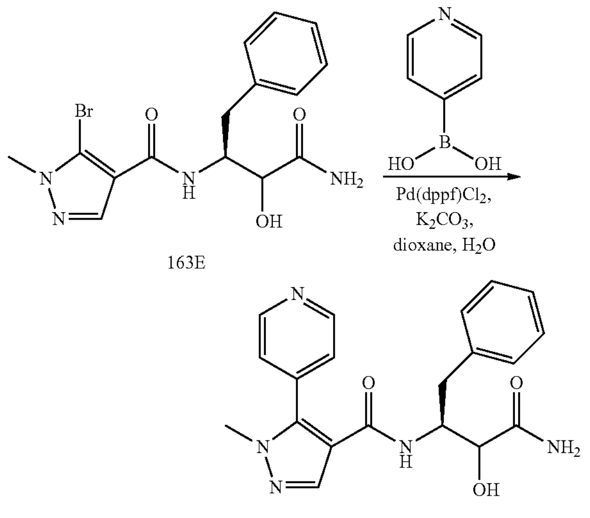

163E

165A

To a mixture of compound 163E (200 mg, 525 umol), 4-pyridylboronic acid (129 mg, 1.05 mmol) and $K_2CO_3$ (218 mg, 1.57 mmol) in dioxane (9 mL) and $H_2O$ (1 mL) was added Pd(dppf)$Cl_2$ (76.8 mg, 105 umol) under $N_2$. The mixture was stirred at 130° C. under microwave conditions for 2 h. The solvent was removed under vacuum. The residue was purified by prep-TLC (Dichloromethane:Methanol=10:1, $R_f$=0.5) to give 165A (90 mg, yield: 45.2%) as a white solid. Compound 165A: $^1$H NMR (400 MHz, DMSO-$d_6$) δ 8.55-8.70 (m, 2H), 7.96 (br dd, J=15.55, 5.40 Hz, 1H), 7.79 (br d, J=7.94 Hz, 1H), 7.03-7.44 (m, 10H), 5.74-5.87 (m, 1H), 4.25-4.45 (m, 1H), 3.75-4.02 (m, 1H), 3.68 (br t, J=5.40 Hz, 3H), 2.57-2.91 (m, 3H).

Compound 165 was prepared as in Example 61 from the corresponding intermediate compound 165A. Compound 165: $^1$H NMR (400 MHz, DMSO-$d_6$) δ 8.60-8.65 (m, 2H), 8.40 (d, J=7.50 Hz, 1H), 8.00 (s, 2H), 7.77 (s, 1H), 7.32-7.36 (m, 2H), 7.18-7.31 (m, 5H), 5.14-5.25 (m, 1H), 3.68 (s, 3H), 3.14 (dd, J=13.89, 3.75 Hz, 1H), 2.83 (dd, J=13.67, 10.14 Hz, 1H). MS (ESI) m/z $(M+H)^+$378.1.

(S)—N-(4-amino-3,4-dioxo-1-phenylbutan-2-yl)-1-methyl-3-(p-tolyl)-1H-pyrazole-4-carboxamide (166)

Compound 166 (17.5 mg, yield: 27.9%, off-white solid) was prepared as in Example 97 from the corresponding starting materials, compound 163G and p-tolylboronic acid. Compound 166: $^1$H NMR (400 MHz, DMSO-$d_6$) δ 8.28 (d, J=7.3 Hz, 1H), 8.09-7.99 (m, 2H), 7.81 (br s, 1H), 7.46 (d, J=8.2 Hz, 2H), 7.33-7.19 (m, 5H), 7.11 (d, J=7.9 Hz, 2H), 5.33-5.23 (m, 1H), 3.93-3.81 (m, 3H), 3.15 (dd, J=3.6, 13.8 Hz, 1H), 2.82 (dd, J=10.0, 13.8 Hz, 1H), 2.30 (s, 3H). MS (ESI) m/z $(M+H)^+$391.1.

(S)—N-(4-amino-3,4-dioxo-1-phenylbutan-2-yl)-1-methyl-5-(p-tolyl)-1H-pyrazole-4-carboxamide (167)

Compound 167 (40.0 mg, yield: 66.9%, white solid) was prepared as in Example 97 from the corresponding starting materials, compound 163E and p-tolylboronic acid. Compound 167: $^1$H NMR (400 MHz, DMSO-$d_6$) δ 7.98-7.91 (m, 2H), 7.89 (s, 1H), 7.73 (s, 1H), 7.30-7.08 (m, 9H), 5.24-5.11 (m, 1H), 3.58 (s, 3H), 3.08 (dd, J=3.6, 14.0 Hz, 1H), 2.77 (dd, J=9.8, 13.6 Hz, 1H), 2.32 (s, 3H). MS (ESI) m/z $(M+H)^+$391.1.

(S)—N-(4-amino-3,4-dioxo-1-phenylbutan-2-yl)-1-methyl-3-(pyridin-4-yl)-1H-pyrazole-4-carboxamide (170)

Compound 170 (15.6 mg, yield: 17.3%, off-white solid) was prepared as in Example 97 from the corresponding starting materials, compound 163G and 4-pyridylboronic acid. Compound 170: $^1$H NMR (400 MHz, DMSO-$d_6$) δ 8.61 (br d, J=7.50 Hz, 1H), 8.49 (d, J=4.85 Hz, 2H), 8.03-8.15 (m, 2H), 7.82 (br s, 1H), 7.56 (d, J=4.85 Hz, 2H), 7.19-7.34 (m, 5H), 5.22-5.36 (m, 1H), 3.87-3.96 (m, 3H), 3.18 (br dd, J=14.00, 3.42 Hz, 1H), 3.12-3.22 (m, 1H), 2.83 (br dd, J=13.56, 10.25 Hz, 1H). MS (ESI) m/z $(M+H_2O+H)^+$396.1.

(S)—N-(4-amino-3,4-dioxo-1-phenylbutan-2-yl)-1-methyl-3-(o-tolyl)-1H-pyrazole-4-carboxamide (171)

Compound 171 (16 mg, 41 umol, yield: 14.6%, purity: 100.0%, white solid) was prepared as in Example 97 from the corresponding starting materials, compound 163G and o-tolylboronic acid. Compound 171: $^1$H NMR (400 MHz, $CDCl_3$) δ 7.95 (s, 1H), 7.38-7.33 (m, 1H), 7.30-7.26 (m, 1H), 7.25-7.21 (m, 2H), 7.19-7.12 (m, 3H), 6.75-6.71 (m, 2H), 6.68 (br s, 1H), 5.81 (br d, J=5.7 Hz, 1H), 5.57 (br s, 1H), 5.47-5.39 (m, 1H), 3.94-3.87 (m, 3H), 3.15 (dd, J=4.4, 14.1 Hz, 1H), 2.62 (dd, J=8.5, 14.2 Hz, 1H), 2.11 (s, 3H). MS (ESI) m/z $(M+H)^+$391.1.

(S)—N-(4-amino-3,4-dioxo-1-phenylbutan-2-yl)-1-methyl-5-(m-tolyl)-1H-pyrazole-4-carboxamide (172)

Compound 172 (25.3 mg, yield: 21.2%, yellow solid) was prepared as in Example 97 from the corresponding starting materials, compound 163E and m-tolylboronic acid. Compound 172: $^1$H NMR (400 MHz, DMSO-$d_6$) δ 7.98 (br s, 1H), 7.91 (s, 1H), 7.88 (br d, J=7.3 Hz, 1H), 7.75 (br s, 1H), 7.33-7.21 (m, 4H), 7.20-7.10 (m, 4H), 7.07 (br d, J=7.3 Hz, 1H), 5.19 (br s, 1H), 3.58 (s, 3H), 3.09 (br dd, J=3.3, 13.7 Hz, 1H), 2.77 (br dd, J=9.7, 13.7 Hz, 1H), 2.29 (s, 3H). MS (ESI) m/z $(M+H)^+$391.1.

(S)—N-(4-amino-3,4-dioxo-1-phenylbutan-2-yl)-1-methyl-3-(pyrimidin-5-yl)-1H-pyrazole-4-carboxamide (173)

Compound 173 (6.9 mg, yield: 18.6%, light yellow solid) was prepared as in Example 97 from the corresponding starting materials, compound 163G and pyrimidin-5-ylboronic acid. Compound 173: $^1$H NMR (400 MHz, DMSO-$d_6$) δ 9.15-9.06 (m, 1H), 8.97-8.77 (m, 1H), 8.62 (d, J=7.5 Hz, 1H), 8.34-8.22 (m, 1H), 8.09 (s, 1H), 7.86-7.62 (m, 1H), 7.40-7.07 (m, 6H), 5.36-5.25 (m, 1H), 3.98-3.90 (m, 3H), 3.17 (dd, J=4.0, 13.7 Hz, 1H), 2.83 (br dd, J=10.3, 13.8 Hz, 1H). MS (ESI) m/z $(M+H)^+$379.1.

(S)—N-(4-amino-3,4-dioxo-1-phenylbutan-2-yl)-1-methyl-5-(pyrimidin-5-yl)-1H-pyrazole-4-carboxamide (176)

Compound 176 (15 mg, yield: 12.19%, white solid) was prepared as in Example 97 from the corresponding starting materials, compound 163E and pyrimidin-5-ylboronic acid. $^1$H NMR (400 MHz, $CD_3CN$) δ 9.24-9.17 (m, 1H), 8.77-8.68 (m, 1H), 7.87 (s, 1H), 7.61 (s, 1H), 7.34-7.18 (m, 5H), 6.97 (br s, 2H), 6.24-6.09 (m, 1H), 5.38-5.33 (m, 1H), 3.73 (s, 3H), 3.25 (dd, J=5.0, 14.0 Hz, 1H), 2.92 (dd, J=9.0, 13.9 Hz, 1H). MS (ESI) m/z $(M+H)^+$379.1.

(S)—N-(4-amino-3,4-dioxo-1-phenylbutan-2-yl)-3-(3-methoxyphenyl)-1-methyl-1H-pyrazole-4-carboxamide (177)

Compound 177 (46 mg, yield: 74.2%, white solid) was prepared as in Example 97 from the corresponding starting materials, compound 163G and (3-methoxyphenyl) boronic acid. Compound 177: $^1$H NMR (400 MHz, DMSO-$d_6$) δ 8.02 (s, 1H), 7.85 (br d, J=7.3 Hz, 1H), 7.78-7.65 (m, 1H), 7.54 (br s, 1H), 7.30-7.25 (m, 3H), 7.24-7.18 (m, 5H), 6.92-6.87 (m, 1H), 5.38-5.31 (m, 1H), 3.89 (s, 3H), 3.78-3.74 (m, 3H), 3.20 (dd, J=4.5, 14.1 Hz, 1H), 2.90 (dd, J=9.0, 14.1 Hz, 11).

(S)—N-(4-amino-3,4-dioxo-1-phenylbutan-2-yl)-3-(3-fluorophenyl)-1-methyl-1H-pyrazole-4-carboxamide (178)

Compound 178 (26 mg, yield: 49.4% white solid) was prepared as in Example 97 from the corresponding starting materials. $^1$H NMR (400 MHz, DMSO-$d_6$) δ 8.46 (br d, J=7.3 Hz, 1H), 8.07 (s, 2H), 7.80 (br s, 1H), 7.42 (d, J=8.2 Hz, 2H), 7.36-7.31 (m, 1H), 7.30-7.25 (m, 4H), 7.22-7.18 (m, 1H), 7.11 (br t, J=8.3 Hz, 1H), 5.33-5.25 (m, 1H), 3.88 (s, 3H), 3.15 (br dd, J=3.5, 13.7 Hz, 1H), 2.80 (dd, J=10.1, 13.9 Hz, 1H). MS (ESI) m/z $(M+H)^+$395.1.

(S)—N-(4-amino-3,4-dioxo-1-phenylbutan-2-yl)-3-(4-fluorophenyl)-1-methyl-1H-pyrazole-4-carboxamide (179)

Compound 179 (15 mg, yield: 36.7%, light yellow solid) was prepared as in Example 97 from the corresponding starting materials. $^1$H NMR (400 MHz, DMSO-$d_6$) δ 8.42 (d, J=7.5 Hz, 1H), 8.07 (s, 2H), 7.81 (s, 1H), 7.61 (dd, J=5.7, 8.8 Hz, 2H), 7.34-7.19 (m, 5H), 7.12 (br t, J=8.9 Hz, 2H), 5.37-5.22 (m, 1H), 3.89 (s, 3H), 3.16 (br dd, J=3.5, 14.1 Hz, 1H), 2.82 (br dd, J=10.1, 13.7 Hz, 1H). MS (ESI) m/z $(M+H)^+$395.1.

(S)—N-(4-amino-3,4-dioxo-1-phenylbutan-2-yl)-3-(3-isopropylphenyl)-1-methyl-1H-pyrazole-4-carboxamide (180)

Compound 180 (58 mg, yield: 60.95%, white solid) was prepared as in Example 97 from the corresponding starting materials. $^1$H NMR (400 MHz, DMSO-$d_6$) δ 8.29 (d, J=7.5 Hz, 1H), 8.11-7.98 (m, 2H), 7.81 (s, 1H), 7.48 (s, 1H), 7.37-7.16 (m, 9H), 5.38-5.23 (m, 1H), 3.89 (s, 3H), 3.15 (dd, J=3.6, 14.0 Hz, 1H), 2.91-2.77 (m, 3H), 1.18 (d, J=6.8 Hz, 6H). MS (ESI) m/z $(M+H)^+$419.2.

(S)—N-(4-amino-3,4-dioxo-1-phenylbutan-2-yl)-3-(2-fluorophenyl)-1-methyl-1H-pyrazole-4-carboxamide (181)

Compound 181 (46 mg, yield: 70.7%, white solid) was prepared as in Example 97 from the corresponding starting materials. $^1$H NMR (400 MHz, DMSO-$d_6$) δ 8.26-8.16 (m, 2H), 8.01 (s, 1H), 7.77 (s, 1H), 7.43-7.07 (m, 9H), 5.28-5.18 (m, 1H), 3.96-3.85 (m, 3H), 3.12 (dd, J=3.6, 14.0 Hz, 1H), 2.81 (dd, J=9.7, 13.9 Hz, 1H). MS (ESI) m/z $(M+H)^+$395.1.

(S)—N-(4-amino-3,4-dioxo-1-phenylbutan-2-yl)-3-(3-ethylphenyl)-1-methyl-1H-pyrazole-4-carboxamide (182)

Compound 182 (24 mg, yield: 65.4%, white solid) was prepared as in Example 97 from the corresponding starting materials. $^1$H NMR (400 MHz, DMSO-$d_6$) δ 8.13 (s, 1H), 7.94 (br d, J=7.0 Hz, 1H), 7.60 (s, 1H), 7.52 (d, J=7.8 Hz, 1H), 7.40-7.36 (m, 2H), 7.35-7.26 (m, 6H), 5.48-5.43 (m, 1H), 4.01 (s, 3H), 3.30 (dd, J=4.5, 14.1 Hz, 1H), 3.00 (dd, J=9.0, 14.1 Hz, 1H), 2.74 (q, J=7.5 Hz, 3H), 1.32 (t, J=7.7 Hz, 4H).

(S)—N-(4-amino-3,4-dioxo-1-phenylbutan-2-yl)-1-methyl-3-(3-(trifluoromethyl)phenyl)-1H-pyrazole-4-carboxamide (183)

Compound 183 (38 mg, yield: 61.9%, white solid) was prepared as in Example 97 from the corresponding starting materials. $^1$H NMR (400 MHz, DMSO-$d_6$) δ 8.51 (d, J=7.5 Hz, 1H), 8.12 (s, 1H), 8.03 (s, 1H), 7.97 (s, 1H), 7.84 (br d, J=7.9 Hz, 1H), 7.80 (s, 1H), 7.63 (br d, J=7.7 Hz, 1H), 7.55-7.48 (m, 1H), 7.26 (d, J=4.2 Hz, 4H), 7.21-7.16 (m, 1H), 5.32-5.25 (m, 1H), 3.89 (s, 3H), 3.17-3.11 (m, 1H), 2.83-2.76 (m, 1H). MS (ESI) m/z $(M+H)^+$445.1.

(S)—N-(4-amino-3,4-dioxo-1-phenylbutan-2-yl)-1-methyl-3-(3-(trifluoromethoxy)phenyl)-1H-pyrazole-4-carboxamide (184)

Compound 184 (18 mg, yield: 53.5%, white solid) was prepared as in Example 97 from the corresponding starting materials. $^1$H NMR (400 MHz, DMSO-$d_6$) δ 8.48 (d, J=7.7 Hz, 1H), 8.10 (s, 1H), 8.03 (s, 1H), 7.79 (s, 1H), 7.64-7.56 (m, 2H), 7.41 (t, J=8.2 Hz, 1H), 7.30-7.24 (m, 5H), 7.12-7.16 (m, 1H), 5.33-5.27 (m, 1H), 3.89 (s, 3H), 3.15 (dd, J=3.9, 13.8 Hz, 1H), 2.81 (dd, J=10.1, 13.9 Hz, 1H). MS (ESI) m/z $(M+H)^+$461.1.

(S)—N-(4-amino-3,4-dioxo-1-phenylbutan-2-yl)-3-(3-cyanophenyl)-1-methyl-1H-pyrazole-4-carboxamide (185)

Compound 185 (20 mg, yield: 43.2%, white solid) was prepared as in Example 97 from the corresponding starting materials. $^1$H NMR (400 MHz, DMSO-$d_6$) δ 8.65 (dd, J=7.3 Hz, 1H), 8.28 (s, 1H), 8.07 (s, 1H), 8.00 (s, 1H), 7.89 (dd, J=7.5 Hz, 1H), 7.82 (s, 1H), 7.77 (dd, J=8.2 Hz, 1H), 7.52 (t, J=7.9 Hz, 1H), 7.31-7.19 (m, 5H), 5.31 (dd, J=6.8 Hz, 1H), 3.91 (s, 3H), 3.16 (dd, J=9.9 Hz, 1H), 2.91-2.81 (m, 1H). MS (ESI) m/z $(M+H)^+$402.1.

(S)—N-(4-amino-3,4-dioxo-1-phenylbutan-2-yl)-3-(3-cyclopropylphenyl)-1-methyl-1H-pyrazole-4-carboxamide (186)

Compound 186 (30 mg, yield: 53.72%, yellow solid) was prepared as in Example 97 from the corresponding starting materials. $^1$H NMR (400 MHz, DMSO-$d_6$) δ 8.36 (dd, J=6.8 Hz, 1H), 8.14-8.01 (m, 2H), 7.82 (s, 1H), 7.30-7.14 (m, 8H), 6.99 (dd, J=7.5 Hz, 1H), 5.28 (s, 1H), 3.88 (s, 3H), 3.14 (dd, J=11.0 Hz, 1H), 2.87-2.80 (m, 1H), 1.89 (s, 1H), 0.92 (dd, J=6.6 Hz, 2H), 0.62 (s, 2H). MS (ESI) m/z $(M+H)^+$417.1.

(S)—N-(4-amino-3,4-dioxo-1-phenylbutan-2-yl)-3-(3-chlorophenyl)-1-methyl-1H-pyrazole-4-carboxamide (187)

Compound 187 (35 mg, yield: 53.0%, white solid) was prepared as in Example 97 from the corresponding starting materials. $^1$H NMR (400 MHz, DMSO-$d_6$) δ 8.52-8.44 (m, 1H), 8.11 (s, 1H), 8.06 (s, 1H), 7.81 (s, 1H), 7.74-7.65 (m, 1H), 7.60-7.50 (m, 1H), 7.39-7.33 (m, 2H), 7.30-7.28 (m, 3H), 7.25-7.18 (m, 2H), 5.38-5.25 (m, 1H), 3.90 (s, 3H), 3.17 (dd, J=3.6, 14.0 Hz, 1H), 2.89-2.80 (m, 1H). MS (ESI) m/z $(M+H)^+$411.1.

(S)—N-(4-amino-3,4-dioxo-1-phenylbutan-2-yl)-1-methyl-3-(pyridin-3-yl)-1H-pyrazole-4-carboxamide (188)

Compound 188 (15.8 mg, yield: 26.5%, white solid) was prepared as in Example 97 from the corresponding starting materials, compound 163G and pyridin-3-ylboronic acid. Compound 188: $^1$H NMR (400 MHz, DMSO-$d_6$) δ 8.77 (d, J=1.6 Hz, 1H), 8.53-8.47 (m, 2H), 8.19 (s, 1H), 8.06 (br s, 1H), 7.92 (td, J=1.9, 7.9 Hz, 1H), 7.80 (br s, 1H), 7.34 (dd, J=5.1, 7.6 Hz, 1H), 7.32-7.28 (m, 4H), 7.26-7.18 (m, 1H), 5.35-5.26 (m, 1H), 3.93 (s, 3H), 3.18 (dd, J=3.8, 13.8 Hz, 1H), 2.84 (dd, J=10.1, 13.9 Hz, 1H). MS (ESI) m/z $(M+H)^+$ 378.1.

(S)—N-(4-amino-3,4-dioxo-1-phenylbutan-2-yl)-1-methyl-5-(pyridin-3-yl)-1H-pyrazole-4-carboxamide (189)

Compound 189 (16 mg, 42.4 umol, yield: 30.9%, white solid) was prepared as in Example 97 from the corresponding starting materials, compound 163E and pyridin-3-ylboronic acid. Compound 189: $^1$H NMR (400 MHz, $CDCl_3$) δ 8.74 (br d, J=4.2 Hz, 1H), 8.60 (s, 1H), 7.86 (s, 1H), 7.69 (br d, J=7.9 Hz, 1H), 7.42-7.36 (m, 1H), 7.25 (br d, J=3.3 Hz, 2H), 6.94 (br d, J=3.5 Hz, 2H), 6.74 (br s, 1H), 5.93 (br d, J=6.6 Hz, 1H), 5.63 (br s, 1H), 5.52 (q, J=6.5 Hz, 1H), 3.73 (s, 3H), 3.32 (dd, J=5.3, 13.9 Hz, 1H), 3.08 (dd, J=6.8, 13.9 Hz, 1H). MS (ESI) m/z $(M+H)^+$378.1.

(S)—N-(4-amino-3,4-dioxo-1-phenylbutan-2-yl)-1-methyl-5-(o-tolyl)-1H-pyrazole-4-carboxamide (190)

Compound 190 (28.4 mg, yield: 30.7%, white solid) was prepared as in Example 97 from the corresponding starting materials, compound 163E and o-tolylboronic acid. Compound 190: $^1$H NMR (400 MHz, DMSO-$d_6$) δ 7.94 (d, J=4.8 Hz, 1H), 7.43-7.31 (m, 3H), 7.30-7.15 (m, 5H), 7.15-7.05 (m, 4H), 5.30-5.19 (m, 1H), 3.48 (s, 3H), 3.12 (dd, J=4.4, 14.0 Hz, 1H), 2.76 (ddd, J=4.8, 9.0, 13.8 Hz, 1H), 1.96 (d, J=10.1 Hz, 3H). MS (ESI) m/z $(M+H)^+$391.1.

N-(4-amino-3,4-dioxo-1-phenylbutan-2-yl)-1-methyl-3-(6-(trifluoromethyl)pyridin-3-yl)-1H-pyrazole-4-carboxamide (315)

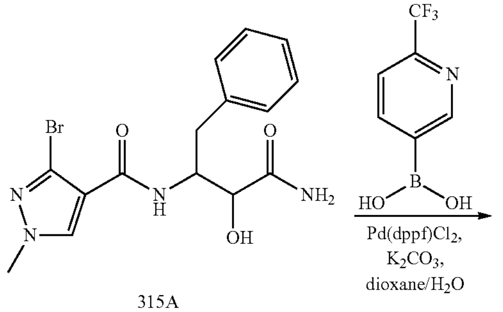

315A

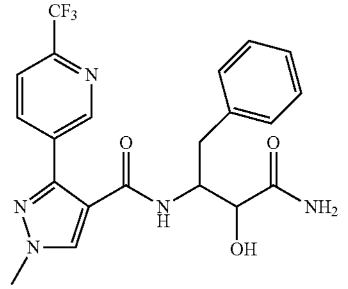

315B

To a mixture of 3-amino-2-hydroxy-4-phenylbutanamide hydrochloride (1.35 g, 5.86 mmol, HCl) and compound 163F (1 g, 4.88 mmol), HOBt (659 mg, 4.88 mmol) in DMF (20 mL) was added DIEA (1.58 g, 12.20 mmol, 2 mL) and EDCI (1.4 g, 7.32 mmol) in portion at 20° C. and stirred for 16 h. The reaction mixture was treated with EA (40 mL), washed with $H_2O$ (50 mL×2). The organic layer was washed with 0.5N HCl (40 mL), saturated aqueous $NaHCO_3$ (40 mL) and brine (30 mL), dried over $Na_2SO_4$, filtered and the solvent was removed in vacuo. The residue was triturated with DCM (2 mL) and PE (10 mL), the precipitate was formed, the solid was collected and was dried in vacuo to give compound 315A (900 mg, yield: 45.38%) as yellow solid. $^1$H NMR (400 MHz, DMSO-$d_6$) δ 8.25 (s, 1H), 7.85-7.42 (m, 1H), 7.35 (dd, J=7.3 Hz, 1H), 7.28-7.18 (m, 5H), 6.15 (d, J=6.2 Hz, 1H), 5.95 (d, J=5.5 Hz, 1H), 4.56-4.32 (m, 1H), 3.86-3.78 (m, 4H), 2.95-2.84 (m, 1H), 2.82-2.73 (m, 1H), 2.69-2.58 (m, 1H). MS (ESI) m/z $(M+H)^+$381.0.

Compound 315 (30 mg, yield: 28.27%, white solid) was prepared as in Example 97 from the corresponding intermediate compounds, 315A and (6-(trifluoromethyl)pyridin-3-yl)boronic acid and through intermediate compound 315B. Compound 315: $^1$H NMR (400 MHz, DMSO-$d_6$) δ 8.92 (s, 1H), 8.65 (dd, J=7.3 Hz, 1H), 8.26 (s, 1H), 8.20 (dd, J=8.4 Hz, 1H), 8.05 (s, 1H), 7.88-7.76 (m, 2H), 7.28 (d, J=3.7 Hz, 4H), 7.24-7.16 (m, 1H), 5.27 (t, J=3.1 Hz, 1H), 3.94 (s, 3H), 3.16 (dd, J=3.7, 14.1 Hz, 1H), 2.83 (dd, J=10.4, 13.7 Hz, 1H). MS (ESI) m/z $(M+H)^+$446.1.

N-(4-amino-3,4-dioxo-1-phenylbutan-2-yl)-3-(3-methoxyphenyl)-1-methyl-1H-pyrazole-4-carboxamide (407)

Compound 407 (3.9 g, yield: 94.15%, white solid) was prepared as in Example 97 from the corresponding starting materials, compound 163C, (3-methoxyphenyl) boronic acid, and 274D. Compound 407: $^1H$ NMR (400 MHz, DMSO-$d_6$) δ 8.44-8.25 (m, 1H), 8.15-7.97 (m, 2H), 7.84 (br s, 1H), 7.37-7.11 (m, 8H), 6.96-6.80 (m, 1H), 5.44-5.19 (m, 1H), 3.90 (br s, 3H), 3.73 (br s, 3H), 3.26-3.07 (m, 1H), 2.92-2.72 (m, 1H). MS (ESI) m/z $(M+H)^+$407.1.

3-((1H-pyrazolo[4,3-c]pyridin-1-yl)methyl)-N-(4-amino-3,4-dioxo-1-phenylbutan-2-yl)-1-methyl-1H-pyrazole-4-carboxamide (408)

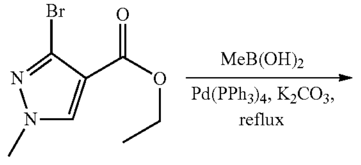

163C

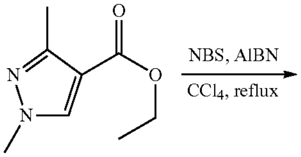

408A

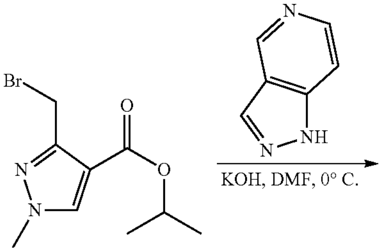

408B

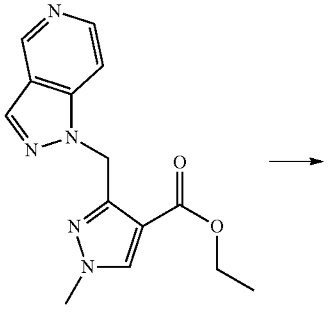

408C

-continued

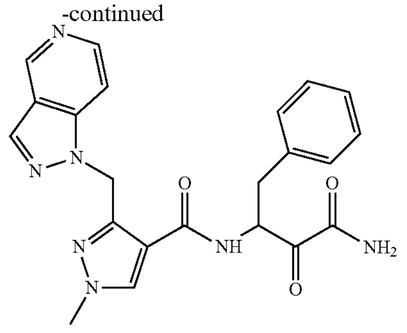

408

A mixture of compound 163C (2 g, 8.58 mmol), MeB$(OH)_2$ (2.05 g, 34.3 mmol), Pd$(PPh_3)_4$ (793 mg, 687 umol), $K_2CO_3$ (2.37 g, 17.2 mmol) in dioxane (50 mL) and $H_2O$ (10 mL) was degassed and purged with $N_2$ for 3 times, and then the mixture was stirred at 120° C. for 12 hour under $N_2$ atmosphere. The reaction mixture was extracted with Ethyl acetate 50 mL (50 mL×2). The combined organic layers were dried over $Na_2SO_4$, filtered and concentrated under reduced pressure to give a residue. The residue was purified by column chromatography ($SiO_2$, Petroleum ether:Ethyl acetate=100:1 to 80:1). Compound 408A (1.4 g, yield: 97.0%) was obtained as a yellow solid. $^1H$ NMR (400 MHz, $CDCl_3$) δ 7.87-7.73 (m, 1H), 4.27 (q, J=7.1 Hz, 2H), 3.91-3.75 (m, 3H), 2.51-2.40 (m, 3H), 1.33 (t, J=7.1 Hz, 3H).

A mixture of compound 408A (1.2 g, 7.13 mmol), NBS (1.9 g, 10.7 mmol), AIBN (586 mg, 3.57 mmol) in $CCl_4$ (30 mL) was stirred at 80° C. for 12 hours. The reaction mixture was filtered and concentrated under reduced pressure to give a residue. The residue was purified by column chromatography ($SiO_2$, Petroleum ether:Ethyl acetate=98:1 to 90:1). Compound 408B (600 mg, yield: 34.1%) was obtained as a yellow oil. $^1H$ NMR (400 MHz, $CDCl_3$) δ 7.76 (s, 1H), 4.66 (s, 2H), 4.30-4.21 (m, 2H), 3.90-3.79 (m, 3H), 1.38-1.22 (m, 3H).

To a mixture of 1H-pyrazolo [4,3-c]pyridine (797 mg, 6.69 mmol) in DMF (20 mL) was added KOH (501 mg, 8.92 mmol). The mixture was stirred at 15° C. for 30 min. And then to the mixture was added compound 408B (550 mg, 2.23 mmol) in DMF (10 mL) drop-wise at 0° C. over 10 min, and the mixture was stirred at 0° C. for 2 hr. The desired product was confirmed by NOE. The reaction mixture was concentrated under reduced pressure to give a residue. The residue was purified by preparatory-HPLC (basic condition). Compound 408C (300 mg, yield: 47.2%) was obtained as a yellow oil. $^1H$ NMR (400 MHz, $CDCl_3$) δ 9.14-8.99 (m, 1H), 8.40 (d, J=6.2 Hz, 1H), 8.15 (s, 1H), 7.92-7.75 (m, 1H), 7.51 (d, J=6.0 Hz, 1H), 5.85 (s, 2H), 4.26 (q, J=7.2 Hz, 2H), 3.93-3.75 (m, 3H), 1.29 (t, J=7.1 Hz, 3H).

Compound 408 (24.1 mg, yield: 40.4%, white solid) was prepared as in Example 95 from the corresponding starting materials, compound 408C and 274D.

Compound 408: $^1H$ NMR (400 MHz, DMSO-$d_6$) δ 9.07 (s, 1H), 8.91 (br d, J=5.5 Hz, 1H), 8.46 (br d, J=5.5 Hz, 1H), 7.93 (s, 1H), 7.69 (s, 1H), 7.59 (br d, J=5.5 Hz, 1H), 7.24-7.17 (m, 1H), 7.23 (br s, 2H), 7.25-7.15 (m, 1H), 6.79 (br s, 1H), 5.69-5.51 (m, 1H), 5.73-5.38 (m, 1H), 5.49-5.37 (m, 1H), 5.50-5.37 (m, 1H), 5.74-5.33 (m, 1H), 3.79 (s, 3H), 3.56-3.42 (m, 1H), 3.17 (br dd, J=9.5, 14.1 Hz, 1H). MS (ESI) m/z $(M+H)^+$432.3.

N-(4-amino-3-hydroxy-4-oxo-1-phenylbutan-2-yl)-3-(4-fluorophenyl)-1-methyl-1H-pyrazole-4-carboxamide (446) and N-(4-amino-3,4-dioxo-1-phenylbutan-2-yl)-3-(4-fluorophenyl)-1-methyl-1H-pyrazole-4-carboxamide (447)

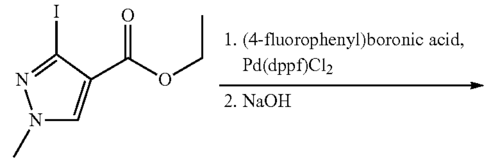

446A

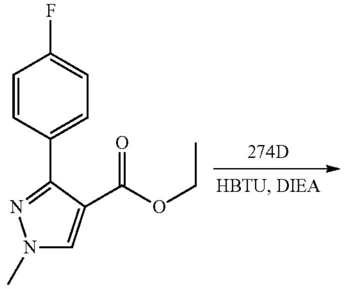

446A

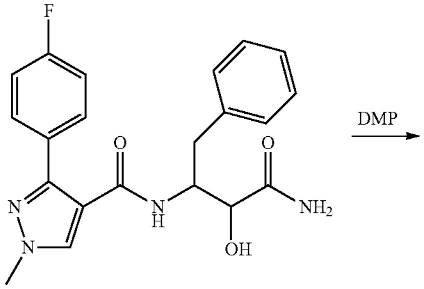

446

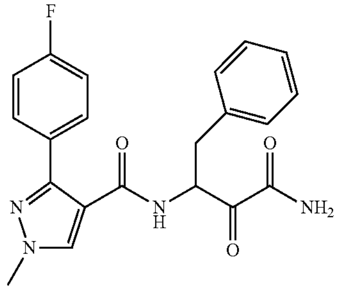

447

Compound 446A was treated with (4-fluorophenyl)boronic acid using procedure as in compound 163E followed by subjecting the resulting product to ester hydrolysis using sodium hydroxide and coupling with intermediate 274D using the procedures as in compound 12 to yield compounds 446 and compound 447. Compound 446 (550 mg, yield: 75.9%) was obtained as a white solid. $^1$H NMR (400 MHz, DMSO-$d_6$) δ 8.08-8.00 (m, 1H), 7.75 (d, J=9.0 Hz, 1H), 7.56 (dd, J=5.6, 8.7 Hz, 2H), 7.33-7.08 (m, 8H), 5.83 (d, J=5.7 Hz, 1H), 4.59-4.37 (m, 1H), 4.00 (d, J=1.8 Hz, 1H), 3.86 (s, 3H), 2.80-2.73 (m, 1H), 2.68 (s, 1H), 2.66 (d, J=5.1 Hz, 1H). MS (ESI) m/z $(M+H)^+$397.1. Compound 447 (80 mg, yield: 39.9%) was obtained as a white solid. $^1$H NMR (400 MHz, DMSO-$d_6$) δ 8.42 (d, J=7.3 Hz, 1H), 8.11-8.03 (m, 2H), 7.81 (s, 1H), 7.65-7.57 (m, 2H), 7.32-7.18 (m, 5H), 7.12 (t, J=8.8 Hz, 2H), 5.27 (d, J=3.1 Hz, 1H), 3.89 (s, 3H), 3.30-3.12 (m, 1H), 2.83 (dd, J=9.9, 13.7 Hz, 1H). MS (ESI) m/z $(M+H)^+$ 395.1.

Example 98

Compounds 174-175, 191-193, 313, 293

(S)—N-(4-amino-3,4-dioxo-1-phenylbutan-2-yl)-1-methyl-3-(pyrimidin-5-yl)-1H-pyrazole-4-carboxamide (174)

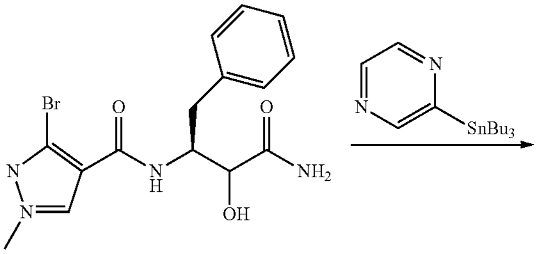

163E

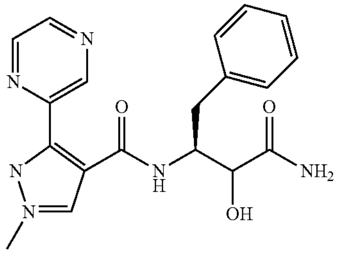

174A

To a solution of Compound 163E (150 mg, 393.47 umol) and tributyl(pyrazin-2-yl)stannane (217 mg, 590.21 umol) in dioxane (15 mL) was added palladium; tritert-butylphosphane (100 mg, 196.74 umol). The mixture was stirred at 90° C. for 16 h. The mixture was quenched with aqueous KF (20 mL), filtered, washed with ethyl acetate (20 mL), the filtrate was extracted with ethyl acetate (20 mL×2). The organic phase was dried over $Na_2SO_4$, concentrated to give a residue. The residue was purified by preparatory-HPLC (basic condition) and by preparatory-TLC ($SiO_2$, DCM: MeOH=10:1). Compound 174A (70 mg, yield: 45.6%) was obtained as a white solid. $^1$H NMR (400 MHz, MeOD) δ 8.77-8.69 (m, 1H), 8.66-8.54 (m, 2H), 7.94-7.78 (m, 1H), 7.25-7.12 (m, 5H), 4.63-4.58 (m, 1H), 4.26-4.02 (m, 1H), 3.91-3.84 (m, 3H), 3.01-2.83 (m, 2H). MS (ESI) m/z $(M+H)^+$381.1.

Compound 174 (25 mg, yield: 34.93%, white solid) was prepared as in Example 61 from the intermediate compound 174A. Compound 174A: $^1$H NMR (400 MHz, DMSO-$d_6$) δ 8.75 (d, J=1.5 Hz, 1H), 8.71 (dd, J=1.6, 2.6 Hz, 1H), 8.66-8.64 (m, 1H), 8.31 (d, J=7.5 Hz, 1H), 7.99 (s, 1H), 7.70 (br s, 1H), 7.51 (br s, 1H), 7.28-7.23 (m, 4H), 7.22-7.17 (m, 1H), 5.33-5.28 (m, 1H), 3.83 (s, 3H), 3.20 (dd, J=4.5, 14.1 Hz, 1H), 2.93 (dd, J=9.3, 14.1 Hz, 1H). MS (ESI) m/z $(M+H)^+$379.1.

(S)—N-(4-amino-3,4-dioxo-1-phenylbutan-2-yl)-1-methyl-5-(pyrimidin-4-yl)-1H-pyrazole-4-carboxamide (175)

Compound 175 (35 mg, yield: 47.75%, white solid) was prepared as in Example 98 from the corresponding starting materials, compound 163E and tributyl(pyrimidin-4-yl)stannane. Compound 175: $^1$H NMR (400 MHz, DMSO-$d_6$) δ 9.24 (d, J=1.1 Hz, 1H), 8.82 (d, J=5.3 Hz, 1H), 8.71 (d, J=7.5 Hz, 1H), 8.03 (s, 1H), 7.93 (s, 1H), 7.78 (s, 1H), 7.54 (dd, J=1.3, 5.3 Hz, 1H), 7.27-7.17 (m, 6H), 5.28-5.19 (m, 1H), 3.85 (s, 3H), 3.15 (dd, J=4.0, 13.9 Hz, 1H), 2.83 (dd, J=10.1, 13.9 Hz, 1H). MS (ESI) m/z $(M+H)^+$379.1.

(S)—N-(4-amino-3,4-dioxo-1-phenylbutan-2-yl)-1-methyl-5-(pyrimidin-2-yl)-1H-pyrazole-4-carboxamide (191)

Compound 191 (20 mg, yield: 38.77%, white solid) was prepared as in Example 98 from the corresponding starting materials, compound 163E and tributyl(pyrimidin-2-yl)stannane. Compound 191: $^1$H NMR (400 MHz, DMSO-$d_6$) δ 9.63 (d, J=6.3 Hz, 1H), 8.86 (d, J=5.0 Hz, 2H), 7.90 (s, 1H), 7.81-7.56 (m, 2H), 7.55 (t, J=4.9 Hz, 1H), 7.21-7.14 (m, 3H), 7.12-7.06 (m, 2H), 5.47 (t, J=5.1, 7.5 Hz, 1H), 4.05 (s, 3H), 3.24 (dd, J=5.1, 14.2 Hz, 1H), 3.05-3.00 (m, 1H). MS (ESI) m/z $(M+H)^+$379.1.

(S)—N-(4-amino-3,4-dioxo-1-phenylbutan-2-yl)-1-methyl-3-(pyrimidin-4-yl)-1H-pyrazole-4-carboxamide (192)

Compound 192 (15 mg, yield: 29.82%, white solid) was prepared as in Example 98 from the corresponding starting materials, compound 163G and 4-(tributylstannyl)pyrimidine. Compound 192: $^1$H NMR (400 MHz, $CD_3CN$) δ 11.76-11.65 (m, 1H), 8.81-8.73 (m, 2H), 8.14 (s, 1H), 8.07 (dd, J=1.1, 5.3 Hz, 1H), 7.59 (s, 1H), 7.15 (s, 4H), 7.04 (s, 1H), 6.24 (s, 1H), 5.65-5.59 (m, 1H), 3.93 (s, 3H), 3.33 (dd, J=5.1, 14.1 Hz, 1H), 3.14 (dd, J=7.7, 14.1 Hz, 1H). MS (ESI) m/z $(M+H)^+$379.1.

(S)—N-(4-amino-3,4-dioxo-1-phenylbutan-2-yl)-1-methyl-3-(pyrimidin-4-yl)-1H-pyrazole-4-carboxamide (193)

Compound 193 (25 mg, yield: 54.29%, white solid) was prepared as in Example 98 from the corresponding starting materials, compound 163G and tributyl(pyrimidin-2-yl) stannane. Compound 193: $^1$H NMR (400 MHz, DMSO-$d_6$) δ 11.24 (d, J=7.3 Hz, 1H), 8.69 (d, J=4.9 Hz, 2H), 8.29 (s, 1H), 8.08 (s, 1H), 7.82 (s, 1H), 7.47 (t, J=4.9 Hz, 1H), 7.16-7.09 (m, 3H), 7.07-7.03 (m, 2H), 5.61-5.49 (m, 1H), 3.92 (s, 3H), 3.23 (dd, J=5.1, 14.1 Hz, 1H), 3.07 (dd, J=7.3, 14.1 Hz, 1H). MS (ESI) m/z $(M+H)^+$379.0.

(S)—N-(4-amino-3,4-dioxo-1-phenylbutan-2-yl)-1-methyl-3-(pyrazin-2-yl)-1H-pyrazole-4-carboxamide (313)

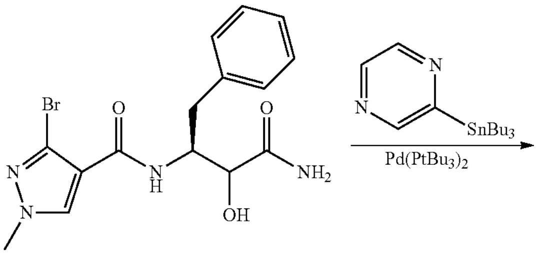

163G

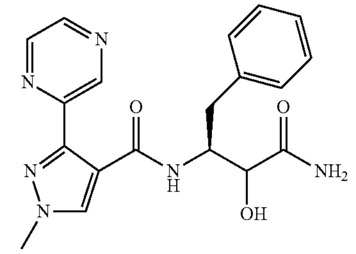

313A

Compound 313 was prepared as in Example 98 from the corresponding starting materials, compound 163G and 2-(tributylstannyl)pyrazine, through intermediate compound 313A. Compound 313 (70 mg, yield: 69.7%, white solid): $^1$H NMR (400 MHz, $CD_3CN$) δ 11.26 (d, J=6.0 Hz, 1H), 9.34 (d, J=1.3 Hz, 1H), 8.54 (d, J=2.6 Hz, 1H), 8.23-8.10 (m, 2H), 7.17-7.11 (m, 5H), 7.01 (br s, 1H), 6.19 (br s, 1H), 5.67-5.55 (m, 1H), 3.94 (s, 3H), 3.33 (dd, J=5.3, 14.1 Hz, 1H), 3.13 (dd, J=7.7, 14.1 Hz, 1H). MS (ESI) m/z $(M+H)^+$ 379.1.

N-(4-amino-3,4-dioxo-1-phenylbutan-2-yl)-1-methyl-3-(6-methylpyridin-2-yl)-1H-pyrazole-4-carboxamide (316

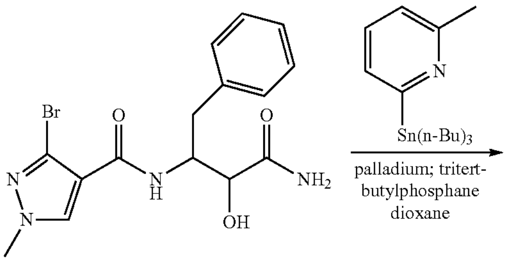

315A

-continued

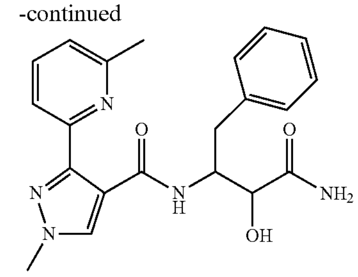

316A

Compound 316 was prepared as in Example 98 from the corresponding starting materials, compound 315A and 2-methyl-6-(tributylstannyl)pyridine, through intermediate compound 316A. Compound 316 (20 mg, yield: 21.64%, white solid): $^1$H NMR (400 MHz, DMSO-$d_6$) δ 11.79 (d, J=7.7 Hz, 1H), 8.24 (s, 1H), 8.02 (s, 1H), 7.92-7.86 (m, 1H), 7.84-7.78 (m, 1H), 7.75 (s, 1H), 7.24 (d, J=7.7 Hz, 1H), 7.15-7.08 (m, 3H), 7.08-7.02 (m, 2H), 5.52 (t, J=5.2, 8.1 Hz, 1H), 3.89 (s, 3H), 3.22 (dd, J=4.7, 13.8 Hz, 1H), 2.99 (dd, J=8.4, 13.7 Hz, 1H), 2.28 (s, 3H). MS (ESI) m/z $(M+H)^+$ 392.2.

Example 99

(S)—N-(4-amino-3,4-dioxo-1-phenylbutan-2-yl)-1-methyl-5-(6-(trifluoromethyl)pyridin-2-yl)-1H-pyrazole-4-carboxamide (194)

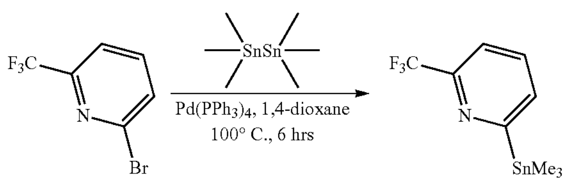

194A

To a mixture of 2-bromo-6-(trifluoromethyl)pyridine (3 g, 13.27 mmol) and 1,1,1,2,2,2-hexamethyldistannane (5.7 g, 17.40 mmol) in 1,4-dioxane (96 mL) was added $Pd(PPh_3)_4$ (3.07 g, 2.65 mmol) at 25° C. under nitrogen atmosphere and the resultant mixture was stirred at 100° C. for 6 hours. The reaction mixture was cooled to room temperature, and filtered through a thin layer of celite. The filter cake was washed with DCM. The filtrate was concentrated in vacuum to give a dark solid, which was purified by column chromatography ($SiO_2$, Petroleum ether/Ethyl acetate=100:1 to 10:1) to afford crude compound 194A (3.2 g, 26.46% purity by LCMS) as a white solid. MS (ESI) m/z $(M+H)^+$311.8.

Compound 194 (32.1 mg, 62.15% yield, white solid) was prepared as in Example 98 from the corresponding starting materials, intermediate compounds 163E and 194A. Compound 194: $^1$H NMR (400 MHz, $CDCl_3$): δ 7.98-7.91 (m, 1H), 7.85 (d, J=7.6 Hz, 1H), 7.75 (s, 1H), 7.72 (d, J=7.6 Hz, 1H), 7.26-7.21 (m, 3H), 7.07-7.02 (m, 2H), 6.74 (br s, 1H), 6.63-6.56 (m, 1H), 5.60-5.54 (m, 1H), 5.51 (br s, 1H), 3.94 (s, 3H), 3.41-3.31 (m, 1H), 3.14-3.06 (m, 1H). MS (ESI) m/z $(M+H)^+$446.0.

Example 100

N-(1-amino-1,2-dioxohex-5-EN-3-yl)-1-methyl-3-phenyl-1H-pyrazole-4-carboxamide (195)

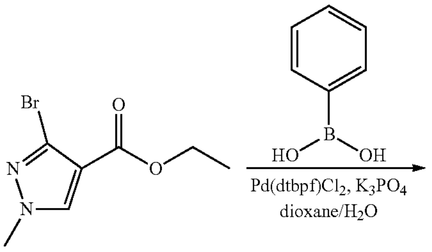

163B

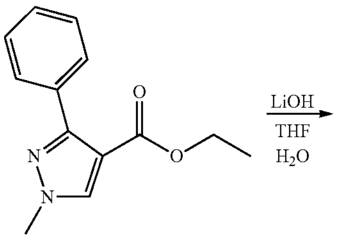

195A

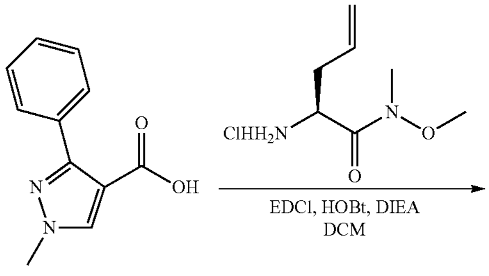

195B

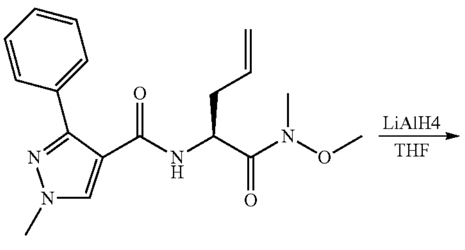

195C

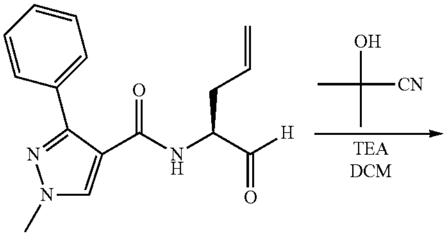

195D

-continued

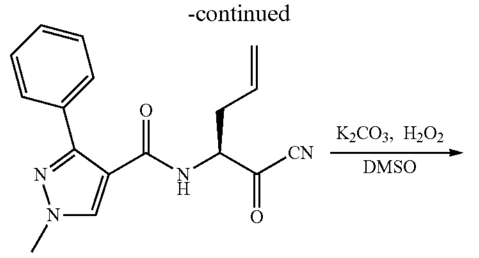

195E

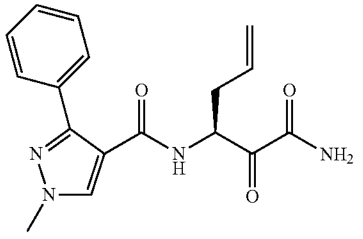

195F

To a solution of compound 163B (2 g, 8.58 mmol) and phenylboronic acid (1.26 g, 10.30 mmol) in dioxane (30 mL) and $H_2O$ (10 mL) was added Pd(dtbpf)$Cl_2$ (280 mg, 0.43 mmol) and $K_3PO_4$ (5.46 g, 25.74 mmol). The mixture was stirred at 70° C. under $N_2$ for 3 h. The reaction was washed with $H_2O$ (20 mL), extracted with EtOAc (15 mL×2). The organics were collected and concentrated. The residue was purified by column (Petroleum Ether:Ethyl Acetate=10:1) to afford compound 195A (1.9 g, yield: 96.17%) as yellow oil.

To a solution of compound 195A (1.9 g, 8.25 mmol) in THF (20 mL) and $H_2O$ (20 mL) was added LiOH.$H_2O$ (1.73 g, 41.25 mmol). The mixture was stirred at 25° C. for 24 h. The reaction was acidified with 1N HCl to pH ~4. The mixture was extracted with EtOAc (25 mL×2). The organics were collected, washed with brine (30 mL), dried with $Na_2SO_4$, filtered and concentrated to afford compound 195B (1.3 g, yield: 77.93%) as light yellow solid. MS (ESI) m/z $(M+1)^+$202.9.

To a solution of compound 195B (800 mg, 3.96 mmol) and (S)-2-amino-N-methoxy-N-methylpent-4-enamide hydrochloride (926 mg, 4.75 mmol) in DCM (20 mL) was added DIEA (1.73 mL, 9.90 mmol), HOBt (1.07 g, 7.92 mmol) and EDCI (1.52 g, 7.92 mmol). The mixture was stirred at 25° C. for 12 h. The solvent was removed in vacuo. The reaction was diluted with EtOAc (30 mL), washed with 1N HCl (20 mL). The organics were collected and concentrated. The residue was purified by column chromatography (Petroleum Ether:Ethyl Acetate=1:1) to afford compound 195C (1.2 g, yield: 88.50%) as colorless oil. MS (ESI) m/z $(M+1)^+$343.1.

To a solution of compound 195C (1 g, 2.92 mmol) in THF (10 mL) at −40° C. was added $LiAlH_4$ (1M, 3.1 mL) dropwise. After addition, the mixture was stirred at 0° C. for 1 h. The reaction was quenched with 1N HCl (30 mL) dropwise, extracted with EtOAc (20 mL×3). The organics were collected, washed with brine (30 mL), dried with $Na_2SO_4$, filtered and concentrated to afford intermediate compound 195D (800 mg, crude) as white solid. MS (ESI) m/z $(M+1)^+$284.0.

To a solution of compound 195D (280 mg, 0.99 mmol) and 2-hydroxy-2-methylpropanenitrile (0.54 mL, 5.88 mmol) in DCM (20 mL) was added TEA (0.17 mL, 1.19 mmol). The mixture was stirred at 25° C. for 12 h. The solvent was removed in vacuo. The residue was purified by column (Petroleum Ether:Ethyl Acetate=1:1) to give compound 195E (200 mg, yield: 65.21%) as yellow oil. MS (ESI) m/z $(M+1)^+$311.0.

To a solution of compound 195E (736 mg, 2.37 mmol) in DMSO (5 mL) at 0° C. was added $K_2CO_3$ (656 mg, 4.74 mmol). Then $H_2O_2$ (2.28 mL, 23.72 mmol, 30% purity) was added dropwise. The mixture was stirred at 25° C. for 1 h. The reaction was quenched with 10% aq. $Na_2S_2O_3$ (30 mL) dropwise. The mixture was extracted with EtOAc (20 mL×3). The organics were collected, washed with brine (30 mL), dried with $Na_2SO_4$, filtered and concentrated. The residue was washed with $CH_3CN$ (5 mL). The solid was filtered, collected and dried in vacuo to afford compound 195F (200 mg, yield: 25.60%) as white solid. $^1$H NMR (DMSO-$d_6$, 400 MHz): δ 8.09 (s, 1H), 7.72-7.61 (m, 2H), 7.48-7.42 (m, 1H), 7.40-7.26 (m, 3H), 7.25-7.12 (m, 2H), 5.81-5.60 (m, 2H), 5.12-4.93 (m, 2H), 4.33-4.17 (m, 1H), 3.96-3.93 (m, 1H), 3.86 (s, 3H), 2.34-2.05 (m, 2H). MS (ESI) m/z $(M+1)^+$329.0.

To a solution of compound 195F (200 mg, 609.07 umol) in DCM (15 mL) and DMSO (5 mL) was added DMP (775 mg, 1.83 mmol). The mixture was stirred at 25° C. for 30 min. The reaction was diluted with DCM (20 mL), quenched with a solution of 10% aqueous $Na_2S_2O_3$ and saturated $NaHCO_3$ (v/v=1/1) (40 mL). The organics were collected, washed with brine (30 mL×3). The organics were collected, dried with $Na_2SO_4$, filtered and concentrated. The residue was washed with $CH_3CN$ (5 mL). The solid was filtered, collected and dried in vacuo to afford 195 (38 mg, yield: 18.72%) as white solid. $^1$H NMR (DMSO-$d_6$, 400 MHz): δ 8.23 (d, J=6.8 Hz, 1H), 8.13 (s, 1H), 7.98 (br. s, 1H), 7.73 (br. s, 1H), 7.68-7.61 (m, 2H), 7.38-7.25 (m, 3H), 5.89-5.71 (m, 1H), 5.11-4.98 (m, 3H), 3.88 (s, 3H), 2.57-2.50 (m, 1H), 2.40-2.31 (m, 1H). MS (ESI) m/z $(M+1)^+$327.1.

Example 101

(S)—N-(4-amino-3,4-dioxo-1-phenylbutan-2-yl)-3-bromo-1-methyl-1H-pyrazole-4-carboxamide (196)

Compound 196 (54 mg, yield: 50.44%, white solid) was prepared as in Example 61 from the corresponding intermediate compound 163G. Compound 196: $^1$H NMR (400 MHz, DMSO-$d_6$) δ 8.21-8.15 (m, 2H), 8.06 (br s, 1H), 7.80 (br s, 1H), 7.28-7.23 (m, 4H), 7.20-7.16 (m, 1H), 5.33-5.26 (m, 1H), 3.82 (s, 3H), 3.15 (br dd, J=3.7, 13.9 Hz, 1H), 2.83 (br dd, J=9.8, 13.8 Hz, 1H). MS (ESI) m/z $(M+H)^+$379.0 & 381.0.

Example 102

N-(1-amino-1,2-dioxohex-5-EN-3-yl)-1-methyl-3-phenyl-1H-pyrazole-4-carboxamide (197)

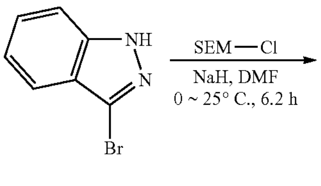

-continued

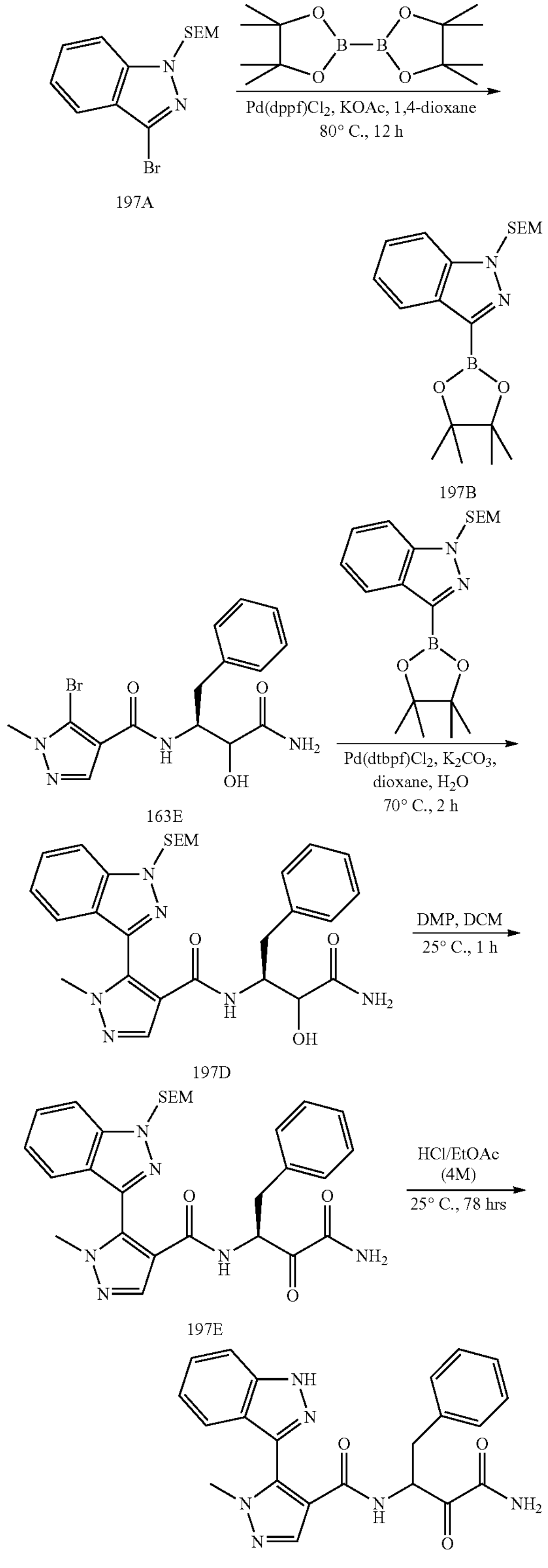

197A

197B

163E

197D

197E

197

To a cold (0° C.), stirred solution of 3-bromo-1H-indazole (5 g, 25.38 mmol) in DMF (130 mL) was added NaH (1.22 g, 50.76 mmol) in portions. After 0.2 h, SEM-Cl (5.08 g, 30.46 mmol) was added and then the mixture was stirred at 25° C. for 6 hours under $N_2$ atmosphere. The reaction was quenched with a saturated aqueous solution of $NH_4Cl$ and the resulting layer was extracted with EtOAc (100 mL×2). The combined organic layers were dried, filtered and concentrated under reduced pressure to leave a residue. The residue which was purified by flash chromatography on silica (elution with 100:1 to 10:1 Petroleum Ether:EtOAc) to give compound compound 197A (5.5 g, 66.21% yield) as an oil. $^1$H NMR ($CDCl_3$, 400 MHz): δ 7.71-7.69 (m, 1H), 7.65-7.60 (m, 1H), 7.57-7.51 (m, 1H), 7.37-7.29 (m, 1H), 5.76 (d, J=3.2 Hz, 2H), 3.70-3.55 (m, 2H), 1.02-0.87 (m, 2H), 0.00 (d, J=3.2 Hz, 9H). MS (ESI) m/z $(M+H)^+$338.3.

To a mixture of compound 197A (2 g, 6.11 mmol), compound 4,4,4',4',5,5,5',5'-octamethyl-2,2'-bi(1,3,2-dioxaborolane) (1.86 g, 7.33 mmol), KOAc (2.4 g, 24.44 mmol), Pd (dppf) $Cl_2$ (894.3 mg, 1.22 mmol) in dioxane (80 mL) was heated at 80° C. for 12 hours under $N_2$ atmosphere. Compound 197B (crude) was obtained as a solution (15.8 mg/mL in dioxane).

To a mixture of compound 197B (461.6 mg, 1.23 mmol, 30 mL in dioxane), compound 163E (100 mg, 262.3 umol), Pd(dtbpf)$Cl_2$ (34.19 mg, 52.46 umol) and $K_3PO_4$ (111.4 mg, 524.6 umol) in $H_2O$ (2 mL) was degassed and purged with $N_2$ for 3 times, and then the mixture was stirred at 70° C. for 2 hours under $N_2$ atmosphere. The reaction solution was purified by preparatory-HPLC (basic condition) to give compound 197D (50 mg, 16.54% yield) as a brown solid. $^1$H NMR ($CDCl_3$, 400 MHz): δ 8.14-8.02 (m, 1H), 8.01-7.82 (m, 1H), 7.70-7.63 (m, 1H), 7.58 (t, J=7.6 Hz, 1H), 7.51 (d, J=8.4 Hz, 1H), 7.39-7.32 (m, 1H), 7.02-6.89 (m, 1H), 6.88-6.69 (m, 5H), 6.42 (br s, 1H), 5.70-5.48 (m, 2H), 5.34 (br s, 1H), 4.39-4.27 (m, 1H), 4.24-4.08 (m, 1H), 3.84 (s, 3H), 3.58 (t, J=8.0 Hz, 2H), 3.04-2.74 (m, 2H), 0.92-0.87 (m, 2H), −0.07 (s, 9H). MS (ESI) m/z $(M+H)^+$549.2.

A mixture of compound 197D (50 mg, 91.12 umol) in DCM (10 mL) was added DMP (116 mg, 273.4 umol) in one portion at 0° C. under $N_2$, and then the mixture was stirred at 0° C. for 1 hour under $N_2$ atmosphere. The mixture was quenched with saturated aqueous $NaHCO_3$ (15 mL) and saturated aqueous $Na_2S_2O_3$ (15 mL), and stirred for 20 min, then diluted with dichloromethane (100 mL). The mixture was stirred for 20 mins and washed with water (2×20 mL). The combined organic layers were dried over $Na_2SO_4$ and concentrated under reduced pressure to give the crude product. The residue was purified by preparatory-HPLC (basic condition) to give compound 197E (30 mg, 55.67% yield) as white solid. $^1$H NMR ($CDCl_3$, 400 MHz): δ 8.23 (s, 1H), 7.98 (d, J=6.8 Hz, 1H), 7.74 (d, J=8.8 Hz, 1H), 7.70-7.60 (m, 2H), 7.48-7.38 (m, 1H), 7.03 (t, J=7.2 Hz, 1H), 6.89-6.75 (m, 3H), 6.74-6.67 (m, 2H), 5.84-5.75 (m, 1H), 5.63 (d, J=11.6 Hz, 2H), 5.45 (d, J=11.2 Hz, 1H), 4.01-3.87 (m, 3H), 3.78-3.57 (m, 2H), 3.39-3.12 (m, 2H), 1.02-0.92 (m, 2H), 0.16-0.07 (m, 9H). MS (ESI) m/z $(M+H)^+$547.2.

A mixture of compound 197E (30 mg, 54.88 umol) in HCl/EtOAc (4 M, 1.50 mL) was stirred at 25° C. for 78 hours. The reaction mixture was concentrated under reduced pressure to give a residue, which was purified by preparatory-HPLC (basic condition) to afford compound 197 (1.6 mg, 6.68% yield) as a white solid. $^1$H NMR (400 MHz, $CDCl_3$): δ 10.35 (br s, 1H), 8.12 (s, 1H), 7.77 (br s, 1H), 7.61-7.50 (m, 3H), 7.34-7.28 (m, 1H), 7.10-7.04 (m, 1H), 6.98-6.90 (m, 2H), 6.84-6.68 (m, 3H), 5.62-5.42 (m, 2H), 3.83 (s, 3H), 3.29-3.19 (m, 1H), 3.08-2.97 (m, 1H). MS (ESI) m/z $(M+H)^+$417.2.

Example 103

N-(4-amino-3,4-dioxo-1-phenylbutan-2-yl)-1-methyl-3-(6-(trifluoromethyl)pyridin-2-yl)-1H-pyrazole-4-carboxamide (198)

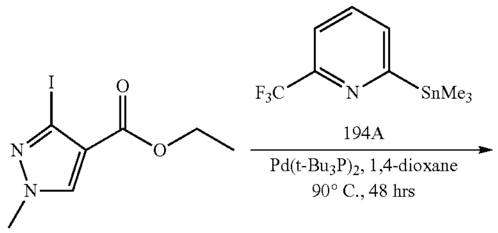

198A

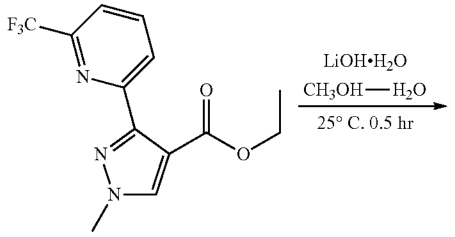

198B

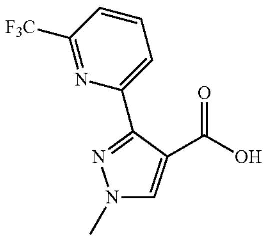

198C

A mixture of compound ethyl 3-iodo-1-methyl-H-pyrazole-4-carboxylate (200 mg, 714.13 umol) and compound 194A (1.91 g, 856.96 umol) in dioxane (3 mL) was added $Pd(t-Bu_3P)_2$ (110 mg, 214.24 umol) under nitrogen atmosphere. The mixture was stirred at 90° C. for 48 hours. The mixture was diluted with $CH_2Cl_2$ (30 mL), filtered to remove the precipitate and the filtrate was concentrated under reduced pressure to give a residue. The residue was purified by flash column chromatography (Petroleum Ether:Ethyl Acetate=10/1 to 5/1) to afford compound (175.00 mg, 77.93% yield) as brown solid. $^1H$ NMR (400 MHz, $CDCl_3$) δ 8.01-7.91 (m, 3H), 7.72-7.67 (m, 1H), 4.26-4.20 (m, 2H), 4.00 (s, 3H), 1.25-1.19 (s, 3H).

To a mixture of compound 198B (170 mg, 568.09 umol) in MeOH (8 mL) and $H_2O$ (4 mL) was added $LiOH.H_2O$ (191 mg, 4.54 mmol) in one portion and the mixture was stirred at 25° C. for 12 hours. The reaction mixture was concentrated under reduced pressure to remove MeOH. The residue was diluted with $H_2O$ (20 mL), adjusted to pH ~3 with 1N HCl, and then extracted with EtOAc (20 mL×3). The combined organic layers were washed with brine (30 mL), dried over anhydrous $Na_2SO_4$, filtered and concentrated under reduced pressure to give intermediate compound 198C (150 mg, 97.36% yield) as a brown solid. $^1H$ NMR (400 MHz, DMSO-$d_6$) δ 8.44 (s 1H), 8.25 (d, J=4 Hz, 1H), 8.00-7.98 (m, 2H), 3.95 (s, 3H).

Compound 198 (94.2 mg, 63.09% yield, white solid) was prepared as in Example 5 from the corresponding intermediate carboxylic acid, compound 198C. Compound 198: $^1H$ NMR (400 MHz, $CDCl_3$) δ 10.92 (d, J=6.80 Hz, 1H), 8.39 (d, J=8.40 Hz, 1H), 8.08 (s, 1H) 7.92-8.02 (m, 1H), 7.65 (d, J=8.00 Hz, 1H), 7.06-7.23 (m, 5H), 6.72 (s, 1H), 5.51 (br s, 1H), 5.31-5.43 (m, 1H), 3.93 (s, 3H), 3.38-3.49 (m, 1H), 2.96-3.11 (m, 1H). MS (ESI) m/z $(M+1)^+$446.1.

Example 104

(S)—N-(4-amino-3,4-dioxo-1-phenylbutan-2-yl)-3-methyl-1-(3'-methyl-[1,1'-biphenyl]-3-yl)-1H-pyrazole-5-carboxamide (199)

Compound 199 (35.0 mg, yield 53.6%, white solid) was prepared as in Example 61 from the corresponding starting materials, compound 103A and m-tolylboronic acid. Compound 199: $^1H$ NMR (DMSO-$d_6$, 400 MHz) δ 9.08 (d, J=7.7 Hz, 1H), 8.08-8.00 (m, 1H), 7.84 (br s, 1H), 7.60-7.52 (m, 2H), 7.45-7.37 (m, 3H), 7.36-7.30 (m, 1H), 7.28-7.25 (m, 3H), 7.23-7.16 (m, 3H), 7.12-7.06 (m, 1H), 6.60 (br s, 1H), 5.29 (br s, 1H), 3.22-3.14 (m, 1H), 2.86-2.76 (m, 1H), 2.35 (s, 3H), 2.28-2.22 (m, 3H). MS (ESI) m/z $(M+H)^+$467.2.

Example 105

(S)—N-(4-amino-3,4-dioxo-1-phenylbutan-2-yl)-1-(6-phenylpyridazin-3-yl)-1H-imidazole-5-carboxamide (200)

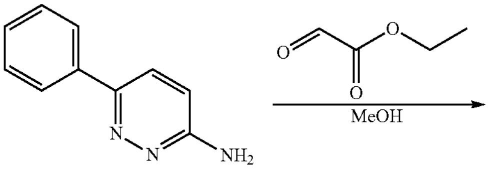

200A

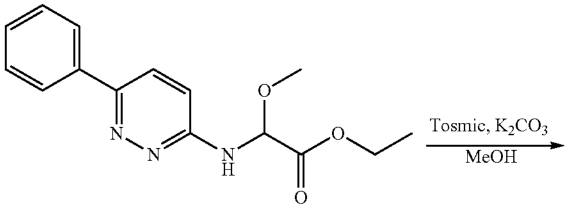

200B

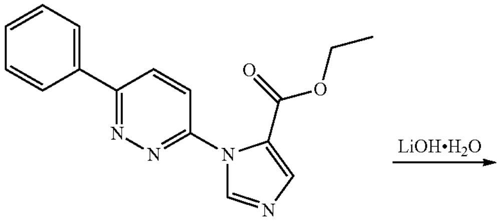

200C

-continued

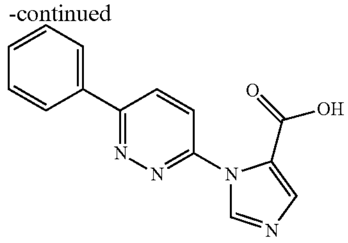

200D

To a mixture of 6-bromopyridazin-3-amine (10 g, 57 mmol) and phenylboronic acid (10.5 g, 86 mmol) in toluene (150 mL) and EtOH (150 mL) was added LiCl (7.3 g, 172.4 mmol). Then $Na_2CO_3$ (1M, 155 mL) was added, followed by $Pd(PPh_3)_2Cl_2$ (403 mg, 0.57 mmol). The mixture was heated to reflux for 16 h. The mixture was filtered through Celite. The filtrate was diluted with $H_2O$ (15 mL), extracted with ethyl acetate (15 mL×3). The combined organic layer was washed with brine (15 mL), dried over $MgSO_4$, filtered and concentrated. The residue was triturated with TBME/ethyl acetate (v/v=1/1, 50 mL). The cake was dried in vacuum to afford compound 2 (4.4 g, yield 44.7%) as off-white solid. $^1$H NMR (DMSO-$d_6$, 400 MHz) δ 7.94 (d, J=7.2 Hz, 2H), 7.79 (d, J=9.2 Hz, 1H), 7.46-7.42 (m, 2H), 7.38-7.36 (m, 1H), 6.86 (d, J=9.2 Hz, 2H), 6.52 (s, 2H). MS (ESI) m/z $(M+H)^+$172.0.

Ethyl 2-oxoacetate (26 mL, 128.50 mmol) was added to a solution of compound 200A (4.4 g, 25.7 mmol) in MeOH (100 mL). The mixture was heated to 65° C. and stirred for 15 h. The mixture was concentrated. The residue was purified by Flash Column Chromatography (Petroleum Ether/Ethyl Acetate=3/1) to afford compound 200B (5.5 g, yield 52%, 69.8% purity) as brown oil. MS (ESI) m/z $(M+H)^+$288.1.

$K_2CO_3$ (6.61 g, 47.85 mmol) was added to a solution of compound 200B (5.5 g, 19.14 mmol) and tosylmethyl isocyanide (5.04 g, 25.84 mmol) in EtOH (190 mL). The mixture was heated to 65° C. and stirred for 3 h. The mixture was concentrated in vacuum and the residue was treated with Ethyl Acetate (100 mL) and $H_2O$ (75 mL). The organic layer was separated and the aqueous layer was extracted with Ethyl Acetate (50 mL×2). The combined organic layer was washed with brine (100 mL), dried over $MgSO_4$, filtered and concentrated. The residue was purified by Flash Column Chromatography (Petroleum Ether/Ethyl Acetate=5/1 to 1/1) to afford (1.80 g, yield 30%) as yellow solid. $^1$H NMR ($CDCl_3$, 400 MHz) δ 8.22 (s, 1H), 8.12-8.10 (m, 2H), 8.01 (d, J=7.2 Hz, 1H), 7.94, (s, 1H), 7.76-7.74 (m, 1H), 7.56-7.54 (m, 3H), 4.29 (q, J=6.8 Hz, 2H), 1.33 (t, J=6.8 Hz, 3H). MS (ESI) m/z $(M+H)^+$295.0.

$LiOH.H_2O$ (114 mg, 2.72 mmol) was added to a solution of compound 200C (100 mg, 0.34 mmol) in MeOH (5 mL). Then $H_2O$ (0.5 mL) was added. The mixture was stirred at 25° C. for 3 h. The mixture was diluted with $H_2O$ (25 mL) and the volatile solvent was evaporated in vacuum. The residue was acidified to pH ~3 with 1N HCl. The mixture was extracted with Ethyl Acetate (25 mL×3). The combined organic layer was washed with brine (20 mL), dried over $MgSO_4$, filtered and concentrated to afford compound 200D (90 mg, yield 99.5%) as yellow solid, which was used for next step directly. $^1$H NMR (DMSO-$d_6$, 400 MHz) δ 8.50 (d, J=9.3 Hz, 1H), 8.38 (d, J=1.0 Hz, 1H), 8.24 (dd, J=1.9, 7.7 Hz, 2H), 8.13 (d, J=9.0 Hz, 1H), 7.85 (d, J=1.0 Hz, 1H), 7.66-7.55 (m, 3H).

Compound 200 (35 mg, yield 35.2%, white solid) was prepared as in Example 5 from the corresponding intermediate carboxylic acid, compound 200D. Hydrate was observed in $^1$H NMR. Compound 200: $^1$H NMR (DMSO-$d_6$, 400 MHz) δ 8.83 (br s, 1H), 8.34-8.25 (m, 2H), 8.19 (dd, J=1.8, 7.8 Hz, 2H), 7.81 (br s, 1H), 7.75 (s, 1H), 7.66-7.48 (m, 5H), 7.34-7.20 (m, 5H), 5.32-5.23 (m, 1H), 3.24 (dd, J=4.3, 14.1 Hz, 1H), 2.94 (dd, J=9.7, 13.9 Hz, 1H). MS (ESI) m/z $(M+H)^+$441.1.

Example 106

(S)—N-(4-(cyclopropylamino)-3,4-dioxo-1-phenylbutan-2-yl)-1-(6-phenylpyridazin-3-yl)-1H-imidazole-5-carboxamide (201)

Compound 201 (89 mg, yield 54.5%, yellow solid) was prepared as in Example 20 from the corresponding intermediate carboxylic acid, compound 200D. Hydrate was observed on $^1$H NMR. Compound 201: $^1$H NMR (DMSO-$d_6$, 400 MHz) δ 8.82 (br s, 0.8H), 8.51 (br s, 0.9H), 8.31-8.22 (m, 2.7H), 8.20-8.14 (m, 2.3H), 7.93 (s, 0.9H), 7.79-7.70 (m, 1.7H), 7.69-7.64 (m, 1.7H), 7.63-7.54 (m, 5.7H), 7.37 (br d, J=8.5 Hz, 0.9H), 7.31 (d, J=4.5 Hz, 3.6H), 7.28-7.17 (m, 5.2H), 5.35-5.28 (m, 1H), 4.42-4.35 (m, 0.9H), 3.23 (dd, J=4.0, 14.1 Hz, 0.7H), 3.07 (br s, 1.7H), 2.97-2.89 (m, 1.1H), 2.80-2.74 (m, 1.7H), 2.68-2.64 (m, 1.0H), 0.71-0.63 (m, 2.0H), 0.62-0.55 (m, 3.2H), 0.48 (br s, 1.6H). MS (ESI) m/z $(M+H)^+$481.1.

Example 107

(S)—N-(4-amino-3,4-dioxo-1-phenylbutan-2-yl)-3-methyl-1-(2'-methyl-[1,1'-biphenyl]-4-yl)-1H-pyrazole-5-carboxamide (202)

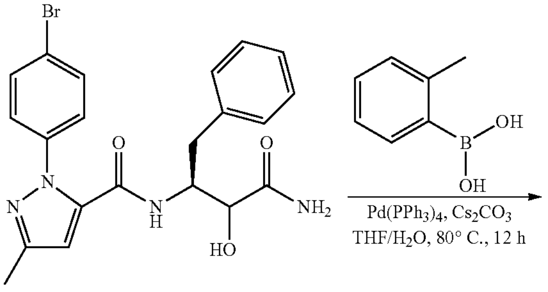

83D

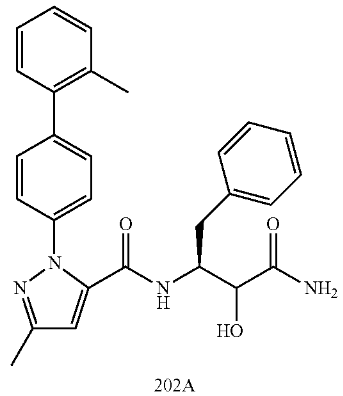

202A

To a solution of compound 83D (150 mg, 0.33 mmol) in THF (6 mL) and $H_2O$ (3 mL) was added $Cs_2CO_3$ (168 mg, 0.51 mmol) and o-tolylboronic acid (89 mg, 0.66 mmol), followed by $Pd(PPh_3)_4$ (38 mg, 0.033 mmol). Then the mixture was heated to 80° C. and stirred for 12 h. The reaction mixture was cooled to the room temperature and $H_2O$ (10 mL) was added to quenched the reaction and then the mixture was evaporated under reduced pressure. The water phase was extracted with ethyl acetate (10 mL×3). The combined organic layer was washed with $NaHCO_3$ (10 ml), $H_2O$ (10 mL), brine (10 mL), dried over $Na_2SO_4$, filtered, evaporated under reduced pressure. The crude product was triturated with isopropyl ether/acetonitrile (10/1, 5 mL) to afford compound 202A (50 mg, yield 32.5%) as yellow solid. $^1H$ NMR (DMSO-$d_6$, 400 MHz) δ 8.54 (br d, J=9.3 Hz, 1H), 8.20 (br d, J=9.7 Hz, 1H), 7.66-7.46 (m, 1H), 7.38 (br s, 1H), 7.35-7.19 (m, 12H), 7.14 (br d, J=8.4 Hz, 1H), 6.61-6.51 (m, 1H), 6.01-5.66 (m, 1H), 4.45 (br s, 1H), 4.04-3.90 (m, 1H), 3.00-2.62 (m, 2H), 2.37-2.17 (m, 6H).

To a solution of compound 202A (46 mg, 98.2 umol) in DCM (10 mL) was added DMP (125 mg, 294.5 umol) and the mixture was at 25° C. for 2 h. The reaction mixture was diluted with DCM (10 mL) and quenched with $NaHCO_3$/$Na_2S_2O_3$ (1/1, 20 mL), then the mixture was stirred for 0.25 h. The mixture was extracted with DCM (10 mL×2), the combined organic layer was washed with $NaHCO_3$ (10 mL×3) and brine (10 mL×3), dried over anhydrous $Na_2SO_4$, filtered, evaporated under reduced pressure. The crude product was purified by preparatory-HPLC (base) to afford 202 (30 mg, yield 60.65%) was obtained as white solid. $^1H$ NMR ($CDCl_3$, 400 MHz) δ 7.43-7.39 (m, 2H), 7.39-7.35 (m, 2H), 7.30-7.28 (m, 3H), 7.26-7.21 (m, 4H), 7.03 (dd, J=1.9, 7.6 Hz, 2H), 6.72 (br s, 1H), 6.52 (s, 1H), 6.37 (br d, J=7.5 Hz, 1H), 5.66-5.60 (m, 1H), 5.55 (br s, 1H), 3.38 (dd, J=5.4, 14.2 Hz, 1H), 3.16 (dd, J=7.3, 14.3 Hz, 1H), 2.36 (s, 3H), 2.29-2.27 (m, 3H). MS (ESI) m/z $(M+H)^+$467.1.

Example 108

(S)—N-(4-(cyclopropylamino)-3,4-dioxo-1-phenylbutan-2-yl)-3-methyl-1-(6-methyl-4-(trifluoromethyl)pyridin-2-yl)-1H-pyrazole-5-carboxamide (206)

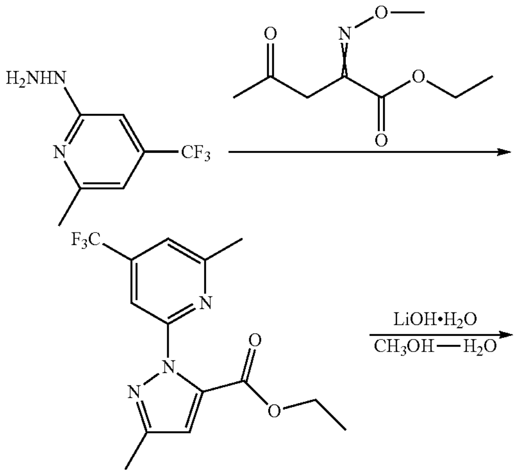

206A

-continued

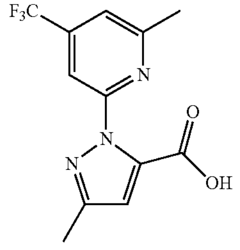

206B

To a solution of 2-hydrazinyl-6-methyl-4-(trifluoromethyl)pyridine (500 mg, 2.62 mmol) in $CH_3COOH$ (10 mL) was added ethyl 2-(methoxyimino)-4-oxopentanoate (490.4 mg, 2.62 mmol), then the mixture was stirred at 120° C. for 2 hours. The mixture was diluted with $CH_2Cl_2$ (100 mL) and washed by saturated sodium bicarbonate (30 mL×2) and saturated brine (30 mL×2), dried with anhydrous $Na_2SO_4$, filtered and concentrated in vacuum. The residue was purified by flash column chromatography ($SiO_2$, Petroleum Ether:Ethyl Acetate=10/1 to 3/1). Compound 206A (200.0 mg, 24.37% yield) was obtained as white solid. $^1H$ NMR (400 MHz, $CDCl_3$) δ 7.72 (s, 1H), 7.33 (s, 1H), 6.68 (s, 1H), 4.33-4.28 (m. 2H), 2.60 (s, 3H), 3.23 (s, 3H), 1.31-1.20 (m, 3H).

To a mixture of compound 206A (180.0 mg, 574.58 umol) in MeOH (6 mL) and $H_2O$ (3 mL) was added $LiOH.H_2O$ (96.4 mg, 2.30 mmol) in one portion and the mixture was stirred at 25° C. for 6 hours. The reaction mixture was concentrated under reduced pressure to remove MeOH. Then the mixture was diluted with $H_2O$ (10 mL) and the pH was adjusted to 3 with 1N HCl and then extracted with EtOAc (40 mL×3). The combined organic layers were washed with brine (30 mL), dried over anhydrous $Na_2SO_4$, filtered and concentrated under reduced pressure to give intermediate compound 206B (145.0 mg, 88.48% yield) as white solid. $^1H$ NMR (400 MHz, DMSO-$d_6$) δ 7.80 (s, 1H), 7.73 (s, 1H), 6.79 (d, J=4 Hz, 1H), 2.56 (s, 3H), 2.29 (s, 3H).

Compound 206 (52.0 mg, 52.16% yield, pale yellow solid) was prepared as in Example 41 from the corresponding intermediate carboxylic acid, compound 206B. Compound 206: $^1H$ NMR (400 MHz, $CDCl_3$) δ 8.65 (J=7.6 Hz, 1H), 7.86 (s, 1H), 7.22 (s, 1H), 7.18-7.16 (m, 3H), 7.04-7.03 (m, 2H), 6.88 (s, 1H), 6.70 (s, 1H), 5.77-5.72 (m, 1H), 3.46-3.41 (m, 1H), 3.35-3.30 (m, 1H), 2.83-2.79 (m, 1H), 2.34 (s, 3H), 2.32 (s, 3H), 0.91-0.86 (m, 2H), 0.63-0.60 (m, 2H). MS (ESI) m/z $(M+1)^+$500.2.

Example 109

(S)—N-(4-(cyclopropylamino)-3,4-dioxo-1-phenylbutan-2-yl)-3-methyl-1-(6-methyl-4-(trifluoromethyl)pyridin-2-yl)-1H-pyrazole-5-carboxamide (208)

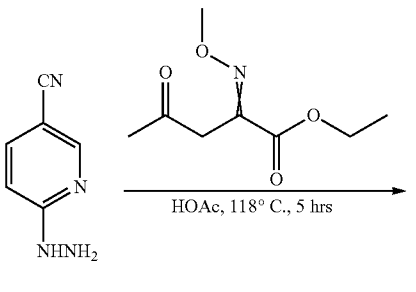

-continued

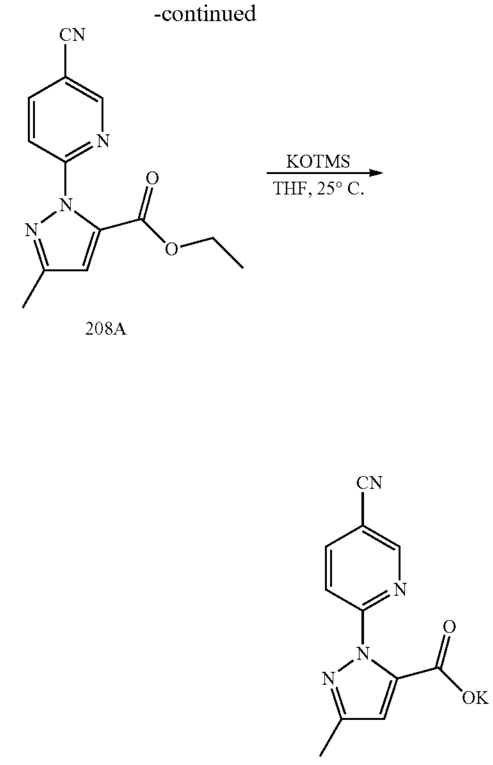

208A

208B

A mixture of ethyl 2-(methoxyimino)-4-oxopentanoate (558.2 mg, 2.98 mmol) and 6-hydrazinylnicotinonitrile (400 mg, 2.98 mmol) in AcOH (5 mL) was stirred at 118° C. for 5 hours. The reaction mixture was cooled to 25° C. and concentrated under reduced pressure to give a residue, which was diluted with $CH_2Cl_2$ (100 mL). The organic phase was washed with saturated aqueous $NaHCO_3$ (20 mL), dried over anhydrous $Na_2SO_4$, filtered and concentrated under reduced pressure to give a residue, which was purified by column chromatography ($SiO_2$, Petroleum ether/Ethyl acetate=1:0 to 5:1) to afford compound 208A (160 mg, 19.09% yield) as a white solid, but structure (proposed structure) could not be confirmed by N—H HMBC. $^1H$ NMR (400 MHz, $CDCl_3$): δ 8.66 (dd, J=0.8, 2.4 Hz, 1H), 8.07 (dd, J=2.4, 8.4 Hz, 1H), 7.88 (dd, J=0.8, 8.4 Hz, 1H), 6.67 (s, 1H), 4.35 (q, J=6.8 Hz, 2H), 2.37 (s, 3H), 1.32 (t, J=7.2 Hz, 3H). MS (ESI) m/z $(M+1)^+$257.1.

To a solution of compound 208A (100 mg, 390.23 umol) in THF (4 mL) was added KOTMS (100 mg, 780.46 umol), then the mixture was stirred at 25° C. for 0.3 hour. The mixture was diluted by petroleum ether (20 mL), the precipitate was filtered to afford the residue. The mixture was diluted by petroleum ether (20 mL), the precipitate was filtered to afford intermediate compound 208B (80 mg, 76.98% yield) as white solid.

Compound 208 (13.5 mg, 27.13% yield, white solid) was prepared as in Example 5 from the corresponding starting materials, compounds 208B and 12G. Compound 208: $^1H$ NMR (400 MHz, DMSO-$d_6$): δ 9.09 (d, J=7.2 Hz, 1H), 8.49 (d, J=1.6 Hz, 1H), 8.40-8.36 (m, 1H), 8.10 (br s, 1H), 7.86 (br s, 1H), 7.82 (d, J=8.4 Hz, 1H), 7.31-7.23 (m, 5H), 6.51 (s, 1H), 5.35-5.29 (m, 1H), 3.19-3.13 (m, 1H), 2.84-2.76 (m, 1H). MS (ESI) m/z $(M+1)^+$403.1.

Example 110

Compounds 209, 439-441, 443-444

(S)—N-(4-amino-3,4-dioxo-1-phenylbutan-2-yl)-3-methyl-1-(pyridin-4-yl)-1H-pyrazole-5-carboxamide (209)

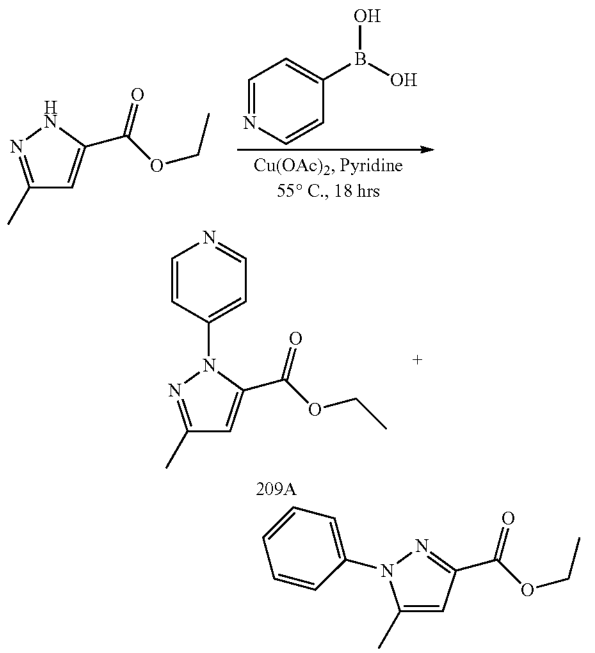

+

209A

209B

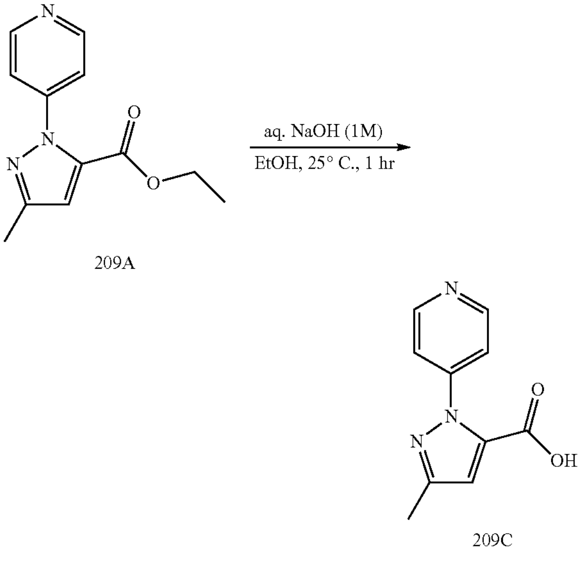

209A

209C

To a solution of ethyl 3-methyl-1H-pyrazole-5-carboxylate (3.0 g, 19.46 mmol), pyridin-4-ylboronic acid (5.98 g, 48.65 mmol) in Pyridine (40 mL) was added $Cu(OAc)_2$ (1.8 g, 9.73 mmol). The mixture was stirred at 55° C. for 18 hrs. The mixture was filtered and concentrated in vacuum. The residue was purified by flash silica gel chromatography (ISCO®; 120 g SepaFlash® Silica Flash Column, Eluent of 050% Ethyl acetate/Petroleum ether gradient @ 40 mL/min). Compound 209A (850 mg, 18.91% yield) was obtained as white solid. Compound 209B (850 mg, 18.91% yield) was obtained as white solid. Compound 209A (850 mg, 18.91% yield, white solid): $^1$H NMR (400 MHz, $CDCl_3$) δ 8.75-8.65 (m, 2H), 7.42 (d, J=6.0 Hz, 2H), 6.87 (s, 1H), 4.33-4.25 (m, 2H), 2.36 (s, 3H), 1.32-1.28 (m, 3H).

To a mixture of compound 209A (600 mg, 2.59 mmol) in EtOH (5 mL) was added aq. NaOH (1 M, 2.59 mL) in one portion and the mixture was stirred at 25° C. for 1 hour. The reaction mixture was concentrated under reduced pressure to remove EtOH. The residue was adjusted to pH ~3 with 1N HCl, and then extracted with EtOAc (200 mL×4). The combined organic layers were washed with brine (80 mL), dried over anhydrous $Na_2SO_4$, filtered and concentrated under reduced pressure to afford intermediate compound 209C (390 mg, 74.10% yield) as a white solid. $^1$H NMR (400 MHz, DMSO-$d_6$): δ 8.63 (br s, 2H), 7.50 (br d, J=5.2 Hz, 2H), 6.90 (s, 1H), 2.26 (s, 3H).

Compound 209 (27.1 mg, 25.46% yield, white solid) was prepared as in Example 5 from the corresponding intermediate carboxylic acid, compound 209C. Compound 209: $^1$H NMR (400 MHz, DMSO-$d_6$) δ 9.33 (d, J=7.8 Hz, 1H), 8.55-8.49 (m, 2H), 8.17 (s, 1H), 7.92 (s, 1H), 7.37-7.27 (m, 5H), 7.22-7.18 (m, 2H), 6.60 (s, 1H), 5.33 (s, 1H), 3.28-3.21 (m, 1H), 2.88-2.79 (m, 1H), 2.28 (s, 3H). MS (ESI) m/z $(M+H)^+$378.1.

N-(4-amino-3,4-dioxo-1-phenylbutan-2-yl)-3-methyl-1-(4-phenoxyphenyl)-1H-pyrazole-5-carboxamide (439)

Compound 439 (65 mg, yield: 61.4%, yellow solid) was prepared from ethyl 3-methyl-1H-pyrazole-5-carboxylate which was subjected to coupling with (4-phenoxyphenyl) boronic acid as in compound 209 followed by ester hydrolysis and coupling with intermediate 274D using procedures as in compound 12 to obtain compound 439. Compound 439: $^1$H NMR (400 MHz, DMSO-$d_6$) δ 9.08 (br d, J=7.3 Hz, 1H), 8.12 (br s, 1H), 7.87 (br s, 1H), 7.44 (br t, J=7.4 Hz, 2H), 7.31-7.13 (m, 8H), 7.06 (br d, J=7.9 Hz, 2H), 6.93 (br d, J=8.4 Hz, 2H), 6.57 (s, 1H), 5.26 (br s, 1H), 3.20 (br d, J=14.6 Hz, 1H), 2.81 (br t, J=12.3 Hz, 1H), 2.24 (s, 3H). MS (ESI) m/z $(M+H)^+$469.2.

N-(4-amino-3,4-dioxo-1-phenylbutan-2-yl)-3-methyl-1-(4-((tetrahydro-2H-pyran-4-yl)oxy)phenyl)-1H-pyrazole-5-carboxamide (440)

Compound 440 (90 mg, yield: 58%, white solid) was prepared from ethyl 1-(4-hydroxyphenyl)-3-methyl-1H-pyrazole-5-carboxylate which was subjected to mitsunobu coupling with tetrahydro-2H-pyran-4-ol followed by ester hydrolysis and coupling with intermediate 274D using procedures as in compound 12 to obtain compound 440. Compound 440: $^1$H NMR (400 MHz, DMSO-$d_6$) δ 9.03 (d, J=7.8 Hz, 1H), 8.11 (s, 1H), 7.87 (s, 1H), 7.35-7.23 (m, 5H), 7.07 (d, J=8.8 Hz, 2H), 6.92 (d, J=9.0 Hz, 2H), 6.53 (s, 1H), 5.27-5.14 (m, 1H), 4.59-4.54 (m, 1H), 3.89-3.82 (m, 2H), 3.49 (t, J=9.3 Hz, 2H), 3.19 (dd, J=3.1, 13.9 Hz, 1H), 2.81 (dd, J=10.8, 13.8 Hz, 1H), 2.23 (s, 3H), 1.97 (d, J=12.0 Hz, 2H), 1.58 (d, J=7.8 Hz, 2H). MS (ESI) m/z $(M+H)^+$477.2.

N-(4-amino-3,4-dioxo-1-phenylbutan-2-yl)-1-(4-(4-((diethylamino)methyl)phenoxy)phenyl)-3-methyl-1H-pyrazole-5-carboxamide hydrochloride (441)

Compound 441 (14 mg, yield: 26.21%, white solid) was prepared from ethyl 1-(4-hydroxyphenyl)-3-methyl-1H-pyrazole-5-carboxylate which was subjected to coupling with (4-((diethylamino)methyl)phenyl)boronic acid as in compound 209 followed by ester hydrolysis and coupling with intermediate 274D using procedures as in compound 12 to obtain compound 441. Compound 441: $^1$H NMR (400 MHz, DMSO-$d_6$) δ 11.55 (br. s, 1H), 7.77-7.71 (m, 2H), 7.37-7.15 (m, 8H), 7.12-7.06 (m, 2H), 6.99 (d, J=9.0 Hz, 2H), 6.57 (s, 2H), 6.13-5.96 (m, 1H), 4.72-4.63 (m, 1H), 4.23-4.13 (m, 2H), 3.27-3.18 (m, 1H), 3.13-2.92 (m, 5H), 2.28 (s, 3H), 1.34 (t, J=3.5, 7.3 Hz, 6H). MS (ESI) m/z $(M+H)^+$554.3.

N-(4-amino-3,4-dioxo-1-phenylbutan-2-yl)-1-(4-(2-(2-methoxyethoxy)ethoxy)phenyl)-3-methyl-1H-pyrazole-5-carboxamide (443)

Compound 443 (75 mg, yield: 61.3%, white solid) was prepared from ethyl 3-methyl-1H-pyrazole-5-carboxylate which was subjected to coupling with (4-(benzyloxy)phenyl)boronic acid as in compound 209 followed by hydrogenolysis to yield the phenolic derivative which was subjected to mitsunobu coupling with 2-(2-methoxyethoxy)ethan-1-ol followed by ester hydrolysis and coupling with intermediate 274D using procedures as in compound 12 to obtain compound 443. Compound 443: $^1$H NMR (400 MHz, DMSO-$d_6$) δ 9.02 (br d, J=7.8 Hz, 1H), 8.10 (s, 1H), 7.86 (s, 1H), 7.37-7.20 (m, 5H), 7.08 (br d, J=8.8 Hz, 2H), 6.89 (br d, J=9.0 Hz, 2H), 6.53 (s, 1H), 5.28-5.17 (m, 1H), 4.16-4.06 (m, 2H), 3.80-3.71 (m, 2H), 3.65-3.56 (m, 2H), 3.51-3.44 (m, 2H), 3.25 (s, 3H), 3.21-3.14 (m, 1H), 2.81 (br dd, J=10.7, 13.7 Hz, 1H), 2.23 (s, 3H). MS (ESI) m/z $(M+H)^+$ 495.2.

N-(4-amino-3,4-dioxo-1-phenylbutan-2-yl)-1-(3-(2-(2-methoxyethoxy)ethoxy)phenyl)-3-methyl-1H-pyrazole-5-carboxamide (444)

Compound 444 (60 mg, yield: 39.58%, white solid) was prepared from ethyl 3-methyl-1H-pyrazole-5-carboxylate which was subjected to coupling with (3-(benzyloxy)phenyl)boronic acid as in compound 209 followed by hydrogenolysis to yield the phenolic derivative which was subjected to mitsunobu coupling with 2-(2-methoxyethoxy)ethan-1-ol followed by ester hydrolysis and coupling with intermediate 274D using procedures as in compound 12 to obtain compound 444. Compound 444: $^1$H NMR (400 MHz, DMSO-$d_6$) δ 9.07 (d, J=7.3 Hz, 1H), 8.09 (s, 1H), 7.85 (s, 1H), 7.35-7.18 (m, 6H), 6.93-6.81 (m, 2H), 6.71 (d, J=8.2 Hz, 1H), 6.54 (s, 1H), 5.28 (s, 1H), 4.05 (s, 2H), 3.72 (s, 2H), 3.57 (d, J=4.2 Hz, 2H), 3.46 (d, J=4.2 Hz, 2H), 3.24 (s, 3H), 3.18 (s, 1H), 2.88-2.77 (m, 1H), 2.24 (s, 3H). MS (ESI) m/z $(M+H)^+$495.2.

Example 111

(S)—N-(4-amino-3,4-dioxo-1-phenylbutan-2-yl)-3-methyl-5-(3-phenyl-1H-pyrazol-1-yl)isoxazole-4-carboxamide (211)

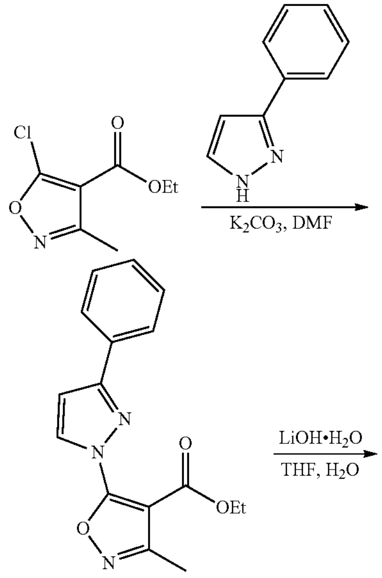

211A 211B

To a mixture of ethyl 5-chloro-3-methylisoxazole-4-carboxylate (400 mg, 2.1 mmol) and 3-phenyl-1H-pyrazole (365 mg, 2.5 mmol) in DMF (3 mL) was added $K_2CO_3$ (1.2 g, 8.4 mmol) in one portion. Then the mixture was stirred at 80° C. for 12 hours. Then $H_2O$ (9 mL) was added into the mixture, and the aqueous phase was extracted with EtOAc (15 mL×3), and the combined organic layer was concentrated to give a residue. The residue was purified by column chromatography ($SiO_2$, Petroleum ether:Ethyl acetate=300:1 to 30:1). Compound 211A (256 mg, yield: 40.8%, pale yellow solid): $^1$H NMR (400 MHz, $CDCl_3$) δ 8.62 (d, J=2.6 Hz, 1H), 7.93 (d, J=6.8 Hz, 2H), 7.49-7.37 (m, 3H), 6.86 (d, J=2.6 Hz, 1H), 4.37 (q, J=7.1 Hz, 2H), 2.53 (s, 3H), 1.40-1.34 (m, 2H), 1.41-1.33 (m, 1H).

To a solution of compound 211A (150 mg, 504.5 umol) in THF (2 mL) and $H_2O$ (500 uL) was added LiOH.$H_2O$ (31.8 mg, 756.8 umol) in one portion. Then the mixture was stirred at 25° C. for 3 hours. TLC (Petroleum ether:Ethyl acetate=1:1, $R_f$~0.45) indicated compound 211A was consumed completely and one new main spot formed. The pH of the aqueous phase was adjusted to around 5 by adding HCl (1M), and then the residue was concentrated on a rotary evaporator to give intermediate compound 211B (92 mg, yield: 67.7%) as a white solid. $^1$H NMR (400 MHz, DMSO-$d_6$) δ 9.39 (br s, 1H), 7.92 (d, J=7.0 Hz, 2H), 7.50-7.43 (m, 2H), 7.42-7.36 (m, 1H), 7.02 (s, 1H), 2.51-2.51 (m, 3H). MS (ESI) m/z $(M+H)^+$269.9.

Compound 211 (20 mg, yield: 44.7%, white solid) was prepared as in Example 5 from the corresponding intermediate carboxylic acid, compound 211B. Compound 211: $^1$H NMR (400 MHz, $CDCl_3$) δ 10.59 (br d, J=6.8 Hz, 1H), 8.19 (d, J=2.6 Hz, 1H), 7.74-7.65 (m, 2H), 7.45-7.38 (m, 3H), 7.12-7.05 (m, 3H), 7.03-6.98 (m, 2H), 6.89 (d, J=2.4 Hz, 1H), 6.72 (br s, 1H), 5.73-5.64 (m, 1H), 5.47 (br s, 1H), 3.38 (dd, J=5.3, 14.1 Hz, 1H), 3.06 (dd, J=8.4, 13.9 Hz, 1H), 2.56 (s, 3H). MS (ESI) m/z $(M+H)^+$444.1.

Example 112

(S)—N-(4-amino-3,4-dioxo-1-phenylbutan-2-yl)-3-methyl-1-(5-phenyloxazol-2-yl)-1H-pyrazole-5-carboxamide (212)

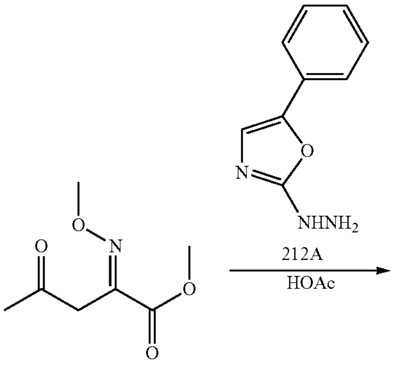

212B

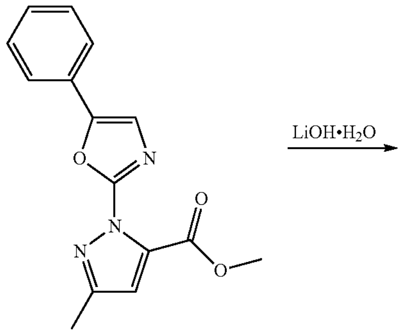

212C

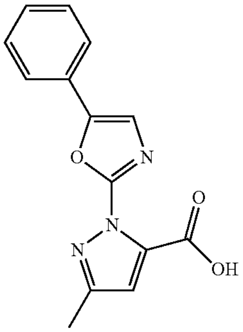

212D

A solution of 2-chloro-5-phenyloxazole (compound 114A) (560 mg, 3.12 mmol) and $NH_2NH_2.H_2O$ (468 mg, 9.35 mmol) in dioxane (10 mL) was heated to reflux for 3 hr. The mixture was concentrated to give compound 212A (610 mg, crude) as yellow solid. $^1$H NMR (400 MHz, DMSO-$d_6$) δ 8.27 (br s, 1H), 7.48 (br d, J=7.9 Hz, 1H), 7.36 (br t, J=7.7 Hz, 2H), 7.29 (s, 1H), 7.19 (br t, J=7.4 Hz, 2H), 4.53-4.12 (m, 1H), 4.35 (br s, 1H).

A solution of O-methylhydroxylamine (1.74 g, 20.8 mmol) in $H_2O$ (20 mL) was added dropwise to a solution of methyl 2,4-dioxopentanoate (5 g, 34.7 mmol) in ethanol (45 mL), $H_2O$ (25 mL), the mixture was stirred at 25° C. for 12 hrs. The organic solvent was removed under vacuum, the water layer was extracted with ethyl acetate (20 mL×2), the combined organic layer was washed with brine (20 mL), dried over $Na_2SO_4$, filtered and concentrated, the residue was purified by silica gel chromatography to give compound 212B (3.3 g, yield: 54.9%), as yellow oil. $^1H$ NMR (400 MHz, $CDCl_3$-d) δ 4.06 (s, 3H), 3.87 (s, 3H), 3.72 (s, 2H), 2.21 (s, 2H).

A mixture of compound 212B (360 mg, 2.05 mmol) and compound 212A (355 mg, 2.05 mmol) in dioxane (5 mL) was heated to 110° C. for 12 hrs. The mixture was concentrated, the residue was purified by TLC (Petroleum ether: Ethyl acetate=5:1) to give compound 212C (140 mg, yield: 24.1%) as yellow oil.

A mixture of compound 212C (140 mg, 494 umol) and $LiOH.H_2O$ (31.1 mg, 741 umol) in THF (5 mL), $H_2O$ (1 mL) was stirred at 25° C. for 2 hrs. TLC (Petroleum ether:Ethyl acetate=1:1, $R_f$~0) showed the reaction was complete, the organic solvent was removed under reduced pressure, the water layer extracted with ethyl acetate (3 mL), then the water layer was adjusted to pH ~3 with 1N HCl to give a precipitate, the solid was filtered and dried to give compound 212D (100 mg, yield: 75.2%) as yellow solid. $^1H$ NMR (400 MHz, DMSO-$d_6$) δ 7.85 (s, 1H), 7.74-7.69 (m, 2H), 7.48 (t, J=7.7 Hz, 2H), 7.44-7.37 (m, 1H), 6.91 (s, 1H), 2.28 (s, 3H).

Compound 212 (34 mg, yield: 52.6%, white solid) was prepared as in Example 5 from the corresponding intermediate carboxylic acid, compound 212D. Compound 212: $^1H$ NMR (400 MHz, DMSO-$d_6$) δ 9.17 (br d, J=7.5 Hz, 1H), 8.08 (br s, 1H), 7.83 (br s, 1H), 7.73 (s, 1H), 7.62 (br d, J=7.5 Hz, 2H), 7.48-7.41 (m, 2H), 7.40-7.34 (m, 1H), 7.25 (s, 4H), 7.19 (br d, J=4.0 Hz, 1H), 6.92 (s, 1H), 5.28 (br d, J=7.7 Hz, 1H), 3.16 (br dd, J=3.0, 14.0 Hz, 1H), 2.81 (br dd, J=10.6, 13.7 Hz, 1H), 2.27 (s, 3H). MS (ESI) m/z $(M+H)^+$444.1.

Example 113

(S)—N-(4-amino-3,4-dioxo-1-phenylbutan-2-yl)-3-chloro-5-phenylisothiazole-4-carboxamide (213)

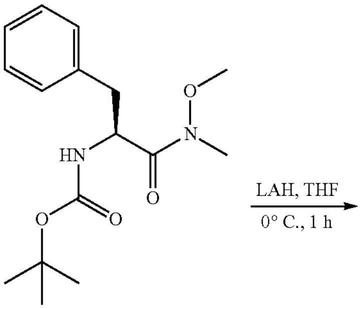

213A

-continued

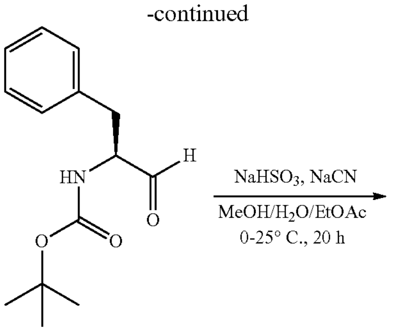

213B

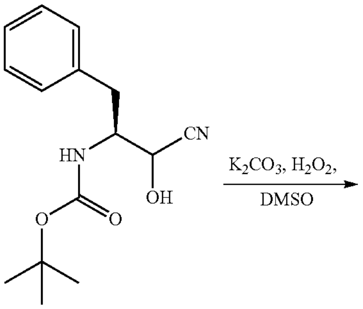

213C

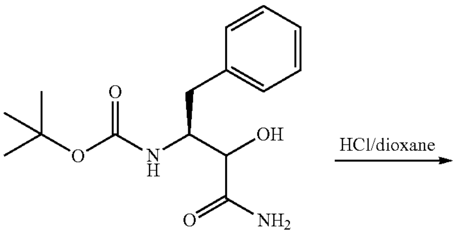

213D

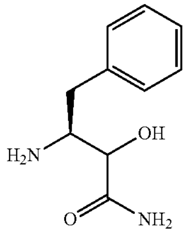

12G

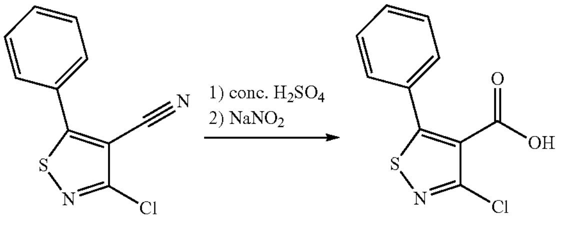

96B 213F

A mixture of (tert-butoxycarbonyl)-L-phenylalanine (50 g, 188.47 mmol), N-methoxymethanamine (20 g, 207.32 mmol, HCl), NMM (57 g, 565.41 mmol) and HOBT (25 g, 188.47 mmol) in $CHCl_3$ (700 mL) was degassed and purged with $N_2$ for 3 times at 0° C., then EDCI (54 g, 282.71 mmol) was added in portions. The mixture was stirred at 25° C. for 16 h under $N_2$ atmosphere. The reaction mixture was quenched by addition $H_2O$ (500 mL). The organic layer was separated, washed with 1N HCl (300 mL×2), saturated aqueous $NaHCO_3$ (300 mL×3), and brine (300 mL), dried over $Na_2SO_4$, filtered and concentrated under reduced pressure to give a residue. The residue was dissolved with petroleum ether (300 mL) and stirred for 2 h, filtered and concentrated under reduced pressure to give compound 213A (46 g, yield: 79.15%) as a colorless oil. $^1$H NMR (400 MHz, $CDCl_3$) δ 7.27-7.13 (m, 5H), 5.26-4.85 (m, 2H), 3.64 (s, 3H), 3.15 (br s, 3H), 3.04 (br dd, J=5.8, 13.6 Hz, 1H), 2.91-2.81 (m, 1H), 1.37 (s, 9H). MS (ESI) m/z $(M+23)^+$ 331.0.

To a solution of $LiAlH_4$ (5.32 g, 140.09 mmol) in THF (1 L) was added a solution of compound 213A (36 g, 116.74 mmol) in THF (500 mL) at 0° C. After addition, the reaction mixture was stirred for 1 h at 0° C. The reaction mixture was quenched by addition ethyl acetate (200 mL) and 1N HCl (200 mL), and then extracted with EtOAc (300 mL×3). The combined organic layers were washed with 1N HCl (300 mL×2), saturated aqueous $NaHCO_3$ (300 mL×3), and brine (300 mL), dried over $Na_2SO_4$, filtered and concentrated under reduced pressure to give compound 213B (25.3 g, yield: 86.93%) as a white solid. $^1$H NMR (400 MHz, $CDCl_3$) δ 9.61 (s, 1H), 7.33-7.24 (m, 3H), 7.16 (br d, J=7.1 Hz, 2H), 5.16-5.03 (m, 1H), 4.40 (q, J=6.6 Hz, 1H), 3.10 (br d, J=5.3 Hz, 2H), 1.42 (s, 9H).

To a solution of compound 213B (32 g, 128.36 mmol) in MeOH (250 mL) was added dropwise a solution of $NaHSO_3$ (13.5 g) in $H_2O$ (400 mL) at 0-5° C. After that, the reaction mixture was stirred at 28° C. for 5 h. NaCN (6.6 g, 134.78 mmol) in $H_2O$ (600 mL) was added into the reaction mixture followed by EtOAc (1.2 L). After that, the reaction mixture was stirred at 28° C. for 14 h. The mixture was separated and the organic layer was washed with brine (500 mL). The mixture was dried over $Na_2SO_4$ and concentrated to afford compound 213C (35 g, yield: 98.68%) as a light yellow gum. $^1$H NMR (400 MHz, DMSO-$d_6$) δ 7.26-7.14 (m, 6H), 6.82-6.70 (m, 1H), 4.57-4.28 (m, 1H), 3.88-3.72 (m, 1H), 3.01-2.58 (m, 2H), 1.31-1.22 (m, 9H). MS (ESI) m/z $(M-55)^+$220.9.

To a solution of compound 213C (35 g, 126.66 mmol) and $K_2CO_3$ (35 g, 253.32 mmol) in DMSO (400 mL) was added $H_2O_2$ (148 g, 4.35 mol) at 0° C. After addition, the reaction mixture was stirred at 25° C. for 2 h. The reaction mixture was filtered to give a residue. The residue was washed with saturated aqueous $Na_2S_2O_3$ (100 mL×2) and $H_2O$ (100 mL), dissolved with toluene (200 mL), concentrated under reduced pressure to remove $H_2O$. The filtrate was quenched with saturated aqueous $Na_2SO_3$ slowly at 0° C. The mixture was extracted with EtOAc (200 mL×3) and the combined extracts were washed with saturated aqueous $Na_2SO_3$ (300 mL×3), brine (200 mL). The organic layer was dried over $Na_2SO_4$, filtered and concentrated under reduced pressure to give compound 213D (37.5 g, yield: 88.51%) as a white solid. $^1$H NMR (400 MHz, DMSO-$d_6$) δ 7.29-7.16 (m, 7H), 6.64-6.09 (m, 1H), 5.74-5.61 (m, 1H), 4.09-3.67 (m, 2H), 2.86-2.56 (m, 2H), 1.36-1.22 (m, 9H). MS (ESI) m/z $(M-100+H)^+$194.9.

To a solution of compound 213D (41 g, 139.29 mmol) in EtOAc (300 mL) was added HCl/EtOAc (4M, 696.45 mL) at 0° C. After addition, the reaction mixture was stirred at 25° C. for 2 h. The reaction mixture was filtered to give a residue. The residue was washed with ethyl acetate (30 mL), concentrated under reduced pressure to give compound 12G (26 g, yield: 66.35%, HCl) as a brown solid. $^1$H NMR (400 MHz, DMSO-$d_6$) δ 8.42-7.95 (m, 3H), 7.60-7.43 (m, 2H), 7.37-7.12 (m, 6H), 4.38-3.79 (m, 2H), 3.73-3.62 (m, 1H), 3.03-2.73 (m, 2H). MS (ESI) m/z $(M+H)^+$195.1.

To a 100 mL round-bottom placed compound 96B (2.00 g, 9.06 mmol) was added $H_2SO_4$ (27.60 g, 281.40 mmol) dropwise, and stirred at 135° C. for 1 h. Then, the mixture was added $NaNO_2$ (907 mg, 13.14 mmol) in $H_2O$ (10 mL) dropwise at 0° C. The resulting solution was stirred at 50° C. for 0.5 h. The reaction mixture was diluted with $H_2O$ (50 mL) and extracted with ethyl acetate (50 mL×3). The combined organic layers were extracted with 10% NaOH (50 mL×2). The aqueous phase was adjusted to 3 with 1N HCl, extracted with ethyl acetate (50 mL×3). The combined organic layers were washed with brines (50 mL), dried $Na_2SO_4$, filtered and concentrated under reduced pressure to give a compound 213F (1.17 g, yield: 49.13%) as a yellow solid. $^1$H NMR (400 MHz, DMSO-$d_6$) δ 7.55 (d, J=1.3 Hz, 5H). MS (ESI) m/z $(M+H)^+$239.9.

Compound 213 (65 mg, yield: 40.23%, gray solid) was prepared as in Example 5 from the corresponding starting materials, compounds 12G and 213F. $^1$H NMR (400 MHz, DMSO-$d_6$) δ 9.35 (d, J=7.3 Hz, 1H), 8.19 (br s, 1H), 7.91 (br s, 1H), 7.51-7.32 (m, 5H), 7.27-7.17 (m, 5H), 5.71-5.21 (m, 1H), 3.17 (dd, J=3.4, 14.2 Hz, 1H), 2.72 (dd, J=10.4, 14.1 Hz, 1H). MS (ESI) m/z $(M+H)^+$414.0.

Example 114

(S)—N-(4-amino-3,4-dioxo-1-phenylbutan-2-yl)-3-methyl-1-(thiazol-2-yl)-1H-pyrazole-5-carboxamide (215)

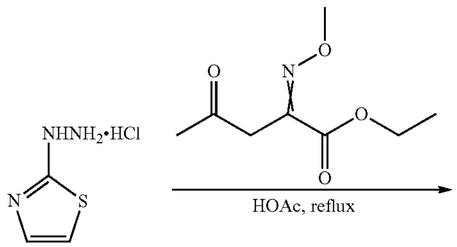

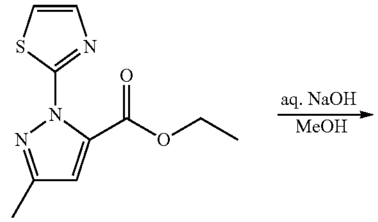

215A

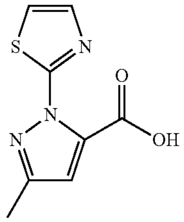

215B

A mixture of 2-hydrazinylthiazole hydrochloride (600 mg, 3.9 mmol, HCl salt) and ethyl 2-(methoxyimino)-4-oxopentanoate (815 mg, 4.35 mmol) in AcOH (15 mL) was stirred at 110° C. for 2 h. The reaction mixture was concentrated under reduced pressure to remove AcOH. The residue was treated with $H_2O$ (50 mL) and ethyl acetate (50 mL), and then the mixture was acidified with saturated aqueous $NaHCO_3$ till the aqueous phase pH ~7-8. The separated aqueous layer was extracted with ethyl acetate (80 mL×3), the combined organic layers were washed with saturated aqueous. NaCl (100 mL), dried over $Na_2SO_4$, filtered under reduced pressure to give crude product, which was purified by Flash Column Chromatography (petroleum ether:ethyl acetate=19) to afford compound 215A (138 mg, yield 12.6%) as white solid. Compound 215A: $^1$H NMR (DMSO-$d_6$, 400 MHz) δ 7.71-7.69 (m, 1H), 7.66 (d, J=3.5 Hz, 1H), 6.87 (s, 1H), 4.23 (q, J=7.1 Hz, 2H), 2.26 (s, 3H), 1.20-1.15 (m, 3H). MS (ESI) m/z $(M+H)^+$237.9.

To a mixture of compound 215A (130 mg, 0.55 mmol) in MeOH (10 mL) was added NaOH (2M, 1.4 mL) in one portion at 25° C. After stirred at 25° C. for 1.5 h, the reaction mixture was concentrated under reduced pressure to remove MeOH. The residue was added $H_2O$ (10 mL) and extracted with ethyl acetate (10 mL), the separated aqueous phase was acidified with 1M HCl till pH ~5-6. The solid was separated and filtered under reduced pressure to afford compound 215B (70 mg, crude) as white solid. Compound 215B: $^1$H NMR ($CDCl_3$, 400 MHz) δ 7.56 (d, J=3.7 Hz, 1H), 7.21-7.17 (m, 2H), 2.37 (s, 3H).

Compound 215 (10 mg, yield 53.7%, white solid) was prepared as in Example 5 from the corresponding intermediate carboxylic acid, compound 215B. Compound 215: $^1$H NMR ($CDCl_3$, 400 MHz) δ 11.76 (s, 1H), 7.27-7.18 (m, 5H), 7.17-7.12 (m, 1H), 7.10-7.00 (m, 2H), 6.78 (s, 1H), 5.83-5.74 (m, 1H), 5.50 (s, 1H), 3.48-3.40 (m, 1H), 3.28-3.18 (m, 1H), 2.32 (s, 3H). MS (ESI) m/z $(M+H)^+$384.0.

Example 115

(S)—N-(4-amino-3,4-dioxo-1-phenylbutan-2-yl)-5-methyl-1-(thiazol-2-yl)-1H-pyrazole-3-carboxamide (219)

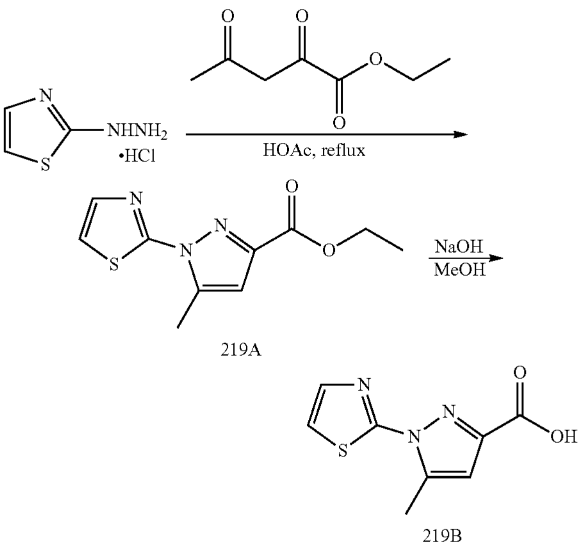

219A

219B

To a solution of 2-hydrazinylthiazole hydrochloride (700 mg, 4.39 mmol, HCl salt) in $CH_3COOH$ (15 mL) was added ethyl 2,4-dioxopentanoate (632 uL, 4.48 mmol) drop wise, then the mixture was heated to 120° C. and stirred for 2 h. Remove the solvent under reduced pressure, the residue was dissolve in ethyl acetate (5 mL) and treated with $NaHCO_3$ until pH ~8. The organic layer was collected and evaporated under reduced pressure. The residue was purified by Flash Column Chromatography (Petroleum Ether/Ethyl Acetate=1/0 to 10/1) to afford compound 219A (160 mg, yield 15.4%) as white solid. Compound 219A: $^1$H NMR ($CDCl_3$, 400 MHz) δ 7.60 (d, J=3.5 Hz, 1H), 7.18 (d, J=3.5 Hz, 1H), 6.70 (d, J=0.9 Hz, 1H), 4.42 (q, J=7.1 Hz, 2H), 2.74 (d, J=0.9 Hz, 3H), 1.42 (t, J=7.1 Hz, 3H).

To a solution of compound 219A (160 mg, 674.31 umol) in MeOH (10 mL) was added NaOH (2M, 2.00 mL) drop-wise and then the mixture was stirred at 25° C. for 2 h. The reaction mixture was diluted with $H_2O$ (5 mL), evaporated under reduced pressure and then the water phase was extracted with MBTE (5 mL). The water phase (acidified with HCl, pH ~3) was extracted with Ethyl Acetate (10 mL×3), then the organic (Ethyl Acetate) was collected, washed with saturate brine, dried over anhydrous $Na_2SO_4$ and filtered, concentrated under reduced pressure. Compound 219B (110 mg, yield 78%, white solid): $^1$H NMR (DMSO-$d_6$, 400 MHz) δ 7.72 (d, J=3.5 Hz, 1H), 7.64 (d, J=3.5 Hz, 1H), 6.77 (d, J=0.7 Hz, 1H), 2.67 (s, 3H).

Compound 219 (15 mg, yield 31.8%, white solid) was prepared as in Example 5 from the corresponding intermediate carboxylic acid, compound 219B. Compound 219: $^1$H NMR (DMSO-$d_6$, 400 MHz) δ 7.58 (d, J=3.5 Hz, 1H), 7.37-7.26 (m, 3H), 7.26-7.24 (m, 1H), 7.22-7.15 (m, 3H), 6.78 (br s, 1H), 6.65 (s, 1H), 5.73-5.64 (m, 1H), 5.58 (br s, 1H), 3.43 (dd, J=5.4, 14.0 Hz, 1H), 3.26 (dd, J=6.9, 14.2 Hz, 1H), 2.71 (s, 3H). MS (ESI) m/z $(M+H)^+$384.1.

Example 116

(2S,4R)—N—((S)-4-amino-3,4-dioxo-1-phenylbutan-2-yl)-4-(benzyloxy)-1-phenylpyrrolidine-2-carboxamide (220)

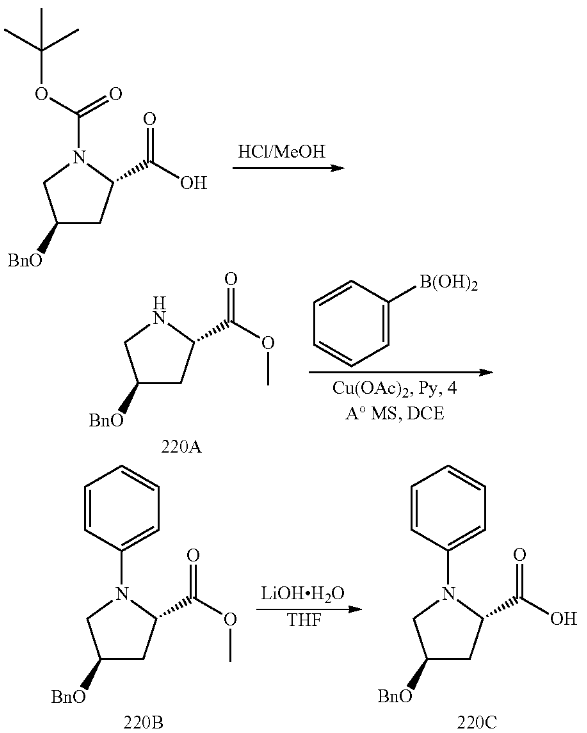

220A

220B

220C

A mixture of (2S,4R)-4-(benzyloxy)-1-(tert-butoxycarbonyl)pyrrolidine-2-carboxylic acid (500 mg, 1.56 mmol) in MeOH (3 mL), HCl/MeOH (15 mL) was stirred at 20° C. for 12 hours. LCMS showed starting material was consumed completely and one main peak with desired MS was detected. The reaction mixture was diluted with aqueous $NaHCO_3$, adjusted the pH ~7, and extracted with DCM (30 mL×2). The combined organic layers were dried over $Na_2SO_4$, filtered and concentrated under reduced pressure to give a residue. Compound 220A (340 mg, crude, yellow oil): $^1$H NMR (400 MHz, $CDCl_3$) δ 7.37-7.20 (m, 5H), 4.52-4.41 (m, 2H), 4.12 (br s, 1H), 4.00 (br t, J=7.6 Hz, 1H), 3.77-3.62 (m, 3H), 3.11 (br s, 2H), 2.66 (br s, 1H), 2.29 (br dd, J=7.8, 13.1 Hz, 1H), 1.98 (td, J=6.6, 13.4 Hz, 1H). MS (ESI) m/z $(M+H)^+$236.1.

A mixture of compound 220A (240 mg, 1.02 mmol), phenylboronic acid (249 mg, 2.04 mmol), $Cu(OAc)_2$ (278 mg, 1.53 mmol), pyridine (161 mg, 2.04 mmol) and 4A° MS (400 mg) in DCE (20 mL) was degassed and purged with 02 for 3 times, and then the mixture was stirred at 60° C. for 12 hours under 02 atmosphere. The reaction mixture was filtered and concentrated under reduced pressure to give a residue. The residue was purified by column chromatography ($SiO_2$, Petroleum ether:Ethyl acetate=50:1 to 10:1). Compound 220B (130 mg, yellow oil): $^1$H NMR (400 MHz, $CDCl_3$) δ 7.36-7.16 (m, 5H), 7.16-7.06 (m, 2H), 6.68-6.57 (m, 1H), 6.42 (d, J=8.1 Hz, 2H), 4.45 (s, 2H), 4.39-4.25 (m, 2H), 3.77-3.67 (m, 1H), 3.66-3.56 (m, 3H), 3.34 (dd, J=4.4, 9.5 Hz, 1H), 2.42-2.28 (m, 1H), 2.28-2.15 (m, 1H). MS (ESI) m/z $(M+H)^+$312.0.

A mixture of compound 220B (130 mg, 418 umol), $LiOH.H_2O$ (26.3 mg, 626 umol) in THF (5 mL), $H_2O$ (2 mL) was stirred at 20° C. for 12 hours. The reaction mixture was added aqueous HCl to adjust the pH ~5. And then the mixture was filtered, and the filter cake was dried by freeze dryer. Compound 220C (130 mg, crude, white solid: $^1$H NMR (400 MHz, DMSO-$d_6$) δ 7.36-7.15 (m, 6H), 7.13-6.98 (m, 2H), 6.57-6.47 (m, 1H), 6.40 (br d, J=7.9 Hz, 2H), 4.48-4.40 (m, 2H), 4.28 (br s, 1H), 4.15-4.05 (m, 1H), 3.29-3.26 (m, 1H), 3.27-3.17 (m, 1H), 2.33-2.22 (m, 1H), 2.21-2.09 (m, 1H). MS (ESI) m/z $(M+H)^+$298.2.

Compound 220 (18.6 mg, yield: 70.3%, brown solid) was prepared as in Example 12 from the corresponding intermediate carboxylic acid, compound 220C. Compound 220: $^1$H NMR (400 MHz, $CDCl_3$) δ 7.33-7.07 (m, 11H), 6.93 (br s, 2H), 6.84-6.70 (m, 2H), 6.59 (br s, 1H), 6.49 (br d, J=8.4 Hz, 2H), 5.35 (br s, 1H), 5.30-5.13 (m, 1H), 4.50-4.29 (m, 2H), 4.01 (br dd, J=4.2, 9.0 Hz, 1H), 3.95-3.85 (m, 1H), 3.62 (dd, J=5.8, 8.9 Hz, 1H), 3.30 (br dd, J=5.0, 14.0 Hz, 1H), 3.17 (dd, J=6.4, 9.0 Hz, 1H), 2.80 (dd, J=9.0, 13.9 Hz, 1H), 2.31-2.17 (m, 1H), 2.16-2.03 (m, 1H). MS (ESI) m/z $(M+H)^+$472.2.

Example 117

(S)—N-(4-amino-3,4-dioxo-1-phenylbutan-2-yl)-1-phenyl-1H-imidazole-2-carboxamide (221)

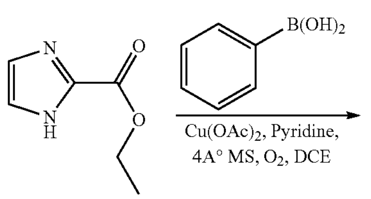

-continued

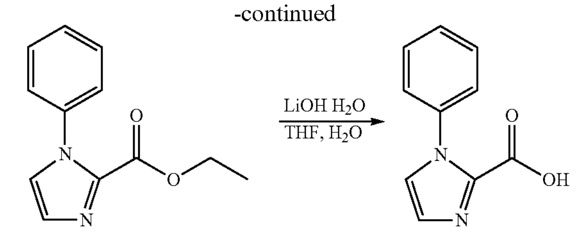

221A 221B

To a mixture of ethyl 1H-imidazole-2-carboxylate (5 g, 35.7 mmol) and phenylboronic acid (8.7 g, 71.4 mmol) in DCE (150 mL) was added $Cu(OAc)_2$ (7.13 g, 39.25 mmol), pyridine (5.64 g, 71.36 mmol, 5.76 mL), 4A° MS (3 g). The mixture was stirred at 60° C. for 16 hours under 02. The reaction mixture was filtered and the filtrate was concentrated. The crude product was purified by silica gel chromatography eluted with Petroleum ether:Ethyl acetate=10:1, 4:1 to give compound 221A (3 g, 13.9 mmol, yield: 38.9%) as a yellow solid. Compound 221A: $^1$H NMR (400 MHz, $CDCl_3$-d) δ 7.43-7.39 (m, 3H), 7.27-7.23 (m, 2H), 7.22-7.19 (m, 1H), 7.11 (d, J=1.0 Hz, 1H), 4.22 (q, J=7.2 Hz, 2H), 1.24 (t, J=7.2 Hz, 3H).

To a mixture of compound 221A (300 mg, 1.39 mmol) in THF (3 mL) and $H_2O$ (1 mL) was added $LiOH.H_2O$ (52 mg, 1.25 mmol). The mixture was stirred at 25° C. for 12 hours. The residue was extracted with ethyl acetate (5 mL×2). The mixture was adjusted to pH ~5 with aqueous HCl (1M) and concentrated by lyophilization to give intermediate compound 221B (550 mg, crude) as a white solid.

Compound 221 (17.1 mg, yield: 30.9%, yellow solid) was prepared as in Example 5 from the corresponding intermediate carboxylic acid, compound 221B.

Compound 221: $^1$H NMR (400 MHz, $CDCl_3$) δ 7.76 (br d, J=7.9 Hz, 1H), 7.35 (br d, J=2.6 Hz, 3H), 7.24-7.16 (m, 5H), 7.12 (br d, J=7.1 Hz, 2H), 7.08 (s, 1H), 7.04 (s, 1H), 6.67 (br s, 1H), 5.60-5.47 (m, 2H), 3.32 (dd, J=4.9, 13.9 Hz, 1H), 3.08 (dd, J=7.4, 14.0 Hz, 1H). MS (ESI) m/z $(M+H)^+$ 363.1.

Example 118

(S)—N-(4-amino-3,4-dioxo-1-phenylbutan-2-yl)-5-methyl-2-phenylthiophene-3-carboxamide (222)

N-(4-amino-3,4-dioxo-1-phenylbutan-2-yl)-2-(2H-indazol-2-yl)-5-methylthiophene-3-carboxamide (428), and N-(4-amino-3,4-dioxo-1-phenylbutan-2-yl)-2-(1H-benzo[d]imidazol-2-yl)-5-methylthiophene-3-carboxamide (429)

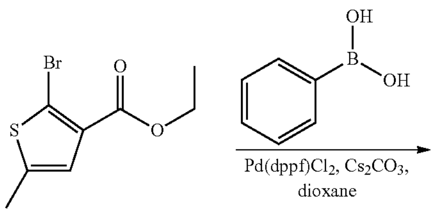

222A

-continued

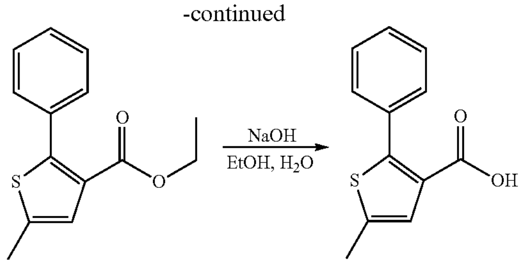

222B

222C

A mixture of ethyl 2-amino-5-methylthiophene-3-carboxylate (9 g, 48.6 mmol) and $CuBr_2$ (13 g, 58.3 mmol) in MeCN (150 mL) was stirred at 0° C.-5° C. t-BuONO (5.5 g, 53.5 mmol) was added dropwise. The reaction mixture was stirred for 0.5 hour at 0-5° C. and 2 hours at 20° C. The reaction mixture was diluted with EtOAc (400 mL), washed with water (100 mL) and brine (100 mL), dried over $MgSO_4$, filtered, and concentrated in vacuo. The residue was purified by column chromatography ($SiO_2$, Petroleum ether:Ethyl acetate=100:1) to give compound 222A (2 g, yield: 16.5%) as yellow oil. Compound 222A: $^1H$ NMR (400 MHz, $CDCl_3$-d) δ 7.01 (s, 1H), 4.30 (q, J=7.1 Hz, 2H), 2.38 (s, 3H), 1.40-1.29 (m, 3H).

To a mixture of compound 222A (400 mg, 1.61 mmol) and phenylboronic acid (393 mg, 3.22 mmol), $Cs_2CO_3$ (1.05 g, 3.22 mmol) in dioxane (20 mL) and $H_2O$ (2 mL) was added Pd(dppf)$Cl_2$ (118 mg, 161 umol) under $N_2$. The mixture was stirred at 110° C. for 12 hours under $N_2$. The reaction mixture was filtered and the filter was concentrated. The residue was purified by preparatory-TLC ($SiO_2$, Petroleum ether:Ethyl acetate=5:1) to give compound 222B (350 mg, yield: 88.3%) as a white solid. Compound 222B: $^1H$ NMR (400 MHz, $CDCl_3$) δ 7.48 (br s, 2H), 7.38 (br s, 3H), 7.19 (br s, 1H), 4.19 (q, J=6.9 Hz, 2H), 2.50 (br s, 3H), 1.23-1.15 (m, 3H).

To a mixture of compound 222B (350 mg, 1.42 mmol) in EtOH (10 mL) and $H_2O$ (5 mL) was added NaOH (142 mg, 3.55 mmol). The mixture was stirred at 80° C. for 3 hours. The mixture was concentrated to remove solvent and adjusted to pH ~5 with aqueous HCl (1M). The mixture was filtered and the solid was washed with $H_2O$ (3 mL) to give intermediate compound 222C (250 mg, yield: 81.0%) as a white solid. Compound 222C: $^1H$ NMR (400 MHz, DMSO-$d_6$) δ 12.47 (br s, 1H), 7.43-7.38 (m, 2H), 7.37-7.32 (m, 3H), 7.10 (d, J=0.9 Hz, 1H), 2.41 (s, 3H).

Compound 222 (15.7 mg, yield: 29.6%, white solid) was prepared as in Example 12 from the corresponding intermediate carboxylic acid, compound 222C. Compound 222: $^1H$ NMR (400 MHz, $CDCl_3$) δ 7.36-7.30 (m, 4H), 7.19 (s, 1H), 7.13-7.07 (m, 3H), 6.97 (s, 1H), 6.71-6.60 (m, 3H), 5.89 (br d, J=5.3 Hz, 1H), 5.49-5.34 (m, 2H), 3.10 (dd, J=5.0, 14.0 Hz, 1H), 2.81 (dd, J=7.9, 13.9 Hz, 1H), 2.37 (s, 3H). MS (ESI) m/z $(M+H)^+$393.1.

Compound 428 (44.7 mg, yield: 40.5%, white solid) was prepared using intermediate 222A to synthesize the intermediate carboxylic acid, 2-(2H-indazol-2-yl)-5-methylthiophene-3-carboxylic acid which was converted to compound 428 using the procedures as for compound 12. Compound 428: $^1H$ NMR (400 MHz, $CDCl_3$) δ 9.17 (br d, J=5.6 Hz, 1H), 8.25 (s, 1H), 7.70 (br d, J=8.3 Hz, 1H), 7.61 (br d, J=8.7 Hz, 1H), 7.34 (br t, J=7.5 Hz, 1H), 7.21-7.13 (m, 2H), 7.00 (br s, 3H), 6.85 (br s, 2H), 6.69 (br s, 1H), 5.69-5.58 (m, 1H), 5.43 (br s, 1H), 3.27 (br dd, J=4.8, 14.0 Hz, 1H), 2.95 (br dd, J=7.3, 14.1 Hz, 1H), 2.48 (s, 3H). MS (ESI) m/z $(M+H)^+$433.1.

Compound 429 (31.6 mg, yield: 35.7%, yellow solid) was prepared using intermediate 222A to synthesize the intermediate carboxylic acid, 5-methyl-2-(1-((2-(trimethylsilyl)ethoxy)methyl)-1H-benzo[d]imidazol-2-yl)thiophene-3-carboxylic acid which was converted to compound 429 using the procedures as for compound 12. Compound 429: $^1H$ NMR (400 MHz, $CDCl_3$) δ 12.80 (br s, 1H), 10.05 (br d, J=6.8 Hz, 1H), 8.18 (br s, 1H), 7.85 (br s, 1H), 7.66-7.57 (m, 2H), 7.32-7.19 (m, 7H), 7.17-7.11 (m, 1H), 5.44 (br s, 1H), 3.27 (br s, 1H), 3.03-2.93 (m, 1H). MS (ESI) m/z $(M+H)^+$433.1.

Example 119

(S)—N-(4-amino-3,4-dioxo-1-phenylbutan-2-yl)-4-methyl-1-phenyl-1H-pyrazole-5-carboxamide (223)

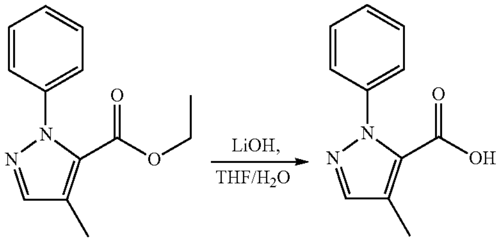

223A

223C

To a mixture of ethyl 4-methyl-1H-pyrazole-5-carboxylate (2.00 g, 12.97 mmol), phenylboronic acid (2.37 g, 19.45 mmol), Py (1.13 g, 14.27 mmol, 1.2 mL) in DCM (40.00 mL) was added 4A° MS (10.00 g)(activated 4A° MS) and $Cu(OAc)_2$ (2.59 g, 14.27 mmol), the mixture was stirred at 40° C. for 63 h. The reaction mixture was filtered, the filtrate was concentrated in vacuo. The residue was purified by flash silica gel chromatography (PE:EA=1:0 to 5:1) to give the compound 223A (725 mg, yield: 24.3%) was obtained as a colorless oil. Compound 223A: $^1H$ NMR (400 MHz, DMSO-$d_6$) δ 8.44 (s, 1H), 7.83 (d, J=7.7 Hz, 2H), 7.52 (t, J=7.9 Hz, 2H), 7.43-7.32 (m, 1H), 4.31 (q, J=7.1 Hz, 2H), 2.27 (s, 3H), 1.32 (t, J=7.1 Hz, 3H).

To a solution of compound 223A (720 mg, 3.13 mmol) in THF (20.00 mL) was added LiOH.$H_2O$ (700 mg, 16.68 mmol) in $H_2O$ (6.00 mL). The reaction was stirred at 25° C. for 27 h and then a solution of NaOH (626 mg, 15.65 mmol) in $H_2O$ (5.00 mL) and MeOH (4.00 mL) was added in the mixture. The mixture was stirred at 25° C. for 3.5 h. The reaction mixture was diluted with $H_2O$ (25 mL) and extracted with MTBE (15 mL). The aqueous layers were adjusted pH ~3 by addition 1N HCl, and then the aqueous layer was extracted with EA (20 mL×3). The combine organic layer was washed with brine (20 mL), dried over $Na_2SO_4$, filtered and concentrated under reduced pressure to give the compound 223C (526 mg, yield: 83.1%) was obtained as a white solid. Compound 223C: $^1H$ NMR (400 MHz, DMSO-$d_6$) δ 7.63 (s, 1H), 7.51-7.28 (m, 5H), 2.25 (s, 3H).

Compound 223 (34 mg, yield: 68.3%, white solid) was prepared as in Example 12 from the corresponding intermediate carboxylic acid, compound 223C. Compound 223: $^1H$ NMR (400 MHz, DMSO-$d_6$) δ 9.18 (d, J=7.8 Hz, 1H), 8.21

(s, 1H), 7.94 (s, 1H), 7.54 (s, 1H), 7.37-7.22 (m, 10H), 5.46-5.36 (m, 1H), 3.26 (br dd, J=3.0, 13.8 Hz, 1H), 2.78 (dd, J=11.2, 13.9 Hz, 1H), 2.00-1.93 (m, 3H).

Example 120

Compounds 224-225

224A

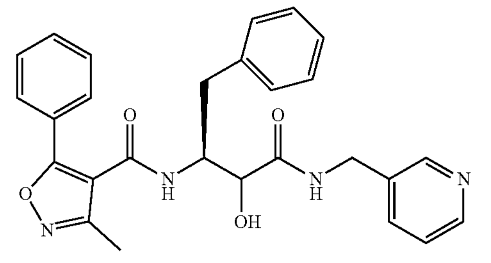

225A

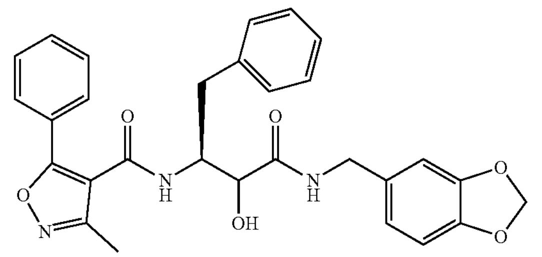

(S)—N-(3,4-dioxo-1-phenyl-4-((pyridin-3-ylmethyl)amino)butan-2-yl)-3-methyl-5-phenylisoxazole-4-carboxamide (224)

(S)—N-(4-((benzo[d][1,3]dioxol-5-ylmethyl)amino)-3,4-dioxo-1-phenylbutan-2-yl)-3-methyl-5-phenylisoxazole-4-carboxamide (225)

To a solution of compound 101E (350.0 mg, 920.11 umol) in DMF (10 mL) was added 3-pyridylmethanamine (119.4 mg, 1.10 mmol, 110 uL), DIEA (0.5 mL), HOBt (124.33 mg, 920.11 umol) and EDCI (211.66 mg, 1.10 mmol). After stirred at 25° C. for 48 h, the mixture was added HBTU (418.7 mg, 1.10 mmol) and DIEA (0.5 mL), and then stirred at 25° C. for 12 h. The mixture was diluted with $H_2O$ (100 mL), extracted with EA (30 mL), washed with HCl (1M, 30 mL), saturated $NaHCO_3$ (aq, 30 mL), brine (30 mL), dried over $Na_2SO_4$ and concentrated. The residue was purified by column chromatography ($SiO_2$, Petroleum ether/Ethyl acetate=5/1 to 0:1) to give compound 224A.

Compound 224A (60.0 mg, yield 13.9%, white solid): $^1H$ NMR (400 MHz, DMSO-$d_6$) δ 8.67-8.50 (m, 1H), 8.48-8.45 (m, 1H), 8.42-8.37 (m, 1H), 8.30-8.24 (m, 1H), 7.73-7.33 (m, 6H), 7.31-7.09 (m, 6H), 6.14-5.86 (m, 1H), 4.69-4.55 (m, 1H), 4.36-4.14 (m, 2H), 4.08-4.01 (m, 1H), 2.97-2.87 (m, 1H), 2.77-2.66 (m, 1H), 2.08-1.96 (m, 3H). MS (ESI) m/z $(M+H)^+$471.2.

Compound 225A (130.0 mg, 27.5% yield, white solid) was synthesized as shown above for 224A from the corresponding amine. Compound 225A: $^1H$ NMR (400 MHz, DMSO-$d_6$) δ 8.35-8.28 (m, 1H), 8.26-8.21 (m, 1H), 7.57-7.51 (m, 2H), 7.48-7.42 (m, 1H), 7.41-7.35 (m, 2H), 7.29-7.12 (m, 5H), 6.89-6.79 (m, 1H), 6.79-6.68 (m, 2H), 5.94-5.88 (m, 2H), 5.87-5.81 (m, 1H), 4.66-4.57 (m, 1H), 4.23-4.09 (m, 2H), 4.04-3.99 (m, 1H), 4.04-3.99 (m, 1H), 2.95-2.86 (m, 1H), 2.78-2.66 (m, 1H), 2.07-1.98 (m, 3H). MS (ESI) m/z $(M+H)^+$514.2.

To a solution of compound 225A (120.0 mg, 233.67 umol) in DMSO (10 mL) and DCM (1 mL) was added DMP (297.3 mg, 701.01 umol). After stirred at 25° C. for 1 hour, the mixture was quenched with 10% $Na_2S_2O_3$ (aqueous):saturated aqueous $NaHCO_3$ (1:1, 50 mL), the organic layer was washed with brine (50 mL×3). The combined organic layers were dried over $Na_2SO_4$ and concentrated. The crude product was triturated with $CH_3CN$ (5 mL) and filtered to obtain compound 225 (62.0 mg, yield 51.9%) as yellow solid. Compound 225: $^1H$ NMR (400 MHz, DMSO-$d_6$) δ 9.41-9.32 (m, 1H), 9.10 (d, J=7.6 Hz, 1H), 7.66-7.62 (m, 2H), 7.53-7.48 (m, 1H), 7.46-7.40 (m, 2H), 7.33-7.23 (m, 5H), 6.89-6.83 (m, 2H), 6.79-6.76 (m, 1H), 5.98 (s, 2H), 5.54-5.47 (m, 1H), 4.27 (d, J=6.4 Hz, 2H), 3.30-3.23 (m, 1H), 2.83-2.74 (m, 1H), 2.09-2.06 (m, 3H). MS(ESI) m/z $(M+H)^+$ 512.2.

Compound 224 was synthesized from the corresponding intermediate compound 224A as shown above for compound 225. Compound 224 (25.0 mg, 50.2% yield) has been obtained as white solid. $^1H$ NMR (400 MHz, DMSO-$d_6$) δ 9.53-9.45 (m, 1H), 9.11 (d, J=7.6 Hz, 1H), 8.54 (s, 1H), 8.49-8.46 (m, 1H), 7.72-7.67 (m, 1H), 7.67-7.62 (m, 2H), 7.54-7.48 (m, 1H), 7.46-7.40 (m, 2H), 7.38-7.33 (m, 1H), 7.32-7.23 (m, 5H), 5.54-5.47 (m, 1H), 4.40 (d, J=6.3 Hz, 2H), 3.30-3.23 (m, 1H), 2.83-2.75 (m, 1H), 2.09-2.05 (m, 3H). MS(ESI) m/z $(M+H)^+$469.1.

Example 121

(S)—N-(4-amino-3,4-dioxo-1-phenylbutan-2-yl)-2-ethyl-4-phenyloxazole-5-carboxamide (226)

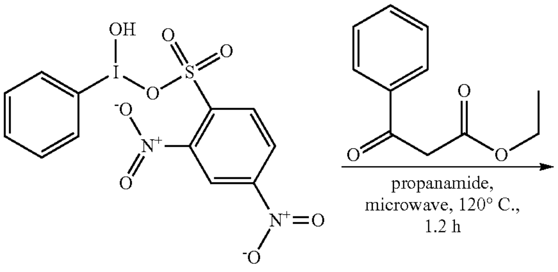

226A

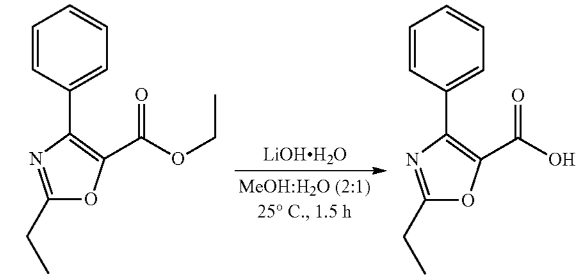

226B

226C

To a mixture of iodobenzene (5 g, 24.51 mmol) and 2,4-dinitrobenzenesulfonic acid (7.83 g, 29.41 mmol, $H_2O$) in $CHCl_3$ (20 mL), was added m-CPBA (4.23 g, 24.51 mmol). The mixture was stirred for 2 hours at 25° C. under an $N_2$ atmosphere. After the reaction, MTBE (20 mL) was added to the reaction mixture, and the resulting mixture was filtered and the solid was washed with MTBE (30 mL) and compound 226A (8.9 g, 77.6% yield) was obtained as a white solid. Compound 226A: $^1H$ NMR ($CDCl_3$, 400 MHz): δ 9.76 (br s, 1H), 8.57 (d, J=2.4 Hz, 1H), 8.43-8.40 (m, 1H), 8.23 (d, J=7.6 Hz, 2H), 8.10 (d, J=8.4 Hz, 1H), 7.75-7.69 (m, 1H), 7.66-7.59 (m, 2H).

Ethyl 3-oxo-3-phenylpropanoate (1.3 g, 6.76 mmol) and compound 226A (4.12 g, 8.79 mmol) in $CH_3CN$ (50 mL) were stirred at 80° C. for 1 h, and propanamide (5.93 g, 81.1 mmol) was added to the mixture, then the mixture was stirred at 120° C. for 0.2 hour under microwave irradiation. After being cooled to 25° C., the suspension was diluted with saturated $NaHCO_3$ solution (30 mL), extracted with EtOAc (100 mL×2), dried over $Na_2SO_4$, filtered, and concentrated in vacuo. The residue was purified by column chromatography ($SiO_2$, Petroleum ether/Ethyl acetate=10/1) to obtain compound 226B (200 mg, 11.22% yield) as white solid. Compound 226B: $^1H$ NMR ($CDCl_3$, 400 MHz): δ 8.03-7.96 (m, 2H), 7.46-7.35 (m, 3H), 4.36 (q, J=7.2 Hz, 2H), 2.88 (q, J=7.6 Hz, 2H), 1.40 (t, J=7.6 Hz, 3H), 1.35 (t, J=7.2 Hz, 3H).

Compound 226C (170 mg, 93.71% yield, yellow solid) was prepared as in Example 51 from the corresponding intermediate compound 226B. Compound 226C: $^1H$ NMR ($CDCl_3$, 400 MHz): δ 7.99-7.97 (m, 2H), 7.47-7.35 (m, 3H), 2.83 (q, J=7.6 Hz, 2H), 1.27 (t, J=7.6 Hz, 3H). MS (ESI) m/z $(M+H)^+$217.9.

Compound 226 (59.7 mg, 58.17% yield, white solid) was prepared as in Example 5 from the corresponding carboxylic acid, compound 226C. Compound 226: $^1H$ NMR ($CDCl_3$, 400 MHz): δ 8.12-8.04 (m, 2H), 7.45-7.35 (m, 3H), 7.32-7.23 (m, 3H), 7.13 (d, J=6.4 Hz, 2H), 6.81-6.68 (m, 2H), 5.74-5.59 (m, 2H), 3.46-3.41 (m, 1H), 3.26-3.21 (m, 1H), 2.91-2.80 (m, 2H), 1.40 (t, J=7.6 Hz, 3H). MS (ESI) m/z $(M+H)^+$392.1.

Example 122

Compounds 268-269

(S)—N-(4-amino-3,4-dioxo-1-phenylbutan-2-yl)-1-methyl-4-phenyl-1H-imidazole-5-carboxamide (268)

(S)—N-(4-amino-3,4-dioxo-1-phenylbutan-2-yl)-1-methyl-5-phenyl-1H-imidazole-4-carboxamide (269)

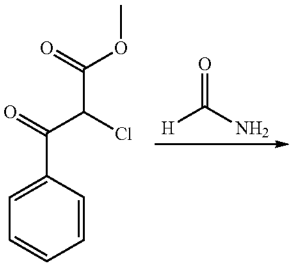

268A

-continued

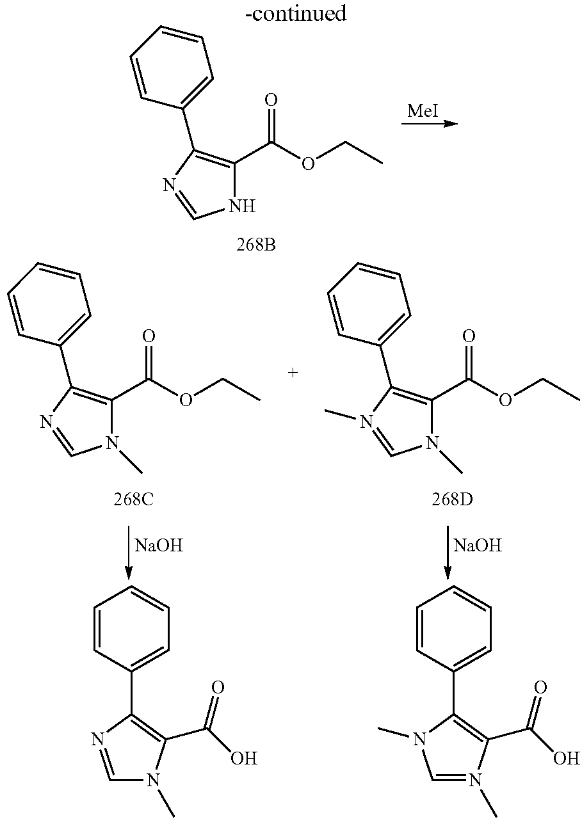

268B 268C 268D 268E 269A

Sulfuryl chloride (33.7 g, 250 mmol) was added drop wise to ethyl 3-oxo-3-phenylpropanoate (40 g, 208 mmol) in $CHCl_3$ (200 mL) at 0° C. The mixture was warmed to 25° C. for 30 min, and then heated to 80° C. for 3.5 h. TLC (Petroleum ether:Ethyl acetate=10:1, $R_f$~0.45) showed the reaction was complete. LCMS showed desired MS after cooling to room temperature, the reaction mixture was diluted with chloroform (40 mL), washed with $NaHCO_3$ (aqueous; 40 mL×2), water (40 mL) and then brine (30 mL) successively. The organic phase was dried over $Na_2SO_4$, filtered and evaporated to give the crude product compound 268A (48 g, crude), as yellow oil. Compound 268A: $^1H$ NMR (400 MHz, $CDCl_3$-d) δ 8.10-7.96 (m, 2H), 7.73-7.58 (m, 1H), 7.57-7.39 (m, 2H), 5.62 (s, 1H), 4.39-4.25 (m, 2H), 1.32-1.13 (m, 3H).

A solution of compound 268A (20 g, 88.2 mmol), formamide (39.7 g, 882 mmol) and $H_2O$ (3.18 g, 176 mmol) was heated to 180° C. for 3.5 h. After cooling, the mixture was added water (100 mL) and extracted with DCM (50 mL×3), the organic phase give a precipitate, the solid was filtered and dried to give compound 268B (1.45 g, yield: 7.6%), as off white solid. Compound 268B: $^1H$ NMR (400 MHz, DMSO-$d_6$) δ 13.26-12.66 (m, 1H), 7.96-7.78 (m, 1H), 7.81 (s, 1H), 7.63 (br d, J=7.2 Hz, 1H), 7.53-7.26 (m, 3H), 4.33-4.09 (m, 2H), 1.33-1.13 (m, 3H).

To a solution of NaH (277 mg, 6.94 mmol, 60% purity) in DMF (5 mL) was added compound 268B (1.25 g, 5.78 mmol) in portions and stirred for 30 min, then $CH_3I$ (903 mg, 6.36 mmol) was added, the mixture was stirred at 15° C. for 2 h. The mixture was quenched with water (15 mL) and extracted with ethyl acetate (20 mL×3), the organic phases were dried over $Na_2SO_4$, filtered and concentrated, the residue was purified by prep-HPLC (neutral) to give compounds 268C and 268D. Compound 268C (430 mg, yield: 64.7%, yellow solid): $^1H$ NMR (400 MHz, $CDCl_3$-d) δ 7.67 (br d, J=7.1 Hz, 2H), 7.57 (s, 1H), 7.43-7.30 (m, 3H), 4.25 (q, J=7.1 Hz, 2H), 3.93 (s, 3H), 1.22 (t, J=7.2 Hz, 3H).

Compound 268D (380 mg, yield: 57.1%, yellow solid): $^1H$ NMR (400 MHz, $CDCl_3$-d) δ 7.54 (s, 1H), 7.52-7.44 (m, 3H), 7.41-7.34 (m, 2H), 4.24 (q, J=7.1 Hz, 2H), 3.50 (s, 3H), 1.25 (t, J=7.2 Hz, 3H).

A mixture of compound 268C (200 mg, 869 umol) and NaOH (69.5 mg, 1.74 mmol) in THF (5 mL), $H_2O$ (1 mL) was stirred at 15° C. for 12 h. TLC (ethyl acetate, $R_f$~0) showed the reaction was complete, the organic solvent was removed under vacuum, the water layer was adjusted to pH ~5 with 1N HCl to give a precipitate, the solid was filtered and dried to give compound 268E (120 mg, yield: 68.3%) as white solid. Compound 268E: $^1H$ NMR (400 MHz, DMSO-$d_6$) δ 12.90 (br s, 1H), 7.86 (s, 1H), 7.62 (br d, J=7.1 Hz, 2H), 7.38-7.21 (m, 3H), 3.80 (s, 3H).

Compound 268 (40.2 mg, yield: 27.2%, white solid) was prepared as in Example 5 from the corresponding intermediate carboxylic acid, compound 268E. Compound 268: $^1H$ NMR (400 MHz, DMSO-$d_6$) δ 8.96 (d, J=7.5 Hz, 1H), 8.19 (s, 1H), 7.92 (s, 1H), 7.66 (s, 1H), 7.55 (d, J=6.8 Hz, 2H), 7.31-7.18 (m, 8H), 5.52 (ddd, J=3.5, 7.4, 10.5 Hz, 1H), 3.40 (s, 3H), 3.21 (dd, J=3.5, 14.1 Hz, 1H), 2.75 (dd, J=10.6, 14.1 Hz, 1H). MS (ESI) m/z $(M+H)^+$377.1.

Following the procedure used for intermediate compound 268E and compound 268, intermediate compound 269A and compound 269 were prepared. Compound 269A (130 mg, yield: 74%, white solid): $^1H$ NMR (400 MHz, DMSO-$d_6$) δ 7.76 (s, 1H), 7.47-7.30 (m, 5H), 3.40 (s, 3H). Compound 269 (32.4 mg, yield: 37.5%, white solid): $^1H$ NMR (400 MHz, $CDCl_3$-d) δ 7.67 (br d, J=7.2 Hz, 1H), 7.51-7.43 (m, 4H), 7.42-7.35 (m, 2H), 7.32-7.29 (m, 1H), 7.28 (s, 1H), 7.26-7.23 (m, 1H), 7.22-7.18 (m, 2H), 6.72 (br s, 1H), 5.64 (dt, J=5.3, 7.5 Hz, 1H), 5.44 (br s, 1H), 3.51 (s, 3H), 3.41 (dd, J=5.3, 14.1 Hz, 1H), 3.20 (dd, J=7.4, 14.0 Hz, 1H). MS (ESI) m/z $(M+H)^+$377.1.

Example 123

Compounds 227-228

(S)—N-(4-amino-3,4-dioxo-1-phenylbutan-2-yl)-1-(4-(ethoxymethyl)phenyl)-3-methyl-1H-pyrazole-5-carboxamide (227)

(S)—N-(4-amino-3,4-dioxo-1-phenylbutan-2-yl)-1-(4-((benzyloxy)methyl)phenyl)-3-methyl-1H-pyrazole-5-carboxamide (228)

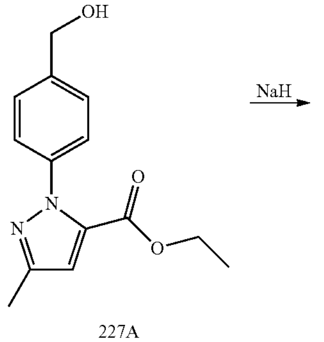

227A

-continued

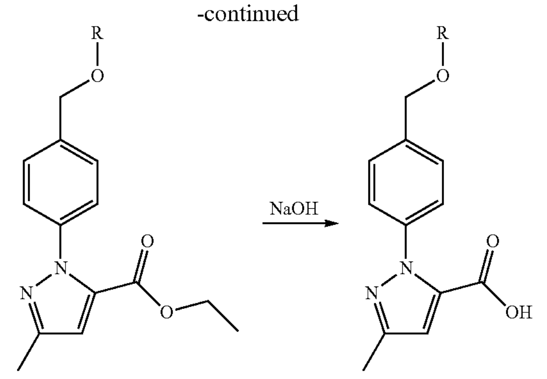

227B: R = Et
228B: R = $CH_2Ph$

227C: R = Et
228C: R = $CH_2Ph$

To a solution of ethyl 3-methyl-1H-pyrazole-5-carboxylate (2 g, 12.97 mmol), [4-(hydroxymethyl)phenyl]boronic acid (3.94 g, 25.94 mmol) in NMP (200 mL) was added pyridine (2.05 g, 25.94 mmol, 2.09 mL), $Cu(OAc)_2$ (3.53 g, 19.45 mmol), 4A° MS (20 g, 12.97 mmol). After stirred at 25° C. for 24 h, the mixture was filtered. The filtrate was washed with $H_2O$ (500 mL), extracted with ethyl acetate (50 mL×3). The organic phase was washed brine (500 mL), dried over $Na_2SO_4$, concentrated to give a residue. The residue was purified by column chromatography ($SiO_2$, Petroleum ether/Ethyl acetate=5/1 to 3/1) to obtain intermediate Compound 227A (1 g, yield: 29.62%) as white solid. Compound 227A: $^1H$ NMR (400 MHz, $CDCl_3$) δ 7.41-7.34 (m, 4H), 6.80 (s, 1H), 4.71 (s, 2H), 4.22 (q, J=7.1 Hz, 2H), 2.35 (s, 3H), 1.24 (t, J=7.2 Hz, 3H). MS (ESI) m/z $(M+H)^+$ 261.0.

To a solution of compound 227A (350 mg, 1.34 mmol) and benzyl bromide (458 mg, 2.68 mmol, 318 uL) in DMF (10 mL) was added NaH (160 mg, 4.02 mmol, 60% purity) at 0° C. The mixture was stirred at 25° C. for 1 h. The mixture was quenched with $NH_4Cl$ (1 mL), diluted with $H_2O$ (30 mL), extracted with ethyl acetate (20 mL×3), the organic phase was combined, washed with NaCl (50 mL×2), dried over $Na_2SO_4$, and concentrated to give a residue. The residue was purified by column chromatography ($SiO_2$, Petroleum ether/Ethyl acetate=10/1 to 5:1) to obtain compound 228B (350 mg, yield: 64.85%, yellow oil). Compound 228B: $^1H$ NMR (400 MHz, $CDCl_3$) δ 7.47-7.28 (m, 9H), 6.87-6.78 (m, 1H), 4.66-4.60 (m, 2H), 4.56 (s, 2H), 4.23 (q, J=7.1 Hz, 2H), 2.36 (s, 3H), 1.24 (t, J=7.2 Hz, 3H). MS (ESI) m/z $(M+H)^+$351.0.

To a solution of compound 228B (350 mg, 998.83 umol) in MeOH (10 mL) and $H_2O$ (10 mL) was added NaOH (119 mg, 3.00 mmol). The mixture was stirred at 25° C. for 3 h. The reaction mixture was concentrated and added 20 mL of water, the mixture was extracted with MTBE (10 mL×2), the aqueous layer was acidified by 1N HCl to pH ~2-3 at 0° C., and extracted with EtOAc (20 mL×2), the organic phase was dried over $Na_2SO_4$, concentrated to give a residue. Compound 228C (270 mg, yield: 83.86%, white solid): $^1H$ NMR (400 MHz, DMSO-$d_6$) δ 13.58-12.95 (m, 1H), 7.45-7.24 (m, 9H), 6.79 (s, 1H), 4.57 (d, J=6.8 Hz, 4H), 2.23 (s, 3H). MS (ESI) m/z $(M+H)^+$323.0.

Compound 228 (37.6 mg, yield: 51.78%, white solid) was prepared as in Example 5 from the corresponding intermediate carboxylic acid, compound 228C. Compound 228: $^1H$ NMR (400 MHz, DMSO-$d_6$) δ 9.09 (d, J=7.9 Hz, 1H), 8.11 (s, 1H), 7.86 (s, 1H), 7.39-7.21 (m, 12H), 7.14 (d, J=8.2 Hz, 2H), 6.58-6.50 (m, 1H), 5.33-5.17 (m, 1H), 4.53 (d, J=6.0 Hz, 4H), 3.18 (dd, J=3.2, 13.6 Hz, 1H), 2.80 (dd, J=10.8, 13.7 Hz, 1H), 2.23 (s, 3H). MS (ESI) m/z $(M+H)^+$497.2.

Intermediate compound 227C (300 mg, yield: 95.04%) was obtained as a white solid using the same procedure as for compound 228C. Compound 227C: $^1$H NMR (400 MHz, DMSO-$d_6$) δ 13.20 (br s, 1H), 7.47-7.24 (m, 4H), 6.79 (s, 1H), 4.49 (s, 2H), 3.50 (q, J=7.0 Hz, 2H), 2.23 (s, 3H), 1.16 (t, J=7.1 Hz, 3H). MS (ESI) m/z $(M+H)^+$261.0.

Compound 227 (31 mg, yield: 54.75%, light yellow solid) was prepared as in Example 5 from the corresponding intermediate carboxylic acid, compound 227C. Compound 227: $^1$H NMR (400 MHz, DMSO-$d_6$) δ 9.07 (d, J=7.7 Hz, 1H), 8.11 (d, J=3.1 Hz, 1H), 7.87-7.84 (m, 1H), 7.31-7.24 (m, 7H), 7.13 (br d, J=8.2 Hz, 2H), 6.53 (s, 1H), 5.25 (t, J=7.4 Hz, 1H), 4.44 (s, 2H), 3.52-3.44 (m, 2H), 3.19 (dd, J=3.0, 13.6 Hz, 1H), 2.84-2.76 (m, 1H), 2.23 (s, 3H), 1.15 (t, J=6.9 Hz, 3H). MS (ESI) m/z $(M+H)^+$435.1.

Example 124

(S)—N-(4-amino-3,4-dioxo-1-phenylbutan-2-yl)-1-(3-(ethoxymethyl)phenyl)-3-methyl-1H-pyrazole-5-carboxamide (229)

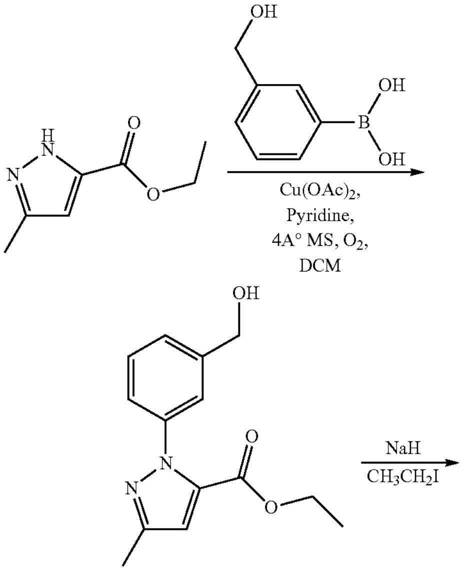

229A

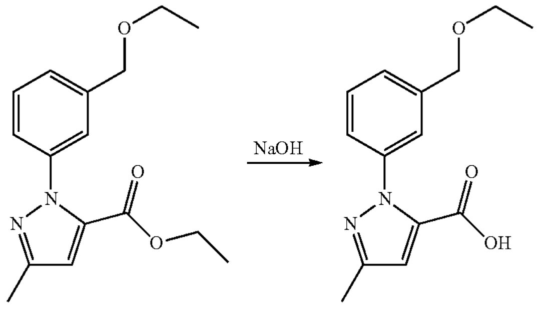

229B

229C

To ethyl 3-methyl-1H-pyrazole-5-carboxylate (3 g, 19.46 mmol), [3-(hydroxymethyl)phenyl]boronic acid (4.44 g, 29.19 mmol), 4A° MS (8 g) and Pyridine (1.69 g, 21.41 mmol, 1.8 mL) in DCM (70 mL) was added $Cu(OAc)_2$ (4.59 g, 25.30 mmol), the mixture was stirred at 25° C. for 16 h under 02 balloon (15 psi). The reaction mixture was filtered to get rid of 4A° MS and catalyst, and then the filtrate was concentrated. The residue was purified by preparatory-HPLC (TFA condition). Compound 229A (1.8 g, yield: 35.54%) was obtained as a colorless oil. $^1$H NMR (400 MHz, $CDCl_3$) δ 7.48-7.35 (m, 3H), 7.32-7.28 (m, 1H), 6.81 (s, 1H), 4.71 (s, 2H), 4.22 (q, J=7.0 Hz, 2H), 2.35 (s, 3H), 1.24 (t, J=7.0 Hz, 3H).

To a solution of compound 229A (465 mg, 1.79 mmol) and iodoethane (1.4 g, 8.95 mmol, 0.75 mL) in dry DMF (10 mL) was added NaH (214.8 mg, 5.37 mmol, 60% purity) at 0° C., then the mixture was reaction at 25° C. for 2 h. The reaction mixture was quenched with 50 mL saturated $NH_4Cl$ at 0° C., extracted with ethyl acetate (30 mL×2), the organic phase was dried over $Na_2SO_4$, filtered and concentrated under reduced pressure to give a residue. The residue was purified by column chromatography ($SiO_2$, Petroleum ether/Ethyl acetate=5/1). Compound 229B (443 mg, yield: 85.83%) was obtained as a colorless oil. $^1$H NMR (400 MHz, $CDCl_3$) δ 7.43-7.36 (m, 3H), 7.33-7.28 (m, 1H), 6.80 (s, 1H), 4.56 (s, 2H), 4.21 (q, J=7.3 Hz, 2H), 3.54 (q, J=7.0 Hz, 2H), 2.35 (s, 3H), 1.23 (t, J=2.4, 7.1 Hz, 6H).

To a solution of compound 229B (443 mg, 1.54 mmol) in MeOH (10 mL) and $H_2O$ (6 mL) was added NaOH (184.8 mg, 4.62 mmol). The mixture was stirred at 25° C. for 2 h. The reaction mixture was concentrated and added 20 mL of water and the mixture was extracted with MTBE (10 mL×2), the aqueous layer was acidified by 1N HCl to pH ~2 to 3 at 0° C., and extracted with EtOAc (10 mL×2), the organic phase was dried over $Na_2SO_4$, filtered and concentrated to give a residue. Compound 229C (400 mg, yield: 99.79%) was obtained as a white solid, which was used for next step directly. $^1$H NMR (400 MHz, DMSO-$d_6$) δ 7.43-7.37 (m, 1H), 7.35-7.26 (m, 3H), 6.79 (s, 1H), 4.48 (s, 2H), 3.48 (q, J=6.9 Hz, 2H), 2.23 (s, 3H), 1.16-1.12 (m, 3H).

Compound 229 (30.1 mg, yield: 47.21%, white solid) was prepared as in Example 5 from the corresponding intermediate carboxylic acid, compound 229C. Compound 229: $^1$H NMR (400 MHz, DMSO-$d_6$) δ 9.07 (br d, J=7.7 Hz, 1H), 8.08 (s, 1H), 7.84 (s, 1H), 7.32-7.22 (m, 8H), 6.99 (br d, J=7.5 Hz, 1H), 6.54 (s, 1H), 5.31-5.20 (m, 1H), 4.42 (s, 2H), 3.47-3.43 (m, 2H), 3.17 (br dd, J=3.4, 13.8 Hz, 1H), 2.80 (br dd, J=10.6, 13.7 Hz, 1H), 2.23 (s, 3H), 1.11 (t, J=6.9 Hz, 3H). MS (ESI) m/z $(M+H)^+$435.1.

Example 125

(S)—N-(4-amino-3,4-dioxo-1-phenylbutan-2-yl)-1-(3-((benzyloxy)methyl)phenyl)-3-methyl-1H-pyrazole-5-carboxamide (230)

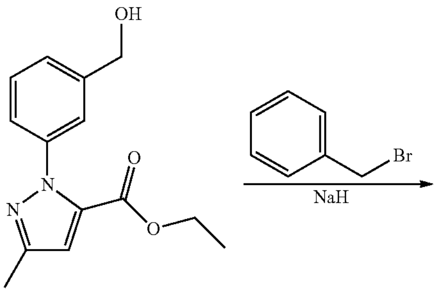

229A

-continued

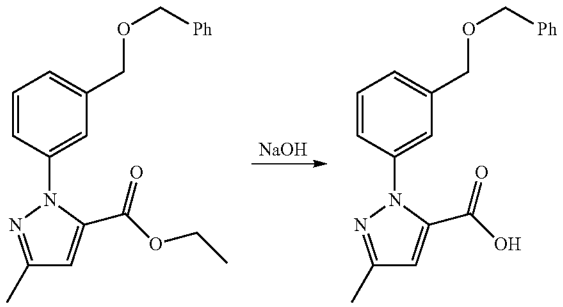

230A 230B

To a solution of compound 229A (472 mg, 1.81 mmol) and bromomethylbenzene (1.55 g, 9.05 mmol, 1.1 mL) in dry DMF (15 mL) was added NaH (218 mg, 5.43 mmol, 60% purity) at 0° C. and then the mixture was reaction at 25° C. for 2 h. The reaction mixture was quenched with 50 mL saturated $NH_4Cl$ at 0° C., extracted with ethyl acetate (30 mL×2), dried over $Na_2SO_4$, filtered and concentrated under reduced pressure to give a residue. The residue was purified by column chromatography ($SiO_2$, Petroleum ether/Ethyl acetate=5/1). Compound 230A (623 mg, yield: 98.23%) was obtained as a colorless oil. $^1H$ NMR (400 MHz, $CDCl_3$) δ 7.43-7.41 (m, 3H), 7.37-7.34 (m, 5H), 7.31 (d, J=2.0 Hz, 1H), 6.81 (s, 1H), 4.62 (s, 2H), 4.57 (s, 2H), 4.23-4.18 (m, 2H), 2.36 (s, 3H), 1.22 (t, J=7.1 Hz, 3H).

To a solution of compound 230A (623 mg, 1.78 mmol) in MeOH (15 mL) and $H_2O$ (8 mL) was added NaOH (214 mg, 5.34 mmol). The mixture was stirred at 25° C. for 2 h. The reaction mixture was concentrated and added 20 mL of water, the mixture was extracted with MTBE (10 mL×2), the aqueous layer was acidified by 1N HCl to pH ~2-3 at 0° C., and extracted with EtOAc (10 mL×2), the organic phase was dried over $Na_2SO_4$, concentrated to give a residue. Compound 230B (569 mg, yield: 99.16%) was obtained as a white solid, which was used for next step directly. $^1H$ NMR (400 MHz, DMSO-$d_6$) δ 7.45-7.23 (m, 10H), 6.80 (s, 1H), 4.57 (s, 2H), 4.54 (s, 2H), 2.24 (s, 3H).

Compound 230 (33.3 mg, yield: 54.97%, white solid) was prepared as in Example 5 from the corresponding intermediate carboxylic acid, compound 230B. Compound 230: $^1H$ NMR (400 MHz, DMSO-$d_6$) δ 9.08 (d, J=7.7 Hz, 1H), 8.08 (s, 1H), 7.85 (s, 1H), 7.35-7.25 (m, 12H), 7.23-7.20 (m, 1H), 7.03-6.98 (m, 1H), 6.55 (s, 1H), 5.30-5.21 (m, 1H), 4.51 (d, J=2.9 Hz, 4H), 3.17 (dd, J=3.4, 13.8 Hz, 1H), 2.80 (dd, J=10.6, 13.7 Hz, 1H), 2.23 (s, 3H). MS (ESI) m/z $(M+H)^+$ 497.1.

Example 126

Compounds 231, 438, 442

(S)—N-(4-amino-3,4-dioxo-1-phenylbutan-2-yl)-3-methyl-1-(3-(phenoxymethyl)phenyl)-1H-pyrazole-5-carboxamide (231)

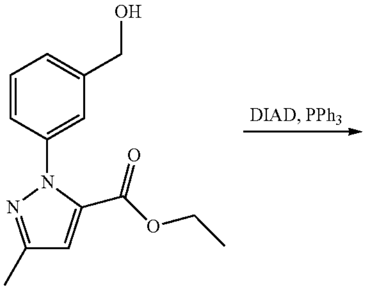

229A

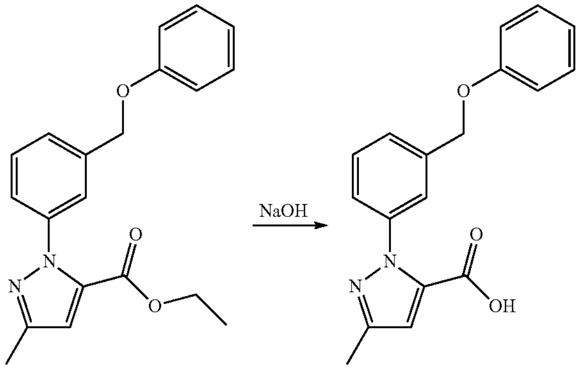

231A 231B

To a suspended solution of compound 229A (400 mg, 1.54 mmol) and phenol (174 mg, 1.85 mmol) in dry THF (10 mL) was added $PPh_3$ (605 mg, 2.31 mmol) and then slowly added DIAD (467 mg, 2.31 mmol, 449 uL) under $N_2$. The mixture was reaction at 25° C. for 12 h under $N_2$. The reaction mixture dissolved in DCM (30 mL) and $H_2O$ (20 mL), then extracted with DCM (20 mL×2), the organic layer was combined and the mixture was dried over $Na_2SO_4$, filtered and concentrated. The residue was purified by column chromatography ($SiO_2$, Petroleum ether/Ethyl acetate=4/1). Compound 231A (489.7 mg, yield: 94.53%) was obtained as a colorless oil. $^1H$ NMR (400 MHz, DMSO-$d_6$) δ 7.51-7.43 (m, 3H), 7.36 (d, J=7.7 Hz, 1H), 7.31-7.24 (m, 2H), 7.13 (t, J=7.8 Hz, 1H), 7.00 (d, J=7.7 Hz, 2H), 6.87 (s, 1H), 5.14 (s, 2H), 4.13 (q, J=7.1 Hz, 2H), 2.25 (s, 3H), 1.11 (t, J=7.1 Hz, 3H).

To a solution of compound 231A (551 mg, 1.64 mmol) in MeOH (5 mL) and $H_2O$ (5 mL) was added NaOH (262 mg, 6.56 mmol). The mixture was stirred at 25° C. for 1 h. The reaction mixture was concentrated and added 10 mL of water and the mixture was extracted with MTBE (10 mL×2), the aqueous layer was acidified by 1N HCl to pH ~2-3 at 0° C., and extracted with EtOAc (10 mL×2), the organic phase was dried over $Na_2SO_4$, filtered and concentrated to give a residue. Compound 231B (490 mg, yield: 96.90%) was obtained as a white solid, which was used for next step directly. $^1H$ NMR (400 MHz, DMSO-$d_6$) δ 7.50-7.42 (m, 3H), 7.36-7.32 (m, 1H), 7.31-7.25 (m, 2H), 7.01 (dd, J=1.0, 8.7 Hz, 2H), 6.95-6.90 (m, 1H), 6.81 (s, 1H), 5.13 (s, 2H), 2.24 (s, 3H).

Compound 231 (68 mg, yield: 65.87%, white solid) was prepared as in Example 5 from the corresponding intermediate carboxylic acid, compound 231B. Compound 231: $^1$H NMR (400 MHz, DMSO-$d_6$) δ 9.08 (d, J=7.7 Hz, 1H), 8.07 (s, 1H), 7.84 (s, 1H), 7.40-7.23 (m, 10H), 7.21-7.17 (m, 1H), 7.04-6.95 (m, 3H), 6.91 (br t, J=7.3 Hz, 1H), 6.55 (s, 1H), 5.28-5.20 (m, 1H), 5.08 (s, 2H), 3.17 (dd, J=3.3, 13.9 Hz, 1H), 2.80 (br dd, J=10.5, 13.8 Hz, 1H), 2.22 (s, 3H).

N-(4-amino-3,4-dioxo-1-phenylbutan-2-yl)-1-(3-((benzyloxy)methyl)phenyl)-3-methyl-1H-pyrazole-5-carboxamide (438)

Compound 438 (2.9 g, yield: 86.54%, white solid) was prepared from the corresponding intermediate compound 229A by alkylating with benzyl bromide followed by ester hydrolysis and coupling with intermediate 274D as in compound 12. Compound 438: $^1$H NMR (400 MHz, DMSO-$d_6$) δ 9.10 (d, J=7.7 Hz, 1H), 8.11 (s, 1H), 7.87 (s, 1H), 7.39-7.23 (m, 13H), 7.10-6.99 (m, 1H), 6.58 (s, 1H), 5.28 (s, 1H), 4.53 (d, J=3.1 Hz, 4H), 3.32-3.16 (m, 1H), 2.83 (dd, J=10.6, 13.7 Hz, 1H), 2.25 (s, 3H). MS (ESI) m/z $(M+H)^+$497.2.

N-(4-amino-3,4-dioxo-1-phenylbutan-2-yl)-3-methyl-1-(4-(morpholinomethyl)phenyl)-1H-pyrazole-5-carboxamide (442)

Compound 442 (50 mg, yield: 50.01%, yellow solid) was prepared from the corresponding intermediate compound 229A by converting it to the morpholino derivative via the mesylate. The morpholino derivative was subjected to ester hydrolysis and coupling with intermediate 274D as in compound 12. Compound 442: $^1$H NMR (400 MHz, $CD_3CN$) δ 7.34-7.15 (m, 11H), 7.07-6.96 (m, 1H), 6.50 (s, 1H), 6.24 (s, 1H), 5.39 (dd, J=4.6, 8.0, 9.4 Hz, 1H), 3.64-3.60 (m, 4H), 3.50 (s, 2H), 3.30-3.25 (m, 1H), 2.89 (dd, J=9.4, 14.0 Hz, 1H), 2.40 (s, 4H), 2.26 (s, 3H). MS (ESI) m/z $(M+H)^+$476.2.

Example 127

(S)—N-(4-amino-3,4-dioxo-1-phenylbutan-2-yl)-1-(2,6-dimethylpyrimidin-4-yl)-5-methyl-1H-pyrazole-3-carboxamide (232)

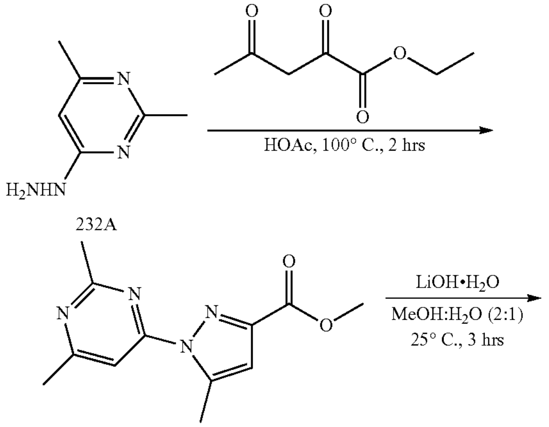

232A

232C

-continued

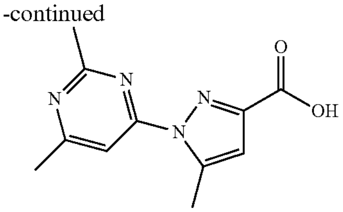

232D

To a solution of 4-chloro-2,6-dimethylpyrimidine (3.0 g, 21.04 mmol) and $NH_2NH_2.H_2O$ (10.5 g, 210.40 mmol) in EtOH (40 mL). The mixture was stirred at 70° C. for 2 hours. The mixture was cooled to room-temperature and concentrated under reduced pressure to afford intermediate compound 232A (2.30 g, 62.60% yield) as a yellow solid. $^1$H NMR (400 MHz, DMSO-$d_6$): δ 6.33 (br s, 1H), 2.24 (s, 3H), 2.15 (s, 3H).

To a solution of compound 232A (2.30 g, 13.17 mmol, HCl) and ethyl 2,4-dioxopentanoate (2.08 g, 13.17 mmol) in AcOH (30 mL). The mixture was stirred at 100° C. for 2 hrs. The reaction mixture was concentrated under reduced pressure to remove AcOH, then diluted with $H_2O$, the pH was adjusted to around 9 by progressively adding $NaHCO_3$, then partitioned between EtOAc (20 mL×3), dried over $Na_2SO_4$. The residue was purified by flash silica gel chromatography (ISCO®; 40 g SepaFlash® Silica Flash Column, Eluent of 0~50% Ethyl acetate/Petroleum ethergradient @ 30 mL/min), then the residue was purified by preparatory-HPLC (basic condition). Compound 232C (50 mg, 1.46% yield) was obtained as a white solid. Compound 232C: $^1$H NMR (400 MHz, $CDCl_3$) δ 7.76-7.71 (m, 1H), 6.72-6.66 (m, 1H), 4.48-4.37 (m, 2H), 2.82-2.74 (m, 3H), 2.73-2.66 (m, 3H), 2.58-2.52 (m, 3H), 1.47-1.38 (m, 3H)[1169]. Compound 232D (38 mg, 85.18% yield, white solid) was prepared as in Example 85 from the corresponding intermediate compound 232C. $^1$H NMR (400 MHz, DMSO-$d_6$) δ 7.63 (s, 1H), 6.74 (s, 1H), 2.68 (s, 3H), 2.60 (s, 3H), 2.50 (s, 3H).

Compound 232 (48.4 mg, 57.40% yield, white solid) was prepared as in Example 5 from the corresponding intermediate carboxylic acid, compound 232D. Compound 232: $^1$H NMR (400 MHz, $CDCl_3$) δ 7.53 (s, 1H), 7.40 (br d, J=7.2 Hz, 1H), 7.33-7.23 (m, 3H), 7.21-7.15 (m, 2H), 6.80 (br s, 1H), 6.66 (s, 1H), 5.77-5.69 (m, 2H), 3.49-3.40 (m, 1H), 3.34-3.24 (m, 1H), 2.75 (s, 3H), 2.69 (s, 3H), 2.58 (s, 3H). MS (ESI) m/z $(M+H)^+$ 407.1.

Example 128

(S)—N-(4-amino-3,4-dioxo-1-phenylbutan-2-yl)-3-methyl-1-(6-phenylpyridazin-3-yl)-1H-pyrazole-5-carboxamide (233)

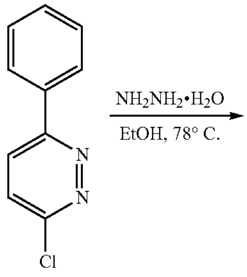

-continued

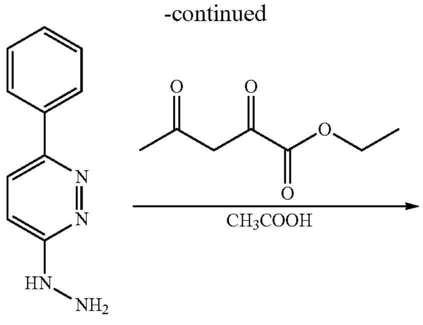

233A

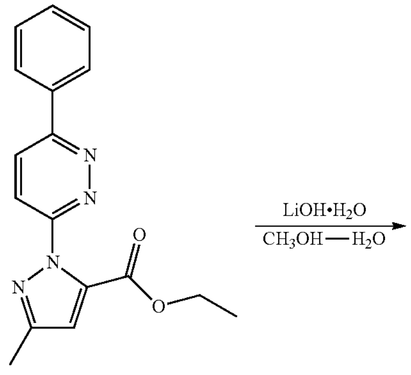

233B

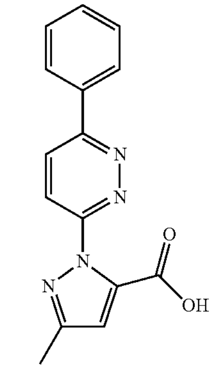

233D

To a solution of 3-chloro-6-phenylpyridazine (1.00 g, 5.25 mmol) in EtOH (20 mL) was added $N_2H_4.H_2O$ (2.63 g, 52.46 mmol, 2.55 mL). After stirred at 78° C. for 10 hours, the reaction mixture was concentrated under reduced pressure to remove the solvent. The residue was diluted with petroleum ether 30 mL, stirred for 30 min, and then filtered to give crude intermediate product 233A as grey residue. $^1H$ NMR (400 MHz, DMSO-$d_6$): δ 7.96 (d, J=7.2 Hz, 1H), 7.85 (d, J=9.6 Hz, 1H), 7.47-7.43 (m, 2H), 7.39-7.35 (m, 1H), 7.09 (d, J=9.2 Hz, 1H).

To a solution of compound 233A (1.30 g, 6.98 mmol) in $CH_3COOH$ (12 mL) was added ethyl 2,4-dioxopentanoate (1.10 g, 6.98 mmol, 985.61 uL), then the mixture was stirred at 120° C. for 2 hours. The reaction mixture was concentrated under reduced pressure to remove solvent. The residue was diluted with solvent ethyl acetate (70 mL) and washed with solvent saturated aqueous $NaHCO_3$ solution (20 mL×3), dried over anhydrous $Na_2SO_4$, filtered and concentrated under reduced pressure to give a residue. The residue was purified by column chromatography (Petroleum Ether: Ethyl Acetate=30/1 to 10/1) to afford a residue. The crude was further separated by preparatory-HPLC (Acid condition). Compound 233B was obtained as a white solid (270.00 mg, 875.69 umol, 12.55% yield).

To a mixture of compound 233B (180.0 mg, 583.79 umol) in MeOH (6 mL) and $H_2O$ (3.00 mL) was added $LiOH.H_2O$ (73.5 mg, 1.75 mmol) in one portion and the mixture was stirred at 25° C. for 6 hours. The reaction mixture was concentrated under reduced pressure to remove MeOH. The residue was diluted with $H_2O$ (20 mL), adjusted to pH ~3 with 1N HCl, and then extracted with EtOAc (60 mL×3). The combined organic layers were washed with brine (30 mL), dried over anhydrous $Na_2SO_4$, filtered and concentrated under reduced pressure to give intermediate compound 233D (160.00 mg, 97.78% yield) as a white solid. $^1H$ NMR (400 MHz, DMSO-$d_6$) δ 8.52 (d, J=9.2 Hz, 1H), 8.27-8.22 (m, 2H), 7.63-7.56 (m, 2H), 6.85 (s, 1H), 2.73 (s, 3H).

Compound 233 (67.0 mg, 63.93% yield white solid) was prepared as in Example 5 from the corresponding intermediate carboxylic acid, compound 233D. Compound 233: $^1H$ NMR (400 MHz, $CDCl_3$) δ 8.16 (d, J=9.2 Hz, 1H), 8.13-8.11 (m, 2H), 8.03 (d, J=9.2 Hz, 1H), 7.59-7.54 (m, 3H), 7.42 (d, J=7.2 Hz, 1H), 7.32-7.27 (m, 3H), 7.20-7.18 (m, 1H), 6.77 (s, 1H), 6.75 (d, J=0.4 Hz, 1H), 5.76-5.71 (m, 1H), 5.55 (s, 1H), 3.49-3.44 (m, 1H), 3.32-3.27 (m, 1H), 2.85 (s, 3H). MS (ESI) m/z $(M+1)^+$455.1.

Example 129

(S)—N-(4-amino-3,4-dioxo-1-phenylbutan-2-yl)-3-methyl-1-(6-methyl-4-(trifluoromethyl)pyridin-2-yl)-1H-pyrazole-5-carboxamide (234)

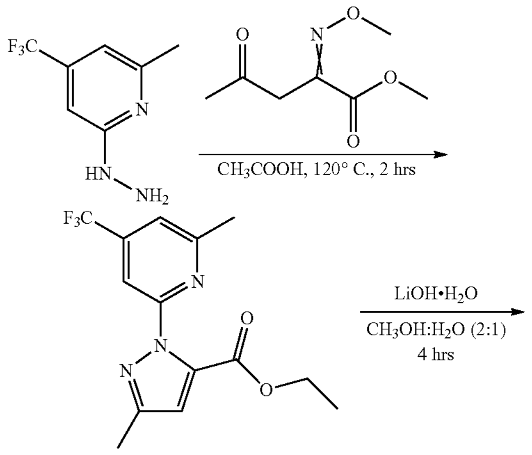

234A

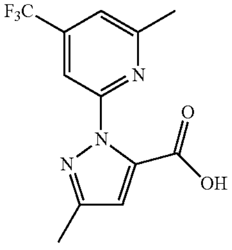

234B

To a solution of 2-hydrazineyl-6-methyl-4-(trifluoromethyl)pyridine (400 mg, 2.09 mmol) in $CH_3COOH$ (4 mL) was added ethyl 2-(methoxyimino)-4-oxopentanoate (391 mg, 2.09 mmol), then he mixture was stirred at 120° C. for 2 hours. The mixture was diluted with $CH_2Cl_2$ (70 mL) and washed by saturated sodium bicarbonate (20 mL×2) and saturated brine (20 mL×2), dried with anhydrous $Na_2SO_4$, filtered and concentrated in vacuum. The residue was purified by flash column chromatography ($SiO_2$, Petroleum Ether:Ethyl Acetate=10:1 to 3:1) to afford proposed compound 3 (150 mg, 22.91% yield) as white solid. $^1H$ NMR (400 MHz, $CDCl_3$): δ 8.08 (s, 1H), 7.32 (s, 1H), 6.72 (s, 1H), 4.46-4.36 (m, 2H), 2.72 (s, 3H), 2.65 (s, 3H), 1.44-1.41 (m, 3H).

To a solution of compound 234A (100 mg, 319.21 umol) in MeOH (4 mL) and $H_2O$ (2 mL) was added $LiOH.H_2O$ (53 mg, 1.28 mmol), then the mixture was stirred at 25° C. for 4 hours. The reaction mixture was concentrated under reduced pressure to remove MeOH. The residue was diluted with $H_2O$ (10 mL), adjusted to pH ~3 with 1N HCl, and extracted with EtOAc (40 mL×3). The combined organic layers were washed with brine (30 mL), dried over anhydrous $Na_2SO_4$, filtered and concentrated under reduced pressure to afford intermediate compound 234B (80 mg, 87.87% yield) as a white solid. $^1H$ NMR (400 MHz, DMSO-$d_6$): δ 7.79 (s, 1H), 7.72 (s, 1H), 6.79 (s, 1H), 2.56 (s, 3H), 2.28 (s, 3H).

Compound 234 (24.1 mg, 34.58% yield, white solid) was prepared as in Example 5 from the corresponding carboxylic acid, compound 234B. Compound 234: $^1H$ NMR (400 MHz, DMSO-$d_6$, t=80° C.) δ 8.81 (d, J=6.4 Hz, 1H), 7.75 (br s, 1H), 7.67 (s, 1H), 7.59 (br, s, 1H), 7.52 (s, 1H), 7.27-7.19 (m, 5H), 6.53 (s, 1H), 5.43-5.35 (m, 1H), 3.23-3.16 (m, 1H), 2.96-2.87 (m, 1H), 2.39 (s, 3H), 2.30 (s, 3H). MS (ESI) m/z $(M+1)^+$460.1.

Example 130

(S)—N-(4-amino-3,4-dioxo-1-phenylbutan-2-yl)-1-(benzo[d]oxazol-2-yl)-3-methyl-1H-pyrazole-5-carboxamide (238)

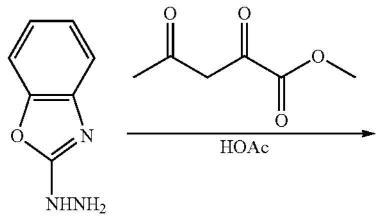

238A

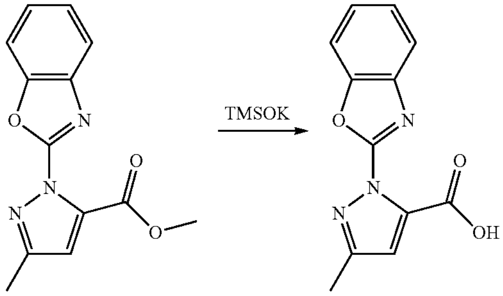

238B 238C

A solution of 2-chlorobenzo[d]oxazole (2.5 g, 16.3 mmol) in dioxane (4 mL) was added to a solution of $N_2H_4.H_2O$ (4.07 g, 81.4 mmol) in dioxane (20 mL) dropwise keeping the reaction temperature below 30° C. The reaction mixture was stirred at 20° C. for 1 hr. The solvent was evaporated. Water (50 mL) was added and the mixture was stirred for 10 min. The solid was collected by filtration and the cake was washed by water (50 mL). The cake was dried to give pure product 238A (2 g, yield: 82.4%) as a white solid. $^1H$ NMR (400 MHz, DMSO-$d_6$) δ 8.76 (br s, 1H), 7.31 (d, J=7.7 Hz, 1H), 7.22 (d, J=7.3 Hz, 1H), 7.09 (dt, J=1.0, 7.7 Hz, 1H), 6.95 (dt, J=1.1, 7.7 Hz, 1H), 4.47 (br s, 2H).

A mixture of compound 238A (1 g, 6.70 mmol) and methyl 2,4-dioxopentanoate (966 mg, 6.70 mmol) in AcOH (5 mL) was stirred at 120° C. for 16 hrs. The solvent was evaporated. The crude product was purified by silica gel column chromatography (petroleum ether:ethyl acetate=20:1-3:1) to give compound 238B (900 mg, crude) as off-white solid.

A solution of compound 238B (200 mg, 777 umol) in toluene (5 mL) was added TMSOK (199 mg, 1.55 mmol). The reaction mixture was stirred at 80° C. for 5 hrs. The reaction mixture was poured into saturated $NH_4Cl$(5 mL). The product was extracted with EtOAc (10 mL×3). The combined organic layer was purified by preparatory-HPLC (HCOOH) to give compound 238C (30 mg, yield: 15.9%) as a white solid. $^1H$ NMR (400 MHz, DMSO-$d_6$) δ 13.30 (br s, 1H), 7.80 (td, J=4.2, 8.4 Hz, 2H), 7.52-7.37 (m, 2H), 6.83 (s, 1H), 5.72 (s, 1H), 2.69 (s, 3H).

Compound 238 (21 mg, yield: 70%, white solid) was prepared as in Example 5 from the corresponding carboxylic acid, compound 238C. Possible isomer could not confirmed by 2DNMR. Compound 238: $^1H$ NMR (400 MHz, $CDCl_3$) δ 7.78-7.69 (m, 1H), 7.61 (dd, J=3.2, 5.8 Hz, 1H), 7.51 (br d, J=7.1 Hz, 1H), 7.43-7.35 (m, 2H), 7.32-7.16 (m, 6H), 6.80-6.70 (m, 2H), 5.81-5.71 (m, 1H), 5.55 (br s, 1H), 3.45 (dd, J=5.4, 14.0 Hz, 1H), 3.22 (dd, J=7.3, 14.1 Hz, 1H), 2.75 (s, 3H). MS (ESI) m/z $(M+H)^+$418.1.

Example 131

Compounds 239-242, 469-474

(S)—N-(4-amino-3,4-dioxo-1-phenylbutan-2-yl)-1-ethyl-3-phenyl-1H-pyrazole-4-carboxamide (239)

(S)—N-(4-amino-3,4-dioxo-1-phenylbutan-2-yl)-1-isopropyl-3-phenyl-1H-pyrazole-4-carboxamide (242)

A solution of p-$TsOH.H_2O$ (61.3 g, 322.27 mmol) in $H_2O$ (20 mL) was added to a suspension of compound 1 (20.0 g, 128.91 mmol) in $CH_3CN$ (400 mL) at 0° C. The mixture turned clear. The mixture was stirred at 0° C. for 30 min. Then a solution of $NaNO_2$ (13.3 g, 193.4 mmol) and KI (32.1 g, 193.4 mmol) in H2O (20 mL) was added dropwise to the mixture at 0° C. After addition, the mixture was stirred at 20° C. for 1 h. The mixture was quenched by the addition of saturated $Na_2SO_3$ (~100 mL) at 0° C. The black mixture turned yellow. The mixture was concentrated to 200 mL and then extracted with DCM (75 mL×3). The combined organic layer was washed with brine (75 mL×2), dried over $MgSO_4$, filtered and concentrated. The residue was treated with 100 mL ethyl acetate. The insoluble substance was removed off by filter. The filtrate was concentrated and purified by FCC (PE/EA=1/1) to afford compound 239A (17.50 g, yield 48.4%) as white solid. $^1H$ NMR (DMSO-$d_6$, 400 MHz): δ

13.01-12.65 (m, 1H), 8.13-8.11 (m, 1H), 4.38-4.32 (m, 2H), 1.41-1.37 (m, 3H). MS (ESI) m/z $(M+H)^+$266.8.

$Cs_2CO_3$ (7.35 g, 22.56 mmol) was added to a solution of compound 239A (2.0 g, 7.52 mmol) in DMF (15 mL). Then EtI (1.50 mL, 18.8 mmol) was added. The mixture was stirred at 25° C. for 2.5 h. The mixture was treated with EA (50 mL) and $H_2O$ (50 mL). The organic layer was separated and the aqueous layer was extracted with EA (25 mL×2). The combined organic layer was washed brine (30 mL×3), dried over $MgSO_4$, filtered and concentrated. The residue was purified by FCC (PE/EA=8/1) to afford compound 239B (1.31 g, yield 59.2%) as colorless oil. Compound 239B ($R_f$=0.24, PE/EA=8/1): $^1$H NMR (DMSO-$d_6$, 400 MHz): δ 8.28 (s, 1H), 4.21-4.12 (m, 4H), 1.34 (t, J=7.3 Hz, 3H), 1.25 (t, J=7.1 Hz, 3H).

was acidified to pH ~2 with 1N HCl. The precipitate was collected by filter and dried in vacuum to afford compound 239E (250 mg, yield 74.1%) was obtained as white solid, which was used for next step directly. $^1$H NMR (DMSO-$d_6$, 400 MHz): δ 12.19 (br.s., 1H), 8.32 (s, 1H), 7.72 (dd, J=1.4, 7.8 Hz, 2H), 7.41-7.24 (m, 3H), 4.17 (q, J=7.3 Hz, 2H), 1.39 (t, J=7.3 Hz, 3H).

Compound 239 (80 mg, yield 51.3%, white solid) was prepared as in Example 5 from the corresponding intermediate carboxylic acid, compound 239E. Compound 239: $^1$H NMR ($CDCl_3$, 400 MHz): δ 8.32 (d, J=7.2 Hz, 1H), 8.07 (s, 1H), 8.05 (br.s., 1H), 7.79 (br.s., 1H), 7.62-7.51 (m, 2H), 7.32-7.17 (m, 8H), 5.32-5.22 (m, 1H), 4.16 (q, J=7.2 Hz, 2H), 3.14 (dd, J=4.0, 14.0 Hz, 1H), 2.81 (dd, J=10.0, 14.0 Hz, 1H), 1.40 (t, J=7.2 Hz, 3H). MS (ESI) m/z $(M+H)^+$ 391.1.

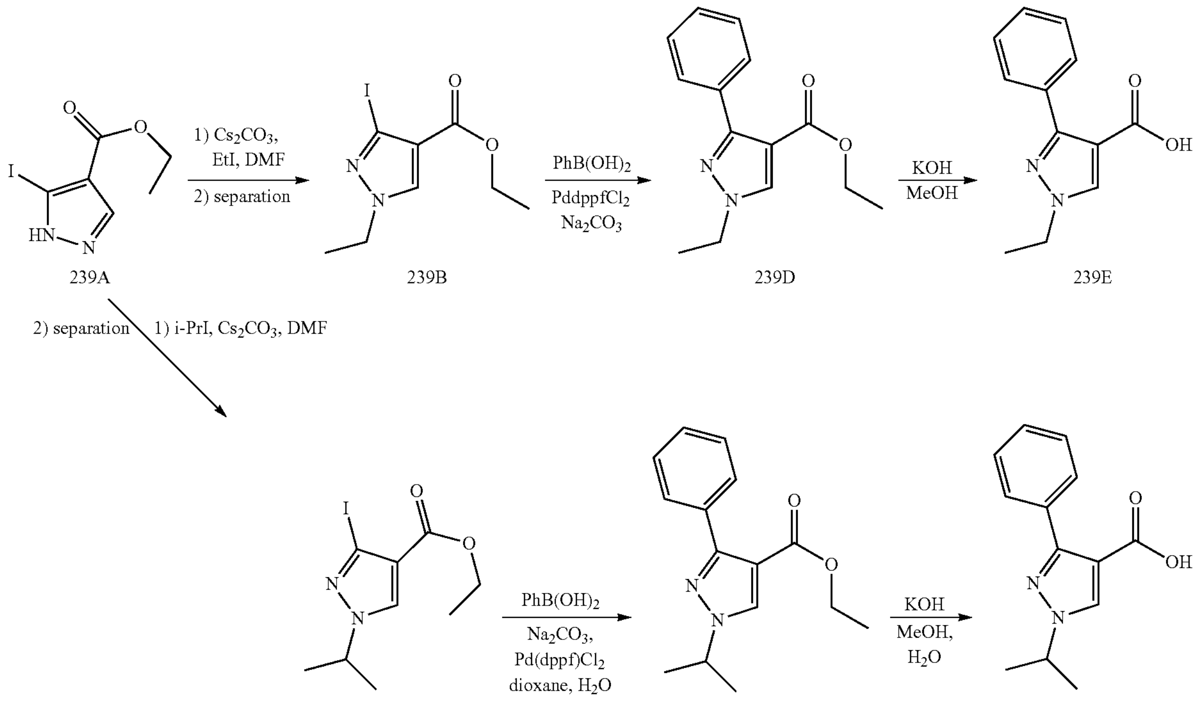

239A 239B 239D 239E
242A 242C 242D $Na_2CO_3$ (360 mg, 3.4 mmol) was added to a solution of compound 239B (500 mg, 1.7 mmol) and phenylboronic acid (311 mg, 2.6 mmol) in dioxane (10 mL). Then $H_2O$ (2 mL) was added, followed by Pd(dppf)$Cl_2$ (124 mg, 0.17 mmol). The mixture was de-gassed 3 times and heated to 80° C. and stirred for 22 h at 80° C. The mixture was filtered through a pad of Celite, the solid was washed with EA (25 mL×3). The organic layer was separated from the filtrate, and then washed with brine (30 mL×2), dried over $MgSO_4$, filtered and concentrated. The residue was purified by FCC (PE/EA=10/1) to afford compound 239D (380 mg, yield 91.5%) as pale yellow oil. $^1$H NMR ($CDCl_3$, 400 MHz): δ 7.99 (s, 1H), 7.76 (dd, J=1.5, 7.9 Hz, 2H), 7.44-7.32 (m, 3H), 4.28-4.17 (m, 4H), 1.55 (t, J=7.3 Hz, 3H), 1.27 (t, J=7.2 Hz, 3H).

To a solution of compound 239D (380 mg, 1.56 mmol) in MeOH (15 mL) was added a solution of KOH (875 mg, 15.6 mmol) in $H_2O$ (3 mL). The mixture was stirred at 70° C. for 2 h. The mixture was diluted with $H_2O$ (15 mL), and then the volatile solvent was removed by evaporation. The residue Following the procedure used for compound 239, intermediate compounds 242A, 242C and 242D were successively prepared. Compound 242A (1.41 g, yield 60.9%, colorless oil): $^1$H NMR (DMSO-$d_6$, 400 MHz): δ 8.31 (s, 1H), 4.60-4.53 (m, 1H), 4.22 (q, J=7.2 Hz, 2H), 1.41 (d, J=6.4 Hz, 6H), 1.28 (t, J=7.2 Hz, 3H).

Compound 242C (318 mg, yield 76.0%, colorless liquid): $^1$H NMR (DMSO-$d_6$, 400 MHz): δ 8.39 (s, 1H), 7.73-7.67 (m, 2H), 7.42-7.34 (m, 3H), 4.64-4.52 (m, 1H), 4.16 (q, J=7.0 Hz, 2H), 1.46 (d, J=6.8 Hz, 6H), 1.21 (t, J=7.2 Hz, 3H). Compound 242D (119 mg, crude, white solid): $^1$H NMR (DMSO-$d_6$, 400 MHz): δ 12.19 (s, 1H), 8.33 (s, 1H), 7.76-7.71 (m, 2H), 7.41-7.32 (m, 3H), 4.61-4.51 (m, 1H), 1.46 (d, J=6.8 Hz, 3H).

Compound 242 (47 mg, yield 46.7%, white solid) was prepared as in Example 5 from the corresponding intermediate carboxylic acid, compound 242D. Compound 242: $^1$H NMR ($CDCl_3$, 400 MHz): δ 7.99 (s, 1H), 7.55-7.49 (m, 2H), 7.47-7.37 (m, 3H), 7.23-7.14 (m, 3H), 6.85-6.78 (m, 2H), 6.73 (s, 1H), 6.13-6.05 (m, J=6.2 Hz, 1H), 5.57-5.42 (m, 2H), 4.51 (spt, J=6.7 Hz, 1H), 3.25 (dd, J=4.7, 14.0 Hz, 1H), 2.90 (dd, J=8.0, 14.2 Hz, 1H), 1.53 (d, J=6.6 Hz, 6H). MS (ESI) m/z $(M+H)^+$405.2.

N-(4-amino-3,4-dioxo-1-phenylbutan-2-yl)-1-ethyl-3-(2-fluorophenyl)-1H-pyrazole-4-carboxamide (469)

Compound 469 (130 mg, yield 49%, white solid) was prepared as in compound 12 from the corresponding intermediate carboxylic acid, 1-ethyl-3-(2-fluorophenyl)-1H-pyrazole-4-carboxylic acid which was prepared using procedure similar to compound 239E. Compound 469: $^1H$ NMR (DMSO-$d_6$, 400 MHz): δ 8.21 (s, 1H), 7.89-7.45 (m, 3H), 7.43-7.31 (m, 2H), 7.30-7.10 (m, 7H), 5.33-5.22 (m, 1H), 4.20 (q, J=7.1 Hz, 2H), 3.22-3.15 (m, 1H), 2.92-2.82 (m, 1H), 1.45 (br t, J=7.2 Hz, 3H). MS (ESI) m/z $(M+H)^+$ 409.1.

N-(4-amino-3,4-dioxo-1-phenylbutan-2-yl)-1-ethyl-3-(3-fluorophenyl)-1H-pyrazole-4-carboxamide (470)

Compound 470 (140 mg, yield 66.8%, white solid) was prepared as in compound 12 from the corresponding intermediate carboxylic acid, 1-ethyl-3-(3-fluorophenyl)-1H-pyrazole-4-carboxylic acid which was prepared using procedure similar to compound 239E. Compound 470: $^1H$ NMR (DMSO-$d_6$, 400 MHz): δ 8.44 (d, J=7.5 Hz, 1H), 8.11 (s, 1H), 8.04 (s, 1H), 7.78 (s, 1H), 7.47-7.39 (m, 2H), 7.36-7.29 (m, 1H), 7.28-7.23 (m, 4H), 7.22-7.16 (m, 1H), 7.14-7.07 (m, 1H), 5.35-5.25 (m, 1H), 4.21-4.11 (m, 2H), 3.15 (dd, J=3.9, 14.0 Hz, 1H), 2.81 (dd, J=9.9, 13.9 Hz, 1H), 1.40 (t, J=7.3 Hz, 3H). MS (ESI) m/z $(M+H)^+$409.1.

N-(4-amino-3,4-dioxo-1-phenylbutan-2-yl)-1-ethyl-3-(4-fluorophenyl)-1H-pyrazole-4-carboxamide (471)

Compound 471 (90 mg, yield 32.9%, white solid) was prepared as in compound 12 from the corresponding intermediate carboxylic acid, 1-ethyl-3-(4-fluorophenyl)-1H-pyrazole-4-carboxylic acid which was prepared using procedure similar to compound 239E. Compound 471: $^1H$ NMR (DMSO-$d_6$, 400 MHz): δ 8.37 (d, J=7.5 Hz, 1H), 8.08 (s, 1H), 8.05-7.96 (m, 1H), 7.77 (s, 1H), 7.63-7.52 (m, 2H), 7.31-7.14 (m, 5H), 7.13-7.01 (m, 2H), 5.31-5.16 (m, 1H), 4.24-4.03 (m, 2H), 3.18-3.06 (m, 1H), 2.87-2.75 (m, 1H), 1.38 (t, J=7.3 Hz, 3H). MS (ESI) m/z $(M+H)^+$409.1.

N-(4-amino-3,4-dioxo-1-phenylbutan-2-yl)-3-(2-fluorophenyl)-1-isopropyl-1H-pyrazole-4-carboxamide (472)

Compound 472 (88 mg, yield 45.8%, white solid) was prepared as in compound 12 from the corresponding intermediate carboxylic acid, 3-(2-fluorophenyl)-1-isopropyl-1H-pyrazole-4-carboxylic acid which was prepared using procedure similar to compound 242D. Compound 472: $^1H$ NMR (DMSO-$d_6$, 400 MHz): δ 8.25 (s, 1H), 8.17 (d, J=7.5 Hz, 1H), 7.96 (s, 1H), 7.73 (s, 1H), 7.40-7.05 (m, 9H), 5.26-5.16 (m, 1H), 4.52 (td, J=6.8, 13.2 Hz, 1H), 3.09 (br, dd, J=3.9, 14.2 Hz, 1H), 2.78 (br.dd, J=9.7, 13.9 Hz, 1H), 1.48-1.39 (m, 6H). MS (ESI) m/z $(M+H)^+$423.2.

N-(4-amino-3,4-dioxo-1-phenylbutan-2-yl)-3-(3-fluorophenyl)-1-isopropyl-1H-pyrazole-4-carboxamide (473)

Compound 473 (51 mg, yield 41.2%, pale yellow solid) was prepared as in compound 12 from the corresponding intermediate carboxylic acid, 3-(3-fluorophenyl)-1-isopropyl-1H-pyrazole-4-carboxylic acid which was prepared using procedure similar to compound 242D. Compound 473: $^1H$ NMR (DMSO-$d_6$, 400 MHz): δ 8.42 (d, J=7.3 Hz, 1H), 8.14 (s, 1H), 8.07-8.01 (m, 1H), 7.78 (s, 1H), 7.51-7.42 (m, 2H), 7.36-7.29 (m, 1H), 7.28-7.24 (m, 4H), 7.22-7.16 (m, 1H), 7.14-7.05 (m, 1H), 5.34-5.25 (m, 1H), 4.60-4.48 (m, 1H), 3.15 (dd, J=4.0, 14.1 Hz, 1H), 2.82 (dd, J=9.8, 14.0 Hz, 1H), 1.44 (d, J=6.4 Hz, 6H). MS (ESI) m/z $(M+H)^+$ 423.2.

N-(4-amino-3,4-dioxo-1-phenylbutan-2-yl)-3-(4-fluorophenyl)-1-isopropyl-1H-pyrazole-4-carboxamide (474)

Compound 474 (80 mg, yield 52.6%, white solid) was prepared as in compound 12 from the corresponding intermediate carboxylic acid, 3-(4-fluorophenyl)-1-isopropyl-1H-pyrazole-4-carboxylic acid which was prepared using procedure similar to compound 242D. Compound 474: $^1H$ NMR (DMSO-$d_6$, 400 MHz): δ 8.10 (s, 1H), 7.97 (s, 1H), 7.85-7.39 (m, 4H), 7.34-7.17 (m, 5H), 7.15-7.03 (m, 2H), 5.37-5.27 (m, 1H), 4.59-4.47 (m, 1H), 3.26-3.16 (m, 1H), 2.97-2.87 (m, 1H), 1.49 (d, J=6.8 Hz, 6H). MS (ESI) m/z $(M+H)^+$423.2.

Example 132

Compounds 240-241

(S)—N-(4-amino-3,4-dioxo-1-phenylbutan-2-yl)-1-ethyl-3-phenyl-1H-pyrazole-4-carboxamide (240)

(S)—N-(4-amino-3,4-dioxo-1-phenylbutan-2-yl)-1-methyl-4-phenyl-1H-pyrazole-3-carboxamide (241)

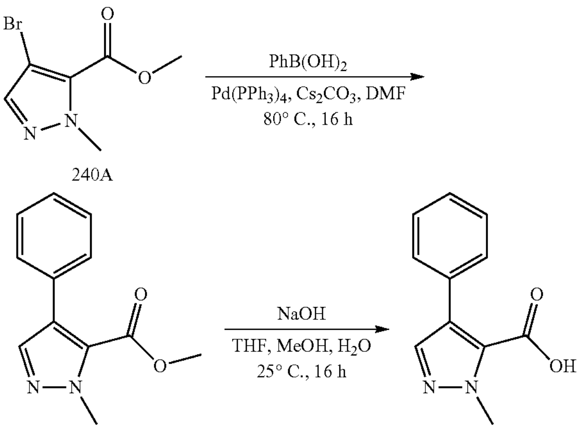

240A 240C 240D

-continued

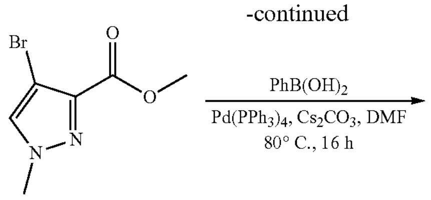

240B

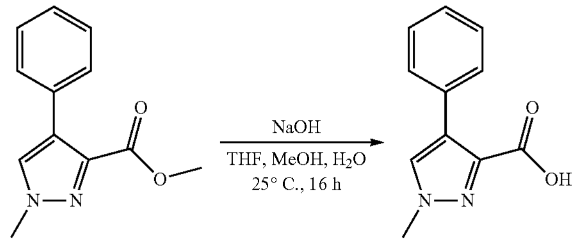

241A 241B

To a mixture of methyl 4-bromo-1H-pyrazole-3-carboxylate (15.0 g, 73.2 mmol) and $Cs_2CO_3$ (59.6 g, 182.9 mmol) in DMF (150 mL) was added MeI (14.7 mL, 236.0 mmol) drop-wise at 0° C. under $N_2$. The mixture was stirred at 25° C. for 16 hours. The reaction mixture was filtered, the cake washed with ethyl acetate (200 mL×2). The filtrate was washed with water (70 mL×4) and the aqueous phase extracted with ethyl acetate (150 mL). The combined organic extracts were dried over $Na_2SO_4$, filtered and concentrated to dryness under reduced pressure to dryness. The crude product which was purified by FCC (gradient eluent: petroleum ether/ethyl acetate from 100/0 to 50/50) to afford the title compound 240A (8.3 g, yield 51.8%) as a white solid and the title compound 240B (7.0 g, yield 43.7%) as white solid. Compound 240A: $^1H$ NMR (400 MHz, $CDCl_3$): δ 7.48 (s, 1H), 4.15 (s, 3H), 3.93 (s, 3H). MS (ESI) m/z $(M+H)^+$219.0. Compound 240B: $^1H$ NMR (400 MHz, $CDCl_3$): δ 7.47 (s, 1H), 3.95 (s, 3H), 3.92 (s, 3H). MS (ESI) m/z $(M+H)^+$219.0.

Compound 240A (2.0 g, 9.1 mmol), phenylboronic acid (1.3 g, 11.0 mmol), $Cs_2CO_3$ (8.9 g, 27.4 mmol) and $Pd(PPh_3)_4$ (211 mg, 183 umol) in DMF (30 mL) was de-gassed and then heated to 80° C. for 16 hours under $N_2$. The reaction mixture was filtered, the cake washed with ethyl acetate (30 mL×2). The filtrate was washed with water (20 mL×4) and the aqueous phase extracted with ethyl acetate (50 mL). The combined organic extracts were dried over $Na_2SO_4$, filtered and concentrated to dryness under reduced pressure to dryness. The crude product which was purified by FCC (gradient eluent: petroleum ether/ethyl acetate from 100/0 to 50/50) to afford the title compound 240C (1.0 g, yield 47.3%) as a light yellow solid. Compound 240C: $^1H$ NMR (400 MHz, $CDCl_3$): δ 7.52 (s, 1H), 7.40-7.36 (m, 4H), 7.35-7.31 (m, 1H), 4.20 (s, 3H), 3.76 (s, 3H). MS (ESI) m/z $(M+H)^+$217.0.

A solution of NaOH (370 mg, 9.2 mmol) in $H_2O$ (10 mL) was added to a solution of compound 240C (1.0 g, 4.6 mmol) in THF (10 mL) and MeOH (10 mL) at 25° C. The mixture was stirred at 25° C. for 16 hours. The mixture was adjusted to pH ~6 with 1N HCl (10 mL) at 25° C., and extracted with ethyl acetate (30 mL×3). The combined organic extracts were dried over $Na_2SO_4$, filtered, and concentrated to afford compound 240D (900 mg, yield 94.1%) as light yellow solid. Compound 240D: $^1H$ NMR (400 MHz, $CD_3OD$): δ 7.54-7.49 (m, 1H), 7.44-7.38 (m, 2H), 7.37-7.27 (m, 3H), 4.14 (s, 3H). MS (ESI) m/z $(M+H)^+$ 202.9.

Compound 240 (68.6 mg, yield 41.4%) was prepared as in Example 12 from the corresponding intermediate carboxylic acid, compound 240D. Compound 240: $^1H$ NMR (400 MHz, DMSO-$d_6$): δ 7.46-7.39 (m, 4H), 7.39-7.34 (m, 2H), 7.20-7.13 (m, 3H), 6.73-6.68 (m, 2H), 6.14-6.07 (m, 1H), 5.57-5.46 (m, 2H), 4.09 (s, 3H), 3.19 (dd, J=4.8, 14.0 Hz, 1H), 2.80 (dd, J=8.0, 14.0 Hz, 1H). MS (ESI) m/z $(M+H)^+$ 377.1.

Following the procedure used for compound 240, compound 241 (90 mg, yield 58.5%, white solid) was prepared from intermediate compound 241B. Compound 241: $^1H$ NMR (400 MHz, $CDCl_3$): δ 7.53-7.47 (m, 2H), 7.41 (s, 1H), 7.37-7.27 (m, 6H), 7.19-7.13 (m, 2H), 6.72 (br s, 1H), 5.69-5.62 (m, 1H), 5.43 (br s, 1H), 3.94 (s, 3H), 3.42 (dd, J=5.2, 14.0 Hz, 1H), 3.20 (dd, J=7.6, 14.0 Hz, 1H). MS (ESI) m/z $(M+H)^+$377.1.

Example 133

Compounds 244-245

(S)—N-(4-amino-3,4-dioxo-1-phenylbutan-2-yl)-3-methyl-1-(2-methylpyrimidin-4-yl)-1H-pyrazole-5-carboxamide (244)

(S)—N-(4-amino-3,4-dioxo-1-phenylbutan-2-yl)-3-methyl-1-(pyrimidin-4-yl)-1H-pyrazole-5-carboxamide (245)

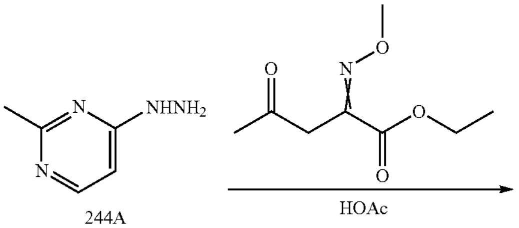

244A

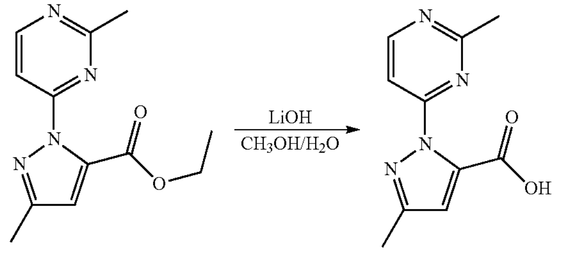

244B 244D

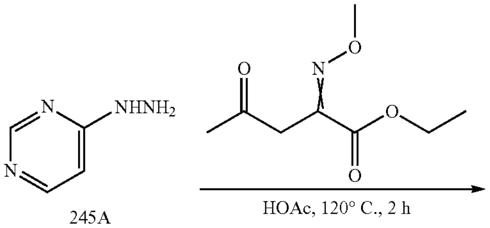

245A

-continued

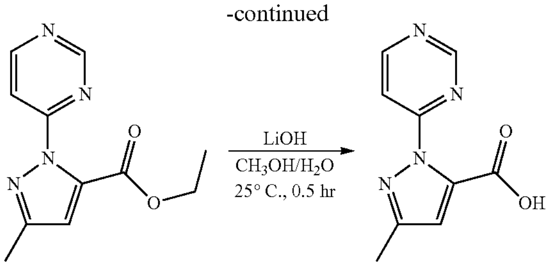

245B

245D

A mixture of 4-chloro-2-methylpyrimidine (5.00 g, 38.89 mmol) and $N_2H_4.H_2O$ (22.91 g, 388.90 mmol, 22.24 mL, 85% purity) in EtOH (100 mL) was degassed and purged with $N_2$ for 3 times, then the mixture was stirred at 70° C. for 2 hour under $N_2$ atmosphere. The mixture was concentrated under reduced pressure to give a crude, the crude was washed by PE (50 mL) and filtered, the residue was purified by column chromatography (DCM:$CH_3OH$=10:1) to obtain compound 244A (1.60 g, 33.14% yield) as a yellow solid. $^1H$ NMR (400 MHz, DMSO-$d_6$) δ 8.21 (s, 1H), 7.99 (d, J=5.6 Hz, 1H), 6.48 (br s, 1H), 4.31 (br s, 2H), 2.30 (s, 3H).

To a solution of compound 244A (900.0 mg, 7.25 mmol) in $CH_3COOH$ (12 mL) was added ethyl 2-(methoxyimino)-4-oxopentanoate (1.36 g, 7.25 mmol), then the mixture was stirred at 120° C. for 2 hours. The residue was diluted with solvent EtOAc (70 mL) and washed with solvent saturated $NaHCO_3$ solution (20 mL×3), dried over anhydrous $Na_2SO_4$, filtered and concentrated under reduced pressure to give a residue. The residue was purified by column chromatography (PE:EA=30/1 to 10/1) to afford crude. The crude was further separated by preparatory-HPLC (Basic condition) to give compound 244B (158.0 mg, 8.85% yield) as a white solid. $^1H$ NMR (400 MHz, $CDCl_3$) δ 8.66 (d, J=5.6 Hz, 1H), 7.53 (d, J=3.6 Hz, 1H), 6.59 (s, 1H), 4.39-4.33 (m, 2H), 2.66 (s, 3H), 2.35 (s, 3H), 1.35-1.32 (m, 3H). MS (ESI) m/z $(M+1)^+$247.1.

To a mixture of compound 244B (130.0 mg, 527.90 umol) in MeOH (8 mL) and $H_2O$ (4 mL) was added $LiOH.H_2O$ (88.6 mg, 2.11 mmol) in one portion and the mixture was stirred at 25° C. for 0.5 hours. The reaction mixture was concentrated under reduced pressure to remove MeOH. The residue was diluted with $H_2O$ (10 mL), adjusted to pH ~3 with 1N HCl, and then extracted with EtOAc (40 mL×3). The combined organic layers were washed with brine (30 mL), dried over anhydrous $Na_2SO_4$, filtered and concentrated under reduced pressure to give intermediate compound 244D (110.00 mg, 95.49% yield) as a white solid. $^1H$ NMR (400 MHz, DMSO-$d_6$) δ 8.77 (d, J=5.6 Hz, 1H), 7.56 (d, J=3.6 Hz, 1H), 6.76 (s, 1H), 2.65 (s, 3H), 2.27 (s, 3H). MS (ESI) m/z $(M+1)^+$219.1.

Compound 244 (40.0 mg, 33.17% yield, white solid) was prepared as in Example 5 from the corresponding intermediate carboxylic acid, compound 244D. Compound 244: $^1H$ NMR (400 MHz, $CDCl_3$) δ 9.48 (d, J=5.2 Hz, 1H), 8.66 (d, J=4.8 Hz, 1H), 7.70 (d, J=5.2 Hz, 1H), 7.26-7.20 (m, 3H), 7.10 (s, 2H), 6.84 (s, 1H), 6.78 (s, 1H), 5.81 (d, J=6.0 Hz, 1H), 5.58 (s, 1H), 3.47-3.38 (m, 1H), 3.39-3.34 (m, 1H), 2.37 (s, 3H), 2.34 (s, 3H). MS (ESI) m/z $(M+1)^+$393.1.

Following the procedure used for compound 244A, compound 245A (1.80 g, 49.37% yield, brown solid) was obtained from 4-chloropyrimidine and $NH_2NH_2.H_2O$. Compound 245A: $^1H$ NMR (400 MHz, DMSO-$d_6$): δ 8.32 (s, 2H), 8.06 (d, J=5.2 Hz, 1H), 6.65 (s, 1H), 4.32 (m, 2H).

Following the procedure used for compound 244B, compound 245B (586.0 mg, 2.52 mmol, 17.39% yield) was obtained as a white solid. $^1H$ NMR (400 MHz, $CDCl_3$) δ 8.92 (s, 1H), 8.71 (d, J=5.6 Hz, 1H), 7.70-7.69 (m, 1H), 6.56 (s, 1H), 4.34-4.38 (m, 2H), 2.29 (s, 1H), 1.31-1.24 (m, 3H). MS (ESI) m/z $(M+1)^+$233.1.

Following the procedure for compound 244D, compound 245D (476.0 mg, 2.33 mmol, 93.30% yield) was obtained as white solid. $^1H$ NMR (400 MHz, DMSO-$d_6$) δ 9.04 (s, 1H), 8.90 (d, J=5.2 Hz, 1H), 7.81 (d, J=5.6 Hz, 1H), 6.79 (s, 1H), 2.27 (s, 3H).

Compound 245 (35.0 mg, 28.33% yield, white solid) was prepared as in Example 5 from the corresponding carboxylic acid, compound 245D. Compound 245: $^1H$ NMR (400 MHz, DMSO-$d_6$) δ 9.18 (d, J=7.2 Hz, 1H), 8.83 (d, J=5.6 Hz, 1H), 8.74 (s, 1H), 8.11 (s, 1H), 7.87 (s, 1H), 7.73 (d, J=4.8 Hz, 1H), 7.28-7.23 (m, 5H), 6.50 (s, 1H), 5.38 (s, 1H), 3.19-3.16 (m, 1H), 2.88-2.82 (m, 1H), 2.29 (s, 3H). MS (ESI) m/z $(M+1)^+$379.1.

Example 134

Compounds 246, 431-437, 448

(S)—N-(4-amino-3,4-dioxo-1-phenylbutan-2-yl)-1-(2-chloropyrimidin-4-yl)-3-methyl-1H-pyrazole-5-carboxamide (246)

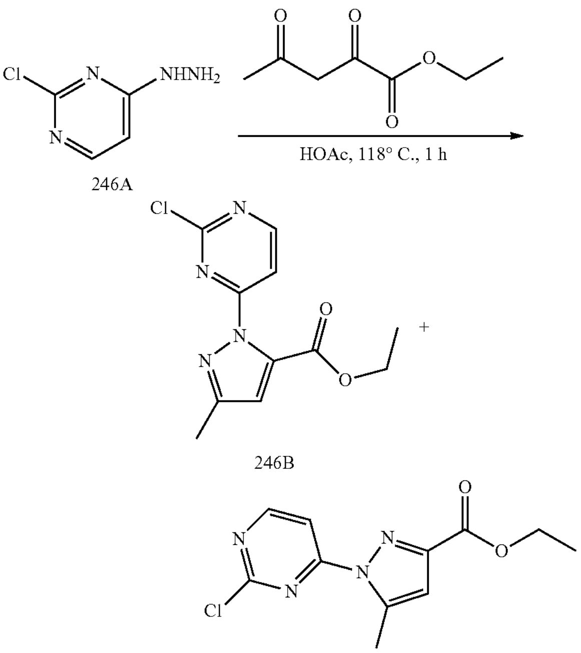

246A

246B

246C

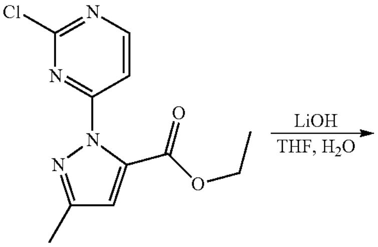

246B

-continued

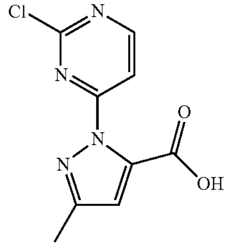

246D

To a solution of 2,4-dichloropyrimidine (10 g, 67.12 mmol) and $Et_3N$ (10.2 mL, 73.83 mmol) in EtOH (120 mL) was added $NH_2NH_2.H_2O$ (4.6 mL, 80.54 mmol) at 05° C. The mixture was stirred at 5° C. for 1.5 h. The mixture was concentrated. The residue was triturated in EtOH (15 mL) and water (15 mL) to afford compound compound 246A (4 g, 41.22% yield) as yellow oil. $^1$H NMR (400 MHz, DMSO-$d_6$) δ 9.00-8.79 (m, 1H), 8.09-7.63 (m, 1H), 6.82-6.59 (m, 1H), 4.82-4.30 (m, 2H).

A mixture of ethyl 2,4-dioxopentanoate (4.38 g, 27.67 mmol), compound 246A (4 g, 27.67 mmol) in AcOH (60 mL) was stirred at 118° C. for 1 h. The mixture was in DCM (50 mL). The organic layer was washed with water (10 mL), $NaHCO_3$ to pH ~89 and dried over $Na_2SO_4$ and concentrated. The residue was purified by column chromatography ($SiO_2$, Petroleum ether/Ethyl acetate=10/1 to 5:1). Compound 246B (650 mg, 8.81% yield) was obtained as white solid. Compound 246C (240 mg, 3.25% yield) was obtained as white solid. Compound 246B: $^1$H NMR (400 MHz, DMSO-$d_6$) δ 8.87 (d, J=5.6 Hz, 1H), 7.98 (d, J=5.6 Hz, 1H), 6.89 (s, 1H), 4.34 (q, J=7.2 Hz, 2H), 2.71 (s, 3H), 1.32 (t, J=7.2 Hz, 3H). Compound 246C: $^1$H NMR (400 MHz, DMSO-$d_6$) δ 8.84 (d, J=5.6 Hz, 1H), 7.86 (d, J=5.6 Hz, 1H), 6.91 (s, 1H), 4.32 (q, J=7.2 Hz, 2H), 2.31 (s, 3H), 1.30-1.20 (m, 3H).

A mixture of compound 246B (300 mg, 1.12 mmol) in THF (36 mL) and $H_2O$ (12 mL) was added $LiOH.H_2O$ (27.1 mg, 645.87 umol). The mixture was stirred at 31° C. for 1 h. The mixture was concentrated and acidified to pH ~5 with 1M HCl, then extracted with chloroform:isopropyl alcohol=10:1 (10 ml×2). This combined organic phase was washed with saturated aqueous NaCl and dried over $Na_2SO_4$, filtered and the solvent was removed in vacuo to give compound 246D (200 mg, 74.83% yield) as white solid. $^1$H NMR (400 MHz, DMSO-$d_6$): δ 14.19-13.39 (m, 1H), 8.83 (d, J=5.4 Hz, 1H), 7.83 (d, J=5.6 Hz, 1H), 6.84 (s, 1H), 2.28 (s, 3H).

Compound 246 (2.7 mg, yield, 12.35%, white solid) was prepared as in Example 5 from the corresponding carboxylic acid, compound 246D. Compound 246: $^1$H NMR (400 MHz, DMSO-$d_6$): δ 9.16-9.11 (m, 1H), 8.77-8.72 (m, 1H), 8.03 (br s, 1H), 7.80 (br s, 1H), 7.73-7.68 (m, 1H), 7.23 (br s, 4H), 7.21-7.17 (m, 1H), 6.53 (s, 1H), 5.42 (br s, 1H), 3.17-3.13 (m, 1H), 2.88-2.84 (m, 1H), 2.27 (s, 3H). MS (ESI) m/z $(M+H)^+$413.1.

N-(4-amino-3,4-dioxo-1-phenylbutan-2-yl)-1-(2-isopropylpyrimidin-4-yl)-3-methyl-1H-pyrazole-5-carboxamide (431)

Compound 431 (65 mg, yield, 87.0%, white solid) was prepared using intermediate 246B which was subjected to suzuki coupling using 4,4,5,5-tetramethyl-2-(prop-1-en-2-yl)-1,3,2-dioxaborolane followed by ester hydrolysis using procedure as for compound 12 and hydrogenation and coupling with intermediate 274D as in compound 12 to obtain compound 431. Compound 431: $^1$H NMR (400 MHz, DMSO-$d_6$): δ 9.11 (d, J=7.5 Hz, 1H), 8.74 (d, J=5.5 Hz, 1H), 8.12 (s, 1H), 7.87 (s, 1H), 7.52 (d, J=5.5 Hz, 1H), 7.32-7.20 (m, 5H), 6.47 (s, 1H), 5.52-5.41 (m, 1H), 3.16 (dd, J=3.6, 13.8 Hz, 1H), 2.80-2.75 (m, 1H), 2.29 (s, 3H), 1.04 (dd, J=6.9, 12.2 Hz, 6H). MS (ESI) m/z $(M+H)^+$421.2.

N-(4-amino-3,4-dioxo-1-phenylbutan-2-yl)-1-(2-ethynylpyrimidin-4-yl)-3-methyl-1H-pyrazole-5-carboxamide (432)

Compound 432 (35 mg, yield, 43.5%, white solid) was prepared using intermediate 246B which was subjected to coupling with 4ethynyltrimethylsilane followed by removal of trimethylsilyl group and then ester hydrolysis using procedure as for compound 12 and coupling with intermediate 274D as in compound 12 to obtain compound 432. Compound 432: $^1$H NMR (400 MHz, DMSO-$d_6$): δ 9.14 (d, J=7.0 Hz, 1H), 8.82 (d, J=5.5 Hz, 1H), 8.02 (s, 1H), 7.80 (s, 1H), 7.70 (d, J=5.5 Hz, 1H), 7.31-7.17 (m, 5H), 6.55 (s, 1H), 5.46-5.35 (m, 1H), 4.39 (s, 1H), 3.19 (dd, J=4.8, 14.1 Hz, 1H), 2.93 (dd, J=9.0, 14.1 Hz, 1H), 2.29 (s, 3H). MS (ESI) m/z $(M+H)^+$403.1.

(S)-1-(2-ethynylpyrimidin-4-yl)-N-(4-fluoro-3-oxo-1-phenylbutan-2-yl)-3-methyl-1H-pyrazole-5-carboxamide (433)

Compound 433 (35 mg, yield, 43.5%, white solid) was prepared using intermediate 246B which was subjected to coupling with 4ethynyltrimethylsilane followed by removal of trimethylsilyl group and then ester hydrolysis using procedure as for compound 12 and coupling with (2S,3S)-3-amino-1-fluoro-4-phenylbutan-2-ol hydrochloride using procedure as in compound 12 to obtain compound 433. Compound 433: $^1$H NMR (400 MHz, DMSO-$d_6$): δ 9.24 (d, J=7.8 Hz, 1H), 8.85 (d, J=5.5 Hz, 1H), 7.78 (d, J=5.5 Hz, 1H), 7.34-7.29 (m, 2H), 7.29-7.21 (m, 3H), 6.38 s, 1H), 5.50-5.21 (m, 2H), 4.73-4.64 (m, 1H), 4.45 (s, 1H), 3.19 (dd, J=4.9, 13.9 Hz, 1H), 2.93 (dd, J=9.8, 14.1 Hz, 1H), 2.28 (s, 3H). MS (ESI) m/z $(M+H)^+$392.1.

N-(4-amino-3-hydroxy-4-oxo-1-phenylbutan-2-yl)-1-(2-chloropyrimidin-4-yl)-3-methyl-1H-pyrazole-5-carboxamide (434)

Compound 434 (80 mg, yield, 15.2%, white solid) was prepared using intermediate 246B which was subjected to coupling with intermediate 274D using procedure as in compound 12 to obtain compound 434. Compound 434: $^1$H NMR (400 MHz, DMSO-$d_6$): δ 8.76 (t, J=5.6 Hz, 1H), 8.63 (d, J=8.8 Hz, 1H), 8.36 (d, J=9.0 Hz, 1H), 7.68 (dd, J=5.5, 19.6 Hz, 1H), 7.39-7.14 (m, 7H), 6.55-6.41 (m, 1H), 4.57-4.31 (m, 1H), 4.19 (d, J=3.3 Hz, 1H), 3.85 (d, J=2.4 Hz, 1H), 3.04-2.66 (m, 2H), 2.28 (d, J=5.5 Hz, 3H). MS (ESI) m/z $(M+H)^+$415.0.

(S)—N-(4-amino-3,4-dioxo-1-phenylbutan-2-yl)-1-(2-chloropyrimidin-4-yl)-5-methyl-1H-pyrazole-3-carboxamide (435)

Compound 435 (160 mg, yield, 46.02%, white solid) was prepared using intermediate 246C which was subjected to coupling with intermediate 12G using procedure as in compound 12 to obtain compound 435. Compound 435: $^1$H NMR (400 MHz, DMSO-$d_6$): δ 8.88 (d, J=5.7 Hz, 1H), 8.09 (d, J=5.5 Hz, 1H), 7.82 (d, J=9.3 Hz, 1H), 7.42 (s, 1H), 7.27 (d, J=4.4 Hz, 4H), 7.23-7.13 (m, 1H), 6.72 (s, 1H), 6.21 (s, 1H), 4.49 (d, J=7.3 Hz, 1H), 3.88 (d, J=2.4 Hz, 1H), 3.02-2.87 (m, 1H), 2.86-2.74 (m, 1H), 2.68 (s, 3H). MS (ESI) m/z $(M+H)^+$415.0.

N-(4-amino-3,4-dioxo-1-phenylbutan-2-yl)-1-(2-methoxypyrimidin-4-yl)-3-methyl-1H-pyrazole-5-carboxamide (436)

Compound 436 (25 mg, yield, 57.7%, white solid) was prepared using intermediate 246D which was subjected to treatment with sodium methoxide and coupling with intermediate 274D using procedure as in compound 12 to obtain compound 436. Compound 436: $^1H$ NMR (400 MHz, DMSO-$d_6$): δ 9.14 (d, J=7.5 Hz, 1H), 8.60 (d, J=5.3 Hz, 1H), 8.15 (s, 1H), 7.91 (s, 1H), 7.34 (d, J=5.3 Hz, 1H), 7.30-7.19 (m, 5H), 6.50 (s, 1H), 5.45-5.36 (m, 1H), 3.48 (s, 3H), 3.16 (dd, J=3.3, 13.9 Hz, 1H), 2.77 (dd, J=10.1, 13.9 Hz, 1H), 2.29 (s, 3H). MS (ESI) m/z $(M+H)^+$409.2.

N-(4-amino-3,4-dioxo-1-phenylbutan-2-yl)-1-(2-cyanopyrimidin-4-yl)-3-methyl-1H-pyrazole-5-carboxamide (437)

Compound 437 (30 mg, yield, 81.32%, white solid) was prepared using intermediate 246D which was subjected to treatment with zinc cyanide using palladium catalyzed coupling conditions followed by coupling with intermediate 274D using procedure as in compound 12 to obtain compound 437. Compound 437: $^1H$ NMR (400 MHz, DMSO-$d_6$): δ 9.13 (d, J=7.3 Hz, 1H), 8.96 (d, J=5.5 Hz, 1H), 8.05-7.93 (m, 2H), 7.84 (s, 1H), 7.27-7.15 (m, 5H), 6.57 (s, 1H), 5.51-5.31 (m, 1H), 3.15 (dd, J=4.2, 13.9 Hz, 1H), 2.79 (dd, J=9.4, 14.0 Hz, 1H), 2.30-2.24 (m, 3H). MS (ESI) m/z $(M+H)^+$404.1.

N-(4-amino-3,4-dioxo-1-phenylbutan-2-yl)-1-(2-cyanopyrimidin-4-yl)-3-methyl-1H-pyrazole-5-carboxamide (448)

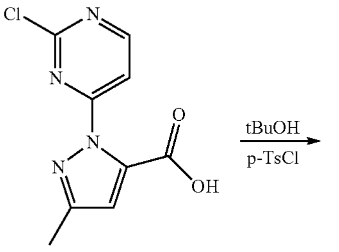

246D

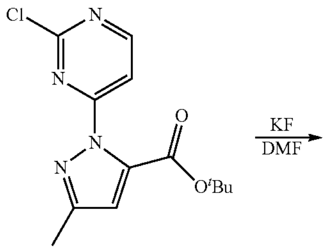

448A

-continued

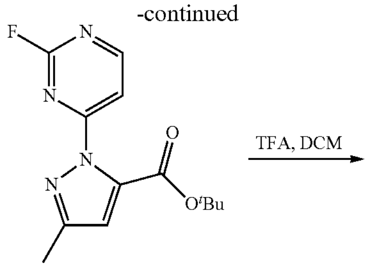

448B

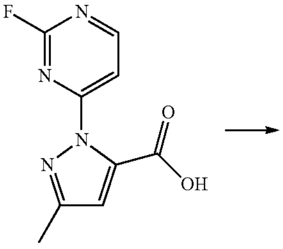

448C

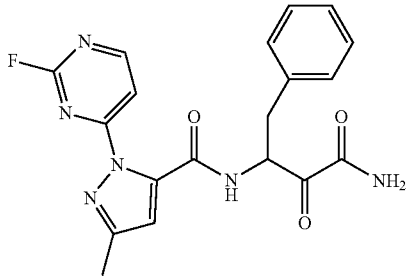

448

To a solution of compound 246D (400 mg, 1.68 mmol) in 2-methylpropan-2-ol (6.2 g, 83.65 mmol, 8.00 mL) and THF (10 mL) was added pyridine (928 mg, 11.73 mmol, 947 uL) and then added p-TsCl (799 mg, 4.19 mmol) in one portion at 0° C. The mixture was stirred at 25° C. for 48 h. The reaction was quenched with sat. $NaHCO_3$ at 0° C., the mixture was extracted with EA (20 mL×2), dried over $Na_2SO_4$, filtered, and concentrated to give a residue. The residue was purified by flash silica gel chromatography (ISCO®; 24 g SepaFlash® Silica Flash Column, eluent of 0-10%-20% Ethyl acetate/Petroleum ethergradient @ 35 mL/min). Compound 448A (400 mg, yield 81.0%) was obtained as a white solid. $^1H$ NMR (400 MHz, $CDCl_3$) δ 8.63 (d, J=5.3 Hz, 1H), 7.80-7.63 (m, 1H), 6.59 (s, 1H), 2.34 (m, 3H), 1.59 (m, 9H). MS (ESI) m/z $(M+H)^+$295.1.

To a solution of compound 448A (400 mg, 1.36 mmol) in DMF (13 mL) was added KF (788 mg, 13.57 mmol) and Dicyclohexano-18-crown-6 (51 mg, 135.71 umol). The mixture was stirred at 120° C. for 3 h under $N_2$. The reaction was cooled to rt and added ice-water (80 mL), white precipitate was formed. The solid was collected by filtration. The residue was purified by preparatory-HPLC (HCl condition). Column: YMC-Actus Triart C18 100*30 mm*5 um; mobile phase: [water (0.05% HCl)-ACN]; B %: 55%-85%, 9.5 min. Compound 448B (130 mg, yield: 34.4%) was obtained as a white solid. $^1H$ NMR (400 MHz, $CDCl_3$) δ 8.63 (dd, J=2.0, 5.3 Hz, 1H), 7.72 (dd, J=3.2, 5.4 Hz, 1H), 6.57 (s, 1H), 2.36 (s, 3H), 1.59 (s, 9H). MS (ESI) m/z $(M+H)^+$279.1.

To a solution of compound 448B (130 mg, 467.15 umol) in DCM (15 mL) was added TFA (2.31 g, 20.26 mmol, 1.5 mL). The mixture was stirred at 25° C. for 5 h. The reaction was concentrated to give a residue. The residue was used to the next step without purification. Compound 448C (105 mg, crude) was obtained as a yellow solid. $^1$H NMR (400 MHz, DMSO-$d_6$) δ 8.84 (dd, J=2.1, 5.4 Hz, 1H), 7.81 (dd, J=3.5, 5.5 Hz, 1H), 6.89-6.78 (m, 1H), 2.25 (s, 3H). MS (ESI) m/z $(M+H)^+$222.9.

Compound 448 (35 mg, yield, 69.7%, white solid) was prepared using intermediate 246D and 448C using procedure as in compound 12 to obtain compound 448. Compound 448: $^1$H NMR (400 MHz, DMSO-$d_6$): δ 9.14 (d, J=7.3 Hz, 1H), 8.76 (dd, J=2.0, 5.5 Hz, 1H), 8.06 (s, 1H), 7.83 (s, 1H), 7.70 (dd, J=3.5, 5.5 Hz, 1H), 7.27-7.17 (m, 5H), 6.53 (s, 1H), 5.42-5.37 (m, 1H), 3.14 (dd, J=4.0, 14.1 Hz, 1H), 2.82 (dd, J=9.3, 14.1 Hz, 1H), 2.28 (s, 3H). MS (ESI) m/z $(M+H)^+$397.1.

Example 135

(S)—N-(3,4-dioxo-1-phenyl-4-((4-(trifluoromethoxy)benzyl)amino)butan-2-yl)-3-methyl-5-phenylisoxazole-4-carboxamide (247)

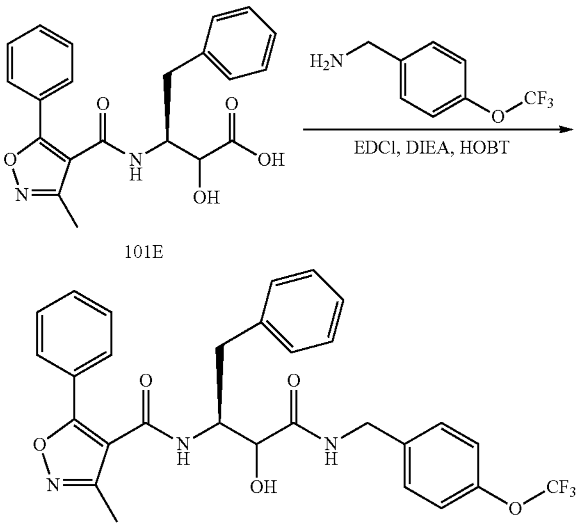

101E

247A

To a solution of compound 101E (500.0 mg, 1.31 mmol) in DMF (10 mL) was added [4-(trifluoromethoxy)phenyl]methanamine (250.4 mg, 1.31 mmol, 200 uL), DIEA (507.9 mg, 3.93 mmol, 690 uL), HOBt (53.1 mg, 393.00 umol) and EDCI (301.4 mg, 1.57 mmol). The mixture was stirred at 25° C. for 12 hours. The mixture was diluted with $H_2O$ (100 mL), extracted with EA (30 mL), washed with HCl (1M, 30 mL), saturated $NaHCO_3$ (aq, 30 mL), brine (30 mL), dried over $Na_2SO_4$ and concentrated. The residue was purified by preparatory-HPLC (basic condition). Compound 247A (80.0 mg, crude) was obtained as a white solid. $^1$H NMR (400 MHz, DMSO-$d_6$) δ 8.46-8.20 (m, 1H), 7.57-7.11 (m, 15H), 5.90-5.64 (m, 1H), 4.71-4.56 (m, 1H), 4.10-3.90 (m, 2H), 2.99-2.89 (m, 1H), 2.86-2.74 (m, 1H), 2.11-2.01 (m, 3H).

To a solution of compound 247A (80.0 mg, 144.53 umol) in DCM (10 mL) and DMSO (1 mL) was added DMP (183.9 mg, 433.59 umol). The mixture was stirred at 25° C. for 3 hours. The mixture quenched with 10% $Na_2S_2O_3$ (aqueous): saturated $NaHCO_3$ (aqueous) (1:1, 20 mL), extracted with DCM (10 mL) and washed with brine (20 mL×3). The combined organic layers were dried over $Na_2SO_4$ and concentrated. The crude product was triturated with $CH_3CN$ (5 mL) and filtered. Compound 247 (20.0 mg, yield 25.1%) was obtained as a white solid. $^1$H NMR (400 MHz, DMSO-$d_6$) δ 9.50-9.43 (m, 1H), 9.12-9.06 (m, 1H), 7.66-7.57 (m, 2H), 7.51-7.36 (m, 5H), 7.34-7.19 (m, 7H), 5.53-5.45 (m, 1H), 4.41-4.16 (m, 2H), 3.27-3.20 (m, 1H), 2.82-2.72 (m, 1H), 2.10-2.01 (m, 1H), 2.05 (s, 2H). MS (ESI) m/z $(M+H)^+$ 552.1.

Example 136

(S)—N-(4-amino-3,4-dioxo-1-phenylbutan-2-yl)-4-(4-fluorophenyl)-2-methyloxazole-5-carboxamide (248)

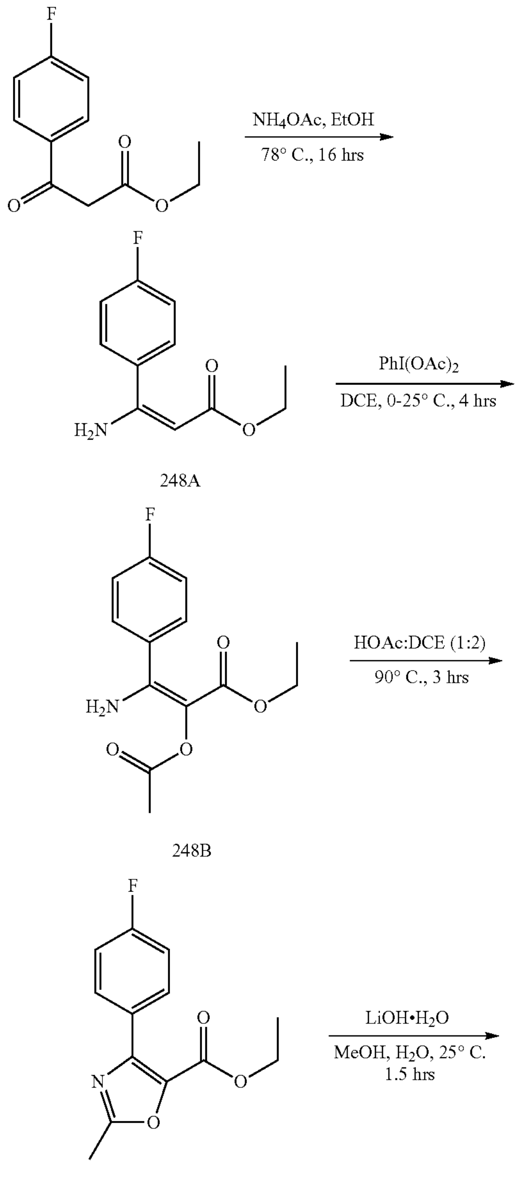

248A

248B

248C

-continued

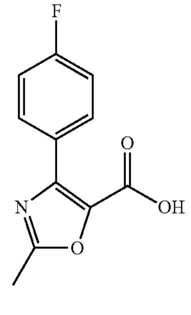

248D

A mixture of ethyl 3-(4-fluorophenyl)-3-oxopropanoate (8 g, 38.06 mmol) and $NH_4OAc$ (5.87 g, 76.12 mmol) in EtOH (450 mL) was stirred at 78° C. for 16 hours. The reaction mixture was concentrated under reduced pressure, and the residue was diluted with water (60 mL) and then extracted with EtOAc (100 mL×3). The combined organic phase was washed with sat. $NaHCO_3$ (50 mL×3) and brine (50 mL), dried over anhydrous $Na_2SO_4$, filtered and the solvent was removed under reduced pressure to give a residue, which was purified by column chromatography ($SiO_2$, petroleum ether/ethyl acetate=100:1 to 10:1) to afford compound 248A (7.10 g, 89.16% yield) as a light yellow oil. $^1H$ NMR (400 MHz, $CDCl_3$): δ 7.56-7.48 (m, 2H), 7.12-7.04 (m, 2H), 4.90 (s, 1H), 4.16 (q, J=7.2 Hz, 2H), 1.32-1.24 (m, 3H).

To a mixture of compound 248A (9 g, 43.02 mmol) in DCE (90 mL) was added $PhI(OAc)_2$ (18.0 g, 55.93 mmol) in three portions at 0° C. under $N_2$, the mixture was stirred at 0° C. for 3 hours and then warmed to 25° C. slowly. The mixture was then stirred at 25° C. for 1 hour. The reaction mixture was quenched with saturated aqueous $NaHCO_3$ (200 mL) and extracted with DCM (200 mL×3). The combined organic layers were dried over anhydrous $Na_2SO_4$, filtered and concentrated under reduced pressure to give a residue. The residue was purified by column chromatography ($SiO_2$, petroleum ether/ethyl acetate=20:1 to 5:1) to afford compound 248B (6.0 g, 52.19% yield) as a yellow oil. $^1H$ NMR (400 MHz, $CDCl_3$): δ 7.49-7.35 (m, 2H), 7.12-7.00 (m, 2H), 4.27-4.16 (m, 2H), 1.93 (s, 3H), 1.27 (t, J=7.2 Hz, 3H).

A mixture of ethyl compound 248B (6.0 g, 22.45 mmol) in DCE (30 mL) and AcOH (15 mL) was stirred at 90° C. for 3 hours. The reaction mixture was cooled to room-temperature and then concentrated to dryness under reduced pressure to afford a residue, which was purified by column chromatography ($SiO_2$, Petroleum ether/Ethyl acetate=100:1 to 10:1) to afford compound 248C (2.80 g, 50.04% yield) as a white solid. $^1H$ NMR (400 MHz, $CDCl_3$): δ 8.10-8.00 (m, 2H), 7.11 (t, J=8.4 Hz, 2H), 4.38 (q, J=7.2 Hz, 2H), 2.57 (s, 3H), 1.37 (t, J=7.2 Hz, 3H).

To a mixture of compound 248C (1 g, 4.01 mmol) in MeOH (30 mL) and $H_2O$ (15 mL) was added LiOH.H2O (505.1 mg, 12.03 mmol) in one portion and the mixture was stirred at 25° C. for 1.5 hours. The reaction mixture was concentrated under reduced pressure to remove MeOH. The residue was adjusted to pH ~3 with 1N HCl, diluted with water (30 mL) and then extracted with EtOAc (100 mL×4). The combined organic layers were washed with brine (80 mL), dried over anhydrous $Na_2SO_4$, filtered and concentrated under reduced pressure to afford intermediate compound 248D (820 mg, 92.45% yield) as a white solid. $^1H$ NMR (400 MHz, $CDCl_3$): δ 8.10-8.00 (m, 2H), 7.17-7.07 (m, 2H), 2.60 (s, 3H).

Compound 248 (36.1 mg, 24.19% yield, white solid) was prepared as in Example 5 from the corresponding intermediate carboxylic acid, compound 248D. Compound 248: $^1H$ NMR (400 MHz, $CDCl_3$): δ 8.19-8.12 (m, 2H), 7.34-7.26 (m, 3H), 7.17-7.11 (m, 2H), 7.10-7.03 (m, 2H), 6.80-6.71 (m, 2H), 5.74-5.68 (m, 1H), 5.58 (br s, 1H), 3.48-3.40 (m, 1H), 3.28-3.19 (m, 1H), 2.53 (s, 3H). MS (ESI) m/z $(M+H)^+$ 396.0.

Example 137

(S)—N-(4-amino-3,4-dioxo-1-phenylbutan-2-yl)-2-phenylbenzofuran-3-carboxamide (249)

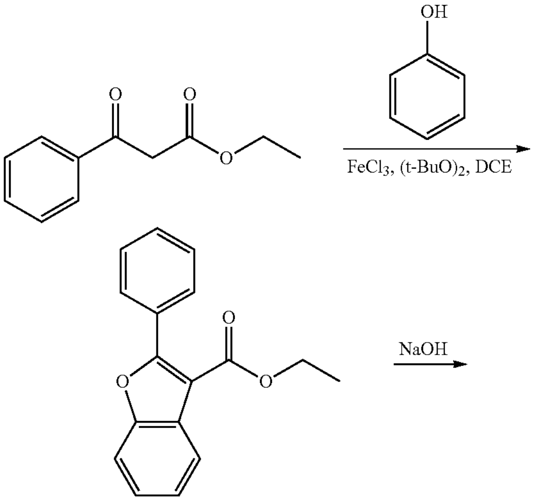

249A

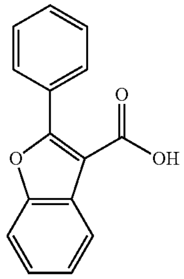

249B

To a mixture of ethyl 3-oxo-3-phenylpropanoate (2 g, 10.41 mmol, 1.8 mL), phenol (2.94 g, 31.23 mmol, 2.75 mL), and $FeCl_3.6H_2O$ (281 mg, 1.04 mmol) was added DCE (70 mL) under nitrogen at 25° C. Then di-tert-butylperoxide (3.04 g, 20.82 mmol, 3.85 mL) was dropped into the mixture under nitrogen. The reaction temperature was raised to 100° C. for 3 h. The temperature of the reaction was cooled to room temperature. The resulting reaction solution was quenched with 30 mL of saturated $NaHCO_3$ and extracted with DCM (20 mL×3). The extract was washed with 100 mL of saturated $NaHCO_3$ and 100 mL of 10% $Na_2S_2O_3$. The extract was dried over $Na_2SO_4$. The solvent was evaporated in vacuo to afford the crude products. The residue was purified by column chromatography ($SiO_2$, PE Petroleum ether/Ethyl acetate=10/1) to give compound 249A (1.5 g, yield: 54.08%) as a yellow oil. $^1H$ NMR (400 MHz, $CDCl_3$)

δ 8.09-7.99 (m, 3H), 7.57-7.45 (m, 4H), 7.39-7.32 (m, 2H), 4.41 (q, J=7.1 Hz, 2H), 1.43-1.39 (m, 3H). MS (ESI) m/z $(M+H)^+$267.0.

To a solution of compound 249A (600 mg, 2.25 mmol) in MeOH (30 mL) and $H_2O$ (15 mL) was added NaOH (270 mg, 6.75 mmol). The mixture was stirred at 25° C. for 16 h. The reaction mixture was concentrated and added 20 mL of water, the mixture was extracted with MTBE (10 mL×2), the aqueous layer was acidified by 1N HCl to pH ~2-3 at 0° C., and extracted with EtOAc (20 mL×2), the organic phase was dried over $Na_2SO_4$, concentrated to give a residue. Compound 249B (330 mg, yield: 61.78%) was obtained as a white solid, which was used to the next step without purification. $^1$H NMR (400 MHz, DMSO-$d_6$) δ 13.10 (br s, 1H), 8.05-7.92 (m, 3H), 7.72-7.62 (m, 1H), 7.57-7.47 (m, 3H), 7.41-7.34 (m, 2H). MS (ESI) m/z $(M+H)^+$239.0.

Compound 249 (65 mg, yield: 60.09%, white solid) was prepared as in Example 5 from the corresponding intermediate carboxylic acid, compound 249B. Compound 249: $^1$H NMR (400 MHz, DMSO-$d_6$) δ 9.08 (d, J=7.3 Hz, 1H), 8.23 (br s, 1H), 7.94 (br s, 1H), 7.69 (br s, 2H), 7.63 (d, J=7.9 Hz, 1H), 7.40 (br s, 3H), 7.39-7.20 (m, 8H), 5.56 (br s, 1H), 3.26 (br s, 1H), 2.79 (t, J=12.2 Hz, 1H). MS (ESI) m/z $(M+H)^+$ 413.1.

Example 138

Compounds 250-251

(S)—N-(4-amino-3,4-dioxo-1-phenylbutan-2-yl)-1-cyclopropyl-3-phenyl-1H-pyrazole-4-carboxamide (250)

(S)—N-(4-amino-3,4-dioxo-1-phenylbutan-2-yl)-1-(cyclopropylmethyl)-3-phenyl-1H-pyrazole-4-carboxamide (251)

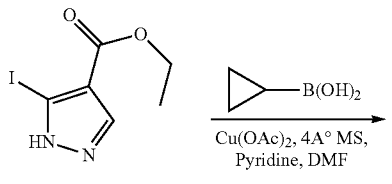

239A

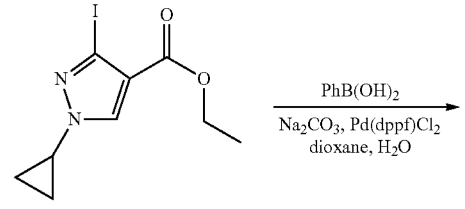

250A

-continued

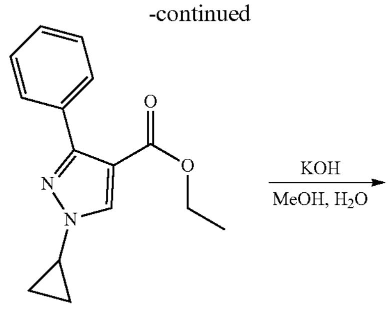

250C

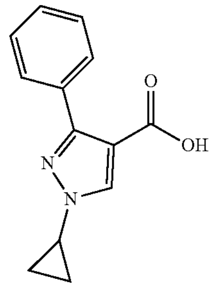

250D

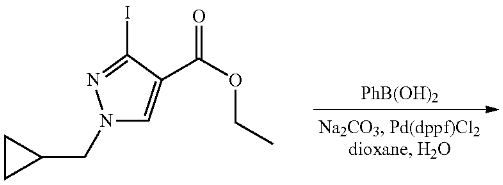

251A

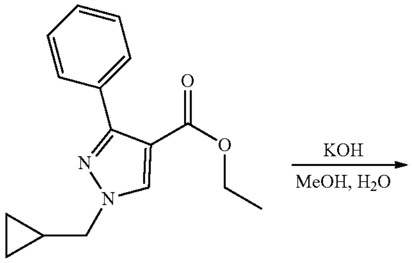

251C

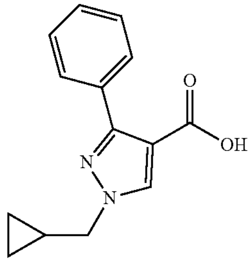

251D

To a mixture of compound 239A (2.0 g, 7.5 mmol) and cyclopropylboronic acid (1.29 g, 15.0 mmol) in DMF (40 mL) was added $Cu(OAc)_2$ (2.05 g, 11.28 mmol), 4A° MS (20 g) and pyridine (1.2 mL 15.0 mmol) at 25° C. under 02 (15 psi). The mixture was stirred at 25° C. for 38 h. Additional cyclopropylboronic acid (1.29 g, 15.04 mmol) was added to the mixture, which was stirred at 70-80° C. for 20 h. The reaction mixture was added $Cu(OAc)_2$ (2.05 g, 11.28 mmol) and stirred at 70-80° C. for 22 h. The mixture was filtered, the filtrate was diluted with $H_2O$ (200 mL), extracted with EA (150 mL×3), the combined organic phase was washed with brine (100 mL), dried over $Na_2SO_4$ and concentrated to give a residue. The residue was purified by FCC ($SiO_2$, Petroleum ether/Ethyl acetate=1:0 to 10:1) to afford compound 250A (552 mg, yield 24.0%) as white solid. Compound 250A: $^1$H NMR (DMSO-$d_6$, 400 MHz): δ 8.32 (s, 1H), 4.20 (q, J=7.1 Hz, 2H), 3.82 (tt, J=3.8, 7.4 Hz, 1H), 1.27 (t, J=7.1 Hz, 3H), 1.12-1.07 (m, 2H), 1.00-0.94 (m, 2H). MS (ESI) m/z $(M+H)^+$307.0.

To a mixture of compound 250A (544 mg, 1.7 mmol) and phenylboronic acid (434 mg, 3.5 mmol) in dioxane (50 mL) and $H_2O$ (10 mL) was added Pd(dppf)$Cl_2$ (130 mg, 0.18 mmol) and $Na_2CO_3$ (377 mg, 3.5 mmol) at 25° C. under $N_2$. The mixture was stirred at 80° C. for 12 h. The mixture was filtered over Celite. The filtrate was added EA (150 mL), and then washed with $H_2O$ (100 mL×3). The organic layer was dried over $Na_2SO_4$ and concentrated. The residue was purified by FCC ($SiO_2$, Petroleum ether/Ethyl acetate=1:0 to 5:1) to afford compound 250C (431 mg, yield 94.5%) as light yellow liquid. $^1$H NMR (DMSO-$d_6$, 400 MHz): δ 8.42 (s, 1H), 7.71-7.65 (m, 2H), 7.42-7.36 (m, 3H), 4.16 (q, J=7.1 Hz, 2H), 3.85 (tt, J=3.8, 7.4 Hz, 1H), 1.21 (t, J=7.1 Hz, 3H), 1.18-1.13 (m, 2H), 1.04-0.96 (m, 2H). MS (ESI) m/z $(M+H)^+$257.0.

To a mixture of compound 250C (425 mg, 1.7 mmol) in MeOH (10 mL) was added the mixture of KOH (931 mg, 16.6 mmol) and $H_2O$ (2 mL) in one portion at 25° C. The mixture was stirred at 70° C. for 1 h 40 mins. The reaction mixture was concentrated under reduced pressure to move MeOH, the aqueous phase was acidified with aqueous HCl (0.5M) till pH ~4-5. The precipitate was filtered and dried to afford compound 250D (333 mg, crude) as white solid, which was used directly for the next step without purification. $^1$H NMR (DMSO-$d_6$, 400 MHz): δ 12.24 (s, 1H), 8.35 (s, 1H), 7.73-7.69 (m, 2H), 7.41-7.34 (m, 3H), 3.83 (tt, J=3.7, 7.5 Hz, 1H), 1.17-1.12 (m, 2H), 1.02-0.97 (m, 2H).

Compound 250 (70.0 mg, yield 46.3%, yellow solid) was prepared as in Example 5 from the corresponding intermediate carboxylic acid, compound 250D. Compound 250: $^1$H NMR (DMSO-$d_6$, 400 MHz): δ 8.09 (s, 1H), 7.95-7.86 (m, 1H), 7.81-7.46 (m, 4H), 7.42-7.12 (m, 8H), 5.33 (s, 1H), 3.79 (s, 1H), 3.25-3.16 (m, 1H), 2.96-2.84 (m, 1H), 1.16-0.97 (m, 4H). MS (ESI) m/z $(M+H)^+$403.1.

Following the procedure used for compound 250D, compound 251D (150 mg, yield 95.64%, white solid) was prepared from the corresponding starting materials, compound 239A and bromomethylcyclopropane. Compound 251D: $^1$H NMR (DMSO-$d_6$, 400 MHz) δ 8.33 (s, 1H), 7.73 (dd, J=1.5, 7.9 Hz, 2H), 7.40-7.34 (m, 3H), 4.01 (d, J=7.1 Hz, 2H), 1.31 (br d, J=7.7 Hz, 1H), 0.57-0.52 (m, 2H), 0.42-0.37 (m, 2H).

Compound 251 (70 mg, yield 43.27%, white solid) was prepared as in Example 5 from the corresponding intermediate carboxylic acid, compound 251D. Compound 251: $^1$H NMR (DMSO-$d_6$, 400 MHz) δ 8.40 (br d, J=7.3 Hz, 1H), 8.15-8.05 (m, 2H), 7.82 (br s, 1H), 7.62-7.52 (m, 2H), 7.30 (br s, 4H), 7.28-7.20 (m, 4H), 5.33-5.24 (m, 1H), 4.06-3.95 (m, 2H), 3.17 (br dd, J=3.5, 13.9 Hz, 1H), 2.84 (br dd, J=9.9, 13.7 Hz, 1H), 1.34-1.18 (m, 1H), 0.58 (br d, J=6.8 Hz, 2H), 0.42 (br d, J=4.4 Hz, 2H). MS (ESI) m/z $(M+H)^+$417.2.

Example 139

(S)—N-(4-amino-3,4-dioxo-1-phenylbutan-2-yl)-1-(phenylethynyl)-1H-indole-3-carboxamide (252)

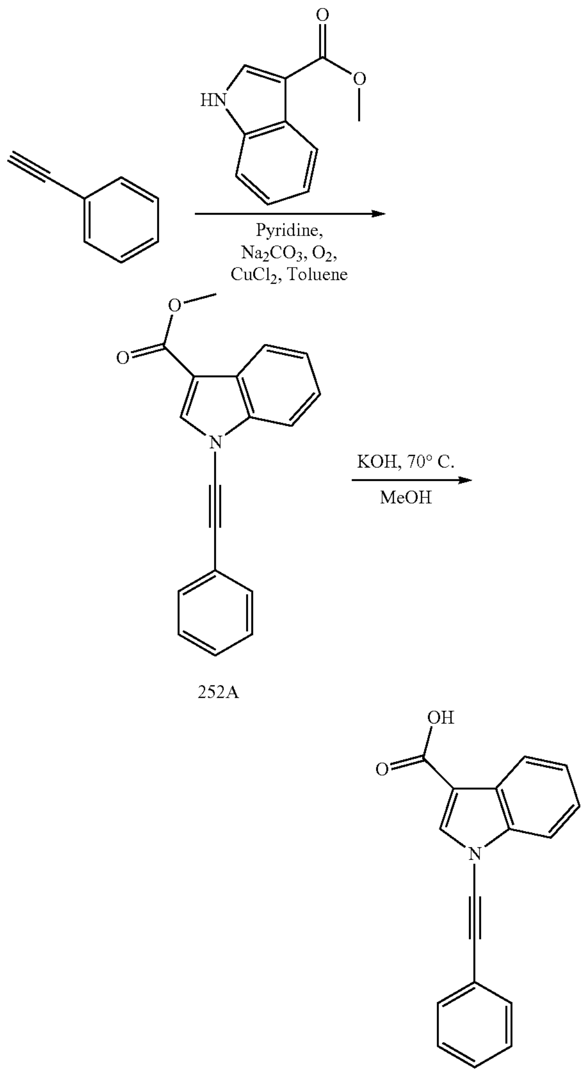

252A

252B

To a solution of methyl 1H-indole-3-carboxylate (5.0 g, 28.55 mmol) in toluene (50 mL) was added $Na_2CO_3$ (1.2 g, 11.42 mmol), $CuCl_2$ (153 mg, 1.14 mmol), pyridine (922 uL, 11.42 mmol), then ethynylbenzene (627 uL, 5.71 mmol) was added to the mixture. The mixture was heated to 70° C. and stirred for 4 h under 02 atmosphere. The reaction was diluted with $H_2O$ (15 mL) and EA (15 mL), filtered. The mixture was extracted with EA (15 mL×2), the organic layer was collected and washed with $NaHCO_3$ (25 mL×2), washed with brine (20 mL), dried over anhydrous $Na_2SO_4$, filtered, concentrated under reduced pressure. The product was purified by FCC (PE/EA:0 to 10/1) to afford compound 252A (630 mg, yield 40.08%) as light red solid. $^1$H NMR (DMSO-$d_6$, 400 MHz) δ 8.46 (s, 1H), 8.09 (d, J=7.7 Hz, 1H), 7.75 (d, J=7.9 Hz, 1H), 7.68-7.65 (m, 2H), 7.49-7.44 (m, 4H), 7.43-7.38 (m, 1H), 3.86 (s, 3H).

To a solution of compound 252A (300 mg, 1.09 mmol) in MeOH (10 mL) was added KOH (611 mg, 10.90 mmol) and then the mixture was stirred at 70° C. for 3 h. The reaction was diluted with $H_2O$ (5 mL) and evaporated under reduced pressure, the water phase was extracted with TBME (5 mL) and then the water phase was treat with HCl (1 M) until pH ~4. The mixture was extracted with EA (10 mL×3), the organic layer was collected, washed with brine (10 mL), dried over anhydrous $Na_2SO_4$, filtered and concentrated under reduced pressure. Compound 252B (240 mg, yield 84.27%) was obtained as white solid. $^1H$ NMR (DMSO-$d_6$, 400 MHz) δ 8.37 (s, 1H), 8.11 (d, J=7.5 Hz, 1H), 7.75 (d, J=7.9 Hz, 1H), 7.69-7.65 (m, 2H), 7.50-7.45 (m, 4H), 7.45-7.36 (m, 2H).

Compound 252 (70 mg, yield 24.39%, yellow solid) was prepared as in Example 5 from intermediate compound 252B. Compound 252: $^1H$ NMR (DMSO-$d_6$, 400 MHz) δ8.61 (d, J=7.5 Hz, 1H), 8.45 (s, 1H), 8.14-8.05 (m, 2H), 7.85 (s, 1H), 7.73 (d, J=8.2 Hz, 1H), 7.67 (dd, J=2.4, 7.3 Hz, 2H), 7.50-7.46 (m, 3H), 7.42 (t, J=7.7 Hz, 1H), 7.38-7.35 (m, 2H), 7.33-7.29 (m, 3H), 7.23-7.19 (m, 1H), 5.47-5.36 (m, 1H), 3.23 (dd, J=3.6, 14.0 Hz, 1H), 2.91 (dd, J=10.0, 13.8 Hz, 1H). MS (ESI) m/z $(M+H)^+$436.1.

Example 140

(S)—N-(4-amino-3,4-dioxo-1-phenylbutan-2-yl)-4-(3-fluorophenyl)-2-methyloxazole-5-carboxamide (254)

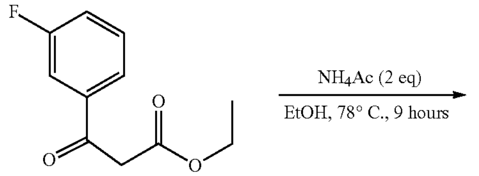

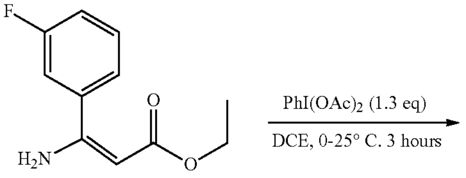

254A

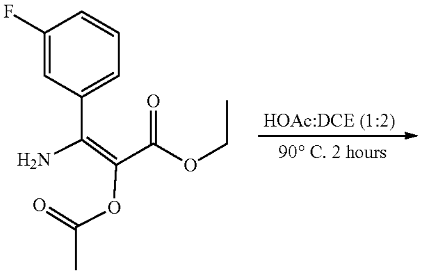

254B

-continued

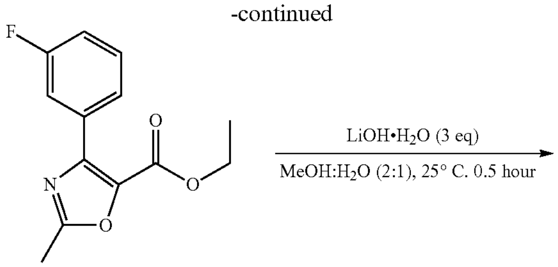

544

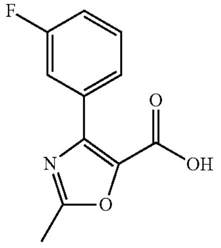

254D

To a solution of ethyl 3-(3-fluorophenyl)-3-oxopropanoate (3.00 g, 14.27 mmol) in EtOH (40 mL) was added $CH_3COONH_4$ (2.20 g, 28.54 mmol), then the mixture was stirred at 78° C. for 9 hours. The reaction mixture was concentrated under reduced pressure to remove the solvent. The residue was diluted with EA (100 mL) and washed with sat. $NaHCO_3$ solution (30 mL×3) and saturated aqueous NaCl (30 mL×3). The organic layer were dried over anhydrous $Na_2SO_4$, filtered and concentrated under reduced pressure to give a residue. The residue was purified flash column chromatography (PE:EA=20/1 to 10:1). Compound 254A (2.40 g, 80.39% yield) was obtained as yellow oil. $^1H$ NMR (400 MHz, $CDCl_3$): δ 7.38-7.35 (m, 1H), 7.35-7.32 (m, 1H), 7.22 (d, J=9.6 Hz, 1H), 7.13-7.09 (m, 1H), 4.93 (s, 1H), 4.19-4.13 (m, 2H), 1.29-1.26 (m, 3H). MS (ESI) m/z $(M+1)^+$210.1.

To a mixture of compound 254A (2.00 g, 9.56 mmol) in DCE (25 mL) was added $PhI(OAc)_2$ (4.00 g, 12.43 mmol) at 0° C. under $N_2$ in five portions, the mixture was stirred at 0° C. for 3 h and then warmed to 25° C. slowly. The mixture was then stirred at 25° C. for 0.5 h. The reaction mixture was quenched with saturated aqueous $NaHCO_3$ (150 mL) at 0° C., warmed to 25° C. slowly, and extracted with DCM (70 mL×3). The combined organic layers were dried over anhydrous $Na_2SO_4$, filtered and concentrated under reduced pressure to give the residue. The residue was purified by column chromatography ($SiO_2$, Petroleum ether/Ethyl acetate=20:1 to 10:1). Compound 254B (1.24 g, 48.53% yield) was obtained as white solid. $^1H$ NMR (400 MHz, $CDCl_3$): δ 7.37-7.34 (m, 1H), 7.22-7.00 (m, 1H), 7.17-7.13 (m, 1H), 7.12-7.09 (m, 1H), 4.23-4.18 (m, 2H), 1.94 (s, 3H), 1.29-1.26 (m, 3H). MS (ESI) m/z $(M+1)^+$268.1.

A mixture of compound 254B (1.20 g, 4.49 mmol) in DCE (20 mL) and $CH_3COOH$ (10 mL) was stirred at 90° C. for 2 hrs. The reaction mixture was concentrated under reduced pressure to remove the solvent and to give the residue. The residue was purified by flash column chromatography (PE:EA=20/1 to 10/1). Compound 544 (360.0 mg, 32.07% yield) was obtained as a white solid. $^1H$ NMR (400 MHz, $CDCl_3$) δ 7.87-7.86 (m, 1H), 7.83-7.80 (m, 1H), 7.41-7.39 (m, 1H), 7.13-7.09 (m, 1H), 4.43-4.37 (m, 2H), 2.58 (s, 3H), 1.40-1.37 (m, 3H). MS (ESI) m/z $(M+1)^+$250.1.

To a mixture of ethyl compound 544 (350.0 mg, 1.40 mmol) in MeOH (10 mL) and $H_2O$ (5 mL) was added $LiOH.H_2O$ (235.0 mg, 5.60 mmol) in one portion and the mixture was stirred at 25° C. for 0.5 hours. The reaction mixture was concentrated under reduced pressure to remove MeOH. The residue was diluted with $H_2O$ (20 mL), adjusted to pH ~3 with 1N HCl, and then extracted with EtOAc (50 mL×3). The combined organic layers were washed with brine (30 mL), dried over anhydrous $Na_2SO_4$, filtered and concentrated under reduced pressure to give intermediate compound 254D (300.0 mg, 96.88% yield) as a white solid. $^1$H NMR (400 MHz, DMSO-$d_6$) δ 7.92-7.87 (m, 1H), 7.52-7.46 (m, 1H), 7.29-7.24 (m, 1H), 2.51 (s, 3H).

Compound 254 (90.3 mg, 58.91% yield, white solid) was prepared as in Example 5 from the corresponding intermediate carboxylic acid, compound 254D. Compound 254: $^1$H NMR (400 MHz, $CDCl_3$) δ 7.98-7.95 (m, 1H), 7.94-7.91 (m, 1H), 7.39-7.35 (m, 1H), 7.33-7.30 (m, 1H), 7.29-7.26 (m, 2H), 7.15-7.13 (m, 2H), 7.09-7.04 (m, 1H), 6.79 (d, J=7.2 Hz, 1H), 6.76 (s, 1H), 5.74-5.69 (m, 1H), 5.53 (s, 1H), 3.47-3.42 (m, 1H), 3.27-3.22 (m, 1H), 2.54 (s, 3H). MS (ESI) m/z $(M+1)^+$396.1.

Example 141

(S)—N-(4-amino-3,4-dioxo-1-phenylbutan-2-yl)-4-phenyl-2-(trifluoromethyl)oxazole-5-carboxamide (255)

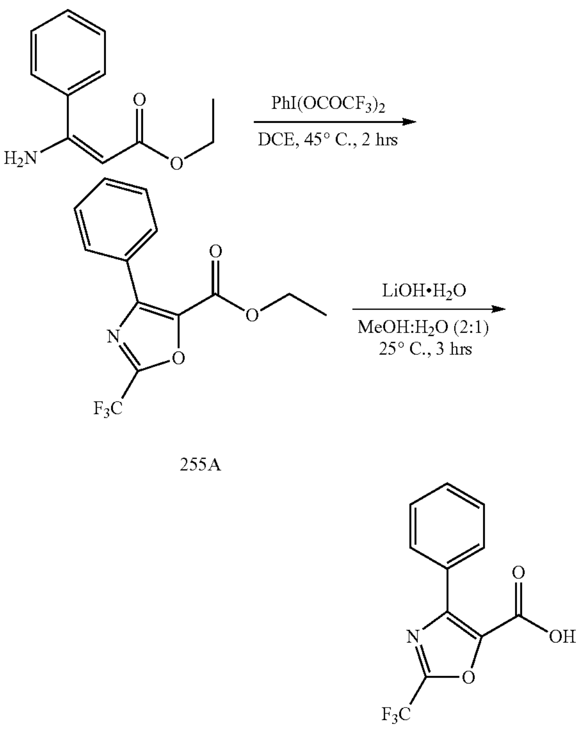

255A

255B

To a mixture of ethyl (E)-3-amino-3-phenylacrylate (1.5 g, 7.84 mmol) in DCE (400 mL) was added phenyliodine bis(2,2,2-trifluoroacetate) (4.38 g, 10.19 mmol) in three portions at 45° C. under $N_2$, the mixture was stirred at 45° C. for 2 hours. The reaction mixture was cooled to 25° C. and concentrated under reduced pressure to give a residue, which was purified by column chromatography ($SiO_2$, Petroleum ether/Ethyl acetate=100:1 to 10:1) to afford compound 255A (650 mg, 28.43% yield) as a white solid. $^1$H NMR (400 MHz, $CDCl_3$): δ 8.11-8.05 (m, 2H), 7.50-7.45 (m, 3H), 4.44 (q, J=7.2 Hz, 2H), 1.40 (t, J=7.2 Hz, 3H). MS (ESI) m/z $(M+H)^+$285.9.

Compound 255B (200 mg, 51.2% purity, yellow oil) was prepared as in Example 85 from compound 255A. Compound 255B: MS (ESI) m/z $(M+H)^+$258.0.

Compound 255 (7.0 mg, 9.89% yield, off-white solid) was prepared as in Example 5 from the corresponding intermediate carboxylic acid, compound 255B. Compound 255: $^1$H NMR (400 MHz, $CDCl_3$): δ 8.17-8.08 (m, 2H), 7.48-7.41 (m, 3H), 7.34-7.28 (m, 3H), 7.17-7.10 (m, 2H), 6.88-6.80 (m, 1H), 6.77 (br s, 1H), 5.78-5.71 (m, 1H), 5.55 (br s, 1H), 3.50-3.42 (m, 1H), 3.27-3.20 (m, 1H). MS (ESI) m/z $(M+H)^+$432.2.

Example 142

(S)—N-(4-amino-3,4-dioxo-1-phenylbutan-2-yl)-1-(benzo[d]oxazol-2-yl)-5-methyl-1H-pyrazole-3-carboxamide (256)

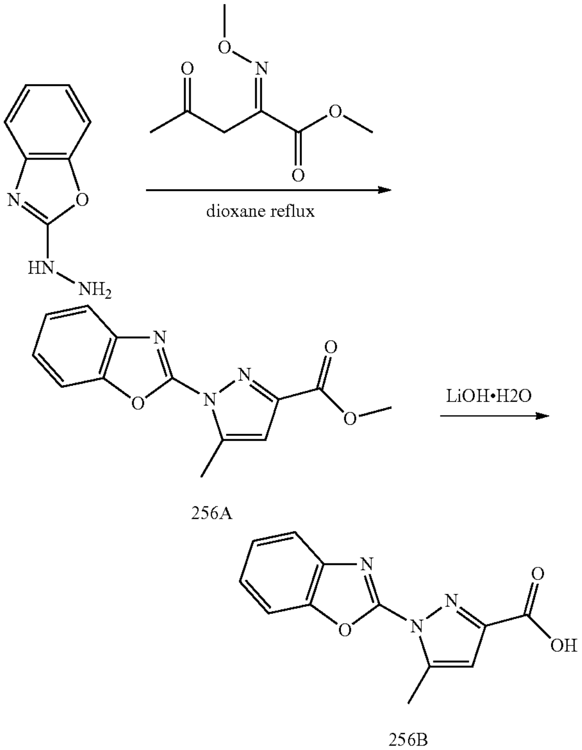

256A

256B

A mixture of 2-hydrazineylbenzo[d]oxazole (320 mg, 2.15 mmol) and methyl (E)-2-(methoxyimino)-4-oxopentanoate (447 mg, 2.58 mmol) in dioxane (10 mL) was heated to 110° C. for 12 hrs. The mixture was concentrated, the residue was purified by preparatory-TLC (Petroleum ether: Ethyl acetate=2:1) to give compound 256A (0.12 g, yield: 16.6%) as yellow oil.

A mixture of compound 256A (120 mg, 466 umol) and $LiOH.H_2O$ (17.6 mg, 420 umol) in THF (5 mL), $H_2O$ (1 mL) was stirred at 25° C. for 20 min. The organic solvent was removed under reduced pressure, the water layer was extracted with ethyl acetate (2 mL), and then adjusted to pH ~6 with 1N HCl to give a precipitate, the solid was filtered and dried to give compound 256B (90 mg, yield: 79.3%) as white solid. $^1H$ NMR (400 MHz, DMSO-$d_6$) δ 8.02-7.87 (m, 2H), 7.61 (dq, J=1.4, 7.7 Hz, 2H), 7.11 (s, 1H), 2.43 (s, 3H).

Compound 256 (22.2 mg, yield: 44.6%, white solid) was prepared as in Example 5 from the corresponding intermediate carboxylic acid, compound 256B. Compound 256: $^1H$ NMR (400 MHz, DMSO-$d_6$) δ 8.97 (s, 1H), 7.82 (br s, 1H), 7.64 (br s, 1H), 7.55-7.44 (m, 2H), 7.30-7.21 (m, 2H), 6.94 (q, J=7.9 Hz, 4H), 6.90-6.83 (m, 1H), 6.64 (s, 1H), 5.37 (dd, J=4.1, 8.0 Hz, 1H), 3.39 (dd, J=4.1, 14.2 Hz, 1H), 2.83 (dd, J=8.4, 14.1 Hz, 1H), 2.24 (s, 3H). MS (ESI) m/z $(M+H)^+$ 418.1.

Example 143

(S)—N-(4-amino-3,4-dioxo-1-phenylbutan-2-yl)-3-methyl-5-phenyl-1H-pyrazole-4-carboxamide (257)

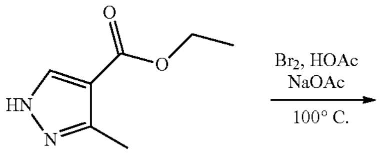

257A

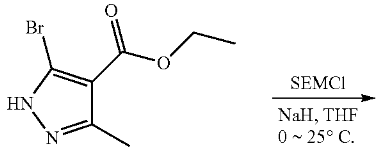

257B

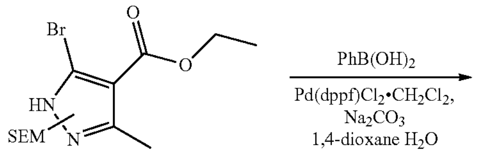

257C

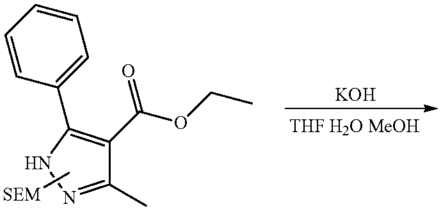

257D

-continued

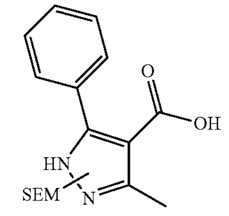

257E

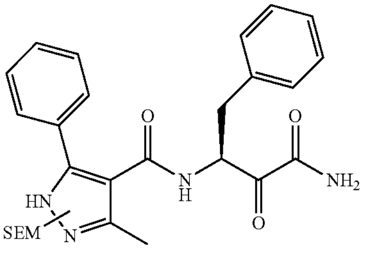

257G

To a solution of ethyl 3-oxobutanoate (20.0 g, 153.7 mmol) in THF (150 mL) was added DMF-DMA (19.2 g, 161.4 mmol). The mixture was stirred at 70° C. for 2 hours. The reaction mixture was concentrated under reduced pressure to give a residue. To a solution of the crude product dissolving in EtOH (150 mL) was added drop-wise $NH_2NH_2.H_2O$ (9.2 g, 184.4 mmol). The mixture was stirred at 80° C. for 16 hours. The reaction mixture was concentrated under reduced pressure to remove EtOH. The residue was diluted with brine 80 mL and extracted with ethyl acetate (200 mL×2). The combined organic layers were dried over $MgSO_4$, filtered and concentrated under reduced pressure to afford compound 257A (21.0 g, yield 87.8%) as light green solid. $^1H$ NMR ($CDCl_3$, 400 MHz): δ 7.96 (s, 1H), 4.29 (q, J=7.2 Hz, 2H), 2.55 (s, 3H), 1.34 (t, J=7.2 Hz, 3H). MS (ESI) m/z $(M+H)^+$154.8.

To a solution of compound 257A (12.0 g, 77.8 mmol) in AcOH (120 mL) was added NaOAc (19.2 g, 233.5 mmol) and $Br_2$ (12 mL, 233.5 mmol) at 25° C. The mixture was stirred at 100° C. for 16 hours under $N_2$. The reaction mixture was concentrated under reduced pressure to remove solvent. The residue was diluted with water 150 mL and extracted with ethyl acetate (200 mL×2). The combined organic extracts were washed with saturated aqueous $NaHCO_3$ (80 mL×2), dried over $Na_2SO_4$, filtered and concentrated to dryness under reduced pressure to dryness. The crude product was purified by flash column (gradient eluent: petroleum ether/ethyl acetate from 100/0 to 50/50) to afford compound 257B (8.2 g, yield 43.3%) as light yellow solid. $^1H$ NMR ($CDCl_3$, 400 MHz): δ 10.89 (br s, 1H), 4.34 (q, J=7.2 Hz, 2H), 2.64 (s, 3H), 1.38 (t, J=7.2 Hz, 3H). MS (ESI) m/z $(M+H)^+$235.1

To a solution of compound 257B (5.0 g, 21.5 mmol) in THF (50 mL) was added NaH (944 mg, 23.6 mmol, 60% purity) at 0° C. and the reaction stirred for 30 minutes. SEM-Cl (3.9 g, 23.6 mmol) was added, and the reaction stirred at 25° C. for 16 hours. The reaction was quenched with water (30 ml) and extracted with ethyl acetate (50 mL×3). The organic extract was dried over $MgSO_4$ and concentrated in vacuo. Compound 257C (6.2 g, yield 78.1%, colorless oil): $^1H$ NMR ($CDCl_3$, 400 MHz): δ 5.52-5.39 (m, 2H), 4.35 (q, J=7.2 Hz, 2H), 3.62 (td, J=8.4, 17.2 Hz, 2H), 2.66-2.44 (m, 3H), 1.40 (dt, J=2.4, 7.2 Hz, 3H), 0.92 (td, J=8.4, 13.6 Hz, 2H), 0.08--0.05 (m, 9H). MS (ESI) m/z $(M+H)^+$364.9.

To a solution consisting of compound 257C (2.0 g, 5.5 mmol), phenylboronic acid (871.8 mg, 7.2 mmol), $Na_2CO_3$ (1.8 g, 16.5 mmol) in 1,4-dioxane (20 mL) and $H_2O$ (4 mL) was added $Pd(dppf)Cl_2.CH_2Cl_2$ (89.9 mg, 110.0 umol) at 25° C. and the reaction mixture stirred for 10 minutes. The reaction mixture was heated to 80° C. for 16 hours under $N_2$. The mixture was concentrated under reduced pressure at 40° C. The reaction mixture was quenched with brine (40 mL) and extracted with ethyl acetate (30 mL×3). The combined organic extracts were dried over $Na_2SO_4$, filtered, and concentrated to dryness under reduced pressure. The crude product was purified by flash column (Petroleum ether:Ethyl acetate=100:01:1) to give compound 257D (1.6 g, yield 79.4%) as light yellow solid. $^1H$ NMR ($CDCl_3$, 400 MHz): δ 7.62-7.53 (m, 1H), 7.48-7.34 (m, 4H), 5.48 (s, 1H), 5.18 (s, 1H), 4.25-4.06 (m, 2H), 3.62 (td, J=8.0, 15.6 Hz, 2H), 2.67-2.50 (m, 3H), 1.23-1.03 (m, 3H), 0.96-0.83 (m, 2H), 0.03-0.07 (m, 9H). MS (ESI) m/z $(M+H)^+$361.1.

KOH (2.5 g, 44.4 mmol) was added to a solution consisting of compound 257D (1.6 g, 4.4 mmol), THF (10 mL), $H_2O$ (5 mL) and MeOH (10 mL). The resultant mixture was stirred at 25° C. for 16 hours. The resultant mixture was stirred at 75° C. for 48 hours. The reaction solution was concentrated under reduced pressure. 2N HCl (30 mL) was added, and extracted with EtOAc (30 mL×3). Combined EtOAc extractions were washed with brine (20 mL), dried over $MgSO_4$, filtered and concentrated. The crude product was purified by flash column (Petroleum ether:Ethyl acetate=100: 0-3:2) to give compound 257E (1.0 g, yield 62.8%) as a colorless oil. $^1H$ NMR ($CDCl_3$, 400 MHz): δ 7.63-7.58 (m, 1H), 7.48-7.36 (m, 4H), 5.49 (s, 1H), 5.17 (s, 1H), 3.62 (td, J=8.4, 18.4 Hz, 2H), 2.66 (s, 1.5H), 2.52 (s, 1.5H), 0.95-0.83 (m, 2H), 0.00--0.06 (m, 9H). MS (ESI) m/z $(M+H)^+$333.2.

Intermediate compound 257G (150 mg, crude, white solid) was prepared as in Example 5 from the corresponding intermediate carboxylic acid, compound 257E. Compound 257G: $^1H$ NMR (DMSO-$d_6$, 400 MHz): δ 8.68-8.61 (m, 0.1H), 8.26-7.88 (m, 1H), 7.59-7.09 (m, 10H), 5.52-5.41 (m, 1H), 5.24 (s, 1H), 3.69-3.52 (m, 1H), 2.42-2.28 (m, 1H), 2.27-2.19 (m, 2H), 0.96-0.79 (m, 2H), 0.08-0.02 (m, 4.4H), 0.02--0.06 (m, 4.3H). MS (ESI) m/z $(M+H)^+$507.2.

To a solution consisting of compound 257G (100 mg, 0.20 mmol), in EA (20 mL) was added HCl/EtOAc (4M, 2 mL) at 25° C. The mixture was stirred at 25° C. under $N_2$ for 16 hours. The reaction solution was concentrated under reduced pressure to give the crude product. The crude product was purified by preparatory-HPLC (0.05% ammonia hydroxide) to give 257 (15 mg, yield 19.3%) as a white solid. Compound 257: $^1H$ NMR (DMSO-$d_6$, 400 MHz): δ 12.67 (br.s., 1H), 7.85-7.72 (m, 2H), 7.64-7.57 (m, 1H), 7.57-7.49 (m, 2H), 7.38-7.17 (m, 8H), 5.45-5.32 (m, 1H), 3.21 (dd, J=4.0, 14.0 Hz, 1H), 2.85 (dd, J=9.2, 14.0 Hz, 1H), 2.19 (s, 3H). MS (ESI) m/z $(M+H)^+$377.1.

Example 144

(S)—N-(4-amino-3,4-dioxo-1-phenylbutan-2-yl)-4-fluoro-1-phenyl-1H-pyrazole-5-carboxamide (258)

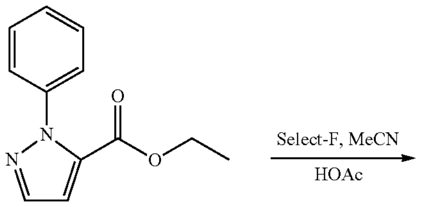

258A

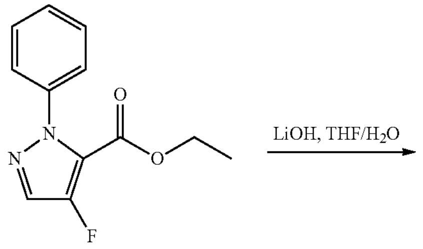

258C

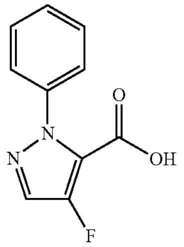

258D

To a mixture of ethyl 1H-pyrazole-5-carboxylate (5.00 g, 35.68 mmol), phenylboronic acid (6.53 g, 53.52 mmol), Py (3.10 g, 39.25 mmol, 3.17 mL) in DCM (70 mL) was added 4A° MS (20.0 g) and $Cu(OAc)_2$ (7.13 g, 39.25 mmol), the mixture was stirred at 30° C. for 20 h. The reaction mixture was filtered, the filtrate was concentrated in vacuo. The residue was purified by flash silica gel chromatography (PE:EA=1:0 to 0:1) to give the compound 258A (1.10 g, yield: 14.3%) was obtained as a rofous oil. Compound 258A: $^1H$ NMR (400 MHz, DMSO-d6) δ 7.81 (d, J=2.0 Hz, 1H), 7.53-7.40 (m, 5H), 7.09 (d, J=2.0 Hz, 1H), 4.17 (q, J=7.0 Hz, 2H), 1.15 (t, J=7.0 Hz, 3H).

To a solution of compound 258A (1.00 g, 4.62 mmol) in MeCN (60 mL) was added $CH_3COOH$ (20 mL), and then Select F (4.91 g, 13.86 mmol) was added in the mixture. The mixture was stirred at 105° C. for 21 h under $N_2$ atmosphere. The mixture was cooled to room temperature and the volatiles were removed in vacuo. The residue was purified by flash silica gel chromatography (PE:EA=1:0 to 10:1) to give the compound 258C (194 mg, yield: 17.9%) was obtained as a colorless oil. $^1H$ NMR (400 MHz, CHLOROFORM-d) δ 7.71-7.56 (m, 1H), 7.51-7.36 (m, 5H), 4.29 (q, J=7.2 Hz, 2H), 1.27 (t, J=7.1 Hz, 3H).

To a solution of compound 258C (190 mg, 811.17 umol) in THF (15 mL) was added $LiOH.H_2O$ (170 mg, 4.06 mmol) in $H_2O$ (5 mL). The mixture was stirred at 25° C. for 20.3 h. The reaction mixture was diluted with MTBE (15 mL) and extracted with $H_2O$ (15 mL×3). The combined aqueous layers were adjusted pH ~3 by addition 1N HCl, and then the aqueous layer was extracted with EA (20 mL×3). The combine organic layer was washed with brine (15 mL×2), dried over $Na_2SO_4$, filtered and concentrated under reduced pressure to give the compound 258D (160 mg, yield: 95.7%) was obtained as a white solid. $^1H$ NMR (400 MHz, CHLOROFORM-d) δ 7.76-7.60 (m, 1H), 7.55-7.33 (m, 5H).

Compound 258 (25 mg, yield: 44.3%, light yellow solid) was prepared as in Example 5 from the corresponding starting materials, compounds 258D and 12G. Compound 258: $^1H$ NMR (400 MHz, DMSO-$d_6$) δ 9.33 (d, J=7.7 Hz, 1H), 8.18 (s, 1H), 8.00-7.85 (m, 2H), 7.39-7.36 (m, 2H), 7.33-7.27 (m, 5H), 7.26-7.19 (m, 3H), 5.42-5.28 (m, 1H), 3.22 (br dd, J=3.3, 14.1 Hz, 1H), 2.82 (br dd, J=10.5, 13.8 Hz, 1H).

Example 145

Compounds 259-261

(S)—N-(4-amino-3,4-dioxo-1-phenylbutan-2-yl)-2-methyl-5-phenyl-2H-1,2,3-triazole-4-carboxamide (259)

(S)—N-(4-amino-3,4-dioxo-1-phenylbutan-2-yl)-1-methyl-5-phenyl-1H-1,2,3-triazole-4-carboxamide (260)

(S)—N-(4-amino-3,4-dioxo-1-phenylbutan-2-yl)-1-methyl-4-phenyl-1H-1,2,3-triazole-5-carboxamide (261)

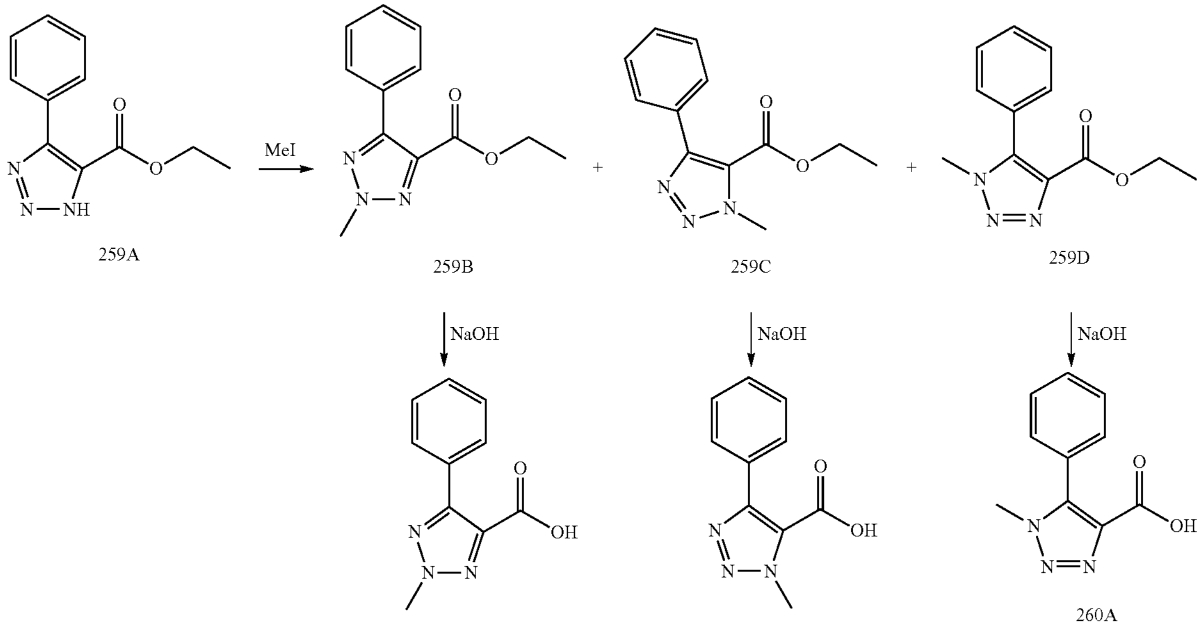

259A 259B 259C 259D 259E 261A 260A

To a solution of benzaldehyde (5 g, 47.12 mmol, 4.76 mL) in DMF (100 mL) was added N,N-diethylethanamine; hydrochloride (19.46 g, 141.36 mmol) $NaN_3$ (9.19 g, 141.36 mmol) and ethyl 2-cyanoacetate (5.33 g, 47.12 mmol, 5.03 mL). The reaction mixture was heated at 70 C for 18 h under nitrogen protection. After completion of the reaction, the mixture was poured into water (500 mL) and extracted with $CHCl_3$:i-PrOH=3:1 (50 mL×4). The organic layers were dried over $Na_2SO_4$, filtered and concentrated. The residue was purified by chromatography (PE:EA=5:1). Compound 259A (4 g, yield: 38.3%) was obtained as a yellow oil. $^1H$ NMR (400 MHz, $CDCl_3$) δ 7.81 (dd, J=2.9, 6.4 Hz, 2H), 7.49-7.38 (m, 3H), 4.38 (q, J=7.2 Hz, 2H), 1.43-1.26 (m, 3H). MS (ESI) m/z $(M+H)^+$217.9.

MeI (6.53 g, 46.03 mmol, 2.86 mL) was added to a solution of compound 259A (4 g, 18.41 mmol) and $K_2CO_3$ (5.09 g, 36.82 mmol) in $CH_3CN$ (50 mL) and DMF (50 mL). The reaction mixture was stirred at 25° C. for 16 h. The mixture was filtered, the filtrate was added with $H_2O$ (200 mL), extracted with EA (50 mL×3). The organic phase was dried over $Na_2SO_4$, filtered and concentrated to give a residue. The residue was purified by column chromatography ($SiO_2$, Petroleum ether/Ethyl acetate=PE ~10/1 to 2/1). Compound 259B (1.8 g, yield: 41.9%, white solid): $^1H$ NMR (400 MHz, $CDCl_3$) δ 7.83-7.77 (m, 2H), 7.45-7.36 (m, 3H), 4.45-4.35 (m, 2H), 4.27 (s, 3H), 1.40-1.31 (m, 3H). Compound 259C (1.2 g, yield: 27.9%, white solid): $^1H$ NMR (400 MHz, $CDCl_3$) δ 7.75-7.67 (m, 2H), 7.48-7.38 (m, 3H), 4.37-4.30 (m, 5H), 1.27 (t, J=7.1 Hz, 3H). Compound 259D (700 mg, yield: 16.3%, white solid): $^1H$ NMR (400 MHz, $CDCl_3$) δ 7.55-7.48 (m, 3H), 7.40-7.35 (m, 2H), 4.36-4.25 (m, 2H), 3.95 (s, 3H), 1.31-1.23 (m, 3H).

To a solution of compound 259B (400 mg, 1.73 mmol) in MeOH (15 mL) and $H_2O$ (15 mL) was added NaOH (345.95 mg, 8.65 mmol). The mixture was stirred at 25° C. for 1 h. The reaction mixture was acidified by 1N HCl to pH ~2~3 at 0° C. and white precipitate was formed. The solid was collected by filtration, the filtrate was extracted with EtOAc (20 mL×2), the organic phase was dried over $Na_2SO_4$, filtered and concentrated to give a residue, the residue was combined with the solid to give compound 259E (337 mg, yield: 95.9%) as a white solid. $^1H$ NMR (400 MHz, DMSO-$d_6$) δ 7.82-7.69 (m, 2H), 7.46-7.34 (m, 3H), 4.22 (s, 3H). MS (ESI) m/z $(M+H)^+$204.0.

Compound 259 (78 mg, yield: 77.2%, white solid) was prepared as in Example 5 from the corresponding intermediate carboxylic acid, compound 259E. Compound 259: $^1H$ NMR (400 MHz, DMSO-$d_6$) δ 8.81 (br d, J=7.5 Hz, 1H), 8.13 (br s, 1H), 7.87 (br s, 1H), 7.70 (br s, 2H), 7.38 (br s, 3H), 7.29 (br d, J=4.0 Hz, 4H), 7.23 (br d, J=4.3 Hz, 1H), 5.47 (br s, 1H), 4.25 (s, 3H), 3.21 (br d, J=10.8 Hz, 1H), 3.04-2.91 (m, 1H). MS (ESI) m/z $(M+H)^+$378.1.

Following the procedure used for compound 259E, intermediate compounds 261A and 260A were prepared from compound 259C and 259D, respectively. Compound 261A (240 mg, yield: 91.6%, white solid): $^1$H NMR (400 MHz, $CDCl_3$) δ 7.69-7.63 (m, 2H), 7.38-7.29 (m, 3H), 4.26 (s, 3H). MS (ESI) m/z $(M+H)^+$203.9. Compound 260A (260 mg, yield: 98.5%, white solid): $^1$H NMR (400 MHz, DMSO-$d_6$) δ 12.81 (br s, 1H), 7.60-7.42 (m, 5H), 4.02-3.74 (m, 3H). MS (ESI) m/z $(M+H)^+$204.0.

Following the procedure used for compound 259, compounds 261 and 260 were prepared from the corresponding intermediate carboxylic acid, compounds 261A and 260A, respectively. Compound 260 (75 mg, yield: 72.4%, white solid): $^1$H NMR (400 MHz, DMSO-$d_6$) δ 8.63 (d, J=7.5 Hz, 1H), 8.09 (s, 1H), 7.84 (s, 1H), 7.51-7.41 (m, 5H), 7.32-7.20 (m, 5H), 5.45-5.33 (m, 1H), 3.91 (s, 3H), 3.23-3.14 (m, 1H), 3.11-2.97 (m, 1H). MS (ESI) m/z $(M+H)^+$378.1.

Compound 261 (52 mg, yield: 59.5%, yellow solid): $^1$H NMR (400 MHz, DMSO-$d_6$) δ 9.54 (dd, J=7.9 Hz, 1H), 8.26 (s, 1H), 7.99 (s, 1H), 7.60 (dd, J=3.0, 6.5 Hz, 2H), 7.36-7.25 (m, 8H), 5.58 (dd, J=3.3, 7.7, 10.9 Hz, 1H), 3.83 (s, 3H), 3.29 (dd, J=3.3 Hz, 1H), 2.77 (dd, J=10.9, 14.0 Hz, 1H). MS (ESI) m/z $(M+H)^+$378.1.

Example 146

(S)—N-(4-amino-3,4-dioxo-1-phenylbutan-2-yl)-5-phenyl-1H-1,2,3-triazole-4-carboxamide (262)

Compound 262 (8.1 mg, 20.36% yield, white solid) was prepared as in Example 5 from the corresponding intermediate carboxylic acid, compound 204A. Compound 262: $^1$H NMR (400 MHz, DMSO-$d_6$) δ 8.38-7.89 (m, 2H), 7.87-7.69 (m, 2H), 7.63-7.34 (m, 4H), 7.31-7.06 (m, 6H), 5.55-5.42 (m, 1H), 3.32-3.24 (m, 1H), 3.12-3.06 (m, 1H). MS (ESI) m/z $(M+H)^+$364.1.

Example 147

(S)—N-(4-amino-3,4-dioxo-1-phenylbutan-2-yl)-1-phenyl-1H-1,2,3-triazole-5-carboxamide (263)

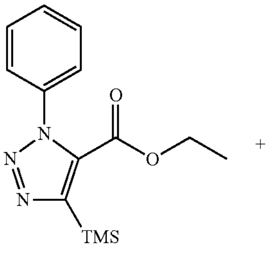

263A

-continued

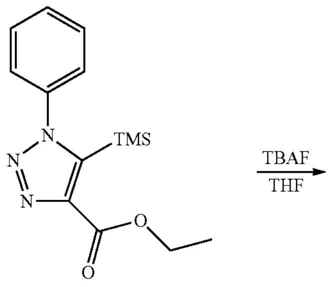

263B

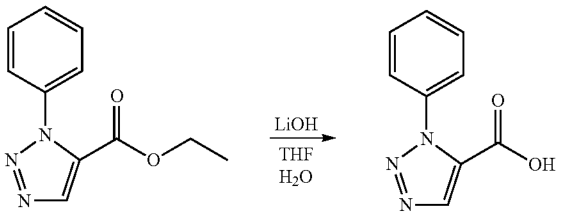

263C

263E

To a solution of azidobenzene (0.5M, 11.8 mL) in toluene (20 mL) was added ethyl 3-(trimethylsilyl)propiolate (1 g, 5.87 mmol). The mixture was stirred at 100° C. for 12 h. The solvent was removed in vacuo to afford a mixture of compound 263A and 263B (1.7 g, crude) as yellow oil, which was used directly for the next step without purification. MS (ESI) m/z $(M+H)^+$290.1.

To a mixture of 263A and 263B (1.7 g, 5.87 mmol) in THF (20 mL) was added TBAF (1M, 8.8 mL). The mixture was stirred at 25° C. for 12 h. The reaction was washed with $H_2O$ (40 mL), extracted with EtOAc (20 mL×3). The organics were collected and concentrated. The residue was purified by column (PE:EA=5:1) to give compound 263C (400 mg, yield: 31.37%) as yellow oil; $^1$H NMR ($CDCl_3$, 400 MHz): δ 8.26 (s, 1H), 7.56-7.47 (m, 5H), 4.29 (q, J=7.2 Hz, 2H), 1.28 (t, J=7.2 Hz, 3H).

To a solution of compound 263C (400 mg, 1.84 mmol) in $H_2O$ (5 mL) and THF (5 mL) was added $LiOH.H_2O$ (386 mg, 9.20 mmol). The mixture was stirred at 25° C. for 12 h. The reaction was acidified with 1N HCl to pH ~3. The mixture was extracted with EtOAc (20 mL×2). The organics were collected, washed with brine (20 mL), dried with $Na_2SO_4$, filtered and concentrated to afford compound 263E (340 mg, yield: 97.68%) as yellow solid. MS (ESI) m/z $(M+1)^+$189.9.

Compound 263 (6.5 mg, yield: 6.10%, white solid) was prepared as in Example 5 from the corresponding intermediate carboxylic acid, compound 263E. Compound 263: MS (ESI) m/z $(M+1)^+$364.1. $^1$H NMR (DMSO-$d_6$, 400 MHz): δ 9.39 (d, J=8.0 Hz, 1H), 8.16 (s, 1H), 8.12 (br. s, 1H), 7.87 (br. s, 1H), 7.53-7.43 (m, 3H), 7.34-7.20 (m, 7H), 5.35-5.26 (m, 1H), 3.23-3.14 (m, 1H), 2.85-2.75 (m, 1H).

Example 148

(S)—N-(4-amino-3,4-dioxo-1-phenylbutan-2-yl)-2-methyl-4-(pyridin-2-yl)oxazole-5-carboxamide (266)

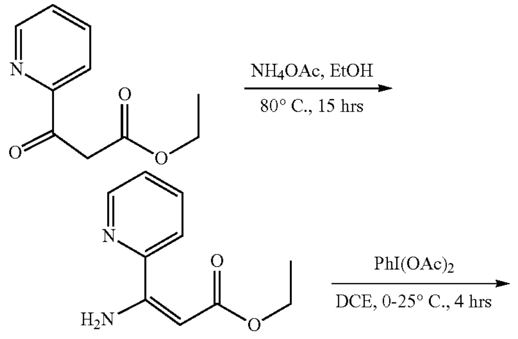

266A

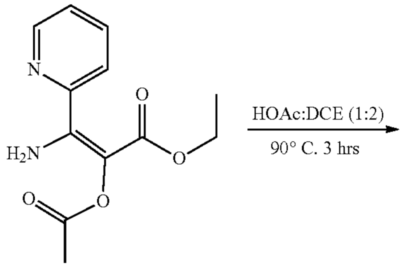

266B

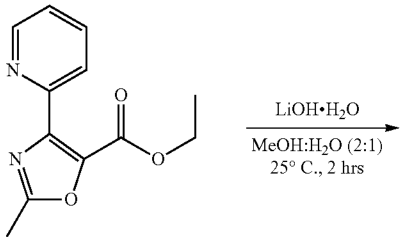

266C

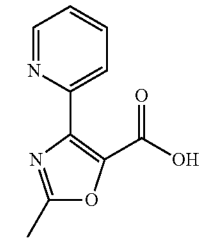

266D

To a mixture of ethyl 3-oxo-3-(pyridin-2-yl)propanoate (5 g, 25.88 mmol) in EtOH (50 mL) was added $NH_4OAc$ (3.99 g, 51.76 mmol) and purged with $N_2$ for 3 times, and then the mixture was stirred at 80° C. for 15 hours under $N_2$ atmosphere. After removal of the solvent, the residue was dissolved in water (50 mL), extracted with EtOAc (100 mL×2). This combined organic phase was washed with saturated aqueous $NaHCO_3$ (50 mL×2) and brine (50 mL), dried over $Na_2SO_4$, filtered and the solvent was removed in vacuum. The residue was purified by column chromatography ($SiO_2$, Petroleum ether/Ethyl acetate=0:1 to 10:1) to give compound 266A (3.80 g, 69.23% yield) as a yellow solid. $^1$H NMR ($CDCl_3$, 400 MHz): δ 8.62 (d, J=4.4 Hz, 1H), 7.78-7.71 (m, 2H), 7.37-7.29 (m, 1H), 5.33 (s, 1H), 4.20 (q, J=7.2 Hz, 2H), 1.31 (t, J=7.2 Hz, 3H). MS (ESI) m/z $(M+H)^+$193.1.

To a mixture of iodosobenzene diacetate (2 g, 10.41 mmol) in DCE (21 mL) was added compound 266A (4.36 g, 13.53 mmol) in six portions at 0° C. under $N_2$, the mixture was stirred at 0° C. for 3 hours and then warmed to 25° C. slowly. The mixture was stirred at 25° C. for 1 h. The reaction mixture was quenched with saturated aqueous $NaHCO_3$ (60 mL) and extracted with DCM (60 mL×3). The combined organic layers were dried over anhydrous $Na_2SO_4$, filtered and concentrated under reduced pressure to give a residue, which was purified by column chromatography ($SiO_2$, Petroleum ether/Ethyl acetate=20:1 to 1:1) to afford compound 266B (1.30 g, 49.90% yield) as a yellow oil. $^1$H NMR (400 MHz, $CDCl_3$): δ 8.72-8.61 (m, 1H), 7.81-7.69 (m, 2H), 7.36-7.29 (m, 1H), 4.24 (q, J=7.2 Hz, 2H), 2.13 (s, 3H), 1.29 (t, J=7.2 Hz, 3H).

A solution of compound 266B (1.30 g, 5.19 mmol) in DCE (20 mL) and AcOH (10 mL) was stirred at 90° C. for 3 hours. The reaction mixture was cooled to room-temperature and the mixture concentrated under reduced pressure to give a residue which was purified by column chromatography ($SiO_2$, Petroleum ether/Ethyl acetate=10:1 to 0:1) to afford compound 266C (300 mg, 23.06% yield) as a yellow solid. $^1$H NMR (400 MHz, $CDCl_3$): δ 8.78-8.73 (m, 1H), 8.13-8.08 (m, 1H), 7.80-7.74 (m, 1H), 7.33-7.28 (m, 1H), 4.40-4.34 (m, 2H), 2.60 (s, 3H), 1.37-1.33 (m, 3H). MS (ESI) m/z $(M+H)^+$233.1.

To a mixture of compound 266C (300 mg, 1.29 mmol) in MeOH (10 mL) and $H_2O$ (5 mL) was added $LiOH.H_2O$ (162.4 mg, 3.87 mmol) in one portion and the mixture was stirred at 25° C. for 2 hours. The reaction mixture was concentrated under reduced pressure to remove MeOH. The residue was adjusted to pH ~3 with 1 N HCl, diluted with water (20 mL) and then extracted with EtOAc (50 mL×4). The combined organic layers were washed with brine (50 mL), dried over anhydrous $Na_2SO_4$, filtered and concentrated under reduced pressure to afford intermediate compound 266D (170 mg, 64.54% yield) as a yellow solid. $^1$H NMR (400 MHz, $CDCl_3$: δ 8.59 (d, J=4.8 Hz, 1H), 8.31 (d, J=8.0 Hz, 1H), 8.11-8.03 (m, 1H), 7.54-7.49 (m, 1H), 2.61 (s, 3H). MS (ESI) m/z $(M+H)^+$204.8.

Compound 266 (15.3 mg, 14.91% yield, light yellow solid) was prepared as in Example 5 from the corresponding intermediate carboxylic acid, compound 266D. Compound 266: $^1$H NMR ($CDCl_3$, 400 MHz): δ12.79 (d, J=6.0 Hz, 1H), 8.17 (d, J=8.0 Hz, 1H), 8.00 (d, J=4.4 Hz, 1H), 7.82 (t, J=7.6 Hz, 1H), 7.23-7.19 (m, 1H), 7.14-7.04 (m, 5H), 6.76 (br s, 1H), 5.89 (q, J=6.0 Hz, 1H), 5.56 (br s, 1H), 3.47-3.30 (m, 2H), 2.59-2.54 (m, 3H). MS (ESI) m/z $(M+H)^+$379.1.

Example 149

(S)—N-(4-amino-3,4-dioxo-1-phenylbutan-2-yl)-4-(2-fluorophenyl)-2-methyloxazole-5-carboxamide (267)

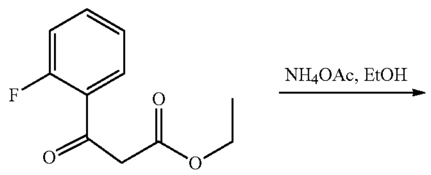

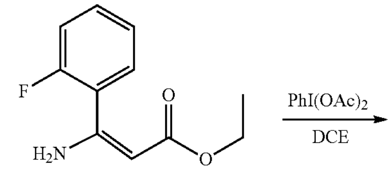

267A

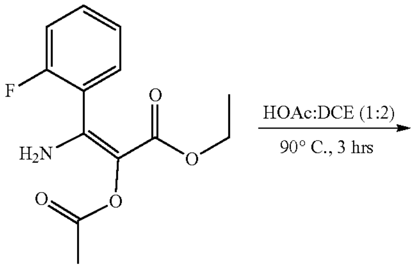

267B

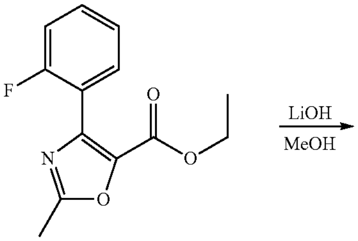

267C

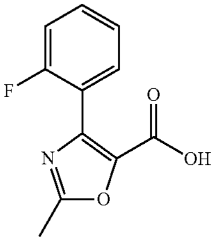

267D

To a mixture of ethyl 3-oxo-3-(pyridin-2-yl)propanoate (5 g, 25.88 mmol) in EtOH (50 mL) was added $NH_4OAc$ (3.99 g, 51.76 mmol) and purged with $N_2$ for 3 times, and then the mixture was stirred at 80° C. for 15 hours under $N_2$ atmosphere. After removal of the solvent, the residue was dissolved in water (50 mL), extracted with EtOAc (100 mL×2). This combined organic phase was washed with saturated aqueous $NaHCO_3$ (50 mL×2) and brine (50 mL), dried over $Na_2SO_4$, filtered and the solvent was removed in vacuum. The residue was purified by column chromatography ($SiO_2$, Petroleum ether/Ethyl acetate=0:1 to 10:1) to give compound 266A (3.80 g, 69.23% yield) as a yellow solid. $^1H$ NMR ($CDCl_3$, 400 MHz): δ 8.62 (d, J=4.4 Hz, 1H), 7.78-7.71 (m, 2H), 7.37-7.29 (m, 1H), 5.33 (s, 1H), 4.20 (q, J=7.2 Hz, 2H), 1.31 (t, J=7.2 Hz, 3H). MS (ESI) m/z $(M+H)^+$193.1.

To a mixture of iodosobenzene diacetate (2 g, 10.41 mmol) in DCE (21 mL) was added compound 266A (4.36 g, 13.53 mmol) in six portions at 0° C. under $N_2$, the mixture was stirred at 0° C. for 3 hours and then warmed to 25° C. slowly. The mixture was stirred at 25° C. for 1 h. The reaction mixture was quenched with saturated aqueous $NaHCO_3$ (60 mL) and extracted with DCM (60 mL×3). The combined organic layers were dried over anhydrous $Na_2SO_4$, filtered and concentrated under reduced pressure to give a residue, which was purified by column chromatography ($SiO_2$, Petroleum ether/Ethyl acetate=20:1 to 1:1) to afford compound 266B (1.30 g, 49.90% yield) as a yellow oil. $^1H$ NMR (400 MHz, $CDCl_3$): δ 8.72-8.61 (m, 1H), 7.81-7.69 (m, 2H), 7.36-7.29 (m, 1H), 4.24 (q, J=7.2 Hz, 2H), 2.13 (s, 3H), 1.29 (t, J=7.2 Hz, 3H).

A solution of compound 266B (1.30 g, 5.19 mmol) in DCE (20 mL) and AcOH (10 mL) was stirred at 90° C. for 3 hours. The reaction mixture was cooled to room-temperature and the mixture concentrated under reduced pressure to give a residue which was purified by column chromatography ($SiO_2$, Petroleum ether/Ethyl acetate=10:1 to 0:1) to afford compound 266C (300 mg, 23.06% yield) as a yellow solid. $^1H$ NMR (400 MHz, $CDCl_3$): δ 8.78-8.73 (m, 1H), 8.13-8.08 (m, 1H), 7.80-7.74 (m, 1H), 7.33-7.28 (m, 1H), 4.40-4.34 (m, 2H), 2.60 (s, 3H), 1.37-1.33 (m, 3H). MS (ESI) m/z $(M+H)^+$233.1.

To a mixture of compound 266C (300 mg, 1.29 mmol) in MeOH (10 mL) and $H_2O$ (5 mL) was added $LiOH.H_2O$ (162.4 mg, 3.87 mmol) in one portion and the mixture was stirred at 25° C. for 2 hours. The reaction mixture was concentrated under reduced pressure to remove MeOH. The residue was adjusted to pH ~3 with 1 N HCl, diluted with water (20 mL) and then extracted with EtOAc (50 mL×4). The combined organic layers were washed with brine (50 mL), dried over anhydrous $Na_2SO_4$, filtered and concentrated under reduced pressure to afford intermediate compound 266D (170 mg, 64.54% yield) as a yellow solid. $^1H$ NMR (400 MHz, $CDCl_3$: δ 8.59 (d, J=4.8 Hz, 1H), 8.31 (d, J=8.0 Hz, 1H), 8.11-8.03 (m, 1H), 7.54-7.49 (m, 1H), 2.61 (s, 3H). MS (ESI) m/z $(M+H)^+$204.8.

Compound 267 (15.3 mg, 14.91% yield, light yellow solid) was prepared as in Example 5 from the corresponding intermediate carboxylic acid, compound 267D. Compound 267: $^1H$ NMR ($CDCl_3$, 400 MHz): δ12.79 (d, J=6.0 Hz, 1H), 8.17 (d, J=8.0 Hz, 1H), 8.00 (d, J=4.4 Hz, 1H), 7.82 (t, J=7.6 Hz, 1H), 7.23-7.19 (m, 1H), 7.14-7.04 (m, 5H), 6.76 (br s, 1H), 5.89 (q, J=6.0 Hz, 1H), 5.56 (br s, 1H), 3.47-3.30 (m, 2H), 2.59-2.54 (m, 3H). MS (ESI) m/z $(M+H)^+$379.1.

Example 150

(S)—N-(4-amino-3,4-dioxo-1-phenylbutan-2-yl)-2-phenylthiophene-3-carboxamide (270)

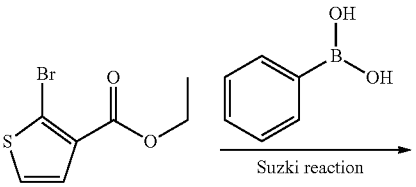

-continued

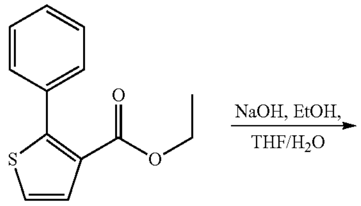

270A

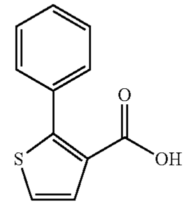

270B

Ethyl 2-bromothiophene-3-carboxylate (2 g, 8.51 mmol), phenylboronic acid (1.35 g, 11.1 mmol), $K_2CO_3$ (2.35 g, 17 mmol) and Pd(dppf)$Cl_2$ (622 mg, 851 umol) in dioxane (30 mL), $H_2O$ (3 mL) was de-gassed and then heated to 100° C. for 6 hours under $N_2$. The mixture was concentrated, the residue was purified by silica gel chromatography (Petroleum ether to Petroleum ether:Ethyl acetate=25:1) to give compound 270A (1.9 g, yield: 96.11%), as yellow oil. $^1$H NMR (400 MHz, $CDCl_3$-d) δ 7.53 (d, J=5.4 Hz, 1H), 7.52-7.47 (m, 2H), 7.44-7.38 (m, 3H), 7.25 (d, J=5.4 Hz, 1H), 4.20 (q, J=7.1 Hz, 2H), 1.19 (t, J=7.1 Hz, 3H).

A mixture of 270A (150 mg, 646 umol) and NaOH (51.7 mg, 1.29 mmol) in THF (5 mL), EtOH (3 mL), $H_2O$ (2 mL) was stirred at 15° C. for 12 hrs. TLC (petroleum ether/ethyl acetate=10:1) showed unreacted starting material and then the mixture was heated to 60° C. for another 3 hrs. The organic solvent was removed under reduced pressure, the water layer was adjusted to pH 6 with 1N HCl to give a precipitate, the solid was filtered and dried to give 270B (100 mg, yield: 75.8%), as white solid. $^1$H NMR (400 MHz, DMSO-$d_6$) δ 12.63 (br s, 1H), 7.55 (d, J=5.3 Hz, 1H), 7.49-7.41 (m, 2H), 7.41-7.31 (m, 4H).

Compound 270 (16.00 mg, yield: 20.1%, white solid) was prepared as in Example 5 from the corresponding intermediate carboxylic acid, compound 270B. Compound 270: $^1$H NMR (400 MHz, DMSO-$d_6$) δ 8.73 (d, J=7.5 Hz, 1H), 8.12 (s, 1H), 7.87 (s, 1H), 7.58 (d, J=5.3 Hz, 1H), 7.36-7.20 (m, 10H), 7.09 (d, J=5.3 Hz, 1H), 5.29 (ddd, J=3.6, 7.3, 10.4 Hz, 1H), 3.17 (dd, J=3.6, 13.8 Hz, 1H), 2.80 (dd, J=10.4, 13.9 Hz, 1H). MS (ESI) m/z (M+H)$^+$379.1.

Example 151

(S)—N-(4-amino-3,4-dioxo-1-phenylbutan-2-yl)-5-chloro-2-phenylthiophene-3-carboxamide (271)

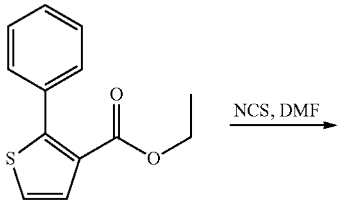

270A

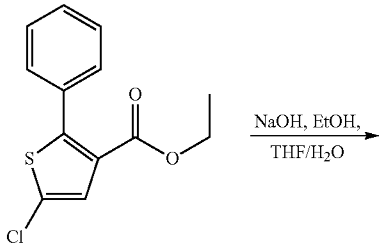

271A

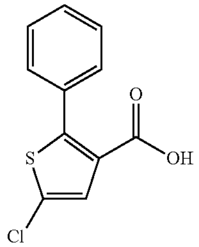

271B

To a solution of 270A (300 mg, 1.29 mmol) in DMF (5 mL) was added NCS (345 mg, 2.58 mmol) at 80° C., and the mixture was stirred at 80° C. for 1.5 hrs. The mixture was poured into water (20 mL) and extracted with ethyl acetate (10 mL×2), the combined organic layer was washed with brine (10 mL), dried over $Na_2SO_4$, filtered and concentrated. The residue was purified by silica gel chromatography (Petroleum ether to Petroleum ether:Ethyl acetate=20:1) to give 271A (0.38 g, yield: 82.8%), as white solid (combined with page 158). $^1$H NMR (400 MHz, $CDCl_3$) δ 7.50-7.44 (m, 2H), 7.43-7.37 (m, 3H), 7.34 (s, 1H), 4.19 (q, J=7.1 Hz, 2H), 1.18 (t, J=7.2 Hz, 3H).

A mixture of 271A (380 mg, 1.42 mmol) and NaOH (114 mg, 2.84 mmol) in THF (5 mL), EtOH (3 mL), $H_2O$ (2 mL) was stirred at 15° C. for 12 hrs. The organic solvent was removed under vacuum, the water layer was adjusted to pH ~3 with 1N HCl and extracted with ethyl acetated (10 mL×2), the organic layer was washed with brine (10 mL), dried over $Na_2SO_4$, filtered and concentrated to give 271B (330 mg, yield: 97.4%), as white solid. $^1$H NMR (400 MHz, $CDCl_3$-d) δ 7.43-7.36 (m, 2H), 7.36-7.29 (m, 3H), 7.28 (s, 1H).

Compound 271 (28.2 mg, yield: 30.4%, white solid) was prepared as in Example 5 from the corresponding intermediate carboxylic acid, compound 271B. Compound 271: $^1$H NMR (400 MHz, $CDCl_3$) δ 7.40 (br s, 5H), 7.19 (br s, 4H), 6.76 (br s, 2H), 6.66 (br s, 1H), 5.93 (br s, 1H), 5.44 (br d, J=19.3 Hz, 2H), 3.18 (br d, J=16.7 Hz, 1H), 2.94-2.81 (m, 1H). MS (ESI) m/z $(M+H)^+$413.0, 415.0.

Example 152

Compounds 272-273

(S)—N-(4-amino-3,4-dioxo-1-phenylbutan-2-yl)-3-CYANO-1-phenyl-1H-pyrazole-5-carboxamide (272)

(S)—N-(4-amino-3,4-dioxo-1-phenylbutan-2-yl)-5-CYANO-1-phenyl-1H-pyrazole-3-carboxamide (273)

residue was purified by flash silica gel chromatography (ISCO®; 20 g SepaFlash® Silica Flash Column, Eluent of 0-30% Ethyl acetate/Petroleum ethergradient) and then by prep-HPLC (HCl condition) to give 272B (170 mg, yield: 8.23%) and 272C (264 mg, yield: 12.78%) as white solid.

Compound 272B: $^1$H NMR (400 MHz, CHLOROFORM-d) δ 7.73 (dd, J=1.3, 8.3 Hz, 2H), 7.64-7.46 (m, 4H), 4.46 (q, J=7.2 Hz, 2H), 1.42 (t, J=7.0 Hz, 3H). MS (ESI) m/z $(M+H)^+$241.9.

Compound 272C: $^1$H NMR (400 MHz, CHLOROFORM-d) δ 7.55-7.47 (m, 3H), 7.45-7.39 (m, 2H), 7.37 (s, 1H), 4.27 (q, J=7.0 Hz, 2H), 1.25 (t, J=7.2 Hz, 3H). MS (ESI) m/z $(M+H)^+$241.9.

To a solution of 272B (170 mg, 704.69 umol) in THF (5 mL) and MeOH (5 mL) was added a solution of $LiOH.H_2O$

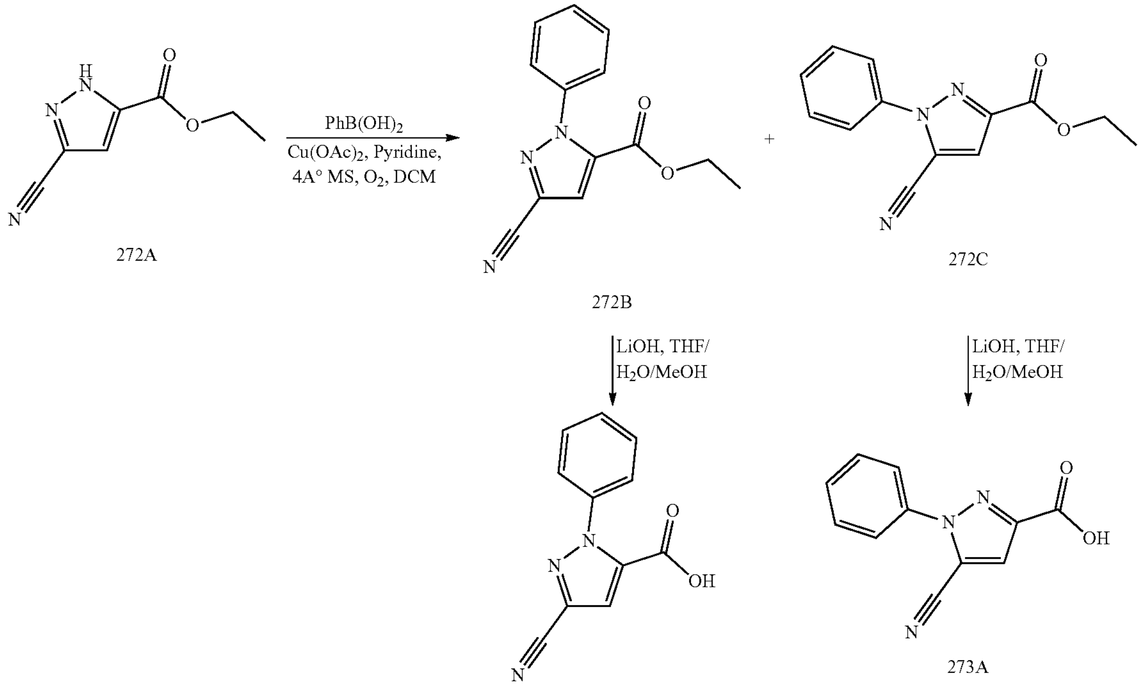

272A 272B 272C 272D 273A

To a solution of ethyl propiolate (4.30 g, 43.83 mmol) and 2-aminoacetonitrile hydrochloride (8.11 g, 87.67 mmol, HCl) in $CHCl_3$ (250 mL) and $H_2O$ (10 mL) was added $NaNO_2$ (9.07 g, 131.50 mmol). The mixture was stirred for 14 h at 25° C. Then, the reaction mixture was diluted with DCM (50 mL) and filtered. The filtrate was washed with $H_2O$ (20 mL) and brine (20 mL), dried over $Na_2SO_4$, filtered and concentrated under reduced pressure to give a residue. The residue was purified by flash silica gel chromatography (ISCO®; 20 g SepaFlash® Silica Flash Column, Eluent of 0-30% Ethylacetate/Petroleum ethergradient) to give 272A (1.40 g yield: 19.34%) as a white solid. $^1$H NMR (400 MHz, CHLOROFORM-d) δ 12.19 (br s, 1H), 7.21 (s, 1H), 4.45 (q, J=7.2 Hz, 2H), 1.41 (t, J=7.2 Hz, 3H).

To a mixture of 272A (1.40 g, 8.48 mmol), phenylboronic acid (1.55 g, 12.72 mmol), pyridine (737.60 mg, 9.32 mmol) in DCM (50 mL) was added 4A° MS (20 g) (activated 4A° MS) and $Cu(OAc)_2$ (1.69 g, 9.32 mmol). After that, the mixture was stirred at 40° C. for 72 hours under 02 atmosphere (15 psi). The reaction mixture was filtered and concentrated under reduced pressure to give a residue. The (148 mg, 3.52 mmol) in $H_2O$ (5 mL) at 0° C. After addition, the reaction mixture was stirred for 3 h at 25° C., and then diluted with $H_2O$ (10 mL) and extracted with MTBE (30 mL). The aqueous phase was neutralized by 1N HCl to the pH ~4, and then extracted with EtOAc (30 mL×3). The combined organic layers were washed with brine (30 mL), dried over $Na_2SO_4$, filtered and concentrated under reduced pressure. Compound 272D (98 mg, yield: 64.58%, white solid): $^1$H NMR (400 MHz, CHLOROFORM-d) δ 7.76-7.74 (m, 2H), 7.61-7.52 (m, 4H), 2.83 (br s, 1H).

Compound 272 (40 mg, yield: 53.56%, white solid) was prepared as in Example 6 from the corresponding starting materials, compounds 272D and 12G. Compound 272: $^1$H NMR (400 MHz, DMSO-$d_6$) δ 8.88 (br d, J=7.8 Hz, 1H), 8.12 (br s, 1H), 7.91-7.74 (m, 4H), 7.71-7.57 (m, 3H), 7.31-7.15 (m, 5H), 5.47 (br s, 1H), 3.25-2.96 (m, 2H). MS (ESI) m/z $(M+H)^+$388.1.

Following the procedure used for compound 274, compound 273 (19 mg, yield: 44.44%, white solid) was prepared from the corresponding intermediate carboxylic acid, compound 273A. Compound 273A (201 mg, yield: 55.94%, white solid): $^1$H NMR (400 MHz, CHLOROFORM-d) δ 7.58-7.53 (m, 1H), 7.46-7.42 (m, 5H), 4.05 (br s, 1H). Compound 273: $^1$H NMR (400 MHz, DMSO-$d_6$) δ 9.43 (br d, J=7.8 Hz, 1H), 8.15 (br s, 1H), 7.90 (br s, 1H), 7.44 (br d, J=8.5 Hz, 4H), 7.36-7.25 (m, 7H), 5.42-5.22 (m, 1H), 3.21 (br d, J=11.5 Hz, 1H), 2.90-2.75 (m, 1H). MS (ESI) m/z $(M+H)^+$388.1.

Example 153

Compounds 274, 320

N-(4-amino-3,4-dioxo-1-phenylbutan-2-yl)-3-bromo-5-chloro-1-methyl-1H-pyrazole-4-carboxamide (274)

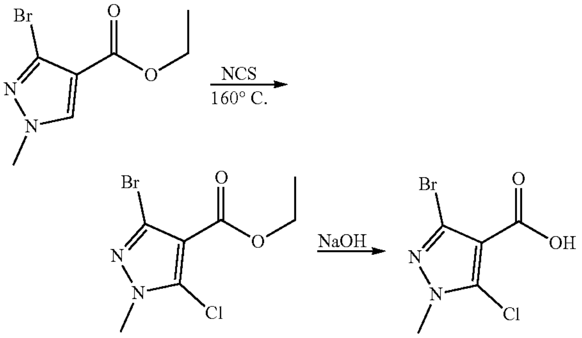

274A 274B

To a solution of ethyl 3-bromo-1-methyl-1H-pyrazole-4-carboxylate (500 mg, 2.15 mmol) and NCS (574 mg, 4.30 mmol) was stirred. The mixture was stirred at 160° C. for 3 h under $N_2$. The reaction mixture was added by addition of $CCl_4$ (20 mL), and then diluted with $NaHCO_3$ (30 mL). The mixture was extracted with DCM (20 mL×3). The combined organic layers were dried over $Na_2SO_4$, filtered and concentrated under reduced pressure to give a residue. The residue was purified by preparatory-TLC ($SiO_2$, PE:EA=5:1). Compound 274A (180 mg, yield: 31.30%) was obtained as a yellow oil. $^1$H NMR (400 MHz, $CDCl_3$) δ 4.34 (q, J=7.1 Hz, 2H), 3.85 (s, 3H), 1.46-1.24 (m, 3H). MS (ESI) m/z $(M+H)^+$266.9.

To a solution of compound 274A (300 mg, 1.12 mmol) in MeOH (10 mL) and $H_2O$ (10 mL) was added NaOH (134 mg, 3.36 mmol). The mixture was stirred at 25° C. for 3 h. The reaction mixture was concentrated and added 20 mL of water, the mixture was extracted with MTBE (10 mL×2), the aqueous layer was acidified by 1N HCl to pH ~2~3 at 0° C., and extracted with EtOAc (20 mL×2), the organic phase was dried over $Na_2SO_4$, filtered and concentrated to give a residue. Compound 274B (250 mg, yield: 93.22%) was obtained as a white solid, which was used to the next step without purification. $^1$H NMR (400 MHz, $CDCl_3$) δ 4.02-3.72 (m, 3H). MS (ESI) m/z $(M+H)^+$238.9.

Compound 274 (70 mg, yield: 66.75%, light yellow solid) was prepared as in Example 5 from the corresponding starting materials, compounds 274B and 3-amino-2-hydroxy-4-phenyl-butanamide (274D). Compound 274: $^1$H NMR (400 MHz, DMSO-$d_6$) δ 8.41-8.27 (m, 1H), 8.12 (s, 1H), 7.87 (s, 1H), 7.29 (dd, J=4.0 Hz, 4H), 7.22 (dd, J=4.0 Hz, 1H), 5.36 (s, 1H), 3.78 (s, 3H), 3.20 (dd, J=10.4 Hz, 1H), 2.90-2.81 (m, 1H). MS (ESI) m/z $(M+H)^+$415.0.

N-(4-amino-3,4-dioxo-1-phenylbutan-2-yl)-5-methyl-2-(3-phenyl-1H-pyrazol-1-yl)thiophene-3-carboxamide (320)

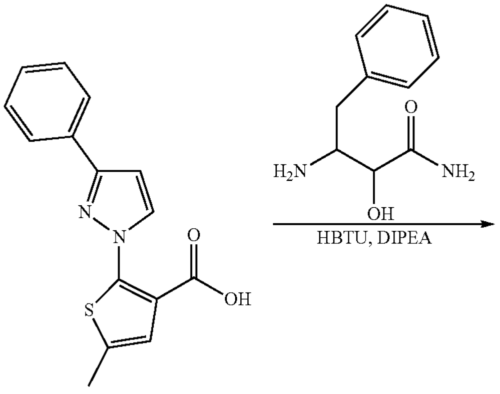

320A

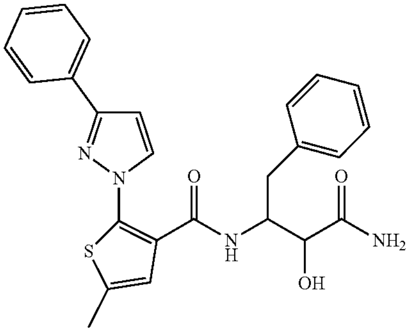

320B

Compound 320 (33.7 mg, yield: 51.5%, white solid) was prepared as in Example 153 from the corresponding carboxylic acid, compound 320A, and 3-amino-2-hydroxy-4-phenyl-butanamide (274D). Compound 320: $^1$H NMR (400 MHz, DMSO-$d_6$) δ 8.88 (d, J=7.6 Hz, 1H), 8.12 (s, 1H), 7.97 (d, J=2.6 Hz, 1H), 7.85 (br d, J=7.1 Hz, 3H), 7.50-7.42 (m, 2H), 7.41-7.34 (m, 1H), 7.33-7.19 (m, 5H), 6.92 (d, J=2.6 Hz, 1H), 6.84 (d, J=1.0 Hz, 1H), 5.40-5.31 (m, 1H), 3.19 (dd, J=3.6, 14.0 Hz, 1H), 2.80 (dd, J=10.3, 13.8 Hz, 1H), 2.44 (s, 3H). MS (ESI) m/z $(M+H)^+$459.1.

Example 154

(S)—N-(4-amino-3,4-dioxo-1-phenylbutan-2-yl)-3-methyl-1-phenyl-1H-pyrazole-5-carboxamide (276)

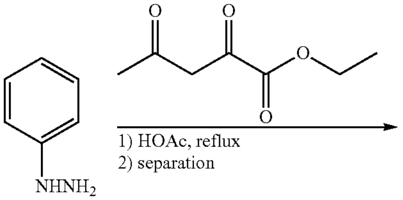

-continued

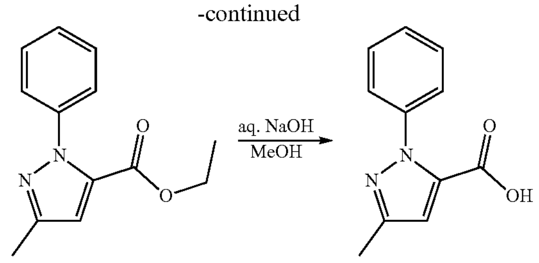

276A

276C

To a mixture of phenylhydrazine (50 g, 462.3 mmol) and ethyl 2,4-dioxopentanoate (76.8 g, 485.5 mmol) in AcOH (600 mL) at 25° C. The mixture was stirred at 100° C. for 16 h. The reaction mixture was concentrated under reduced pressure to remove AcOH. The residue was added $H_2O$ (200 mL) and EA (200 mL), and then the mixture was alkalized with saturated aqueous $NaHCO_3$ till the aqueous phase pH ~7-8. The separated aqueous layer was extracted with EA (150 mLx3), the combined organic layers were washed with saturated aqueous $NaHCO_3$ (200 mL), saturated aqueous NaCl (200 mL), dried over $Na_2SO_4$, filtered under reduced pressure to give crude product. The crude product was purified by FCC (SiO2, Petroleum ether:Ethyl acetate=1:0 3:1). Compound 276A (39.0 g, yield: 36.7%, yellow solid): $^1H$ NMR (DMSO-$d_6$, 400 MHz): δ 7.50-7.37 (m, 5H), 6.88 (s, 1H), 4.16 (q, J=7.0 Hz, 2H), 2.26 (s, 3H), 1.14 (t, J=7.2 Hz, 3H).

To a mixture of compound 276A (250 mg, 1.1 mmol) in MeOH (10 mL) was added NaOH (2M, 3 mL) in one portion at 25° C. The mixture was stirred at 25° C. for 2 h. The reaction mixture was concentrated under reduced pressure to move MeOH. $H_2O$ (10 mL) was added into the mixture, which was acidified with aqueous HCl (1M) till pH ~3-4. The aqueous phase was extracted with EA (10 mLx3). The combined organic phase was washed with saturated aqueous NaCl (15 mLx2), dried over $Na_2SO_4$ and filtered under reduced pressure to afford compound 276C (170 mg, crude) as yellow solid, which was used directly for next step without purification. $^1H$ NMR (DMSO-$d_6$, 400 MHz): δ 7.49-7.37 (m, 5H), 6.82 (s, 1H), 2.25 (s, 3H).

Compound 276 (100 mg, yield: 65.68%, white solid) was prepared as in Example 5 from the corresponding intermediate carboxylic acid, compound 276C. Compound 276: $^1H$ NMR ($CDCl_3$, 400 MHz): δ 9.14-9.00 (m, 1H), 8.09 (s, 1H), 7.85 (s, 1H), 7.44-7.11 (m, 10H), 6.56 (s, 1H), 5.28 (s, 1H), 3.26-3.16 (m, 1H), 2.91-2.76 (m, 1H), 2.26 (s, 3H). MS (ESI) m/z $(M+H)^+$377.1.

Example 155

(S)—N-(4-amino-3,4-dioxo-1-phenylbutan-2-yl)-3-(2-fluorophenyl)isoxazole-4-carboxamide (277)

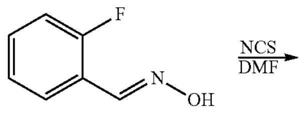

277A

-continued

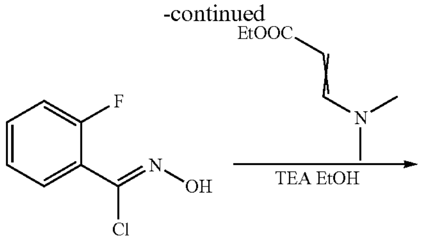

277B

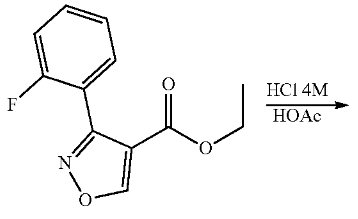

277C

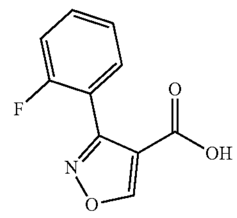

277D

To a suspension of 2-fluorobenzaldehyde (10 g 80.6 mmol) and $NH_2OH.HCl$ (6.2 g, 88.6 mmol) in EtOH (10 mL) and 1120 (20 mL) was added ice (50 g). Then an aqueous solution of NaOH (8 g, 201 mmol) in $H_2O$ (25 mL) was added dropwise within a 10 min period where upon most of the solid dissolves. Then the mixture was stirred 2 hours at 16° C. The resulting mixture was then acidified with HCl (5N). The mixture was then extracted with dichloromethane (100 mL) for two times. The residue was purified by column chromatography ($SiO_2$, Petroleum ether:Ethyl acetate=1:0 to 200:1) to give compound 277A (10 g, yield: 89.2%) as a pale yellow solid. $^1H$ NMR (400 MHz, $CDCl_3$) δ 8.68 (s, 1H), 8.39 (s, 1H), 7.74 (br t, J=7.5 Hz, 1H), 7.39 (q, J=6.8 Hz, 1H), 7.18 (t, J=7.4 Hz, 1H), 7.14-7.06 (m, 1H).

A solution of compound 277A (5 g, 35.9 mmol) in DMF (20 mL) was added 1-chloropyrrolidine-2,5-dione (5.3 g, 39.5 mmol) followed by stirring at 20° C. for 3 hours. The reaction mixture was diluted with $H_2O$ (60 mL), and extracted with ethyl acetate (100 mLx2). The organic layers were dried over $Na_2SO_4$, filtered and concentrated under reduced pressure to give intermediate compound 277B (5 g, yield: 80.2%) as a yellow solid. $^1H$ NMR (400 MHz, $CDCl_3$) δ 9.15 (s, 1H), 7.68 (br t, J=7.5 Hz, 1H), 7.50-7.39 (m, 1H), 7.23 (t, J=7.6 Hz, 1H), 7.20-7.13 (m, 1H).

To a solution of ethyl 3-(dimethylamino)acrylate (165 mg, 1.2 mmol) and TEA (233 mg, 2.3 mmol) in THF (15 mL) was added a solution of compound 277B (400 mg, 2.3 mmol) in THF (5 mL) drop-wise over 30 mins. The mixture was stirred at 20° C. for 12 hours. The reaction mixture was concentrated under reduced pressure to give a residue. The residue was purified by preparatory-TLC ($SiO_2$, Petroleum ether:Ethyl acetate=1:1) to give compound 277C (240 mg, yield: 44.4%) as a pale yellow oil. $^1H$ NMR (400 MHz, $CDCl_3$) δ 8.94 (s, 1H), 7.51-7.36 (m, 2H), 7.21-7.14 (m, 1H), 7.13-7.04 (m, 1H), 4.17 (q, J=7.1 Hz, 2H), 1.15 (t, J=7.2 Hz, 3H).

A mixture of compound 277C (230 mg, 977.9 umol) in $H_2O$ (2.00 mL), HOAc (1.5 mL) and HCl (3 mL) was heated to 130° C. and stirred for 12 hours. The reaction mixture was concentrated under reduced pressure to give compound 277D (120 mg, yield: 59.2%) as a brown solid. The product was used into the next step without future purification. MS (ESI) m/z $(M+H)^+$208.1.

Compound 277 (33 mg, yield: 37.7%, white solid) was prepared as in Example 5 from the corresponding intermediate carboxylic acid, compound 277D. Compound 277: $^1$H NMR (400 MHz, DMSO-$d_6$) δ 9.43 (br s, 1H), 8.94 (br d, J=6.8 Hz, 1H), 8.09 (br s, 1H), 7.83 (br s, 1H), 7.54 (br d, J=5.3 Hz, 1H), 7.47-7.40 (m, 1H), 7.36-7.16 (m, 9H), 5.31 (br s, 1H), 3.17 (br d, J=13.5 Hz, 1H), 2.89-2.75 (m, 1H), 2.89-2.75 (m, 1H). MS (ESI) m/z $(M+H)^+$382.1.

Example 156

(S)—N-(4-amino-3,4-dioxo-1-phenylbutan-2-yl)-3-phenyl-5-(trifluoromethyl)isoxazole-4-carboxamide (278)

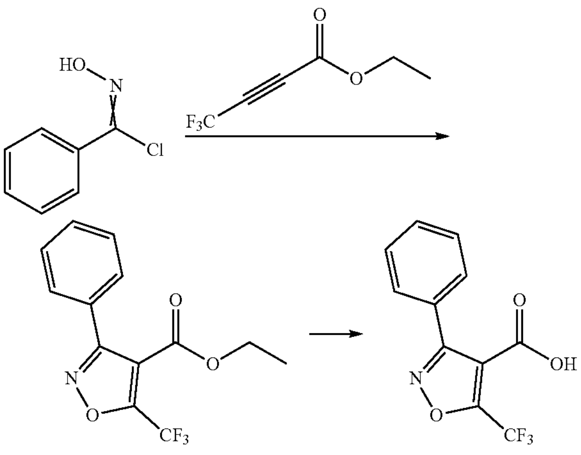

278A 278B

To a mixture of N-hydroxybenzimidoyl chloride (1 g, 6.43 mmol) and ethyl 4,4,4-trifluorobut-2-ynoate (1.28 g, 7.71 mmol) in THF (10 mL) was added TEA (1.3 g, 12.9 mmol) at 25° C. The mixture was stirred at 25° C. for 1 h and $H_2O$ (10 mL) was added to the mixture and extracted with ethyl acetate (10 mL×2). The combined organic phase was washed with brine (10 mL×2), dried with anhydrous $Na_2SO_4$, filtered and concentrated in vacuum. The residue was purified by preparatory-TLC to get compound 278A (1 g, yield: 54.5%) as yellow oil. $^1$H NMR (400 MHz, $CDCl_3$) δ 7.68 (dd, J=1.3, 7.9 Hz, 2H), 7.56-7.47 (m, 3H), 4.39-4.31 (m, 2H), 1.34-1.28 (m, 3H).

To a mixture of compound 278A (750 mg, 2.63 mmol) in HOAc (2 mL) was added HCl (12M, 939 uL). The mixture was stirred at 130° C. for 48 h. TLC (dichloromethane: methanol=10:1, $R_f$~0.09) showed desired point. The mixture was concentrated to get crude product compound 278B (450 mg, crude) as yellow solid. $^1$H NMR (400 MHz, DMSO-$d_6$) δ 7.68 (br d, J=7.9 Hz, 2H), 7.62-7.50 (m, 3H).

Compound 278 (15 mg, yield: 12.6%, white solid) was prepared as in Example 5 from the corresponding intermediate carboxylic acid, compound 278B. Compound 278: $^1$H NMR (400 MHz, DMSO-$d_6$) δ 9.17 (br d, J=9.2 Hz, 1H), 7.55-7.48 (m, 3H), 7.43-7.36 (m, 4H), 7.28-7.14 (m, 5H), 5.88 (d, J=5.3 Hz, 1H), 4.60 (br s, 1H), 4.04 (br s, 1H), 3.31 (s, 12H), 2.73-2.61 (m, 1H). MS (ESI) m/z $(M+H)^+$432.1.

Example 157

N-(4-amino-3,4-dioxo-1-phenylbutan-2-yl)-4-chloro-1-phenyl-1H-pyrazole-5-carboxamide (280)

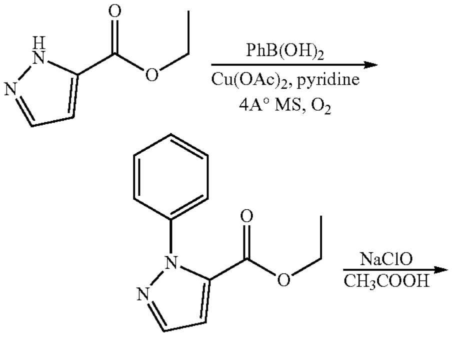

280A

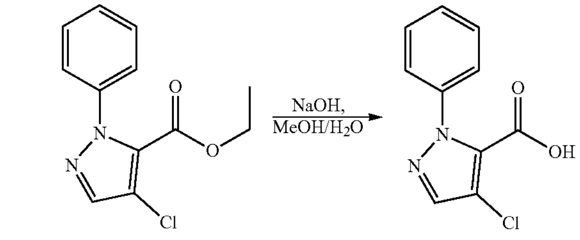

280C 280D

To a mixture of ethyl 1H-pyrazole-5-carboxylate (10.00 g, 71.36 mmol), phenylboronic acid (13.05 g, 107.04 mmol), Py (8.82 g, 111.50 mmol, 9.0 mL) in DCM (120 mL) was added 4A° MS (40.00 g) and $Cu(OAc)_2$ (14.26 g, 78.50 mmol), the mixture was stirred at 30° C. for 154 h. The reaction mixture was filtered, the filtrate was concentrated in vacuo. The residue was purified by flash silica gel chromatography (PE:EA=1:0 to 10:1) to give the compound 280A (3.10 g, yield: 19.1%) as a yellow oil. Compound 280A: $^1$H NMR (400 MHz, DMSO-$d_6$) δ 7.81 (d, J=2.0 Hz, 1H), 7.57-7.37 (m, 5H), 7.09 (d, J=2.0 Hz, 1H), 4.17 (q, J=7.0 Hz, 2H), 1.15 (t, J=7.0 Hz, 3H).

To a solution of compound 280A (1.0 g, 4.62 mmol) in $CH_3COOH$ (15 mL) was added NaClO (24.2 g, 47.12 mmol, 20.00 mL, 14.5% purity). The mixture was stirred at 25° C. for 21 h under $N_2$ atmosphere. The reaction mixture was quenched by addition $H_2O$ (25 mL), and diluted with EA (20 mL) and stirred for 30 min, and then extracted with EA (25 mL). The combined organic layers were washed with $H_2O$ (20 mL×2), and then washed with $NaHCO_3$ (20 mL×2), and then washed with brine (15 mL×2), dried over $Na_2SO_4$, filtered and concentrated under reduced pressure to give a residue. The residue was purified by flash silica gel chromatography (PE:EA=1:0 to 1:1) to give the compound 280C (327 mg, yield: 28.1%) as a white solid. $^1$H NMR (400 MHz, CHLOROFORM-d) δ 7.69 (s, 1H), 7.53-7.31 (m, 5H), 4.27 (q, J=7.1 Hz, 2H), 1.22 (t, J=7.2 Hz, 3H).

To a solution of compound 280C (300 mg, 1.20 mmol) in MeOH (15 mL) was added NaOH (240 mg, 6.00 mmol) in $H_2O$ (5 mL). The mixture was stirred at 20° C. for 2 h. The reaction mixture was diluted with MTBE (15 mL) and $H_2O$ (15 mL), and then stirred for 10 mins. The water layer was separated, and the organic layer was extracted with $H_2O$ (15 mL×2). The combined aqueous layers were adjusted pH ~3 by addition 1N HCl, and then the aqueous layer was extracted with EA (20 mL×3). The combine organic layer was washed with brine (20 mL), dried over $Na_2SO_4$, filtered and concentrated under reduced pressure to give the compound 280D (252 mg, yield: 94.1%) as a white solid. $^1$H NMR (400 MHz, METHANOL-$d_4$) δ 7.76 (s, 1H), 7.52-7.38 (m, 5H).

Compound 280 (61 mg, yield: 61.2%, light yellow solid) was prepared as in Example 5 from the corresponding intermediate carboxylic acid, compound 280D. Compound 280: $^1$H NMR (400 MHz, DMSO-$d_6$) δ 9.46 (d, J=7.5 Hz, 1H), 8.20 (s, 1H), 7.97-7.86 (m, 2H), 7.41-7.24 (m, 10H), 5.48-5.35 (m, 1H), 3.21 (br dd, J=3.2, 14.0 Hz, 1H), 2.80 (dd, J=10.5, 14.0 Hz, 1H). MS (ESI) m/z $(M+H)^+$397.1.

Example 158

(S)—N-(4-amino-3,4-dioxo-1-phenylbutan-2-yl)-3-chloro-1-phenyl-1H-pyrazole-5-carboxamide (281)

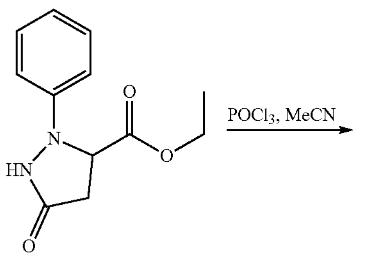

281A

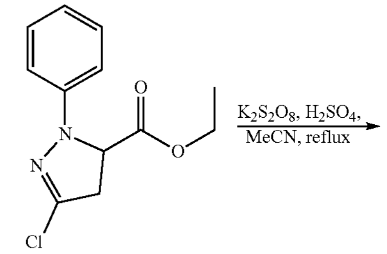

281B

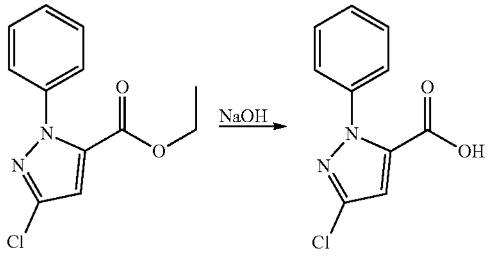

281C 281D

To EtOH (40 mL) was added Na (470 mg, 20.34 mmol) at 20° C. After all sodium was reacted, the mixture was heated to 78° C. and phenylhydrazine (2.0 g, 18.49 mmol, 1.82 mL) was added, and stirred for 0.1 h and then diethyl maleate (3.5 g, 20.34 mmol, 3.27 mL) was added dropwise. The mixture was stirred at 78° C. for 4 h. After being cooled to 65° C., the reaction mixture was treated with AcOH (2.0 g, 33.28 mmol, 1.9 mL). The reaction mixture was concentrated under reduced pressure to remove solvent. The residue was diluted with $H_2O$ (80 mL) and extracted with EtOAc (80 mL×2). The combined organic layers were washed with brine (50 mL×2), dried over $Na_2SO_4$, filtered and concentrated under reduced pressure to give a residue. The residue was purified by column chromatography ($SiO_2$, Petroleum ether/Ethyl acetate=5/1 to 1:1) to give the compound 281A (2.72 g, yield: 58.40%) as a yellow solid. $^1$H NMR (400 MHz, DMSO-$d_6$) δ10.24 (s, 1H), 7.34-7.24 (m, 2H), 7.02-6.92 (m, 3H), 4.59 (dd, J=2.0, 9.7 Hz, 1H), 4.24-4.13 (m, 2H), 3.00-2.86 (m, 1H), 2.46-2.39 (m, 1H), 1.23 (t, J=7.1 Hz, 3H). MS (ESI) m/z $(M+H)^+$235.0.

To a solution of Compound 281A (2.7 g, 11.53 mmol) in MeCN (50 mL) was added $POCl_3$ (2.15 g, 14.02 mmol). The mixture was stirred at 85° C. for 5 h. The reaction mixture was concentrated under reduced pressure to remove solvent. The residue was neutralized by sat. $NaHCO_3$ to pH-8, then extracted with DCM (50 mL×2). The combined organic layers were washed with brine (50 mL), dried over $Na_2SO_4$, filtered and concentrated under reduced pressure to give a residue. The residue was purified by column chromatography ($SiO_2$, Petroleum ether/Ethyl acetate=10/1 to 5:1) to give the Compound 281B (1.9 g, yield: 65.21%) as a yellow solid. $^1$H NMR (400 MHz, $CDCl_3$) δ 7.31-7.17 (m, 2H), 6.98 (br d, J=7.3 Hz, 2H), 6.89 (br t, J=7.2 Hz, 1H), 4.86-4.60 (m, 1H), 4.34-4.14 (m, 2H), 3.62-3.37 (m, 1H), 3.33-3.17 (m, 1H), 1.37-1.11 (m, 3H). MS (ESI) m/z $(M+H)^+$252.9.

To a solution of Compound 281B (800 mg, 3.17 mmol) in MeCN (20 mL) was added $H_2SO_4$ (620 mg, 6.34 mmol, 337.95 uL) and $K_2S_2O_8$ (1.29 g, 4.76 mmol). The mixture was stirred at 80° C. for 6 h. The reaction mixture was concentrated under reduced pressure to remove most solvent. The residue was dropped in $H_2O$ (30 mL), filtered and concentrated under reduced pressure to give a residue. The residue was washed with 30% MeCN (5 mL×2). The residue was purified by column chromatography ($SiO_2$, Petroleum ether/Ethyl acetate=20/1 to 15:1) to give the compound 281C (190 mg, yield: 21.52%) as a white solid. $^1$H NMR (400 MHz, DMSO-$d_6$) δ 7.47 (d, J=1.3 Hz, 4H), 7.23-7.14 (m, 1H), 4.15 (q, J=7.1 Hz, 2H), 1.12 (t, J=7.2 Hz, 3H). MS (ESI) m/z $(M+H)^+$250.9.

To a solution of Compound 281C (150 mg, 598.37 umol) in THF/$H_2O$ (5 mL/5 mL) was added NaOH (120 mg, 2.99 mmol). The mixture was stirred at 25° C. for 4 h. The reaction mixture was diluted with $H_2O$ (20 mL), then the mixture was concentrated under reduced pressure to remove THF, and extracted with MTBE (15 mL×2). The water layers were neutralized by 1N HCl to pH ~3 and then extracted with DCM (20 mL×2). The combined organic layers were washed with brine (20 mL), dried over $Na_2SO_4$, filtered and concentrated under reduced pressure to give the Compound 281D (120 mg, yield: 90.08%) as a white solid. $^1$H NMR (400 MHz, $CDCl_3$) δ 7.50-7.34 (m, 5H), 6.97 (s, 1H).

Compound 281 (20 mg, yield: 40.20%, white solid) was prepared as in Example 5 from the corresponding intermediate carboxylic acid, compound 281D. Compound 281: $^1$H NMR (400 MHz, DMSO-$d_6$) δ 9.27 (d, J=7.7 Hz, 1H), 8.11 (s, 1H), 7.87 (s, 1H), 7.41-7.34 (m, 3H), 7.30 (br d, J=7.1 Hz, 2H), 7.28-7.23 (m, 3H), 7.21-7.16 (m, 2H), 6.80 (s, 1H), 5.31-5.19 (m, 1H), 3.24-3.

Example 159

N-(4-amino-3,4-dioxo-1-phenylbutan-2-yl)-3,5-dichloro-1-methyl-1H-pyrazole-4-carboxamide (282)

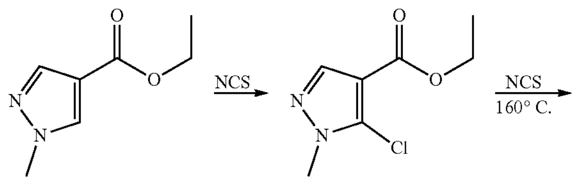

282A 282B

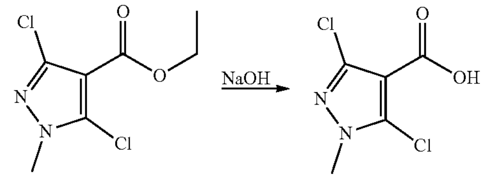

282C 282D

To a solution of ethyl 1H-pyrazole-4-carboxylate (5 g, 35.68 mmol) and $Cs_2CO_3$ (23.25 g, 71.36 mmol) in DMF (100 mL) was added MeI (10.13 g, 71.36 mmol, 4.44 mL). The mixture was stirred at 25° C. for 16 h. The mixture was filtered, the filtrate was diluted with $H_2O$ (500 mL), extracted with EA (50 mL×3), dried over $Na_2SO_4$, filtered and concentrated to give a residue. The residue was purified by column chromatography ($SiO_2$, Petroleum ether/Ethyl acetate=5/1). Compound 282A (4.5 g, yield: 81.81%) was obtained as a yellow oil. $^1$H NMR (400 MHz, $CDCl_3$) δ 7.84 (d, J=8.5 Hz, 2H), 4.24 (q, J=7.3 Hz, 2H), 4.03-3.70 (m, 3H), 1.30 (t, J=7.2 Hz, 3H). MS (ESI) m/z $(M+H)^+$155.0.

To a solution of compound 282A (1.5 g, 9.73 mmol) was added NCS (2.6 g, 19.46 mmol) under $N_2$. The mixture was stirred at 160° C. for 3 h. The reaction mixture was added $CCl_4$ (10 mL) and saturated aqueous $NaHCO_3$ (10 mL). The mixture was extracted with DCM (20 mL×2), and then combined the organic layers and the organic phase was dried with over $Na_2SO_4$, filtered and the filtrate was concentrated in vacuum. Compound 282B (1.84 g, crude) was obtained as a brown oil, which was used for next step directly. MS (ESI) m/z $(M+H)^+$188.9.

To a solution of compound 282B (1.84 g, 9.76 mmol) was added NCS (2.61 g, 19.52 mmol) under $N_2$ and the mixture was stirred at 160° C. for 4 h under $N_2$. To the reaction mixture was added $CCl_4$ (10 mL) and saturated aqueous $NaHCO_3$ (10 mL) and the mixture was extracted with DCM (20 mL×2), and then combined the organic layers and the organic phase was dried with over $Na_2SO_4$, filtered and the filtrate was concentrated in vacuum. The residue was purified by column chromatography ($SiO_2$, Petroleum ether/Ethyl acetate=5/1). Compound 282C (482 mg, yield: 22.14%) was obtained as a yellow solid. $^1$H NMR (400 MHz, $CDCl_3$) δ 4.35 (q, J=7.1 Hz, 2H), 3.84 (s, 3H), 1.38 (t, J=7.2 Hz, 3H). MS (ESI) m/z $(M+H)^+$222.9.

To a mixture of compound 282C (480 mg, 2.15 mmol) in $H_2O$ (5 mL) and MeOH (10 mL) was added NaOH (258 mg, 6.45 mmol) in portion at 20° C. and stirred for 2 h. The mixture was concentrated to remove MeOH, then the mixture was diluted with $H_2O$ (20 mL) and extracted with MTBE (50 mL×2). The water layers were acidified to pH ~2 with 1N HCl, then the solution was extracted with EA (50 mL×3). The organic layers were dried over $Na_2SO_4$ and concentrated to give intermediate compound 282D (390 mg, yield: 93.02%) as white solid. $^1$H NMR (400 MHz, $CDCl_3$) δ 7.27 (s, 1H), 3.77 (s, 3H). MS (ESI) m/z $(M+H)^+$194.8 & 196.8.

Compound 282 (50 mg, yield: 46.25%, off-white solid) was prepared as in Example 5 from the corresponding intermediate carboxylic acid, compound 282D. Compound 282: $^1$H NMR (400 MHz, DMSO-$d_6$) δ 8.32 (dd, J=7.7 Hz, 1H), 8.21-8.07 (m, 1H), 7.87 (s, 1H), 7.36-7.16 (m, 5H), 5.33 (s, 1H), 3.82-3.69 (m, 3H), 3.19 (dd, J=13.2 Hz, 1H), 2.95-2.78 (m, 1H). MS (ESI) m/z $(M+H)^+$369.1 & 371.1.

Example 160

Compounds 283-284

N-(4-amino-3,4-dioxo-1-phenylbutan-2-yl)-1-benzyl-1H-pyrazole-5-carboxamide (283)

N-(4-amino-3,4-dioxo-1-phenylbutan-2-yl)-1-benzyl-1H-pyrazole-3-carboxamide (284)

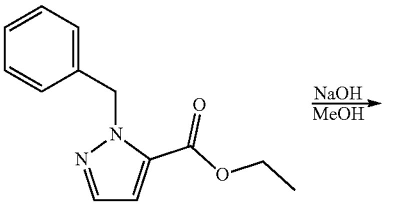

283A

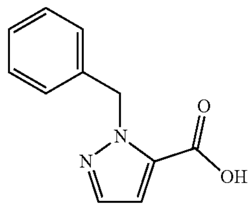

283C

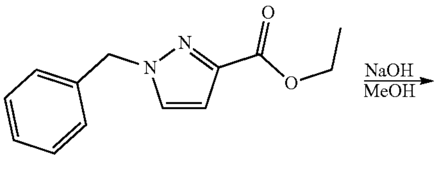

283B

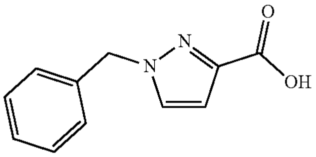

284A

To a mixture of ethyl 1H-pyrazole-5-carboxylate (1 g, 7.14 mmol) and benzyl bromide (0.93 mL, 7.8 mmol) in DMF (30 mL) was added $K_2CO_3$ (1.18 g, 8.6 mmol) in one portion at 25° C. The mixture was stirred at 25° C. for 14 h. The reaction mixture was added $H_2O$ (80 mL) and extracted by EA (50 mL×3). The combined organic phase was washed with Sat. NaCl (50 mL×2). The organic phase was dried over $Na_2SO_4$, filtered and concentrated. The residue was purified by FCC ($SiO_2$, Petroleum ether/Ethyl acetate=I/O to 3/1) to afford compound 283A (523 mg, yield 31.7%) as colorless liquid and compound 283B (989 mg, yield 60.1%) as white solid.

Compound 283A: $^1H$ NMR (DMSO-$d_6$, 400 MHz) δ 7.65 (d, J=2.0 Hz, 1H), 7.36-7.23 (m, 3H), 7.13 (d, J=7.0 Hz, 2H), 6.95 (d, J=2.0 Hz, 1H), 5.72 (s, 2H), 4.27 (q, J=7.2 Hz, 2H), 1.26 (t, J=7.0 Hz, 3H). MS (ESI) m/z $(M+H)^+$231.0.

Compound 283B: $^1H$ NMR (DMSO-$d_6$, 400 MHz) δ 7.99 (d, J=2.5 Hz, 1H), 7.40-7.29 (m, 3H), 7.28-7.23 (m, 2H), 6.77 (d, J=2.3 Hz, 1H), 5.43 (s, 2H), 4.25 (q, J=7.0 Hz, 2H), 1.27 (t, J=7.0 Hz, 3H). MS (ESI) m/z $(M+H)^+$231.0.

To a mixture of compound 283A (517 mg, 2.2 mmol) in MeOH (10 mL) was added NaOH (2M, 6 mL, 12.0 mmol) in one portion at 25° C. After stirred at 25° C. for 2 h, the reaction mixture was concentrated under reduced pressure to move MeOH, the aqueous phase was acidified with aqueous HCl (1M) till pH ~4-5. The precipitate was filtered and dried to afford compound 283C (389 mg, crude) as white solid, which was used directly for next step without purification. $^1H$ NMR (DMSO-$d_6$, 400 MHz) δ 7.60 (d, J=2.0 Hz, 1H), 7.34-7.22 (m, 3H), 7.15-7.08 (m, 2H), 6.88 (d, J=2.0 Hz, 1H), 5.73 (s, 2H).

Compound 283 (177 mg, yield 89.0%) was prepared as in Example 12 from the corresponding intermediate carboxylic acid, compound 283C. Compound 283: $^1H$ NMR (DMSO-$d_6$, 400 MHz) δ 8.91 (d, J=7.1 Hz, 1H), 8.11 (s, 1H), 7.84 (s, 1H), 7.52 (s, 1H), 7.26 (s, 8H), 7.14-7.01 (m, 2H), 6.89 (s, 1H), 5.60 (s, 2H), 5.40-5.24 (m, 1H), 3.27-3.13 (m, 1H), 2.95-2.80 (m, 1H). MS (ESI) m/z $(M+H)^+$377.1.

Following the same procedure as is used for compound 283, compound 284 (35 mg, yield 35.7%, white solid) was prepared from the corresponding intermediate carboxylic acid, compound 284A. Compound 284: $^1H$ NMR (DMSO-$d_6$, 400 MHz) δ 8.18 (br d, J=7.5 Hz, 1H), 8.05 (br s, 1H), 7.94-7.79 (m, 2H), 7.40-7.30 (m, 3H), 7.28-7.18 (m, 7H), 6.64 (s, 1H), 5.40 (s, 3H), 3.19 (br dd, J=3.7, 13.7 Hz, 1H), 3.04 (br dd, J=8.9, 13.8 Hz, 1H). MS (ESI) m/z $(M+H)^+$ 377.1.

Example 161

(S)-3-methyl-N-(1-oxo-3-phenylpropan-2-yl)-1-(pyrazin-2-yl)-1H-pyrazole-5-carboxamide (285)

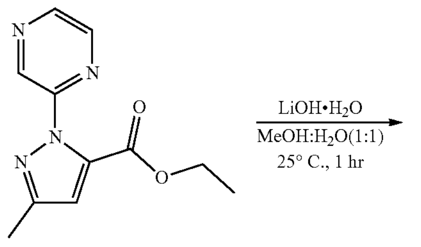

285A

-continued

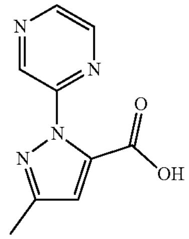

285C

A mixture of 2-hydrazineylpyrazine (2 g, 18.16 mmol) and ethyl 2,4-dioxopentanoate (2.87 g, 18.16 mmol) in AcOH (40 mL) was stirred at 118° C. for 1 hour. The reaction mixture was concentrated under reduced pressure to remove AcOH. The residue was diluted with $H_2O$ (8 mL), adjusted to pH ~7 with $Na_2CO_3$, and then extracted with DCM (200 mL×3). The combined organic layers were washed with brine (20 mL), dried over anhydrous $Na_2SO_4$, filtered and concentrated under reduced pressure to give the crude product. The residue was purified by flash silica gel chromatography (ISCO®; 40 g SepaFlash® Silica Flash Column, Eluent of 0~20% Ethyl acetate/Petroleum ether-gradient @ 40 mL/min). Compound 285A (1.5 g, 35.57% yield) was obtained as a white solid. Compound 285A: $^1H$ NMR (400 MHz, $CDCl_3$) δ 8.98-8.93 (m, 1H), 8.60-8.54 (m, 1H), 8.46-8.41 (m, 1H), 6.78 (s, 1H), 4.34-4.25 (m, 2H), 2.38 (s, 3H), 1.27 (t, J=7.2 Hz, 3H).

Intermediate compound 285C (1.2 g, 92.84% yield, white solid) was deprotected as in Example 85 from compound 285A. Compound 285C: $^1H$ NMR (400 MHz, DMSO-$d_6$): δ 8.96-8.92 (m, 1H), 8.70-8.66 (m, 1H), 8.58-8.54 (m, 1H), 6.84 (s, 1H), 2.25-2.24 (m, 1H), 2.26 (s, 2H).

Compound 285 (143.0 mg, 53.28% yield, white solid) was prepared as in Example 6 from the corresponding intermediate compounds 285C and 21G ((S)-2-amino-3-phenylpropan-1-ol). Compound 285: $^1H$ NMR (400 MHz, $CDCl_3$) δ 9.74 (s, 1H), 9.19-9.16 (m, 1H), 9.03-8.96 (m, 1H), 8.48-8.43 (m, 1H), 8.06-8.03 (m, 1H), 7.27-7.25 (m, 1H), 7.24-7.20 (m, 3H), 7.17-7.12 (m, 2H), 6.80 (s, 1H), 5.00-4.91 (m, 1H), 3.39-3.31 (m, 1H), 3.30-3.23 (m, 1H), 2.37 (s, 3H). MS (ESI) m/z $(M+H_2O+H)^+$354.2.

Example 162

(S)-3-methyl-N-(1-oxo-3-phenylpropan-2-yl)-1-(pyrazin-2-yl)-1H-pyrazole-5-carboxamide (286)

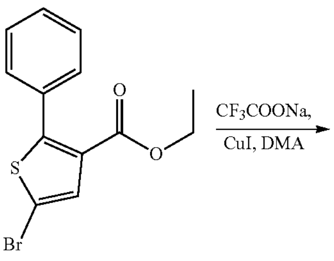

286A

-continued

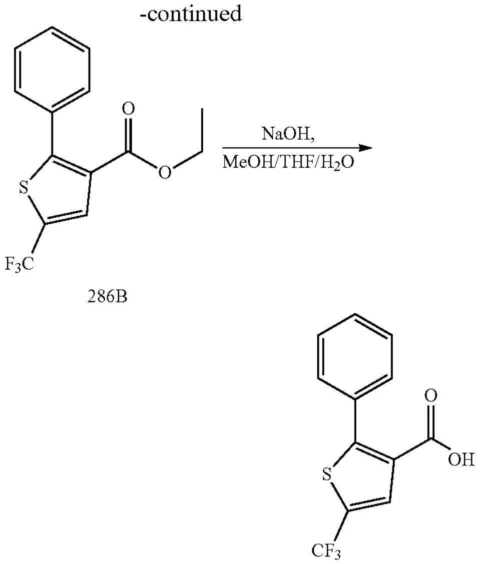

286B

286C

To a solution of compound 270A (1 g, 4.30 mmol) in DMF (20 mL) was added NBS (1.53 g, 8.60 mmol) at 80° C., and the mixture was stirred at 80° C. for 1.5 hrs. The mixture was poured into water (40 mL) and extracted with ethyl acetate (20 mL×2), the combined organic layer was washed with saturated $NaHCO_3$ (20 mL), brine (20 mL), dried over $Na_2SO_4$, filtered and concentrated. The residue was purified by silica gel chromatography (Petroleum ether to Petroleum ether:Ethyl acetate=20:1) to give compound 286A (1.3 g, yield: 97.2%) as white solid. $^1H$ NMR (400 MHz, $CDCl_3$) δ 7.49-7.41 (m, 3H), 7.40-7.34 (m, 3H), 4.16 (q, J=7.2 Hz, 2H), 1.16 (t, J=7.1 Hz, 3H).

A mixture of compound 286A (1 g, 3.21 mmol), CuI (1.22 g, 6.42 mmol) and sodium 2,2,2-trifluoroacetate (4.37 g, 32.1 mmol) in DMA (20 mL) was heated to 160° C. for 5 hrs. The mixture was added ethyl acetate (30 mL), water (50 mL), 1N HCl (50 mL), the mixture was filtered, and the filtrate was separated. The organic solvent was washed with water (30 mL), brine (30 mL), dried over $Na_2SO_4$, filtered and concentrated. The residue was purified by MPLC (Petroleum ether to Petroleum ether:Ethyl acetate=30:1) to give compound 286B (210 mg, yield: 21.8%), as yellow oil. $^1H$ NMR (400 MHz, $CDCl_3$) δ 7.85 (d, J=1.1 Hz, 1H), 7.53-7.47 (m, 2H), 7.47-7.37 (m, 3H), 4.21 (q, J=7.2 Hz, 2H), 1.20 (t, J=7.1 Hz, 3H).

A mixture of compound 286B (210 mg, 699 umol) and NaOH (55.9 mg, 1.40 mmol) in THF (5 mL), EtOH (3 mL), $H_2O$ (2 mL) was stirred at 10° C. for 12 hrs. The organic solvents was removed under vacuum, the water layer was adjusted to pH ~5 with 1N HCl, and extracted with ethyl acetate (20 mL), the organic layer was dried over $Na_2SO_4$, filtered and concentrated to give compound 286C (160 mg, yield: 84%), as yellow solid. $^1H$ NMR (400 MHz, $CDCl_3$) δ 7.81 (d, J=1.1 Hz, 1H), 7.46-7.41 (m, 2H), 7.40-7.31 (m, 3H).

Compound 286 (28.3 mg, yield: 45.5%, white solid) was prepared as in Example 5 from the corresponding starting materials, compounds 286C and 3-amino-2-hydroxy-4-phenyl-butanamide (274D). Compound 286: $^1H$ NMR (400 MHz, $CDCl_3$) δ 7.76 (s, 1H), 7.61-7.38 (m, 5H), 7.26-7.16 (m, 3H), 6.80 (br d, J=5.6 Hz, 2H), 6.70 (br s, 1H), 6.01 (br d, J=5.9 Hz, 1H), 5.61-5.47 (m, 2H), 3.24 (dd, J=5.0, 14.2 Hz, 1H), 2.93 (dd, J=7.6, 14.2 Hz, 1H). MS (ESI) m/z $(M+H)^+$447.1.

Example 163

(S)-3-methyl-N-(1-oxo-3-phenylpropan-2-yl)-1-(pyrazin-2-yl)-1H-pyrazole-5-carboxamide (287)

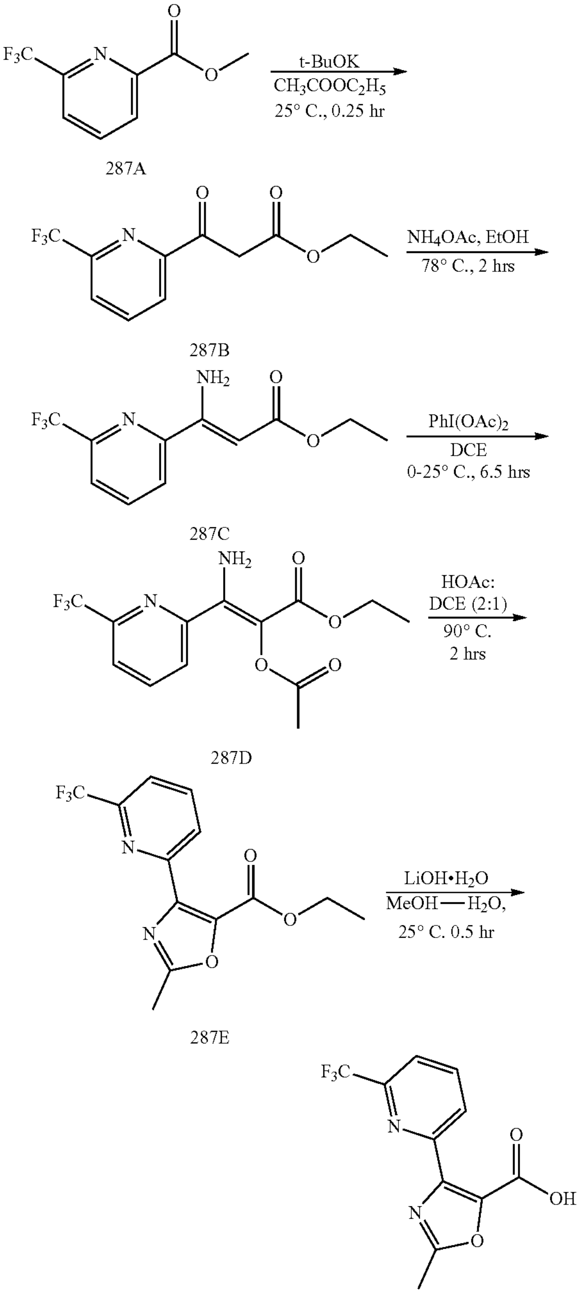

287A

287B

287C

287D

287E

287F

To a solution of 6-(trifluoromethyl)picolinic acid (10 g, 52.33 mmol) in MeOH (150 mL) was added $H_2SO_4$ (1.03 g, 10.47 mmol, 557.88 uL) dropwise. After stirred at 65° C. for 10 hours, the mixture was cooled to room temperature, neutralized with a saturated aqueous $NaHCO_3$ solution, and extracted with $CH_2Cl_2$ (70 mL×3). The organic phases were combined, dried with anhydrous $Na_2SO_4$, and evaporated to afford crude intermediate compound 287A (9.20 g, 85.71% yield) as white solid. $^1$H NMR (400 MHz, $CDCl_3$) δ 8.32 (d, J=8.0 Hz, 1H), 8.09-8.05 (m, 1H), 7.88 (d, J=8.0 Hz, 1H), 4.03 (s, 3H).

A solution of compound 287A (4.5 g, 21.94 mmol) in $CH_3COOC_2H_5$ (150 mL) was added t-BuOK (3.20 g, 28.52 mmol). The mixture was stirred for 0.25 hour at 25° C. The mixture was quenched with $H_2O$ (150 mL). The organic layer was separated and the aqueous was extracted with EA (70 mL×3). The organic phases were combined, dried with anhydrous $Na_2SO_4$, filtered and evaporated to afford intermediate compound 287B (3.95 g, 66.86% yield) as yellow oil. $^1$H NMR (400 MHz, $CDCl_3$) δ 8.24 (d, J=8.0 Hz, 1H), 8.09-8.06 (m, 1H), 7.87 (d, J=7.2 Hz, 1H), 4.22-4.16 (m, 4H), 1.26-1.23 (m, 3H).

To a solution of compound 287B (3.90 g, 14.93 mmol) in EtOH (80 mL) was added $NH_4OAc$ (5.75 g, 74.65 mmol), then the mixture was stirred at 78° C. for 2 hours. The reaction mixture was concentrated under reduced pressure to remove the solvent. The residue was diluted with EA (500 mL) and washed with saturated aqueous $NaHCO_3$ solution (30 mL×3) and brine (30 mL×3). The organic layer were dried over anhydrous $Na_2SO_4$, filtered and concentrated under reduced pressure to give a residue. The residue was purified by flash column chromatography (PE:EA=30/1 to 10/1) to afford compound 287C (2.52 g, 64.87% yield) as white solid. $^1$H NMR (400 MHz, $CDCl_3$) δ 7.94-7.93 (m, 2H), 7.73-7.71 (m, 1H), 5.38 (s, 1H), 4.23-4.18 (m, 2H), 1.33-1.29 (m, 3H).

To a mixture of compound 287C (2.5 g, 9.61 mmol) in DCE (60.00 mL) was added $PhI(OAc)_2$ (4.02 g, 12.49 mmol) at 0° C. under $N_2$ in four portions, the mixture was stirred at 0° C. for 6 h and then warmed to 25° C. slowly. The mixture was then stirred at 25° C. for 0.5 h. The reaction mixture was quenched with saturated aqueous $NaHCO_3$ (150 mL) at 0° C., warmed to 25° C. slowly, and extracted with DCM (100 mL×3). The combined organic layers were dried over anhydrous $Na_2SO_4$, filtered and concentrated under reduced pressure to give a residue. The residue was purified by flash column chromatography (PE:EA=20/1 to 10/1) to afford compound 287D (650 mg, 21.23% yield) as yellow oil. $^1$H NMR (400 MHz, $CDCl_3$) δ 8.34-8.18 (m, 1H), 8.16-8.13 (s, 1H), 7.96-7.90 (m, 1H), 4.28-4.23 (m, 2H), 2.13 (s, 3H), 1.28-1.23 (m, 3H).

A mixture of compound 287D (600 mg, 1.89 mmol) in DCE (5 mL) and $CH_3COOH$ (10 mL) was stirred at 90° C. for 2 hours. The reaction mixture was concentrated under reduced pressure to remove the solvent and to give the residue. The residue was purified by flash column chromatography (PE:EA=30/1 to 10/1) to afford compound 287E (120 mg, 221.31 umol, 11.71% yield, 55.37% purity) as yellow solid. $^1$H NMR (400 MHz, $CDCl_3$) δ 8.42-8.33 (m, 1H), 8.17-8.15 (m, 1H), 7.99-7.26 (m, 1H), 4.40-4.37 (m, 2H), 2.62 (s, 3H), 1.35-1.32 (m, 3H).

To a solution of compound 287E (110 mg, 366.39 umol) in MeOH (6 mL) and $H_2O$ (3 mL) was added $LiOH.H_2O$ (61 mg, 1.47 mmol), then the mixture was stirred at 25° C. for 0.5 hour. The reaction mixture was concentrated under reduced pressure to remove MeOH. The residue was diluted with $H_2O$ (20 mL), adjusted to pH ~3 with 1N HCl, then extracted with EtOAc (30 mL×3). The combined organic layers were washed with brine (30 mL), dried over anhydrous $Na_2SO_4$, filtered and concentrated under reduced pressure to give intermediate compound 287F (86 mg, 59.17% yield) as a white solid. $^1$H NMR (400 MHz, DMSO-$d_6$) δ 8.45-8.26 (m, 2H), 8.10-8.07 (m, 1H), 2.58 (s, 3H).

Compound 287 (12.1 mg, 20.26% yield, off-white solid) was prepared as in Example 5 from the corresponding starting materials, compounds 287F and 3-amino-2-hydroxy-4-phenyl-butanamide (274D). Compound 287: $^1$H NMR (400 MHz, $CDCl_3$): δ 11.10 (d, J=7.2 Hz, 1H), 8.46 (d, J=8.0 Hz, 1H), 8.18-7.99 (m, 1H), 7.72 (d, J=8.0 Hz, 1H), 7.23-7.04 (m, 5H), 6.70 (br s, 1H), 5.64-5.52 (m, 1H), 5.45 (br s, 1H), 3.57-3.47 (m, 1H), 3.10-2.94 (m, 1H), 2.55 (d, J=0.80 Hz, 3H). MS (ESI) m/z $(M+1)^+$447.2.

Example 164

Compounds 288-289

(S)—N-(4-amino-3,4-dioxo-1-phenylbutan-2-yl)-3-(pyridin-2-yl)isoxazole-4-carboxamide (288)

(S)—N-(4-amino-3,4-dioxo-1-phenylbutan-2-yl)-3-(4-fluorophenyl)isoxazole-4-carboxamide (289)

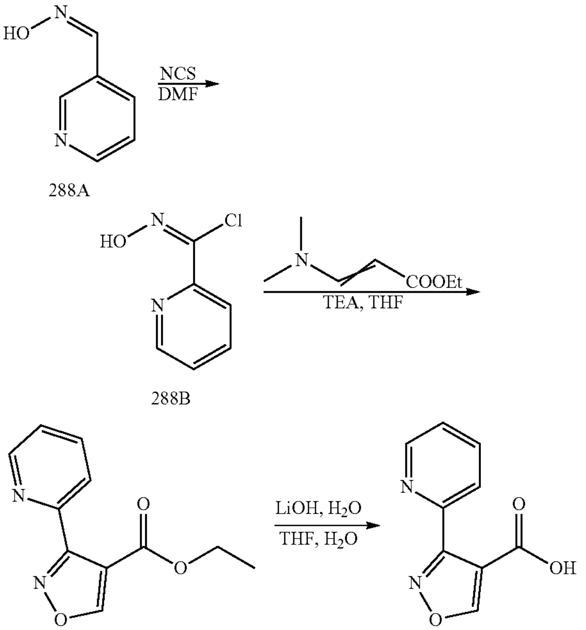

288A 288B 288C 288D

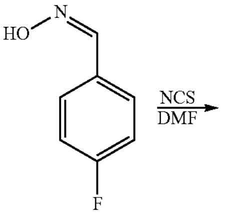

289A

-continued

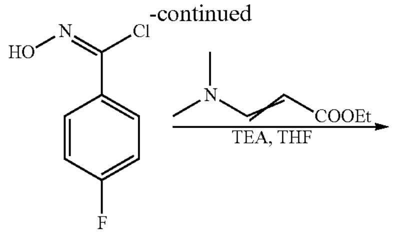

289B

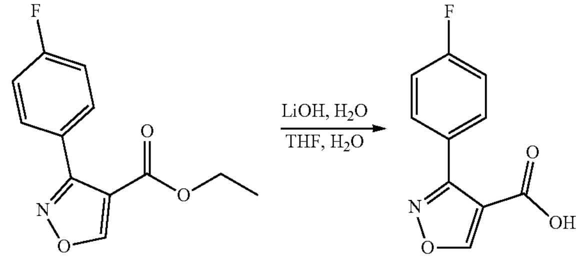

289C

289D $NH_2OH$.HCl (156 mg, 2.24 mmol) and NaOAc (184 mg, 2.24 mmol) was added in a solution of picolinaldehyde (200 mg, 1.87 mmol) in EtOH (15 mL). The mixture was heated at 60° C. for 2 hours. The reaction mixture was concentrated. Dichloromethane (50 mL) was added. The organic phase was washed with $H_2O$ (10 mL) and brine (10 mL), dried with anhydrous $Na_2SO_4$, filtered and concentrated in vacuum to give intermediate compound 288A (180 mg, yield: 78.8%) as a yellow solid. $^1H$ NMR (400 MHz, $CDCl_3$) δ 9.47 (br s, 1H), 8.57 (br d, J=4.2 Hz, 1H), 8.50 (br d, J=4.4 Hz, 1H), 8.26 (s, 1H), 7.85 (t, J=7.7 Hz, 1H), 7.76 (d, J=7.9 Hz, 1H), 7.69-7.62 (m, 1H), 7.40-7.32 (m, 1H), 7.26-7.17 (m, 1H).

To a mixture of compound 288A (180 mg, 1.47 mmol) in DMF (2 mL) was added NCS (216 mg, 1.62 mmol) in one portion at 20° C. The mixture was stirred at 20° C. for 12 hours. The reaction mixture was concentrated. The residue was poured into water (20 mL). The aqueous phase was extracted with ethyl acetate (50 mL×3). The combined organic phase was washed with brine (20 mL×2), dried with anhydrous $Na_2SO_4$, filtered and concentrated in vacuum to give intermediate compound 288B (200 mg, yield: 87.1%) as a brown solid. $^1H$ NMR (400 MHz, $CDCl_3$) δ 10.79 (br s, 1H), 8.72 (d, J=4.2 Hz, 1H), 7.94 (d, J=8.2 Hz, 1H), 7.80 (dt, J=1.7, 7.8 Hz, 1H), 7.39 (ddd, J=0.8, 5.0, 7.4 Hz, 1H), 2.79 (s, 1H).

To a mixture of ethyl 3-(dimethylamino)acrylate (92 mg, 639 umol), TEA (129 mg, 1.28 mmol) in THF (10 mL) was added a solution of compound 288B (200 mg, 1.28 mmol) in THF (10 mL) over a period of 20 min. The mixture was stirred at 20° C. and stirred for 12 hours. The reaction mixture was concentrated. The residue was purified by preparatory-TLC ($SiO_2$, Petroleum ether:Ethyl acetate=1:1) to give compound 288C (150 mg, yield: 53.8%) as yellow oil. $^1H$ NMR (400 MHz, $CDCl_3$-d) δ 9.02-8.97 (m, 1H), 8.75 (d, J=4.6 Hz, 1H), 7.87-7.76 (m, 2H), 7.45-7.36 (m, 1H), 4.27 (q, J=7.3 Hz, 2H), 1.26 (t, J=7.2 Hz, 3H).

To a mixture of compound 288C (150 mg, 687 umol) in THF (5 mL) and $H_2O$ (1 mL) was added LiOH.$H_2O$ (58 mg, 1.4 mmol). The mixture was stirred at 15° C. for 12 hours. The mixture was concentrated to remove solvent. The mixture was adjusted to pH ~5 with aqueous HCl (1M) and concentrated to give intermediate compound 288D (130 mg, yield: 99.5%) as a brown solid. $^1H$ NMR (400 MHz, DMSO-$d_6$) δ 9.57 (s, 1H), 8.76 (d, J=4.9 Hz, 1H), 8.11-8.05 (m, 2H), 7.65 (dt, J=3.1, 5.3 Hz, 1H).

Compound 288 (73.8 mg, yield: 81.7%, yellow solid) was prepared as in Example 5 from the corresponding intermediate carboxylic acid, compound 288D. Compound 288: $^1H$ NMR (400 MHz, DMSO-$d_6$) δ 11.10 (br d, J=7.0 Hz, 1H), 9.44 (s, 1H), 8.46 (d, J=4.4 Hz, 1H), 8.11-8.01 (m, 2H), 7.81 (br s, 1H), 7.65-7.51 (m, 2H), 7.17-7.08 (m, 5H), 5.62-5.52 (m, 1H), 3.27 (dd, J=5.0, 13.8 Hz, 1H), 3.13-3.06 (m, 1H). MS (ESI) m/z $(M+H)^+$365.1.

Following the procedure used for compound 288, compound 289 (83.1 mg, yield: 70.9%, white solid) was prepared from the corresponding intermediate carboxylic acid, compound 289D. Intermediate compound 289D (100 mg, yield: 56.8%, white solid): $^1H$ NMR (400 MHz, DMSO-$d_6$) δ 9.55 (s, 1H), 7.89-7.81 (m, 2H), 7.39-7.28 (m, 2H). Compound 289: $^1H$ NMR (400 MHz, DMSO-$d_6$) δ 9.32 (s, 1H), 9.10 (d, J=7.6 Hz, 1H), 8.11 (s, 1H), 7.86 (s, 1H), 7.65-7.56 (m, 2H), 7.33-7.21 (m, 7H), 5.40-5.29 (m, 1H), 3.19 (dd, J=3.9, 13.9 Hz, 1H), 2.84 (dd, J=10.0, 13.9 Hz, 1H). MS (ESI) m/z $(M+H)^+$382.1.

Example 165

(S)—N-(4-amino-3,4-dioxo-1-phenylbutan-2-yl)-4-methyl-1-phenyl-1H-imidazole-5-carboxamide (290)

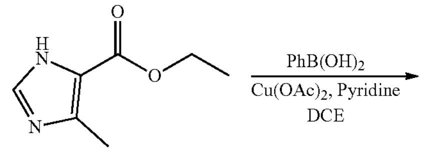

290A

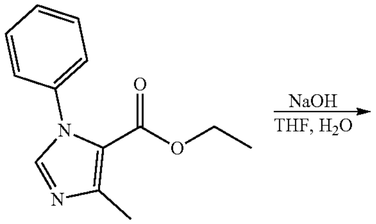

290B

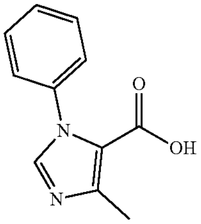

290C

A mixture of ethyl 2-chloro-3-oxobutanoate (16 g, 97.2 mmol), formamide (43.8 g, 972 mmol), $H_2O$ (3.50 g, 194 mmol) in autoclave was stirred at 180° C. for 3.5 hours. The reaction mixture was filtered and the filtered cake was dissolved in DCM (200 mL). The mixture was filtered and the filtrate was concentrated under reduced pressure to give a residue. Compound 290A (2 g, crude) was obtained as a yellow solid. MS (ESI) m/z $(M+H)^+$154.8.

A mixture of 290A (1.8 g, 11.7 mmol), phenylboronic acid (2.85 g, 23.4 mmol), $Cu(OAc)_2$ (3.18 g, 17.5 mmol), pyridine (1.85 g, 23.4 mmol) and 4A° MS (2 g) in DCE (60 mL) was degassed and purged with 02 for 3 times, and then the mixture was stirred at 60° C. for 12 hours under 02 atmosphere. The reaction mixture was filtered and concentrated under reduced pressure to give a residue. The residue was purified by column chromatography (Petroleum ether:Ethyl acetate=50:1 to 2:1). Compound 290B (1.15 g, yield: 42.7%) was obtained as a yellow solid. $^1H$ NMR (400 MHz, $CDCl_3$) δ 7.53 (s, 1H), 7.45-7.35 (m, 3H), 7.27-7.16 (m, 2H), 4.18-4.05 (m, 2H), 2.53 (s, 3H), 1.10 (t, J=7.1 Hz, 3H). MS (ESI) m/z $(M+H)^+$231.0.

A mixture of 290B (300 mg, 1.30 mmol), $LiOH.H_2O$ (109 mg, 2.60 mmol) in THF (10 mL), $H_2O$ (10 mL) was stirred at 15° C. for 12 hrs. LCMS showed most of 290B was remained. To the mixture was added NaOH (416 mg, 10.4 mmol), and the mixture was stirred at 70° C. for 12 hrs. The reaction mixture was added aq. HCl to adjust the pH ~5. And then the mixture was filtered, and the filter cake was concentrated to give the product. Compound 290C (300 mg, crude) was obtained as a yellow solid. $^1H$ NMR (400 MHz, DMSO-$d_6$) δ 7.90 (s, 1H), 7.50-7.37 (m, 3H), 7.36-7.28 (m, 2H), 2.39 (s, 3H). MS (ESI) m/z $(M+H)^+$203.1.

Compound 290 (15.3 mg, yield: 11.5%, white solid) was prepared as in Example 5 from the corresponding intermediate carboxylic acid, compound 290C. Compound 290: $^1H$ NMR (400 MHz, DMSO-$d_6$) δ 8.23 (br d, J=7.0 Hz, 1H), 7.73 (s, 1H), 7.80-7.56 (m, 1H), 7.41-7.13 (m, 11H), 5.31 (br s, 1H), 3.20 (dd, J=3.7, 13.8 Hz, 1H), 2.92-2.80 (m, 1H), 2.18-2.13 (m, 3H). MS (ESI) m/z $(M+H)^+$377.2.

Example 166

(S)—N-(4-amino-3,4-dioxo-1-phenylbutan-2-yl)-4-chloro-1-phenyl-1H-imidazole-5-carboxamide (291)

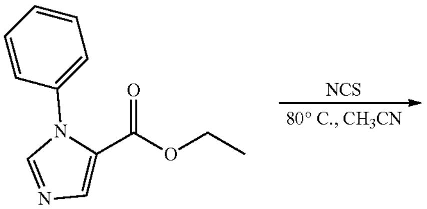

291A

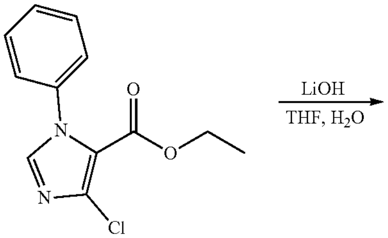

291B

-continued

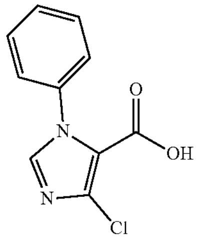

291C

A mixture of ethyl 1H-imidazole-5-carboxylate (10 g, 71.4 mmol), phenylboronic acid (13.1 g, 107 mmol), $Cu(OAc)_2$ (19.4 g, 107 mmol), pyridine (11.3 g, 142.72 mmol) and 4A MS (4.0 g) in DCE (200 mL) was degassed and purged with 02 for 3 times, and then the mixture was stirred at 60° C. for 12 hours under 02 atmosphere. The reaction mixture was filtered and concentrated under reduced pressure to give a residue. The residue was purified by column chromatography ($SiO_2$, Petroleum ether:Ethyl acetate=20:1 to 5:1). Compound 291A (2.8 g, yield: 18.2%) was obtained as a yellow solid. (Note: The structure was confirmed by NOE). $^1H$ NMR (400 MHz, $CDCl_3$) δ 7.79 (s, 1H), 7.63 (s, 1H), 7.47-7.33 (m, 3H), 7.32-7.22 (m, 2H), 4.14 (q, J=7.2 Hz, 2H), 1.16 (t, J=7.1 Hz, 3H).

To a solution of 291A (1 g, 4.62 mmol) in $CH_3CN$ (20 mL) was added NCS (925 mg, 6.93 mmol) at 80° C. The mixture was stirred at 80° C. for 2 hrs. The reaction mixture was concentrated under reduced pressure to give a residue. The residue was dissolved in DCM (50 mL), filtered, and the filtrate was concentrated under reduced pressure to give a residue. The residue was purified by column chromatography (SiO2, Petroleum ether:Ethyl acetate=80:1 to 50:1) and then purified by preparatory-TLC (Petroleum ether:Ethyl acetate=3:1). Compound 291B (150 mg, yield: 13.0%) was obtained as a yellow oil. (Note: The structure was confirmed by HMBC). $^1H$ NMR (400 MHz, $CDCl_3$) δ 7.77-7.62 (m, 1H), 7.54-7.37 (m, 3H), 7.29-7.10 (m, 2H), 4.09 (q, J=7.1 Hz, 2H), 1.11 (t, J=7.2 Hz, 3H).

A mixture of 291B (150 mg, 598 umol), $LiOH.H_2O$ (50.2 mg, 1.20 mmol) in THF (5 mL), $H_2O$ (5 mL) was stirred at 15° C. for 12 hours. The reaction mixture was added aq. HCl to adjust the pH ~5. And then the mixture was filtered, and the filter cake was concentrated to give the product. Compound 291C (130 mg, crude) was obtained as a white solid. $^1H$ NMR (400 MHz, DMSO-$d_6$) δ 7.45 (br d, J=2.2 Hz, 4H), 7.29 (br s, 2H). MS (ESI) m/z $(M+H)^+$222.8.

Compound 291 (47.1 mg, yield: 47.6%, brown solid) was prepared as in Example 5 from the corresponding intermediate carboxylic acid, compound 291C. Compound 291: $^1H$ NMR (400 MHz, DMSO-$d_6$) δ 8.74 (br d, J=7.7 Hz, 1H), 8.02 (br s, 1H), 7.79 (br s, 1H), 7.66 (s, 1H), 7.43 (br d, J=4.0 Hz, 3H), 7.37-7.10 (m, 7H), 5.16 (br t, J=6.8 Hz, 1H), 3.13 (br d, J=10.8 Hz, 1H), 2.86-2.68 (m, 1H). MS (ESI) m/z $(M+H)^+$397.1.

Example 167

(2S,4R)—N-(4-amino-3,4-dioxo-1-phenylbutan-2-yl)-4-methyl-1-phenylpyrrolidine-2-carboxamide (292)

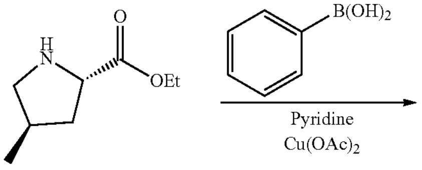

292A

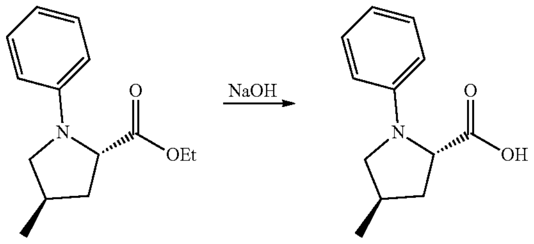

292B 292C

To the mixture of 1-(tert-butyl) 2-ethyl (2S,4R)-4-methylpyrrolidine-1,2-dicarboxylate (2 g, 7.77 mmol) in EtOAc (5 mL) was added HCl/EtOAc (4M, 20 mL) at 25° C. The mixture was stirred at 25° C. for 10 h. The mixture was concentrated to get residue and saturated aqueous $Na_2CO_3$ (1.5 mL) was added to the residue, then DCM (200 mL) was added. Then the mixture was dried with anhydrous $Na_2SO_4$, filtered and concentrated in vacuum to get crude compound 292A (1.9 g, crude) as yellow oil. $^1H$ NMR (400 MHz, $CDCl_3$) δ 8.76 (br s, 2H), 5.29 (s, 1H), 4.48 (dd, J=4.1, 9.2 Hz, 1H), 4.27 (q, J=7.2 Hz, 2H), 3.73 (dd, J=7.4, 11.3 Hz, 1H), 2.95 (dd, J=9.1, 11.3 Hz, 1H), 2.48-2.28 (m, 2H), 2.05-1.95 (m, 1H), 1.31 (t, J=7.2 Hz, 3H), 1.13 (d, J=6.6 Hz, 3H).

To a mixture of compound 292A (1.9 g, 12.1 mmol) and phenylboronic acid (2.95 g, 24.2 mmol) in DCE (15 mL) was added 4A° MS (4 g), pyridine (1.91 g, 24.2 mmol), $Cu(OAc)_2$ (3.29 g, 18.1 mmol) in one portion at 25° C. The mixture was stirred at 60° C. for 10 h under 02 (15 psi). The reaction was filtered and the filtrate was concentrated in vacuum. The residue was purified by silica gel chromatography (petroleum ether/ethyl acetate=100/1, 50/1) to get compound 292B (900 mg, yield: 31.9%) as light oil. $^1H$ NMR (400 MHz, $CDCl_3$) δ 7.42-7.32 (m, 2H), 7.29-7.17 (m, 3H), 4.28-4.08 (m, 3H), 3.67 (t, J=8.0 Hz, 1H), 2.90 (t, J=8.7 Hz, 1H), 2.69-2.55 (m, 1H), 2.24-2.14 (m, 1H), 1.96-1.83 (m, 1H), 1.24 (t, J=7.1 Hz, 3H), 1.12 (d, J=6.6 Hz, 3H).

To the mixture of compound 292B (300 mg, 1.29 mmol) in EtOH (5 mL) and $H_2O$ (1 mL) was added NaOH (129 mg, 3.23 mmol) at 25° C. The mixture was stirred at 25° C. for 10 h. The reaction was concentrated and the aqueous phase was extracted with ethyl acetate (15 mL×2). Then to the aqueous phase was added HCl (1M) till pH ~3. Desired product was extracted with ethyl acetate (15 mL×2). The combined organic phase was washed with brine (20 mL×2), dried with anhydrous $Na_2SO_4$, filtered and concentrated in vacuum to get crude compound 292C (100 mg, crude) as yellow oil.

Compound 292 (12.7 mg, yield: 25.5%, off-white solid) was prepared as in Example 5 from the corresponding intermediate carboxylic acid, compound 292C. Compound 292: $^1H$ NMR (400 MHz, $CDCl_3$) δ 7.30-7.19 (m, 4H), 7.16-7.09 (m, 1H), 7.09-6.97 (m, 3H), 6.88-6.77 (m, 2H), 6.73 (br s, 1H), 6.55 (dd, J=8.2, 18.3 Hz, 2H), 5.75-5.61 (m, 1H), 5.61-5.36 (m, 1H), 4.04-3.92 (m, 1H), 3.65-3.47 (m, 1H), 3.42 (dd, J=5.0, 14.0 Hz, 1H), 3.23-3.02 (m, 1H), 2.90 (dd, J=8.9, 14.0 Hz, 1H), 2.82-2.68 (m, 1H), 2.41-2.29 (m, 1H), 2.28-2.04 (m, 1H), 2.03-1.89 (m, 1H), 1.88-1.70 (m, 1H), 1.13-1.00 (m, 3H). MS (ESI) m/z $(M+H)^+$380.2.

Example 168

(S)—N-(4-amino-3,4-dioxo-1-phenylbutan-2-yl)-4-phenyl-1,2,5-oxadiazole-3-carboxamide (293)

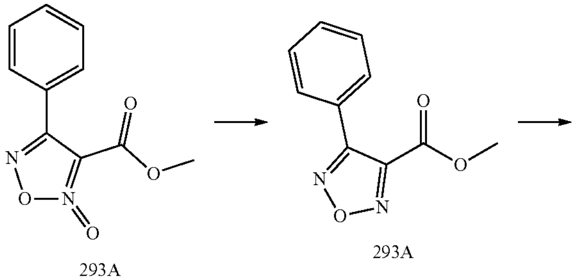

293A 293A

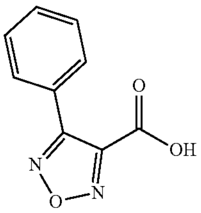

293C

To a solution of methyl cinnamate (1 g, 1 eq) in pyridine (20 mL) was added $NOBF_4$ (2.34 g, 3.2 eq) at 0° C. The reaction mixture was stirred at 0° C. for 2 days. The solution was poured into ice water and extracted with EtOAc (3 times). The combined organic phase was washed with water, dried over $NaSO_4$ and concentrated under reduced pressure. The residue was purified on ISCO to afford compound 293A.

The solution of compound 293A (0.5 g) in trimethyl phosphite (5 mL) was heated at 100° C. under $N_2$ overnight. The reaction was cooled to room temperature and quenched with 1N HCl (10 mL). The mixture was extracted with EtOAc (3 times). The combined organic phase was washed with water, dried over $NaSO_4$ and concentrated under reduced pressure. The residue was purified on ISCO to afford compound 293B.

Compound 293 was prepared as in Example 5 from the corresponding acid, intermediate compound 293C, which was obtained by treating compound 293B (720 mg) with LiOH in MeOH and water. $^1H$ NMR (400 MHz, DMSO): δ 9.81 (d, 1H), 8.22 (s, 1H), 7.95 (s, 1H), 7.6-7.2 (m, 10H), 5.53 (m, 1H), 3.25 (dd, 1H), 2.83 (dd, 1H) ppm. MS (ESI) m/z $(M+Na)^+$387.2.

Example 169

(S)—N-(4-amino-3,4-dioxo-1-phenylbutan-2-yl)-3-methyl-1-(1-methyl-1H-benzo[d]imidazol-2-yl)-1H-pyrazole-5-carboxamide (294)

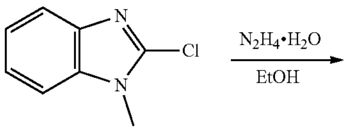

294A

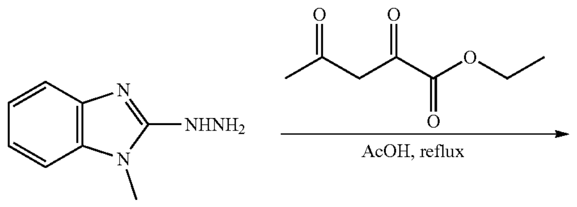

294B

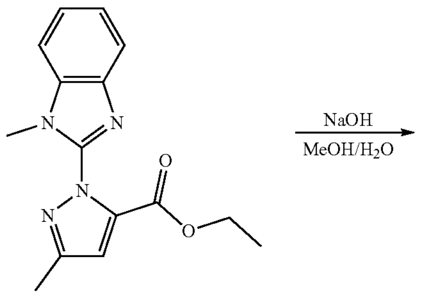

294C

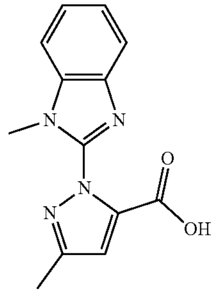

294E

MeI (6.1 mL, 98.3 mmol) was added to a mixture of 2-chloro-1H-benzo[d]imidazole (5.0 g, 32.8 mmol) and $K_2CO_3$ (13.6 g, 98.3 mmol) in DMF (20 mL). The mixture was stirred at 25° C. for 1 h. The insoluble substance was removed by filtration and the filtrate was treated with EA (50 mL), $H_2O$ (50 mL). The organic layer was separated and the aqueous layer was extracted with EA (35 mL×3). The combined organic layer was washed with $H_2O$ (35 mL×2), brine (35 mL×2), dried over $MgSO_4$, filtered and concentrated. The residue was triturated with TBME/PE (v/v=1/1, ~20 mL) to afford compound 294A (3.3 g, yield 60.38%) as pale yellow solid. $^1$H NMR (DMSO-$d_6$, 400 MHz) δ 7.60-7.56 (m, 2H), 7.31-7.24 (m, 2H), 3.80 (s, 3H). MS (ESI) m/z $(M+H)^+$167.0.

To a mixture of compound 294A (3.3 g, 19.8 mmol in EtOH (10 mL) was added $N_2H_4$.$H_2O$ (5.8 g, 99.1 mmol, 85% purity) in one portion. The mixture was stirred at 110° C. for 12 h. The reaction mixture was concentrated under reduced pressure. The residue was triturated with MTBE (20 mL), the precipitate was filtered and dried in vacuum to afford compound 294B (2.4 g, yield 73.1%) as white solid. $^1$H NMR (DMSO-$d_6$, 400 MHz) δ 7.25-7.21 (m, 1H), 7.17-7.13 (m, 1H), 6.98-6.89 (m, 2H), 3.45 (s, 3H).

To a mixture of compound 294B (1.0 g, 6.17 mmol) and ethyl 2,4-dioxopentanoate (1.0 g, 6.48 mmol) in AcOH (20 mL) was stirred at 110° C. for 5 h. The reaction mixture was concentrated under reduced pressure to remove AcOH. The residue was added $H_2O$ (50 mL) and EA (50 mL), and then the mixture was acidified with saturated aqueous $NaHCO_3$ till the aqueous phase pH ~7-8. The separated aqueous layer was extracted with EA (100 mL×3), the combined organic layers were washed with saturated aqueous NaCl (150 mL), dried over $Na_2SO_4$, filtered under reduced pressure to give crude product. The crude product was purified by FCC ($SiO_2$, Petroleum ether:Ethyl acetate=1:0 3:1) to afford compound 294C (494 mg, yield 27.9%) as yellow liquid.

Compound 294C: $^1$H NMR (DMSO-$d_6$, 400 MHz) δ 7.69-7.63 (m, 2H), 7.41-7.35 (m, 1H), 7.33-7.28 (m, 1H), 7.05 (s, 1H), 4.10 (q, J=7.1 Hz, 2H), 3.55 (s, 3H), 2.32 (s, 3H), 0.99 (t, J=7.2 Hz, 3H). MS (ESI) m/z $(M+H)^+$285.1.

To a mixture of compound 294C (645 mg, 2.3 mmol) in MeOH (10 mL) was added NaOH (2 M, 5.7 mL) in one portion at 25° C. The mixture was stirred at 25° C. for 1.5 h. The reaction mixture was concentrated under reduced pressure to move MeOH, the residue was added $H_2O$ (10 mL) and acidified with 1N HCl solution till the aqueous phase pH ~6-7. The solid was separated and filtered under reduced pressure to afford compound 294E (482 mg, crude) as white solid, which was used directly for the next step without purification. $^1$H NMR (DMSO-$d_6$, 400 MHz) δ 13.58 (s, 1H), 7.69-7.61 (m, 2H), 7.40-7.34 (m, 1H), 7.33-7.26 (m, 1H), 6.96 (s, 1H), 3.54 (s, 3H), 2.31 (s, 3H). MS (ESI) m/z $(M+H)^+$257.0.

Compound 294 (27 mg, yield 57.7%, white solid) was prepared as in Example 5 from the corresponding intermediate carboxylic acid, compound 294E. Compound 294: $^1$H NMR ($CDCl_3$, 400 MHz) δ 9.98 (d, J=6.0 Hz, 1H), 7.63 (d, J=7.9 Hz, 1H), 7.44-7.29 (m, 4H), 7.04 (m, 3H), 6.99 (m, 2H), 6.90-6.85 (m, 1H), 6.78-6.71 (m, 1H), 5.74-5.65 (m, 1H), 3.81 (s, 3H), 3.36 (m, 1H), 3.09 (m, 1H), 2.37 (s, 3H). MS (ESI) m/z $(M+H)^+$431.1.

Example 170

(S)—N-(4-(cyclopropylamino)-3,4-dioxo-1-phenylbutan-2-yl)-3-methyl-1-(1-methyl-1H-benzo[d]imidazol-2-yl)-1H-pyrazole-5-carboxamide (295)

Compound 295 (50.0 mg, yield: 50.16%, white solid) was prepared as in Example 20 from the corresponding intermediate carboxylic acid, compound 294E. Compound 295: $^1$H NMR ($CDCl_3$, 400 MHz) δ 9.89-9.76 (m, 1H), 7.66-7.62 (m, 1H), 7.43-7.37 (m, 2H), 7.36-7.30 (m, 1H), 7.06-7.00 (m, 3H), 7.00-6.94 (m, 2H), 6.92-6.85 (m, 2H), 5.77-5.65 (m, 1H), 3.79 (s, 3H), 3.43-3.32 (m, 1H), 3.13-3.02 (m, 1H), 2.86-2.73 (m, 1H), 2.37 (s, 3H), 0.91-0.81 (m, 2H), 0.65-0.52 (m, 2H). MS (ESI) m/z $(M+H)^+$ 471.1.

Example 171

Compounds 296-297

(S)—N-(4-amino-3,4-dioxo-1-phenylbutan-2-yl)-1-(6-methoxybenzo[d]thiazol-2-yl)-5-methyl-1H-pyrazole-3-carboxamide (296)

(S)—N-(4-amino-3,4-dioxo-1-phenylbutan-2-yl)-1-(6-methoxybenzo[d]thiazol-2-yl)-3-methyl-1H-pyrazole-5-carboxamide (297)

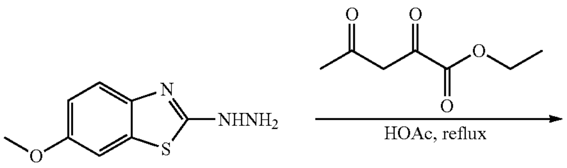

296A

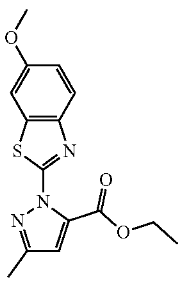

+

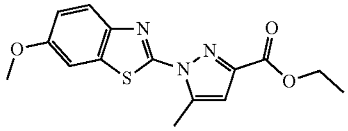

296B

296C

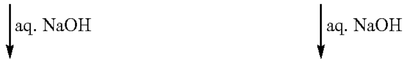

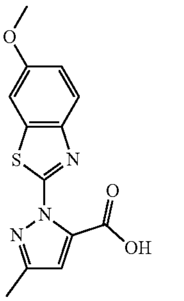

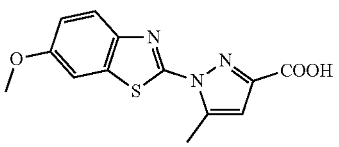

297A

296D

HCl (12 M, 5.50 mL) was added to $NH_2NH_2.H_2O$ (6.9 mL, 120 mmol) with stirring at 0-5° C., followed by ethylene glycol (30 mL). Then 6-methoxybenzo[d]thiazol-2-amine (3.6 g, 20.0 mmol) was added in portions. The mixture was heated to 125° C. and stirred for 3 h. After cooling to room temperature, the precipitate was collected by filtration. The cake was washed with EtOH (5 mL×3) to afford compound 296A (3.0 g, 15.37 mmol, yield 76.8%) was obtained as pale green solid.

A mixture of compound 296A (1.0 g, 5.1 mmol) and ethyl 2,4-dioxopentanoate (0.7 mL, 5.1 mmol) in HOAc (20 mL) was heated to 120° C. and stirred for 3 h. The mixture was concentrated. The residue was treated with MeOH (15 mL). The insoluble substance was removed by filter. The filtrate was concentrated and the residue was purified by preparatory-HPLC to afford compound 296C (670 mg, yield 41.2%) as pale yellow solid and compound 296B (74 mg, yield 4.6%) as pink solid. The insoluble substance (0.5 g, impure) as pink solid was treated with DCM (50 mL). The insoluble substance was removed off by filtration. The filtrate was washed with saturated $NaHCO_3$ (15 mL×3), brine (15 mL×2), dried over $MgSO_4$, filter and concentrated to afford compound 296B (0.35 g, yield 21.5%) as pink solid.

Compound 296B: $^1$H NMR ($CDCl_3$, 400 MHz) δ 7.80 (d, J=9.2 Hz, 1H), 7.30 (d, J=2.4 Hz, 1H), 7.06 (dd, J=2.4, 8.8 Hz, 1H), 6.72 (s, 1H), 4.42 (q, J=6.8 Hz, 2H), 3.89 (s, 3H), 2.82 (s, 3H), 1.42 (t, J=7.2 Hz, 3H). MS (ESI) m/z $(M+H)^+$ 317.9.

Compound 296C: $^1$H NMR ($CDCl_3$, 400 MHz) δ 7.80 (d, J=8.8 Hz, 1H), 7.30 (d, J=2.4 Hz, 1H), 7.80 (dd, J=2.0, 8.8 Hz, 1H) 6.71 (s, 1H), 4.37 (q, J=7.2 Hz, 2H), 3.88 (s, 3H), 2.37 (s, 3H), 1.30 (t, J=7.2 Hz, 3H). MS (ESI) m/z $(M+H)^+$ 317.9.

NaOH (2 M, 3.15 mL, 6.3 mmol) was added to a solution of compound 296C (400 mg, 1.26 mmol) in MeOH (15 mL). The mixture was stirred at 25° C. for 12 h. The mixture was diluted with $H_2O$ (50 mL) and the volatile solvent was removed by evaporation. The resulting aqueous solution was acidified to pH ~3 with 1N HCl. The precipitate was collected and azeotroped with toluene to afford compound 296D (320 mg, yield 87.8%) was obtained as white solid. $^1$H NMR (DMSO-$d_6$, 400 MHz) δ 7.78 (d, J=9.0 Hz, 1H), 7.70 (d, J=2.6 Hz, 1H), 7.11 (dd, J=2.5, 8.9 Hz, 1H), 6.86 (s, 1H), 3.82 (s, 3H), 2.28 (s, 3H).

Compound 296 (100 mg, yield 43.9%, pale yellow solid) was prepared as in Example 5 from the corresponding intermediate carboxylic acid, compound 296D. Compound 296: $^1$H NMR (DMSO-$d_6$, 400 MHz) δ 10.20 (br d, J=7.3 Hz, 1H), 8.12 (s, 1H), 7.86 (br s, 1H), 7.64 (d, J=2.4 Hz, 1H), 7.56 (d, J=9.0 Hz, 1H), 7.18 (q, J=7.8 Hz, 4H), 7.12 (br d, J=6.8 Hz, 1H), 7.05 (dd, J=2.6, 9.0 Hz, 1H), 6.73 (s, 1H), 5.59-5.49 (m, 1H), 3.81 (s, 3H), 3.22 (br dd, J=4.5, 14.0 Hz, 1H), 3.02 (br dd, J=8.5, 14.4 Hz, 1H), 2.27 (s, 3H). MS (ESI) m/z $(M+H)^+$464.1.

Following the same procedure as is used for compound 296, compound 297 (30 mg, yield 54.3%, white solid) was prepared from the corresponding intermediate carboxylic acid, compound 297A. Compound 297: $^1$H NMR (DMSO-$d_6$, 400 MHz) δ 8.55 (br d, J=7.5 Hz, 1H), 8.12 (s, 1H), 7.88-7.80 (m, 2H), 7.72 (d, J=2.6 Hz, 1H), 7.31-7.25 (m, 4H), 7.22-7.17 (m, 1H), 7.11 (dd, J=2.6, 8.8 Hz, 1H), 6.76 (s, 1H), 5.45-5.35 (m, 1H), 3.83 (s, 3H), 3.22 (br dd, J=4.1, 13.8 Hz, 1H), 3.04 (dd, J=9.4, 13.8 Hz, 1H), 2.73 (s, 3H). MS (ESI) m/z $(M+H)^+$464.1.

Example 172

Compounds 298-299

(S)—N-(4-amino-3,4-dioxo-1-phenylbutan-2-yl)-3-methyl-1-(4-methylbenzo[d]thiazol-2-yl)-1H-pyrazole-5-carboxamide (298)

(S)—N-(4-amino-3,4-dioxo-1-phenylbutan-2-yl)-5-methyl-1-(4-methylbenzo[d]thiazol-2-yl)-1H-pyrazole-3-carboxamide (299)

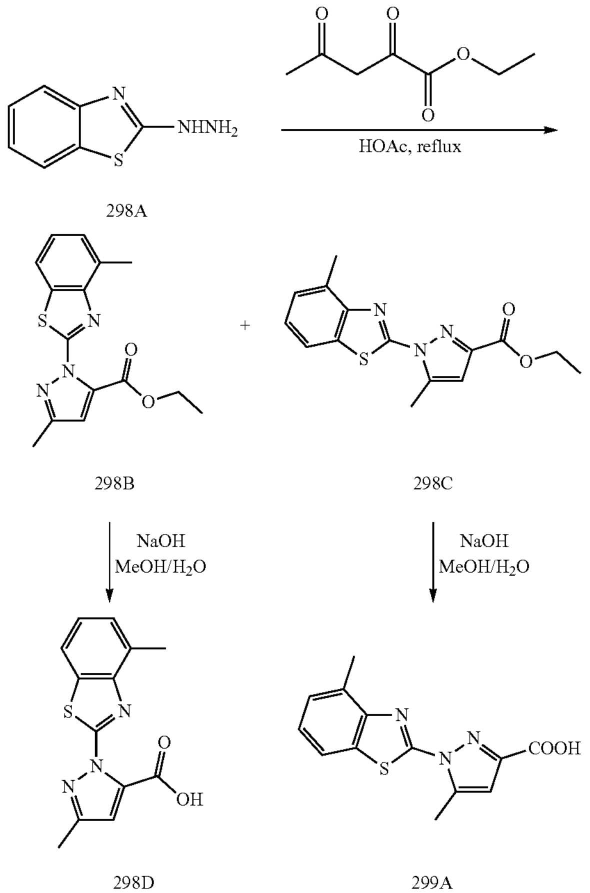

HCl (12M, 2.5 mL) was added to a mixture of 4-methylbenzo[d]thiazol-2-amine (5.0 g, 30.5 mmol) and $NH_2NH_2.H_2O$ (19.2 mL, 335 mmol) in ethylene glycol (30 mL). The mixture was heated 120° C. and stirred for 5 h. After cooling to room temperature, precipitation was observed. The precipitate was collected by filtration, and washed with EtOH (15 mL) to afford compound 298A (2.3 g, yield 41.7%) as white needle crystal. $^1H$ NMR (DMSO-$d_6$, 400 MHz) δ 8.98 (br.s., 1H), 7.46 (d, J=8.0 Hz, 1H), 7.00 (d, J=7.6 Hz, 1H), 6.88-6.84 (m, 2H), 4.98 (s, 2H), 2.38 (s, 3H). MS (ESI) m/z $(M+H)^+$179.8.

A mixture of compound 298A (1.7 g, 9.5 mmol) and ethyl 2,4-dioxopentanoate (1.5 g, 9.5 mmol) in AcOH (30 mL) was heated to 125° C. and stirred for 3 h. The mixture was concentrated. The residue was treated with MeOH (15 mL). The insoluble substance was removed by filtration. The filtrate was concentrated and the residue was purified by prep-HPLC (FA) to afford compound 298B (260 mg, 9.1% yield) was obtained as yellow solid and compound 298C (1.12 g, yield 39.2%). The insoluble substance (1.4 g, impure) was treated with DCM (50 mL) and saturated aqueous $NaHCO_3$ (15 mL). The organic layer was separated, and then washed with saturated $NaHCO_3$ (15 mL×2), brine (15 mL×3), dried over $MgSO_4$, filtered and concentrated. The residue was purified by FCC (PE/EA=10/1) to afford compound 298B (620 mg, 21.7% yield) as yellow solid.

Compound 298B: $^1H$ NMR ($CDCl_3$, 400 MHz) δ 7.71-7.65 (m, 1H), 7.28 (d, J=5.3 Hz, 2H), 6.74 (d, J=0.9 Hz, 1H), 4.43 (q, J=7.3 Hz, 2H), 2.87 (d, J=0.9 Hz, 3H), 2.69 (s, 3H), 1.43 (t, J=7.2 Hz, 3H). MS (ESI) m/z $(M+H)^+$302.0.

Compound 298C: $^1H$ NMR ($CDCl_3$, 400 MHz) δ 7.681-7.66 (m, 1H), 7.30-7.26 (m, 2H), 6.66 (s, 1H), 4.39 (q, J=7.2 Hz, 2H), 2.65 (s, 3H), 2.38 (s, 3H), 1.30 (t, J=6.8 Hz, 3H). MS (ESI) m/z $(M+H)^+$301.9.

NaOH (2M, 2.5 mL, 5.0 mmol) was added to a solution of ethyl compound 298B (300 mg, 1.0 mmol) in MeOH (10 mL). The mixture was stirred at 25° C. for 2 h. Thick white precipitate was observed. The mixture was diluted with $H_2O$ (30 mL). And the volatile solvent was removed by evaporated. The residue was acidified to pH ~3 with 1N HCl. The precipitate was collected and azeotroped with toluene to afford compound 298D (190 mg, yield 69.8%) as white solid. $^1H$ NMR (DMSO-$d_6$, 400 MHz) δ 13.32 (br s, 1H), 7.93-7.87 (m, 1H), 7.37-7.31 (m, 2H), 6.83 (s, 1H), 2.79 (s, 3H), 2.62 (s, 3H).

Compound 298 (35 mg, yield 42.1%, white solid) was prepared as in Example 5 from the corresponding intermediate carboxylic acid, compound 298D. Compound 298: $^1H$ NMR (DMSO-$d_6$, 400 MHz) δ 8.60 (br d, J=7.0 Hz, 1H), 8.14 (br s, 1H), 7.94 (br s, 1H), 7.88 (br s, 1H), 7.41-7.17 (m, 8H), 6.81 (s, 1H), 5.44 (br s, 1H), 3.23 (br s, 1H), 3.27-3.23 (m, 1H), 3.13-3.02 (m, 1H), 2.81 (br s, 3H), 2.65 (br s, 3H). MS (ESI) m/z $(M+H)^+$448.1.

Following the same procedure as is used for compound 298, compound 299 (30 mg, yield 25.0%, white solid) was prepared from the corresponding intermediate carboxylic acid, compound 299A. Compound 299: $^1H$ NMR (DMSO-$d_6$, 400 MHz) δ 11.49 (d, J=6.8 Hz, 1H), 7.68-7.62 (m, 1H), 7.32-7.28 (m, 1H), 7.26-7.21 (m, 1H), 7.20-7.04 (m, 6H), 6.73 (s, 1H), 5.56-5.43 (m, 2H), 3.55-3.47 (m, 1H), 3.25-3.16 (m, 1H), 2.39 (s, 3H), 2.36 (s, 3H). MS (ESI) m/z $(M+H)^+$448.1.

Example 173

Compounds 306-307

(S)—N-(4-amino-3,4-dioxo-1-phenylbutan-2-yl)-3-cyclopropyl-1-phenyl-1H-pyrazole-5-carboxamide (306)

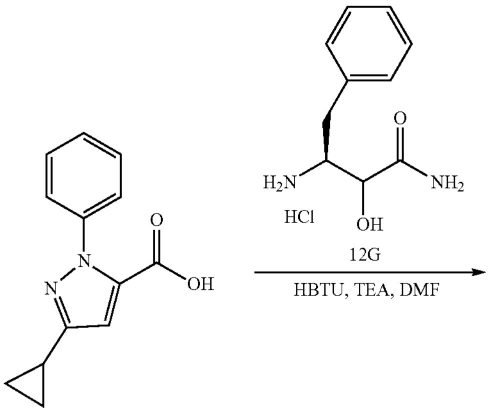

306A

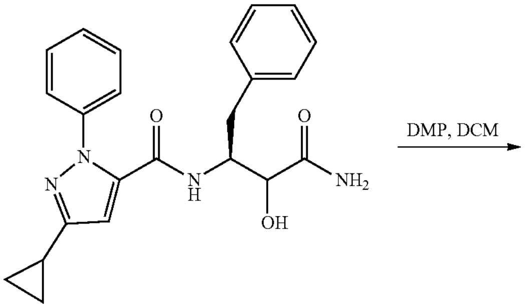

306B

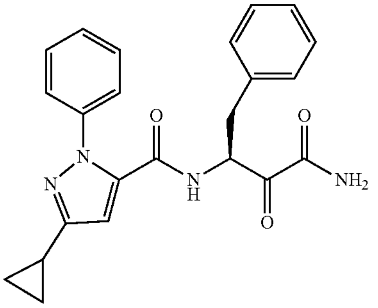

306

Compound 306 (25 mg, 24%, white solid) was prepared as in Example 5 from the corresponding starting materials, compounds 306A and 12G. Compound 306: MS (ESI) m/z $(M+H)^+$ 403.

(S)—N-(4-amino-3,4-dioxo-1-phenylbutan-2-yl)-1-phenyl-1H-indole-2-carboxamide (307)

Compound 307 was synthesized from the corresponding starting materials using same procedures as described earlier for compound 306.

Example 174

Compounds 314, 494

N-(4-amino-3,4-dioxo-1-phenylbutan-2-yl)-2-methyl-5-(pyridin-2-yl)oxazole-4-carboxamide (314)

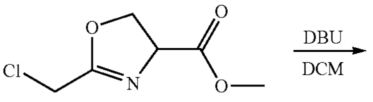

314A

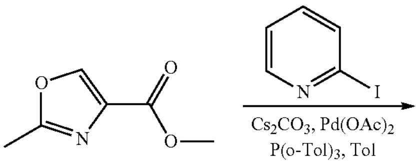

314B

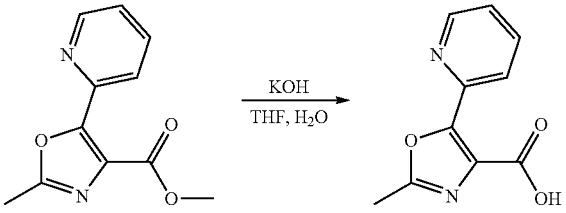

314C

314D

Na (29.55 mg, 1.29 mmol) was dissolved in MeOH (90 mg). The solution was added to a mixture of MeOH (10 mL) and DCM (90 mL) at 0-5° C. and 5 mins later, 2-chloroacetonitrile (10.2 mL, 160.7 mmol) was added, and the mixture was stirred at 0-5° C. for 1.5 h. Then ethyl acetamidate hydrochloride (20 g, 128.55 mmol, HCl salt) was added at 0-5° C. The slurry was allowed to warm to 20° C. and stirred for 18 h. $H_2O$ (50 mL) was added to the mixture and the mixture was stirred for 15 mins to ensure the precipitate was dissolved. The organic layer was separated, washed with brine (30 mL), dried over $MgSO_4$, filtered and concentrated to afford compound 314A (20.2 g, yield 88.5%) as clear oil, which was used for next step directly. $^1H$ NMR (DMSO-$d_6$, 400 MHz) δ 4.87-4.82 (m, 1H), 4.55-4.46 (m, 2H), 4.39 (s, 2H), 3.71 (s, 3H).

DBU (17.2 mL, 113.75 mmol) was added to a solution of compound 314A (20.2 g, 113.75 mmol) in DCM (100 mL) slowly. The mixture was stirred at 25° C. for 1 h. The mixture was treated with 2N HCl (40 mL). The organic layer was separated and then washed with $H_2O$ (30 mL), brine (30 mL), dried over $MgSO_4$, filtered and concentrated to afford compound 314B (13.5 g, yield 84.1%) as white solid, which was used for next step directly. $^1H$ NMR (DMSO-$d_6$, 400 MHz) δ 8.68 (s, 1H), 3.76 (s, 3H), 2.42 (s, 3H).

$Cs_2CO_3$ (4.6 g, 14.2 mmol) was added to a mixture of compound 314B (1.0 g, 7.1 mmol) and 2-iodopyridine (2.9 g, 14.2 mmol) in toluene (20.00 mL). Then P(o-tolyl)$_3$ (216 mg, 0.71 mmol) and Pd(OAc)$_2$ (80 mg, 0.35 mmol) was added. The mixture was de-gassed for 3 times. Then the mixture was heated to 110° C. and stirred for 18 h. The mixture was filtered through Celite; the cake was washed with EA (15 mL×2). The combined filtrates were concentrated. The residue was purified by Flash Column Chromatography (PE/EA=10/1 to 1/1) to afford compound 314C (1.0 g, yield 64.6%) as pale yellow solid. $^1$H NMR (DMSO-$d_6$, 400 MHz) δ 8.69-8.67 (m, 1H), 8.08-8.06 (m, 1H), 7.96-7.91 (m, 1H), 7.48-7.45 (m, 1H), 3.77 (s, 3H), 2.50 (s, 3H).

To a mixture of compound 314C (500 mg, 2.3 mmol) in THF (10 mL) and $H_2O$ (2 mL) was added KOH (1.28 g, 22.9 mmol) in one portion at 25° C. The mixture was stirred at 25° C. for 1.5 h. The reaction mixture was concentrated under reduced pressure to move THF. The aqueous phase was acidified with aqueous HCl (1M) till pH ~4-5, and then extracted with DCM (20 mL×5). The combined organic phase was dried over $Na_2SO_4$, filtered and concentrated to afford compound 314D (600 mg, crude) as light yellow solid, which was used directly for next step without purification. $^1$H NMR (DMSO-$d_6$, 400 MHz) δ 8.84-8.75 (m, 1H), 8.25-8.19 (m, 1H), 8.06 (d, J=8.2 Hz, 1H), 7.71-7.66 (m, 1H), 2.56 (s, 3H).

Compound 314 (30 mg, yield 26.2%, white solid) was prepared as in compound 12 from the corresponding starting materials, compounds 314D and 3-amino-2-hydroxy-4-phenyl-butanamide (274D). Compound 314: $^1$H NMR ($CDCl_3$, 400 MHz) δ 11.59 (d, J=6.2 Hz, 1H), 8.14-8.09 (m, 1H), 8.03-7.98 (m, 1H), 7.87-7.80 (m, 1H), 7.26-7.22 (m, 1H), 7.18-7.05 (m, 5H), 6.81 (s, 1H), 5.86-5.78 (m, 1H), 5.64 (s, 1H), 3.50-3.41 (m, 1H), 3.37-3.29 (m, 1H), 2.58 (s, 3H). MS (ESI) m/z $(M+H)^+$379.1.

N-(4-amino-3,4-dioxo-1-phenylbutan-2-yl)-2-methyl-5-phenyloxazole-4-carboxamide (494)

Compound 494 (40 mg, yield 25.1%, white solid) was prepared as in compound 314 from the corresponding starting materials, compounds 314B and iodobenzene followed by using procedures as in compound 12 to obtain compound 494. Compound 494: $^1$H NMR ($CDCl_3$, 400 MHz) δ 8.20-7.97 (m, 3H), 7.80 (br s, 1H), 7.61 (br d, J=10.0 Hz, 1H), 7.49-7.34 (m, 5H), 7.31-7.04 (m, 5H), 6.22 (br s, 0.22H), 6.09 (br s, 0.22H), 5.46 (dt, J=4.8, 8.0 Hz, 0.75H), 4.59 (dt, J=3.0, 10.3 Hz, 0.28H), 3.27 (dd, J=5.0, 14.1 Hz, 1H), 3.11 (br dd, J=8.3, 14.1 Hz, 1H), 2.54-2.50 (m, 3H). MS (ESI) m/z $(M+H)^+$378.1.

Example 175

(S)-1-methyl-N-(1-oxo-3-phenylpropan-2-yl)-3-phenyl-1H-pyrazole-4-carboxamide (317)

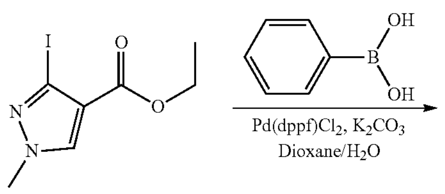

317B

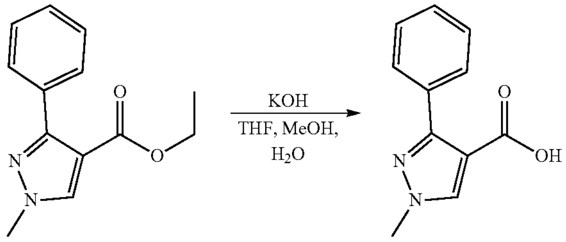

317C

317D

To a mixture of ethyl 3-iodo-1H-pyrazole-4-carboxylate (30 g, 112.7 mmol) in DMF (200 mL) was added $Cs_2CO_3$ (110.22 g, 338.28 mmol) in one portion at 25° C. Then iodomethane (18.83 mL, 302.45 mmol) was added. The mixture was stirred at 25° C. for 3 h. The reaction mixture was concentrated under reduced pressure to remove most of DMF. The mixture was treated with EA (100 mL) and $H_2O$ (100 mL). The organic layer was separated and the aqueous layer was extracted with EA (50 mL×3). The combined organic layer was washed with brine (100 mL×2), dried over $Na_2SO_4$, filtered and concentrated. The residue was purified by FCC ($SiO_2$, PE:EA=1: 0-5:1) to afford compound 317B (17.24 g, yield 54.59%) as white solid. Compound 317B: $^1$H NMR (DMSO-$d_6$, 400 MHz) δ 8.25 (s, 1H), 4.20 (q, J=7.1 Hz, 2H), 3.87 (s, 3H), 1.29-1.23 (m, 3H).

To a mixture of compound 317B (10.0 g, 35.7 mmol) and phenylboronic acid (8.71 g, 71.4 mmol) in 1,4-dioxane (300 mL) and $H_2O$ (80 mL) was added $K_2CO_3$ (9.87 g, 71.4 mmol) and Pd(dppf)$Cl_2$ (2.61 g, 3.57 mmol). The mixture was degassed and purged with $N_2$ for 3 times, and then stirred at 80° C. for 18 h. The reaction mixture was concentrated under reduced pressure to move 1,4-dioxane. The mixture was added EA (150 mL), and then washed with $H_2O$ (100 mL×3). The organic layer was dried over $Na_2SO_4$ and concentrated. The residue was purified by Flash Column Chromatography ($SiO_2$, Petroleum ether:Ethyl acetate=1:0 to 3:1) to afford compound 317C (8.30 g, crude) as light red solid. $^1$H NMR (DMSO-$d_6$, 400 MHz) δ 8.34 (s, 1H), 7.71-7.64 (m, 2H), 7.41-7.33 (m, 3H), 4.20-4.06 (m, 2H), 3.88 (s, 3H), 1.26-1.12 (m, 3H). MS (ESI) m/z $(M+H)^+$ 231.0.

To a mixture of compound 317C (8.29 g, 36.0 mmol) in THF (15 mL) and MeOH (10 mL) was added the mixture of KOH (20.20 g, 360.0 mmol) and $H_2O$ (10 mL) at 25° C. The mixture was stirred at 70° C. for 1.5 h. The reaction mixture was concentrated under reduced pressure to move MeOH and THF, the aqueous phase was acidified with concentrated HCl (36-38%) till pH ~3-4, precipitated solid was filtered and dried to afford compound 317D (5.95 g, yield 81.72%) as white solid, which was used directly for the next step without purification. $^1$H NMR (DMSO-$d_6$, 400 MHz) δ 8.29 (s, 1H), 7.75-7.70 (m, 2H), 7.42-7.30 (m, 3H), 3.89 (s, 3H).

Compound 317 (1.29 g, yield 63.83%) was prepared as in Example 6 from the corresponding intermediate compounds 317D and 21G ((S)-2-amino-3-phenylpropan-1-ol). Compound 317: $^1$H NMR (DMSO-$d_6$, 400 MHz) δ 9.56 (s, 1H), 8.38 (d, J=7.5 Hz, 1H), 8.05 (s, 1H), 7.60-7.48 (m, 2H), 7.34-7.13 (m, 8H), 4.51-4.37 (m, 1H), 3.87 (s, 3H), 3.26-3.15 (m, 1H), 2.90-2.76 (m, 1H). MS (ESI) m/z $(M+H)^+$ 334.1.

Example 176

N-(4-amino-3,4-dioxo-1-phenylbutan-2-yl)-2-methyl-1-phenyl-1H-imidazole-5-carboxamide (318)

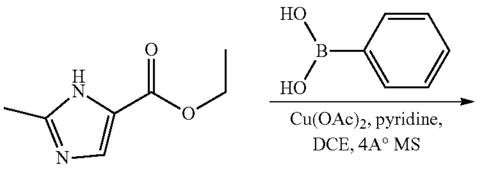

318A

-continued

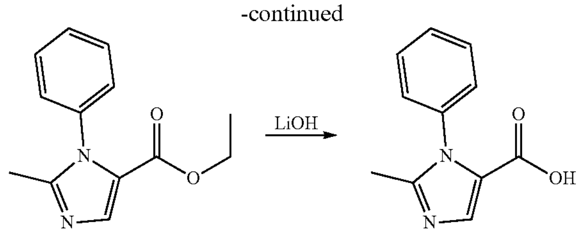

318B 318C

A mixture of N'-hydroxyacetimidamide (5 g, 67.5 mmol) and ethyl prop-2-ynoate (8.94 g, 91.1 mmol) in MeOH (50 mL) was stirred at 65° C. for 4 h. Then the solvent was evaporated and $Ph_2O$ (25 mL) was added. The reaction mixture was stirred at 250° C. for 4 h. The mixture was cooled to 70° C. and poured into MTBE (100 mL) portion-wise. The mixture was stirred for 10 min. Filtered and the filter cake was collected. The solid was dissolved in EtOAc (200 mL) and MeOH (50 mL). Filtered and the filtrate was collected. The filtrate was concentrated to give the crude product as brown oil. The residue was suspended in MTBE (100 mL) and stirred for 10 mins. Filtered and the filter cake was collected to give compound 318A (2 g, yield: 19.2%) as a brown solid. $^1H$ NMR (400 MHz, DMSO-$d_6$) δ 12.32 (br s, 1H), 7.72-7.49 (m, 1H), 4.25-4.10 (m, 2H), 3.33 (br d, J=8.8 Hz, 1H), 2.33-2.23 (m, 3H), 1.25 (t, J=7.2 Hz, 3H).

To a mixture of compound 318A (2 g, 13.0 mmol), phenylboronic acid (3.16 g, 25.9 mmol), pyridine (2.05 g, 25.9 mmol) and 4A° molecular sieve (2 g) in DCE (50 mL) was added $Cu(OAc)_2$ (3.53 g, 19.5 mmol). The mixture was stirred at 60° C. for 12 h under 02 (15 psi). Filtered and the filtrate was purified by silica gel chromatography eluting with Petroleum ether:Ethyl acetate=4:1 to give the crude product. The crude product was then purified again by preparatory-TLC (EtOAc, $R_f$~0.5) twice to give compound 318B (160 mg, yield: 5.36%) as a yellow solid. $^1H$ NMR (400 MHz, $CDCl_3$) δ 7.77 (s, 1H), 7.53-7.48 (m, 3H), 7.26-7.20 (m, 2H), 4.15 (q, J=7.2 Hz, 2H), 2.24 (s, 3H), 1.19 (t, J=7.1 Hz, 3H).

To a solution of compound 318B (100 mg, 434 umol) in THF (6 mL) and $H_2O$ (2 mL) was added $LiOH.H_2O$ (36.5 mg, 869 umol). The mixture was stirred at 15° C. for 24 hr. TLC (EtOAc, $R_f$~0) showed the reaction was completed. The pH of the mixture was adjusted to 7.0 using 1N HCl. Then solvent was removed under vacuum to give crude compound 318C (87.0 mg, crude) as yellow oil.

Compound 318 (30.3 mg, yield: 28.0%, white solid) was prepared as in Example 5 from the corresponding starting materials, compounds 318C and 3-amino-2-hydroxy-4-phenyl-butanamide (274D). Compound 318: $^1H$ NMR (400 MHz, $CDCl_3$) δ 7.57-7.39 (m, 5H), 7.30 (br s, 2H), 7.24-7.17 (m, 2H), 7.11-6.96 (m, 2H), 6.70 (br s, 1H), 6.13 (br s, 1H), 5.63-5.46 (m, 2H), 3.34 (dd, J=5.5, 14.2 Hz, 1H), 3.12 (dd, J=6.8, 14.1 Hz, 1H), 2.22 (s, 3H). MS (ESI) m/z $(M+H)^+$377.1.

Example 177

(S)—N-(4-amino-3,4-dioxo-1-phenylbutan-2-yl)-4-methyl-1-phenyl-1H-imidazole-2-carboxamide (319)

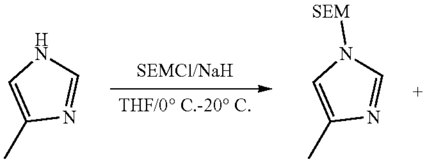

319A

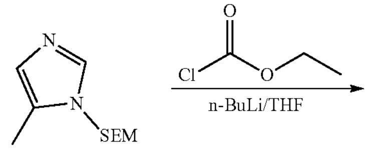

319B

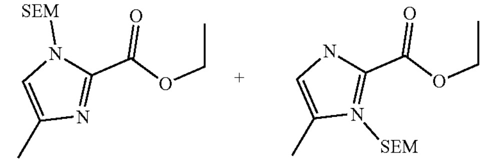

319C 319D

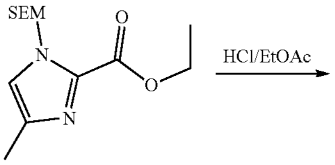

319C

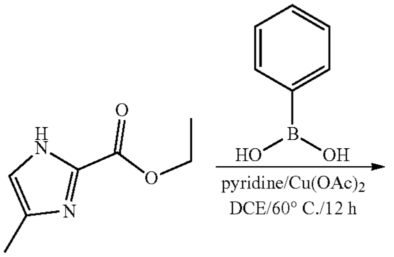

319E

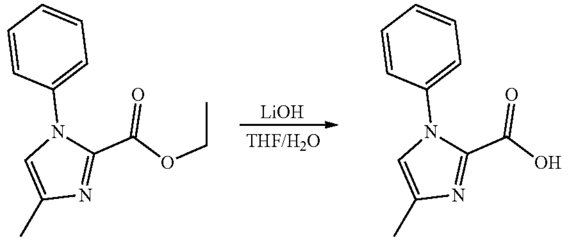

319F 319G

To a solution of 4-methyl-1H-imidazole (5 g, 60.9 mmol) in THF (100 mL) was slowly added NaH (2.68 g, 67 mmol) at 0° C. The suspension was stirred at 0° C. for 30 mins and then SEM-Cl (12.2 g, 73.1 mmol) was added. The reaction mixture was stirred at 20° C. for 12 hours. The mixture was quenched with saturated aqueous $NaHCO_3$ (200 ml) and extracted with EtOAc (300 mL×2). The combined organics were dried over $Na_2SO_4$, concentrated to give crude product.

The crude product was purified by silica gel chromatography eluting with EtOAc to give a mixture of compound 319A and 319B (10 g, crude) as yellow oil.

To a solution of compound 319A and 319B (10 g, 47.1 mmol) in THF (40 mL) was added n-BuLi (2.5 M, 28.3 mL) at −78° C. The mixture was stirred at −78° C. for 1 h. Ethyl carbonochloridate (7.67 g, 70.6 mmol) was added to the solution and stirred at 20° C. for 12 h. The mixture was quenched with $NH_4Cl$(aqueous; 200 ml), extracted with EtOAc (300 mL×2). The combined organics were dried over $Na_2SO_4$, concentrated to give the crude product as orange oil. The crude product was purified by silica gel chromatography eluting with Petroleum ether:Ethyl acetate=5:1 to give a mixture of compound 319C and 319D (2.9 g, crude) as yellow oil.

A solution of 319C and 319D (2 g, 7.03 mmol) in HC/EtOAc (50 mL) was stirred at 20° C. for 24 h. LCMS showed most 319C and 319D were consumed. The solvent was removed and the residue was extracted with EtOAc (50 ml) and water (50 mL). Then the pH of water layer was adjusted to 8.0 using saturated aqueous $NaHCO_3$ and the residue was extracted with EtOAc (50 ml×6). The combined organics were dried over $Na_2SO_4$, concentrated to give 319E (900 mg, crude) as a brown solid. The crude product was used directly in the next step. $^1$H NMR (400 MHz, $CDCl_3$) δ 10.42 (br s, 1H), 10.62-10.25 (m, 1H), 6.96 (s, 1H), 4.42 (q, J=7.3 Hz, 2H), 2.33 (s, 3H), 1.41 (t, J=7.2 Hz, 3H).

To a mixture of compound 319E (405 mg, 2.63 mmol), phenylboronic acid (480 mg, 3.94 mmol), pyridine (416 mg, 5.25 mmol) and 4A° molecular sieve (500 mg) in DCE (30 mL) was added $Cu(OAc)_2$ (716 mg, 3.94 mmol). The mixture was stirred at 60° C. for 12 h under 02 (15 psi). Filtered and the residue was purified by silica gel chromatography eluting with Petroleum ether:Ethyl acetate=5:1 to give compound 319F (400 mg, crude) as a clear oil. $^1$H NMR (400 MHz, $CDCl_3$) δ 7.49-7.44 (m, 3H), 7.33-7.28 (m, 2H), 6.93 (s, 1H), 4.30 (q, J=7.1 Hz, 2H), 2.35 (s, 3H), 1.31 (t, J=7.1 Hz, 4H).

A solution of compound 319F (75 mg, 326 umol) and $LiOH.H_2O$ (13.7 mg, 326 umol) in THF (3 mL) and $H_2O$ (1 mL) was stirred at 15° C. for 12 h. TLC (Petroleum ether:Ethyl acetate=1:1, $R_f$~0.01) and LCMS showed the reaction was completed. The pH of the mixture was adjusted to ~7.0 and THF was removed by $N_2$. Then the residue was lyophilized to give crude compound 319G (130 mg, crude) as a white solid. The crude product was used directly in the next step. MS (ESI) m/z $(M+H)^+$202.8.

Compound 319 (38.3 mg, yield: 42.3%, off-white solid) was prepared as in Example 5 from the corresponding intermediate carboxylic acid, compound 319G. Compound 319: $^1$H NMR (400 MHz, $CDCl_3$) δ 7.80 (br s, 1H), 7.41 (br s, 3H), 7.33-7.28 (m, 2H), 7.21 (br d, J=7.2 Hz, 4H), 6.85 (s, 1H), 6.70 (br s, 1H), 5.69-5.57 (m, 1H), 5.42 (br s, 1H), 3.39 (br dd, J=5.0, 14.2 Hz, 1H), 3.15 (br dd, J=7.6, 14.1 Hz, 1H), 2.28 (s, 3H). MS (ESI) m/z $(M+H)^+$377.2.

Example 178

Compounds 321, 519-520

N-(4-amino-3,4-dioxo-1-phenylbutan-2-yl)-4-(3-fluorophenyl)-1,2,5-thiadiazole-3-carboxamide (321)

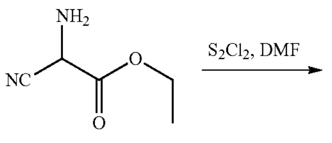

321A

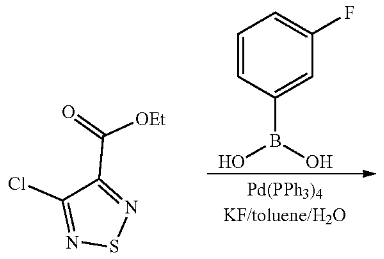

321B

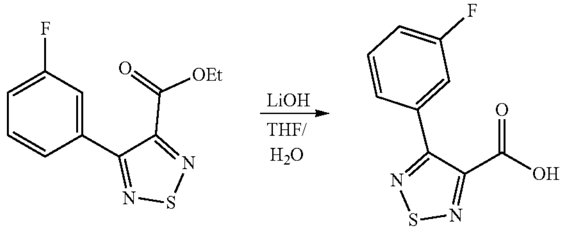

321C 321D

To a mixture of ethyl (E)-2-cyano-2-(hydroxyimino)acetate (25 g, 1.76 mol) in EtOH (100 mL) was added $PtO_2$ (2 g, 8.8 mmol). The mixture was stirred at 25° C. for 12 h under $H_2$ (50 psi). Filtered and the filtrate was concentrated to give compound 321A (44 g, crude) as red oil. The crude product was used directly in the next step.

To a solution of compound 321A (22 g, 172 mmol) in DMF (500 mL) was added chlorosulfanyl thiohypochlorite (69.6 g, 515 mmol). The mixture was stirred at 20° C. for 12 h. The mixture was poured into ice-water (1000 mL), extracted with EtOAc (500 mL×3). The combined organic layers were dried over sodium sulfate, filtered and concentrated under vacuum. The crude product was purified by silica gel column chromatography eluting with Petroleum ether:Ethyl acetate=30:1. Compound 321B (12 g, yield: 18.1%, yellow clear oil): $^1$H NMR (400 MHz, $CDCl_3$) δ 4.50 (q, J=7.1 Hz, 2H), 1.46 (t, J=7.2 Hz, 3H).

A mixture of compound 321B (1 g, 5.19 mmol) and (3-fluorophenyl)boronic acid (1.09 g, 7.79 mmol) in $H_2O$ (2 mL) and toluene (20 mL) was added KF (603 mg, 10.38 mmol) and $Pd(PPh_3)_4$ (300 mg, 260 umol) under $N_2$. Then the reaction mixture was stirred at 100° C. under $N_2$ for 16 h. The solvent was evaporated. The crude product was purified by preparatory-TLC (petroleum ether:ethyl acetate=5:1, $R_f$=0.69) to give compound 321C (100 mg, yield: 7.64%) as white solid.

A mixture of compound 321C (120 mg, 476 umol) in THF (4 mL) and $H_2O$ (2 mL) was added $LiOH.H_2O$ (39.9 mg, 951 umol). Then the reaction mixture was stirred at 20° C.

for 16 h. 1M HCl was added to the reaction mixture until pH ~6. The solvent was removed under vacuum to give crude compound 321D (100 mg, crude) as a white solid. The crude product was used in the next step without purification. $^1$H NMR (400 MHz, $CDCl_3$) δ 7.70-7.50 (m, 3H), 7.36-7.33 (m, 1H).

Compound 321 (43.8 mg, yield: 61.6%, white solid) was prepared as in Example 6 from the corresponding starting materials, compounds 321D and 3-amino-2-hydroxy-4-phenyl-butanamide (274D). Compound 321: $^1$H NMR (400 MHz, DMSO-$d_6$) δ 9.39 (d, J=7.7 Hz, 1H), 8.16 (s, 1H), 7.91 (s, 1H), 7.48-7.17 (m, 8H), 5.73 (s, 1H), 5.55-5.43 (m, 1H), 3.21 (dd, J=3.6, 14.0 Hz, 1H), 2.85 (dd, J=10.0, 14.0 Hz, 1H). MS (ESI) m/z $(M+H)^+$399.1.

3-(2-fluorophenyl)-1-methyl-N-(2-oxo-1-(2-(trifluoromethyl)phenyl)ethyl)-1H-pyrazole-4-carboxamide (519)

Compound 519 (50 mg, yield: 17.5%, white solid) was prepared as in compound 21 from the corresponding starting materials, 3-(2-fluorophenyl)-1-methyl-1H-pyrazole-4-carboxylic acid and 2-amino-2-(2-(trifluoromethyl)phenyl)ethan-1-ol. Compound 519: $^1$H NMR (400 MHz, DMSO-$d_6$) δ 9.61 (s, 1H), 8.98 (d, J=6.8 Hz, 1H), 8.37 (s, 1H), 7.80 (d, J=8.0 Hz, 1H), 7.75-7.70 (m, 1H), 7.62-7.56 (m, 2H), 7.49-7.40 (m, 2H), 7.26-7.17 (m, 2H), 5.77 (d, J=6.8 Hz, 1H), 3.95 (s, 3H). MS (ESI) m/z $(M+H)^+$406.1.

3-(2-fluorophenyl)-1-methyl-N-(1-oxo-3-phenylpropan-2-yl)-1H-pyrazole-4-carboxamide (520)

Compound 520 (60 mg, yield: 39.6%, light yellow solid) was prepared as in compound 21 from the corresponding starting materials, 3-(2-fluorophenyl)-1-methyl-1H-pyrazole-4-carboxylic acid and 3-amino-2-hydroxy-4-phenylbutanamide (274D). Compound 520: $^1$H NMR (400 MHz, DMSO-$d_6$) δ 9.56 (s, 1H), 7.93 (s, 1H), 7.47-7.33 (m, 2H), 7.23-7.08 (m, 5H), 6.95 (dd, J=2.9, 6.6 Hz, 2H), 6.00 (d, J=6.2 Hz, 1H), 4.70 (q, J=6.7 Hz, 1H), 3.96 (s, 3H), 3.07 (d, J=6.4 Hz, 2H). MS (ESI) m/z $(M+H)^+$392.0.

Example 179

(S)—N-(4-amino-3,4-dioxo-1-phenylbutan-2-yl)-3-(3-fluorophenyl)isoxazole-4-carboxamide (323)

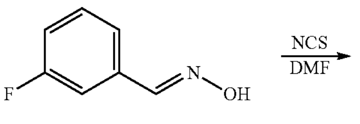

323A

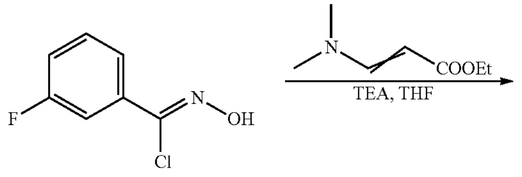

323B

-continued

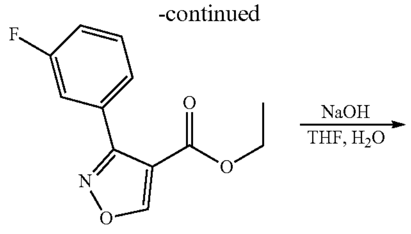

323C

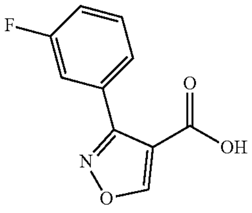

323D

To a suspension of 3-fluorobenzaldehyde (10 g, 80.6 mmol) and $NH_2OH.HCl$ (6.2 g, 88.6 mmol) in EtOH (10 mL) and $H_2O$ (20 mL) was added ice (50 g). Then an aqueous solution of NaOH (8.1 g, 201.4 mmol) in $H_2O$ (20 mL) was added dropwise over a period of 10 min where upon most of the solid dissolves. Then the mixture was stirred 2 hours at 16° C. The resulting mixture was then acidified with HCl (5N). The mixture was then extracted with dichloromethane (80 mL) for three times to give compound 323A (10 g, yield: 89.2%) as a light yellow solid. The product was used into the next step without future purification. $^1$H NMR (400 MHz, $CDCl_3$) δ 8.13 (s, 1H), 7.95 (br s, 1H), 7.39-7.30 (m, 3H), 7.13-7.06 (m, 1H).

NCS (5.3 g, 39.5 mmol) was added to a solution of compound 323A (5 g, 35.9 mmol) in DMF (20 mL) followed by stirring at 20° C. for 3 hours. The reaction mixture was diluted with $H_2O$ (60 mL), and extracted with Ethyl acetate (100 mL×2). The organic layers were dried over $Na_2SO_4$, filtered and concentrated under reduced pressure to give compound 323B (5.7 g, yield: 91.4%) as a yellow solid. The product was used into the next step without future purification. $^1$H NMR (400 MHz, $CDCl_3$) δ 8.21 (s, 1H), 7.66 (d, J=7.9 Hz, 1H), 7.57 (br d, J=10.1 Hz, 1H), 7.43-7.33 (m, 1H), 7.16 (tt, J=1.1, 8.3 Hz, 1H).

To a solution of ethyl 3-(dimethylamino)acrylate (825 mg, 5.8 mmol) and TEA (583 mg, 5.8 mmol) in THF (15 mL) was added a solution of compound 323B (1 g, 5.8 mmol) in THF (35 mL) dropwise over a period of 30 mins. The mixture was stirred at 16° C. for 12 hours. The reaction mixture was concentrated under reduced pressure to give a residue. The residue was purified by column chromatography ($SiO_2$, Petroleum ether:Ethyl acetate=1:0 to 30:1) to give compound 323C (800 mg, yield: 59%) as a pale yellow oil. $^1$H NMR (400 MHz, $CDCl_3$) δ 9.03 (s, 1H), 7.62-7.51 (m, 2H), 7.45 (dt, J=5.8, 8.0 Hz, 1H), 7.25-7.17 (m, 1H), 4.32 (q, J=7.1 Hz, 2H), 1.33 (t, J=7.2 Hz, 3H).

To a mixture of compound 323C (224 mg, 952 umol) in THF (5 mL) and $H_2O$ (1 mL) was added $LiOH.H_2O$ (80 mg, 1.90 mmol). The mixture was stirred at 15° C. for 12 hours. The mixture was concentrated to remove solvent and adjusted to pH ~5 with aqueous HCl (1M). The mixture was filtered and the solid was washed with $H_2O$ (3 mL) to give intermediate compound 323D (200 mg, crude) as a white solid. $^1$H NMR (400 MHz, DMSO-$d_6$) δ 9.40 (s, 1H), 7.74

(td, J=1.9, 10.3 Hz, 1H), 7.66 (d, J=7.7 Hz, 1H), 7.52 (dt, J=6.2, 7.9 Hz, 1H), 7.34 (dt, J=2.2, 8.4 Hz, 1H).

Compound 323 (68.9 mg, yield: 66.0%, white solid) was prepared as in Example 5 from the corresponding starting materials, compounds 323D and 12G. Compound 323: $^1$H NMR (400 MHz, DMSO-$d_6$) δ 9.31 (s, 1H), 9.05 (br d, J=7.5 Hz, 1H), 8.13 (br s, 1H), 7.87 (br s, 1H), 7.54-7.17 (m, 9H), 5.38 (br s, 1H), 3.26-3.15 (m, 1H), 2.81 (br dd, J=10.6, 13.2 Hz, 1H). MS (ESI) m/z $(M+H)^+$382.1.

Example 180

N-(4-amino-3,4-dioxo-1-phenylbutan-2-yl)-3-(pyrimidin-2-yl)isoxazole-4-carboxamide (324)

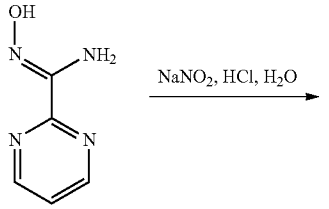

324A

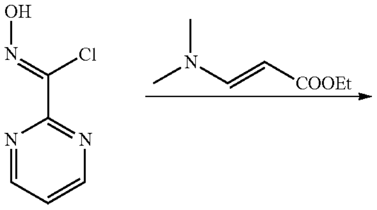

324B

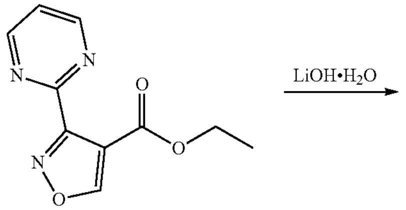

324C

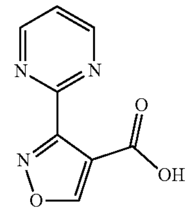

324D

A mixture of pyrimidine-2-carbonitrile (10 g, 95.2 mmol), $NH_2OH.HCl$ (6.94 g, 99.9 mmol) and $CH_3ONa$ (5.40 g, 99.9 mmol) in MeOH (100 mL) was heated to 70° C. for 2 h. The mixture was concentrated, the residue was added water (50 mL) to give a precipitate, the solid was filtered, washed with water (5 mL×2), MTBE (10 mL) to give compound 324A (10.4 g, yield: 79.1%) as white solid. $^1$H NMR (400 MHz, DMSO-$d_6$) δ 10.18 (s, 1H), 8.84 (d, J=4.9 Hz, 2H), 7.51 (t, J=4.9 Hz, 1H), 5.84 (br s, 2H).

$NaNO_2$ (1.25 g, 18.1 mmol) in $H_2O$ (7 mL) was added to a solution of compound 324A (2 g, 14.5 mmol) in HCl (40 mL) at 0° C., the mixture was stirred at 0° C. for 2 h. The mixture was adjusted to pH ~6 with saturated aqueous $NaHCO_3$ to give a precipitate. The solid was filtered, washed with water (5 mL×2) and dried to give compound 324B (1.40 g, yield: 61.4%), as white solid. $^1$H NMR (400 MHz, DMSO-$d_6$) δ 12.95 (s, 1H), 8.92 (d, J=4.9 Hz, 2H), 7.60 (t, J=5.0 Hz, 1H).

A suspension of compound 324B (500 mg, 3.17 mmol) in THF (4 mL) was added in portions to a mixture of 3-amino-2-hydroxy-4-phenylbutanamide (454 mg, 3.17 mmol) and TEA (321 mg, 3.17 mmol) in THF (6 mL), the mixture was stirred at 10° C. for 12 h. The mixture was filtered and the filtrate was concentrated, the residue was purified by preparatory-TLC (Petroleum ether:Ethyl acetate=1:1) to give compound 324C (300 mg, yield: 43.2%) as yellow oil. $^1$H NMR (400 MHz, $CDCl_3$) δ 7.46-7.39 (m, 1H), 7.39-7.32 (m, 2H), 7.30-7.27 (m, 1H), 7.25-7.19 (m, 4H), 7.05-7.00 (m, 2H), 6.87 (br s, 1H), 5.92-5.85 (m, 2H), 5.40 (br s, 1H), 4.22 (dd, J=1.3, 4.9 Hz, 1H), 4.17-4.09 (m, 1H), 2.92-2.81 (m, 2H).

A mixture of compound 324C (150 mg, 684 umol) and $LiOH.H_2O$ (43.1 mg, 1.03 mmol) in THF (5 mL), EtOH (3 mL), $H_2O$ (2 mL) was stirred at 10° C. for 12 h. LCMS showed desired MS, the organic solvent was removed under vacuum, the water layer was extracted with MTBE (5 mL) and then adjusted to pH ~4 with 1N HCl, the mixture was concentrated to give crude compound 324D (130 mg, crude) as black solid.

Compound 324 (27.9 mg, yield: 62.3%, yellow solid) was prepared as in Example 6 from the corresponding starting materials, compounds 324D and 3-amino-2-hydroxy-4-phenyl-butanamide (274D). Compound 324: $^1$H NMR (400 MHz, DMSO-$d_6$) δ 10.16 (d, J=7.3 Hz, 1H), 9.56 (s, 1H), 8.84 (d, J=5.1 Hz, 2H), 8.13 (s, 1H), 7.88 (s, 1H), 7.66 (t, J=5.0 Hz, 1H), 7.27-7.05 (m, 5H), 5.51 (dt, J=5.0, 7.6 Hz, 1H), 3.21 (dd, J=4.9, 14.1 Hz, 1H), 3.00 (dd, J=7.8, 14.0 Hz, 1H). MS (ESI) m/z $(M+H)^+$366.1.

Example 181

(S)—N—((S)-4-amino-3,4-dioxo-1-phenylbutan-2-yl)-1-phenylpyrrolidine-2-carboxamide (308)

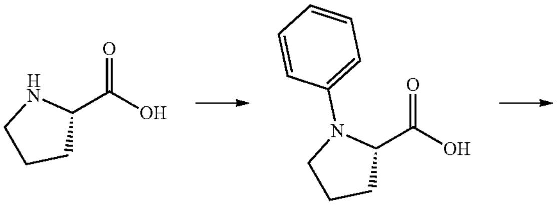

308A

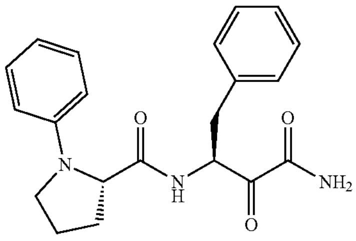

308

The mixture of L-proline (1.15 g, 1 eq) and iodobenzene (2.04 g, 1 eq), $K_2CO_3$ (2.07 g, 1.5 eq) and CuI (0.19 g, 0.1 eq) in DMA (15 mL) was heated to 90° C. under $N_2$ atmosphere for 48 hours. The reaction mixture was diluted with ethyl acetate and water after cooling to room temperature and adjusted pH to 3 with HCl. The organic layer was separated and the aqueous layer was extracted with ethyl acetate (5 times). The combined organic layer was washed with brine, dried over $Na_2SO_4$ and concentrated. The residue was purified on ISCO to afford compound acid 308A.

Compound 308 was prepared as in Example 5 from acid, intermediate compound 308A. $^1H$ NMR (400 MHz, DMSO): $^1H$ NMR (400 MHz, DMSO): δ 8.3-7.5 (m, 2H), 7.38-7 (m, 7H), 6.7-6.2 (m, 4H), 5.2 (m, 0.5H), 4.35 (m, 0.5H), 3.9-3.3 (m, 3H), 3.2-2.8 (m, 2H) 2.2-1.7 (m, 4H) ppm. MS (ESI) m/z $(M+H)^+$356.9.

Example 182

Compounds 325-327

Compounds 325-327 were synthesized from the corresponding starting materials using same procedures as described earlier for compound 321.

Compound 325: N-(4-amino-3,4-dioxo-1-phenylbutan-2-yl)-4-(M-tolyl)-1,2,5-thiadiazole-3-carboxamide: $^1H$ NMR (400 MHz, DMSO-$d_6$) δ 9.42 (br d, J=7.3 Hz, 1H), 8.17 (br s, 1H), 7.92 (br s, 1H), 7.49 (s, 1H), 7.39-7.13 (m, 8H), 5.55-5.43 (m, 1H), 3.20 (br dd, J=3.0, 14.2 Hz, 1H), 2.85 (br dd, J=10.0, 14.0 Hz, 1H), 2.30 (s, 3H). MS (ESI) m/z $(M+H)^+$395.1.

Compound 326: N-(4-amino-3,4-dioxo-1-phenylbutan-2-yl)-4-(o-tolyl)-1,2,5-thiadiazole-3-carboxamide: $^1H$ NMR (400 MHz, $CDCl_3$) δ 7.52 (br d, J=7.7 Hz, 1H), 7.39-7.32 (m, 1H), 7.31-7.19 (m, 6H), 7.13 (br d, J=6.6 Hz, 2H), 6.71 (br s, 1H), 5.66 (dt, J=5.3, 7.5 Hz, 1H), 5.59 (br s, 1H), 3.41 (dd, J=5.1, 14.1 Hz, 1H), 3.18 (dd, J=7.3, 14.1 Hz, 1H), 2.17-2.01 (m, 3H). MS (ESI) m/z $(M+H)^+$395.1.

Compound 327: N-(4-amino-3,4-dioxo-1-phenylbutan-2-yl)-4-(2-fluorophenyl)-1,2,5-thiadiazole-3-carboxamide: $^1H$ NMR (400 MHz, $CDCl_3$) δ 7.58-7.41 (m, 3H), 7.33-7.21 (m, 4H), 7.19-7.08 (m, 3H), 6.74 (br s, 1H), 5.79-5.68 (m, 1H), 5.65 (br s, 1H), 3.50-3.37 (m, 1H), 3.36-3.23 (m, 1H). MS (ESI) m/z $(M+H)^+$399.1.

Example 183

Compounds 328-329

Compounds 328-329 were synthesized from the corresponding starting materials using same procedures as described earlier for compound 317.

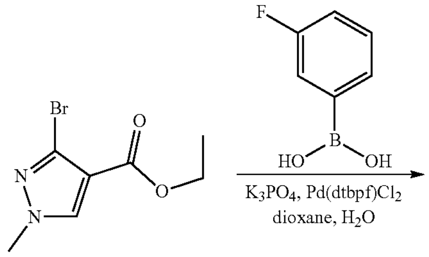

-continued

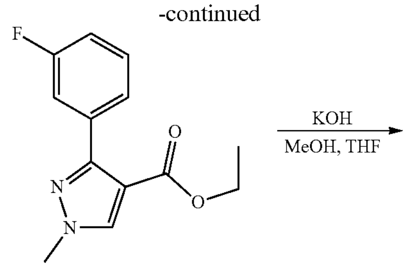

545

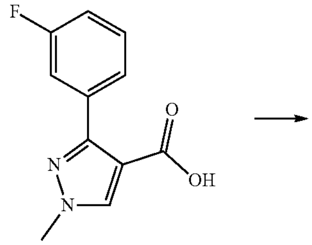

589

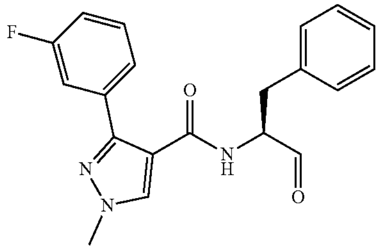

328

Compound 328 was synthesized using ethyl 3-bromo-1-methyl-1H-pyrazole-4-carboxylate and (3-fluorophenyl)boronic acid via intermediates 545 and 589 using the same procedures as in compound 317. Compound 328: (S)-3-(3-fluorophenyl)-1-methyl-N-(1-oxo-3-phenylpropan-2-yl)-1H-pyrazole-4-carboxamide: $^1H$ NMR (400 MHz, DMSO-$d_6$) δ 9.57 (s, 1H), 8.51 (d, J=8.0 Hz, 1H), 8.08 (s, 1H), 7.48-7.41 (m, 2H), 7.37-7.29 (m, 1H), 7.29-7.21 (m, 4H), 7.21-7.09 (m, 2H), 4.50-4.42 (m, 1H), 3.88 (s, 3H), 3.24-3.18 (m, 1H), 2.85-2.77 (m, 1H). MS (ESI) m/z $(M+H)^+$ 352.1.

Compound 329: (S)-1-methyl-N-(1-oxo-3-phenylpropan-2-yl)-3-(M-tolyl)-1H-pyrazole-4-carboxamide: $^1H$ NMR (400 MHz, DMSO-$d_6$) δ 9.56 (s, 1H), 8.35 (d, J=7.2 Hz, 1H), 8.03 (s, 1H), 7.42 (s, 1H), 7.32 (d, J=7.6 Hz, 1H), 7.29-7.18 (m, 5H), 7.17-7.14 (m, 1H), 7.12-7.07 (m, 1H), 4.47-4.40 (m, 1H), 3.86 (s, 3H), 3.22-3.16 (m, 1H), 2.85-2.78 (m, 1H), 2.29-2.25 (m, 1H), 2.27 (s, 2H). MS (ESI) m/z $(M+H)^+$348.1.

Example 184

Compounds 330

Compound 330 was synthesized from the intermediate 250D and using same procedures as described earlier for compound 317.

Compound 330: (S)-1-cyclopropyl-N-(1-oxo-3-phenyl-propan-2-yl)-3-phenyl-1H-pyrazole-4-carboxamide: $^1H$ NMR (400 MHz, $CD_3CN$) δ 9.59 (s, 1H), 7.92 (s, 1H), 7.56-7.08 (m, 10H), 6.65 (s, 1H), 4.58-4.44 (m, 1H), 3.77-

3.58 (m, 1H), 3.30-3.15 (m, 1H), 2.95-2.86 (m, 1H), 1.15-0.99 (m, 4H). MS (ESI) m/z $(M+H)^+$360.1.

Example 185

Compounds 331-333, 415-424

Compounds 331-333 were synthesized from the intermediate 32F and using same procedures as described earlier for compound 168

Compound 331: (S)—N-(4-amino-3,4-dioxo-1-(m-tolyl)butan-2-yl)-1-methyl-3-phenyl-1H-pyrazole-4-carboxamide: $^1$H NMR (400 MHz, DMSO-$d_6$) δ 8.25 (d, J=7.3 Hz, 1H), 8.09-8.01 (m, 2H), 7.80 (s, 1H), 7.61-7.56 (m, 2H), 7.40-7.22 (m, 3H), 6.85 (s, 3H), 5.28 (br s, 1H), 3.90 (s, 3H), 3.11-3.04 (m, 1H), 2.77-2.68 (m, 1H), 2.22 (s, 6H). MS (ESI) m/z $(M+H)^+$405.2.

Compound 332: (S)—N-(1-amino-1,2-dioxopentan-3-yl)-1-methyl-3-phenyl-1H-pyrazole-4-carboxamide: $^1$H NMR (400 MHz, DMSO-$d_6$) δ 8.26 (br d, J=6.8 Hz, 1H), 8.19 (s, 1H), 8.02 (br s, 1H), 7.76 (br s, 1H), 7.69 (br d, J=7.0 Hz, 2H), 7.39-7.28 (m, 3H), 4.95 (br t, J=10.0 Hz, 1H), 3.91 (s, 3H), 1.90-1.75 (m, 1H), 1.66-1.50 (m, 1H), 0.94 (t, J=7.3 Hz, 3H). MS (ESI) m/z $(M+H)^+$315.1.

Compound 333: N-((3S,4R)-1-amino-4-methyl-1,2-dioxohexan-3-yl)-1-methyl-3-phenyl-1H-pyrazole-4-carboxamide: $^1$H NMR (400 MHz, DMSO-$d_6$) δ 8.19 (s, 1H), 8.07-7.94 (m, 2H), 7.75-7.59 (m, 3H), 7.43-7.27 (m, 3H), 5.06 (t, J=6.9 Hz, 1H), 3.90 (s, 3H), 2.11-1.88 (m, 1H), 1.36 (ddd, J=3.9, 7.3, 13.7 Hz, 1H), 1.20-1.04 (m, 1H), 0.91-0.79 (m, 6H). MS (ESI) m/z $(M+H)^+$343.2.

Compound 415 (45 mg, yield: 60.98%): (S)—N-(1-amino-5-methyl-1,2-dioxohexan-3-yl)-1-methyl-3-phenyl-1H-pyrazole-4-carboxamide: $^1$H NMR (400 MHz, DMSO-$d_6$) δ 8.24 (d, J=6.8 Hz, 1H), 8.14 (s, 1H), 8.00 (s, 1H), 7.73 (s, 1H), 7.66 (d, J=7.4 Hz, 2H), 7.35-7.26 (m, 3H), 5.13-5.07 (m, 1H), 3.88 (s, 3H), 1.75-1.65 (m, 1H), 1.51-1.42 (m, 2H), 0.88 (d, J=6.6 Hz, 6H). MS (ESI) m/z $(M+H)^+$343.1.

Compound 416 (25 mg, yield: 34.6%): (S)—N-(1-amino-5,5-dimethyl-1,2-dioxohexan-3-yl)-1-methyl-3-phenyl-1H-pyrazole-4-carboxamide: $^1$H NMR (400 MHz, DMSO-$d_6$) δ 8.26 (d, J=7.5 Hz, 1H), 8.13-8.09 (m, 1H), 8.04 (s, 1H), 7.78-7.66 (m, 3H), 7.38-7.28 (m, 3H), 5.19 (br t, J=6.9 Hz, 1H), 3.93-3.87 (m, 3H), 1.61-1.46 (m, 2H), 0.95 (s, 9H). MS (ESI) m/z $(M+H)^+$357.2.

Compound 417 (25 mg, yield: 71.7%): N-(1-amino-1,2-dioxo-5-phenylpentan-3-yl)-1-methyl-3-phenyl-1H-pyrazole-4-carboxamide: $^1$H NMR (400 MHz, DMSO-$d_6$) δ 8.44 (d, J=6.8 Hz, 1H), 8.19 (s, 1H), 8.00 (s, 1H), 7.74 (s, 1H), 7.68 (d, J=6.8 Hz, 2H), 7.36-7.23 (m, 5H), 7.22-7.14 (m, 3H), 4.99-4.91 (m, 1H), 3.90 (s, 3H), 2.79-2.69 (m, 1H), 2.67-2.59 (m, 1H), 2.10-1.99 (m, 1H), 1.87-1.76 (m, 1H). MS (ESI) m/z $(M+H)^+$391.2.

Compound 418 (25.1 mg, yield: 22.25%): N-(4-amino-1-(3,5-dichlorophenyl)-3,4-dioxobutan-2-yl)-1-methyl-3-phenyl-1H-pyrazole-4-carboxamide: $^1$H NMR (400 MHz, DMSO-$d_6$) δ 8.47 (d, J=7.6 Hz, 1H), 8.05 (br. s, 1H), 7.98 (s, 1H), 7.79 (br. s, 1H), 7.55-7.44 (m, 3H), 7.32-7.21 (m, 5H), 5.25-5.17 (m, 1H), 3.87 (s, 3H), 3.19-3.11 (m, 1H), 2.88-2.77 (m, 1H). MS (ESI) m/z $(M+H)^+$445.0.

Compound 419 (10 mg, yield: 17.6%): (S)—N-(1-amino-1,2-dioxoheptan-3-yl)-1-methyl-3-phenyl-1H-pyrazole-4-carboxamide: $^1$H NMR (400 MHz, DMSO-$d_6$) δ 8.23 (br d, J=6.6 Hz, 1H), 8.15 (s, 1H), 8.00 (s, 1H), 7.74 (s, 1H), 7.65 (br d, J=6.6 Hz, 2H), 7.36-7.25 (m, 3H), 5.07-4.93 (m, 1H), 3.88 (s, 3H), 1.79-1.67 (m, 1H), 1.57-1.44 (m, 1H), 1.37-1.20 (m, 4H), 0.84 (br t, J=6.9 Hz, 3H). MS (ESI) m/z $(M+H)^+$343.2.

Compound 420 (25 mg, yield: 38.7%): (S)—N-(4-amino-1-(4-methoxyphenyl)-3,4-dioxobutan-2-yl)-1-methyl-3-phenyl-1H-pyrazole-4-carboxamide: $^1$H NMR (400 MHz, DMSO-$d_6$) δ 8.04 (s, 1H), 7.85-7.67 (m, 2H), 7.66-7.46 (m, 3H), 7.37-7.29 (m, 3H), 7.17-7.09 (m, 2H), 6.89-6.77 (m, 2H), 5.33-5.24 (m, 1H), 3.94-3.85 (m, 3H), 3.76-3.71 (m, 3H), 3.16-3.10 (m, 1H), 2.88-2.80 (m, 1H). MS (ESI) m/z $(M+H)^+$407.1.

Compound 421 (10 mg, yield: 28.2%): (S)—N-(4-amino-1-(4-hydroxyphenyl)-3,4-dioxobutan-2-yl)-1-methyl-3-phenyl-1H-pyrazole-4-carboxamide: $^1$H NMR (400 MHz, DMSO-$d_6$) δ 9.25 (s, 1H), 8.25 (br d, J=7.3 Hz, 1H), 8.06 (s, 2H), 7.80 (s, 1H), 7.60-7.52 (m, 2H), 7.36-7.26 (m, 3H), 7.03 (d, J=8.6 Hz, 2H), 6.67 (d, J=8.6 Hz, 2H), 5.28-5.17 (m, 1H), 3.92-3.85 (m, 3H), 3.03 (dd, J=4.1, 13.8 Hz, 1H), 2.73-2.68 (m, 1H). MS (ESI) m/z $(M+H)^+$393.1.

Compound 422 (20.3 mg, yield: 27.2%): N-(1-amino-6,6,6-trifluoro-1,2-dioxohexan-3-yl)-1-methyl-3-phenyl-1H-pyrazole-4-carboxamide: $^1$H NMR (400 MHz, DMSO-$d_6$) δ 8.54 (br d, J=6.8 Hz, 1H), 8.20 (s, 1H), 8.03 (br s, 1H), 7.78 (br s, 1H), 7.68 (br d, J=7.6 Hz, 2H), 7.39-7.27 (m, 3H), 5.00-4.90 (m, 1H), 3.91 (s, 3H), 2.43-2.36 (m, 2H), 2.12-1.98 (m, 1H), 1.87-1.72 (m, 1H). MS (ESI) m/z $(M+1)^+$ 383.1.

Compound 423 (23 mg, yield: 35.5%): (S)—N-(4-amino-1-(1H-indol-3-yl)-3,4-dioxobutan-2-yl)-1-methyl-3-phenyl-1H-pyrazole-4-carboxamide: $^1$H NMR (400 MHz, DMSO-$d_6$) δ 10.81 (s, 1H), 8.18 (d, J=6.8 Hz, 1H), 8.11-8.01 (m, 2H), 7.80 (s, 1H), 7.62 (d, J=7.6 Hz, 1H), 7.56-7.46 (m, 2H), 7.32 (d, J=7.6 Hz, 1H), 7.28-7.21 (m, 3H), 7.14-7.08 (m, 1H), 7.08-7.02 (m, 1H), 6.99-6.93 (m, 1H), 5.39-5.31 (m, 1H), 3.85 (s, 3H), 3.30-3.23 (m, 1H), 2.96-2.87 (m, 1H). MS (ESI) m/z $(M+H)^+$416.2.

Compound 424 (23.6 mg, yield: 24.48%): N-(5-amino-1,1,1-trifluoro-4,5-dioxopentan-3-yl)-1-methyl-3-phenyl-1H-pyrazole-4-carboxamide: $^1$H NMR (400 MHz, DMSO-$d_6$) δ 8.78 (d, J=7.2 Hz, 1H), 8.14-8.02 (m, 2H), 7.81 (s, 1H), 7.70-7.63 (m, 2H), 7.39-7.29 (m, 3H), 5.20-5.13 (m, 1H), 3.91 (s, 3H), 2.97-2.80 (m, 1H), 2.74-2.60 (m, 1H). MS (ESI) m/z $(M+1)^+$369.1.

Example 186

Compounds 334-340

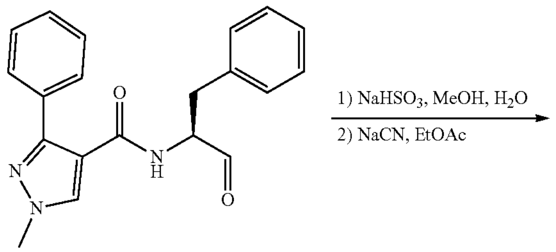

317

-continued

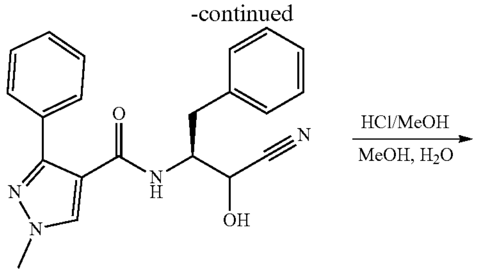

334A

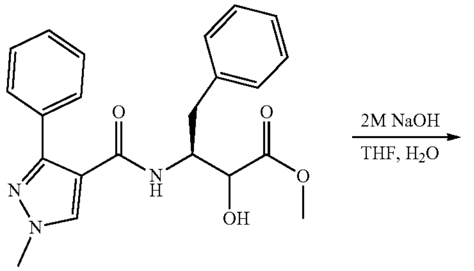

334B

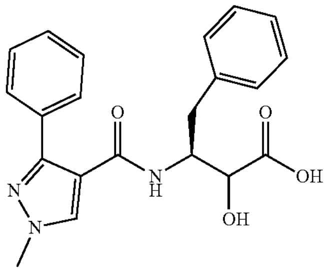

334C

Compound 317 was subjected to reaction conditions as used for converting intermediate 98C to 98D to obtain the intermediate 334A (1.82 g, yield 89.9%) as white solid, which was used directly for the next step without purification. $^1$H NMR (DMSO-$d_6$, 400 MHz) δ 8.17-8.05 (m, 1H), 8.03-7.89 (m, 1H), 7.51-7.40 (m, 2H), 7.29-7.13 (m, 8H), 6.89-6.76 (m, 1H), 4.69-4.42 (m, 1H), 4.40-4.26 (m, 1H), 3.85 (s, 3H), 3.10-2.94 (m, 1H), 2.84-2.60 (m, 1H). MS (ESI) m/z $(M+H)^+$361.1.

To a mixture of compound 334A (1.82 g, 5.1 mmol) in MeOH (20 mL) was added HCl/MeOH (20 mL) at 25° C. The mixture was stirred at 25° C. for 15 h. After solvent of the reaction mixture was removed under reduced pressure, MeOH (25 mL) and $H_2O$ (25 mL) were added, and then the mixture was stirred at 25° C. for 1 h. The reaction mixture was concentrated under reduced pressure to remove solvents to afford compound 334B (2 g, crude) as white solid, which was used directly for next step without purification.

To a mixture of compound 334B (2 g, 5.1 mmol) in THF (15 mL) and MeOH (15 mL) was added aqueous NaOH (2M, 13 mL) at 25° C. The mixture was stirred at 25° C. for 6 h. The reaction mixture was concentrated under reduced pressure to move MeOH and THF. $H_2O$ (10 mL) was added into the mixture, which was washed with TBME (10 mL×2), and then the aqueous phase was acidified with aqueous HCl (1M) till pH ~4-5. The precipitate was filtered and dried to afford compound 334C (1.33 g, yield 69.1%) as white solid, which was used directly for next step without purification. $^1$H NMR (DMSO-$d_6$, 400 MHz) δ 12.55 (s, 1H), 8.03-7.93 (m, 1H), 7.90-7.39 (m, 3H), 7.32-7.14 (m, 8H), 5.74-5.25

(m, 1H), 4.54-4.36 (m, 1H), 4.10-3.94 (m, 1H), 3.85 (d, J=4.9 Hz, 3H), 2.92-2.71 (m, 2H). MS (ESI) m/z $(M+H)^+$ 380.1.

Compounds 334-340 were synthesized from the intermediate 334C and the corresponding amine and using same procedures as described earlier for compound 168.

Compound 334: (S)-1-methyl-N-(4-((oxazol-2-ylmethyl)amino)-3,4-dioxo-1-phenylbutan-2-yl)-3-phenyl-1H-pyrazole-4-carboxamide: $^1$H NMR (400 MHz, $CDCl_3$) δ 7.90 (s, 1H), 7.64 (s, 1H), 7.54-7.33 (m, 6H), 7.22-7.12 (m, 3H), 7.10 (s, 1H), 6.84-6.77 (m, 2H), 6.10 (d, J=6.0 Hz, 1H), 5.60-5.46 (m, 1H), 4.76-4.53 (m, 2H), 3.92 (s, 3H), 3.33-3.22 (m, 1H), 2.96-2.87 (m, 1H). MS (ESI) m/z $(M+H)^+$ 458.2.

Compound 335: (S)—N-(4-((2-(2-methoxyethoxy)ethyl)amino)-3,4-dioxo-1-phenylbutan-2-yl)-1-methyl-3-phenyl-1H-pyrazole-4-carboxamide: $^1$H NMR ($CDCl_3$, 400 MHz) δ 7.89 (s, 1H), 7.53-7.45 (m, 2H), 7.44-7.29 (m, 4H), 7.18 (s, 3H), 6.80 (s, 2H), 6.09 (d, J=4.5 Hz, 1H), 5.58 (d, J=4.8 Hz, 1H), 3.91 (s, 3H), 3.68-3.48 (m, 8H), 3.38 (s, 3H), 3.28 (d, J=10.3 Hz, 1H), 2.97-2.84 (m, 1H). MS (ESI) m/z $(M+H)^+$ 479.2.

Compound 336: (S)-1-methyl-N-(4-((2-(methylamino)-2-oxoethyl)amino)-3,4-dioxo-1-phenylbutan-2-yl)-3-phenyl-1H-pyrazole-4-carboxamide: $^1$H NMR ($CDCl_3$, 400 MHz) δ 7.83 (s, 1H), 7.58-7.32 (m, 6H), 7.18 (s, 3H), 6.82 (s, 2H), 6.32 (s, 1H), 6.11 (s, 1H), 5.31 (s, 1H), 4.15-3.80 (m, 5H), 3.28-3.08 (m, 1H), 2.93-2.64 (m, 4H). MS (ESI) m/z $(M+H)^+$448.2.

Compound 337: (S)—N-(4-((2-(dimethylamino)-2-oxoethyl)amino)-3,4-dioxo-1-phenylbutan-2-yl)-1-methyl-3-phenyl-1H-pyrazole-4-carboxamide: $^1$H NMR ($CDCl_3$, 400 MHz) δ 7.92-7.79 (m, 2H), 7.52-7.44 (m, 2H), 7.44-7.33 (m, 3H), 7.21-7.11 (m, 3H), 6.85-6.74 (m, 2H), 6.09 (d, J=6.3 Hz, 1H), 5.62 (q, J=6.5 Hz, 1H), 4.18-3.99 (m, 2H), 3.91 (s, 3H), 3.31-3.22 (m, 1H), 3.01 (d, J=3.3 Hz, 6H), 2.95-2.86 (m, 1H). MS (ESI) m/z $(M+H)^+$462.2.

Compound 338: (S)—N-(4-((3-amino-3-oxopropyl)amino)-3,4-dioxo-1-phenylbutan-2-yl)-1-methyl-3-phenyl-1H-pyrazole-4-carboxamide: $^1$H NMR ($CDCl_3$, 400 MHz) δ 7.86 (s, 1H), 7.52-7.46 (m, 2H), 7.45-7.35 (m, 4H), 7.21-7.13 (m, 3H), 6.86-6.74 (m, 2H), 6.08 (d, J=5.8 Hz, 1H), 5.71 (s, 1H), 5.58-5.46 (m, 1H), 5.34 (s, 1H), 3.91 (s, 3H), 3.73-3.51 (m, 2H), 3.24 (dd, J=4.8, 14.1 Hz, 1H), 2.86 (dd, J=7.8, 14.3 Hz, 1H), 2.49 (t, J=5.9 Hz, 2H). MS (ESI) m/z $(M+H)^+$448.2.

Compound 339: (S)—N-(4-((2-amino-2-oxoethyl)amino)-3,4-dioxo-1-phenylbutan-2-yl)-1-methyl-3-phenyl-1H-pyrazole-4-carboxamide: $^1$H NMR ($CDCl_3$, 400 MHz) δ 7.83 (s, 1H), 7.55-7.34 (m, 6H), 7.22-7.14 (m, 3H), 6.89-6.77 (m, 2H), 6.33 (s, 1H), 6.14 (d, J=4.6 Hz, 1H), 5.52 (s, 1H), 5.37-5.19 (m, 1H), 4.12-4.02 (m, 1H), 3.99-3.94 (m, 1H), 3.90 (s, 3H), 3.28-3.13 (m, 1H), 2.99-2.77 (m, 1H). MS (ESI) m/z $(M+H)^+$434.2.

Compound 340: Tert-butyl (S)-(2-(3-(1-methyl-3-phenyl-1H-pyrazole-4-carboxamido)-2-oxo-4-phenylbutanamido)ethyl)carbamate: $^1$H NMR ($CDCl_3$, 400 MHz) δ 7.89 (s, 1H), 7.50-7.35 (m, 5H), 7.26-7.23 (m, 1H), 7.20-7.13 (m, 3H), 6.86-6.70 (m, 2H), 6.09 (d, J=6.0 Hz, 1H), 5.58-5.42 (m, 1H), 4.97-4.82 (m, 1H), 3.91 (s, 3H), 3.48-3.39 (m, 2H), 3.35-3.20 (m, 3H), 2.93-2.85 (m, 1H), 1.44 (s, 9H). MS (ESI) m/z $(M+H)^+$520.3.

Example 187

Compound 341

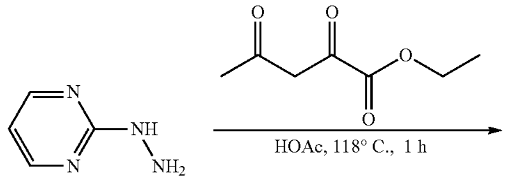

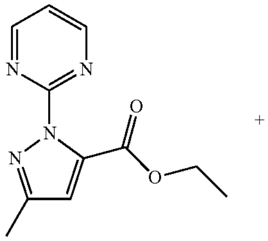

341A

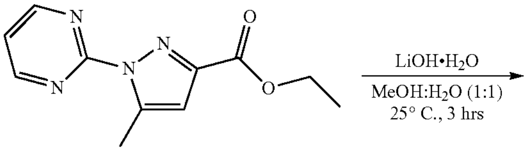

341B

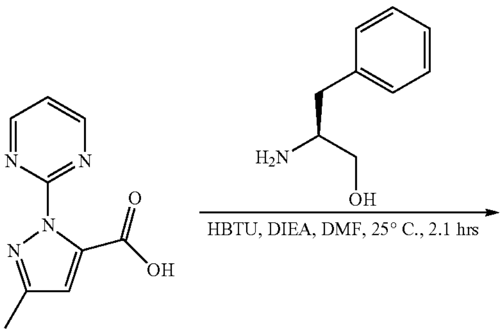

341C

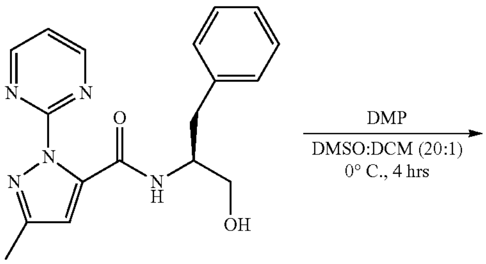

341D

-continued

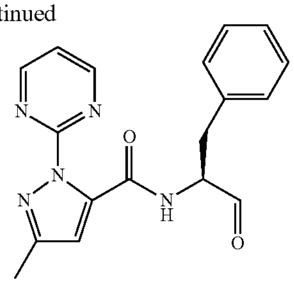

341

Compounds 341C was synthesized from 2-hydrazinylpyrimidine and using same procedures as described earlier for compound 38.

Compound 341 was synthesized from 341C using same procedures as described earlier for compound 317. Compound 341: (S)-3-methyl-N-(1-oxo-3-phenylpropan-2-yl)-1-(pyrimidin-2-yl)-1H-pyrazole-5-carboxamide: $^1$H NMR (400 MHz, $CDCl_3$) δ 9.75 (d, J=1.8 Hz, 1H), 8.70-8.60 (m, 3H), 7.28-7.26 (m, 1H), 7.25-7.16 (m, 5H), 6.74 (s, 1H), 5.00-4.94 (m, 1H), 3.40-3.33 (m, 1H), 3.32-3.24 (m, 1H), 2.42-2.39 (m, 3H). MS (ESI) m/z $(M+H_2O+H)^+$354.2.

Example 188

Compound 342

Compounds 342 was synthesized from 2,2,3,3,3-pentafluoropropan-1-amine hydrochloride and using same procedures as described earlier for compound 272.

Compound 342: N-(4-amino-3,4-dioxo-1-phenylbutan-2-yl)-3-(perfluoroethyl)-1-phenyl-1H-pyrazole-5-carboxamide: $^1$H NMR (400 MHz, DMSO-d6) δ 9.36 (d, J=7.7 Hz, 1H), 8.10 (s, 1H), 7.85 (s, 1H), 7.48-7.34 (m, 4H), 7.32-7.18 (m, 9H), 5.31-5.24 (m, 1H), 3.24-3.13 (m, 1H), 2.85-2.69 (m, 1H). MS (ESI) m/z $(M+H)^+$481.1.

Example 189

Compound 343

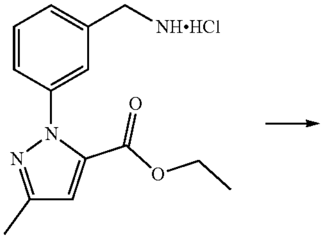

343A

-continued

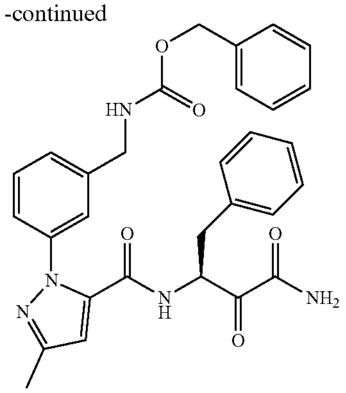

343

Compound 343 was synthesized from ethyl 1-(3-(aminomethyl)phenyl)-3-methyl-1H-pyrazole-5-carboxylate hydrochloride (343A) and using same procedures as described earlier for compound 153. Compound 343: Benzyl (S)-(3-(5-((4-amino-3,4-dioxo-1-phenylbutan-2-yl)carbamoyl)-3-methyl-1H-pyrazol-1-yl)benzyl)carbamate: $^1$H NMR (400 MHz, DMSO-d6) δ 9.14-9.05 (m, 0.4H), 8.16-8.00 (m, 0.9H), 7.93-7.82 (m, 1.3H), 7.59-7.06 (m, 14.2H), 7.00-6.87 (m, 0.5H), 6.77-6.64 (m, 0.5H), 6.31-6.50 (m, 0.9H), 6.49-6.40 (m, 0.4H), 6.29-6.17 (m, 0.4H), 5.34-5.23 (m, 0.4H), 5.04 (s, 1.9H), 4.53-4.34 (m, 0.5H), 4.31-4.09 (m, 1.9H), 3.24-2.99 (m, 0.8H), 2.90-2.63 (m, 1.4H), 2.30-2.16 (m, 3H). MS (ESI) m/z $(M+H)^+$540.2.

Example 190

Compound 344

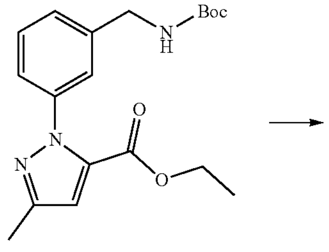

344A

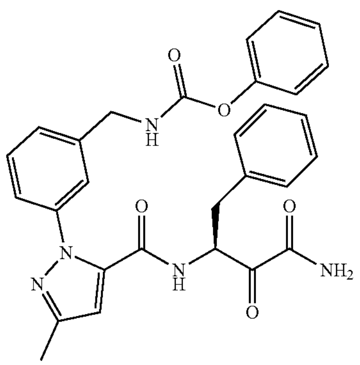

344

Compound 344 was synthesized from ethyl 1-(3-(((tert-butoxycarbonyl)amino)methyl)phenyl)-3-methyl-1H-pyrazole-5-carboxylate 344A and using same procedures as described earlier for compound 162. Compound 344: Phenyl (S)-(3-(5-((4-amino-3,4-dioxo-1-phenylbutan-2-yl)carbamoyl)-3-methyl-1H-pyrazol-1-yl)benzyl)carbamate: $^1$H NMR (400 MHz, DMSO-d6) δ 9.14-9.08 (m, 1H), 8.40-8.33 (m, 1H), 8.13-8.04 (m, 1H), 7.87 (s, 1H), 7.45-7.09 (m, 13H), 6.99-6.71 (m, 1H), 6.60-6.20 (m, 1H), 5.31-5.23 (m, 1H), 4.46-3.97 (m, 2H), 3.26-3.01 (m, 1H), 2.90-2.68 (m, 1H), 2.31-2.19 (m, 3H). MS (ESI) m/z $(M+H)^+$526.2.

Example 191

Compounds 345-346

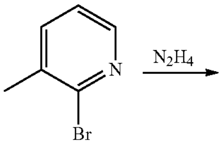

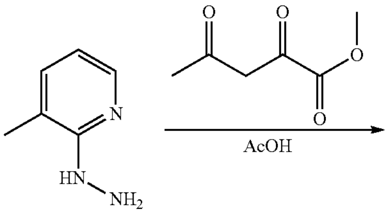

345A

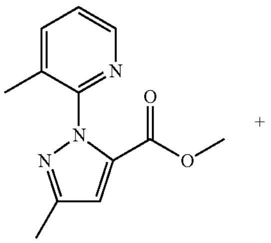

345B

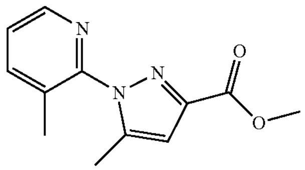

346A

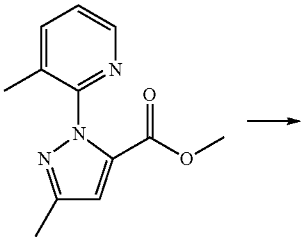

345B

-continued

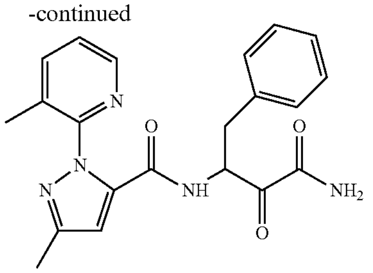

345

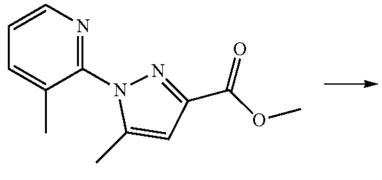

346A

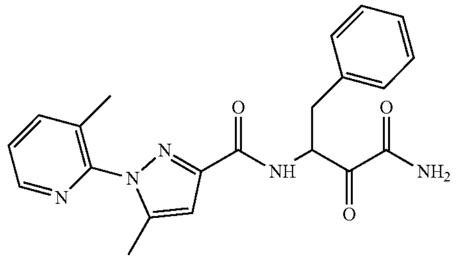

346

Compounds 345 and 346 were prepared from 2-hydrazinyl-3-methylpyridine and methyl 2,4-dioxopentanoate using procedures for compounds 38 and 317.

Compound 345: N-(4-amino-3,4-dioxo-1-phenylbutan-2-yl)-3-methyl-1-(3-methylpyridin-2-yl)-1H-pyrazole-5-carboxamide: $^1H$ NMR (400 MHz, $CDCl_3$) δ 8.36 (br d, J=4.0 Hz, 1H), 7.67 (br d, J=7.6 Hz, 1H), 7.33-7.24 (m, 2H), 7.18-7.05 (m, 5H), 6.67 (br s, 1H), 6.62 (s, 1H), 5.69-5.60 (m, 1H), 5.46 (br s, 1H), 3.35 (dd, J=5.3, 14.0 Hz, 1H), 3.13 (dd, J=7.2, 14.0 Hz, 1H), 2.19 (s, 3H), 2.12 (s, 3H).

Compound 346: N-(4-amino-3,4-dioxo-1-phenylbutan-2-yl)-5-methyl-1-(3-methylpyridin-2-yl)-1H-pyrazole-3-carboxamide: $^1H$ NMR (400 MHz, $CDCl_3$) δ 8.23 (br d, J=4.6 Hz, 1H), 7.67 (d, J=7.5 Hz, 1H), 7.33 (br d, J=7.3 Hz, 1H), 7.26-7.18 (m, 4H), 7.01 (br d, J=3.7 Hz, 2H), 6.68 (br s, 1H), 6.57 (s, 1H), 5.62 (q, J=6.5 Hz, 1H), 5.50 (br s, 1H), 3.34 (dd, J=5.3, 14.1 Hz, 1H), 3.17 (dd, J=6.5, 14.2 Hz, 1H), 2.34 (s, 3H), 2.17 (s, 3H). MS (ESI) m/z $(M+H)^+$392.2.

Example 192

Compound 347

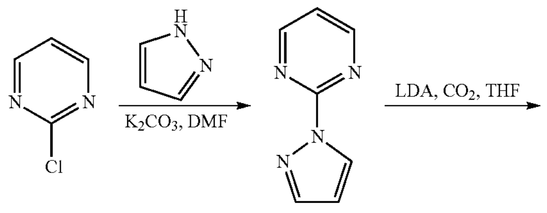

347A

-continued

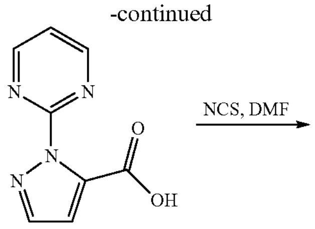

347B

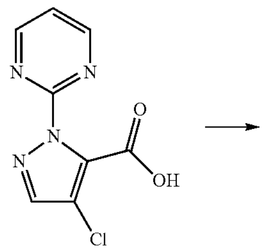

347C

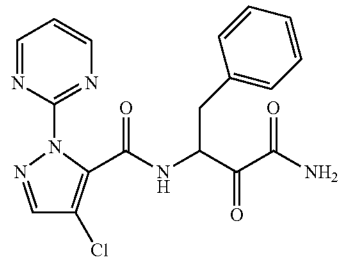

347

A mixture of 2-chloropyrimidine (10 g, 87.3 mmol), 1H-pyrazole (7.73 g, 114 mmol) and $K_2CO_3$ (24.1 g, 175 mmol) in DMF (150 mL) was heated to 120° C. for 12 hr. LCMS showed desired MS. TLC (Petroleum ether:Ethyl acetate=3:1, $R_f$~0) showed new point, after cooling the mixture was filtered and the filtrate was concentrated, the residue was purified by MPLC (Petroleum ether:Ethyl acetate=1:1) to give Compound 347A (10.4 g, yield: 81.5%) as yellow solid. $^1H$ NMR (400 MHz, $CDCl_3$) δ 8.76 (d, J=4.8 Hz, 2H), 8.60 (d, J=2.4 Hz, 1H), 7.84 (s, 1H), 7.21 (t, J=4.8 Hz, 1H), 6.51 (s, 1H).

To a solution of compound 347A (500 mg, 3.42 mmol) in THF (10 mL) was added LDA (1M, 4.45 mL) dropwise at −70° C. and stirred for 10 min, then carbon dioxide was bubbled to the mixture for 30 min, the mixture was slowly warm to 15° C. for 20 min. The mixture was added MTBE (20 mL) and $H_2O$ (20 mL), the water layer was adjusted to pH ~4 with 1N HCl and extracted with ethyl acetate (20 mL×4), the organic layer was dried over $Na_2SO_4$, filtered and concentrated to give compound 347B (480 mg, yield: 73.8%) as brown solid. $^1H$ NMR (400 MHz, DMSO-$d_6$) δ 13.49 (br s, 1H), 8.94 (d, J=4.9 Hz, 2H), 7.83 (d, J=1.8 Hz, 1H), 7.63 (t, J=4.9 Hz, 1H), 6.98 (d, J=1.8 Hz, 1H).

A mixture of compound 347B (200 mg, 1.05 mmol) and NCS (154 mg, 1.16 mmol) in DMF (3 mL) was heated to 90° C. for 4 hr. LCMS showed desired MS, the mixture was purified by preparatory-HPLC (TFA) to give compound 347C (0.2 g, yield: 56.5%) as yellow solid. $^1H$ NMR (400 MHz, DMSO-$d_6$) δ 14.05 (br s, 1H), 8.96 (d, J=4.9 Hz, 2H), 8.07 (s, 1H), 7.66 (t, J=4.9 Hz, 1H).

Compound 347 was synthesized from 347C and using same procedures described earlier for converting compound 321D to compound 321. Compound 347: N-(4-amino-3,4- dioxo-1-phenylbutan-2-yl)-4-chloro-1-(pyrimidin-2-yl)-1H-pyrazole-5-carboxamide: $^1$H NMR (400 MHz, DMSO-d6) δ 9.25 (d, J=7.3 Hz, 1H), 8.67 (d, J=4.9 Hz, 2H), 8.12 (s, 1H), 7.96 (s, 1H), 7.86 (s, 1H), 7.46 (t, J=4.9 Hz, 1H), 7.32-7.15 (m, 5H), 5.50-5.38 (m, 1H), 3.13 (dd, J=3.6, 14.2 Hz, 1H), 2.77 (dd, J=9.9, 14.1 Hz, 1H). MS (ESI) m/z (M+H)$^+$399.1.

Example 193

Compound 348

Compound 348 was synthesized from 2,3-difluoropyridine and using same procedures described earlier for Example 313. Compound 348: N-(4-amino-3,4-dioxo-1-phenylbutan-2-yl)-1-(3-fluoropyridin-2-yl)-3-methyl-1H-pyrazole-5-carboxamide: $^1$H NMR (400 MHz, DMSO-d6) δ 8.97 (d, J=7.5 Hz, 1H), 8.29 (d, J=4.6 Hz, 1H), 8.07 (s, 1H), 7.92-7.80 (m, 2H), 7.57 (td, J=4.2, 8.4 Hz, 1H), 7.32-7.25 (m, 4H), 7.21 (dt, J=2.5, 6.1 Hz, 1H), 6.91 (s, 1H), 5.26-5.17 (m, 1H), 3.16 (dd, J=3.3, 13.9 Hz, 1H), 2.91-2.79 (m, 1H), 2.27 (s, 3H). MS (ESI) m/z (M+H)$^+$396.1.

Example 194

Compound 349

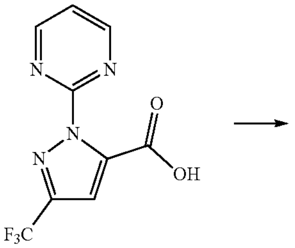

349B

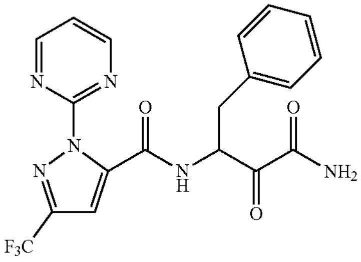

349

Compound 349B was prepared 3-(trifluoromethyl)-1H-pyrazole using the same procedure as described for Compound 347B.

Compound 349 was synthesized from 349B and using same procedures described earlier for converting compound 347C to compound 347. Compound 349: N-(4-amino-3,4-dioxo-1-phenylbutan-2-yl)-1-(pyrimidin-2-yl)-3-(trifluoromethyl)-1H-pyrazole-5-carboxamide: $^1$H NMR (400 MHz, $CDCl_3$) δ 8.69 (br s, 2H), 8.11 (br s, 1H), 7.33 (br s, 1H), 7.38-7.31 (m, 1H), 7.24 (br s, 4H), 7.15-7.08 (m, 1H), 7.15-7.08 (m, 1H), 7.15-7.01 (m, 1H), 6.77 (br s, 1H), 5.82 (br s, 1H), 5.63 (br s, 1H), 3.47 (br s, 1H), 3.35 (br s, 1H). MS (ESI) m/z (M+H)$^+$433.1.

Example 195

Compounds 350, 457

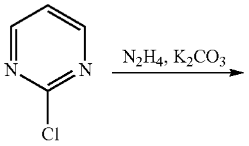

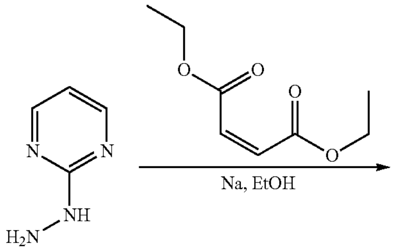

350A

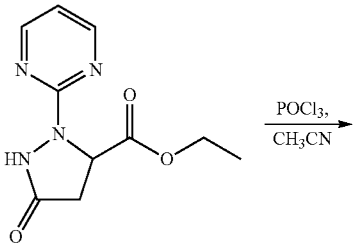

350B

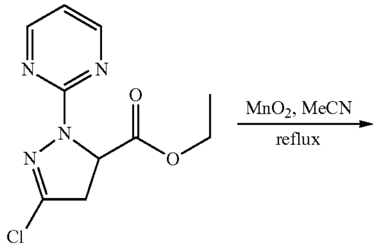

350C

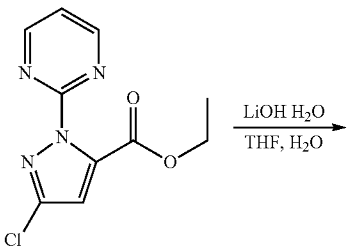

350D

-continued

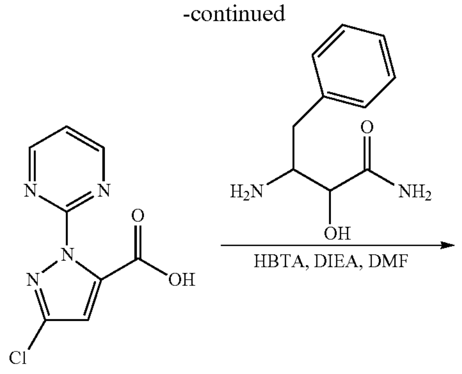

350E

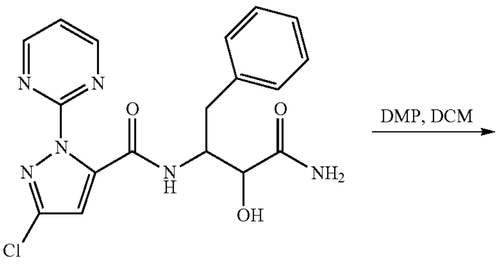

350F

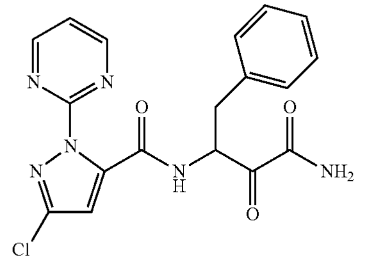

350

A mixture of 2-chloropyrimidine (15 g, 131 mmol), $NH_2NH_2.H_2O$ (30 mL), $K_2CO_3$ (15 g, 109 mmol) was stirred at 100° C. for 30 min. The mixture was ice cooled and the resulting crude crystals were collected by filtration. The crystals were washed with cold water, air dried, and recrystallized from Petroleum ether (150 mL) to give compound 350A (14.4 g, 131 mmol, yield: 99.8%) as a yellow solid. $^1$H NMR (400 MHz, DMSO-$d_6$) δ 8.30 (d, J=4.8 Hz, 2H), 8.12 (br s, 1H), 6.59 (t, J=4.7 Hz, 1H), 4.13 (s, 2H).

To a mixture of compound 350A (2 g, 18.2 mmol) and Na (1.46 g, 63.6 mmol) in EtOH (60 mL) was added diethyl maleate (3.75 g, 21.8 mmol) at 15° C. The mixture was stirred at 60° C. for 3 hours. The reaction was cooled to 15° C. and quenched with acetic acid to pH ~7. The mixture was concentrated to give residue. The residue was purified by prep-HPLC (TFA condition) to give compound 350B (3.5 g, 14.8 mmol, yield: 81.6%) as brown oil. $^1$H NMR (400 MHz, $CDCl_3$) δ 8.49 (d, J=4.9 Hz, 2H), 6.85 (t, J=5.0 Hz, 1H), 5.23 (dd, J=4.2, 11.0 Hz, 1H), 4.33-4.20 (m, 2H), 3.41-3.28 (m, 1H), 3.01 (dd, J=4.2, 17.6 Hz, 1H), 2.05-1.96 (m, 1H), 1.32-1.21 (m, 3H).

To a mixture of compound 350B (3.5 g, 14.8 mmol) in MeCN (40 mL) was added $POCl_3$ (2.73 g, 17.8 mmol, 1.65 mL). The mixture was stirred at 80° C. for 12 hours. The reaction mixture was concentrated. The residue was poured into saturated $NaHCO_3$ (30 mL) and stirred for 10 min. The aqueous phase was extracted with ethyl acetate (50 mL×4).

The combined organic phase was dried with anhydrous $Na_2SO_4$, filtered and concentrated in vacuum. The residue was purified by column chromatography ($SiO_2$, Petroleum ether:Ethyl acetate=0:1 to 1:1) to give compound 350C (900 mg, yield: 23.9%) as a yellow solid. $^1$H NMR (400 MHz, $CDCl_3$) δ 8.44 (d, J=4.9 Hz, 2H), 6.75 (t, J=4.9 Hz, 1H), 5.11 (dd, J=6.5, 12.7 Hz, 1H), 4.27-4.16 (m, 2H), 3.56 (dd, J=12.7, 18.0 Hz, 1H), 3.21 (dd, J=6.6, 18.1 Hz, 1H), 1.23 (t, J=7.2 Hz, 3H).

To a mixture of compound 350C (900 mg, 3.53 mmol) in MeCN (15 mL) was added $MnO_2$ (3.07 g, 35.3 mmol). The mixture was stirred at 80° C. for 12 hours. The reaction mixture was filtered and the filtrate was concentrated. The residue was purified by column chromatography ($SiO_2$, Petroleum ether:Ethyl acetate=1:0 to 0:1) to give compound 350D (215 mg, yield: 24.1%) as brown oil. $^1$H NMR (400 MHz, $CDCl_3$) δ 8.81 (d, J=4.9 Hz, 2H), 7.36 (t, J=4.9 Hz, 1H), 6.80 (s, 1H), 4.35 (q, J=7.2 Hz, 2H), 1.31 (t, J=7.2 Hz, 3H).

Compounds 350 were synthesized from the intermediate 350D and using same procedures as described earlier for converting compound 38B to compound 38. Compound 350: N-(4-amino-3,4-dioxo-1-phenylbutan-2-yl)-3-chloro-1-(pyrimidin-2-yl)-1H-pyrazole-5-carboxamide: $^1$H NMR (400 MHz, DMSO-$d_6$) δ 9.23 (d, J=7.3 Hz, 1H), 8.78 (d, J=4.9 Hz, 2H), 8.09 (s, 1H), 7.85 (s, 1H), 7.55 (t, J=4.9 Hz, 1H), 7.33-7.19 (m, 5H), 6.84 (s, 1H), 5.35-5.25 (m, 1H), 3.16 (dd, J=3.6, 14.0 Hz, 1H), 2.82 (dd, J=10.0, 14.0 Hz, 1H). MS (ESI) m/z $(M+H)^+$399.1.

Compound 457 were synthesized from the intermediate 350E and 3-amino-N-cyclopropyl-2-hydroxy-4-phenylbutanamide hydrochloride using same procedures as described earlier for compound 350. Compound 457 (70.21 g, yield: 70.32%): 3-chloro-N-(4-(cyclopropylamino)-3,4-dioxo-1-phenylbutan-2-yl)-1-(pyrimidin-2-yl)-1H-pyrazole-5-carboxamide: $^1$H NMR (400 MHz, DMSO-$d_6$) δ 9.29 (d, J=7.5 Hz, 1H), 8.84 (d, J=5.1 Hz, 1H), 8.77 (d, J=4.9 Hz, 2H), 7.56 (t, J=4.7 Hz, 1H), 7.32-7.20 (m, 5H), 6.90 (s, 1H), 5.36-5.29 (m, 1H), 3.16 (dd, J=3.6, 14.0 Hz, 1H), 2.83 (dd, J=9.9, 13.9 Hz, 1H), 2.79-2.72 (m, 1H), 0.71-0.56 (m, 4H). MS (ESI) m/z $(M+H)^+$439.1.

Example 196

Compound 351

Compound 351 was synthesized from 341C using same procedures as described earlier for converting compound 321D to compound 321. Compound 341: N-(4-amino-3,4-dioxo-1-phenylbutan-2-yl)-3-methyl-1-(pyrimidin-2-yl)-1H-pyrazole-5-carboxamide: $^1$H NMR (400 MHz, DMSO-$d_6$) δ 9.05 (d, J=7.2 Hz, 1H), 8.71 (d, J=4.8 Hz, 2H), 8.07 (s, 1H), 7.83 (s, 1H), 7.47-7.42 (m, 1H), 7.32-7.17 (m, 5H), 6.56 (s, 1H), 5.29-5.21 (m, 1H), 3.16-3.08 (m, 1H), 2.85-2.77 (m, 1H), 2.25 (s, 3H). MS (ESI) m/z $(M+H)^+$379.0.

Example 197

Compound 352

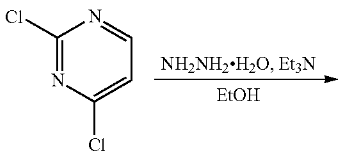

-continued

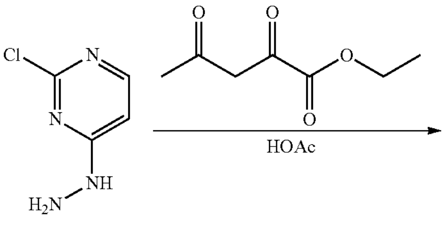

352A

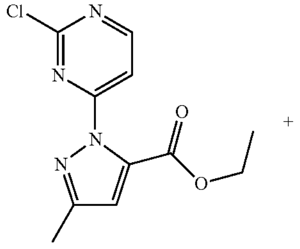

352B

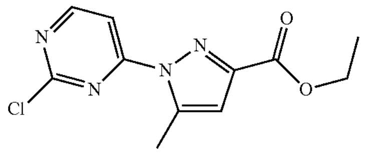

352C

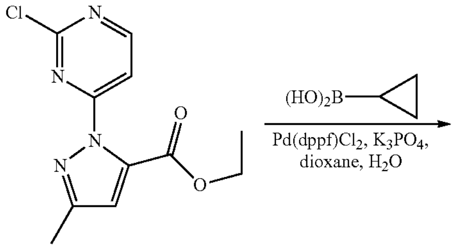

352B

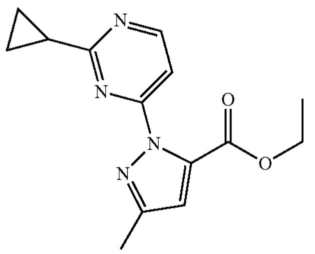

352D

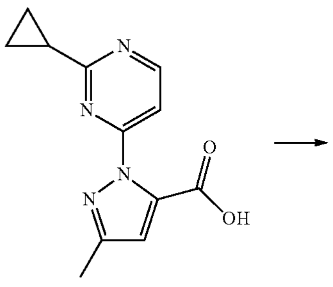

352D

-continued

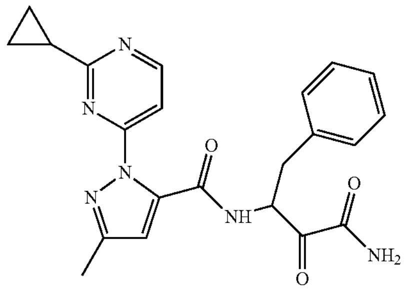

352

Compound 352 was prepared from 2-chloro-4-hydrazinylpyrimidine and ethyl 2,4-dioxopentanoate using procedures for compounds 345 and 321. Compound 352: N-(4-amino-3,4-dioxo-1-phenylbutan-2-yl)-1-(2-cyclopropylpyrimidin-4-yl)-3-methyl-1H-pyrazole-5-carboxamide: $^1$H NMR (400 MHz, DMSO-$d_6$) δ 9.10 (br d, J=7.0 Hz, 1H), 8.62 (d, J=5.5 Hz, 1H), 8.12 (br s, 1H), 7.87 (br s, 1H), 7.45 (d, J=5.5 Hz, 1H), 7.35-7.19 (m, 5H), 6.44 (s, 1H), 5.56-5.48 (m, 1H), 3.18 (br dd, J=3.8, 13.8 Hz, 1H), 2.81 (br dd, J=9.8, 13.8 Hz, 1H), 2.28 (s, 3H), 2.00-1.90 (m, 1H), 0.94-0.67 (m, 4H). MS (ESI) m/z $(M+H)^+$419.2.

Example 198

Compound 353

Compound 353 was synthesized from 254D using same procedures as described earlier for synthesis of compound 322. Compound 353: (S)-4-(3-fluorophenyl)-2-methyl-N-(1-oxo-3-phenylpropan-2-yl)oxazole-5-carboxamide: $^1$H NMR (400 MHz, $CDCl_3$) δ 9.71 (s, 1H), 8.05-7.94 (m, 2H), 7.43-7.27 (m, 4H), 7.21 (br d, J=6.8 Hz, 2H), 7.13-7.05 (m, 1H), 6.89-6.84 (m, 1H), 4.98-4.90 (m, 1H), 3.37-3.31 (m, 1H), 3.29-3.20 (m, 1H), 2.55 (s, 3H). MS (ESI) m/z $(M+H_2O+H)^+$353.1.

Example 199

Compound 354

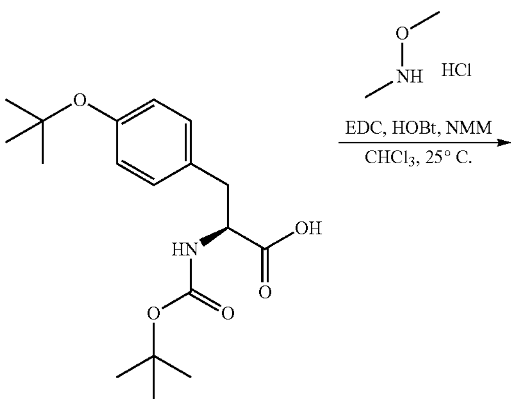

-continued

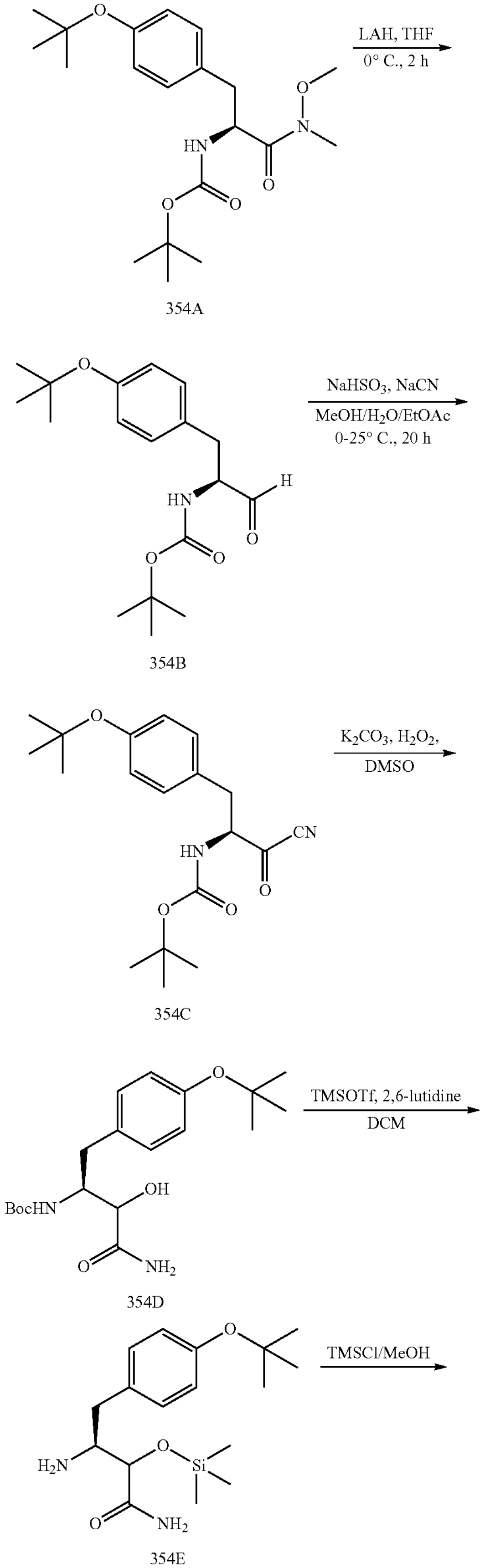

354A

354B

354C

354D

354E

-continued

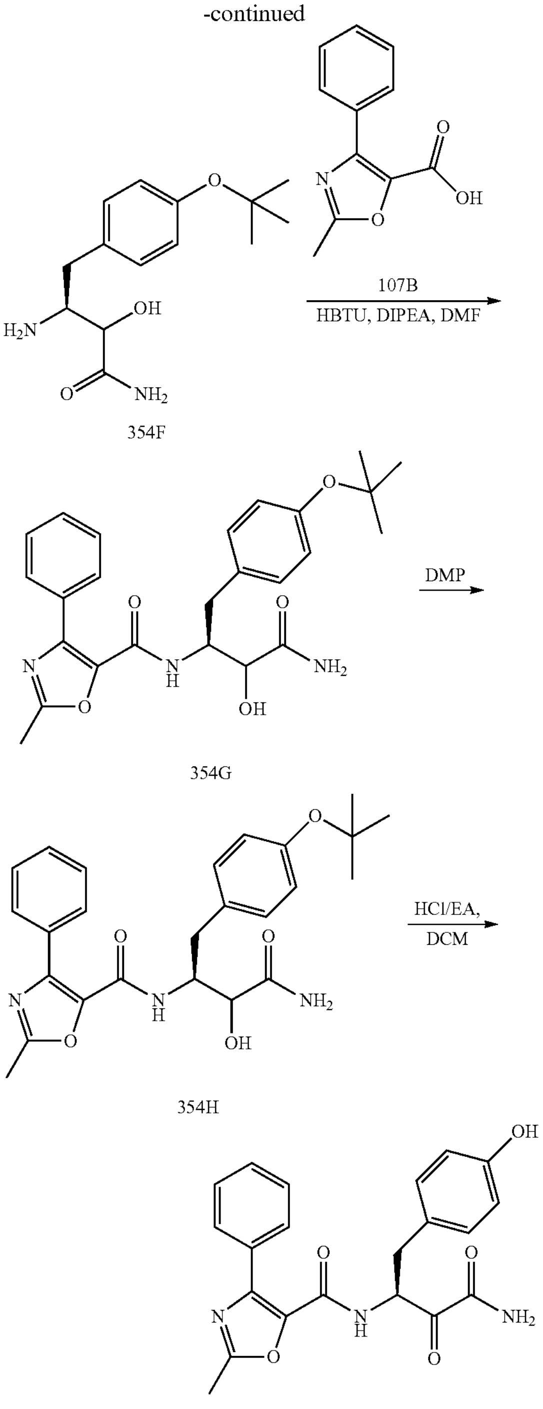

354F

354G

354H

354

Compound 354D was prepared using procedure for compound 213D. To a solution of compound 354D (2.50 g, 6.82 mmol) and 2,6-lutidine (6.36 mL, 54.56 mmol) in DCM (25 mL) was added trimethylsilyl trifluoromethanesulfonate (7.40 mL, 40.92 mmol) at 0° C. under $N_2$ atmosphere. After addition, the reaction mixture was stirred at 0° C. for 0.25 h, then stirred at 20° C. for 3 h. The reaction mixture was cooled to 0° C. and added into cooled sat.$NH_4Cl$(50 mL), then the mixture was extracted with EtOAc (100 mL×2), the combined extracts were washed with sat.$NaHCO_3$ (100 mL), then the mixture was dried over $Na_2SO_4$ and filtered, the filtrate was concentrated in vacuum to afford compound 354E (2.50 g, crude) as red oil. MS (ESI) m/z $(M+H)^+$339.1.

To a solution of compound 354E (2.50 g, 7.39 mmol) in MeOH (40 mL) was added TMSCl (1.50 mL, 11.87 mmol) at 0° C. After addition, the reaction mixture was stirred at 0° C. for 0.5 h. TEA was added into the reaction mixture to pH ~8, then the mixture was concentrated in vacuum to afford crude compound 354F (2.50 g, crude) as red solid. MS (ESI) m/z $(M+H)^+$266.9.

To a solution of compound 107B (700 mg, 3.45 mmol), compound 354F (1.01 g, 3.80 mmol) and HBTU (1.57 g, 4.13 mmol) in DMF (40 mL) was added DIEA (2.41 mL, 13.78 mmol) at 0-10° C. After addition, the reaction mixture was stirred at 20° C. for 2 h. 5 mL of water was added into the reaction mixture and the mixture was concentrated in vacuum to remove the most of DMF. Then 100 mL of water and 80 mL of EtOAc were added into the mixture and stirred for 2 min. The mixture was separated and the aqueous layer was extracted with EtOAc (80 mL). The combined extracts were washed with 0.3N HCl (80 mL×2), sat.$NaHCO_3$ (80 mL×2) and brine (80 mL). Then the mixture was dried over $Na_2SO_4$ and filtered, the mixture was concentrated in vacuum to afford crude product. The residue was purified by preparatory-HPLC (neutral condition) to afford compound 354G (1.0 g, yield 63.55%) as white solid. $^1$H NMR (400 MHz, DMSO-$d_6$) δ 8.12-7.55 (m, 3H), 7.45-7.25 (m, 5H), 7.22-7.05 (m, 2H), 6.91-6.77 (m, 2H), 6.10-5.84 (m, 1H), 4.64-4.46 (m, 1H), 4.11-3.99 (m, 1H), 2.94-2.80 (m, 1H), 2.79-2.61 (m, 1H), 2.56-2.52 (m, 3H), 1.23-1.17 (m, 9H). MS (ESI) m/z $(M+H)^+$452.1.

To a solution of compound 354G (863.1 mg, 1.91 mmol) in DCM (200 mL) was added DMP (3.24 g, 7.65 mmol) at 0° C. under $N_2$ atmosphere. After addition, the reaction mixture was stirred at 10° C. for 1 h. 50 mL of sat.$Na_2S_2O_3$ and 50 mL of $NaHCO_3$ was added into the reaction mixture, the mixture was stirred for 20 min. Then the mixture was separated, the organic layer was washed with 50 mL of sat.$Na_2S_2O_3$ and 50 mL of $NaHCO_3$, then water (80 mL), brine (80 mL). The mixture was dried over $Na_2SO_4$ and filtered, then the mixture was concentrated in vacuum to afford compound 354H (640 mg, yield 74.45%) as white solid. $^1$H NMR (400 MHz, DMSO-$d_6$) δ 8.77 (d, J=7.5 Hz, 1H), 8.17-7.94 (m, 3H), 7.87-7.74 (m, 1H), 7.45-7.31 (m, 3H), 7.16 (d, J=8.4 Hz, 2H), 6.88-6.81 (m, 2H), 5.45-5.31 (m, 1H), 3.18-3.05 (m, 1H), 2.99-2.86 (m, 1H), 2.55-2.49 (m, 3H), 1.23-1.18 (m, 9H). MS (ESI) m/z $(M+H)^+$448.2.

To a solution of compound 354H (440 mg, 978.87 umol) in DCM (30 mL) was added HCl/EtOAc (4M, 22 mL) at 0° C. After addition, the reaction mixture was stirred at 10° C. for 2 h. The reaction mixture was concentrated and the residue was dissolved into 80 mL of EtOAc, the mixture was washed with water (80 mL), 0.1% $NaHCO_3$ (80 mL) and brine (80 mL). Then the mixture was dried over $Na_2SO_4$ and filtered, then concentrated in vacuum to afford compound 354. Compound 354 (650 mg, 1.49 mmol) was dissolved into 3 mL of $CH_3CN$ and 15 mL of 2-isopropoxypropane was added into the stirring mixture. After that, the mixture was filtered to afford pure compound 354 (450 mg, yield 71.40%) as light yellow solid. $^1$H NMR (400 MHz, DMSO-$d_6$) δ 9.25 (s, 1H), 8.70 (d, J=7.5 Hz, 1H), 8.11 (s, 1H), 8.07-8.00 (m, 2H), 7.84 (s, 1H), 7.42-7.36 (m, 3H), 7.08 (d, J=8.5 Hz, 2H), 6.67 (d, J=8.5 Hz, 2H), 5.45-5.29 (m, 1H), 3.13-3.05 (m, 1H), 2.93-2.84 (m, 1H), 2.56 (s, 3H). MS (ESI) m/z $(M+H)^+$394.1.

Example 200

Compound 355

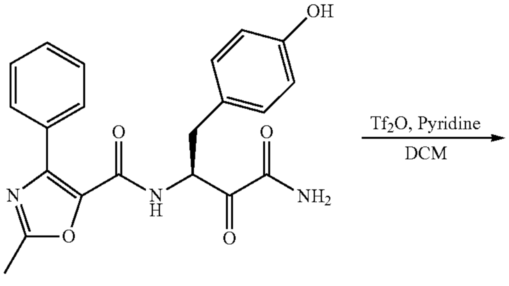

354

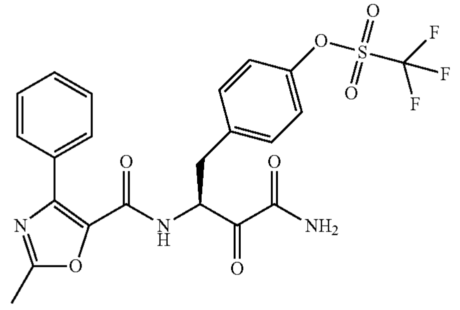

355

To a solution of compound 354 (40 mg, 101.68 umol) and pyridine (19 mg, 233.86 umol) in DCM (2 mL) was added $Tf_2O$ (34 mg, 122.02 umol) in DCM (0.5 mL) at 0° C. under $N_2$ atmosphere. After addition, the reaction mixture was stirred at 0° C. for 4 h. The reaction mixture was diluted with EtOAc (50 mL), the mixture was washed with 0.2N HCl (20 mL), $NaHCO_3$ (20 mL) and brine (20 mL), then the mixture was dried over $Na_2SO_4$ and filtered, the mixture was concentrated in vacuum to afford compound 355 (40 mg, yield 63.64%) as yellow solid. $^1$H NMR (400 MHz, DMSO-$d_6$) δ 8.89 (d, J=7.5 Hz, 1H), 8.09 (s, 1H), 8.01-7.95 (m, 2H), 7.82 (s, 1H), 7.47-7.42 (m, 2H), 7.42-7.38 (m, 2H), 7.37-7.32 (m, 3H), 5.44-5.28 (m, 1H), 3.26-3.21 (m, 1H), 3.06-2.96 (m, 1H), 2.52 (s, 3H). MS (ESI) m/z $(M+H)^+$526.1.

Example 201

Compound 356

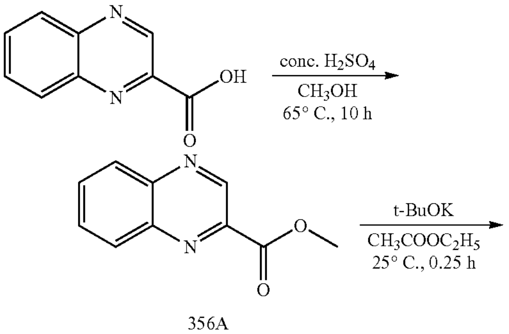

356A

-continued

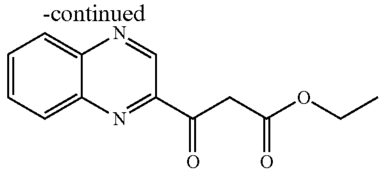

356B

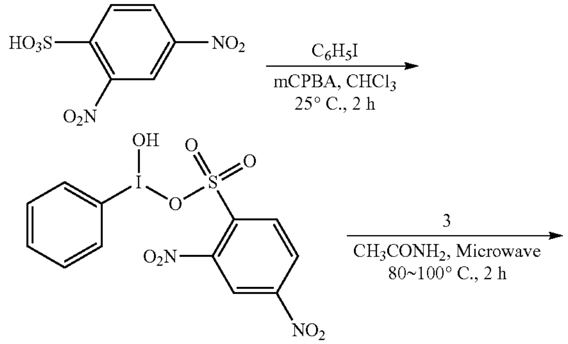

356C

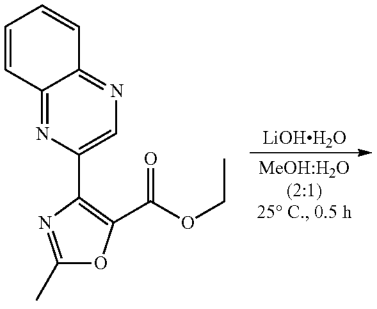

356D

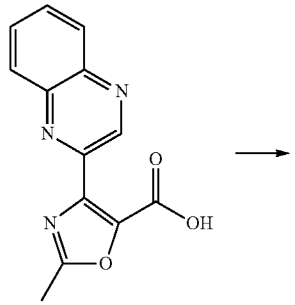

356E

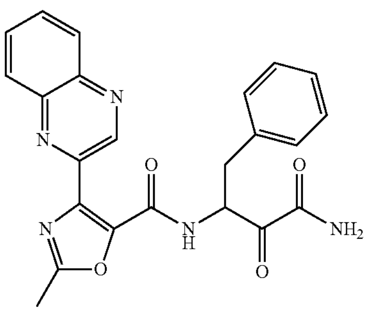

356

To a solution of quinoxaline-2-carboxylic acid (6 g, 34.45 mmol) in MeOH (80 mL) was added con. $H_2SO_4$ (675.8 mg, 6.89 mmol) dropwise, then the mixture was stirred at 65° C. for 10 hours. After cooling to room temperature, the mixture was neutralized with a sat. $NaHCO_3$ and extracted with DCM (60 mL×3). The organic phases were combined, dried with anhydrous $Na_2SO_4$, and evaporated to afford compound 356A (5.80 g, yield: 89.47%) as a brown solid. The crude product was used directly in the next step without further purification. $^1H$ NMR ($CDCl_3$, 400 MHz) δ 9.56 (s, 1H), 8.31 (d, J=7.6 Hz, 1H), 8.20 (d, J=8.0 Hz, 1H), 7.97-7.84 (m, 2H), 4.13 (s, 3H).

A solution of compound 356A (2.5 g, 13.29 mmol) in $CH_3COOC_2H_5$ (60 mL) was added t-BuOK (1.94 g, 17.28 mmol). The mixture was stirred for 0.25 hour at 25° C. The mixture was quenched with $H_2O$ (50 mL). The organic layer was separated and the aqueous was extracted with EA (50 mL×3). The organic phases were combined, dried with anhydrous $Na_2SO_4$, filtered and evaporated. The residue was purified by flash chromatography (PE:EA=20/1 to 10/1) to afford compound 356B (2.45 g, 75.48% yield) as pale yellow solid. $^1H$ NMR ($CDCl_3$, 400 MHz) δ 9.57-9.33 (m, 1H), 8.19-8.06 (m, 2H), 7.96-7.74 (m, 2H), 4.35-4.26 (m, 2H), 4.24-4.13 (m, 2H), 1.28-1.18 (m, 3H).

A mixture of 2,4-dinitrobenzenesulfonic acid (7.83 g, 29.41 mmol, $H_2O$) and iodobenzene (5 g, 24.51 mmol) in $CHCl_3$ (20 mL) was added m-CPBA (4.23 g, 24.51 mmol), the mixture was stirred at 25° C. for 2 hours under $N_2$ atmosphere. After the reaction, MTBE (20 mL) was added to the reaction mixture, and the resulting mixture was filtered and the solid was washed with MTBE (30 mL). The resulting mixture was filtered and the solid was washed with MTBE (30 mL) to give compound 356C (8.7 g, 75.82% yield) as a white solid. $^1H$ NMR (400 MHz, DMSO-$d_6$) δ 9.60 (br s, 1H), 8.53 (d, J=2.0 Hz, 1H), 8.39-8.36 (m, 1H), 8.18 (d, J=7.6 Hz, 2H), 8.07 (d, J=8.8 Hz, 1H), 7.71-7.64 (m, 1H), 7.63-7.55 (m, 2H).

A mixture of compound 356C (3.49 g, 7.45 mmol) and compound 356B (1.4 g, 5.73 mmol) were stirred at 80° C. for 1 h, and acetamide (4.06 g, 68.76 mmol) was added to the mixture, then the mixture was stirred at 120° C. for 1 h under microwave irradiation. The reaction mixture was concentrated under reduced pressure to remove solvent and concentrated under reduced pressure to give a residue. The residue was purified by column chromatography ($SiO_2$, Petroleum ether/Ethyl acetate=I/O to 0:1) to give compound 356D (300 mg, crude) as dull-red solid. MS (ESI) m/z $(M+H)^+$284.1.

Compound 356 was synthesized from 356D and using same procedures described earlier for converting compound 321C to compound 321. Compound 356: N-(4-amino-3,4-dioxo-1-phenylbutan-2-yl)-2-methyl-4-(quinoxalin-2-yl) oxazole-5-carboxamide: $^1H$ NMR (400 MHz, DMSO-$d_6$) δ 11.39 (d, J=8.4 Hz, 1H), 9.58 (s, 1H), 8.24 (br s, 1H), 8.12 (d, J=8.0 Hz, 1H), 7.95 (br s, 1H), 7.89 (t, J=7.6 Hz, 1H), 7.76 (t, J=7.6 Hz, 1H), 7.60 (d, J=8.4 Hz, 1H), 6.98-6.86 (m, 4H), 6.85-6.78 (m, 1H), 5.90-5.78 (m, 1H), 3.27-3.19 (m, 2H), 2.59 (s, 3H). MS (ESI) m/z $(M+H)^+$430.1.

Example 202

Compound 357

Compound 357 was synthesized from 107B and using same procedures described earlier for converting compound 321D to compound 321. Compound 357: N-(4-amino-3,4-dioxo-1-phenylbutan-2-yl)-2-methyl-4-phenyloxazole-5-carboxamide: $^1H$ NMR (400 MHz, $CDCl_3$) δ 8.12-8.05 (m, 2H), 7.43-7.37 (m, 3H), 7.32-7.26 (m, 3H), 7.15-7.10 (m, 2H), 6.78-6.71 (m, 2H), 5.75-5.68 (m, 1H), 5.54 (br s, 1H), 3.50-3.38 (m, 1H), 3.29-3.18 (m, 1H), 2.55 (s, 3H). $^1H$ NMR (400 MHz, DMSO-$d_6$) δ 8.82 (d, J=7.2 Hz, 1H), 8.15-7.92 (m, 3H), 7.86 (s, 1H), 7.41-7.35 (m, 3H), 7.32-7.26 (m, 4H), 7.25-7.17 (m, 1H), 5.48-5.38 (m, 1H), 3.27-3.15 (m, 1H), 3.06-2.93 (m, 1H), 2.55 (s, 3H). MS (ESI) m/z $(M+1)^+$378.1.

Example 203

Compounds 358-359

Compounds 358 and 359 were synthesized using same procedures described earlier for compound 255. Compound 358: N-(4-amino-3,4-dioxo-1-phenylbutan-2-yl)-4-(2-fluorophenyl)-2-(trifluoromethyl)oxazole-5-carboxamide: $^1$H NMR ($CDCl_3$, 400 MHz) δ 7.52 (t, J=7.6 Hz, 1H), 7.45-7.35 (m, 1H), 7.28-7.20 (m, 3H), 7.19-7.07 (m, 2H), 7.02 (d, J=7.6 Hz, 2H), 6.68 (d, J=4.8 Hz, 2H), 5.70-5.60 (m, 1H), 5.49 (br s, 1H), 3.42-3.32 (m, 1H), 3.24-3.14 (m, 1H). MS (ESI) m/z $(M+H)^+$450.1. Compound 359: N-(4-amino-3,4-dioxo-1-phenylbutan-2-yl)-4-(o-tolyl)-2-(trifluoromethyl)oxazole-5-carboxamide: $^1$H NMR ($CDCl_3$, 400 MHz) δ 7.43-7.34 (m, 1H), 7.33-7.26 (m, 2H), 7.25-7.19 (m, 4H), 6.92 (br s, 2H), 6.69 (br s, 1H), 6.44 (d, J=6.4 Hz, 1H), 5.66-5.58 (m, 1H), 5.50 (br s, 1H), 3.41-3.28 (m, 1H), 3.08-2.97 (m, 1H), 2.21 (s, 3H). MS (ESI) m/z $(M+H)^+$ 446.1.

Example 204

Compound 360

Compound 360 was synthesized using same procedures described earlier for compound 26. Compound 360: N-((2S)-4-amino-3-hydroxy-4-oxo-1-phenylbutan-2-yl)-2-methyl-4-phenyloxazole-5-carboxamide: $^1$H NMR (400 MHz, DMSO-$d_6$) δ 8.19-7.58 (m, 3H), 7.47-7.34 (m, 5H), 7.32-7.26 (m, 2H), 7.25-7.06 (m, 3H), 6.16-5.82 (m, 1H), 4.73-4.39 (m, 1H), 4.06-3.88 (m, 1H), 3.04-2.65 (m, 2H), 2.59-2.53 (m, 3H). MS (ESI) m/z $(M+1)^+$380.0.

Example 205

Compound 361

Compound 361 was synthesized from ethyl 3-(2,3-difluorophenyl)-3-oxopropanoate using same procedures described earlier for compound 267. Compound 361: N-(4-amino-3,4-dioxo-1-phenylbutan-2-yl)-4-(2,3-difluorophenyl)-2-methyloxazole-5-carboxamide: $^1$H NMR ($CDCl_3$, 400 MHz) δ 7.36-7.27 (m, 3H), 7.26-7.17 (m, 2H), 7.15-7.06 (m, 3H), 6.78-6.63 (m, 2H), 5.74-5.62 (m, 1H), 5.55 (br s, 1H), 3.42 (dd, J=5.5, 14.3 Hz, 1H), 3.25 (dd, J=6.6, 14.3 Hz, 1H), 2.57 (s, 3H). MS (ESI) m/z $(M+H)^+$414.1.

Example 206

Compounds 362-377, 462-468

Compounds 362-377, 462-468 were synthesized from the corresponding intermediate or intermediate 321B and using same procedures as described earlier for compound 321.

Compound 362 (35.2 mg, 47.49% yield, 94% purity, EE %: 97%): (S)—N-(4-fluoro-3-oxo-1-phenylbutan-2-yl)-4-(4-((prop-2-yn-1-yloxy)methyl)phenyl)-1,2,5-thiadiazole-3-carboxamide: $^1$H NMR (400 MHz, DMSO-$d_6$) δ 9.50-9.40 (m, 1H), 9.45 (d, J=7.7 Hz, 1H), 7.50 (d, J=8.2 Hz, 2H), 7.38-7.22 (m, 7H), 5.44-5.14 (m, 2H), 4.99-4.88 (m, 1H), 4.58 (s, 2H), 4.23 (d, J=2.4 Hz, 2H), 3.53 (t, J=2.3 Hz, 1H), 3.21 (dd, J=4.1, 14.2 Hz, 1H), 2.89 (dd, J=10.5, 14.0 Hz, 1H). MS (ESI) m/z $(M+H)^+$438.1, $(M+Na)^+$460.0.

Compound 363 (39.2 mg, 36.85% yield, 94% purity): N-(4-amino-3,4-dioxo-1-phenylbutan-2-yl)-4-(4-((4-fluorobenzamido)methyl)phenyl)-1,2,5-thiadiazole-3-carboxamide: $^1$H NMR (400 MHz, DMSO-$d_6$) δ 9.44 (d, J=7.7 Hz, 1H), 9.14 (t, J=6.0 Hz, 1H), 8.21 (s, 1H), 8.06-7.97 (m, 2H), 7.93 (s, 1H), 7.51 (d, J=8.2 Hz, 2H), 7.37-7.23 (m, 8H), 7.20-7.12 (m, 1H), 5.60-5.44 (m, 1H), 4.52 (d, J=6.0 Hz, 2H), 3.24 (dd, J=3.2, 14.0 Hz, 1H), 2.85 (dd, J=10.3, 14.0 Hz, 1H). MS (ESI) m/z $(M+H)^+$532.2.

Compound 364 (27.5 mg, 26.56% yield, 96% purity): N-(4-amino-3,4-dioxo-1-phenylbutan-2-yl)-4-chloro-1,2,5-thiadiazole-3-carboxamide: $^1$H NMR (400 MHz, DMSO-d6) δ 9.24 (d, J=7.5 Hz, 1H), 8.19 (s, 1H), 7.92 (s, 1H), 7.49-7.19 (m, 5H), 5.47 (ddd, J=3.9, 7.7, 9.6 Hz, 1H), 3.24 (dd, J=3.9, 14.0 Hz, 1H), 2.95 (dd, J=9.8, 14.0 Hz, 1H). MS (ESI) m/z $(M+H)^+$339.0.

Compound 365 (60 mg, 39.4% yield): N-(4-amino-3,4-dioxo-1-phenylbutan-2-yl)-4-(pyrazin-2-yl)-1,2,5-thiadiazole-3-carboxamide: $^1$H NMR (400 MHz, DMSO-d6) δ 9.23 (d, J=7.3 Hz, 1H), 9.06 (d, J=1.5 Hz, 1H), 8.69 (d, J=2.4 Hz, 1H), 8.51 (dd, J=1.5, 2.4 Hz, 1H), 8.13 (s, 1H), 7.87 (s, 1H), 7.29-7.14 (m, 6H), 5.47 (ddd, J=4.1, 7.6, 9.3 Hz, 1H), 3.16 (dd, J=4.0, 14.1 Hz, 1H), 2.87 (dd, J=9.3, 14.3 Hz, 1H). MS (ESI) m/z $(M+H)^+$383.1.

Compound 366 (50 mg, 36.9% yield): N-(4-amino-3,4-dioxo-1-phenylbutan-2-yl)-4-bromo-1,2,5-thiadiazole-3-carboxamide: $^1$H NMR (400 MHz, DMSO-$d_6$) δ 9.23 (d, J=7.5 Hz, 1H), 8.18 (s, 1H), 7.91 (s, 1H), 7.35-7.17 (m, 4H), 5.54-5.41 (m, 1H), 3.23 (dd, J=3.9, 14.2 Hz, 1H), 2.95 (dd, J=9.7, 13.9 Hz, 1H). MS (ESI) m/z $(M+H)^+$383.0.

Compound 367 (50 mg, 18.43% yield): N-(4-amino-3,4-dioxo-1-phenylbutan-2-yl)-4-(benzo[d][1,3]dioxol-4-yl)-1,2,5-thiadiazole-3-carboxamide: $^1$H NMR (400 MHz, DMSO-$d_6$) δ 8.92 (d, J=8.0 Hz, 1H), 7.94-7.52 (m, 2H), 7.36-7.18 (m, 5H), 7.08-6.93 (m, 2H), 6.92-6.79 (m, 1H), 5.87 (d, J=10.0 Hz, 2H), 5.55-5.38 (m, 1H), 3.23 (dd, J=3.5, 14.1 Hz, 1H), 3.03-2.97 (m, 1H). MS (ESI) m/z $(M+H)^+$ 425.1.

Compound 368 (130 mg, 60.3% yield): N-(4-amino-3,4-dioxo-1-phenylbutan-2-yl)-4-(2-fluoro-3-methylphenyl)-1,2,5-thiadiazole-3-carboxamide: $^1$H NMR (400 MHz, DMSO-$d_6$) δ 9.22 (d, J=7.7 Hz, 1H), 8.12 (s, 1H), 7.87 (s, 1H), 7.39 (t, J=6.9 Hz, 1H), 7.31-7.19 (m, 6H), 7.17-7.10 (m, 1H), 5.42 (ddd, J=3.7, 7.7, 9.7 Hz, 1H), 3.19 (dd, J=3.7, 14.1 Hz, 1H), 2.96 (dd, J=9.7, 13.9 Hz, 1H), 2.22 (d, J=2.0 Hz, 3H). MS (ESI) m/z $(M+H)^+$413.1.

Compound 369 (55 mg, 27.8% yield): N-(4-amino-3-hydroxy-4-oxo-1-phenylbutan-2-yl)-4-(4-((benzyloxy)methyl)phenyl)-1,2,5-thiadiazole-3-carboxamide: $^1$H NMR (400 MHz, DMSO-$d_6$) δ 9.45 (d, J=7.5 Hz, 1H), 8.21 (s, 1H), 7.94 (s, 1H), 7.63-7.52 (m, 2H), 7.44-7.16 (m, 12H), 5.54-5.49 (m, 1H), 4.62-4.56 (m, 4H), 3.24 (dd, J=3.6, 14.0 Hz, 1H), 2.86 (dd, J=10.1, 13.9 Hz, 1H). MS (ESI) m/z $(M+H)^+$501.1.

Compound 370 (55 mg, 20.1% yield): N-(4-amino-3,4-dioxo-1-phenylbutan-2-yl)-4-(3-((benzyloxy)methyl)phenyl)-1,2,5-thiadiazole-3-carboxamide: $^1$H NMR (400 MHz, DMSO-$d_6$) δ 9.42 (d, J=7.7 Hz, 1H), 8.18 (s, 1H), 7.93 (s, 1H), 7.71 (s, 1H), 7.49-7.43 (m, 2H), 7.42-7.33 (m, 5H), 7.32-7.24 (m, 5H), 7.24-7.19 (m, 1H), 6.49-6.39 (m, 1H), 5.55-5.48 (m, 1H), 4.55 (d, J=5.7 Hz, 4H), 3.22 (dd, J=3.6, 14.0 Hz, 1H), 2.88 (dd, J=9.9, 13.9 Hz, 1H). MS (ESI) m/z $(M+H_2O)^+$518.2.

Compound 371 (90 mg, 63.2% yield): N-(4-amino-3,4-dioxo-1-phenylbutan-2-yl)-4-(pyridin-4-yl)-1,2,5-thiadiazole-3-carboxamide: $^1$H NMR (400 MHz, DMSO-$d_6$) δ 9.47 (d, J=7.8 Hz, 1H), 8.65-8.55 (m, 2H), 8.21 (s, 1H), 7.95 (s, 1H), 7.52-7.38 (m, 2H), 7.33-7.22 (m, 5H), 6.53-6.39 (m, 1H), 5.55-5.47 (m, 1H), 3.28-3.22 (m, 1H), 2.92-2.83 (m, 1H). MS (ESI) m/z (M+H)$^+$382.1.

Compound 372 (50 mg, 22.8% yield): N-(4-amino-3,4-dioxo-1-phenylbutan-2-yl)-4-(2,3-difluorophenyl)-1,2,5-thiadiazole-3-carboxamide: $^1$H NMR (400 MHz, DMSO-$d_6$) δ 9.24 (d, J=7.6 Hz, 1H), 8.12 (s, 1H), 7.86 (s, 1H), 7.59-7.50 (m, 1H), 7.29-7.16 (m, 7H), 5.44-5.37 (m, 1H), 3.21-3.14 (m, 1H), 2.98-2.90 (m, 1H). MS (ESI) m/z (M+H)$^+$417.1.

Compound 373 (85 mg, 44.6% yield): N-(4-amino-3,4-dioxo-1-phenylbutan-2-yl)-4-(pyridin-2-yl)-1,2,5-thiadiazole-3-carboxamide: $^1$H NMR (400 MHz, DMSO-$d_6$) δ 9.36 (d, J=7.1 Hz, 1H), 8.42 (d, J=5.6 Hz, 1H), 8.10 (s, 1H), 7.97-7.79 (m, 3H), 7.50-7.34 (m, 1H), 7.21 (s, 5H), 5.54-5.46 (m, 1H), 3.20-3.11 (m, 1H), 2.90 (dd, J=8.8, 14.1 Hz, 1H). MS (ESI) m/z (M+H)$^+$382.1.

Compound 374 (100 mg, 49.9% yield): N-(4-amino-3,4-dioxo-1-phenylbutan-2-yl)-4-(pyrimidin-4-yl)-1,2,5-thiadiazole-3-carboxamide: $^1$H NMR (400 MHz, DMSO-$d_6$) δ 9.27 (d, J=7.5 Hz, 1H), 9.05 (d, J=1.3 Hz, 1H), 8.94 (d, J=5.1 Hz, 1H), 8.14 (s, 1H), 7.94-7.83 (m, 2H), 7.28-7.16 (m, 5H), 5.50 (ddd, J=4.2, 7.5, 9.3 Hz, 1H), 3.18 (dd, J=4.1, 14.2 Hz, 1H), 2.88 (dd, J=9.5, 14.1 Hz, 1H). MS (ESI) m/z (M+H)$^+$ 383.1.

Compound 375 (60 mg, 28.5% yield): N-(4-amino-3,4-dioxo-1-phenylbutan-2-yl)-4-(3-fluoro-2-methylphenyl)-1,2,5-thiadiazole-3-carboxamide: $^1$H NMR (400 MHz, DMSO-$d_6$) δ 9.19 (d, J=8.0 Hz, 1H), 8.10 (s, 1H), 7.84 (s, 1H), 7.27-7.15 (m, 7H), 6.98-6.94 (m, 1H), 5.39-5.31 (m, 1H), 3.18-3.12 (m, 1H), 2.93-2.85 (m, 1H), 1.87-1.83 (m, 3H). MS (ESI) m/z (M+H)$^+$413.1.

Compound 376 (300 mg, 47.9% yield): (S)—N-(4-amino-3,4-dioxo-1-phenylbutan-2-yl)-4-phenyl-1,2,5-thiadiazole-3-carboxamide: $^1$H NMR (400 MHz, DMSO-$d_6$) δ 9.46 (d, J=8.0 Hz, 1H), 8.22 (s, 1H), 7.95 (s, 1H), 7.58 (d, J=6.8 Hz, 2H), 7.50-7.45 (m, 1H), 7.44-7.38 (m, 2H), 7.35-7.24 (m, 5H), 5.56-5.49 (m, 1H), 3.29-3.21 (m, 1H), 2.93-2.83 (m, 1H). (ESI) m/z (M+H)$^+$-381.1.

Compound 377 (80 mg, 39.9% yield): N-(4-amino-3,4-dioxo-1-phenylbutan-2-yl)-4-(pyridin-3-yl)-1,2,5-thiadiazole-3-carboxamide: $^1$H NMR (400 MHz, DMSO-$d_6$) δ 9.39 (d, J=7.7 Hz, 1H), 8.82 (d, J=2.2 Hz, 1H), 8.65 (dd, J=1.5, 4.9 Hz, 1H), 8.19 (s, 1H), 7.96-7.82 (m, 2H), 7.43 (dd, J=4.9, 7.9 Hz, 1H), 7.33-7.20 (m, 5H), 5.53-5.45 (m, 1H), 3.23 (dd, J=3.6, 14.0 Hz, 1H), 2.90 (dd, J=10.0, 14.0 Hz, 1H). MS (ESI) m/z (M+H)$^+$382.1.

Compound 462 (150 mg, 73.8% yield): N-(4-(cyclopropylamino)-3,4-dioxo-1-phenylbutan-2-yl)-4-phenyl-1,2,5-thiadiazole-3-carboxamide: $^1$H NMR (400 MHz, DMSO-$d_6$) δ 9.45 (d, J=7.7 Hz, 1H), 8.91 (br d, J=5.1 Hz, 1H), 7.57 (d, J=7.1 Hz, 2H), 7.50-7.43 (m, 1H), 7.42-7.34 (m, 2H), 7.34-7.25 (m, 5H), 5.59-5.48 (m, 1H), 3.24 (dd, J=3.1, 13.9 Hz, 1H), 2.93-2.76 (m, 2H), 0.72-0.59 (m, 4H). MS (ESI) m/z (M+H)$^+$421.1.

Compound 463 was prepared from the corresponding intermediates, 4-phenyl-1,2,5-thiadiazole-3-carboxylic acid and 3-amino-2-hydroxy-5-phenylpentanamide hydrochloride using same procedures as for compound 321. Compound 463 (120 mg, 35% yield): N-(1-amino-1,2-dioxo-5-phenylpentan-3-yl)-4-phenyl-1,2,5-thiadiazole-3-carboxamide: $^1$H NMR (400 MHz, DMSO-$d_6$) δ 9.49 (br d, J=7.1 Hz, 1H), 8.14 (br s, 1H), 7.91-7.78 (m, 3H), 7.56-7.45 (m, 3H), 7.33-7.25 (m, 2H), 7.22-7.15 (m, 3H), 5.15 (br t, J=6.6 Hz, 1H), 2.77-2.58 (m, 2H), 2.21-2.08 (m, 1H), 1.96-1.81 (m, 1H). MS (ESI) m/z (M+H)$^+$395.1.

Compound 464 was prepared from the corresponding intermediates, 4-phenyl-1,2,5-thiadiazole-3-carboxylic acid and 3-amino-4-(4-fluorophenyl)-2-hydroxybutanamide hydrochloride using same procedures as for compound 321. Compound 464 (120 mg, 47% yield): N-(4-amino-1-(4-fluorophenyl)-3,4-dioxobutan-2-yl)-4-phenyl-1,2,5-thiadiazole-3-carboxamide: $^1$H NMR (400 MHz, DMSO-$d_6$) δ 9.45 (d, J=6.4 Hz, 1H), 8.20 (s, 1H), 7.94 (s, 1H), 7.56 (d, J=7.1 Hz, 2H), 7.50-7.37 (m, 3H), 7.31 (s, 2H), 7.18-7.05 (m, 2H), 5.47 (s, 1H), 3.29-3.15 (m, 1H), 2.91-2.78 (m, 1H). MS (ESI) m/z (M+H)$^+$399.0.

Compound 465 was prepared from the corresponding intermediates, 4-phenyl-1,2,5-thiadiazole-3-carboxylic acid and 3-amino-2-hydroxy-5-methylhexanamide hydrochloride using same procedures as for compound 321. Compound 465 (110 mg, 38.2% yield): N-(1-amino-5-methyl-1,2-dioxohexan-3-yl)-4-phenyl-1,2,5-thiadiazole-3-carboxamide: $^1$H NMR (400 MHz, DMSO-$d_6$) δ 9.32 (d, J=6.6 Hz, 1H), 8.14 (s, 1H), 7.95-7.69 (m, 3H), 7.51 (s, 3H), 5.30 (s, 1H), 1.78-1.39 (m, 3H), 0.90 (dd, J=5.8, 15.3 Hz, 6H). MS (ESI) m/z (M+H)$^+$347.1.

Compound 466 was prepared from the corresponding intermediates, 4-phenyl-1,2,5-thiadiazole-3-carboxylic acid and 3-amino-4-(3,5-dimethylphenyl)-2-hydroxybutanamide hydrochloride using same procedures as for compound 321. Compound 466 (70 mg, 39.2% yield): N-(4-amino-1-(3,5-dimethylphenyl)-3,4-dioxobutan-2-yl)-4-phenyl-1,2,5-thiadiazole-3-carboxamide: $^1$H NMR (400 MHz, DMSO-$d_6$) δ 9.40 (d, J=7.5 Hz, 1H), 8.19 (s, 1H), 7.92 (s, 1H), 7.62 (d, J=7.3 Hz, 2H), 7.53-7.35 (m, 3H), 6.89 (s, 3H), 5.56-5.40 (m, 1H), 3.20-3.08 (m, 1H), 2.85-2.71 (m, 1H), 2.21 (s, 6H). MS (ESI) m/z (M+H)$^+$409.1.

Compound 467 was prepared from the corresponding intermediates, 4-phenyl-1,2,5-thiadiazole-3-carboxylic acid and 3-amino-2-hydroxyheptanamide hydrochloride using same procedures as for compound 321. Compound 467 (80 mg, 73% yield): N-(1-amino-1,2-dioxoheptan-3-yl)-4-phenyl-1,2,5-thiadiazole-3-carboxamide: $^1$H NMR (400 MHz, DMSO-$d_6$) δ 9.31 (br d, J=7.0 Hz, 1H), 8.14 (br s, 1H), 7.94-7.69 (m, 3H), 7.58-7.43 (m, 3H), 5.30-5.15 (m, 1H), 1.82 (br d, J=7.5 Hz, 1H), 1.57 (br d, J=4.8 Hz, 1H), 1.40-1.39 (m, 1H), 1.36-1.22 (m, 1H), 1.36-1.20 (m, 3H), 0.88-0.81 (m, 3H). MS (ESI) m/z (M+H)$^+$347.1.

Compound 468 was prepared from the corresponding intermediates, 4-phenyl-1,2,5-thiadiazole-3-carboxylic acid and 3-amino-2-hydroxybutanamide hydrochloride using same procedures as for compound 321. Compound 468 (70 mg, 54.2% yield): N-(4-amino-3,4-dioxobutan-2-yl)-4-phenyl-1,2,5-thiadiazole-3-carboxamide: $^1$H NMR (400 MHz, DMSO-$d_6$) δ 9.40 (d, J=6.4 Hz, 1H), 8.12 (br s, 1H), 7.92-7.75 (m, 3H), 7.58-7.43 (m, 3H), 5.25-5.18 (m, 1H), 1.36 (d, J=7.3 Hz, 3H). MS (ESI) m/z (M+H)$^+$305.1.

Example 207

Compounds 378, 578, 599

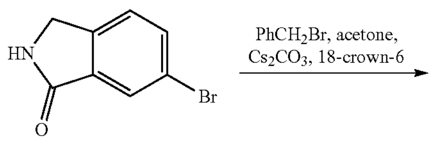

-continued

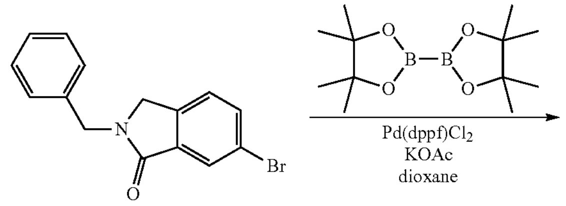

378A

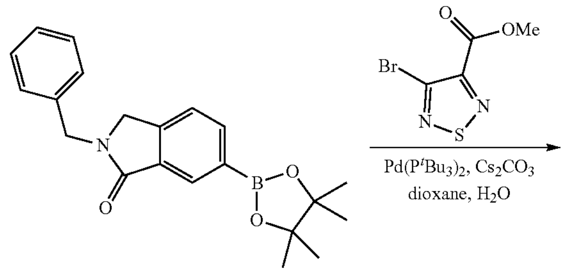

378B

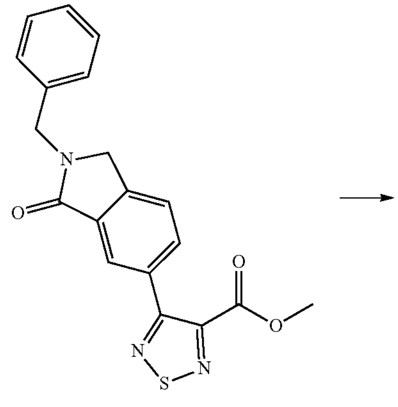

378C

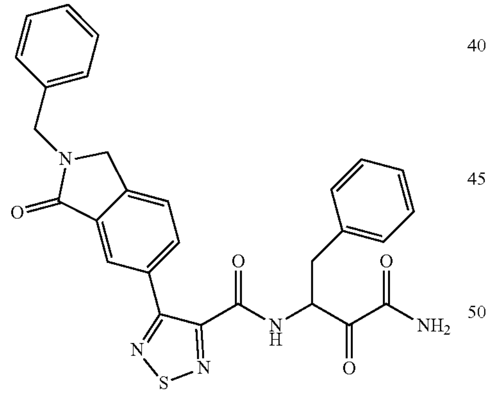

378

To a solution of 6-bromoisoindolin-1-one (0.5 g, 2.36 mmol) in acetone (20 mL) was added BnBr (605 mg, 3.54 mmol, 0.420 mL), $Cs_2CO_3$ (1.92 g, 5.90 mmol) and 18-crown-6 (62 mg, 235.80 umol), then the mixture was stirred at 70° C. for 16 h. The reaction mixture was concentrated to remove solvent, then diluted with water (50 mL) and extracted with EA (40 mL×2), and the organic layers were dried over $Na_2SO_4$, filtered and concentrated to give a residue. The residue was purified by flash silica gel chromatography (ISCO®; 12 g SepaFlash® Silica Flash Column, Eluent of 0-20% Ethyl acetate/Petroleum ethergradient @ 30 mL/min). Compound 378A (0.46 g, yield: 59.5%) was obtained as white solid. $^1H$ NMR (400 MHz, $CDCl_3$) δ 8.02 (d, J=1.8 Hz, 1H), 7.63 (dd, J=1.9, 8.0 Hz, 1H), 7.39-7.16 (m, 6H), 4.79 (s, 2H), 4.21 (s, 2H). MS (ESI) m/z $(M+H)^+$ 302.0.

To a solution of compound 378A (0.46 g, 1.52 mmol) and 4,4,4',4',5,5,5',5'-octamethyl-2,2'-bi(1,3,2-dioxaborolane) (580 mg, 2.28 mmol) in dioxane (20 mL) was added KOAc (299 mg, 3.04 mmol), and then $Pd(dppf)Cl_2$ (111 mg, 152.23 umol) was added under $N_2$ atmosphere, the mixture was stirred at 85° C. for 16 h. The reaction mixture was diluted with EA (20 mL), then filtered and washed with EA (20 mL×3), the filtrate was concentrated to give a residue. The residue was purified by flash silica gel chromatography (ISCO®; 12 g SepaFlash® Silica Flash Column, Eluent of 0 30% Ethyl acetate/Petroleum ethergradient @ 30 mL/min). Then further purified by preparatory-TLC (PE: EA=2:1). Compound 378B (0.35 g, yield: 46.1%) was obtained as light yellow solid. $^1H$ NMR (400 MHz, DMSO-$d_6$) δ 7.98 (t, J=0.9 Hz, 1H), 7.86 (dd, J=1.1, 7.5 Hz, 1H), 7.57 (dd, J=0.9, 7.5 Hz, 1H), 7.38-7.32 (m, 2H), 7.31-7.23 (m, 3H), 4.77-4.69 (m, 2H), 4.39 (s, 2H), 1.31 (s, 12H). MS (ESI) m/z $(M+H)^+$349.9.

To a solution of methyl 4-bromo-1,2,5-thiadiazole-3-carboxylate (186 mg, 835.17 umol) and compound 378B (0.35 g, 1.00 mmol) in dioxane (20 mL) and $H_2O$ (2 mL) was added $K_2CO_3$ (231 mg, 1.67 mmol), then $Pd(dppf)Cl_2$ (61 mg, 83.52 umol) was added under $N_2$ atmosphere, then the mixture was stirred at 85° C. for 16 h under $N_2$ atmosphere. The reaction mixture was diluted with EA (30 mL), then filtered and concentrated to give a residue. The residue was purified by flash silica gel chromatography (ISCO®; 12 g SepaFlash® Silica Flash Column, Eluent of 030% Ethyl acetate/Petroleum ethergradient @ 30 mL/min). Compound 378C (0.13 g, yield: 37.3%) was obtained as a white solid. $^1H$ NMR (400 MHz, $CDCl_3$) δ 8.20 (d, J=1.8 Hz, 1H), 7.87 (dd, J=1.8, 7.9 Hz, 1H), 7.51 (d, J=7.7 Hz, 1H), 7.41-7.28 (m, 5H), 4.84 (s, 2H), 4.35 (s, 2H), 4.03-3.95 (m, 3H). MS (ESI) m/z $(M+H)^+$366.0.

Compound 378 was synthesized from 378C and using same procedures described earlier for compound 321. Compound 378 (20 mg, 13.5% yield): N-(4-amino-3,4-dioxo-1-phenylbutan-2-yl)-4-(2-benzyl-3-oxoisoindolin-5-yl)-1,2,5-thiadiazole-3-carboxamide: $^1H$ NMR (400 MHz, DMSO-$d_6$) δ 9.07 (br s, 1H), 8.20-8.00 (m, 1H), 7.96-7.48 (m, 4H), 7.42-7.12 (m, 10H), 5.58-5.38 (m, 1H), 4.78 (s, 2H), 4.45 (s, 2H), 3.26 (dd, J=3.8, 14.3 Hz, 1H), 2.98 (d, J=14.1 Hz, 1H). MS (ESI) m/z $(M+H)^+$526.1.

Compound 578 was synthesized by the coupling of methyl 4-bromo-1,2,5-thiadiazole-3-carboxylate and (2,2-difluorobenzo[d][1,3]dioxol-4-yl)boronic acid followed by subjecting the product to same procedures described earlier for compound 321. Compound 578 (100 mg, 57.9% yield): N-(4-amino-3,4-dioxo-1-phenylbutan-2-yl)-4-(2,2-difluorobenzo[d][1,3]dioxol-4-yl)-1,2,5-thiadiazole-3-carboxamide: $^1H$ NMR (400 MHz, DMSO-$d_6$) δ 9.36-9.32 (m, 1H), 8.12 (s, 1H), 7.88 (s, 1H), 7.52-7.49 (m, 1H), 7.28-7.17 (m, 7H), 5.50-5.43 (m, 1H), 3.22-3.15 (m, 1H), 2.94-2.86 (m, 1H). MS (ESI) m/z $(M+H)^+$461.0.

Compound 599 was synthesized by the coupling of methyl 4-bromo-1,2,5-thiadiazole-3-carboxylate and (2,2-difluorobenzo[d][1,3]dioxol-5-yl)boronic acid followed by subjecting the product to same procedures described earlier for compound 321. Compound 599 (140 mg, 69.6% yield): N-(4-amino-3,4-dioxo-1-phenylbutan-2-yl)-4-(2,2-difluorobenzo[d][1,3]dioxol-5-yl)-1,2,5-thiadiazole-3-carboxamide: $^1H$ NMR (400 MHz, DMSO-$d_6$) δ 9.40 (d, J=7.7 Hz, 1H), 8.19 (s, 1H), 7.93 (s, 1H), 7.59 (s, 1H), 7.42 (d, J=0.9 Hz, 2H), 7.29-7.18 (m, 5H), 5.55-5.41 (m, 1H), 3.23 (dd, J=3.5, 13.9 Hz, 1H), 2.86 (dd, J=10.1, 14.1 Hz, 1H). MS (ESI) m/z $(M+H)^+$461.0.

Example 208

Compounds 379-380

Compounds 379-380 were synthesized from the corresponding intermediate 1-(difluoromethyl)-3-phenyl-1H-pyrazole-4-carboxylic acid using same procedures as described earlier for Example 5.

Compound 379 (240 mg, 76.2% yield): (S)—N-(4-amino-3,4-dioxo-1-phenylbutan-2-yl)-1-(difluoromethyl)-3-phenyl-1H-pyrazole-4-carboxamide: $^1$H NMR (400 MHz, DMSO-$d_6$) δ 8.79 (d, J=7.5 Hz, 1H), 8.48 (s, 1H), 8.14-7.72 (m, 3H), 7.55 (dd, J=2.0, 7.3 Hz, 2H), 7.37-7.20 (m, 8H), 5.40-5.26 (m, 1H), 3.18 (dd, J=3.6, 14.0 Hz, 1H), 2.80 (dd, J=10.1, 13.9 Hz, 1H). MS (ESI) m/z $(M+H)^+$413.1.

Compound 380 (50 mg, 61.7% yield): (R)—N-(4-amino-3,4-dioxo-1-phenylbutan-2-yl)-1-(difluoromethyl)-3-phenyl-1H-pyrazole-4-carboxamide: $^1$H NMR (400 MHz, DMSO-$d_6$) δ 8.79 (d, J=7.3 Hz, 1H), 8.47 (s, 1H), 8.15-7.71 (m, 3H), 7.60-7.48 (m, 2H), 7.39-7.21 (m, 8H), 5.40-5.25 (m, 1H), 3.17 (dd, J=3.7, 13.9 Hz, 1H), 2.80 (dd, J=10.0, 14.0 Hz, 1H). MS (ESI) m/z $(M+H)^+$413.1.

Example 209

Compounds 381-384, 403, 522-524, 546-547, 550-552, 554-555, 575-577, 588, 596, 598, 608, 610, 622, 630

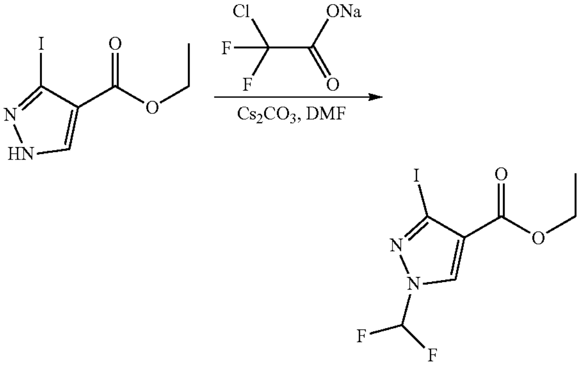

381A

To a solution of ethyl 3-iodo-1H-pyrazole-4-carboxylate (20 g, 75.18 mmol) in DMF (100 mL) was added sodium 2-chloro-2,2-difluoroacetate (22.92 g, 150.36 mmol) and $Cs_2CO_3$ (48.99 g, 150.36 mmol). The mixture was stirred at 100° C. for 16 h. The reaction mixture was concentrated, the residue was diluted with $H_2O$ (200 mL) and extracted with EtOAc (100 mL×3). The combined organic layers were washed with brine (200 mL), dried over $Na_2SO_4$, filtered and concentrated under reduced pressure to give a residue. The residue was purified by flash silica gel chromatography (ISCO®; X g SepaFlash® Silica Flash Column, eluent of 0%~10%~20% Ethyl acetate/Petroleum ether gradient). Compound 381A (9.1 g, yield: 38.30%) was obtained as a white solid. $^1$H NMR (400 MHz, $CDCl_3$) δ 8.47-7.95 (m, 1H), 7.44-6.95 (m, 1H), 4.53-4.17 (m, 2H), 1.54-1.17 (m, 3H).

Compounds 381-384, 403, 522-524, 546-547, 550-552, 554-555, 561, 563-566, 575-577, 581-582, 586, 588, 596, 598, 608, 610, 622, and 630 were synthesized from the corresponding intermediate ethyl 1-(difluoromethyl)-3-iodo-1H-pyrazole-4-carboxylate (381A) using same procedures as described earlier for Compound 242.

Compound 381 (125 mg, 43.5% yield): N-(4-amino-3,4-dioxo-1-phenylbutan-2-yl)-1-(difluoromethyl)-3-(3-fluorophenyl)-1H-pyrazole-4-carboxamide: $^1$H NMR (400 MHz, DMSO-$d_6$) δ 8.87 (br d, J=7.3 Hz, 1H), 8.56 (s, 1H), 8.18-8.04 (m, 1H), 7.99-7.75 (m, 2H), 7.51-7.36 (m, 3H), 7.33-7.18 (m, 6H), 5.35 (br s, 1H), 3.20 (br dd, J=3.0, 13.8 Hz, 1H), 2.89-2.76 (m, 1H). MS (ESI) m/z $(M+H)^+$431.1.

Compound 382 (70 mg, 40.9% yield): N-(4-amino-3,4-dioxo-1-phenylbutan-2-yl)-1-(difluoromethyl)-3-(o-tolyl)-1H-pyrazole-4-carboxamide: $^1$H NMR (400 MHz, DMSO-$d_6$) δ 8.69 (s, 1H), 8.35 (br d, J=7.3 Hz, 1H), 8.06 (br s, 1H), 7.95-7.75 (m, 2H), 7.27 (br d, J=6.8 Hz, 3H), 7.25-7.10 (m, 6H), 5.26 (br s, 1H), 3.19-3.10 (m, 1H), 2.81-2.70 (m, 1H), 2.02 (s, 3H). MS (ESI) m/z $(M+H)^+$427.1.

Compound 383 (150 mg, 58.2% yield): N-(4-amino-3,4-dioxo-1-phenylbutan-2-yl)-1-(difluoromethyl)-3-(2-fluorophenyl)-1H-pyrazole-4-carboxamide: $^1$H NMR (400 MHz, DMSO-$d_6$) δ 8.77-8.62 (m, 2H), 8.16-7.76 (m, 3H), 7.50-7.17 (m, 9H), 5.36-5.23 (m, 1H), 3.17 (dd, J=3.9, 14.0 Hz, 1H), 2.82 (dd, J=10.0, 13.8 Hz, 1H). MS (ESI) m/z $(M+H)^+$ 431.1.

Compound 384 (130 mg, 39.4% yield): N-(4-amino-3,4-dioxo-1-phenylbutan-2-yl)-1-(difluoromethyl)-3-(3-methoxyphenyl)-1H-pyrazole-4-carboxamide: $^1$H NMR (400 MHz, DMSO-$d_6$) δ 8.54-8.35 (m, 2H), 8.03-7.51 (m, 3H), 7.35-7.14 (m, 8H), 6.96 (d, J=7.8 Hz, 1H), 5.37 (br s, 1H), 3.76 (s, 3H), 3.22 (d, J=14.3 Hz, 1H), 2.97-2.83 (m, 1H). MS (ESI) m/z $(M+H)^+$443.1.

Compound 403 (3.1 g, 49.74% yield): N-(4-amino-3,4-dioxo-1-phenylbutan-2-yl)-1-(difluoromethyl)-3-phenyl-1H-pyrazole-4-carboxamide: $^1$H NMR (400 MHz, DMSO-$d_6$) δ 8.80 (d, J=7.5 Hz, 1H), 8.58-8.37 (m, 1H), 8.10 (s, 1H), 8.05-7.69 (m, 2H), 7.58-7.47 (m, 2H), 7.36-7.19 (m, 8H), 5.47-5.19 (m, 1H), 3.19-3.14 (m, 1H), 2.82-2.75 (m, 1H). MS (ESI) m/z $(M+H)^+$413.2.

Compound 522 (25 mg, 16.6% yield; white solid): N-(4-amino-3,4-dioxo-1-phenylbutan-2-yl)-1-(difluoromethyl)-3-(4-methylpyridin-3-yl)-1H-pyrazole-4-carboxamide: $^1$H NMR (400 MHz, DMSO-$d_6$) δ 8.77 (s, 1H), 8.65 (d, J=7.3 Hz, 1H), 8.39 (d, J=5.1 Hz, 1H), 8.24 (s, 1H), 8.09-8.02 (m, 1H), 7.93 (s, 1H), 7.78 (d, J=6.2 Hz, 1H), 7.29-7.13 (m, 7H), 5.27-5.19 (m, 1H), 3.13 (dd, J=3.7, 13.9 Hz, 1H), 2.76 (dd, J=9.9, 13.9 Hz, 1H), 1.99 (s, 3H). MS (ESI) m/z $(M+H)^+$ 428.1.

Compound 523 (63 mg, 63.6% yield; light yellow solid): N-(4-amino-3,4-dioxo-1-phenylbutan-2-yl)-1-(difluoromethyl)-3-(3,5-difluorophenyl)-1H-pyrazole-4-carboxamide: $^1$H NMR (400 MHz, DMSO-$d_6$) δ 8.89 (d, J=7.5 Hz, 1H), 8.62 (s, 1H), 8.14-8.08 (m, 1H), 7.97-7.79 (m, 2H), 7.39-7.25 (m, 7H), 7.23-7.19 (m, 1H), 5.42-5.33 (m, 1H), 3.20 (dd, J=3.7, 13.9 Hz, 1H), 2.82 (dd, J=10.3, 14.0 Hz, 1H). MS (ESI) m/z $(M+H)^+$449.0.

Compound 524 (50 mg, 31.5% yield): N-(4-amino-3,4-dioxo-1-phenylbutan-2-yl)-1-(difluoromethyl)-3-(2,5-dimethylphenyl)-1H-pyrazole-4-carboxamide: $^1$H NMR (400 MHz, DMSO-$d_6$) δ 8.69 (s, 1H), 8.23 (d, J=7.3 Hz, 1H), 8.05 (s, 1H), 7.92-7.73 (m, 2H), 7.31-7.24 (m, 2H), 7.24-7.15 (m, 3H), 7.13-7.09 (m, 2H), 6.97 (s, 1H), 5.28-5.24 (m, 1H), 3.14 (dd, J=3.6, 14.0 Hz, 1H), 2.75 (dd, J=9.7, 14.1 Hz, 1H), 2.25 (s, 3H), 1.96 (s, 3H). MS (ESI) m/z $(M+H)^+$441.1.

Compound 546 (120 mg, 47.9% yield; white solid): N-(4-amino-3,4-dioxo-1-phenylbutan-2-yl)-3-(2,2-difluorobenzo[d][1,3]dioxol-4-yl)-1-(difluoromethyl)-1H-pyrazole-4-carboxamide: $^1$H NMR (400 MHz, DMSO-$d_6$) δδ 8.87 (d, J=7.5 Hz, 1H), 8.72 (s, 1H), 8.19-7.79 (m, 3H), 7.44 (d, J=7.7 Hz, 1H), 7.32-7.17 (m, 7H), 5.42-5.24 (m, 1H), 3.17 (dd, J=3.5, 13.7 Hz, 1H), 2.81 (dd, J=10.1, 13.9 Hz, 1H). MS (ESI) m/z $(M+H)^+$493.1.

Compound 547 (140 mg, 67.0% yield; white solid): N-(4-amino-3,4-dioxo-1-phenylbutan-2-yl)-1-(difluoromethyl)-3-(naphthalen-1-yl)-1H-pyrazole-4-carboxamide: $^1$H NMR (400 MHz, DMSO-$d_6$) δ 8.79 (s, 1H), 8.46 (d, J=7.5 Hz, 1H), 8.15-7.71 (m, 5H), 7.62 (d, J=7.9 Hz, 1H), 7.54-7.45 (m, 2H), 7.44-7.35 (m, 2H), 7.28-7.13 (m, 5H), 5.19-5.15 (m, 1H), 3.08 (dd, J=3.7, 13.9 Hz, 1H), 2.72 (dd, J=9.9, 13.9 Hz, 1H). MS (ESI) m/z $(M+H)^+$463.1.

Compound 550 (25 mg, 30.3% yield; light yellow solid): N-(4-amino-3,4-dioxo-1-phenylbutan-2-yl)-1-(difluoromethyl)-3-(pyridin-2-yl)-1H-pyrazole-4-carboxamide: $^1$H NMR (400 MHz, DMSO-$d_6$) δ 11.78 (s, 1H), 8.71 (s, 1H), 8.40 (d, J=4.5 Hz, 1H), 8.15 (d, J=8.0 Hz, 1H), 8.03-7.99 (m, 1H), 7.91-7.56 (m, 3H), 7.55-7.46 (m, 1H), 7.23-7.08 (m, 5H), 5.67-5.53 (m, 1H), 3.31 (dd, J=5.0, 14.3 Hz, 1H), 3.18-3.11 (m, 1H). MS (ESI) m/z $(M+H)^+$414.1.

Compound 551 (65 mg, 82.3% yield; white solid): N-(4-amino-3,4-dioxo-1-phenylbutan-2-yl)-1-(difluoromethyl)-3-(naphthalen-2-yl)-1H-pyrazole-4-carboxamide: $^1$H NMR (400 MHz, DMSO-$d_6$) δ 8.90 (d, J=7.3 Hz, 1H), 8.53 (s, 1H), 8.16 (d, J=9.9 Hz, 2H), 8.09-7.79 (m, 5H), 7.67 (dd, J=1.7, 8.5 Hz, 1H), 7.56-7.50 (m, 2H), 7.30-7.25 (m, 4H), 7.23-7.18 (m, 1H), 5.39-5.29 (m, 1H), 3.18 (dd, J=3.9, 13.8 Hz, 1H), 2.82 (dd, J=10.3, 14.0 Hz, 1H). MS (ESI) m/z $(M+H)^+$463.1.

Compound 552 (60 mg, 53.6% yield; white solid): N-(4-amino-3,4-dioxo-1-phenylbutan-2-yl)-1-(difluoromethyl)-3-(2,5-difluorophenyl)-1H-pyrazole-4-carboxamide: $^1$H NMR (400 MHz, DMSO-$d_6$) δ 8.75-8.67 (m, 2H), 8.09-7.76 (m, 3H), 7.32-7.15 (m, 8H), 5.30-5.22 (m, 1H), 3.16-3.09 (m, 1H), 2.82-2.73 (m, 1H). MS (ESI) m/z $(M+H)^+$449.1.

Compound 554 (174 mg, 86.6% yield; white solid): N-(4-amino-3,4-dioxo-1-phenylbutan-2-yl)-1-(difluoromethyl)-3-(3-fluoro-5-methylphenyl)-1H-pyrazole-4-carboxamide: $^1$H NMR (400 MHz, DMSO-$d_6$) δ 8.83 (d, J=7.3 Hz, 1H), 8.53 (s, 1H), 8.21-7.72 (m, 3H), 7.34-7.23 (m, 5H), 7.21 (br dd, J=2.5, 8.5 Hz, 2H), 7.06 (br d, J=9.9 Hz, 1H), 5.46-5.22 (m, 1H), 3.17 (dd, J=3.9, 14.0 Hz, 1H), 2.80 (dd, J=10.1, 13.9 Hz, 1H), 2.31 (s, 3H). MS (ESI) m/z $(M+H)^+$ 445.1.

Compound 555 (85 mg, 57.0% yield; white solid): N-(4-amino-3,4-dioxo-1-phenylbutan-2-yl)-3-(2,2-difluorobenzo[d][1,3]dioxol-4-yl)-1-(difluoromethyl)-1H-pyrazole-4-carboxamide: $^1$H NMR (400 MHz, DMSO-$d_6$) δ 8.34 (s, 1H), 7.57-7.27 (m, 1H), 7.24 (br s, 3H), 7.05-6.97 (m, 4H), 6.96-6.92 (m, 1H), 6.90 (t, J=6.9 Hz, 1H), 6.71 (d, J=6.6 Hz, 1H), 6.26 (br s, 1H), 5.55-5.42 (m, 1H), 4.16 (br s, 2H), 4.11-4.05 (m, 1H), 4.11-4.05 (m, 1H), 4.00-3.92 (m, 1H), 3.22 (m, J=4.7, 14.2 Hz, 1H), 2.93-2.82 (m, 1H). MS (ESI) m/z $(M+H)^+$471.1.

Compound 561 (100 mg, 46.4% yield; white solid): N-(4-amino-3,4-dioxo-1-phenylbutan-2-yl)-1-(difluoromethyl)-3-(isoquinolin-4-yl)-1H-pyrazole-4-carboxamide: $^1$H NMR (400 MHz, DMSO-$d_6$) δ 9.35 (s, 1H), 8.89 (s, 1H), 8.73 (d, J=7.5 Hz, 1H), 8.39 (s, 1H), 8.24-7.88 (s, 3H), 7.78 (s, 1H), 7.74-7.66 (m, 2H), 7.66-7.59 (m, 1H), 7.33-7.15 (m, 5H), 5.25-5.14 (m, 1H), 3.21-3.05 (m, 1H), 2.83-2.72 (m, 1H). MS (ESI) m/z $(M+H)^+$464.1.

Compound 563 (110 mg, 84.1% yield; light yellow solid): N-(4-amino-3,4-dioxo-1-phenylbutan-2-yl)-3-(benzo[d][1,3]dioxol-4-yl)-1-(difluoromethyl)-1H-pyrazole-4-carboxamide: $^1$H NMR (400 MHz, DMSO-$d_6$) δ 8.67 (d, J=7.3 Hz, 1H), 8.53 (s, 1H), 8.08 (s, 1H), 7.97-7.76 (m, 2H), 7.34-7.19 (m, 5H), 6.97-6.91 (m, 1H), 6.90-6.80 (m, 2H), 5.90 (s, 1H), 5.78 (s, 1H), 5.33-5.23 (m, 1H), 3.15 (dd, J=3.9, 14.0 Hz, 1H), 2.81 (dd, J=9.7, 13.9 Hz, 1H). MS (ESI) m/z $(M+H)^+$ 457.1.

Compound 564 (128 mg, 79.3% yield; white solid): N-(4-amino-3,4-dioxo-1-phenylbutan-2-yl)-1-(difluoromethyl)-3-(2-fluoro-5-methylphenyl)-1H-pyrazole-4-carboxamide: $^1$H NMR (400 MHz, DMSO-$d_6$) δ 8.71-8.60 (m, 2H), 8.11-8.02 (m, 1H), 7.97-7.76 (m, 2H), 7.33-7.16 (m, 7H), 7.11-7.02 (m, 1H), 5.32-5.23 (m, 1H), 3.15 (dd, J=3.9, 14.0 Hz, 1H), 2.81 (dd, J=9.9, 13.9 Hz, 1H), 2.29 (s, 3H). MS (ESI) m/z $(M+H)^+$445.1.

Compound 565 (75 mg, 80.2% yield; white solid): N-(4-amino-3,4-dioxo-1-phenylbutan-2-yl)-1-(difluoromethyl)-3-(3,5-dimethylphenyl)-1H-pyrazole-4-carboxamide: $^1$H NMR (400 MHz, DMSO-$d_6$) δ 8.42 (s, 1H), 8.34-8.23 (m, 1H), 7.98-7.47 (m, 3H), 7.28-7.20 (m, 7H), 7.03 (s, 1H), 5.39-5.33 (m, 1H), 3.23-3.19 (m, 1H), 2.90 (dd, J=9.2, 13.9 Hz, 1H), 2.29 (s, 6H). MS (ESI) m/z $(M+H)^+$441.1.

Compound 566 (135 mg, 78.7% yield; white solid): N-(4-amino-3,4-dioxo-1-phenylbutan-2-yl)-1-(difluoromethyl)-3-(5-fluoro-2-methylphenyl)-1H-pyrazole-4-carboxamide: $^1$H NMR (400 MHz, DMSO-$d_6$) δ 8.74 (s, 1H), 8.49 (d, J=7.7 Hz, 1H), 8.10-7.77 (m, 3H), 7.31-7.18 (m, 6H), 7.17-7.10 (m, 1H), 6.96 (dd, J=2.9, 9.5 Hz, 1H), 5.32-5.23 (m, 1H), 3.15 (dd, J=3.7, 13.9 Hz, 1H), 2.78 (dd, J=9.9, 13.9 Hz, 1H), 1.97 (s, 3H). MS (ESI) m/z $(M+H)^+$445.1.

Compound 575 (20 mg, 66.9% yield; white solid): N-(4-amino-3,4-dioxo-1-phenylbutan-2-yl)-1-(difluoromethyl)-3-(quinolin-7-yl)-1H-pyrazole-4-carboxamide: $^1$H NMR (400 MHz, DMSO-$d_6$) δ 8.94 (dd, J=1.6, 4.1 Hz, 1H), 8.67-8.48 (m, 2H), 8.43-8.33 (m, 2H), 7.98-7.71 (m, 4H), 7.58-7.53 (m, 1H), 7.31-7.17 (m, 6H), 5.48-5.28 (m, 1H), 3.24 (dd, J=4.5, 14.1 Hz, 1H), 2.93 (dd, J=9.3, 14.1 Hz, 1H). MS (ESI) m/z $(M+H)^+$464.1.

Compound 576 (125 mg, 66.2% yield; white solid): N-(4-amino-3,4-dioxo-1-phenylbutan-2-yl)-1-(difluoromethyl)-3-(quinolin-5-yl)-1H-pyrazole-4-carboxamide: $^1$H NMR (400 MHz, DMSO-$d_6$) δ 8.94-8.82 (m, 2H), 8.66 (br d, J=7.5 Hz, 1H), 8.20-7.98 (m, 4H), 7.87-7.72 (m, 2H), 7.55-7.40 (m, 2H), 7.32-7.17 (m, 5H), 5.27-5.14 (m, 1H), 3.13 (br dd, J=3.5, 13.9 Hz, 1H), 2.78 (br dd, J=10.0, 13.8 Hz, 1H). MS (ESI) m/z $(M+H)^+$471.1.

Compound 577 (110 mg, 47.2% yield; white solid): N-(4-amino-3,4-dioxo-1-phenylbutan-2-yl)-1-(difluoromethyl)-3-(isoquinolin-6-yl)-1H-pyrazole-4-carboxamide: $^1$H NMR (400 MHz, DMSO-$d_6$) δ 9.31 (s, 1H), 8.93 (d, J=7.5 Hz, 1H), 8.58 (s, 1H), 8.51 (d, J=5.7 Hz, 1H), 8.23-8.17 (m, 1H), 8.15-7.81 (m, 6H), 7.31-7.25 (m, 4H), 7.24-7.17 (m, 1H), 5.45-5.26 (m, 1H), 3.19 (dd, J=4.0, 13.9 Hz, 1H), 2.90-2.77 (m, 1H). MS (ESI) m/z $(M+H)^+$471.1.

Compound 581 (30 mg, 37.5% yield; white solid): N-(4-amino-3,4-dioxo-1-phenylbutan-2-yl)-1-(difluoromethyl)-3-(pyrazin-2-yl)-1H-pyrazole-4-carboxamide: $^1$H NMR (400 MHz, DMSO-$d_6$) δ 10.55 (d, J=7.0 Hz, 1H), 9.40-9.27 (m, 1H), 8.91-8.83 (m, 2H), 8.73-8.15 (m, 1H), 8.06-7.67 (m, 3H), 7.30-7.23 (m, 5H), 5.75-5.62 (m, 1H), 3.28-3.16 (m, 2H). MS (ESI) m/z $(M+H)^+$415.1.

Compound 582 (11.4 mg, 13.6% yield; white solid): N-(4-amino-3,4-dioxo-1-phenylbutan-2-yl)-1-(difluoromethyl)-3-(5-methylpyridin-3-yl)-1H-pyrazole-4-carboxamide: $^1$H NMR (400 MHz, DMSO-$d_6$) δ 8.83 (d, J=7.5 Hz, 1H), 8.62 (s, 1H), 8.55 (d, J=2.0 Hz, 1H), 8.40 (d, J=1.3 Hz, 1H), 8.08-7.79 (m, 3H), 7.76 (s, 1H), 7.30-7.25 (m, 4H), 7.21 (td, J=4.5, 8.8 Hz, 1H), 5.36-5.27 (m, 1H), 3.17 (dd, J=3.7, 13.7 Hz, 1H), 2.81 (dd, J=10.0, 14.0 Hz, 1H), 2.29 (s, 3H). MS (ESI) m/z $(M+H)^+$428.1.

Compound 586 (56 mg, 32.4% yield; white solid): N-(4-amino-3,4-dioxo-1-phenylbutan-2-yl)-1-(difluoromethyl)-3-(5-fluoropyridin-3-yl)-1H-pyrazole-4-carboxamide: $^1$H NMR (400 MHz, DMSO-$d_6$) δ 8.94-8.86 (m, 1H), 8.74 (s, 1H), 8.69-8.58 (m, 2H), 8.15-8.08 (m, 1H), 8.01-7.81 (m, 3H), 7.29 (br d, J=4.2 Hz, 4H), 7.21 (br d, J=4.4 Hz, 1H), 5.36 (br s, 1H), 3.23-3.14 (m, 1H), 2.87-2.77 (m, 1H). MS (ESI) m/z $(M+H)^+$431.0.

Compound 588 (95 mg, 63.0% yield; white solid): N-(4-amino-3,4-dioxo-1-phenylbutan-2-yl)-1-(difluoromethyl)-3-(quinolin-2-yl)-1H-pyrazole-4-carboxamide: $^1$H NMR (400 MHz, DMSO-$d_6$) δ 11.90 (d, J=8.2 Hz, 1H), 8.87 (s, 1H), 8.59 (d, J=8.6 Hz, 1H), 8.27 (d, J=8.6 Hz, 1H), 8.20-8.04 (m, 2H), 7.98-7.79 (m, 2H), 7.76-7.64 (m, 3H), 7.02-6.91 (m, 5H), 5.78-5.70 (m, 1H), 3.32-3.27 (m, 1H), 3.14 (dd, J=8.0, 14.0 Hz, 1H). MS (ESI) m/z $(M+H)^+$464.1.

Compound 596 (110 mg, 58.1% yield; white solid): N-(4-amino-3,4-dioxo-1-phenylbutan-2-yl)-1-(difluoromethyl)-3-(quinolin-4-yl)-1H-pyrazole-4-carboxamide: $^1$H NMR (400 MHz, DMSO-$d_6$) δ 8.94-8.77 (m, 3H), 8.19-7.86 (m, 3H), 7.83-7.69 (m, 3H), 7.55-7.51 (m, 1H), 7.41-7.20 (m, 6H), 5.28-5.12 (m, 1H), 3.14 (dd, J=3.6, 14.0 Hz, 1H), 2.79 (dd, J=9.9, 14.1 Hz, 1H). MS (ESI) m/z $(M+H)^+$464.1.

Compound 598 (85 mg, 53.3% yield; white solid): N-(4-amino-3,4-dioxo-1-phenylbutan-2-yl)-1-(difluoromethyl)-3-(isoquinolin-5-yl)-1H-pyrazole-4-carboxamide: $^1$H NMR (400 MHz, DMSO-$d_6$) δ 9.35 (s, 1H), 8.90-8.63 (m, 2H), 8.41 (d, J=6.0 Hz, 1H), 8.30-7.94 (m, 3H), 7.90-7.64 (m, 3H), 7.51 (d, J=6.0 Hz, 1H), 7.32-7.17 (m, 5H), 5.29-5.12 (m, 1H), 3.13 (dd, J=3.9, 14.0 Hz, 1H), 2.77 (dd, J=10.0, 13.8 Hz, 1H). MS (ESI) m/z $(M+H)^+$464.1.

Compound 608 (25 mg, 37.2% yield; white solid): N-(4-amino-3,4-dioxo-1-phenylbutan-2-yl)-1-(difluoromethyl)-3-(isoquinolin-3-yl)-1H-pyrazole-4-carboxamide: $^1$H NMR (400 MHz, DMSO-$d_6$) δ 11.96 (d, J=7.1 Hz, 1H), 9.03 (s, 1H), 8.78 (s, 1H), 8.60 (s, 1H), 8.22-7.84 (m, 6H), 7.80-7.75 (m, 1H), 7.12-7.05 (m, 4H), 7.03-6.96 (m, 1H), 5.69-5.55 (m, 1H), 3.30-3.24 (m, 1H), 3.12 (dd, J=7.6, 14.0 Hz, 1H). MS (ESI) m/z $(M+H)^+$464.1.

Compound 610 (42 mg, 15.5% yield; pale yellow solid): N-(4-amino-3,4-dioxo-1-phenylbutan-2-yl)-1-(difluoromethyl)-3-(quinolin-3-yl)-1H-pyrazole-4-carboxamide: $^1$H NMR (400 MHz, DMSO-$d_6$) δ 9.12 (s, 1H), 8.73-8.55 (m, 3H), 8.13-7.89 (m, 3H), 7.79 (d, J=8.8 Hz, 2H), 7.65 (d, J=7.0 Hz, 2H), 7.28 (s, 5H), 5.39 (s, 1H), 3.00-2.82 (m, 1H), 3.3-3.15 (m, 1H). MS (ESI) m/z $(M+H)^+$464.1.

Compound 622 (25 mg, 22.7% yield; white solid): N-(4-amino-3,4-dioxo-1-phenylbutan-2-yl)-1-(difluoromethyl)-3-(quinolin-6-yl)-1H-pyrazole-4-carboxamide hydrochloride: $^1$H NMR (400 MHz, DMSO-$d_6$) δ 9.13 (d, J=3.7 Hz, 1H), 8.99 (d, J=7.5 Hz, 1H), 8.86-8.75 (m, 1H), 8.67 (s, 1H), 8.44 (s, 1H), 8.19-8.12 (m, 2H), 8.12-8.07 (m, 1H), 8.00-7.80 (m, 3H), 7.32-7.25 (m, 4H), 7.24-7.18 (m, 1H), 5.43-5.26 (m, 1H), 3.26-3.12 (m, 1H), 2.90-2.80 (m, 1H). MS (ESI) m/z $(M+H)^+$464.1.

Compound 630 (20 mg, 42.58% yield; pale yellow solid): N-(4-amino-3,4-dioxo-1-phenylbutan-2-yl)-1-(difluoromethyl)-3-(isoquinolin-7-yl)-1H-pyrazole-4-carboxamide: $^1$H NMR (400 MHz, DMSO-$d_6$) δ 9.31 (s, 1H), 8.68-8.48 (m, 3H), 8.41 (s, 1H), 8.08-7.71 (m, 5H), 7.60 (br s, 1H), 7.31-7.16 (m, 5H), 5.39 (br t, J=10.5 Hz, 1H), 3.24 (br dd, J=4.3, 14.1 Hz, 1H), 2.99-2.86 (m, 1H). MS (ESI) m/z $(M+H)^+$464.2.

Example 210

Compounds 385-391, 532

Compounds 385-391, 532 were synthesized from the corresponding starting material using same procedures as described earlier for Compound 265.

Compound 385 (25 mg, 38.7% yield): (S)—N-(4-amino-1-(4-methoxyphenyl)-3,4-dioxobutan-2-yl)-2-methyl-4-phenyloxazole-5-carboxamide: $^1$H NMR (400 MHz, DMSO-$d_6$) δ 8.74 (br d, J=7.6 Hz, 1H), 8.10 (br s, 1H), 8.06-7.95 (m, 2H), 7.83 (s, 1H), 7.43-7.29 (m, 3H), 7.18 (br d, J=8.4 Hz, 2H), 6.83 (br d, J=8.4 Hz, 2H), 5.40-5.29 (m, 1H), 3.73-3.62 (m, 3H), 3.15-3.06 (m, 1H), 2.97-2.86 (m, 1H), 2.53 (s, 3H). MS (ESI) m/z $(M+H)^+$408.1.

Compound 386 (14 mg, 22.8% yield): (S)—N-(1-amino-1,2-dioxo-5-phenylpentan-3-yl)-2-methyl-4-phenyloxazole-5-carboxamide: $^1$H NMR (400 MHz, DMSO-$d_6$) δ 8.87 (br d, J=7.2 Hz, 1H), 8.13-8.04 (m, 3H), 7.77 (br s, 1H), 7.43-7.34 (m, 3H), 7.30-7.13 (m, 5H), 5.09 (br s, 1H), 2.81-2.70 (m, 1H), 2.67-2.61 (m, 1H), 2.56 (s, 3H), 2.15-1.90 (m, 2H). MS (ESI) m/z $(M+H)^+$392.1.

Compound 387 (18 mg, 29.4% yield): N-((3S,4R)-1-amino-4-methyl-1,2-dioxohexan-3-yl)-2-methyl-4-phenyloxazole-5-carboxamide: $^1$H NMR (400 MHz, DMSO-$d_6$) δ 8.48 (br d, J=7.2 Hz, 1H), 8.09-8.03 (m, 3H), 7.77 (br s, 1H), 7.43-7.32 (m, 3H), 5.17-5.09 (m, 1H), 2.53 (s, 3H), 2.04 (br s, 1H), 1.41 (br s, 1H), 1.24-1.13 (m, 1H), 0.91-0.78 (m, 6H). MS (ESI) m/z $(M+H)^+$344.2.

Compound 388 (35 mg, 47.8% yield): (S)—N-(4-amino-1-(3,5-dimethylphenyl)-3,4-dioxobutan-2-yl)-2-methyl-4-phenyloxazole-5-carboxamide: $^1$H NMR (400 MHz, DMSO-$d_6$) δ 8.71 (d, J=7.2 Hz, 1H), 8.10 (s, 1H), 8.06-7.98 (m, 2H), 7.82 (s, 1H), 7.42-7.32 (m, 3H), 6.87 (s, 2H), 6.81 (s, 1H), 5.41-5.35 (m, 1H), 3.13-3.06 (m, 1H), 2.92-2.84 (m, 1H), 2.52 (s, 3H), 2.18 (s, 6H). MS (ESI) m/z $(M+H)^+$406.1.

Compound 389 (55 mg, 15.9% yield): (S)—N-(4-amino-1-(1H-indol-3-yl)-3,4-dioxobutan-2-yl)-2-methyl-4-phenyloxazole-5-carboxamide: $^1$H NMR (400 MHz, DMSO-$d_6$) δ 10.83 (s, 1H), 8.60 (d, J=7.2 Hz, 1H), 8.11 (s, 1H), 8.04-7.99 (m, 2H), 7.85 (s, 1H), 7.66 (d, J=8.0 Hz, 1H), 7.38-7.28 (m, 4H), 7.19-7.16 (m, 1H), 7.08-7.01 (m, 1H), 7.00-6.94 (m, 1H), 5.51-5.44 (m, 1H), 3.36-3.32 (m, 1H), 3.15-3.06 (m, 1H), 2.50 (s, 3H). MS (ESI) m/z $(M+H)^+$417.1.

Compound 390 (50.1 mg, 83.9% yield): N-(4-amino-1-(3,5-dichlorophenyl)-3,4-dioxobutan-2-yl)-2-methyl-4-phenyloxazole-5-carboxamide: $^1$H NMR (400 MHz, DMSO-$d_6$) δ 8.93 (d, J=7.6 Hz, 1H), 8.09 (br. s, 1H), 8.02-7.92 (m, 2H), 7.81 (br. s, 1H), 7.46-7.29 (m, 6H), 5.38-5.26 (m, 1H), 3.25-3.17 (m, 1H), 3.02-2.88 (m, 1H), 2.52 (s, 3H). MS (ESI) m/z $(M+H)^+$446.0.

Compound 391 (60 mg, 45.63% yield): (S)—N-(1-amino-5,5-dimethyl-1,2-dioxohexan-3-yl)-2-methyl-4-phenyloxazole-5-carboxamide: $^1$H NMR (400 MHz, DMSO-$d_6$) δ 8.06 (br. s, 0.23H), 7.78 (br. s, 0.23H), 7.65 (d, J=10.0 Hz, 0.73H), 7.43-7.33 (m, 3H), 7.32-7.26 (m, 1.4H), 6.39-6.14 (m, 1H), 5.31-5.24 (m, 0.25H), 4.35-4.28 (m, 0.74H), 2.55-2.50 (m, 3H), 1.74-1.66 (m, 0.3H), 1.62-1.50 (m, 1H), 1.33-1.24 (m, 0.79H), 0.95-0.82 (m, 9H). MS (ESI) m/z $(M+H)^+$358.1.

Compound 532 (65 mg, 27.6% yield; light yellow solid): N-(4-amino-1-(1H-indol-3-yl)-3,4-dioxobutan-2-yl)-4-phenyl-1,2,5-thiadiazole-3-carboxamide: $^1$H NMR (400 MHz, DMSO-$d_6$) δ 10.67 (br s, 1H), 9.00 (br d, J=7.3 Hz, 1H), 7.87 (br s, 1H), 7.73-7.58 (m, 4H), 7.46-7.39 (m, 1H), 7.34 (q, J=7.5 Hz, 3H), 7.15 (d, J=2.3 Hz, 1H), 7.09 (t, J=7.2 Hz, 1H), 7.02-6.96 (m, 1H), 5.59 (ddd, J=4.3, 7.3, 9.0 Hz, 1H), 3.40 (dd, J=4.1, 14.7 Hz, 1H), 3.16-3.10 (m, 1H). MS (ESI) m/z $(M+H)^+$420.1.

Example 211

Compound 392

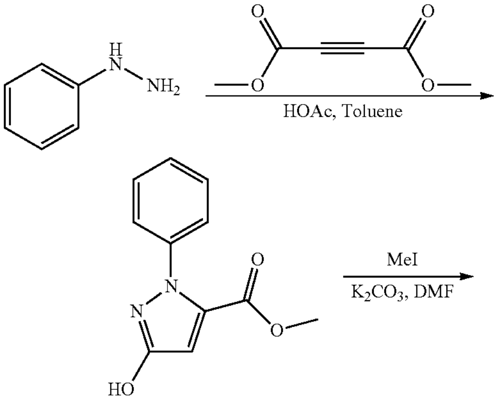

392A

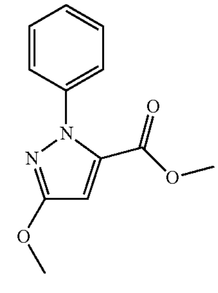

392B

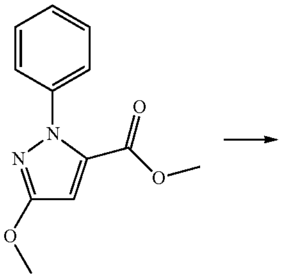

392B

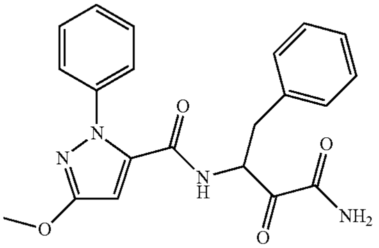

392

A stirred solution of dimethyl but-2-ynedioate (5.4 mL, 44.7 mmol) in toluene (35 mL) and AcOH (35 mL, 612.0 mmol) at 0° C. was treated cautiously with phenylhydrazine (4 mL, 40.6 mmol). The mixture was stirred at 20° C. for 1 h. Then the mixture was heated to 115° C. and stirred for 4 h. The reaction was on standing at 20° C. for 12 h. The reaction was filtered and the filtered cake was washed with EtOH (30 mL×3). The cake was dried under reduced pressure to afford compound 392A (2.2 g, yield 24.7%) was obtained as white solid, which was used directly in next step. $^1$H NMR (DMSO-$d_6$, 400 MHz): δ 12.16 (br s, 1H), 7.77-7.70 (m, 2H), 7.54-7.47 (m, 2H), 7.40-7.37 (m, 1H), 5.97 (s, 1H), 3.80 (s, 3H).

To a solution of compound 392A (1 g, 4.5 mmol) in DMF (20 mL) was added $K_2CO_3$ (1.2 g, 9.1 mmol) and MeI (855 uL, 13.7 mmol). Then mixture was stirred at 15° C. for 12 h. The mixture was filtered and the residue was washed with EA (20 mL×2). $H_2O$ (20 mL) was added to the mixture and the organic layer was separated, the aqueous was extracted with EA (20 mL×2). The combined organic layer was washed with brine, dried over anhydrous $Na_2SO_4$, filtered, concentrated under reduced pressure to afford compound 392B (0.515 g, yield 48.3%) as white solid, which was used directly in next step. $^1$H NMR (DMSO-$d_6$, 400 MHz): δ 7.67 (d, J=7.9 Hz, 2H), 7.51 (t, J=7.8 Hz, 2H), 7.44-7.37 (m, 1H), 6.41 (s, 1H), 3.98 (s, 3H), 3.83 (s, 3H).

Compound 392 was synthesized from 392B and using same procedures described earlier for compound 66. Compound 392 (40 mg, 21.8% yield): N-(4-amino-3,4-dioxo-1-phenylbutan-2-yl)-3-methoxy-1-phenyl-1H-pyrazole-5-carboxamide: $^1$H NMR (400 MHz, DMSO-$d_6$) δ 8.38 (br d, J=7.8 Hz, 1H), 8.11 (br s, 1H), 7.86 (br s, 1H), 7.71 (br d, J=8.0 Hz, 2H), 7.53 (br t, J=7.7 Hz, 2H), 7.44-7.35 (m, 1H), 7.32-7.15 (m, 5H), 6.26 (s, 1H), 5.44 (br d, J=3.3 Hz, 1H), 3.96 (s, 3H), 3.21 (br dd, J=3.8, 14.1 Hz, 1H), 3.11-3.00 (m, 1H). MS (ESI) m/z (M+H)+393.1.

Example 212

Compound 393

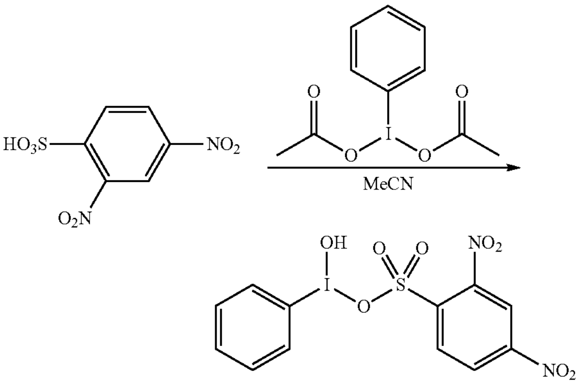

393A

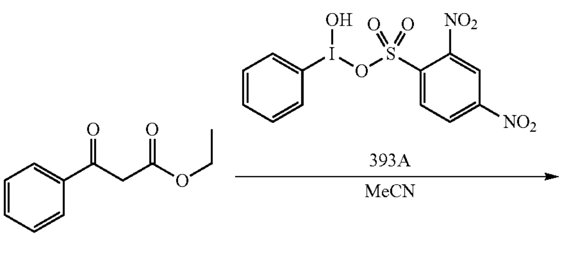

-continued

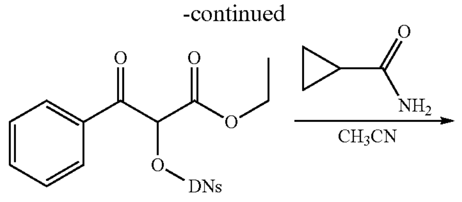

393B

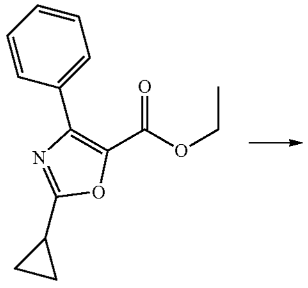

393C

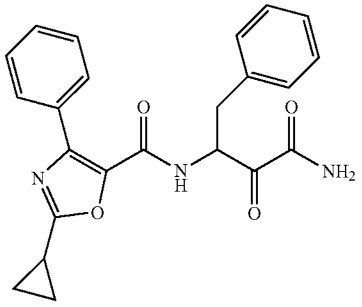

393

To a solution of 2,4-dinitrobenzenesulfonic acid (10.0 g, 31.05 mmol) in $CH_3CN$ (150 mL) was added phenyliodosobenzene diacetate (15.4 g, 62.09 mmol). The mixture was stirred at 25° C. for 1 h. The mixture was added MTBE (400 mL), cooled by ice water 10 min. Then the mixture was filtered and the filter was collected. Compound 393A (11 g, crude) was obtained as a yellow solid. The crude product was used in next step directly.

To a solution of compound 393A (11.3 g, 24.14 mmol) in $CH_3CN$ (100 mL) was added ethyl 3-oxo-3-phenylpropanoate (4.23 g, 21.98 mmol). The mixture was stirred at 90° C. for 1 h. The reaction mixture was used in next step directly.

To a solution of compound 393B (9.69 g, 21.95 mmol) in $CH_3CN$ (100 mL) was added cyclopropanecarboxamide (2.24 g, 26.34 mmol). The mixture was stirred at 90° C. for 12 h. The mixture was concentrated. The residue was purified by column chromatography $SiO_2$, Petroleum ether/Ethyl acetate=10/1. Compound 393C (800.0 mg, crude) was obtained as a colorless oil. The crude product was used in next step directly.

Compound 393 was synthesized from 393C and using same procedures described earlier for compound 66. Compound 393 (60 mg, 29.0% yield): N-(4-amino-3,4-dioxo-1-phenylbutan-2-yl)-2-cyclopropyl-4-phenyloxazole-5-carboxamide: $^1$H NMR (400 MHz, DMSO-$d_6$) δ 8.71 (d, J=7.6 Hz, 1H), 8.11 (s, 1H), 8.04-7.96 (m, 2H), 7.84 (s, 1H), 7.40-7.14 (m, 8H), 5.39-5.31 (m, 1H), 3.23-3.15 (m, 1H), 2.99-2.91 (m, 1H), 2.24-2.14 (m, 1H), 1.23-1.03 (m, 4H). MS (ESI) m/z $(M+H)^+$404.1.

Example 213

Compound 394

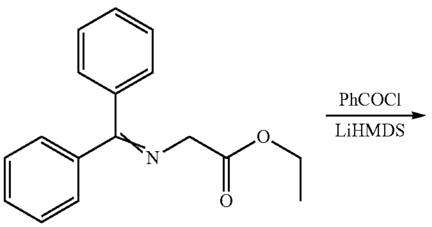

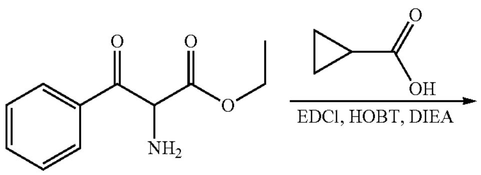

394A

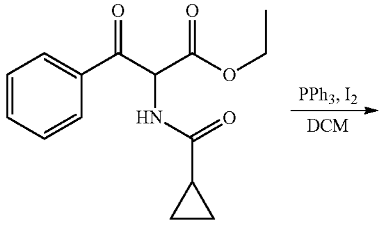

394B

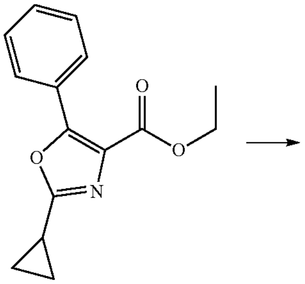

394C

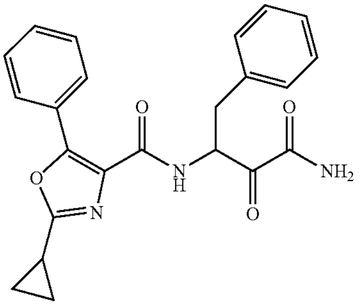

394

A mixture of ethyl 2-((diphenylmethylene)amino)acetate (5.00 g, 18.70 mmol) in THF (100 mL) was degassed and purged with $N_2$ for 3 times, and LiHMDS (1M, 22 mL) was added at −78° C., then the mixture was stirred for 0.5 h, then benzoyl chloride (22.44 mmol, 2.61 mL) was added at −78° C., and the mixture was stirred at 25° C. for 2 h under $N_2$ atmosphere. The mixture was quenched with HCl (2N, 240 mL), and stirred for 1 h, then washed with EA (50 mL). The aqueous phase was collected, added $NaHCO_3$ (aqueous) to pH ~9, then extracted with EA (100 mL). The organic layer was washed with brine (100 mL), dried over $Na_2SO_4$ and concentrated. Compound 394A (2.6 g, crude) was obtained as a yellow oil. The crude product was used in next step directly.

To a solution of compound 394A (1.30 g, 6.27 mmol) in DMF (20 mL) was added DIEA (25.09 mmol, 4.4 mL), cyclopropanecarboxylic acid (648.1 mg, 7.53 mmol), and HBTU (2.62 g, 6.90 mmol). The mixture was stirred at 25° C. for 1 hr. The mixture was concentrated, diluted with EA (200 mL), washed with HCl (1M, 200 mL), $NaHCO_3$ (aqueous, 200 mL), brine (200 mL), dried over $Na_2SO_4$ and concentrated. The residue was purified by preparatory-HPLC (TFA condition). Compound 394B (400.0 mg, 1.45 mmol, 23.2% yield) was obtained as a white solid. $^1$H NMR (400 MHz, DMSO-$d_6$) δ 9.13 (d, J=8.0 Hz, 1H), 7.98-7.92 (m, 2H), 7.71-7.64 (m, 1H), 7.58-7.50 (m, 2H), 6.17 (d, J=8.0 Hz, 1H), 4.16-4.05 (m, 2H), 1.83-1.74 (m, 1H), 1.11-1.04 (m, 3H), 0.74-0.60 (m, 4H).

To a solution of compound 394B (400.0 mg, 1.45 mmol) in DCM (15 mL) was added $Et_3N$ (5.96 mmol, 800 uL), 12 (737.6 mg, 2.91 mmol) and $PPh_3$ (762.2 mg, 2.91 mmol). The mixture was stirred at 25° C. for 2 h. The mixture was concentrated. The residue was purified by column chromatography ($SiO_2$, Petroleum ether/Ethyl acetate=5/1 to 0:1). Compound 394C (300.0 mg, crude) was obtained as a yellow oil. The crude product was used in next step without further purification.

Compound 394 was synthesized from 394C and using same procedures described earlier for compound 66. Compound 394 (50 mg, 31.4% yield): N-(4-amino-3,4-dioxo-1-phenylbutan-2-yl)-2-cyclopropyl-5-phenyloxazole-4-carboxamide: $^1$H NMR (400 MHz, DMSO-$d_6$) δ 8.31 (d, J=7.6 Hz, 1H), 8.11 (s, 1H), 8.05-7.99 (m, 2H), 7.86 (s, 1H), 7.45-7.36 (m, 3H), 7.29-7.16 (m, 5H), 5.45-5.38 (m, 1H), 3.23-3.16 (m, 1H), 3.11-3.03 (m, 1H), 2.22-2.13 (m, 1H), 1.13-1.04 (m, 4H). MS (ESI) m/z $(M+H)^+$404.2.

Example 214

Compound 395

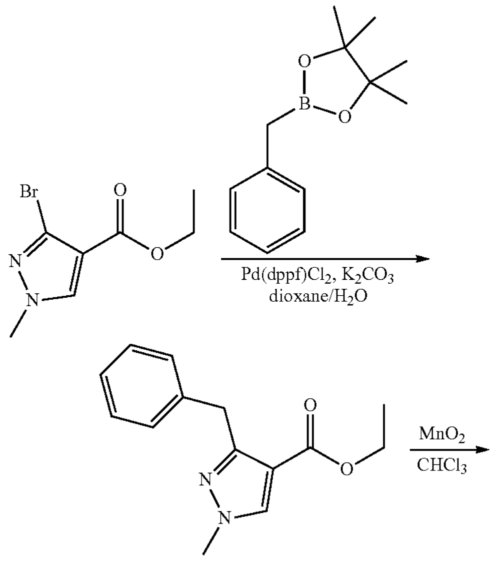

395A

-continued

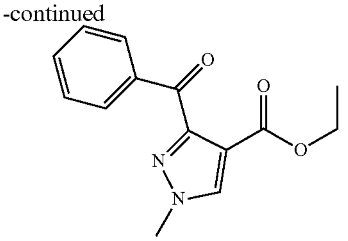

395B

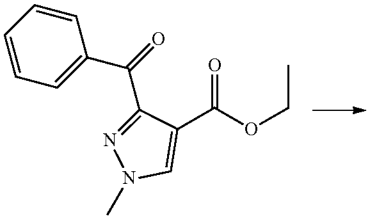

395B

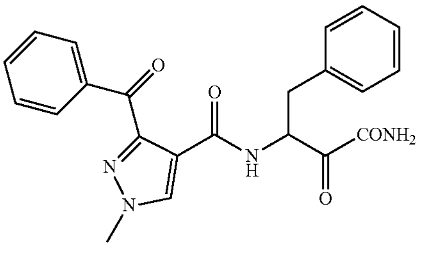

395

To a mixture of ethyl 3-bromo-1-methyl-1H-pyrazole-4-carboxylate (1 g, 4.29 mmol), 2-benzyl-4,4,5,5-tetramethyl-1,3,2-dioxaborolane (1.12 g, 5.15 mmol), $K_2CO_3$ (1.19 g, 8.58 mmol) in dioxane (15 mL) and $H_2O$ (5 mL) was added Pd(dppf)$Cl_2$ (314 mg, 429.07 umol) in portion at 15° C. under $N_2$. The mixture was stirred at 90° C. for 16 h. The reaction was diluted with $H_2O$ (20 mL), extracted with EtOAc (40 mL×2), the organic phase was dried over $Na_2SO_4$, filtered and concentrated to give a residue. The residue was purified by column chromatography ($SiO_2$, Petroleum ether:Ethyl acetate=5:1 to 3:1) to give compound 395A (1 g, yield: 35.4%) as yellow solid. $^1$H NMR (400 MHz, $CDCl_3$) δ 7.82 (s, 1H), 7.82 (s, 1H), 7.38-7.10 (m, 5H), 4.25-4.19 (m, 2H), 3.89 (s, 3H), 3.85 (s, 2H), 1.34 (t, J=7.1 Hz, 3H). MS (ESI) m/z $(M+H)^+$245.0.

To a mixture of compound 395A (0.85 g, 3.48 mmol) in $CHCl_3$ (30 mL) was added $MnO_2$ (4.54 g, 52.19 mmol) in one portion at 15° C. The mixture was stirred at 70° C. for 36 h. The reaction mixture was filtered and concentrated under reduced pressure to give a residue. The residue was purified by column chromatography ($SiO_2$, Petroleum ether: Ethyl acetate=5:1 to 1:1) to give compound 395B (0.25 g, yield: 24.12%) as a white solid. $^1$H NMR (400 MHz, $CDCl_3$) δ 7.97 (s, 1H), 7.95-7.91 (m, 2H), 7.59 (t, J=6.9 Hz, 1H), 7.46 (t, J=7.2 Hz, 2H), 4.12-4.06 (m, 2H), 4.01 (s, 3H), 1.03 (t, J=7.2 Hz, 3H). MS (ESI) m/z $(M+H)^+$258.9.

Compound 395 was synthesized from 395B and using same procedures described earlier for compound 66. Compound 395 (20 mg, 18.61% yield): N-(4-amino-3,4-dioxo-1-phenylbutan-2-yl)-3-benzoyl-1-methyl-1H-pyrazole-4-carboxamide: $^1$H NMR (400 MHz, $CD_3CN$) δ 9.77 (d, J=5.3 Hz, 1H), 8.13 (s, 1H), 8.02 (d, J=7.9 Hz, 2H), 7.75-7.62 (m, 1H), 7.52 (t, J=7.3 Hz, 2H), 7.24-7.16 (m, 5H), 7.07-6.95

(m, 1H), 6.22 (s, 1H), 5.62-5.44 (m, 1H), 3.92 (s, 3H), 3.33 (dd, J=4.5, 13.8 Hz, 1H), 3.03 (dd, J=8.4, 13.9 Hz, 1H). MS (ESI) m/z $(M+H)^+$405.1.

Example 215

Compounds 396-402

Compounds 396-402 were synthesized from the corresponding starting material using same procedures as described earlier for Compound 21.

Compound 396 (260 mg, 81.12% yield): 1-(difluoromethyl)-N-(1-oxo-3-phenylpropan-2-yl)-3-phenyl-1H-pyrazole-4-carboxamide: $^1$H NMR (400 MHz, $CD_3CN$) δ 9.61 (s, 1H), 8.27 (s, 1H), 7.59-7.51 (m, 2H), 7.44-7.35 (m, 3H), 7.33-7.23 (m, 3H), 7.22-7.16 (m, 2H), 6.93 (d, J=7.7 Hz, 1H), 4.60 (ddd, J=5.0, 7.6, 9.1 Hz, 1H), 3.26 (dd, J=5.1, 14.1 Hz, 1H), 2.92 (dd, J=9.0, 14.1 Hz, 1H). MS (ESI) m/z $(M+H)^+$370.0.

Compound 397 (153 mg, 50.5% yield): N-(1-oxo-3-phenylpropan-2-yl)-5-phenylisoxazole-4-carboxamide: $^1$H NMR (400 MHz, DMSO-$d_6$) δ 9.61 (s, 1H), 8.96 (d, J=7.3 Hz, 1H), 8.83 (s, 1H), 7.82 (d, J=7.3 Hz, 2H), 7.57-7.39 (m, 3H), 7.31-7.13 (m, 5H), 4.55 (s, 1H), 3.28-3.19 (m, 1H), 2.92-2.76 (m, 1H). MS (ESI) m/z $(M+H)^+$321.0.

Compound 398 (180 mg, 52.4% yield): 3-methyl-N-(1-oxo-3-phenylpropan-2-yl)-1-(pyridin-2-yl)-1H-pyrazole-5-carboxamide: $^1$H NMR (400 MHz, $CD_3CN$) δ 9.59 (s, 1H), 9.17 (d, J=7.2 Hz, 1H), 8.29-8.24 (m, 1H), 7.94-7.87 (m, 1H), 7.61 (d, J=8.0 Hz, 1H), 7.34-7.23 (m, 5H), 7.22-7.16 (m, 1H), 6.46 (s, 1H), 4.37-4.29 (m, 1H), 3.20-3.12 (m, 1H), 2.89-2.80 (m, 1H), 2.24 (s, 3H). MS (ESI) m/z $(M+H)^+$ 375.0.

Compound 399 (580 mg, 85.67% yield): 3-methyl-N-(1-oxo-3-phenylpropan-2-yl)-1-(5-(trifluoromethyl)pyridin-2-yl)-1H-pyrazole-5-carboxamide: $^1$H NMR (400 MHz, $CD_3CN$) δ 9.69 (s, 1H), 8.52-8.40 (m, 1H), 8.16 (dd, J=2.4, 8.6 Hz, 1H), 7.99 (br d, J=6.2 Hz, 1H), 7.89 (d, J=8.6 Hz, 1H), 7.34-7.16 (m, 5H), 6.55 (s, 1H), 4.57 (ddd, J=5.1, 7.2, 8.9 Hz, 1H), 3.28 (dd, J=5.1, 14.3 Hz, 1H), 3.01 (dd, J=8.9, 14.2 Hz, 1H), 2.31 (s, 3H). MS (ESI) m/z $(M+H)^+$403.1.

Compound 400 (135 mg, 46.3% yield): 1-(3-((benzyloxy)methyl)phenyl)-3-methyl-N-(1-oxo-3-phenylpropan-2-yl)-1H-pyrazole-5-carboxamide: $^1$H NMR (400 MHz, $CDCl_3$) δ 9.60 (s, 1H), 7.45 (s, 1H), 7.42-7.28 (m, 10H), 7.09-7.04 (m, 2H), 6.51 (s, 1H), 6.32 (d, J=6.0 Hz, 1H), 4.78 (q, J=6.6 Hz, 1H), 4.59 (d, J=14.3 Hz, 5H), 3.22-3.10 (m, 2H), 2.35 (s, 3H). MS (ESI) m/z $(M+H)^+$454.2.

Compound 401 (180 mg, 37.0% yield): N-(1-oxo-3-phenylpropan-2-yl)-4-phenyl-1,2,5-thiadiazole-3-carboxamide: $^1$H NMR (400 MHz, DMSO-$d_6$) δ 9.64 (s, 1H), 9.35 (br d, J=8.0 Hz, 1H), 7.57-7.53 (m, 2H), 7.47-7.41 (m, 1H), 7.40-7.34 (m, 2H), 7.29-7.18 (m, 5H), 4.75-4.68 (m, 1H), 3.29-3.25 (m, 1H), 2.89-2.81 (m, 1H). MS (ESI) m/z $(M+H)^+$338.0.

Compound 402 (250 mg, 35.9% yield): 4-(2-fluorophenyl)-2-methyl-N-(1-oxo-3-phenylpropan-2-yl)oxazole-5-carboxamide: $^1$H NMR (400 MHz, DMSO-$d_6$) δ 9.53 (s, 1H), 8.85 (d, J=7.6 Hz, 1H), 7.49-7.40 (m, 2H), 7.28-7.14 (m, 7H), 4.50-4.44 (m, 1H), 3.25-3.18 (m, 1H), 2.94-2.86 (m, 1H), 2.52 (s, 3H). MS (ESI) m/z $(M+H)^+$353.1.

Example 216

Compounds 404-405, 609, 618

Compounds 404-405, 609, and 618 were synthesized from the corresponding starting materials using same procedures as described earlier for Example 254.

Compound 404 (3.69 g, 85.6% yield): N-(4-amino-3,4-dioxo-1-phenylbutan-2-yl)-4-(3-fluorophenyl)-2-methyloxazole-5-carboxamide: $^1$H NMR (400 MHz, $CDCl_3$) δ 8.02-7.89 (m, 2H), 7.44-7.26 (m, 4H), 7.21-7.01 (m, 3H), 6.88-6.69 (m, 2H), 5.79-5.70 (m, 1H), 5.66 (br s, 1H), 3.53-3.39 (m, 1H), 3.35-3.18 (m, 1H), 2.56 (s, 3H). MS (ESI) m/z $(M+1)^+$396.1.

Compound 405 was prepared by oxidation of N-(4-amino-3-hydroxy-4-oxo-1-phenylbutan-2-yl)-4-(2-fluorophenyl)-2-methyloxazole-5-carboxamide using the same conditons as used for oxidation of intermediate 12H to 12. Compound 405 (3.97 g, 34.6% yield): N-(4-amino-3,4-dioxo-1-phenylbutan-2-yl)-4-(2-fluorophenyl)-2-methyloxazole-5-carboxamide: $^1$H NMR (400 MHz, DMSO-$d_6$) δ 8.78 (d, J=7.2 Hz, 1H), 8.07 (br. s, 1H), 7.82 (br. s, 1H), 7.48-7.38 (m, 2H), 7.31-7.14 (m, 7H), 5.38-5.29 (m, 1H), 3.17-3.09 (m, 1H), 2.98-2.88 (m, 1H), 2.53 (s, 3H). MS (ESI) m/z $(M+H)^+$396.1.

Alternately, N-(4-amino-3-hydroxy-4-oxo-1-phenylbutan-2-yl)-4-(2-fluorophenyl)-2-methyloxazole-5-carboxamide was oxidized using EDC and dichloroacetic acid as shown below to yield compound 405.

N-(3-Dimethylaminopropyl)-N'-ethylcarbodiimide hydrochloride (351.5 mg, 2.3 mmol, 9 eq) was added to a solution of compound N-(4-amino-3-hydroxy-4-oxo-1-phenylbutan-2-yl)-4-(2-fluorophenyl)-2-methyloxazole-5-carboxamide (100 mg, 0.25 mmol, 1.0 equiv) in DMSO (5 mL) at room temperature. After stirring for 10 minutes, dichloroacetic acid (0.083 mL, 1 mmol, 4 equiv) was added. The reaction was stirred at room temperature for 1 hour, at which point LC-MS indicated the reaction was complete. The mixture was diluted with dichloromethane (10 mL) and sequentially washed with saturated sodium bicarbonate (2×10 mL), 1N HCl (2×10 mL) and saturated brine (10 mL). The organic layer was dried over sodium sulfate and concentrated under reduced pressure. The resulting solid was triturated with ethyl acetate (2×1 mL) at room temperature for 2 hours and dried under vacuum at 45° C. overnight to give compound 405 as a white solid (69 mg, 70% yield; $(M+H)^+$396.1.

Compound 609 (70 mg, 35.13% yield, white solid): N-(4-amino-3,4-dioxo-1-phenylbutan-2-yl)-4-(benzo[d][1,3]dioxol-4-yl)-2-methyloxazole-5-carboxamide: $^1$H NMR (400 MHz, DMSO-$d_6$) δ 8.31-8.18 (m, 1H), 7.80 (br. s, 1H), 7.61 (br. s, 1H), 7.33-7.14 (m, 5H), 7.06-6.98 (m, 1H), 6.94-6.79 (m, 2H), 5.96-5.85 (m, 2H), 5.45-5.34 (m, 1H), 3.27-3.18 (m, 1H), 3.05-2.95 (m, 1H). MS (ESI) m/z $(M+H)^+$422.1.

Compound 618 (80 mg, 39.73% yield, white solid): N-(4-amino-3,4-dioxo-1-phenylbutan-2-yl)-4-(2,2-difluorobenzo[d][1,3]dioxol-4-yl)-2-methyloxazole-5-carboxamide: $^1$H NMR (400 MHz, DMSO-$d_6$) δ 7.52-7.45 (m, 1H), 7.32-7.26 (m, 2H), 7.25-7.18 (m, 1H), 7.13-7.05 (m, 4H), 6.79-6.68 (m, 2H), 5.71-5.63 (m, 1H), 5.56 (br. s, 1H), 3.48-3.40 (m, 1H), 3.30-3.21 (m, 1H), 2.57 (s, 3H). MS (ESI) m/z $(M+H)^+$458.1.

Example 217

Compound 406

Compounds 406 was synthesized from the corresponding starting intermediates 274D and 250D using same procedures as described earlier for Example 306. Compound 406 (3.3 g): N-(4-amino-3,4-dioxo-1-phenylbutan-2-yl)-1-cyclopropyl-3-phenyl-1H-pyrazole-4-carboxamide: $^1$H NMR (400 MHz, DMSO-$d_6$) δ 8.34 (br d, J=7.1 Hz, 1H), 8.12 (s, 1H), 8.06 (br s, 1H), 7.80 (br.s., 1H), 7.53 (br d, J=3.1 Hz, 2H), 7.35-7.09 (m, 8H), 5.26 (br s, 1H), 3.78 (br s, 1H), 3.14 (br d, J=11.5 Hz, 1H), 2.87-2.73 (m, 1H), 2.05 (s, 1H), 1.11-0.92 (m, 4H). MS (ESI) m/z $(M+H)^+$403.4.

Example 218

Compound 410

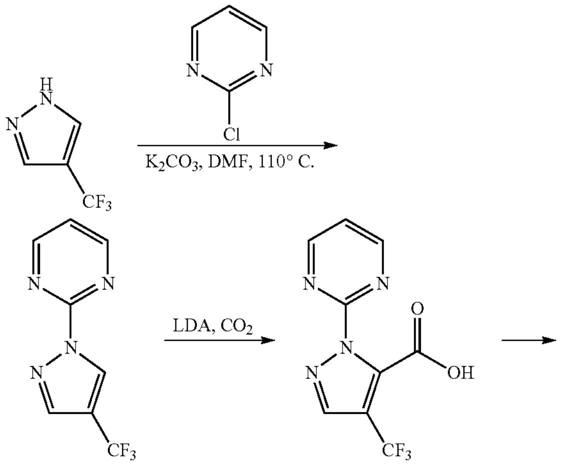

410A

410B

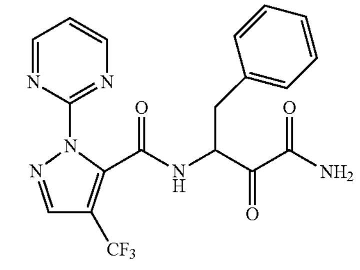

410

A mixture of 4-(trifluoromethyl)-1H-pyrazole compound (1 g, 7.35 mmol), 2-chloropyrimidine (926 mg, 8.09 mmol) and $K_2CO_3$ (2.03 g, 14.7 mmol) in DMF (15 mL) was heated to 110° C. for 12 hr. The mixture was added water (20 mL) and extracted with ethyl acetate (20 mL×2), the organic phases were washed with brine (10 mL), dried over $Na_2SO_4$, filtered and concentrated. The residue was recrystallized by MTBE to give compound 410A (800 mg, yield: 50.8%) as yellow solid. $^1H$ NMR (400 MHz, $CDCl_3$) δ 8.94 (s, 1H), 8.83 (d, J=4.8 Hz, 2H), 8.03 (s, 1H), 7.34 (t, J=4.8 Hz, 1H).

To a solution of compound 410A (350 mg, 1.63 mmol) in THF (10 mL) was added LDA (2M, 1.06 mL) dropwise at −78° C. and stirred for 10 min, then $CO_2$ was bubbled into the mixture for 20 min at −78° C., then slowly warmed to 15° C. for 1 hr. The mixture was added water (20 mL) and extracted with ethyl acetate (10 mL×2), the water layer was adjusted to pH 3 with 1N HCl and extracted with ethyl acetate (10 mL×2), the organic phases were dried and concentrated to give compound 410B (140 mg, yield: 33.3%), as yellow solid. $^1H$ NMR (400 MHz, $CDCl_3$) δ 8.79 (d, J=4.9 Hz, 2H), 7.93 (s, 1H), 7.34 (t, J=4.7 Hz, 1H).

Compounds 410 was synthesized from the corresponding starting intermediates 274D and 410B using same procedures as described earlier for Example 305. Compound 410

(3.3 g): N-(4-amino-3,4-dioxo-1-phenylbutan-2-yl)-1-(pyrimidin-2-yl)-4-(trifluoromethyl)-1H-pyrazole-5-carboxamide: $^1H$ NMR (400 MHz, DMSO-$d_6$) δ 8.68 (d, J=4.6 Hz, 2H), 7.94 (s, 1H), 7.32-7.26 (m, 2H), 7.24-7.14 (m, 4H), 6.81 (br d, J=7.1 Hz, 1H), 6.71 (br s, 1H), 5.85 (q, J=6.4 Hz, 1H), 5.51 (br s, 1H), 3.49-3.40 (m, 1H), 3.39-3.29 (m, 1H). MS (ESI) m/z $(M+H)^+$ 433.1.

Example 219

Compound 411

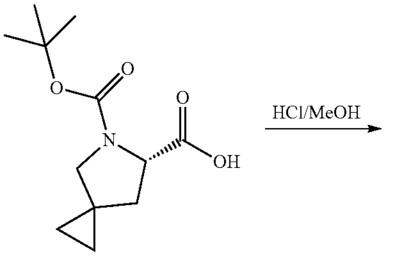

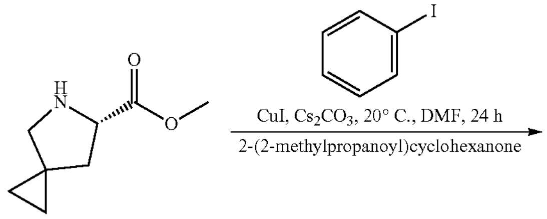

411A

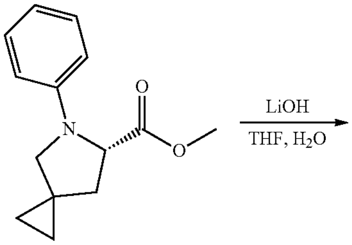

411B

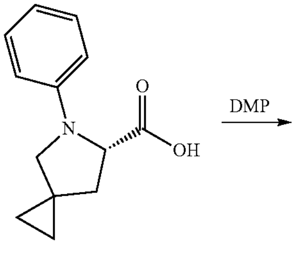

411C

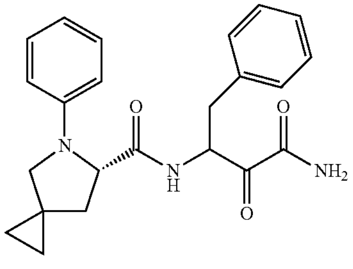

411

A mixture of(S)-5-(tert-butoxycarbonyl)-5-azaspiro[2.4]heptane-6-carboxylic acid (2 g, 8.29 mmol) in MeOH (5 mL), HCl/MeOH (50 mL) was stirred at 1° C. for 12 hour. The reaction mixture was concentrated under reduced pressure to give a residue. Compound 411A (1.3 g, crude) was obtained as a yellow solid. $^1$H NMR (400 MHz, $CDCl_3$) δ 11.09 (br s, 1H), 9.14 (br s, 1H), 4.64 (br s, 1H), 3.85 (s, 3H), 3.55-3.33 (m, 3H), 2.87-2.64 (m, 2H), 2.38 (br dd, J=8.2, 13.0 Hz, 1H), 2.10 (br dd, J=5.3, 13.0 Hz, 1H), 0.87-0.71 (m, 3H), 0.71-0.61 (m, 1H).

A mixture of compound 411A (1 g, 6.44 mmol), iodobenzene (5.26 g, 25.8 mmol), $Cs_2CO_3$ (6.30 g, 19.3 mmol), CuI (981.76 mg, 5.15 mmol) in DMF (40 mL) was degassed and purged with $N_2$ for 3 times, and then the mixture was stirred at 110° C. for 12 hours under $N_2$ atmosphere. The reaction mixture was filtered and concentrated under reduced pressure to give a residue. The residue was purified by column chromatography ($SiO_2$, Petroleum ether:Ethyl acetate=95:1 to 90:1). And then the residue was purified by preparatory-HPLC (TFA condition). Compound 411B (120 mg, yield: 8.06%) was obtained as a yellow oil. $^1$H NMR (400 MHz, $CDCl_3$) δ 7.32-7.12 (m, 2H), 6.72 (t, J=7.3 Hz, 1H), 6.50 (d, J=7.9 Hz, 2H), 4.40 (dd, J=2.4, 8.6 Hz, 1H), 3.80-3.62 (m, 3H), 3.48 (d, J=8.6 Hz, 1H), 3.29 (d, J=8.6 Hz, 1H), 2.50 (dd, J=8.8, 12.6 Hz, 1H), 1.87 (dd, J=2.4, 12.6 Hz, 1H), 0.79-0.51 (m, 4H).

Compounds 411 was synthesized from the corresponding starting intermediates 274D and 411B using same procedures as described earlier for Example 321. Compound 411 (53.2 mg, yield: 50.5%): (6S)—N-(4-amino-3,4-dioxo-1-phenylbutan-2-yl)-5-phenyl-5-azaspiro[2.4]heptane-6-carboxamide: $^1$H NMR (400 MHz, $CDCl_3$) δ 7.16-7.06 (m, 4H), 7.04-6.87 (m, 3H), 6.77-6.66 (m, 2H), 6.60 (br s, 1H), 6.54-6.38 (m, 2H), 5.58-5.21 (m, 2H), 4.05-3.93 (m, 1H), 3.39-3.22 (m, 1H), 3.09-2.90 (m, 2H), 2.82-2.69 (m, 1H), 2.45-2.30 (m, 1H), 1.68-1.53 (m, 1H), 0.56-0.34 (m, 3H), 0.17-0.05 (m, 1H). MS (ESI) m/z $(M+H)^+$392.2.

Example 220

2-(1,1-dioxido-1,2-thiazinan-2-yl)-3-methyl-N-(4-methyl-1-oxopentan-2-yl)butanamide (412)

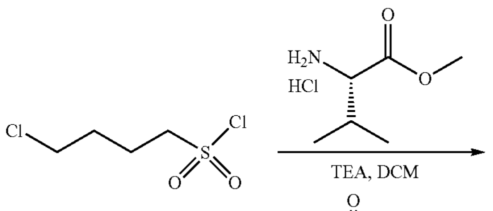

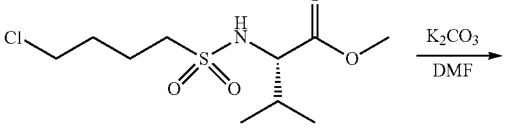

412A

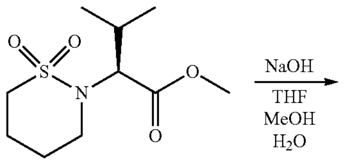

412B

-continued

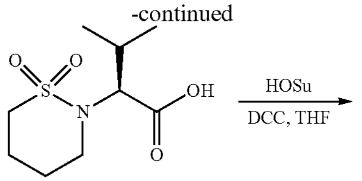

412C

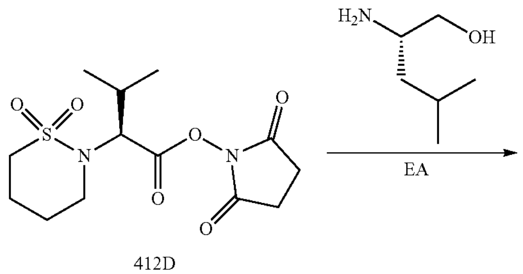

412D

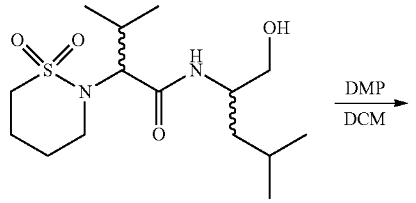

412E

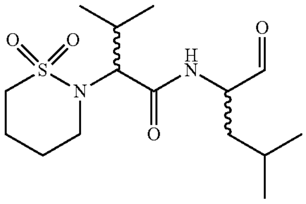

412

To a mixture of methyl L-valinate (2.63 g, 15.7 mmol, HCl) in DCM (50 mL) was added TEA (4.5 mL, 32.3 mmol) in one portion. After 4-chlorobutane-1-sulfonyl chloride (2.5 g, 13.1 mmol) was dropwise added at 0° C., the mixture was stirred for 30 min at 0° C., then stirred at 15° C. for 1.5 h. The reaction mixture was washed with 0.5N HCl (20 mL), sat. $NaHCO_3$ (20 mL) and sat. NaCl (20 mL). The separated organic layer was dried over $Na_2SO_4$, filtered and concentrated under reduced pressure to afford compound 412A (2.26 g, yield 60.4%) as light yellow viscous oil, which was used directly for next step without purification. MS (ESI) m/z $(M+H)^+$286.1.

To a mixture of compound 412A (3.16 g, 11.1 mmol) in DMF (150 mL) was added $K_2CO_3$ (3.82 g, 27.6 mmol) in one portion. The mixture was stirred at 15° C. for 18 h. $H_2O$ (200 mL) was added into the mixture, which was extracted with EA (150 mL×3). The combined organic phase was washed with sat. NaCl (200 mL×2) and dried over $Na_2SO_4$. The solvent was evaporated under reduced pressure to afford compound 412B (2.7 g, crude) as light yellow liquid, which was used directly for next step without purification. $^1$H NMR (DMSO-$d_6$, 400 MHz): δ 3.94 (d, J=10.6 Hz, 1H), 3.69-3.64 (m, 3H), 3.40-3.34 (m, 0.72H), 3.33-3.30 (m, 0.24H), 3.29-3.20 (m, 1H), 3.16-3.07 (m, 1H), 3.06-2.97 (m, 1H), 2.11-1.95 (m, 3H), 1.61-1.47 (m, 2H), 0.87 (dd, J=6.7, 14.0 Hz, 6H). MS (ESI) m/z $(M+H)^+$250.1.

To a mixture of compound 412B (1 g, 4.0 mmol) in THF (10 mL) and MeOH (10 mL) was added a solution of NaOH (802.1 mg, 20.0 mmol) in $H_2O$ (2 mL) in one portion. The mixture was stirred at 55° C. for 1 h. The reaction mixture was added $H_2O$ (15 mL), and then concentrated under reduced pressure to move MeOH. The aqueous phase was washed with TBME (10 mL). The separated aqueous phase was acidified with aqueous HCl (1 M) till pH ~5-6 before extracting with EA (15 mL×5). Then the organic phase was dried over anhydrous $Na_2SO_4$, filtered and concentrated in vacuo to afford compound 412C (88.6 mg, crude) as yellow solid, which was used directly for next step without purification. $^1$H NMR (DMSO-$d_6$, 400 MHz): δ 12.83 (s, 1H), 3.82 (d, J=10.4 Hz, 1H), 3.29-3.23 (m, 2H), 3.14-2.90 (m, 2H), 2.10-1.89 (m, 3H), 1.65-1.44 (m, 2H), 0.85 (dd, J=4.2, 6.6 Hz, 6H).

To a mixture of compound 412C (88.5 mg, 3.7 mmol) in THF (20 mL) was added 1-hydroxypyrrolidine-2,5-dione (HOSu) (432.9 mg, 3.8 mmol), followed by DCC (776.0 mg, 3.7 mmol) in one portion at 0° C. The mixture was stirred at 15° C. for 12 h. The insoluble substance was removed by filter. The filtrate was concentrated in vacuum. The residue was triturated with isopropanol (10 mL). The solid was collected and dried in vacuum to afford compound 412D (95.8 mg, yield 76.6%) as colorless liquid. $^1$H NMR (DMSO-$d_6$, 400 MHz): δ 4.26 (d, J=11.0 Hz, 1H), 3.45-3.37 (m, 2H), 3.28-3.22 (m, 1H), 3.15-3.05 (m, 1H), 2.81 (s, 4H), 2.19-2.09 (m, 1H), 2.08-2.02 (m, 2H), 1.58-1.45 (m, 2H), 0.93 (dd, J=6.6, 18.7 Hz, 6H).

To a mixture of compound 412D (950 mg, 2.9 mmol) in EA (25 mL) was added (S)-2-amino-4-methylpentan-1-ol (40.2 mg, 3.4 mmol) in one portion. The mixture was stirred at 15° C. for 12 h. The mixture was washed with aq. HCl (0.5N, 10 mL), sat. $NaHCO_3$ (10 mL), sat. NaCl (10 mL). The separated organic phase was dried over $Na_2SO_4$, filtered and concentrated. The residue was purified by preparatory-HPLC (basic condition) to afford compound 412E (220 mg, yield 23.0%) as white solid. $^1$H NMR (DMSO-$d_6$, 400 MHz): δ 7.78 (d, J=8.8 Hz, 1H), 4.57 (t, J=5.5 Hz, 1H), 3.85-3.70 (m, 2H), 3.55-3.44 (m, 1H), 3.41-3.37 (m, 0.52H), 3.32-3.25 (m, 1.45H), 3.20-3.06 (m, 2H), 2.88-2.75 (m, 1H), 2.08-1.88 (m, 3H), 1.73-1.61 (m, 1H), 1.60-1.41 (m, 2H), 1.38-1.21 (m, 2H), 0.84 (td, J=6.6, 17.4 Hz, 12H).

To a mixture of compound 412E (0.1 g, 299 umol) in DCM (15 mL) was added DMP (380.4 mg, 896.93 umol) in one portion. The mixture was stirred at 15° C. for 1.5 h. The reaction was quenched by 30 mL of 10% $Na_2S_2O_3$ solution and 30 mL of sat. $NaHCO_3$ solution and stirred for 10 min. After quenching the reaction, the reaction mixture was poured into separatory funnel and separated. The separated aqueous phase was extracted with DCM (20 mL×3). The combined organic phase was washed with brine (30 mL×2), dried over anhydrous $Na_2SO_4$, filtered and concentrated in vacuo. The residue was triturated with $CH_3CN$: i-propyl ether (1:8, 2 mL). The solid was collected and dried in vacuum to afford compound 412 (45 mg, yield 45.1%) as white solid. $^1$H NMR (DMSO-$d_6$, 400 MHz): δ 9.39 (s, 1H), 8.64 (d, J=6.5 Hz, 1H), 4.06 (s, 1H), 3.88 (d, J=10.8 Hz, 1H), 3.50-3.37 (m, 2H), 3.19-3.06 (m, 1H), 2.96-2.83 (m, 1H), 2.03 (s, 3H), 1.77-1.38 (m, 5H), 0.97-0.79 (m, 12H). MS (ESI) m/z $(M+H)^+$333.1.

Example 221

Compounds 413-414, 525-529

Compounds 413-414 were synthesized from the corresponding starting intermediates 274D and 250A using same procedures as described earlier for Example 250.

Compound 413 (55 mg, yield: 53.4%): N-(4-amino-3,4-dioxo-1-phenylbutan-2-yl)-3-(6-cyanopyridin-3-yl)-1-cyclopropyl-1H-pyrazole-4-carboxamide: $^1$H NMR (400 MHz, DMSO-$d_6$) δ 9.04-8.86 (m, 1H), 8.36-8.06 (m, 3H), 7.95-7.86 (m, 1H), 7.76 (s, 1H), 7.62-7.43 (m, 1H), 7.35-7.04 (m, 5H), 5.40-5.24 (m, 1H), 3.94-3.73 (m, 1H), 3.26-3.18 (m, 1H), 2.95-2.86 (m, 1H), 1.19-1.02 (m, 4H). MS (ESI) m/z $(M+H)^+$429.1.

Compound 414 (42 mg, yield: 26.9%): N-(4-amino-3,4-dioxo-1-phenylbutan-2-yl)-1-cyclopropyl-3-(6-(trifluoromethyl)pyridin-3-yl)-1H-pyrazole-4-carboxamide: $^1$H NMR (400 MHz, DMSO-$d_6$) δ 8.98 (s, 1H), 8.34-8.11 (m, 3H), 7.82 (d, J=8.0 Hz, 1H), 7.78-7.66 (m, 1H), 7.54 (s, 1H), 7.34-7.06 (m, 5H), 5.39-5.24 (m, 1H), 3.94-3.57 (m, 1H), 3.28-3.16 (m, 1H), 2.97-2.84 (m, 1H), 1.18-1.04 (m, 4H). MS (ESI) m/z $(M+H)^+$472.1.

Compounds 525-526 were synthesized from the corresponding starting intermediate 250A and the corresponding alkylating agent followed by subjecting the resulting intermediates to the procedures as in compound 12 to obtain the final compounds.

Compound 525 (13 mg, yield: 5.84%; white solid): N-(4-amino-3,4-dioxo-1-phenylbutan-2-yl)-1-cyclopentyl-3-phenyl-1H-pyrazole-4-carboxamide: $^1$H NMR (400 MHz, DMSO-$d_6$) δ 8.33 (d, J=7.3 Hz, 1H), 8.09 (s, 1H), 8.05 (s, 1H), 7.79 (s, 1H), 7.59-7.54 (m, 2H), 7.33-7.18 (m, 8H), 5.27 (ddd, J=4.0, 7.4, 9.8 Hz, 1H), 4.73 (quin, J=6.8 Hz, 1H), 3.16 (dd, J=4.1, 14.0 Hz, 1H), 2.82 (dd, J=9.9, 13.9 Hz, 1H), 2.16-2.06 (m, 2H), 1.94 (td, J=6.1, 12.2 Hz, 2H), 1.85-1.77 (m, 2H), 1.72-1.60 (m, 2H). MS (ESI) m/z $(M+H)^+$431.2.

Compound 526 (69.7 mg, yield: 22.7%; pale yellow solid): N-(4-amino-3,4-dioxo-1-phenylbutan-2-yl)-1-cyclobutyl-3-phenyl-1H-pyrazole-4-carboxamide: $^1$H NMR (400 MHz, DMSO-$d_6$) δ 8.35 (d, J=7.3 Hz, 1H), 8.15 (s, 1H), 8.06 (s, 1H), 7.80 (s, 1H), 7.60-7.54 (m, 2H), 7.33-7.17 (m, 8H), 5.29 (ddd, J=4.0, 7.4, 9.8 Hz, 1H), 4.92-4.84 (m, 1H), 3.16 (dd, J=4.0, 13.9 Hz, 1H), 2.82 (dd, J=9.7, 13.9 Hz, 1H), 2.48-2.30 (m, 4H), 1.86-1.75 (m, 2H). MS (ESI) m/z $(M+Na)^+$441.1.

Compounds 527-529 were synthesized from the corresponding starting intermediate 250A and the corresponding boronic acids agent as in compound 250 followed by subjecting the resulting intermediates to the procedures as in compound 12 to obtain the final compounds.

Compound 527 (69.9 mg, yield: 23.4%; white solid): N-(4-amino-3,4-dioxo-1-phenylbutan-2-yl)-1-(2-fluorophenyl)-3-phenyl-1H-pyrazole-4-carboxamide: $^1$H NMR (400 MHz, DMSO-$d_6$) δ 8.70 (d, J=7.5 Hz, 1H), 8.53 (d, J=2.2 Hz, 1H), 8.09 (s, 1H), 7.91 (dt, J=1.7, 8.0 Hz, 1H), 7.83 (s, 1H), 7.68-7.63 (m, 2H), 7.58-7.46 (m, 2H), 7.43-7.33 (m, 4H), 7.31-7.27 (m, 4H), 7.25-7.20 (m, 1H), 5.33 (ddd, J=4.2, 7.4, 10.0 Hz, 1H), 3.20 (dd, J=4.0, 13.9 Hz, 1H), 2.85 (dd, J=10.1, 13.9 Hz, 1H). MS (ESI) m/z $(M+H)^+$457.1.

Compound 528 (50 mg, yield: 16.2%; white solid): N-(4-amino-3,4-dioxo-1-phenylbutan-2-yl)-1-(3-fluorophenyl)-3-phenyl-1H-pyrazole-4-carboxamide: $^1$H NMR (400 MHz, DMSO-$d_6$) δ 8.87 (s, 1H), 8.59 (d, J=7.3 Hz, 1H), 8.10 (s, 1H), 7.84 (s, 1H), 7.80-7.72 (m, 2H), 7.70-7.57 (m, 3H), 7.40-7.20 (m, 9H), 5.49-5.31 (m, 1H), 3.24-3.16 (m, 1H), 2.91-2.82 (m, 1H). MS (ESI) m/z $(M+H)^+$457.2.

Compound 529 (17.5 mg, yield: 10%; white solid): N-(4-amino-3,4-dioxo-1-phenylbutan-2-yl)-1-(4-fluorophenyl)-3-phenyl-1H-pyrazole-4-carboxamide: $^1$H NMR (400 MHz, DMSO-$d_6$) δ 8.76 (s, 1H), 8.54 (d, J=7.3 Hz, 1H), 8.09 (s, 1H), 7.95-7.81 (m, 3H), 7.67 (dd, J=3.0, 6.5 Hz, 2H), 7.46-7.21 (m, 10H), 5.43-5.31 (m, 1H), 3.20 (dd, J=4.0, 14.1 Hz, 1H), 2.90-2.82 (m, 1H). MS (ESI) m/z $(M+H)^+$457.2.

Example 222

Compounds 425-427

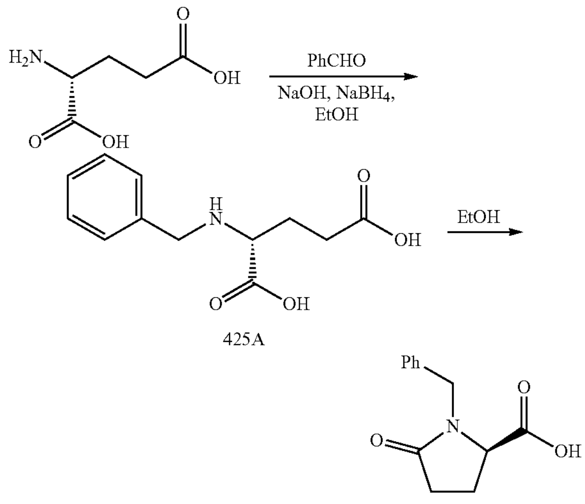

425A

425B

D-glutamic acid (15.0 g, 101.9 mmol) was dissolved in aqueous NaOH (2M, 100 mL) and stirred for 15 minutes. The mixture was added a solution of benzaldehyde (11 mL, 108.84 mmol) in EtOH (30 mL) and stirred at 15° C. for 30 minutes. The mixture was cooled to 0° C. $NaBH_4$ (1.16 g, 30.6 mmol) was added into the mixture, which was allowed to warm to 15° C. with stirring over 3 hrs. The mixture was washed with TBME (30 mL×2) before acidifying with concentrated hydrochloric acid to pH ~4-5. The resulting precipitate was filtered off and dried over to afford compound 425A (10.26 g, crude) as white solid, which was used directly for the next step without purification. MS (ESI) m/z $(M+H)^+$238.0.

The suspension of compound 425A (4.2 g, 17.7 mmol) in EtOH (400 mL) was heated to reflux at 95° C. for 10 hours. The reaction mixture was concentrated under reduced pressure to move EtOH. The residue was purified by preparatory-HPLC (TFA condition: column: Phenomenex Synergi Max-RP 250×50 mm×10 um; mobile phase: [water (0.1% TFA)-ACN]; B %: 2%-30%, 20 min) to afford compound 3 (2.7 g, yield 69.44%) as white solid. $^1H$ NMR (DMSO-$d_6$, 400 MHz): δ 7.36-7.24 (m, 3H), 7.22-7.16 (m, 2H), 4.88 (d, J=15.2 Hz, 1H), 3.96-3.81 (m, 2H), 2.41-2.21 (m, 3H), 2.01-1.89 (m, 1H). MS (ESI) m/z $(M+H)^+$219.9.

Compound 425 was synthesized from the corresponding starting intermediate 3-amino-N-cyclopropyl-2-hydroxy-4-phenylbutanamide hydrochloride and 425B using same procedures as described earlier for compound 65 followed by SFC separation to yield compounds 426 and 427.

Compound 425: (2R)-1-benzyl-N-(4-(cyclopropylamino)-3,4-dioxo-1-phenylbutan-2-yl)-5-oxopyrrolidine-2-carboxamide: $^1H$ NMR (400 MHz, DMSO-$d_6$) δ 8.83 (s, 1H), 8.66 (s, 1H), 7.38-7.18 (m, 8H), 7.17-6.97 (m, 2H), 5.18 (s, 1H), 4.90-4.67 (m, 1H), 3.87 (s, 1H), 3.56-3.41 (m, 1H), 3.26-3.13 (m, 1H), 2.85-2.65 (m, 2H), 2.30-1.97 (m, 3H), 1.77-1.45 (m, 1H), 0.73-0.52 (m, 4H). MS (ESI) m/z $(M+H)^+$434.2.

Compound 426 (129 mg, yield: 49.5%): (2R)-1-benzyl-N-(4-(cyclopropylamino)-3,4-dioxo-1-phenylbutan-2-yl)-5-oxopyrrolidine-2-carboxamide: $^1H$ NMR (400 MHz, DMSO-$d_6$) δ 8.85 (d, J=5.1 Hz, 1H), 8.68 (d, J=7.5 Hz, 1H), 7.36-7.18 (m, 8H), 7.13 (d, J=7.1 Hz, 2H), 5.24-5.11 (m, 1H), 4.84 (d, J=15.0 Hz, 1H), 3.92-3.83 (m, 1H), 3.49 (d, J=15.0 Hz, 1H), 3.18 (dd, J=3.5, 13.9 Hz, 1H), 2.84-2.69 (m, 2H), 2.22 (t, J=7.9 Hz, 2H), 2.12-1.97 (m, 1H), 1.59-1.47 (m, 1H), 0.73-0.56 (m, 4H). MS (ESI) m/z $(M+H)^+$434.2.

Compound 427 (63.2 mg, yield: 25.2%): (2R)-1-benzyl-N-(4-(cyclopropylamino)-3,4-dioxo-1-phenylbutan-2-yl)-5-oxopyrrolidine-2-carboxamide: $^1H$ NMR (400 MHz, DMSO-$d_6$) δ 8.83 (d, J=5.1 Hz, 1H), 8.67 (d, J=7.5 Hz, 1H), 7.34-7.21 (m, 8H), 7.02 (d, J=6.6 Hz, 2H), 5.27-5.16 (m, 1H), 4.75 (d, J=15.0 Hz, 1H), 3.86 (dd, J=3.3, 8.8 Hz, 1H), 3.33 (s, 1H), 3.19 (dd, J=4.0, 14.1 Hz, 1H), 2.83-2.69 (m, 2H), 2.32-2.06 (m, 3H), 1.77-1.61 (m, 1H), 0.73-0.50 (m, 4H). MS (ESI) m/z $(M+H)^+$434.2.

Example 223

Compound 430

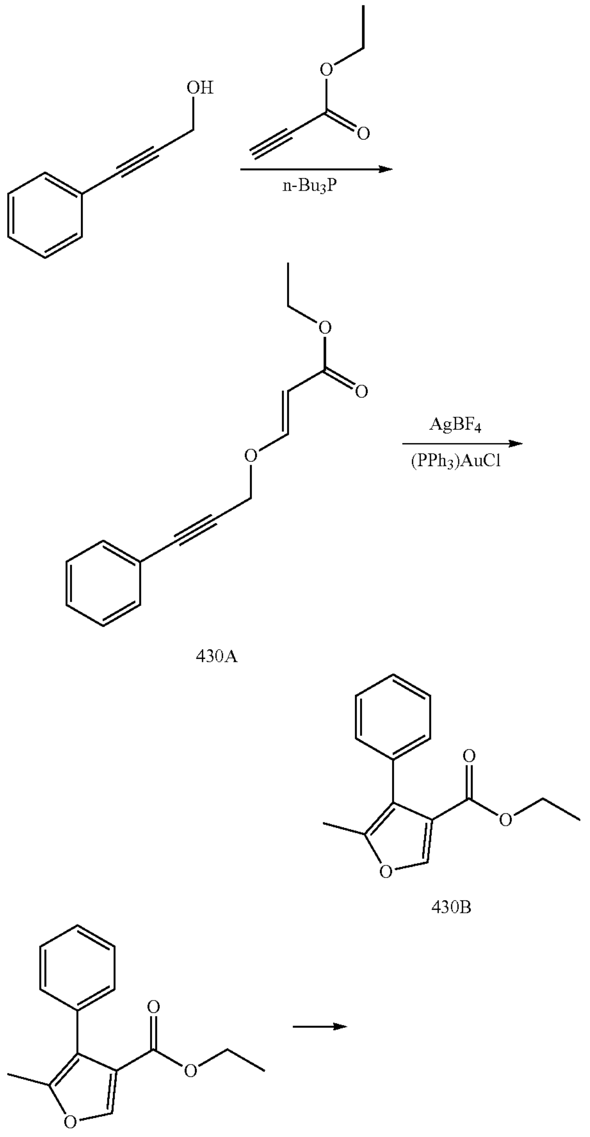

430A

430B

430B

-continued

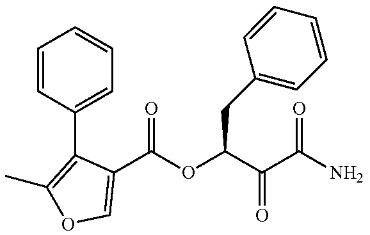

430

-continued

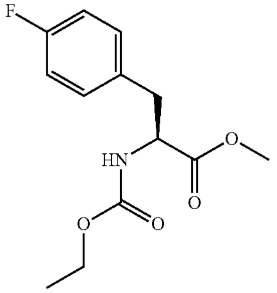

449

To a solution of 3-phenylprop-2-yn-1-ol (2 g, 15.13 mmol) and ethyl propiolate (1.48 g, 15.13 mmol) in DCM (20 mL) was added n-$Bu_3P$ (307 mg, 1.51 mmol) dropwise. The mixture was stirred at 25° C. for 12 h. The solvent was removed in vacuo. The residue was purified by column (PE:EA=10:1) to give compound 425A (3.4 g, crude) as light yellow oil. MS (ESI) m/z $(M+H)^+$231.0.

To a solution of compound 425A (500 mg, 2.17 mmol) in toluene (10 mL) was added $(PPh_3)AuCl$ (22 mg, 43.40 umol) and $AgBF_4$ (9 mg, 43.40 umol). The mixture was stirred at 25° C. for 12 h. The solvent was removed in vacuo. The residue was purified by column (PE:EA=10:1) to afford compound 425B (120 mg, yield: 24.02%) as colorless oil. $^1H$ NMR ($CDCl_3$, 400 MHz): δ 7.95 (s, 1H), 7.45-7.29 (m, 5H), 4.20-4.14 (m, 2H), 2.26 (s, 3H), 1.22-1.17 (m, 3H).

Compound 430 was synthesized from the intermediate 430B using same procedures as described earlier for compound 65 to yield compound 430.

Compound 430 (35 mg, yield: 33.25%) (S)—N-(4-amino-3,4-dioxo-1-phenylbutan-2-yl)-5-methyl-4-phenylfuran-3-carboxamide: $^1H$ NMR (400 MHz, DMSO-$d_6$) δ 7.82 (s, 1H), 7.38-7.14 (m, 11H), 7.04-6.94 (m, 2H), 6.35 (s, 1H), 6.11 (s, 1H), 4.43-4.30 (m, 1H), 3.04-2.85 (m, 1H), 2.61-2.53 (m, 1H), 2.21 (s, 3H). MS (ESI) m/z $(M+H)^+$377.1.

Example 224

Compound 449

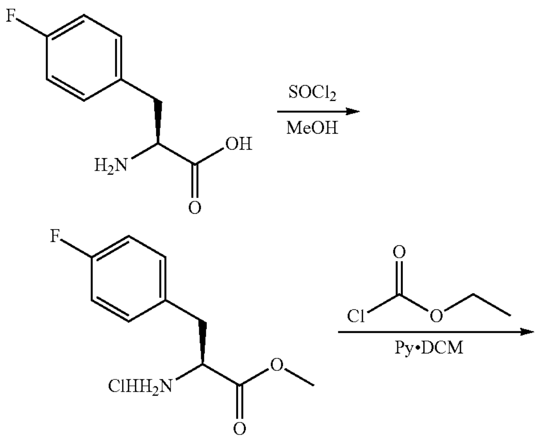

449A

To a mixture of (S)-2-amino-3-(4-fluorophenyl)propanoic acid (1 g, 5.46 mmol) in MeOH (10 mL) was added $SOCl_2$ (2.60 g, 21.84 mmol, 1.6 mL) in portions at 0° C. under $N_2$. The mixture was stirred at 60° C. for 1.5 h. The solvent was removed in vacuo to give compound 449A (1.2 g, yield: 94.1%, HCl) as white solid which was used directly for next step without further purification. $^1H$ NMR (400 MHz, DMSO-$d_6$) δ 8.59 (s, 3H), 7.29 (t, J=5.9 Hz, 2H), 7.17 (t, J=8.2 Hz, 2H), 4.28 (s, 1H), 3.68 (s, 3H), 3.19-3.07 (m, 2H). MS (ESI) m/z $(M+H)^+$197.9.

To a mixture of compound 449A (1.2 g, 5.46 mmol, HCl) and ethyl carbonochloridate (712 mg, 6.56 mmol, 0.6 mL) in DCM (20 mL) was added pyridine (1.30 g, 16.39 mmol, 1.3 mL) in one portion at 0° C. under $N_2$. The mixture was stirred at 20° C. for 2 h. The reaction mixture was treated with DCM (30 mL), washed with 0.5N HCl (50 mL×2) and brine (50 mL), dried over anhydrous $Na_2SO_4$, filtered and concentrated. The residue was purified by column chromatography ($SiO_2$, Petroleum ether:Ethyl acetate=10:1 to 4:1) to give compound 449 (1.2 g, yield: 80.6%) as colorless oil. Methyl (S)-2-((ethoxycarbonyl)amino)-3-(4-fluorophenyl) propanoate: $^1H$ NMR (400 MHz, DMSO-$d_6$) δ 7.64 (d, J=8.0 Hz, 1H), 7.27 (dd, J=5.8, 8.3 Hz, 2H), 7.10 (t, J=8.8 Hz, 2H), 4.24-4.07 (m, 1H), 3.92 (dd, J=4.0, 7.0 Hz, 2H), 3.61 (s, 3H), 3.00 (dd, J=5.0, 14.1 Hz, 1H), 2.83 (dd, J=10.5, 13.6 Hz, 1H), 1.14-0.97 (m, 3H). MS (ESI) m/z $(M+H)^+$ 269.9.

Example 225

Compound 450

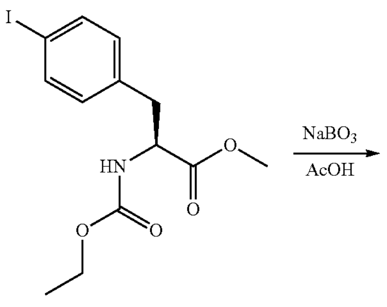

450A

-continued

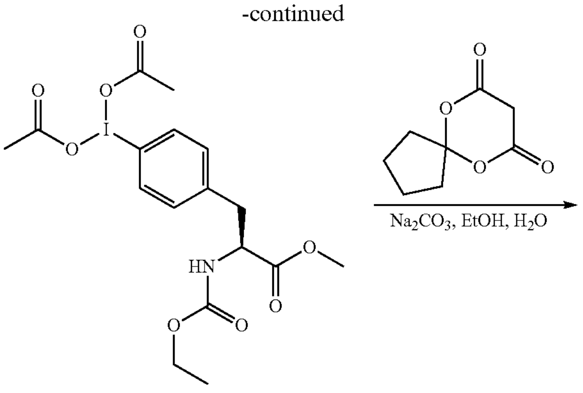

450B

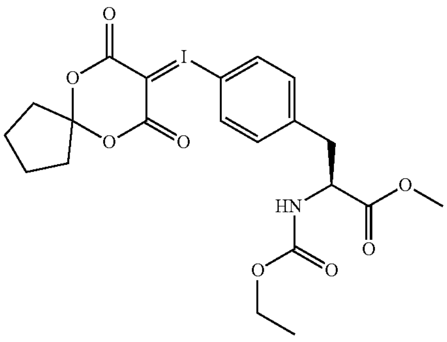

450

Compound 450A was prepared from (S)-2-amino-3-(4-iodophenyl)propanoic acid using procedures as in compound 449.

$NaBO_3$ (1.63 g, 10.61 mmol) was added in portions to a solution of compound 450A (400 mg, 1.06 mmol) in AcOH (8.5 mL) and heated to 50° C. The reaction mixture was stirred at 50° C. for 6 h. The reaction mixture was cooled to room temperature, diluted with DCM (20 mL), filtered, the filtrate was diluted with water (30 mL), and extracted with DCM (10 mL×2). The combined organic extracts were dried with anhydrous sodium sulfate, filtered, and concentrated. The residue was triturated in DCM:PE=1:10 (10 mL×2) to induce precipitation, solids was collected. Compound 450B (380 mg, yield: 72.4%) was obtained as a white solid. $^1H$ NMR (400 MHz, $CDCl_3$) δ 7.99 (d, J=8.4 Hz, 2H), 7.29-7.23 (m, 2H), 5.20 (d, J=7.7 Hz, 1H), 4.72-4.64 (m, 1H), 4.11 (q, J=6.9 Hz, 2H), 3.76-3.72 (m, 3H), 3.25-3.08 (m, 2H), 2.00 (s, 6H), 1.23 (t, J=7.1 Hz, 3H).

To a solution of compound 450B (380 mg, 767.27 umol) in $Na_2CO_3$ (243.97 mg, 2.30 mmol) in $H_2O$ (3 mL) was added EtOH (3 mL) followed quickly by 6,10-dioxaspiro[4.5]decane-7,9-dione (130.56 mg, 767.27 umol). The reaction mixture was vigorously stirred at 18° C. for 4 h. The reaction mixture was then diluted with water (10 mL), and extracted with DCM (10 mL×3). The combined organic extracts were dried with anhydrous $Na_2SO_4$, filtered, and concentrated. To the residue was added DCM (1 mL) and PE (15 mL) to induce precipitation, solids was collected. Compound 450 (300 mg, yield: 71.7%) was obtained as a white solid. Methyl (S)-3-(4-((7,9-dioxo-6,10-dioxaspiro[4.5]decan-8-ylidene)-3-iodanyl)phenyl)-2-((ethoxycarbonyl)amino)propanoate $^1H$ NMR (400 MHz, $CDCl_3$) δ 7.78 (d, J=8.4 Hz, 2H), 7.18 (d, J=8.4 Hz, 2H), 5.18 (d, J=7.7 Hz, 1H), 4.67-4.55 (m, 1H), 4.12-4.02 (m, 2H), 3.71 (s, 3H), 3.26-3.13 (m, 1H), 3.11-2.99 (m, 1H), 2.13 (t, J=7.4 Hz, 4H), 1.84-1.74 (m, 4H), 1.21 (t, J=7.1 Hz, 3H). MS (ESI) m/z $(M-H)^+$544.0.

Example 226

Compounds 451-453, 533-540

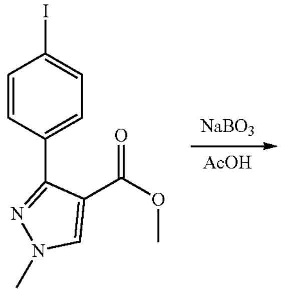

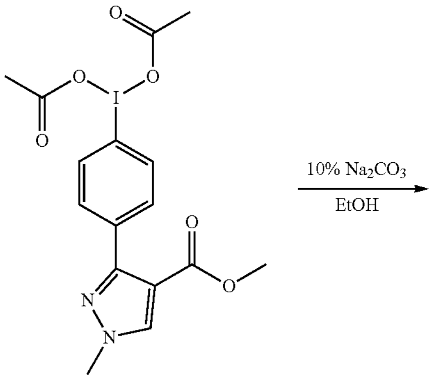

451A

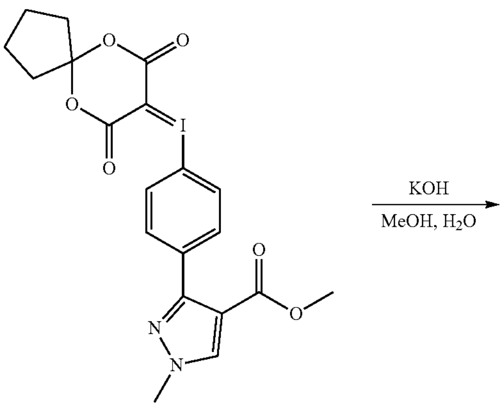

451B

-continued

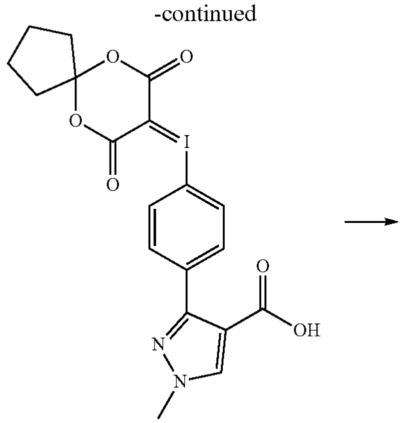

451

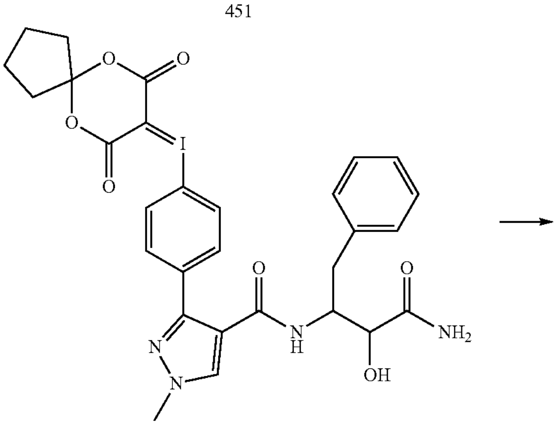

452

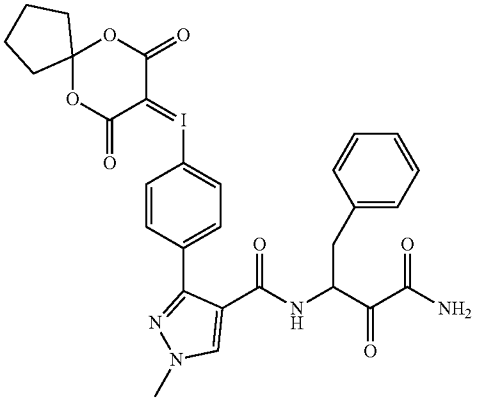

453

Sodium perborate tetrahydrate (8.99 g, 58.46 mmol) was added in portions to a solution of methyl 3-(4-iodophenyl)-1-methyl-1H-pyrazole-4-carboxylate (2 g, 5.85 mmol) in AcOH (40 mL) and heated to 50° C. The reaction mixture was stirred at 50° C. for 8 h, cooled to room temperature, diluted with DCM (50 mL), filtered, the filtrate was diluted with water (100 mL), and extracted with methylenechloride (30 mL×2). The combined organic extracts were dried with anhydrous sodium sulfate, filtered, and concentrated. The residue was triturated in DCM:PE (1:20) (100 mL), filtered to give compound 451A (2.1 g, yield: 78.1%) as a white solid. $^1$H NMR (400 MHz, $CDCl_3$) δ 8.30-8.01 (m, 2H), 7.98-7.84 (m, 3H), 4.10-3.90 (m, 3H), 3.86-3.70 (m, 3H), 2.17-1.83 (m, 6H).

To a solution of compound 451A (2.1 g, 4.56 mmol) in EtOH (60 mL) was added $Na_2CO_3$ (1.93 g, 18.25 mmol) in $H_2O$ (30 mL) and 6,10-dioxaspiro[4.5]decane-7,9-dione (932 mg, 5.48 mmol). The mixture was stirred at 25° C. for 4 h. The reaction mixture was then diluted with water (50 mL), and extracted with DCM (20 mL×3). The combined organic extracts were dried with anhydrous $Na_2SO_4$, filtered, and concentrated. The residue was added DCM (5 mL) and PE (50 mL) to induce precipitation. Solids were collected to give compound 451B (1.6 g, yield: 68.7%) as a white solid. $^1$H NMR (400 MHz, $CDCl_3$) δ 7.95 (s, 1H), 7.90-7.80 (m, 4H), 3.94 (s, 3H), 3.79-3.72 (m, 3H), 2.14 (t, J=7.5 Hz, 4H), 1.81-1.75 (m, 4H).

Compounds 451-453 were was synthesized from the intermediate 451B using same procedures as described earlier for compound 12 to yield compounds 451-453.

Compound 451 (220 mg, yield: 58.1%) 3-(4-((7,9-dioxo-6,10-dioxaspiro[4.5]decan-8-ylidene)-λ3-iodanyl)phenyl)-1-methyl-1H-pyrazole-4-carboxylic acid: $^1$H NMR (400 MHz, DMSO-$d_6$) δ 12.31 (br s, 1H), 8.35-8.28 (m, 1H), 7.82-7.73 (m, 4H), 3.88 (s, 3H), 2.02-1.93 (m, 4H), 1.70-1.62 (m, 4H). MS (ESI) m/z $(M-H)^+$495.01.

Compound 452 (250 mg, yield: 35.1%) N-(4-amino-3-hydroxy-4-oxo-1-phenylbutan-2-yl)-3-(4-((7,9-dioxo-6,10-dioxaspiro[4.5]decan-8-ylidene)-$\lambda^3$-iodanyl)phenyl)-1-methyl-1H-pyrazole-4-carboxamide: $^1$H NMR (400 MHz, DMSO-$d_6$) δ 8.13-7.98 (m, 1H), 7.93-7.78 (m, 1H), 7.72-7.62 (m, 2H), 7.59-7.46 (m, 2H), 7.33 (d, J=7.8 Hz, 2H), 7.28-7.17 (m, 6H), 5.87-5.73 (m, 1H), 4.49 (d, J=9.5 Hz, 1H), 4.02 (br s, 1H), 3.89 (s, 3H), 2.84-2.65 (m, 2H), 2.01 (br s, 4H), 1.70 (br s, 4H). MS (ESI) m/z $(M+H)^+$673.11.

Compound 453 (32 mg, yield: 64.2%) N-(4-amino-3,4-dioxo-1-phenylbutan-2-yl)-3-(4-((7,9-dioxo-6,10-dioxaspiro[4.5]decan-8-ylidene)-$\lambda^3$-iodanyl)phenyl)-1-methyl-1H-pyrazole-4-carboxamide: $^1$H NMR (400 MHz, DMSO-$d_6$) δ 8.52 (d, J=7.5 Hz, 1H), 8.11-8.02 (m, 2H), 7.81-7.76 (m, 1H), 7.72-7.65 (m, 2H), 7.56 (d, J=8.6 Hz, 2H), 7.29-7.24 (m, 4H), 7.21 (dd, J=4.5, 8.7 Hz, 1H), 5.34-5.19 (m, 1H), 3.91-3.86 (m, 3H), 3.18-3.14 (m, 1H), 2.79 (dd, J=10.3, 13.8 Hz, 1H), 1.97 (t, J=7.3 Hz, 4H), 1.68-1.64 (m, 4H). MS (ESI) m/z $(M+H)^+$671.09.

533

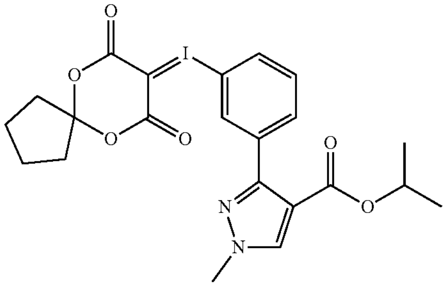

534

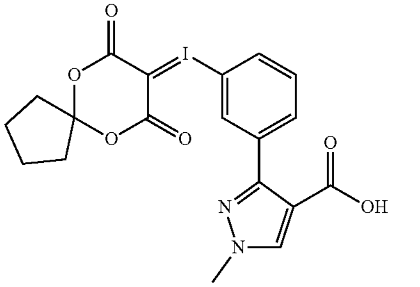

-continued

535

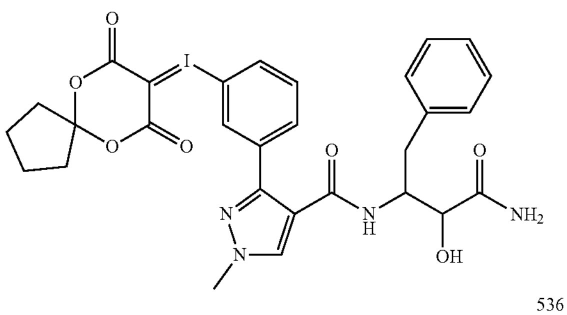

536

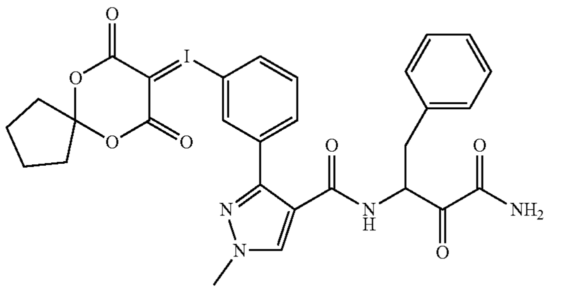

Compounds 533-536 were was synthesized from the corresponding intermediate, ethyl 3-(3-iodophenyl)-1-methyl-1H-pyrazole-4-carboxylate using same procedures as described earlier for compounds 451B and 451-453 to yield compounds 533-536.

Compound 533 (1.3 g, yield: 67.8%; yellow solid) Ethyl 3-(3-((7,9-dioxo-6,10-dioxaspiro[4.5]decan-8-ylidene)-$\lambda^3$-iodanyl)phenyl)-1-methyl-1H-pyrazole-4-carboxylate: $^1$H NMR (400 MHz, $CDCl_3$) δ 8.35 (s, 1H), 8.07 (d, J=8.2 Hz, 1H), 7.94 (s, 1H), 7.85 (dd, J=0.9, 8.2 Hz, 1H), 7.43 (t, J=7.9 Hz, 1H), 4.24 (q, J=7.1 Hz, 2H), 3.94 (s, 3H), 2.14 (t, J=7.5 Hz, 4H), 1.83-1.70 (m, 4H), 1.28 (t, J=7.2 Hz, 3H).

Compound 534 (78 mg; white solid) 3-(3-((7,9-dioxo-6,10-dioxaspiro[4.5]decan-8-ylidene)-$\lambda^3$-iodanyl)phenyl)-1-methyl-1H-pyrazole-4-carboxylic acid: $^1$H NMR (400 MHz, DMSO-$d_6$) δ 12.46-12.28 (m, 1H), 8.31 (s, 1H), 8.11 (t, J=1.7 Hz, 1H), 7.94 (d, J=8.2 Hz, 1H), 7.75 (d, J=8.8 Hz, 1H), 7.46 (t, J=7.9 Hz, 1H), 3.88 (s, 3H), 2.01-1.94 (m, 4H), 1.69-1.63 (m, 4H). MS (ESI) m/z $(M-H)^+$495.0.

Compound 535 (250 mg, yield: 48%; white solid) N-(4-amino-3-hydroxy-4-oxo-1-phenylbutan-2-yl)-3-(3-((7,9-dioxo-6,10-dioxaspiro[4.5]decan-8-ylidene)-$\Delta^3$-iodanyl)phenyl)-1-methyl-1H-pyrazole-4-carboxamide: $^1$H NMR (400 MHz, DMSO-$d_6$) δ 8.14-8.00 (m, 2H), 7.87 (d, J=8.8 Hz, 0.5H), 7.66 (d, J=7.9 Hz, 1H), 7.60-7.55 (m, 1H), 7.53 (d, J=9.3 Hz, 0.5H), 7.35-7.10 (m, 8H), 5.86-5.68 (m, 1H), 4.49-4.33 (m, 1H), 4.02-3.98 (m, 0.5H), 3.88-3.81 (m, 3.5H), 2.90-2.83 (m, 0.5H), 2.79-2.71 (m, 1H), 2.67-2.62 (m, 0.5H), 2.00-1.94 (m, 4H), 1.69-1.62 (m, 4H). MS (ESI) m/z $(M+H)^+$673.1.

Compound 536 (200 mg, yield: 69.8%; pale yellow solid) N-(4-amino-3,4-dioxo-1-phenylbutan-2-yl)-3-(3-((7,9-dioxo-6,10-dioxaspiro[4.5]decan-8-ylidene)-$\Delta^3$-iodanyl)phenyl)-1-methyl-1H-pyrazole-4-carboxamide: $^1$H NMR (400 MHz, DMSO-$d_6$) δ 8.49 (d, J=7.5 Hz, 1H), 8.16-7.92 (m, 3H), 7.82-7.72 (m, 1H), 7.71-7.54 (m, 2H), 7.33 (t, J=7.7 Hz, 1H), 7.29-7.21 (m, 4H), 7.19 (d, J=3.7 Hz, 1H), 5.24 (br s, 1H), 3.95-3.80 (m, 3H), 3.21-3.07 (m, 1H), 2.80 (dd, J 10.0, 13.8 Hz, 1H), 2.02-1.91 (m, 4H), 1.65 (br s, 4H). MS (ESI) m/z $(M+H)^+$671.1.

537

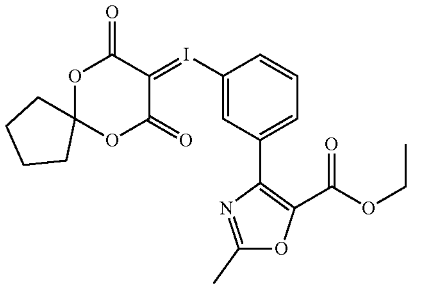

538

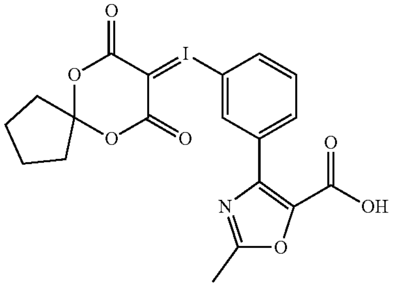

539

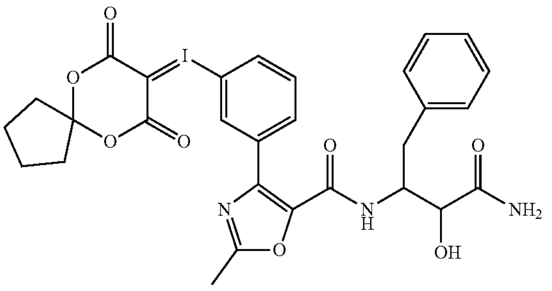

540

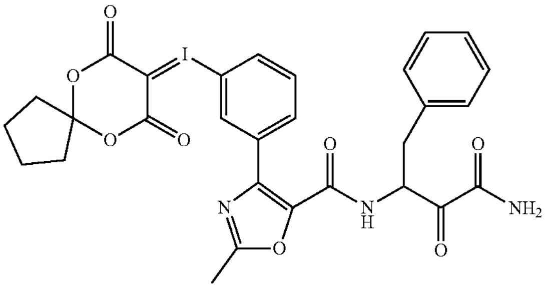

Compounds 537-540 were was synthesized from the corresponding intermediate, ethyl 3-(3-iodophenyl)-3-oxopropanoate to convert it to ethyl 4-(3-iodophenyl)-2-methyloxazole-5-carboxylate using the procedures as for compound 248C and then ethyl 4-(3-iodophenyl)-2-methyloxazole-5-carboxylate was converted to compounds 537-540 using same procedures as described earlier for compounds 451B and 451-453.

Compound 537 (1.3 g, yield: 41.5%; white solid) Ethyl 4-(3-((7,9-dioxo-6,10-dioxaspiro[4.5]decan-8-ylidene)-$\lambda^3$-iodanyl)phenyl)-2-methyloxazole-5-carboxylate: $^1$H NMR (400 MHz, $CDCl_3$) δ 8.64 (t, J=1.7 Hz, 1H), 8.42-8.35 (m, 1H), 7.98-7.80 (m, 1H), 7.50 (t, J=7.9 Hz, 1H), 4.42 (q, J=7.1 Hz, 2H), 2.59 (s, 3H), 2.21-2.14 (m, 4H), 1.83-1.76 (m, 4H), 1.41 (t, J=7.2 Hz, 3H).

Compound 538 (300 mg; yield: 63.1% white solid) 4-(3-((7,9-dioxo-6,10-dioxaspiro[4.5]decan-8-ylidene)-2-iodanyl)phenyl)-2-methyloxazole-5-carboxylic acid: $^1$H NMR (400 MHz, DMSO-$d_6$) δ 8.37 (t, J=1.7 Hz, 1H), 8.28-8.23 (m, 1H), 7.85-7.78 (m, 1H), 7.53 (t, J=7.9 Hz, 1H), 2.52 (s, 3H), 2.00-1.96 (m, 4H), 1.69-1.64 (m, 4H). MS (ESI) m/z $(M-H)^+$495.99.

Compound 539 (360 mg, yield: 68.7%; pale yellow solid) N-(4-amino-3-hydroxy-4-oxo-1-phenylbutan-2-yl)-4-(3-((7,9-dioxo-6,10-dioxaspiro[4.5]decan-8-ylidene)-$\lambda^3$-iodanyl)phenyl)-2-methyloxazole-5-carboxamide: $^1$H NMR (400 MHz, DMSO-$d_6$) δ 8.47-8.38 (m, 1H), 8.29 (d, J=8.2 Hz, 0.5H), 8.22 (t, J=8.8 Hz, 1H), 7.83-7.68 (m, 1.5H), 7.44 (td, J=7.9, 13.0 Hz, 1H), 7.34 (d, J=9.3 Hz, 1H), 7.27-7.08 (m, 6H), 6.03 (d, J=6.0 Hz, 0.5H), 5.87 (d, J=5.7 Hz, 0.5H), 4.69-4.41 (m, 1H), 4.03 (t, J=4.6 Hz, 0.5H), 3.90-3.83 (m, 0.5H), 2.98-2.85 (m, 1H), 2.82-2.71 (m, 1H), 2.52 (d, J=3.7 Hz, 3H), 2.01-1.96 (m, 4H), 1.69-1.64 (m, 4H). MS (ESI) m/z $(M-H)^+$672.0.

Compound 540 (150 mg, yield: 65.2%; white solid) N-(4-amino-3,4-dioxo-1-phenylbutan-2-yl)-4-(3-((7,9-dioxo-6,10-dioxaspiro[4.5]decan-8-ylidene)-$\lambda^3$-iodanyl)phenyl)-2-methyloxazole-5-carboxamide: $^1$H NMR (400 MHz, DMSO-$d_6$) δ 8.56 (br s, 1H), 8.50-8.42 (m, 1H), 8.33-8.21 (m, 1H), 7.92-7.73 (m, 2H), 7.63 (br s, 1H), 7.50-7.41 (m, 1H), 7.30-7.20 (m, 5H), 5.50-5.39 (m, 1H), 3.28 (dd, J=4.4, 14.2 Hz, 1H), 3.08-3.02 (m, 1H), 2.56-2.54 (m, 3H), 2.02 (t, J=7.4 Hz, 4H), 1.75-1.67 (m, 4H). MS (ESI) m/z $(M+H)^+$ 672.0.

Example 227

Compound 489

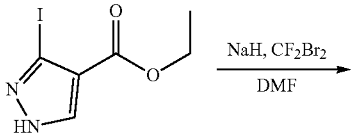

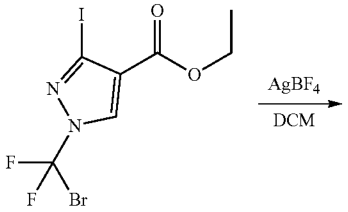

489A

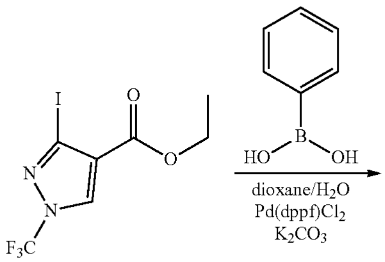

489B

-continued

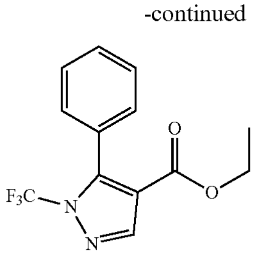

489C

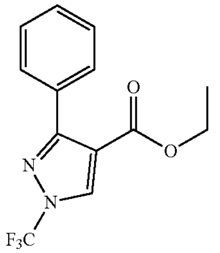

489D

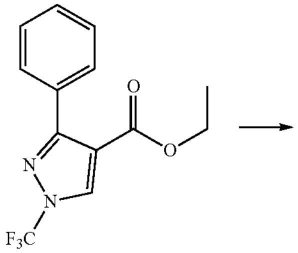

489D

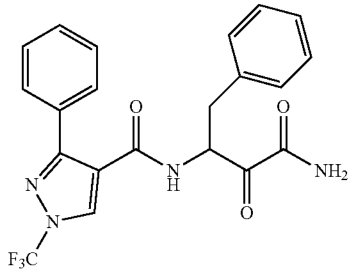

489

To a solution of ethyl 3-iodo-1H-pyrazole-4-carboxylate (4.3 g, 16.16 mmol) in DMF (50 mL) was added NaH (1.29 g, 32.32 mmol, 60% purity) at 0° C., the mixture was stirred at 15° C. for 30 min, then added dibromo(difluoro)methane (10.17 g, 48.48 mmol, 4.5 mL) at 0° C. The mixture was stirred at 15° C. for 16 h. The mixture was quenched with $NH_4Cl$(15 mL), diluted with $H_2O$ (30 mL), extracted with EA (50 mL×3), the organic phase was combined, washed with NaCl (50 mL), dried over $Na_2SO_4$, filtered and concentrated to give a residue. The residue was purified by column chromatography ($SiO_2$, Petroleum ether:Ethyl acetate=1:0 to 10:1) to give compound 489A (4.4 g, yield: 61.15%) as a yellow oil. $^1$H NMR (400 MHz, $CDCl_3$) δ 8.25-8.08 (m, 1H), 4.42-4.31 (m, 2H), 1.39 (t, J=3.3, 7.2 Hz, 3H). MS (ESI) m/z $(M+H)^+$394.9.

To a mixture of compound 489A (2.6 g, 6.58 mmol) in DCM (30 mL) was added $AgBF_4$ (3.84 g, 19.74 mmol) in portion at −78° C. under $N_2$. The mixture was stirred at 15° C. for 16 h. The reaction mixture was diluted with DCM (50 mL), then, the mixture was wash with $H_2O$ (60 mL) and brine (60 ml), the organic was dried over $Na_2SO_4$, and concentrated under reduced pressure to give a residue. The residue was purified by column chromatography ($SiO_2$, Petroleum ether:Ethyl acetate=1:0 to 10:1) to give compound 489B (1.7 g, yield: 45.17%) as a colorless oil. $^1$H NMR (400 MHz, $CDCl_3$) δ 8.24-8.03 (m, 1H), 4.44-4.31 (m, 2H), 1.46-1.34 (m, 3H). MS (ESI) m/z $(M+H)^+$334.9.

To a mixture of compound 489B (200 mg, 598.75 umol), phenylboronic acid (110 mg, 898.13 umol), $K_2CO_3$ (166 mg, 1.20 mmol) in dioxane (10 mL) and $H_2O$ (0.5 mL) was added Pd(dppf)$Cl_2$ (44 mg, 59.88 umol) in portion at 15° C. under $N_2$. The mixture was stirred at 90° C. for 16 h. The reaction mixture was concentrated. The residue was purified by preparatory-TLC ($SiO_2$, PE:EA=15:1) to give compound 489D (40 mg, yield: 9.31%) as yellow oil and compound 489C (40 mg, yield: 20.97%) as yellow oil. Compound 489D: $^1$H NMR (400 MHz, $CDCl_3$) δ 8.43 (s, 1H), 7.83-7.77 (m, 2H), 7.48-7.43 (m, 3H), 4.30 (q, J=7.1 Hz, 2H), 1.31 (t, J=7.2 Hz, 4H). MS (ESI) m/z $(M+H)^+$285.0. Compound 489C: $^1$H NMR (400 MHz, $CDCl_3$) δ 8.16 (s, 1H), 7.55-7.44 (m, 3H), 7.38 (d, J=7.3 Hz, 2H), 4.15 (q, J=7.2 Hz, 2H), 1.14 (t, J=7.2 Hz, 3H). MS (ESI) m/z $(M+H)^+$285.0.

Compound 489 were was synthesized from the intermediate 489D using same procedures as described earlier for compound 12 to yield compound 489. Compound 489 (55 mg, yield: 73.01%) N-(4-amino-3,4-dioxo-1-phenylbutan-2-yl)-3-phenyl-1-(trifluoromethyl)-1H-pyrazole-4-carboxamide: $^1$H NMR (400 MHz, DMSO-$d_6$) δ 8.93 (dd, J=7.3 Hz, 1H), 8.76 (s, 1H), 8.11 (s, 1H), 7.85 (s, 1H), 7.54 (dd, J=7.1 Hz, 2H), 7.41-7.31 (m, 3H), 7.29-7.20 (m, 5H), 5.39-5.32 (m, 1H), 3.17 (dd, J=3.6, 14.0 Hz, 1H), 2.82 (dd, J=10.0, 14.0 Hz, 1H). MS (ESI) m/z $(M+H)^+$431.1.

Example 228

Compound 490

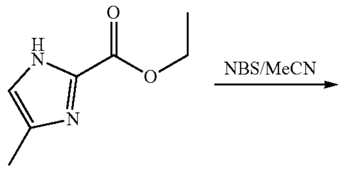

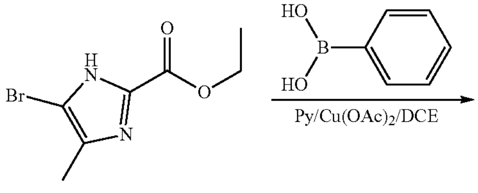

490A

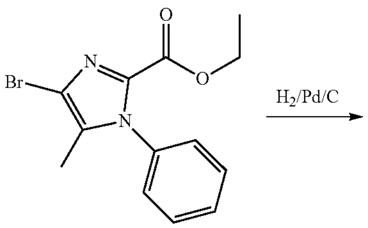

490B

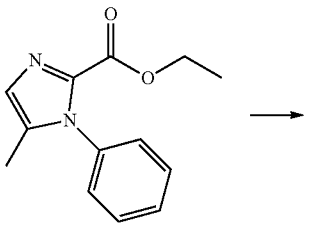

490C

-continued

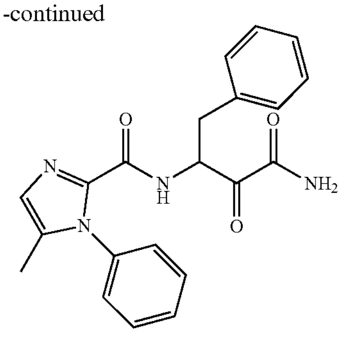

490

A solution of ethyl 4-methyl-1H-imidazole-2-carboxylate (800 mg, 5.19 mmol) in MeCN (20 mL) was added NBS (970 mg, 5.45 mmol). The reaction mixture was stirred at 20° C. for 5 hr. The solvent was evaporated under vacuum. The crude product was purified by silica gel column chromatography (petroleum ether:ethyl acetate=20:1~3:1) to give compound 490A (1.50 g, crude) as a yellow solid. $^1$H NMR (400 MHz, $CDCl_3$) δ 4.42 (q, J=7.2 Hz, 2H), 2.32 (s, 3H), 1.40 (t, J=7.1 Hz, 3H).

A mixture of compound 490A (1.5 g, 6.44 mmol), phenylboronic acid (1.57 g, 12.9 mmol), $Cu(OAc)_2$ (2.34 g, 12.9 mmol), pyridine (1.53 g, 19.3 mmol) and 4A° MS in DCE (20 mL) was stirred at 70° C. under 02 for 12 hr. The mixture was filtered and the filtrate was concentrated, the residue was purified by FCC (Petroleum ether:Ethyl acetate=15:1) to give compound 490B (300 mg, yield: 15.1%) as yellow solid. $^1$H NMR (400 MHz, $CDCl_3$) δ7.57-7.47 (m, 3H), 7.23-7.17 (m, 2H), 4.24 (q, J=7.1 Hz, 2H), 2.02 (s, 3H), 1.25 (t, J=7.2 Hz, 3H).

To a solution of compound 490B (50 mg, 162 umol) in EtOH (10 mL) was added Pd—C (0.1 g) under $N_2$. The suspension was degassed under vacuum and purged with $H_2$ several times. The mixture was stirred under $H_2$ (15 psi) at 15° C. for 12 hours. The mixture was filtered and the filtrate was concentrated to give compound 490C (40 mg, crude) as yellow oil. $^1$H NMR (400 MHz, $CDCl_3$) δ 7.72-7.56 (m, 4H), 7.33 (br d, J=7.1 Hz, 2H), 4.40 (q, J=7.1 Hz, 2H), 1.40 (t, J=7.2 Hz, 3H).

Compound 490 were was synthesized from the intermediate 490C using same procedures as described earlier for compound 12 to yield compound 490. Compound 490 (26 mg, yield: 52.3%) N-(4-amino-3,4-dioxo-1-phenylbutan-2-yl)-5-methyl-1-phenyl-1H-imidazole-2-carboxamide: $^1$H NMR (400 MHz, DMSO-$d_6$) δ 7.74 (br d, J=7.9 Hz, 1H), 7.55-7.45 (m, 3H), 7.35-7.29 (m, 1H), 7.27-7.14 (m, 6H), 6.93 (d, J=0.9 Hz, 1H), 6.70 (br s, 1H), 5.63 (dt, J=5.2, 7.7 Hz, 1H), 5.44 (br s, 1H), 3.38 (dd, J=5.3, 14.1 Hz, 1H), 3.17 (dd, J=7.3, 14.1 Hz, 1H), 2.02 (d, J=0.9 Hz, 3H). MS (ESI) m/z $(M+H)^+$377.1.

Example 229

Compound 491

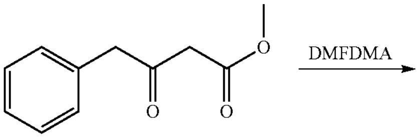

-continued

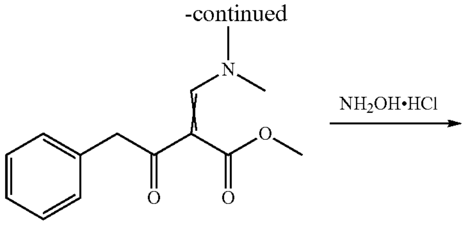

491A

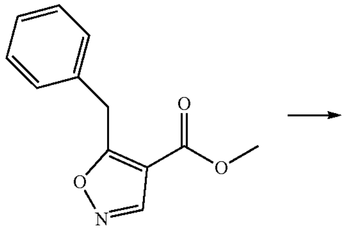

491B

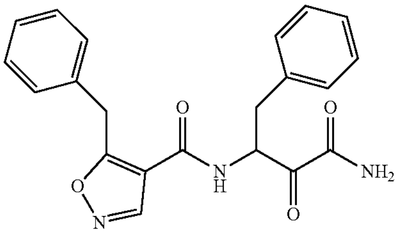

491

A mixture of methyl 3-oxo-4-phenylbutanoate (1 g, 5.20 mmol) and DMF-DMA (682 mg, 5.72 mmol) was stirred at 20° C. for hr. The crude product was purified by silica gel column chromatography (petroleum ether:ethyl acetate=20:1 to 5:1) to give compound 491A (900 mg, yield: 70.0%) as yellow oil. $^1$H NMR (400 MHz, $CDCl_3$) δ 7.70 (s, 1H), 7.37-7.16 (m, 5H), 4.06 (s, 2H), 3.75 (s, 3H), 3.33-2.57 (m, 6H).

A solution of compound 491A (900 mg, 3.64 mmol) in MeOH (20 mL) was added $NH_2OH$.HCl (253 mg, 3.64 mmol). The reaction mixture was stirred at 65° C. for 1 hr. The solvent was evaporated. The crude residue was purified by preparatory-TLC (petroleum ether:ethyl acetate=3:1) to give compound 491B (500 mg, yield: 63.2%) as a yellow oil. $^1$H NMR (400 MHz, $CDCl_3$) δ 8.50 (s, 1H), 7.35-7.27 (m, 5H), 4.48 (s, 2H), 3.90 (s, 3H).

Compound 491 were was synthesized from the intermediate 491B using same procedures as described earlier for compound 12 to yield compound 491. Compound 491 (20.4 mg, yield: 41.0%) N-(4-amino-3,4-dioxo-1-phenylbutan-2-yl)-5-benzylisoxazole-4-carboxamide: $^1$H NMR (400 MHz, $CDCl_3$) δ 8.30 (s, 1H), 7.39-7.23 (m, 9H), 7.14-7.03 (m, 2H), 6.78 (br s, 1H), 6.21 (br d, J=7.0 Hz, 1H), 5.72-5.66 (m, 1H), 5.59 (br s, 1H), 4.41 (s, 2H), 3.43 (dd, J=5.5, 14.2 Hz, 1H), 3.21 (dd, J=6.8, 14.2 Hz, 1H).

Example 230

Compound 497

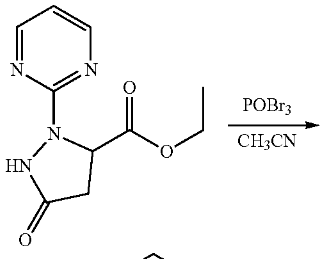

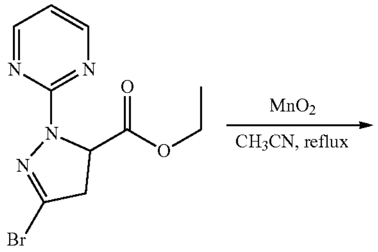

497A

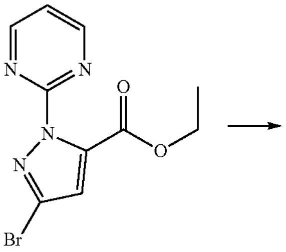

497B

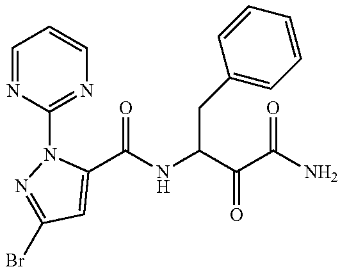

497

To a solution of ethyl 5-oxo-2-(pyrimidin-2-yl)pyrazolidine-3-carboxylate (300 mg, 1.27 mmol) in $CH_3CN$ (10 mL) was added $POBr_3$ (291.26 mg, 1.02 mmol). The mixture was stirred at 80° C. for 2 h. The reaction mixture was concentrated under reduced pressure to remove $CH_3CN$. The residue was diluted with $H_2O$ (10 mL) and extracted with DCM (10 mL×2). The combined organic layers were washed with brine (20 mL), dried over $Na_2SO_4$, filtered and concentrated under reduced pressure to give a residue. The residue was used in the next step without purification. Compound 497A (300 mg, crude) was obtained as a yellow oil. $^1$H NMR (400 MHz, $CDCl_3$) δ 8.42 (d, J=4.9 Hz, 2H), 6.74 (t, J=4.9 Hz, 1H), 5.03 (dd, J=6.6, 12.6 Hz, 1H), 4.27-4.10 (m, 2H), 3.60 (dd, J=12.7, 18.0 Hz, 1H), 3.25 (dd, J=6.6, 18.1 Hz, 1H), 1.20 (t, J=7.2 Hz, 3H). MS (ESI) m/z $(M+H)^+$298.7.

To a solution of compound 497A (300 mg, 1.00 mmol) in $CH_3CN$ (10 mL) was added $MnO_2$ (871.92 mg, 10.03 mmol). The mixture was stirred at 80° C. for 48 h. The mixture was filtered. The filtrate was concentrated to give a residue. The residue was purified by preparatory-TLC ($SiO_2$, PE:EA=2:1). Compound 497B (150 mg, yield 50.3%) was obtained as a yellow oil. $^1H$ NMR (400 MHz, $CDCl_3$) δ 8.79 (d, J=4.9 Hz, 2H), 7.34 (t, J=4.9 Hz, 1H), 6.95-6.78 (m, 1H), 4.33 (q, J=7.1 Hz, 2H), 1.28 (t, J=7.2 Hz, 3H). MS (ESI) m/z $(M+H)^+$296.8.

Compound 497 were was synthesized from the intermediates, 497B and 3-amino-2-hydroxy-4-phenylbutanamide hydrochloride and using same procedures as described earlier for compound 12 to yield compound 497. Compound 497 (6 mg, yield: 41.0%) N-(4-amino-3,4-dioxo-1-phenylbutan-2-yl)-3-bromo-1-(pyrimidin-2-yl)-1H-pyrazole-5-carboxamide: $^1H$ NMR (400 MHz, $CDCl_3$) δ 8.72 (d, J=4.8 Hz, 2H), 7.70 (br.d, J=7.3 Hz, 1H), 7.42 (t, J=4.8 Hz, 1H), 7.35-7.20 (m, 5H), 7.03 (br.s, 1H), 6.76 (s, 1H), 6.27 (br s, 1H), 5.50 (dt, J=4.8, 8.0 Hz, 1H), 3.31 (dd, J=4.9, 13.9 Hz, 1H), 2.99 (dd, J=8.5, 14.1 Hz, 1H). MS (ESI) m/z $(M+H)^+$ 443.0.

Example 231

Compounds 549, 556-560, 584, 594, 595, 600, 619

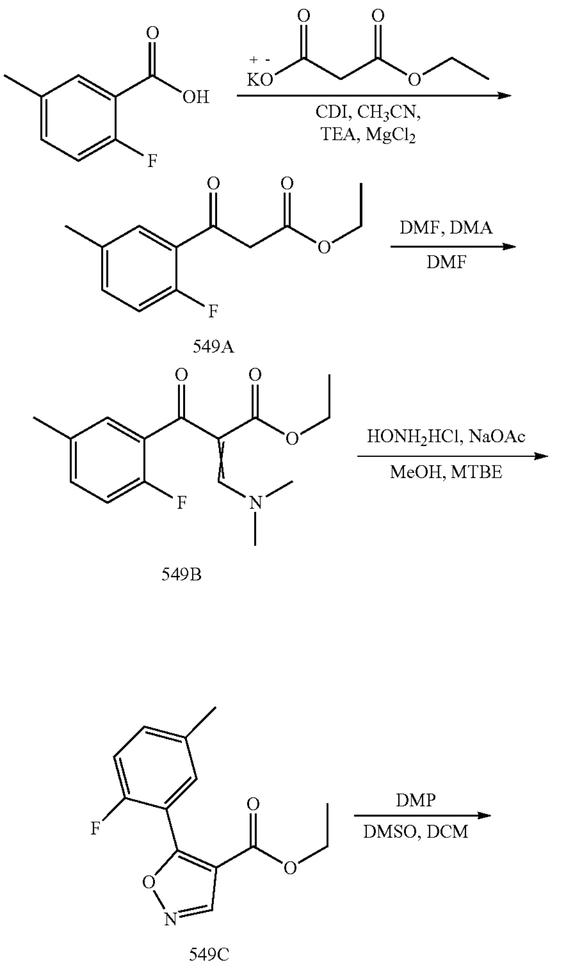

-continued

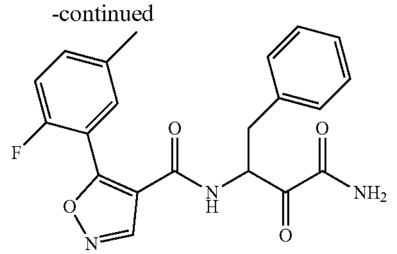

549

In a round bottom flask a solution of 2-fluoro-5-methylbenzoic acid (10 g, 64.9 mmol) in $CH_3CN$ (40 mL) was added CDI (11.8 g, 72.7 mmol). The mixture was stirred at 25° C. for 4 h. In another flask a solution of potassium 3-ethoxy-3-oxopropanoate (14.6 g, 85.6 mmol) in $CH_3CN$ (130 mL) was added $MgCl_2$ (6.2 g, 64.9 mmol) in portions over 15 min. The mixture was stirred at 25° C. for 0.5 h, then TEA (27 mL, 194.0 mmol) was added and the slurry was stirred for 0.5 h. The solution in the first round-bottom flask was transferred to the slurry of the second flask. The mixture was stirred at 25° C. for 12 h. The reaction mixture was quenched with HCl (3 N, 180 mL) and the solution was concentrated under reduce pressure. The resulting was extracted with MTBE (200 mL×2). The organic layer was washed with $H_2O$ (200 mL), sat. $NaHCO_3$ (200 mL×2), sat. NaCl (200 mL), dried over anhydrous $Na_2SO_4$, filtered and concentrated under reduced pressure to afford compound 549A (6.7 g, yield 45.5%) as colorless liquid, which was used in next step without further purification. $^1H$ NMR (DMSO-$d_6$, 400 MHz): δ 7.68-7.63 (m, 1H), 7.53-7.46 (m, 1H), 7.28-7.19 (m, 1H), 4.11 (q, J=7.1 Hz, 2H), 4.03 (d, J=3.1 Hz, 2H), 2.33 (s, 3H), 1.16 (t, J=7.1 Hz, 3H). MS (ESI) m/z $(M+H)^+$224.9.

A mixture of compound 549A (6.7 g, 29.9 mmol) and DMF-DMA (16 mL, 120.4 mmol) in DMF (60 mL) was stirred at 80° C. for 12 h. The mixture was concentrated in vacuum to afford compound 549B (8.4 g, yield 97.6%) as red liquid, which was used in next step without further purification. MS (ESI) m/z $(M+H)^+$280.1

To a mixture of compound 549B (8.4 g, 30.1 mmol) and hydroxylamine hydrochloride (4.2 g, 60.2 mmol) in MTBE (70 mL) and MeOH (70 mL) was added NaOAc (4.9 g, 60.2 mmol) in one portion. The mixture was stirred at 25° C. for 12 h. The reaction mixture was filtered and the solvent removed from the filtrate by concentration in vacuo. The residue was purified by flash silica gel chromatography (Eluent of 010% Ethyl acetate/Petroleum ether gradient) to afford compound 549C (3.6 g, yield 46.7%) as colorless liquid. $^1H$ NMR (DMSO-$d_6$, 400 MHz): δ 9.11 (s, 1H), 7.60-7.54 (m, 1H), 7.52-7.44 (m, 1H), 7.37-7.28 (m, 1H), 4.20 (q, J=7.2 Hz, 2H), 2.36 (s, 3H), 1.17 (t, J=7.2 Hz, 3H). MS (ESI) m/z $(M+H)^+$250.1.

Compound 549 was synthesized from the intermediates, 549C and 3-amino-2-hydroxy-4-phenylbutanamide hydrochloride and using same procedures as described earlier for compound 12 to yield compound 549. Compound 549 (100 mg, yield: 68.0%, white solid) N-(4-amino-3,4-dioxo-1-phenylbutan-2-yl)-5-(2-fluoro-5-methylphenyl)isoxazole-4-carboxamide: $^1H$ NMR (400 MHz, DMSO-$d_6$) δ 8.96 (s, 1H), 8.92-8.81 (m, 1H), 8.08 (s, 1H), 7.83 (s, 1H), 7.40 (s, 2H), 7.33-7.11 (m, 6H), 5.33 (s, 1H), 3.24-3.05 (m, 1H), 2.93-2.75 (m, 1H), 2.31 (s, 3H). MS (ESI) m/z $(M+H)^+$ 396.1.

Compound 556 was synthesized from ethyl 3-(2-fluorophenyl)-3-oxopropanoate using the procedures as in compound 549 followed by using same procedures as described earlier for compound 12 to yield compound 556. Compound 556 (60 mg, yield: 39.8%, white solid) N-(4-amino-3,4-dioxo-1-phenylbutan-2-yl)-5-(2-fluorophenyl)isoxazole-4-carboxamide: $^1$H NMR (400 MHz, DMSO-$d_6$) δ 9.00-8.89 (m, 2H), 8.11 (s, 1H), 7.85 (s, 1H), 7.65-7.55 (m, 2H), 7.38-7.19 (m, 7H), 5.37-5.28 (m, 1H), 3.18 (dd, J=3.6, 14.0 Hz, 1H), 2.91-2.63 (m, 1H). MS (ESI) m/z $(M+H)^+$382.1.

Compound 557 was synthesized from ethyl 3-oxo-3-(o-tolyl)propanoate using the procedures as in compound 549 followed by using same procedures as described earlier for compound 12 to yield compound 557. Compound 557 (80 mg, yield: 52.5%, white solid) N-(4-amino-3,4-dioxo-1-phenylbutan-2-yl)-5-(o-tolyl)isoxazole-4-carboxamide: $^1$H NMR (400 MHz, DMSO-$d_6$) δ 8.99 (s, 1H), 8.73 (d, J=7.3 Hz, 1H), 8.10 (s, 1H), 7.84 (s, 1H), 7.45-7.39 (m, 1H), 7.34-7.19 (m, 8H), 5.33-5.26 (m, 1H), 3.17 (dd, J=3.7, 13.9 Hz, 1H), 2.80 (dd, J=9.9, 13.9 Hz, 1H), 2.08 (s, 3H). MS (ESI) m/z $(M+H)^+$378.1.

Compound 558 was synthesized from ethyl 3-(5-fluoro-2-methylphenyl)-3-oxopropanoate using the procedures as in compound 549 followed by using same procedures as described earlier for compound 12 to yield compound 558. Compound 558 (100 mg, yield: 48.0%, white solid) N-(4-amino-3,4-dioxo-1-phenylbutan-2-yl)-5-(5-fluoro-2-methylphenyl)isoxazole-4-carboxamide: $^1$H NMR (400 MHz, DMSO-$d_6$) δ 9.04 (s, 1H), 8.79 (d, J=7.5 Hz, 1H), 8.10 (s, 1H), 7.84 (s, 1H), 7.39-7.33 (m, 1H), 7.39-7.19 (m, 7H), 5.38-5.27 (m, 1H), 3.18 (dd, J=3.9, 13.9 Hz, 1H), 2.91-2.72 (m, 1H), 2.04 (s, 3H). MS (ESI) m/z $(M+H)^+$396.1.

Compound 559 was synthesized from ethyl 3-(3-fluorophenyl)-3-oxopropanoate using the procedures as in compound 549 followed by using same procedures as described earlier for compound 12 to yield compound 559. Compound 559 (150 mg, yield: 74.3%, white solid) N-(4-amino-3,4-dioxo-1-phenylbutan-2-yl)-5-(3-fluorophenyl)isoxazole-4-carboxamide: $^1$H NMR (400 MHz, DMSO-$d_6$) δ 9.04 (d, J=7.3 Hz, 1H), 8.88 (s, 1H), 8.14 (s, 1H), 7.86 (s, 1H), 7.76 (d, J=9.8 Hz, 1H), 7.70 (d, J=7.8 Hz, 1H), 7.59-7.48 (m, 1H), 7.46-7.37 (m, 1H), 7.36-7.25 (m, 4H), 7.25-7.17 (m, 1H), 5.46-5.32 (m, 1H), 3.27-3.15 (m, 1H), 2.92-2.77 (m, 1H). MS (ESI) m/z $(M+H)^+$382.1.

Compound 560 was synthesized from ethyl 3-oxo-3-(m-tolyl)propanoate using the procedures as in compound 549 followed by using same procedures as described earlier for compound 12 to yield compound 560. Compound 560 (160 mg, yield: 61.3%, white solid) N-(4-amino-3,4-dioxo-1-phenylbutan-2-yl)-5-(m-tolyl)isoxazole-4-carboxamide: $^1$H NMR (400 MHz, DMSO-$d_6$) δ 9.08-8.88 (m, 1H), 8.80 (s, 1H), 8.15 (s, 1H), 7.88 (s, 1H), 7.73-7.52 (m, 2H), 7.43-7.11 (m, 7H), 5.43-5.29 (m, 1H), 3.27-3.15 (m, 1H), 2.91-2.78 (m, 1H), 2.34 (br s, 3H). MS (ESI) m/z $(M+H)^+$378.1.

Compound 584 was synthesized from ethyl 3-(2-fluoro-3-methylphenyl)-3-oxopropanoate using the procedures as in compound 549 followed by using same procedures as described earlier for compound 12 to yield compound 584. Compound 584 (130 mg, yield: 60.1%, white solid) N-(4-amino-3,4-dioxo-1-phenylbutan-2-yl)-5-(2-fluoro-3-methylphenyl)isoxazole-4-carboxamide: $^1$H NMR (400 MHz, DMSO-$d_6$) δ 8.93 (s, 1H), 8.84 (d, J=7.5 Hz, 1H), 8.06 (s, 1H), 7.81 (s, 1H), 7.46 (t, J=7.1 Hz, 1H), 7.40-7.33 (m, 1H), 7.30-7.15 (m, 6H), 5.31 (ddd, J=4.0, 7.4, 9.8 Hz, 1H), 3.15 (dd, J=4.0, 13.9 Hz, 1H), 2.80 (dd, J=9.9, 13.9 Hz, 1H), 2.23 (d, J=1.8 Hz, 3H). MS (ESI) m/z $(M+H)^+$396.1.

Compound 594 was synthesized from ethyl 3-(3-fluoro-2-methylphenyl)-3-oxopropanoate using the procedures as in compound 549 followed by using same procedures as described earlier for compound 12 to yield compound 594. Compound 594 (30 mg, yield: 18.1%, white solid) N-(4-amino-3,4-dioxo-1-phenylbutan-2-yl)-5-(3-fluoro-2-methylphenyl)isoxazole-4-carboxamide: $^1$H NMR (400 MHz, DMSO-$d_6$) δ 9.00 (s, 1H), 8.77 (d, J=7.3 Hz, 1H), 8.06 (s, 1H), 7.80 (s, 1H), 7.36-7.13 (m, 8H), 5.32-5.24 (m, 1H), 3.16 (dd, J=4.1, 14.0 Hz, 1H), 2.79 (br dd, J=10.0, 13.6 Hz, 1H), 1.93 (d, J=2.2 Hz, 3H). $^{19}$F NMR (400 MHz, DMSO-$d_6$) δ−115.508-−115.531 (s, 1F). MS (ESI) m/z $(M+H)^+$ 396.0.

Compound 595 was synthesized from ethyl 3-(2-fluoro-3-methoxyphenyl)-3-oxopropanoate using the procedures as in compound 549 followed by using same procedures as described earlier for compound 12 to yield compound 595. Compound 595 (86 mg, yield: 68.2%, light yellow solid) N-(4-amino-3,4-dioxo-1-phenylbutan-2-yl)-5-(2-fluoro-3-methoxyphenyl)isoxazole-4-carboxamide: $^1$H NMR (400 MHz, DMSO-$d_6$) δ 8.97 (s, 1H), 8.89 (d, J=7.5 Hz, 1H), 8.09 (s, 1H), 7.84 (s, 1H), 7.40-7.33 (m, 1H), 7.32-7.17 (m, 6H), 7.12-7.04 (m, 1H), 5.43-5.25 (m, 1H), 3.87 (s, 3H), 3.22-3.13 (m, 1H), 2.89-2.75 (m, 1H). MS (ESI) m/z $(M+H)^+$ 412.1.

Compound 600 was synthesized from ethyl 3-(5-methylpyridin-3-yl)-3-oxopropanoate using the procedures as in compound 549 followed by using same procedures as described earlier for compound 12 to yield compound 600. Compound 600 (90 mg, yield: 49.1%, yellow solid) N-(4-amino-3,4-dioxo-1-phenylbutan-2-yl)-5-(5-methylpyridin-3-yl)isoxazole-4-carboxamide: $^1$H NMR (400 MHz, DMSO-$d_6$) δ 9.04 (d, J=7.5 Hz, 1H), 8.96 (s, 1H), 8.81 (d, J=1.8 Hz, 1H), 8.56 (d, J=1.5 Hz, 1H), 8.15 (s, 1H), 8.06 (s, 1H), 7.86 (s, 1H), 7.29 (d, J=4.3 Hz, 3H), 7.27-7.17 (m, 2H), 5.42-5.34 (m, 1H), 3.21 (dd, J=3.8, 13.8 Hz, 1H), 2.85 (dd, J=10.0, 14.1 Hz, 1H), 2.35 (s, 3H). MS (ESI) m/z $(M+H)^+$ 412.1.

Compound 619 was synthesized from ethyl 3-(2-fluoro-5-methoxyphenyl)-3-oxopropanoate using the procedures as in compound 549 followed by using same procedures as described earlier for compound 12 to yield compound 619. Compound 619 (72 mg, yield: 71.5%, white solid) N-(4-amino-3,4-dioxo-1-phenylbutan-2-yl)-5-(2-fluoro-5-methoxyphenyl)isoxazole-4-carboxamide: $^1$H NMR (400 MHz, DMSO-$d_6$) δ 8.97 (s, 1H), 8.88 (d, J=7.5 Hz, 1H), 8.08 (s, 1H), 7.83 (s, 1H), 7.31-7.12 (m, 8H), 5.38-5.30 (m, 1H), 3.75 (s, 3H), 3.17 (dd, J=3.8, 14.1 Hz, 1H), 2.83 (dd, J=9.9, 13.9 Hz, 1H). MS (ESI) m/z $(M+H)^+$412.1.

Example 232

Compounds 553, 574, 579, 580, 592, 623

Compounds 553, 574, 579, 580, 592, 623 were synthesized by coupling corresponding intermediates which in turn were synthesized using procedures as used for intermediates 62F and 32F respectively followed by subjecting the coupled product with conditions as in compound 107 to obtain the final product.

Compound 553 (100 mg, 66.9% yield, white solid) was synthesized from intermediate (3S)-3-amino-3-(2,3-dihydro-1H-inden-2-yl)-2-hydroxypropanamide and 3-(2-fluorophenyl)-1-methyl-1H-pyrazole-4-carboxylic acid. Compound 553: (S)—N-(3-amino-1-(2,3-dihydro-1H-inden-2-yl)-2,3-dioxopropyl)-3-(2-fluorophenyl)-1-methyl-1H-pyrazole-4-carboxamide: $^1$H NMR (400 MHz, DMSO- $d_6$) δ 8.24-8.19 (m, 2H), 7.97-7.91 (m, 1H), 7.70 (s, 1H), 7.40-7.33 (m, 2H), 7.19-7.05 (m, 6H), 5.16-5.10 (m, 1H), 3.87 (s, 3H), 2.89-2.67 (m, 5H). MS (ESI) m/z $(M+H)^+$ 421.1.

Compound 574 (100 mg, 45.0% yield, light yellow solid) was synthesized from intermediate (3S)-3-amino-2-hydroxyhex-5-ynamide and 3-(2-fluorophenyl)-1-methyl-1H-pyrazole-4-carboxylic acid. Compound 574: (S)—N-(1-amino-1,2-dioxohex-5-yn-3-yl)-3-(2-fluorophenyl)-1-methyl-1H-pyrazole-4-carboxamide: $^1H$ NMR (400 MHz, DMSO-$d_6$) δ 8.31-8.24 (m, 2H), 7.97 (s, 1H), 7.74 (s, 1H), 7.44-7.37 (m, 2H), 7.23-7.15 (m, 2H), 5.11-5.02 (m, 1H), 3.92 (s, 3H), 2.88 (t, J=2.5 Hz, 1H), 2.75-2.57 (m, 2H). MS (ESI) m/z $(M+H)^+$343.1.

Compound 579 (52 mg, 33.85% yield, white solid) was synthesized from intermediate 3-amino-2-hydroxy-3-(naphthalen-2-yl)propanamide hydrochloride and 3-(2-fluorophenyl)-1-methyl-1H-pyrazole-4-carboxylic acid. Compound 579: N-(3-amino-1-(naphthalen-2-yl)-2,3-dioxopropyl)-3-(2-fluorophenyl)-1-methyl-1H-pyrazole-4-carboxamide: $^1H$ NMR (400 MHz, DMSO-$d_6$) δ 8.53 (d, J=6.0 Hz, 1H), 8.34 (s, 1H), 8.01 (br. s, 1H), 7.93-7.85 (m, 3H), 7.81 (s, 1H), 7.68 (br. s, 1H), 7.55-7.36 (m, 5H), 7.23-7.13 (m, 2H), 6.45 (d, J=6.0 Hz, 1H), 3.87 (s, 3H). MS (ESI) m/z $(M+H)^+$431.1.

Compound 580 (60 mg, 40.15% yield, white solid) was synthesized from intermediate (3S)-3-amino-4-(3,5-difluorophenyl)-2-hydroxybutanamide hydrochloride and 3-(2-fluorophenyl)-1-methyl-1H-pyrazole-4-carboxylic acid. Compound 580: N-(4-amino-1-(3,5-difluorophenyl)-3,4-dioxobutan-2-yl)-3-(2-fluorophenyl)-1-methyl-1H-pyrazole-4-carboxamide: $^1H$ NMR (400 MHz, DMSO-$d_6$) δ 8.31 (d, J=7.6 Hz, 1H), 8.13 (s, 1H), 7.95 (br. s, 1H), 7.72 (br. s, 1H), 7.39-7.27 (m, 2H), 7.17-7.00 (m, 3H), 6.96-6.87 (m, 2H), 5.20-5.11 (m, 1H), 3.88 (s, 3H), 3.17-3.09 (m, 1H), 2.89-2.79 (m, 1H). MS (ESI) m/z $(M+H)^+$431.1.

Compound 592 (320 mg, 60.69% yield, white solid) was synthesized from intermediate (3R)-3-amino-2-hydroxy-4-phenylbutanamide hydrochloride and 3-(2-fluorophenyl)-1-methyl-1H-pyrazole-4-carboxylic acid. Compound 592: (R)—N-(4-amino-3,4-dioxo-1-phenylbutan-2-yl)-4-(2-fluorophenyl)-2-methyloxazole-5-carboxamide: $^1H$ NMR (400 MHz, DMSO-$d_6$) δ 8.78 (d, J=7.6 Hz, 1H), 8.06 (br. s, 1H), 7.81 (br. s, 1H), 7.47-7.37 (m, 2H), 7.30-7.13 (m, 7H), 5.37-5.28 (m, 1H), 3.16-3.09 (m, 1H), 2.97-2.88 (m, 1H), 2.52 (s, 3H). MS (ESI) m/z $(M+H)^+$396.1.

Compound 623 (60 mg, 59.9% yield, white solid) was synthesized from intermediate 3-amino-2-hydroxy-4-(3-(trifluoromethyl)phenyl)butanamide hydrochloride and 3-(2-fluorophenyl)-1-methyl-1H-pyrazole-4-carboxylic acid. Compound 623: N-(4-amino-3,4-dioxo-1-(3-(trifluoromethyl)phenyl)butan-2-yl)-3-(2-fluorophenyl)-1-methyl-1H-pyrazole-4-carboxamide: $^1H$ NMR (400 MHz, DMSO-$d_6$) δ 8.35 (br d, J=6.6 Hz, 1H), 8.15 (s, 1H), 8.00 (br s, 1H), 7.76 (br s, 1H), 7.64-7.48 (m, 4H), 7.33 (br dd, J=7.3, 15.4 Hz, 2H), 7.20-7.08 (m, 2H), 5.22 (br s, 1H), 3.90 (s, 3H), 3.28-2.84 (m, 2H). MS (ESI) m/z $(M+H)^+$363.1.

Example 233

Compound 562

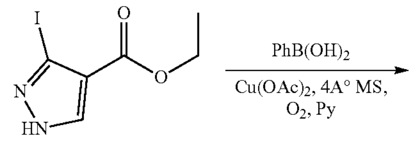

-continued

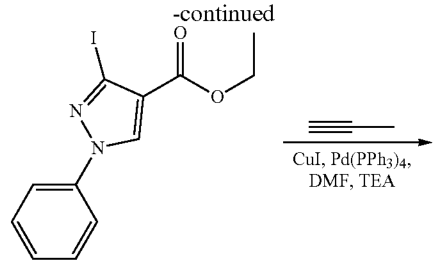

562A

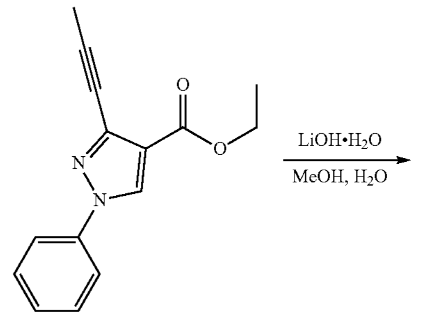

562B

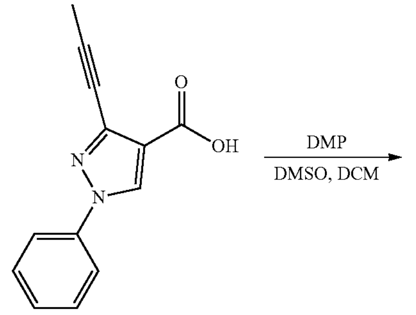

562C

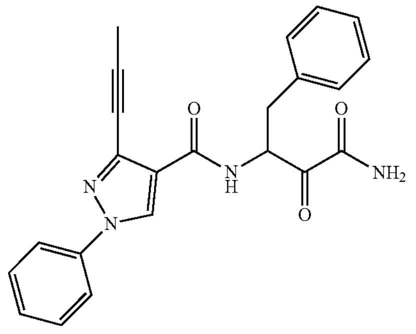

562

To a mixture of ethyl 3-iodo-1H-pyrazole-4-carboxylate compound (1 g, 3.8 mmol) and phenylboronic acid (504.1 mg, 4.1 mmol) in pyridine (20 mL) were added $Cu(OAc)_2$ (751 mg, 4.1 mmol, 1.1 eq), and 4A° molecular sieve (1 g). The mixture was stirred at 80° C. for 12 h under 02 atmosphere (~15 psi). The mixture was diluted with EA (40 mL), filtered through Celite. The filtrate was concentrated under reduce pressure to move solvent, then $H_2O$ (60 mL) and EA (50 mL) was added. The black insoluble substance was separated out and filtered through Celite two times. The cake was washed with EA (40 mL×2). The combined filtrate was separated and aqueous phase was extracted with EA (40 mL×2). The combined organic phase was washed with brine (50 mL×2), dried over $Na_2SO_4$, filtered and concentrated.

The crude product was purified by column chromatography ($SiO_2$, petroleum ether/ethyl acetate=20/1 to 5/1), then the fraction was collected and concentrated. The residue was triturated with PE (40 mL). The solid was collected and dried in vacuum to afford compound 2 (0.8 g, yield 61.4%) as white solid. $^1H$ NMR (DMSO-$d_6$, 400 MHz) δ 9.01 (s, 1H), 7.89 (d, J=8.4 Hz, 2H), 7.58-7.49 (m, 2H), 7.44-7.36 (m, 1H), 4.28 (q, J=7.2 Hz, 2H), 1.35-1.27 (m, 3H). MS (ESI) m/z $(M+H)^+$342.9.

To a mixture of compound 562A (0.3 g, 876.9 umol) and prop-1-yne (1M in DMF, 1.8 mL, 1.8 mmol) in DMF (6 mL) was added TEA (2 mL), CuI (33.4 mg, 175.4 umol), followed by $Pd(PPh_3)_4$ (101 mg, 87.7 umol). The mixture was degassed and purged with $N_2$ for 3 times, and then stirred at 55° C. for 12 h. The reaction mixture was combined with the reaction mixture on page ES5524-401-P1 for concentrating under reduce pressure. The residue was purified by flash silica gel chromatography (eluent of 015% ethyl acetate/petroleum ether gradient) to afford compound 562B (204.2 mg, yield 91.5%) as light yellow solid. $^1H$ NMR (DMSO-$d_6$, 400 MHz): δ 9.07 (s, 1H), 7.98-7.85 (m, 2H), 7.59-7.47 (m, 2H), 7.45-7.33 (m, 1H), 4.26 (q, J=7.0 Hz, 2H), 2.11 (s, 3H), 1.31 (t, J=7.2 Hz, 3H). MS (ESI) m/z $(M+H)^+$255.1

Compound 562 was synthesized from the intermediates, 562B by converting it to 562C and treatment with (3S)-3-amino-2-hydroxy-4-phenylbutanamide hydrochloride and using same procedures as described earlier for compound 12 to yield compound 562. Compound 549 (100 mg, yield: 35.7%, white solid) N-(4-amino-3,4-dioxo-1-phenylbutan-2-yl)-1-phenyl-3-(prop-1-yn-1-yl)-1H-pyrazole-4-carboxamide: $^1H$ NMR (400 MHz, DMSO-$d_6$) δ 8.85 (s, 1H), 7.92-7.76 (m, 4H), 7.66 (s, 1H), 7.57-7.48 (m, 2H), 7.43-7.36 (m, 1H), 7.33-7.26 (m, 2H), 7.26-7.17 (m, 3H), 5.63-5.48 (m, 1H), 3.34-3.26 (m, 1H), 3.15-3.09 (m, 1H), 2.03 (s, 3H). MS (ESI) m/z $(M+H)^+$401.2.

Example 234

Compound 583

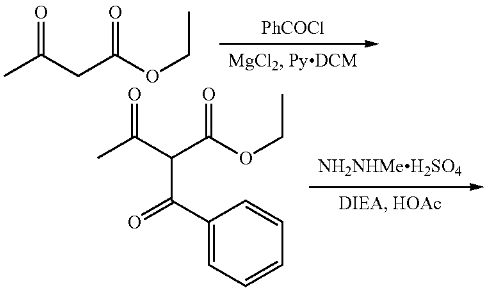

583A

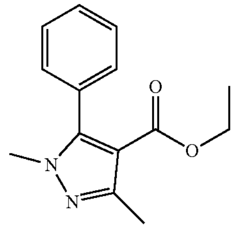

583B

+

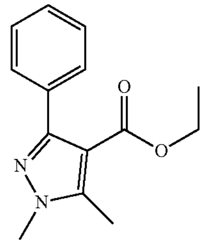

583C

-continued

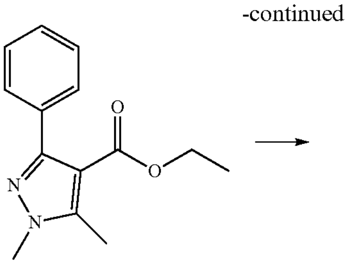

583

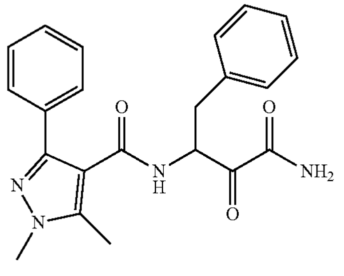

583

A mixture of ethyl 3-oxobutanoate (5 g, 38.42 mmol) and $MgCl_2$ (4.39 g, 46.10 mmol) and pyridine (6.8 mL, 84.52 mmol) in DCM (100 mL) was stirred at 0° C. for 30 min. Then a solution of benzoyl chloride (4.9 mL, 42.26 mmol) in DCM (20 mL) was added slowly. The mixture was stirred at 25° C. for 10 h. The reaction was quenched by the addition of 6N HCl (~20 mL). Then the mixture was diluted with $H_2O$ (60 mL). The organic layer was separated and the aqueous solution was extracted with DCM (35 mL×2). The combined organic layer was washed with saturated $NaHCO_3$ (50 mL), brine (50 mL), dried over $Na_2SO_4$, filtered and concentrated. The residue was purified by silica gel column chromatography (petroleum ether/ethyl acetate=8:1) to afford compound 583A (6.2 g, yield 68.9%) as colorless oil.

To a suspension of methylhydrazine (14.6 g, 101.6 mmol, $H_2SO_4$ salt) in DMF (15 mL) was added DIEA (35.3 mL, 203.2 mmol). The mixture was stirred at 25° C. for 15 min. Then the mixture was added to mixture of compound 583A (11.9 g, 50.8 mmol) in HOAc (150 mL). The mixture was stirred at 25° C. for 8 h. The mixture was concentrated. The residue was treated with $H_2O$ (300 mL) and EA (100 mL). The organic layer was separated and the aqueous layer was extracted with EA (100 mL). The combined organic layer was washed with saturated $NaHCO_3$ (100 mL), brine (100 mL), dried over $MgSO_4$, filtered and concentrated. The residue was purified by silica gel column chromatography (petroleum ether/ethyl acetate=10:1 to 5:1) to afford compound 583B (2.3 g, yield 18.5%) as colorless oil and compound 583C (6 g, yield 48.3%) as pale yellow oil. Compound 583B: $^1H$ NMR (DMSO-$d_6$, 400 MHz): δ 7.49-7.43 (m, 3H), 7.39-7.34 (m, 2H), 3.95 (q, J=7.1 Hz, 2H), 3.56-3.51 (m, 3H), 2.34 (s, 3H), 0.96 (t, J=7.1 Hz, 3H). Compound 583C: $^1H$ NMR (DMSO-$d_6$, 400 MHz): δ 7.51-7.47 (m, 2H), 7.38-7.31 (m, 3H), 4.09 (q, J=7.1 Hz, 2H), 3.78 (s, 3H), 2.47 (br s, 3H), 1.11 (t, J=7.1 Hz, 3H).

Compound 583 was synthesized from the intermediates, 583C and 3-amino-2-hydroxy-4-phenylbutanamide hydrochloride and using same procedures as described earlier for compound 12 to yield compound 583. Compound 583 (100 mg, yield: 46.2%, white solid) N-(4-amino-3,4-dioxo-1-phenylbutan-2-yl)-1-phenyl-3-(prop-1-yn-1-yl)-1H-pyrazole-4-carboxamide: $^1H$ NMR (400 MHz, DMSO-$d_6$) δ 8.38

(d, J=7.5 Hz, 1H), 8.12 (s, 1H), 7.86 (s, 1H), 7.47-7.41 (m, 2H), 7.31-7.21 (m, 8H), 5.38 (ddd, J=3.6, 7.4, 10.6 Hz, 1H), 3.72 (s, 3H), 3.19 (dd, J=3.4, 14.0 Hz, 1H), 2.74 (dd, J=10.6, 13.9 Hz, 1H), 2.12 (s, 3H). MS (ESI) m/z $(M+H)^+$391.1.

Biological Data

Example 235

Calpain 1, 2, and 9 activity and inhibition thereof was assessed by means of a continuous fluorescence assay. The SensoLyte 520 Calpain substrate (Anaspec Inc) was optimized for detecting calpain activity. This substrate contains an internally quenched 5-FAM/QXLTM 520 FRET pair. Calpains 1, 2, and 9 cleave the FRET substrate into two separate fragments resulting in an increase of 5-FAM fluorescence that is proportional to calpain activity Assays were typically setup in black 384-well plates using automated liquid handling as follows. Calpain assay base buffer typically contains 50 mM Tris, pH 7.5, 100 mM NaCl and 1 mM DTT. Inhibitors were serially diluted in DMSO and used to setup 2× mixtures with calpains in the aforementioned buffer. After incubation at ambient temperature (25C), the reaction was initiated by adding a 2× mix of the fluorescent peptide substrate and CaCl2) (required for in-situ calpain activation) in the same buffer. Reaction progress curve data were typically collected for 10 min using excitation/emission wavelengths of 490 nm/520 nm on SpectraMax i3× or the FLIPR-Tetra plate readers (Molecular Devices Inc). Reaction rates were calculated from progress curve slopes typically over 1-5 min. Dose response curves (rate vs. log inhibitor concentration) were typically fit to a 4-parameter logistic function to extract IC50 values.

Calpain activity in SH-SY5Y cells and inhibition thereof were assessed by means of a homogeneous, fluorescence assay that uses the cell-permeable and pro-fluorescent calpain substrate Suc-LLVY-AMC (Sigma-Aldrich Inc). Upon intracellular calpain cleavage of Suc-LLVY-AMC, fluorescent amino-methyl-coumarin (AMC) is released into the media resulting in a continuous increase in fluorescence signal that is proportional to intra-cellular calpain activity.

Assays were typically setup by seeding SH-SY5Y cells in black 384-well plates at 40 k/per well in RPMI-1640 containing 1% serum followed by 37C overnight incubation. Next morning, cells were pre-incubated for 30 min with serially diluted compounds followed by addition of 100 uM of Suc-LLVY-AMC substrate. The continuous increase in AMC fluorescence is monitored using a FLIPR Tetra plate reader (Molecular Devices Inc) and slopes measured to report calpain activity. Dose response curves (slopes vs. log inhibitor concentration) were typically fit to a 4-parameter logistic function to extract IC50 values.

Calpain activity in SH-SY5Y cells and inhibition thereof were also assessed by a western blot based assay that measures a calpain-specific breakdown product of the alpha chain of non-erythrocytic spectrin (SBDP-150). Addition of the calcium ionophore A23187 was used to induce calpain activity and SBDP-150 formation.

These assays were typically setup by seeding SH-SY5Y cells in 96-well plates at 150 k/per well in DMEM containing 10% serum, followed by 37C incubation for 24 hrs. The cells were then pre-incubated for 60 min with serially diluted compounds followed by addition of 25 uM A23187 and further incubation for 90 min. Total cellular protein was extracted in RIPA buffer, boiled in gel loading buffer and run on SDS-PAGE gel. The gel was processed via Western Blotting (dry transfer) to quantify SBDP-150 (AA6 antibody, Enzo Inc) and either GAPDH or HSP90 as loading controls. Normalized SBDP-150 levels vs. log inhibitor concentration were plotted to get dose response curves that are typically fit to a 4-parameter logistic function to extract IC50 values.

Calpain Inhibition

TABLE 2

Calpain inhibition assay
Column A: Human Calpain 1/NS1 IC50
Column B: Human Calpain 2/NS1 IC50
Column C: Human Calpain 9/NS1 IC50
Column D: SH-SY5Y Spectrin IC50
Column E: SH-SY5Y + AMC IC50

| Compound No. | Column A | Column B | Column C | Column D | Column E |
|---|---|---|---|---|---|
| 1 | A | A | A | ND | ND |
| 2 | A | A | A | E | ND |
| 3 | A | A | A | ND | ND |
| 4 | A | A | A | ND | ND |
| 5 | C | B | B | ND | ND |
| 6 | A | A | A | ND | F |
| 7 | A | A | A | ND | ND |
| 8 | A | A | A | ND | ND |
| 9 | A | A | A | ND | E |
| 10 | A | A | A | ND | ND |
| 11 | A | A | A | ND | ND |
| 12 | A | A | A | E | D |
| 13 | A | A | A | F | ND |
| 14 | A | A | A | ND | ND |
| 15 | A | A | A | D | E |
| 16 | A | A | A | E | E |
| 17 | A | A | A | D | F |
| 18 | A | A | A | ND | ND |
| 19 | A | A | A | E | F |
| 20 | A | A | A | ND | ND |
| 21 | A | A | A | ND | ND |
| 22 | A | A | A | ND | ND |
| 23 | A | A | A | E | F |
| 24 | A | A | A | F | F |
| 25 | A | A | A | ND | E |
| 26 | A | A | A | D | D |
| 27 | A | A | A | E | F |
| 28 | A | A | A | D | D |
| 29 | A | A | A | ND | ND |
| 30 | A | A | A | D | E |
| 31 | A | A | A | ND | ND |
| 32 | A | A | A | D | F |
| 33 | A | A | A | D | D |
| 34 | A | A | A | ND | ND |
| 35 | A | A | A | ND | ND |
| 36 | C | B | B | ND | ND |
| 37 | A | A | A | ND | ND |
| 38 | A | A | A | ND | ND |
| 39 | A | A | A | ND | ND |
| 40 | A | A | A | ND | ND |
| 41 | B | A | B | ND | ND |
| 42 | A | A | C | ND | ND |
| 43 | A | A | A | ND | ND |
| 44 | A | A | A | E | F |
| 45 | A | A | A | F | E |
| 46 | A | A | A | ND | ND |
| 47 | A | A | A | ND | ND |
| 48 | B | B | B | ND | ND |
| 49 | A | A | A | D | D |
| 50 | A | A | A | D | F |
| 51 | B | B | C | ND | ND |
| 52 | A | A | A | ND | ND |
| 53 | A | A | B | ND | ND |
| 54 | A | A | A | ND | ND |
| 55 | A | A | A | D | F |
| 56 | A | A | A | ND | ND |
| 57 | A | A | A | D | E |
| 58 | A | A | A | E | F |
| 59 | A | A | A | ND | D |

TABLE 2-continued

Calpain inhibition assay
Column A: Human Calpain 1/NS1 IC50
Column B: Human Calpain 2/NS1 IC50
Column C: Human Calpain 9/NS1 IC50
Column D: SH-SY5Y Spectrin IC50
Column E: SH-SY5Y + AMC IC50

| Compound No. | Column A | Column B | Column C | Column D | Column E |
|---|---|---|---|---|---|
| 60 | A | A | A | D | D |
| 61 | A | A | A | ND | ND |
| 62 | A | A | A | ND | ND |
| 63 | A | A | A | D | D |
| 64 | A | A | A | ND | ND |
| 65 | C | C | C | ND | ND |
| 66 | B | A | A | ND | ND |
| 67 | C | C | C | ND | ND |
| 68 | A | A | A | ND | ND |
| 69 | A | A | A | ND | ND |
| 70 | A | A | A | ND | ND |
| 71 | B | B | C | ND | ND |
| 72 | A | A | A | D | D |
| 73 | A | A | C | ND | ND |
| 74 | A | A | A | ND | ND |
| 75 | A | A | B | ND | ND |
| 76 | A | A | B | ND | ND |
| 77 | A | B | C | ND | ND |
| 78 | C | B | A | ND | ND |
| 79 | A | A | A | ND | ND |
| 80 | B | A | B | ND | ND |
| 81 | A | A | A | D | E |
| 82 | A | A | A | D | F |
| 83 | A | A | A | D | F |
| 84 | A | A | A | D | D |
| 85 | A | A | A | ND | ND |
| 86 | A | A | A | ND | ND |
| 87 | C | A | A | ND | ND |
| 88 | A | A | A | ND | ND |
| 89 | A | A | B | ND | ND |
| 90 | A | A | B | ND | ND |
| 91 | B | A | B | ND | ND |
| 92 | B | B | A | ND | ND |
| 93 | A | A | A | ND | ND |
| 94 | A | A | A | ND | ND |
| 96 | A | A | A | ND | ND |
| 97 | A | A | A | ND | ND |
| 98 | A | A | A | ND | ND |
| 99 | A | A | A | E | E |
| 100 | A | A | A | ND | ND |
| 101 | C | C | C | ND | ND |
| 102 | A | A | A | ND | ND |
| 103 | A | A | A | F | F |
| 104 | A | A | A | ND | ND |
| 105 | A | A | A | F | F |
| 106 | A | A | A | D | F |
| 107 | A | A | A | D | D |
| 108 | A | A | A | ND | ND |
| 109 | A | A | A | ND | ND |
| 110 | A | A | B | ND | ND |
| 111 | A | A | A | ND | ND |
| 112 | A | A | A | D | F |
| 113 | A | A | A | D | F |
| 114 | B | A | B | ND | ND |
| 115 | C | A | C | ND | ND |
| 116 | A | B | C | ND | ND |
| 117 | B | B | B | ND | ND |
| 118 | A | A | A | D | F |
| 119 | A | A | A | ND | ND |
| 120 | A | A | A | D | E |
| 121 | A | A | A | D | E |
| 122 | A | A | A | ND | ND |
| 123 | A | A | A | ND | ND |
| 124 | A | A | A | ND | ND |
| 125 | C | C | C | ND | ND |
| 126 | A | A | A | D | F |
| 127 | A | A | A | ND | ND |
| 128 | B | C | B | ND | ND |
| 129 | B | C | B | ND | ND |
| 130 | A | A | A | D | F |
| 131 | A | A | A | E | F |
| 132 | A | A | A | ND | ND |
| 133 | A | A | A | ND | ND |
| 134 | B | B | B | ND | ND |
| 135 | A | A | C | ND | ND |
| 136 | A | A | A | E | E |
| 137 | C | C | C | ND | ND |
| 138 | A | A | A | ND | ND |
| 139 | A | A | A | ND | ND |
| 140 | A | A | A | ND | E |
| 141 | A | A | A | E | ND |
| 142 | A | A | A | E | D |
| 143 | A | A | A | E | D |
| 144 | A | A | A | D | D |
| 145 | A | A | A | D | D |
| 146 | A | A | A | E | D |
| 147 | A | A | A | E | E |
| 148 | A | A | A | ND | ND |
| 149 | C | C | C | ND | ND |
| 150 | C | C | C | ND | ND |
| 151 | A | A | A | ND | ND |
| 152 | A | A | A | ND | ND |
| 153 | A | A | A | D | F |
| 154 | A | A | A | E | F |
| 155 | A | A | A | F | ND |
| 156 | A | A | A | D | F |
| 157 | A | A | A | F | F |
| 158 | A | A | A | E | F |
| 159 | A | A | A | E | F |
| 160 | A | A | A | E | F |
| 161 | A | A | A | D | F |
| 162 | A | A | A | F | F |
| 163 | A | A | A | E | E |
| 164 | A | A | A | F | F |
| 165 | A | A | A | ND | ND |
| 166 | A | A | A | E | F |
| 167 | A | A | A | ND | ND |
| 168 | A | A | A | E | D |
| 169 | A | A | A | ND | ND |
| 170 | A | A | A | F | F |
| 171 | A | B | A | F | E |
| 172 | A | A | A | D | F |
| 173 | A | A | A | F | F |
| 174 | A | A | A | F | F |
| 175 | A | A | A | F | D |
| 176 | A | A | A | ND | ND |
| 177 | A | A | A | E | D |
| 178 | A | A | A | D | D |
| 179 | A | A | A | E | F |
| 180 | A | A | A | D | E |
| 181 | A | A | A | D | D |
| 182 | A | A | A | E | D |
| 183 | A | A | A | D | E |
| 184 | A | A | A | ND | F |
| 185 | C | B | B | F | F |
| 186 | B | B | B | F | F |
| 187 | A | A | A | E | F |
| 188 | A | A | A | E | F |
| 189 | A | A | A | ND | ND |
| 190 | B | C | B | ND | ND |
| 191 | A | A | A | ND | ND |
| 192 | A | A | A | ND | ND |
| 193 | B | A | B | ND | F |
| 194 | A | A | A | ND | ND |
| 195 | A | B | A | ND | ND |
| 196 | A | A | B | ND | ND |
| 197 | B | C | B | ND | ND |
| 198 | A | A | A | F | F |
| 199 | A | A | A | F | ND |
| 200 | A | A | A | E | F |

TABLE 2-continued

Calpain inhibition assay
Column A: Human Calpain 1/NS1 IC50
Column B: Human Calpain 2/NS1 IC50
Column C: Human Calpain 9/NS1 IC50
Column D: SH-SY5Y Spectrin IC50
Column E: SH-SY5Y + AMC IC50

| Compound No. | Column A | Column B | Column C | Column D | Column E |
|---|---|---|---|---|---|
| 201 | A | A | B | ND | ND |
| 202 | A | A | A | E | F |
| 203 | A | A | C | ND | F |
| 204 | C | C | C | ND | ND |
| 205 | A | A | A | ND | ND |
| 206 | A | C | C | ND | ND |
| 207 | A | A | A | E | D |
| 208 | A | A | A | D | F |
| 209 | A | A | A | ND | ND |
| 210 | A | A | A | ND | ND |
| 211 | A | A | A | ND | ND |
| 212 | A | A | A | E | D |
| 213 | A | A | A | ND | ND |
| 214 | A | A | A | ND | F |
| 215 | A | A | A | ND | ND |
| 216 | A | A | A | D | F |
| 217 | A | A | A | D | F |
| 218 | A | A | A | E | F |
| 219 | B | B | B | ND | ND |
| 220 | A | A | B | ND | ND |
| 221 | A | A | A | F | ND |
| 222 | A | A | A | E | F |
| 223 | A | A | A | E | F |
| 224 | A | B | B | ND | ND |
| 225 | A | C | C | ND | ND |
| 226 | A | A | A | D | D |
| 227 | A | A | A | D | F |
| 228 | A | A | A | D | F |
| 229 | A | A | A | D | D |
| 230 | A | A | A | D | D |
| 231 | A | A | A | F | F |
| 232 | C | C | B | ND | ND |
| 233 | A | A | B | ND | ND |
| 234 | A | A | A | ND | ND |
| 235 | A | A | A | ND | ND |
| 238 | B | B | A | ND | ND |
| 239 | A | A | A | E | D |
| 240 | A | A | A | ND | ND |
| 241 | A | A | A | ND | ND |
| 242 | A | A | A | F | D |
| 243 | A | A | A | E | F |
| 244 | A | A | A | F | D |
| 245 | A | A | A | E | D |
| 246 | A | A | A | E | D |
| 247 | B | B | B | ND | ND |
| 248 | A | A | A | D | D |
| 249 | A | A | A | E | F |
| 250 | A | A | A | E | E |
| 251 | A | A | A | F | F |
| 252 | C | C | C | F | F |
| 253 | A | A | A | E | F |
| 254 | A | ND | A | E | D |
| 255 | A | A | A | D | D |
| 256 | C | C | A | ND | ND |
| 257 | A | A | A | E | D |
| 258 | A | A | A | ND | ND |
| 259 | A | A | A | D | E |
| 260 | A | A | A | ND | ND |
| 261 | A | A | A | ND | ND |
| 262 | B | B | A | ND | ND |
| 263 | A | A | A | ND | ND |
| 264 | B | B | C | ND | ND |
| 265 | A | A | A | D | F |
| 266 | A | A | A | F | F |
| 267 | A | A | A | E | D |
| 268 | A | A | A | F | F |
| 269 | B | B | A | ND | ND |
| 270 | A | A | A | ND | ND |
| 271 | A | A | A | ND | F |
| 272 | C | B | B | ND | ND |
| 273 | C | A | A | ND | ND |
| 274 | A | A | A | ND | ND |
| 276 | A | A | A | D | D |
| 277 | A | A | A | E | D |
| 278 | A | A | A | D | F |
| 279 | A | A | B | E | D |
| 280 | A | A | A | ND | ND |
| 281 | A | A | A | ND | E |
| 282 | A | A | A | E | D |
| 283 | A | A | A | ND | ND |
| 284 | C | C | C | ND | ND |
| 285 | A | A | A | F | E |
| 286 | A | A | A | D | F |
| 287 | A | B | A | ND | ND |
| 288 | A | A | A | F | F |
| 289 | A | A | A | E | F |
| 290 | A | A | A | ND | ND |
| 291 | A | A | A | ND | ND |
| 292 | A | A | A | ND | F |
| 293 | A | A | A | E | D |
| 294 | B | B | A | E | F |
| 295 | C | C | C | ND | ND |
| 296 | A | A | A | D | F |
| 297 | C | B | A | ND | ND |
| 298 | C | C | C | ND | ND |
| 299 | A | A | A | E | ND |
| 303 | A | A | A | E | D |
| 304 | A | A | A | ND | ND |
| 305 | A | A | A | ND | D |
| 306 | B | B | B | ND | D |
| 307 | A | A | A | ND | ND |
| 308 | A | A | A | ND | F |
| 309 | A | A | A | E | D |
| 310 | A | A | B | ND | ND |
| 311 | A | A | A | ND | ND |
| 312 | A | A | B | ND | ND |
| 313 | A | A | A | F | F |
| 314 | B | B | B | ND | ND |
| 315 | B | B | A | ND | ND |
| 316 | C | C | B | ND | ND |
| 317 | A | A | A | E | F |
| 318 | A | B | A | ND | ND |
| 319 | A | A | A | ND | ND |
| 320 | A | A | A | E | F |
| 321 | A | A | A | D | F |
| 322 | A | A | A | E | F |
| 323 | A | A | A | ND | F |
| 324 | A | A | B | ND | ND |
| 325 | A | A | A | F | F |
| 326 | A | A | A | E | D |
| 327 | A | A | A | D | D |
| 328 | A | A | A | E | F |
| 329 | A | A | A | F | F |
| 330 | A | A | A | E | E |
| 331 | A | A | A | D | F |
| 332 | A | A | A | F | F |
| 333 | A | A | A | F | F |
| 334 | A | A | A | F | D |
| 335 | A | A | A | ND | D |
| 336 | A | A | A | ND | D |
| 337 | A | A | A | D | D |
| 338 | A | A | A | F | D |
| 339 | A | A | A | F | E |
| 340 | A | A | A | F | ND |
| 341 | A | A | B | F | E |
| 342 | A | A | A | E | E |
| 343 | A | A | A | E | ND |
| 344 | A | A | A | F | E |
| 345 | C | C | C | F | ND |
| 346 | C | B | B | F | ND |

TABLE 2-continued

Calpain inhibition assay
Column A: Human Calpain 1/NS1 IC50
Column B: Human Calpain 2/NS1 IC50
Column C: Human Calpain 9/NS1 IC50
Column D: SH-SY5Y Spectrin IC50
Column E: SH-SY5Y + AMC IC50

| Compound No. | Column A | Column B | Column C | Column D | Column E |
|---|---|---|---|---|---|
| 347 | A | A | A | E | F |
| 348 | A | A | A | F | D |
| 349 | A | A | A | F | D |
| 350 | A | A | A | E | D |
| 351 | A | A | A | E | D |
| 352 | A | A | A | F | E |
| 353 | A | A | A | E | F |
| 354 | A | A | A | D | D |
| 355 | A | A | A | ND | E |
| 356 | A | A | A | F | F |
| 357 | A | A | A | D | D |
| 358 | A | A | A | E | D |
| 359 | A | A | A | ND | E |
| 360 | C | C | C | F | F |
| 361 | A | A | A | D | D |
| 362 | A | A | A | D | F |
| 363 | A | A | A | D | F |
| 364 | A | A | A | E | ND |
| 365 | A | A | A | D | D |
| 366 | A | A | A | E | D |
| 367 | A | A | A | D | D |
| 368 | A | A | A | ND | D |
| 369 | A | A | A | D | F |
| 370 | A | A | A | E | F |
| 371 | A | A | A | D | D |
| 372 | A | A | A | D | D |
| 373 | A | A | A | D | D |
| 374 | A | A | A | D | D |
| 375 | A | A | A | D | D |
| 376 | A | A | A | D | D |
| 377 | A | A | A | D | E |
| 378 | A | A | A | D | F |
| 379 | A | ND | A | D | D |
| 380 | A | A | A | D | D |
| 381 | A | A | A | D | D |
| 382 | A | A | A | E | D |
| 383 | A | A | A | D | D |
| 384 | A | A | A | D | D |
| 385 | A | A | A | D | F |
| 386 | A | A | A | F | E |
| 387 | A | A | A | F | F |
| 388 | A | A | A | D | E |
| 389 | A | A | A | D | D |
| 390 | A | A | A | ND | ND |
| 391 | A | A | A | ND | ND |
| 392 | C | C | C | E | D |
| 393 | A | A | A | E | D |
| 394 | A | A | A | F | F |
| 395 | C | B | B | ND | ND |
| 396 | A | A | A | D | E |
| 397 | A | A | A | D | F |
| 398 | A | A | A | F | F |
| 399 | A | A | B | F | F |
| 400 | A | A | A | F | F |
| 401 | A | A | A | D | F |
| 402 | A | A | A | E | F |
| 403 | A | A | A | D | D |
| 404 | A | A | A | D | D |
| 405 | A | A | A | ND | ND |
| 406 | A | A | A | E | D |
| 407 | A | A | A | E | E |
| 408 | C | B | C | E | D |
| 409 | A | A | A | ND | ND |
| 410 | B | B | B | ND | ND |
| 411 | A | A | A | ND | E |
| 413 | A | A | A | F | F |
| 414 | A | A | A | ND | F |
| 415 | A | A | A | F | F |
| 416 | A | A | A | F | F |
| 417 | A | A | A | F | F |
| 418 | A | A | A | E | E |
| 419 | A | A | A | E | F |
| 420 | A | A | A | D | F |
| 421 | A | A | A | E | D |
| 422 | C | B | B | F | F |
| 423 | A | A | A | D | D |
| 424 | B | A | A | E | F |
| 428 | A | A | A | D | F |
| 429 | A | A | A | ND | ND |
| 430 | A | A | A | D | D |
| 431 | A | A | A | F | D |
| 432 | A | A | A | D | D |
| 433 | B | B | C | E | F |
| 434 | C | C | C | ND | F |
| 435 | C | B | B | F | D |
| 436 | A | A | A | F | D |
| 437 | A | A | A | F | E |
| 438 | A | A | A | E | E |
| 439 | A | A | A | D | F |
| 440 | A | A | A | D | F |
| 441 | C | C | C | F | F |
| 442 | A | A | A | E | F |
| 443 | A | A | A | D | E |
| 444 | A | A | A | E | D |
| 445 | A | A | A | D | F |
| 447 | A | A | A | E | E |
| 448 | A | A | A | D | D |
| 454 | A | A | B | E | D |
| 455 | B | A | C | F | D |
| 456 | A | A | A | F | D |
| 457 | A | A | B | ND | D |
| 458 | A | A | A | E | D |
| 459 | A | A | A | E | D |
| 460 | A | A | A | F | F |
| 461 | A | A | A | D | F |
| 462 | A | A | A | E | ND |
| 463 | A | A | A | D | F |
| 464 | A | A | A | D | D |
| 465 | A | A | A | D | F |
| 466 | A | A | A | D | F |
| 467 | A | A | A | D | F |
| 468 | A | A | A | D | F |
| 469 | A | A | A | E | D |
| 470 | A | A | ND | E | D |
| 471 | A | A | A | E | E |
| 472 | A | A | A | E | D |
| 473 | A | A | A | E | E |
| 474 | A | A | A | E | E |
| 475 | B | A | B | D | F |
| 476 | A | A | A | E | F |
| 477 | B | A | B | E | F |
| 478 | A | A | B | F | F |
| 479 | A | A | A | E | F |
| 480 | A | A | A | E | E |
| 481 | A | A | A | F | ND |
| 482 | B | B | A | ND | ND |
| 483 | C | B | A | F | ND |
| 484 | A | A | A | E | D |
| 485 | A | A | A | E | E |
| 486 | A | A | A | E | D |
| 487 | B | A | A | ND | ND |
| 488 | B | B | B | ND | ND |
| 489 | A | A | A | E | E |
| 490 | C | B | A | ND | ND |
| 491 | A | A | B | ND | ND |
| 492 | A | A | A | E | F |
| 493 | A | A | B | F | ND |
| 494 | A | A | A | ND | F |
| 495 | A | A | A | E | D |
| 496 | A | A | A | E | F |

TABLE 2-continued

Calpain inhibition assay
Column A: Human Calpain 1/NS1 IC50
Column B: Human Calpain 2/NS1 IC50
Column C: Human Calpain 9/NS1 IC50
Column D: SH-SY5Y Spectrin IC50
Column E: SH-SY5Y + AMC IC50

| Compound No. | Column A | Column B | Column C | Column D | Column E |
|---|---|---|---|---|---|
| 497 | A | A | A | E | D |
| 498 | A | A | A | F | E |
| 499 | A | A | A | E | D |
| 500 | A | A | A | E | D |
| 501 | A | A | A | E | D |
| 502 | A | A | A | E | D |
| 503 | A | A | A | ND | E |
| 504 | A | A | A | F | F |
| 505 | A | A | A | D | F |
| 506 | A | A | A | E | E |
| 507 | A | A | A | E | D |
| 508 | A | A | A | D | D |
| 509 | A | A | A | E | E |
| 510 | A | A | A | E | E |
| 511 | A | A | A | ND | F |
| 512 | B | B | B | F | D |
| 513 | B | B | B | F | D |
| 514 | A | A | A | F | D |
| 515 | A | A | A | F | F |
| 516 | A | A | A | F | ND |
| 517 | A | A | A | E | E |
| 518 | A | A | A | E | D |
| 519 | C | C | C | ND | F |
| 520 | A | A | A | F | E |
| 521 | A | A | B | E | ND |
| 522 | A | A | A | F | D |
| 523 | A | ND | ND | E | D |
| 524 | A | A | A | E | D |
| 525 | A | A | A | F | D |
| 526 | A | A | A | F | D |
| 527 | A | A | A | F | D |
| 528 | A | A | A | F | |
| 529 | A | A | A | F | D |
| 530 | A | A | A | F | F |
| 531 | A | A | A | E | F |
| 532 | A | A | A | D | D |
| 541 | A | A | A | E | F |
| 546 | A | A | A | D | D |
| 547 | A | A | A | D | D |
| 548 | A | A | A | F | F |
| 549 | A | A | A | F | D |
| 550 | A | A | A | F | E |
| 551 | A | A | A | E | F |
| 552 | A | A | A | D | D |
| 553 | A | A | A | F | D |
| 554 | A | A | A | D | D |
| 555 | A | A | A | F | D |
| 556 | A | A | A | D | D |
| 557 | A | A | A | F | D |
| 558 | A | A | A | E | D |
| 559 | A | A | A | E | F |
| 560 | A | A | A | E | F |
| 561 | A | A | A | E | E |
| 562 | C | C | C | F | D |
| 563 | A | A | A | D | D |
| 564 | A | A | A | D | D |
| 565 | A | A | A | D | F |
| 566 | A | A | A | E | D |
| 567 | A | A | A | D | D |
| 568 | A | A | A | F | D |
| 569 | A | A | A | F | E |
| 570 | A | A | A | F | F |
| 571 | A | A | A | F | F |
| 572 | A | A | A | F | D |
| 573 | A | A | A | F | D |
| 574 | A | A | A | F | F |
| 575 | A | A | A | D | F |
| 576 | A | A | A | D | D |
| 577 | A | A | A | D | D |
| 578 | A | A | A | D | D |
| 579 | A | A | A | F | D |
| 580 | A | A | A | E | D |
| 581 | A | A | A | F | E |
| 582 | A | A | A | D | E |
| 583 | A | A | A | F | F |
| 584 | A | A | A | D | E |
| 585 | A | A | A | E | F |
| 586 | A | A | A | E | E |
| 587 | A | A | B | F | F |
| 588 | A | A | A | E | F |
| 591 | A | A | A | F | F |
| 592 | A | A | A | E | D |
| 593 | A | A | A | F | F |
| 594 | A | A | A | E | D |
| 595 | A | A | A | E | F |
| 596 | A | A | A | E | D |
| 597 | A | A | A | E | E |
| 598 | A | A | A | D | D |
| 599 | ND | ND | A | F | F |
| 600 | A | A | A | E | F |
| 601 | B | A | B | F | F |
| 602 | A | A | A | E | F |
| 603 | B | B | B | F | F |
| 604 | A | A | A | F | D |
| 605 | A | A | A | F | F |
| 607 | A | A | A | E | F |
| 608 | A | A | A | F | ND |
| 609 | A | A | A | D | ND |
| 610 | A | A | A | D | ND |
| 611 | A | A | A | E | ND |
| 613 | B | B | A | ND | ND |
| 614 | B | B | B | ND | ND |
| 615 | A | A | A | ND | ND |
| 616 | B | A | B | ND | ND |
| 617 | B | A | A | ND | ND |
| 618 | A | A | A | ND | ND |
| 619 | A | A | A | ND | ND |
| 620 | A | A | B | ND | ND |
| 621 | A | A | A | ND | ND |
| 622 | A | A | A | ND | ND |
| 623 | A | A | A | ND | ND |
| 624 | A | A | A | ND | ND |
| 625 | A | A | A | ND | ND |
| 626 | A | A | A | ND | ND |
| 627 | B | A | B | ND | ND |
| 628 | A | A | A | ND | ND |
| 629 | A | A | A | ND | ND |
| 630 | A | A | A | ND | ND |

A: <3 uM;
B: 3-10 uM;
C: >10 uM;
D: <10 uM;
E: 10-25 uM;
F: >25 uM
ND: Not Determined

Example 236: Animal Models & Studies

Bleomycin-Induced Pulmonary Fibrosis in Mice or Rats

The method for inducing pulmonary fibrosis in mice is described in Current Protocols in Pharmacology: 5.46.1, entitled "Mouse Models of Bleomycin-induced Pulmonary Fibrosis". In order to induce pulmonary fibrosis, 6-8 week old C57Bl/6 mice or Wistar rats are instilled once oropharyngeally with ~1.5 U/kg of bleomycin sulfate (Calbiochem, Billerica, Mass.). Briefly, for oropharyngeal administration of bleomycin, mice or rats are anesthetized with isofluorane and then suspended on its back at a 60 degree angle on an inclined surface with a rubber band running under the upper incisors. The airway is opened while securing the tongue with one arm of padded forceps and bleomycin is administered into the back of the oral cavity with a syringe. The animal's tongue and mouth were held open until the liquid disappeared from the oral cavity. The animal was then returned to its cage and monitored until fully recovered from the anesthesia. The study is terminated on day 14-28 for oropharyngeally administered bleomycin in mice and rats.

In-Vivo Efficacy Data

TABLE 3

Bleomycin-induced pulmonary fibrosis in mice (14 d)

| Compound ID | % reduction compared to vehicle |
|---|---|
| 60 | −24% |
| 72 | −35% |
| 403 | −29% |
| 484 | −35% |
| 357 | −13% |
| 485 | −41% |
| 406 | −25% |
| 404 | −24% |
| 405 | −33% |
| 495 | −27% |
| pirfenidone | −14% |

Alternatively, for systemic bleomycin administration by osmotic pumps in mice, the pumps are loaded with bleomycin and implanted subcutaneously under isofluorane anesthesia as described in Lee, Am J Physiol Lung Cell Mol Physiol, 2014. Briefly, mice are systemically administered ~50-100 U/kg bleomycin (Blenoxane; Teva Pharma, North Wales, Pa.) via osmotic pumps for 7 days. On day 10, the osmotic pumps are removed, and the study is continued until day 35.

All animals are euthanized at the termination of the studies by cervical dislocation for gross necropsy, and blood collected by cardiac puncture. The lungs from each animal are dissected from the animal and weighed. The BAL cells and fluid are collected by lavaging the lung twice with 0.5 ml Hanks Balanced Salt Solution (HBSS; VWR, Radnor, Pa.). After collection of BAL cells and fluid, lungs are dissected and removed from each animal. Whole lungs are inflated with 10% NBF and then fixed in 10% NBF for histology. Severity of fibrosis in the lungs is evaluated using a modified Ashcroft score (Hubner, Biotechniques, 2008) and subjective fibrosis scores. Lung sections were graded by averaging 5 microscopic fields at 20× on an Ashcroft scale as follows: Grade 0=normal lung; Grade 1=minimally detectable thickening of alveolar walls; Grade 2=Mild thickening of alveolar walls. Grade 3=moderate contiguous thickening of walls with fibrous nodules; Grade 4=Thickened septae and confluent fibrotic masses that total less than 10% of microscopic field. Grade 5=increased fibrosis with definite damage to lung structure and formation of fibrous bands or small fibrous masses between 10 and 50% of microscopic field; Grade 6=Large contiguous fibrotic masses consolidating more than 50% of microscopic field. Grade 7=severe distortion of structure and large fibrous areas; Grade 8=total fibrous obliteration of lung within microscopic field. Each slide was examined at 20× magnification and the score for 5 separate representative fields was averaged for each animal. Subjective scores (H&E and Trichrome-stained slides) were evaluated at 2× magnification for an overall assessment of pathologic change. A score of 0=no detectable findings to 5=complete involvement of consolidation. Scores in each group were averaged and standard error was calculated using Excel 2010. Dense, organized inflammatory exudates were scored as fibrosis. Other tissues were evaluated microscopically and scored routinely.

Carbon Tetrachloride-Induced Liver Fibrosis in Mice or Rats

Carbon tetrachloride-induced liver fibrosis is a widely used and accepted model for evaluating novel antifibrotic therapies. The methods for inducing liver fibrosis by carbon tetrachloride administration is described in Lee, J Clin Invest, 1995 and Tsukamoto, Semin Liver Dis, 1990. Briefly, male C57BL/6 mice are challenged with 1 mg/kg carbon tetrachloride (Sigma Aldrich, diluted 1:7 in corn or olive oil) administered by intraperitoneal injection twice weekly for a period of 4 weeks. Mice are euthanized on day 28. In an alternative implementation, Wistar rats are administered carbon tetrachloride by intraperitoneal injection three times per week for 8-12 weeks. Rats are euthanized at the termination of the experiment, 8-12 after study initiation.

Blood is collected by cardiac puncture and processed into serum for evaluation of liver enzymes (including ALT, AST, ALP, etc) at several timepoints throughout the study and at termination of the study. The liver tissues from all animals are collected and fixed by immersion in 10% neutral buffered formalin, processed, paraffin embedded, sectioned, mounted, and stained with Masson's Trichrome (Tri) or Picrosirius Red (PSR) using standard histological methods for evaluation of fibrosis severity.

Mouse Unilateral Ureteral Obstruction Kidney Fibrosis Model

Female C57BL/6 mice (Harlan, 4-6 weeks of age) will be given free access to food and water and allowed to acclimate for at least 7 days prior to test initiation. After acclimation, mice are anesthetized and undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. All animals are euthanized 4, 8, 14, 21, or 28 days after UUO surgery. Following sacrifice blood is collected via cardiac puncture, the kidneys are harvested and one half of the kidney is frozen at −80° C. and the other half is fixed in 10% neutral buffered formalin for histopathological assessment of kidney fibrosis.

Bleomycin Dermal Fibrosis Model

Bleomycin (Calbiochem, Billerica Mass.) is dissolved in phosphate buffered saline (PBS) at 10 ug/ml, and sterilized by filtration. Bleomycin or PBS control is injected subcutaneously into two locations on the shaved back of C57/BL6 or 5129 mice (Charles River/Harlan Labs, 20-25 g) once daily for 28 days while under isoflourane anesthesia (5% in 100% 02). After 28 days, mice are euthanized and 6 mm-full thickness punch biopsies are obtained from each injection site. Dermal fibrosis is assessed by standard histopathology and hydroxyproline biochemical assays.

Example 237: Targeting Calpains

Inhibition of EpMT

For assessment of in vitro EMT, NMuMG cells (ATCC) are grown to confluence in 10% serum (Fetal Bovine Serum)

growth media (Dubecco's Modified Eagles Medium supplemented with 10 ug/mL insulin) and then are followed by 24 h starvation in 0.5% serum media +/− drug inhibitors. Cells are then treated with recombinant human TGFbl (R&D Systems 5 ng/mL) +/− drug inhibitors in 0.5% serum media. For time points greater than 24 h, the aforementioned media is refreshed every 24 hours. Cell lysates were analyzed for aSMA protein expression by western blot.

Miettinen et al. (1994). "TGF-beta induced transdifferentiation of mammary epithelial cells to mesenchymal cells: involvement of type I receptors." J Cell Biol 127 (6 Pt 2):2021-36.

Lamouille et al. (2014). "Molecular mechanisms of epithelial-mesenchymal transition." Nat Rev Mol Cell Biol 15(3):178-96.

For assessment of in vitro FMT, Normal Human Lung Fibroblasts (NHLF) cells (Lonza) were grown in Fibroblast Growth Media-2 (Lonza CC-3131/with CC-4126 bullet kit) and then were followed by 24 h starvation in serum/growth factor free Fibroblast Basal Media-2 (Lonza CC-3131)$^+$/− drug inhibitors. Cells were then treated with TGFbl (5 ng/mL) Fibroblast Basal Media +/− drug inhibitors. Cell lysates are analyzed for aSMA protein expression by western blot.

Further details may be found in Pegorier et al. (2010). "Bone Morphogenetic Protein (BMP)-4 and BMP-7 regulate differentially Transforming Growth Factor (TGF)-B1 in normal human lung fibroblasts (NHLF)" Respir Res 11:85, which is incorporated herein by reference in its entirety.

Example 238: Human Treatment

The efficacy of treatment with a compound of a preferred embodiment compared with placebo in patients with idiopathic pulmonary fibrosis (IPF) and the safety of treatment with a compound of a preferred embodiment compared with placebo in patients with IPF is assessed. The primary outcome variable is the absolute change in percent predicted forced vital capacity (FVC) from baseline to Week 52. Other possible end-points would include, but are not limited to: mortality, progression free survival, change in rate of FVC decline, change in Sp02, and change in biomarkers (HRCT image analysis; molecular and cellular markers of disease activity). Secondary outcome measures include: composite outcomes of important IPF-related events; progression-free survival; the rate of death from any cause; the rate of death from IPF; categorical assessment of absolute change in percent predicted FVC from baseline to Week 52; change in Shortness-of-Breath from baseline to Week 52; change in percent predicted hemoglobin (Hb)-corrected carbon monoxide diffusing capacity (DLco) of the lungs from baseline to Week 52; change in oxygen saturation during the 6 minute walk test (6MWT) from baseline to Week 52; change in high-resolution computed tomography (HRCT) assessment from baseline to Week 52; change in distance walked in the 6MWT from baseline to Week 52. Patients eligible for this study include, but are not limited to: those patients that satisfy the following inclusion criteria: diagnosis of IPF; 40 to 80 years of age; FVC≥50% predicted value; DLco≥35% predicted value; either FVC or DLco≤90% predicted value; no improvement in past year; a ratio of the forced expiratory volume in 1 second (FEV1) to the FVC of 0.80 or more; able to walk 150 meters in 6 minutes and maintain saturation ≥83% while on no more than 6 L/min supplemental oxygen. Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 52 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials. Patients are orally dosed with either placebo or an amount of a compound of a preferred embodiment (1 mg/day-1000 mg/day). The primary outcome variable will be the absolute change in percent predicted FVC from Baseline to Week 52. Patients will receive blinded study treatment from the time of randomization until the last patient randomized has been treated for 52 weeks. Physical and clinical laboratory assessments will be performed at defined intervals during the treatment duration, for example at weeks 2, 4, 8, 13, 26, 39, and 52. Pulmonary function, exercise tolerance, and shortness-of-breath will be assessed at defined intervals during the treatment duration, for example at weeks 13, 26, 39, and 52. A Data Monitoring Committee (DMC) will periodically review safety and efficacy data to ensure patient safety.

Example Trial in SSc

The efficacy of treatment with a compound of a preferred embodiment compared with placebo in patients with systemic sclerosis (SSc) and the safety of treatment with a compound of a preferred embodiment compared with placebo in patients with SSc is assessed. The primary outcome variable is the absolute change in Modified Rodnan Skin Score (mRSS) from baseline to Week 48. Other possible end-points would include, but are not limited to: mortality, percentage of patients with treatment-emergent adverse events (AEs) and serious adverse events (SAEs), composite measurement of disease progression, and change in biomarkers (molecular and cellular markers of disease activity, such as C-reactive protein). Secondary outcome measures include, but are not limited to: Scleroderma Health Assessment Questionnaire (SHAQ) score; the Health Assessment Questionnaire Disability Index (HAQ-DI); Functional Assessment of Chronic Illness Therapy-Fatigue (FACIT) score; severity of pruritus as measured by a standardized scale, such as the 5-D Itch Scale; St. George's Respiratory Questionnaire (SGRQ) score; Tender Joint Count 28 (TCJ28); lung function parameters; standard vital signs (including blood pressure, heart rate, and temperature); electrocardiogram measurements (ECGs); laboratory tests (clinical chemistry, hematology, and urinalysis); pharmacokinetics (PK) measurements. Included in these measurements and in addition, clinical and biomarker samples, such as skin biopsies and blood (or serum and/or plasma), will also be collected prior to initiation of treatment. Additionally, patients eligible for this study include, but are not limited to, those patients that satisfy the following criteria: Patients at least 18 years of age; diagnosis of SSc according to the American College of Rheumatology (ACR) and European League Against Rheumatism (EULAR) Criteria, meeting criteria for active disease and with a total disease duration of less than or equal to 60 months; 10≤mRSS≤35. Patients are excluded from this study if they satisfy any of the following criteria: major surgery within 8 weeks prior to screening; scleroderma limited to area distal to the elbows or knees; rheumatic autoimmune disease other than SSc; use of any investigational, biologic, or immunosuppressive therapies, including intra-articular or parenteral corticosteroids within 4 weeks of screening. Patients are orally dosed with either placebo or an amount of a compound of a preferred embodiment (1 mg/day-1000 mg/day). The primary outcome variable will be the absolute change in mRSS from Baseline to Week 48. Patients will receive blinded study treatment from the time of randomization until the last patient randomized has been treated for 48 weeks. Physical and clinical laboratory assessments will be performed at defined intervals during the treatment duration, such as Weeks 2, 4, 8, 12, 24, 36, and 48. Clinical and biomarker samples will also be collected at Week 48. A Data Monitoring Committee (DMC) will periodically review safety and efficacy data to ensure patient safety.

Example 239: Calpain Binding

Calpain 9 Protein Preparation: N-terminally hexa-histidine-tagged human calpain 9, residues 27-347, was over expressed in *E. coli* BL21 (DE3) and purified via Ni-NTA and size-exclusion chromatography with yields >10 mg/liter of culture and >99% purity. The calpain 9 sequence is accession number 014815 at uniprot.org.

Calpain 9 Crystallization: A 10 mg/ml solution of rat calpain 1 or human calpain 9 (obtained as described above) was prepared in 50 mM tris (pH 8), 0.5 M NaCl, 1 mM EDTA, 1 mM CaCl2), and 1 mM beta-mercaptoethanol against MCSG1 screen condition C2 (Anatrace, Maumee, Ohio) containing 0.2 M LiSO4, 0.1 M bis-tris (pH 5.5), and 25% PEG 3350. The solution contained 2.5 mM of test compound supplemented with 20% ethylene glycol as a cryo-protectant. The bound protein was crystallized using vapor diffusion, sitting drop, at 289° K. The space group was P 41 21 2, with unit cell dimensions of 97.2 Å, 97.2 Å, 173.4 Å.

Calpain 9 Crystallography data collection and refinement: Data was collected at the APS synchrotron, beamline 21-ID-F at 1000 K. Reflections were collect between 45.0-2.1 Å with completeness of 100%. Reflection data was analyzed using XDS and Xscale (Heidelberg, Germany). Structure was solved using molecular replacement and was refined with PHENIX (Berkeley, Calif.) to an R value of 0.168, Rfree=0.210.

Calpain 9 modeling: The experimental distances measured from crystal structures were supplemented with computational models of calpain 9 binding. The calpain 9/test compound crystal structure was used for the initial coordinates. It was stripped of solvent and minimized in MOE 2016.08 (CCG, Montreal) using the standard quickprep protocol and the Amber10:EHT force field. Various test compounds were then minimized in the active site. The distances showed good agreement with the available crystal data.

Calpain 1 preparation, crystallization, and data collection: Suitable constructs for expression of rat calpain 1 had been previously established. Expression was performed according to previously established protocols. A purification protocol was established and homogeneous protein was produced in preparative amounts. The calpain 1 protein was purified comprising affinity and gel filtration chromatography steps. This procedure yielded homogenous protein with a purity greater 95% as judged from Coomassie stained SDS-PAGE. The purified protein was used in crystallization trials with test compounds employing both, a standard screen with approximately 1200 different conditions, as well as crystallization conditions identified using literature data. Conditions initially obtained were optimised using standard strategies, systematically varying parameters critically influencing crystallization, such as temperature, protein concentration, drop ratio, and others. These conditions were also refined by systematically varying pH or precipitant concentrations. Crystals were flashfrozen and measured at a temperature of 100 K. The X-ray diffraction data were collected from complex crystals ligands at a synchrotron source using cryogenic conditions. Data were processed using software programs XDS and XSCALE Key interactions between test compound moieties (with reference to the variables of Formula II) and calpain 1 or calpain 9 residues were determined as set forth in Tables 4-7 below.

TABLE 4

Polar interactions with human calpain 9

| Compound | Interaction Distances/Å $R^{10}$-Gly253 | $R^{11}$-Gly190 | $R^{12}$-His254 | $R^{13}$-Gln91 | $R^{13}$-Cys97 |
|---|---|---|---|---|---|
| 32 | 3.2 | 2.9 | 2.7 | 2.8 | 2.9 |
| 72 | 3.2 | 2.9 | 2.6 | 2.8 | 2.9 |
| 44 | 2.9 | 3.2 | 2.5 | 2.8 | 3.0 |
| 265 | 2.9 | 3.2 | 2.4 | 2.9 | 3.1 |

TABLE 5

Polar interactions with rat calpain 1

| Compound | Interaction Distances/Å $R^{10}$-Gly271 | $R^{11}$-Gly208 | $R^{12}$-His272 | $R^{13}$-Gln109 | $R^{13}$-Cys115 |
|---|---|---|---|---|---|
| 60 | 3.21 | 2.9 | 2.9 | 2.91 | 2.91 |
| 250 | 3.28 | 2.98 | 2.81 | 3 | 2.96 |

TABLE 6

Non-polar interactions with human calpain 9

| Compound | Interaction Distances/Å $P_2$-Gly190 | $P_2$-Phe233 | $P_2$-Gly253 | $P_2$-His254 | $P_2$-Ala255 | $P_3$-Gly189 | $P_3$-Gly190 | $P_3$-Ser191 | $P_1$-Gly95 | $P_1$-Lys188 | $P_1$-Gly189 | $P_1$-Ser242 |
|---|---|---|---|---|---|---|---|---|---|---|---|---|
| 32 | 3.3 | 3.3 | 3.1 | 4.2 | 4.3 | 3.7 | 3.5 | 4.4 | 4.0 | 3.8 | 3.5 | 3.6 |
| 72 | 3.0 | 4.1 | 3.2 | 3.7 | 3.6 | 3.8 | 3.3 | 4.2 | 3.9 | 4.0 | 3.5 | 3.5 |
| 44 | 3.0 | 4.4 | 3.4 | 4.2 | 3.9 | 4.0 | 3.3 | 4.2 | 3.6 | 3.7 | 3.4 | 3.7 |
| 265 | 3.2 | 3.3 | 2.9 | 4.2 | 4.1 | 3.8 | 3.4 | 3.8 | 3.7 | 4.4 | 3.7 | 4.0 |
| 403* | 3.1 | 2.9 | 3.1 | 4.4 | 4.1 | 3.5 | 3.6 | 4.4 | 3.9 | 4.2 | 3.4 | 3.5 |
| 484* | 3.2 | 3.2 | 3.1 | 4.5 | 4.3 | 3.4 | 3.4 | 4.5 | 3.8 | 4.1 | 3.5 | 3.5 |
| 405* | 3.2 | 3.2 | 3.0 | 4.1 | 4.3 | 3.7 | 3.5 | 4.4 | 3.9 | 4.2 | 3.6 | 3.5 |

*Based on computational modelling

TABLE 7

| Non-polar interactions with rat calpain 1 | | | | | | | | | | | | |
|---|---|---|---|---|---|---|---|---|---|---|---|---|
| | Interaction Distances/Å | | | | | | | | | | | |
| Compound | $P_2$- Gly208 | $P_2$- Ser251 | $P_2$- Gly271 | $P_2$- His272 | $P_2$- Ala273 | $P_3$- Gly207 | $P_3$- Gly208 | $P_3$- Ser209 | $P_1$- Gly113 | $P_1$- Ser206 | $P_1$- Gly207 | $P_1$- Met260 |
| 60 | 3.2 | 4.4 | 3.2 | 4.2 | 4.1 | 3.7 | 3.3 | 4.4 | 4.0 | 4.4 | 3.7 | 3.3 |
| 250 | 3.3 | 3.7 | 3.4 | 4.6 | 4.4 | 3.6 | 3.5 | 3.8 | 3.8 | 4.1 | 3.5 | 3.5 |

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Although the invention has been described with reference to embodiments and examples, it should be understood that numerous and various modifications can be made without departing from the spirit of the invention. Accordingly, the invention is limited only by the following claims.

REFERENCES CITED

1. U.S. Pat. No. 5,145,684
2. Goll et al. (2003). "The calpain system." Physiol Rev 83(3):731-801.
3. Schad et al. (2002). "A novel human small subunit of calpains." Biochem J 362 (Pt 2):383-8.
4. Ravulapalli et al. (2009). "Distinguishing between calpain heterodimerization and homodimerization." FEBS J 276 (4):973-82.
5. Dourdin et al. (2001). "Reduced cell migration and disruption of the actin cytoskeleton in calpain-deficient embryonic fibroblasts." J Biol Chem 276(51):48382-8.
6. Leloup et al. (2006). "Involvement of calpains in growth factor-mediated migration." Int J Biochem Cell Biol 38(12):2049-63.
7. Janossy et al. (2004). "Calpain as a multi-site regulator of cell cycle." Biochem Pharmacol 67(8):1513-21.
8. Santos et al. (2012). "Distinct regulatory functions of calpain 1 and 2 during neural stem cell self-renewal and differentiation." PLoS One 7(3):e33468.
9. Miettinen et al. (1994). "TGF-beta induced transdifferentiation of mammary epithelial cells to mesenchymal cells: involvement of type I receptors." J Cell Biol 127 (6 Pt 2):2021-36.

10. Lamouille et al. (2014). "Molecular mechanisms of epithelial-mesenchymal transition." Nat Rev Mol Cell Biol 15(3):178-96.

11. Pegorier et al. (2010). "Bone Morphogenetic Protein (BMP)-4 and BMP-7 regulate differentially Transforming Growth Factor (TGF)-B1 in normal human lung fibroblasts (NHLF)" Respir Res 11:85.

What is claimed is:

1. A compound having the structure of formula:

I-h

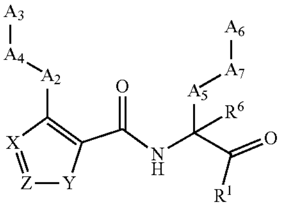

or a pharmaceutically acceptable salt thereof, wherein:

$A_2$ is a single bond;

$A_4$ is a single bond;

$A_3$ is directly attached to the ring-atom to which $A_2$ is attached;

$A_3$ is selected from the group consisting of optionally substituted $C_{6-10}$ aryl, optionally substituted 5-10 membered heteroaryl, optionally substituted 3-10 membered heterocyclyl, and optionally substituted $C_{3-10}$ carbocyclyl;

$A_5$ is selected from the group consisting of optionally substituted 3-10 membered heterocyclyl, optionally substituted $C_{6-10}$ aryl, optionally substituted 5-10 membered heteroaryl, optionally substituted $C_{3-10}$ carbocyclyl, optionally substituted $C_{1-8}$ alkyl, —S—, —S(═O)—, —$SO_2$—, —O—, —C(═S)—, —C(═O)—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;

$A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, optionally substituted $C_{1-8}$ alkyl, optionally substituted $C_{2-8}$ alkenyl, optionally substituted —O—$C_{1-6}$ alkyl, optionally substituted —$OC_{2-6}$ alkenyl, —$OSO_2CF_3$, and any natural or non-natural amino acid side chain;

$A_7$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, optionally substituted $C_{1-8}$ alkyl, —S—, S(═O)—, —$SO_2$—, —O—, —C(═S)—, —C(═O)—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;

when $A_5$ and $A_7$ are single bond, $A_6$ is directly attached to the carbon to which —$COR^1$ is attached;

$R^1$ is selected from the group consisting of H, —COOH, —$CH_2NO_2$, —C(═O)NOR, —$CONR^2R^3$, —$CH(CH_3)$═$CH_2$, —$CH(CF_3)NR^2R^3$, —C(F)═$CHCH_2CH_3$,

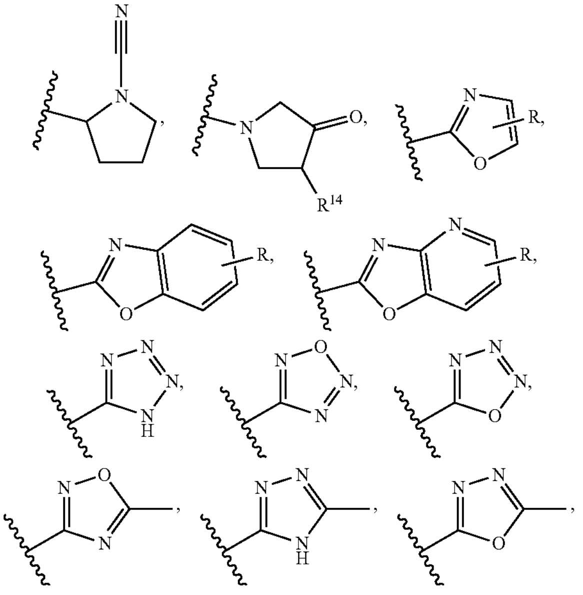

and

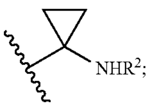

$R^{14}$ is halo;

each R, $R^2$, and $R^3$ are independently selected from —H, optionally substituted $C_{1-4}$ alkyl, optionally substituted $C_{1-8}$ alkoxyalkyl, optionally substituted 2- to 5-membered polyethylene glycol, optionally substituted $C_{3-7}$ carbocyclyl, optionally substituted 5-10 membered heterocyclyl, optionally substituted $C_{6-10}$ aryl, optionally substituted $C_{6-10}$ aryl($C_1$-$C_6$)alkyl, and optionally substituted 5-10 membered heteroaryl;

$R^6$ is independently selected from —H and optionally substituted $C_{1-4}$ alkyl;

X and Z are each independently selected from the group consisting of $C(R^4)$ and N;

each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy;

Y is selected from the group consisting of $NR^5$, O, S, and $SO_2$; and $R^5$ is selected from the group consisting of —H, $C_{1-4}$ alkyl, $C_{1-4}$ haloalkyl, and $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy).

2. The compound of claim 1, wherein:

$A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, optionally substituted $C_{1-8}$ alkyl, optionally substituted —O—$C_{1-6}$ alkyl, optionally substituted —$OC_{2-6}$ alkenyl, and any natural or non-natural amino acid side chain; and each R, $R^2$, and $R^3$ are independently selected from —H, optionally substituted $C_{1-4}$ alkyl, optionally substituted $C_{3-7}$ carbocyclyl, optionally substituted 5-10 membered heterocyclyl, optionally substituted $C_{6-10}$ aryl, and optionally substituted 5-10 membered heteroaryl.

3. The compound of claim 1, wherein X and Z are independently selected from the group consisting of CH and N.

4. The compound of claim 1, wherein X is CH, Z is N, and Y is $NR^5$.

5. The compound of claim 1, wherein X is N, Z is $C(R^4)$, and Y is O.

6. The compound of claim 5, wherein $R^4$ is selected from —H and $C_{1-4}$ alkyl.

7. The compound of claim 1, wherein X is N, Z is $C(R^4)$, and Y is S.

8. The compound of claim 1, wherein X is N, Z is N, and Y is S.

9. The compound of claim 1, wherein $A_3$ is substituted with $^{18}F$.

10. The compound of claim 1, wherein $A_3$ is substituted with $C_1$-$C_6$ alkyl containing one or more $^{11}C$.

11. The compound of claim 1, wherein $A_3$ is selected from the group consisting of

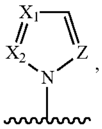 , 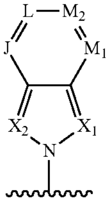 , 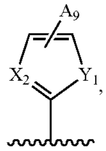 , 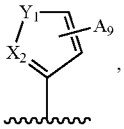 ,

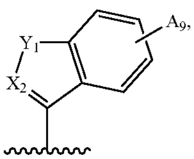 , 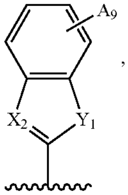 , 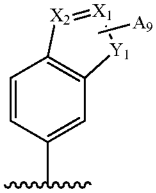 ,

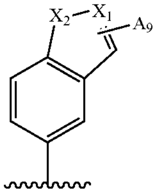 , 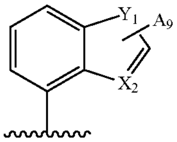 and

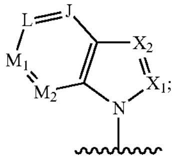 ;

and $A_9$ is selected from the group consisting of H, $C_{6-10}$ aryl, 5-10 membered heteroaryl, 3-10 membered heterocyclyl, $C_{3-10}$ carbocyclyl, and $C_{1-4}$ alkyl;

$X_2$, $X_1$, and Z are each independently selected from the group consisting of $C(R^4)$ and N;

$Y_1$ is selected from the group consisting of $NR^5$, O, and S;

J, L, $M_1$ and $M_2$ are each independently selected from the group consisting of $C(R^4)$ and N;

$R^4$ is selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy;

$R^5$ is selected from the group consisting of —H, $C_{1-4}$ alkyl, $C_{1-4}$ haloalkyl, and $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy).

12. The compound of claim 1, wherein $A_3$ is selected from the group consisting of

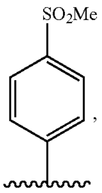 , 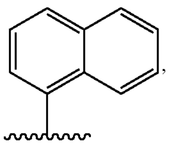 , 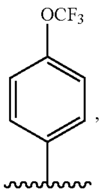 ,

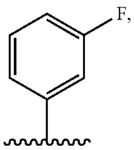 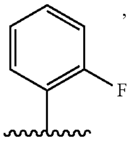 , and 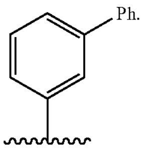

13. The compound of claim 1, wherein $A_3$ is selected from the group consisting of

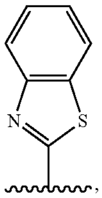 , 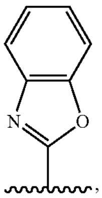 , 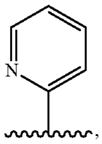 , 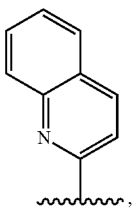 ,

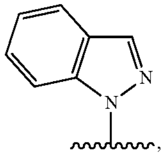 , 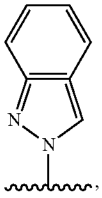 , and 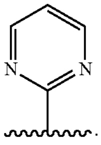 .

14. The compound of claim 1, wherein $A_3$ is an optionally substituted $C_{6-10}$ aryl or an optionally substituted 5-10 membered heteroaryl.

15. The compound of claim 14, wherein $A_3$ has the structure:

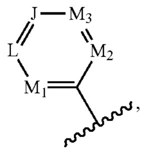 , wherein

J, L, $M_1$, $M_2$, and $M_3$ are each independently selected from the group consisting of $C(R^4)$ and N; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

16. The compound of claim 15, wherein each of J, L, $M_1$, $M_2$, and $M_3$ are $C(R^4)$.

17. The compound of claim 16, wherein each $R^4$ is independently selected from —H and halo.

18. The compound of claim 15, wherein $M_1$ is $C(R^4)$; $R^4$ is halo and each of J, L, $M_2$, and $M_3$ are CH.

19. The compound of claim 15, wherein L is $C(R^4)$; $R^4$ is halo and each of J, $M_1$, $M_2$, and $M_3$ are CH.

20. The compound of claim 14, wherein $A_3$ has a structure selected from the group consisting of:

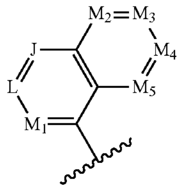

and

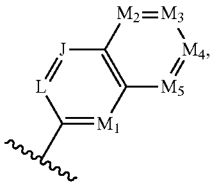

wherein

J, L, $M_1$, $M_2$, $M_3$, $M_4$, and $M_5$ are each independently selected from the group consisting of $C(R^4)$ and N; and each $R^4$ is independently selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

21. The compound of claim 14, wherein $A_3$ has the structure:

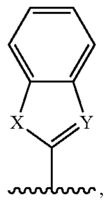

wherein

X is selected from the group consisting of $C(R^4)$ and N;

Y is selected from O and S; and $R^4$ is selected from the group consisting of —H, $C_{1-4}$ alkyl, $C_{1-4}$ haloalkyl, $C_{3-7}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, hydroxy, and $C_1$-$C_6$ alkoxy.

22. The compound of claim 1, wherein at least one of the optionally substituted moieties of $A_5$, $A_7$, and $A_6$ is substituted with $^{18}F$.

23. The compound of claim 1, wherein at least one of the optionally substituted moieties of $A_5$, $A_7$, and $A_6$ is substituted with $C_1$-$C_6$ alkyl containing one or more $^{11}C$.

24. The compound of claim 1, wherein $A_6$ is phenyl.

25. The compound of claim 1, wherein $A_7$ is selected from the group consisting of single bond, —$CH_2$—, O, —CH═CH—, and —S.

26. The compound of claim 1, wherein $A_7$ is selected from the group consisting of single bond, optionally substituted $C_{6-10}$ aryl, and phenyl.

27. The compound of claim 1, wherein $A_5$ is —$CH_2$—.

28. The compound of claim 1, wherein $A_5$ is —$CH_2$— or —$CH_2CH_2$—; $A_7$ is a single bond; and $A_6$ is selected from the group consisting of $C_1$-$C_4$ alkyl, optionally substituted phenyl, optionally substituted 5-10 membered heteroaryl.

29. The compound of claim 28, wherein $A_6$ is selected from the group consisting of optionally substituted phenyl, phenyl and phenyl optionally substituted with one or more $C_{1-4}$ alkyl, $C_{3-7}$ carbocyclyl, halo, hydroxy, and $C_1$-$C_6$ alkoxy.

30. The compound of claim 28, wherein $A_6$ has the structure:

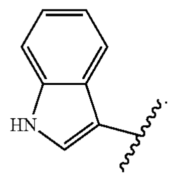

31. The compound of claim 1, wherein $A_5$ is a single bond, $A_7$ is a single bond; and $A_6$ is $C_1$-$C_5$ alkyl.

32. The compound of claim 31, wherein $A_6$ is selected from the group consisting of ethyl, n-propyl, isopropyl, isobutyl, 2,2-dimethylpropyl, and 1,2-dimethylpropyl.

33. The compound of claim 1, wherein $R^1$ is $CONR^2R^3$.

34. The compound of claim 33, wherein $R^2$ is —H and $R^3$ is optionally substituted $C_{1-4}$ alkyl.

35. The compound of claim 33, wherein $R^2$ is —H and $R^3$ is selected from the group consisting of —H, $C_1$-$C_4$ alkyl optionally substituted with C-amido, and $C_3$-$C_6$ cycloalkyl.

36. The compound of claim 35, wherein $R^3$ is selected from the group consisting of —H, ethyl, cyclopropyl, and methyl substituted with C-amido.

37. The compound of claim 33, wherein $R^3$ is selected from the group consisting of optionally substituted $C_{1-4}$ alkyl and benzyl.

38. The compound of claim 1, wherein $R^6$ is selected from the group consisting of —H, methyl, and optionally substituted $C_{1-4}$ alkyl.

39. A compound having the structure selected from the group consisting of:

6

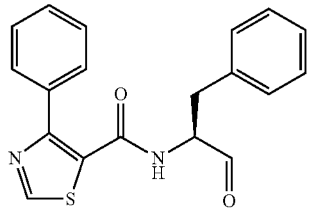

18

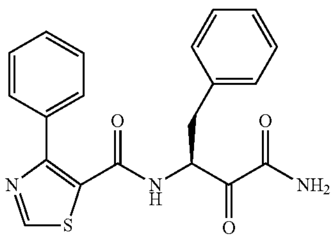

-continued
21
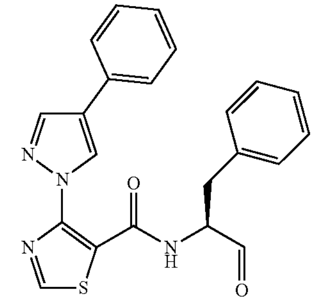
22
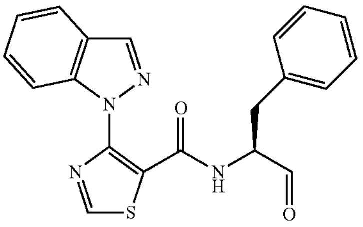
25
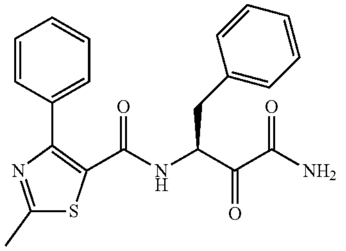
26
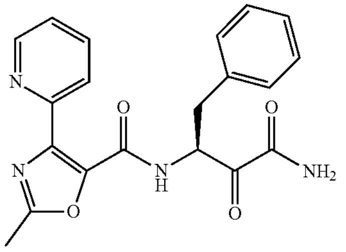
37
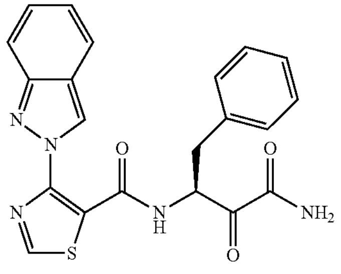
39
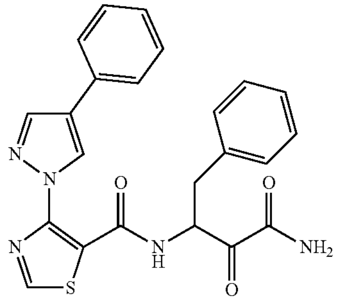
-continued
40
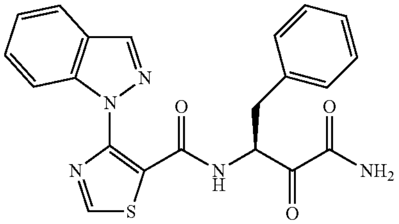
44
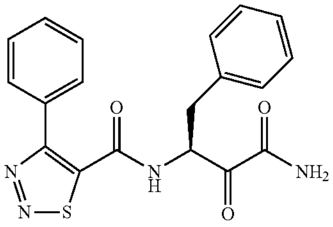
48
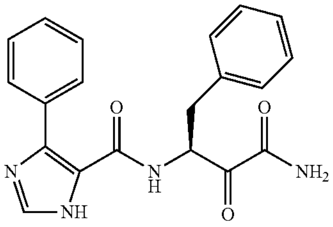
61
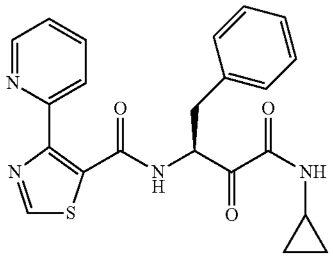
64
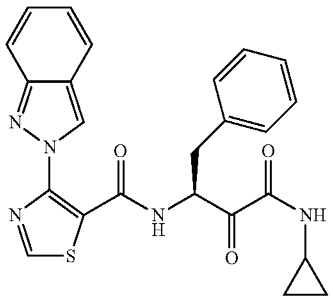
86
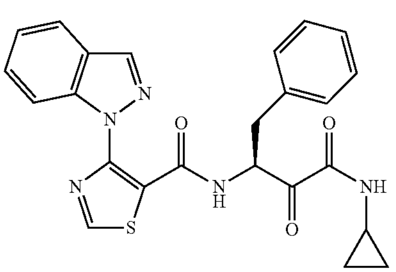

-continued
87
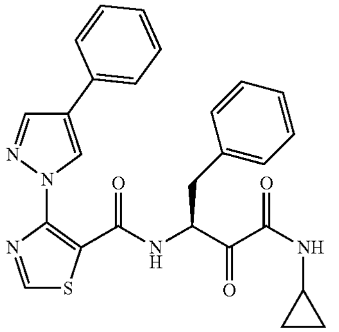
104
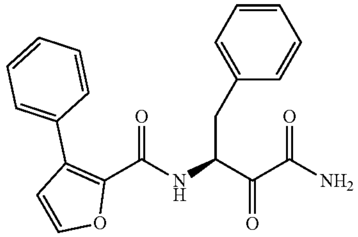
107
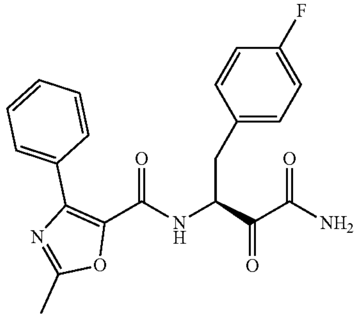
109
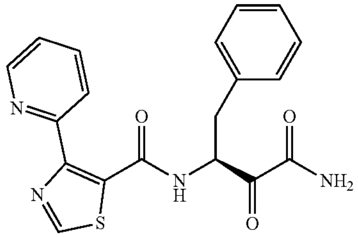
124
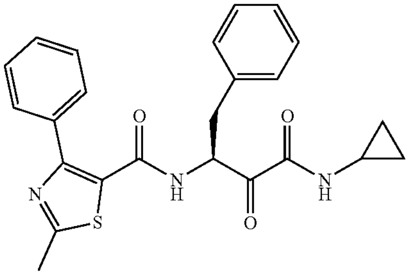
-continued
129
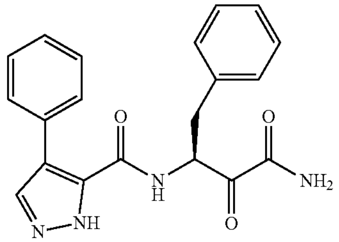
135
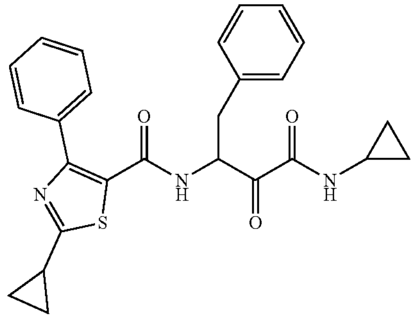
207
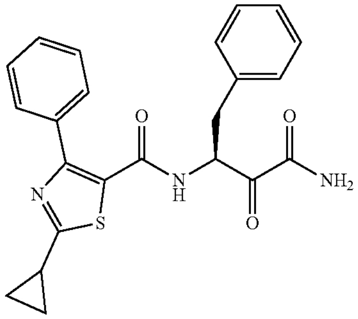
226
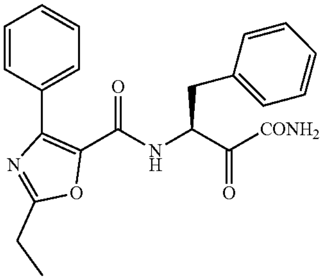
240
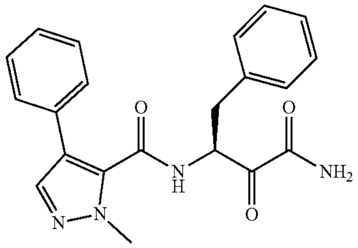

-continued
243
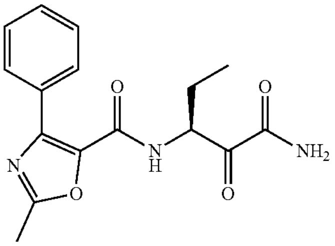
248
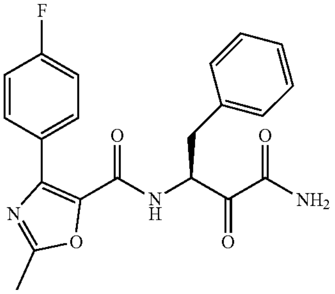
253
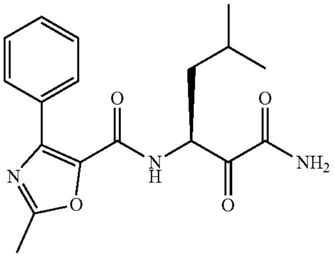
254
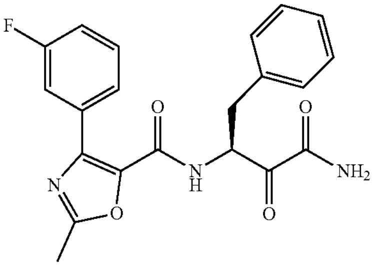
255
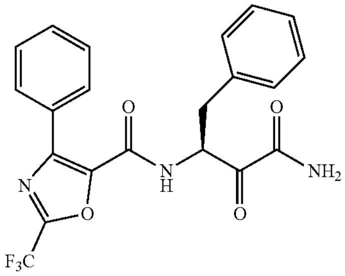
261
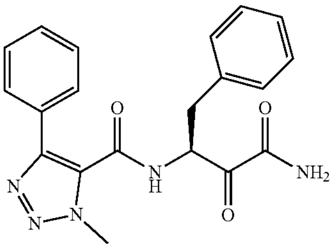
-continued
265
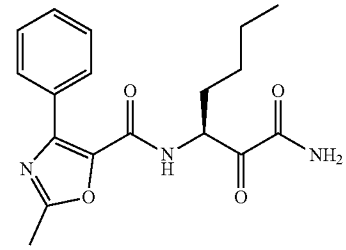
266
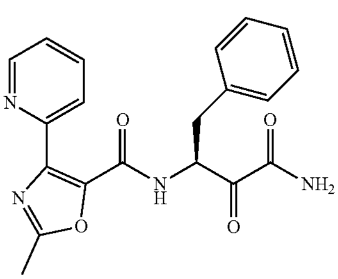
267
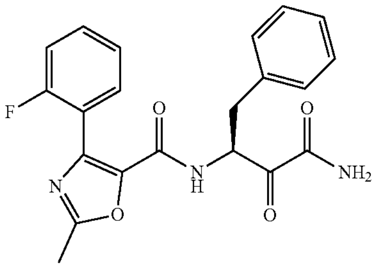
268
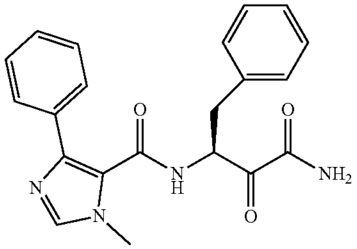
287
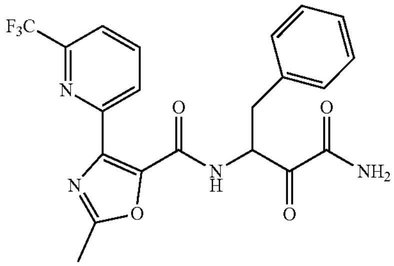
303
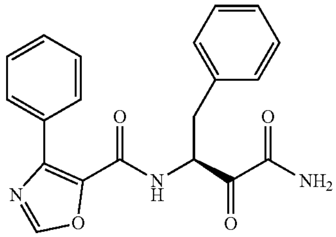

-continued
322
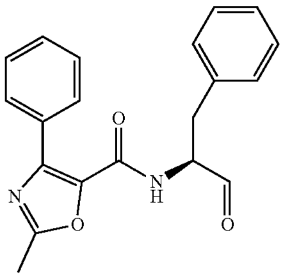
353
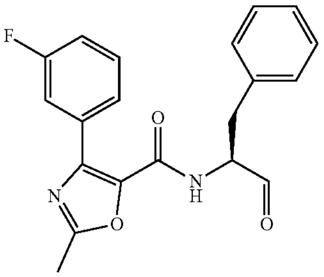
354
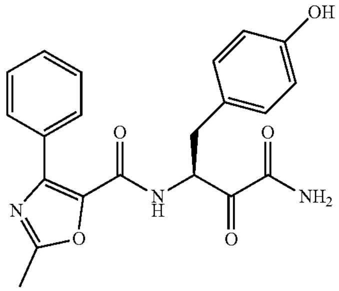
355
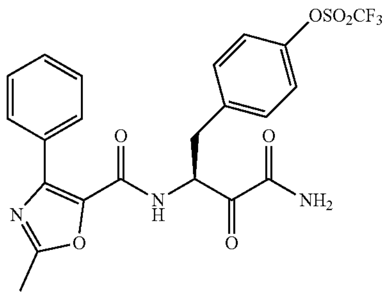
356
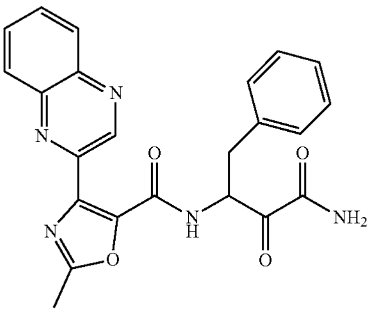
-continued
357
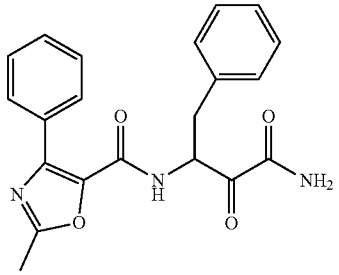
358
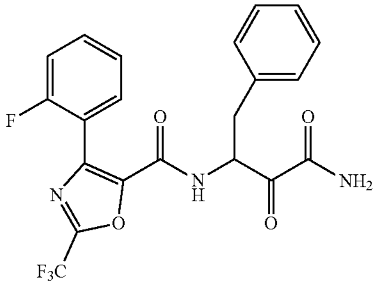
359
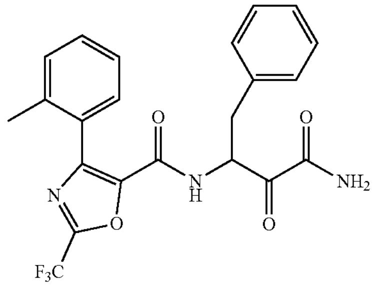
360
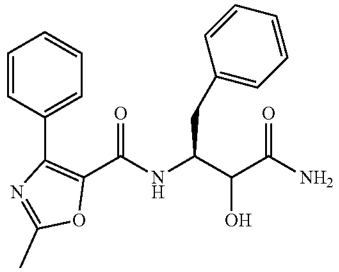
361
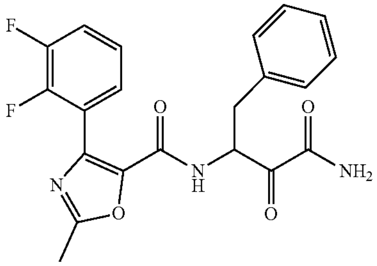

385
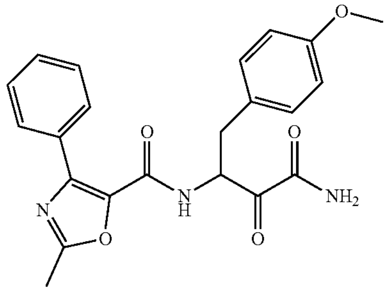
386
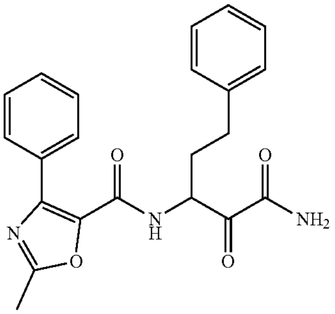
387
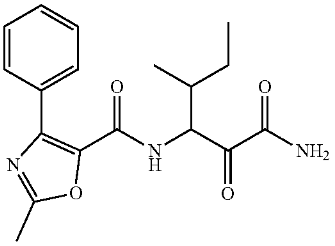
388
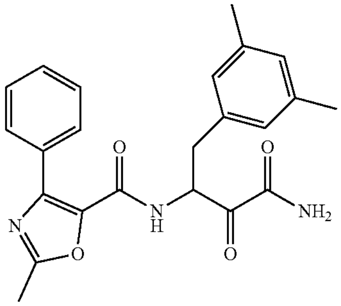
389
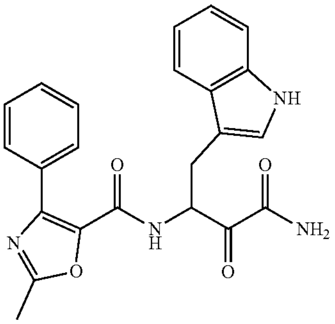
390
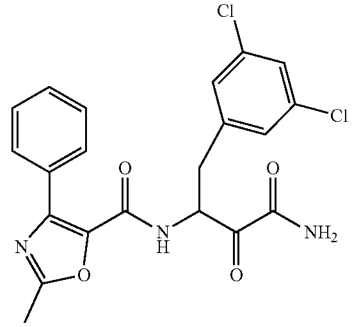
391
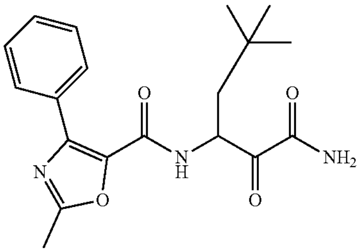
393
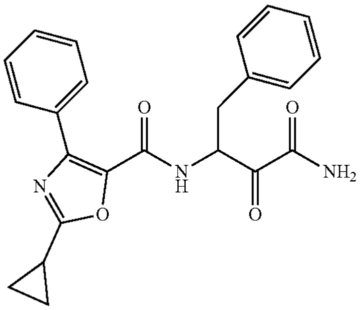
402
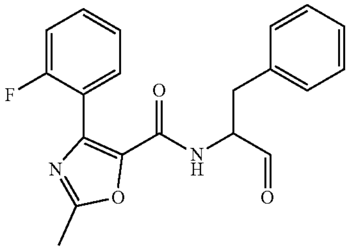
404
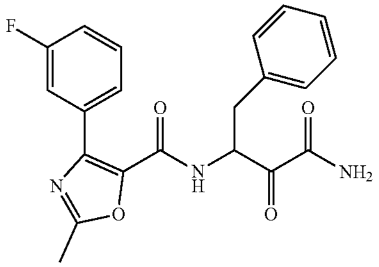

-continued

405

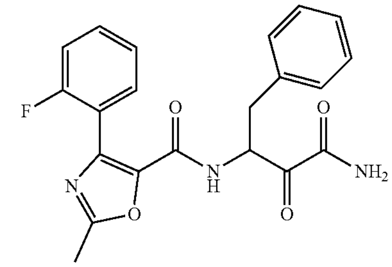

459

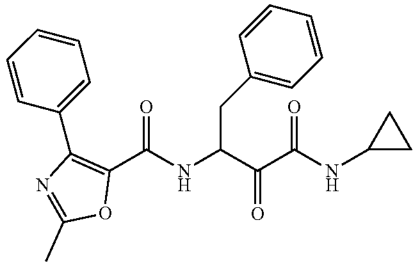

460

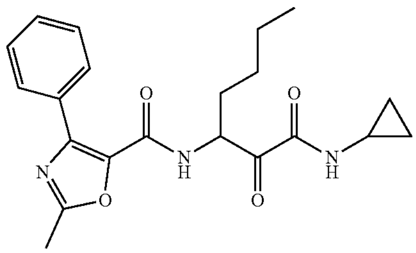

475

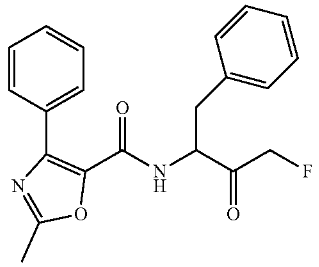

592

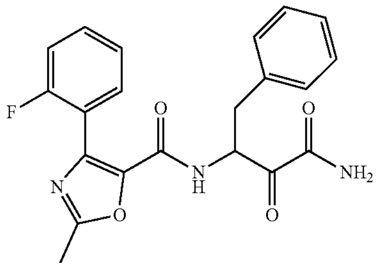

609

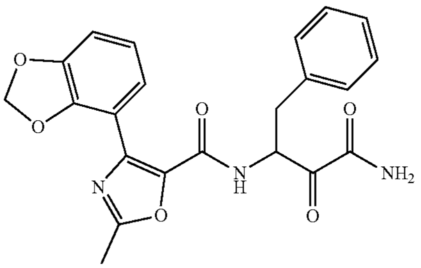

-continued

618

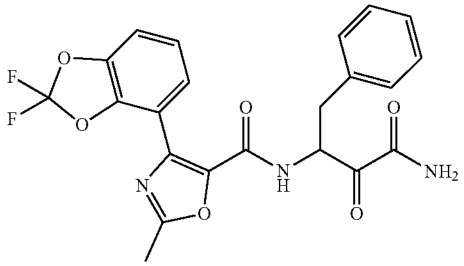

and pharmaceutically acceptable salts thereof.

40. A pharmaceutical composition comprising a compound of claim 1 and a pharmaceutically acceptable excipient.

41. A method of treating fibrotic disease comprising administering to a subject in need thereof, a compound according to claim 1.

42. The method of claim 41, wherein the disease is selected from the group consisting of liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis.

43. A compound having the structure selected from the group consisting of:

6

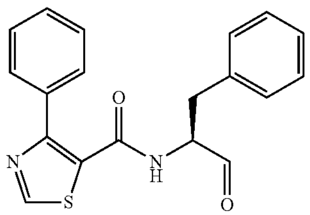

26

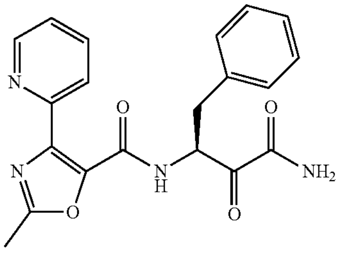

-continued
39
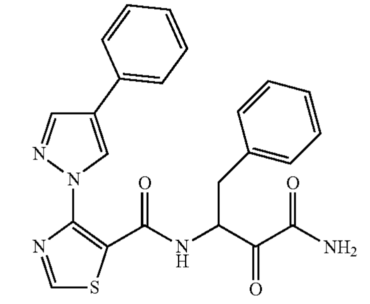
44
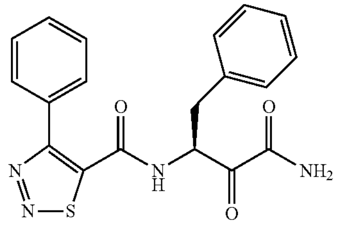
48
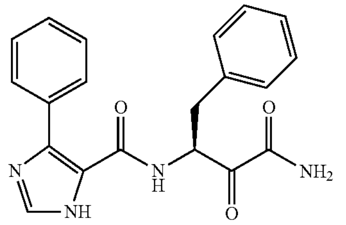
104
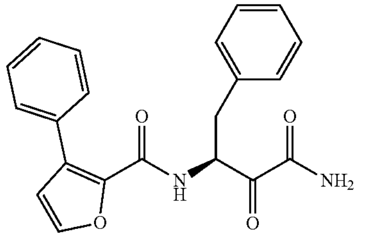
129
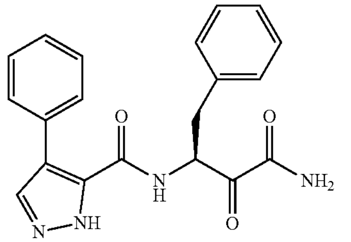
226
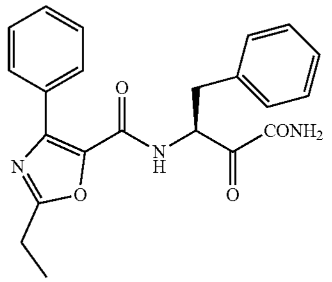
-continued
240
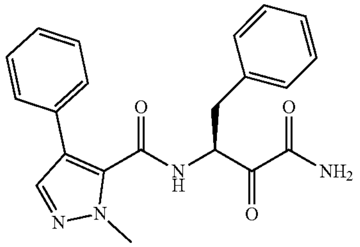
243
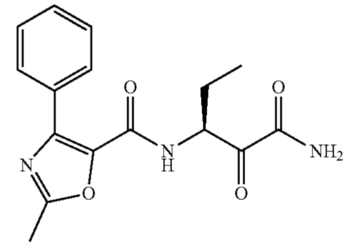
255
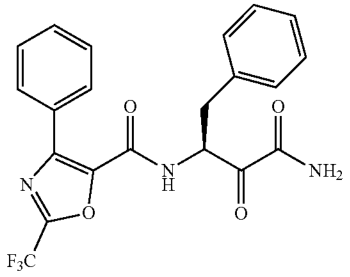
303
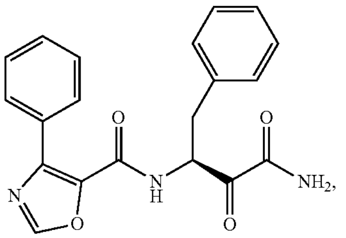
and pharmaceutically acceptable salts thereof.
44. A compound having the structure selected from the group consisting of:
37
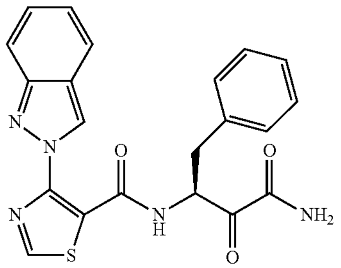

-continued
86
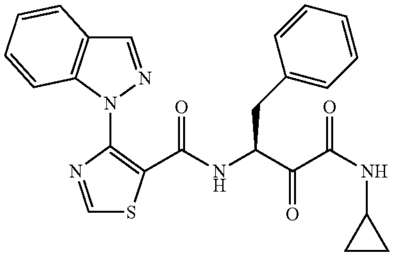
129
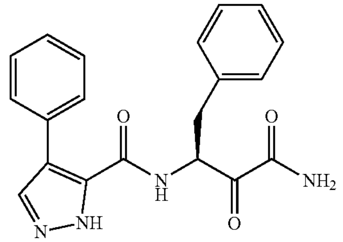
207
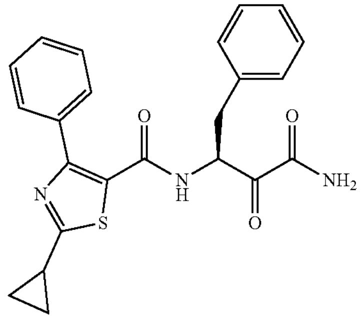
240
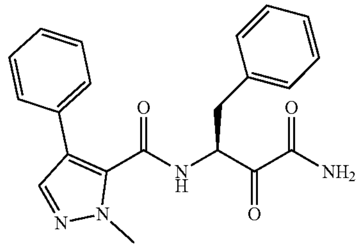
261
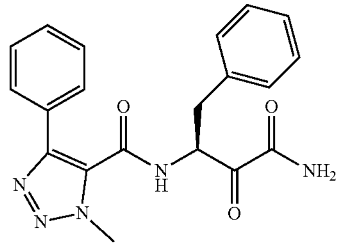
353
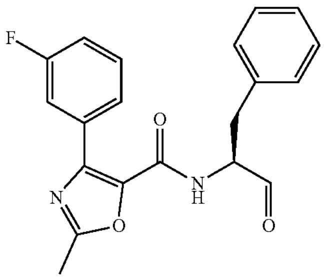
-continued
358
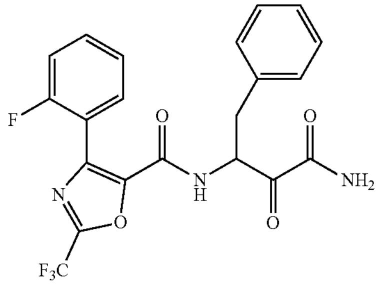
360
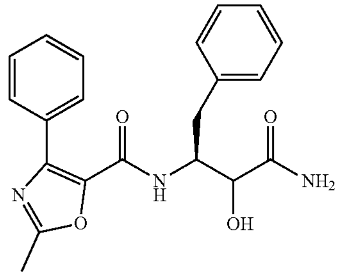
386
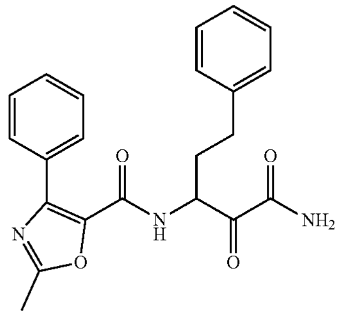
393
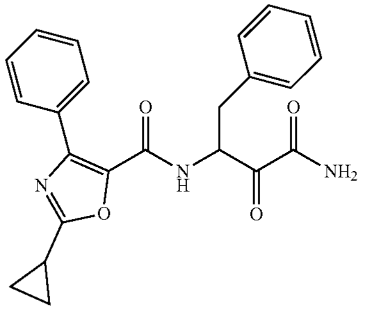
405
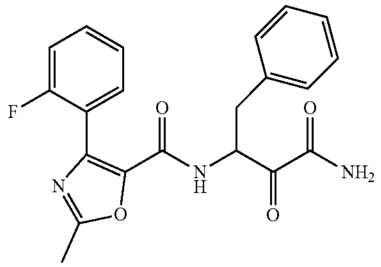

-continued
460
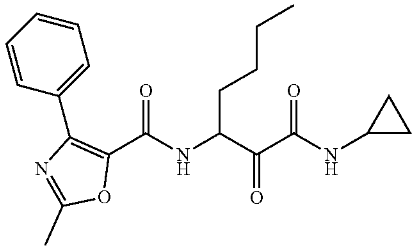
,
and pharmaceutically acceptable salts thereof.
* * * * *